United States Patent
Liang et al.

(10) Patent No.: US 11,612,606 B2
(45) Date of Patent: Mar. 28, 2023

(54) 8-AMINOISOQUINOLINE COMPOUNDS AND USES THEREOF

(71) Applicant: Genentech, Inc., South San Francisco, CA (US)

(72) Inventors: Jun Liang, Los Altos Hills, CA (US); Rohan V. Mendonca, Pleasanton, CA (US); Michael Siu, San Francisco, CA (US); John Tellis, San Mateo, CA (US); Weiru Wang, Orinda, CA (US); BinQing Wei, Belmont, CA (US); Bryan Chan, Foster City, CA (US); Edna F. Choo, San Francisco, CA (US); Joy Drobnick, Daly City, CA (US); Lewis J. Gazzard, Belmont, CA (US); Timothy Heffron, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 11 days.

(21) Appl. No.: 16/592,502

(22) Filed: Oct. 3, 2019

(65) Prior Publication Data
US 2020/0108075 A1    Apr. 9, 2020

Related U.S. Application Data

(63) Continuation of application No. PCT/US2019/054359, filed on Oct. 2, 2019.

(60) Provisional application No. 62/870,529, filed on Jul. 3, 2019, provisional application No. 62/740,894, filed on Oct. 3, 2018.

(51) Int. Cl.
| | |
|---|---|
| *A61K 31/5383* | (2006.01) |
| *A61K 31/4725* | (2006.01) |
| *C07D 498/04* | (2006.01) |
| *C07D 498/08* | (2006.01) |
| *A61K 31/4375* | (2006.01) |
| *C07D 491/052* | (2006.01) |
| *A61K 31/436* | (2006.01) |
| *A61K 31/551* | (2006.01) |
| *C07D 471/04* | (2006.01) |
| *A61K 31/439* | (2006.01) |

(52) U.S. Cl.
CPC ........ *A61K 31/5383* (2013.01); *A61K 31/436* (2013.01); *A61K 31/439* (2013.01); *A61K 31/4375* (2013.01); *A61K 31/4725* (2013.01); *A61K 31/551* (2013.01); *C07D 471/04* (2013.01); *C07D 491/052* (2013.01); *C07D 498/04* (2013.01); *C07D 498/08* (2013.01)

(58) Field of Classification Search
CPC ............ A61K 31/5383; A61K 31/4725; A61K 31/4375; A61K 31/436; A61K 31/551; A61K 31/439; A61K 45/06; C07D 498/04; C07D 498/08; C07D 491/052; C07D 471/04; C07D 519/00; C07D 401/14
USPC ........................................................ 546/143
See application file for complete search history.

(56) References Cited

U.S. PATENT DOCUMENTS

| | | | |
|---|---|---|---|
| 4,590,273 A | 5/1986 | Konz et al. | |
| 7,863,291 B2 | 1/2011 | Cook, II et al. | |
| 8,309,577 B2 | 11/2012 | Cook, II et al. | |
| 8,461,339 B2 | 6/2013 | Boyle et al. | |
| 8,530,468 B2 | 9/2013 | Collins et al. | |
| 2006/0156485 A1 | 7/2006 | Lim | |
| 2009/0143399 A1 | 6/2009 | Hurley et al. | |
| 2010/0081671 A1 | 4/2010 | Plettenburg et al. | |
| 2010/0113467 A1 | 5/2010 | Manley et al. | |
| 2010/0331328 A1 | 12/2010 | Collins et al. | |
| 2011/0245248 A1 | 10/2011 | Plettenburg et al. | |
| 2013/0096119 A1 | 4/2013 | Bur et al. | |
| 2013/0302303 A1 | 11/2013 | Hurley et al. | |
| 2014/0066453 A1 | 3/2014 | Blake et al. | |
| 2016/0060262 A1 | 3/2016 | Lyssikatos et al. | |
| 2018/0072719 A1 | 3/2018 | Ye et al. | |

(Continued)

FOREIGN PATENT DOCUMENTS

| | | |
|---|---|---|
| CN | 107266421 A | 10/2017 |
| EA | 018163 B1 | 5/2013 |

(Continued)

OTHER PUBLICATIONS

Bartmann, W., et al., "Synthesis of di- and tetraalkyl-3-piperazinoisoquinolines and related compounds as potential antidepressant agents" J Heterocyclic 24(3):677-682 (May 30, 1987).

(Continued)

*Primary Examiner* — Taylor V Oh

(57) ABSTRACT

3-Carbonylamino-8-aminoisoquinoline compounds of formula (I):

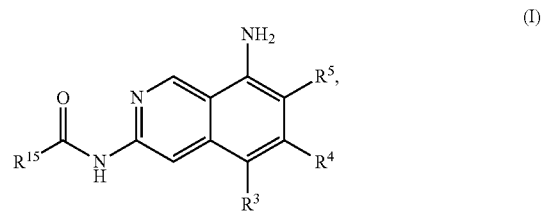

variations thereof, and their use as inhibitors of HPK1 (hematopoietic kinase 1) are described. The compounds are useful in treating HPK1-dependent disorders and enhancing an immune response. Also described are methods of inhibiting HPK1, methods of treating HPK1-dependent disorders, (Continued)

methods for enhancing an immune response, and methods for preparing the 3-carbonylamino-8-aminoisoquinoline compounds.

29 Claims, No Drawings

(56) References Cited

U.S. PATENT DOCUMENTS

| | | |
|---|---|---|
| 2018/0072720 A1 | 3/2018 | Vechorkin et al. |
| 2018/0282282 A1 | 4/2018 | Chan et al. |
| 2021/0163417 A1 | 6/2021 | Chan et al. |
| 2021/0253580 A1 | 8/2021 | Liang et al. |
| 2021/0332064 A1 | 10/2021 | Liang et al. |

FOREIGN PATENT DOCUMENTS

| | | | |
|---|---|---|---|
| EP | 2937345 | A2 | 10/2015 |
| PL | 176081 | B1 | 4/1999 |
| WO | 2000/071508 | A2 | 11/2000 |
| WO | 2000/071508 | A3 | 11/2000 |
| WO | 2000/071510 | A2 | 11/2000 |
| WO | 2000/071510 | A3 | 11/2000 |
| WO | 2005/032468 | A2 | 4/2005 |
| WO | 2005/032468 | A3 | 4/2005 |
| WO | 2005/035503 | A1 | 4/2005 |
| WO | 2006/048248 | A2 | 5/2006 |
| WO | 2006/048248 | A3 | 5/2006 |
| WO | 2006/048251 | A1 | 5/2006 |
| WO | 2007/000240 | A1 | 1/2007 |
| WO | 2007/041511 | A2 | 4/2007 |
| WO | 2007/053346 | A1 | 5/2007 |
| WO | 2007/071348 | A1 | 6/2007 |
| WO | 2007/084391 | A2 | 7/2007 |
| WO | 2007/125405 | A2 | 11/2007 |
| WO | 2007/125405 | A3 | 11/2007 |
| WO | 2008/077554 | A1 | 7/2008 |
| WO | 2008/119569 | A1 | 10/2008 |
| WO | 2009/000558 | A1 | 12/2008 |
| WO | 2009/023193 | A1 | 2/2009 |
| WO | 2009/103966 | A1 | 8/2009 |
| WO | 2009/131926 | A1 | 10/2009 |
| WO | 2010/007374 | A1 | 1/2010 |
| WO | 2010/042699 | A1 | 4/2010 |
| WO | 2011/073845 | A1 | 6/2011 |
| WO | 2011/075607 | A1 | 6/2011 |
| WO | 2011/121555 | A1 | 10/2011 |
| WO | 2012/056372 | A1 | 5/2012 |
| WO | 2012/080284 | A2 | 6/2012 |
| WO | 2012/080284 | A3 | 6/2012 |
| WO | 2012/137099 | A1 | 10/2012 |
| WO | 2012/177725 | A1 | 12/2012 |
| WO | 2012/177728 | A1 | 12/2012 |
| WO | 2013/003315 | A2 | 1/2013 |
| WO | 2013/169793 | A2 | 11/2013 |
| WO | 2013/169793 | A3 | 11/2013 |
| WO | 2014/036015 | A1 | 3/2014 |
| WO | 2014/037751 | A1 | 3/2014 |
| WO | 2014/043296 | A1 | 3/2014 |
| WO | 2014/123900 | A1 | 8/2014 |
| WO | 2015/003166 | A1 | 1/2015 |
| WO | 2016/014674 | A1 | 1/2016 |
| WO | 2016/046530 | A1 | 3/2016 |
| WO | 2016/090300 | A1 | 6/2016 |
| WO | 2016/205942 | A1 | 12/2016 |
| WO | 2017/069980 | A1 | 4/2017 |
| WO | 2017/106556 | A1 | 6/2017 |
| WO | 2017/152821 | A1 | 9/2017 |
| WO | 2017/155765 | A1 | 9/2017 |
| WO | 2017/158388 | A1 | 9/2017 |
| WO | 2017/189823 | A2 | 11/2017 |
| WO | 2017/189829 | A1 | 11/2017 |
| WO | 2018/065768 | A1 | 4/2018 |
| WO | 2018/102366 | A1 | 6/2018 |
| WO | 2018/119263 | A1 | 6/2018 |
| WO | 2018/136700 | A1 | 7/2018 |
| WO | 2018/182051 | A1 | 10/2018 |
| WO | 2018/183418 | A1 | 10/2018 |
| WO | 2018/183964 | A1 | 10/2018 |
| WO | 2018/231745 | A1 | 12/2018 |
| WO | 2019/079626 | A1 | 4/2019 |
| WO | 2019/084497 | A1 | 5/2019 |
| WO | 2019/155066 | A1 | 8/2019 |
| WO | 2020/023560 | A1 | 1/2020 |
| WO | 2020/072627 | A1 | 4/2020 |
| WO | 2020/072695 | A1 | 4/2020 |

OTHER PUBLICATIONS

Collins, I., et al., CAS Registry Database, 1184844-45-8, CAPLUS Accession No. 2009:1042183Document No. 151:289187, Entitled: Bicyclylaryl-aryl-amine compounds, their preparation, and their use as CHK1 kinase inhibitors for treating proliferative diseases, pp. 1-3 (2009).

Dibartolo, V., et al., "A novel pathway down-modulating T cell activation involves HPK-1-dependent recruitment of 14-3-3 proteins on SLP-76" J Exp Med 204(3):681-691 (Mar. 19, 2007).

Dong, X. et al., "QSAR study of Akt/protein kinase B (PKB) inhibitors using support vector machine" Eur J Med Chem 44(10):4090-4097 (Oct. 1, 2009).

"International Preliminary Report on Patentability—PCT/US2019/054359" (Report dated Mar. 23, 2021, Chapter I),pp. 1-7 (dated Apr. 15, 2021).

"International Search Report—PCT/US2019/054359" pp. 1-22 (dated Dec. 13, 2019).

Johnson, C.N. et al., "Structure-Based Design of Type II Inhibitors Applied to Maternal Embryonic Leucine Zipper Kinase" ACS Med Chem Lett 6(1):31-36 (Jan. 8, 2015).

Lasserre, R., et al., "Release of serine/threonine-phosphorylated adaptors from signaling microclusters down-regulates T cell activation" J Cell Biol 195(5):839-853 (Nov. 28, 2011).

Liang, J. et al., "Identification of an imidazopyridine scaffold to generate potent and selective TYK2 inhibitors that demonstrate activity in an in vivo psoriasis model" Bioorg Med Chem Lett 27(18):4370-4376 (Sep. 15, 2017).

Lu, B. et al., "Discovery of EBI-907: A highly potent and orally active B-RafV600E inhibitor for the treatment of melanoma and associated cancers" Bioorg Med Chem Lett 26(3):819-823 (Feb. 1, 2016).

Ma, X. et al., "Identification of New FLT3 Inhibitors That Potently Inhibit AML Cell Lines via an Azo Click-It/Staple-It Approach" ACS Med Chem Lett 8(5):492-497 (Apr. 14, 2017).

Panchaud, P. et al., "Discovery and Optimization of Isoquinoline Ethyl Ureas as Antibacterial Agents" J Med Chem 60(9):3755-3775 (May 11, 2017).

USPTO, Chan, B., et al., "U.S. Appl. No. 16/921,297, entitled 'Isoquinolines as Inhibitors of HPK1' filed Jul. 6, 2020".

USPTO, Liang, J., et al., "U.S. Appl. No. 17/220,307, entitled 'Isoquinoline Compounds for the Treatment of Cancer,' filed Apr. 1, 2021".

USPTO, Liang, J., et al., "U.S. Appl. No. 17/156,387, entitled 'Isoquinoline Compounds and Uses Thereof' filed Jan. 22, 2021".

Yule, I.A. et al., "Pyridine-3-carboxamide-6-yl-ureas as novel inhibitors of bacterial DNA gyrase: Structure based design, synthesis, SAR and antimicrobial activity" Eur J Med Chem 86:31-38 (Oct. 30, 2014).

Zdrojewski, T. et al., "A general approach to 3-aminoisoquinoline, its N-mono- and N,N-disubstituted derivatives" Tetrahedron 51(45):12439-12444 (Nov. 6, 1995).

Zeng, Q. et al., "Azole-based inhibitors of AKT/PKB for the treatment of cancer" Bioorg Med Chem Lett 20(5):1559-1564 (Mar. 1, 2010).

Zhu, G. et al., "Isoquinoline-pyridine-based protein kinase B/Akt antagonists: SAR and in vivo antitumor activity" Bioorg Med Chem Lett 16(12):3150-3155 (Jun. 15, 2006).

(56) References Cited

OTHER PUBLICATIONS

Belikov et al., Pharmaceutical Chemistry (Text in Russian with English translation attached), Moscow, MEDpress-inform, pp. 27-29 (2007).
Dyson et al., Chemistry of Synthetic Medicinal Substances (Text in Russian with English translation attached), Moscow, pp. 12-19 (1964).
Kharkevich, D.A., Pharmacology (Text in Russian with English translation attached), 10th edition, Moscow, GEOTAR-Media, pp. 73-74 (2010).
Mashkovsky, M.D., Medicine "'Medicines'" (Text in Russian with English translation attached), Moscow (Part 1), p. 8 (1993).
Linney, I. D. et al., "Inhibitors of immuno-oncology target HPK1—a patent review (2016 to 2020)," Expert Opin Ther Pat, 31(10):893-910 (2021).

8-AMINOISOQUINOLINE COMPOUNDS AND USES THEREOF

CROSS-REFERENCE TO RELATED APPLICATIONS

This application claims is a continuation of PCT/US2019/054359 filed Oct. 2, 2019 which claims the benefit of priority to U.S. Provisional Application No. 62/740,894 filed 3 Oct. 2018, and U.S. Provisional Application No. 62/870,529 filed 3 Jul. 2019, the contents of which applications are hereby incorporated by reference in their entireties.

BACKGROUND OF THE INVENTION

The major treatment modalities used by oncologists to treat cancer are surgical resection, radiation therapy, and classical chemotherapeutic drugs. Unfortunately, surgical resection is not a viable option for many tumors or forms of cancers. Further, radiation therapy and chemotherapeutic drugs do not target only diseased cells and therefore, end up damaging healthy cells. Therapeutics that more specifically target tumor cells are being developed by taking advantage of tumor-specific expression of antigens or inappropriate overexpression or activation of specific proteins within tumor cells, but tumor cells are prone to mutation and can become resistant to drugs that specifically target tumor cells.

A new cancer treatment paradigm has emerged that harnesses the patient's own immune system to overcome immunoevasive strategies utilized by many cancers and to enhance anti-tumor immunity. One such strategy is to inhibit negative regulators of immune responses that normally function to maintain peripheral tolerance, allowing tumor antigens to be recognized as non-self entities.

The hematopoietic progenitor kinase 1 (HPK1) is an example of a negative regulator of dendritic cell activation, and T and B cell responses that can be targeted to enhance anti-tumor immunity. HPK1 is expressed predominantly by hematopoietic cells, including early progenitors. In T cells, it is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters (Lasserre et al. (2011) *J Cell Biol* 195(5):839-853). HPK1 can also become activated in response to prostaglandin E2, which is often secreted by tumors, contributing to the escape of tumor cells from the immune system.

BRIEF SUMMARY OF THE INVENTION

Disclosed are 3-carbonylamino-8-aminoisoquinoline compounds that are inhibitors of HPK1, compositions containing these compounds, and methods for enhacing an immune response and treating HPK1-dependent disorders such as cancer.

In one aspect, provided is a compound of Formula (I), or any variation thereof, or a salt thereof (e.g., a pharmaceutically acceptable salt thereof), as detailed herein. Also provided is a pharmaceutical composition comprising a compound of Formula (I), or any variation thereof detailed herein, or a pharmaceutically acceptable salt thereof, and a pharmaceutically acceptable carrier or excipient.

In another aspect, provided is a method for inhibiting HPK1, comprising contacting HPK1 in a subject with an effective amount of the compound of Formula (I), or any variation thereof detailed herein, or a pharmaceutically acceptable salt thereof. Also provided is a method for enhancing an immune response in a subject in need thereof, comprising administering to the subject an effective amount of the compound of Formula (I), or any variation thereof detailed herein, or a pharmaceutically acceptable salt thereof.

Further provided is a method for treating a HPK1-dependent disorder, comprising administering to a subject in need thereof an effective amount of the compound of Formula (I), or any variation thereof detailed herein, or a pharmaceutically acceptable salt thereof. In some embodiments, the subject is a human. In some embodiments, the HPK1-dependent disorder is a cancer, for example, colorectal cancer, melanoma, non-small cell lung cancer, ovarian cancer, breast cancer, pancreatic cancer, a hematological malignancy, and a renal cell carcinoma. In some embodiments, the method further comprises administering a chemotherapeutic agent to the subject.

Also provided is a compound of Formula (I), or any variation thereof detailed herein, or a pharmaceutically acceptable salt thereof, for use in a method of inhibiting HPK1, enhancing an immune response, or treating a HPK1-dependent disorder such as cancer.

Also provided is use of a compound of Formula (I), or any variation thereof detailed herein, or a pharmaceutically acceptable salt thereof, in a method detailed herein (e.g., treatment of a HPK1-dependent disorder such as cancer.

Also provided is use of a compound of Formula (I), or any variation thereof detailed herein, or a pharmaceutically acceptable salt thereof, for the manufacture of a medicament for use in a method detailed herein (e.g., treatment of a HPK1-dependent disorder such as cancer.

Also provided is a kit for treating a HPK1-dependent disorder, the kit comprising a pharmaceutical composition comprising a the compound of Formula (I), or any variation thereof detailed herein, or a pharmaceutically acceptable salt thereof; and instructions for use.

In another aspect, provided is a method of making a compound of Formula (I) or any variation thereof. Also provided are compound intermediates useful in synthesis of a compound of Formula (I), or any variation thereof.

DETAILED DESCRIPTION OF THE INVENTION

Disclosed herein, are compounds of Formula (I), or variations thereof such as Formula (IA), (IB) and (IC), and pharmaceutical compositions thereof that are inhibitors or modulators of HPK1 (hematopoietic progenitor kinase 1). As such, the compounds and compositions are useful in treating diseases and disorders mediated by HPK1. An example of a method of treating is in the case of a subject who is suffering from cancer. The compounds can be used not only to combat cancer, but can also advantageously be used to enhance an immune response in a subject in need thereof.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

Definitions

"Alkyl" as used herein refers to a saturated linear (i.e. unbranched) or branched univalent hydrocarbon chain or combination thereof, having the number of carbon atoms designated (i.e., $C_{1-10}$ means one to ten carbon atoms). Particular alkyl groups are those having 1 to 20 carbon atoms (a "$C_{1-20}$ alkyl"), having a 1 to 8 carbon atoms (a "$C_{1-8}$ alkyl"), having 1 to 6 carbon atoms (a "$C_{1-6}$ alkyl"), having 2 to 6 carbon atoms (a "$C_{2-6}$ alkyl"), or having 1 to 4 carbon atoms (a "$C_{1-4}$ alkyl"). Examples of alkyl group include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_{2-10}$ means two to ten carbon atoms). The alkenyl group may be in "cis" or "trans" configurations, or alternatively in "E" or "Z" configurations. Particular alkenyl groups are those having 2 to 20 carbon atoms (a "$C_{2-20}$ alkenyl"), having a 2 to 8 carbon atoms (a "$C_{2-8}$ alkenyl"), having 2 to 6 carbon atoms (a "$C_{2-6}$ alkenyl"), or having 2 to 4 carbon atoms (a "$C_{2-4}$ alkenyl"). Example of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkynyl" as used herein refers to an unsaturated linear (i.e. unbranched) or branched univalent hydrocarbon chain or combination thereof, having at least one site of acetylenic unsaturation (i.e., having at least one moiety of the formula C≡C) having the number of carbon atoms designated (i.e., $C_{2-10}$ means two to ten carbon atoms). Particular alkynyl groups are those having 2 to 20 carbon atoms (a "$C_{2-20}$ alkynyl"), having a 2 to 8 carbon atoms (a "$C_{2-8}$ alkynyl"), having 2 to 6 carbon atoms (a "$C_{2-6}$ alkynyl"), having 2 to 4 carbon atoms (a "$C_{2-4}$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Alkylene" as used herein refers to the same residues as alkyl, but having bivalency. Particular alkylene groups are those having 1 to 6 carbon atoms (a "$C_{1-6}$ alkylene"), 1 to 5 carbon atoms (a "$C_{1-5}$ alkylene"), having 1 to 4 carbon atoms (a "$C_{1-4}$ alkylene"), or 1 to 3 carbon atoms (a "$C_{1-3}$ alkylene"). Examples of alkylene include, but are not limited to, groups such as methylene (—$CH_2$—), ethylene (—$CH_2$—$CH_2$—), 1,3-propylene (—$CH_2$—$CH_2$—$CH_2$—), 1,2-propylene (—CH($CH_3$)—$CH_2$—), 1,4-butylene (—$CH_2$—$CH_2$—$CH_2$—$CH_2$—), and the like.

"Alkylidene" as used herein refers to the same residues as alkyl, but having bivalency at the attachment point and is attached to the parent structure via a double bond. Particular alkylidene groups are those having 1 to 6 carbon atoms (a "$C_{1-6}$ alkylidene"), 1 to 5 carbon atoms (a "$C_{1-5}$ alkylidene"), having 1 to 4 carbon atoms (a "$C_{1-4}$ alkylidene"), or 1 to 3 carbon atoms (a "$C_{1-3}$ alkylidene"). Examples of alkylene include, but are not limited to, groups such as methylidene (=$CH_2$), ethylidene (=CH—$CH_3$), 1-propylidene (=CH—$CH_2$—$CH_3$), 2-propylidene (=C($CH_3$)$_2$), 1-butylidene (=$CH_2$—$CH_2$—$CH_2$—$CH_3$), and the like.

"Cycloalkyl" as used herein refers to non-aromatic, saturated or unsaturated cyclic univalent hydrocarbon structures having the number of carbon atoms designated (i.e., $C_{3-10}$ means three to ten carbon atoms). Cycloalkyl can consist of one ring, such as cyclohexyl, or multiple rings, such as adamantyl, but excludes aryl groups. A cycloalkyl comprising more than one ring may be fused, spiro, or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_{3-8}$ cycloalkyl"), or having 3 to 6 carbon atoms (a "$C_{3-6}$ alkynyl"). Examples of cycloalkyl include, but are not limited to, cyclopropyl, cyclobutyl, cyclopentyl, cyclohyxyl, 1-cyclohexenyl, 3-cyclohexenyl, cycloheptyl, norbornyl, and the like.

"Aryl" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular (i.e., ring) carbon atoms (a "$C_{6-14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" as used herein refers to an unsaturated aromatic cyclic group having from 1 to 14 annular (i.e., ring) carbon atoms and at least one annular heteroatom, including but not limited to heteroatoms such as nitrogen, phosphorus, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5- to 14-membered rings having 1 to 12 annular (i.e., ring) carbon atoms and 1 to 6 annular (i.e., ring) heteroatoms independently selected from nitrogen, phosphorus, oxygen and sulfur; 5- to 10-membered rings having 1 to 8 annular carbon atoms and 1 to 4 annular heteroatoms independently selected from nitrogen, phosphorus, oxygen and sulfur; and 5-, 6- or 7-membered rings having 1 to 5 annular carbon atoms and 1 to 4 annular heteroatoms independently selected from nitrogen, oxygen and sulfur In one variation, heteroaryl include monocyclic aromatic 5-, 6- or 7-membered rings having from 1 to 6 annular carbon atoms and 1 to 4 annular heteroatoms independently selected from nitrogen, oxygen and sulfur. In another variation, heteroaryl includes polycyclic aromatic rings having from 1 to 12 annular carbon atoms and 1 to 6 annular heteroatoms independently selected from nitrogen, phosphorus, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Heterocycle", "heterocyclic", or "heterocyclyl" as used herein refers to a saturated or an unsaturated non-aromatic cyclic group having a single ring or multiple condensed rings, and having from 1 to 14 annular (i.e., ring) carbon atoms and from 1 to 6 annular (i.e., ring) heteroatoms, such as nitrogen, phosphorus, sulfur or oxygen, and the like. A heterocycle comprising more than one ring may be fused, spiro or bridged, or any combination thereof. In fused ring systems, one or more may be fused rings can be cycloalkyl. Particular heterocyclyl groups are 3- to 14-membered rings having 1 to 13 annular carbon atoms and 1 to 6 annular heteroatoms independently selected from nitrogen, phosphorus, oxygen and sulfur; 3- to 12-membered rings having 1 to 11 annular carbon atoms and 1 to 6 annular heteroatoms independently selected from nitrogen, phosphorus, oxygen and sulfur; 3- to 10-membered rings having 1 to 9 annular carbon atoms and 1 to 4 annular heteroatoms independently selected from nitrogen, phosphorus, oxygen and sulfur; 3- to 8-membered rings having 1 to 7 annular carbon atoms and 1 to 4 annular heteroatoms independently selected from nitrogen, phosphorus, oxygen and sulfur; and 3- to 6-membered rings having 1 to 5 annular carbon atoms and 1 to 4 annular heteroatoms independently selected from nitrogen, phosphorus, oxygen and sulfur. In one variation, heterocyclyl include monocyclic 3-, 4-, 5-, 6- or 7-membered rings having from 1 to 2, 1 to 3, 1 to 4, 1 to 5 or 1 to 6 annular carbon atoms and 1 to 2, 1 to 3 or 1 to 4 annular heteroatoms independently selected from from nitrogen, phosphorus, oxygen and sulfur. In another variation, heterocyclyl includes polycyclic non-aromatic rings having from 1 to 12 annular carbon atoms and 1 to 6 annular heteroatoms independently selected from nitrogen, phosphorus, oxygen and sulfur.

"Halo" or Halogen" refers to fluoro, chloro, bromo and/or iodo. "Haloalkyl" refers to an alkyl group substituted with one or more halogen that may be the same or different. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Oxo" refers to the moiety =O.

"Geminal" refers to the relationship between two moieties that are attached to the same atom. For example, in the residue $CH_2$—$CR^xR^y$—, $R^x$ and $R^y$ are geminal and $R^x$ may be referred to as a geminal R group to $R^y$.

"Vicinal" refers to the relationship between two moieties that are attached to adjacent atoms. For example, in the residue —$CHR^x$—$CHR^y$—, $R^x$ and $R^y$ are vicinal and $R^x$ may be referred to as a vicinal R group to $R^y$.

"Optionally substituted" unless otherwise specified means that a group may be unsubstituted or substituted by one or more (e.g., 1, 2, 3, 4 or 5) of the substituents listed for that group in which the substituents may be the same or different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4 or 1 to 5 substituents.

Use of the word "inhibitor" herein is meant to mean a molecule that inhibits activity of HPK1. By "inhibit" herein is meant to decrease the activity of the target enzyme, as compared to the activity of that enzyme in the absence of the inhibitor. In some embodiments, the term "inhibit" means a decrease in HPK1 activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in HPK1 activity of about 5% to about 25%, about 25% to about 50%, about 50% to about 75%, or about 75% to 100%. In some embodiments, inhibit means a decrease in HPK1 activity of about 95% to 100%, e.g., a decrease in activity of 95%, 96%, 97%, 98%, 99%, or 100%. Such decreases can be measured using a variety of techniques that would be recognizable by one of skill in the art, including in vitro kinase assays.

As used herein, a "HPK1 antagonist" or a "HPK1 inhibitor" is a molecule that reduces, inhibits, or otherwise diminishes one or more of the biological activities of HPK1 (e.g., serine/threonine kinase activity, recruitment to the TCR complex upon TCR activation, interaction with a protein binding partner, such as SLP76). Antagonism using the HPK1 antagonist does not necessarily indicate a total elimination of the HPK1 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of HPK1 compared to an appropriate control. In some embodiments, the HPK1 antagonist reduces, inhibits, or otherwise diminishes the serine/threonine kinase activity of HPK1. In some of these embodiments, the HPK1 antagonist reduces, inhibits, or otherwise diminishes the HPK1-mediated phosphorylation of SLP76 and/or Gads. The presently disclosed compounds bind directly to HPK1 and inhibit its kinase activity.

By "specific antagonist" is intended an agent that reduces, inhibits, or otherwise diminishes the activity of a defined target greater than that of an unrelated target. For example, a HPK1 specific antagonist reduces at least one biological activity of HPK1 by an amount that is statistically greater than the inhibitory effect of the antagonist on any other protein (e.g., other serine/threonine kinases). In some embodiments, the $IC_{50}$ of the antagonist for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the HPK1 antagonist specifically inhibits the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

As used herein, "treatment" or "treating" is an approach for obtaining beneficial or desired results including clinical results. For purposes of this invention, beneficial or desired clinical results include, but are not limited to, one or more of the following: decreasing one or more symptoms resulting from the disease, diminishing the extent of the disease, stabilizing the disease (e.g., preventing or delaying the worsening of the disease), preventing or delaying the spread (e.g., metastasis) or the disease, delay or slowing the progression of the disease, ameliorating the disease state, providing a remission (whether partial or total) of the disease, decreasing the dose of one or more medications required to treat the disease, enhancing effect of another medication, delaying the progression of the disease, increasing the quality of life, and/or prolonging survival. Also encompassed by "treatment" is a reduction of pathological consequence of cancer. The methods of the invention contemplate any one or more of these aspects of treatment.

As used here, "delaying" the development of cancer means to defer, hinder, slow, retard, stabilize, and/or postpone development of the disease. This delay can be of varying lengths of time, depending on the history of the disease and/or subject being treated. As is evident to one skilled in the art, a sufficient or significant delay can, in effect, encompass prevention, in that the subject does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of subjects. Cancer development can be detectable using standard methods, such as routine physical exams, mammography, imaging, or biopsy. Development may also refer to disease progression that may be initially undetectable and includes occurrence, recurrence, and onset.

As used herein, an "at risk" subject is a subject who is at risk of developing cancer. A subject "at risk" may or may not have detectable disease, and may or may not have displayed detectable disease prior to the treatment methods described herein. "At risk" denotes that a subject has one or more so-called risk factors, which are measurable parameters that correlate with development or cancer, which are described herein. A subject having one or more of these risk factors has a higher probability of developing cancer than a subject without these risk factor(s).

As used herein, by "combination therapy" is meant a therapy that includes two or more different compounds. Thus, in one aspect, a combination therapy comprising a compound detailed herein and another compound is provided. In some variations, the combination therapy optionally includes one or more pharmaceutically acceptable carriers or excipients, non-pharmaceutically active compounds, and/or inert substances.

As used herein, the term "effective amount" intends such amount of a compound of the invention which in combination with its parameters of efficacy and toxicity, should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial results may be or is achieved. Suitable doses of any of the co-administered compounds may optionally be lowered due to the combined action (e.g., additive or synergistic effects) of the compounds. In various embodiments, an effective amount of the composition or therapy may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

As is understood in the art, an "effective amount" may be in one or more doses, i.e., a single dose or multiple doses may be required to achieve the desired treatment endpoint. An effective amount may be considered in the context of administering one or more therapeutic agents, and a compound, or pharmaceutically acceptable salt thereof, may be considered to be given in an effective amount if, in conjunction with one or more other agents a desirable or beneficial result may be or is achieved.

A "therapeutically effective amount" refers to an amount of a compound or salt thereof sufficient to produce a desired therapeutic outcome (e.g., reducing the severity or duration of, stabilizing the severity of, or eliminating one or more symptoms of cancer). For therapeutic use, beneficial or desired results include, e.g., decreasing one or more symptoms resulting from the disease (biochemical, histologic and/or behavioral), including its complications and intermediate pathological phenotypes presenting during development of the disease, increasing the quality of life of those suffering from the disease, decreasing the dose of other medications required to treat the disease, enhancing effect of another medication, delaying the progression of the disease, and/or prolonging survival of patients.

A "prophylactically effective amount" refers to an amount of a compound, or pharmaceutically acceptable salt thereof, sufficient to prevent or reduce the severity of one or more future symptoms of cancer when administered to a subject who is susceptible and/or who may develop cancer. For prophylactic use, beneficial or desired results include, e.g., results such as eliminating or reducing the risk, lessening the severity of future disease, or delaying the onset of the disease (e.g., delaying biochemical, histologic and/or behavioral symptoms of the disease, its complications, and intermediate pathological phenotype presenting during future development of the disease).

It is understood that an effective amount of a compound or pharmaceutically acceptable salt thereof, including a prophylactically effective amount, may be given to a subject in the adjuvant setting, which refers to a clinical setting in which a subject has had a history of cancer, and generally (but not necessarily) has been responsive to therapy, which includes, but is not limited to, surgery (e.g., surgical resection), radiotherapy, and chemotherapy. However, because of their history of the cancer, these subjects are considered at risk of developing cancer. Treatment or administration in the "adjuvant setting" refers to a subsequent mode of treatment.

As used herein, "unit dosage form refers to physically discrete units, suitable as unit dosages, each unit containing predetermined quantity of active ingredient calculated to produce the desired therapeutic effect in association with the required pharmaceutical carrier or excipient. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulation can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug Administration.

In some embodiments, the salts of the compounds of the invention are pharmaceutically acceptable salts. "Pharmaceutically acceptable salts" are those salts which retain at least some of the biological activity of the free (non-salt) compound and which can be administered as drugs or pharmaceuticals to a subject. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include e.g. calcium carbonate, dextrose, fructose dc (dc—"directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g. dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc. In some cases, the terms "excipient" and "carrier" are used interchangeably.

The term "subject" or "patient" refers to animals such as mammals, including, but not limited to, primates (e.g., humans), cows, sheep, goats, horses, dogs, cats, rabbits, rats, mice and the like. In certain embodiments, the subject is a human or a human patient.

The terms "abnormal cell growth," "unregulated cell growth," and "hyperproliferative disorder" are used interchangeably in this application. "Abnormal cell growth", as used herein, unless otherwise indicated, refers to cell growth that is independent of normal regulatory mechanisms (e.g., loss of contact inhibition).

The term "cancer" refers to the condition in a subject that is characterized by unregulated cell growth, wherein the cancerous cells are capable of local invasion and/or metastasis to noncontiguous sites. As used herein, "cancer cells," "cancerous cells," or "tumor cells" refer to the cells that are characterized by this unregulated cell growth and invasive property. The term "cancer" encompasses all types of cancers, including, but not limited to, all forms of carcinomas, melanomas, blastomas, sarcomas, lymphomas and leukemias, including without limitation, bladder cancer, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer, acute lymphocytic leukemia, acute myeloid leukemia, ependymoma, Ewing's sarcoma, glioblastoma, medulloblastoma, neuroblastoma, osteosarcoma, rhabdomyosarcoma, rhabdoid cancer, and nephroblastoma (Wilm's tumor).

A "chemotherapeutic agent" is a chemical compound or biologic useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1I (see, e.g., Nicolaou et al., Angew. Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, and floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovorin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and predniso-lone, and FOLFOX, an abbreviation for a treatment regimen with oxaliplatin (ELOXATIN™) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); anti-sense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; EGFR inhibitor such as erlotinib or cetuximab; an anti-VEGF inhibitor such as bevacizumab; arinotecan; rmRH (e.g., ABARELIX®); 17AAG (geldanamycin derivative that is a heat shock protein (Hsp) 90 poison), and pharmaceutically acceptable salts, acids or derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

In some embodiments, the chemotherapeutic agent is an immunotherapeutic agent. As used herein, an "immunotherapeutic agent" is a compound that enhances the immune system to help fight cancer, specifically or non-specifically. Immunotherapeutics include monoclonal antibodies and non-specific immunotherapies that boost the immune system, such as cytokines, interleukins (e.g., IL-2, IL-7, IL-12, IL-15, IL-21), interferons (e.g., IFN-α, IFN-β, IFN-γ), GM-CSF, thalidomide, (THALOMID®, Celgene), lenalidomide (REVLIMID®, Celgene), pomalidomide (POMALYST®, Celgene), imiquimod (ZYCLARA®, Valeant). Non-limiting examples of monoclonal antibodies that are useful as a chemotherapeutic agent include trastuzumab (HERCEPTIN®, Genentech), bevacizumab (AVASTIN®, Genentech), cetuximab (ERBITUX®, Bristol-Myers Squibb), panitumumab (VECTIBIX®, Amgen), ipilimumab (YERVOY®, Bristol-Myers Squibb), rituximab (RITUXAN®, Genentech), alemtuzumab (CAMPATH®, Genzyme), ofatumumab (ARZERRA®, Genmab), gemtuzumab ozogamicin (MYLOTARG®, Wyeth), brentuximab vedotin (ADCETRIS®, Seattle Genetics), $^{90}$Y-labelled ibritumomab tiuxetan (ZEVALIN®, Biogen Idec), $^{131}$I-labelled tositumomab (BEXXAR®, GlaxoSmithKline), ado-trastuzumab emtansine (KADCYLA®, Genentech) blinatumomab (BLINCYTO®, Amgen), pertuzumab (PERJETA®, Genentech), obinutuzumab (GAZYVA®, Genentech), nivolumab (OPDIVO®) Bristol-Myers Squibb), pembrolizumab (KEYTRUDA®, Merck), pidilizumab (CureTech), MPDL3280A (described in WO2010/077634, herein incorporated by reference in its entirety), MDX-1105 (described in WO2007/005874, herein incorporated by reference in its entirety), and MEDI4736 (described in WO2011/066389 and US2013/034559, each of which is herein incorporated by reference in its entirety). Another useful immunotherapeutic agent is AMP-224 (described in WO2010/027827 and WO2011/066342, each of which is incorporated herein in its entirety).

Compounds

The compounds disclosed herein are 3-carbonylamino-8-aminoisoquinoline compounds of Formula (I), or salts (e.g., pharmaceutically acceptable salts), solvates (e.g., hydrates), prodrugs, metabolites, or derivatives thereof. These compounds are useful inhibitors of HPK1.

In one aspect, provided is a compound of Formula (I):

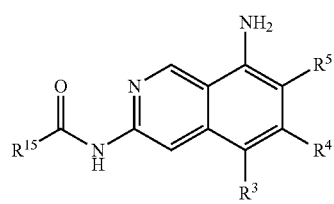

(I)

or a salt (e.g., a pharmaceutically acceptable salt), solvate (e.g., hydrate), prodrug, metabolites or derivative thereof, wherein:

$R^{15}$ is —$OR^{16}$, —$SR^{16}$ or —$NR^{17}R^{18}$;

each $R^{16}$ is independently $C_{1-6}$ alkyl, $C_{3-10}$ cycloalkyl, 7- to 14-membered heteroaryl, or 3- to 14-membered heterocyclyl; wherein the $C_{1-6}$ alkyl, $C_{3-10}$ cycloalkyl, 7- to 14-membered heteroaryl and 3- to 14-membered heterocyclyl of $R^{16}$ are each independently optionally substituted with 1, 2, 3, 4 or 5 substituents independently selected from $R^{10}$;

$R^{17}$ is hydrogen or $C_{1-6}$ alkyl;

$R^{18}$ is $C_{1-6}$ alkyl, $C_{3-10}$ cycloalkyl, or 3- to 14-membered heterocyclyl; wherein the $C_{1-6}$ alkyl, $C_{3-10}$ cycloalkyl and 3- to 14-membered heterocyclyl of $R^{18}$ are each independently optionally substituted with 1, 2, 3, 4 or 5 substituents independently selected from $R^{10}$;

or $R^{17}$ and $R^{18}$ are taken together with the nitrogen atom to which they are attached to form a 4- to 12-membered heterocyclyl optionally substituted with 1, 2, 3, 4 or 5 substituents independently selected from $R^{10}$;

$R^3$ is hydrogen, halogen, cyano, $C_{1-6}$ alkyl, $C_{3-8}$ cycloalkyl, 3- to 14-membered heterocyclyl, or —$OR^7$; wherein the $C_{1-6}$ alkyl, $C_{3-8}$ cycloalkyl and 3- to 14-membered heterocyclyl of $R^3$ are each optionally substituted with 1, 2, 3, 4 or 5 substituents independently selected from $R^{10}$;

$R^4$ is 5- to 14-membered heteroaryl optionally substituted with 1, 2, 3, 4 or 5 substituents independently selected from $R^{10}$;

$R^5$ is hydrogen, halogen, cyano, $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, —$C(O)R^6$, —$C(O)OR^7$, —$C(O)NR^{8a}R^{8b}$, —$OR^7$, —$OC(O)R^6$, —$OC(O)NR^{8a}R^{8b}$, —$SR^7$, —$S(O)R^9$, —$S(O)_2R^9$, —$S(O)_2NR^{8a}R^{8b}$, —$P(O)R^{9a}R^{9b}$, —$N(R^8)C(O)R^6$, —$N(R^8)C(O)OR^7$, —$N(R^8)C(O)NR^{8a}R^{8b}$, —$N(R^8)S(O)_2R^9$, or —$N(R^8)S(O)_2NR^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^5$ are each optionally substituted with 1, 2, 3, 4 or 5 substituents independently selected from $R^{10}$;

each $R^6$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl and 3- to 12-membered heterocyclyl of $R^6$ are each optionally substituted with 1, 2, 3, 4 or 5 substituents independently selected from $R^{10}$;

each $R^7$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^7$ are each optionally substituted with 1, 2, 3, 4 or 5 substituents independently selected from $R^{10}$;

each $R^8$ is independently hydrogen or $C_{1-6}$ alkyl;

each $R^{8a}$ and $R^{8b}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{8a}$ and $R^{8b}$ are each optionally substituted with 1, 2, 3, 4 or 5 substituents independently selected from $R^{10}$;

or $R^{8a}$ and $R^{8b}$ are taken together with the nitrogen atom to which they are attached to form a 4- to 12-membered heterocyclyl optionally substituted with 1, 2, 3, 4 or 5 substituents independently selected from $R^{10}$;

each $R^9$ is independently $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^9$ are each optionally substituted with 1, 2, 3, 4 or 5 substituents independently selected from $R^{10}$;

each $R^{9a}$ and $R^{9b}$ is independently $C_{1-6}$ alkyl, $C_{3-8}$ cycloalkyl, $C_{6-10}$ aryl, 5- to 14-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{9a}$ and $R^{9b}$ are each optionally substituted with 1, 2, 3, 4 or 5 substituents independently selected from $R^{10}$;

or $R^{9a}$ and $R^{9b}$ are taken together with the phosphorus atom to which they are attached to form a 4- to 12-membered heterocyclyl optionally substituted with 1, 2, 3, 4 or 5 substituents independently selected from $R^{10}$;

each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)$R^a$, —C(O)O$R^b$, —C(O)N$R^cR^d$, —O$R^b$, —OC(O)$R^a$, —OC(O)N$R^cR^d$, —S$R^b$, —S(O)$R^e$, —S(O)$_2R^e$, —S(O)(=NH)$R^e$, —S(O)$_2$N$R^cR^d$, —N$R^cR^d$, —N($R^f$)C(O)$R^a$, —N($R^f$)C(O)O$R^b$, —N($R^f$)C(O)N$R^cR^d$, —N($R^f$)S(O)$_2R^e$, —N($R^f$)S(O)$_2$N$R^cR^d$, or —P(O)$R^gR^h$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^{11}$;

each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of IV are each optionally substituted with 1, 2, 3 or 4 substituents independently selected from $R^{11}$;

each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$;

each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$;

or $R^c$ and $R^d$ are taken together with the nitrogen atom to which they are attached to form a 4- to 12-membered heterocyclyl optionally substituted with 1, 2, 3 or 4 substituents independently selected from $R^{11}$;

each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$;

each $R^f$ is independently hydrogen or $C_{1-6}$ alkyl;

each $R^g$ and $R^h$ is independently $C_{1-6}$ alkyl, $C_{3-8}$ cycloalkyl, $C_{6-10}$ aryl, 5- to 10-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^g$ and $R^h$ are each optionally substituted with 1, 2, 3 or 4 substituents independently selected from $R^{11}$;

or $R^g$ and $R^h$ are taken together with the phosphorus atom to which they are attached to form a 4- to 12-membered heterocyclyl optionally substituted with 1, 2, 3 or 4 substituents independently selected from $R^{11}$;

each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)$R^{a1}$, —C(O)O$R^{b1}$, —C(O)N$R^{c1}R^{d1}$, —O$R^{b1}$, —OC(O)$R^{a1}$, —OC(O)N$R^{c1}R^{d1}$, —S$R^{b1}$, —S(O)$R^{e1}$, —S(O)$_2R^{e1}$, —S(O)$_2$N$R^{c1}R^{d1}$, —N$R^{c1}R^{d1}$, —N($R^{f1}$)C(O)$R^{a1}$, —N($R^{f1}$)C(O)O$R^{b1}$, —N($R^{f1}$)C(O)N$R^{c1}R^{d1}$, —N($R^{f1}$)S(O)$_2R^{e1}$, —N($R^{f1}$)S(O)$_2$N$R^{c1}R^{d1}$, or —P(O)$R^{g1}R^{h1}$; wherein $C_{1-6}$ alkyl, alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)R$^{a2}$, —C(O)OR$^{b2}$, —C(O)NR$^{c2}$R$^{d2}$, —OR$^{b2}$, —OC(O)R$^{a2}$, —OC(O)NR$^{c2}$R$^{d2}$, —S(O)$_2$R$^{e2}$, —S(O)$_2$NR$^{c2}$R$^{d2}$, —NR$^{c2}$R$^{d2}$, —N(R$^{f2}$)C(O) R$^{a2}$, —N(R$^{f2}$)C(O)OR$^{b2}$, —N(R$^{f2}$)C(O)NR$^{c2}$R$^{d2}$, —N(R$^{f2}$) S(O)$_2$R$^{e2}$, —N(R$^{f2}$)S(O)$_2$NR$^{c2}$R$^{d2}$, or —P(O)R$^{g2}$R$^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{a2}$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_{1-6}$ alkyl, $C_{3-6}$ cycloalkyl, and 3- to 8-membered heterocyclyl of $R^{g2}$ and $R^{h2}$ are each optionally substituted with 1, 2, 3 or 4 substituents independently selected from $R^{13}$;

or $R^{g2}$ and $R^{h2}$ are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl.

In some embodiments, the compound is of the Formula (I), or a salt (e.g., a pharmaceutically acceptable salt), solvate (e.g., hydrate), prodrug, metabolites or derivative thereof, wherein $R^{15}$ is —OR$^{16}$, —SR$^{16}$ or —NR$^{17}$R$^{18}$.

In some embodiments, $R^{15}$ is —OR$^{16}$ or —SR$^{16}$; wherein each $R^{16}$ is independently $C_{1-6}$ alkyl, $C_{3-10}$ cycloalkyl, 7- to 14-membered heteroaryl, or 3- to 14-membered heterocyclyl; wherein the $C_{1-6}$ alkyl, $C_{3-10}$ cycloalkyl, 7- to 14-membered heteroaryl and 3- to 14-membered heterocyclyl of $R^{16}$ are each independently optionally substituted with 1, 2, 3 or 4 or 5 substituents independently selected from $R^{10}$. In some of these embodiments, $R^{15}$ is —OR$^{16}$. In some of these embodiments, $R^{15}$ is —SR$^{16}$.

In one aspect, provided is a compound of Formula (IA) or (IC):

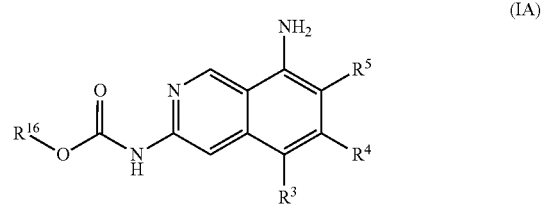

(IA)

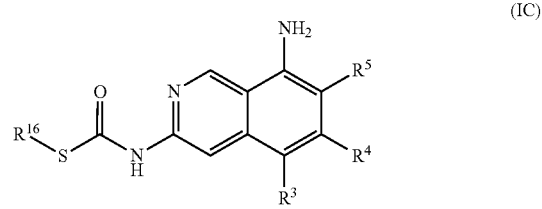

(IC)

or a salt (e.g., a pharmaceutically acceptable salt) thereof, wherein:

each $R^{16}$ is independently $C_{1-6}$ alkyl, $C_{3-10}$ cycloalkyl, 7- to 14-membered heteroaryl, or 3- to 14-membered heterocyclyl; wherein the $C_{1-6}$ alkyl, $C_{3-10}$ cycloalkyl, 7- to 14-membered heteroaryl and 3- to 14-membered heterocyclyl of $R^{16}$ are each independently optionally substituted with 1, 2, 3, 4 or 5 substituents independently selected from $R^{10}$; and $R^3$, $R^4$, $R^5$ and $R^{10}$ are as defined for Formula (I), or variations detailed herein.

In some embodiments, the compound is of the Formula (I), (IA) or (IC), or a salt (e.g., a pharmaceutically acceptable salt), solvate (e.g., hydrate), prodrug, metabolites or derivative thereof, wherein $R^{16}$ is independently $C_{1-6}$ alkyl optionally substituted with 1, 2, 3, 4 or 5 substituents independently selected from $R^{10}$; $C_{3-10}$ cycloalkyl optionally substituted with 1, 2, 3, 4 or 5 substituents independently selected from $R^{10}$; 7- to 14-membered heteroaryl optionally substituted with 1, 2, 3, 4 or 5 substituents independently selected from $R^{10}$; or 3- to 14-membered heterocyclyl optionally substituted with 1, 2, 3, 4 or 5 substituents independently selected from $R^{10}$. In some embodiments, $R^{16}$ is $C_{1-6}$ alkyl substituted with 1, 2, 3, 4 or 5 substituents independently selected from $R^{10}$; $C_{3-10}$ cycloalkyl optionally substituted with 1, 2, 3, 4 or 5 substituents independently selected from $R^{10}$; or 3- to 14-membered heterocyclyl optionally substituted with 1, 2, 3, 4 or 5 substituents independently selected from $R^{10}$.

In some embodiments, $R^{16}$ is 3- to 14-membered heterocyclyl optionally substituted with 1, 2, 3, 4 or 5 substituents independently selected from $R^{10}$. In some of these embodiments, $R^{16}$ is a 4- to 10-membered heterocyclyl having 1 or 2 heteroatoms independently selected from the group consisting of N, O and S, and optionally substituted with 1, 2, 3, 4 or 5 substituents independently selected from $R^{10}$. In some of these embodiments, $R^{16}$ is a 4- to 7-membered monocyclic heterocyclyl having 1 or 2 heteroatoms independently selected from the group consisting of N, O and S, and optionally substituted with 1, 2, 3, 4 or 5 substituents independently selected from $R^{10}$. In some of these embodiments, $R^{16}$ is 6- to 10-membered bicyclic heterocyclyl having 1 or 2 heteroatoms independently selected from the group consisting of N, O and S, and optionally substituted with 1, 2, 3, 4 or 5 substituents independently selected from $R^{10}$.

In some embodiments, $R^{16}$ is $C_{3-10}$ cycloalkyl optionally substituted with 1, 2, 3, 4 or 5 substituents independently selected from $R^{10}$. In some embodiments, $R^{16}$ is $C_{3-8}$ cycloalkyl optionally substituted with 1, 2, 3, 4 or 5 substituents independently selected from $R^{10}$.

In some embodiments, $R^{16}$ is 7- to 14-membered heteroaryl optionally substituted with 1, 2, 3, 4 or 5 substituents independently selected from $R^{10}$. In some embodiments, $R^{16}$ is a fused 7- to 14-membered heteroaryl optionally substituted with 1, 2, 3, 4 or 5 substituents independently selected from $R^{10}$; wherein the heteroaryl contains a partially saturated ring, and the point of attachment is at the partially saturated ring. In one variation, $R^{16}$ is 5H-pyrrolo[1,2-a] imidazol-6-yl.

In some embodiments, $R^{16}$ is $C_{1-6}$ alkyl optionally substituted with 1, 2, 3, 4 or 5 substituents independently selected from $R^{10}$. In some of these embodiments, $R^{16}$ is $C_{1-6}$ alkyl or $C_{1-6}$ haloalkyl. In some of these embodiments, $R^{16}$ is $C_{1-6}$ alkyl (e.g., isopropyl or neopentyl). In some of these embodiments, $R^{16}$ is $C_{1-6}$ alkyl substituted with 1, 2, 3, 4 or 5 substituents independently selected from $R^{10}$. In one variation, $R^{1-6}$ is $C_{1-6}$ haloalkyl (e.g., 2,2,2-trifluoroethyl).

In some of these embodiments, $R^{16}$ is —($C_{1-6}$ alkylene)-$R^{19}$, wherein $R^{19}$ is $C_{3-10}$ cycloalkyl, $C_{6-14}$ aryl, 5- to 14-membered heteroaryl, 3- to 14-membered heterocyclyl, cyano, —$OR^7$, —$NR^{8a}R^{8b}$, or —$S(O)_2R^9$; wherein the $C_{3-10}$ cycloalkyl, $C_{6-14}$ aryl, 5- to 14-membered heteroaryl and 3- to 14-membered heterocyclyl of $R^{19}$ are each independently optionally substituted with 1, 2, 3, 4 or 5 substituents independently selected from $R^{10}$. In one variation, $R^{19}$ is a 5- or 6-membered heteroaryl optionally substituted with 1, 2, 3 or 4 substituents independently selected from $R^{10}$; or 3- to 10-membered heterocyclyl optionally substituted with 1, 2, 3 or 4 substituents independently selected from $R^{10}$. In one variation, $R^{19}$ is a $C_{3-10}$ cycloalkyl optionally substituted with 1, 2, 3 or 4 substituents independently selected from $R^{10}$; or phenyl optionally substituted with 1, 2, 3 or 4 substituents independently selected from $R^{10}$. In another variation, $R^{19}$ is cyano, —$OR^7$, —$NR^{8a}R^{8b}$, or —$S(O)_2R^9$. In another variation, $R^{19}$ is —$OCH_3$, —$NH_2$, or —$S(O)_2CH_3$.

In some of these embodiments, $R^{16}$ is selected from the group consisting of:

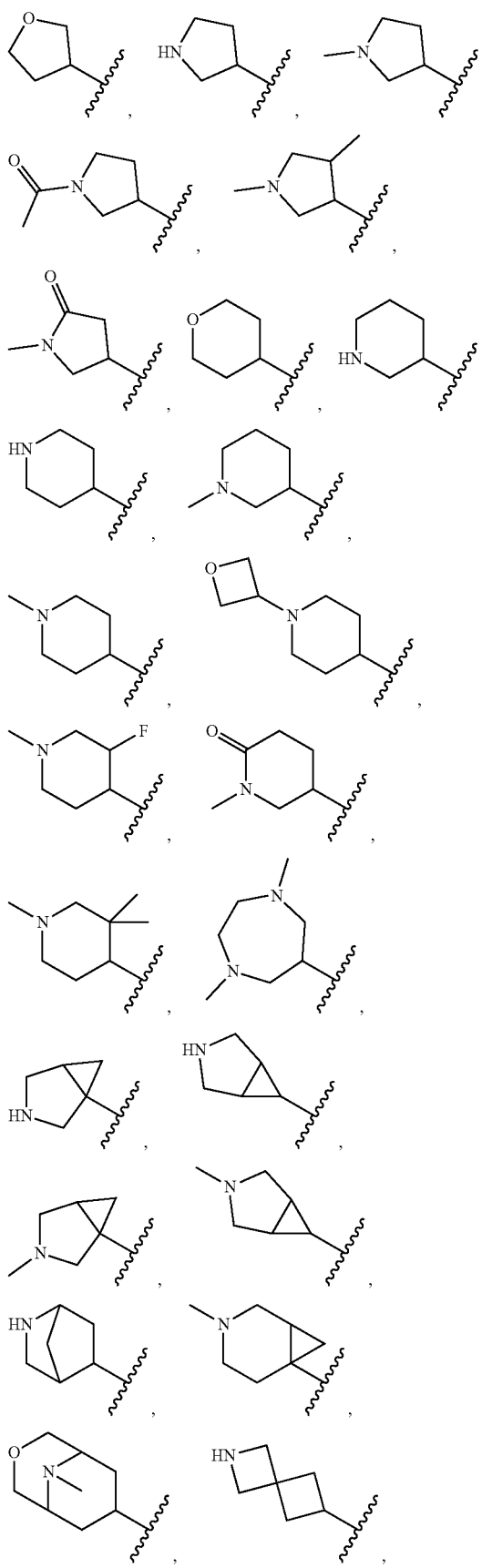

-continued
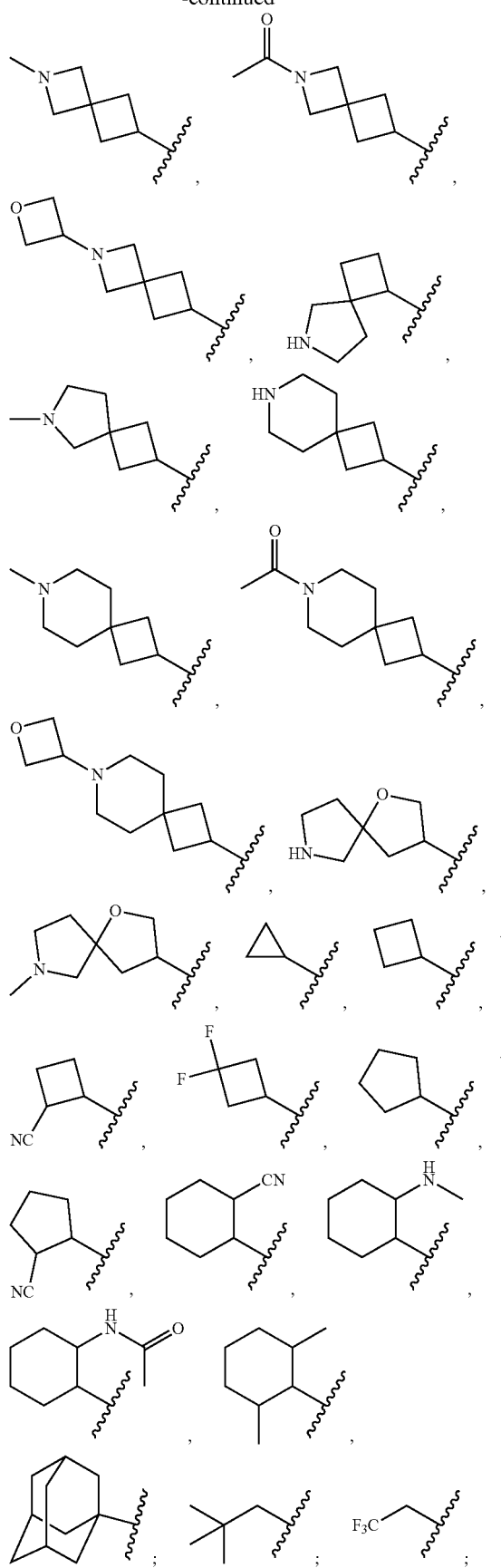
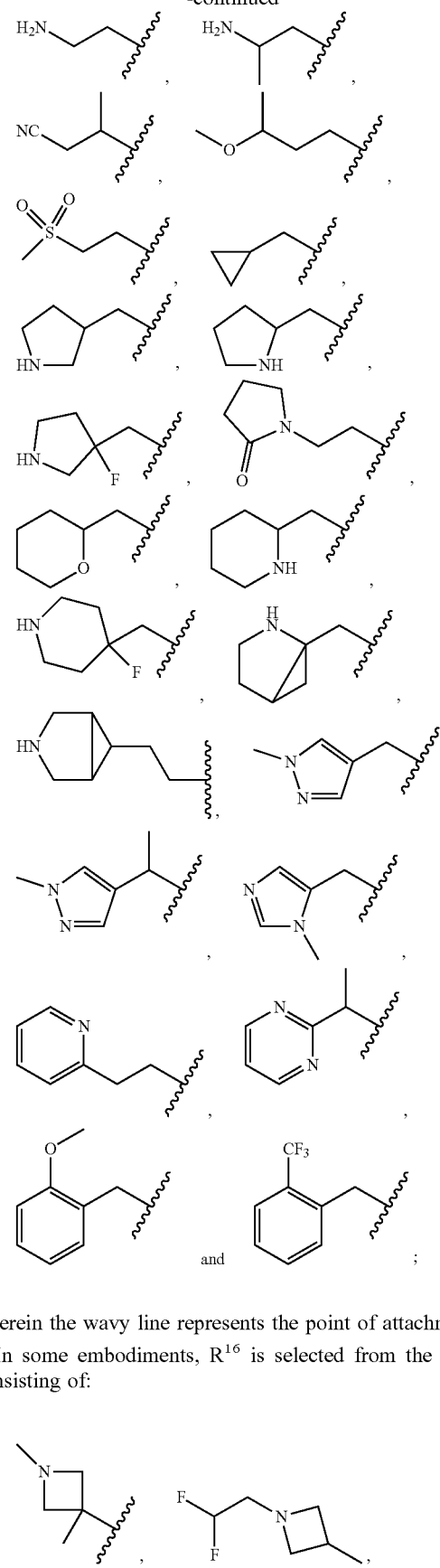
wherein the wavy line represents the point of attachment.
In some embodiments, $R^{16}$ is selected from the group consisting of:
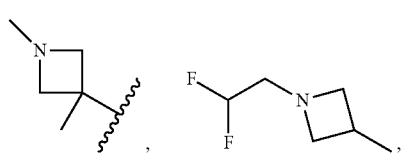

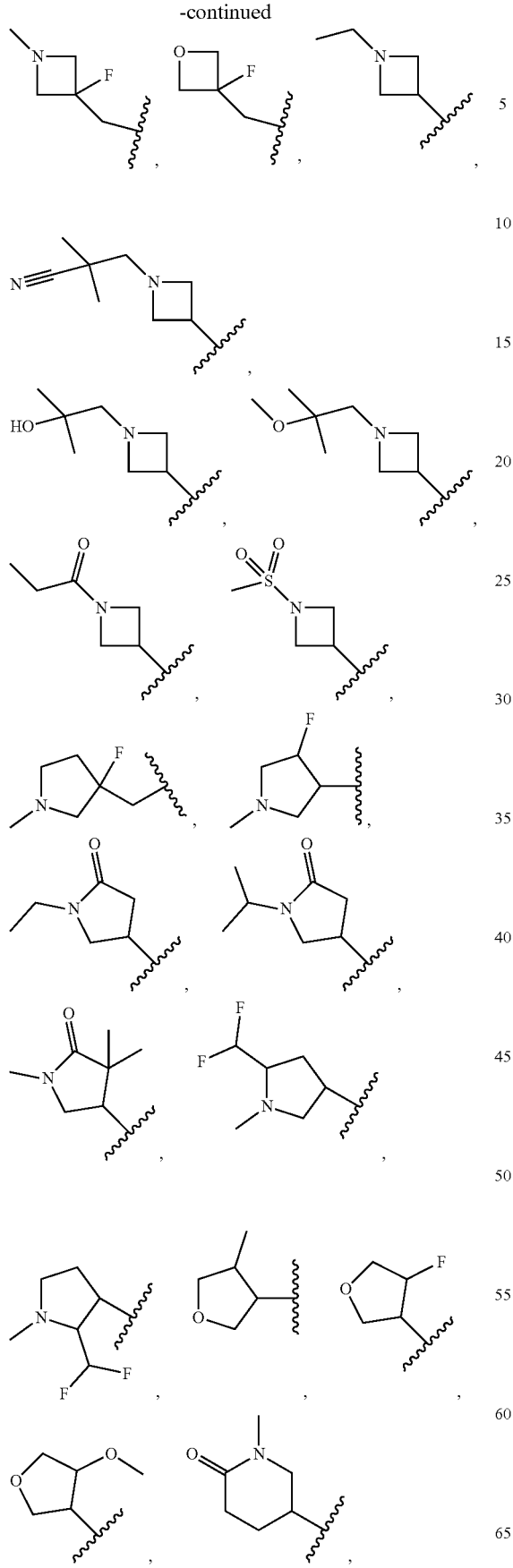
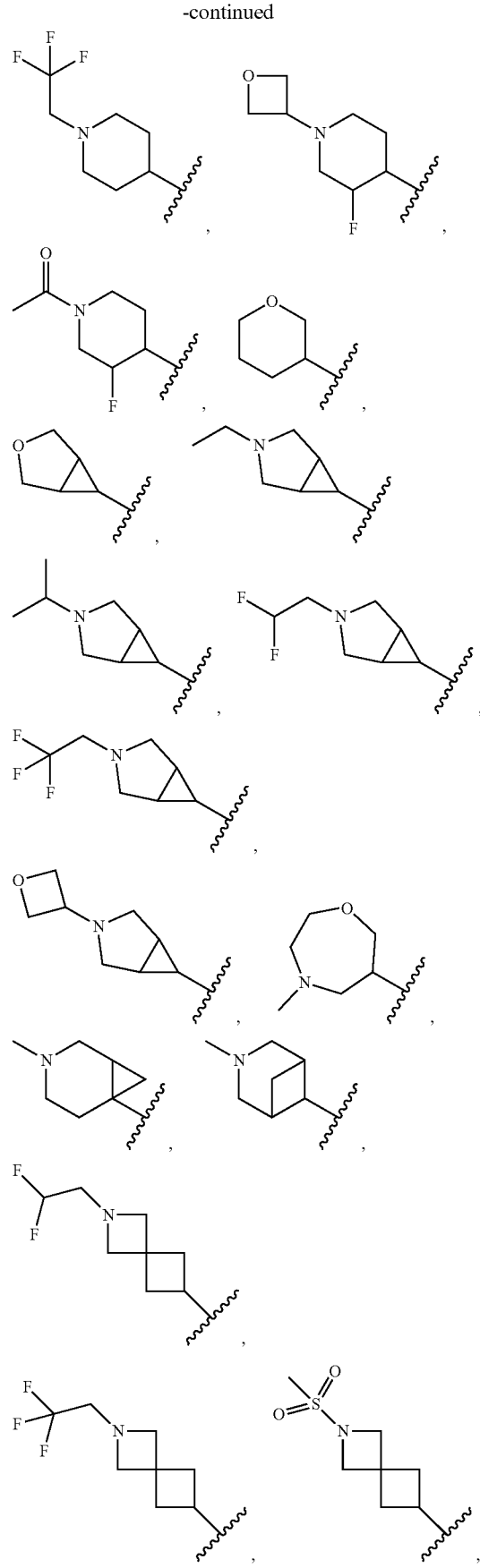

-continued

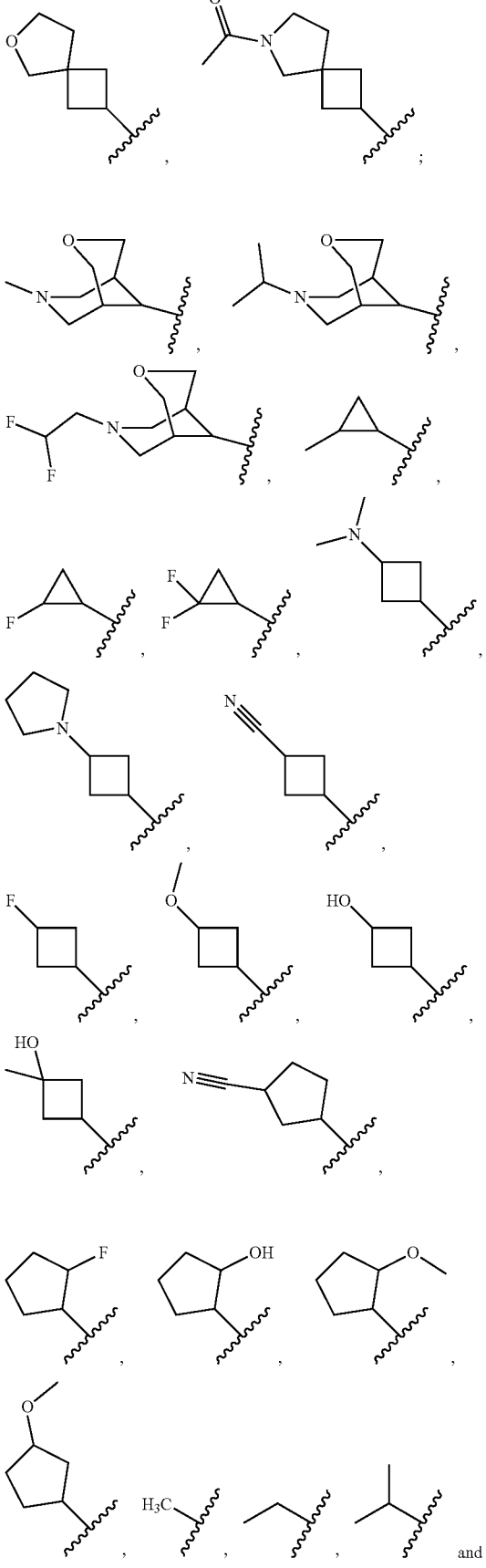

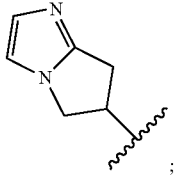

wherein the wavy line represents the point of attachment.

In some of these embodiments, $R^{16}$ is selected from the group consisting of:

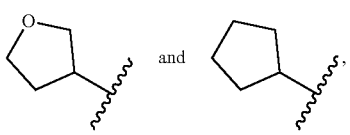 [SMILES: *C1CCOC1 ; *C1CCCC1]

each independently optionally substituted with 1, 2, 3, 4 or 5 substituents independently selected from $R^{10}$; wherein the wavy line represents the point of attachment. In some embodiments, each is independently optionally substituted with 1 substituent independently selected from $R^{10}$. In some of these embodiments, $R^{10}$ is independently $C_{1-6}$ alkyl (e.g., methyl) or cyano. In some of these embodiments, $R^{10}$ is independently $C_{1-6}$ alkyl (e.g., methyl).

In some embodiments, $R^{15}$ is $-NR^{17}R^{18}$, wherein $R^{17}$ is hydrogen or $C_{1-6}$ alkyl; $R^{18}$ is 3- to 14-membered heterocyclyl optionally substituted with 1, 2, 3, 4 or 5 substituents independently selected from $R^{10}$, $C_{3-10}$ cycloalkyl optionally substituted with 1, 2, 3, 4 or 5 substituents independently selected from $R^{10}$; or $C_{1-6}$ alkyl optionally substituted with 1, 2, 3, 4 or 5 substituents independently selected from $R^{10}$; or $R^{17}$ and $R^{18}$ are taken together with the nitrogen atom to which they are attached to form a 4- to 12-membered heterocyclyl optionally substituted with 1, 2, 3, 4 or 5 substituents independently selected from $R^{10}$.

In one aspect, provided is a compound of Formula (IB):

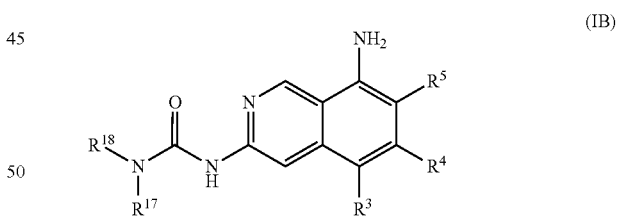

(IB)

or a salt (e.g., a pharmaceutically acceptable salt) thereof, wherein:

$R^{17}$ is hydrogen or $C_{1-6}$ alkyl;

$R^{18}$ is $C_{1-6}$ alkyl, $C_{3-10}$ cycloalkyl, or 3- to 14-membered heterocyclyl; wherein the $C_{1-6}$ alkyl, $C_{3-10}$ cycloalkyl and 3- to 14-membered heterocyclyl of $R^{18}$ are each independently optionally substituted with 1, 2, 3, 4 or 5 substituents independently selected from $R^{10}$;

or $R^{17}$ and $R^{18}$ are taken together with the nitrogen atom to which they are attached to form a 4- to 12-membered heterocyclyl optionally substituted with 1, 2, 3, 4 or 5 substituents independently selected from $R^{10}$; and $R^3$, $R^4$, $R^5$ and $R^{10}$ are as defined for Formula (I), or variations detailed herein.

In some embodiments, the compound is of the Formula (I) or (IB), or a salt (e.g., a pharmaceutically acceptable salt), solvate (e.g., hydrate), prodrug, metabolites or derivative thereof, wherein $R^{17}$ is hydrogen or $C_{1-6}$ alkyl. In some of these embodiments, $R^{17}$ is hydrogen.

In some embodiments, the compound is of the Formula (I) or (IB), or a salt (e.g., a pharmaceutically acceptable salt), solvate (e.g., hydrate), prodrug, metabolites or derivative thereof, wherein $R^{18}$ is 3- to 14-membered heterocyclyl optionally substituted with 1, 2, 3, 4 or 5 substituents independently selected from $R^{10}$; $C_{3-10}$ cycloalkyl optionally substituted with 1, 2, 3, 4 or 5 substituents independently selected from $R^{10}$; or $C_{1-6}$ alkyl optionally substituted with 1, 2, 3, 4 or 5 substituents independently selected from $R^{10}$.

In some embodiments, $R^{10}$ is 3- to 14-membered heterocyclyl optionally substituted with 1, 2, 3, 4 or 5 substituents independently selected from $R^{10}$. In some of these embodiments, $R^{18}$ is selected from the group consisting of:

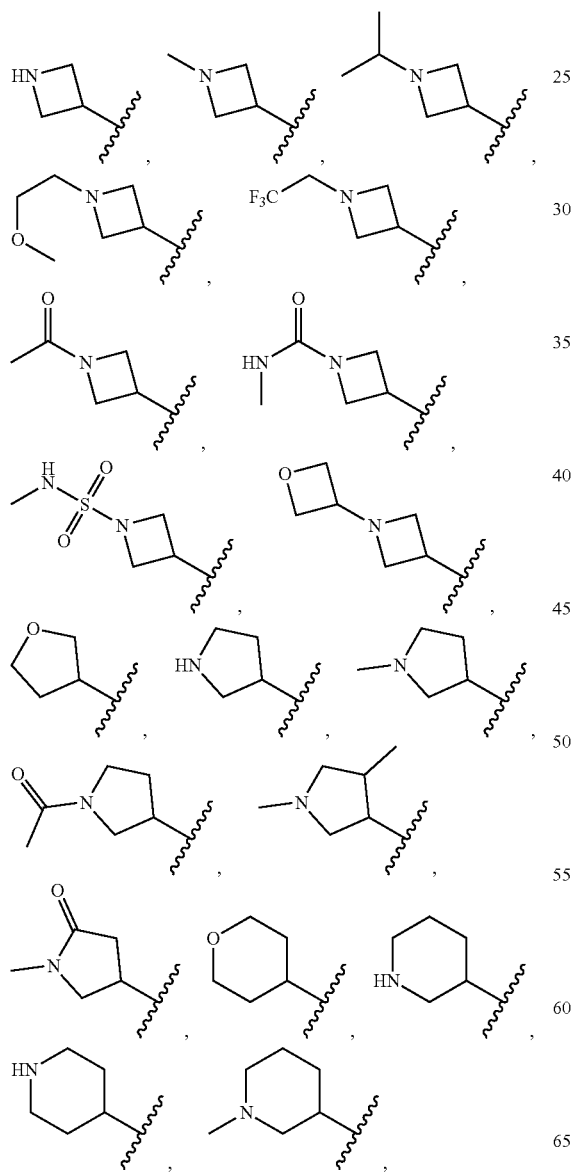

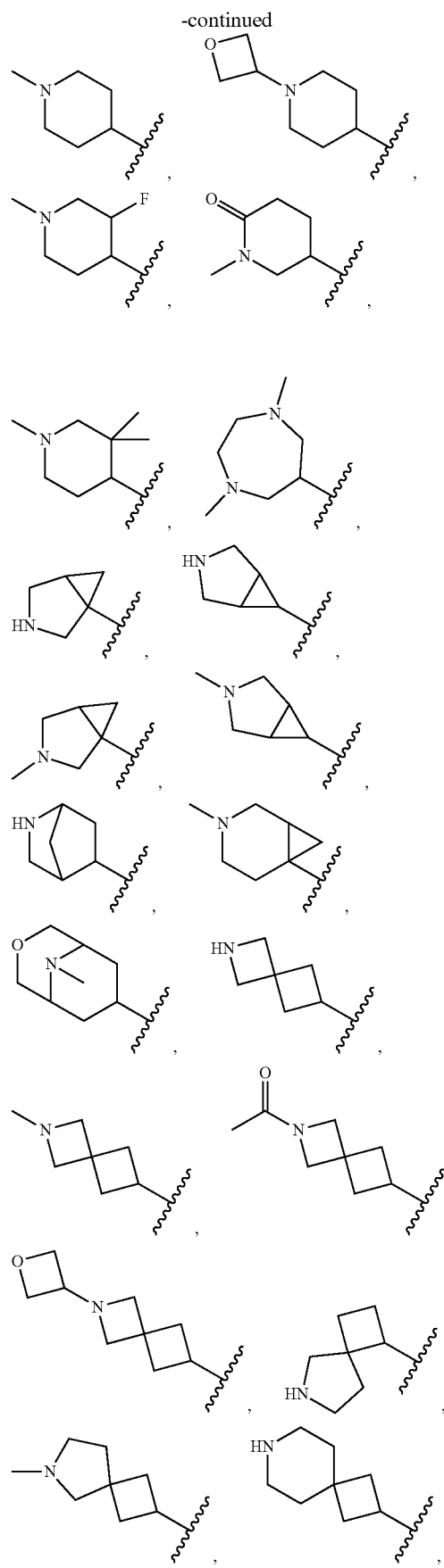

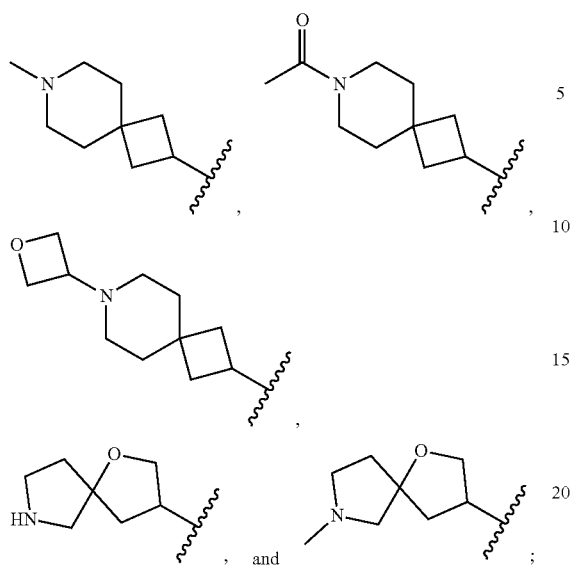
wherein the wavy line represents the point of attachment.
In some embodiments, $R^{18}$ is selected from the group consisting of:
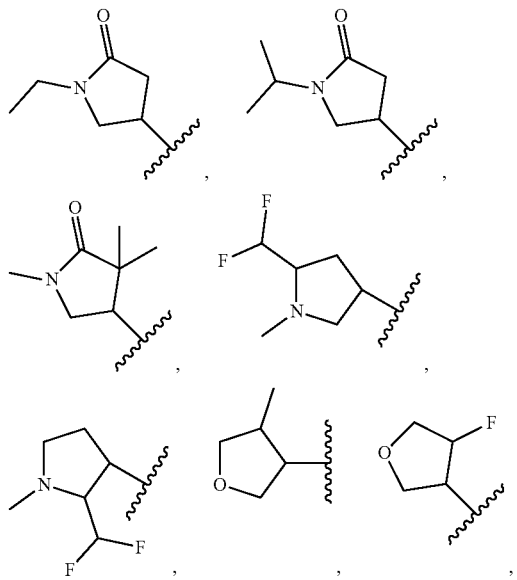
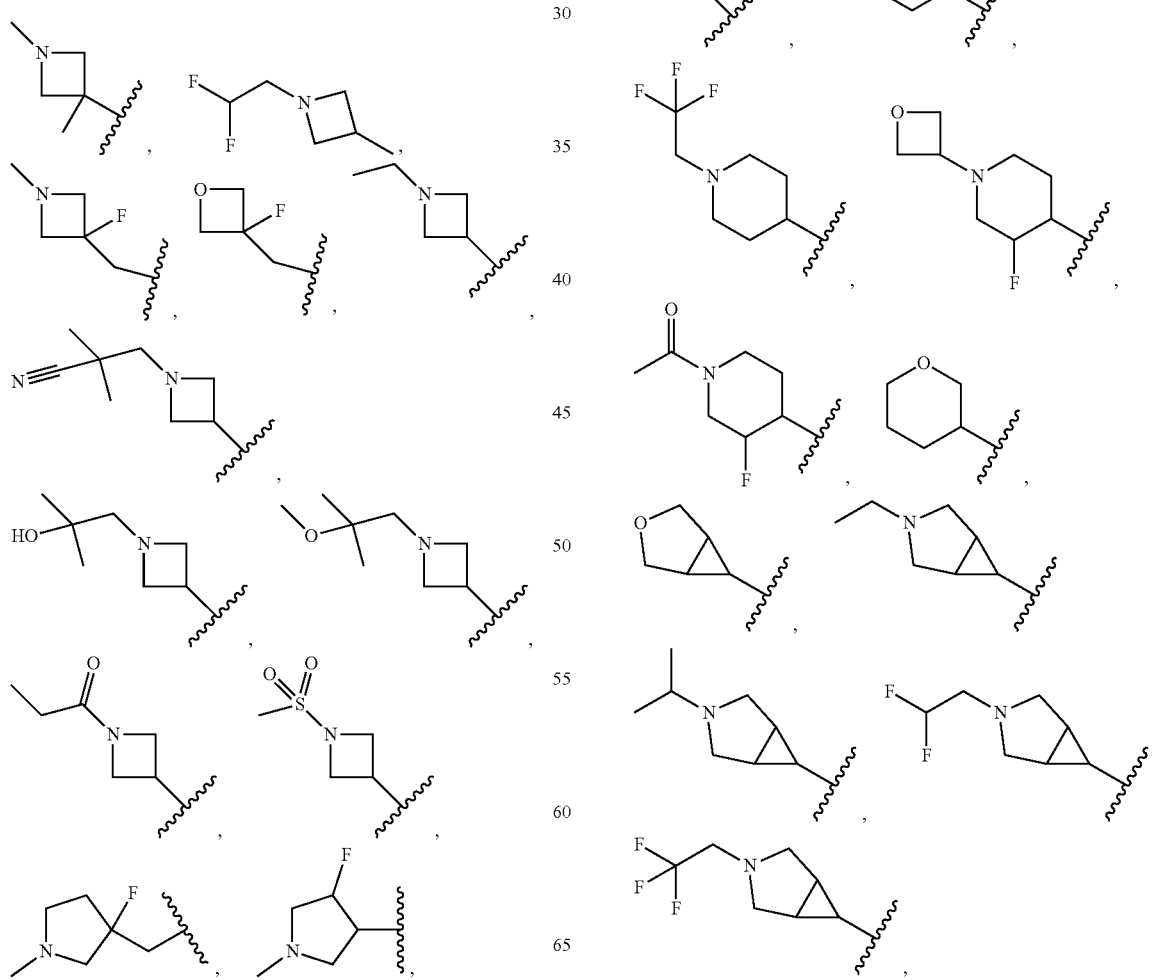

-continued

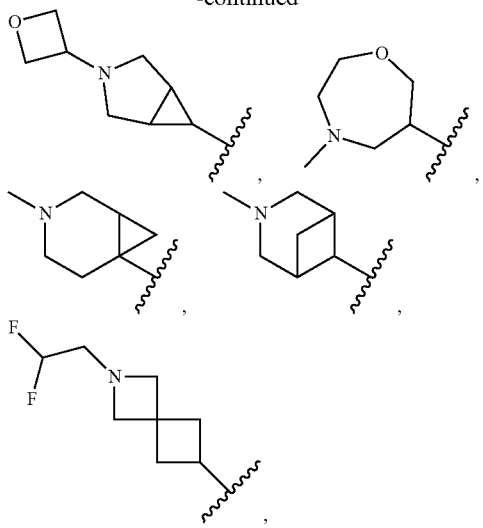

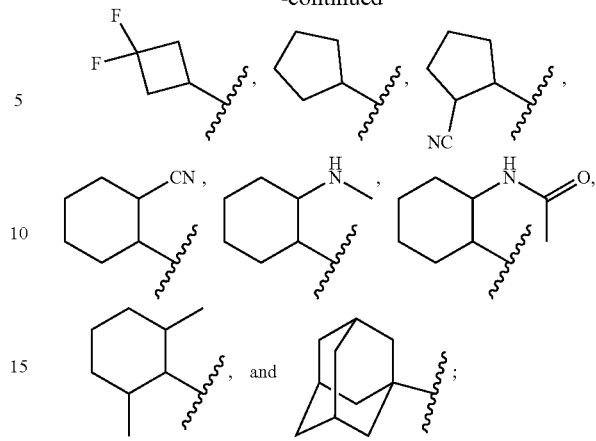

wherein the wavy line represents the point of attachment.

In some embodiments, R$^{18}$ is selected from the group consisting of:

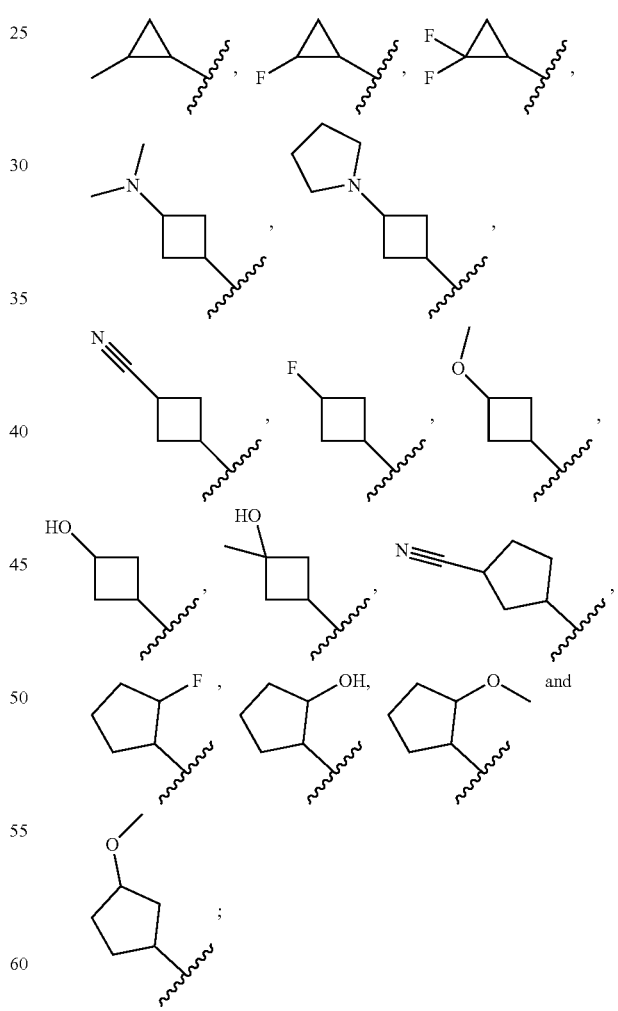

wherein the wavy line represents the point of attachment.

In some embodiments, R$^{18}$ is C$_{3-10}$ cycloalkyl optionally substituted with 1, 2, 3, 4 or 5 substituents independently selected from R$^{10}$. In some of these embodiments, R$^{18}$ is selected from the group consisting of:

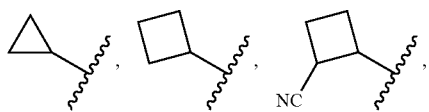

wherein the wavy line represents the point of attachment.

In some embodiments, R$^{18}$ is C$_{1-6}$ alkyl, C$_{1-6}$ haloalkyl or —(C$_{1-6}$ alkylene)-R$^{19}$, wherein R$^{19}$ is C$_{3-10}$ cycloalkyl, C$_{6-14}$ aryl, 5- to 14-membered heteroaryl, 3- to 14-membered

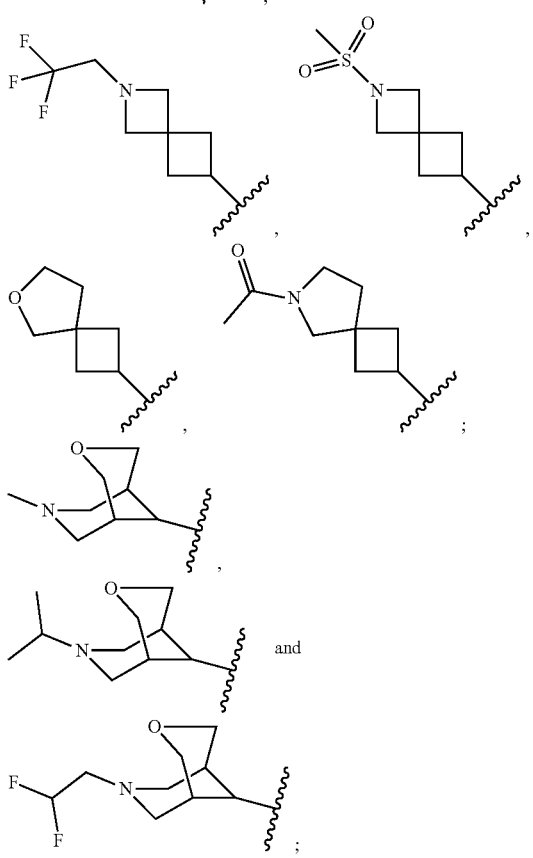

heterocyclyl, cyano, —OR$^7$, —NR$^{8a}$R$^{8b}$, or —S(O)$_2$R$^9$; wherein the C$_{3-10}$ cycloalkyl, C$_{6-14}$ aryl, 5- to 14-membered heteroaryl and 3- to 14-membered heterocyclyl of R$^{19}$ are each independently optionally substituted with 1, 2, 3, 4 or 5 substituents independently selected from R$^{10}$. In some of these embodiments, R$^{19}$ is 3- to 14-membered heterocyclyl optionally substituted with 1, 2, 3, 4 or 5 substituents independently selected from R$^{10}$. In some of these embodiments, R$^{19}$ is C$_{3-10}$ cycloalkyl optionally substituted with 1, 2, 3, 4 or 5 substituents independently selected from R$^{10}$. In one variation, R$^{19}$ is optionally substituted pyrazolyl (e.g., 1-methylpyrazol-4-yl), cyclopropyl, or cyano.

In some embodiments, R$^{18}$ is selected from the group consisting of:

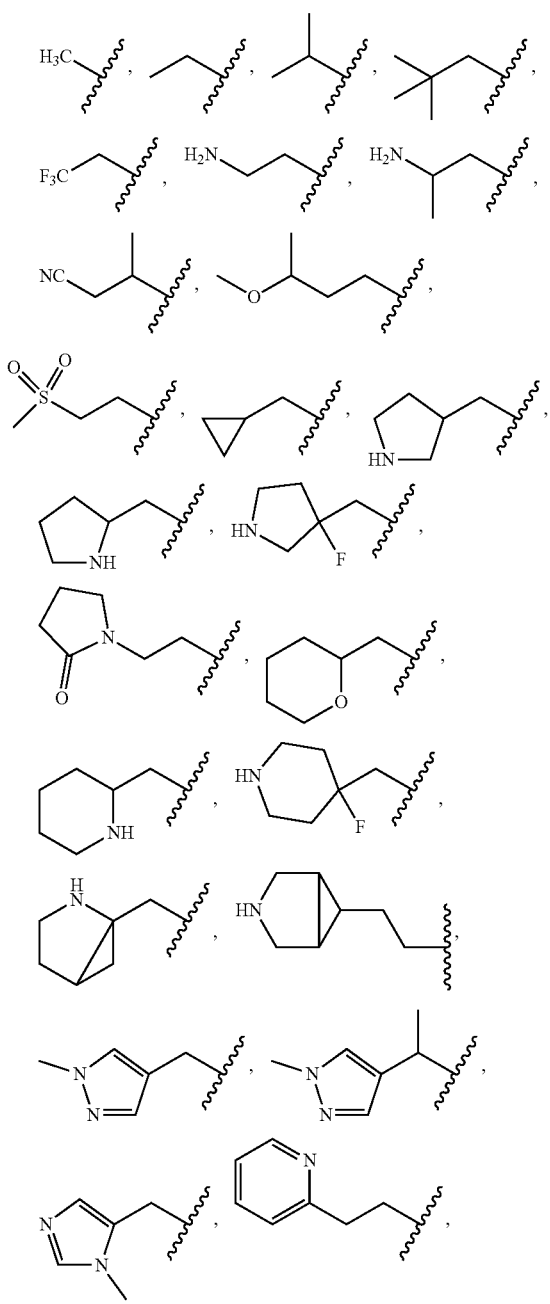

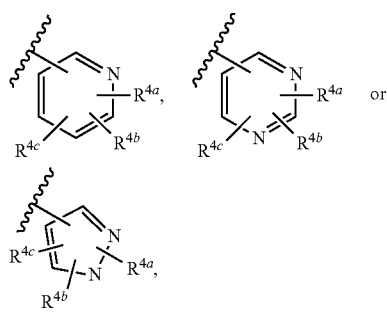

wherein the wavy line represents the point of attachment.

In some embodiments, the compound is of the Formula (I) or (IB), or a salt (e.g., a pharmaceutically acceptable salt), solvate (e.g., hydrate), prodrug, metabolites or derivative thereof, wherein R$^{17}$ and R$^{18}$ are taken together with the nitrogen atom to which they are attached to form a 4- to 12-membered heterocyclyl optionally substituted with 1, 2, 3, 4 or 5 substituents independently selected from R$^{10}$. In one variation, R$^{17}$ and R$^{18}$ are taken together with the nitrogen atom to which they are attached to form a 5- or 6-membered heterocyclyl optionally substituted with 1, 2, 3, 4 or 5 substituents independently selected from R$^{10}$. In one variation, R$^{17}$ and R$^{18}$ are taken together with the nitrogen atom to which they are attached to form a 5- or 6-membered heterocyclyl (e.g., pyrrolidin-1-yl or piperidin-1-yl).

In some embodiments, the compound is of the Formula (I), or variations thereof such as Formula (IA), (IB) and (IC), or a salt (e.g., a pharmaceutically acceptable salt) thereof, wherein R$^4$ is 5- to 14-membered heteroaryl optionally substituted with 1, 2, 3, 4 or 5 substituents independently selected from R$^{10}$. In some embodiments, R$^4$ is 5- to 10-membered heteroaryl optionally substituted with 1, 2, 3, 4 or 5 substituents independently selected from R$^{10}$. In some embodiments, R$^4$ is 5- or 6-membered heteroaryl optionally substituted with 1, 2, 3, 4 or 5 substituents independently selected from R$^{10}$. In some embodiments, R$^4$ is 5-membered heteroaryl optionally substituted with 1, 2, 3, 4 or 5 substituents independently selected from R$^{10}$. In some embodiments, R$^4$ is 6-membered heteroaryl optionally substituted with 1, 2, 3, 4 or 5 substituents independently selected from R$^{10}$.

In some embodiments, R$^4$ is wherein the wavy line represents the point of attachment, R$^{4a}$, R$^{4b}$ and R$^{4c}$ are each independently hydrogen or R$^{10}$, or two vicinal R$^{4(a-c)}$ are taken together with the atoms to which they are attached form a fused 5- or 6-membered heteroaryl optionally substituted with 1, 2, 3 or 4 substituents independently selected from R$^{10}$ or a fused 5- or 6-membered heterocyclyl optionally substituted with 1, 2, 3 or 4 substituents independently selected from $R^{10}$.

In some embodiments, $R^4$ is

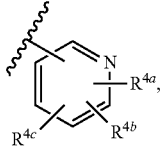

wherein the wavy line represents the point of attachment, $R^{4a}$, $R^{4b}$ and $R^{4c}$ are each independently hydrogen or $R^{10}$, or two vicinal $R^{4(a-c)}$ are taken together with the atoms to which they are attached form a fused 5- to 10-membered heterocyclyl optionally substituted with 1, 2, 3 or 4 substituents independently selected from $R^{10}$ or a fused $C_{5-8}$ cycloalkyl optionally substituted with 1, 2, 3 or 4 substituents independently selected from $R^{10}$.

In some of these embodiments, $R^4$ is elected from the group consisting of:

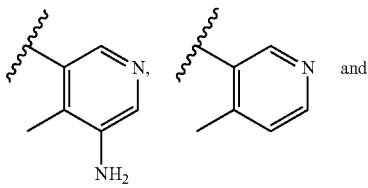

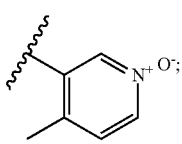

wherein the wavy line represents the point of attachment.

In some embodiments, $R^4$ is

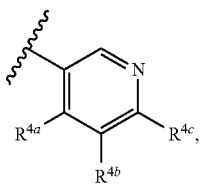

wherein the wavy line represents the point of attachment; $R^{4a}$ is halogen, $C_{1-6}$ alkyl or $C_{3-6}$ cycloalkyl; and $R^{4b}$ and $R^{4c}$ are taken together with the atoms to which they are attached form a fused 5- to 10-membered heterocyclyl optionally substituted with 1, 2, 3 or 4 substituents independently selected from the group consisting of $C_{1-6}$ alkyl, hydroxyl, halogen and cyano, or a fused $C_{5-8}$ cycloalkyl optionally substituted with 1, 2, 3 or 4 substituents independently selected from the group consisting of $C_{1-6}$ alkyl, hydroxyl, halogen and cyano.

In some embodiments, $R^4$ is

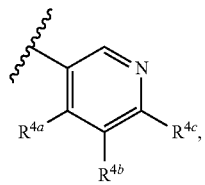

wherein the wavy line represents the point of attachment; $R^{4a}$ is $C_{1-6}$ alkyl (e.g., methyl or ethyl), and $R^{4b}$ and $R^{4c}$ are taken together with the atoms to which they are attached form a fused 5- to 10-membered heterocyclyl.

In some of these embodiments, $R^4$ is selected from the group consisting of:

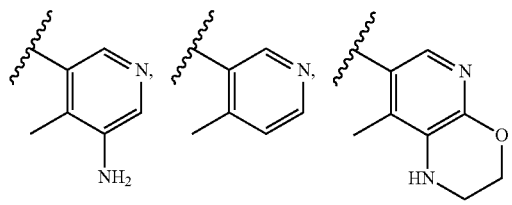

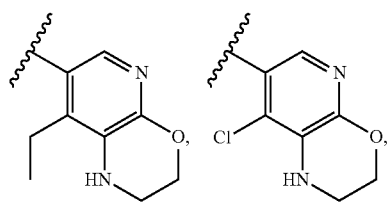

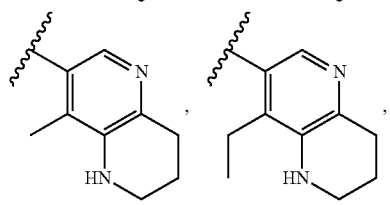

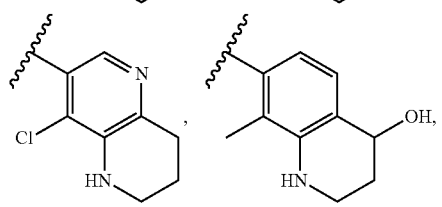

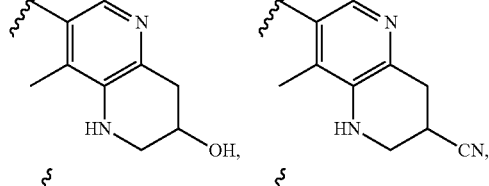

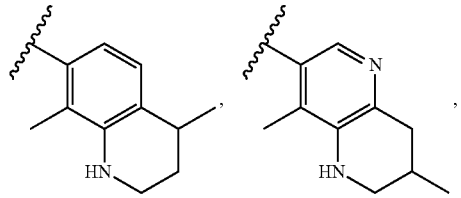

-continued

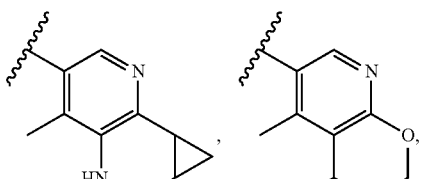

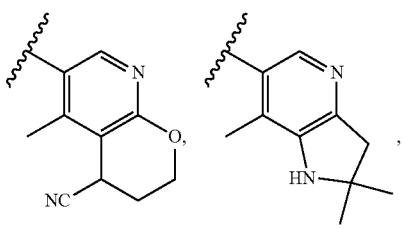

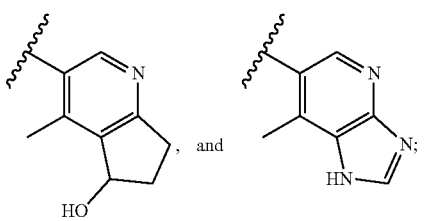

wherein the wavy line represents the point of attachment.

In some of these embodiments, $R^4$ is elected from the group consisting of:

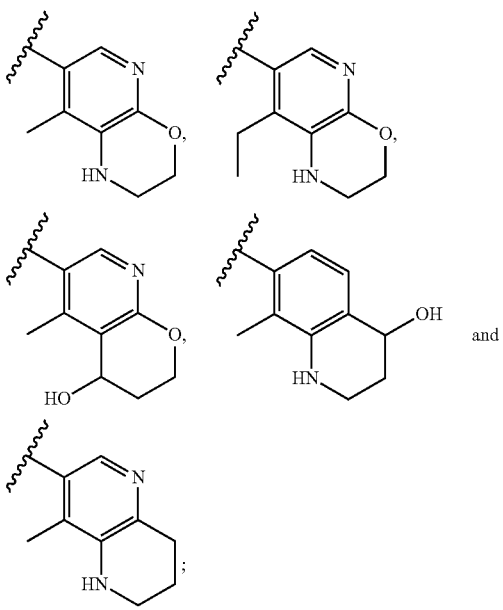

wherein the wavy line represents the point of attachment.

In some of these embodiments, $R^4$ is

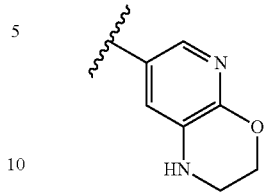

substituted with 1 substituent selected from $R^{10}$, wherein the wavy line represents the point of attachment. In some of these embodiments, $R^{10}$ is independently $C_{1-6}$ alkyl (e.g., methyl or ethyl). In some of these embodiments, $R^4$ is

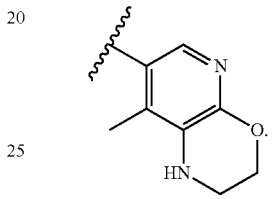

It is intended and understood that each and every variation of $R^{15}$ described for the Formula (I), or variations thereof such as Formula (IA), (IB) or (IC), may be combined with each and every variation of $R^4$ described for the Formula (I), (IA), (IB) or (IC), the same as if each and every combination is specifically and individually described. For example, in some embodiments, wherein $R^{15}$ is (a), (b) or (c):

(a) —$OR^{16}$, wherein $R^{16}$ is (i), (ii), (iii), (iv) or (v):
  (i) a 4- to 10-membered heterocyclyl having 1 or 2 heteroatoms independently selected from the group consisting of N, O and S, and optionally substituted with 1, 2, 3, 4 or 5 substituents independently selected from $R^{10}$;
  (ii) $C_{3-10}$ cycloalkyl optionally substituted with 1, 2, 3, 4 or 5 substituents independently selected from $R^{10}$;
  (iii) $C_{1-6}$ alkyl,
  (iv) $C_{1-6}$ haloalkyl, or
  (v) —($C_{1-6}$ alkylene)-$R^{19}$ where $R^{19}$ is 5- or 6-membered heteroaryl optionally substituted with 1, 2, 3 or 4 substituents independently selected from $R^{10}$; 3- to 10-membered heterocyclyl optionally substituted with 1, 2, 3 or 4 substituents independently selected from $R^{10}$; $C_{3-10}$ cycloalkyl optionally substituted with 1, 2, 3 or 4 substituents independently selected from $R^{10}$; phenyl optionally substituted with 1, 2, 3 or 4 substituents independently selected from $R^{10}$; cyano, —$OR^7$, —$NR^{8a}R^{8b}$, or —$S(O)_2R^9$;

(b) —$NR^{17}R^{18}$, wherein $R^{17}$ is hydrogen, and $R^{18}$ is 3- to 14-membered heterocyclyl optionally substituted with 1, 2, 3, 4 or 5 substituents independently selected from $R^{10}$, $C_{3-10}$ cycloalkyl optionally substituted with 1, 2, 3, 4 or 5 substituents independently selected from $R^{10}$; $C_{1-6}$ haloalkyl, or —($C_{1-6}$ alkylene)-$R^{19}$, where $R^{19}$ is optionally substituted pyrazolyl (e.g., 1-methylpyrazol-4-yl), cyclopropyl, or cyano; or (c) —SR$^{16}$;

and R$^4$ is elected from the group consisting of

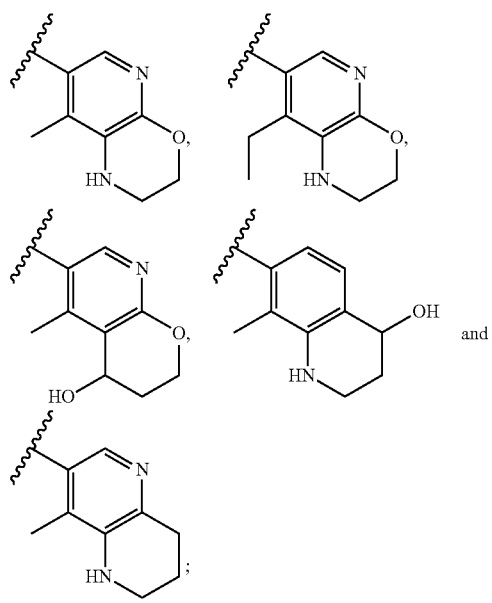

wherein the wavy line represents the point of attachment. In some of these embodiments, R$^4$ is

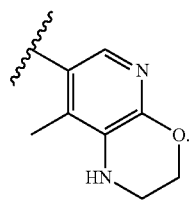 [SMILES: *c1cnc2c(c1C)NCCO2]

In some embodiments, the compound is of the Formula (I), or variations thereof such as Formula (IA), (IB) and (IC), or a salt (e.g., a pharmaceutically acceptable salt) thereof, wherein R$^3$ is hydrogen, halogen, cyano, C$_{1-6}$ alkyl, C$_{3-8}$ cycloalkyl, 3- to 14-membered heterocyclyl, or —OR$^7$; wherein the C$_{1-6}$ alkyl, C$_{3-8}$ cycloalkyl and 3- to 14-membered heterocyclyl of R$^3$ are each optionally substituted with 1, 2, 3, 4 or 5 substituents independently selected from R$^{10}$. In some embodiments, R$^3$ is hydrogen, fluoro, chloro, cyano, hydroxyl, C$_{3-4}$ cycloalkyl, C$_{1-6}$ alkyl, C$_{1-6}$ haloalkyl, —O(C$_{1-6}$ alkyl) or —O(C$_{1-6}$ haloalkyl). In one variation, R$^3$ is hydrogen, fluoro, cyano, or C$_{1-6}$ alkyl (e.g., methyl). In another variation, R$^3$ is hydrogen or fluoro. In another variation, R$^3$ is hydrogen.

In some embodiments, the compound is of the Formula (I), or variations thereof such as Formula (IA), (IB) and (IC), or a salt (e.g., a pharmaceutically acceptable salt) thereof, wherein R$^5$ is hydrogen, halogen, cyano, C$_{1-6}$ alkyl, C$_{2-6}$ alkenyl, C$_{2-6}$ alkynyl, C$_{3-8}$ cycloalkyl, C$_{6-14}$ aryl, 5- to 14-membered heteroaryl, 3- to 14-membered heterocyclyl, —C(O)R$^6$, —C(O)OR$^7$, —C(O)NR$^{8a}$R$^{8b}$, —OR$^7$, —OC(O)R$^6$, —OC(O)NR$^{8a}$R$^{8b}$, —SR$^7$, —S(O)R$^9$, —S(O)$_2$R$^9$, —S(O)$_2$NR$^{8a}$R$^{8b}$, —P(O)R$^{9a}$R$^{9b}$, —NR$^{8a}$R$^{8b}$, —N(R$^8$)C(O)R$^6$, —N(R$^8$)C(O)NR$^7$, —N(R$^8$)C(O)NR$^{8a}$R$^{8b}$, —N(R$^8$)S(O)$_2$R$^9$, or —N(R$^8$)S(O)$_2$NR$^{8a}$R$^{8b}$; wherein the C$_{1-6}$ alkyl, C$_{2-6}$ alkenyl, C$_{2-6}$ alkynyl, C$_{3-8}$ cycloalkyl, C$_{6-14}$ aryl, 5- to 14-membered heteroaryl and 3- to 14-membered heterocyclyl of R$^5$ are each optionally substituted with 1, 2, 3, 4 or 5 substituents independently selected from R$^{10}$. In some embodiments, R$^5$ is hydrogen, halogen, cyano, C$_{1-6}$ alkyl, C$_{3-8}$ cycloalkyl, 3- to 14-membered heterocyclyl, —OR$^7$, —NR$^{8a}$R$^{8b}$, or —N(R$^8$)C(O)R$^6$; wherein the C$_{1-6}$ alkyl, C$_{3-8}$ cycloalkyl and 3- to 14-membered heterocyclyl of R$^5$ are each optionally substituted with 1, 2, 3, 4 or 5 substituents independently selected from R$^{10}$. In some embodiments, R$^5$ is hydrogen, fluoro, chloro, cyano, hydroxyl, C$_{3-4}$ cycloalkyl, C$_{1-6}$ alkyl, C$_{1-6}$ haloalkyl, —O(C$_{1-6}$ alkyl) or —O(C$_{1-6}$ haloalkyl). In one variation, R$^5$ is hydrogen, fluoro, cyano, or C$_{1-6}$ alkyl. In another variation, R$^5$ is hydrogen, fluoro, or chloro. In another variation, R$^5$ is hydrogen. In another variation, R$^5$ is fluoro.

It is intended and understood that each and every variation of R$^{15}$ and R$^4$, or a combination thereof, described for the Formula (I) may be combined with each and every variation of R$^3$ and R$^5$, or a combination thereof, described for the Formula (I), or the Formula (IA), (IB) or (IC), the same as if each and every combination is specifically and individually described. For example, in some embodiments, R$^3$ is hydrogen; R$^5$ is fluoro; and R$^4$ is as detailed herein for the Formula (I), or variations thereof such as Formula (IA), (IB) and (IC). In some embodiments of the compound of the Formula (I), or a salt (e.g., a pharmaceutically acceptable salt) thereof, R$^{15}$ is (a), (b) or (c) as detailed above; R$^3$ is hydrogen; R$^5$ is fluoro; and R$^4$ is elected from the group consisting of

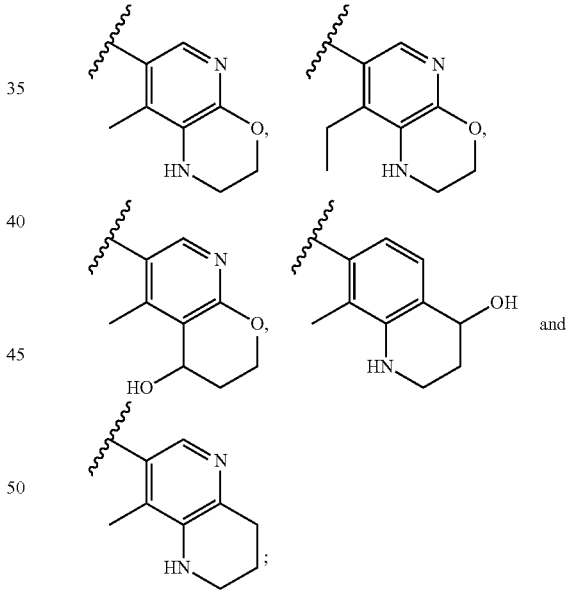

wherein the wavy line represents the point of attachment.

In some embodiments of the compound of the Formula (I), or variations thereof such as Formula (IA), (IB) and (IC) where applicable, or a salt (e.g., a pharmaceutically acceptable salt) thereof, each R$^6$ is independently hydrogen, C$_{1-6}$ alkyl, C$_{2-6}$ alkenyl, C$_{2-6}$ alkynyl, C$_{3-8}$ cycloalkyl, C$_{6-10}$ aryl, 5- to 14-membered heteroaryl or 3- to 12-membered heterocyclyl; wherein the C$_{1-6}$ alkyl, C$_{2-6}$ alkenyl, C$_{2-6}$ alkynyl, C$_{3-8}$ cycloalkyl, C$_{6-10}$ aryl, 5- to 14-membered heteroaryl and 3- to 12-membered heterocyclyl of R$^6$ are each optionally substituted with 1, 2, 3, 4 or 5 substituents independently selected from R$^{10}$. In one variation, R$^6$ is C$_{1-6}$ alkyl, $C_{3-8}$ cycloalkyl, or 3- to 12-membered heterocyclyl; wherein the $C_{1-6}$ alkyl, $C_{3-8}$ cycloalkyl, and 3- to 12-membered heterocyclyl of $R^6$ are each optionally substituted with 1, 2, 3, 4 or 5 substituents independently selected from $R^{10}$. In one variation, $R^6$ is $C_{1-6}$ alkyl (e.g., methyl). In one variation, $R^6$ is 3- to 12-membered heterocyclyl optionally substituted with 1, 2, 3, 4 or 5 substituents independently selected from $R^{10}$.

In some embodiments of the compound of the Formula (I), or variations thereof such as Formula (IA), (IB) and (IC) where applicable, or a salt (e.g., a pharmaceutically acceptable salt) thereof, each $R^7$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^7$ are each optionally substituted with 1, 2, 3, 4 or 5 substituents independently selected from $R^{10}$. In one variation, $R^7$ is hydrogen, $C_{1-6}$ alkyl optionally substituted with $R^{10}$. In one variation, $R^7$ is $C_{1-6}$ alkyl. In one variation, $R^7$ is 3- to 12-membered heterocyclyl.

In some embodiments of the compound of the Formula (I), or variations thereof such as Formula (IA), (IB) and (IC) where applicable, or a salt (e.g., a pharmaceutically acceptable salt) thereof, each $R^8$ is independently hydrogen or $C_{1-6}$ alkyl; and each $R^{8a}$ and $R^{8b}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{8a}$ and $R^{8b}$ are each optionally substituted with 1, 2, 3, 4 or 5 substituents independently selected from $R^{10}$; or $R^{8a}$ and $R^{8b}$ are taken together with the nitrogen atom to which they are attached to form a 4- to 12-membered heterocyclyl optionally substituted with 1, 2, 3, 4 or 5 substituents independently selected from $R^{10}$. In one variation, le is hydrogen or $C_{1-6}$ alkyl (e.g., methyl). In one variation, each $R^{8a}$ and $R^{8b}$ is independently hydrogen or $C_{1-6}$ alkyl. In one variation, each $R^{8a}$ and $R^{8b}$ is hydrogen. In one variation, $R^{8a}$ and $R^{8b}$ are taken together with the nitrogen atom to which they are attached to form a 5- to 7-membered heterocyclyl optionally substituted with $R^{10}$.

In some embodiments of the compound of the Formula (I), or variations thereof such as Formula (IA), (IB) and (IC) where applicable, or a salt (e.g., a pharmaceutically acceptable salt) thereof, each $R^9$ is independently $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^9$ are each optionally substituted with 1, 2, 3, 4 or 5 substituents independently selected from $R^{10}$. In one variation, $R^9$ is $C_{1-6}$ alkyl optionally substituted with $R^{10}$; or $C_{6-10}$ aryl optionally substituted with $R^{10}$. In one variation, $R^9$ is $C_{1-6}$ alkyl (e.g., methyl).

In some embodiments of the compound of the Formula (I), or variations thereof such as Formula (IA), (IB) and (IC) where applicable, or a salt (e.g., a pharmaceutically acceptable salt) thereof, each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)$R^a$, —C(O)O$R^b$, —C(O)N$R^cR^d$, —O$R^b$, —OC(O)$R^a$, —OC(O)N$R^cR^d$, —S$R^b$, —S(O)$R^e$, —S(O)$_2R^e$, —S(O)(=NH)$R^e$, —S(O)$_2$N$R^cR^d$, —N$R^cR^d$, —N($R^f$)C(O)$R^a$, —N($R^f$)C(O)O$R^b$, —N($R^f$)C(O)N$R^cR^d$, —N($R^f$)S(O)$_2R^e$, or —N($R^f$)S(O)$_2$N$R^cR^d$; wherein the $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl and 3- to 14-membered heterocyclyl of $R^{10}$ are each optionally substituted with 1, 2, 3 or 4 substituents independently selected from $R^{11}$.

In one variation, $R^{10}$ is independently oxo, $C_{1-6}$ alkyl, $C_{3-8}$ cycloalkyl, $C_{6-10}$ aryl, 5- to 10-membered heteroaryl, 3- to 12-membered heterocyclyl, halogen, cyano, —C(O)$R^a$, —C(O)N$R^cR^d$, —O$R^b$, —S(O)$_2R^e$, —S(O)$_2$N$R^cR^d$, —N$R^cR^d$; wherein the $C_{1-6}$ alkyl, $C_{3-8}$ cycloalkyl, $C_{6-10}$ aryl, 5- to 14-membered heteroaryl and 3- to 14-membered heterocyclyl of $R^{10}$ are each optionally substituted with 1, 2, 3 or 4 substituents independently selected from $R^{11}$.

In one variation, $R^{10}$ is independently oxo; $C_{1-6}$ alkyl optionally substituted with 1, 2, 3 or 4 substituents independently selected from $R^{11}$; 5- to 10-membered heteroaryl optionally substituted with 1, 2, 3 or 4 substituents independently selected from $R^{11}$; halogen, —O$R^b$, —S(O)(=NH)$R^e$, —N$R^cR^d$, —N($R^f$)C(O)$R^a$, or —N($R^f$)S(O)$_2$N$R^cR^d$.

In one variation, $R^{10}$ is independently oxo, halogen, cyano, $C_{1-6}$ alkyl optionally substituted with 1, 2, 3 or 4 substituents independently selected from $R^{11}$, or —O$R^b$.

In one variation, $R^{10}$ is independently —N$R^cR^d$, —N($R^f$)C(O)$R^a$, —N($R^f$)C(O)O$R^b$, —N($R^f$)C(O)N$R^cR^d$, —N($R^f$)S(O)$_2R^e$, or —N($R^f$)S(O)$_2$N$R^cR^d$.

In one variation, $R^{10}$ is independently oxo, —O$R^b$, —OC(O)$R^a$, —OC(O)N$R^cR^d$, —S$R^b$, —S(O)$R^e$, —S(O)$_2R^e$, —S(O)(=NH)$R^e$, or —S(O)$_2$N$R^cR^d$.

In one variation, each $R^{10}$ is independently $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)$R^a$, —C(O)O$R^b$, —C(O)N$R^cR^d$; wherein the $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl and 3- to 14-membered heterocyclyl of $R^{10}$ are each optionally substituted with 1, 2, 3 or 4 substituents independently selected from $R^{11}$.

In one variation, each $R^{10}$ is independently $C_{1-6}$ alkyl, $C_{2-6}$ alkenyl, $C_{2-6}$ alkynyl, each optionally substituted with 1, 2, 3 or 4 substituents independently selected from $R^{11}$.

In one variation, $R^{10}$ is $C_{1-6}$ alkyl optionally substituted with 1, 2, 3 or 4 substituents independently selected from $R^{11}$. In one variation, $R^{10}$ is 3- to 12-membered heterocyclyl optionally substituted with 1, 2, 3 or 4 substituents independently selected from $R^{11}$.

In one variation, $R^{10}$ is halogen, cyano, —N$R^cR^d$, —C(O)N$R^cR^d$, —O$R^b$, —S(O)$_2R^e$, $C_{1-6}$ haloalkyl, —($C_{1-6}$ alkylene)-OH, or —($C_{1-6}$ alkylene)-OH.

In one variation, $R^{10}$ is hydroxyl, cyano, halogen, —CHF$_2$, —CF$_3$, —NH$_2$, —NH($C_{1-6}$ alkyl), —N($C_{1-6}$ alkyl)$_2$, —O($C_{1-6}$ alkyl), SO$_2$($C_{1-6}$ alkyl), —S(O)$_2$N$R^cR^d$, —C(O)N$R^cR^d$, or —N($R^f$)C(O)$R^a$.

In one variation, $R^{10}$ is independently $C_{1-6}$ alkyl (e.g., methyl) or cyano. In one variation, $R^{10}$ is independently $C_{1-6}$ alkyl (e.g., methyl).

In some embodiments, each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl $R^a$ are each optionally substituted with 1, 2, 3 or 4 substituents independently selected from $R^{11}$. In one variation, $R^a$ is independently hydrogen or $C_{1-6}$ alkyl. In one variation, $R^a$ is hydrogen. In one variation, $R^a$ is $C_{1-6}$ alkyl (e.g., methyl).

In some embodiments, each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$. In one variation, $R^b$ is independently hydrogen or $C_{1-6}$ alkyl. In one variation, $R^b$ is hydrogen. In one variation, $R^b$ is $C_{1-6}$ alkyl (e.g., methyl).

In some embodiments, each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$; or $R^c$ and $R^d$ are taken together with the nitrogen atom to which they are attached to form a 4- to 12-membered heterocyclyl optionally substituted with 1, 2, 3 or 4 substituents independently selected from $R^{11}$. In one variation, each $R^c$ and $R^d$ is independently hydrogen or $C_{1-6}$ alkyl. In one variation, one of $R^c$ and $R^d$ is hydrogen and the other one of $R^c$ and $R^d$ is $C_{1-6}$ alkyl. In one variation, each $R^c$ and $R^d$ is hydrogen. In one variation, each $R^c$ and $R^d$ is independently $C_{1-6}$ alkyl.

In some embodiments, each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$. In one variation, $R^e$ is independently $C_{1-6}$ alkyl (e.g., methyl).

In some embodiments, each $R^f$ is independently hydrogen or $C_{1-6}$ alkyl. In one variation, $R^f$ is hydrogen.

In some embodiments, each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)$R^{a1}$, —C(O)O$R^{b1}$, —C(O)N$R^{c1}R^{d1}$, —O$R^{b1}$, —OR(O)$R^{a1}$, —OC(O)N$R^{c1}R^{d1}$, —S$R^{b1}$, —S(O)$R^{e1}$, —S(O)$R^{e1}$, —S(O)$_2$N$R^{c1}_R{}^{d1}$, —N($R^{f1}$)C($R^{a1}$, —N($R^{f1}$)C(O)O$R^{b1}$, —N($R^{f1}$)C(O)N$R^{c1}R^{d1}$, —N($R^{f1}$)S(O)$_2R^{e1}$, or —N($R^{f1}$)S(O)$_2$N$R^{c1}R^{d1}$; wherein the $C_{1-6}$ alkyl, $C_{2-6}$ alkenyl, $C_{2-6}$ alkynyl, $C_{3-6}$ cycloalkyl, $C_{6-10}$ aryl, 5- to 14-membered heteroaryl and 3- to 14-membered heterocyclyl of $R^{11}$ are each optionally substituted with 1, 2, 3 or 4 substituents independently selected from $R^{12}$.

In one variation, each $R^{11}$ is independently oxo, $C_{1-6}$ alkyl optionally substituted with 1, 2, 3 or 4 substituents independently selected from $R^{12}$, or —O$R^{b1}$.

In one variation, each $R^{11}$ is independently oxo, $C_{1-6}$ alkyl, $C_{3-6}$ cycloalkyl, 3- to 8-membered heterocyclyl, halogen, cyano, or —O$R^{b1}$; wherein the $C_{1-6}$ alkyl, $C_{3-6}$ cycloalkyl, and 3- to 14-membered heterocyclyl of $R^{11}$ are each optionally substituted with 1, 2, 3 or 4 substituents independently selected from $R^{12}$.

In one variation, $R^{11}$ is $C_{1-6}$ alkyl optionally substituted with 1, 2, 3 or 4 substituents independently selected from $R^{12}$. In one variation, $R^{11}$ is 3- to 8-membered heterocyclyl optionally substituted with 1, 2, 3 or 4 substituents independently selected from $R^{12}$.

In one variation, $R^{11}$ is halogen, cyano, —N$R^{c1}R^{d1}$, —C(O)N$R^{c1}R^{d1}$, —O$R^{b1}$, —S(O)$_2R^{e1}$, $C_{1-6}$ haloalkyl, —($C_{1-6}$ alkylene)-OH, or —($C_{1-6}$ alkylene)-OH.

In one variation, $R^{11}$ is hydroxyl, cyano, halogen, —CHF$_2$, —CF$_3$, —NH$_2$, —NH($C_{1-6}$ alkyl), —N($C_{1-6}$ alkyl)$_2$, —O($C_{1-6}$ alkyl), —SO$_2$($C_{1-6}$ alkyl), —S(O)$_2$N$R^{c1}R^{d1}$, —C(O)N$R^{c1}R^{d1}$, or —N($R^{f1}$)C(O)$R^{a1}$.

In one variation, $R^{11}$ is halogen, cyano, —O($C_{1-6}$ alkyl), —O($C_{1-6}$alkylene)-NH$_2$, or —($C_{1-6}$ alkylene)-OH.

In some embodiments, each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$. In one variation, $R^{a1}$ is independently hydrogen or $C_{1-6}$ alkyl (e.g., methyl).

In some embodiments, each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$. In one variation, $R^{b1}$ is independently hydrogen or $C_{1-6}$ alkyl. In one variation, $R^{b1}$ is hydrogen. In one variation, $R^{b1}$ is $C_{1-6}$ alkyl (e.g., methyl).

In some embodiments, each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$; or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$. In one variation, each $R^{c1}$ and $R^{d1}$ is independently hydrogen or $C_{1-6}$ alkyl.

In some embodiments, each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$. In one variation, $R^{e1}$ is independently $C_{1-6}$ alkyl.

In some embodiments, each $R^{f1}$ is independently hydrogen or $C_{1-6}$ alkyl. In one variation, $R^{f1}$ is hydrogen.

In some embodiments, each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)N$R^{c2}R^{d2}$, —O$R^{b2}$, —OC(O)$R^{a2}$, —OC(O)N$R^{c2}R^{d2}$, —S(O)$_2R^{e2}$, —S(O)$_2$N$R^{c2}R^{d2}$, —N$R^{c2}R^{d2}$, —N($R^{f2}$)C(O)$R^{a2}$, —N($R^{f2}$)C(O)O$R^{b2}$, —N($R^{f2}$)C(O)N$R^{c2}R^{d2}$, —N($R^{f2}$)S(O)$_2R^{e2}$, or —N($R^{f2}$)S(O)$_2$N$R^{c2}R^{d2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$.

In one variation, each $R^{12}$ is independently oxo, halogen, cyano, —O$R^{b2}$, or $C_{1-6}$ alkyl optionally substituted with 1, 2, 3 or 4 substituents independently selected from $R^{13}$. In one variation, each $R^{12}$ is independently oxo, halogen, cyano, or hydroxyl.

In one variation, $R^{12}$ is $C_{1-6}$ alkyl optionally substituted with 1, 2, 3 or 4 substituents independently selected from $R^{13}$.

In one variation, $R^{12}$ is oxo, hydroxyl, $C_{1-6}$ alkyl, or —O($C_{1-6}$ alkyl).

In some embodiments, each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{a2}$ are each optionally substituted with 1, 2, 3 or 4 substituents independently selected from $R^{13}$. In one variation, $R^{a2}$ is independently hydrogen or $C_{1-6}$ alkyl.

In some embodiments, each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$. In one variation, $R^{b2}$ is hydrogen.

In some embodiments, each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$; or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$. In one variation, each $R^{c2}$ and $R^{d2}$ is independently hydrogen or $C_{1-6}$ alkyl.

In some embodiments, each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$. In one variation, $R^{e2}$ is independently $C_{1-6}$ alkyl.

In some embodiments, each $R^{f2}$ is independently hydrogen or $C_{1-6}$ alkyl. In one variation, $R^{f2}$ is hydrogen.

In some embodiments, each $R^{13}$ is independently oxo, halogen, hydroxyl, —O($C_{1-6}$ alkyl), cyano, $C_{1-6}$ alkyl or $C_{1-6}$ haloalkyl.

In one variation, each $R^{13}$ is independently halogen, hydroxyl, —O($C_{1-6}$ alkyl), cyano, or $C_{1-6}$ alkyl.

In one variation, $R^{13}$ is oxo, hydroxyl, $C_{1-6}$ alkyl, or —O($C_{1-6}$ alkyl).

Further provided is a compound of the formula (IA):

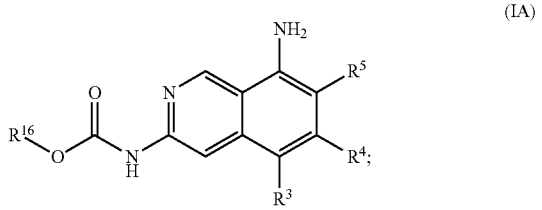

(IA)

or a salt (e.g., a pharmaceutically acceptable salt) thereof, wherein $R^3$, $R^4$, $R^5$ and $R^{16}$ are as detailed herein for the formula (I), or applicable variations thereof.

In some embodiments, provided is a compound of the formula (IA-1):

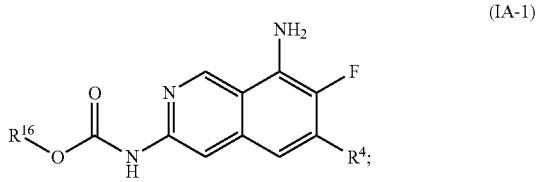

(IA-1)

or a salt (e.g., a pharmaceutically acceptable salt) thereof, wherein $R^4$ and $R^{16}$ are as detailed herein for the Formula (IA), or applicable variations thereof.

In some embodiments, provided is a compound of the formula (IA-2):

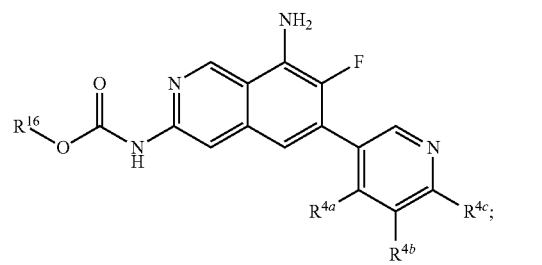

(IA-2)

or a salt (e.g., a pharmaceutically acceptable salt) thereof, wherein $R^{4a}$ is $C_{1-6}$ alkyl; $R^{4b}$ and $R^{4c}$ are independently hydrogen or $R^{10}$, or $R^{4b}$ and $R^{4c}$ are taken together with the atoms to which they are attached form a fused 5- to 10-membered heterocyclyl optionally substituted with 1, 2, 3 or 4 substituents independently selected from the group consisting of $C_{1-6}$ alkyl, hydroxyl, halogen and cyano, or a fused $C_{5-8}$ cycloalkyl optionally substituted with 1, 2, 3 or 4 substituents independently selected from the group consisting of $C_{1-6}$ alkyl, hydroxyl, halogen and cyano; and $R^{10}$ and $R^{16}$ are as detailed herein for the Formula (IA), or applicable variations thereof. In one variation, $R^{16}$ is 5- or 6-membered heterocyclyl having 1 or 2 heteroatoms independently selected from the group consisting of N, O and S, and optionally substituted with 1, 2, 3, 4 or 5 substituents independently selected from $R^{10}$; $R^{4a}$ is $C_{1-6}$ alkyl (e.g., methyl); and $R^{4b}$ and $R^{4c}$ are taken together with the atoms to which they are attached form a fused 6-membered heterocyclyl optionally substituted with 1, 2, 3 or 4 substituents independently selected from the group consisting of $C_{1-6}$ alkyl, hydroxyl, halogen and cyano.

Also provided is a compound of the formula (IB):

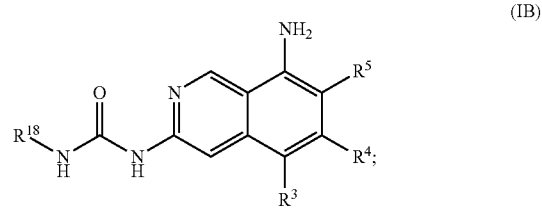

(IB)

or a salt (e.g., a pharmaceutically acceptable salt) thereof, wherein $R^3$, $R^4$, $R^5$, $R^{17}$ and $R^{18}$ are as detailed herein for the Formula (I), or applicable variations thereof.

In some embodiments, provided is a compound of the formula (IB-1):

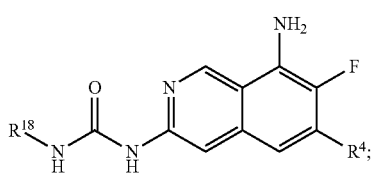
(IB-1)

or a salt (e.g., a pharmaceutically acceptable salt) thereof, wherein $R^3$, $R^4$, $R^5$ and $R^{18}$ are as detailed herein for the Formula (IB), or applicable variations thereof.

In some embodiments, provided is a compound of the formula (IB-2):

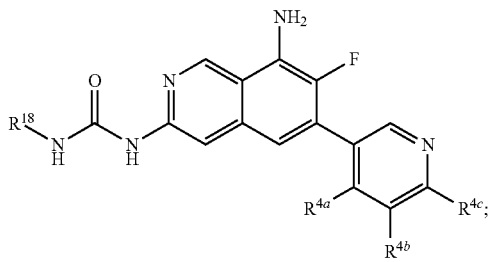
(IB-2)

or a salt (e.g., a pharmaceutically acceptable salt) thereof, wherein $R^{4a}$ is $C_{1-6}$ alkyl; $R^{4b}$ and $R^{4c}$ are independently hydrogen or $R^{10}$, or $R^{4b}$ and $R^{4c}$ are taken together with the atoms to which they are attached form a fused 5- to 10-membered heterocyclyl optionally substituted with 1, 2, 3 or 4 substituents independently selected from the group consisting of $C_{1-6}$ alkyl, hydroxyl, halogen and cyano, or a fused $C_{5-8}$ cycloalkyl optionally substituted with 1, 2, 3 or 4 substituents independently selected from the group consisting of $C_{1-6}$ alkyl, hydroxyl, halogen and cyano; and $R^{10}$ and $R^{18}$ are as detailed herein for the Formula (IB), or applicable variations thereof.

Also provided is a compound of the formula (IC):

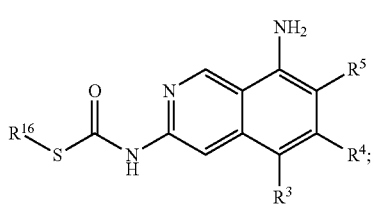
(IC)

or a salt (e.g., a pharmaceutically acceptable salt) thereof, wherein $R^3$, $R^4$, $R^5$ and $R^{16}$ are as detailed herein for the Formula (I), or applicable variations thereof.

In some embodiments, provided is a compound of the formula (IC-1):

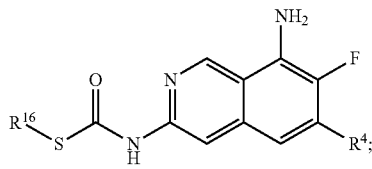
(IC-1)

or a salt (e.g., a pharmaceutically acceptable salt) thereof, wherein $R^4$ and $R^{16}$ are as detailed herein for the Formula (IC), or applicable variations thereof.

In some embodiments, provided is a compound of the formula (IC-2):

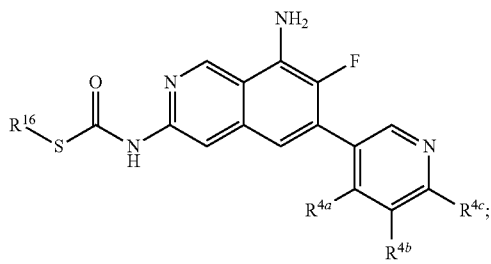
(IC-2)

or a salt (e.g., a pharmaceutically acceptable salt) thereof, wherein $R^{4a}$ is $C_{1-6}$ alkyl; $R^{4b}$ and $R^{4c}$ are independently hydrogen or $R^{10}$, or $R^{4b}$ and $R^{4c}$ are taken together with the atoms to which they are attached form a fused 5- to 10-membered heterocyclyl optionally substituted with 1, 2, 3 or 4 substituents independently selected from the group consisting of $C_{1-6}$ alkyl, hydroxyl, halogen and cyano, or a fused $C_{5-8}$ cycloalkyl optionally substituted with 1, 2, 3 or 4 substituents independently selected from the group consisting of $C_{1-6}$ alkyl, hydroxyl, halogen and cyano; and $R^{10}$ and $R^{16}$ are as detailed herein for the Formula (IC), or applicable variations thereof. In some embodiments, $R^{16}$ is a 4- to 10-membered heterocyclyl having 1 or 2 heteroatoms independently selected from the group consisting of N, O and S, and optionally substituted with 1, 2, 3, 4 or 5 substituents independently selected from $R^{10}$. In one variation, $R^{16}$ is 5- or 6-membered heterocyclyl (e.g., tetrahydro-2H-pyran-4-yl); $R^{4a}$ is $C_{1-6}$ alkyl (e.g., methyl); and $R^{4b}$ and $R^{4c}$ are taken together with the atoms to which they are attached form a fused 6-membered heterocyclyl.

Representative compounds are listed in Table 1. It is understood that individual enantiomers and diastereomers are included in the table below by Compound No. and Compound Name, and their corresponding structures can be readily determined therefrom. In some instances, the enantiomers or diastereomers are identified by their respective perperties, for example, retention times on a chiral HPLC or its biological activities, and the absolute stereo configurations of the chiral centers are arbitrarily assigned.

TABLE 1

| No. | Structure | Name |
|---|---|---|
| 401 | 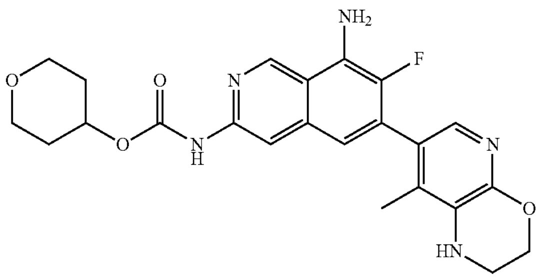 [SMILES: Cc1c(-c2cc3cc(NC(=O)OC4CCOCC4)ncc3c(N)c2F)cnc2c1NCCO2] | Tetrahydro-2H-pyran-4-yl(8-amino-7-fluoro-6-(8-methyl-2,3-dihydro-1H-pyrido[2,3-b][1,4]oxazin-7-yl)isoquinolin-3-yl)carbamate |
| 402 | 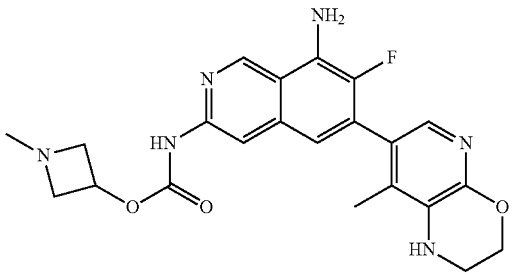 [SMILES: Cc1c(-c2cc3cc(NC(=O)OC4CN(C)C4)ncc3c(N)c2F)cnc2c1NCCO2] | 1-Methylazetidin-3-yl(8-amino-7-fluoro-6-(8-methyl-2,3-dihydro-1H-pyrido[2,3-b][1,4]oxazin-7-yl)isoquinolin-3-yl)carbamate |
| 403 | 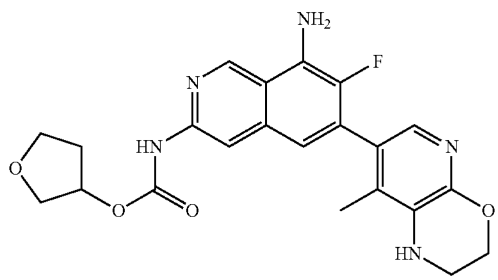 [SMILES: Cc1c(-c2cc3cc(NC(=O)OC4CCOC4)ncc3c(N)c2F)cnc2c1NCCO2] | Tetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 403a 403b | | (R)-Tetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (S)-Tetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 404 | 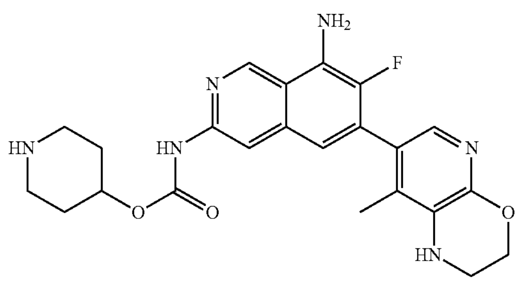 [SMILES: Cc1c(-c2cc3cc(NC(=O)OC4CCNCC4)ncc3c(N)c2F)cnc2c1NCCO2] | Piperidin-4-yl(8-amino-7-fluoro-6-(8-methyl-2,3-dihydro-1H-pyrido[2,3-b][1,4]oxazin-7-yl)isoquinolin-3-yl)carbamate |
| 405 | 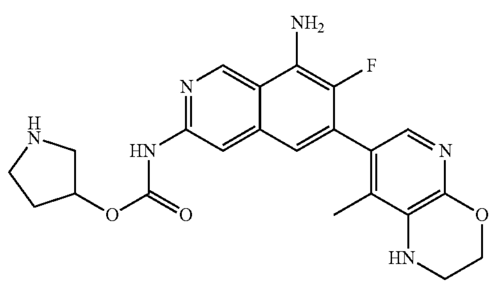 [SMILES: Cc1c(-c2cc3cc(NC(=O)OC4CCNC4)ncc3c(N)c2F)cnc2c1NCCO2] | Pyrrolidin-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 405a 405b | | (S)-Pyrrolidin-3-yl(8-amino-7-fluoro-6-(8-methyl-2,3-dihydro-1H-pyrido[2,3-b][1,4]oxazin-7-yl)isoquinolin-3-yl)carbamate; (R)-Pyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 406 | 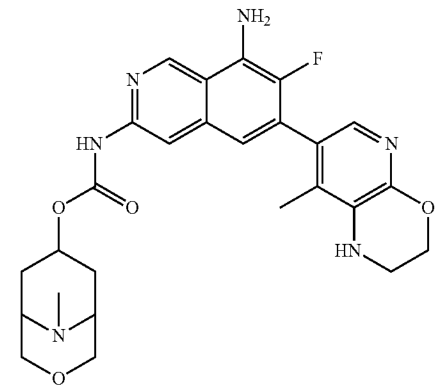 [SMILES: Cc1c(-c2cc3cc(NC(=O)OC4CC5COCC(C4)N5C)ncc3c(N)c2F)cnc2c1NCCO2] | 9-Methyl-3-oxa-9-azabicyclo[3.3.1]nonan-7-yl(8-amino-7-fluoro-6-(8-methyl-2,3-dihydro-1H-pyrido[2,3-b][1,4]oxazin-7-yl)isoquinolin-3-yl)carbamate |
| 407 | 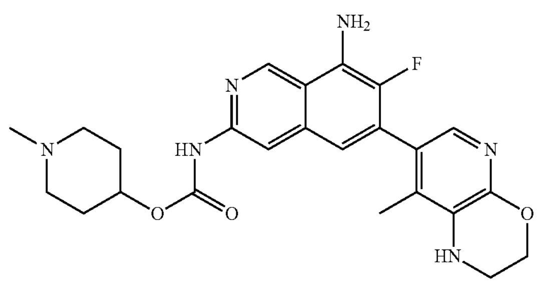 [SMILES: Cc1c(-c2cc3cc(NC(=O)OC4CCN(C)CC4)ncc3c(N)c2F)cnc2c1NCCO2] | 1-Methylpiperidin-4-yl(8-amino-7-fluoro-6-(8-methyl-2,3-dihydro-1H-pyrido[2,3-b][1,4]oxazin-7-yl)isoquinolin-3-yl)carbamate |
| 408 | 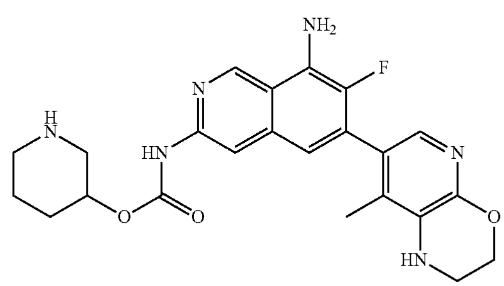 | Piperidin-3-yl(8-amino-7-fluoro-6-(8-methyl-2,3-dihydro-1H-pyrido[2,3-b][1,4]oxazin-7-yl)isoquinolin-3-yl)carbamate |
| 408a 408b | | (R)-Piperidin-3-yl(8-amino-7-fluoro-6-(8-methyl-2,3-dihydro-1H-pyrido[2,3-b][1,4]oxazin-7-yl)isoquinolin-3-yl)carbamate; (S)-Piperidin-3-yl(8-amino-7-fluoro-6-(8-methyl-2,3-dihydro-1H-pyrido[2,3-b][1,4]oxazin-7-yl)isoquinolin-3-yl)carbamate |
| 409 | 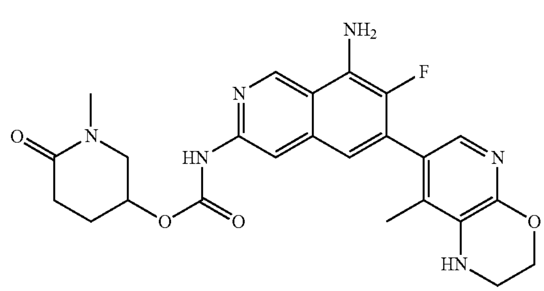 [SMILES: Cc1c(-c2cc3cc(NC(=O)OC4CCC(=O)N(C)C4)ncc3c(N)c2F)cnc2c1NCCO2] | 1-Methyl-6-oxopiperidin-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 409a 409b | | (R)-1-Methyl-6-oxopiperidin-3-yl(8-amino-7-fluoro-6-(8-methyl-2,3-dihydro-1H-pyrido[2,3-b][1,4]oxazin-7-yl)isoquinolin-3-yl)carbamate; (S)-1-Methyl-6-oxopiperidin-3-yl(8-amino-7-fluoro-6-(8-methyl-2,3-dihydro-1H-pyrido[2,3-b][1,4]oxazin-7-yl)isoquinolin-3-yl)carbamate |
| 410 | | 1-Methyl-5-oxopyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 410a 410b | | (R)-1-Methyl-5-oxopyrrolidin-3-yl(8-amino-7-fluoro-6-(8-methyl-2,3-dihydro-1H-pyrido[2,3-b][1,4]oxazin-7-yl)isoquinolin-3-yl)carbamate; (S)-1-Methyl-5-oxopyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 411 | | 1-Methylpyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 411a 411b | | (R)-1-Methylpyrrolidin-3-yl(8-amino-7-fluoro-6-(8-methyl-2,3-dihydro-1H-pyrido[2,3-b][1,4]oxazin-7-yl)isoquinolin-3-yl)carbamate; (S)-1-Methylpyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 412 | | Tetrahydro-2H-pyran-4-yl(8-amino-7-fluoro-6-(4-hydroxy-5-methyl-3,4-dihydro-2H-pyrano[2,3-b]pyridin-6-yl)isoquinolin-3-yl)carbamate |
| 412a 412b | | Tetrahydro-2H-pyran-4-yl(R)-(8-amino-7-fluoro-6-(4-hydroxy-5-methyl-3,4-dihydro-2H-pyrano[2,3-b]pyridin-6-yl)isoquinolin-3-yl)carbamate; Tetrahydro-2H-pyran-4-yl(S)-(8-amino-7-fluoro-6-(4-hydroxy-5-methyl-3,4-dihydro-2H-pyrano[2,3-b]pyridin-6-yl)isoquinolin-3-yl)carbamate |

TABLE 1-continued

| No. | Structure | Name |
|---|---|---|
| 413 | 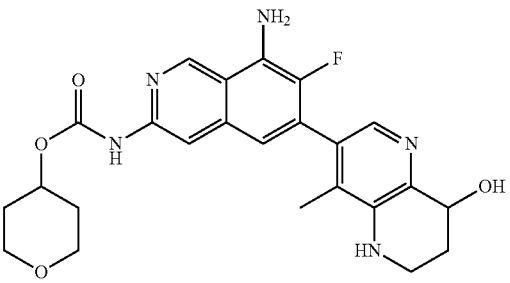 [SMILES: Cc1c(-c2cc3cc(NC(=O)OC4CCOCC4)ncc3c(N)c2F)cnc2c1NCCC2O] | Tetrahydro-2H-pyran-4-yl(8-amino-7-fluoro-6-(8-hydroxy-4-methyl-5,6,7,8-tetrahydro-1,5-naphthyridin-3-yl)isoquinolin-3-yl)carbamate |
| 414 | 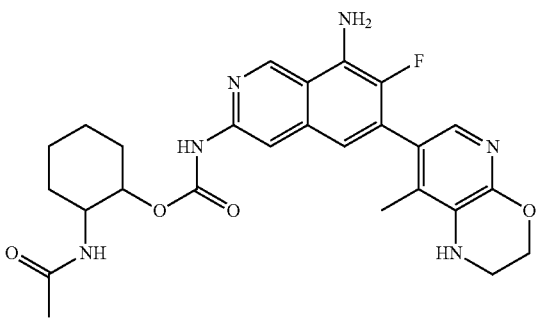 [SMILES: CC(=O)NC1CCCCC1OC(=O)Nc1cc2cc(-c3cnc4c(c3C)NCCO4)c(F)c(N)c2cn1] | (trans)-2-Acetamidocyclohexyl(8-amino-7-fluoro-6-(8-methyl-2,3-dihydro-1H-pyrido[2,3-b][1,4]oxazin-7-yl)isoquinolin-3-yl)carbamate |
| 414a 414b | | (1S,2S)-2-Acetamidocyclohexyl(8-amino-7-fluoro-6-(8-methyl-2,3-dihydro-1H-pyrido[2,3-b][1,4]oxazin-7-yl)isoquinolin-3-yl)carbamate; (1R,2R)-2-Acetamidocyclohexyl(8-amino-7-fluoro-6-(8-methyl-2,3-dihydro-1H-pyrido[2,3-b][1,4]oxazin-7-yl)isoquinolin-3-yl)carbamate |
| 415 | 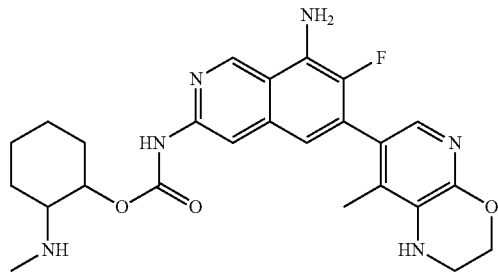 [SMILES: CNC1CCCCC1OC(=O)Nc1cc2cc(-c3cnc4c(c3C)NCCO4)c(F)c(N)c2cn1] | (trans)-2-(Methylamino)cyclohexyl(8-amino-7-fluoro-6-(8-methyl-2,3-dihydro-1H-pyrido[2,3-b][1,4]oxazin-7-yl)isoquinolin-3-yl)carbamate |
| 415a 415b | | (1S,2S)-2-(Methylamino)cyclohexyl(8-amino-7-fluoro-6-(8-methyl-2,3-dihydro-1H-pyrido[2,3-b][1,4]oxazin-7-yl)isoquinolin-3-yl)carbamate; (1R,2R)-2-(Methylamino)cyclohexyl(8-amino-7-fluoro-6-(8-methyl-2,3-dihydro-1H-pyrido[2,3-b][1,4]oxazin-7-yl)isoquinolin-3-yl)carbamate |
| 416 | 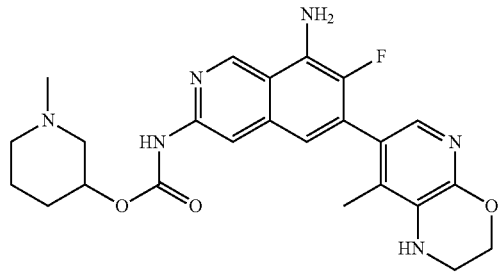 [SMILES: Cc1c(-c2cc3cc(NC(=O)OC4CCCN(C)C4)ncc3c(N)c2F)cnc2c1NCCO2] | 1-Methylpiperidin-3-yl(8-amino-7-fluoro-6-(8-methyl-2,3-dihydro-1H-pyrido[2,3-b][1,4]oxazin-7-yl)isoquinolin-3-yl)carbamate |
| 416a 416b | | (R)-1-Methylpiperidin-3-yl(8-amino-7-fluoro-6-(8-methyl-2,3-dihydro-1H-pyrido[2,3-b][1,4]oxazin-7- |

TABLE 1-continued

| No. | Structure | Name |
|---|---|---|
| | | yl)isoquinolin-3-yl)carbamate; (S)-1-Methylpiperidin-3-yl(8-amino-7-fluoro-6-(8-methyl-2,3-dihydro-1H-pyrido[2,3-b][1,4]oxazin-7-yl)isoquinolin-3-yl)carbamate |
| 417 | 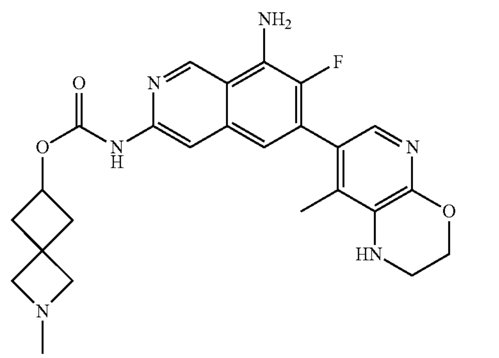 [SMILES: Cc1c(-c2cc3cc(NC(=O)OC4CC5(C4)CN(C)C5)ncc3c(N)c2F)cnc2c1NCCO2] | 2-Methyl-2-azaspiro[3.3]heptan-6-yl(8-amino-7-fluoro-6-(8-methyl-2,3-dihydro-1H-pyrido[2,3-b][1,4]oxazin-7-yl)isoquinolin-3-yl)carbamate |
| 418 | 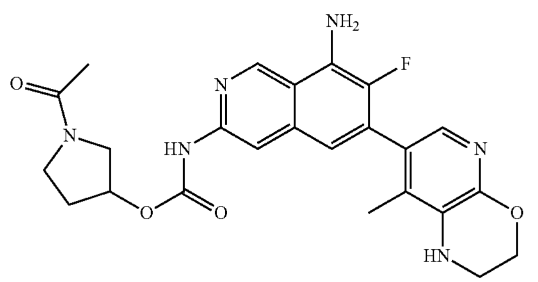 [SMILES: CC(=O)N1CCC(OC(=O)Nc2cc3cc(-c4cnc5c(c4C)NCCO5)c(F)c(N)c3cn2)C1] | 1-Acetylpyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 418a 418b | | (R)-1-Acetylpyrrolidin-3-yl(8-amino-7-fluoro-6-(8-methyl-2,3-dihydro-1H-pyrido[2,3-b][1,4]oxazin-7-yl)isoquinolin-3-yl)carbamate; (S)-1-Acetylpyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 419 | 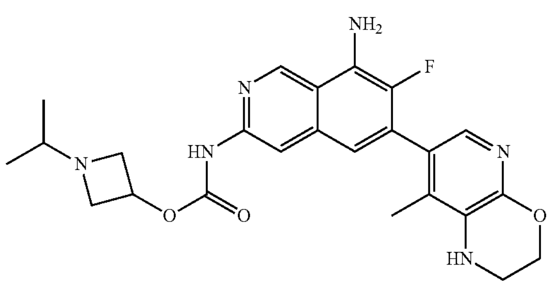 [SMILES: Cc1c(-c2cc3cc(NC(=O)OC4CN(C(C)C)C4)ncc3c(N)c2F)cnc2c1NCCO2] | 1-Isopropylazetidin-3-yl(8-amino-7-fluoro-6-(8-methyl-2,3-dihydro-1H-pyrido[2,3-b][1,4]oxazin-7-yl)isoquinolin-3-yl)carbamate |
| 420 | 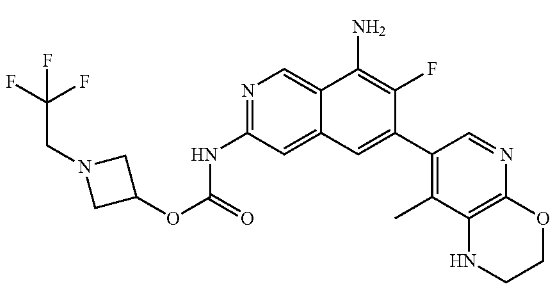 [SMILES: Cc1c(-c2cc3cc(NC(=O)OC4CN(CC(F)(F)F)C4)ncc3c(N)c2F)cnc2c1NCCO2] | 1-(2,2,2-Trifluoroethyl)azetidin-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 421 | 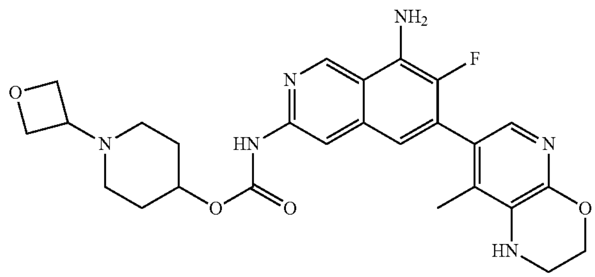 [SMILES: Cc1c(-c2cc3cc(NC(=O)OC4CCN(C5COC5)CC4)ncc3c(N)c2F)cnc2c1NCCO2] | 1-(Oxetan-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate |
| 422 | 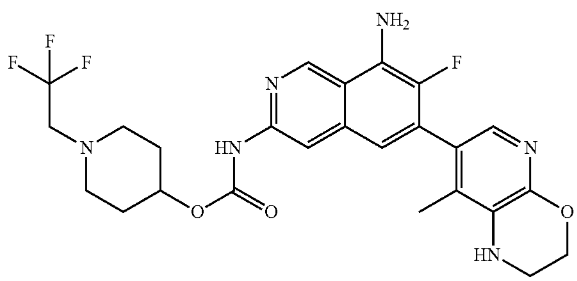 [SMILES: Cc1c(-c2cc3cc(NC(=O)OC4CCN(CC(F)(F)F)CC4)ncc3c(N)c2F)cnc2c1NCCO2] | 1-(2,2,2-Trifluoroethyl)piperidin-4-yl(8-amino-7-fluoro-6-(8-methyl-2,3-dihydro-1H-pyrido[2,3-b][1,4]oxazin-7-yl)isoquinolin-3-yl)carbamate |
| 423 | 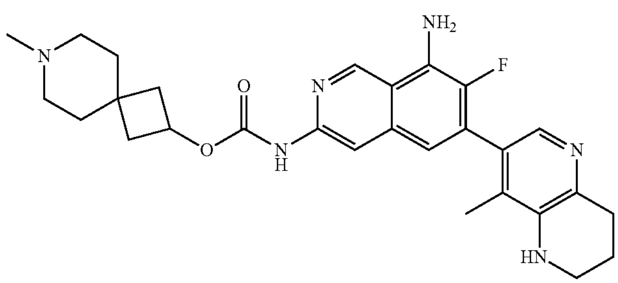 [SMILES: Cc1c(-c2cc3cc(NC(=O)OC4CC5(CCN(C)CC5)C4)ncc3c(N)c2F)cnc2c1NCCC2] | 7-Methyl-7-azaspiro[3.5]nonan-2-yl(8-amino-7-fluoro-6-(4-methyl-5,6,7,8-tetrahydro-1,5-naphthyridin-3-yl)isoquinolin-3-yl)carbamate |
| 424 | 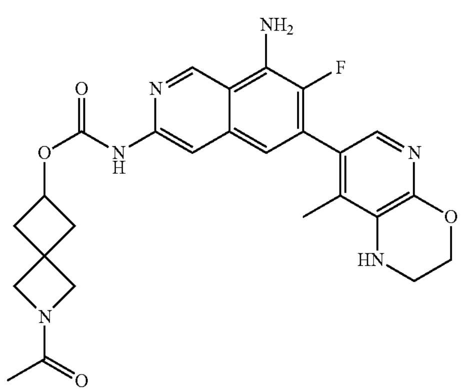 [SMILES: CC(=O)N1CC2(CC(OC(=O)Nc3cc4cc(-c5cnc6c(c5C)NCCO6)c(F)c(N)c4cn3)C2)C1] | 2-Acetyl-2-azaspiro[3.3]heptan-6-yl(8-amino-7-fluoro-6-(8-methyl-2,3-dihydro-1H-pyrido[2,3-b][1,4]oxazin-7-yl)isoquinolin-3-yl)carbamate |
| 425 | 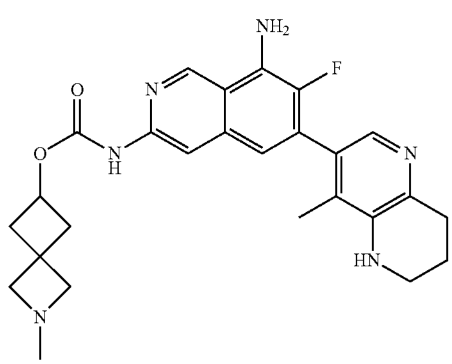 [SMILES: Cc1c(-c2cc3cc(NC(=O)OC4CC5(C4)CN(C)C5)ncc3c(N)c2F)cnc2c1NCCC2] | 2-Methyl-2-azaspiro[3.3]heptan-6-yl(8-amino-7-fluoro-6-(4-methyl-5,6,7,8-tetrahydro-1,5-naphthyridin-3-yl)isoquinolin-3-yl)carbamate |

TABLE 1-continued

| No. | Structure | Name |
|---|---|---|
| 426 | 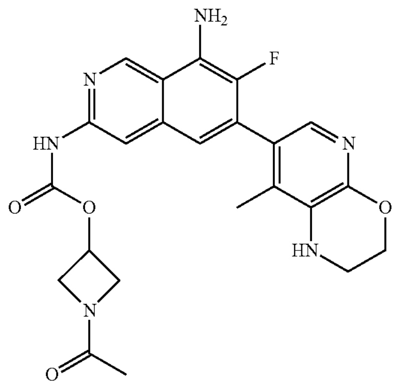 [SMILES: CC(=O)N1CC(OC(=O)Nc2cc3cc(-c4cnc5c(c4C)NCCO5)c(F)c(N)c3cn2)C1] | 1-Acetylazetidin-3-yl(8-amino-7-fluoro-6-(8-methyl-2,3-dihydro-1H-pyrido[2,3-b][1,4]oxazin-7-yl)isoquinolin-3-yl)carbamate |
| 427 | 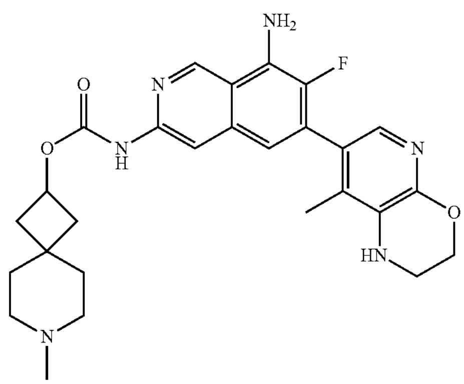 [SMILES: Cc1c(-c2cc3cc(NC(=O)OC4CC5(CCN(C)CC5)C4)ncc3c(N)c2F)cnc2c1NCCO2] | 7-Methyl-7-azaspiro[3.5]nonan-2-yl(8-amino-7-fluoro-6-(8-methyl-2,3-dihydro-1H-pyrido[2,3-b][1,4]oxazin-7-yl)isoquinolin-3-yl)carbamate |
| 428 | 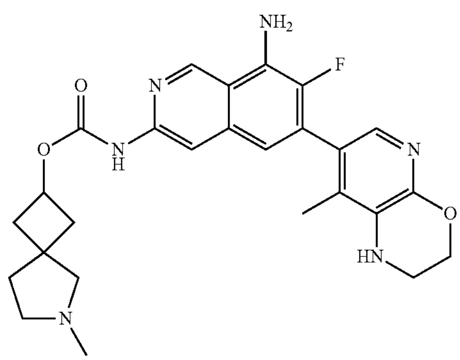 [SMILES: Cc1c(-c2cc3cc(NC(=O)OC4CC5(CCN(C)C5)C4)ncc3c(N)c2F)cnc2c1NCCO2] | 6-Methyl-6-azaspiro[3.4]octan-2-yl(8-amino-7-fluoro-6-(8-methyl-2,3-dihydro-1H-pyrido[2,3-b][1,4]oxazin-7-yl)isoquinolin-3-yl)carbamate |
| 429 | 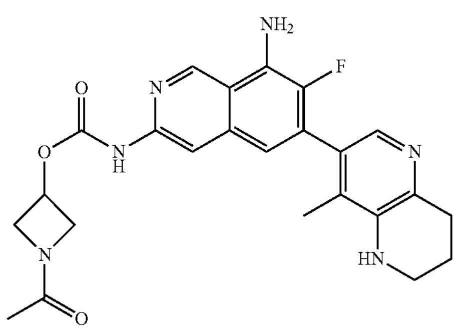 [SMILES: CC(=O)N1CC(OC(=O)Nc2cc3cc(-c4cnc5c(c4C)NCCC5)c(F)c(N)c3cn2)C1] | 1-Acetylazetidin-3-yl(8-amino-7-fluoro-6-(4-methyl-5,6,7,8-tetrahydro-1,5-naphthyridin-3-yl)isoquinolin-3-yl)carbamate |

TABLE 1-continued

| No. | Structure | Name |
|---|---|---|
| 430 | 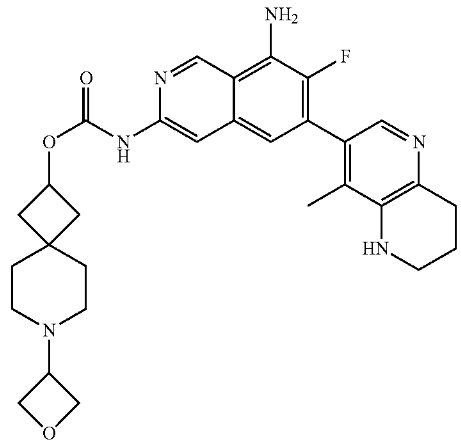 [SMILES: Cc1c(-c2cc3cc(NC(=O)OC4CC5(CCN(C6COC6)CC5)C4)ncc3c(N)c2F)cnc2c1NCCC2] | 7-(Oxetan-3-yl)-7-azaspiro[3.5]nonan-2-yl(8-amino-7-fluoro-6-(4-methyl-5,6,7,8-tetrahydro-1,5-naphthyridin-3-yl)isoquinolin-3-yl)carbamate |
| 431 | 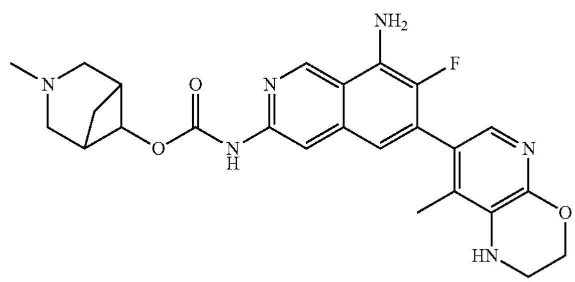 [SMILES: Cc1c(-c2cc3cc(NC(=O)OC4C5CC4CN(C)C5)ncc3c(N)c2F)cnc2c1NCCO2] | 3-Methyl-3-azabicyclo[3.1.1]heptan-6-yl (8-amino-7-fluoro-6-(8-methyl-2,3-dihydro-1H-pyrido[2,3-b][1,4]oxazin-7-yl)isoquinolin-3-yl)carbamate |
| 432 | 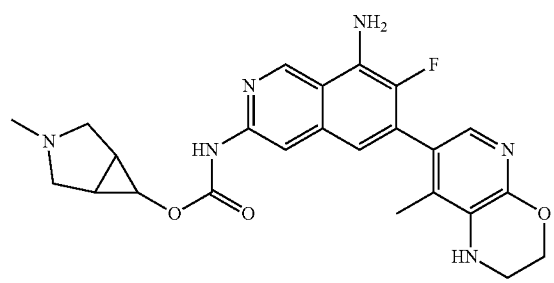 [SMILES: Cc1c(-c2cc3cc(NC(=O)OC4C5CN(C)CC54)ncc3c(N)c2F)cnc2c1NCCO2] | 3-Methyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate |
| 432a 432b | | (1R,5S,6r)-3-Methyl-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate; (1R,5S,6s)-3-Methyl-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate |
| 433 | 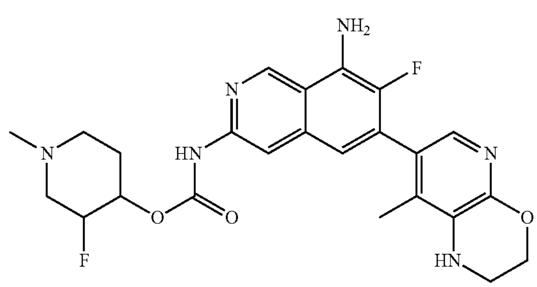 [SMILES: Cc1c(-c2cc3cc(NC(=O)OC4CCN(C)CC4F)ncc3c(N)c2F)cnc2c1NCCO2] | (cis)-3-Fluoro-1-methylpiperidin-4-yl(8-amino-7-fluoro-6-(8-methyl-2,3-dihydro-1H-pyrido[2,3-b][1,4]oxazin-7-yl)isoquinolin-3-yl)carbamate |
| 433a 433b | | (3R,4S)-3-Fluoro-1-methylpiperidin-4-yl (8-amino-7-fluoro-6-(8-methyl-2,3-dihydro-1H-pyrido[2,3-b][1,4]oxazin-7-yl)isoquinolin-3-yl)carbamate; |

TABLE 1-continued

| No. | Structure | Name |
|---|---|---|
| | | (3S,4R)-3-Fluoro-1-methylpiperidin-4-yl (8-amino-7-fluoro-6-(8-methyl-2,3-dihydro-1H-pyrido[2,3-b][1,4]oxazin-7-yl)isoquinolin-3-yl)carbamate |
| 434 | 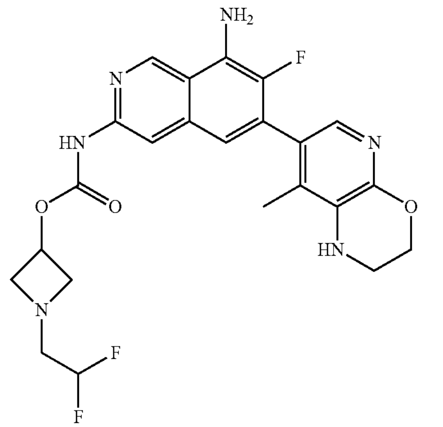 [SMILES: Cc1c(-c2cc3cc(NC(=O)OC4CN(CC(F)F)C4)ncc3c(N)c2F)cnc2c1NCCO2] | 1-(2,2-Difluoroethyl)azetidin-3-yl(8-amino-7-fluoro-6-(8-methyl-2,3-dihydro-1H-pyrido[2,3-b][1,4]oxazin-7-yl)isoquinolin-3-yl)carbamate |
| 435 | 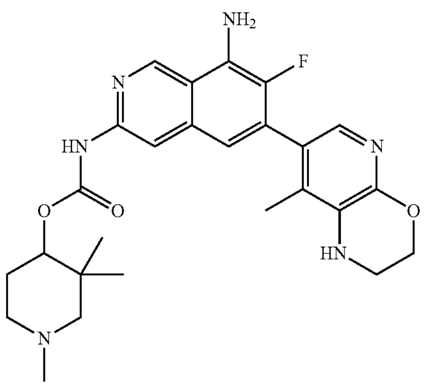 [SMILES: Cc1c(-c2cc3cc(NC(=O)OC4CCN(C)CC4(C)C)ncc3c(N)c2F)cnc2c1NCCO2] | 1,3,3-Trimethylpiperidin-4-yl(8-amino-7-fluoro-6-(8-methyl-2,3-dihydro-1H-pyrido[2,3-b][1,4]oxazin-7-yl)isoquinolin-3-yl)carbamate |
| 436 | 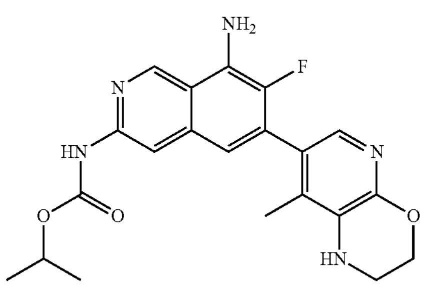 | Isopropyl(8-amino-7-fluoro-6-(8-methyl-2,3-dihydro-1H-pyrido[2,3-b][1,4]oxazin-7-yl)isoquinolin-3-yl)carbamate |
| 437 | 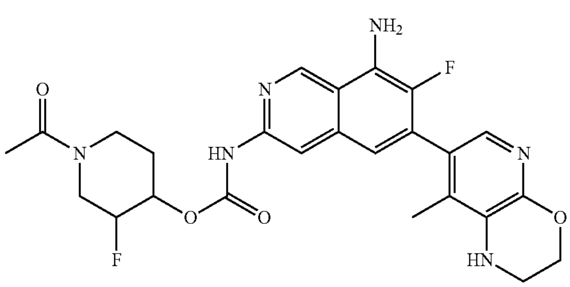 [SMILES: CC(=O)N1CCC(OC(=O)Nc2cc3cc(-c4cnc5c(c4C)NCCO5)c(F)c(N)c3cn2)C(F)C1] | (cis)-1-Acetyl-3-fluoropiperidin-4-yl(8-amino-7-fluoro-6-(8-methyl-2,3-dihydro-1H-pyrido[2,3-b][1,4]oxazin-7-yl)isoquinolin-3-yl)carbamate |
| 437a 437b | | (3S,4R)-1-Acetyl-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate; (3R,4S)-1-Acetyl-3-fluoropiperidin-4-yl (8-amino-7-fluoro-6-(8-methyl-2,3- |

TABLE 1-continued

| No. | Structure | Name |
|---|---|---|
| | | dihydro-1H-pyrido[2,3-b][1,4]oxazin-7-yl)isoquinolin-3-yl)carbamate |
| 438 | 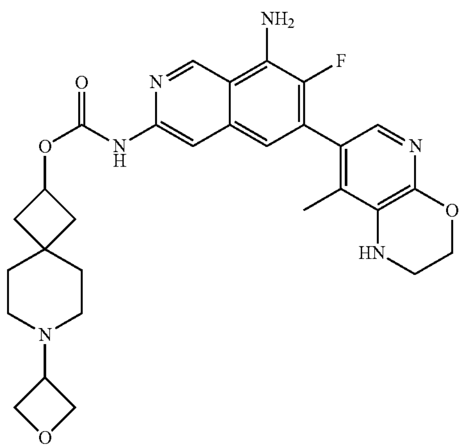 [SMILES: Cc1c(-c2cc3cc(NC(=O)OC4CC5(CCN(C6COC6)CC5)C4)ncc3c(N)c2F)cnc2c1NCCO2] | 7-(Oxetan-3-yl)-7-azaspiro[3.5]nonan-2-yl(8-amino-7-fluoro-6-(8-methyl-2,3-dihydro-1H-pyrido[2,3-b][1,4]oxazin-7-yl)isoquinolin-3-yl)carbamate |
| 439 | 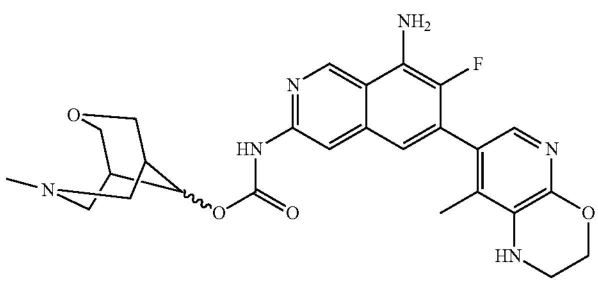 [SMILES: Cc1c(-c2cc3cc(NC(=O)OC4C5COCC4CN(C)C5)ncc3c(N)c2F)cnc2c1NCCO2] | 7-Methyl-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl)carbamate |
| 439a<br>439b | | (1R,5S,9s)-7-Methyl-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl)carbamate<br>(1R,5S,9r)-7-Methyl-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl)carbamate |
| 440 | 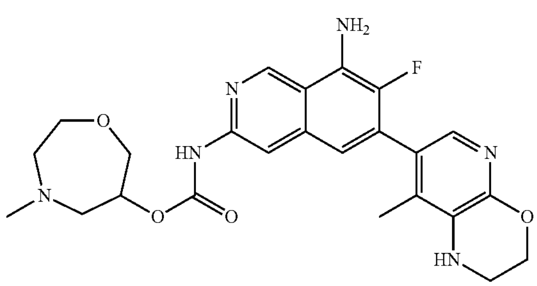 [SMILES: Cc1c(-c2cc3cc(NC(=O)OC4COCCN(C)C4)ncc3c(N)c2F)cnc2c1NCCO2] | 4-Methyl-1,4-oxazepan-6-yl(8-amino-7-fluoro-6-(8-methyl-2,3-dihydro-1H-pyrido[2,3-b][1,4]oxazin-7-yl)isoquinolin-3-yl)carbamate |
| 440a<br>440b | | (R)-4-Methyl-1,4-oxazepan-6-yl(8-amino-7-fluoro-6-(8-methyl-2,3-dihydro-1H-pyrido[2,3-b][1,4]oxazin-7-yl)isoquinolin-3-yl)carbamate;<br>(S)-4-Methyl-1,4-oxazepan-6-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 441 | | 4-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 441a 441b | | (trans)-4-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate (3R,4S)-4-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (3S,4R)-4-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 441c 441d | | (cis)-4-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate (3R,4R)-4-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (3S,4S)-4-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 442 | | 1,4-Dimethylpyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 442a 442b | | (cis)-1,4-Dimethylpyrrolidin-3-yl(8-amino-7-fluoro-6-(8-methyl-2,3-dihydro-1H-pyrido[2,3-b][1,4]oxazin-7-yl)isoquinolin-3-yl)carbamate; [(3S,4S)-1,4-Dimethylpyrrolidin-3-yl]N-[8-amino-7-fluoro-6-(8-methyl-2,3-dihydro-1H-pyrido[2,3-b][1,4]oxazin-7-yl)-3-isoquinolyl]carbamate; [(3R,4R)-1,4-Dimethylpyrrolidin-3-yl]N-[8-amino-7-fluoro-6-(8-methyl-2,3-dihydro-1H-pyrido[2,3-b][1,4]oxazin-7-yl)-3-isoquinolyl]carbamate |
| 442c 442d | | (trans)-1,4-Dimethylpyrrolidin-3-yl(8-amino-7-fluoro-6-(8-methyl-2,3-dihydro-1H-pyrido[2,3-b][1,4]oxazin-7-yl)isoquinolin-3-yl)carbamate; (3S,4R)-1,4-Dimethylpyrrolidin-3-yl(8-amino-7-fluoro-6-(8-methyl-2,3-dihydro-1H-pyrido[2,3-b][1,4]oxazin-7-yl)isoquinolin-3-yl)carbamate; (3R,4S)-1,4-dimethylpyrrolidin-3-yl(8-amino-7-fluoro-6-(8-methyl-2,3-dihydro- |

| No. | Structure | Name |
|---|---|---|
| | | 1H-pyrido[2,3-b][1,4]oxazin-7-yl)isoquinolin-3-yl)carbamate |
| 443 | 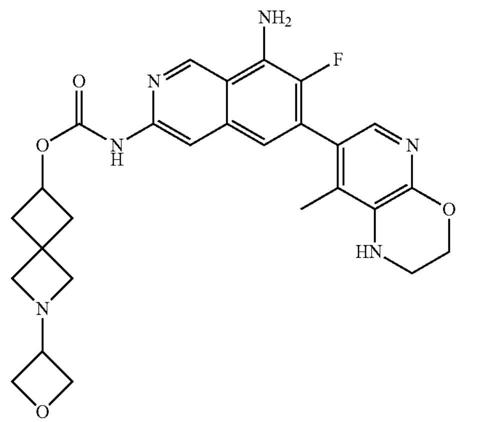 [SMILES: Cc1c(-c2cc3cc(NC(=O)OC4CC5(C4)CN(C4COC4)C5)ncc3c(N)c2F)cnc2c1NCCO2] | 2-(Oxetan-3-yl)-2-azaspiro[3.3]heptan-6-yl(8-amino-7-fluoro-6-(8-methyl-2,3-dihydro-1H-pyrido[2,3-b][1,4]oxazin-7-yl)isoquinolin-3-yl)carbamate |
| 444 | 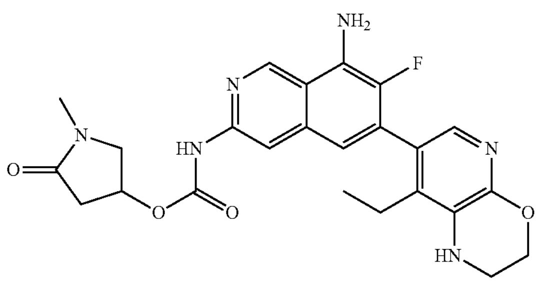 [SMILES: CCc1c(-c2cc3cc(NC(=O)OC4CC(=O)N(C)C4)ncc3c(N)c2F)cnc2c1NCCO2] | 1-Methyl-5-oxopyrrolidin-3-yl(8-amino-6-(8-ethyl-2,3-dihydro-1H-pyrido[2,3-b][1,4]oxazin-7-yl)-7-fluoroisoquinolin-3-yl)carbamate |
| 444a 444b | | (S)-1-Methyl-5-oxopyrrolidin-3-yl(8-amino-6-(8-ethyl-2,3-dihydro-1H-pyrido[2,3-b][1,4]oxazin-7-yl)-7-fluoroisoquinolin-3-yl)carbamate; (R)-1-Methyl-5-oxopyrrolidin-3-yl(8-amino-6-(8-ethyl-2,3-dihydro-1H-pyrido[2,3-b][1,4]oxazin-7-yl)-7-fluoroisoquinolin-3-yl)carbamate |
| 445 | 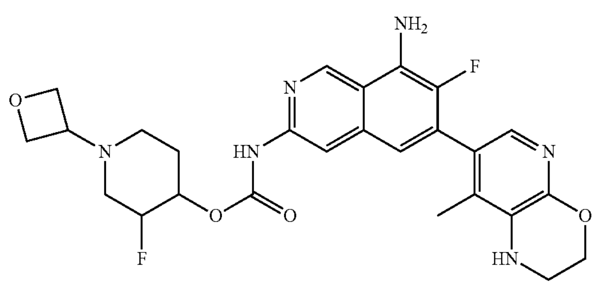 [SMILES: Cc1c(-c2cc3cc(NC(=O)OC4CCN(C5COC5)CC4F)ncc3c(N)c2F)cnc2c1NCCO2] | 3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate |
| 445a 445b | | 4-yl(8-amino-7-fluoro-6-(8-methyl-2,3-dihydro-1H-pyrido[2,3-b][1,4]oxazin-7-yl)isoquinolin-3-yl)carbamate trans-3-Fluoro-1-(oxetan-3-yl)piperidin-(3S,4S)-3-Fluoro-1-(oxetan-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate; (3R,4R)-3-Fluoro-1-(oxetan-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate |
| 445c 445d | | cis-3-Fluoro-1-(oxetan-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| | | (3S,4R)-3-Fluoro-1-(oxetan-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate; (3R,4S)-3-Fluoro-1-(oxetan-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate |
| 446 | 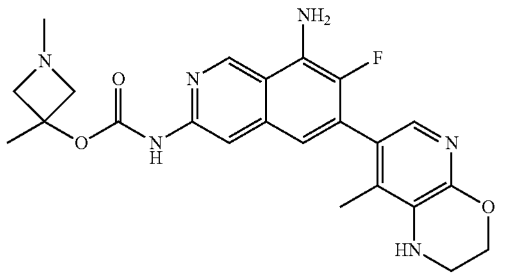 [SMILES: Cc1c(-c2cc3cc(NC(=O)OC4(C)CN(C)C4)ncc3c(N)c2F)cnc2c1NCCO2] | 1,3-Dimethylazetidin-3-yl(8-amino-7-fluoro-6-(8-methyl-2,3-dihydro-1H-pyrido[2,3-b][1,4]oxazin-7-yl)isoquinolin-3-yl)carbamate |
| 447 | 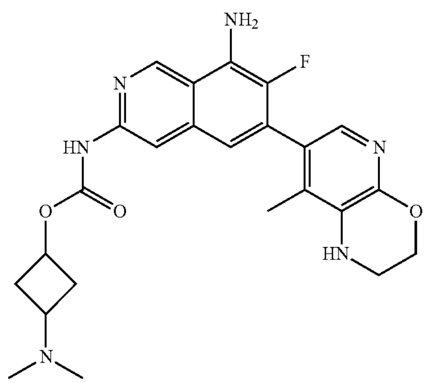 | 3-(Dimethylamino)cyclobutyl(8-amino-7-fluoro-6-(8-methyl-2,3 dihydro-1H-pyrido[2,3-b][1,4]oxazin-7-yl)isoquinolin-3-yl)carbamate |
| 447a | | (1r,3r)-3-(Dimethylamino)cyclobutyl(8-amino-7-fluoro-6-(8-methyl-2,3-dihydro-1H-pyrido[2,3-b][1,4]oxazin-7-yl)isoquinolin-3-yl)carbamate |
| 447b | | (1s,3s)-3-(Dimethylamino)cyclobutyl(8-amino-7-fluoro-6-(8-methyl-2,3-dihydro-1H-pyrido[2,3-b][1,4]oxazin-7-yl)isoquinolin-3-yl)carbamate |
| 448 | 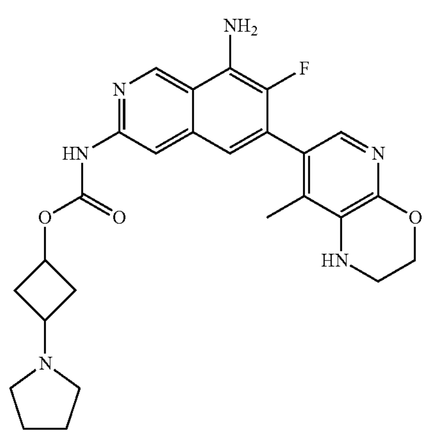 [SMILES: Cc1c(-c2cc3cc(NC(=O)OC4CC(N5CCCC5)C4)ncc3c(N)c2F)cnc2c1NCCO2] | 3-(Pyrrolidin-1-yl)cyclobutyl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 449 | 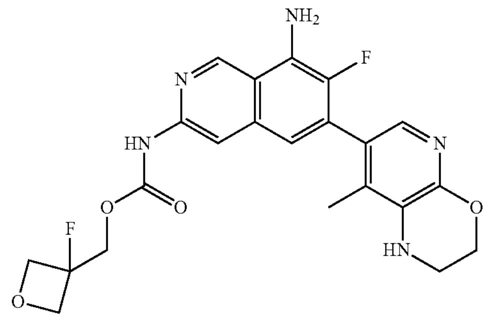 [SMILES: Cc1c(-c2cc3cc(NC(=O)OCC4(F)COC4)ncc3c(N)c2F)cnc2c1NCCO2] | (3-Fluorooxetan-3-yl)methyl(8-amino-7-fluoro-6-(8-methyl-2,3-dihydro-1H-pyrido[2,3-b][1,4]oxazin-7-yl)isoquinolin-3-yl)carbamate |
| 450 | 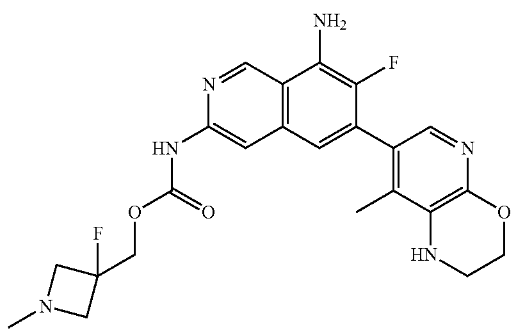 [SMILES: Cc1c(-c2cc3cc(NC(=O)OCC4(F)CN(C)C4)ncc3c(N)c2F)cnc2c1NCCO2] | (3-Fluoro-1-methylazetidin-3-yl)methyl (8-amino-7-fluoro-6-(8-methyl-2,3-dihydro-1H-pyrido[2,3-b][1,4]oxazin-7-yl)isoquinolin-3-yl)carbamate |
| 451 | 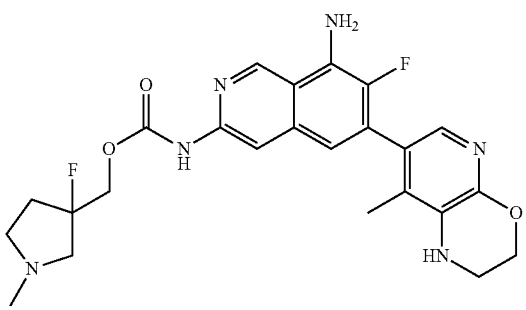 [SMILES: Cc1c(-c2cc3cc(NC(=O)OCC4(F)CCN(C)C4)ncc3c(N)c2F)cnc2c1NCCO2] | (3-Fluoro-1-methylpyrrolidin-3-yl)methyl (8-amino-7-fluoro-6-(8-methyl-2,3-dihydro-1H-pyrido[2,3-b][1,4]oxazin-7-yl)isoquinolin-3-yl)carbamate |
| 451a 451b | | (R)-(3-Fluoro-1-methylpyrrolidin-3-yl)methyl(8-amino-7-fluoro-6-(8-methyl-2,3-dihydro-1H-pyrido[2,3-b][1,4]oxazin-7-yl)isoquinolin-3-yl)carbamate; (S)-(3-Fluoro-1-methylpyrrolidin-3-yl)methyl(8-amino-7-fluoro-6-(8-methyl-2,3-dihydro-1H-pyrido[2,3-b][1,4]oxazin-7-yl)isoquinolin-3-yl)carbamate |
| 452 | 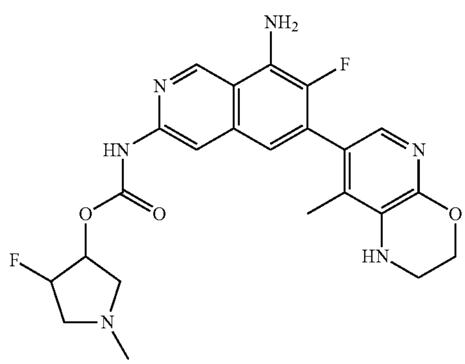 [SMILES: Cc1c(-c2cc3cc(NC(=O)OC4CN(C)CC4F)ncc3c(N)c2F)cnc2c1NCCO2] | 4-Fluoro-1-methylpyrrolidin-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 452a<br>452b | | trans-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate<br>(3S,4S)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate;<br>(3R,4R)-4-Fluoro-1-methylpyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 452c<br>452d | | cis-4-Fluoro-1-methylpyrrolidin-3-yl(8-amino-7-fluoro-6-(8-methyl-2,3-dihydro-1H-pyrido[2,3-b][1,4]oxazin-7-yl)isoquinolin-3-yl)carbamate<br>(3S,4R)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate;<br>(3R,4S)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate |
| 453 | 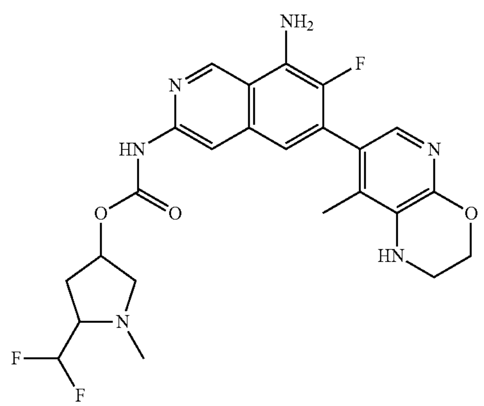 [SMILES: Cc1c(-c2cc3cc(NC(=O)OC4CC(C(F)F)N(C)C4)ncc3c(N)c2F)cnc2c1NCCO2] | 5-(Difluoromethyl)-1-methylpyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 454 | 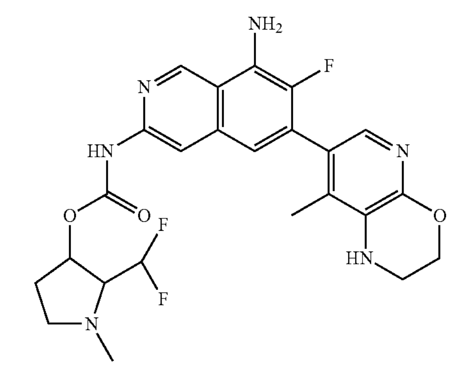 [SMILES: Cc1c(-c2cc3cc(NC(=O)OC4CCN(C)C4C(F)F)ncc3c(N)c2F)cnc2c1NCCO2] | 2-(Difluoromethyl)-1-methylpyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 455 | 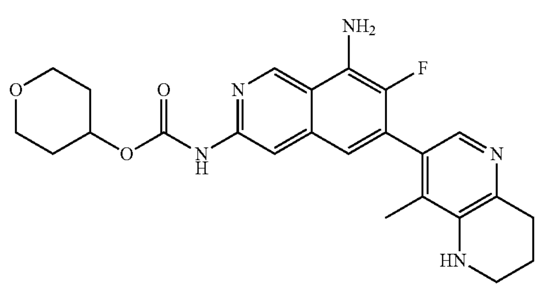 [SMILES: Cc1c(-c2cc3cc(NC(=O)OC4CCOCC4)ncc3c(N)c2F)cnc2c1NCCC2] | Tetrahydro-2H-pyran-4-yl(8-amino-7-fluoro-6-(4-methyl-5,6,7,8-tetrahydro-1,5-naphthyridin-3-yl)isoquinolin-3-yl)carbamate |

TABLE 1-continued

| No. | Structure | Name |
|---|---|---|
| 456 | 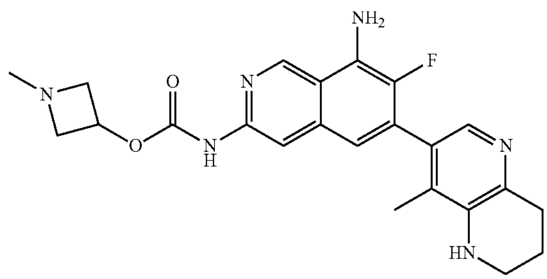 [SMILES: Cc1c(-c2cc3cc(NC(=O)OC4CN(C)C4)ncc3c(N)c2F)cnc2c1NCCC2] | 1-Methyl-3-yl(8-amino-7-fluoro-6-(4-methyl-5,6,7,8-tetrahydro-1,5-naphthyridin-3-yl)isoquinolin-3-yl)carbamate |
| 457 | 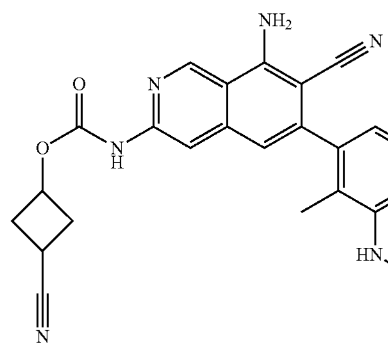 | 3-Cyanocyclobutyl(8-amino-7-cyano-6-(8-methyl-2,3-dihydro-1H-pyrido[2,3-b][1,4]oxazin-7-yl)isoquinolin-3-yl)carbamate |
| 458 | 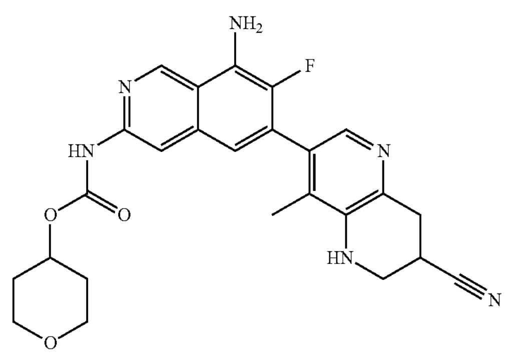 [SMILES: Cc1c(-c2cc3cc(NC(=O)OC4CCOCC4)ncc3c(N)c2F)cnc2c1NCC(C#N)C2] | Tetrahydro-2H-pyran-4-yl(8-amino-6-(7-cyano-4-methyl-5,6,7,8-tetrahydro-1,5-naphthyridin-3-yl)-7-fluoroisoquinolin-3-yl)carbamate |
| 459 | 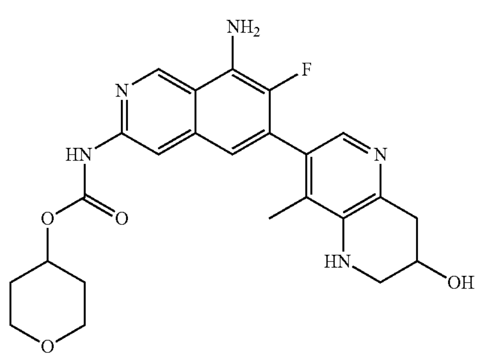 [SMILES: Cc1c(-c2cc3cc(NC(=O)OC4CCOCC4)ncc3c(N)c2F)cnc2c1NCC(O)C2] | Tetrahydro-2H-pyran-4-yl(8-amino-7-fluoro-6-(7-hydroxy-4-methyl-5,6,7,8-tetrahydro-1,5-naphthyridin-3-yl)isoquinolin-3-yl)carbamate |

TABLE 1-continued

| No. | Structure | Name |
|---|---|---|
| 460 | 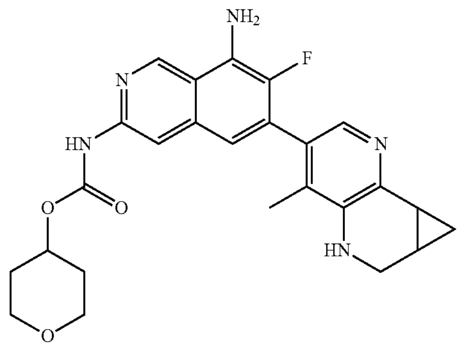 [SMILES: Cc1c(-c2cc3cc(NC(=O)OC4CCOCC4)ncc3c(N)c2F)cnc2c1NCC1CC21] | Tetrahydro-2H-pyran-4-yl(8-amino-7-fluoro-6-(4-methyl-6,6a,7,7a-tetrahydro-5H-cyclopropa[c][1,5]naphthyridin-3-yl)isoquinolin-3-yl)carbamate |
| 461 | 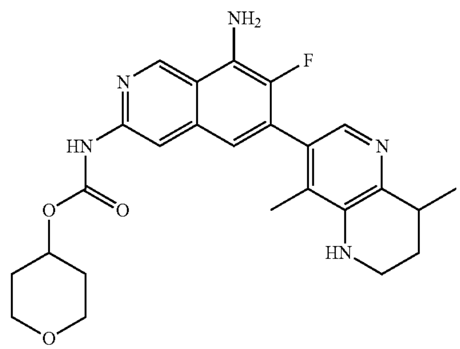 [SMILES: Cc1c(-c2cc3cc(NC(=O)OC4CCOCC4)ncc3c(N)c2F)cnc2c1NCCC2C] | Tetrahydro-2H-pyran-4-yl(8-amino-6-(4,8-dimethyl-5,6,7,8-tetrahydro-1,5-naphthyridin-3-yl)-7-fluoroisoquinolin-3-yl)carbamate |
| 461a 461b | | Tetrahydro-2H-pyran-4-yl(R)-(8-amino-6-(4,8-dimethyl-5,6,7,8-tetrahydro-1,5-naphthyridin-3-yl)-7-fluoroisoquinolin-3-yl)carbamate; Tetrahydro-2H-pyran-4-yl(S)-(8-amino-6-(4,8-dimethyl-5,6,7,8-tetrahydro-1,5-naphthyridin-3-yl)-7-fluoroisoquinolin-3-yl)carbamate |
| 462 | 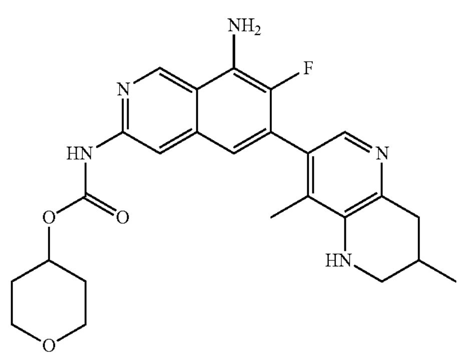 [SMILES: Cc1c(-c2cc3cc(NC(=O)OC4CCOCC4)ncc3c(N)c2F)cnc2c1NCC(C)C2] | Tetrahydro-2H-pyran-4-yl(8-amino-6-(4,7-dimethyl-5,6,7,8-tetrahydro-1,5-naphthyridin-3-yl)-7-fluoroisoquinolin-3-yl)carbamate |
| 463 | 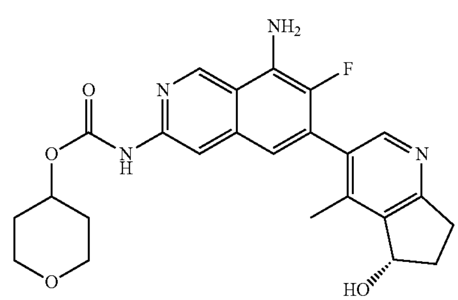 [SMILES: Cc1c(-c2cc3cc(NC(=O)OC4CCOCC4)ncc3c(N)c2F)cnc2c1[C@@H](O)CC2] | Tetrahydro-2H-pyran-4-yl-(8-amino-7-fluoro-6-(5-hydroxy-4-methyl-6,7-dihydro-5H-cyclopenta[b]pyridin-3-yl)isoquinolin-3-yl)carbamate |

TABLE 1-continued

| No. | Structure | Name |
|---|---|---|
| 464 | 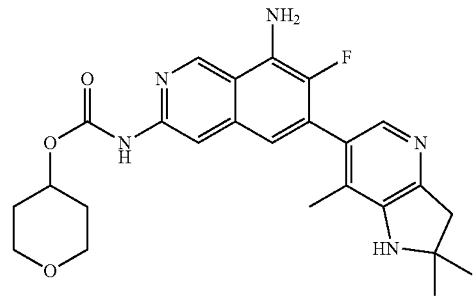 [SMILES: Cc1c(-c2cc3cc(NC(=O)OC4CCOCC4)ncc3c(N)c2F)cnc2c1NC(C)(C)C2] | Tetrahydro-2H-pyran-4-yl(8-amino-7-fluoro-6-(2,2,7-trimethyl-2,3-dihydro-1H-pyrrolo[3,2-b]pyridin-6-yl)isoquinolin-3-yl)carbamate |
| 465 | 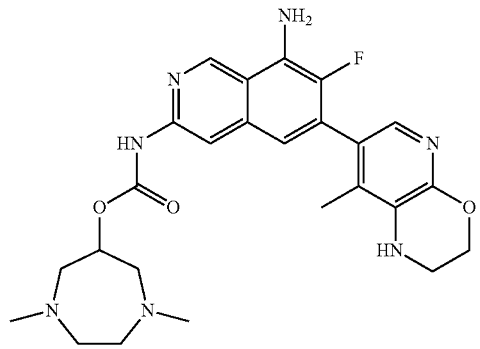 [SMILES: Cc1c(-c2cc3cc(NC(=O)OC4CN(C)CCN(C)C4)ncc3c(N)c2F)cnc2c1NCCO2] | 1,4-Dimethyl-1,4-diazepan-6-yl(8-amino-7-fluoro-6-(8-methyl-2,3-dihydro-1H-pyrido[2,3-b][1,4]oxazin-7-yl)isoquinolin-3-yl)carbamate |
| 466 | 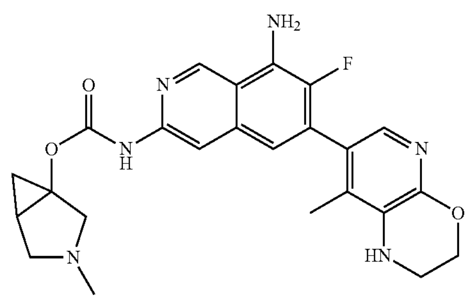 [SMILES: Cc1c(-c2cc3cc(NC(=O)OC45CC4CN(C)C5)ncc3c(N)c2F)cnc2c1NCCO2] | 3-Methyl-3-azabicyclo[3.1.0]hexan-1-yl (8-amino-7-fluoro-6-(8-methyl-2,3-dihydro-1H-pyrido[2,3-b][1,4]oxazin-7-yl)isoquinolin-3-yl)carbamate |
| 467 | 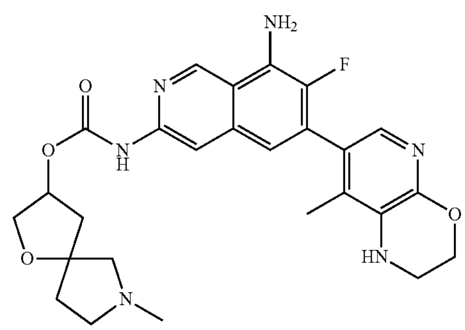 [SMILES: Cc1c(-c2cc3cc(NC(=O)OC4COC5(CCN(C)C5)C4)ncc3c(N)c2F)cnc2c1NCCO2] | 7-Methyl-1-oxa-7-azaspiro[4.4]nonan-3-yl(8-amino-7-fluoro-6-(8-methyl-2,3-dihydro-1H-pyrido[2,3-b][1,4]oxazin-7-yl)isoquinolin-3-yl)carbamate |
| 467a 467b | | (3S,5S)-7-Methyl-1-oxa-7-azaspiro[4.4]nonan-3-yl(8-amino-7-fluoro-6-(8-methyl-2,3-dihydro-1H-pyrido[2,3-b][1,4]oxazin-7-yl)isoquinolin-3-yl)carbamate; (3R,5R)-7-Methyl-1-oxa-7-azaspiro[4.4]nonan-3-yl(8-amino-7-fluoro-6-(8-methyl-2,3-dihydro-1H-pyrido[2,3-b][1,4]oxazin-7-yl)isoquinolin-3-yl)carbamate |
| 467c 467d | | (3S,5R)-7-Methyl-1-oxa-7-azaspiro[4.4]nonan-3-yl(8-amino-7-fluoro-6-(8-methyl-2,3-dihydro-1H-pyrido[2,3-b][1,4]oxazin-7-yl)isoquinolin-3-yl)carbamate; |

TABLE 1-continued

| No. | Structure | Name |
|---|---|---|
| | | (3R,5S)-7-Methyl-1-oxa-7-azaspiro[4.4]nonan-3-yl(8-amino-7-fluoro-6-(8-methyl-2,3-dihydro-1H-pyrido[2,3-b][1,4]oxazin-7-yl)isoquinolin-3-yl)carbamate |
| 468 | 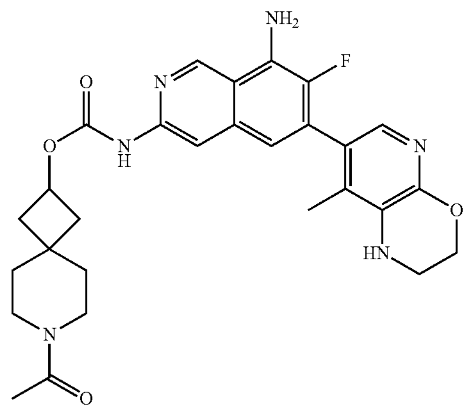 [SMILES: CC(=O)N1CCC2(CC1)CC(OC(=O)Nc1cc3cc(-c4cnc5c(c4C)NCCO5)c(F)c(N)c3cn1)C2] | 7-Acetyl-7-azaspiro[3.5]nonan-2-yl(8-amino-7-fluoro-6-(8-methyl-2,3-dihydro-1H-pyrido[2,3-b][1,4]oxazin-7-yl)isoquinolin-3-yl)carbamate |
| 469 | 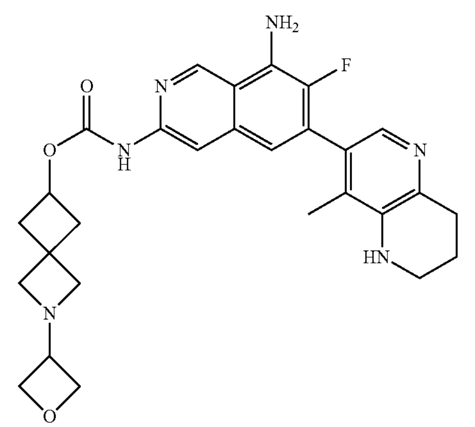 [SMILES: Cc1c(-c2cc3cc(NC(=O)OC4CC5(C4)CN(C4COC4)C5)ncc3c(N)c2F)cnc2c1NCCC2] | 2-(Oxetan-3-yl)-2-azaspiro[3.3]heptan-6-yl(8-amino-7-fluoro-6-(4-methyl-5,6,7,8-tetrahydro-1,5-naphthyridin-3-yl)isoquinolin-3-yl)carbamate |
| 470 | 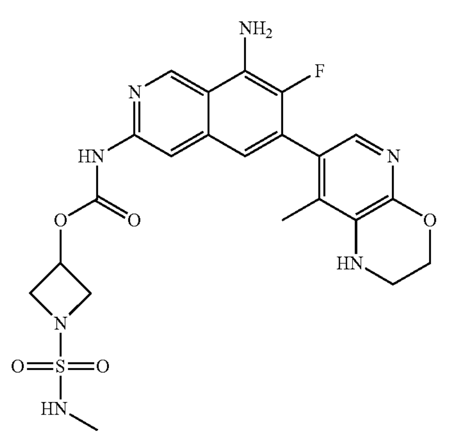 [SMILES: CNS(=O)(=O)N1CC(OC(=O)Nc2cc3cc(-c4cnc5c(c4C)NCCO5)c(F)c(N)c3cn2)C1] | 1-(N-Methylsulfamoyl)azetidin-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 471 | 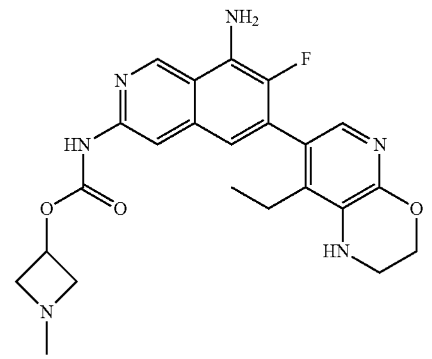 [SMILES: CCc1c(-c2cc3cc(NC(=O)OC4CN(C)C4)ncc3c(N)c2F)cnc2c1NCCO2] | 1-Methylazetidin-3-yl(8-amino-6-(8-ethyl-2,3-dihydro-1H-pyrido[2,3-b][1,4]oxazin-7-yl)-7-fluoroisoquinolin-3-yl)carbamate |
| 472 | 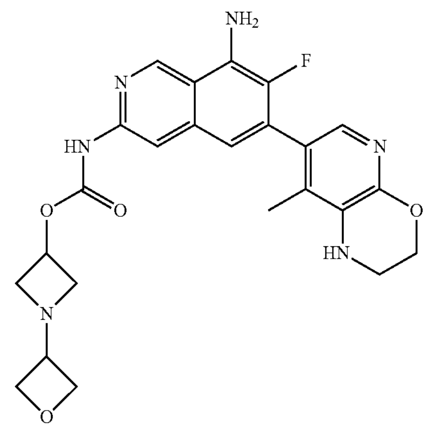 [SMILES: Cc1c(-c2cc3cc(NC(=O)OC4CN(C5COC5)C4)ncc3c(N)c2F)cnc2c1NCCO2] | 1-(Oxetan-3-yl)azetidin-3-yl(8-amino-7-fluoro-6-(8-methyl-2,3-dihydro-1H-pyrido[2,3-b][1,4]oxazin-7-yl)isoquinolin-3-yl)carbamate |
| 473 | 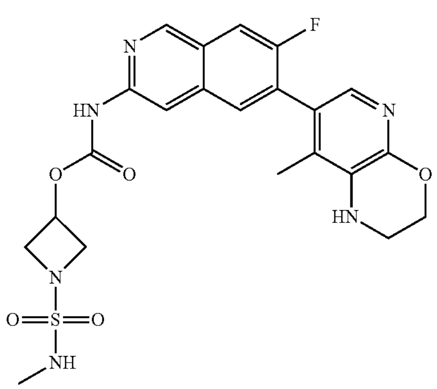 [SMILES: CNS(=O)(=O)N1CC(OC(=O)Nc2cc3cc(-c4cnc5c(c4C)NCCO5)c(F)cc3cn2)C1] | 1-(N-Methylsulfamoyl)azetidin-3-yl(7-fluoro-6-(8-methyl-2,3-dihydro-1H-pyrido[2,3-b][1,4]oxazin-7-yl)isoquinolin-3-yl)carbamate |
| 474 | 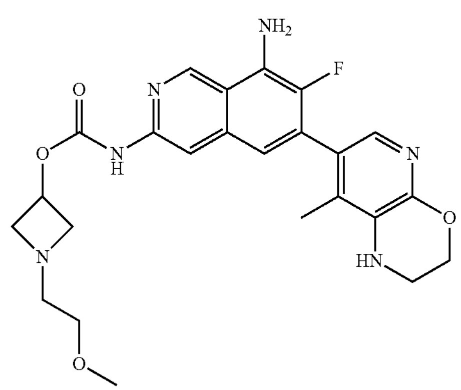 [SMILES: COCCN1CC(OC(=O)Nc2cc3cc(-c4cnc5c(c4C)NCCO5)c(F)c(N)c3cn2)C1] | 1-(2-Methoxyethyl)azetidin-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 475 | 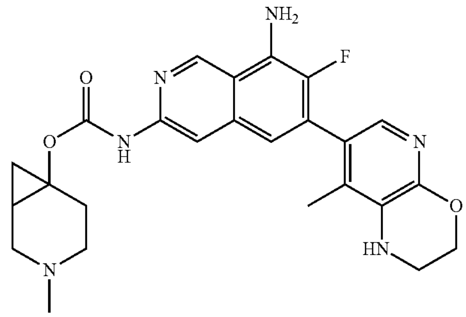 [SMILES: Cc1c(-c2cc3cc(NC(=O)OC45CCN(C)CC4C5)ncc3c(N)c2F)cnc2c1NCCO2] | 3-Methyl-3-azabicyclo[4.1.0]heptan-6-yl (8-amino-7-fluoro-6-(8-methyl-2,3-dihydro-1H-pyrido[2,3-b][1,4]oxazin-7-yl)isoquinolin-3-yl)carbamate |
| 476 | 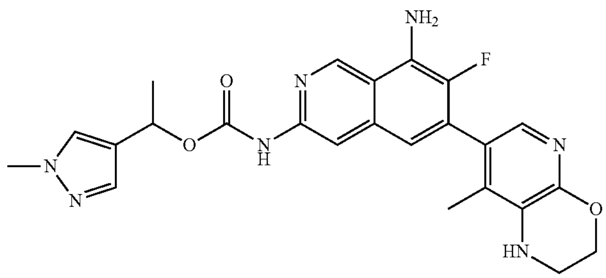 [SMILES: Cc1c(-c2cc3cc(NC(=O)OC(C)c4cnn(C)c4)ncc3c(N)c2F)cnc2c1NCCO2] | 1-(1-Methyl-1H-pyrazol-4-yl)ethyl(8-amino-7-fluoro-6-(8-methyl-2,3-dihydro-1H-pyrido[2,3-b][1,4]oxazin-7-yl)isoquinolin-3-yl)carbamate |
| 477 | 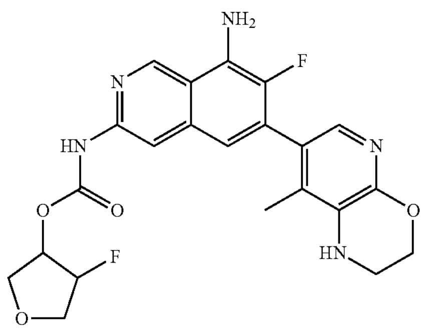 [SMILES: Cc1c(-c2cc3cc(NC(=O)OC4COCC4F)ncc3c(N)c2F)cnc2c1NCCO2] | 4-Fluorotetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 477a 477b | | (trans)-4-Fluorotetrahydrofuran-3-yl(8-amino-7-fluoro-6-(8-methyl-2,3-dihydro-1H-pyrido[2,3-b][1,4]oxazin-7-yl)isoquinolin-3-yl)carbamate (3R,4R)-4-Fluorotetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (3S,4S)-4-Fluorotetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 477c 477d | | (cis)-4-Fluorotetrahydrofuran-3-yl(8-amino-7-fluoro-6-(8-methyl-2,3-dihydro-1H-pyrido[2,3-b][1,4]oxazin-7-yl)isoquinolin-3-yl)carbamate (3S,4R)-4-Fluorotetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (3R,4S)-4-Fluorotetrahydrofuran-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Name |
|---|---|
| 478 | 1-Ethyl-5-oxopyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 478a 478b | (R)-1-Ethyl-5-oxopyrrolidin-3-yl(8-amino-7-fluoro-6-(8-methyl-2,3-dihydro-1H-pyrido[2,3-b][1,4]oxazin-7-yl)isoquinolin-3-yl)carbamate (S)-1-Ethyl-5-oxopyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 479 | 1-Isopropyl-5-oxopyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 479a 479b | (S)-1-Isopropyl-5-oxopyrrolidin-3-yl(8-amino-7-fluoro-6-(8-methyl-2,3-dihydro-1H-pyrido[2,3-b][1,4]oxazin-7-yl)isoquinolin-3-yl)carbamate; (R)-1-Isopropyl-5-oxopyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 480 | 1,4,4-Trimethyl-5-oxopyrrolidin-3-yl(8-amino-7-fluoro-6-(8-methyl-2,3-dihydro-1H-pyrido[2,3-b][1,4]oxazin-7-yl)isoquinolin-3-yl)carbamate |
| 480a 480b | (S)-1,4,4-Trimethyl-5-oxopyrrolidin-3-yl(8-amino-7-fluoro-6-(8-methyl-2,3-dihydro-1H-pyrido[2,3-b][1,4]oxazin-7-yl)isoquinolin-3-yl)carbamate; |

TABLE 1-continued

| No. | Structure | Name |
|---|---|---|
| | | (R)-1,4,4-Trimethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate |
| 481 | | 1-Methyl-5-oxopyrrolidin-3-yl(8-amino-7-fluoro-6-(4-methyl-5,6,7,8-tetrahydro-1,5-naphthyridin-3-yl)isoquinolin-3-yl)carbamate |
| 481a 481b | | (S)-1-Methyl-5-oxopyrrolidin-3-yl(8-amino-7-fluoro-6-(4-methyl-5,6,7,8-tetrahydro-1,5-naphthyridin-3-yl)isoquinolin-3-yl)carbamate; (R)-1-Methyl-5-oxopyrrolidin-3-yl(8-amino-7-fluoro-6-(4-methyl-5,6,7,8-tetrahydro-1,5-naphthyridin-3-yl)isoquinolin-3-yl)carbamate |
| 482 | | 2-Cyanocyclopentyl(8-amino-7-fluoro-6-(8-methyl-2,3-dihydro-1H-pyrido[2,3-b][1,4]oxazin-7-yl)isoquinolin-3-yl)carbamate |
| 482a 482b | | (trans)-2-Cyanocyclopentyl(8-amino-7-fluoro-6-(8-methyl-2,3-dihydro-1H-pyrido[2,3-b][1,4]oxazin-7-yl)isoquinolin-3-yl)carbamate (1R,2S)-2-Cyanocyclopentyl(8-amino-7-fluoro-6-(8-methyl-2,3-dihydro-1H-pyrido[2,3-b][1,4]oxazin-7-yl)isoquinolin-3-yl)carbamate; (1S,2R)-2-Cyanocyclopentyl(8-amino-7-fluoro-6-(8-methyl-2,3-dihydro-1H-pyrido[2,3-b][1,4]oxazin-7-yl)isoquinolin-3-yl)carbamate |
| 482c 482d | | (cis)-2-Cyanocyclopentyl(8-amino-7-fluoro-6-(8-methyl-2,3-dihydro-1H-pyrido[2,3-b][1,4]oxazin-7-yl)isoquinolin-3-yl)carbamate (1S,2S)-2-Cyanocyclopentyl(8-amino-7-fluoro-6-(8-methyl-2,3-dihydro-1H-pyrido[2,3-b][1,4]oxazin-7-yl)isoquinolin-3-yl)carbamate; (1R,2R)-2-Cyanocyclopentyl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 483 | 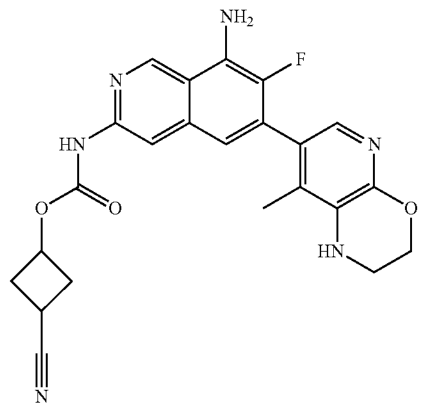 [SMILES: Cc1c(-c2cc3cc(NC(=O)OC4CC(C#N)C4)ncc3c(N)c2F)cnc2c1NCCO2] | 3-Cyanocyclobutyl(8-amino-7-fluoro-6-(4-methyl-5,6,7,8-tetrahydro-1,5-naphthyridin-3-yl)isoquinolin-3-yl)carbamate |
| 483a | | (1s,3s)-3-cyanocyclobutyl (8-amino-7-fluoro-6-(4-methyl-5,6,7,8-tetrahydro-1,5-naphthyridin-3-yl)isoquinolin-3-yl)carbamate |
| 483b | | (1r,3r)-3-cyanocyclobutyl(8-amino-7-fluoro-6-(4-methyl-5,6,7,8-tetrahydro-1,5-naphthyridin-3-yl)isoquinolin-3-yl)carbamate |
| 484 | 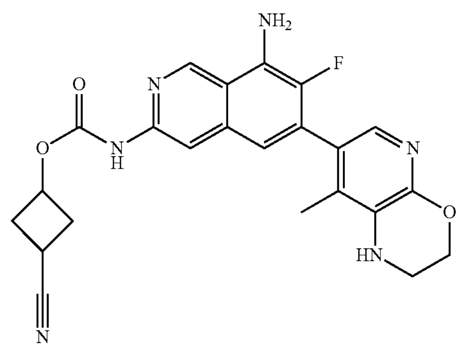 [SMILES: Cc1c(-c2cc3cc(NC(=O)OC4CC(C#N)C4)ncc3c(N)c2F)cnc2c1NCCO2] | 3-Cyanocyclobutyl(8-amino-7-fluoro-6-(8-methyl-2,3-dihydro-1H-pyrido[2,3-b][1,4]oxazin-7-yl)isoquinolin-3-yl)carbamate |
| 484a | | (1s,3s)-3-Cyanocyclobutyl(8-amino-7-fluoro-6-(8-methyl-2,3-dihydro-1H-pyrido[2,3-b][1,4]oxazin-7-yl)isoquinolin-3-yl)carbamate |
| 484b | | (1r,3r)-3-Cyanocyclobutyl(8-amino-7-fluoro-6-(8-methyl-2,3-dihydro-1H-pyrido[2,3-b][1,4]oxazin-7-yl)isoquinolin-3-yl)carbamate |
| 485 | 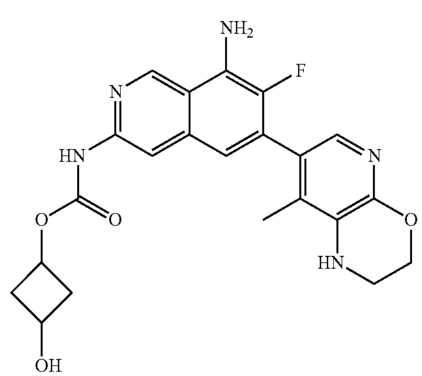 [SMILES: Cc1c(-c2cc3cc(NC(=O)OC4CC(O)C4)ncc3c(N)c2F)cnc2c1NCCO2] | 3-Hydroxycyclobutyl(8-amino-7-fluoro-6-(8-methyl-2,3-dihydro-1H-pyrido[2,3-b][1,4]oxazin-7-yl)isoquinolin-3-yl)carbamate |
| 485a | | (1s,3s)-3-Hydroxycyclobutyl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 485b | | (1r,3r)-3-Hydroxycyclobutyl(8-amino-7-fluoro-6-(8-methyl-2,3-dihydro-1H-pyrido[2,3-b][1,4]oxazin-7-yl)isoquinolin-3-yl)carbamate |
| 486 | (structure) | 3-Hydroxy-3-methylcyclobutyl(8-amino-7-fluoro-6-(8-methyl-2,3-dihydro-1H-pyrido[2,3-b][1,4]oxazin-7-yl)isoquinolin-3-yl)carbamate |
| 486a | | (1s,3s)-3-Hydroxy-3-methylcyclobutyl (8-amino-7-fluoro-6-(8-methyl-2,3-dihydro-1H-pyrido[2,3-b][1,4]oxazin-7-yl)isoquinolin-3-yl)carbamate |
| 486b | | (1r,3r)-3-Hydroxy-3-methylcyclobutyl (8-amino-7-fluoro-6-(8-methyl-2,3-dihydro-1H-pyrido[2,3-b][1,4]oxazin-7-yl)isoquinolin-3-yl)carbamate |
| 487 | (structure) | Cyclobutyl(8-amino-7-fluoro-6-(8-methyl-2,3-dihydro-1H-pyrido[2,3-b][1,4]oxazin-7-yl)isoquinolin-3-yl)carbamate |
| 488 | (structure) | 1-Ethylazetidin-3-yl(8-amino-7-fluoro-6-(8-methyl-2,3-dihydro-1H-pyrido[2,3-b][1,4]oxazin-7-yl)isoquinolin-3-yl)carbamate |
| 489 | (structure) | 1-(2-Cyano-2-methylpropyl)azetidin-3-yl (8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 490 | 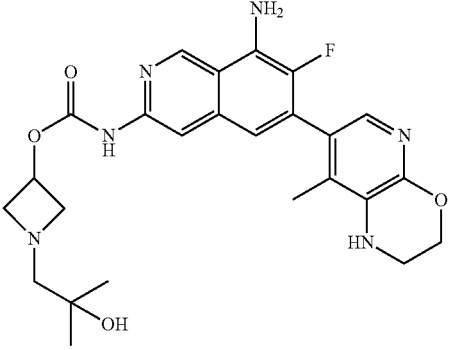 [SMILES: Cc1c(-c2cc3cc(NC(=O)OC4CN(CC(C)(C)O)C4)ncc3c(N)c2F)cnc2c1NCCO2] | 1-(2-Hydroxy-2-methylpropyl)azetidin-3-yl(8-amino-7-fluoro-6-(8-methyl-2,3-dihydro-1H-pyrido[2,3-b][1,4]oxazin-7-yl)isoquinolin-3-yl)carbamate |
| 491 | 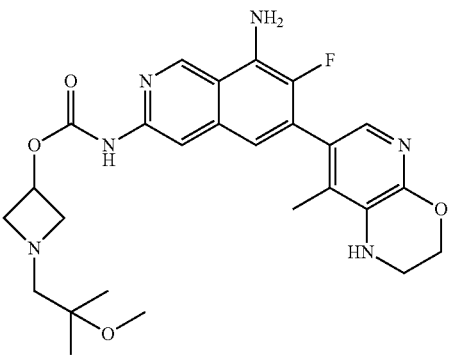 [SMILES: COC(C)(C)CN1CC(OC(=O)Nc2cc3cc(-c4cnc5c(c4C)NCCO5)c(F)c(N)c3cn2)C1] | 1-(2-Methoxy-2-methylpropyl)azetidin-3-yl(8-amino-7-fluoro-6-(8-methyl-2,3-dihydro-1H-pyrido[2,3-b][1,4]oxazin-7-yl)isoquinolin-3-yl)carbamate |
| 492 | 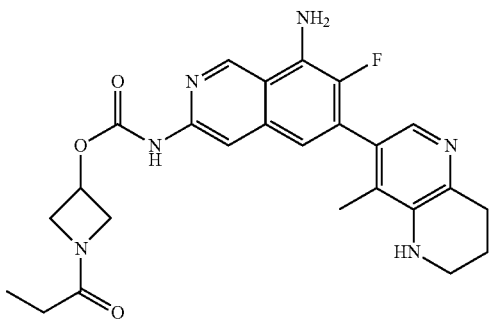 [SMILES: CCC(=O)N1CC(OC(=O)Nc2cc3cc(-c4cnc5c(c4C)NCCC5)c(F)c(N)c3cn2)C1] | 1-Propionylazetidin-3-yl(8-amino-7-fluoro-6-(4-methyl-5,6,7,8-tetrahydro-1,5-naphthyridin-3-yl)isoquinolin-3-yl)carbamate |
| 493 | 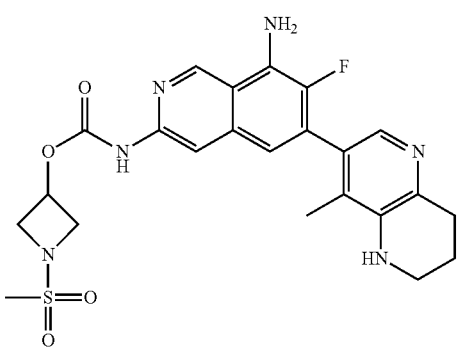 [SMILES: Cc1c(-c2cc3cc(NC(=O)OC4CN(S(C)(=O)=O)C4)ncc3c(N)c2F)cnc2c1NCCC2] | 1-(Methylsulfonyl)azetidin-3-yl(8-amino-7-fluoro-6-(4-methyl-5,6,7,8-tetrahydro-1,5-naphthyridin-3-yl)isoquinolin-3-yl)carbamate |

TABLE 1-continued

| No. | Structure | Name |
|---|---|---|
| 494 | 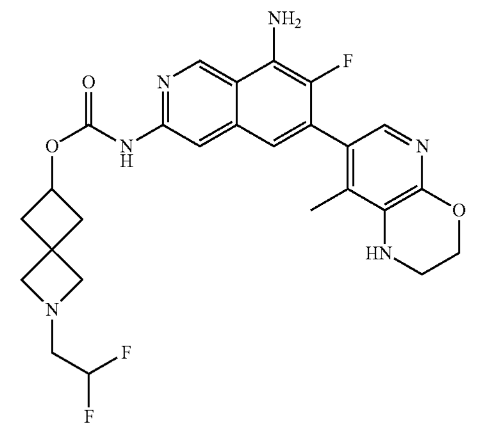 [SMILES: Cc1c(-c2cc3cc(NC(=O)OC4CC5(C4)CN(CC(F)F)C5)ncc3c(N)c2F)cnc2c1NCCO2] | 2-(2,2-Difluoroethyl)-2-azaspiro[3.3]heptan-6-yl(8-amino-7-fluoro-6-(8-methyl-2,3-dihydro-1H-pyrido[2,3-b][1,4]oxazin-7-yl)isoquinolin-3-yl)carbamate |
| 495 | 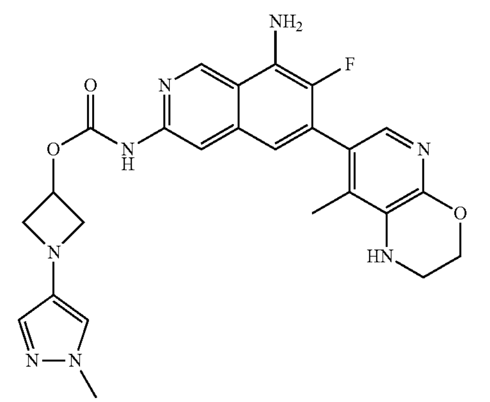 [SMILES: Cc1c(-c2cc3cc(NC(=O)OC4CN(c5cnn(C)c5)C4)ncc3c(N)c2F)cnc2c1NCCO2] | 1-(1-Methyl-1H-pyrazol-4-yl)azetidin-3-yl(8-amino-7-fluoro-6-(8-methyl-2,3-dihydro-1H-pyrido[2,3-b][1,4]oxazin-7-yl)isoquinolin-3-yl)carbamate |
| 496 | 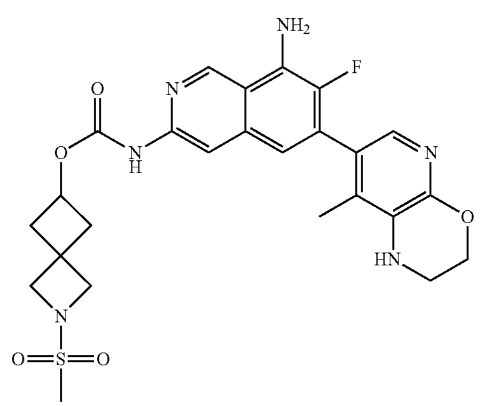 [SMILES: Cc1c(-c2cc3cc(NC(=O)OC4CC5(C4)CN(S(C)(=O)=O)C5)ncc3c(N)c2F)cnc2c1NCCO2] | 2-(Methylsulfonyl)-2-azaspiro[3.3]heptan-6-yl(8-amino-7-fluoro-6-(8-methyl-2,3-dihydro-1H-pyrido[2,3-b][1,4]oxazin-7-yl)isoquinolin-3-yl)carbamate |
| 497 | 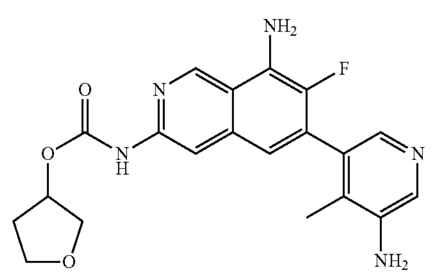 [SMILES: Cc1c(N)cncc1-c1cc2cc(NC(=O)OC3CCOC3)ncc2c(N)c1F] | Tetrahydrofuran-3-yl(8-amino-6-(5-amino-4-methylpyridin-3-yl)-7-fluoroisoquinolin-3-yl)carbamate |

TABLE 1-continued

| No. | Structure | Name |
|---|---|---|
| 498 | 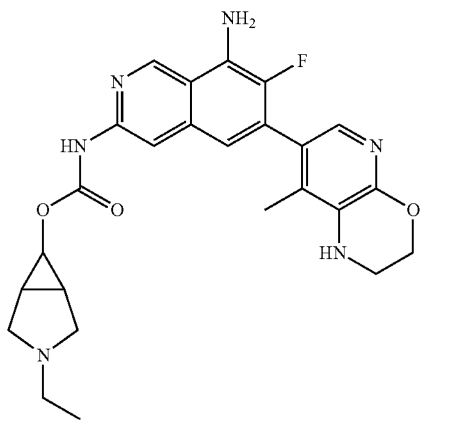 [SMILES: CCN1CC2C(C1)C2OC(=O)Nc1cc2cc(-c3cnc4c(c3C)NCCO4)c(F)c(N)c2cn1] | 3-Ethyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate |
| 499 | 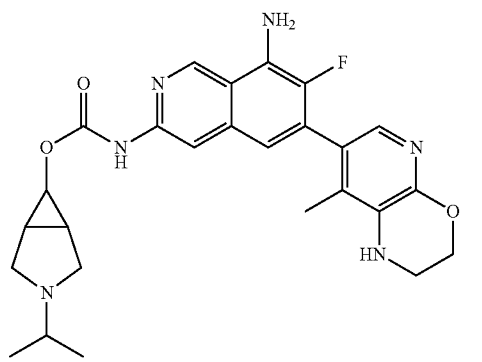 [SMILES: Cc1c(-c2cc3cc(NC(=O)OC4C5CN(C(C)C)CC54)ncc3c(N)c2F)cnc2c1NCCO2] | 3-Isopropyl-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate |
| 499a 499b | | (1R,5S,6r)-3-Isopropyl-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate; (1R,5S,6s)-3-Isopropyl-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl) |
| 500 | 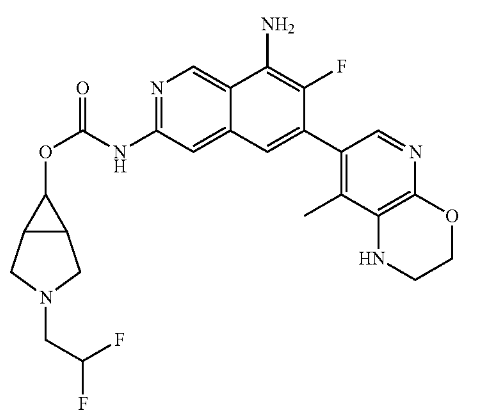 [SMILES: Cc1c(-c2cc3cc(NC(=O)OC4C5CN(CC(F)F)CC54)ncc3c(N)c2F)cnc2c1NCCO2] | 3-(2,2-Difluoroethyl)-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 501 | 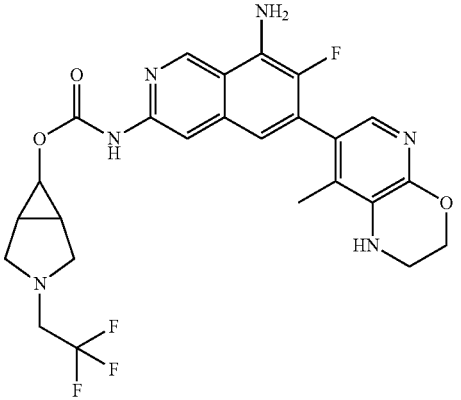 | 3-(2,2,2-Trifluoroethyl)-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate |
| 502 | 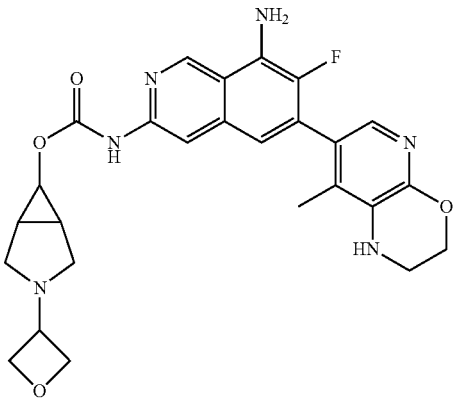 [SMILES: Cc1c(-c2cc3cc(NC(=O)OC4C5CN(C6COC6)CC54)ncc3c(N)c2F)cnc2c1NCCO2] | 3-(Oxetan-3-yl)-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate |
| 502a 502b | | (1R,5S,6r)-3-(oxetan-3-yl)-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate; (1R,5S,6s)-3-(oxetan-3-yl)-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate |
| 503 | 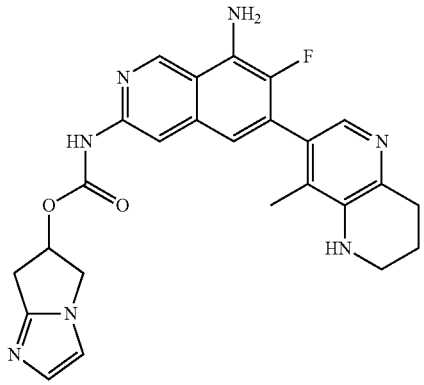 [SMILES: Cc1c(-c2cc3cc(NC(=O)OC4Cc5nccn5C4)ncc3c(N)c2F)cnc2c1NCCC2] | 6,7-Dihydro-5H-pyrrolo[1,2-c]imidazol-6-yl(8-amino-7-fluoro-6-(4-methyl-5,6,7,8-tetrahydro-1,5-naphthyridin-3-yl)isoquinolin-3-yl)carbamate |

TABLE 1-continued

| No. | Structure | Name |
|---|---|---|
| 504 | 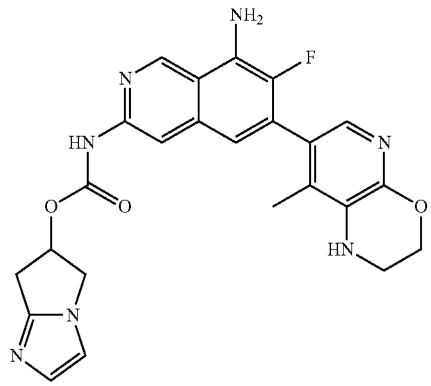 [SMILES: Cc1c(-c2cc3cc(NC(=O)OC4Cc5nccn5C4)ncc3c(N)c2F)cnc2c1NCCO2] | 6,7-Dihydro-5H-pyrrolo[1,2-a]imidazol-6-yl(8-amino-7-fluoro-6-(8-methyl-2,3-dihydro-1H-pyrido[2,3-b][1,4]oxazin-7-yl)isoquinolin-3-yl)carbamate |
| 504a 504b | | (R)-6,7-dihydro-5H-pyrrolo[1,2-a]imidazol-6-yl(8-amino-7-fluoro-6-(8-methyl-2,3-dihydro-1H-pyrido[2,3-b][1,4]oxazin-7-yl)isoquinolin-3-yl)carbamate; (S)-6,7-dihydro-5H-pyrrolo[1,2-a]imidazol-6-yl(8-amino-7-fluoro-6-(8-methyl-2,3-dihydro-1H-pyrido[2,3-b][1,4]oxazin-7-yl)isoquinolin-3-yl)carbamate |
| 505 | 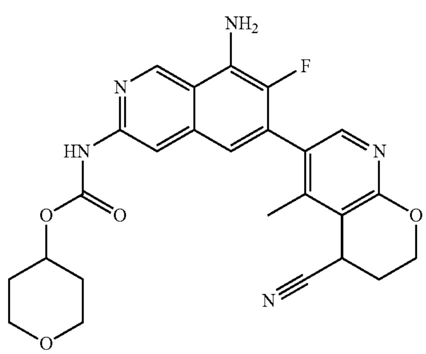 [SMILES: Cc1c(-c2cc3cc(NC(=O)OC4CCOCC4)ncc3c(N)c2F)cnc2c1C(C#N)CCO2] | Tetrahydro-2H-pyran-4-yl(8-amino-6-(4-cyano-5-methyl-3,4-dihydro-2H-pyrano[2,3-b]pyridin-6-yl)-7-fluoroisoquinolin-3-yl)carbamate |
| 506 | 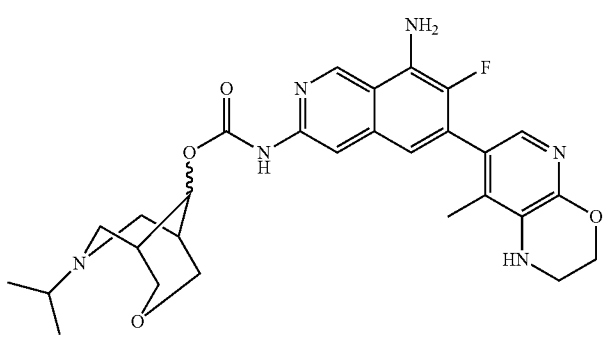 [SMILES: Cc1c(-c2cc3cc(NC(=O)OC4C5COCC4CN(C(C)C)C5)ncc3c(N)c2F)cnc2c1NCCO2] | 7-Isopropyl-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl)carbamate |
| 506a 506b | | (1R,5S,9s)-7-isopropyl-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl (1R,5S,9r)-7-isopropyl-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 507 | 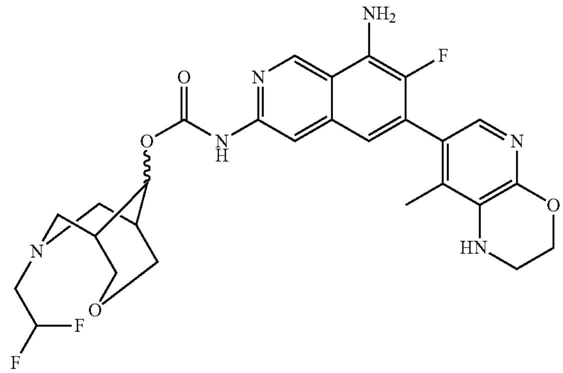 [SMILES: Cc1c(-c2cc3cc(NC(=O)OC4C5COCC4CN(CC(F)F)C5)ncc3c(N)c2F)cnc2c1NCCO2] | 7-(2,2-Difluoroethyl)-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl)carbamate |
| 507a 507b | | (1R,5S,9s)-7-(2,2-difluoroethyl)-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl)carbamate; (1R,5S,9r)-7-(2,2-difluoroethyl)-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl)carbamate |
| 508 | 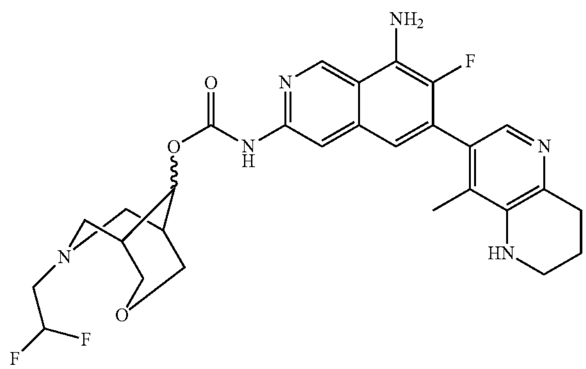 [SMILES: Cc1c(-c2cc3cc(NC(=O)OC4C5COCC4CN(CC(F)F)C5)ncc3c(N)c2F)cnc2c1NCCC2] | 7-(2,2-Difluoroethyl)-3-oxa-7-azabicyclo[3.3.1]nonan-9-yl(8-amino-7-fluoro-6-(4-methyl-5,6,7,8-tetrahydro-1,5-naphthyridin-3-yl)isoquinolin-3-yl)carbamate |
| 509 | 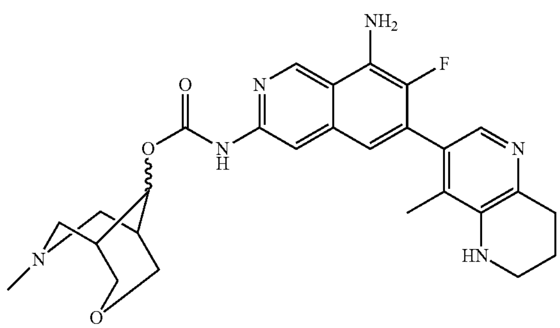 [SMILES: Cc1c(-c2cc3cc(NC(=O)OC4C5COCC4CN(C)C5)ncc3c(N)c2F)cnc2c1NCCC2] | 7-Methyl-3-oxa-7-azabicyclo[3.3.1]nonan-9-yl(8-amino-7-fluoro-6-(4-methyl-5,6,7,8-tetrahydro-1,5-naphthyridin-3-yl)isoquinolin-3-yl)carbamate |
| 510 | 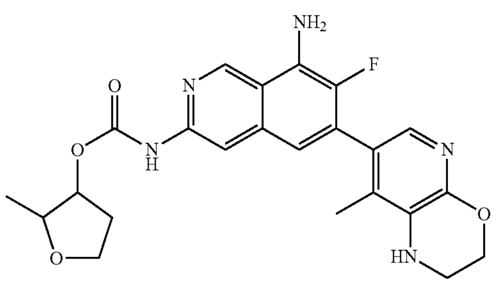 [SMILES: Cc1c(-c2cc3cc(NC(=O)OC4CCOC4C)ncc3c(N)c2F)cnc2c1NCCO2] | 2-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 510a  510b  510c  510d | | (trans)-2-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate (3S,4R)-2-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (3R,4S)-2-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate (cis)-2-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate (3R,4R)-2-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (3S,4S)-2-Methyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 511 | 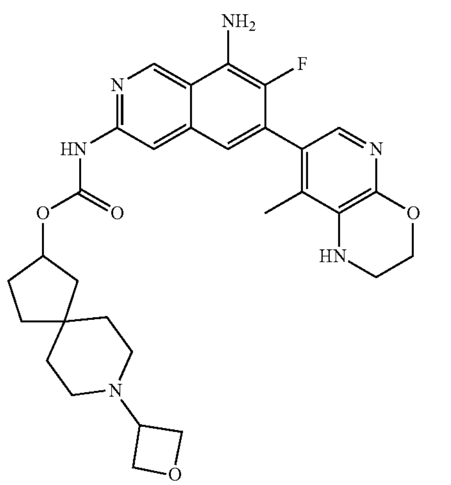 [SMILES: Cc1c(-c2cc3cc(NC(=O)OC4CCC5(CCN(C6COC6)CC5)C4)ncc3c(N)c2F)cnc2c1NCCO2] | 8-(Oxetan-3-yl)-8-azaspiro[4.5]decan-2-yl(8-amino-7-fluoro-6-(8-methyl-2,3-dihydro-1H-pyrido[2,3-b][1,4]oxazin-7-yl)isoquinolin-3-yl)carbamate |
| 511a  511b | | (R)-8-(Oxetan-3-yl)-8-azaspiro[4.5]decan-2-yl(8-amino-7-fluoro-6-(8-methyl-2,3-dihydro-1H-pyrido[2,3-b][1,4]oxazin-7-yl)isoquinolin-3-yl)carbamate (S)-8-(Oxetan-3-yl)-8-azaspiro[4.5]decan-2-yl(8-amino-7-fluoro-6-(8-methyl-2,3-dihydro-1H-pyrido[2,3-b][1,4]oxazin-7-yl)isoquinolin-3-yl)carbamate |
| 512 | 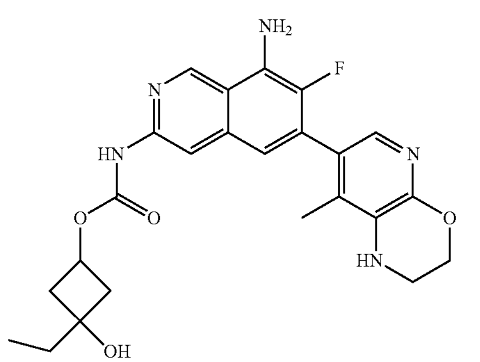 [SMILES: CCC1(O)CC(OC(=O)Nc2cc3cc(-c4cnc5c(c4C)NCCO5)c(F)c(N)c3cn2)C1] | 3-Ethyl-3-hydroxycyclobutyl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 512a<br>512b | | (1s,3r)-3-Ethyl-3-hydroxycyclobutyl(8-amino-7-fluoro-6-(8-methyl-2,3-dihydro-1H-pyrido[2,3-b][1,4]oxazin-7-yl)isoquinolin-3-yl)carbamate<br>(1r,3s)-3-Ethyl-3-hydroxycyclobutyl(8-amino-7-fluoro-6-(8-methyl-2,3-dihydro-1H-pyrido[2,3-b][1,4]oxazin-7-yl)isoquinolin-3-yl)carbamate |
| 513 | 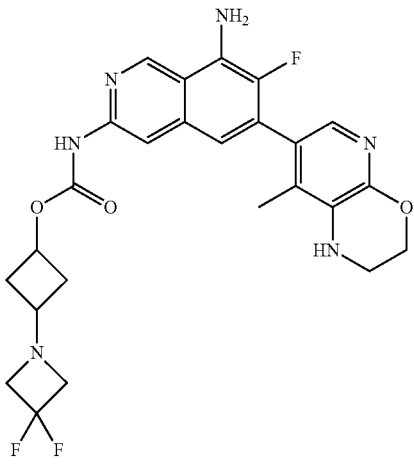 [SMILES: Cc1c(-c2cc3cc(NC(=O)OC4CC(N5CC(F)(F)C5)C4)ncc3c(N)c2F)cnc2c1NCCO2] | 3-(3,3-Difluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate |
| 513a<br>513b | | (1s,3s)-3-(3,3-Difluoroazetidin-1-yl)cyclobutyl(8-amino-7-fluoro-6-(8-methyl-2,3-dihydro-1H-pyrido[2,3-b][1,4]oxazin-7-yl)isoquinolin-3-yl)carbamate;<br>(1r,3r)-3-(3,3-Difluoroazetidin-1-yl)cyclobutyl(8-amino-7-fluoro-6-(8-methyl-2,3-dihydro-1H-pyrido[2,3-b][1,4]oxazin-7-yl)isoquinolin-3-yl)carbamate |
| 514 | 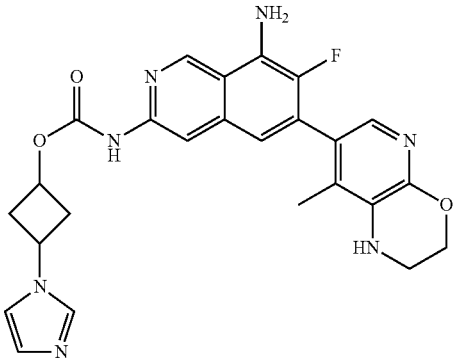 [SMILES: Cc1c(-c2cc3cc(NC(=O)OC4CC(n5ccnc5)C4)ncc3c(N)c2F)cnc2c1NCCO2] | 3-(1H-Imidazol-1-yl)cyclobutyl(8-amino-7-fluoro-6-(8-methyl-2,3-dihydro-1H-pyrido[2,3-b][1,4]oxazin-7-yl)isoquinolin-3-yl)carbamate |
| 514a<br>514b | | (1r,3r)-3-(1H-Imidazol-1-yl)cyclobutyl (8-amino-7-fluoro-6-(8-methyl-2,3-dihydro-1H-pyrido[2,3-b][1,4]oxazin-7-yl)isoquinolin-3-yl)carbamate<br>(1s,3s)-3-(1H-Imidazol-1-yl)cyclobutyl (8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 515 | | 4-Ethyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 515a 515b | | (trans)-4-Ethyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate (3S,4R)-4-Ethyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (3R,4S)-4-Ethyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 515c 515d | | (cis)-4-Ethyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate (3R,4R)-4-Ethyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (3S,4S)-4-Ethyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 516 | | 4-Cyclopropyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 516a 516b | | (trans)-4-Cyclopropyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (3R,4S)-4-Cyclopropyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (3S,4R)-4-Cyclopropyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 516c 516d | | (cis)-4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4R)-4-Cyclopropyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate; (3S,4S)-4-Cyclopropyltetrahydrofuran-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 517 | 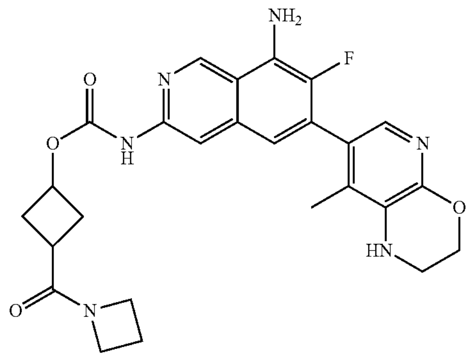 [SMILES: Cc1c(-c2cc3cc(NC(=O)OC4CC(C(=O)N5CCC5)C4)ncc3c(N)c2F)cnc2c1NCCO2] | 3-(Azetidine-1-carbonyl)cyclobutyl(8-amino-7-fluoro-6-(8-methyl-2,3-dihydro-1H-pyrido[2,3-b][1,4]oxazin-7-yl)isoquinolin-3-yl)carbamate |
| 517a | | (1s,3s)-3-(Azetidine-1-carbonyl)cyclobutyl(8-amino-7-fluoro-6-(8-methyl-2,3-dihydro-1H-pyrido[2,3-b][1,4]oxazin-7-yl)isoquinolin-3-yl)carbamate |
| 517b | | (1r,3r)-3-(Azetidine-1-carbonyl)cyclobutyl(8-amino-7-fluoro-6-(8-methyl-2,3-dihydro-1H-pyrido[2,3-b][1,4]oxazin-7-yl)isoquinolin-3-yl)carbamate |
| 518 | 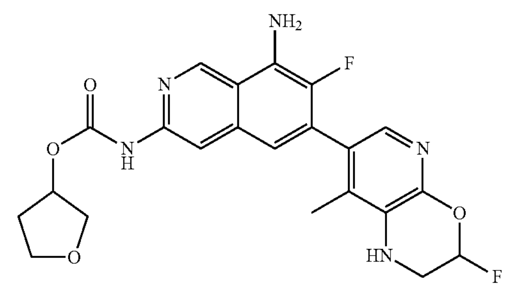 [SMILES: Cc1c(-c2cc3cc(NC(=O)OC4CCOC4)ncc3c(N)c2F)cnc2c1NCC(F)O2] | Tetrahydrofuran-3-yl(8-amino-7-fluoro-6-(3-fluoro-8-methyl-2,3-dihydro-1H-pyrido[2,3-b][1,4]oxazin-7-yl)isoquinolin-3-yl)carbamate |
| 518a | | (R)-Tetrahydrofuran-3-yl(8-amino-7-fluoro-6-(3-fluoro-8-methyl-2,3-dihydro-1H-pyrido[2,3-b][1,4]oxazin-7-yl)isoquinolin-3-yl)carbamate |
| 518b | | (R)-Tetrahydrofuran-3-yl(8-amino-7-fluoro-6-((R)-3-fluoro-8-methyl-2,3-dihydro-1H-pyrido[2,3-b][1,4]oxazin-7-yl)isoquinolin-3-yl)carbamate; (R)-Tetrahydrofuran-3-yl(8-amino-7-fluoro-6-((S)-3-fluoro-8-methyl-2,3-dihydro-1H-pyrido[2,3-b][1,4]oxazin-7-yl)isoquinolin-3-yl)carbamate |
| 518c | | (S)-tetrahydrofuran-3-yl(8-amino-7-fluoro-6-(3-fluoro-8-methyl-2,3-dihydro-1H-pyrido[2,3-b][1,4]oxazin-7-yl)isoquinolin-3-yl)carbamate |
| 518d | | (S)-tetrahydrofuran-3-yl(8-amino-7-fluoro-6-((R)-3-fluoro-8-methyl-2,3-dihydro-1H-pyrido[2,3-b][1,4]oxazin-7-yl)isoquinolin-3-yl)carbamate; (S)-tetrahydrofuran-3-yl(8-amino-7-fluoro-6-((S)-3-fluoro-8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 519 | 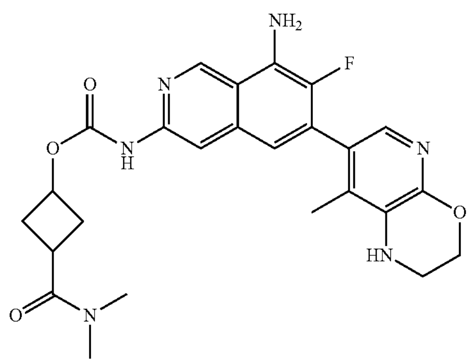 [SMILES: Cc1c(-c2cc3cc(NC(=O)OC4CC(C(=O)N(C)C)C4)ncc3c(N)c2F)cnc2c1NCCO2] | 3-(Dimethylcarbamoyl)cyclobutyl(8-amino-7-fluoro-6-(8-methyl-2,3-dihydro-1H-pyrido[2,3-b][1,4]oxazin-7-yl)isoquinolin-3-yl)carbamate |
| 519a | | (1s,3s)-3-(Dimethylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate |
| 519b | | (1r,3r)-3-(Dimethylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate |
| 520 | 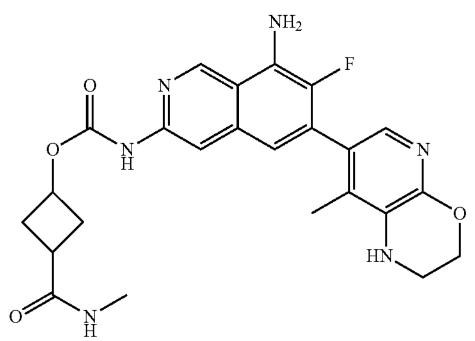 [SMILES: CNC(=O)C1CC(OC(=O)Nc2cc3cc(-c4cnc5c(c4C)NCCO5)c(F)c(N)c3cn2)C1] | 3-(Methylcarbamoyl)cyclobutyl(8-amino-7-fluoro-6-(8-methyl-2,3-dihydro-1H-pyrido[2,3-b][1,4]oxazin-7-yl)isoquinolin-3-yl)carbamate |
| 520a | | (1s,3s)-3-(Methylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate |
| 520b | | (1r,3r)-3-(Methylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate |
| 521 | 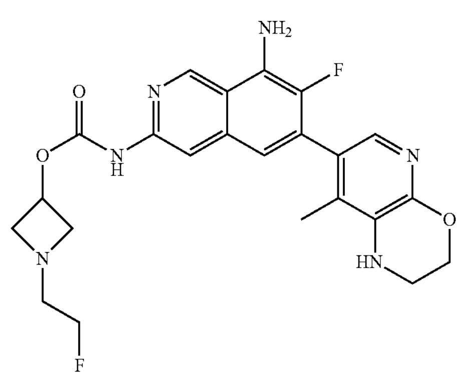 [SMILES: Cc1c(-c2cc3cc(NC(=O)OC4CN(CCF)C4)ncc3c(N)c2F)cnc2c1NCCO2] | 1-(2-Fluoroethyl)azetidin-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 522 | 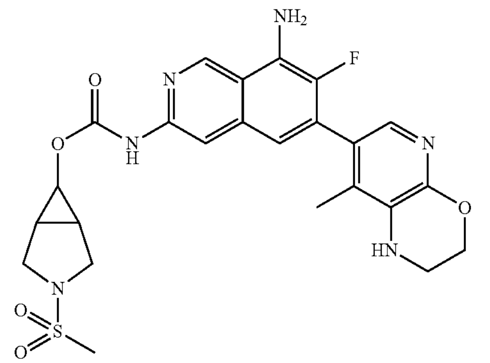 [SMILES: Cc1c(-c2cc3cc(NC(=O)OC4C5CN(S(C)(=O)=O)CC54)ncc3c(N)c2F)cnc2c1NCCO2] | 3-(Methylsulfonyl)-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate |
| 522a | | (1R,5S,6s)-3-(Methylsulfonyl)-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate |
| 522b | | (1R,5S,6r)-3-(Methylsulfonyl)-3-azabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate |
| 523 | 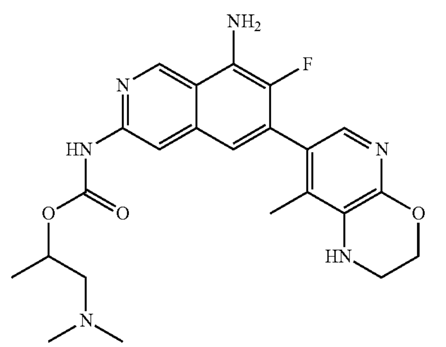 [SMILES: Cc1c(-c2cc3cc(NC(=O)OC(C)CN(C)C)ncc3c(N)c2F)cnc2c1NCCO2] | 1-(Dimethylamino)propan-2-yl(8-amino-7-fluoro-6-(8-methyl-2,3-dihydro-1H-pyrido[2,3-b][1,4]oxazin-7-yl)isoquinolin-3-yl)carbamate |
| 523a 523b | | (R)-1-(Dimethylamino)propan-2-yl(8-amino-7-fluoro-6-(8-methyl-2,3-dihydro-1H-pyrido[2,3-b][1,4]oxazin-7-yl)isoquinolin-3-yl)carbamate; (S)-1-(Dimethylamino)propan-2-yl(8-amino-7-fluoro-6-(8-methyl-2,3-dihydro-1H-pyrido[2,3-b][1,4]oxazin-7-yl)isoquinolin-3-yl)carbamate |
| 524 | 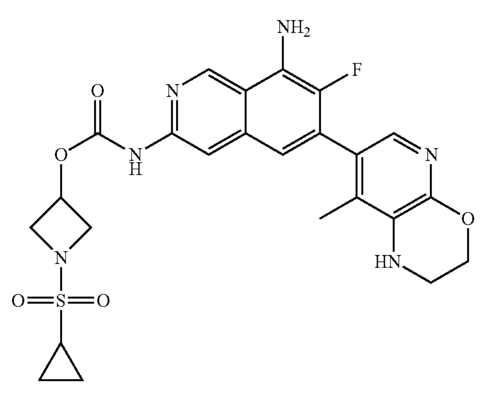 [SMILES: Cc1c(-c2cc3cc(NC(=O)OC4CN(S(=O)(=O)C5CC5)C4)ncc3c(N)c2F)cnc2c1NCCO2] | 1-(Cyclopropylsulfonyl)azetidin-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 525 | | 3-(3-Fluoroazetidin-1-yl)cyclobutyl(8-amino-7-fluoro-6-(8-methyl-2,3-dihydro-1H-pyrido[2,3-b][1,4]oxazin-7-yl)isoquinolin-3-yl)carbamate |
| 525a 525b | | (1s,3s)-3-(3-Fluoroazetidin-1-yl)cyclobutyl(8-amino-7-fluoro-6-(8-methyl-2,3-dihydro-1H-pyrido[2,3-b][1,4]oxazin-7-yl)isoquinolin-3-yl)carbamate; (1r,3r)-3-(3-Fluoroazetidin-1-yl)cyclobutyl(8-amino-7-fluoro-6-(8-methyl-2,3-dihydro-1H-pyrido[2,3-b][1,4]oxazin-7-yl)isoquinolin-3-yl)carbamate |
| 526 | | 3-Hydroxy-2,3-dimethylcyclobutyl(8-amino-7-fluoro-6-(8-methyl-2,3-dihydro-1H-pyrido[2,3-b][1,4]oxazin-7-yl)isoquinolin-3-yl)carbamate |
| 526a 526b | | (1R,2R,3S)-3-Hydroxy-2,3-dimethylcyclobutyl(8-amino-7-fluoro-6-(8-methyl-2,3-dihydro-1H-pyrido[2,3-b][1,4]oxazin-7-yl)isoquinolin-3-yl)carbamate; (1S,2S,3R)-3-Hydroxy-2,3-dimethylcyclobutyl(8-amino-7-fluoro-6-(8-methyl-2,3-dihydro-1H-pyrido[2,3-b][1,4]oxazin-7-yl)isoquinolin-3-yl)carbamate |
| 526c 526d | | (1S,2R,3S)-3-Hydroxy-2,3-dimethylcyclobutyl(8-amino-7-fluoro-6-(8-methyl-2,3-dihydro-1H-pyrido[2,3-b][1,4]oxazin-7-yl)isoquinolin-3-yl)carbamate; (1R,2S,3R)-3-Hydroxy-2,3-dimethylcyclobutyl(8-amino-7-fluoro-6-(8-methyl-2,3-dihydro-1H-pyrido[2,3-b][1,4]oxazin-7-yl)isoquinolin-3-yl)carbamate |
| 526e 526f 526g 526h | | (1R,2S,3S)-3-Hydroxy-2,3-dimethylcyclobutyl(8-amino-7-fluoro-6-(8-methyl-2,3-dihydro-1H-pyrido[2,3-b][1,4]oxazin-7-yl)isoquinolin-3-yl)carbamate; (1S,2R,3R)-3-Hydroxy-2,3-dimethylcyclobutyl(8-amino-7-fluoro-6-(8-methyl-2,3-dihydro-1H-pyrido[2,3-b][1,4]oxazin-7-yl)isoquinolin-3-yl)carbamate (1S,2S,3S)-3-Hydroxy-2,3-dimethylcyclobutyl(8-amino-7-fluoro-6-(8-methyl-2,3-dihydro-1H-pyrido[2,3- |

TABLE 1-continued

| No. | Structure | Name |
|---|---|---|
| | | b][1,4]oxazin-7-yl)isoquinolin-3-yl)carbamate; (1R,2R,3R)-3-Hydroxy-2,3-dimethylcyclobutyl(8-amino-7-fluoro-6-(8-methyl-2,3-dihydro-1H-pyrido[2,3-b][1,4]oxazin-7-yl)isoquinolin-3-yl)carbamate |
| 527 | 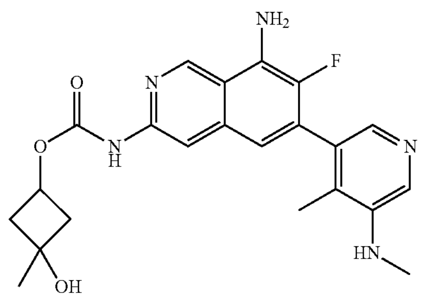 [SMILES: CNc1cncc(-c2cc3cc(NC(=O)OC4CC(C)(O)C4)ncc3c(N)c2F)c1C] | 3-Hydroxy-3-methylcyclobutyl(8-amino-7-fluoro-6-(4-methyl-5-(methylamino)pyridin-3-yl)isoquinolin-3-yl)carbamate |
| 527a 527b | | (1s,3s)-3-Hydroxy-3-methylcyclobutyl (8-amino-7-fluoro-6-(4-methyl-5-(methylamino)pyridin-3-yl)isoquinolin-3-yl)carbamate (1r,3r)-3-hydroxy-3-methylcyclobutyl(8-amino-7-fluoro-6-(4-methyl-5-(methylamino)pyridin-3-yl)isoquinolin-3-yl)carbamate |
| 528 | 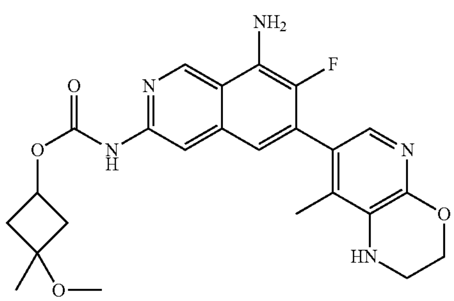 [SMILES: COC1(C)CC(OC(=O)Nc2cc3cc(-c4cnc5c(c4C)NCCO5)c(F)c(N)c3cn2)C1] | 3-Methoxy-3-methylcyclobutyl(8-amino-7-fluoro-6-(8-methyl-2,3-dihydro-1H-pyrido[2,3-b][1,4]oxazin-7-yl)isoquinolin-3-yl)carbamate |
| 528a | | (1s,3s)-3-Methoxy-3-methylcyclobutyl (8-amino-7-fluoro-6-(8-methyl-2,3-dihydro-1H-pyrido[2,3-b][1,4]oxazin-7-yl)isoquinolin-3-yl)carbamate |
| 528b | | (1r,3r)-3-Methoxy-3-methylcyclobutyl (8-amino-7-fluoro-6-(8-methyl-2,3-dihydro-1H-pyrido[2,3-b][1,4]oxazin-7-yl)isoquinolin-3-yl)carbamate |
| 529 | 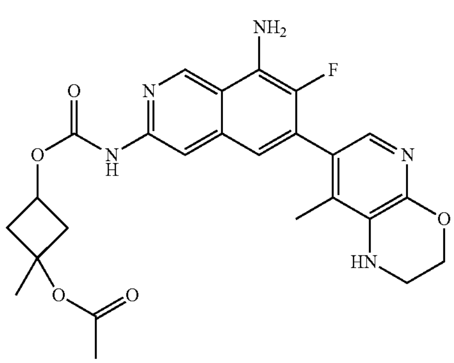 [SMILES: CC(=O)OC1(C)CC(OC(=O)Nc2cc3cc(-c4cnc5c(c4C)NCCO5)c(F)c(N)c3cn2)C1] | 3-(((8-Amino-7-fluoro-6-(8-methyl-2,3-dihydro-1H-pyrido[2,3-b][1,4]oxazin-7-yl)isoquinolin-3-yl)carbamoyl)oxy)-1-methylcyclobutyl acetate |
| 529a | | (1r,3r)-3-(((8-Amino-7-fluoro-6-(8-methyl-2,3-dihydro-1H-pyrido[2,3-b][1,4]oxazin-7-yl)isoquinolin-3-yl)carbamoyl)oxy)-1-methylcyclobutyl acetate |

TABLE 1-continued

| No. | Structure | Name |
|---|---|---|
| 529b | | (1s,3s)-3-(((8-Amino-7-fluoro-6-(8-methyl-2,3-dihydro-1H-pyrido[2,3-b][1,4]oxazin-7-yl)isoquinolin-3-yl)carbamoyl)oxy)-1-methylcyclobutyl acetate |
| 530 | 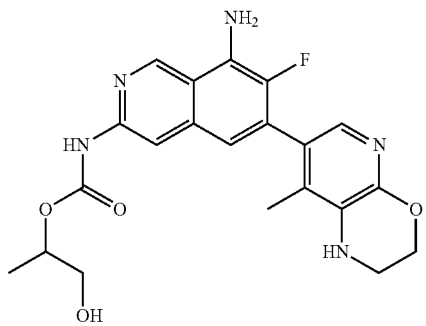 [SMILES: Cc1c(-c2cc3cc(NC(=O)OC(C)CO)ncc3c(N)c2F)cnc2c1NCCO2] | 1-Hydroxypropan-2-yl(8-amino-7-fluoro-6-(8-methyl-2,3-dihydro-1H-pyrido[2,3-b][1,4]oxazin-7-yl)isoquinolin-3-yl)carbamate |
| 530a 530b | | (R)-1-Hydroxypropan-2-yl(8-amino-7-fluoro-6-(8-methyl-2,3-dihydro-1H-pyrido[2,3-b][1,4]oxazin-7-yl)isoquinolin-3-yl)carbamate; (S)-1-Hydroxypropan-2-yl(8-amino-7-fluoro-6-(8-methyl-2,3-dihydro-1H-pyrido[2,3-b][1,4]oxazin-7-yl)isoquinolin-3-yl)carbamate |
| 531 | 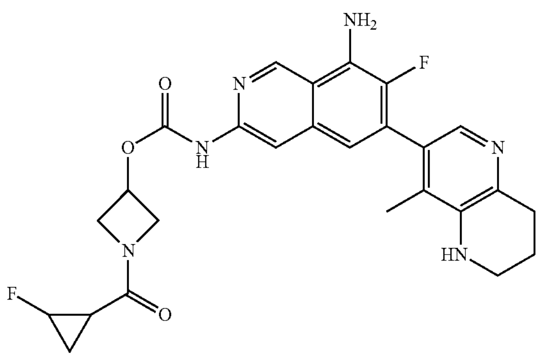 [SMILES: Cc1c(-c2cc3cc(NC(=O)OC4CN(C(=O)C5CC5F)C4)ncc3c(N)c2F)cnc2c1NCCC2] | 1-(2-Fluorocyclopropane-1-carbonyl)azetidin-3-yl(8-amino-7-fluoro-6-(4-methyl-5,6,7,8-tetrahydro-1,5-naphthyridin-3-yl)isoquinolin-3-yl)carbamate |
| 531a 531b | | 1-(trans-2-Fluorocyclopropane-1-carbonyl)azetidin-3-yl(8-amino-7-fluoro-6-(4-methyl-5,6,7,8-tetrahydro-1,5-naphthyridin-3-yl)isoquinolin-3-yl)carbamate 1-((1R,2S)-2-Fluorocyclopropane-1-carbonyl)azetidin-3-yl(8-amino-7-fluoro-6-(4-methyl-5,6,7,8-tetrahydro-1,5-naphthyridin-3-yl)isoquinolin-3-yl)carbamate; 1-((1S,2R)-2-Fluorocyclopropane-1-carbonyl)azetidin-3-yl(8-amino-7-fluoro-6-(4-methyl-5,6,7,8-tetrahydro-1,5-naphthyridin-3-yl)isoquinolin-3-yl)carbamate |
| 531c 531d | | 1-(cis-2-fluorocyclopropane-1-carbonyl)azetidin-3-yl(8-amino-7-fluoro-6-(4-methyl-5,6,7,8-tetrahydro-1,5-naphthyridin-3-yl)isoquinolin-3-yl)carbamate 1-((1R,2R)-2-fluorocyclopropane-1-carbonyl)azetidin-3-yl(8-amino-7-fluoro-6-(4-methyl-5,6,7,8-tetrahydro-1,5-naphthyridin-3-yl)isoquinolin-3-yl)carbamate |

TABLE 1-continued

| No. | Structure | Name |
|---|---|---|
| | | 1-((1S,2S)-2-fluorocyclopropane-1-carbonyl)azetidin-3-yl(8-amino-7-fluoro-6-(4-methyl-5,6,7,8-tetrahydro-1,5-naphthyridin-3-yl)isoquinolin-3-yl)carbamate |
| 532 | 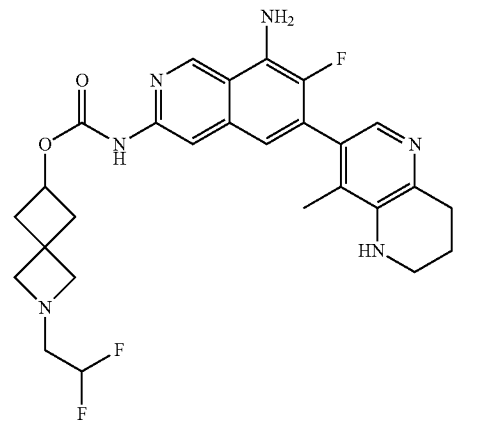 [SMILES: Cc1c(-c2cc3cc(NC(=O)OC4CC5(C4)CN(CC(F)F)C5)ncc3c(N)c2F)cnc2c1NCCC2] | 2-(2,2-Difluoroethyl)-2-azaspiro[3.3]heptan-6-yl(8-amino-7-fluoro-6-(4-methyl-5,6,7,8-tetrahydro-1,5-naphthyridin-3-yl)isoquinolin-3-yl)carbamate |
| 533 | 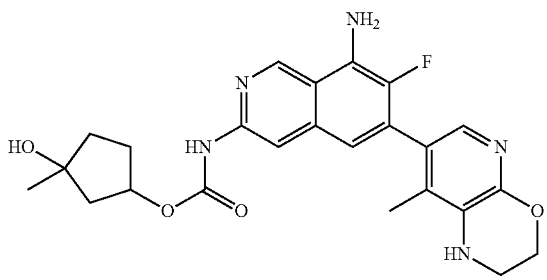 [SMILES: Cc1c(-c2cc3cc(NC(=O)OC4CCC(C)(O)C4)ncc3c(N)c2F)cnc2c1NCCO2] | 3-Hydroxy-3-methylcyclopentyl(8-amino-7-fluoro-6-(8-methyl-2,3-dihydro-1H-pyrido[2,3-b][1,4]oxazin-7-yl)isoquinolin-3-yl)carbamate |
| 533a 533b 533c 533d | | (1R,3S)-3-hydroxy-3-methylcyclopentyl (8-amino-7-fluoro-6-(8-methyl-2,3-dihydro-1H-pyrido[2,3-b][1,4]oxazin-7-yl)isoquinolin-3-yl)carbamate; (1S,3R)-3-hydroxy-3-methylcyclopentyl (8-amino-7-fluoro-6-(8-methyl-2,3-dihydro-1H-pyrido[2,3-b][1,4]oxazin-7-yl)isoquinolin-3-yl)carbamate; (1R,3R)-3-hydroxy-3-methylcyclopentyl (8-amino-7-fluoro-6-(8-methyl-2,3-dihydro-1H-pyrido[2,3-b][1,4]oxazin-7-yl)isoquinolin-3-yl)carbamate; (1S,3S)-3-hydroxy-3-methylcyclopentyl (8-amino-7-fluoro-6-(8-methyl-2,3-dihydro-1H-pyrido[2,3-b][1,4]oxazin-7-yl)isoquinolin-3-yl)carbamate |
| 534 | 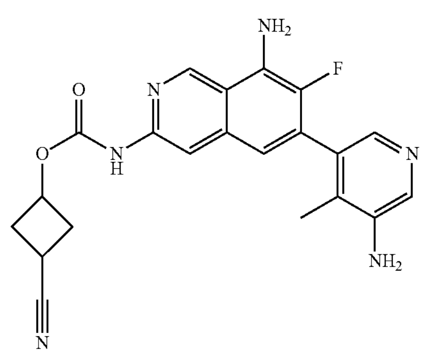 [SMILES: Cc1c(N)cncc1-c1cc2cc(NC(=O)OC3CC(C#N)C3)ncc2c(N)c1F] | 3-Cyanocyclobutyl(8-amino-6-(5-amino-4-methylpyridin-3-yl)-7-fluoroisoquinolin-3-yl)carbamate |

TABLE 1-continued

| No. | Structure | Name |
|---|---|---|
| 534a | | (1s,3s)-3-Cyanocyclobutyl(8-amino-6-(5-amino-4-methylpyridin-3-yl)-7-fluoroisoquinolin-3-yl)carbamate |
| 534b | | (1r,3r)-3-Cyanocyclobutyl(8-amino-6-(5-amino-4-methylpyridin-3-yl)-7-fluoroisoquinolin-3-yl)carbamate |
| 535 | 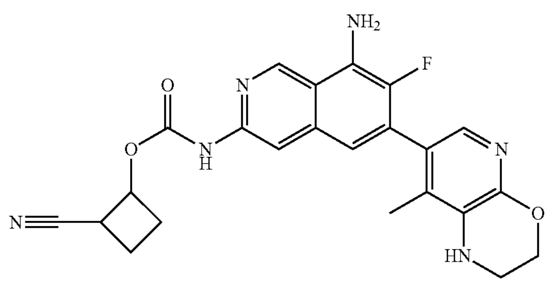 [SMILES: Cc1c(-c2cc3cc(NC(=O)OC4CCC4C#N)ncc3c(N)c2F)cnc2c1NCCO2] | 2-Cyanocyclobutyl(8-amino-7-fluoro-6-(8-methyl-2,3-dihydro-1H-pyrido[2,3-b][1,4]oxazin-7-yl)isoquinolin-3-yl)carbamate |
| 535a 535b | | trans-2-Cyanocyclobutyl(8-amino-7-fluoro-6-(8-methyl-2,3-dihydro-1H-pyrido[2,3-b][1,4]oxazin-7-yl)isoquinolin-3-yl)carbamate (1S,2R)-2-Cyanocyclobutyl(8-amino-7-fluoro-6-(8-methyl-2,3-dihydro-1H-pyrido[2,3-b][1,4]oxazin-7-yl)isoquinolin-3-yl)carbamate; (1R,2S)-2-Cyanocyclobutyl(8-amino-7-fluoro-6-(8-methyl-2,3-dihydro-1H-pyrido[2,3-b][1,4]oxazin-7-yl)isoquinolin-3-yl)carbamate |
| 535c 535d | | cis-2-Cyanocyclobutyl(8-amino-7-fluoro-6-(8-methyl-2,3-dihydro-1H-pyrido [2,3-b ][1,4]oxazin-7-yl)isoquinolin-3-yl)carbamate (1S,2S)-2-Cyanocyclobutyl(8-amino-7-fluoro-6-(8-methyl-2,3-dihydro-1H-pyrido[2,3-b][1,4]oxazin-7-yl)isoquinolin-3-yl)carbamate; (1R,2R)-2-Cyanocyclobutyl(8-amino-7-fluoro-6-(8-methyl-2,3-dihydro-1H-pyrido[2,3-b][1,4]oxazin-7-yl)isoquinolin-3-yl)carbamate |
| 536 | 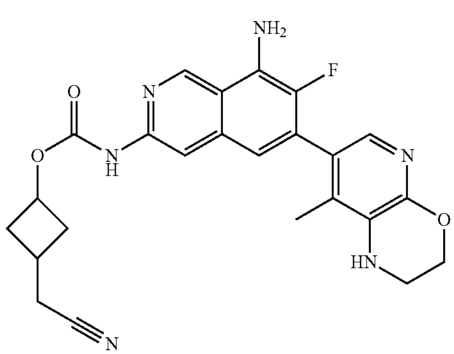 [SMILES: Cc1c(-c2cc3cc(NC(=O)OC4CC(CC#N)C4)ncc3c(N)c2F)cnc2c1NCCO2] | 3-(Cyanomethyl)cyclobutyl(8-amino-7-fluoro-6-(8-methyl-2,3-dihydro-1H-pyrido[2,3-b][1,4]oxazin-7-yl)isoquinolin-3-yl)carbamate |
| 536a 536b | | (1r,3s)-3-(Cyanomethyl)cyclobutyl(8-amino-7-fluoro-6-(8-methyl-2,3-dihydro-1H-pyrido[2,3-b][1,4]oxazin-7-yl)isoquinolin-3-yl)carbamate; (1s,3r)-3-(Cyanomethyl)cyclobutyl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 537 | 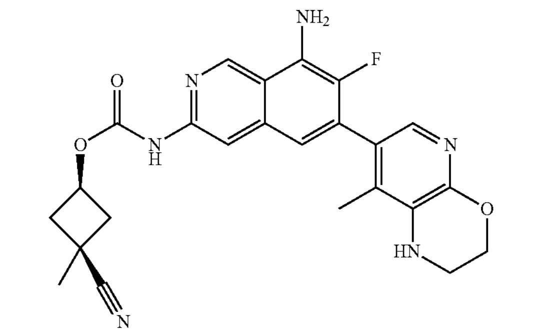 [SMILES: Cc1c(-c2cc3cc(NC(=O)O[C@H]4C[C@@](C)(C#N)C4)ncc3c(N)c2F)cnc2c1NCCO2] | 3-Cyano-3-methylcyclobutyl(8-amino-7-fluoro-6-(8-methyl-2,3-dihydro-1H-pyrido[2,3-b][1,4]oxazin-7-yl)isoquinolin-3-yl)carbamate |
| 537a<br>537b | | (1s,3s)-3-Cyano-3-methylcyclobutyl(8-amino-7-fluoro-6-(8-methyl-2,3-dihydro-1H-pyrido[2,3-b][1,4]oxazin-7-yl)isoquinolin-3-yl)carbamate;<br>(1r,3r)-3-Cyano-3-methylcyclobutyl(8-amino-7-fluoro-6-(8-methyl-2,3-dihydro-1H-pyrido[2,3-b][1,4]oxazin-7-yl)isoquinolin-3-yl)carbamate |
| 538 | 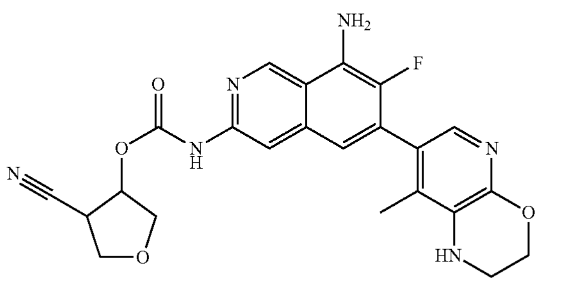 [SMILES: Cc1c(-c2cc3cc(NC(=O)OC4COCC4C#N)ncc3c(N)c2F)cnc2c1NCCO2] | 4-Cyanotetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 538a<br>538b | | trans-4-Cyanotetrahydrofuran-3-yl(8-amino-7-fluoro-6-(8-methyl-2,3-dihydro-1H-pyrido[2,3-b][1,4]oxazin-7-yl)isoquinolin-3-yl)carbamate<br>(3S,4R)-4-Cyanotetrahydrofuran-3-yl(8-amino-7-fluoro-6-(8-methyl-2,3-dihydro-1H-pyrido[2,3-b][1,4]oxazin-7-yl)isoquinolin-3-yl)carbamate;<br>(3R,4S)-4-Cyanotetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 538c<br>538d | | cis-2-4-Cyanotetrahydrofuran-3-yl(8-amino-7-fluoro-6-(8-methyl-2,3-dihydro-1H-pyrido[2,3-b][1,4]oxazin-7-yl)isoquinolin-3-yl)carbamate<br>(3S,4S)-4-Cyanotetrahydrofuran-3-yl(8-amino-7-fluoro-6-(8-methyl-2,3-dihydro-1H-pyrido[2,3-b][1,4]oxazin-7-yl)isoquinolin-3-yl)carbamate;<br>(3R,4R)-4-cyanotetrahydrofuran-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 539 | 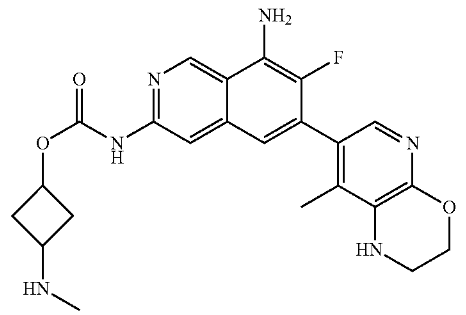 [SMILES: CNC1CC(OC(=O)Nc2cc3cc(-c4cnc5c(c4C)NCCO5)c(F)c(N)c3cn2)C1] | 3-(Methylamino)cyclobutyl(8-amino-7-fluoro-6-(8-methyl-2,3-dihydro-1H-pyrido[2,3-b][1,4]oxazin-7-yl)isoquinolin-3-yl)carbamate |
| 539a | | (1r,3r)-3-(Methylamino)cyclobutyl(8-amino-7-fluoro-6-(8-methyl-2,3-dihydro-1H-pyrido[2,3-b][1,4]oxazin-7-yl)isoquinolin-3-yl)carbamate |
| 539b | | (1s,3s)-3-(Methylamino)cyclobutyl(8-amino-7-fluoro-6-(8-methyl-2,3-dihydro-1H-pyrido[2,3-b][1,4]oxazin-7-yl)isoquinolin-3-yl)carbamate |
| 540 | 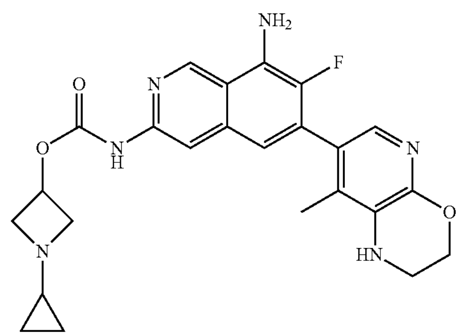 [SMILES: Cc1c(-c2cc3cc(NC(=O)OC4CN(C5CC5)C4)ncc3c(N)c2F)cnc2c1NCCO2] | 1-Cyclopropylazetidin-3-yl(8-amino-7-fluoro-6-(8-methyl-2,3-dihydro-1H-pyrido[2,3-b][1,4]oxazin-7-yl)isoquinolin-3-yl)carbamate |
| 541 | 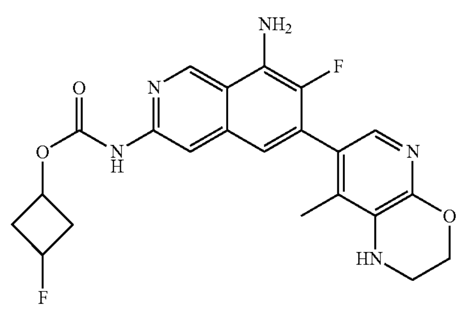 [SMILES: Cc1c(-c2cc3cc(NC(=O)OC4CC(F)C4)ncc3c(N)c2F)cnc2c1NCCO2] | 3-Fluorocyclobutyl(8-amino-7-fluoro-6-(8-methyl-2,3-dihydro-1H-pyrido[2,3-b][1,4]oxazin-7-yl)isoquinolin-3-yl)carbamate |
| 541a | | (1s,3s)-3-Fluorocyclobutyl(8-amino-7-fluoro-6-(8-methyl-2,3-dihydro-1H-pyrido[2,3-b][1,4]oxazin-7-yl)isoquinolin-3-yl)carbamate |
| 541b | | (1r,3r)-3-Fluorocyclobutyl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 542 | | 2-Hydroxycyclobutyl(8-amino-7-fluoro-6-(8-methyl-2,3-dihydro-1H-pyrido[2,3-b][1,4]oxazin-7-yl)isoquinolin-3-yl)carbamate |
| 542a 542b | | cis-2-Hydroxycyclobutyl(8-amino-7-fluoro-6-(8-methyl-2,3-dihydro-1H-pyrido[2,3-b][1,4]oxazin-7-yl)isoquinolin-3-yl)carbamate (1S,2R)-2-Hydroxycyclobutyl(8-amino-7-fluoro-6-(8-methyl-2,3-dihydro-1H-pyrido[2,3-b][1,4]oxazin-7-yl)isoquinolin-3-yl)carbamate; (1R,2S)-2-Hydroxycyclobutyl(8-amino-7-fluoro-6-(8-methyl-2,3-dihydro-1H-pyrido[2,3-b][1,4]oxazin-7-yl)isoquinolin-3-yl)carbamate |
| 542c 542d | | trans-2-Hydroxycyclobutyl(8-amino-7-fluoro-6-(8-methyl-2,3-dihydro-1H-pyrido[2,3-b][1,4]oxazin-7-yl)isoquinolin-3-yl)carbamate (1S,2S)-2-Hydroxycyclobutyl(8-amino-7-fluoro-6-(8-methyl-2,3-dihydro-1H-pyrido[2,3-b][1,4]oxazin-7-yl)isoquinolin-3-yl)carbamate; (1R,2R)-2-Hydroxycyclobutyl(8-amino-7-fluoro-6-(8-methyl-2,3-dihydro-1H-pyrido[2,3-b][1,4]oxazin-7-yl)isoquinolin-3-yl)carbamate |
| 543 | | 3-Oxabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate |
| 543a 543b | | (1R,5S,6s)-3-Oxabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamate; (1R,5S,6r)-3-Oxabicyclo[3.1.0]hexan-6-yl(8-amino-7-fluoro-6-(8-methyl-2,3-dihydro-1H-pyrido[2,3-b][1,4]oxazin-7-yl)isoquinolin-3-yl)carbamat |

TABLE 1-continued

| No. | Structure | Name |
|---|---|---|
| 544 | 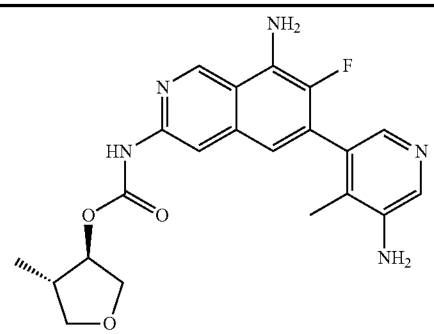 | 4-Methyltetrahydrofuran-3-yl(8-amino-6-(5-amino-4-methylpyridin-3-yl)-7-fluoroisoquinolin-3-yl)carbamate |
| 544a<br>544b | | trans-4-Methyltetrahydrofuran-3-yl(8-amino-6-(5-amino-4-methylpyridin-3-yl)-7-fluoroisoquinolin-3-yl)carbamate<br>(3R,4S)-4-Methyltetrahydrofuran-3-yl(8-amino-6-(5-amino-4-methylpyridin-3-yl)-7-fluoroisoquinolin-3-yl)carbamate;<br>(3S,4R)-4-Methyltetrahydrofuran-3-yl(8-amino-6-(5-amino-4-methylpyridin-3-yl)-7-fluoroisoquinolin-3-yl)carbamate |
| 544c<br>544d | | cis-4-Methyltetrahydrofuran-3-yl(8-amino-6-(5-amino-4-methylpyridin-3-yl)-7-fluoroisoquinolin-3-yl)carbamate<br>(3R,4R)-4-Methyltetrahydrofuran-3-yl(8-amino-6-(5-amino-4-methylpyridin-3-yl)-7-fluoroisoquinolin-3-yl)carbamate;<br>(3S,4S)-4-Methyltetrahydrofuran-3-yl(8-amino-6-(5-amino-4-methylpyridin-3-yl)-7-fluoroisoquinolin-3-yl)carbamate |
| 545 | 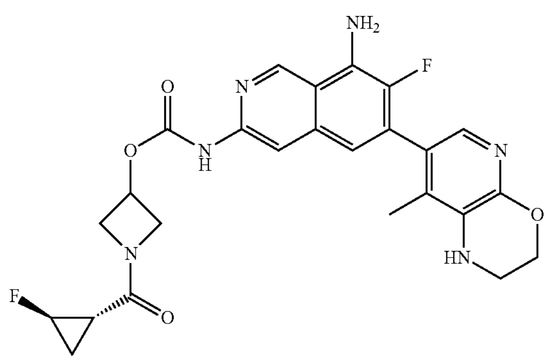 [SMILES: Cc1c(-c2cc3cc(NC(=O)OC4CN(C(=O)[C@@H]5C[C@H]5F)C4)ncc3c(N)c2F)cnc2c1NCCO2] | 1-(2-Fuorocyclopropane-1-carbonyl)azetidin-3-yl(8-amino-7-fluoro-6-(8-methyl-2,3-dihydro-1H-pyrido[2,3-b][1,4]oxazin-7-yl)isoquinolin-3-yl)carbamate |
| 545a<br>545b | | 1-(trans-2-Fuorocyclopropane-1-carbonyl)azetidin-3-yl(8-amino-7-fluoro-6-(8-methyl-2,3-dihydro-1H-pyrido[2,3-b][1,4]oxazin-7-yl)isoquinolin-3-yl)carbamate<br>1-((1R,2S)-2-Fluorocyclopropane-1-carbonyl)azetidin-3-yl(8-amino-7-fluoro-6-(8-methyl-2,3-dihydro-1H-pyrido[2,3-b][1,4]oxazin-7-yl)isoquinolin-3-yl)carbamate<br>1-((1S,2R)-2-fluorocyclopropane-1-carbonyl)azetidin-3-yl(8-amino-7-fluoro-6-(8-methyl-2,3-dihydro-1H-pyrido[2,3-b][1,4]oxazin-7-yl)isoquinolin-3-yl)carbamate |
| 545c<br>545d | | 1-(cis-2-Fuorocyclopropane-1-carbonyl)azetidin-3-yl(8-amino-7-fluoro-6-(8-methyl-2,3-dihydro-1H-pyrido[2,3-b][1,4]oxazin-7-yl)isoquinolin-3-yl)carbamate<br>1-((1R,2R)-2-Fluorocyclopropane-1-carbonyl)azetidin-3-yl(8-amino-7-fluoro-6-(8-methyl-2,3-dihydro-1H-pyrido[2,3-b][1,4]oxazin-7-yl)isoquinolin-3-yl)carbamate; |

TABLE 1-continued

| No. | Structure | Name |
|---|---|---|
| | | 1-((1S,2S)-2-Fluorocyclopropane-1-carbonyl)azetidin-3-yl(8-amino-7-fluoro-6-(8-methyl-2,3-dihydro-1H-pyrido[2,3-b][1,4]oxazin-7-yl)isoquinolin-3-yl)carbamate |
| 546 | (structure) | 4-Methoxytetrahydrofuran-3-yl(8-amino-7-fluoro-6-(8-methyl-2,3-dihydro-1H-pyrido[2,3-b][1,4]oxazin-7-yl)isoquinolin-3-yl)carbamate |
| 546a 546b | | trans-4-Methoxytetrahydrofuran-3-yl(8-amino-7-fluoro-6-(8-methyl-2,3-dihydro-1H-pyrido[2,3-b][1,4]oxazin-7-yl)isoquinolin-3-yl)carbamate (3S,4S)-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4R)-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate |
| 546c 546d | | cis-4-Methoxytetrahydrofuran-3-yl(8-amino-7-fluoro-6-(8-methyl-2,3-dihydro-1H-pyrido[2,3-b][1,4]oxazin-7-yl)isoquinolin-3-yl)carbamate (3S,4R)-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4S)-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate |
| 547 | (structure) | Tetrahydrofuran-3-yl(8-amino-6-(7-cyano-4-methyl-5,6,7,8-tetrahydro-1,5-naphthyridin-3-yl)-7-fluoroisoquinolin-3-yl)carbamate |
| 547a 547b | | (R)-Tetrahydrofuran-3-yl(8-amino-6-(7-cyano-4-methyl-5,6,7,8-tetrahydro-1,5-naphthyridin-3-yl)-7-fluoroisoquinolin-3-yl)carbamate; (S)-Tetrahydrofuran-3-yl(8-amino-6-(7-cyano-4-methyl-5,6,7,8-tetrahydro-1,5-naphthyridin-3-yl)-7-fluoroisoquinolin-3-yl)carbamate |

TABLE 1-continued

| No. | Structure | Name |
|---|---|---|
| 548 | | Tetrahydrofuran-3-yl(8-amino-7-fluoro-6-(5-hydroxy-4-methyl-6,7-dihydro-5H-cyclopenta[b]pyridin-3-yl)isoquinolin-3-yl)carbamate |
| 548a 548b | | (R)-tetrahydrofuran-3-yl(8-amino-7-fluoro-6-(5-hydroxy-4-methyl-6,7-dihydro-5H-cyclopenta[b]pyridin-3-yl)isoquinolin-3-yl)carbamate (R)-tetrahydrofuran-3-yl(8-amino-7-fluoro-6-((S)-5-hydroxy-4-methyl-6,7-dihydro-5H-cyclopenta[b]pyridin-3-yl)isoquinolin-3-yl)carbamate; (R)-tetrahydrofuran-3-yl(8-amino-7-fluoro-6-((R)-5-hydroxy-4-methyl-6,7-dihydro-5H-cyclopenta[b]pyridin-3-yl)isoquinolin-3-yl)carbamate |
| 548c 548d | | (S)-tetrahydrofuran-3-yl(8-amino-7-fluoro-6-(5-hydroxy-4-methyl-6,7-dihydro-5H-cyclopenta[b]pyridin-3-yl)isoquinolin-3-yl)carbamate (S)-tetrahydrofuran-3-yl(8-amino-7-fluoro-6-((S)-5-hydroxy-4-methyl-6,7-dihydro-5H-cyclopenta[b]pyridin-3-yl)isoquinolin-3-yl)carbamate; (S)-tetrahydrofuran-3-yl(8-amino-7-fluoro-6-((R)-5-hydroxy-4-methyl-6,7-dihydro-5H-cyclopenta[b]pyridin-3-yl)isoquinolin-3-yl)carbamate |
| 549 | | 3-(2-Cyanopropan-2-yl)cyclobutyl(8-amino-7-fluoro-6-(8-methyl-2,3-dihydro-1H-pyrido[2,3-b][1,4]oxazin-7-yl)isoquinolin-3-yl)carbamate |
| 549a 549b | | (1s,3s)-3-(2-Cyanopropan-2-yl)cyclobutyl(8-amino-7-fluoro-6-(8-methyl-2,3-dihydro-1H-pyrido[2,3-b][1,4]oxazin-7-yl)isoquinolin-3-yl)carbamate; (1r,3r)-3-(2-Cyanopropan-2-yl)cyclobutyl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 550 | 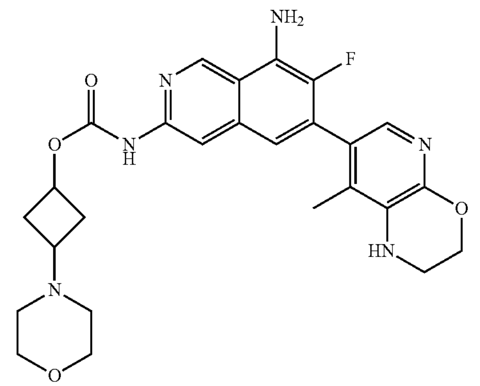 [SMILES: Cc1c(-c2cc3cc(NC(=O)OC4CC(N5CCOCC5)C4)ncc3c(N)c2F)cnc2c1NCCO2] | 3-Morpholinocyclobutyl(8-amino-7-fluoro-6-(8-methyl-2,3-dihydro-1H-pyrido[2,3-b][1,4]oxazin-7-yl)isoquinolin-3-yl)carbamate |
| 550a | | (1r,3r)-3-Morpholinocyclobutyl(8-amino-7-fluoro-6-(8-methyl-2,3-dihydro-1H-pyrido[2,3-b][1,4]oxazin-7-yl)isoquinolin-3-yl)carbamate |
| 550b | | (1s,3s)-3-Morpholinocyclobutyl(8-amino-7-fluoro-6-(8-methyl-2,3-dihydro-1H-pyrido[2,3-b][1,4]oxazin-7-yl)isoquinolin-3-yl)carbamate |
| 551 | 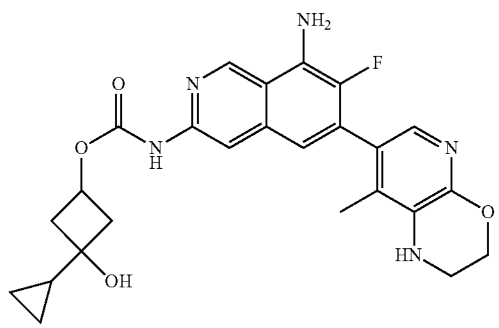 [SMILES: Cc1c(-c2cc3cc(NC(=O)OC4CC(O)(C5CC5)C4)ncc3c(N)c2F)cnc2c1NCCO2] | 3-Cyclopropyl-3-hydroxycyclobutyl(8-amino-7-fluoro-6-(8-methyl-2,3-dihydro-1H-pyrido[2,3-b][1,4]oxazin-7-yl)isoquinolin-3-yl)carbamate |
| 551a 551b | | (1s,3s)-3-Cyclopropyl-3-hydroxycyclobutyl(8-amino-7-fluoro-6-(8-methyl-2,3-dihydro-1H-pyrido[2,3-b][1,4]oxazin-7-yl)isoquinolin-3-yl)carbamate; (1r,3r)-3-Cyclopropyl-3-hydroxycyclobutyl(8-amino-7-fluoro-6-(8-methyl-2,3-dihydro-1H-pyrido[2,3-b][1,4]oxazin-7-yl)isoquinolin-3-yl)carbamate |
| 552 | 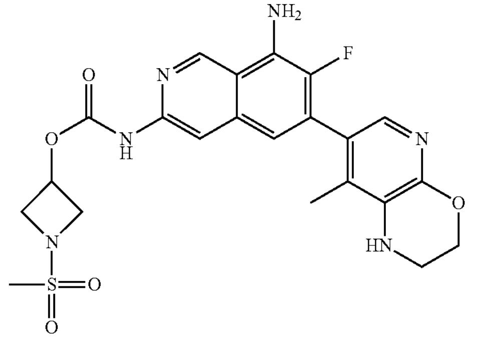 [SMILES: Cc1c(-c2cc3cc(NC(=O)OC4CN(S(C)(=O)=O)C4)ncc3c(N)c2F)cnc2c1NCCO2] | 1-(Methylsulfonyl)azetidin-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 553 | 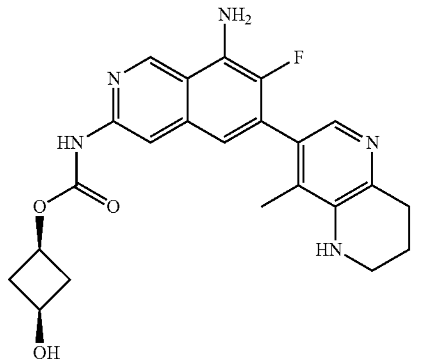 [SMILES: Cc1c(-c2cc3cc(NC(=O)O[C@H]4C[C@@H](O)C4)ncc3c(N)c2F)cnc2c1NCCC2] | 3-Hydroxycyclobutyl(8-amino-7-fluoro-6-(4-methyl-5,6,7,8-tetrahydro-1,5-naphthyridin-3-yl)isoquinolin-3-yl)carbamate |
| 553a | | (1s,3s)-3-hydroxycyclobutyl(8-amino-7-fluoro-6-(4-methyl-5,6,7,8-tetrahydro-1,5-naphthyridin-3-yl)isoquinolin-3-yl)carbamate |
| 553b | | (1r,3r)-3-hydroxycyclobutyl(8-amino-7-fluoro-6-(4-methyl-5,6,7,8-tetrahydro-1,5-naphthyridin-3-yl)isoquinolin-3-yl)carbamate |
| 554 | 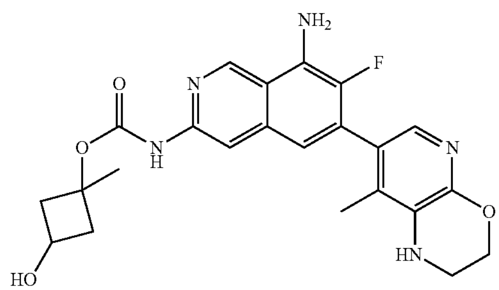 [SMILES: Cc1c(-c2cc3cc(NC(=O)OC4(C)CC(O)C4)ncc3c(N)c2F)cnc2c1NCCO2] | 3-Hydroxy-1-methylcyclobutyl(8-amino-7-fluoro-6-(8-methyl-2,3-dihydro-1H-pyrido[2,3-b][1,4]oxazin-7-yl)isoquinolin-3-yl)carbamate |
| 554a | | (1s,3s)-3-Hydroxy-1-methylcyclobutyl (8-amino-7-fluoro-6-(8-methyl-2,3-dihydro-1H-pyrido[2,3-b][1,4]oxazin-7-yl)isoquinolin-3-yl)carbamate |
| 554b | | (1r,3r)-3-Hydroxy-1-methylcyclobutyl (8-amino-7-fluoro-6-(8-methyl-2,3-dihydro-1H-pyrido[2,3-b][1,4]oxazin-7-yl)isoquinolin-3-yl)carbamate |
| 555 | 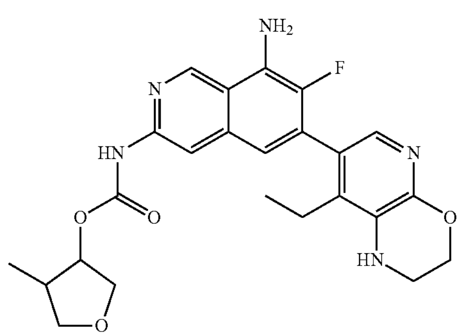 [SMILES: CCc1c(-c2cc3cc(NC(=O)OC4COCC4C)ncc3c(N)c2F)cnc2c1NCCO2] | 4-Methyltetrahydrofuran-3-yl(8-amino-6-(8-ethyl-2,3-dihydro-1H-pyrido[2,3-b][1,4]oxazin-7-yl)-7-fluoroisoquinolin-3-yl)carbamate |
| 555a 555b | | trans-4-Methyltetrahydrofuran-3-yl(8-amino-6-(8-ethyl-2,3-dihydro-1H-pyrido[2,3-b][1,4]oxazin-7-yl)-7-fluoroisoquinolin-3-yl)carbamate (3R,4S)-4-Methyltetrahydrofuran-3-yl(8-amino-6-(8-ethyl-2,3-dihydro-1H-pyrido[2,3-b][1,4]oxazin-7-yl)-7-fluoroisoquinolin-3-yl)carbamate; (3S,4R)-4-Methyltetrahydrofuran-3-yl(8-amino-6-(8-ethyl-2,3-dihydro-1H-pyrido[2,3-b][1,4]oxazin-7-yl)-7-fluoroisoquinolin-3-yl)carbamate |

TABLE 1-continued

| No. | Structure | Name |
|---|---|---|
| 555c 555d | | cis-4-Methyltetrahydrofuran-3-yl(8-amino-6-(8-ethyl-2,3-dihydro-1H-pyrido[2,3-b][1,4]oxazin-7-yl)-7-fluoroisoquinolin-3-yl)carbamate (3R,4R)-4-methyltetrahydrofuran-3-yl(8-amino-6-(8-ethyl-2,3-dihydro-1H-pyrido[2,3-b][1,4]oxazin-7-yl)-7-fluoroisoquinolin-3-yl)carbamate; (3S,4S)-4-methyltetrahydrofuran-3-yl(8-amino-6-(8-ethyl-2,3-dihydro-1H-pyrido[2,3-b][1,4]oxazin-7-yl)-7-fluoroisoquinolin-3-yl)carbamate |
| 556 | 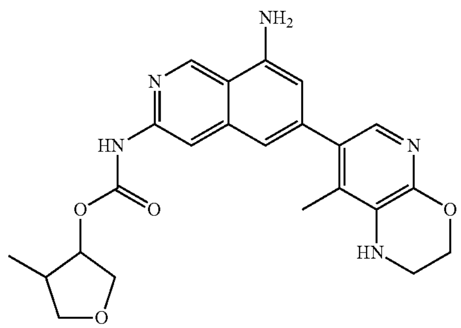 [SMILES: Cc1c(-c2cc(N)c3cnc(NC(=O)OC4COCC4C)cc3c2)cnc2c1NCCO2] | 4-Methyltetrahydrofuran-3-yl(8-amino-6-(8-methyl-2,3-dihydro-1H-pyrido[2,3-b][1,4]oxazin-7-yl)isoquinolin-3-yl)carbamate |
| 556a 556b | | trans-4-Methyltetrahydrofuran-3-yl(8-amino-6-(8-methyl-2,3-dihydro-1H-pyrido[2,3-b][1,4]oxazin-7-yl)isoquinolin-3-yl)carbamate (3R,4S)-4-Methyltetrahydrofuran-3-yl(8-amino-6-(8-methyl-2,3-dihydro-1H-pyrido[2,3-b][1,4]oxazin-7-yl)isoquinolin-3-yl)carbamate; (3S,4R)-4-Methyltetrahydrofuran-3-yl(8-amino-6-(8-methyl-2,3-dihydro-1H-pyrido[2,3-b][1,4]oxazin-7-yl)isoquinolin-3-yl)carbamate |
| 556c 556d | | cis-4-Methyltetrahydrofuran-3-yl(8-amino-6-(8-methyl-2,3-dihydro-1H-pyrido[2,3-b][1,4]oxazin-7-yl)isoquinolin-3-yl)carbamate (3R,4R)-4-Methyltetrahydrofuran-3-yl(8-amino-6-(8-methyl-2,3-dihydro-1H-pyrido[2,3-b][1,4]oxazin-7-yl)isoquinolin-3-yl)carbamate; (3S,4S)-4-Methyltetrahydrofuran-3-yl(8-amino-6-(8-methyl-2,3-dihydro-1H-pyrido[2,3-b][1,4]oxazin-7-yl)isoquinolin-3-yl)carbamate |
| 557 | 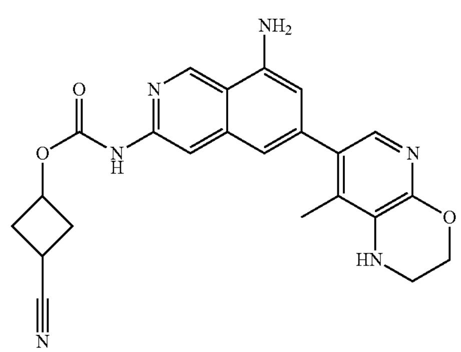 [SMILES: Cc1c(-c2cc(N)c3cnc(NC(=O)OC4CC(C#N)C4)cc3c2)cnc2c1NCCO2] | 3-Cyanocyclobutyl(8-amino-6-(8-methyl-2,3-dihydro-1H-pyrido[2,3-b][1,4]oxazin-7-yl)isoquinolin-3-yl)carbamate |
| 557a | | (1s,3s)-3-Cyanocyclobutyl(8-amino-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 557b | | (1r,3r)-3-Cyanocyclobutyl(8-amino-6-(8-methyl-2,3-dihydro-1H-pyrido[2,3-b][1,4]oxazin-7-yl)isoquinolin-3-yl)carbamate |
| 558 | | 4-Methyltetrahydrofuran-3-yl(8-amino-7-fluoro-6-(8-methyl-2-oxo-2,3-dihydro-1H-pyrido[2,3-b][1,4]oxazin-7-yl)isoquinolin-3-yl)carbamate |
| 558a 558b | | trans-4-Methyltetrahydrofuran-3-yl(8-amino-7-fluoro-6-(8-methyl-2-oxo-2,3-dihydro-1H-pyrido[2,3-b][1,4]oxazin-7-yl)isoquinolin-3-yl)carbamate (3R,4S)-4-Methyltetrahydrofuran-3-yl(8-amino-7-fluoro-6-(8-methyl-2-oxo-2,3-dihydro-1H-pyrido[2,3-b][1,4]oxazin-7-yl)isoquinolin-3-yl)carbamate; (I3S,4R)-4-Methyltetrahydrofuran-3-yl (8-amino-7-fluoro-6-(8-methyl-2-oxo-2,3-dihydro-1H-pyrido[2,3-b][1,4]oxazin-7-yl)isoquinolin-3-yl)carbamate |
| 558c 558d | | cis-4-Methyltetrahydrofuran-3-yl(8-amino-7-fluoro-6-(8-methyl-2-oxo-2,3-dihydro-1H-pyrido[2,3-b][1,4]oxazin-7-yl)isoquinolin-3-yl)carbamate (3R,4R)-4-Methyltetrahydrofuran-3-yl(8-amino-7-fluoro-6-(8-methyl-2-oxo-2,3-dihydro-1H-pyrido[2,3-b][1,4]oxazin-7-yl)isoquinolin-3-yl)carbamate; (3S,4S)-4-Methyltetrahydrofuran-3-yl(8-amino-7-fluoro-6-(8-methyl-2-oxo-2,3-dihydro-1H-pyrido[2,3-b][1,4]oxazin-7-yl)isoquinolin-3-yl)carbamate |
| 559 | | 2-Methylcyclobutyl(8-amino-7-fluoro-6-(8-methyl-2,3-dihydro-1H-pyrido[2,3-b][1,4]oxazin-7-yl)isoquinolin-3-yl)carbamate |
| 559a 559b | | cis-2-Methylcyclobutyl(8-amino-7-fluoro-6-(8-methyl-2,3-dihydro-1H-pyrido[2,3-b][1,4]oxazin-7-yl)isoquinolin-3-yl)carbamate (1R,2S)-2-Methylcyclobutyl(8-amino-7-fluoro-6-(8-methyl-2,3-dihydro-1H-pyrido[2,3-b][1,4]oxazin-7-yl)isoquinolin-3-yl)carbamate; (1S,2R)-2-Methylcyclobutyl(8-amino-7-fluoro-6-(8-methyl-2,3-dihydro-1H-pyrido[2,3-b][1,4]oxazin-7-yl)isoquinolin-3-yl)carbamate |
| 559c 559d | | trans-2-Methylcyclobutyl(8-amino-7-fluoro-6-(8-methyl-2,3-dihydro-1H-pyrido[2,3-b][1,4]oxazin-7- |

US 11,612,606 B2

153                                                                                                          154

TABLE 1-continued

| No. | Structure | Name |
|---|---|---|
|  |  | yl)isoquinolin-3-yl)carbamate (1R,2R)-2-Methylcyclobutyl(8-amino-7-fluoro-6-(8-methyl-2,3-dihydro-1H-pyrido[2,3-b][1,4]oxazin-7-yl)isoquinolin-3-yl)carbamate; (1S,2S)-2-Methylcyclobutyl(8-amino-7-fluoro-6-(8-methyl-2,3-dihydro-1H-pyrido[2,3-b][1,4]oxazin-7-yl)isoquinolin-3-yl)carbamate |
| 560 | 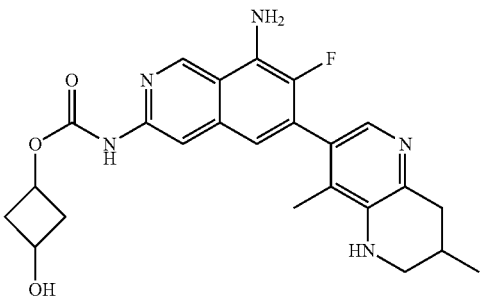 [SMILES: Cc1c(-c2cc3cc(NC(=O)OC4CC(O)C4)ncc3c(N)c2F)cnc2c1NCC(C)C2] | 3-Hydroxycyclobutyl(8-amino-6-(4,7-dimethyl-5,6,7,8-tetrahydro-1,5-naphthyridin-3-yl)-7-fluoroisoquinolin-3-yl)carbamate |
| 560a 560b 560c 560d |  | (1s,3s)-3-Hydroxycyclobutyl(8-amino-6-((S)-4,7-dimethyl-5,6,7,8-tetrahydro-1,5-naphthyridin-3-yl)-7-fluoroisoquinolin-3-yl)carbamate; (1s,3s)-3-Hydroxycyclobutyl(8-amino-6-((R)-4,7-dimethyl-5,6,7,8-tetrahydro-1,5-naphthyridin-3-yl)-7-fluoroisoquinolin-3-yl)carbamate; (1r,3r)-3-Hydroxycyclobutyl(8-amino-6-((S)-4,7-dimethyl-5,6,7,8-tetrahydro-1,5-naphthyridin-3-yl)-7-fluoroisoquinolin-3-yl)carbamate; (1r,3r)-3-Hydroxycyclobutyl(8-amino-6-((R)-4,7-dimethyl-5,6,7,8-tetrahydro-1,5-naphthyridin-3-yl)-7-fluoroisoquinolin-3-yl)carbamate |
| 561 | 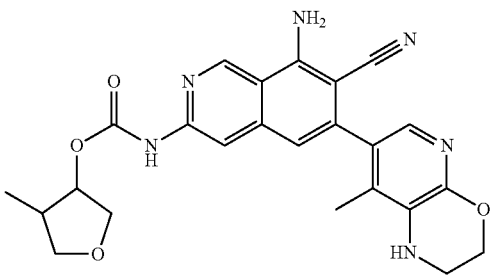 [SMILES: Cc1c(-c2cc3cc(NC(=O)OC4COCC4C)ncc3c(N)c2C#N)cnc2c1NCCO2] | 4-Methyltetrahydrofuran-3-yl(8-amino-7-cyano-6-(8-methyl-2,3-dihydro-1H-pyrido[2,3-b][1,4]oxazin-7-yl)isoquinolin-3-yl)carbamate |
| 561a 561b |  | trans-4-Methyltetrahydrofuran-3-yl(8-amino-7-cyano-6-(8-methyl-2,3-dihydro-1H-pyrido[2,3-b][1,4]oxazin-7-yl)isoquinolin-3-yl)carbamate; (3R,4S)-4-Methyltetrahydrofuran-3-yl(8-amino-7-cyano-6-(8-methyl-2,3-dihydro-1H-pyrido[2,3-b][1,4]oxazin-7-yl)isoquinolin-3-yl)carbamate; (3S,4R)-4-Methyltetrahydrofuran-3-yl(8-amino-7-cyano-6-(8-methyl-2,3-dihydro-1H-pyrido[2,3-b][1,4]oxazin-7-yl)isoquinolin-3-yl)carbamate |
| 561c 561d |  | cis-4-Methyltetrahydrofuran-3-yl(8-amino-7-cyano-6-(8-methyl-2,3-dihydro-1H-pyrido[2,3-b][1,4]oxazin-7-yl)isoquinolin-3-yl)carbamate (3S,4S)-4-Methyltetrahydrofuran-3-yl(8-amino-7-cyano-6-(8-methyl-2,3-dihydro-1H-pyrido[2,3-b][1,4]oxazin-7-yl)isoquinolin-3-yl)carbamate; (3R,4R)-4-Methyltetrahydrofuran-3-yl(8-amino-7-cyano-6-(8-methyl-2,3-dihydro- |

TABLE 1-continued

| No. | Structure | Name |
|---|---|---|
| | | 1H-pyrido[2,3-b][1,4]oxazin-7-yl)isoquinolin-3-yl)carbamate |
| 562 | | Tetrahydrofuran-3-yl(8-amino-6-(4-cyano-5-methyl-3,4-dihydro-2H-pyrano[2,3-b]pyridin-6-yl)-7-fluoroisoquinolin-3-yl)carbamate |
| 562a 562b | | (R)-Tetrahydrofuran-3-yl(8-amino-6-(4-cyano-5-methyl-3,4-dihydro-2H-pyrano[2,3-b]pyridin-6-yl)-7-fluoroisoquinolin-3-yl)carbamate (R)-Tetrahydrofuran-3-yl(8-amino-6-((R)-4-cyano-5-methyl-3,4-dihydro-2H-pyrano[2,3-b]pyridin-6-yl)-7-fluoroisoquinolin-3-yl)carbamate; (R)-Tetrahydrofuran-3-yl(8-amino-6-((S)-4-cyano-5-methyl-3,4-dihydro-2H-pyrano[2,3-b]pyridin-6-yl)-7-fluoroisoquinolin-3-yl)carbamate |
| 562c 562d | | (S)-Tetrahydrofuran-3-yl(8-amino-6-(4-cyano-5-methyl-3,4-dihydro-2H-pyrano[2,3-b]pyridin-6-yl)-7-fluoroisoquinolin-3-yl)carbamate (S)-Tetrahydrofuran-3-yl(8-amino-6-((R)-4-cyano-5-methyl-3,4-dihydro-2H-pyrano[2,3-b]pyridin-6-yl)-7-fluoroisoquinolin-3-yl)carbamate; (S)-tetrahydrofuran-3-yl(8-amino-6-((S)-4-cyano-5-methyl-3,4-dihydro-2H-pyrano[2,3-b]pyridin-6-yl)-7-fluoroisoquinolin-3-yl)carbamate |
| 563 | | Hexahydrofuro[3,4-b]furan-3-yl(8-amino-7-fluoro-6-(8-methyl-2,3-dihydro-1H-pyrido[2,3-b][1,4]oxazin-7-yl)isoquinolin-3-yl)carbamate |
| 563a 563b | | (3S,3aR,6aR)-Hexahydrofuro[3,4-b]furan-3-yl(8-amino-7-fluoro-6-(8-methyl-2,3-dihydro-1H-pyrido[2,3-b][1,4]oxazin-7-yl)isoquinolin-3-yl)carbamate; (3R,3aS,6aS)-Hexahydrofuro[3,4-b]furan-3-yl(8-amino-7-fluoro-6-(8-methyl-2,3-dihydro-1H-pyrido[2,3-b][1,4]oxazin-7-yl)isoquinolin-3-yl)carbamate |
| 563c 563d | | (3R,3aR,6aR)-Hexahydrofuro[3,4-b]furan-3-yl(8-amino-7-fluoro-6-(8-methyl-2,3-dihydro-1H-pyrido[2,3-b][1,4]oxazin-7-yl)isoquinolin-3-yl)carbamate; (3S,3aS,6aS)-Hexahydrofuro[3,4-b]furan-3-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 566 | | 1-(2,2-Difluoroethyl)-3-fluoropiperidin-4-yl(8-amino-7-fluoro-6-(8-methyl-2,3-dihydro-1H-pyrido[2,3-b][1,4]oxazin-7-yl)isoquinolin-3-yl)carbamate |
| 566a 566b | | cis-1-(2,2-Difluoroethyl)-3-fluoropiperidin-4-yl(8-amino-7-fluoro-6-(8-methyl-2,3-dihydro-1H-pyrido[2,3-b][1,4]oxazin-7-yl)isoquinolin-3-yl)carbamate (3S,4R)-1-(2,2-Difluoroethyl)-3-fluoropiperidin-4-yl(8-amino-7-fluoro-6-(8-methyl-2,3-dihydro-1H-pyrido[2,3-b][1,4]oxazin-7-yl)isoquinolin-3-yl)carbamate; (3R,4S)-1-(2,2-Difluoroethyl)-3-fluoropiperidin-4-yl(8-amino-7-fluoro-6-(8-methyl-2,3-dihydro-1H-pyrido[2,3-b][1,4]oxazin-7-yl)isoquinolin-3-yl)carbamate |
| 566c 566d | | trans-1-(2,2-Difluoroethyl)-3-fluoropiperidin-4-yl(8-amino-7-fluoro-6-(8-methyl-2,3-dihydro-1H-pyrido[2,3-b][1,4]oxazin-7-yl)isoquinolin-3-yl)carbamate (3S,4S)-1-(2,2-Difluoroethyl)-3-fluoropiperidin-4-yl(8-amino-7-fluoro-6-(8-methyl-2,3-dihydro-1H-pyrido[2,3-b][1,4]oxazin-7-yl)isoquinolin-3-yl)carbamate; (3R,4R)-1-(2,2-Difluoroethyl)-3-fluoropiperidin-4-yl(8-amino-7-fluoro-6-(8-methyl-2,3-dihydro-1H-pyrido[2,3-b][1,4]oxazin-7-yl)isoquinolin-3-yl)carbamate |
| 567 | | 4-Methyltetrahydrofuran-3-yl(8-amino-7-fluoro-6-(3-fluoro-8-methyl-2,3-dihydro-1H-pyrido[2,3-b][1,4]oxazin-7-yl)isoquinolin-3-yl)carbamate |
| 567a 567b | | (3R,4S)-4-Methyltetrahydrofuran-3-yl(8-amino-7-fluoro-6-(3-fluoro-8-methyl-2,3-dihydro-1H-pyrido[2,3-b][1,4]oxazin-7-yl)isoquinolin-3-yl)carbamate (3R,4S)-4-Methyltetrahydrofuran-3-yl(8-amino-7-fluoro-6-((S)-3-fluoro-8-methyl-2,3-dihydro-1H-pyrido[2,3-b][1,4]oxazin-7-yl)isoquinolin-3-yl)carbamate; (3R,4S)-4-Methyltetrahydrofuran-3-yl(8-amino-7-fluoro-6-((R)-3-fluoro-8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 567c 567d | | (3S,4R)-4-Methyltetrahydrofuran-3-yl(8-amino-7-fluoro-6-(3-fluoro-8-methyl-2,3-dihydro-1H-pyrido[2,3-b][1,4]oxazin-7-yl)isoquinolin-3-yl)carbamate (3S,4R)-4-Methyltetrahydrofuran-3-yl(8-amino-7-fluoro-6-((S)-3-fluoro-8-methyl-2,3-dihydro-1H-pyrido[2,3-b][1,4]oxazin-7-yl)isoquinolin-3-yl)carbamate; (3S,4R)-4-Methyltetrahydrofuran-3-yl(8-amino-7-fluoro-6-((R)-3-fluoro-8-methyl-2,3-dihydro-1H-pyrido[2,3-b][1,4]oxazin-7-yl)isoquinolin-3-yl)carbamate |
| 567e 567f | | (3R,4R)-4-Methyltetrahydrofuran-3-yl(8-amino-7-fluoro-6-(3-fluoro-8-methyl-2,3-dihydro-1H-pyrido[2,3-b][1,4]oxazin-7-yl)isoquinolin-3-yl)carbamate (3R,4R)-4-Methyltetrahydrofuran-3-yl(8-amino-7-fluoro-6-((S)-3-fluoro-8-methyl-2,3-dihydro-1H-pyrido[2,3-b][1,4]oxazin-7-yl)isoquinolin-3-yl)carbamate; (3R,4R)-4-Methyltetrahydrofuran-3-yl(8-amino-7-fluoro-6-((R)-3-fluoro-8-methyl-2,3-dihydro-1H-pyrido[2,3-b][1,4]oxazin-7-yl)isoquinolin-3-yl)carbamate |
| 567g 567h | | (3S,4S)-4-Methyltetrahydrofuran-3-yl(8-amino-7-fluoro-6-(3-fluoro-8-methyl-2,3-dihydro-1H-pyrido[2,3-b][1,4]oxazin-7-yl)isoquinolin-3-yl)carbamate (3S,4S)-4-Methyltetrahydrofuran-3-yl(8-amino-7-fluoro-6-((S)-3-fluoro-8-methyl-2,3-dihydro-1H-pyrido[2,3-b][1,4]oxazin-7-yl)isoquinolin-3-yl)carbamate; (3S,4S)-4-Methyltetrahydrofuran-3-yl(8-amino-7-fluoro-6-((R)-3-fluoro-8-methyl-2,3-dihydro-1H-pyrido[2,3-b][1,4]oxazin-7-yl)isoquinolin-3-yl)carbamate |
| 568 | (structure) | Hexahydrofuro[2,3-b]furan-3-yl(8-amino-7-fluoro-6-(8-methyl-2,3-dihydro-1H-pyrido[2,3-b][1,4]oxazin-7-yl)isoquinolin-3-yl)carbamate |
| 568a 568b | | (3R,3aR,6aS)-Hexahydrofuro[2,3-b]furan-3-yl(8-amino-7-fluoro-6-(8-methyl-2,3-dihydro-1H-pyrido[2,3-b][1,4]oxazin-7-yl)isoquinolin-3-yl)carbamate; (3S,3aS,6aR)-Hexahydrofuro[2,3-b]furan-3-yl(8-amino-7-fluoro-6-(8-methyl-2,3-dihydro-1H-pyrido[2,3-b][1,4]oxazin-7-yl)isoquinolin-3-yl)carbamate |
| 568c 568d | | (3S,3aR,6aS)-Hexahydrofuro[2,3-b]furan-3-yl(8-amino-7-fluoro-6-(8-methyl-2,3-dihydro-1H-pyrido[2,3-b][1,4]oxazin-7-yl)isoquinolin-3-yl)carbamate; (3R,3aS,6aR)-Hexahydrofuro[2,3-b]furan-3-yl(8-amino-7-fluoro-6-(8-methyl-2,3-dihydro-1H-pyrido[2,3-b][1,4]oxazin-7-yl)isoquinolin-3-yl)carbamate |

| No. | Structure | Name |
|---|---|---|
| 569 | 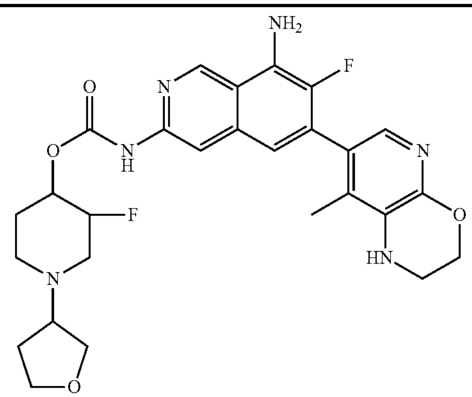 | 3-Fluoro-1-(tetrahydrofuran-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate |
| 569a<br>569b<br>569c<br>569d | | cis-3-Fluoro-1-(tetrahydrofuran-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate<br>(3S,4R)-3-Fluoro-1-((S)-tetrahydrofuran-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate;<br>(3S,4R)-3-Fluoro-1-((R)-tetrahydrofuran-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate;<br>(3R,4S)-3-Fluoro-1-((S)-tetrahydrofuran-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate;<br>(3R,4S)-3-Fluoro-1-((R)-tetrahydrofuran-3-yl)piperidin-4-yl(8-amino-7-fluoro-6-(8-methyl-2,3-dihydro-1H-pyrido[2,3-b][1,4]oxazin-7-yl)isoquinolin-3-yl)carbamate |
| 570 | 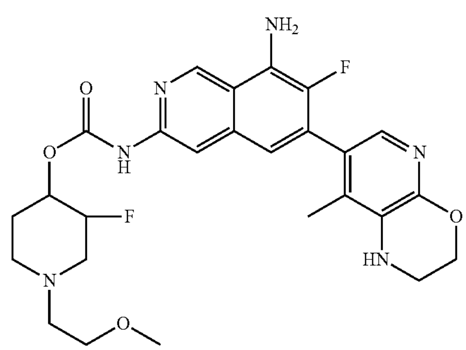 [SMILES: COCCN1CCC(OC(=O)Nc2cc3cc(-c4cnc5c(c4C)NCCO5)c(F)c(N)c3cn2)C(F)C1] | 3-Fluoro-1-(2-methoxyethyl)piperidin-4-yl(8-amino-7-fluoro-6-(8-methyl-2,3-dihydro-1H-pyrido[2,3-b][1,4]oxazin-7-yl)isoquinolin-3-yl)carbamate |
| 570a<br>570b | | (3R,4S)-3-fluoro-1-(2-methoxyethyl)piperidin-4-yl(8-amino-7-fluoro-6-(8-methyl-2,3-dihydro-1H-pyrido[2,3-b][1,4]oxazin-7-yl)isoquinolin-3-yl)carbamate;<br>(3S,4R)-3-Fluoro-1-(2-methoxyethyl)piperidin-4-yl(8-amino-7-fluoro-6-(8-methyl-2,3-dihydro-1H-pyrido[2,3-b][1,4]oxazin-7-yl)isoquinolin-3-yl)carbamate |
| 570c<br>570d | | (3R,4R)-3-Fluoro-1-(2-methoxyethyl)piperidin-4-yl(8-amino-7-fluoro-6-(8-methyl-2,3-dihydro-1H-pyrido[2,3-b][1,4]oxazin-7-yl)isoquinolin-3-yl)carbamate;<br>(3S,4S)-3-fluoro-1-(2- |

TABLE 1-continued

| No. | Structure | Name |
|---|---|---|
| | | methoxyethyl)piperidin-4-yl(8-amino-7-fluoro-6-(8-methyl-2,3-dihydro-1H-pyrido[2,3-b][1,4]oxazin-7-yl)isoquinolin-3-yl)carbamate |
| 571 | 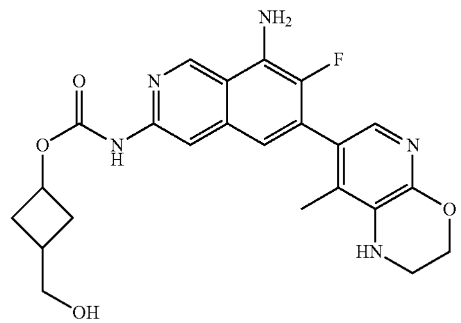 [SMILES: Cc1c(-c2cc3cc(NC(=O)OC4CC(CO)C4)ncc3c(N)c2F)cnc2c1NCCO2] | 3-(Hydroxymethyl)cyclobutyl(8-amino-7-fluoro-6-(8-methyl-2,3-dihydro-1H-pyrido[2,3-b][1,4]oxazin-7-yl)isoquinolin-3-yl)carbamate |
| 571a 571b | | (1r,3r)-3-(Hydroxymethyl)cyclobutyl(8-amino-7-fluoro-6-(8-methyl-2,3-dihydro-1H-pyrido[2,3-b][1,4]oxazin-7-yl)isoquinolin-3-yl)carbamate; (1s,3s)-3-(Hydroxymethyl)cyclobutyl(8-amino-7-fluoro-6-(8-methyl-2,3-dihydro-1H-pyrido[2,3-b][1,4]oxazin-7-yl)isoquinolin-3-yl)carbamate |
| 572 | 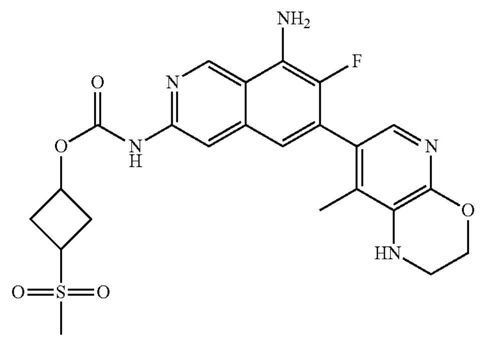 [SMILES: Cc1c(-c2cc3cc(NC(=O)OC4CC(S(C)(=O)=O)C4)ncc3c(N)c2F)cnc2c1NCCO2] | 3-(Methylsulfonyl)cyclobutyl(8-amino-7-fluoro-6-(8-methyl-2,3-dihydro-1H-pyrido[2,3-b][1,4]oxazin-7-yl)isoquinolin-3-yl)carbamate |
| 572a 572b | | (1s,3s)-3-(Methylsulfonyl)cyclobutyl(8-amino-7-fluoro-6-(8-methyl-2,3-dihydro-1H-pyrido[2,3-b][1,4]oxazin-7-yl)isoquinolin-3-yl)carbamate (1r,3r)-3-(Methylsulfonyl)cyclobutyl(8-amino-7-fluoro-6-(8-methyl-2,3-dihydro-1H-pyrido[2,3-b][1,4]oxazin-7-yl)isoquinolin-3-yl)carbamate |
| 573 | 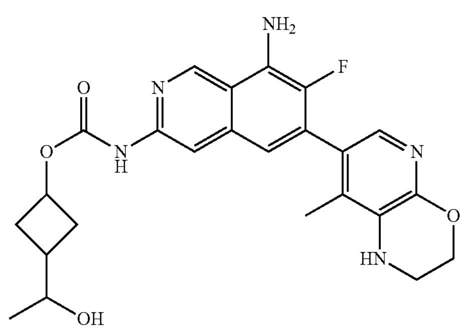 [SMILES: Cc1c(-c2cc3cc(NC(=O)OC4CC(C(C)O)C4)ncc3c(N)c2F)cnc2c1NCCO2] | 3-(1-Hydroxyethyl)cyclobutyl(8-amino-7-fluoro-6-(8-methyl-2,3-dihydro-1H-pyrido[2,3-b][1,4]oxazin-7-yl)isoquinolin-3-yl)carbamate |
| 573a 573b 573c 573d | | (1S,3s)-3-((R)-1-Hydroxyethyl)cyclobutyl(8-amino-7-fluoro-6-(8-methyl-2,3-dihydro-1H-pyrido[2,3-b][1,4]oxazin-7-yl)isoquinolin-3-yl) (1S,3r)-3-((S)-1-Hydroxyethyl)cyclobutyl(8-amino-7-fluoro-6-(8-methyl-2,3- |

TABLE 1-continued

| No. | Structure | Name |
|---|---|---|
| | | dihydro-1H-pyrido[2,3-b][1,4]oxazin-7-yl)isoquinolin-3-yl)carbamate; (1R,3r)-3-((R)-1-Hydroxyethyl)cyclobutyl(8-amino-7-fluoro-6-(8-methyl-2,3-dihydro-1H-pyrido[2,3-b][1,4]oxazin-7-yl)isoquinolin-3-yl)carbamate; (1R,3s)-3-((S)-1-Hydroxyethyl)cyclobutyl(8-amino-7-fluoro-6-(8-methyl-2,3-dihydro-1H-pyrido[2,3-b][1,4]oxazin-7-yl)isoquinolin-3-yl)carbamate |
| 574 | 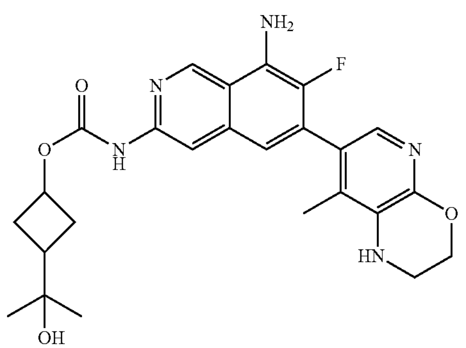 [SMILES: Cc1c(-c2cc3cc(NC(=O)OC4CC(C(C)(C)O)C4)ncc3c(N)c2F)cnc2c1NCCO2] | 3-(2-Hydroxypropan-2-yl)cyclobutyl(8-amino-7-fluoro-6-(8-methyl-2,3-dihydro-1H-pyrido[2,3-b][1,4]oxazin-7-yl)isoquinolin-3-yl)carbamate |
| 574a 574b | | (1r,3r)-3-(2-Hydroxypropan-2-yl)cyclobutyl(8-amino-7-fluoro-6-(8-methyl-2,3-dihydro-1H-pyrido[2,3-b][1,4]oxazin-7-yl)isoquinolin-3-yl)carbamate; (1s,3s)-3-(2-Hydroxypropan-2-yl)cyclobutyl(8-amino-7-fluoro-6-(8-methyl-2,3-dihydro-1H-pyrido[2,3-b][1,4]oxazin-7-yl)isoquinolin-3-yl)carbamate |
| 575 | 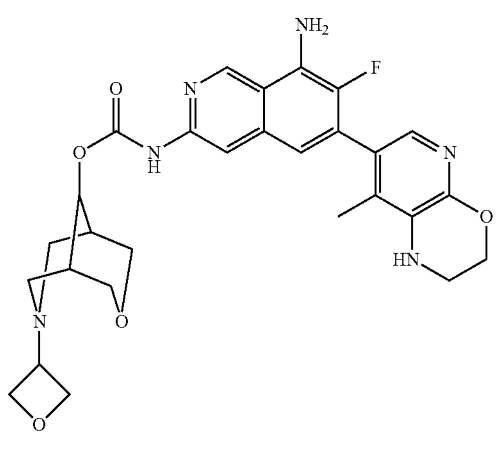 [SMILES: Cc1c(-c2cc3cc(NC(=O)OC4C5COCC4CN(C4COC4)C5)ncc3c(N)c2F)cnc2c1NCCO2] | 7-(Oxetan-3-yl)-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl)carbamate |
| 575a 575b | | (1R,5S,9s)-7-(Oxetan-3-yl)-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl)carbamate; (1R,5S,9r)-7-(oxetan-3-yl)-3-oxa-7-azabicyclo[3.3.1]nonan-9-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 576 | 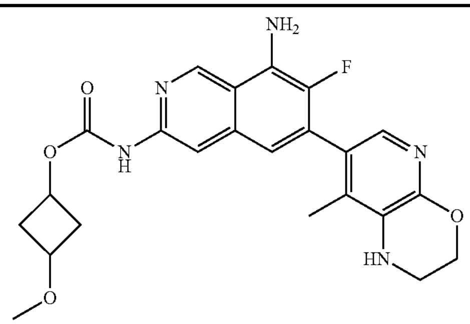 | 3-Methoxycyclobutyl(8-amino-7-fluoro-6-(8-methyl-2,3-dihydro-1H-pyrido[2,3-b][1,4]oxazin-7-yl)isoquinolin-3-yl)carbamate |
| 576a 576b | | (1r,3r)-3-Methoxycyclobutyl(8-amino-7-fluoro-6-(8-methyl-2,3-dihydro-1H-pyrido[2,3-b][1,4]oxazin-7-yl)isoquinolin-3-yl)carbamate; (1s,3s)-3-Methoxycyclobutyl(8-amino-7-fluoro-6-(8-methyl-2,3-dihydro-1H-pyrido[2,3-b][1,4]oxazin-7-yl)isoquinolin-3-yl)carbamate |
| 577 | 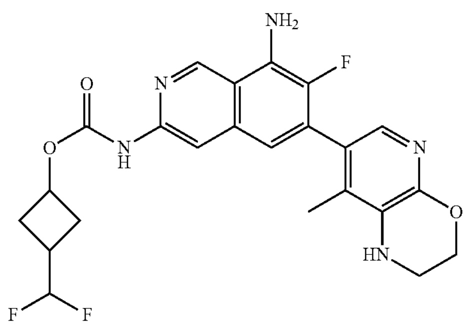 [SMILES: Cc1c(-c2cc3cc(NC(=O)OC4CC(C(F)F)C4)ncc3c(N)c2F)cnc2c1NCCO2] | 3-(Difluoromethyl)cyclobutyl(8-amino-7-fluoro-6-(8-methyl-2,3-dihydro-1H-pyrido[2,3-b][1,4]oxazin-7-yl)isoquinolin-3-yl)carbamate |
| 577a 577b | | (1s,3s)-3-(Difluoromethyl)cyclobutyl(8-amino-7-fluoro-6-(8-methyl-2,3-dihydro-1H-pyrido[2,3-b][1,4]oxazin-7-yl)isoquinolin-3-yl)carbamate; (1r,3r)-3-(Difluoromethyl)cyclobutyl(8-amino-7-fluoro-6-(8-methyl-2,3-dihydro-1H-pyrido[2,3-b][1,4]oxazin-7-yl)isoquinolin-3-yl)carbamate |
| 578 | 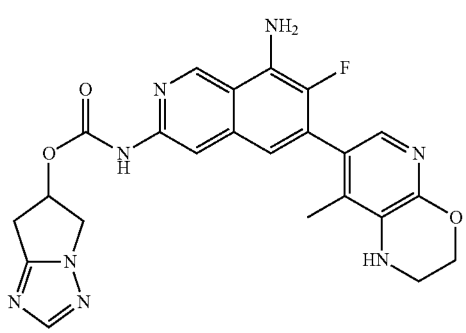 [SMILES: Cc1c(-c2cc3cc(NC(=O)OC4Cc5ncnn5C4)ncc3c(N)c2F)cnc2c1NCCO2] | 6,7-Dihydro-5H-pyrrolo[1,2-b][1,2,4]triazol-6-yl(8-amino-7-fluoro-6-(8-methyl-2,3-dihydro-1H-pyrido[2,3-b][1,4]oxazin-7-yl)isoquinolin-3-yl)carbamate |
| 578a 578b | | (R)-6,7-Dihydro-5H-pyrrolo[1,2-b][1,2,4]triazol-6-yl(8-amino-7-fluoro-6-(8-methyl-2,3-dihydro-1H-pyrido[2,3-b][1,4]oxazin-7-yl)isoquinolin-3-yl)carbamate; (S)-6,7-Dihydro-5H-pyrrolo[1,2-b][1,2,4]triazol-6-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 579 | | 1,1-Dioxidotetrahydro-2H-thiopyran-4-yl (8-amino-7-fluoro-6-(4-methyl-5,6,7,8-tetrahydro-1,5-naphthyridin-3-yl)isoquinolin-3-yl)carbamate |
| 580 | | 7-Azaspiro[3.5]nonan-2-yl(8-amino-7-fluoro-6-(8-methyl-2,3-dihydro-1H-pyrido[2,3-b][1,4]oxazin-7-yl)isoquinolin-3-yl)carbamate |
| 581 | | Tetrahydrofuran-3-yl(8-amino-7-fluoro-6-(7-(hydroxymethyl)-4-methyl-5,6,7,8-tetrahydro-1,5-naphthyridin-3-yl)isoquinolin-3-yl)carbamate |
| 581a | | (R)-tetrahydrofuran-3-yl(8-amino-7-fluoro-6-(7-(hydroxymethyl)-4-methyl-5,6,7,8-tetrahydro-1,5-naphthyridin-3-yl)isoquinolin-3-yl)carbamate |
| 581b | | (R)-tetrahydrofuran-3-yl(8-amino-7-fluoro-6-((R)-7-(hydroxymethyl)-4-methyl-5,6,7,8-tetrahydro-1,5-naphthyridin-3-yl)isoquinolin-3-yl)carbamate (R)-tetrahydrofuran-3-yl(8-amino-7-fluoro-6-((S)-7-(hydroxymethyl)-4-methyl-5,6,7,8-tetrahydro-1,5-naphthyridin-3-yl)isoquinolin-3-yl)carbamate |
| 581c | | (S)-Tetrahydrofuran-3-yl(8-amino-7-fluoro-6-(7-(hydroxymethyl)-4-methyl-5,6,7,8-tetrahydro-1,5-naphthyridin-3-yl)isoquinolin-3-yl)carbamate |
| 581d | | (S)-Tetrahydrofuran-3-yl(8-amino-7-fluoro-6-((R)-7-(hydroxymethyl)-4-methyl-5,6,7,8-tetrahydro-1,5-naphthyridin-3-yl)isoquinolin-3-yl)carbamate; (S)-tetrahydrofuran-3-yl(8-amino-7-fluoro-6-((S)-7-(hydroxymethyl)-4-methyl-5,6,7,8-tetrahydro-1,5-naphthyridin-3-yl)isoquinolin-3-yl)carbamate |

TABLE 1-continued

| No. | Structure | Name |
|---|---|---|
| 582 | | 3-Hydroxycyclopentyl(8-amino-7-fluoro-6-(8-methyl-2,3-dihydro-1H-pyrido[2,3-b][1,4]oxazin-7-yl)isoquinolin-3-yl)carbamate |
| 582a 582b | | cis-3-Hydroxycyclopentyl(8-amino-7-fluoro-6-(8-methyl-2,3-dihydro-1H-pyrido[2,3-b][1,4]oxazin-7-yl)isoquinolin-3-yl)carbamate (1S,3R)-3-Hydroxycyclopentyl(8-amino-7-fluoro-6-(8-methyl-2,3-dihydro-1H-pyrido[2,3-b][1,4]oxazin-7-yl)isoquinolin-3-yl)carbamate; (1R,3S)-3-Hydroxycyclopentyl(8-amino-7-fluoro-6-(8-methyl-2,3-dihydro-1H-pyrido[2,3-b][1,4]oxazin-7-yl)isoquinolin-3-yl)carbamate |
| 582c 582d | | trans-3-Hydroxycyclopentyl(8-amino-7-fluoro-6-(8-methyl-2,3-dihydro-1H-pyrido[2,3-b][1,4]oxazin-7-yl)isoquinolin-3-yl)carbamate (1S,3S)-3-Hydroxycyclopentyl(8-amino-7-fluoro-6-(8-methyl-2,3-dihydro-1H-pyrido[2,3-b][1,4]oxazin-7-yl)isoquinolin-3-yl)carbamate; (1R,3R)-3-Hydroxycyclopentyl(8-amino-7-fluoro-6-(8-methyl-2,3-dihydro-1H-pyrido[2,3-b][1,4]oxazin-7-yl)isoquinolin-3-yl)carbamate |
| 583 | | 3-Methoxytetrahydro-2H-pyran-4-yl(8-amino-7-fluoro-6-(8-methyl-2,3-dihydro-1H-pyrido[2,3-b][1,4]oxazin-7-yl)isoquinolin-3-yl)carbamate |
| 583a 583b 583c 583d | | (3S,4S)-3-Methoxytetrahydro-2H-pyran-4-yl(8-amino-7-fluoro-6-(8-methyl-2,3-dihydro-1H-pyrido[2,3-b][1,4]oxazin-7-yl)isoquinolin-3-yl)carbamate (3S,4R)-3-Methoxytetrahydro-2H-pyran-4-yl(8-amino-7-fluoro-6-(8-methyl-2,3-dihydro-1H-pyrido[2,3-b][1,4]oxazin-7-yl)isoquinolin-3-yl)carbamate (3R,4S)-3-Methoxytetrahydro-2H-pyran-4-yl(8-amino-7-fluoro-6-(8-methyl-2,3-dihydro-1H-pyrido[2,3-b][1,4]oxazin-7-yl)isoquinolin-3-yl)carbamate (3R,4R)-3-Methoxytetrahydro-2H-pyran-4-yl(8-amino-7-fluoro-6-(8-methyl-2,3-dihydro-1H-pyrido[2,3-b][1,4]oxazin-7-yl)isoquinolin-3-yl)carbamate |

TABLE 1-continued

| No. | Structure | Name |
|---|---|---|
| 584 | 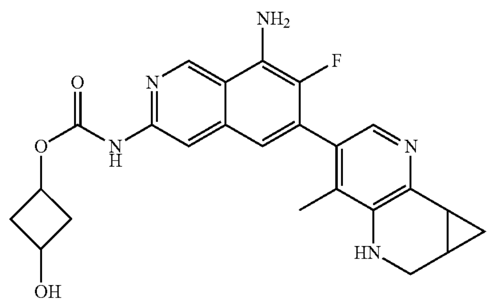 [SMILES: Cc1c(-c2cc3cc(NC(=O)OC4CC(O)C4)ncc3c(N)c2F)cnc2c1NCC1CC21] | 3-Hydroxycyclobutyl(8-amino-7-fluoro-6-(4-methyl-6,6a,7,7a-tetrahydro-5H-cyclopropa[c][1,5]naphthyridin-3-yl)isoquinolin-3-yl)carbamate |
| 584a 584b 584c 584d | | (1s,3R)-3-Hydroxycyclobutyl(8-amino-7-fluoro-6-((6aR,7aS)-4-methyl-6,6a,7,7a-tetrahydro-5H-cyclopropa[c][1,5]naphthyridin-3-yl)isoquinolin-3-yl)carbamate; (1s,3S)-3-Hydroxycyclobutyl(8-amino-7-fluoro-646aS,7aR)-4-methyl-6,6a,7,7a-tetrahydro-5H-cyclopropa[c][1,5]naphthyridin-3-yl)isoquinolin-3-yl)carbamate; (1r,3S)-3-Hydroxycyclobutyl(8-amino-7-fluoro-6-((6aR,7aS)-4-methyl-6,6a,7,7a-tetrahydro-5H-cyclopropa[c][1,5]naphthyridin-3-yl)isoquinolin-3-yl)carbamate (1r,3R)-3-hydroxycyclobutyl(8-amino-7-fluoro-6-((6aS,7aR)-4-methyl-6,6a,7,7a-tetrahydro-5H-cyclopropa[c][1,5]naphthyridin-3-yl)isoquinolin-3-yl)carbamate |
| 601 | 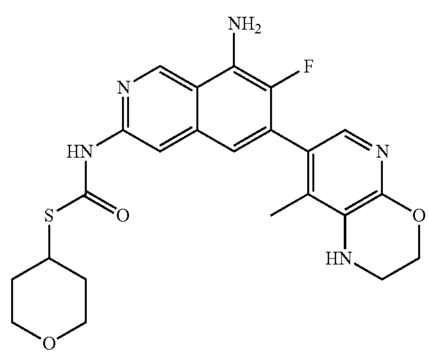 [SMILES: Cc1c(-c2cc3cc(NC(=O)SC4CCOCC4)ncc3c(N)c2F)cnc2c1NCCO2] | S-(Tetrahydro-2H-pyran-4-yl)(8-amino-7-fluoro-6-(8-methyl-2,3-dihydro-1H-pyrido[2,3-b][1,4]oxazin-7-yl)isoquinolin-3-yl)carbamothioate |
| 701 | 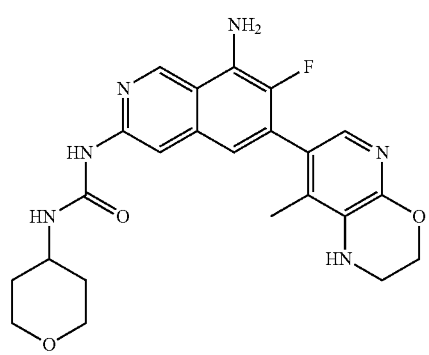 [SMILES: Cc1c(-c2cc3cc(NC(=O)NC4CCOCC4)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(tetrahydro-2H-pyran-4-yl)urea |

TABLE 1-continued

| No. | Structure | Name |
|---|---|---|
| 702 | 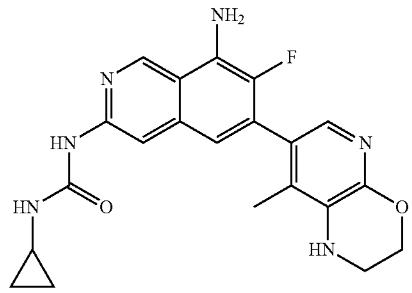 [SMILES: Cc1c(-c2cc3cc(NC(=O)NC4CC4)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-cyclopropylurea |
| 703 | 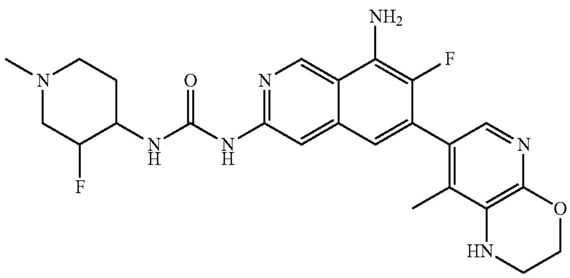 [SMILES: Cc1c(-c2cc3cc(NC(=O)NC4CCN(C)CC4F)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(3-fluoro-1-methylpiperidin-4-yl)urea |
| 703a 703b | | 1-(8-Amino-7-fluoro-6-(8-methyl-2,3-dihydro-1H-pyrido[2,3-b][1,4]oxazin-7-yl)isoquinolin-3-yl)-3-((3R,4R)-3-fluoro-1-methylpiperidin-4-yl)urea; 1-(8-Amino-7-fluoro-6-(8-methyl-2,3-dihydro-1H-pyrido[2,3-b][1,4]oxazin-7-yl)isoquinolin-3-yl)-3-((3S,4S)-3-fluoro-1-methylpiperidin-4-yl)urea |
| 703c | | 1-(8-Amino-7-fluoro-6-(8-methyl-2,3-dihydro-1H-pyrido[2,3-b][1,4]oxazin-7-yl)isoquinolin-3-yl)-3-((cis)-3-fluoro-1-methylpiperidin-4-yl)urea |
| 704 | 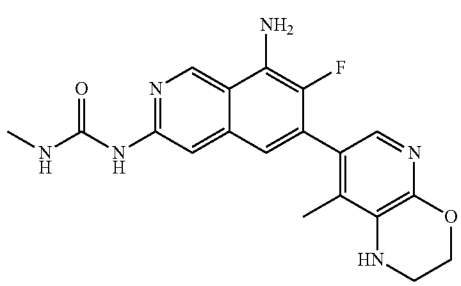 [SMILES: CNC(=O)Nc1cc2cc(-c3cnc4c(c3C)NCCO4)c(F)c(N)c2cn1] | 1-(8-Amino-7-fluoro-6-(8-methyl-2,3-dihydro-1H-pyrido[2,3-b][1,4]oxazin-7-yl)isoquinolin-3-yl)-3-methylurea |
| 705 | 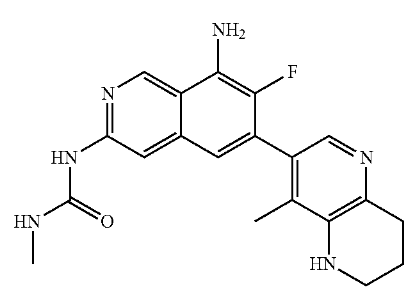 [SMILES: CNC(=O)Nc1cc2cc(-c3cnc4c(c3C)NCCC4)c(F)c(N)c2cn1] | 1-(8-Amino-7-fluoro-6-(4-methyl-5,6,7,8-tetrahydro-1,5-naphthyridin-3-yl)isoquinolin-3-yl)-3-methylurea |

TABLE 1-continued

| No. | Structure | Name |
|---|---|---|
| 706 | 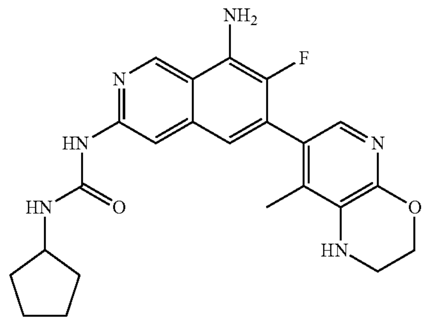 [SMILES: Cc1c(-c2cc3cc(NC(=O)NC4CCCC4)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-cyclopentylurea |
| 707 | 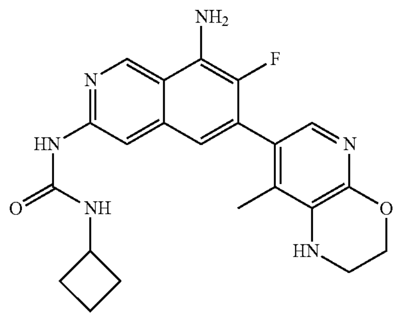 [SMILES: Cc1c(-c2cc3cc(NC(=O)NC4CCC4)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-cyclobutylurea |
| 708 | 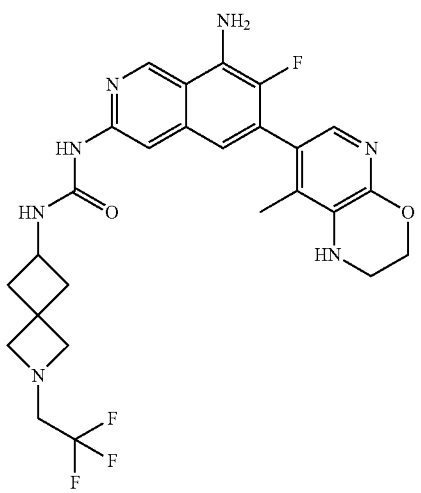 [SMILES: Cc1c(-c2cc3cc(NC(=O)NC4CC5(C4)CN(CC(F)(F)F)C5)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(2-(2,2,2-trifluoroethyl)-2-azaspiro[3.3]heptan-6-yl)urea |
| 709 | 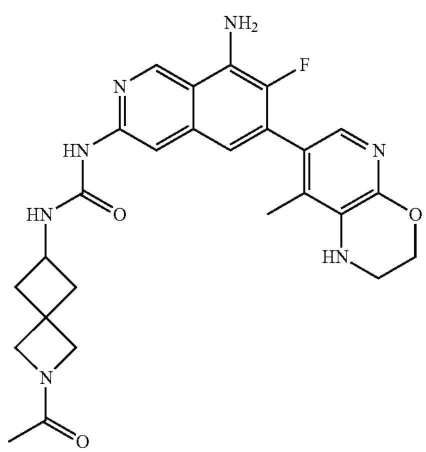 [SMILES: CC(=O)N1CC2(CC(NC(=O)Nc3cc4cc(-c5cnc6c(c5C)NCCO6)c(F)c(N)c4cn3)C2)C1] | 1-(2-Acetyl-2-azaspiro[3.3]heptan-6-yl)-3-(8-amino-7-fluoro-6-(8-methyl-2,3-dihydro-1H-pyrido[2,3-b][1,4]oxazin-7-yl)isoquinolin-3-yl)urea |

TABLE 1-continued

| No. | Structure | Name |
|---|---|---|
| 710 | 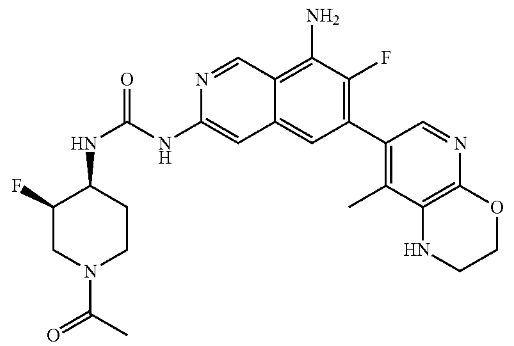 [SMILES: CC(=O)N1CC[C@H](NC(=O)Nc2cc3cc(-c4cnc5c(c4C)NCCO5)c(F)c(N)c3cn2)[C@H](F)C1] | 1-((cis)-1-Acetyl-3-fluoropiperidin-4-yl)-3-(8-amino-7-fluoro-6-(8-methyl-2,3-dihydro-1H-pyrido[2,3-b][1,4]oxazin-7-yl)isoquinolin-3-yl)urea |
| 710a 710b | | 1-((3R,4S)-1-Acetyl-3-fluoropiperidin-4-yl)-3-(8-amino-7-fluoro-6-(8-methyl-2,3-dihydro-1H-pyrido[2,3-b][1,4]oxazin-7-yl)isoquinolin-3-yl)urea; 1-((3S,4R)-1-Acetyl-3-fluoropiperidin-4-yl)-3-(8-amino-7-fluoro-6-(8-methyl-2,3-dihydro-1H-pyrido[2,3-b][1,4]oxazin-7-yl)isoquinolin-3-yl)urea |
| 711 | 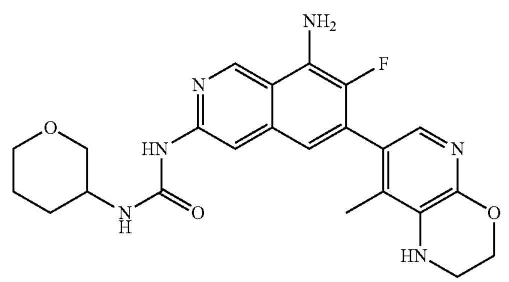 [SMILES: Cc1c(-c2cc3cc(NC(=O)NC4CCCOC4)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(tetrahydro-2H-pyran-3-yl)urea |
| 711a 711b | | (S)-1-(8-Amino-7-fluoro-6-(8-methyl-2,3-dihydro-1H-pyrido[2,3-b][1,4]oxazin-7-yl)isoquinolin-3-yl)-3-(tetrahydro-2H-pyran-3-yl)urea; (R)-1-(8-Amino-7-fluoro-6-(8-methyl-2,3-dihydro-1H-pyrido[2,3-b][1,4]oxazin-7-yl)isoquinolin-3-yl)-3-(tetrahydro-2H-pyran-3-yl)urea |
| 712 | 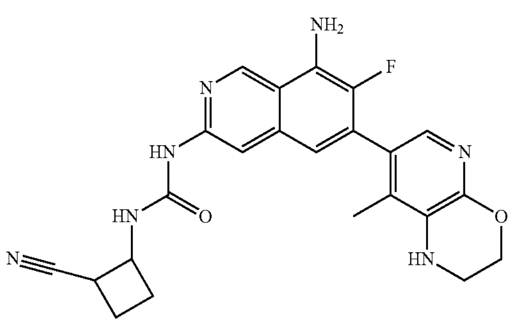 [SMILES: Cc1c(-c2cc3cc(NC(=O)NC4CCC4C#N)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(2-cyanocyclobutyl)urea |
| 712a 712b | | 1-(8-Amino-7-fluoro-6-(8-methyl-2,3-dihydro-1H-pyrido[2,3-b][1,4]oxazin-7-yl)isoquinolin-3-yl)-3-(trans-2-cyanocyclobutyl)urea 1-(8-Amino-7-fluoro-6-(8-methyl-2,3-dihydro-1H-pyrido[2,3-b][1,4]oxazin-7-yl)isoquinolin-3-yl)-3-((1S,2S)-2-cyanocyclobutyl)urea; 1-(8-Amino-7-fluoro-6-(8-methyl-2,3-dihydro-1H-pyrido[2,3-b][1,4]oxazin-7-yl)isoquinolin-3-yl)-3-((1R,2R)-2-cyanocyclobutyl)urea |

TABLE 1-continued

| No. | Structure | Name |
|---|---|---|
| 712c 712d | | 1-(8-Amino-7-fluoro-6-(8-methyl-2,3-dihydro-1H-pyrido[2,3-b][1,4]oxazin-7-yl)isoquinolin-3-yl)-3-(cis-2-cyanocyclobutyl)urea 1-(8-Amino-7-fluoro-6-(8-methyl-2,3-dihydro-1H-pyrido[2,3-b][1,4]oxazin-7-yl)isoquinolin-3-yl)-3-((1S,2R)-2-cyanocyclobutyl)urea; 1-(8-Amino-7-fluoro-6-(8-methyl-2,3-dihydro-1H-pyrido[2,3-b][1,4]oxazin-7-yl)isoquinolin-3-yl)-3-((1R,2S)-2-cyanocyclobutyl)urea |
| 713 | 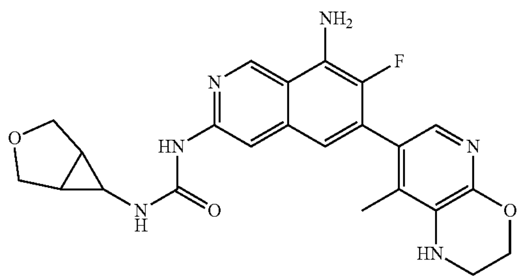 [SMILES: Cc1c(-c2cc3cc(NC(=O)NC4C5COCC54)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(3-oxabicyclo[3.1.0]hexan-6-yl)urea |
| 713a 713b | | 1-(8-Amino-7-fluoro-6-(8-methyl-2,3-dihydro-1H-pyrido[2,3-b][1,4]oxazin-7-yl)isoquinolin-3-yl)-3-((1R,5S,6r)-3-oxabicyclo[3.1.0]hexan-6-yl)urea; 1-(8-Amino-7-fluoro-6-(8-methyl-2,3-dihydro-1H-pyrido[2,3-b][1,4]oxazin-7-yl)isoquinolin-3-yl)-3-((1R,5S,6s)-3-oxabicyclo[3.1.0]hexan-6-yl)urea |
| 714 | 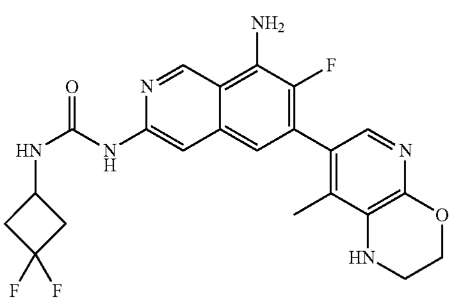 [SMILES: Cc1c(-c2cc3cc(NC(=O)NC4CC(F)(F)C4)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(3,3-difluorocyclobutyl)urea |
| 715 | 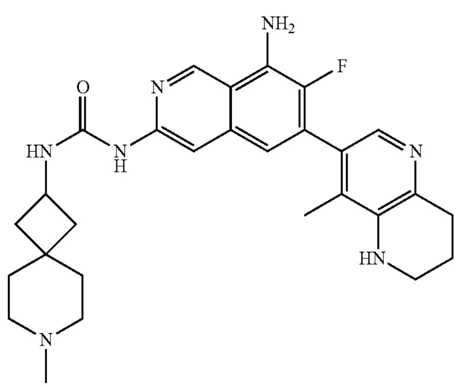 | 1-(8-Amino-7-fluoro-6-(4-methyl-5,6,7,8-tetrahydro-1,5-naphthyridin-3-yl)isoquinolin-3-yl)-3-(7-methyl-7-azaspiro[3.5]nonan-2-yl)urea |

TABLE 1-continued

| No. | Structure | Name |
|---|---|---|
| 716 | 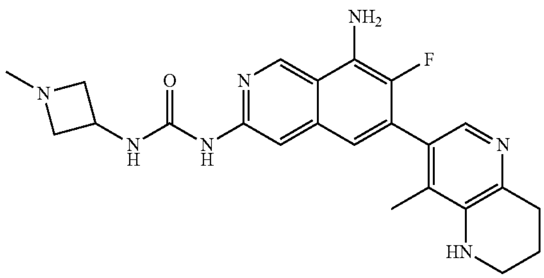 [SMILES: Cc1c(-c2cc3cc(NC(=O)NC4CN(C)C4)ncc3c(N)c2F)cnc2c1NCCC2] | 1-(8-Amino-7-fluoro-6-(4-methyl-5,6,7,8-tetrahydro-1,5-naphthyridin-3-yl)isoquinolin-3-yl)-3-(1-methylazetidin-3-yl)urea |
| 717 | 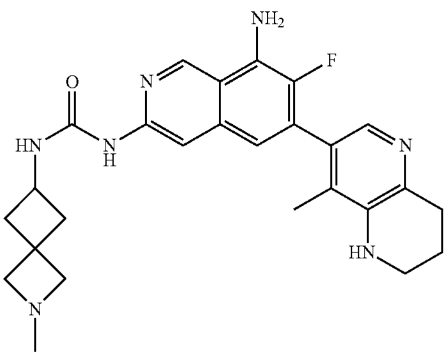 [SMILES: Cc1c(-c2cc3cc(NC(=O)NC4CC5(C4)CN(C)C5)ncc3c(N)c2F)cnc2c1NCCC2] | 1-(8-Amino-7-fluoro-6-(4-methyl-5,6,7,8-tetrahydro-1,5-naphthyridin-3-yl)isoquinolin-3-yl)-3-(2-methyl-2-azaspiro[3.3]heptan-6-yl)urea |
| 718 | 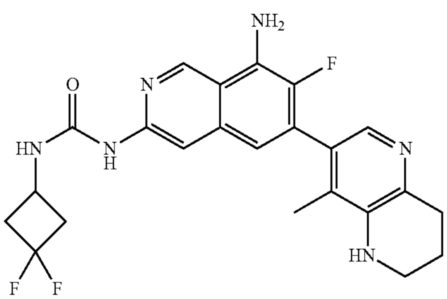 [SMILES: Cc1c(-c2cc3cc(NC(=O)NC4CC(F)(F)C4)ncc3c(N)c2F)cnc2c1NCCC2] | 1-(8-Amino-7-fluoro-6-(4-methyl-5,6,7,8-tetrahydro-1,5-naphthyridin-3-yl)isoquinolin-3-yl)-3-(3,3-difluorocyclobutyl)urea |
| 719 | 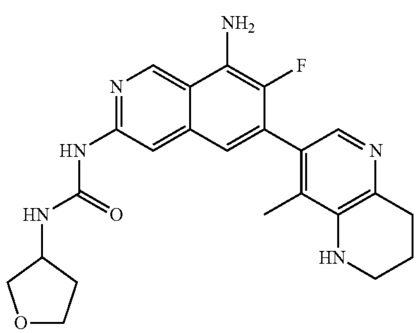 [SMILES: Cc1c(-c2cc3cc(NC(=O)NC4CCOC4)ncc3c(N)c2F)cnc2c1NCCC2] | 1-(8-Amino-7-fluoro-6-(4-methyl-5,6,7,8-tetrahydro-1,5-naphthyridin-3-yl)isoquinolin-3-yl)-3-(tetrahydrofuran-3-yl)urea |
| 719a 719b | | (R)-1-(8-Amino-7-fluoro-6-(4-methyl-5,6,7,8-tetrahydro-1,5-naphthyridin-3-yl)isoquinolin-3-yl)-3-(tetrahydrofuran-3-yl)urea; (S)-1-(8-Amino-7-fluoro-6-(4-methyl-5,6,7,8-tetrahydro-1,5-naphthyridin-3-yl)isoquinolin-3-yl)-3-(tetrahydrofuran-3-yl)urea |

TABLE 1-continued

| No. | Structure | Name |
|---|---|---|
| 720 | 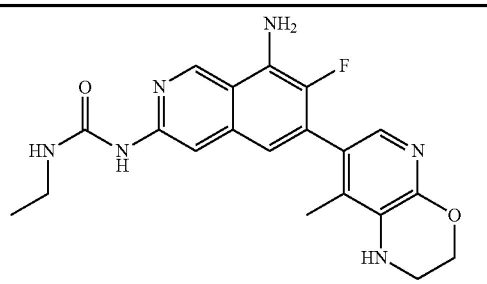 | 1-(8-Amino-7-fluoro-6-(8-methyl-2,3-dihydro-1H-pyrido[2,3-b][1,4]oxazin-7-yl)isoquinolin-3-yl)-3-ethylurea |
| 721 | 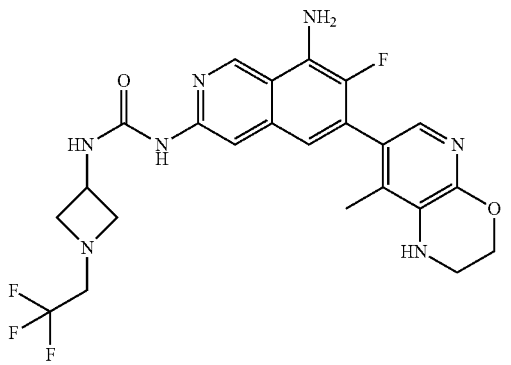 [SMILES: Cc1c(-c2cc3cc(NC(=O)NC4CN(CC(F)(F)F)C4)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(1-(2,2,2-trifluoroethyl)azetidin-3-yl)urea |
| 722 | 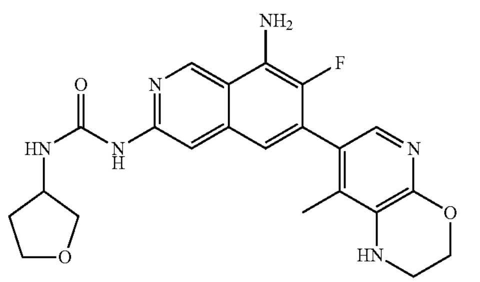 [SMILES: Cc1c(-c2cc3cc(NC(=O)NC4CCOC4)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(tetrahydrofuran-3-yl)urea |
| 722a 722b | | (R)-1-(8-Amino-7-fluoro-6-(8-methyl-2,3-dihydro-1H-pyrido[2,3-b][1,4]oxazin-7-yl)isoquinolin-3-yl)-3-(tetrahydrofuran-3-yl)urea; (S)-1-(8-Amino-7-fluoro-6-(8-methyl-2,3-dihydro-1H-pyrido[2,3-b][1,4]oxazin-7-yl)isoquinolin-3-yl)-3-(tetrahydrofuran-3-yl)urea |
| 723 | 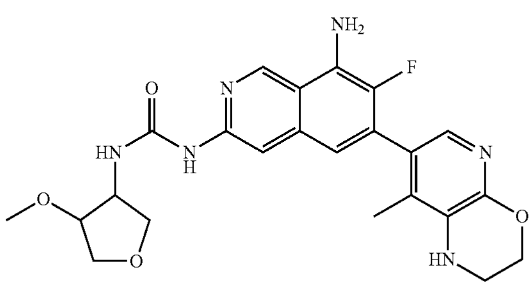 [SMILES: COC1CCCC1NC(=O)Nc1cc2cc(-c3cnc4c(c3C)NCCO4)c(F)c(N)c2cn1] | 1-(8-Amino-7-fluoro-6-(8-methyl-2,3-dihydro-1H-pyrido[2,3-b][1,4]oxazin-7-yl)isoquinolin-3-yl)-3-(4-methoxytetrahydrofuran-3-yl)urea |
| 723a 723b | | 1-(8-Amino-7-fluoro-6-(8-methyl-2,3-dihydro-1H-pyrido[2,3-b][1,4]oxazin-7-yl)isoquinolin-3-yl)-3-((cis-4-methoxytetrahydrofuran-3-yl)urea 1-(8-Amino-7-fluoro-6-(8-methyl-2,3-dihydro-1H-pyrido[2,3-b][1,4]oxazin-7-yl)isoquinolin-3-yl)-3-((3S,4S)-4-methoxytetrahydrofuran-3-yl)urea; 1-(8-Amino-7-fluoro-6-(8-methyl-2,3-dihydro-1H-pyrido[2,3-b][1,4]oxazin-7- |

TABLE 1-continued

| No. | Structure | Name |
|---|---|---|
| 723c | | yl)isoquinolin-3-yl)-3-((3R,4R)-4-methoxytetrahydrofuran-3-yl)urea 1-(8-Amino-7-fluoro-6-(8-methyl-2,3-dihydro-1H-pyrido[2,3-b][1,4]oxazin-7-yl)isoquinolin-3-yl)-3-((trans-4-methoxytetrahydrofuran-3-yl)urea |
| 723d | | 1-(8-Amino-7-fluoro-6-(8-methyl-2,3-dihydro-1H-pyrido[2,3-b][1,4]oxazin-7-yl)isoquinolin-3-yl)-3-((3S,4R)-4-methoxytetrahydrofuran-3-yl)urea; 1-(8-Amino-7-fluoro-6-(8-methyl-2,3-dihydro-1H-pyrido[2,3-b][1,4]oxazin-7-yl)isoquinolin-3-yl)-3-((3R,4S)-4-methoxytetrahydrofuran-3-yl)urea |
| 724 | | 1-(8-Amino-7-fluoro-6-(8-methyl-2,3-dihydro-1H-pyrido[2,3-b][1,4]oxazin-7-yl)isoquinolin-3-yl)-3-(4-fluorotetrahydrofuran-3-yl)urea |
| 724a | | 1-(8-Amino-7-fluoro-6-(8-methyl-2,3-dihydro-1H-pyrido[2,3-b][1,4]oxazin-7-yl)isoquinolin-3-yl)-3-(cis-4-fluorotetrahydrofuran-3-yl)urea |
| 724b | | 1-(8-amino-7-fluoro-6-(8-methyl-2,3-dihydro-1H-pyrido[2,3-b][1,4]oxazin-7-yl)isoquinolin-3-yl)-3-((3S,4S)-4-fluorotetrahydrofuran-3-yl)urea; 1-(8-amino-7-fluoro-6-(8-methyl-2,3-dihydro-1H-pyrido[2,3-b][1,4]oxazin-7-yl)isoquinolin-3-yl)-3-((3R,4R)-4-fluorotetrahydrofuran-3-yl)urea |
| 725 | | 1-(8-Amino-7-fluoro-6-(4-methyl-5,6,7,8-tetrahydro-1,5-naphthyridin-3-yl)isoquinolin-3-yl)-3-(1-methyl-5-oxopyrrolidin-3-yl)urea |
| 726 | | 1-(8-Amino-7-fluoro-6-(8-methyl-2,3-dihydro-1H-pyrido[2,3-b][1,4]oxazin-7-yl)isoquinolin-3-yl)-3-(3-cyanocyclopentyl)urea |
| 726a 726b | | 1-(8-Amino-7-fluoro-6-(8-methyl-2,3-dihydro-1H-pyrido[2,3-b][1,4]oxazin-7- |

| No. | Structure | Name |
|---|---|---|
| | | yl)isoquinolin-3-yl)-3-(cis-3-cyanocyclopentyl)urea |
| | | 1-(8-Amino-7-fluoro-6-(8-methyl-2,3-dihydro-1H-pyrido[2,3-b][1,4]oxazin-7-yl)isoquinolin-3-yl)-3-((1R,3S)-3-cyanocyclopentyl)urea |
| | | 1-(8-Amino-7-fluoro-6-(8-methyl-2,3-dihydro-1H-pyrido[2,3-b][1,4]oxazin-7-yl)isoquinolin-3-yl)-3-((1S,3R)-3-cyanocyclopentyl)urea |
| 726c 726d | | 1-(8-Amino-7-fluoro-6-(8-methyl-2,3-dihydro-1H-pyrido[2,3-b][1,4]oxazin-7-yl)isoquinolin-3-yl)-3-(trans-3-cyanocyclopentyl)urea |
| | | 1-(8-Amino-7-fluoro-6-(8-methyl-2,3-dihydro-1H-pyrido[2,3-b][1,4]oxazin-7-yl)isoquinolin-3-yl)-3-((1R,3R)-3-cyanocyclopentyl)urea |
| | | 1-(8-Amino-7-fluoro-6-(8-methyl-2,3-dihydro-1H-pyrido[2,3-b][1,4]oxazin-7-yl)isoquinolin-3-yl)-3-((1S,3S)-3-cyanocyclopentyl)urea |
| 727 | (structure) | 1-(8-Amino-7-fluoro-6-(8-methyl-2,3-dihydro-1H-pyrido[2,3-b][1,4]oxazin-7-yl)isoquinolin-3-yl)-3-(2-fluorocyclopentyl)urea |
| 727a 727b | | 1-(8-Amino-7-fluoro-6-(8-methyl-2,3-dihydro-1H-pyrido[2,3-b][1,4]oxazin-7-yl)isoquinolin-3-yl)-3-(cis-2-fluorocyclopentyl)urea |
| | | 1-(8-Amino-7-fluoro-6-(8-methyl-2,3-dihydro-1H-pyrido[2,3-b][1,4]oxazin-7-yl)isoquinolin-3-yl)-3-((1R,2S)-2-fluorocyclopentyl)urea; |
| | | 1-(8-Amino-7-fluoro-6-(8-methyl-2,3-dihydro-1H-pyrido[2,3-b][1,4]oxazin-7-yl)isoquinolin-3-yl)-3-((1S,2R)-2-fluorocyclopentyl)urea |
| 727c 727d | | 1-(8-Amino-7-fluoro-6-(8-methyl-2,3-dihydro-1H-pyrido[2,3-b][1,4]oxazin-7-yl)isoquinolin-3-yl)-3-(trans-2-fluorocyclopentyl)urea |
| | | 1-(8-Amino-7-fluoro-6-(8-methyl-2,3-dihydro-1H-pyrido[2,3-b][1,4]oxazin-7-yl)isoquinolin-3-yl)-3-((1R,2R)-2-fluorocyclopentyl)urea; |
| | | 1-(8-Amino-7-fluoro-6-(8-methyl-2,3-dihydro-1H-pyrido[2,3-b][1,4]oxazin-7-yl)isoquinolin-3-yl)-3-((1S,2S)-2-fluorocyclopentyl)urea |
| 728 | (structure) | 1-(8-Amino-7-fluoro-6-(8-methyl-2,3-dihydro-1H-pyrido[2,3-b][1,4]oxazin-7-yl)isoquinolin-3-yl)-3-(2-hydroxycyclopentyl)urea |

TABLE 1-continued

| No. | Structure | Name |
|---|---|---|
| 728a 728b 728c 728d | | 1-(8-Amino-7-fluoro-6-(8-methyl-2,3-dihydro-1H-pyrido[2,3-b][1,4]oxazin-7-yl)isoquinolin-3-yl)-3-((1S,2R)-2-hydroxycyclopentyl)urea; 1-(8-Amino-7-fluoro-6-(8-methyl-2,3-dihydro-1H-pyrido[2,3-b][1,4]oxazin-7-yl)isoquinolin-3-yl)-3-((1R,2S)-2-hydroxycyclopentyl)urea; 1-(8-Amino-7-fluoro-6-(8-methyl-2,3-dihydro-1H-pyrido[2,3-b][1,4]oxazin-7-yl)isoquinolin-3-yl)-3-((1S,2S)-2-hydroxycyclopentyl)urea; 1-(8-Amino-7-fluoro-6-(8-methyl-2,3-dihydro-1H-pyrido[2,3-b][1,4]oxazin-7-yl)isoquinolin-3-yl)-3-((1R,2R)-2-hydroxycyclopentyl)urea |
| 729 | | 1-(8-Amino-7-fluoro-6-(8-methyl-2,3-dihydro-1H-pyrido[2,3-b][1,4]oxazin-7-yl)isoquinolin-3-yl)-3-(2-methoxycyclopentyl)urea |
| 729a 729b | | 1-(8-Amino-7-fluoro-6-(8-methyl-2,3-dihydro-1H-pyrido[2,3-b][1,4]oxazin-7-yl)isoquinolin-3-yl)-3-(cis-2-methoxycyclopentyl)urea 1-(8-Amino-7-fluoro-6-(8-methyl-2,3-dihydro-1H-pyrido[2,3-b][1,4]oxazin-7-yl)isoquinolin-3-yl)-3-((1S,2R)-2-methoxycyclopentyl)urea; 1-(8-Amino-7-fluoro-6-(8-methyl-2,3-dihydro-1H-pyrido[2,3-b][1,4]oxazin-7-yl)isoquinolin-3-yl)-3-((1R,2S)-2-methoxycyclopentyl)urea |
| 729c 729d | | 1-(8-Amino-7-fluoro-6-(8-methyl-2,3-dihydro-1H-pyrido[2,3-b][1,4]oxazin-7-yl)isoquinolin-3-yl)-3-(trans-2-methoxycyclopentyl)urea 1-(8-Amino-7-fluoro-6-(8-methyl-2,3-dihydro-1H-pyrido[2,3-b][1,4]oxazin-7-yl)isoquinolin-3-yl)-3-((1S,2S)-2-methoxycyclopentyl)urea; 1-(8-Amino-7-fluoro-6-(8-methyl-2,3-dihydro-1H-pyrido[2,3-b][1,4]oxazin-7-yl)isoquinolin-3-yl)-3-((1R,2R)-2-methoxycyclopentyl)urea |
| 730 | | 1-(8-Amino-7-fluoro-6-(8-methyl-2,3-dihydro-1H-pyrido[2,3-b][1,4]oxazin-7-yl)isoquinolin-3-yl)-3-(3-methoxycyclopentyl)urea |
| 730a 730b | | 1-(8-Amino-7-fluoro-6-(8-methyl-2,3-dihydro-1H-pyrido[2,3-b][1,4]oxazin-7-yl)isoquinolin-3-yl)-3-(trans-3-methoxycyclopentyl)urea 1-(8-Amino-7-fluoro-6-(8-methyl-2,3- |

| No. | Structure | Name |
|---|---|---|
| | | dihydro-1H-pyrido[2,3-b][1,4]oxazin-7-yl)isoquinolin-3-yl)-3-((1R,3R)-3-methoxycyclopentyl)urea; 1-(8-Amino-7-fluoro-6-(8-methyl-2,3-dihydro-1H-pyrido[2,3-b][1,4]oxazin-7-yl)isoquinolin-3-yl)-3-((1S,3S)-3-methoxycyclopentyl)urea |
| 730c 730d | | 1-(8-Amino-7-fluoro-6-(8-methyl-2,3-dihydro-1H-pyrido[2,3-b][1,4]oxazin-7-yl)isoquinolin-3-yl)-3-(cis-3-methoxycyclopentyl)urea 1-(8-Amino-7-fluoro-6-(8-methyl-2,3-dihydro-1H-pyrido[2,3-b][1,4]oxazin-7-yl)isoquinolin-3-yl)-3-(1R,3S)-3-methoxycyclopentyl)urea; 1-(8-Amino-7-fluoro-6-(8-methyl-2,3-dihydro-1H-pyrido[2,3-b][1,4]oxazin-7-yl)isoquinolin-3-yl)-3((1S,3R)-3-methoxycyclopentyl)urea |
| 731 | 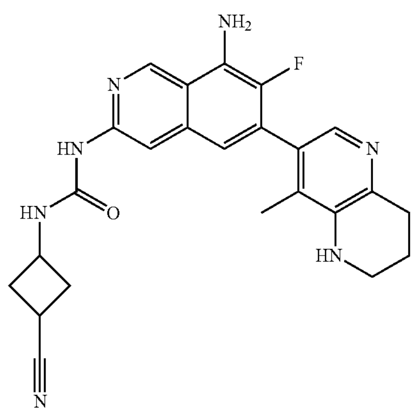 [SMILES: Cc1c(-c2cc3cc(NC(=O)NC4CC(C#N)C4)ncc3c(N)c2F)cnc2c1NCCC2] | 1-(8-Amino-7-fluoro-6-(4-methyl-5,6,7,8-tetrahydro-1,5-naphthyridin-3-yl)isoquinolin-3-yl)-3-(3-cyanocyclobutyl)urea |
| 732 | 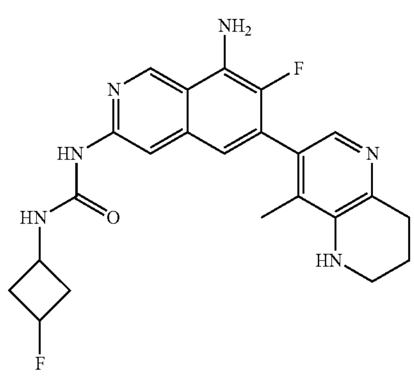 [SMILES: Cc1c(-c2cc3cc(NC(=O)NC4CC(F)C4)ncc3c(N)c2F)cnc2c1NCCC2] | 1-(8-Amino-7-fluoro-6-(4-methyl-5,6,7,8-tetrahydro-1,5-naphthyridin-3-yl)isoquinolin-3-yl)-3-(3-fluorocyclobutyl)urea |
| 732a 732b | | 1-(8-Amino-7-fluoro-6-(4-methyl-5,6,7,8-tetrahydro-1,5-naphthyridin-3-yl)isoquinolin-3-yl)-3-((1r,3r)-3-fluorocyclobutyl)urea; 1-(8-Amino-7-fluoro-6-(4-methyl-5,6,7,8-tetrahydro-1,5-naphthyridin-3-yl)isoquinolin-3-yl)-3-((1s,3s)-3-fluorocyclobutyl)urea |

TABLE 1-continued

| No. | Structure | Name |
|---|---|---|
| 733 | 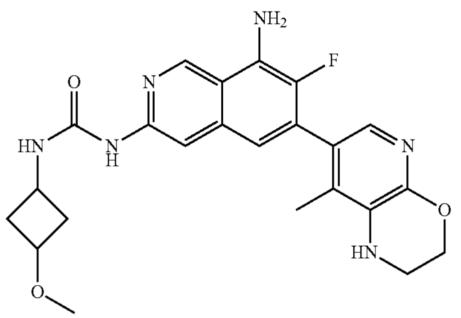 [SMILES: COC1CC(NC(=O)Nc2cc3cc(-c4cnc5c(c4C)NCCO5)c(F)c(N)c3cn2)C1] | 1-(8-Amino-7-fluoro-6-(8-methyl-2,3-dihydro-1H-pyrido[2,3-b][1,4]oxazin-7-yl)isoquinolin-3-yl)-3-(3-methoxycyclobutyl)urea |
| 733a 733b | | 1-(8-Amino-7-fluoro-6-(8-methyl-2,3-dihydro-1H-pyrido[2,3-b][1,4]oxazin-7-yl)isoquinolin-3-yl)-3-((1r,3r)-3-methoxycyclobutyl)urea; 1-(8-Amino-7-fluoro-6-(8-methyl-2,3-dihydro-1H-pyrido[2,3-b][1,4]oxazin-7-yl)isoquinolin-3-yl)-3-((1s,3s)-3-methoxycyclobutyl)urea |
| 734 | 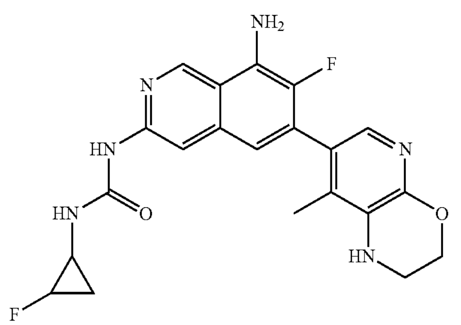 [SMILES: Cc1c(-c2cc3cc(NC(=O)NC4CC4F)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(2-fluorocyclopropyl)urea |
| 734a 734b | | 1-(8-Amino-7-fluoro-6-(8-methyl-2,3-dihydro-1H-pyrido[2,3-b][1,4]oxazin-7-yl)isoquinolin-3-yl)-3-((1S,2R)-2-fluorocyclopropyl)urea; 1-(8-Amino-7-fluoro-6-(8-methyl-2,3-dihydro-1H-pyrido[2,3-b][1,4]oxazin-7-yl)isoquinolin-3-yl)-3-((1R,2S)-2-fluorocyclopropyl)urea |
| 735 | 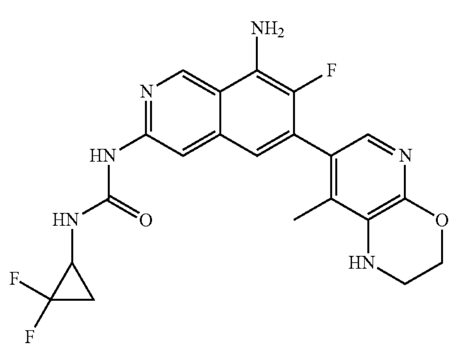 [SMILES: Cc1c(-c2cc3cc(NC(=O)NC4CC4(F)F)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(2,2-difluorocyclopropyl)urea |

TABLE 1-continued

| No. | Structure | Name |
|---|---|---|
| 736 | 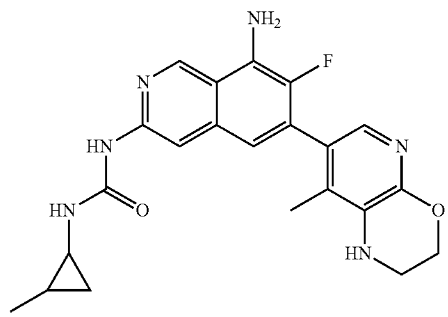 [SMILES: Cc1c(-c2cc3cc(NC(=O)NC4CC4C)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(2-methylcyclopropyl)urea |
| 736a 736b | | 1-(8-Amino-7-fluoro-6-(8-methyl-2,3-dihydro-1H-pyrido[2,3-b][1,4]oxazin-7-yl)isoquinolin-3-yl)-3-(cis-2-methylcyclopropyl)urea 1-(8-Amino-7-fluoro-6-(8-methyl-2,3-dihydro-1H-pyrido[2,3-b][1,4]oxazin-7-yl)isoquinolin-3-yl)-3-((1S,2R)-2-methylcyclopropyl)urea; 1-(8-Amino-7-fluoro-6-(8-methyl-2,3-dihydro-1H-pyrido[2,3-b][1,4]oxazin-7-yl)isoquinolin-3-yl)-3-((1R,2S)-2-methylcyclopropyl)urea |
| 736c 736d | | 1-(8-Amino-7-fluoro-6-(8-methyl-2,3-dihydro-1H-pyrido[2,3-b][1,4]oxazin-7-yl)isoquinolin-3-yl)-3-(trans-2-methylcyclopropyl)urea 1-(8-Amino-7-fluoro-6-(8-methyl-2,3-dihydro-1H-pyrido[2,3-b][1,4]oxazin-7-yl)isoquinolin-3-yl)-3-((1S,2S)-2-methylcyclopropyl)urea; 1-(8-Amino-7-fluoro-6-(8-methyl-2,3-dihydro-1H-pyrido[2,3-b][1,4]oxazin-7-yl)isoquinolin-3-yl)-3-((1R,2R)-2-methylcyclopropyl)urea |
| 737 | 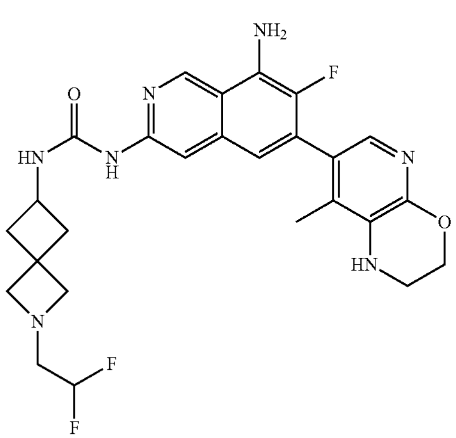 [SMILES: Cc1c(-c2cc3cc(NC(=O)NC4CC5(C4)CN(CC(F)F)C5)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(2-(2,2-difluoroethyl)-2-azaspiro[3.3]heptan-6-yl)urea |

TABLE 1-continued

| No. | Structure | Name |
|---|---|---|
| 738 | 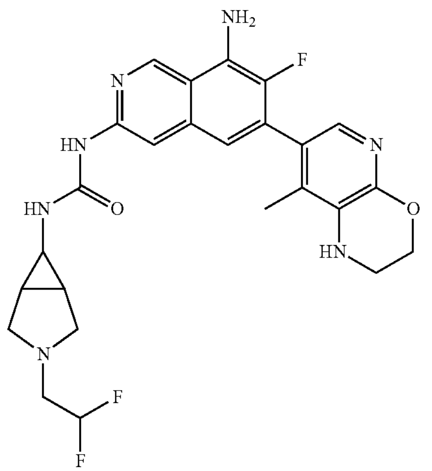 [SMILES: Cc1c(-c2cc3cc(NC(=O)NC4C5CN(CC(F)F)CC54)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(3-(2,2-difluoroethyl)-3-azabicyclo[3.1.0]hexan-6-yl)urea |
| 739 | 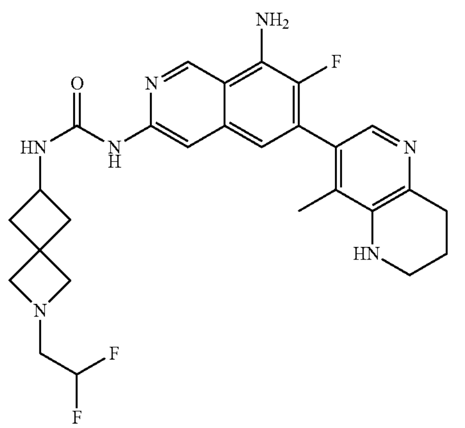 [SMILES: Cc1c(-c2cc3cc(NC(=O)NC4CC5(C4)CN(CC(F)F)C5)ncc3c(N)c2F)cnc2c1NCCC2] | 1-(8-Amino-7-fluoro-6-(4-methyl-5,6,7,8-tetrahydro-1,5-naphthyridin-3-yl)isoquinolin-3-yl)-3-(2-(2,2-difluoroethyl)-2-azaspiro[3.3]heptan-6-yl)urea |
| 740 | 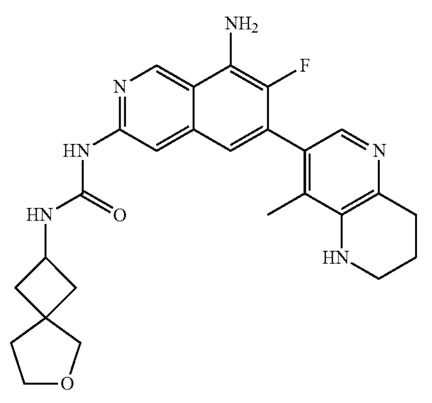 [SMILES: Cc1c(-c2cc3cc(NC(=O)NC4CC5(CCOC5)C4)ncc3c(N)c2F)cnc2c1NCCC2] | 1-(8-Amino-7-fluoro-6-(4-methyl-5,6,7,8-tetrahydro-1,5-naphthyridin-3-yl)isoquinolin-3-yl)-3-(6-oxaspiro[3.4]octan-2-yl)urea |
| 740a 740b | | 1-(8-Amino-7-fluoro-6-(4-methyl-5,6,7,8-tetrahydro-1,5-naphthyridin-3-yl)isoquinolin-3-yl)-3-((2s,4s)-6-oxaspiro[3.4]octan-2-yl)urea; 1-(8-Amino-7-fluoro-6-(4-methyl-5,6,7,8-tetrahydro-1,5-naphthyridin-3-yl)isoquinolin-3-yl)-3-((2r,4r)-6-oxaspiro[3.4]octan-2-yl)urea |

TABLE 1-continued

| No. | Structure | Name |
|---|---|---|
| 741 | 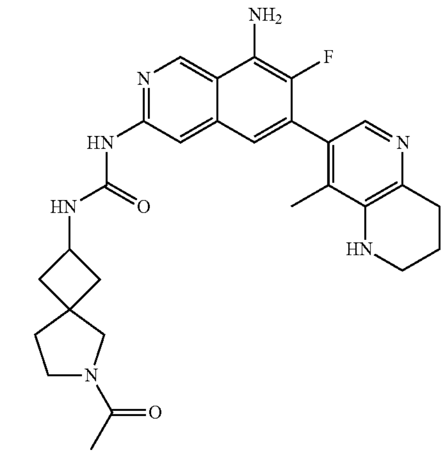 [SMILES: CC(=O)N1CCC2(CC(NC(=O)Nc3cc4cc(-c5cnc6c(c5C)NCCC6)c(F)c(N)c4cn3)C2)C1] | 1-(6-Acetyl-6-azaspiro[3.4]octan-2-yl)-3-(8-amino-7-fluoro-6-(4-methyl-5,6,7,8-tetrahydro-1,5-naphthyridin-3-yl)isoquinolin-3-yl)urea |
| 742 | 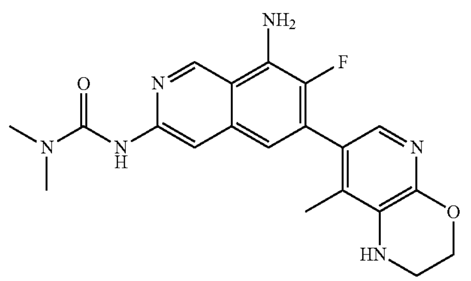 [SMILES: Cc1c(-c2cc3cc(NC(=O)N(C)C)ncc3c(N)c2F)cnc2c1NCCO2] | 3-(8-Amino-7-fluoro-6-(8-methyl-2,3-dihydro-1H-pyrido[2,3-b][1,4]oxazin-7-yl)isoquinolin-3-yl)-1,1-dimethylurea |
| 743 | 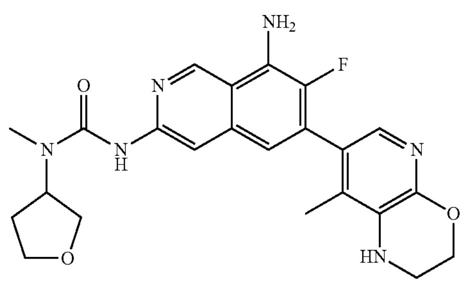 [SMILES: Cc1c(-c2cc3cc(NC(=O)N(C)C4CCOC4)ncc3c(N)c2F)cnc2c1NCCO2] | 3-(8-Amino-7-fluoro-6-(8-methyl-2,3-dihydro-1H-pyrido[2,3-b][1,4]oxazin-7-yl)isoquinolin-3-yl)-1-methyl-1-(tetrahydrofuran-3-yl)urea |
| 744 | 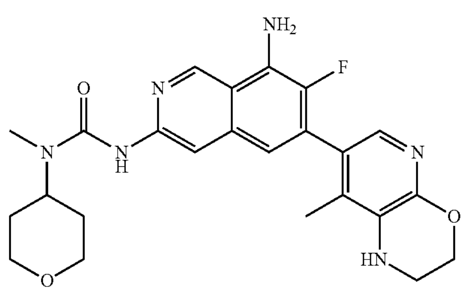 [SMILES: Cc1c(-c2cc3cc(NC(=O)N(C)C4CCOCC4)ncc3c(N)c2F)cnc2c1NCCO2] | 3-(8-Amino-7-fluoro-6-(8-methyl-2,3-dihydro-1H-pyrido[2,3-b][1,4]oxazin-7-yl)isoquinolin-3-yl)-1-methyl-1-(tetrahydro-2H-pyran-4-yl)urea |
| 745 | 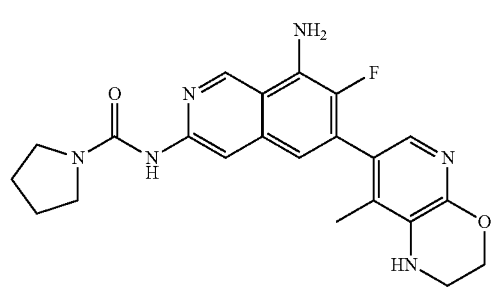 [SMILES: Cc1c(-c2cc3cc(NC(=O)N4CCCC4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)pyrrolidine-1-carboxamide |

TABLE 1-continued

| No. | Structure | Name |
|---|---|---|
| 746 | 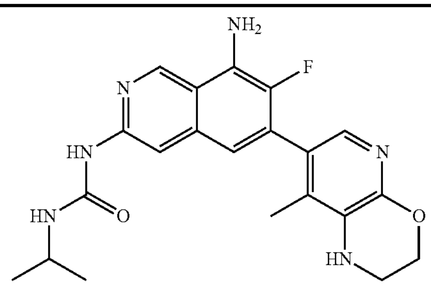 | 1-(8-amino-7-fluoro-6-(8-methyl-2,3-dihydro-1H-pyrido[2,3-b][1,4]oxazin-7-yl)isoquinolin-3-yl)-3-isopropylurea |
| 747 | 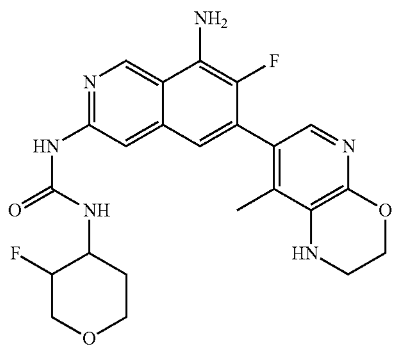 | 1-(8-Amino-7-fluoro-6-(8-methyl-2,3-dihydro-1H-pyrido[2,3-b][1,4]oxazin-7-yl)isoquinolin-3-yl)-3-(3-fluorotetrahydro-2H-pyran-4-yl)urea |
| 747a 747b | | 1-(8-Amino-7-fluoro-6-(8-methyl-2,3-dihydro-1H-pyrido[2,3-b][1,4]oxazin-7-yl)isoquinolin-3-yl)-3-(cis-3-fluorotetrahydro-2H-pyran-4-yl)urea 1-(8-Amino-7-fluoro-6-(8-methyl-2,3-dihydro-1H-pyrido[2,3-b][1,4]oxazin-7-yl)isoquinolin-3-yl)-3-((3S,4S)-3-fluorotetrahydro-2H-pyran-4-yl)urea; 1-(8-Amino-7-fluoro-6-(8-methyl-2,3-dihydro-1H-pyrido[2,3-b][1,4]oxazin-7-yl)isoquinolin-3-yl)-3-((3R,4R)-3-fluorotetrahydro-2H-pyran-4-yl)urea |
| 747c 747d | | 1-(8-Amino-7-fluoro-6-(8-methyl-2,3-dihydro-1H-pyrido[2,3-b][1,4]oxazin-7-yl)isoquinolin-3-yl)-3-(trans-3-fluorotetrahydro-2H-pyran-4-yl)urea 1-(8-Amino-7-fluoro-6-(8-methyl-2,3-dihydro-1H-pyrido[2,3-b][1,4]oxazin-7-yl)isoquinolin-3-yl)-3-((3S,4R)-3-fluorotetrahydro-2H-pyran-4-yl)urea; 1-(8-Amino-7-fluoro-6-(8-methyl-2,3-dihydro-1H-pyrido[2,3-b][1,4]oxazin-7-yl)isoquinolin-3-yl)-3-((3R,4S)-3-fluorotetrahydro-2H-pyran-4-yl)urea |
| 748 | 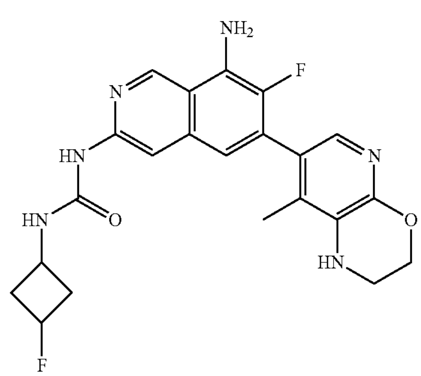 [SMILES: Cc1c(-c2cc3cc(NC(=O)NC4CC(F)C4)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(3-fluorocyclobutyl)urea |
| 748a 748b | | 1-(8-Amino-7-fluoro-6-(8-methyl-2,3-dihydro-1H-pyrido[2,3-b][1,4]oxazin-7-yl)isoquinolin-3-yl)-3-((1s,3s)-3-fluorocyclobutyl)urea; |

TABLE 1-continued

| No. | Structure | Name |
|---|---|---|
| | | 1-(8-Amino-7-fluoro-6-(8-methyl-2,3-dihydro-1H-pyrido[2,3-b][1,4]oxazin-7-yl)isoquinolin-3-yl)-3-((1r,3r)-3-fluorocyclobutyl)urea |
| 749 | 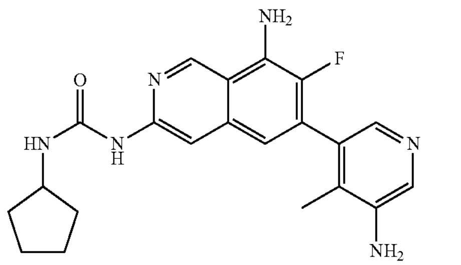 [SMILES: Cc1c(N)cncc1-c1cc2cc(NC(=O)NC3CCCC3)ncc2c(N)c1F] | 1-(8-Amino-6-(5-amino-4-methylpyridin-3-yl)-7-fluoroisoquinolin-3-yl)-3-cyclopentylurea |
| 750 | 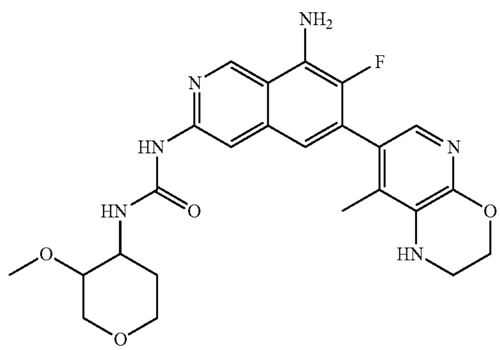 [SMILES: COC1COCCC1NC(=O)Nc1cc2cc(-c3cnc4c(c3C)NCCO4)c(F)c(N)c2cn1] | 1-(8-Amino-7-fluoro-6-(8-methyl-2,3-dihydro-1H-pyrido[2,3-b][1,4]oxazin-7-yl)isoquinolin-3-yl)-3-(3-methoxytetrahydro-2H-pyran-4-yl)urea |
| 750a 750b | | 1-(8-Amino-7-fluoro-6-(8-methyl-2,3-dihydro-1H-pyrido[2,3-b][1,4]oxazin-7-yl)isoquinolin-3-yl)-3-(cis-3-methoxytetrahydro-2H-pyran-4-yl)urea 1-(8-Amino-7-fluoro-6-(8-methyl-2,3-dihydro-1H-pyrido[2,3-b][1,4]oxazin-7-yl)isoquinolin-3-yl)-3-((3S,4S)-3-methoxytetrahydro-2H-pyran-4-yl)urea; 1-(8-Amino-7-fluoro-6-(8-methyl-2,3-dihydro-1H-pyrido[2,3-b][1,4]oxazin-7-yl)isoquinolin-3-yl)-3-((3R,4R)-3-methoxytetrahydro-2H-pyran-4-yl)urea |
| 750c 750d | | 1-(8-Amino-7-fluoro-6-(8-methyl-2,3-dihydro-1H-pyrido[2,3-b][1,4]oxazin-7-yl)isoquinolin-3-yl)-3-(trans-3-methoxytetrahydro-2H-pyran-4-yl)urea 1-(8-Amino-7-fluoro-6-(8-methyl-2,3-dihydro-1H-pyrido[2,3-b][1,4]oxazin-7-yl)isoquinolin-3-yl)-3-((3S,4R)-3-methoxytetrahydro-2H-pyran-4-yl)urea; 1-(8-Amino-7-fluoro-6-(8-methyl-2,3-dihydro-1H-pyrido[2,3-b][1,4]oxazin-7-yl)isoquinolin-3-yl)-3-((3R,4S)-3-methoxytetrahydro-2H-pyran-4-yl)urea |
| 751 | 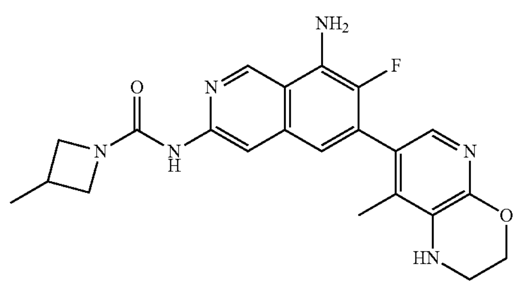 [SMILES: Cc1c(-c2cc3cc(NC(=O)N4CC(C)C4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)-3-methylazetidine-1-carboxamide |

TABLE 1-continued

| No. | Structure | Name |
|---|---|---|
| 752 | 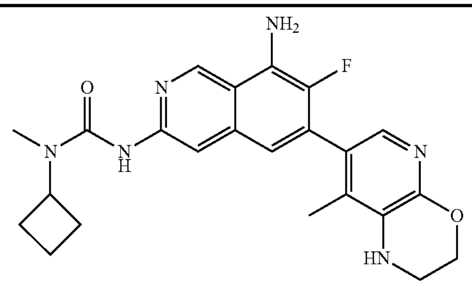 | 3-(8-Amino-7-fluoro-6-(8-methyl-2,3-dihydro-1H-pyrido[2,3-b][1,4]oxazin-7-yl)isoquinolin-3-yl)-1-cyclobutyl-1-methylurea |
| 753 | 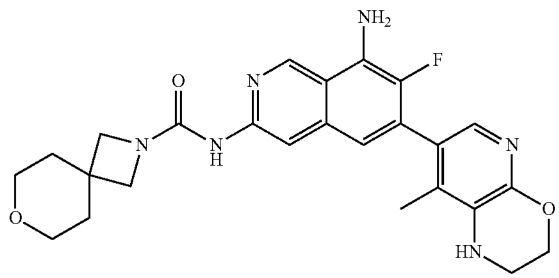 [SMILES: Cc1c(-c2cc3cc(NC(=O)N4CC5(CCOCC5)C4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)-7-oxa-2-azaspiro[3.5]nonane-2-carboxamide |
| 754 | 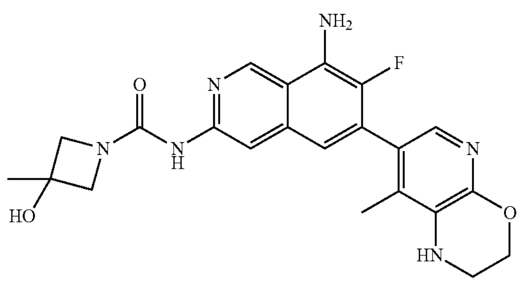 [SMILES: Cc1c(-c2cc3cc(NC(=O)N4CC(C)(O)C4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)-3-hydroxy-3-methylazetidine-1-carboxamide |
| 755 | 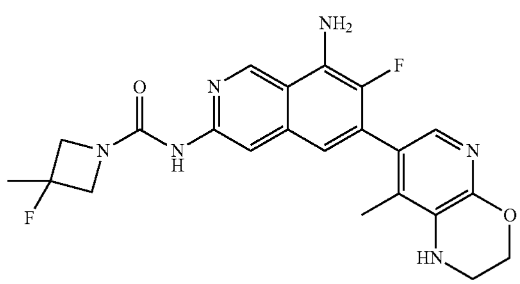 [SMILES: Cc1c(-c2cc3cc(NC(=O)N4CC(C)(F)C4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)-3-fluoro-3-methylazetidine-1-carboxamide |
| 756 | 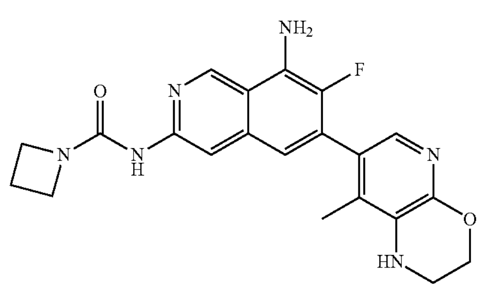 [SMILES: Cc1c(-c2cc3cc(NC(=O)N4CCC4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)azetidine-1-carboxamide |

In some embodiments, provided is a compound selected from Compound Nos. 401-584, 601 and 701-756 in Table 1, or a salt (e.g., a pharmaceutically acceptable salt) thereof. In some embodiments, the compound is selected from Compound Nos. 401, 402, 403, 403a, 403b, 404, 405, 405a, 405b, 406, 407, 408, 408a, 408b, 409, 409a, 409b, 410, 410a, 410b, 411, 411a, 411b, 412, 412a, 412b, 413, 414, 414a, 414b, 415, 415a, 415b, 416, 416a, 416b, 417, 418, 418a, 418b, 419, 420, 421, 422, 423, 424, 425, 426, 427, 428, 429, 430, 431, 432, 432a, 432b, 433, 433a, 433b, 434, 435, 436, 437, 437a, 437b, 438, 439, 439a, 439b, 440, 440a, 440b, 441, 441a, 441b, 441c, 441d, 442, 442a, 442b, 442c, 442d, 443, 444, 444a, 444b, 445, 445a, 445b, 445c, 445d, 446, 447, 447a, 447b, 448, 449, 450, 451, 451a, 451b, 452, 452a, 452b, 452c, 452d, 453, 454, 455, 456, 457, 458, 459, 460, 461, 461a, 461b, 462, 463, 464, 465, 466, 467, 467a, 467b, 467c, 467d, 468, 469, 470, 471, 472, 473, 474, 475, 476, 477, 477a, 477b, 477c, 477d, 478, 478a, 478b, 479, 479a, 479b, 480, 480a, 480b, 481, 481a, 481b, 482, 482a, 482b, 482c, 482d, 483, 483a, 483b, 484, 484a, 484b, 485, 485a, 485b, 486, 486a, 486b, 487, 488, 489, 490, 491, 492, 493, 494, 495, 496, 497, 498, 499, 499a, 499b, 500, 501, 502, 502a, 502b, 503, 504, 504a, 504b, 505, 506, 506a, 506b, 507, 507a, 507b, 508, 509, 510, 510a, 510b, 510c, 510d, 511, 511a, 511b, 512, 512a, 512b, 513, 513a, 513b, 514, 514a, 514b, 515, 515a, 515b, 515c, 515d, 516, 516a, 516b, 516c, 516d, 517, 517a, 517b, 518, 518a, 518b, 518c, 518d, 519, 519a, 519b, 520, 520a, 520b, 521, 522, 522a, 522b, 523, 523a, 523b, 524, 525, 525a, 525b, 526, 526a, 526b, 526c, 526d, 527, 527a, 527b, 528, 528a, 528b, 529, 529a, 529b, 530, 530a, 530b, 531, 531a, 531b, 531c, 531d, 532, 533, 533a, 533b, 533c, 533d, 534, 534a, 534b, 535, 535a, 535b, 535c, 535d, 536, 536a, 536b, 537, 537a, 537b, 538, 538a, 538b, 538c, 538d, 539, 539a, 539b, 540, 541, 541a, 541b, 542, 542a, 542b, 542c, 542d, 543, 543a, 543b, 544, 544a, 544b, 544c, 544d, 545, 545a, 545b, 545c, 545d, 546, 546a, 546b, 546c, 546d, 547, 547a, 547b, 548, 548a, 548b, 548c, 548d, 549, 549a, 549b, 550, 550a, 550b, 551, 551a, 551b, 552, 553, 553a, 553b, 554, 554a, 554b, 555, 555a, 555b, 555c, 555d, 556, 556a, 556b, 556c, 556d, 557, 557a, 557b, 558, 558a, 558b, 558c, 558d, 559, 559a, 559b, 559c, 559d, 560, 560a, 560b, 560c, 560d, 561, 561a, 561b, 561c, 561d, 562, 562a, 562b, 562c, 562d, 563, 563a, 563b, 563c, 563d, 566, 566a, 566b, 566c, 566d, 567, 567a, 567b, 567c, 567d, 567e, 567f, 567g, 567h, 568, 568a, 568b, 568c, 568d, 569, 569a, 569b, 569c, 569d, 570, 570a, 570b, 570c, 570d, 571, 571a, 571b, 572, 572a, 572b, 573, 573a, 573b, 573c, 573d, 574, 574a, 574b, 575, 575a, 575b, 576, 576a, 576b, 577, 577a, 577b, 578, 578a, 578b, 579, 580, 581, 581a, 581b, 581c, 581d, 582, 582a, 582b, 582c, 582d, 583, 583a, 583b, 583c, 583d, 584, 584a, 584b, 584c, 584d, 601, 701, 702, 703, 703a, 703b, 703c, 704, 705, 706, 707, 708, 709, 710, 710a, 710b, 711, 711a, 711b, 712, 712a, 712b, 712c, 713, 713a, 713b, 714, 715, 716, 717, 718, 719, 720, 721, 722, 722a, 722b, 723, 723a, 723b, 723c, 723d, 724, 724a, 724b, 725, 726, 726a, 726b, 726c, 726d, 727, 727a, 727b, 727c, 727d, 728, 728a, 728b, 728c, 728d, 729, 729a, 729b, 729c, 729d, 730, 730a, 730b, 730c, 730d, 731, 732, 732a, 732b, 733, 733a, 733b, 734, 734a, 734b, 735, 736, 736a, 736b, 736c, 736d, 737, 738, 739, 740, 740a, 740b, 741, 742, 743, 744, 745, 746, 747, 747a, 747b, 747c, 747d, 748, 748a, 748b, 749, 750, 750a, 750b, 750c, 750d, 751, 752, 753, 754, 755 and 756 in Table 1, or a salt (e.g., a pharmaceutically acceptable salt) thereof.

In some embodiments, provided is a compound selected from Compound Nos. 401-456, 458-494 and 496-509, 601, 701-720 and 722-745 in Table 1, or a salt (e.g., a pharmaceutically acceptable salt) thereof. In some embodiments, the compound is selected from Compound Nos. 401, 402, 403, 403a, 403b, 404, 405, 405a, 405b, 406, 407, 408, 408a, 408b, 409, 409a, 409b, 410, 410a, 410b, 411, 411a, 411b, 412, 412a, 412b, 413, 414, 414a, 414b, 415, 415a, 415b, 416, 416a, 416b, 417, 418, 418a, 418b, 419, 420, 421, 422, 423, 424, 425, 426, 427, 428, 429, 430, 431, 432, 432a, 432b, 433, 433a, 433b, 434, 435, 436, 437, 437a, 437b, 438, 439, 439a, 439b, 440, 440a, 440b, 441, 441a, 441b, 441c, 441d, 442, 442a, 442b, 442c, 442d, 443, 444, 444a, 444b, 445, 445a, 445b, 445c, 445d, 446, 447, 447a, 447b, 448, 449, 450, 451, 451a, 451b, 452, 452a, 452b, 452c, 452d, 453, 454, 455, 456, 457, 458, 459, 460, 461, 461a, 461b, 462, 463, 464, 465, 466, 467, 467a, 467b, 467c, 467d, 468, 469, 470, 471, 472, 473, 474, 475, 476, 477, 477a, 477b, 477c, 477d, 478, 478a, 478b, 479, 479a, 479b, 480, 480a, 480b, 481, 481a, 481b, 482, 482a, 482b, 482c, 482d, 483, 483a, 483b, 484, 484a, 484b, 485, 485a, 485b, 486, 486a, 486b, 487, 488, 489, 490, 491, 492, 493, 494, 495, 496, 497, 498, 499, 499a, 499b, 500, 501, 502, 502a, 502b, 503, 504, 504a, 504b, 505, 506, 506a, 506b, 507, 507a, 507b, 508, 509, 601, 701, 702, 703, 703a, 703b, 703c, 704, 705, 706, 707, 708, 709, 710, 710a, 710b, 711, 711a, 711b, 712, 712a, 712b, 712c, 713, 713a, 713b, 714, 715, 716, 717, 718, 719, 720, 722, 723, 724, 725, 726, 727, 728, 729, 730, 731, 732, 733, 734, 735, 736, 737, 738, 739, 740, 741, 742, 743, 744 and 745 in Table 1, or a salt (e.g., a pharmaceutically acceptable salt) thereof.

In some embodiments, provided is a compound selected from Compound Nos. 457, 495, 510-563 and 566-584 in Table 1, or a salt (e.g., a pharmaceutically acceptable salt) thereof.

In some embodiments, provided is a compound selected from Compound Nos. 401-563 and 566-584 in Table 1, or a salt (e.g., a pharmaceutically acceptable salt) thereof. In some embodiments, the compound is selected from Compound Nos. 401, 402, 403, 403a, 403b, 404, 405, 405a, 405b, 406, 407, 408, 408a, 408b, 409, 409a, 409b, 410, 410a, 410b, 411, 411a, 411b, 412, 412a, 412b, 413, 414, 414a, 414b, 415, 415a, 415b, 416, 416a, 416b, 417, 418, 418a, 418b, 419, 420, 421, 422, 423, 424, 425, 426, 427, 428, 429, 430, 431, 432, 432a, 432b, 433, 433a, 433b, 434, 435, 436, 437, 437a, 437b, 438, 439, 439a, 439b, 440, 440a, 440b, 441, 441a, 441b, 441c, 441d, 442, 442a, 442b, 442c, 442d, 443, 444, 444a, 444b, 445, 445a, 445b, 445c, 445d, 446, 447, 447a, 447b, 448, 449, 450, 451, 451a, 451b, 452, 452a, 452b, 452c, 452d, 453, 454, 455, 456, 457, 458, 459, 460, 461, 461a, 461b, 462, 463, 464, 465, 466, 467, 467a, 467b, 467c, 467d, 468, 469, 470, 471, 472, 473, 474, 475, 476, 477, 477a, 477b, 477c, 477d, 478, 478a, 478b, 479, 479a, 479b, 480, 480a, 480b, 481, 481a, 481b, 482, 482a, 482b, 482c, 482d, 483, 483a, 483b, 484, 484a, 484b, 485, 485a, 485b, 486, 486a, 486b, 487, 488, 489, 490, 491, 492, 493, 494, 495, 496, 497, 498, 499, 499a, 499b, 500, 501, 502, 502a, 502b, 503, 504, 504a, 504b, 505, 506, 506a, 506b, 507, 507a, 507b, 508, 509, 510, 510a, 510b, 510c, 510d, 511, 511a, 511b, 512, 512a, 512b, 513, 513a, 513b, 514, 514a, 514b, 515, 515a, 515b, 515c, 515d, 516, 516a, 516b, 516c, 516d, 517, 517a, 517b, 518, 518a, 518b, 518c, 518d, 519, 519a, 519b, 520, 520a, 520b, 521, 522, 522a, 522b, 523, 523a, 523b, 524, 525, 525a, 525b, 526, 526a, 526b, 526c, 526d, 527, 527a, 527b, 528, 528a, 528b, 529, 529a, 529b, 530, 530a, 530b, 531, 531a, 531b, 531c, 531d, 532, 533, 533a, 533b, 533c, 533d, 534, 534a, 534b, 535, 535a, 535b, 535c, 535d, 536, 536a, 536b, 537, 537a, 537b, 538, 538a, 538b, 538c, 538d, 539, 539a, 539b, 540, 541, 541a, 541b, 542, 542a, 542b, 542c, 542d, 543, 543a, 543b, 544, 544a, 544b, 544c, 544d, 545, 545a, 545b, 545c, 545d, 546, 546a, 546b, 546c, 546d, 547, 547a, 547b, 548, 548a, 548b, 548c, 548d, 549, 549a, 549b, 550, 550a, 550b, 551, 551a, 551b, 552, 553, 553a, 553b, 554, 554a, 554b, 555, 555a, 555b, 555c, 555d, 556, 556a, 556b, 556c, 556d, 557, 557a, 557b, 558, 558a, 558b, 558c, 558d, 559, 559a, 559b, 559c, 559d, 560, 560a, 560b, 560c, 560d, 561, 561a, 561b, 561c, 561d, 562, 562a, 562b, 562c, 562d, 563, 563a, 563b, 563c, 563d, 566, 566a, 566b, 566c, 566d, 567, 567a, 567b, 567c, 567d, 567e, 567f, 567g, 567h, 568, 568a, 568b, 568c, 568d, 569, 569a, 569b, 569c, 569d, 570, 570a, 570b, 570c, 570d, 571, 571a, 571b, 572, 572a, 572b, 573, 573a, 573b, 573c, 573d, 574, 574a, 574b, 575, 575a, 575b, 576, 576a, 576b, 577, 577a, 577b, 578, 578a, 578b, 579, 580, 581, 581a, 581b, 581c, 581d, 582, 582a, 582b, 582c, 582d, 583, 583a, 583b, 583c, 583d, 584, 584a, 584b, 584c and 584d in Table 1, or a salt (e.g., a pharmaceutically acceptable salt) thereof.

In some embodiments, provided is a compound selected from Compound Nos. 401-456, 458-494 and 496-509 in Table 1, or a salt (e.g., a pharmaceutically acceptable salt)

thereof. In some embodiments, the compound is selected from Compound Nos. 401, 402, 403, 403a, 403b, 404, 405, 405a, 405b, 406, 407, 408, 408a, 408b, 409, 409a, 409b, 410, 410a, 410b, 411, 411a, 411b, 412, 412a, 412b, 413, 414, 414a, 414b, 415, 415a, 415b, 416, 416a, 416b, 417, 418, 418a, 418b, 419, 420, 421, 422, 423, 424, 425, 426, 427, 428, 429, 430, 431, 432, 432a, 432b, 433, 433a, 433b, 434, 435, 436, 437, 437a, 437b, 438, 439, 439a, 439b, 440, 440a, 440b, 441, 441a, 441b, 442, 442a, 442b, 442c, 442d, 443, 444, 444a, 444b, 445, 445a, 445b, 446, 447, 448, 449, 450, 451, 452, 453, 454, 455, 456, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 496, 497, 498, 499, 500, 501, 502, 503, 504, 505, 506, 507, 508 and 509 in Table 1, or a salt (e.g., a pharmaceutically acceptable salt) thereof.

In some embodiments, provided is a compound selected from Compound Nos. 457, 495, 510-563 and 566-584 in Table 1, or a salt (e.g., a pharmaceutically acceptable salt) thereof.

In some embodiments, provided is a compound selected from Compound Nos. 701-756 in Table 1, or a salt (e.g., a pharmaceutically acceptable salt) thereof. In some embodiments, the compound is selected from Compound Nos. 701, 702, 703, 703a, 703b, 703c, 704, 705, 706, 707, 708, 709, 710, 710a, 710b, 711, 711a, 711b, 712, 712a, 712b, 712c, 712d, 713, 713a, 713b, 714, 715, 716, 717, 718, 719, 719a, 719b, 720, 721, 722, 722a, 722b, 723, 723a, 723b, 723c, 723d, 724, 724a, 724b, 725, 726, 726a, 726b, 726c, 726d, 727, 727a, 727b, 727c, 727d, 728, 728a, 728b, 728c, 728d, 729, 729a, 729b, 729c, 729d, 730, 730a, 730b, 730c, 730d, 731, 732, 732a, 732b, 733, 733a, 733b, 734, 734a, 734b, 735, 736, 736a, 736b, 736c, 736d, 737, 738, 739, 740, 740a, 740b, 741, 742, 743, 744, 745, 746, 747, 747a, 747b, 747c, 747d, 748, 748a, 748b, 749, 750, 750a, 750b, 750c, 750d, 751, 752, 753, 754, 755 and 756 in Table 1, or a salt (e.g., a pharmaceutically acceptable salt) thereof.

In some embodiments, provided is a compound selected from Compound Nos. 701-720 and 722-745 in Table 1, or a salt (e.g., a pharmaceutically acceptable salt) thereof. In some embodiments, the compound is selected from Compound Nos. 701, 702, 703, 703a, 703b, 703c, 704, 705, 706, 707, 708, 709, 710, 710a, 710b, 711, 711a, 711b, 712, 712a, 712b, 712c, 713, 713a, 713b, 714, 715, 716, 717, 718, 719, 720, 722, 723, 724, 725, 726, 727, 728, 729, 730, 731, 732, 733, 734, 735, 736, 737, 738, 739, 740, 741, 742, 743, 744 and 745 in Table 1, or a salt (e.g., a pharmaceutically acceptable salt) thereof.

In some embodiments, provided is a compound selected from Compound Nos. 721 and 746-756 in Table 1, or a salt (e.g., a pharmaceutically acceptable salt) thereof.

In some embodiments, provided is a compound which is Compound No. 601 in Table 1, or a salt (e.g., a pharmaceutically acceptable salt) thereof.

Compounds of Formula (I) described herein or a salt thereof may exist in stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound or salt of Formulas (I) may exist in tautomeric forms other than that shown in the formula and these are also included within the scope of the subject matter disclosed herein. It is to be understood that the subject matter disclosed herein includes combinations and subsets of the particular groups described herein. The scope of the subject matter disclosed herein includes mixtures of stereoisomers as well as purified enantiomers or enantiomerically/diastereomerically enriched mixtures. It is to be understood that the subject matter disclosed herein includes combinations and subsets of the particular groups defined herein.

The subject matter disclosed herein also includes isotopically-labelled forms of the compounds described herein, but for the fact that one or more atoms are replaced by an atom having an atomic mass or mass number different from the atomic mass or mass number usually found in nature. Examples of isotopes that can be incorporated into compounds described herein and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I. For example, compounds disclosed herein include forms wherein one or more of the hydrogen atoms are replaced or enriched with deuterium.

The subject matter disclosed herein includes prodrugs, metabolites, derivatives, and pharmaceutically acceptable salts of compounds of Formula (I). Metabolites of the compounds of Formula (I) include compounds produced by a process comprising contacting a compound of Formula (I) with a mammal for a period of time sufficient to yield a metabolic product thereof.

If the compound of Formula (I) is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of Formula (I) is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of Formula (I) can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

Compounds of Formula (I) can be prepared by procedures described in the general synthetic methods, and Examples as described herein, as well as methods known in the art.

Pharmaceutical Compositions and Formulations

The presently disclosed compounds can be formulated into pharmaceutical compositions along with a pharmaceutically acceptable carrier or excipient.

Compounds of Formula (I), or variations thereof such as Formula (IA), (IB) and (IC), can be formulated in accordance with standard pharmaceutical practice as a pharmaceutical composition. According to this aspect, there is provided a pharmaceutical composition comprising a compound of Formula (I), or variations thereof such as Formula (IA), (IB) and (IC), in association with a pharmaceutically acceptable excipient, diluent or carrier.

A typical formulation is prepared by mixing a compound of Formula (I), or variations thereof such as Formula (IA), (IB) and (IC), and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of Formula (I), or variations thereof such as Formula (IA), (IB) and (IC), is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of Formula (I), or variations thereof such as Formula (IA), (IB) and (IC), or pharmaceutical composition thereof) or aid in the manufacturing of the pharmaceutical product (i.e., medicament).

The formulations may be prepared using conventional dissolution and mixing procedures. For example, the bulk drug substance (i.e., compound of Formula (I), or variations thereof such as Formula (IA), (IB) and (IC), or stabilized form of the Compound of Formula (I), or variations thereof such as Formula (IA), (IB) and (IC), (e.g., complex with a cyclodextrin derivative or other known complexation agent) is dissolved in a suitable solvent in the presence of one or more of the excipients described above. The compound of Formula (I) is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations may be prepared for various routes and types of administration. For example, a compound of Formula (I) having the desired degree of purity may optionally be mixed with pharmaceutically acceptable diluents, carriers, excipients or stabilizers (Remington's Pharmaceutical Sciences (1980) 16$^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable excipients or carriers, i.e., excipients or carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compounds of Formula (I) can be sterile. In particular, formulations to be used for in vivo administration should be sterile. Such sterilization is readily accomplished by filtration through sterile filtration membranes.

The compound ordinarily can be stored as a solid composition, a lyophilized formulation or as an aqueous solution.

The pharmaceutical compositions comprising a compound of Formula (I) can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. In some embodiments, the amount is below the amount that is toxic to the host or renders the host more susceptible to bleeding.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

Sustained-release preparations of Formula (I) compounds may be prepared. Suitable examples of sustained-release preparations include semipermeable matrices of solid hydrophobic polymers containing a compound of Formula (I), which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3773919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the excipient or carrier which constitutes one or more accessory ingredients. In general the formulations are prepared by uniformly and intimately bringing into association the active ingredient with liquid excipients or carriers or finely divided solid excipients or carriers or both, and then, if necessary, shaping the product.

Formulations of a compound of Formula (I) suitable for oral administration may be prepared as discrete units such as pills, capsules, cachets or tablets each containing a predetermined amount of a compound of Formula (I).

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula (I) intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400), and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise solely an emulsifier, it may also comprise a mixture of at least one emulsifier and a fat or oil, or both a fat and an oil. A hydrophilic emulsifier included together with a lipophilic emulsifier may act as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation include Tween® 60, Span® 80, cetostearyl alcohol, benzyl alcohol, myristyl alcohol, glyceryl mono-stearate and sodium lauryl sulfate.

Aqueous suspensions of Formula (I) compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula (I), or variations thereof such as Formula (IA), (IB) and (IC), may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the excipient or carrier material to produce a single dosage form will vary depending upon the host treated and the particular mode of administration. For example, a time-release formulation intended for oral administration to humans may contain approximately 1 to 1000 mg of active material compounded with an appropriate and convenient amount of excipient or carrier material which may vary from about 5 to about 95% of the total compositions (weight: weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable excipient or carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid excipient or carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of disorders as described below.

Formulations suitable for vaginal administration may be presented as pessaries, tampons, creams, gels, pastes, foams or spray formulations containing in addition to the active ingredient such excipients or carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid excipient or carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary excipient or carrier therefore. Veterinary excipients or carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

In particular embodiments the pharmaceutical composition comprising the presently disclosed compounds further comprise a chemotherapeutic agent. In some of these embodiments, the chemotherapeutic agent is an immunotherapeutic agent.

Methods of Use

The presently disclosed compounds find use in inhibiting the activity of the enzyme HPK1. HPK1, also referred to as mitogen activated protein kinase kinase kinase kinase 1 or MAP4K1, is a member of the germinal center kinase subfamily of Ste20-related serine/threnonine kinases. HPK1 functions as a MAP4K by phosphorylating and activating MAP3K proteins, including MEKK1, MLK3 and TAK1, leading to the activation of the MAPK Jnk.

In an embodiment, the subject matter disclosed herein is directed to a method of inhibiting HPK1, the method comprising contacting HPK1 with an effective amount of a compound of Formula (I), or variations thereof such as Formula (IA), (IB) and (IC), or a pharmaceutical composition described herein.

In an embodiment, the subject matter disclosed herein is directed to a method for enhancing an immune response in a subject in need thereof, wherein the method comprises administering to said subject an effective amount of a compound of Formula (I), or variations thereof such as Formula (IA), (IB) and (IC), or a pharmaceutical composition described herein. In certain aspects of this embodiment, the T cells in the subject have at least one of enhanced priming, enhanced activation, enhanced migration, enhanced proliferation, enhanced survival, and enhanced cytolytic activity relative to prior to the administration of the compound or pharmaceutical composition. In certain aspects of this embodiment, the T cell activation is characterized by an elevated frequency of γ-IFN+CD8 T cells, an elevated frequency of γ-IFN+CD4 T cells, or enhanced levels of IL-2 or granzyme B production by T cells, relative to prior to administration of the compound or pharmaceutical composition. In certain aspects of this embodiment, the number of T cells is elevated relative to prior to administration of the compound or pharmaceutical composition. In certain aspects of this embodiment, the T cell is an antigen-specific CD8 T cell. In certain aspects of this embodiment, the T cell is an antigen-specific CD4 T cell. In certain aspects of this embodiment, the antigen presenting cells in the subject have enhanced maturation and activation relative prior to the administration of the compound or pharmaceutical composition. In certain aspects of this embodiment, the antigen presenting cells are dendritic cells. In certain aspects of this embodiment, the maturation of the antigen presenting cells is characterized by increased frequency of CD83+ dendritic cells. In certain aspects of this embodiment, the activation of the antigen presenting cells is characterized by elevated expression of CD80 and CD86 on dendritic cells. In some aspects, compounds of Formula (I), or variations thereof such as Formula (IA), (IB) and (IC), or a pharmaceutical composition thereof provides general priming of the immune response (i.e., vaccines) to tumors or viruses for boosting/generating anti-viral/tumor immunity.

In the methods described herein, a compound of Formula (I), or variations thereof such as Formula (IA), (IB) and (IC), or a pharmaceutical composition thereof is administered to a subject that has cancer as described elsewhere herein.

In an embodiment, the subject matter disclosed herein is directed to a method for treating a HPK1-dependent disorder, the method comprising administering to a subject in need thereof an effective amount of a compound of Formula (I), or variations thereof such as Formula (IA), (IB) and (IC), or a pharmaceutical composition described herein. In certain aspects of this embodiment, the HPK1-dependent disorder is a cancer. In certain aspects of this embodiment, the cancer comprises at least one cancer selected from the group consisting of colorectal cancer, melanoma, non-small cell lung cancer, ovarian cancer, breast cancer, pancreatic cancer, a hematological malignancy, and a renal cell carcinoma. In certain aspects of this embodiment, the cancer has elevated levels of T-cell infiltration. In certain aspects of this embodiment, the cancer cells in the subject selectively have elevated expression of MHC class I antigen expression relative to prior to the administration of the compound or composition.

In the methods described herein, the method can further comprise administering a chemotherapeutic agent to said subject. In certain aspects of this embodiment, the chemotherapeutic agent is administered to the subject simultaneously with the compound or the composition. In certain aspects of this embodiment, the chemotherapeutic agent is administered to the subject prior to administration of the compound or the composition. In certain aspects of this embodiment, the chemotherapeutic agent is administered to the subject after administration of the compound or said composition.

HPK1 polynucleotides and polypeptides are known in the art (Hu et al. (1996) *Genes Dev.* 10: 2251-2264, which is herein incorporated by reference in its entirety). Certain HPK1 polynucleotides and polypeptides comprise the human HPK1 polynucleotide are accessible and the sequences are known, for example, nucleotides 141-2642 of GenBank Accession No. NM_007181.5 and the encoded human HPK1 polypeptide (Accession No. NP_009112.1); and nucleotides 141-2606 of GenBank Accession No. NM_001042600.2 and the encoded human HPK1 polypeptide (Accession No. NP_001036065.1).

HPK1 polypeptides comprise a variety of conserved structural motifs. HPK1 polypeptides comprise an amino-terminal Ste20-like kinase domain, which includes the ATP-binding site. The kinase domain is followed by four proline-rich (PR) motifs that serve as binding sites for SH3-containing proteins, such as CrkL, Grb2, HIP-55, Gads, Nck, and Crk. HPK1 becomes phosphorylated and activated in response to TCR or BCR stimulation. TCR- and BCR-induced phosphorylation of a tyrosine residue located between PR1 and PR2, mediates binding to SLP-76 in T cells or BLNK in B cells via a SLP-76 or BLNK SH2 domain, and is required for activation of the kinase. A citron homology domain found in the C-terminus of HPK1 may act as a regulatory domain and may be involved in macromolecular interactions.

The presently disclosed compounds bind directly to HPK1 and inhibit its kinase activity. In some embodiments, the presently disclosed compounds reduce, inhibit, or otherwise diminish the HPK1-mediated phosphorylation of SLP76 and/or Gads.

The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the presently disclosed compounds specifically inhibit the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

The presently disclosed compounds can be used in a method for inhibiting HPK1. Such methods comprise contacting HPK1 with an effective amount of a presently disclosed compound. By "contact" is intended bringing the compound within close enough proximity to an isolated HPK1 enzyme or a cell expressing HPK1 (e.g., T cell, B cell, dendritic cell) such that the compound is able to bind to and inhibit the activity of HPK1. The compound can be contacted with HPK1 in vitro or in vivo via administration of the compound to a subject.

Any method known in the art to measure the kinase activity of HPK1 may be used to determine if HPK1 has been inhibited, including in vitro kinase assays, immunoblots with antibodies specific for phosphorylated targets of HPK1, such as SLP76 and Gads, or the measurement of a downstream biological effect of HPK1 kinase activity, such as the recruitment of 14-3-3 proteins to phosphorylated SLP7 and Gads, release of the SLP76-Gads-14-3-3 complex from LAT-containing microclusters, or T or B cell activation.

The presently disclosed compounds can be used to treat a HPK1-dependent disorder. As used herein, a "HPK1-dependent disorder" is a pathological condition in which HPK1 activity is necessary for the genesis or maintenance of the pathological condition. In some embodiments, the HPK1-dependent disorder is cancer.

The presently disclosed compounds also find use in enhancing an immune response in a subject in need thereof. Such methods comprise administering an effective amount of a presently disclosed compound (i.e., compound of Formula (I), or variations thereof such as Formula (IA), (IB) and (IC), or a pharmaceutically acceptable salt, prodrug, metabolite, or derivative thereof).

As used herein, "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CD8 T cells), enhanced T cell (e.g., CD4 T cell, CD8 T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2-induced immune suppression, and enhanced priming and/or cytolytic activity of CD8 T cells.

In some embodiments, the CD8 T cells in the subject have enhanced priming, activation, proliferation and/or cytolytic activity relative to prior to the administration of the compound of Formula (I), or variations thereof such as Formula (IA), (IB) and (IC), or a pharmaceutically acceptable salt, prodrug, metabolite, or derivative thereof. In some embodiments, the CD8 T cell priming is characterized by elevated CD44 expression and/or enhanced cytolytic activity in CD8 T cells. In some embodiments, the CD8 T cell activation is characterized by an elevated frequency of $\gamma$-IFN$^+$ CD8 T cells. In some embodiments, the CD8 T cell is an antigen-specific T-cell.

In some embodiments, the CD4 T cells in the subject have enhanced priming, activation, proliferation and/or cytolytic activity relative to prior to the administration of the compound of Formula (I), or variations thereof such as Formula (IA), (IB) and (IC), or a pharmaceutically acceptable salt, prodrug, metabolite, or derivative thereof. In some embodiments, the CD4 T cell priming is characterized by elevated CD44 expression and/or enhanced cytolytic activity in CD4 T cells. In some embodiments, the CD4 T cell activation is characterized by an elevated frequency of $\gamma$-IFN$^+$ CD4 T cells. In some embodiments, the CD4 T cell is an antigen-specific T-cell.

In some embodiments, the antigen presenting cells in the subject have enhanced maturation and activation relative to prior to the administration of the compound of Formula (I), or variations thereof such as Formula (IA), (IB) and (IC), or a pharmaceutically acceptable salt, prodrug, metabolite, or derivative thereof. In some embodiments, the antigen presenting cells are dendritic cells. In some embodiments, the maturation of the antigen presenting cells is characterized by an increased frequency of CD83$^+$ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the subject are reduced relative to prior to the administration of the compound of Formula (I), or variations thereof such as Formula (IA), (IB) and (IC), or a pharmaceutically acceptable salt, prodrug, metabolite, or derivative thereof.

Engagement of the TCR leads to HPK1 activation, which functions as a negative regulator of TCR-induced AP-1 response pathway. It is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters, which leads to T cell dysfunction, including anergy and exhaustion (Lasserre et al. (2011) *J Cell Biol* 195(5):839-853).

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growthours.

The term "dysfunctional", as used herein, also includes refractory or unresponsive to antigen recognition, specifically, impaired capacity to translate antigen recognition into downstream T-cell effector functions, such as proliferation, cytokine production (e.g., IL-2, $\gamma$-IFN) and/or target cell killing.

The term "anergy" refers to the state of unresponsiveness to antigen stimulation resulting from incomplete or insufficient signals delivered through the T-cell receptor (e.g. increase in intracellular Ca$^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

In some embodiments, administration of a compound of Formula (I), or variations thereof such as Formula (IA), (IB) and (IC), or a pharmaceutically acceptable salt, prodrug, metabolite, or derivative thereof to a subject results in an enhancement of T cell function. In some embodiments, administration of HPK1 inhibitors described herein may enhance/renew/reactivate immune response or activate de nove immune response.

"Enhancing T cell function" means to induce, cause or stimulate a T cell to have a sustained or amplified biological function, or renew or reactivate exhausted or inactive T cells. Examples of enhancing T cell function include: increased secretion of cytokines (e.g., $\gamma$-interferon, IL-2, IL-12, and TNF$\alpha$), increased proliferation, increased antigen responsiveness (e.g., viral, pathogen, or tumor clearance) relative to such levels before the intervention, and increased effector granule production by CD8 T cells or CD4 T cells, such as granzyme B. In one embodiment, the level of enhancement is as least 50%, alternatively 60%, 70%, 80%, 90%, 100%, 120%, 150%, 200%. The manner of measuring this enhancement is known to one of ordinary skill in the art.

Accordingly, the presently disclosed compounds of Formula (I), or variations thereof such as Formula (IA), (IB) and (IC), or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation. In a particular embodiment, a T cell dysfunctional disorder is a disorder that is specifically associated with increased kinase activity of HPK1. In another embodiment, a T cell dysfunctional disorder is one in which T cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

Thus, the presently disclosed compounds can be used in treating conditions where enhanced immunogenicity is desired, such as increasing tumor immunogenicity for the treatment of cancer.

"Immunogenecity" refers to the ability of a particular substance to provoke an immune response. Tumors are immunogenic and enhancing tumor immunogenicity aids in the clearance of the tumor cells by the immune response. Viruses may also be immunogenic and enhancing/activating immunogenicity may aid in clearance of viral particles by the immune response.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

In one aspect, provided herein is a method for treating of cancer in a subject in need thereof comprising administering to the subject an effective amount of a compound of Formula (I), or variations thereof such as Formula (IA), (IB) and (IC), or a pharmaceutically acceptable salt, prodrug, metabolite, or derivative thereof. In some embodiments, the subject has melanoma. The melanoma may be at early stage or at late stage. In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or late state. In some embodiments, the subject has a hematological malignancy. The hematological malignancy may be at early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

In one aspect, provided is a method for treating viral infection in a subject in need thereof comprising administering to the subject an effective amount of a compound of Formula (I), or variations thereof such as Formula (IA), (IB) and (IC), or a pharmaceutically acceptable salt, prodrug, metabolite, or derivative thereof. In one aspect, provided is a method for enhacing or boosting response to a vaccine (such as a cancer vaccine or a personalized cancer vaccine (PCV)) or a CAR-T cell therapy in a subject in need thereof comprising administering to the subject an effective amount of a compound of Formula (I), or variations thereof such as Formula (IA), (IB) and (IC), or a pharmaceutically acceptable salt, prodrug, metabolite, or derivative thereof.

The presently disclosed compounds may be administered in any suitable manner known in the art. In some embodiments, the compound of Formula (I), or variations thereof such as Formula (IA), (IB) and (IC), or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the HPK1 antagonist is administered continuously. In other embodiments, the HPK1 antagonist is administered intermittently. Moreover, treatment of a subject with an effective amount of a HPK1 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of Formula (I), or variations thereof such as Formula (IA), (IB) and (IC), or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the HPK1 antagonist is administered to the subject at a dose of between about 0.001 µg/kg and about 1000 mg/kg, including but not limited to about 0.001 µg/kg, about 0.01 µg/kg, about 0.05 µg/kg, about 0.1 µg/kg, about 0.5 µg/kg, about 1 µg/kg, about 10 µg/kg, about 25 µg/kg, about 50 µg/kg, about 100 µg/kg, about 250 µg/kg, about 500 µg/kg, about 1 mg/kg, about 5 mg/kg, about 10 mg/kg, about 25 mg/kg, about 50 mg/kg, about 100 mg/kg, and about 200 mg/kg.

In some embodiments, provided is a method for treating a cancer in a subject in need thereof comprising administering to the subject an effective amount of a compound of Formula (I), or variations thereof such as Formula (IA), (TB) and (IC), or a pharmaceutically acceptable salt, prodrug, metabolite, or derivative thereof, further comprising administering an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of an anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting the PI3K/AKT/mTOR pathway, HSP90 inhibitor, tubulin inhibitor, apoptosis inhibitor, and/or chemopreventative agent.

The additional therapy may be one or more of a chemotherapeutic agent. Thus, the method of treating cancer can comprise administering the presently disclosed HPK1 antagonists in conjunction with at least one chemotherapeutic agent.

As used herein, "in conjunction with" refers to administration of one treatment modality in addition to another treatment modality. As such, "in conjunction with" refers to administration of one treatment modality before, during, or after administration of the other treatment modality to the subject.

For example, the HPK1 antagonist and chemotherapeutic agent may be administered sequentially (at different times) or concurrently (at the same time). The HPK1 antagonist and chemotherapeutic agent may be administered by the same route of administration or by different routes of administration.

In certain embodiments, the HPK1 antagonist is administered in conjunction with another immunotherapy. For example, the HPK1 antagonist can be combined with a chemotherapeutic agent or biologic that targets the PD-L1/PD-1 pathway. A known inhibitory checkpoint pathway involves signaling through PD-1 receptors. The programmed-death 1 (PD-1) receptor and its ligands PD-L1 and PD-L2 are part of the same family of coregulatory molecules as CTLA-4.—See more at: http://www.onclive.com/web-exclusives/the-role-of-anti-pd-11-immunotherapy-in-cancer/2#sthash.cGfYa1T1.dpuf Chemotherapeutic agents or biologics that block PD-L1 binding to PD-1 and CD80 can prevent PD-L1-mediated inhibition/suppression of T-cell activation. Programmed cell death ligand-1 (PD-L1) is widely expressed on antigen-presenting cells (APC) and other immune cells. It is upregulated on tumor cells from a broad range of human cancers, and has been implicated with inhibition of antitumor T-cell immunity. PD-L1 is a cell surface protein that binds to the receptors PD-1 and CD80 on activated T cells, B cells, and other myeloid cells. PD-L1 binding to PD-1 on activated T-cells has been found to interfere with T-cell proliferation and inhibit immune responses. Overexpression of PD-L1 on cancer cells may allow these cells to avoid immune detection and elimination. High levels of PD-L1 expression on tumor cells have been associated with increased tumor aggressiveness and a poor prognosis. Chemotherapeutic agents or biologics that block PD-L1 binding to PD-1 include anti-PD-L1 antibodies, such as durvalumab, nivolumab, pidlizumab, MPDL3280A, MK-3475 and BMS-936559, among others. In some embodiments, the HPK1 antagonist is administered in conjunction with a PD-1 antagonist such as an anti-PD-1 antibody, a PD-L1 antagonist such as an anti-PD-L1 antibody, and/or a PD-L2 antagonist such as an anti-PD-L2 antibody. Examples of anti-PD-L1 antibodies include but are not limited to avelumab, atezolizumab (also known as MPDL3280A), pembrolizumab (also known as MK-3475), LY3300054 (Eli Lilly), STI-A1014 (Sorrento), KN035 (Suzhou Alphamab) and BMS-936559 (Bristol Myers Squibb). Examples of anti-PD-1 antibodies include but are not limited to nivolumab, pidlizumab, PDR001 (Novartis), REGN2810 (Regeneron), BGB-108 (BeiGene), BGB-A317 (BeiGene), JS-001 (Shanghai Junshi), STI-A1110 (Sorrento), INCSHR-1210 (Incyte), PF-06801591 (Pfizer), TSR-042 (also known as ANB011; Tesaro/AnaptysBio), AM0001 (ARMO Biosciences), and ENUM 244C8 (Enumeral Biomedical Holdings).

In another example, the HPK1 antagonist can be combined with a chemotherapeutic agent or biologic that targets OX40 and its ligand, OX40L, are members of the TNF superfamily. OX40 is expressed on activated CD4(+) and CD8(+) T cells as well as on a number of other lymphoid and non-lymphoid cells. Costimulatory signals from OX40 to a conventional T cell promote division and survival, augmenting the clonal expansion of effector and memory populations as they are being generated to antigen. OX40 additionally suppresses the differentiation and activity of T-regulatory cells, further amplifying this process. OX40 and OX40L also regulate cytokine production from T cells, antigen-presenting cells, natural killer cells, and natural killer T cells, and modulate cytokine receptor signaling. As one of the most prominent costimulatory molecules known to control T cells, stimulating OX40 has been shown be a target for therapeutic immunization strategies for cancer. Certain OX40 agonists include GBR 830, and those disclosed in Linch, et al., Frontiers in Oncology, v. 5, pp. 1-10 (2015), herein incorporated by reference in its entirety.

In other examples, the HPK1 antagonist can be combined with a chemotherapeutic agent or biologic that targets a CD28, OX40, GITR, CD137, CD27, CD40, ICOS, HVEM, NKG2D, MICA, 2B4, IL-2, IL-12, IFNγ, IFNα, TNFα, IL-1, CDN, HMGB1, TLR, PD-L1 axis, CTLA-4, TIM-3, BTLA, VISTA, LAG-3, B7H4, CD96, CD226, prostaglandin, VEGF, endothelin B, IDO, arginase, MICA/MICB, TIM-3, IL-10, IL-4, IL-13, TIGIT or TGFβ. In other examples, the HPK1 antagonist can be combined with an immunotherapy comprising a PD-L1 axis, CTLA-4, TIM-3, BTLA, VISTA, LAG-3, B7H4, CD96, TIGIT, CD226, prostaglandin, VEGF, endothelin B, IDO, arginase, MICA/MICB, TIM-3, IL-10, IL-4, or IL-13 antagonis. In other examples, the HPK1 antagonist can be combined with an immunotherapy comprising a CD28, OX40, GITR, CD137, CD27, CD40, ICOS, HVEM, NKG2D, MICA, 2B4, IL-2, IL-12, IFNγ, IFNα, TNFα, IL-1, CDN, HMGB1, or TLR agonist.

In another example, the HPK1 antagonist can be combined with a PCV. In another example, the HPK1 antagonist can be combined with an adoptive T cell therapy.

Provided is a method of inhibiting HPK1, said method comprising contacting HPK1 in a subject with an effective amount of a compound Formula (I), or variations thereof such as Formula (IA), (IB) and (IC), or a pharmaceutically acceptable salt thereof; or a pharmaceutical composition comprising a compound Formula (I), or variations thereof such as Formula (IA), (IB) and (IC), or a pharmaceutically acceptable salt thereof.

A method for enhancing an immune response in a subject in need thereof, wherein the method comprises administering to said subject an effective amount of a compound Formula (I), or variations thereof such as Formula (IA), (IB) and (IC), or a pharmaceutically acceptable salt thereof; or a pharmaceutical composition comprising a compound Formula (I), or variations thereof such as Formula (IA), (IB) and (IC), or a pharmaceutically acceptable salt thereof.

In some embodiments, said subject has cancer.

Also provided is a method for treating a HPK1-dependent disorder, said method comprising administering to a subject in need thereof an effective amount of a compound Formula (I), or variations thereof such as Formula (IA), (IB) and (IC), or a pharmaceutically acceptable salt thereof; or a pharmaceutical composition comprising a compound Formula (I), or variations thereof such as Formula (IA), (IB) and (IC), or a pharmaceutically acceptable salt thereof.

In some embodiments, said HPK1-dependent disorder is a cancer.

In some embodiments, wherein the cancer comprises at least one cancer selected from the group consisting of colorectal cancer, melanoma, non-small cell lung cancer, ovarian cancer, breast cancer, pancreatic cancer, a hematological malignancy, and a renal cell carcinoma.

In some embodiments, said method further comprises administering a chemotherapeutic agent to said subject.

In some embodiments, the invention also provides compounds of Formula (I), or variations thereof such as Formula (IA), (IB) and (IC), described herein or pharmaceutical compositions described herein for use in a method for inhibiting HPK1 as described herein, in a method for enhancing an immune response in a subject in need thereof as described herein and/or in a method for treating a HPK1-dependent disorder as described herein.

In some embodiments, the invention also provides compounds of Formula (I), or variations thereof such as Formula (IA), (IB) and (IC), described herein or pharmaceutical compositions described herein for use in a method for inhibiting HPK1 as described herein.

In some embodiments, the invention also provides compounds of Formula (I), or variations thereof such as Formula (IA), (IB) and (IC), described herein or pharmaceutical compositions described herein for use in a method for enhancing an immune response in a subject in need thereof as described herein.

In some embodiments, the invention also provides compounds of Formula (I), or variations thereof such as Formula (IA), (IB) and (IC), described herein or pharmaceutical compositions described herein for use in a method for treating a HPK1-dependent disorder as described herein.

In some embodiments, the invention also provides the use of a compound of Formula (I), or variations thereof such as Formula (IA), (IB) and (IC), described herein or a pharmaceutical composition described herein for the manufacture of a medicament for inhibiting HPK1, a medicament for enhancing an immune response in a subject in need thereof and/or a medicament for treating a HPK1-dependent disorder.

In some embodiments, the invention also provides the use of a compound of Formula (I), or variations thereof such as Formula (IA), (IB) and (IC), described herein or a pharmaceutical composition described herein for the manufacture of a medicament for inhibiting HPK1.

In some embodiments, the invention also provides the use of a compound of Formula (I), or variations thereof such as Formula (IA), (IB) and (IC), described herein or a pharmaceutical composition described herein for the manufacture of a medicament for enhancing an immune response in a subject in need thereof.

In some embodiments, the invention also provides the use of a compound of Formula (I), or variations thereof such as Formula (IA), (IB) and (IC), described herein or a pharmaceutical composition described herein for the manufacture of a medicament treating a HPK1-dependent disorder.

In some embodiments, the invention also provides the use of compounds of Formula (I), or variations thereof such as Formula (IA), (IB) and (IC), described herein or pharmaceutical compositions described herein in a method for inhibiting HPK1 as described herein, in a method for enhancing an immune response in a subject in need thereof as described herein and/or in a method for treating a HPK1-dependent disorder as described herein.

In some embodiments, the invention also provides the use of compounds of Formula (I), or variations thereof such as Formula (IA), (IB) and (IC), described herein or pharmaceutical compositions described herein in a method for inhibiting HPK1 as described herein.

In some embodiments, the invention also provides the use of compounds of Formula (I), or variations thereof such as Formula (IA), (IB) and (IC), described herein or pharmaceutical compositions described herein in a method for enhancing an immune response in a subject in need thereof as described herein.

In some embodiments, the invention also provides the use of compounds of Formula (I), or variations thereof such as Formula (IA), (IB) and (IC), described herein or pharmaceutical compositions described herein in a method for treating a HPK1-dependent disorder as described herein.

In some embodiments, the treatment results in a sustained response in the subject after cessation of the treatment. "Sustained response" refers to the sustained effect on reducing tumor growth after cessation of a treatment. For example, the tumor size may remain the same or smaller as compared to the size at the beginning of the administration phase. In some embodiments, the sustained response has a duration at least the same as the treatment duration, at least 1.5×, 2.0×, 2.5×, or 3.0× length of the treatment duration.

The treatment methods disclosed herein may result in a partial or complete response. As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started. As used herein, "overall response rate" (ORR) refers to the sum of complete response (CR) rate and partial response (PR) rate.

The treatment methods disclosed herein can lead to an increase in progression free survival and overall survival of the subject administered the HPK1 antagonist. As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" refers to the percentage of subjects in a group who are likely to be alive after a particular duration of time.

In some embodiments, the subject that is administered a HPK1 antagonist is a mammal, such as domesticated animals (e.g., cows, sheep, cats, dogs, and horses), primates (e.g., humans and non-human primates such as monkeys), rabbits, and rodents (e.g., mice and rats). In some embodiments, the subject treated is a human.

The subject in need of treatment for cancer may be a person demonstrating symptoms of cancer, one that has been diagnosed with cancer, a subject that is in remission from cancer, or a subject having an increased risk for developing cancer (e.g., a genetic predisposition, certain dietary or environmental exposures).

In any of the described methods, in one aspect the subject is a human, such as a human in need of the method. The subject may be a human who has been diagnosed with or is suspected of having an HPK1-dependent disorder such as cancer. The individual may be a human who does not have detectable disease but who has one or more risk factors for developing a cancer.

Further provided are kits for carrying out the methods detailed herein, which comprises one or more compounds described herein or a pharmaceutical composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for use in the treatment of an HPK1-dependent disorder such as cancer. In some embodiments, the kit contains instructions for use in the treatment of a cancer.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or sub-unit doses. For example, kits may be provided that contain sufficient dosages of a compound as disclosed herein (e.g., a therapeutically effective amount) and/or a second pharmaceutically active compound useful for an HPK1-dependent disorder (e.g., cancer) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to a subject.

The following examples are offered by way of illustration and not by way of limitation.

EXAMPLES

Abbreviations

| | |
|---|---|
| ACN | acetonitrile |
| aq. | aqueous |
| DCM | dichloromethane |
| DIEA | diisopropylethylamine |
| DMAP | 4-Dimethylaminopyridine |
| DMF | N,N-dimethylformamide |
| DMSO | dimethylsulfoxide |
| DMSO-$d_6$ | deuterated dimethylsulfoxide |
| ESI | electrospray ionization |
| EtOAc | ethyl acetate |
| Et$_2$O | diethyl ether |
| FA | formic acid |
| h. | hours |
| HATU | O-(7-azabenzotriazol-1-yl)-N,N,N',N'-tetramethyluronium hexafluorophosphate |
| HCl | hydrochloric acid |
| LCMS | liquid chromatography—mass spectrometry |
| NaOH | sodium hydroxide |
| NMR | nuclear magnetic resonance |
| MeCN | acetonitrile |
| MeOH | methanol |
| MeOH•NH$_3$ | 2N methanolic ammonia |
| mg | milligram |
| mmol | millimole |
| min | minutes |
| mL | millilitre |
| RT | room temperature |
| Rt or R$_T$ | retention time |
| SFC | supercritical fluid chromatography |
| TBAF | tetrabutylammonium fluoride |
| TFA | Trifluoroacetic acid |
| TMEDA | N,N,N',N'-tetramethylethylenediamine |
| THF | tetrahydrofuran |
| Brettphos Pd G3 | [(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate |

All samples were pre-purified by achiral systems and purity checked before SFC chiral purification.

LCMS Analytical Methods

Method J: Experiments were performed on a Shimadzu 20AD HPLC with Shimadzu LCMS2020 mass spectrometer using ESI as ionization source, a Shim-Pack XR-ODS C18 2.2 μm, 3.0×50 column, and a 1.2 ml/minute flow rate. The solvent system was a gradient starting with 95% water with 0.05% TFA (solvent A) and 5% acetonitrile with 0.05% TFA (solvent B), ramping up to 95% solvent B over 2.0 minutes. The final solvent system was held constant for a further 0.7 minutes.

Method K: Experiments were performed on a Shimadzu 20AD HPLC with Shimadzu LCMS2020 mass spectrometer using ESI as ionization source, a Shim-Pack XR-ODS C18 2.2 μm, 3.0×50 column, and a 1.2 ml/minute flow rate. The solvent system was a gradient starting with 95% water with 0.05% TFA (solvent A) and 5% acetonitrile with 0.05% TFA (solvent B), ramping up to 95% solvent B over 2.0 minutes. The final solvent system was held constant for a further 0.7 minutes.

Method L: Experiments were performed on a Shimadzu 30AD HPLC with Shimadzu LCMS2020 mass spectrometer using ESI as ionization source, an Ascentis Express C18 2.7 μm, 2.1×50 column, and a 1.0 ml/minute flow rate. The solvent system was a gradient starting with 95% water with 0.05% TFA (solvent A) and 5% acetonitrile with 0.05% TFA (solvent B), ramping up to 95% solvent B over 2.0 minutes. The final solvent system was held constant for a further 0.7 minutes.

Method M: Experiments were performed on a Shimadzu 20AD XR HPLC with Shimadzu LCMS2020 mass spectrometer using ESI as ionization source, a Poroshell HPH-C18 2.7 μm, 3.0×50 column, and a 1.2 ml/minute flow rate. The solvent system was a gradient starting with 95% water with 5 mM Ammonium bicarbonate (solvent A) and 5% acetonitrile (solvent B), ramping up to 95% solvent B over 2.0 minutes. The final solvent system was held constant for a further 0.7 minutes.

Method N: Experiments performed on an Agilent 1290 UHPLC coupled with Agilent MSD (6140) mass spectrometer using ESI as ionization source. The LC separation used a Phenomenex XB-C18, 1.7 mm, 50×2.1 mm column with a 0.4 ml/minute flow rate. Solvent A was water with 0.1% FA and solvent B was acetonitrile with 0.1% FA. The gradient consisted with 2-98% solvent B over 7 min and hold 98% B for 1.5 min following equilibration for 1.5 min. LC column temperature is 40° C. UV absorbance was collected at 220 nm and 254 nm and mass spec full scan was applied to all experiment.

SYNTHETIC EXAMPLES

The following are procedures to prepare the intermediates used to prepare the compounds described in the General Methods and in the Tables.

Example 1

Intermediate 1: tert-Butyl 8-methyl-7-(4,4,5,5-tetramethyl-1,3,2-dioxaborolan-2-yl)-2,3-dihydropyrido[2,3-b][1,4]oxazine-1-carboxylate

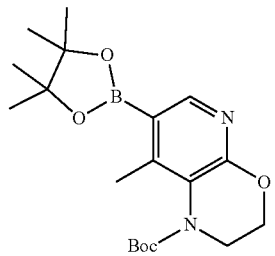 [SMILES: Cc1c(B2OC(C)(C)C(C)(C)O2)cnc2c1N(C(=O)OC(C)(C)C)CCO2]

Step 1: tert-Butyl 7-bromo-8-methyl-2,3-dihydropyrido[2,3-b][1,4]oxazine-1-carboxylate

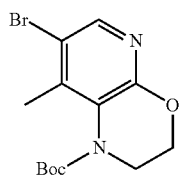

To a solution of 7-bromo-8-methyl-2,3-dihydro-1H-pyrido[2,3-b][1,4]oxazine (1 g, 4.37 mmol) in tetrahydrofuran (2 mL) was added dropwise LiHMDS (8.73 mL, 8.73 mmol, 1 mol/L) at 0° C. The resulting solution was stirred under nitrogen for 0.5 h at 0° C. Then di-tert-butyl dicarbonate (2.85 g, 13.07 mmol) was added and the reaction was stirred at room temperature for 2 h. The reaction was quenched by the addition of methanol (50 mL). The reaction mixture was concentrated under vacuum. The residue was purified by silica gel flash chromatography (ethyl acetate/petroleum ether, 1/4) to afford tert-butyl 7-bromo-8-methyl-2,3-dihydropyrido[2,3-b][1,4]oxazine-1-carboxylate (800 mg, 2.43 mmol) as a yellow oil. LCMS (ESI) [M+H]$^+$= 329.2.

Step 2: tert-Butyl 8-methyl-7-(4,4,5,5-tetramethyl-1,3,2-dioxaborolan-2-yl)-2,3-dihydropyrido[2,3-b][1,4]oxazine-1-carboxylate

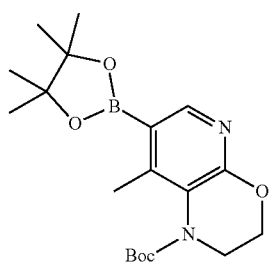 [SMILES: Cc1c(B2OC(C)(C)C(C)(C)O2)cnc2c1N(C(=O)OC(C)(C)C)CCO2]

A mixture of tert-butyl 7-bromo-8-methyl-2,3-dihydropyrido[2,3-b][1,4]oxazine-1-carboxylate (6.2 g, 18.83 mmol), bis(pinacolato)diboron (23.93 g, 94.22 mmol), [1,1'-bis(diphenylphosphino)ferrocene]dichloropalladium(II) (2.76 g, 3.77 mmol) and potassium acetate (5.55 g, 56.62 mmol) in 1,4-dioxane (2 mL) was stirred under nitrogen for 2.5 h at 90° C. The reaction mixture was concentrated under vacuum. The residue was purified by flash chromatography on silica gel eluting with ethyl acetate/petroleum ether (30%) to afford tert-butyl 8-methyl-7-(4,4,5,5-tetramethyl-1,3,2-dioxaborolan-2-yl)-2,3-dihydropyrido[2,3-b][1,4]oxazine-1-carboxylate (5 g, 13.29 mmol) as a yellow oil. LCMS (ESI) [M+H]$^+$=376.3.

Example 2

Intermediate 2:
7-Bromo-8-chloro-6-iodoisoquinolin-3-amine

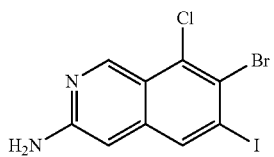

Step 1: 4-Amino-3-bromo-2-chlorobenzonitrile

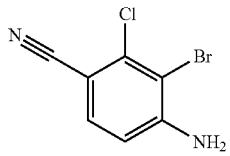 [SMILES: N#Cc1ccc(N)c(Br)c1Cl]

To a solution of 4-amino-2-chlorobenzonitrile (1.5 g, 9.83 mmol) in acetonitrile (30 mL) was added 1,3-dibromo-5,5-dimethyl-2,4-imidazolidinedione (1.5 g, 5.25 mmol). The solution was stirred at 25° C. for 2 hours. The reaction was quenched by the addition of a saturated solution of NaHSO$_3$ (30 mL) and extracted with ethyl acetate (50 mL×2). The organic layer was concentrated, then purified by flash chromatography (10% ethyl acetate in petroleum ether) to give a mixture of 4-amino-3-bromo-2-chlorobenzonitrile and 4-amino-5-bromo-2-chlorobenzonitrile (850 mg, 5/2 ratio of regio-isomers, 26% yield) as a yellow solid which was used directly in the next step. $^1$H NMR (400 MHz, CDCl$_3$) δ 7.67 (s, 1H), 7.38 (d, J=8.4 Hz, 2.6H), 6.80 (s, 1H), 6.65 (d, J=8.4 Hz, 2.6H), 4.81 (bs, 5H), 4.71 (bs, 2H).

Step 2: 3-Bromo-2-chloro-4-iodobenzonitrile

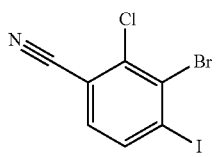 [SMILES: N#Cc1ccc(I)c(Br)c1Cl]

To a suspension of CuI (51.63 g, 271.74 mmol) in acetonitrile (300 mL) was added tert-butyl nitrite (33.59 g, 326.09 mmol). The mixture was stirred at 65° C. for 10 minutes. A mixture of 4-amino-3-bromo-2-chlorobenzonitrile and 4-amino-5-bromo-2-chlorobenzonitrile (3/4 ratio, 25 g, 108.7 mmol) was added, then the reaction mixture was stirred at 65° C. for 12 hours. Upon cooling to room temperature, the mixture was quenched with saturated Na$_2$S$_2$O$_4$ solution (30 mL) and extracted with ethyl acetate (3×50 mL). The combined organic layers were washed with brine (10 mL), dried over by Na$_2$SO$_4$ and filtered. The filtrate was concentrated and purified by flash column chromatography (5% ethyl acetate in petroleum ether) to give 3-bromo-2-chloro-4-iodobenzonitrile (5 g, 31% yield) as a yellow solid. $^1$H NMR (400 MHz, CDCl$_3$) 7.91 (d, J=8.0 Hz, 1H), 7.30 (d, J=8.0 Hz, 1H).

Step 3:
(3-Bromo-2-chloro-4-iodophenyl)methanamine

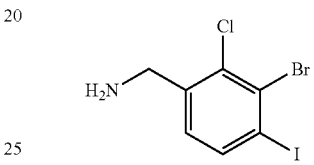

To a solution of 3-bromo-2-chloro-4-iodobenzonitrile (3 g, 8.76 mmol) in THF (30 mL) was added borane-THF (30 mL, 1 M in THF, 30 mmol). The mixture was stirred at 65° C. for 3 h under N$_2$. Upon cooling to room temperature, the mixture was quenched by the addition of methanol (10 mL) and HCl (12 N, 10 mL). The reaction was concentrated to dryness. The residue was taken up in ethyl acetate (100 mL) and extracted with water (50 mL×2). The organic layer was discarded and the aqueous layer was adjusted to pH 9 through the addition of a saturated aqueous solution of NaHCO$_3$. The mixture was extracted with ethyl acetate (50 mL×3). The combined organic layers were washed with water (10 mL×2) and brine (10 mL), dried (Na$_2$SO$_4$), filtered and concentrated to give (3-bromo-2-chloro-4-iodophenyl)methanamine (3 g, 99% yield) as a yellow oil, which was used directly in the next step. LCMS (ESI) [M+H]$^+$=345.9.

Step 4: N-(3-Bromo-2-chloro-4-iodobenzyl)-2,2-diethoxyacetimidamide

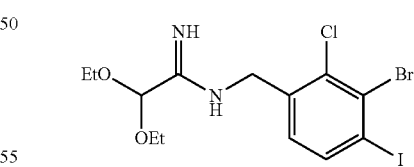

To a solution of (3-bromo-2-chloro-4-iodophenyl)methanamine (2.5 g, 7.22 mmol) in methanol (20 mL) was added methyl 2,2-diethoxyacetimidate (3.75 g, 23.26 mmol). The solution was stirred at 25° C. for 12 hours, then concentrated to dryness. The residue was dissolved in dichloromethane (20 mL), washed with water and brine, dried over MgSO$_4$, filtered and concentrated to give N-(3-bromo-2-chloro-4-iodobenzyl)-2,2-diethoxyacetimidamide (3 g, 87% yield) as a yellow solid, which was used directly in the next step. LCMS (ESI) [M+H]$^+$=474.9.

Step 5:
7-Bromo-8-chloro-6-iodoisoquinolin-3-amine

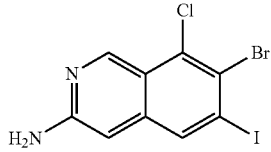

A mixture of sulfuric acid (10 mL) and N-(3-bromo-2-chloro-4-iodobenzyl)-2,2-diethoxyacetimidamide (3 g, 6.31 mmol) was stirred at 60° C. for 12 hours. The reaction mixture was cooled to 0° C. and then a NaOH solution was added to adjust the pH to 9. The resulting solution was extracted with dichloromethane (100 mL×3). The combined organic layers were washed with brine, dried over $Na_2SO_4$, filtered and concentrated to give 7-bromo-8-chloro-6-iodoisoquinolin-3-amine (2.4 g, 99% yield) as a yellow solid. LCMS (ESI) $[M+H]^+=382.8$. $^1$H NMR (400 MHz, DMSO-$d_6$) δ 8.99 (s, 1H), 8.32 (s, 1H), 6.56 (s, 1H), 6.49 (s, 2H).

Example 3

Intermediate 3:
8-Chloro-7-fluoro-6-iodoisoquinolin-3-amine

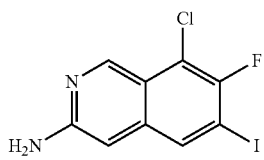 [SMILES: Nc1cc2cc(I)c(F)c(Cl)c2cn1]

Step 1: 4-Amino-2-chloro-3-fluorobenzonitrile

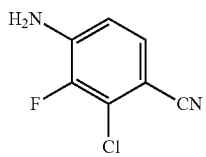 [SMILES: N#Cc1ccc(N)c(F)c1Cl]

To a pressure reaction tube were added copper (I) cyanide (1.2 g, 13.37 mmol), 4-bromo-3-chloro-2-fluoroaniline (1 g, 4.46 mmol) and 1-methyl-2-pyrrolidinone (8 mL). The mixture was heated at 170° C. for 1 hour in a microwave reactor. The reaction mixture was quenched by addition of a saturated solution of $NH_4Cl$ (20 mL) and filtered. The filtrate was extracted with ethyl acetate (3×100 mL). The combined organic layers were washed with brine (3×10 mL), dried with $Na_2SO_4$, filtered through a pad of silica gel, and concentrated to dryness to give 4-amino-2-chloro-3-fluorobenzonitrile (700 mg, 92% yield) as a yellow solid. LCMS (ESI) $[M+H]^+=171.1$.

Step 2: 2-Chloro-3-fluoro-4-iodobenzonitrile

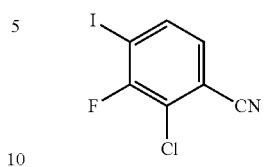

To a suspension of CuI (3341 mg, 17.59 mmol) in acetonitrile (50 mL) was added tert-butyl nitrite (1811 mg, 17.59 mmol) at 65° C. under $N_2$. The mixture was stirred at 65° C. for 10 minutes, then 4-amino-2-chloro-3-fluorobenzonitrile (2 g, 11.73 mmol) was added. The mixture was stirred at 65° C. for 12 hours. Upon cooling to room temperature, the mixture was quenched with saturated aqueous $Na_2S_2O_4$ (30 mL) and aqueous $NH_4Cl$ (30 mL) and extracted with ethyl acetate (3×300 mL). The combined organic layers were washed with brine (2×10 mL), dried over $Na_2SO_4$ and filtered. The filtrate was concentrated to give crude product, which was purified by flash chromatography (petroleum ether/ethyl acetate=5/1) to give 2-chloro-3-fluoro-4-iodobenzonitrile (1 g, 30% yield) as a yellow solid. $^1$H NMR (400 MHz, CDCl$_3$) δ 7.80 (dd, J=5.6, 8.2 Hz, 1H), 7.22 (dd, J=1.4, 8.2 Hz, 1H).

Step 3:
(2-Chloro-3-fluoro-4-iodophenyl)methanamine

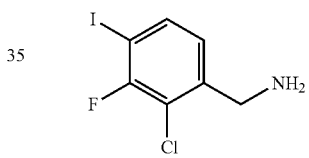

2-Chloro-3-fluoro-4-iodobenzonitrile (1 g, 3.55 mmol) was added to a solution of borane-THF (35.53 mL, 1 M in THF, 35.53 mmol) in THF (30 mL) at 0° C. The mixture was then warmed to room temperature and stirred overnight. The reaction solution was quenched by the dropwise addition of a solution of HCl (6 M, 2 mL) then neutralized with an aqueous solution of $NaHCO_3$ to pH 8 and extracted with dichloromethane (2×200 mL). The combined organic layer was washed with water (2×10 mL) and brine (1×10 mL), dried ($Na_2SO_4$), filtered and concentrated to give (2-chloro-3-fluoro-4-iodophenyl)methanamine (400 mg, crude), which was used directly in the next step without further purification. LCMS (ESI) $[M+H]^+=285.9$.

Step 4: N-(2-Chloro-3-fluoro-4-iodobenzyl)-2,2-diethoxyacetimidamide

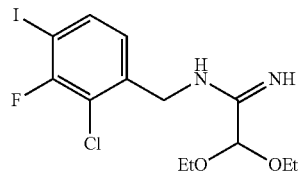 [SMILES: CCOC(OCC)C(=N)NCc1ccc(I)c(F)c1Cl]

To a solution of methyl 2,2-diethoxyacetimidate (0.3 g, 1.88 mmol) in methanol (5 mL) was added (2-chloro-3-fluoro-4-iodophenyl)methanamine (250 mg, 0.88 mmol). The reaction mixture was stirred at 25° C. for 12 hours, and then concentrated to dryness. The residue was taken up in dichloromethane (20 mL), washed with water (2×10 mL) then brine, dried (MgSO$_4$), filtered and concentrated to give N-(2-chloro-3-fluoro-4-iodobenzyl)-2,2-diethoxyacetimidamide (360 mg, crude) as a yellow solid which was used directly in the next step without further purification. LCMS (ESI) [M+H]$^+$=415.0.

Step 5:
8-Chloro-7-fluoro-6-iodoisoquinolin-3-amine

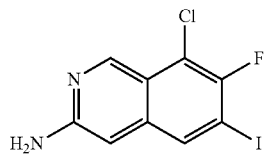 [SMILES: Nc1cc2cc(I)c(F)c(Cl)c2cn1]

A solution of N-(2-Chloro-3-fluoro-4-iodobenzyl)-2,2-diethoxyacetimidamide (0.36 g, 0.87 mmol) and conc. H$_2$SO$_4$ (10 mL, 26.05 mmol) was stirred at 60° C. for 12 hours. The mixture was cooled to 0° C. adjusted to pH 9 with NaOH (10 wt %), then extracted with dichloromethane (5×100 mL). The combined organic layers were washed with brine, dried (Na$_2$SO$_4$), filtered and concentrated to give 8-chloro-7-fluoro-6-iodoisoquinolin-3-amine (0.25 g, crude) as a yellow solid, which was used directly without further purification. LCMS (ESI) [M+H]$^+$=322.9. $^1$H NMR (400 MHz, CD$_3$OD) δ 9.00 (s, 1H), 8.08 (d, J=5.6 Hz, 1H), 6.70 (s, 1H).

Example 4 tert-Butyl 7-(3-amino-8-chloro-7-fluoro-6-isoquinolyl)-8-methyl-2,3-dihydropyrido[2,3-b][1,4]oxazine-1-carboxylate

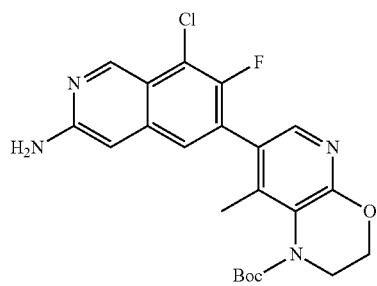 [SMILES: Cc1c(-c2cc3cc(N)ncc3c(Cl)c2F)cnc2c1N(C(=O)OC(C)(C)C)CCO2]

Under nitrogen, a mixture of 8-chloro-7-fluoro-6-iodoisoquinolin-3-amine (249.0 g, 772.07 mmol), tert-butyl 8-methyl-7-(4,4,5,5-tetramethyl-1,3,2-dioxaborolan-2-yl)-2,3-dihydropyrido[2,3-b][1,4]oxazine-1-carboxylate (290.0 g, 770.76 mmol), Pd(dppf)Cl$_2$ (57.0 g, 77.98 mmol) and K$_2$CO$_3$ (320.0 g, 2318.8 mmol) in 1,4-dioxane (3000 mL) and water (300 mL) was stirred at 60° C. for 12 hours. The reaction mixture was slowly cooled to room temperature. Anhydrous sodium sulfate (500 g) was added and stirred for 0.5 hour. The solids were filtered out. The filtrate was concentrated under vacuum. The residue was washed with ethyl acetate (3 L). The solids were collected by filtration and washed with ethyl acetate, dried under vacuum to afford 240 g product. The filtrate was concentrated under vacuum and purified by flash chromatography on silica gel eluting with petroleum ether/ethyl acetate (0-100%) to afford 60 g product. Two batches were combined to afford tert-butyl 7-(3-amino-8-chloro-7-fluoro-6-isoquinolyl)-8-methyl-2,3-dihydropyrido[2,3-b][1,4]oxazine-1-carboxylate (300 g, 674.32 mmol, 87.5% yield) as a yellow solid. LCMS (ESI) [M+H]$^+$=445.

Example 5 tert-Butyl 7-(3-amino-8-((tert-butoxycarbonyl)amino)-7-fluoroisoquinolin-6-yl)-8-methyl-2,3-dihydro-1H-pyrido[2,3-b][1,4]oxazine-1-carboxylate

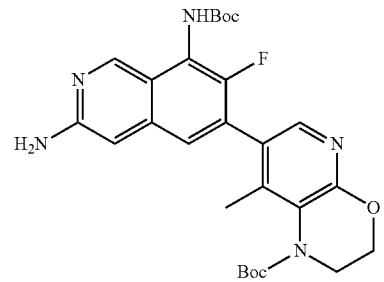 [SMILES: Cc1c(-c2cc3cc(N)ncc3c(NC(=O)OC(C)(C)C)c2F)cnc2c1N(C(=O)OC(C)(C)C)CCO2]

Step 1: tert-Butyl 7-[8-chloro-3-(1,3-dioxoisoindolin-2-yl)-7-fluoro-6-isoquinolyl]-8-methyl-2,3-dihydropyrido[2,3-b][1,4]oxazine-1-carboxylate

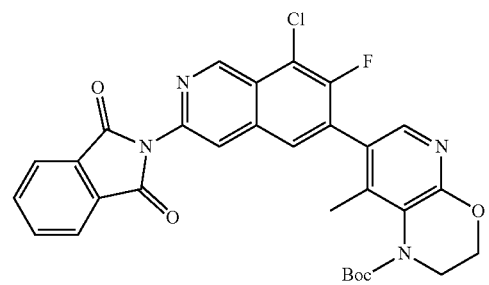 [SMILES: Cc1c(-c2cc3cc(N4C(=O)c5ccccc5C4=O)ncc3c(Cl)c2F)cnc2c1N(C(=O)OC(C)(C)C)CCO2]

A solution of tert-butyl 7-(3-amino-8-chloro-7-fluoro-6-isoquinolyl)-8-methyl-2,3-dihydropyrido[2,3-b][1,4]oxazine-1-carboxylate (300.0 g, 674.32 mmol), fresh-dried 4 Å molecular series (300 g) and phthalic anhydride (150.0 g, 1012.7 mmol) in toluene (3000 mL) was stirred at 100° C. for 3 hours. The reaction was slowly cooled to room temperature and then the resulting mixture was filtered. The filtrate was concentrated under vacuum. The residue was mashed with ethyl acetate (2000 mL). The solids were collected by filtration and dried under vacuum to afford 200 g product. The filtrate was concentrated under vacuum and purified by flash chromatography on silica gel eluting with petroleum ether/ethyl acetate (1/2) to afford 100 g product. Two batches were combined to afford tert-butyl 7-[8-chloro-3-(1,3-dioxoisoindolin-2-yl)-7-fluoro-6-isoquinolyl]-8-methyl-2,3-dihydropyrido[2,3-b][1,4]oxazine-1-carboxylate (300 g, 521.75 mmol, 77.4% yield) as an off white solid. LCMS (ESI) [M+H]$^+$=575.

Step 2: tert-Butyl 7-(8-((tert-butoxycarbonyl)amino)-3-(1,3-dioxoisoindolin-2-yl)-7-fluoroisoquinolin-6-yl)-8-methyl-2,3-dihydro-1H-pyrido[2,3-b][1,4]oxazine-1-carboxylate

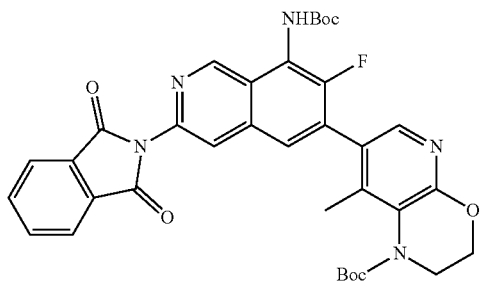 [SMILES: Cc1c(-c2cc3cc(N4C(=O)c5ccccc5C4=O)ncc3c(NC(=O)OC(C)(C)C)c2F)cnc2c1N(C(=O)OC(C)(C)C)CCO2]

Under nitrogen, a mixture of tert-butyl 7-[8-chloro-3-(1,3-dioxoisoindolin-2-yl)-7-fluoro-6-isoquinolyl]-8-methyl-2,3-dihydropyrido[2,3-b][1,4]oxazine-1-carboxylate (300.0 g, 521.75 mmol), NH$_2$Boc (916.0 g, 7829.1 mmol), Brettphos Pd G3 (24.0 g, 26.48 mmol), fresh-dried 4 Å molecular series (300 g) and K$_2$CO$_3$ (227.0 g, 1644.9 mmol) in 1,4-dioxane (3000 mL) was stirred at 90° C. for 2 hours. The reaction was slowly cooled to room temperature and then the mixture was filtered. The filtrate was concentrated under vacuum and the residue was used to the next step without further purification. LCMS (ESI) [M+H]$^+$=656.

Step 3: tert-Butyl 7-(3-amino-8-((tert-butoxycarbonyl)amino)-7-fluoroisoquinolin-6-yl)-8-methyl-2,3-dihydro-1H-pyrido[2,3-b][1,4]oxazine-1-carboxylate

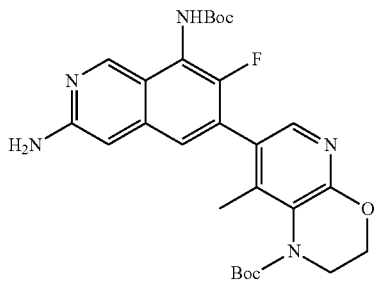 [SMILES: Cc1c(-c2cc3cc(N)ncc3c(NC(=O)OC(C)(C)C)c2F)cnc2c1N(C(=O)OC(C)(C)C)CCO2]

A solution of tert-butyl 7-[8-(tert-butoxycarbonylamino)-3-(1,3-dioxoisoindolin-2-yl)-7-fluoro-6-isoquinolyl]-8-methyl-2,3-dihydropyrido[2,3-b][1,4]oxazine-1-carboxylate (crude product from last step) and hydrazine hydrate (228.0 g, 4560 mmol) in methyl alcohol (3000 mL) was stirred at 40° C. for 2 hours. The product is precipitated, filtered and washed with MeOH (3×500 mL). The solids were dried under vacuum to afford 130 g product. The filtrate was concentrated under vacuum. The residue was purified by flash chromatography on silica gel eluting with DCM/MeOH (5%) to afford 22 g product. Two batches were combined to afford tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (152 g, 288.97 mmol, 55.5% yield) as a yellow solid. LCMS (ESI) [M+H]$^+$= 526.

Example 6 tert-Butyl-7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate

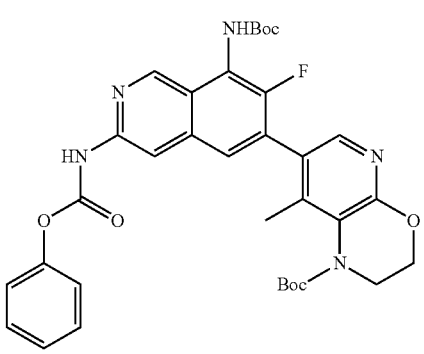 [SMILES: Cc1c(-c2cc3cc(NC(=O)Oc4ccccc4)ncc3c(NC(=O)OC(C)(C)C)c2F)cnc2c1N(C(=O)OC(C)(C)C)CCO2]

A solution of phenyl chloroformate (0.60 g, 3.82 mmol) in dichloromethane (10 mL) was added a suspension of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (1.0 g, 1.9 mmol) and 4-dimethylaminopyridine (0.23 g, 1.88 mmol) in pyridine (5 mL) and dichloromethane (5 mL). The mixture was stirred for 2 hours at 0° C. The resulting solution was washed with water and the organic layer was concentrated under vacuum. The residue was purified by flash chromatography on silica gel eluting with ethyl acetate/petroleum ether (1:1) to afford tert-butyl-7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (1.09 g, 1.553 mmol, 81.7% yield) as a faint yellow solid. LCMS (ESI) [M+H]$^+$=646.2.

Example 7 tert-Butyl 7-(3-amino-8-chloro-7-fluoro-6-isoquinolyl)-8-methyl-3,4-dihydro-2H-1,5-naphthyridine-1-carboxylate

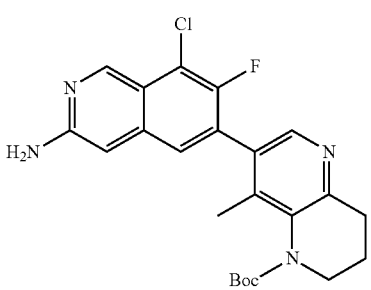 [SMILES: Cc1c(-c2cc3cc(N)ncc3c(Cl)c2F)cnc2c1N(C(=O)OC(C)(C)C)CCC2]

Step 1: 5-bromo-2-iodo-4-methyl-pyridin-3-amine

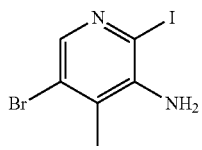

A solution of 5-bromo-4-methyl-pyridin-3-amine (60.0 g, 320.79 mmol) and n-iodosuccinimide (72.2 g, 320.92 mmol) in acetic acid (1000 mL) was stirred at 25° C. for 12 hours. The reaction mixture was concentrated under vacuum. The residue was purified by flash chromatography on silica gel eluting with PE/EA (1/20) to afford 5-bromo-2-iodo-4-methyl-pyridin-3-amine (72 g, 177.16 mmol, 55.2% yield) as a yellow solid.

Step 2: tert-Butyl N-(5-bromo-2-iodo-4-methyl-3-pyridyl)carbamate

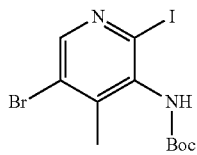

A solution of 5-bromo-2-iodo-4-methyl-pyridin-3-amine (55 g, 175.76 mmol) and NaHMDS (360.mL, 720 mmol) in tetrahydrofuran (500 mL) was stirred at 0° C. for 30 min. Then (Boc)$_2$O (43 g, 197.25 mmol) was added and stirred at 25° C. for 1.5 hours. The resulting solution was diluted with water, then extracted with ethyl acetate. The organic layers were combined and concentrated under vacuum. The residue was purified by flash chromatography on silica gel eluting with ethyl acetate/petroleum ether (1/20) to afford tert-butyl N-(5-bromo-2-iodo-4-methyl-3-pyridyl)carbamate (58 g, 140.42 mmol, 79.9% yield) as a yellow oil.

Step 3: Methyl 3-[5-bromo-3-(tert-butoxycarbonylamino)-4-methyl-2-pyridyl]propanoate

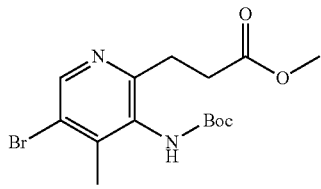 [SMILES: COC(=O)CCc1ncc(Br)c(C)c1NC(=O)OC(C)(C)C]

Under nitrogen, a mixture of tert-butyl N-(5-bromo-2-iodo-4-methyl-3-pyridyl)carbamate (500.0 mg, 1.21 mmol), bromo-(3-methoxy-3-oxo-propyl)zinc (15 mL, 6.89 mmol) and Pd(PPh$_3$)$_4$ (115.0 mg, 0.10 mmol) in tetrahydrofuran (10 mL) was stirred for 2 hours at 70° C. The reaction mixture was diluted with water. The resulting solution was extracted with ethyl acetate and the organic layers were combined. The organic layer was dried over anhydrous sodium sulfate and concentrated under vacuum. The residue was purified by flash chromatography on silica gel eluting with ethyl acetate/petroleum ether (1:1) to afford methyl 3-[5-bromo-3-(tert-butoxycarbonylamino)-4-methyl-2-pyridyl]propanoate (313 mg, 0.79 mmol, 65.1% yield) as a yellow solid. LCMS (ESI) [M+H]$^+$=373.0.

Step 4: 7-Bromo-8-methyl-3,4-dihydro-1H-1,5-naphthyridin-2-one

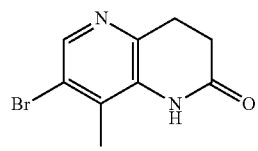

A solution of methyl 3-[5-bromo-3-(tert-butoxycarbonylamino)-4-methyl-2-pyridyl]propanoate (313.0 mg, 0.79 mmol) in trifluoroacetic acid (1 mL) and dichloromethane (4 mL) was stirred at room temperature for 1 hour. The reaction mixture was concentrated under vacuum. The residue was purified by flash chromatography on silica gel eluting with ethyl acetate/petroleum ether (1:1) to afford 7-bromo-8-methyl-3,4-dihydro-1H-1,5-naphthyridin-2-one (140 mg, 0.55 mmol, 70% yield) as a white solid. LCMS (ESI) [M+H]$^+$=241.0.

Step 5: 7-Bromo-8-methyl-1,2,3,4-tetrahydro-1,5-naphthyridine

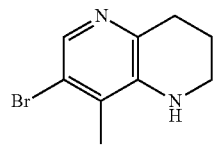

A solution of 7-bromo-8-methyl-3,4-dihydro-1H-1,5-naphthyridin-2-one (120.0 mg, 0.47 mmol) in tetrahydrofuran (10 mL) and BH$_3$.THF (1M) (1.4 mL, 1.42 mmol) was stirred at 60° C. for 2 hours. The reaction was quenched with methanol and diluted hydrochloric acid. The mixture was concentrated under vacuum. The resulting residue was purified by reverse phase chromatography (acetonitrile 0-70/0.1% NH$_4$HCO$_3$ in water) to afford 7-bromo-8-methyl-1,2,3,4-tetrahydro-1,5-naphthyridine (70 mg, 0.29 mmol, 61.9% yield) as a white solid. LCMS (ESI) [M+H]$^+$=227.0. $^1$H NMR (300 MHz, DMSO-d$_6$) δ 7.74 (s, 1H), 5.67 (s, 1H), 3.26-3.21 (m, 2H), 2.76-2.72 (m, 2H), 2.12 (s, 3H), 1.89-1.81 (m, 2H).

Step 6: tert-Butyl 7-bromo-8-methyl-3,4-dihydro-2H-1,5-naphthyridine-1-carboxylate

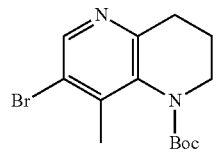 [SMILES: Cc1c(Br)cnc2c1N(C(=O)OC(C)(C)C)CCC2]

NaHDMS (0.5 mL, 0.26 mmol, 0.5 mol/L in THF) was added to a solution of 7-bromo-8-methyl-1,2,3,4-tetrahydro- 1,5-naphthyridine (60.0 mg, 0.26 mmol) in tetrahydrofuran (10 mL) at 0° C., and then the mixture was stirred for 0.5 hour at this temperature. Then (Boc)$_2$O (100.0 mg, 0.46 mmol) was added and stirred at room temperature for 1 hour. The reaction was quenched by methanol (1 mL). The reaction mixture was concentrated under vacuum. The residue was purified by flash chromatography on silica gel eluting with ethyl acetate/petroleum ether (1/4) to afford tert-butyl 7-bromo-8-methyl-3,4-dihydro-2H-1,5-naphthyridine-1-carboxylate (70 mg, 0.20 mmol, 76.9%) as a white solid. LCMS (ESI) [M+H]$^+$=327.0.

Step 7: tert-Butyl 8-methyl-7-(4,4,5,5-tetramethyl-1,3,2-dioxaborolan-2-yl)-3,4-dihydro-2H-1,5-naphthyridine-1-carboxylate

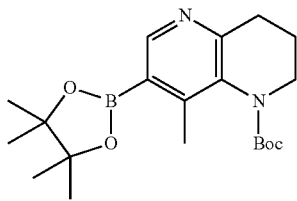 [SMILES: Cc1c(B2OC(C)(C)C(C)(C)O2)cnc2c1N(C(=O)OC(C)(C)C)CCC2]

Under nitrogen, a mixture of tert-butyl 7-bromo-8-methyl-3,4-dihydro-2H-1,5-naphthyridine-1-carboxylate (30.0 g, 91.68 mmol), 4,4,4',4',5,5,5',5'-octamethyl-2,2'-bi(1,3,2-dioxaborolane) (117.0 g, 460.63 mmol), Pd(dppf)Cl$_2$ (6.7 g, 9.17 mmol) and KOAc (27.0 g, 275.51 mmol) in 1,4-dioxane (500 mL) was stirred at 100° C. for 3 hours. The solids were removed by filtration. The mixture was then concentrated under vacuum. The resulting residue was purified by reverse phase chromatography (acetonitrile 5-30/ 0.1% HCl in water) to afford tert-butyl 8-methyl-7-(4,4,5,5-tetramethyl-1,3,2-dioxaborolan-2-yl)-3,4-dihydro-2H-1,5-naphthyridine-1-carboxylate (30 g, 80.154 mmol, 87.4% yield) as a white solid. LCMS (ESI) [M+H]$^+$=375.0.

Step 8: tert-Butyl 7-(3-amino-8-chloro-7-fluoro-6-isoquinolyl)-8-methyl-3,4-dihydro-2H-1,5-naphthyridine-1-carboxylate

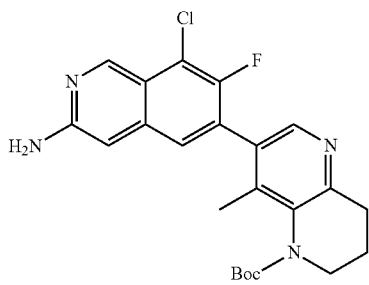 [SMILES: Cc1c(-c2cc3cc(N)ncc3c(Cl)c2F)cnc2c1N(C(=O)OC(C)(C)C)CCC2]

Under nitrogen, a mixture of tert-butyl 8-methyl-7-(4,4,5,5-tetramethyl-1,3,2-dioxaborolan-2-yl)-3,4-dihydro-2H-1,5-naphthyridine-1-carboxylate (30.0 g, 80.15 mmol), 8-chloro-7-fluoro-6-iodo-isoquinolin-3-amine (28.5 g, 88.37 mmol), Pd(dppf)Cl$_2$ (5.9 g, 8.07 mmol) and K$_2$CO$_3$ (33.0 g, 239.13 mmol) in 1,4-dioxane (500 mL) and water (50 mL) was stirred for 16 hours at 60° C. The reaction mixture was diluted with ethyl acetate (1000 mL). The resulting solution was washed with water (3×100 mL) and the organic layers were combined. The organic layer was dried over anhydrous sodium sulfate and concentrated under vacuum. The residue was purified by flash chromatography on silica gel eluting with ethyl acetate/petroleum ether (9:1) to afford tert-butyl 7-(3-amino-8-chloro-7-fluoro-6-isoquinolyl)-8-methyl-3,4-dihydro-2H-1,5-naphthyridine-1-carboxylate (26 g, 58.703 mmol, 73.2% yield) as a yellow solid. LCMS (ESI) [M+H]$^+$=443.

Example 8

Step 1: tert-Butyl 7-[8-chloro-3-(1,3-dioxoisoindolin-2-yl)-7-fluoro-6-isoquinolyl]-8-methyl-3,4-dihydro-2H-1,5-naphthyridine-1-carboxylate

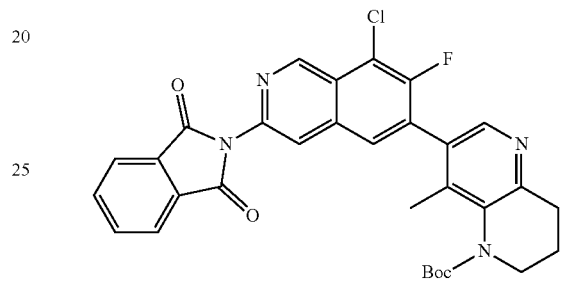

A solution of tert-butyl 7-(3-amino-8-chloro-7-fluoro-6-isoquinolyl)-8-methyl-3,4-dihydro-2H-1,5-naphthyridine-1-carboxylate (26.0 g, 58.7 mmol) and isobenzofuran-1,3-dione (17.5 g, 118.24 mmol) in toluene (300 mL) was stirred at 110° C. for 2 hours. The reaction mixture was concentrated under vacuum. The residue was purified by flash chromatography on silica gel eluting with ethyl acetate/ petroleum ether (1/1) to afford tert-butyl 7-[8-chloro-3-(1,3-dioxoisoindolin-2-yl)-7-fluoro-6-isoquinolyl]-8-methyl-3,4-dihydro-2H-1,5-naphthyridine-1-carboxylate (18 g, 31.41 mmol, 53.5% yield) as a yellow solid. LCMS (ESI) [M+H]$^+$=573.

Step 2: tert-Butyl 7-[8-(tert-butoxycarbonylamino)-3-(1,3-dioxoisoindolin-2-yl)-7-fluoro-6-isoquinolyl]-8-methyl-3,4-dihydro-2H-1,5-naphthyridine-1-carboxylate

Under nitrogen, a mixture of tert-butyl 7-[8-chloro-3-(1,3-dioxoisoindolin-2-yl)-7-fluoro-6-isoquinolyl]-8-methyl-3,4-dihydro-2H-1,5-naphthyridine-1-carboxylate (17.0 g, 29.67 mmol), NH$_2$Boc (104.0 g, 888.89 mmol), Pd$_2$(dba)$_3$·CHCl$_3$ (6.1 g, 5.89 mmol), Brettphos (6.4 g, 11.92 mmol)

and K₂CO₃ (12.3 g, 89.13 mmol) in 1,4-dioxane (300 mL) was stirred at 90° C. for 3 hours. The mixture was filtered and concentrated under vacuum. The crude product was put to the next step without further purification. LCMS (ESI) [M+H]⁺=654.

Step 3: tert-Butyl 7-[3-amino-8-(tert-butoxycarbonylamino)-7-fluoro-6-isoquinolyl]-8-methyl-3,4-dihydro-2H-1,5-naphthyridine-1-carboxylate

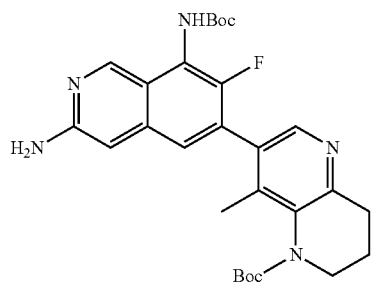 [SMILES: Cc1c(-c2cc3cc(N)ncc3c(NC(=O)OC(C)(C)C)c2F)cnc2c1N(C(=O)OC(C)(C)C)CCC2]

A solution of tert-butyl 7-[8-(tert-butoxycarbonylamino)-3-(1,3-dioxoisoindolin-2-yl)-7-fluoro-6-isoquinolyl]-8-methyl-3,4-dihydro-2H-1,5-naphthyridine-1-carboxylate (13.0 g, 19.89 mmol) and N₂H₄ H₂O (12.5 g, 200 mmol) in ethanol (130 mL) was stirred at 50° C. for 1 hour. The reaction mixture was concentrated under vacuum. The residue was purified by flash chromatography on silica gel eluting with dichloromethane/methanol (20/1) to afford tert-butyl 7-[3-amino-8-(tert-butoxycarbonylamino)-7-fluoro-6-isoquinolyl]-8-methyl-3,4-dihydro-2H-1,5-naphthyridine-1-carboxylate (8 g, 15.279 mmol, 76.8% yield) as a yellow solid. LCMS (ESI) [M+H]⁺=524.

Example 101

Tetrahydropyran-4-yl N-[8-amino-7-fluoro-6-(8-methyl-2,3-dihydro-1H-pyrido[2,3-b][1,4]oxazin-7-yl)-3-isoquinolyl]carbamate (Compound 401)

Step 1: tert-Butyl 7-[8-chloro-7-fluoro-3-(tetrahydropyran-4-yloxycarbonylamino)-6-isoquinolyl]-8-methyl-2,3-dihydropyrido[2,3-b][1,4]oxazine-1-carboxylate

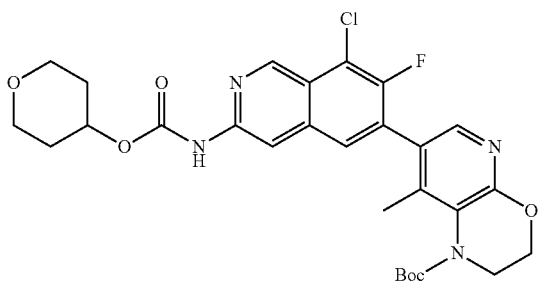

To a solution of tert-butyl 7-(3-amino-8-chloro-7-fluoro-6-isoquinolyl)-8-methyl-2,3-dihydropyrido[2,3-b][1,4]oxazine-1-carboxylate (145 mg, 0.33 mmol) in dichloromethane (1 mL) was added pyridine (1 mL, 12 mmol). To the resulting solution was added drop wise a solution of tetrahydropyran-4-yl carbonochloridate (81 mg, 0.50 mmol) in dichloromethane (0.5 mL). The reaction was then stirred for 90 minutes.

The reaction was then diluted with 20 mL dichloromethane and washed with 40 mL saturated sodium bicarbonate solution. The organic layer was separated and the aqueous layer was further extracted with dichloromethane (2×25 mL). The combined dichloromethane layers were dried with anhydrous powdered magnesium sulfate, filtered and concentrated to give a brown solid. The crude material was purified by flash column chromatography (0-100% isopropyl acetate in heptane) to afford tert-butyl 7-[8-chloro-7-fluoro-3-(tetrahydropyran-4-yloxycarbonylamino)-6-isoquinolyl]-8-methyl-2,3-dihydropyrido[2,3-b][1,4]oxazine-1-carboxylate (181 mg, 0.3 mmol) as a white solid. LCMS (ESI, m/z): 575 [M+H]⁺.

Step 2: tert-Butyl 7-[8-(tert-butoxycarbonylamino)-7-fluoro-3-(tetrahydropyran-4-yloxycarbonylamino)-6-isoquinolyl]-8-methyl-2,3-dihydropyrido[2,3-b][1,4]oxazine-1-carboxylate

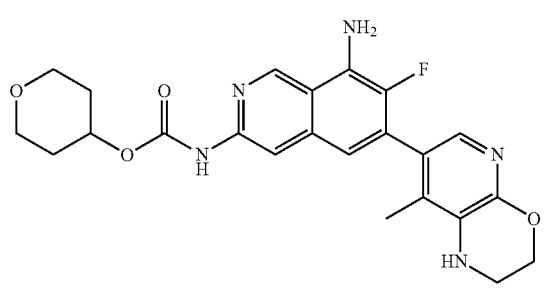 [SMILES: Cc1c(-c2cc3cc(NC(=O)OC4CCOCC4)ncc3c(N)c2F)cnc2c1NCCO2]

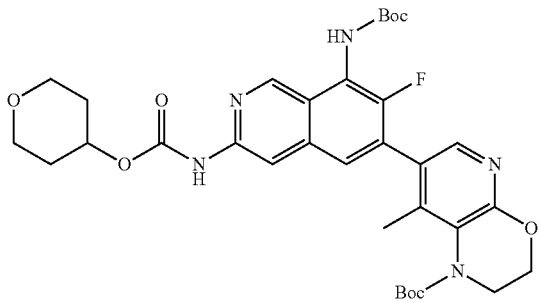 [SMILES: Cc1c(-c2cc3cc(NC(=O)OC4CCOCC4)ncc3c(NC(=O)OC(C)(C)C)c2F)cnc2c1N(C(=O)OC(C)(C)C)CCO2]

tert-Butyl 7-[8-chloro-7-fluoro-3-(tetrahydropyran-4-yloxycarbonylamino)-6-isoquinolyl]-8-methyl-2,3-dihydropyrido[2,3-b][1,4]oxazine-1-carboxylate (181 mg, 0.3 mmol), tert-butyl carbamate (949.3 mg, 8.1 mmol), tris(dibenzylideneacetone)dipalladium-chloroform adduct (83.4 mg, 0.08 mmol), BrettPhos (94.8 mg, 0.17 mmol) and cesium carbonate (624.7 mg, 1.9 mmol) in 1,4-dioxane (4 mL) in a 20 mL pressure tube was purged with nitrogen, sealed and then heated at 90° C. for 3.5 h. The reaction was then cooled to room temperature, diluted with 20 mL dichloromethane and filtered through celite. The filtrate was then concentrated to give a yellowish red solid and purified by column chromatography (0-50% methanol in dichloromethane) to afford tert-butyl 7-[8-(tert-butoxycarbonylamino)-7-fluoro-3-(tetrahydropyran-4-yloxycarbonylamino)-6-isoquinolyl]-8-methyl-2,3-dihydropyrido[2,3-b][1,4]oxazine-1-carboxylate (197 mg, 0.3 mmol) as a brown oil. LCMS (ESI, m/z): 654 [M+H]+.

Step 3: Tetrahydropyran-4-yl N-[8-amino-7-fluoro-6-(8-methyl-2,3-dihydro-1H-pyrido[2,3-b][1,4]oxazin-7-yl)-3-isoquinolyl]carbamate

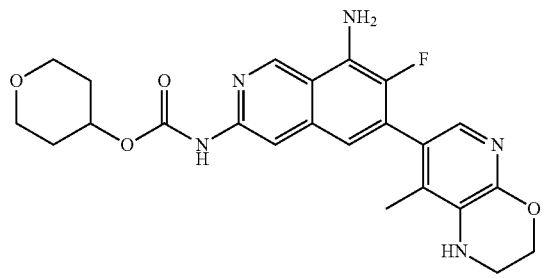 [SMILES: Cc1c(-c2cc3cc(NC(=O)OC4CCOCC4)ncc3c(N)c2F)cnc2c1NCCO2]

To a solution of tert-butyl 7-[8-(tert-butoxycarbonylamino)-7-fluoro-3-(tetrahydropyran-4-yloxycarbonylamino)-6-isoquinolyl]-8-methyl-2,3-dihydropyrido[2,3-b][1,4]oxazine-1-carboxylate (197 mg, 0.3 mmol) in dichloromethane (4 mL) was added tifluoroacetic acid (8 mL). The reaction was then stirred at room temperature for 45 minutes. The reaction was then concentrated and purified by reverse phase HPLC to afford tetrahydropyran-4-yl N-[8-amino-7-fluoro-6-(8-methyl-2,3-dihydro-1H-pyrido[2,3-b][1,4]oxazin-7-yl)-3-isoquinolyl]carbamate (56 mg, 0.12 mmol) as a pale yellow solid. $^1$H NMR (400 MHz, DMSO-$d_6$) δ 10.04 (s, 1H), 9.34 (s, 1H), 7.97 (s, 1H), 7.33 (s, 1H), 6.83 (d, J=6.2 Hz, 1H), 6.20 (s, 2H), 5.66 (d, J=3.0 Hz, 1H), 4.88 (dt, J=8.8, 4.6 Hz, 1H), 4.29 (t, J=4.4 Hz, 2H), 3.88-3.83 (m, 2H), 3.50-3.45 (m, 2H), 3.38-3.36 (m, 2H), 1.92 (d, J=1.6 Hz, 5H), 1.61 (dt, J=12.9, 4.5 Hz, 2H). LCMS (ESI, m/z): 454.2 [M+H]+, Rt=3.502 min, Method N.

Example 102

1-Methylazetidin-3-yl (8-amino-7-fluoro-6-(8-methyl-2,3-dihydro-1H-pyrido[2,3-b][1,4]oxazin-7-yl)isoquinolin-3-yl)carbamate (Compound 402)

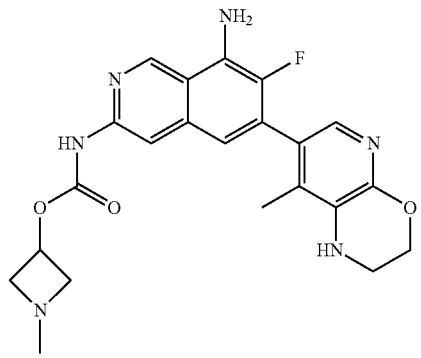 [SMILES: Cc1c(-c2cc3cc(NC(=O)OC4CN(C)C4)ncc3c(N)c2F)cnc2c1NCCO2]

Step 1: tert-Butyl 7-[3-[(1-tert-butoxycarbonylazetidin-3-yl)oxycarbonylamino]-8-chloro-7-fluoro-6-isoquinolyl]-8-methyl-2,3-dihydropyrido[2,3-b][1,4]oxazine-1-carboxylate

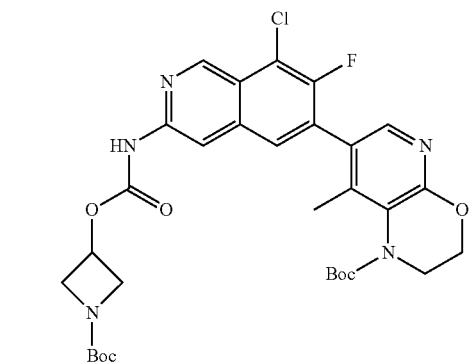 [SMILES: Cc1c(-c2cc3cc(NC(=O)OC4CN(C(=O)OC(C)(C)C)C4)ncc3c(Cl)c2F)cnc2c1N(C(=O)OC(C)(C)C)CCO2]

A solution of triphosgene (203 mg, 0.68 mmol) in dichloromethane (1 mL) was added slowly to a solution of 1-boc-3-hydroxyazetidine (370 mg, 2.14 mmol) and DIEA (275 mg, 2.13 mmol) in dichloromethane (5 mL) at 0° C. The reaction was stirred for 1 hour at 0° C. The resulting mixture was added to a solution of tert-butyl 7-(3-amino-8-chloro-7-fluoro-6-isoquinolyl)-8-methyl-2,3-dihydropyrido[2,3-b][1,4]oxazine-1-carboxylate (190 mg, 0.43 mmol) and DIEA (111 mg, 0.86 mmol) in dichloromethane (5 mL) at 0° C. The reaction was stirred for 2 hours at room temperature. The reaction was quenched with water and then extracted with dichloromethane. The organic layer was dried over anhydrous sodium sulfate and concentrated under vacuum. The residue was purified by flash chromatography on silica gel eluting with dichloromethane/methanol (10/1) to afford tert-butyl 7-[3-[(1-tert-butoxycarbonylazetidin-3-yl)oxycarbonylamino]-8-chloro-7-fluoro-6-isoquinolyl]-8-methyl-2,3-dihydropyrido[2,3-b][1,4]oxazine-1-carboxylate (180 mg, 0.28 mmol, 65.4% yield) as a yellow solid.

Step 2: tert-Butyl 7-[3-[(1-tert-butoxycarbonylazetidin-3-yl)oxycarbonylamino]-8-chloro-7-fluoro-6-isoquinolyl]-8-methyl-2,3-dihydropyrido[2,3-b][1,4]oxazine-1-carboxylate

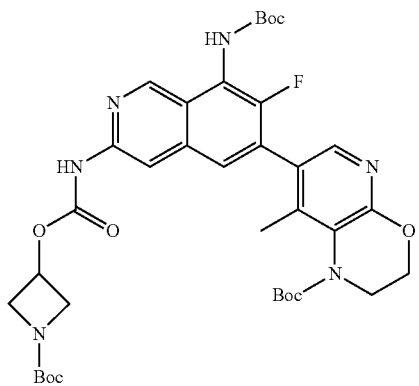 [SMILES: Cc1c(-c2cc3cc(NC(=O)OC4CN(C(=O)OC(C)(C)C)C4)ncc3c(NC(=O)OC(C)(C)C)c2F)cnc2c1N(C(=O)OC(C)(C)C)CCO2]

A mixture of tert-butyl 7-[3-[(1-tert-butoxycarbonylazetidin-3-yl)oxycarbonylamino]-8-chloro-7-fluoro-6-isoquinolyl]-8-methyl-2,3-dihydropyrido[2,3-b][1,4]oxazine-1-carboxylate (180.0 mg, 0.28 mmol), NH$_2$Boc (981.0 mg, 8.38 mmol), Pd$_2$(dba)$_3$·CHCl$_3$ (29.0 mg, 0.03 mmol), Brettphos (27.0 mg, 0.06 mmol), and Cs$_2$CO$_3$ (273.0 mg, 0.84 mmol) in 1,4-dioxane (5 mL) was stirred at 90° C. for 2 h. The reaction was concentrated under vacuum. The residue was purified by flash chromatography on silica gel eluting with dichloromethane/methanol (10:1) to afford tert-butyl 7-[8-(tert-butoxycarbonylamino)-3-[(1-tert-butoxycarbonylazetidin-3-yl)oxycarbonylamino]-7-fluoro-6-isoquinolyl]-8-methyl-2,3-dihydropyrido[2,3-b][1,4]oxazine-1-carboxylate (140 mg, 0.19 mmol, 69.1% yield) as a brown solid.

Step 3: Azetidin-3-yl N-[8-amino-7-fluoro-6-(8-methyl-2,3-dihydro-1H-pyrido[2,3-b][1,4]oxazin-7-yl)-3-isoquinolyl]carbamate

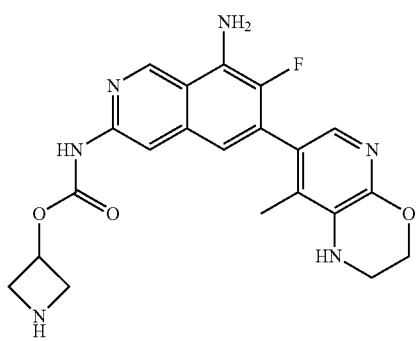 [SMILES: Cc1c(-c2cc3cc(NC(=O)OC4CNC4)ncc3c(N)c2F)cnc2c1NCCO2]

A solution of tert-butyl 7-[8-(tert-butoxycarbonylamino)-3-[(1-tert-butoxycarbonylazetidin-3-yl)oxycarbonylamino]-7-fluoro-6-isoquinolyl]-8-methyl-2,3-dihydropyrido[2,3-b][1,4]oxazine-1-carboxylate (140.0 mg, 0.19 mmol) in dichloromethane (2 mL) and TFA (0.5 mL) was stirred at 25° C. for 2 h. The reaction was concentrated under vacuum and purified by reverse phase chromatography (acetonitrile 0-40/0.1% NH$_4$HCO$_3$ in water) to afford azetidin-3-yl N-[8-amino-7-fluoro-6-(8-methyl-2,3-dihydro-1H-pyrido[2,3-b][1,4]oxazin-7-yl)-3-isoquinolyl]carbamate (40 mg, 0.09 mmol, 48.8% yield) as a yellow solid.

Step 4: (1-Methylazetidin-3-yl) N-[8-amino-7-fluoro-6-(8-methyl-2,3-dihydro-1H-pyrido[2,3-b][1,4]oxazin-7-yl)-3-isoquinolyl]carbamate

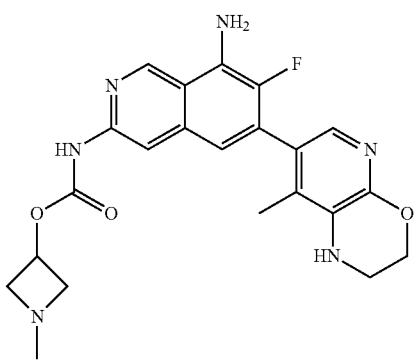 [SMILES: Cc1c(-c2cc3cc(NC(=O)OC4CN(C)C4)ncc3c(N)c2F)cnc2c1NCCO2]

A solution of azetidin-3-yl N-[8-amino-7-fluoro-6-(8-methyl-2,3-dihydro-1H-pyrido[2,3-b][1,4]oxazin-7-yl)-3-isoquinolyl]carbamate (40 mg, 0.09 mmol) and formaldehyde (40% aq., 14 mg, 0.19 mmol) in methyl alcohol (2 mL) was stirred at 25° C. for 1 hour. NaBH$_3$CN (32 mg, 0.28 mmol) was then added and the reaction was stirred at 25° C. for 2 hours. The reaction was concentrated under vacuum and purified by reverse phase chromatography (acetonitrile 0-40/0.1% NH$_4$HCO$_3$ in water) to afford (1-methylazetidin-3-yl) N-[8-amino-7-fluoro-6-(8-methyl-2,3-dihydro-1H-pyrido[2,3-b][1,4]oxazin-7-yl)-3-isoquinolyl]carbamate (9.2 mg, 0.021 mmol, 22.1% yield) as a white solid. LCMS (ESI) [M+H]$^+$=439, Rt=1.574 min, Method K. $^1$H NMR (400 MHz, DMSO-d$_6$) δ 10.25 (s, 1H), 9.35 (s, 1H), 7.96 (s, 1H), 7.33 (s, 1H), 6.84 (d, J=6.1 Hz, 1H), 6.24 (s, 2H), 5.69 (s, 1H), 4.95 (p, J=6.0 Hz, 1H), 4.29 (s, 2H), 3.65 (t, J=7.4 Hz, 2H), 3.36-3.33 (m, 2H), 3.04 (t, J=6.9 Hz, 2H), 2.30 (s, 3H), 1.92 (d, J=1.6 Hz, 3H).

Example 103

(±)-Tetrahydrofuran-3-yl (8-amino-7-fluoro-6-(8-methyl-2,3-dihydro-1H-pyrido[2,3-b][1,4]oxazin-7-yl)isoquinolin-3-yl)carbamate (Compound 403)

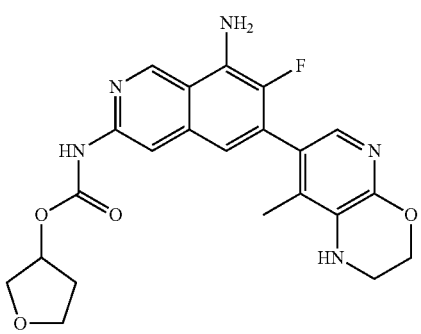 [SMILES: Cc1c(-c2cc3cc(NC(=O)OC4CCOC4)ncc3c(N)c2F)cnc2c1NCCO2]

Step 1: tert-Butyl 7-[8-chloro-7-fluoro-3-(tetrahydrofuran-3-yloxycarbonylamino)-6-isoquinolyl]-8-methyl-2,3-dihydropyrido[2,3-b][1,4]oxazine-1-carboxylate

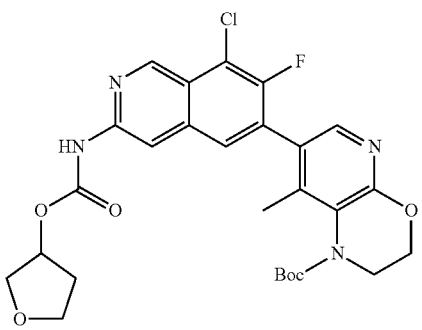 [SMILES: Cc1c(-c2cc3cc(NC(=O)OC4CCOC4)ncc3c(Cl)c2F)cnc2c1N(C(=O)OC(C)(C)C)CCO2]

To a solution of 3-hydroxytetrahydrofuran (790 mg, 8.97 mmol) and N,N-diisopropylethylamine (0.32 mL, 1.86 mmol) in dichloromethane (15 mL) was added triphosgene (414 mg, 1.40 mmol) at 0° C. The reaction was stirred for 30 min. tert-Butyl 7-(3-amino-8-chloro-7-fluoro-6-isoquinolyl)-8-methyl-2,3-dihydropyrido[2,3-b][1,4]oxazine-1-carboxylate (400 mg, 0.90 mmol) was then added. The reaction was stirred at 0° C. for 6 h. The resulting mixture was concentrated under vacuum and purified by flash chromatography on silica gel eluting with petroleum ether/ethyl acetate (5/1) to afford tert-butyl 7-[8-chloro-7-fluoro-3-(tetrahydrofuran-3-yloxycarbonylamino)-6-isoquinolyl]-8-methyl-2,3-dihydropyrido[2,3-b][1,4]oxazine-1-carboxylate (180 mg, 0.32 mmol, 35.8% yield) as a yellow solid. LCMS (ESI) [M+H]$^+$=559.

Step 2: tert-Butyl 7-[8-(tert-butoxycarbonylamino)-7-fluoro-3-(tetrahydrofuran-3-yloxycarbonylamino)-6-isoquinolyl]-8-methyl-2,3-dihydropyrido[2,3-b][1,4]oxazine-1-carboxylate

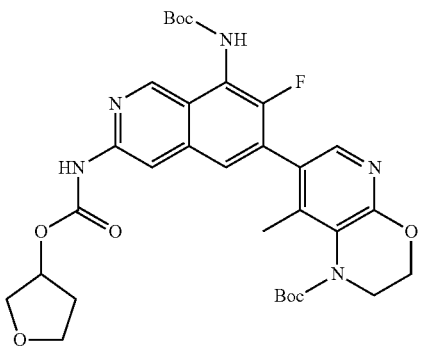 [SMILES: Cc1c(-c2cc3cc(NC(=O)OC4CCOC4)ncc3c(NC(=O)OC(C)(C)C)c2F)cnc2c1N(C(=O)OC(C)(C)C)CCO2]

A mixture of tert-butyl 7-[8-chloro-7-fluoro-3-(tetrahydrofuran-3-yloxycarbonylamino)-6-isoquinolyl]-8-methyl-2,3-dihydropyrido[2,3-b][1,4]oxazine-1-carboxylate (160 mg, 0.29 mmol), tert-butyl carbamate (1.0 g, 8.54 mmol), cesium carbonate (290 mg, 0.88 mmol), 2-(dicyclohexylphosphino)3,6-dimethoxy-2',4',6'-triisopropyl-1,1'-biphenyl (62 mg, 0.12 mmol), and tris(dibenzylideneacetone)dipalladium-chloroform adduct (60 mg, 0.06 mmol) in 1,4-dioxane (20 mL) was stirred at 100° C. for 2 h. After filtration, the filtrate was concentrated under reduced pressure. The residue was purified by flash chromatography on silica gel eluting with methane/dichloromethane (1/10) to afford tert-butyl 7-[8-(tert-butoxycarbonylamino)-7-fluoro-3-(tetrahydrofuran-3-yloxycarbonylamino)-6-isoquinolyl]-8-methyl-2,3-dihydropyrido[2,3-b][1,4]oxazine-1-carboxylate (100 mg, 0.16 mmol, 54.6% yield) as a yellow solid. LCMS (ESI) [M+H]$^+$=640.

Step 3: (±)-Tetrahydrofuran-3-yl N-[8-amino-7-fluoro-6-(8-methyl-2,3-dihydro-1H-pyrido[2,3-b][1,4]oxazin-7-yl)-3-isoquinolyl]carbamate

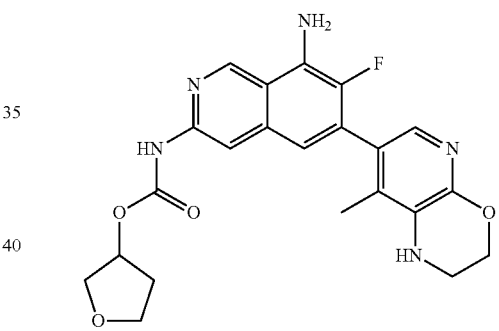

A solution of tert-butyl 7-[8-(tert-butoxycarbonylamino)-7-fluoro-3-(tetrahydrofuran-3-yloxycarbonylamino)-6-isoquinolyl]-8-methyl-2,3-dihydropyrido[2,3-b][1,4]oxazine-1-carboxylate (45 mg, 0.07 mmol) in dichloromethane (5 mL) and TFA (1 mL) was stirred at 25° C. for 30 min. The resulting solution was concentrated under vacuum. The pH of the residue was adjusted to pH 8 with ammonia in methanol (7 mol/L). The resulting solution was concentrated under vacuum and purified by Prep-HPLC (XBridge Shield RP18 OBD Column 30*150 mm, 5 μm; Water (10 mmol/L NH$_4$HCO$_3$): ACN=19% B to 42% B in 7 min; 60 mL/min) to afford tetrahydrofuran-3-yl N-[8-amino-7-fluoro-6-(8-methyl-2,3-dihydro-1H-pyrido[2,3-b][1,4]oxazin-7-yl)-3-isoquinolyl]carbamate (17.8 mg, 0.041 mmol, 57.6% yield) as a yellow solid. LCMS (ESI) [M+H]$^+$=440, 2.216 min, Method M. $^1$H NMR (400 MHz, DMSO-d$_6$) δ 10.12 (s, 1H), 9.33 (s, 1H), 7.97 (s, 1H), 7.33 (s, 1H), 6.84 (d, J=6.1 Hz, 1H), 6.21 (s, 2H), 5.67 (s, 1H), 5.31-5.24 (m, 1H), 4.29 (t, J=4.5 Hz, 2H), 3.89-3.69 (m, 4H), 3.39-3.34 (m, 2H), 2.20-2.18 (m, 1H), 1.98-1.96 (m, 1H), 1.92 (s, 3H).

Example 104

1-Methylpiperidin-4-yl (8-amino-7-fluoro-6-(8-methyl-2,3-dihydro-1H-pyrido[2,3-b][1,4]oxazin-7-yl)isoquinolin-3-yl)carbamate (Compound 407) and Piperidin-4-yl (8-amino-7-fluoro-6-(8-methyl-2,3-dihydro-1H-pyrido[2,3-b][1,4]oxazin-7-yl)isoquinolin-3-yl)carbamate (Compound 404)

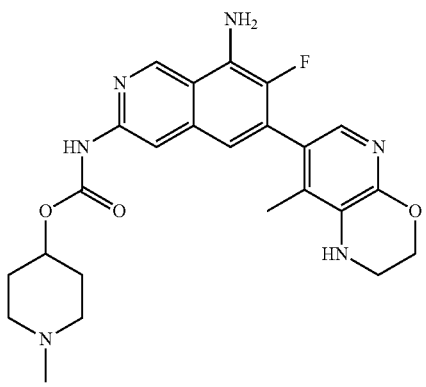

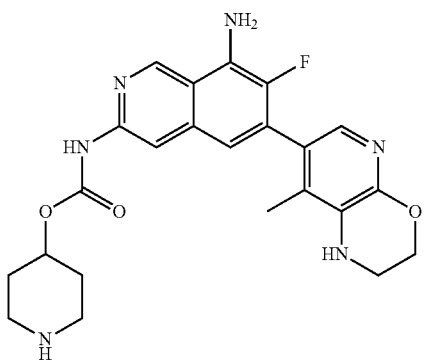

Step 1: tert-Butyl 7-(3-((((1-(tert-butoxycarbonyl)piperidin-4-yl)oxy)carbonyl)amino)-8-chloro-7-fluoroisoquinolin-6-yl)-8-methyl-2,3-dihydro-1H-pyrido[2,3-b][1,4]oxazine-1-carboxylate

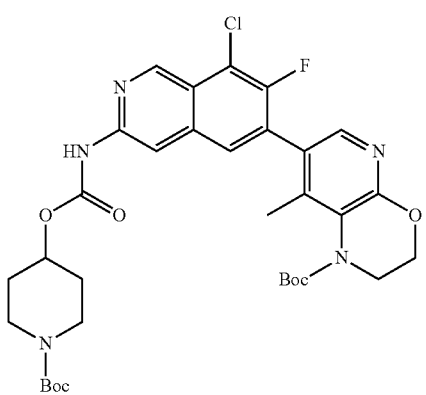 [SMILES: Cc1c(-c2cc3cc(NC(=O)OC4CCN(C(=O)OC(C)(C)C)CC4)ncc3c(Cl)c2F)cnc2c1N(C(=O)OC(C)(C)C)CCO2]

To a solution of tert-butyl 4-hydroxypiperidine-1-carboxylate (2.26 g, 11.23 mmol) and N,N-diisopropylethylamine (1.95 mL, 11.23 mmol) in dichloromethane (5 mL) was added dropwise triphosgene (1 g, 3.43 mmol) in dichloromethane (2 ml) at 0° C. The reaction was stirred at 0° C. for 2 hours. The reaction mixture was then added to a solution of tert-butyl 7-(3-amino-8-chloro-7-fluoro-6-isoquinolyl)-8-methyl-2,3-dihydropyrido[2,3-b][1,4]oxazine-1-carboxylate (500 mg, 1.12 mmol) and N,N-diisopropylethylamine (1.95 mL, 11.23 mmol) in dichloromethane (5 mL) at 0° C. The mixture was stirred at room temperature for 16 h. The reaction was quenched with water and then extracted with dichloromethane. The organic layer was dried over anhydrous sodium sulfate, filtered, and concentrated under vacuum. The residue was purified by flash chromatography on silica gel eluting with petroleum ether/ethyl acetate (1/1) to afford tert-butyl 7-[3-[(1-tert-butoxycarbonyl-4-piperidyl)oxycarbonylamino]-8-chloro-7-fluoro-6-isoquinolyl]-8-methyl-2,3-dihydropyrido[2,3-b][1,4]oxazine-1-carboxylate (500 mg, 0.74 mmol, 66% yield) as a yellow solid. LCMS (ESI) [M+H]$^+$=672.

Step 2: tert-Butyl 7-(8-((tert-butoxycarbonyl)amino)-3-((((1-(tert-butoxycarbonyl)piperidin-4-yl)oxy)carbonyl)amino)-7-fluoroisoquinolin-6-yl)-8-methyl-2,3-dihydro-1H-pyrido[2,3-b][1,4]oxazine-1-carboxylate

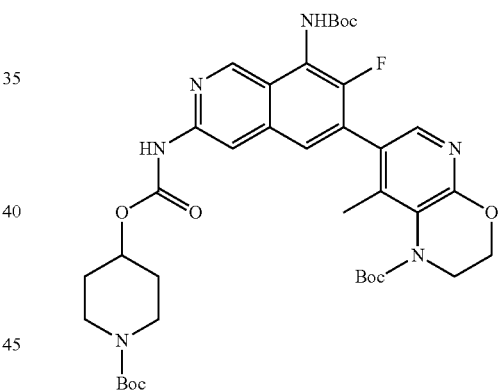

To a mixture of tert-butyl 7-[3-[(1-tert-butoxycarbonyl-4-piperidyl)oxycarbonylamino]-8-chloro-7-fluoro-6-isoquinolyl]-8-methyl-2,3-dihydropyrido[2,3-b][1,4]oxazine-1-carboxylate (500 mg, 0.74 mmol), tert-butyl carbamate (1.75 g, 14.9 mmol), tris(dibenzylideneacetone)dipalladium-chloroform adduct (155 mg, 0.15 mmol) and 2-(dicyclohexylphosphino)3,6-dimethoxy-2',4',6'-triisopropyl-1,1'-biphenyl (160 mg, 0.30 mmol) in 1,4-dioxane (10 mL) was added cesium carbonate (730 mg, 2.23 mmol) at room temperature. The reaction was stirred at 90° C. for 3 hours. The resulting solution was concentrated under vacuum and purified by flash chromatography on silica gel eluting with petroleum ether/ethyl acetate (3/1) to afford tert-butyl 7-[8-(tert-butoxycarbonylamino)-3-[(1-tert-butoxycarbonyl-4-piperidyl)oxycarbonylamino]-7-fluoro-6-isoquinolyl]-8-methyl-2,3-dihydropyrido[2,3-b][1,4]oxazine-1-carboxylate (250 mg, 0.33 mmol, 44.6% yield) as a yellow solid. LCMS (ESI) [M+H]$^+$=753.

Step 3: Piperidin-4-yl (8-amino-7-fluoro-6-(8-methyl-2,3-dihydro-1H-pyrido[2,3-b][1,4]oxazin-7-yl)isoquinolin-3-yl)carbamate

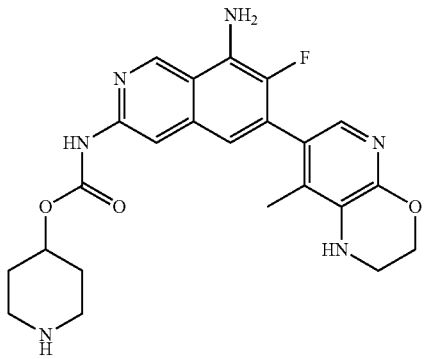 [SMILES: Cc1c(-c2cc3cc(NC(=O)OC4CCNCC4)ncc3c(N)c2F)cnc2c1NCCO2]

A mixture of tert-butyl 7-[8-(tert-butoxycarbonylamino)-3-[(1-tert-butoxycarbonyl-4-piperidyl)oxycarbonylamino]-7-fluoro-6-isoquinolyl]-8-methyl-2,3-dihydropyrido[2,3-b][1,4]oxazine-1-carboxylate (250 mg, 0.33 mmol) and trifluoroacetic acid (2 mL) in dichloromethane (2 mL) was stirred at room temperature for 30 minutes. The reaction solution was concentrated under vacuum. The residue was dissolved in dichloromethane and adjusted pH to 7 with triethylamine. The mixture was concentrated under vacuum and purified by reverse phase chromatography (acetonitrile 0-40/0.1% $NH_4HCO_3$ in water) to afford 4-piperidyl N-[8-amino-7-fluoro-6-(8-methyl-2,3-dihydro-1H-pyrido[2,3-b][1,4]oxazin-7-yl)-3-isoquinolyl]carbamate (70 mg, 0.15 mmol, 45.5% yield) as a yellow solid. LCMS (ESI) $[M+H]^+$= 453, 1.479 min, Method J; $^1$H NMR (400 MHz, DMSO-$d_6$) δ 9.98 (s, 1H), 9.33 (s, 1H), 7.97 (s, 1H), 7.33 (s, 1H), 6.82 (d, J=6.4 Hz, 1H), 6.20 (s, 2H), 5.66 (s, 1H), 4.73-4.71 (m, 1H), 4.29 (t, J=4.0 Hz, 2H), 3.49 (s, 3H), 2.97-2.94 (m, 2H), 2.58-2.55 (m, 2H), 1.92 (s, 3H), 1.89-1.85 (m, 2H), 1.53-1.48 (m, 2H).

Step 4: 1-Methylpiperidin-4-yl (8-amino-7-fluoro-6-(8-methyl-2,3-dihydro-1H-pyrido[2,3-b][1,4]oxazin-7-yl)isoquinolin-3-yl)carbamate

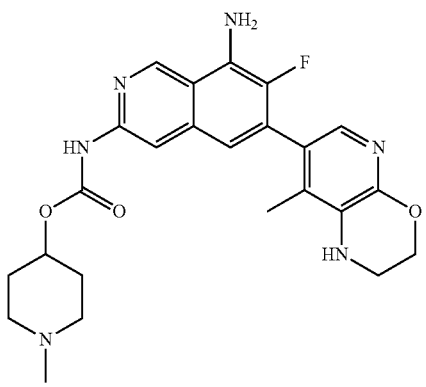 [SMILES: Cc1c(-c2cc3cc(NC(=O)OC4CCN(C)CC4)ncc3c(N)c2F)cnc2c1NCCO2]

A solution of 4-piperidyl N-[8-amino-7-fluoro-6-(8-methyl-2,3-dihydro-1H-pyrido[2,3-b][1,4]oxazin-7-yl)-3-isoquinolyl]carbamate (70 mg, 0.15 mmol) and formaldehyde (9 mg, 0.30 mmol) in methyl alcohol (8 mL) was stirred at room temperature for 2 hours at room temperature. Sodium cyanoborohydride (18.8 mg, 0.30 mmol) was then added. The reaction mixture was stirred at room temperature for 2 hours. The reaction was quenched with water and then extracted with dichloromethane. The organic layer was dried over anhydrous sodium sulfate, filtered, and concentrated under vacuum. The crude product was purified by prep-HPLC (XBridge Prep OBD C18 Column 30×150 mm 5 μm; Water (10 mmol/L $NH_4HCO_3$): $CH_3CN$=31% B to 53% B in 7 min; 60 mL/min) to afford (1-methyl-4-piperidyl) N-[8-amino-7-fluoro-6-(8-methyl-2,3-dihydro-1H-pyrido[2,3-b][1,4]oxazin-7-yl)-3-isoquinolyl]carbamate (24.4 mg, 0.052 mmol, 34.8% yield) as a yellow solid. LCMS (ESI) $[M+H]^+$= 467, Rt=1.545 min, Method K; $^1$H NMR (400 MHz, DMSO-$d_6$) δ 9.99 (s, 1H), 9.33 (s, 1H), 7.97 (s, 1H), 7.33 (s, 1H), 6.82 (d, J=6.4 Hz, 1H), 6.20 (s, 2H), 5.66 (s, 1H), 4.68-4.66 (m, 1H), 4.29 (t, J=4.0 Hz, 2H), 3.36-3.33 (m, 2H), 2.64-2.62 (m, 2H), 2.15-2.12 (m, 5H), 1.90-1.87 (m, 5H), 1.65-1.63 (m, 2H).

Example 105

(R)-Pyrrolidin-3-yl (8-amino-7-fluoro-6-(8-methyl-2,3-dihydro-1H-pyrido[2,3-b][1,4]oxazin-7-yl)isoquinolin-3-yl)carbamate and (S)-Pyrrolidin-3-yl (8-amino-7-fluoro-6-(8-methyl-2,3-dihydro-1H-pyrido[2,3-b][1,4]oxazin-7-yl)isoquinolin-3-yl)carbamate (Compound 405a and Compound 405b)

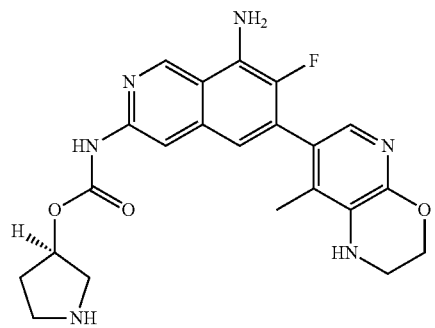

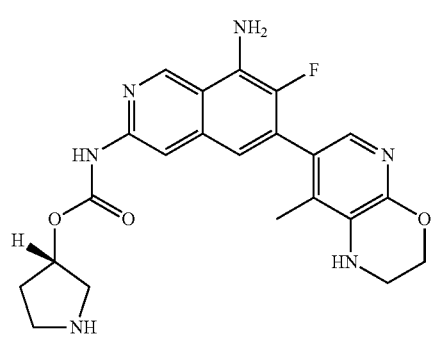

Step 1: tert-Butyl 7-[3-[(1-tert-butoxycarbonylpyr-rolidin-3-yl)oxycarbonylamino]-8-chloro-7-fluoro-6-isoquinolyl]-8-methyl-2,3-dihydropyrido[2,3-b][1,4]oxazine-1-carboxylate

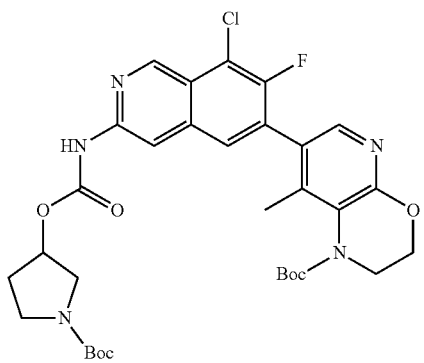 [SMILES: Cc1c(-c2cc3cc(NC(=O)OC4CCN(C(=O)OC(C)(C)C)C4)ncc3c(Cl)c2F)cnc2c1N(C(=O)OC(C)(C)C)CCO2]

A solution of tert-butyl 7-(3-amino-8-chloro-7-fluoro-6-isoquinolyl)-8-methyl-2,3-dihydropyrido[2,3-b][1,4]oxazine-1-carboxylate (250 mg, 0.56 mmol), 1-boc-3-hy-droxypyrrolidine (105 mg, 0.56 mmol), and DIEA (72 mg, 0.56 mmol) in dichloromethane (20 mL) was stirred at 0° C. under nitrogen for 5 minutes. Triphosgene (168 mg, 0.59 mmol) in dichloromethane (1 mL) was then added to the reaction solution at 0° C. The reaction was stirred at room temperature for 1 hour. The reaction was then quenched by water and extracted with dichloromethane (200 mL). The organic layer was dried over anhydrous sodium sulfate, filtered, and concentrated under vacuum. The residue was purified by flash chromatography on silica gel eluting with ethyl acetate/petroleum ether (1/1) to afford tert-butyl 7-[3-[(1-tert-butoxycarbonylpyrrolidin-3-yl)oxycarbonylamino]-8-chloro-7-fluoro-6-isoquinolyl]-8-methyl-2,3-dihydro-pyrido[2,3-b][1,4]oxazine-1-carboxylate (230 mg, 0.33 mmol, 59.1% yield) as a yellow solid. LCMS (ESI) [M+H]$^+$= 658.0.

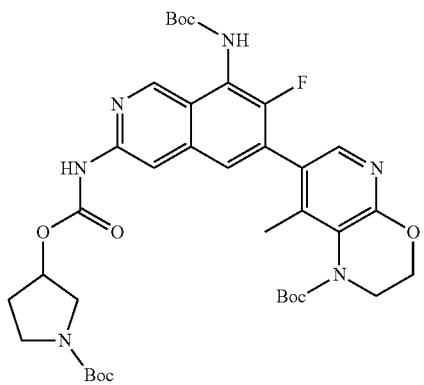 [SMILES: Cc1c(-c2cc3cc(NC(=O)OC4CCN(C(=O)OC(C)(C)C)C4)ncc3c(NC(=O)OC(C)(C)C)c2F)cnc2c1N(C(=O)OC(C)(C)C)CCO2]

A mixture of tert-butyl 7-[3-[(1-tert-butoxycarbonylpyr-rolidin-3-yl)oxycarbonylamino]-8-chloro-7-fluoro-6-iso-quinolyl]-8-methyl-2,3-dihydropyrido[2,3-b][1,4]oxazine-1-carboxylate (230 mg, 0.35 mmol), tert-butylcarbamate (1.2 g, 10.26 mmol), Pd$_2$(dba)$_3$·CHCl$_3$ (36 mg, 0.03 mmol), Brettphos (35 mg, 0.070 mmol) and Cs$_2$CO$_3$ (350 mg, 1.07 mmol) in 1,4-dioxane (15 mL) was stirred under nitrogen at 90° C. for 4 hours. The reaction solution was filtered and the filtrate was concentrated under vacuum. The residue was purified by flash chromatography on silica gel eluting with ethyl acetate/petroleum ether (1/1) to afford tert-butyl 7-[8-(tert-butoxycarbonylamino)-3-[(1-tert-butoxycarbonylpyr-rolidin-3-yl)oxycarbonylamino]-7-fluoro-6-isoquinolyl]-8-methyl-2,3-dihydropyrido[2,3-b][1,4]oxazine-1-carboxylate (220 mg, 0.27 mmol, 76.7% yield) as a yellow solid. LCMS (ESI) [M+H]$^+$=739.0.

Step 3: (R)-Pyrrolidin-3-yl (8-amino-7-fluoro-6-(8-methyl-2,3-dihydro-1H-pyrido[2,3-b][1,4]oxazin-7-yl)isoquinolin-3-yl)carbamate and (S)-Pyrrolidin-3-yl (8-amino-7-fluoro-6-(8-methyl-2,3-dihydro-1H-pyrido[2,3-b][1,4]oxazin-7-yl)isoquinolin-3-yl) carbamate

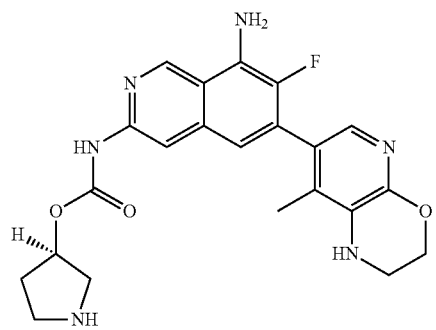

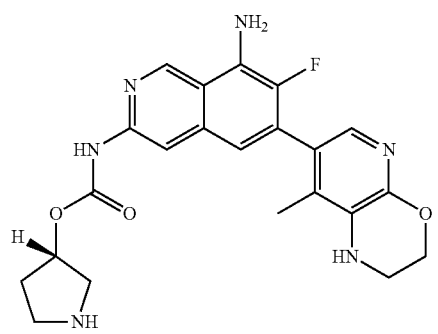

A solution of tert-butyl 7-[8-(tert-butoxycarbonylamino)-3-[(1-tert-butoxycarbonylpyrrolidin-3-yl)oxycarbo-nylamino]-7-fluoro-6-isoquinolyl]-8-methyl-2,3-dihydro-pyrido[2,3-b][1,4]oxazine-1-carboxylate (200 mg, 0.27 mmol) and trifluoroacetic acid (3 mL) in dichloromethane (10 mL) was stirred at 28° C. for 1 hour. The mixture then was concentrated under vacuum. The pH value of the residue was adjusted to pH 9 with triethylamine. The crude product was purified by prep-HPLC (YMC-Actus Triart C18 30*250, 5 μm; water (10 mmol/L NH$_4$HCO$_3$): CH$_3$CN=50% B to 70% B in 7 min; 60 mL/min) to afford the racemic product. The racemic product was separated by Chiral-HPLC to afford two enantiomers. Absolute stereochemistry was arbitrarily assigned.

Enantiomer 1 (Compound 405a) (27.1 mg, 0.062 mmol, 22.8% yield): Retention time: 2.075 min (ChIRALPAK IC-3, 0.46*5 cm, 3 μm; MTBE (0.1% DEA): MeOH=75:25 in 5 min; 1 mL/min). LCMS (ESI) [M+H]⁺=439.2, Rt=0.935 min, Method J; ¹H NMR (400 MHz, DMSO-d₆) δ 9.98 (s, 1H), 9.32 (s, 1H), 7.97 (s, 1H), 7.33 (s, 1H), 6.83 (d, J=6.1 Hz, 1H), 6.20 (s, 2H), 5.67 (s, 1H), 5.14-5.11 (m, 1H), 4.29 (t, J=4.4 Hz, 2H), 3.36 (s, 3H), 3.04 (dd, J=12.4, 5.6 Hz, 1H), 2.92-2.74 (m, 3H), 1.98 (dd, J=14.3, 7.3 Hz, 1H), 1.92 (s, 3H), 1.78 (q, J=6.9, 6.1 Hz, 1H).

Enantiomer 2 (Compound 405b) (25.9 mg, 0.059 mmol, 21.8% yield): Retention time: 3.237 min (ChIRALPAK IC-3, 0.46*5 cm, 3 μm; MTBE (0.1% DEA): MeOH=75:25 in 5 min; 1 mL/min). LCMS (ESI) [M+H]⁺=439.2, Rt=0.935 min, Method J; ¹H NMR (400 MHz, DMSO-d₆) δ 9.98 (s, 1H), 9.32 (s, 1H), 7.97 (s, 1H), 7.33 (s, 1H), 6.83 (d, J=6.1 Hz, 1H), 6.20 (s, 2H), 5.67 (s, 1H), 5.14-5.11 (m, 1H), 4.29 (t, J=4.4 Hz, 2H), 3.36 (s, 3H), 3.04 (dd, J=12.4, 5.6 Hz, 1H), 2.92-2.74 (m, 3H), 1.98 (dd, J=14.3, 7.3 Hz, 1H), 1.92 (s, 3H), 1.78 (q, J=6.9, 6.1 Hz, 1H).

Example 106

(S)-Piperidin-3-yl (8-amino-7-fluoro-6-(8-methyl-2, 3-dihydro-1H-pyrido[2,3-b][1,4]oxazin-7-yl)isoquinolin-3-yl)carbamate and (R)-Piperidin-3-yl (8-amino-7-fluoro-6-(8-methyl-2,3-dihydro-1H-pyrido[2,3-b][1,4]oxazin-7-yl)isoquinolin-3-yl)carbamate (Compound 408a and Compound 408b)

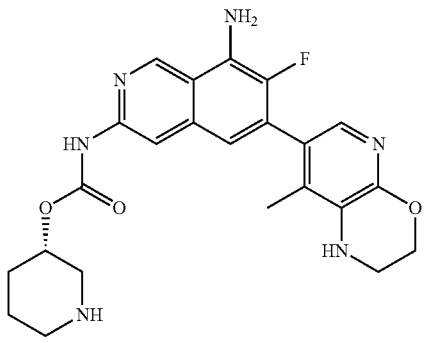

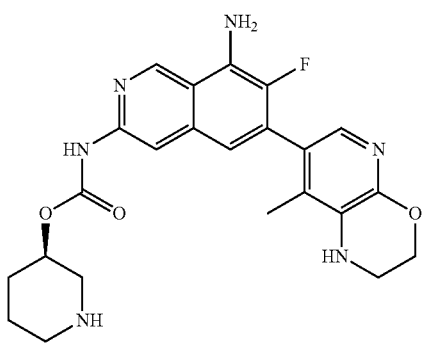

Step 1: tert-Butyl 7-[3-[(1-tert-butoxycarbonyl-3-piperidyl)oxycarbonylamino]-8-chloro-7-fluoro-6-isoquinolyl]-8-methyl-2,3-dihydropyrido[2,3-b][1,4]oxazine-1-carboxylate

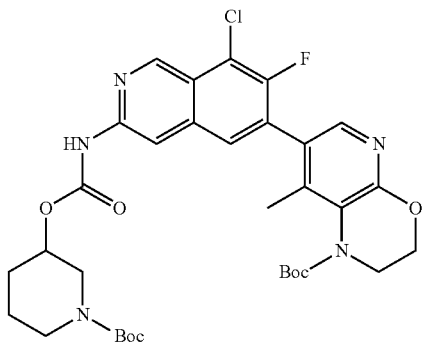 [SMILES: Cc1c(-c2cc3cc(NC(=O)OC4CCCN(C(=O)OC(C)(C)C)C4)ncc3c(Cl)c2F)cnc2c1N(C(=O)OC(C)(C)C)CCO2]

A solution of tert-butyl 7-(3-amino-8-chloro-7-fluoro-6-isoquinolyl)-8-methyl-2,3-dihydropyrido[2,3-b][1,4]oxazine-1-carboxylate (200 mg, 0.45 mmol) and tert-butyl 3-hydroxypiperidine-1-carboxylate (250 mg, 1.24 mmol) in dichloromethane (15 mL) was added DIEA (300 mg, 2.33 mmol) at room temperature. Triphosgene (120 mg, 0.40 mmol) was added and the reaction mixture was stirred at 0° C. for 1 hour. The reaction was diluted with dichloromethane and then washed with water. The organic phase was dried with anhydrous sodium sulfate, filtered, and concentrated under vacuum. The residue was purified by flash chromatography on silica gel eluting with petroleum ether/ethyl acetate (2/1) to afford tert-butyl 7-[3-[(1-tert-butoxycarbonyl-3-piperidyl)oxycarbonylamino]-8-chloro-7-fluoro-6-isoquinolyl]-8-methyl-2,3-dihydropyrido[2,3-b][1,4]oxazine-1-carboxylate (140 mg, 0.21 mmol, 46.3% yield) as a yellow solid. LCMS (ESI) [M+H]⁺=672.2.

Step 2: tert-Butyl 7-[8-(tert-butoxycarbonylamino)-3-[(1-tert-butoxycarbonyl-3-piperidyl)oxycarbonylamino]-7-fluoro-6-isoquinolyl]-8-methyl-2,3-dihydropyrido[2,3-b][1,4]oxazine-1-carboxylate

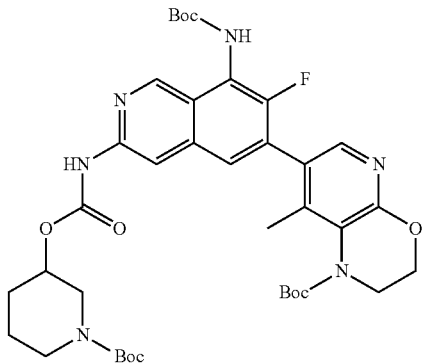 [SMILES: Cc1c(-c2cc3cc(NC(=O)OC4CCCN(C(=O)OC(C)(C)C)C4)ncc3c(NC(=O)OC(C)(C)C)c2F)cnc2c1N(C(=O)OC(C)(C)C)CCO2]

To a solution of tert-butyl 7-[3-[(1-tert-butoxycarbonyl-3-piperidyl)oxycarbonylamino]-8-chloro-7-fluoro-6-isoquinolyl]-8-methyl-2,3-dihydropyrido[2,3-b][1,4]oxazine-1-carboxylate (140 mg, 0.21 mmol) and tert-butyl carbamate (1.5 g, 12.82 mmol) in 1,4-dioxane (7 mL) was added Pd$_2$(dba)$_3$.CHCl$_3$ (50 mg, 0.05 mmol), Brettphos (50 mg, 0.09 mmol), and Cs$_2$CO$_3$ (220 mg, 0.67 mmol) at room temperature. The resulting mixture was stirred at 90° C. for 2 hours. After filtration, the filtrate was concentrated under reduced pressure and purified by flash chromatography on silica gel eluting with petroleum ether/ethyl acetate (1/3) to afford tert-butyl 7-[8-(tert-butoxycarbonylamino)-3-[(1-tert-butoxycarbonyl-3-piperidyl)oxycarbonylamino]-7-fluoro-6-isoquinolyl]-8-methyl-2,3-dihydropyrido[2,3-b][1,4]oxazine-1-carboxylate (150 mg, 0.20 mmol, 95.7% yield) as a yellow solid. LCMS (ESI) [M+H]$^+$=753.2.

Step 3: (S)-Piperidin-3-yl (8-amino-7-fluoro-6-(8-methyl-2,3-dihydro-1H-pyrido[2,3-b][1,4]oxazin-7-yl)isoquinolin-3-yl)carbamate and (R)-Piperidin-3-yl (8-amino-7-fluoro-6-(8-methyl-2,3-dihydro-1H-pyrido[2,3-b][1,4]oxazin-7-yl)isoquinolin-3-yl)carbamate

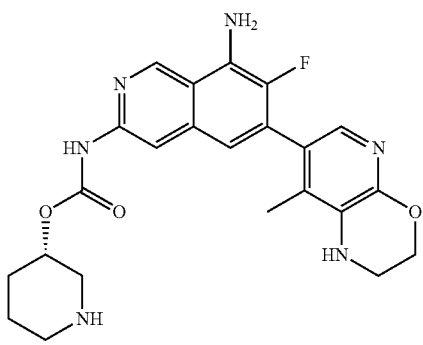

To a solution of tert-Butyl 7-[8-(tert-butoxycarbonylamino)-3-[(1-tert-butoxycarbonyl-3-piperidyl)oxycarbonylamino]-7-fluoro-6-isoquinolyl]-8-methyl-2,3-dihydro-pyrido[2,3-b][1,4]oxazine-1-carboxylate (140 mg, 0.19 mmol) in dichloromethane (4 mL) was added TFA (1 mL) at room temperature. The reaction was stirred at 25° C. for 1 h before concentrated under vacuum. The residue was adjusted to pH 8 with triethylamine and then purified by prep-HPLC (YMC-Actus Triart C18 30*250, 5 μm; water (10 mmol/L NH$_4$HCO$_3$): CH$_3$CN=23%-49% in 7 min; 60 mL/min) to afford the racemic product. The racemic product was isolated by Chiral-HPLC to afford two enantiomers. Absolute stereochemistry was arbitrarily assigned Enantiomer 1 (Compound 408a) (15.9 mg, 0.035 mmol, 18.9% yield): Retention time: 1.937 min (CHIRALPAK IG-3, 0.46*5 cm, 3 μm; DCM (0.1% DEA): MeOH=50:50 in 3 min; 1.0 mL/min). LCMS (ESI) [M+H]$^+$=453.2, 1.814 min, Method K; $^1$H NMR (400 MHz, DMSO-d$_6$) δ 9.95 (s, 1H), 9.33 (s, 1H), 7.96 (s, 1H), 7.33 (s, 1H), 6.83 (d, J=6.2 Hz, 1H), 6.20 (s, 2H), 5.67 (s, 1H), 4.59 (dt, J=8.7, 4.4 Hz, 1H), 4.29 (s, 2H), 2.36-3.32 (m, 3H), 3.06-3.04 (m, 1H), 2.76-2.72 (m, 1H), 2.45-2.40 (m, 2H), 1.98-1.92 (m, 4H), 1.68-1.64 (m, 1H), 1.46 (dt, J=21.7, 10.5 Hz, 2H).

Enantiomer 2 (Compound 408b) (12.6 mg, 0.0278 mmol, 15% yield): Retention time: 1.235 min (CHIRALPAK IG-3, 0.46*5 cm, 3 μm; DCM (0.1% DEA): MeOH=50:50; 1.0 mL/min). LCMS (ESI) [M+H]$^+$=453.2, 1.814 min, Method K; $^1$H NMR (400 MHz, DMSO-d$_6$) δ 9.95 (s, 1H), 9.33 (s, 1H), 7.96 (s, 1H), 7.33 (s, 1H), 6.83 (d, J=6.2 Hz, 1H), 6.20 (s, 2H), 5.67 (s, 1H), 4.59 (dt, J=8.7, 4.4 Hz, 1H), 4.29 (s, 2H), 2.36-3.32 (m, 3H), 3.06-3.04 (m, 1H), 2.76-2.72 (m, 1H), 2.45-2.40 (m, 2H), 1.98-1.92 (m, 4H), 1.68-1.64 (m, 1H), 1.46 (dt, J=21.7, 10.5 Hz, 2H).

Example 107

Tetrahydropyran-4-yl N-[8-amino-7-fluoro-6-[(4S)-4-hydroxy-5-methyl-3,4-dihydro-2H-pyrano[2,3-b]pyridin-6-yl]-3-isoquinolyl]carbamate and tetrahydropyran-4-yl N-[8-amino-7-fluoro-6-[(4R)-4-hydroxy-5-methyl-3,4-dihydro-2H-pyrano[2,3-b]pyridin-6-yl]-3-isoquinolyl]carbamate (Compound 412a and Compound 412b)

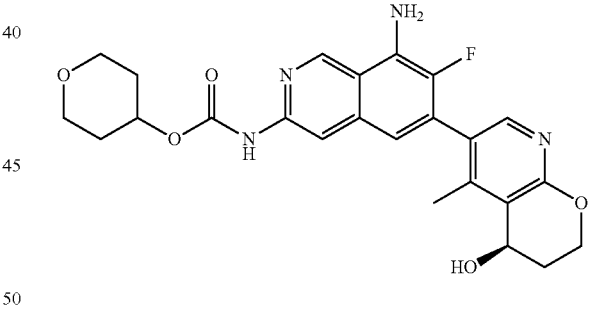

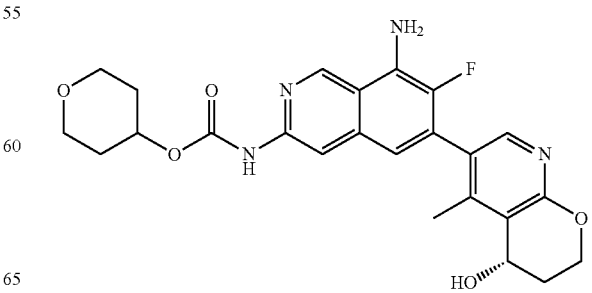

Step 4: 6-[4-[tert-Butyl(dimethyl)silyl]oxy-5-methyl-3,4-dihydro-2H-pyrano[2,3-b]pyridin-6-yl]-8-chloro-7-fluoro-isoquinolin-3-amine

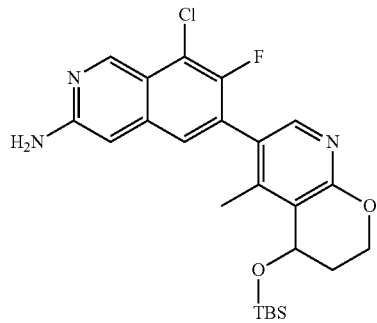

A mixture of 8-chloro-7-fluoro-6-iodo-isoquinolin-3-amine (311 mg, 0.96 mmol), [4-[tert-butyl(dimethyl)silyl]oxy-5-methyl-3,4-dihydro-2H-pyrano[2,3-b]pyridin-6-yl] boronic acid (190 mg, 0.6 mmol), 1,1'-bis(diphenylphosphino)ferrocene-palladium(II)dichloride dichloromethane complex (74.2 mg, 0.09 mmol) and potassium carbonate (294.4 mf, 2.1 mmol) in dioxane (5 mL) and water (1 mL) was purged with nitrogen and heated at 90° C. for 24 h. The reaction was then cooled to room temperature and diluted with 20 mL ethyl acetate and filtered through celite. The filtrate was then concentrated and purified by flash column chromatography (0-100% isopropyl acetate in heptane) to 6-[4-[tert-butyl(dimethyl)silyl]oxy-5-methyl-3,4-dihydro-2H-pyrano[2,3-b]pyridin-6-yl]-8-chloro-7-fluoro-isoquinolin-3-amine (204 mg, 0.4 mmol) as a brown solid. LCMS (ESI, m/z): 474 [M+H]$^+$.

Step 5: Tetrahydropyran-4-yl N-[6-[4-[tert-butyl(dimethyl)silyl]oxy-5-methyl-3,4-dihydro-2H-pyrano[2,3-b]pyridin-6-yl]-8-chloro-7-fluoro-3-isoquinolyl]carbamate

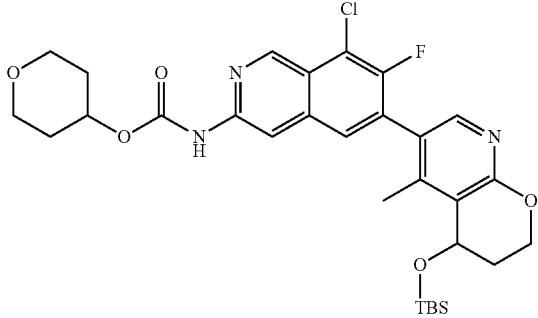

The title compound was prepared using a procedure analogous to Step 1 for Example 101 using 6-[4-[tert-butyl(dimethyl)silyl]oxy-5-methyl-3,4-dihydro-2H-pyrano[2,3-b]pyridin-6-yl]-8-chloro-7-fluoro-isoquinolin-3-amine in place of tert-butyl 7-(3-amino-8-chloro-7-fluoro-6-isoquinolyl)-8-methyl-2,3-dihydropyrido[2,3-b][1,4]oxazine-1-carboxylate (207.8 mg, 0.34 mmol). LCMS (ESI, m/z): 602 [M+H]$^+$.

Step 6: Tetrahydropyran-4-yl N-[8-(tert-butoxycarbonylamino)-6-[4-[tert-butyl(dimethyl)silyl]oxy-5-methyl-3,4-dihydro-2H-pyrano[2,3-b]pyridin-6-yl]-7-fluoro-3-isoquinolyl]carbamate

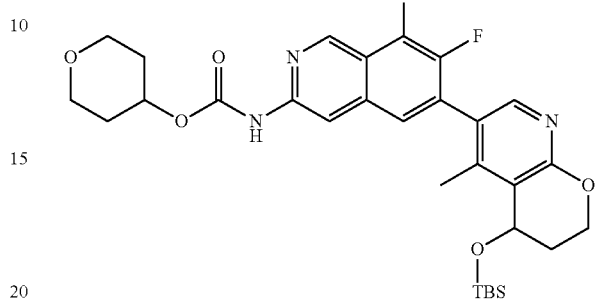

The title compound was prepared using a procedure analogous to Step 2 for Example 101 using tetrahydropyran-4-yl N-[6-[4-[tert-butyl (dimethyl)silyl]oxy-5-methyl-3,4-dihydro-2H-pyrano[2,3-b]pyridin-6-yl]-8-chloro-7-fluoro-3-isoquinolyl]carbamate in place 7-[8-chloro-7-fluoro-3-(tetrahydropyran-4-yloxycarbonylamino)-6-isoquinolyl]-8-methyl-2,3-dihydropyrido[2,3-b][1,4]oxazine-1-carboxylate (207.8 mg, 0.34 mmol). LCMS (ESI, m/z): 602 [M+H]$^+$. Absolute stereochemistry arbitrarily assigned.

Step 7: Tetrahydropyran-4-yl N-[8-amino-7-fluoro-6-[(4S)-4-hydroxy-5-methyl-3,4-dihydro-2H-pyrano[2,3-b]pyridin-6-yl]-3-isoquinolyl]carbamate

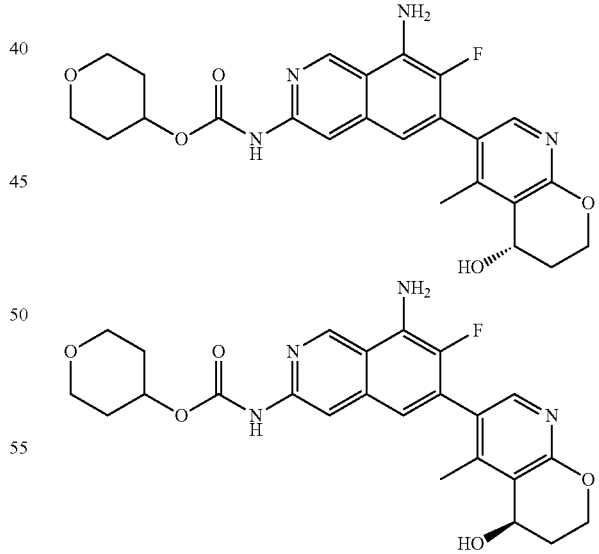

The title compound was prepared using a procedure analogous to step 3 for Example 101 using tetrahydropyran-4-yl N-[8-(tert-butoxy carbonylamino)-6-[4-[tert-butyl(dimethyl)silyl]oxy-5-methyl-3,4-dihydro-2H-pyrano[2,3-b]pyridin-6-yl]-7-fluoro-3-isoquinolyl]carbamate in place 7-[8-(tert-butoxycarbonylamino)-7-fluoro-3-(tetrahydropyran-4-yloxycarbonylamino)-6-isoquinolyl]-8-methyl-2,3- dihydropyrido[2,3-b][1,4]oxazine-1-carboxylate. Absolute stereochemistry was arbitrarily assigned.

Enantiomer 1 (Compound 412b): Retention time: 1.556 min (CHIRALPAK IH, 0.46*5 cm, 3 μm; isocratic 40% MeOH in 2.5 min). $^1$H NMR (400 MHz, DMSO-$d_6$) δ 10.06 (s, 1H), 9.35 (s, 1H), 7.98 (d, J=2.8 Hz, 2H), 6.84 (d, J=6.2 Hz, 1H), 6.24 (s, 2H), 5.40 (d, J=5.5 Hz, 1H), 4.85 (s, 2H), 4.40-4.30 (m, 2H), 3.86 (dt, J=11.7, 4.5 Hz, 2H), 3.48 (ddd, J=11.8, 9.3, 2.9 Hz, 2H), 2.24 (d, J=1.4 Hz, 3H), 1.95 (ddd, J=16.6, 8.0, 3.9 Hz, 4H), 1.65-1.56 (m, 2H). LCMS (ESI, m/z): 469.2 [M+H]$^+$, 3.437 min., Method N.

Enantiomer 2 (Compound 412a): Retention time: 1.082 min (CHIRALPAK IH, 0.46*5 cm, 3 μm; isocratic 40% MeOH in 2.5 min). $^1$H NMR (400 MHz, DMSO-$d_6$) δ 10.06 (s, 1H), 9.35 (s, 1H), 7.98 (d, J=2.8 Hz, 2H), 6.84 (d, J=6.2 Hz, 1H), 6.24 (s, 2H), 5.40 (d, J=5.5 Hz, 1H), 4.85 (s, 2H), 4.40-4.30 (m, 2H), 3.86 (dt, J=11.7, 4.5 Hz, 2H), 3.48 (ddd, J=11.8, 9.3, 2.9 Hz, 2H), 2.24 (d, J=1.4 Hz, 3H), 1.95 (ddd, J=16.6, 8.0, 3.9 Hz, 4H), 1.65-1.56 (m, 2H). LCMS (ESI, m/z): 469.2 [M+H]$^+$, 3.437 min., Method N.

Example 108

1-(8-Amino-7-fluoro-6-(8-methyl-2,3-dihydro-1H-pyrido[2,3-b][1,4]oxazin-7-yl)isoquinolin-3-yl)-3-(tetrahydro-2H-pyran-4-yl)urea (Compound 701)

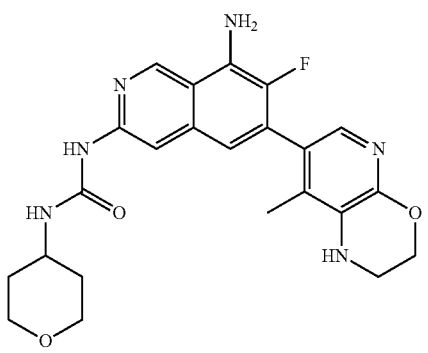

Step 1: tert-Butyl 7-[8-chloro-7-fluoro-3-(tetrahydropyran-4-ylcarbamoylamino)-6-isoquinolyl]-8-methyl-2,3-dihydropyrido[2,3-b][1,4]oxazine-1-carboxylate

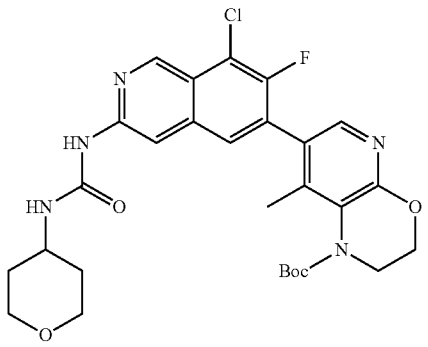 [SMILES: Cc1c(-c2cc3cc(NC(=O)NC4CCOCC4)ncc3c(Cl)c2F)cnc2c1N(C(=O)OC(C)(C)C)CCO2]

Triphosgene (320 mg, 1.08 mmol) in tetrahydrofuran (40 mL) was added to a solution of tert-butyl 7-(3-amino-8-chloro-7-fluoro-6-isoquinolyl)-8-methyl-2,3-dihydropyrido[2,3-b][1,4]oxazine-1-carboxylate (300 mg, 0.67 mmol), and pyridine (0.16 mL, 2.02 mmol) at 0° C. over 10 min. Tetrahydro-2H-pyran-4-amine (700 mg, 6.92 mmol) was added and the reaction mixture was stirred at 0° C. for 2 hours. The resulting mixture was concentrated under vacuum and purified by flash chromatography on silica gel eluting with ethyl acetate/petroleum ether (1/10) to afford tert-butyl 7-[8-chloro-7-fluoro-3-(tetrahydropyran-4-ylcarbamoylamino)-6-isoquinolyl]-8-methyl-2,3-dihydropyrido[2,3-b][1,4]oxazine-1-carboxylate (260 mg, 0.45 mmol, 67.4% yield) as a yellow solid. LCMS (ESI) [M+H]$^+$=572.

Step 2: tert-Butyl 7-[8-(tert-butoxycarbonylamino)-7-fluoro-3-(tetrahydropyran-4-ylcarbamoylamino)-6-isoquinolyl]-8-methyl-2,3-dihydropyrido[2,3-b][1,4]oxazine-1-carboxylate

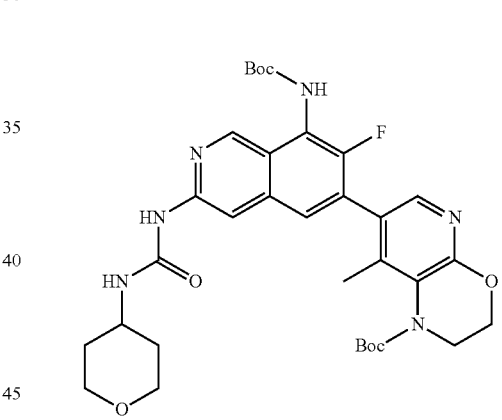

A mixture of tert-butyl 7-[8-chloro-7-fluoro-3-(tetrahydropyran-4-ylcarbamoylamino)-6-isoquinolyl]-8-methyl-2,3-dihydropyrido[2,3-b][1,4]oxazine-1-carboxylate (160 mg, 0.28 mmol), tert-butyl carbamate (1 g, 8.54 mmol), cesium carbonate (284 mg, 0.87 mmol), 2-(dicyclohexylphosphino) 3,6-dimethoxy-2',4',6'-triisopropyl-1,1'-biphenyl (61 mg, 0.11 mmol), and tris(dibenzylideneacetone)dipalladium-chloroform adduct (60 mg, 0.06 mmol) in 1,4-dioxane (20 mL) was stirred at 90° C. for 2 hours. After filtration, the filtrate was concentrated under reduced pressure and purified by flash chromatography on silica gel eluting with methanol/dichloromethane (1/10) to afford tert-butyl 7-[8-(tert-butoxycarbonylamino)-7-fluoro-3-(tetrahydropyran-4-ylcarbamoylamino)-6-isoquinolyl]-8-methyl-2,3-dihydropyrido[2,3-b][1,4]oxazine-1-carboxylate (100 mg, 0.15 mmol, 54.8% yield) as a yellow solid. LCMS (ESI) [M+H]$^+$=653.0.

Step 3: 1-[8-Amino-7-fluoro-6-(8-methyl-2,3-dihydro-1H-pyrido[2,3-b][1,4]oxazin-7-yl)-3-isoquinolyl]-3-tetrahydropyran-4-yl-urea

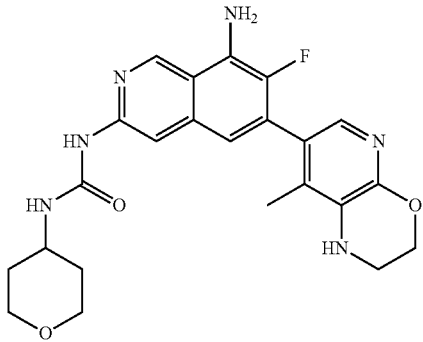

A solution of tert-butyl 7-[8-(tert-butoxycarbonylamino)-7-fluoro-3-(tetrahydropyran-4-ylcarbamoylamino)-6-isoquinolyl]-8-methyl-2,3-dihydropyrido[2,3-b][1,4]oxazine-1-carboxylate (100 mg, 0.15 mmol) in dichloromethane (10 mL) and TFA (2 mL) was stirred at 25° C. for 1 h. The resulting solution was concentrated under vacuum. The pH of the residue was adjusted to pH 8 with ammonia in methanol (7 mol/L). The resulting solution was concentrated under vacuum and purified by prep-HPLC (YMC-Actus Triart C18 30*250, 5 µm; water (10 mmol/L NH$_4$HCO$_3$): CH$_3$CN=37% B to 62% B in 7 min; 60 mL/min) to afford 1-[8-amino-7-fluoro-6-(8-methyl-2,3-dihydro-1H-pyrido[2,3-b][1,4]oxazin-7-yl)-3-isoquinolyl]-3-tetrahydropyran-4-yl-urea (59.8 mg, 0.13 mmol, 86.3% yield) as a yellow solid. LCMS (ESI) [M+H]$^+$=453, Rt=0.893 min., Method M; $^1$H NMR (300 MHz, DMSO-d$_6$) δ 9.29 (s, 1H), 8.87 (s, 1H), 7.84 (s, 1H), 7.33 (s, 1H), 7.20 (d, J=7.5 Hz, 1H), 6.74 (d, J=6.1 Hz, 1H), 6.15 (s, 2H), 5.67 (s, 1H), 4.29 (s, 2H), 3.88-3.75 (m, 3H), 3.42-3.34 (m, 4H), 1.92 (s, 3H), 1.87-1.83 (m, 2H), 1.43-1.39 (m, 2H).

Example 109

9-Methyl-3-oxa-9-azabicyclo[3.3.1]nonan-7-yl (8-amino-7-fluoro-6-(8-methyl-2,3-dihydro-1H-pyrido[2,3-b][1,4]oxazin-7-yl)isoquinolin-3-yl)carbamate (Compound 406)

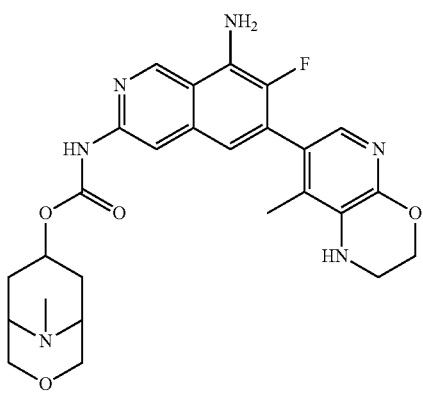 [SMILES: Cc1c(-c2cc3cc(NC(=O)OC4CC5COCC(C4)N5C)ncc3c(N)c2F)cnc2c1NCCO2]

Step 1: tert-butyl 7-[3-[(9-tert-butoxycarbonyl-3-oxa-9-azabicyclo[3.3.1]nonan-7-yl)oxycarbonylamino]-8-chloro-7-fluoro-6-isoquinolyl]-8-methyl-2,3-dihydropyrido[2,3-b][1,4]oxazine-1-carboxylate

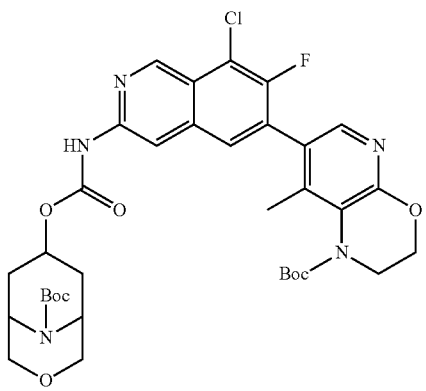 [SMILES: Cc1c(-c2cc3cc(NC(=O)OC4CC5COCC(C4)N5C(=O)OC(C)(C)C)ncc3c(Cl)c2F)cnc2c1N(C(=O)OC(C)(C)C)CCO2]

A solution of tert-butyl 7-(3-amino-8-chloro-7-fluoro-6-isoquinolyl)-8-methyl-2,3-dihydropyrido[2,3-b][1,4]oxazine-1-carboxylate (150 mg, 0.34 mmol), tert-butyl 7-hydroxy-3-oxa-9-azabicyclo[3.3.1]nonane-9-carboxylate (410.2 mg, 1.69 mmol) and DIEA (435.8 mg, 3.37 mmol) in dichloromethane (10 mL) was stirred at 0° C. Then triphosgene (150.1 mg, 0.51 mmol) was added dropwise at 0° C. and then stirred at 25° C. for 2 hours. The reaction was quenched with water. The resulting solution was extracted with dichloromethane and the organic layers were combined. The organic layer was dried over anhydrous sodium sulfate and concentrated under vacuum. The residue was purified by flash chromatography on silica gel eluting with petroleum ether/ethyl acetate (2:1) to afford tert-butyl 7-[3-[(9-tert-butoxycarbonyl-3-oxa-9-azabicyclo[3.3.1]nonan-7-yl)oxycarbonylamino]-8-chloro-7-fluoro-6-isoquinolyl]-8-methyl-2,3-dihydropyrido[2,3-b][1,4]oxazine-1-carboxylate (115 mg, 0.16 mmol, 47.8% yield) as a light yellow solid. LCMS (ESI) [M+H]$^+$=714.2.

Step 2: tert-butyl 7-[8-(tert-butoxycarbonylamino)-3-[(9-tert-butoxycarbonyl-3-oxa-9-azabicyclo[3.3.1]nonan-7-yl)oxycarbonylamino]-7-fluoro-6-isoquinolyl]-8-methyl-2,3-dihydropyrido[2,3-b][1,4]oxazine-1-carboxylate

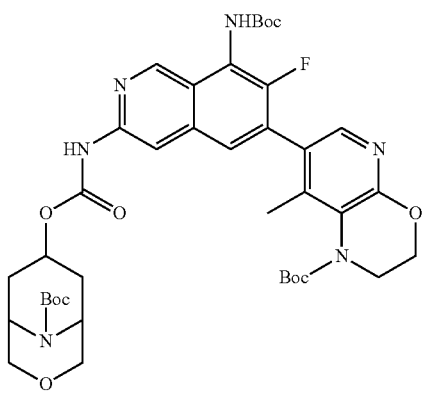 [SMILES: Cc1c(-c2cc3cc(NC(=O)OC4CC5COCC(C4)N5C(=O)OC(C)(C)C)ncc3c(NC(=O)OC(C)(C)C)c2F)cnc2c1N(C(=O)OC(C)(C)C)CCO2]

A solution of tert-butyl 7-[3-[(9-tert-butoxycarbonyl-3-oxa-9-azabicyclo[3.3.1]nonan-7-yl)oxycarbonylamino]-8-chloro-7-fluoro-6-isoquinolyl]-8-methyl-2,3-dihydropyrido[2,3-b][1,4]oxazine-1-carboxylate (105 mg, 0.15 mmol), NH$_2$Boc (516.1 mg, 4.41 mmol), Pd$_2$(dba)$_3$·CHCl$_3$ (31 mg, 0.030 mmol), Brettphos (32 mg, 0.06 mmol) and Cs$_2$CO$_3$ (143.8 mg, 0.44 mmol) in 1,4-dioxane (5 mL) was stirred for 1 hour at 90° C. The resulting solution was concentrated under vacuum. The residue was purified by flash chromatography on silica gel eluting with dichloromethane/methanol (97:3) to afford tert-butyl 7-[8-(tert-butoxycarbonylamino)-3-[(9-tert-butoxycarbonyl-3-oxa-9-azabicyclo[3.3.1]nonan-7-yl)oxycarbonylamino]-7-fluoro-6-isoquinolyl]-8-methyl-2,3-dihydropyrido[2,3-b][1,4]oxazine-1-carboxylate (85 mg, 0.11 mmol, 72.7% yield) as a light yellow solid. LCMS (ESI) [M+H]$^+$=795.5.

Step 3: 3-oxa-9-azabicyclo[3.3.1]nonan-7-yl N-[8-amino-7-fluoro-6-(8-methyl-2,3-dihydro-1H-pyrido[2,3-b][1,4]oxazin-7-yl)-3-isoquinolyl]carbamate

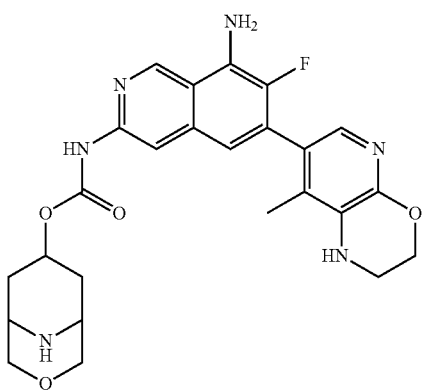 [SMILES: Cc1c(-c2cc3cc(NC(=O)OC4CC5COCC(C4)N5)ncc3c(N)c2F)cnc2c1NCCO2]

A solution of tert-butyl 7-[8-(tert-butoxycarbonylamino)-3-[(9-tert-butoxycarbonyl-3-oxa-9-azabicyclo[3.3.1]nonan-7-yl)oxycarbonylamino]-7-fluoro-6-isoquinolyl]-8-methyl-2,3-dihydropyrido[2,3-b][1,4]oxazine-1-carboxylate (80 mg, 0.10 mmol) and TFA (2 ml) in dichloromethane (2 mL) was stirred for 1 hour at 25° C. The solvent was concentrated under vacuum. The residue was adjusted to pH 8 with TEA. The resulting mixture was diluted with water. The resulting solution was extracted with ethyl acetate and the organic layers were combined. The organic layer was dried over anhydrous sodium sulfate and concentrated under vacuum to afford 3-oxa-9-azabicyclo[3.3.1]nonan-7-yl N-[8-amino-7-fluoro-6-(8-methyl-2,3-dihydro-1H-pyrido[2,3-b][1,4]oxazin-7-yl)-3-isoquinolyl]carbamate (40 mg, 0.08 mmol, 80.4% yield) as a light yellow solid. LCMS (ESI) [M+H]$^+$=495.3.

Step 4: 9-Methyl-3-oxa-9-azabicyclo[3.3.1]nonan-7-yl (8-amino-7-fluoro-6-(8-methyl-2,3-dihydro-1H-pyrido[2,3-b][1,4]oxazin-7-yl)isoquinolin-3-yl)carbamate (Compound 406)

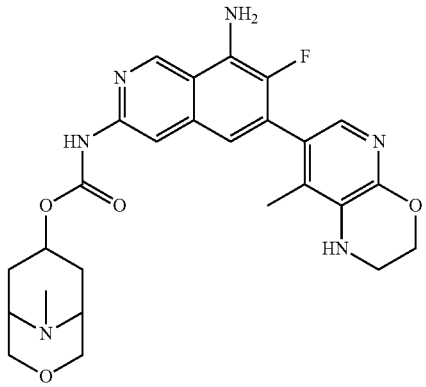 [SMILES: Cc1c(-c2cc3cc(NC(=O)OC4CC5COCC(C4)N5C)ncc3c(N)c2F)cnc2c1NCCO2]

A solution of 3-oxa-9-azabicyclo[3.3.1]nonan-7-yl N-[8-amino-7-fluoro-6-(8-methyl-2,3-dihydro-1H-pyrido[2,3-b][1,4]oxazin-7-yl)-3-isoquinolyl]carbamate (34.5 mg, 0.07 mmol) in methanol (15 mL) was added formaldehyde (10.5 mg, 0.14 mmol, 40%) and was stirred at 25° C. for 2 hours. Then NaBH$_3$CN (8.8 mg, 0.14 mmol) was added and stirred at 25° C. for 2 hours. The reaction was diluted with water. The resulting solution was extracted with ethyl acetate and the organic layers were combined. The organic layer was dried over anhydrous sodium sulfate and concentrated under vacuum. The residue was purified by Prep-HPLC (X Bridge Shield RP18 OBD Column 30*150 mm, 5 μm; Mobile Phase A: Water (10 mmol/L NH$_4$HCO$_3$), Mobile Phase B: ACN; Flow rate: 60 mL/min; Gradient: 17% B to 31% B in 10 min; Rt: 9.87 min) to afford 9-methyl-3-oxa-9-azabicyclo[3.3.1]nonan-7-yl (8-amino-7-fluoro-6-(8-methyl-2,3-dihydro-1H-pyrido[2,3-b][1,4]oxazin-7-yl)isoquinolin-3-yl)carbamate (9.9 mg, 0.02 mmol, 27.9% yield) as a yellow solid. LCMS (ESI) [M+H]$^+$=509.2, R$_T$=0.720 min, Method L; $^1$H NMR (300 MHz, DMSO-d$_6$) δ 9.71 (s, 1H), 9.33 (s, 1H), 8.04 (s, 1H), 7.33 (s, 1H), 6.81 (d, J=6.2 Hz, 1H), 6.21 (s, 2H), 5.69 (s, 1H), 5.05-5.08 (m, 1H), 4.29 (d, J=4.8 Hz, 2H), 3.80 (dd, J=11.0, 2.2 Hz, 2H), 3.42-3.36 (m, 4H), 2.70 (d, J=8.4 Hz, 2H), 2.43-2.33 (m, 5H), 1.93 (d, J=1.6 Hz, 3H), 1.62 (dd, J=13.1, 5.8 Hz, 2H).

Example 110

(S)-1-Methyl-6-oxopiperidin-3-yl (8-amino-7-fluoro-6-(8-methyl-2,3-dihydro-1H-pyrido[2,3-b][1,4]oxazin-7-yl)isoquinolin-3-yl)carbamate and (R)-1-Methyl-6-oxopiperidin-3-yl (8-amino-7-fluoro-6-(8-methyl-2,3-dihydro-1H-pyrido[2,3-b][1,4]oxazin-7-yl)isoquinolin-3-yl)carbamate (Compound 409a and Compound 409b)

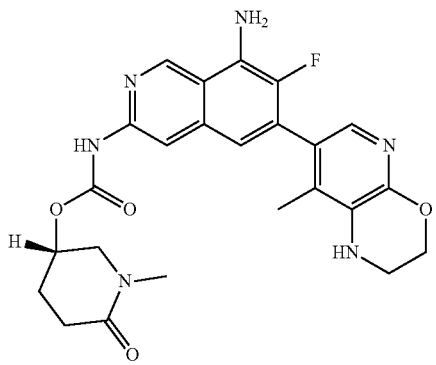

-continued

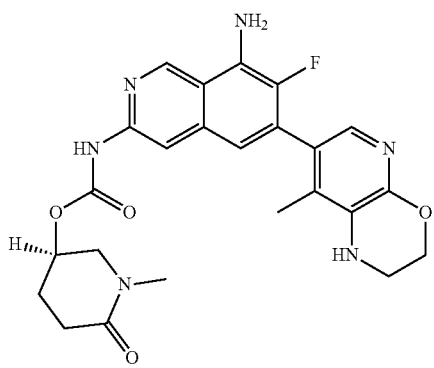

Step 1: tert-Butyl 7-[8-chloro-7-fluoro-3-[(1-methyl-5-oxo-pyrrolidin-3-yl)oxycarbonylamino]-6-isoquinolyl]-8-methyl-2,3-dihydropyrido[2,3-b][1,4]oxazine-1-carboxylate

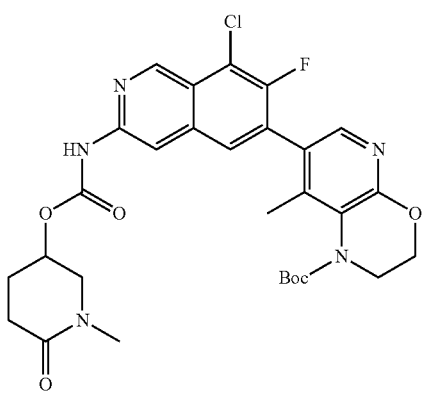 [SMILES: Cc1c(-c2cc3cc(NC(=O)OC4CCC(=O)N(C)C4)ncc3c(Cl)c2F)cnc2c1N(C(=O)OC(C)(C)C)CCO2]

A solution of tert-butyl 7-(3-amino-8-chloro-7-fluoro-6-isoquinolyl)-8-methyl-2,3-dihydropyrido[2,3-b][1,4]oxazine-1-carboxylate (250 mg, 0.56 mmol), 5-hydroxy-1-methyl-piperidin-2-one (90 mg, 0.70 mmol) and DIEA (292 mg, 2.25 mmol) in dichloromethane (25 mL) was added triphosgene (60 mg, 0.20 mmol) in dichloromethane (3 mL) at 0° C. The reaction was stirred for 16 hours at room temperature. The reaction was quenched with water. The resulting solution was extracted with dichloromethane and the organic layers were combined. The organic layer was dried over anhydrous sodium sulfate and concentrated under vacuum. the resulting residue was purified by reverse phase chromatography (acetonitrile 0-40/0.1% NH$_4$HCO$_3$ in water) to afford tert-butyl 7-[8-chloro-7-fluoro-3-[(1-methyl-5-oxo-pyrrolidin-3-yl)oxycarbonylamino]-6-isoquinolyl]-8-methyl-2,3-dihydropyrido[2,3-b][1,4]oxazine-1-carboxylate (290 mg, 0.495 mmol, 88.1% yield) as a yellow solid. LCMS (ESI) [M+H]$^+$=600.

Step 2: tert-Butyl 7-[8-(tert-butoxycarbonylamino)-7-fluoro-3-[(1-methyl-6-oxo-3-piperidyl)oxycarbonylamino]-6-isoquinolyl]-8-methyl-2,3-dihydropyrido[2,3-b][1,4]oxazine-1-carboxylate

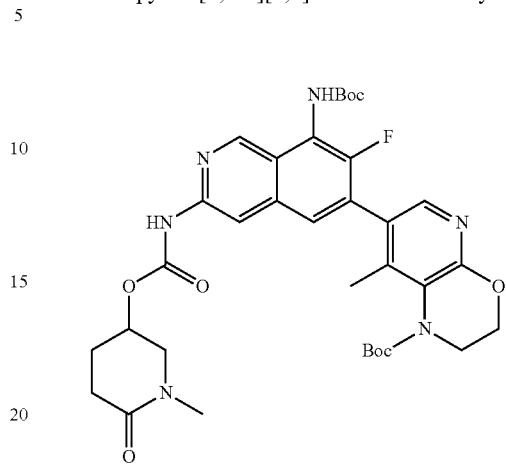

A solution of tert-butyl 7-[8-chloro-7-fluoro-3-[(1-methyl-6-oxo-3-piperidyl)oxycarbonylamino]-6-isoquinolyl]-8-methyl-2,3-dihydropyrido[2,3-b][1,4]oxazine-1-carboxylate (280 mg, 0.47 mmol), NH$_2$Boc (3.28 g, 28.03 mmol), Pd$_2$(dba)$_3$CHCl$_3$ (97 mg, 0.09 mmol), Brettphos (101 mg, 0.19 mmol) and Cs$_2$CO$_3$ (304 mg, 0.94 mmol) in 1,4-dioxane (20 mL) was stirred at 90° C. for 3 hours. The reaction mixture was diluted with water. The resulting solution was extracted with ethyl acetate and the organic layers were combined. The organic layer was dried over anhydrous sodium sulfate and concentrated under vacuum. The residue was purified by flash chromatography on silica gel eluting with dichloromethane/methanol (88/12) to afford tert-butyl 7-[8-(tert-butoxycarbonylamino)-7-fluoro-3-[(1-methyl-6-oxo-3-piperidyl)oxycarbonylamino]-6-isoquinolyl]-8-methyl-2,3-dihydropyrido[2,3-b][1,4]oxazine-1-carboxylate (180 mg, 0.264 mmol, 56.7% yield) as a yellow solid. LCMS (ESI) [M+H]$^+$=681.

Step 3: (S)-1-Methyl-6-oxopiperidin-3-yl (8-amino-7-fluoro-6-(8-methyl-2,3-dihydro-1H-pyrido[2,3-b][1,4]oxazin-7-yl)isoquinolin-3-yl)carbamate and (R)-1-Methyl-6-oxopiperidin-3-yl (8-amino-7-fluoro-6-(8-methyl-2,3-dihydro-1H-pyrido[2,3-b][1,4]oxazin-7-yl)isoquinolin-3-yl)carbamate

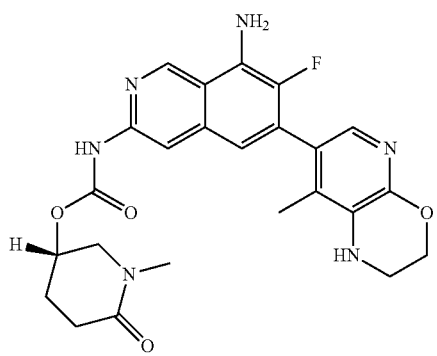

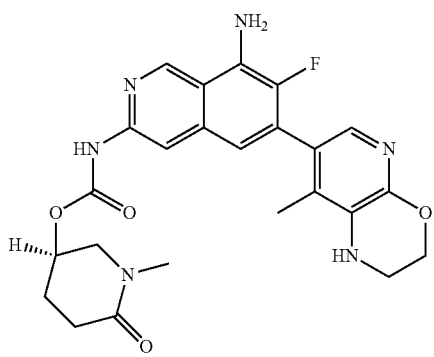

A solution of tert-butyl 7-[8-(tert-butoxycarbonylamino)-7-fluoro-3-[(1-methyl-6-oxo-3-piperidyl)oxycarbonylamino]-6-isoquinolyl]-8-methyl-2,3-dihydropyrido[2,3-b][1,4]oxazine-1-carboxylate (150 mg, 0.22 mmol) in TFA (3 mL) and dichloromethane (10 mL) was stirred at 25° C. for 1 hour. The reaction mixture was concentrated under vacuum. The residue was adjusted to pH 9 with TEA. The crude product was purified by Prep-HPLC with the following condition (Column: X Bridge Shield RP18 OBD Column 30*150 mm, 5 μm; Mobile Phase A: Water (10 mmol/L NH₄HCO₃), Mobile Phase B: ACN; Flow rate: 60 mL/min; Gradient: 14% B to 37% B in 7 min; 220/254 nm; Rt: 6.57 min) and Chiral-HPLC to afford two enantiomers. Absolute stereochemistry arbitrarily assigned.

Enantiomer 1 (Compound 409a) (17.9 mg, 0.0373 mmol, 16.9% yield): Retention time: 2.367 (CHIRALPAK IC-3: 0.46*5 cm; 3 μm; (Hex:DCM=1:1) (0.1% DEA): EtOH=50:50; 1.0 ml/min; Gradient: 50 B to 50 B in 5 min). LCMS (ESI) [M+H]⁺=481.2, $R_T$=1.017 min, Method M. ¹H NMR (300 MHz, DMSO-d₆) δ 10.16 (s, 1H), 9.34 (s, 1H), 7.96 (s, 1H), 7.33 (s, 1H), 6.84 (d, J=6.1 Hz, 1H), 6.21 (s, 2H), 5.67 (s, 1H), 5.12 (s, 1H), 4.29 (s, 2H), 3.64 (dd, J=13.3, 3.9 Hz, 1H), 2.81 (s, 3H), 2.48-2.36 (m, 3H), 2.31-2.20 (m, 2H), 2.02 (s, 2H), 1.92 (d, J=1.6 Hz, 3H).

Enantiomer 2 (Compound 409b) (17.6 mg, 0.0366 mmol, 16.6% yield): Retention time: 3.097 (CHIRALPAK IC-3: 0.46*5 cm; 3 μm; (Hex:DCM=1:1) (0.1% DEA): EtOH=50:50; 1.0 ml/min; Gradient: 50 B to 50 B in 5 min). LCMS (ESI) [M+H]⁺=481.2, $R_T$=1.017 min, Method M. ¹H NMR (300 MHz, DMSO-d₆) δ 10.16 (s, 1H), 9.34 (s, 1H), 7.96 (s, 1H), 7.33 (s, 1H), 6.84 (d, J=6.1 Hz, 1H), 6.21 (s, 2H), 5.67 (s, 1H), 5.12 (s, 1H), 4.29 (s, 2H), 3.64 (dd, J=13.3, 3.9 Hz, 1H), 2.81 (s, 3H), 2.48-2.36 (m, 3H), 2.31-2.20 (m, 2H), 2.02 (s, 2H), 1.92 (d, J=1.6 Hz, 3H).

Example 111

(S)-1-Methyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate and (R)-1-Methyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate (Compound 410a and Compound 410b)

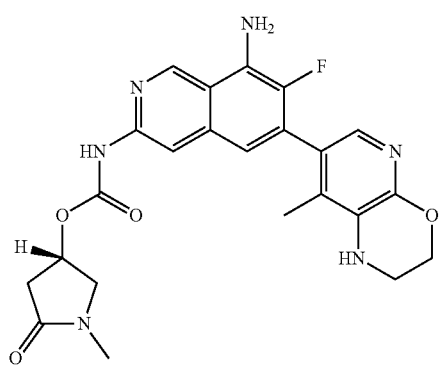

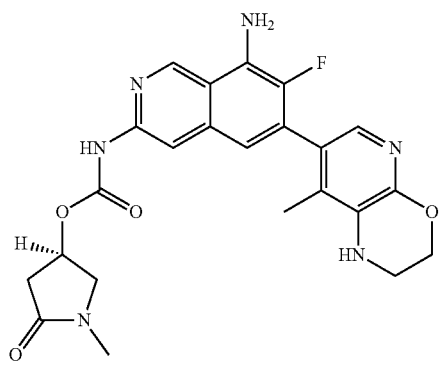

Step 1: tert-Butyl 7-[8-chloro-7-fluoro-3-[(1-methyl-5-oxo-pyrrolidin-3-yl)oxycarbonylamino]-6-isoquinolyl]-8-methyl-2,3-dihydropyrido[2,3-b][1,4]oxazine-1-carboxylate

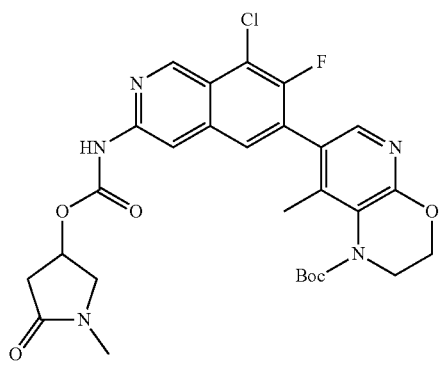 [SMILES: Cc1c(-c2cc3cc(NC(=O)OC4CC(=O)N(C)C4)ncc3c(Cl)c2F)cnc2c1N(C(=O)OC(C)(C)C)CCO2]

Under nitrogen, to a solution of 4-hydroxy-1-methyl-pyrrolidin-2-one (200 mg, 1.74 mmol), tert-butyl 7-(3-amino-8-chloro-7-fluoro-6-isoquinolyl)-8-methyl-2,3-dihydropyrido[2,3-b][1,4]oxazine-1-carboxylate (386 mg, 0.87 mmol) and DIEA (903 mg, 6.95 mmol) in dichloromethane (25 mL) was added triphosgene (155 mg, 0.52 mmol) in dichloromethane (5 mL) slowly at 0° C. The reaction was stirred for 2 hours at room temperature. The reaction was quenched with water. The resulting solution was diluted with dichloromethane and washed with water. The organic layer was dried over anhydrous sodium sulfate and concentrated under vacuum. The residue was purified by reverse phase chromatography (acetonitrile 0-70/0.1% NH$_4$HCO$_3$ in water) to afford tert-butyl 7-[8-chloro-7-fluoro-3-[(1-methyl-5-oxo-pyrrolidin-3-yl)oxycarbonylamino]-6-isoquinolyl]-8-methyl-2,3-dihydropyrido[2,3-b][1,4]oxazine-1-carboxylate (307 mg, 0.5239 mmol, 30.2% yield) as a yellow solid. LCMS (ESI) [M+H]$^+$=586.

Step 2: tert-Butyl 7-[8-(tert-butoxycarbonyl amino)-7-fluoro-3-[(1-methyl-5-oxo-pyrrolidin-3-yl)oxycarbonylamino]-6-isoquinolyl]-8-methyl-2,3-dihydropyrido[2,3-b][1,4]oxazine-1-carboxylate

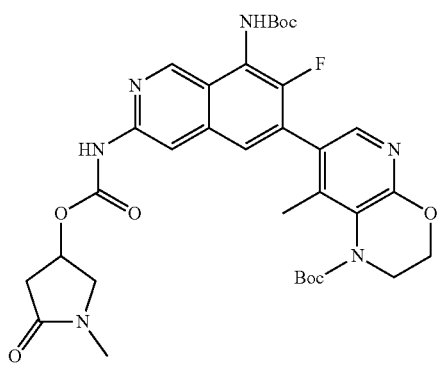 [SMILES: Cc1c(-c2cc3cc(NC(=O)OC4CC(=O)N(C)C4)ncc3c(NC(=O)OC(C)(C)C)c2F)cnc2c1N(C(=O)OC(C)(C)C)CCO2]

Under nitrogen, a mixture of tert-butyl 7-[8-chloro-7-fluoro-3-[(1-methyl-5-oxo-pyrrolidin-3-yl)oxycarbonylamino]-6-isoquinolyl]-8-methyl-2,3-dihydropyrido[2,3-b][1,4]oxazine-1-carboxylate (307 mg, 0.52 mmol), NH$_2$Boc (3.7 g, 31.62 mmol), Brettphos (112 mg, 0.21 mmol), Pd$_2$(dba)$_3$CHCl$_3$ (108 mg, 0.10 mmol) and Cs$_2$CO$_3$ (340 mg, 1.05 mmol) in 1,4-dioxane (30 mL) was stirred at 90° C. for 1 h. The reaction mixture was concentrated under vacuum. The residue was purified by flash chromatography on silica gel eluting with dichloromethane/methanol (9/1) to afford tert-butyl 7-[8-(tert-butoxycarbonylamino)-7-fluoro-3-[(1-methyl-5-oxo-pyrrolidin-3-yl)oxycarbonylamino]-6-isoquinolyl]-8-methyl-2,3-dihydropyrido[2,3-b][1,4]oxazine-1-carboxylate (260 mg, 0.39 mmol, 74.4% yield) as a yellow solid. LCMS (ESI) [M+H]$^+$=667.

Step 3: (S)-1-Methyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate and (R)-1-methyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate

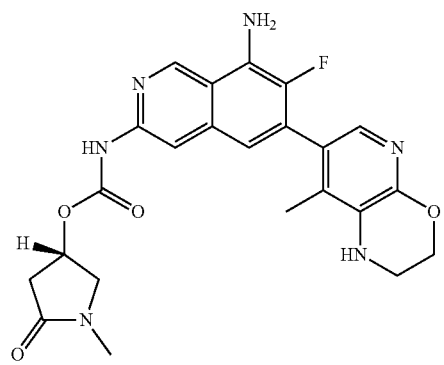

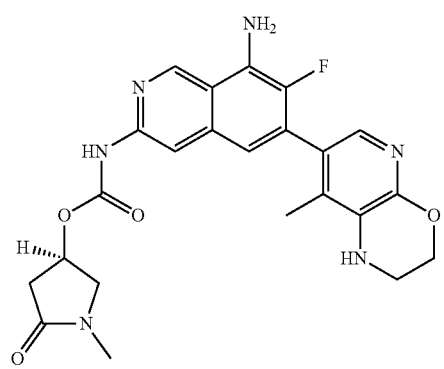

A solution of tert-butyl 7-[8-(tert-butoxycarbonylamino)-7-fluoro-3-[(1-methyl-5-oxo-pyrrolidin-3-yl)oxycarbonylamino]-6-isoquinolyl]-8-methyl-2,3-dihydropyrido[2,3-b][1,4]oxazine-1-carboxylate (150 mg, 0.22 mmol) in TFA (3 mL) and dichloromethane (10 mL) was stirred at room temperature for 1 hour. The reaction mixture was concentrated under vacuum. The crude product was purified by Prep-HPLC (X Bridge Prep OBD C18 Column 30×150 mm 5 μm; Mobile Phase A: Water (10 mmol/L NH$_4$HCO$_3$), Mobile Phase B: ACN; Flow rate: 60 mL/min; Gradient: 10% B to 30% B in 10 min; 254/220 nm; Rt: 9.58 min) and Chiral-HPLC to afford two enantiomers. Absolute stereochemistry was arbitrarily assigned.

Enantiomer 1 (Compound 410a) (37.7 mg, 0.0808 mmol, 35.9% yield). Retention time: 2.589 min (CHIRALPAK IC-3: 0.46*5 cm; 3 μm; MTBE (0.1% DEA): MeOH=75:25; 1.0 ml/min; Gradient: 50 B to 50 B in 5 min). LCMS (ESI) [M+H]$^+$=467.2, 1.659 min., Method M; $^1$H NMR (400 MHz, DMSO-d$_6$) δ 10.22 (s, 1H), 9.34 (s, 1H), 7.98 (s, 1H), 7.34 (s, 1H), 6.85 (d, J=6.2 Hz, 1H), 6.23 (s, 2H), 5.69 (s, 1H), 5.28 (dd, J=7.1, 5.5 Hz, 1H), 4.29 (t, J=4.4 Hz, 2H), 3.79 (dd, J=11.6, 5.7 Hz, 1H), 3.42 (dd, J=11.5, 1.5 Hz, 1H), 2.84-2.75 (m, 2H), 2.76 (s, 4H), 2.30 (d, J=17.3 Hz, 1H), 1.93 (d, J=1.6 Hz, 3H).

Enantiomer 2 (Compound 410b) (41.6 mg, 0.0892 mmol, 39.6% yield). Retention time: 3.581 min (CHIRALPAK IC-3: 0.46*5 cm; 3 μm; MTBE (0.1% DEA):MeOH=75:25; 1.0 ml/min; Gradient: 50 B to 50 B in 5 min), LCMS (ESI) [M+H]$^+$=467.2, 1.659 min., Method M; $^1$H NMR (400 MHz, DMSO-d$_6$) δ 10.22 (s, 1H), 9.34 (s, 1H), 7.98 (s, 1H), 7.34 (s, 1H), 6.85 (d, J=6.2 Hz, 1H), 6.23 (s, 2H), 5.69 (s, 1H), 5.28 (dd, J=7.1, 5.5 Hz, 1H), 4.29 (t, J=4.4 Hz, 2H), 3.79 (dd, J=11.6, 5.7 Hz, 1H), 3.42 (dd, J=11.5, 1.5 Hz, 1H), 2.84-2.75 (m, 2H), 2.76 (s, 4H), 2.30 (d, J=17.3 Hz, 1H), 1.93 (d, J=1.6 Hz, 3H).

Example 112

(S)-1-Methylpyrrolidin-3-yl (8-amino-7-fluoro-6-(8-methyl-2,3-dihydro-1H-pyrido[2,3-b][1,4]oxazin-7-yl)isoquinolin-3-yl)carbamate and (R)-1-Methylpyrrolidin-3-yl (8-amino-7-fluoro-6-(8-methyl-2,3-dihydro-1H-pyrido[2,3-b][1,4]oxazin-7-yl)isoquinolin-3-yl)carbamate (Compound 411a and Compound 411b)

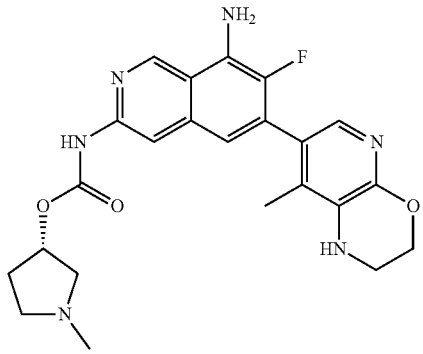

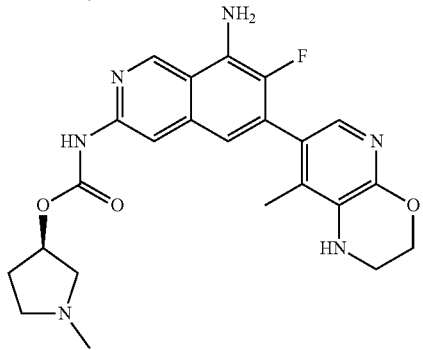

Step 1: tert-Butyl 7-[3-[(1-tert-butoxycarbonylpyrrolidin-3-yl)oxycarbonylamino]-8-chloro-7-fluoro-6-isoquinolyl]-8-methyl-2,3-dihydropyrido[2,3-b][1,4]oxazine-1-carboxylate

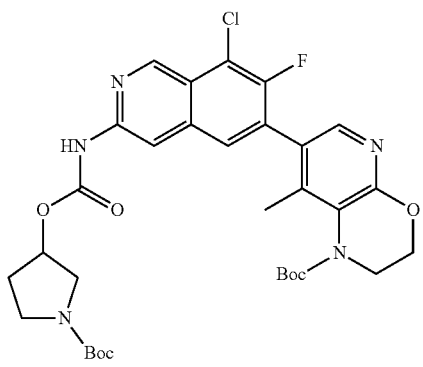 [SMILES: Cc1c(-c2cc3cc(NC(=O)OC4CCN(C(=O)OC(C)(C)C)C4)ncc3c(Cl)c2F)cnc2c1N(C(=O)OC(C)(C)C)CCO2]

A solution of tert-butyl 7-(3-amino-8-chloro-7-fluoro-6-isoquinolyl)-8-methyl-2,3-dihydropyrido[2,3-b][1,4]oxazine-1-carboxylate (1200 mg, 2.7 mmol), 1-Boc-3-hydroxypyrrolidine (660 mg, 3.52 mmol) and DIEA (2000 mg, 15.5 mmol) in dichloromethane (50 mL) was added (COCl$_2$)$_3$ (312 mg, 1.05 mmol) at 0° C. The reaction was stirred for 1 hour at room temperature. The reaction mixture was quenched with water and extracted with ethyl acetate. The organic layer was dried over anhydrous sodium sulfate and concentrated under vacuum. The residue was purified by flash chromatography on silica gel eluting with petroleum ether/ethyl acetate (100/1) to afford tert-butyl 7-[3-[(1-tert-butoxycarbonylpyrrolidin-3-yl)oxycarbonylamino]-8-chloro-7-fluoro-6-isoquinolyl]-8-methyl-2,3-dihydropyrido[2,3-b][1,4]oxazine-1-carboxylate (1600 mg, 2.1881 mmol, 81.1% yield) as a yellow solid. LCMS (ESI) [M+H]$^+$=659.0.

Step 2: tert-Butyl 7-[8-(tert-butoxycarbonylamino)-7-fluoro-3-[(1-methylpyrrolidin-3-yl)oxycarbonylamino]-6-isoquinolyl]-8-methyl-2,3-dihydropyrido[2,3-b][1,4]oxazine-1-carboxylate

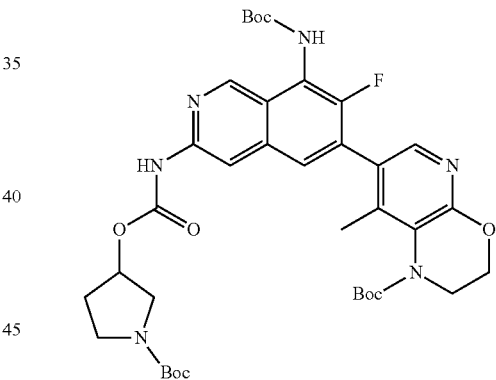

Under nitrogen, a mixture of tert-butyl 7-[8-chloro-7-fluoro-3-[(1-methylpyrrolidin-3-yl)oxycarbonylamino]-6-isoquinolyl]-8-methyl-2,3-dihydropyrido[2,3-b][1,4]oxazine-1-carboxylate (1600 mg, 2.8 mmol), NH$_2$Boc (1.40 g, 119.66 mmol), Pd$_2$(dba)$_3$.CHCl$_3$ (250 mg, 0.24 mmol), Brettphos (240 mg, 0.50 mmol) and Cs$_2$CO$_3$ (2400 mg, 7.36 mmol) in 1,4-dioxane (30 mL) was stirred for 2 hours at 90° C. The reaction mixture was diluted with water and extracted with ethyl acetate. The organic layer was dried over anhydrous sodium sulfate and concentrated under vacuum. The residue was purified by flash chromatography on silica gel eluting with petroleum ether/ethyl acetate (10/1) to afford tert-butyl 7-[8-(tert-butoxycarbonylamino)-7-fluoro-3-[(1-methylpyrrolidin-3-yl)oxycarbonylamino]-6-isoquinolyl]-8-methyl-2,3-dihydropyrido[2,3-b][1,4]oxazine-1-carboxylate (1300 mg, 1.793 mmol, 64.1% yield) as a yellow solid. LCMS (ESI) [M+H]$^+$=739.0.

Step 3: Pyrrolidin-3-yl N-[8-amino-7-fluoro-6-(8-methyl-2,3-dihydro-1H-pyrido[2,3-b][1,4]oxazin-7-yl)-3-isoquinolyl]carbamate

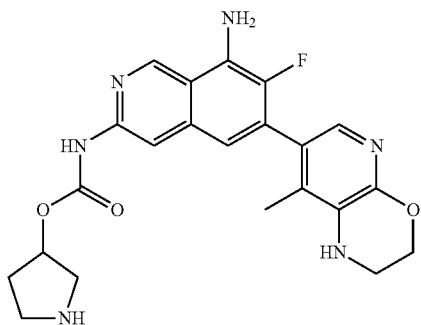 [SMILES: Cc1c(-c2cc3cc(NC(=O)OC4CCNC4)ncc3c(N)c2F)cnc2c1NCCO2]

A solution of tert-butyl 7-[8-(tert-butoxycarbonylamino)-3-[(1-tert-butoxycarbonylpyrrolidin-3-yl)oxycarbonylamino]-7-fluoro-6-isoquinolyl]-8-methyl-2,3-dihydro-pyrido[2,3-b][1,4]oxazine-1-carboxylate (380 mg, 0.51 mmol) in dichloromethane (5 mL) and 2,2,2-trifluoroacetic acid (20 mL) was stirred at room temperature for 1 hour. The reaction mixture was concentrated under vacuum. The residue was purified by reverse phase chromatography (acetonitrile 0-40/0.1% NH$_4$HCO$_3$ in water) to afford pyrrolidin-3-yl N-[8-amino-7-fluoro-6-(8-methyl-2,3-dihydro-1H-pyrido[2,3-b][1,4]oxazin-7-yl)-3-isoquinolyl]carbamate (200 mg, 0.4105 mmol, 79.8% yield) as a yellow solid. LCMS (ESI) [M+H]$^+$=439.0.

Step 4: (S)-1-Methylpyrrolidin-3-yl (8-amino-7-fluoro-6-(8-methyl-2,3-dihydro-1H-pyrido[2,3-b][1,4]oxazin-7-yl)isoquinolin-3-yl)carbamate and (R)-1-Methylpyrrolidin-3-yl (8-amino-7-fluoro-6-(8-methyl-2,3-dihydro-1H-pyrido[2,3-b][1,4]oxazin-7-yl)isoquinolin-3-yl)carbamate

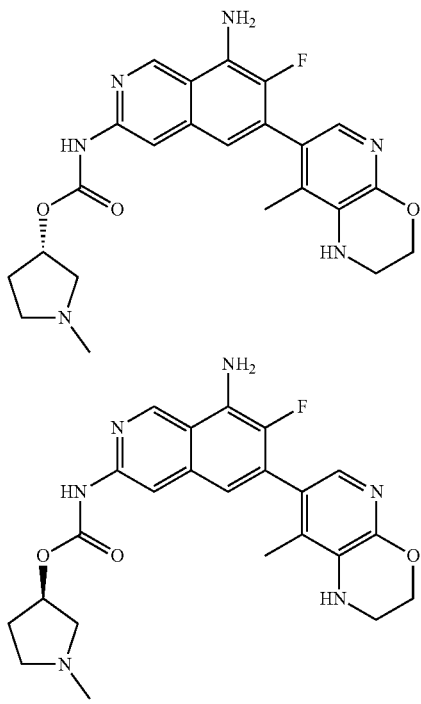

A solution of formaldehyde (20 mg, 0.67 mmol) and pyrrolidin-3-yl N-[8-amino-7-fluoro-6-(8-methyl-2,3-dihydro-1H-pyrido[2,3-b][1,4]oxazin-7-yl)-3-isoquinolyl]carbamate (300 mg, 0.68 mmol) in methyl alcohol (30 mL) was stirred at room temperature for 1 hour. Then NaBH$_3$CN (127 mg, 2.05 mmol) was added and the reaction was stirred at room temperature for 30 min. The reaction mixture was concentrated under vacuum. The residue was purified by reverse phase chromatography (acetonitrile 0-70/0.1% NH$_4$HCO$_3$ in water) and Chiral-HPLC to afford two enantiomers. Absolute stereochemistry was arbitrarily assigned.

Enantiomer 1 (Compound 411a) (25 mg, 0.0553 mmol, 8.1% yield): Retention time: 7.952 (CHIRALPAK IG, 2*25 cm, 5 µm; Mobile Phase A:HEX:DCM=3:1, Mobile Phase B: EtOH; Flow rate: 20 mL/min; Gradient: 50 B to 50 B in 15 min). LCMS (ESI) [M+H]$^+$=453.2, R$_T$ 0.931 min, Method K; $^1$H NMR (300 MHz, DMSO-d$_6$) δ10.06 (s, 1H), 9.33 (s, 1H), 7.97 (s, 1H), 7.33 (s, 1H), 6.83 (d, J=6.2 Hz, 1H), 6.21 (s, 2H), 5.68 (s, 1H), 5.14 (dd, J=8.0, 4.3 Hz, 1H), 4.29 (s, 2H), 3.37 (s, 2H), 2.71 (dt, J=7.6, 3.9 Hz, 1H), 2.65 (d, J=4.5 Hz, 2H), 2.32-2.17 (m, 5H), 1.93 (d, J=1.6 Hz, 3H), 1.85-1.73 (m, 1H).

Enantiomer 2 (Compound 411b) (22 mg, 0.0485 mmol, 7.1% yield). Retention time: 12.08 (CHIRALPAK IG, 2*25 cm, 5 µm; Mobile Phase A:HEX:DCM=3:1, Mobile Phase B: EtOH; Flow rate: 20 mL/min; Gradient: 50 B to 50 B in 15 min). LCMS (ESI) [M+H]$^+$=453.2, R$_T$ 0.931 min., Method K; $^1$H NMR (300 MHz, DMSO-d$_6$) δ10.06 (s, 1H), 9.33 (s, 1H), 7.97 (s, 1H), 7.33 (s, 1H), 6.83 (d, J=6.2 Hz, 1H), 6.21 (s, 2H), 5.68 (s, 1H), 5.14 (dd, J=8.0, 4.3 Hz, 1H), 4.29 (s, 2H), 3.37 (s, 2H), 2.71 (dt, J=7.6, 3.9 Hz, 1H), 2.65 (d, J=4.5 Hz, 2H), 2.32-2.17 (m, 5H), 1.93 (d, J=1.6 Hz, 3H), 1.85-1.73 (m, 1H).

Example 113

Tetrahydro-2H-pyran-4-yl (8-amino-7-fluoro-6-(8-hydroxy-4-methyl-5,6,7,8-tetrahydro-1,5-naphthyridin-3-yl)isoquinolin-3-yl)carbamate (Compound 413)

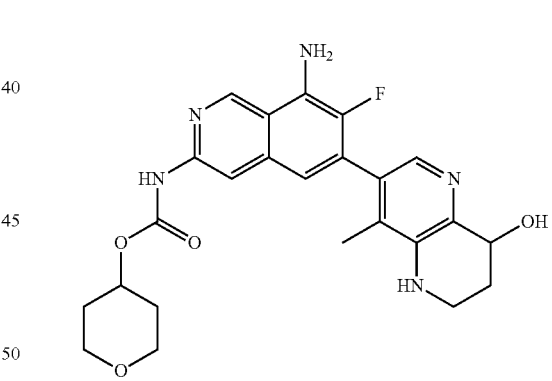

Step 1: tert-Butyl N-(5-bromo-2-iodo-4-methyl-3-pyridyl)-N-but-3-enyl-carbamate

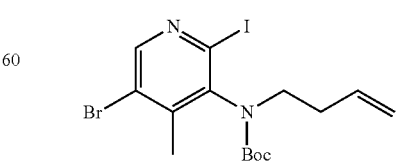

A solution of tert-butyl N-(5-bromo-2-iodo-4-methyl-3-pyridyl)carbamate (58 g, 140.42 mmol) and in tetrahydrofuran (500 mL) was stirred at room temperature for 1 hour. Then 4-bromo-1-butene (50 g, 370.37 mmol) and NaI (55 g, 366.67 mmol) was added and stirred at 95° C. for 16 hours. The reaction was then quenched by adding water and extracted with ethyl acetate. The organic layers were combined, dried and concentrated under vacuum. The residue was purified by flash chromatography on silica gel eluting with petroleum ether/ethyl acetate (4/1) to afford tert-butyl N-(5-bromo-2-iodo-4-methyl-3-pyridyl)-N-but-3-enyl-carbamate (30 g, 64.22 mmol, 45.7% yield) as a yellow oil and 8 g of starting material recovered. LCMS (ESI) [M+H]$^+$= 467.

Step 2: tert-Butyl 7-bromo-8-methyl-4-methylene-2,3-dihydro-1,5-naphthyridine-1-carboxylate

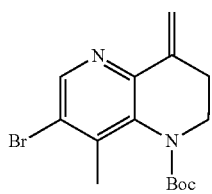 [SMILES: C=C1CCN(C(=O)OC(C)(C)C)c2c1ncc(Br)c2C]

A solution of tert-butyl N-(5-bromo-2-iodo-4-methyl-3-pyridyl)-N-but-3-enyl-carbamate (30 g, 64.22 mmol), Pd(dppf)Cl$_2$ (2.4 g, 3.28 mmol) and TEA (13.1 g, 128.43 mmol) in N,N-dimethylformamide (1500 mL) was stirred at 110° C. under nitrogen for 1 hour. The resulting solution was diluted with water and extracted with ethyl acetate. The organic layers were combined, dried and concentrated under vacuum. The residue was purified by flash chromatography on silica gel eluting with petroleum ether/ethyl acetate (4/1) to afford tert-butyl 7-bromo-8-methyl-4-methylene-2,3-dihydro-1,5-naphthyridine-1-carboxylate (13 g, 38.32 mmol, 59.7% yield) as a yellow. LCMS (ESI) [M+H]$^+$=339.

Step 3: tert-Butyl 7-bromo-8-methyl-4-oxo-2,3-dihydro-1,5-naphthyridine-1-carboxylate

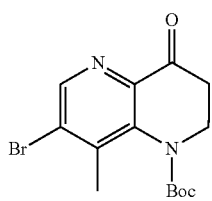 [SMILES: Cc1c(Br)cnc2c1N(C(=O)OC(C)(C)C)CCC2=O]

A solution of tert-butyl 7-bromo-8-methyl-4-methylene-2,3-dihydro-1,5-naphthyridine-1-carboxylate (13 g, 38.32 mmol), RuCl$_3$ (2.4 g, 11.59 mmol) and NaIO$_4$ (20.5 g, 95.79 mmol) in acetonitrile (350 mL), carbon tetrachloride (350 mL) and water (350 mL) was stirred at 25° C. for 1.5 hours. The reaction was then quenched by adding 300 mL of sodium thiosulfate solution. The resulting solution was adjusted to pH 6-7 with sodium bicarbonate and extracted with ethyl acetate. The organic phase was concentrated under vacuum. The residue was purified by flash chromatography on silica gel eluting with petroleum ether/ethyl acetate (1/1) to afford tert-butyl 7-bromo-8-methyl-4-oxo-2,3-dihydro-1,5-naphthyridine-1-carboxylate (7 g, 20.52 mmol, 53.5% yield) as a yellow solid. LCMS (ESI) [M+H]$^+$= 341.

Step 4: tert-butyl 7-bromo-4-hydroxy-8-methyl-3,4-dihydro-2H-1,5-naphthyridine-1-carboxylate

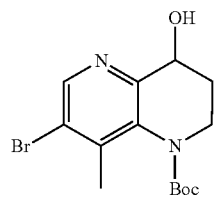 [SMILES: Cc1c(Br)cnc2c1N(C(=O)OC(C)(C)C)CCC2O]

A solution of tert-butyl 7-bromo-8-methyl-4-oxo-2,3-dihydro-1,5-naphthyridine-1-carboxylate (500 mg, 1.47 mmol) and NaBH$_4$ (150 mg, 4.05 mmol) in ethanol (30 mL) was stirred at room temperature for 2 hours. The reaction mixture was diluted with water. The resulting mixture was extracted with ethyl acetate. The organic layers were combined, dried over anhydrous sodium sulfate and concentrated under vacuum to afford tert-butyl 7-bromo-4-hydroxy-8-methyl-3,4-dihydro-2H-1,5-naphthyridine-1-carboxylate (400 mg, 1.049 mmol, 71.6% yield) as a yellow solid. LCMS (ESI) [M+H]$^+$=343.

Step 5: tert-Butyl 7-bromo-4-[tert-butyl(dimethyl)silyl]oxy-8-methyl-3,4-dihydro-2H-1,5-naphthyridine-1-carboxylate

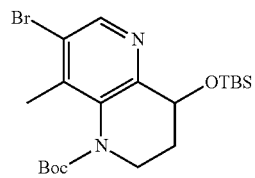 [SMILES: Cc1c(Br)cnc2c1N(C(=O)OC(C)(C)C)CCC2O[Si](C)(C)C(C)(C)C]

Under nitrogen, to a solution of tert-butyl 7-bromo-4-hydroxy-8-methyl-3,4-dihydro-2H-1,5-naphthyridine-1-carboxylate (330 mg, 0.96 mmol) and imidazole (200 mg, 2.94 mmol) in dichloromethane (10 mL) was added TBDMSCl (293 mg, 1.95 mmol) at 25° C. The resulting solution was stirred for 2 h at 25° C. The residue was purified by flash chromatography on silica gel eluting with petroleum ether/ethyl acetate (1/1) to afford tert-butyl 7-bromo-4-[tert-butyl(dimethyl)silyl]oxy-8-methyl-3,4-dihydro-2H-1,5-naphthyridine-1-carboxylate (400 mg, 0.874 mmol, 90.9% yield) as a colorless oil. LCMS (ESI) [M+H]$^+$= 457.

Step 6: tert-Butyl 4-[tert-butyl(dimethyl)silyl]oxy-8-methyl-7-(4,4,5,5-tetramethyl-1,3,2-dioxaborolan-2-yl)-3,4-dihydro-2H-1,5-naphthyridine-1-carboxylate

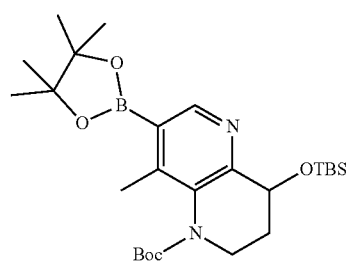 [SMILES: Cc1c(B2OC(C)(C)C(C)(C)O2)cnc2c1N(C(=O)OC(C)(C)C)CCC2O[Si](C)(C)C(C)(C)C]

Under nitrogen, to a mixture of tert-butyl 7-bromo-4-[tert-butyl(dimethyl)silyl]oxy-8-methyl-3,4-dihydro-2H-1,5-naphthyridine-1-carboxylate (400 mg, 0.87 mmol) and bis(pinacolato)diboron (440 mg, 1.73 mmol) in 1,4-dioxane (10 mL) was added Pd(dppf)Cl$_2$ (130 mg, 0.18 mmol) and KOAc (260 mg, 2.65 mmol) at room temperature. The resulting solution was stirred for 2 h at 100° C. After filtration, the filtrate was concentrated under reduced pressure. The resulting residue was purified by reverse phase chromatography (acetonitrile 0-40/0.1% NH$_4$HCO$_3$ in water) to afford tert-butyl 4-[tert-butyl(dimethyl)silyl]oxy-8-methyl-7-(4,4,5,5-tetramethyl-1,3,2-dioxaborolan-2-yl)-3,4-dihydro-2H-1,5-naphthyridine-1-carboxylate (320 mg, 0.634 mmol, 72.5% yield) as a colorless oil. LCMS (ESI) [M+H]$^+$=505.

Step 7: tert-Butyl 7-(3-amino-8-chloro-7-fluoro-6-isoquinolyl)-4-[tert-butyl(dimethyl)silyl]oxy-8-methyl-3,4-dihydro-2H-1,5-naphthyridine-1-carboxylate

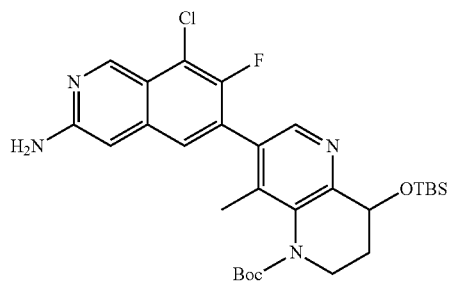 [SMILES: Cc1c(-c2cc3cc(N)ncc3c(Cl)c2F)cnc2c1N(C(=O)OC(C)(C)C)CCC2O[Si](C)(C)C(C)(C)C]

Under nitrogen, to a solution of tert-butyl 4-[tert-butyl(dimethyl)silyl]oxy-8-methyl-7-(4,4,5,5-tetramethyl-1,3,2-dioxaborolan-2-yl)-3,4-dihydro-2H-1,5-naphthyridine-1-carboxylate (400 mg, 0.79 mmol) and 8-chloro-7-fluoro-6-iodo-isoquinolin-3-amine (400 mg, 1.24 mmol) in 1,4-dioxane (12 mL) and water (1.2 mL) was added Pd(dppf)Cl$_2$ (120 mg, 0.16 mmol) and K$_2$CO$_3$ (330 mg, 2.39 mmol) at room temperature. The resulting mixture was stirred for 2 h at 60° C. The residue was purified by flash chromatography on silica gel eluting with petroleum ether/ethyl acetate (2/1) to afford tert-butyl 7-(3-amino-8-chloro-7-fluoro-6-isoquinolyl)-4-[tert-butyl(dimethyl)silyl]oxy-8-methyl-3,4-dihydro-2H-1,5-naphthyridine-1-carboxylate (300 mg, 0.523 mmol, 66% yield) as a colorless oil. LCMS (ESI) [M+H]$^+$=573.

Step 8: tert-Butyl 4-[tert-butyl(dimethyl)silyl]oxy-7-[8-chloro-7-fluoro-3-(tetrahydropyran-4-yloxycarbonylamino)-6-isoquinolyl]-8-methyl-3,4-dihydro-2H-1,5-naphthyridine-1-carboxylate

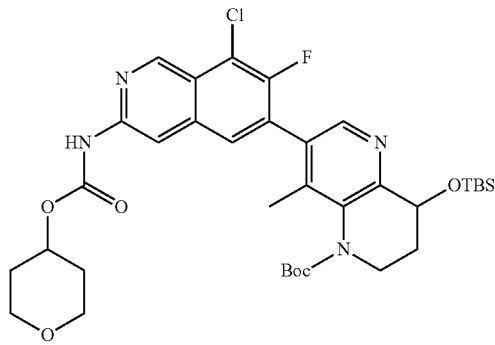 [SMILES: Cc1c(-c2cc3cc(NC(=O)OC4CCOCC4)ncc3c(Cl)c2F)cnc2c1N(C(=O)OC(C)(C)C)CCC2O[Si](C)(C)C(C)(C)C]

Under nitrogen, to a solution of tert-butyl 7-(3-amino-8-chloro-7-fluoro-6-isoquinolyl)-4-[tert-butyl (dimethyl)silyl]oxy-8-methyl-3,4-dihydro-2H-1,5-naphthyridine-1-carboxylate (220 mg, 0.38 mmol) and tetrahydro-2H-pyran-4-yl carbonochloridate (350 mg, 2.13 mmol) in dichloromethane (10 mL) was added DIEA (268 mg, 2.08 mmol) at 0° C. The resulting solution was stirred for 2 h at 0° C. The reaction was diluted with dichloromethane and then washed with water. The organic phase was dried and concentrated under vacuum. The residue was purified by flash chromatography on silica gel eluting with petroleum ether/ethyl acetate (1/1) to afford tert-butyl 4-[tert-butyl (dimethyl)silyl]oxy-7-[8-chloro-7-fluoro-3-(tetrahydropyran-4-yloxycarbonylamino)-6-isoquinolyl]-8-methyl-3,4-dihydro-2H-1,5-naphthyridine-1-carboxylate (150 mg, 0.214 mmol, 55.7% yield) as a brown solid. LCMS (ESI) [M+H]$^+$=701.

Step 9: tert-Butyl 7-[8-(tert-butoxycarbonylamino)-7-fluoro-3-(tetrahydropyran-4-yloxycarbonylamino)-6-isoquinolyl]-4-[tert-butyl(dimethyl)silyl]oxy-8-methyl-3,4-dihydro-2H-1,5-naphthyridine-1-carboxylate

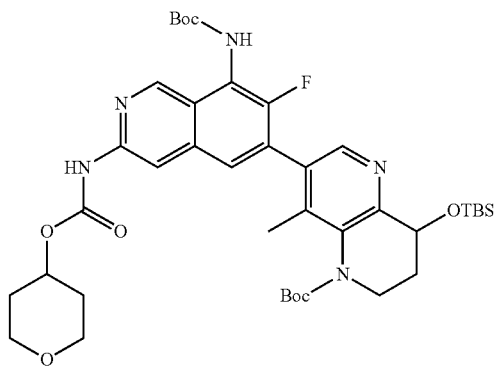 [SMILES: Cc1c(-c2cc3cc(NC(=O)OC4CCOCC4)ncc3c(NC(=O)OC(C)(C)C)c2F)cnc2c1N(C(=O)OC(C)(C)C)CCC2O[Si](C)(C)C(C)(C)C]

Under nitrogen, to a solution of tert-butyl 4-[tert-butyl (dimethyl)silyl]oxy-7-[8-chloro-7-fluoro-3-(tetrahydropyran-4-yloxycarbonylamino)-6-isoquinolyl]-8-methyl-3,4-dihydro-2H-1,5-naphthyridine-1-carboxylate (150 mg, 0.21 mmol) and NH$_2$-Boc (1.5 g, 12.82 mmol) in 1,4-dioxane (8 mL) was added Pd(dba)$_3$CHCl$_3$ (45 mg, 0.04 mmol), Brettphos (45 mg, 0.08 mmol) and Cs$_2$CO$_3$ (225 mg, 0.69 mmol) at room temperature. The resulting mixture was stirred for 2 h at 90° C. After filtration, the filtrate was concentrated under reduced pressure. The residue was purified by flash chromatography on silica gel eluting with petroleum ether/ethyl acetate (1/1) to afford tert-butyl 7-[8-(tert-butoxycarbonylamino)-7-fluoro-3-(tetrahydropyran-4-yloxycarbonylamino)-6-isoquinolyl]-4-[tert-butyl (dimethyl)silyl]oxy-8-methyl-3,4-dihydro-2H-1,5-naphthyridine-1-carboxylate (140 mg, 0.179 mmol, 83.7% yield) as a yellow solid. LCMS (ESI) [M+H]$^+$=782.

Step 10: Tetrahydropyran-4-yl N-[8-amino-6-[8-[tert-butyl(dimethyl)silyl]oxy-4-methyl-5,6,7,8-tetrahydro-1,5-naphthyridin-3-yl]-7-fluoro-3-isoquinolyl]carbamate

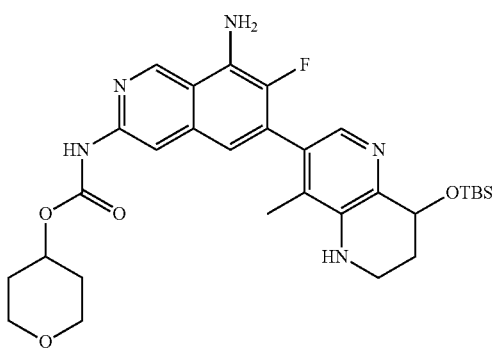 [SMILES: Cc1c(-c2cc3cc(NC(=O)OC4CCOCC4)ncc3c(N)c2F)cnc2c1NCCC2O[Si](C)(C)C(C)(C)C]

To a solution of tert-butyl 7-[8-(tert-butoxycarbonylamino)-7-fluoro-3-(tetrahydropyran-4-yloxycarbonylamino)-6-isoquinolyl]-4-[tert-butyl(dimethyl)silyl]oxy-8-methyl-3,4-dihydro-2H-1,5-naphthyridine-1-carboxylate (140 mg, 0.18 mmol) in dichloromethane (4 mL) was added 2,2,2-trifluoroacetic acid (1 mL) at room temperature. The resulting solution was stirred for 1 hour at 25° C. and then concentrated under vacuum. The residue was adjusted to pH 8 with TEA. The resulting mixture was purified by reverse phase chromatography (acetonitrile 0-40/0.1% HCl in water) to afford tetrahydropyran-4-yl N-[8-amino-6-[8-[tert-butyl(dimethyl)silyl]oxy-4-methyl-5,6,7,8-tetrahydro-1,5-naphthyridin-3-yl]-7-fluoro-3-isoquinolyl]carbamate (60 mg, 0.103 mol, 57.6% yield) as a yellow solid. LCMS (ESI) [M+H]$^+$=58

Step 11: Tetrahydropyran-4-yl N-[8-amino-7-fluoro-6-(8-hydroxy-4-methyl-5,6,7,8-tetrahydro-1,5-naphthyridin-3-yl)-3-isoquinolyl]carbamate

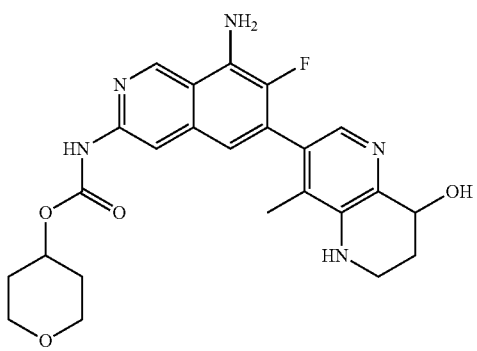 [SMILES: Cc1c(-c2cc3cc(NC(=O)OC4CCOCC4)ncc3c(N)c2F)cnc2c1NCCC2O]

To a solution of tetrahydropyran-4-yl N-[8-amino-6-[8-[tert-butyl(dimethyl)silyl]oxy-4-methyl-5,6,7,8-tetrahydro-1,5-naphthyridin-3-yl]-7-fluoro-3-isoquinolyl]carbamate (60 mg, 0.10 mmol) in tetrahydrofuran (10 mL) was added tetrabutylammonium fluoride (120 mg, 0.46 mmol) at 25° C. The resulting solution was stirred for 2 h at 25° C. The resulting mixture was concentrated and purified by reverse phase chromatography (acetonitrile 0-40/0.1% TFA in water) to afford tetrahydropyran-4-yl N-[8-amino-7-fluoro-6-(8-hydroxy-4-methyl-5,6,7,8-tetrahydro-1,5-naphthyridin-3-yl)-3-isoquinolyl]carbamate (9 mg, 0.019 mmol, 18.7% yield) as a yellow solid. LCMS (ESI) [M+H]$^+$=468.2, 1.275 min, Method J; $^1$H NMR (400 MHz, DMSO-d$_6$) δ10.05 (s, 1H), 9.35 (s, 1H), 7.98 (s, 1H), 7.65 (s, 1H), 6.84 (s, 1H), 6.23 (s, 2H), 5.65 (s, 1H), 5.19 (s, 1H), 4.87 (dq, J=8.7, 4.4 Hz, 1H), 4.61 (d, J=3.9 Hz, 1H), 3.90-3.81 (m, 2H), 3.53-3.42 (m, 2H), 3.34 (m, 2H), 1.97-1.87 (m, 6H), 1.81 (s, 1H), 1.61 (dtd, J=12.9, 9.1, 4.0 Hz, 2H).

Example 114

(1S,2S)-2-Acetamidocyclohexyl (8-amino-7-fluoro-6-(8-methyl-2,3-dihydro-1H-pyrido[2,3-b][1,4]oxazin-7-yl)isoquinolin-3-yl)carbamate and (1R,2R)-2-acetamidocyclohexyl (8-amino-7-fluoro-6-(8-methyl-2,3-dihydro-1H-pyrido[2,3-b][1,4]oxazin-7-yl)isoquinolin-3-yl)carbamate (Compound 414a and Compound 414b)

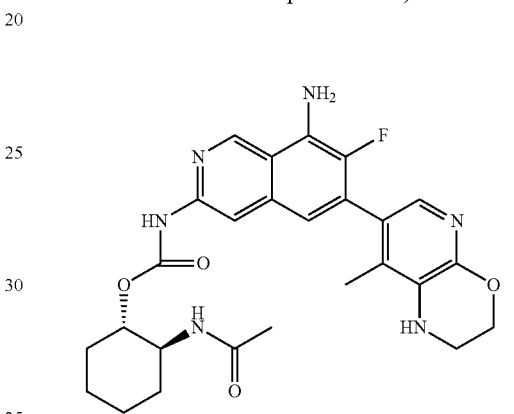

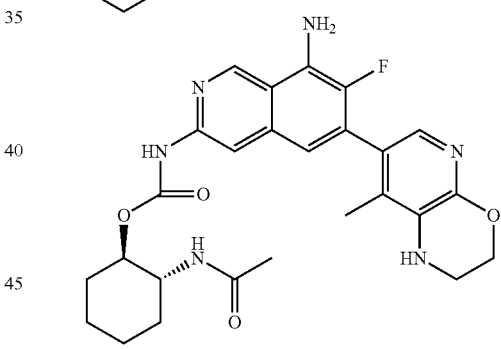

Step 1: (±)-N-((1R,2R)-2-Hydroxycyclohexyl)acetamide

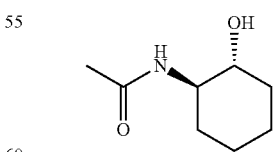

A solution of (±)-(1s,2s)-2-aminocyclohexanol (1.0 g, 8.68 mmol) and MeONa (474.0 mg, 8.62 mmol) in methanol (50 mL) was stirred at room temperature for 15 minutes. Then acetic anhydride (1.0 g, 9.8 mmol) was added and stirred at room temperature for 2 hours. The reaction mixture was concentrated under vacuum and purified by flash chromatography on silica gel eluting with dichloromethane/methanol (9/1) to afford (±)-N-[(trans)-2-hydroxycyclohexyl]acetamide (1 g, 6.361 mmol, 73.3% yield) as a white solid. LCMS (ESI) [M+H]⁺=157.2.

Step 2: (±)-tert-Butyl 7-(3-(((((1R,2R)-2-acetamidocyclohexyl)oxy)carbonyl)amino)-8-chloro-7-fluoroisoquinolin-6-yl)-8-methyl-2,3-dihydro-1H-pyrido[2,3-b][1,4]oxazine-1-carboxylate

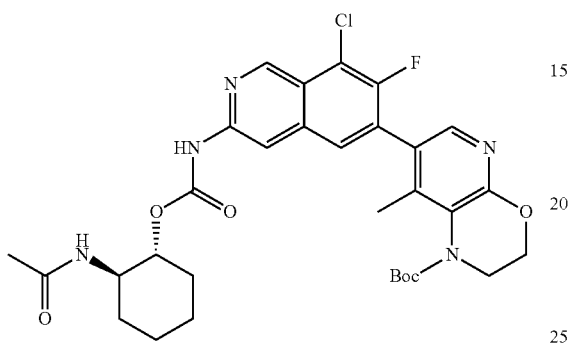

A solution of N-[(trans)-2-hydroxycyclohexyl]acetamide (133 mg, 0.85 mmol), tert-butyl 7-(3-amino-8-chloro-7-fluoro-6-isoquinolyl)-8-methyl-2,3-dihydropyrido[2,3-b][1,4]oxazine-1-carboxylate (250 mg, 0.56 mmol) and DIEA (363 mg, 2.81 mmol) in dichloromethane (20 mL) was stirred at 0° C. Then triphosgene (75.0 mg, 0.25 mmol) was added and the reaction was stirred at room temperature for 3 hours. The reaction mixture was concentrated under vacuum. The residue was purified by flash chromatography on silica gel eluting with dichloromethane/methanol (9:1) to afford (±)-tert-butyl 7-[3-[[(trans)-2-acetamidocyclohexoxy]carbonylamino]-8-chloro-7-fluoro-6-isoquinolyl]-8-methyl-2,3-dihydropyrido[2,3-b][1,4]oxazine-1-carboxylate (310 mg, 0.494 mmol, 87.8% yield) as a yellow solid. LCMS (ESI) [M+H]⁺=628.1.

Step 3: (±)-tert-Butyl 7-(3-(((((trans)-2-acetamidocyclohexyl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

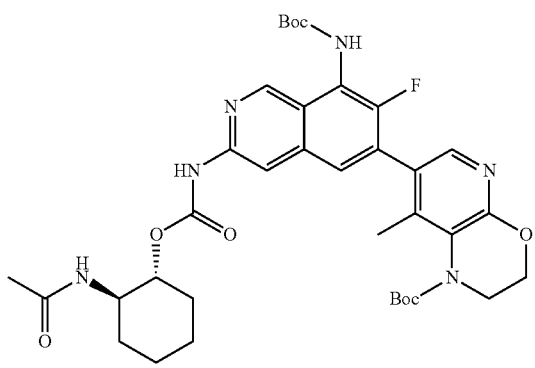 [SMILES: CC(=O)N[C@@H]1CCCC[C@H]1OC(=O)Nc1cc2cc(-c3cnc4c(c3C)N(C(=O)OC(C)(C)C)CCO4)c(F)c(NC(=O)OC(C)(C)C)c2cn1]

A mixture of (±)-tert-butyl 7-[3-[[(trans)-2-acetamidocyclohexoxy]carbonylamino]-8-chloro-7-fluoro-6-isoqui-nolyl]-8-methyl-2,3-dihydropyrido[2,3-b][1,4]oxazine-1-carboxylate (300 mg, 0.48 mmol), tert-butyl carbamate (2800 mg, 23.9 mmol), Pd(dba)₃·CHCl₃ (99 mg, 0.10 mmol), Brettphos (103 mg, 0.19 mmol) and Cs₂CO₃ (467 mg, 1.43 mmol) in 1,4-dioxane (10 mL) was stirred at 90° C. under nitrogen for 5 hours. The reaction mixture was concentrated under vacuum. The residue was purified by flash chromatography on silica gel eluting with dichloromethane/methanol (97:3) to afford (±)-tert-butyl 7-[3-[[(trans)-2-acetamidocyclohexoxy]carbonylamino]-8-(tert-butoxycarbonylamino)-7-fluoro-6-isoquinolyl]-8-methyl-2,3-dihydropyrido[2,3-b][1,4]oxazine-1-carboxylate (220 mg, 0.3104 mmol, 65% yield) as a yellow solid. LCMS (ESI) [M+H]⁺=708.8.

Step 4: (1S,2S)-2-acetamidocyclohexyl (8-amino-7-fluoro-6-(8-methyl-2,3-dihydro-1H-pyrido[2,3-b][1,4]oxazin-7-yl)isoquinolin-3-yl)carbamate and (1R,2R)-2-Acetamidocyclohexyl (8-amino-7-fluoro-6-(8-methyl-2,3-dihydro-1H-pyrido[2,3-b][1,4]oxazin-7-yl)isoquinolin-3-yl)carbamate

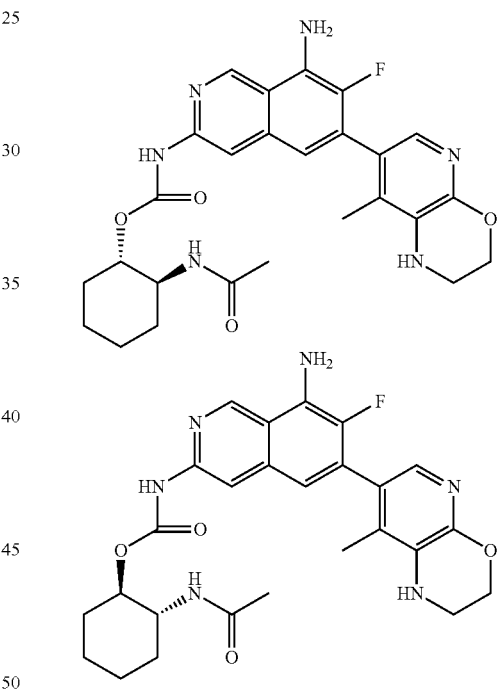

A solution of (±)-tert-butyl 7-[3-[[(trans)-2-acetamidocyclohexoxy]carbonylamino]-8-(tert-butoxycarbonylamino)-7-fluoro-6-isoquinolyl]-8-methyl-2,3-dihydropyrido[2,3-b][1,4]oxazine-1-carboxylate (200 mg, 0.28 mmol) and TFA (1.0 mL, 0.28 mmol) in dichloromethane (3 mL) was stirred at room temperature for 1.5 hours. The reaction was diluted with dichloromethane, then adjusted to pH 6-7 with triethylamine. The mixture was concentrated under vacuum and purified by prep-HPLC (X Bridge Shield RP18 OBD Column, 30*150 mm, 5 μm; Water (10 mmol/L NH₄HCO₃):ACN=20%-45% in 7 min; 60 mL/min) to afford the racemic product. The racemic product was isolated by Chiral-HPLC to afford two enantiomers. Absolute stereochemistry arbitrarily assigned Enantiomer 1 (Compound 414a) (29.6 mg, 0.0582 mmol, 20.6% yield): Retention time: 1.225 min. (CHIRALPAK IG-3, 0.46*5 cm; 3 µm; MTBE (0.2%IPAmine): EtOH=50:50 in 5 min; 1 mL/min). LCMS (ESI) [M+H]$^+$=509.2, R$_T$=2.029 min, Method K; $^1$H NMR (300 MHz, DMSO-d$_6$) δ9.90 (s, 1H), 9.30 (s, 1H), 7.92 (s, 1H), 7.86 (d, J=8.4 Hz, 1H), 7.30 (s, 1H), 6.82 (d, J=6.1 Hz, 1H), 6.19 (s, 2H), 5.67 (s, 1H), 4.61-4.44 (m, 1H), 4.27-4.26 (m, 2H), 3.82-3.76 (m, 1H), 3.34-3.33 (m, 2H), 2.05-2.04 (m, 1H), 1.95 (s, 3H), 1.91-1.90 (m, 1H), 1.84 (s, 3H), 1.74-1.61 (m, 2H), 1.45-1.28 (m, 4H).

Enantiomer 2 (Compound 414b) (28.3 mg, 0.0556 mmol, 19.7% yield): Retention time: 2.338 min. (CHIRALPAK IG-3, 0.46*5 cm; 3 µm; MTBE (0.2% IPAmine): EtOH=50:50 in 5 min; 1 mL/min). LCMS (ESI) [M+H]$^+$=509.2, R$_T$=2.029 min., Method K. $^1$H NMR (300 MHz, DMSO-d$_6$) δ9.90 (s, 1H), 9.30 (s, 1H), 7.92 (s, 1H), 7.86 (d, J=8.4 Hz, 1H), 7.30 (s, 1H), 6.82 (d, J=6.1 Hz, 1H), 6.19 (s, 2H), 5.67 (s, 1H), 4.61-4.44 (m, 1H), 4.27-4.26 (m, 2H), 3.82-3.76 (m, 1H), 3.34-3.33 (m, 2H), 2.05-2.04 (m, 1H), 1.95 (s, 3H), 1.91-1.90 (m, 1H), 1.84 (s, 3H), 1.74-1.61 (m, 2H), 1.45-1.28 (m, 4H).

Example 115

(1S,2S)-2-(Methylamino)cyclohexyl (8-amino-7-fluoro-6-(8-methyl-2,3-dihydro-1H-pyrido[2,3-b][1,4]oxazin-7-yl)isoquinolin-3-yl)carbamate and (1R,2R)-2-(Methylamino)cyclohexyl (8-amino-7-fluoro-6-(8-methyl-2,3-dihydro-1H-pyrido[2,3-b][1,4]oxazin-7-yl)isoquinolin-3-yl)carbamate (Compound 415a and Compound 415b)

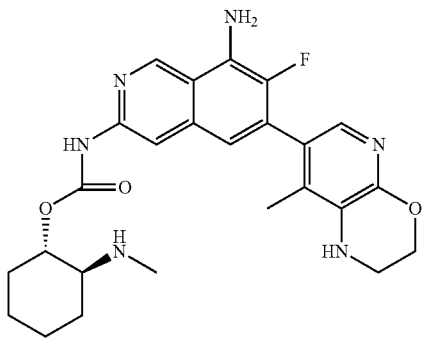

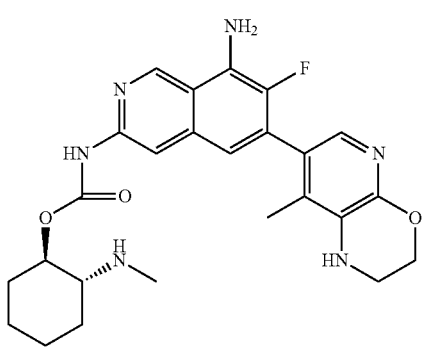

Step 1: trans-tert-butyl (2-hydroxycyclohexyl)(methyl) carbamate

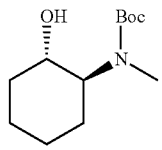 [SMILES: CN(C(=O)OC(C)(C)C)[C@H]1CCCC[C@@H]1O]

To a solution of trans-2-(methylamino)cyclohexanol (200 mg, 1.55 mmol) in 1,4-dioxane was added a solution of sodium hydroxide (80.0 mg, 1.86 mmol) in water (30 ml) and Boc$_2$O (503.0 mg, 2.31 mmol). The mixture was stirred at room temperature for 16 hours. The reaction solution was adjusted to pH 6-7 with 1 N HCl. The resulting mixture was extracted with ethyl acetate. The organic layers were combined, dried and concentrated under vacuum to afford trans-tert-butyl (2-hydroxycyclohexyl)(methyl) carbamate (310 mg, 1.3518 mmol, 87.3% yield) as a white solid. LCMS (ESI) [M+H]$^+$=229.3.

Step 2: trans-tert-Butyl 7-(3-((((2-((tert-butoxycarbonyl)(methyl)amino)cyclohexyl)oxy)carbonyl)amino)-8-chloro-7-fluoroisoquinolin-6-yl)-8-methyl-2,3-dihydro-1H-pyrido[2,3-b][1,4]oxazine-1-carboxylate

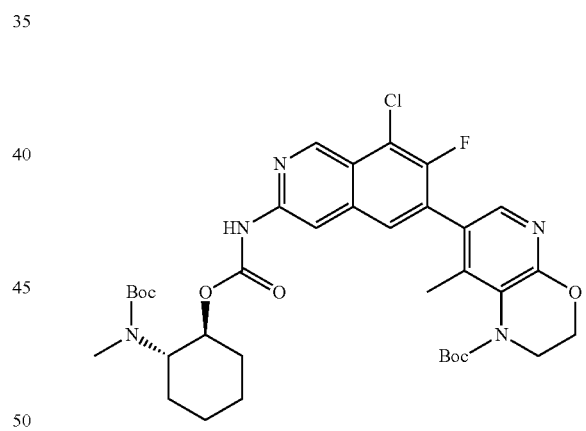

To a solution of tert-butyl 7-(3-amino-8-chloro-7-fluoro-6-isoquinolyl)-8-methyl-2,3-dihydropyrido[2,3-b][1,4]oxazine-1-carboxylate (250.0 mg, 0.560 mmol), trans-tert-butyl (2-hydroxycyclohexyl)(methyl) carbamate (194.0 mg, 0.850 mmol) and DIEA (362.0 mg, 2.81 mmol) in dichloromethane (20 mL) was added triphosgene (75.0 mg, 0.250 mmol) at 0° C. The reaction was stirred at room temperature for 2 hours and then concentrated under vacuum. The residue was purified by flash chromatography on silica gel eluting with petroleum ether/ethyl acetate (1:1) to afford trans-tert-butyl 7-(3-((((2-((tert-butoxycarbonyl)(methyl)amino)cyclohexyl)oxy)carbonyl)amino)-8-chloro-7-fluoroisoquinolin-6-yl)-8-methyl-2,3-dihydro-1H-pyrido[2,3-b][1,4]oxazine-1-carboxylate (330 mg, 0.4713 mmol, 83.9% yield) as a yellow solid. LCMS (ESI) [M+H]$^+$=700.2.

Step 3: trans-tert-Butyl 7-(8-((tert-butoxycarbonyl)amino)-7-fluoro-3-((((2-(methylamino)cyclohexyl)oxy)carbonyl)amino)isoquinolin-6-yl)-8-methyl-2,3-dihydro-1H-pyrido[2,3-b][1,4]oxazine-1-carboxylate

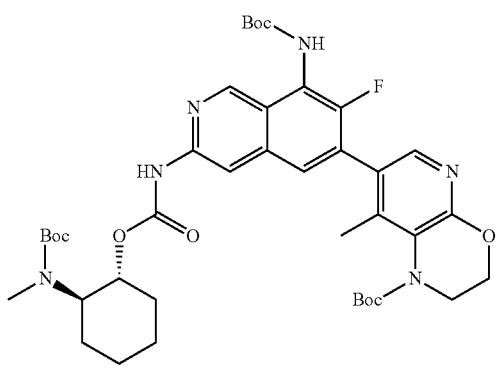 [SMILES: Cc1c(-c2cc3cc(NC(=O)O[C@@H]4CCCC[C@H]4N(C)C(=O)OC(C)(C)C)ncc3c(NC(=O)OC(C)(C)C)c2F)cnc2c1N(C(=O)OC(C)(C)C)CCO2]

A mixture of trans-tert-butyl 7-(3-((((2-((tert-butoxycarbonyl)(methyl)amino)cyclohexyl)oxy)carbonyl)amino)-8-chloro-7-fluoroisoquinolin-6-yl)-8-methyl-2,3-dihydro-1H-pyrido[2,3-b][1,4]oxazine-1-carboxylate (320.0 mg, 0.460 mmol), tert-butyl carbamate (2698.0 mg, 23.03 mmol), Pd(dba)$_3$·CHCl$_3$ (94.0 mg, 0.090 mmol), Brettphos (98.0 mg, 0.180 mmol) and Cs$_2$CO$_3$ (447.0 mg, 1.37 mmol) in 1,4-dioxane (10 mL) was stirred at 90° C. for 5 hours. The reaction mixture was concentrated under vacuum and purified by flash chromatography on silica gel eluting with petroleum ether/ethyl acetate (1:2) to afford trans-tert-butyl 7-(8-((tert-butoxycarbonyl)amino)-7-fluoro-3-((((2-(methylamino)cyclohexyl)oxy)carbonyl)amino)isoquinolin-6-yl)-8-methyl-2,3-dihydro-1H-pyrido[2,3-b][1,4]oxazine-1-carboxylate (250 mg, 0.3202 mmol, 70.1% yield) as a yellow solid. LCMS (ESI) [M+H]$^+$=780.9.

Step 4: (1S,2S)-2-(Methylamino)cyclohexyl (8-amino-7-fluoro-6-(8-methyl-2,3-dihydro-1H-pyrido[2,3-b][1,4]oxazin-7-yl)isoquinolin-3-yl)carbamate and (1R,2R)-2-(Methylamino)cyclohexyl (8-amino-7-fluoro-6-(8-methyl-2,3-dihydro-1H-pyrido[2,3-b][1,4]oxazin-7-yl)isoquinolin-3-yl)carbamate

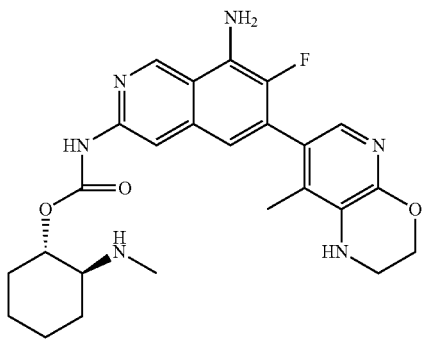

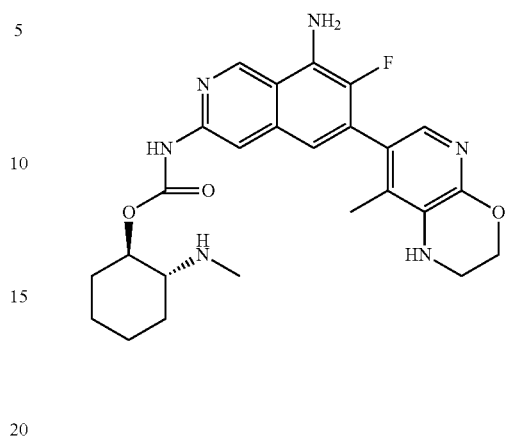

A solution of trans-tert-butyl 7-(8-((tert-butoxycarbonyl)amino)-7-fluoro-3-(((2-(methylamino)cyclohexyl)oxy)carbonyl)amino)isoquinolin-6-yl)-8-methyl-2,3-dihydro-1H-pyrido[2,3-b][1,4]oxazine-1-carboxylate (230.0 mg, 0.290 mmol) and TFA (1.0 mL, 0.290 mmol) in dichloromethane (3 mL) was stirred at room temperature for 1.5 hours. The reaction was diluted with dichloromethane, then adjusted to pH 6-7 with triethylamine. The reaction mixture was concentrated under vacuum and purified by prep-HPLC (YMC-Actus Triart C18 30*250, 5 μm; Water (10 mmol/L NH$_4$HCO$_3$):ACN=31%-44% in 7 min; 60 mL/min) to afford the racemic product. The racemic product was isolated by Chiral-HPLC to afford two enantiomers. Absolute stereochemistry was arbitrarily assigned Enantiomer 1 (Compound 415a) (22.9 mg, 0.0477 mmol, 16.2% yield): Retention time: 1.553 min (CHIRALPAK IG-3, 0.46*5 cm; 3 μm; (Hex:DCM=3:1) (0.1% DEA): EtOH=50:50 in 7 min; 1 mL/min). LCMS (ESI) [M+H]$^+$= 481.3, Rt=1.030 min. Method J. $^1$H NMR (300 MHz, DMSO-d$_6$) δ9.92 (s, 1H), 9.32 (s, 1H), 7.95 (s, 1H), 7.30 (d, J=8.4 Hz, 1H), 6.82 (d, J=6.1 Hz, 1H), 6.19 (s, 2H), 5.67 (s, 1H), 4.46-4.40 (m, 1H), 4.27 (s, 2H), 3.34-3.33 (m, 3H), 2.49-2.42 (m, 1H), 2.33 (s, 3H), 2.06-1.90 (m, 5H), 1.65-1.63 (m, 2H), 1.39-1.33 (m, 4H).

Enantiomer 2 (Compound 415b) (24.6 mg, 0.0512 mmol, 17.4% yield): Retention time: 3.752 min. (CHIRALPAK IG-3, 0.46*5 cm; 3 μm; (Hex:DCM=3:1) (0.1% DEA): EtOH=50:50 in 17 min; 1 mL/min). LCMS (ESI) [M+H]$^+$= 481.3, Rt=1.030 min. Method J. $^1$H NMR (300 MHz, DMSO-d$_6$) δ9.92 (s, 1H), 9.32 (s, 1H), 7.95 (s, 1H), 7.30 (d, J=8.4 Hz, 1H), 6.82 (d, J=6.1 Hz, 1H), 6.19 (s, 2H), 5.67 (s, 1H), 4.46-4.40 (m, 1H), 4.27 (s, 2H), 3.34-3.33 (m, 3H), 2.49-2.42 (m, 1H), 2.33 (s, 3H), 2.06-1.90 (m, 5H), 1.65-1.63 (m, 2H), 1.39-1.33 (m, 4H).

Example 116

(R)-1-Methylpiperidin-3-yl (8-amino-7-fluoro-6-(8-methyl-2,3-dihydro-1H-pyrido[2,3-b][1,4]oxazin-7-yl)isoquinolin-3-yl)carbamate and (S)-1-Methylpiperidin-3-yl (8-amino-7-fluoro-6-(8-methyl-2,3-dihydro-1H-pyrido[2,3-b][1,4]oxazin-7-yl)isoquinolin-3-yl)carbamate (Compound 416a and Compound 416b)

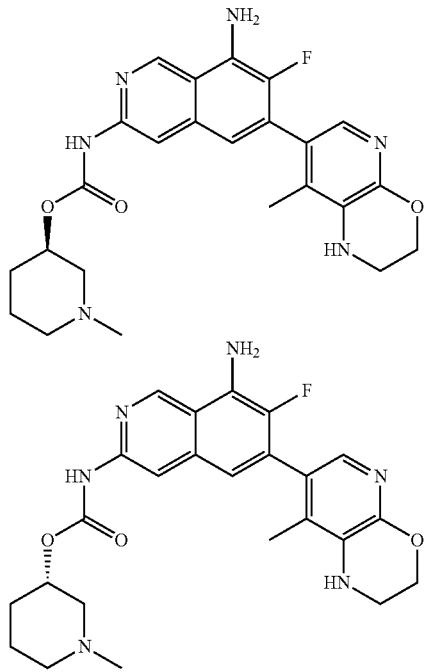

To a solution of 3-piperidyl N-[8-amino-7-fluoro-6-(8-methyl-2,3-dihydro-1H-pyrido[2,3-b][1,4]oxazin-7-yl)-3-isoquinolyl]carbamate (100 mg, 0.22 mmol) (from example 106) in methyl alcohol (10 mL) was added formaldehyde (20 mg, 0.27 mmol, 40%) at room temperature. The resulting solution was stirred for 1 hour at 25° C. Then NaBH$_4$ (20 mg, 0.53 mmol) was added and stirred at 25° C. for 1 hour. The reaction was quenched by adding water, concentrated under vacuum and purified by Prep-HPLC (Column: Kinetex EVO C18 Column 21.2*150, 5 µm; Mobile Phase A: Water (10 mmol/L NH$_4$HCO$_3$), Mobile Phase B: ACN; Flow rate: 25 mL/min; Gradient: 15% B to 41% B in 10 min; 254 nm; Rt: 9.75 min) and chiral-HPLC (Column: CHIRALPAK IE, 2*25 cm, 5 µm; Mobile Phase A:Hex:DCM=3:1 (10 mM NH$_3$-MeOH)—HPLC, Mobile Phase B: EtOH—HPLC; Flow rate: 20 mL/min; Gradient: 50% B to 50% B in 21 min) to afford two enantiomers. Absolute stereochemistry was arbitrarily assigned.

Enantiomer 1 (Compound 416a) (22.6 mg, 0.0484 mmol, 21.9% yield): Retention time: 2.690 min (CHIRALPAK IE-3, 0.46*5 cm; 3 µm, (Hex:DCM=3:1)(0.1% DEA): EtOH=50:50 in 5 min; 1.0 mL/min). LCMS (ESI) [M+H]$^+$= 467.3, R$_T$=1.514 min., Method J; $^1$H NMR (400 MHz, DMSO-d$_6$) δ10.02 (s, 1H), 9.33 (s, 1H), 7.97 (s, 1H), 7.33 (s, 1H), 6.83 (d, J=6.2 Hz, 1H), 6.20 (s, 2H), 5.67 (s, 1H), 4.72 (dt, J=8.4, 4.3 Hz, 1H), 4.29 (t, J=4.4 Hz, 2H), 3.33 (t, J=4.4 Hz, 2H), 2.78 (d, J=10.8 Hz, 1H), 2.48 (d, J=10.8 Hz, 1H), 2.18 (s, 3H), 2.13-2.01 (d, J=10.3 Hz, 2H), 1.92-1.87 (s, 4H), 1.75-1.71 (m, 1H), 1.55-1.34 (m, 2H).

Enantiomer 2 (Compound 416b) (19.8 mg, 0.0424 mmol, 19.2% yield): Retention time: 3.558 min (CHIRALPAK IE-3, 0.46*5 cm, 3 µm; (Hex:DCM=3:1)(0.1% DEA): EtOH=50:50 in 5 min; 1.0 mL/min). LCMS (ESI) [M+H]$^+$= 467.3, R$_T$=1.514 min., Method J; $^1$H NMR (400 MHz, DMSO-d$_6$) δ10.02 (s, 1H), 9.33 (s, 1H), 7.97 (s, 1H), 7.33 (s, 1H), 6.83 (d, J=6.2 Hz, 1H), 6.20 (s, 2H), 5.67 (s, 1H), 4.72 (dt, J=8.4, 4.3 Hz, 1H), 4.29 (t, J=4.4 Hz, 2H), 3.33 (t, J=4.4 Hz, 2H), 2.78 (d, J=10.8 Hz, 1H), 2.48 (d, J=10.8 Hz, 1H), 2.18 (s, 3H), 2.13-2.01 (d, J=10.3 Hz, 2H), 1.92-1.87 (s, 4H), 1.75-1.71 (m, 1H), 1.55-1.34 (m, 2H).

Example 117

2-Methyl-2-azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate (Compound 417)

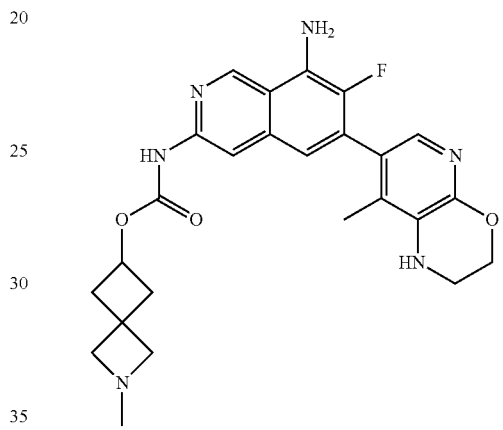

Step 1: tert-Butyl 7-(3-(((((2-(tert-butoxycarbonyl)-2-azaspiro[3.3]heptan-6-yl)oxy)carbonyl)amino)-8-chloro-7-fluoroisoquinolin-6-yl)-8-methyl-2,3-dihydro-1H-pyrido[2,3-b][1,4]oxazine-1-carboxylate

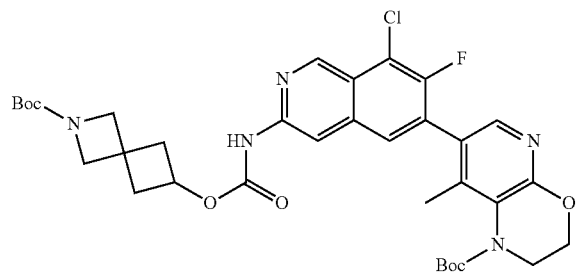 [SMILES: Cc1c(-c2cc3cc(NC(=O)OC4CC5(C4)CN(C(=O)OC(C)(C)C)C5)ncc3c(Cl)c2F)cnc2c1N(C(=O)OC(C)(C)C)CCO2]

Under nitrogen, a solution of tert-butyl 7-(3-amino-8-chloro-7-fluoro-6-isoquinolyl)-8-methyl-2,3-dihydropyrido[2,3-b][1,4]oxazine-1-carboxylate (200 mg, 0.45 mmol), tert-butyl 6-hydroxy-2-azaspiro[3.3]heptane-2-carboxylate (195 mg, 0.91 mmol) and DIEA (285 mg, 2.21 mmol) in dichloromethane (2 mL) was stirred for 10 min at 0° C. Then triphosgene (95 mg, 0.32 mmol) was added and stirred at 0° C. for 2 hours. The reaction was concentrated under vacuum and purified by flash chromatography on silica gel eluting with petroleum ether/ethyl acetate (60/30) to afford tert-butyl 7-[3-[(2-tert-butoxycarbonyl-2-azaspiro[3.3]heptan-6- yl)oxycarbonylamino]-8-chloro-7-fluoro-6-isoquinolyl]-8-methyl-2,3-dihydropyrido[2,3-b][1,4]oxazine-1-carboxylate (190 mg, 0.278 mmol, 61.8% yield) as a yellow solid. LCMS (ESI) [M+H]$^+$=684.

Step 2: tert-Butyl 7-(3-((((2-(tert-butoxycarbonyl)-2-azaspiro[3.3]heptan-6-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

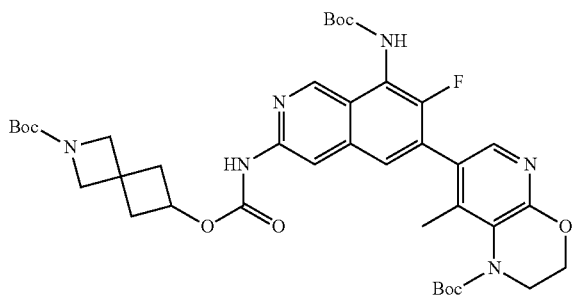 [SMILES: Cc1c(-c2cc3cc(NC(=O)OC4CC5(C4)CN(C(=O)OC(C)(C)C)C5)ncc3c(NC(=O)OC(C)(C)C)c2F)cnc2c1N(C(=O)OC(C)(C)C)CCO2]

A mixture of tert-butyl 7-[3-[(2-tert-butoxycarbonyl-2-azaspiro[3.3]heptan-6-yl)oxycarbonylamino]-8-chloro-7-fluoro-6-isoquinolyl]-8-methyl-2,3-dihydropyrido[2,3-b][1,4]oxazine-1-carboxylate (300 mg, 0.44 mmol), Pd$_2$(dba)$_3$·CHCl$_3$ (90 mg, 0.090 mmol), Brettphos (93 mg, 0.17 mmol), Cs$_2$CO$_3$ (420 mg, 1.29 mmol) and NH$_2$Boc (1250 mg, 10.68 mmol) in 1,4-dioxane (5 mL) was stirred for 2 hours at 90° C. The reaction was concentrated under vacuum and purified by flash chromatography on silica gel eluting with petroleum ether/ethyl acetate (2/1) to afford tert-butyl 7-[8-(tert-butoxycarbonylamino)-3-[(2-tert-butoxycarbonyl-2-azaspiro[3.3]heptan-6-yl)oxycarbonylamino]-7-fluoro-6-isoquinolyl]-8-methyl-2,3-dihydropyrido[2,3-b][1,4]oxazine-1-carboxylate (190 mg, 0.248 mmol, 89.5% yield) as a yellow solid. LCMS (ESI) [M+H]$^+$=765.

Step 3: 2-Azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate

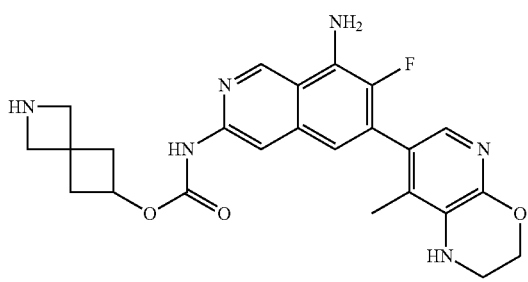 [SMILES: Cc1c(-c2cc3cc(NC(=O)OC4CC5(CNC5)C4)ncc3c(N)c2F)cnc2c1NCCO2]

A solution of tert-butyl 7-[8-(tert-butoxycarbonylamino)-3-[(2-tert-butoxycarbonyl-2-azaspiro[3.3]heptan-6-yl)oxycarbonylamino]-7-fluoro-6-isoquinolyl]-8-methyl-2,3-dihydropyrido[2,3-b][1,4]oxazine-1-carboxylate (190 mg, 0.25 mmol) in dichloromethane (5 mL) and TFA (5 mL, 0.25 mmol) was stirred at room temperature for 2 hours. The organic layer was concentrated under vacuum and purified by reverse-phase HPLC with CH$_3$CN/H$_2$O (10/2) to afford 2-azaspiro[3.3]heptan-6-yl N-[8-amino-7-fluoro-6-(8-methyl-2,3-dihydro-1H-pyrido[2,3-b][1,4]oxazin-7-yl)-3-isoquinolyl[carbamate (90 mg, 0.194 mmol, 78% yield) as a yellow solid. LCMS (ESI) [M+H]$^+$=465.

Step 4: 2-Methyl-2-azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate

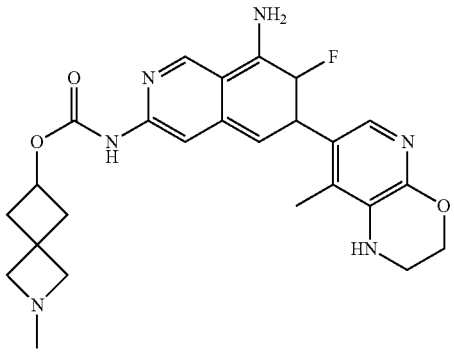 [SMILES: Cc1c(C2C=c3cc(NC(=O)OC4CC5(C4)CN(C)C5)ncc3=C(N)C2F)cnc2c1NCCO2]

A solution of 2-azaspiro[3.3]heptan-6-yl N-[8-amino-7-fluoro-6-(8-methyl-2,3-dihydro-1H-pyrido[2,3-b][1,4]oxazin-7-yl)-3-isoquinolyl]carbamate (20 mg, 0.040 mmol) and formaldehyde (3 mg, 0.10 mmol, 40%) in methyl alcohol (2 mL) was stirred at room temperature for 1 hour. Then NaCNBH$_3$ (8 mg, 0.13 mmol) was added. The reaction was stirred at room temperature for 1 hour. The mixture was concentrated under vacuum and purified by reverse HPLC with ACN/water (10 mmol/L NH$_4$HCO$_3$) (45/15) to afford (2-methyl-2-azaspiro[3.3]heptan-6-yl) N-[8-amino-7-fluoro-6-(8-methyl-2,3-dihydro-1H-pyrido[2,3-b][1,4]oxazin-7-yl)-3-isoquinolyl]carbamate (4.6 mg, 0.0096 mmol, 22.3% yield) as a light yellow solid. LCMS (ESI) [M+H]$^+$=479.2, R$_T$=1.584 min., Method J. $^1$H NMR (300 MHz, DMSO-d$_6$) δ10.10 (s, 1H), 9.34 (s, 1H), 8.19 (s, 1H), 7.95 (s, 1H), 6.87-6.80 (d, J=6 Hz, 1H), 6.20 (s, 2H), 5.67 (s, 1H), 4.89-4.81 (m, 1H), 4.29-4.27 (m, 2H), 3.19-3.07 (d, J=15 Hz, 4H), 2.20-2.14 (m, 5H), 1.96-1.89 (m, 3H), 1.24 (s, 4H).

Example 118

(1-Isopropylazetidin-3-yl) N-[8-amino-7-fluoro-6-(8-methyl-2,3-dihydro-1H-pyrido[2,3-b][1,4]oxazin-7-yl)-3-isoquinolyl]carbamate (Compound 419)

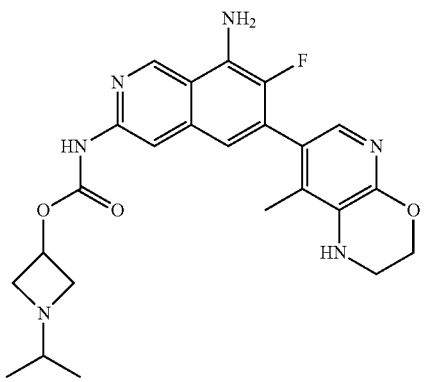 [SMILES: Cc1c(-c2cc3cc(NC(=O)OC4CN(C(C)C)C4)ncc3c(N)c2F)cnc2c1NCCO2]

297

Step 1: tert-Butyl 7-[3-[(1-tert-butoxycarbonylazetidin-3-yl)oxycarbonylamino]-8-chloro-7-fluoro-6-isoquinolyl]-8-methyl-2,3-dihydropyrido[2,3-b][1,4]oxazine-1-carboxylate

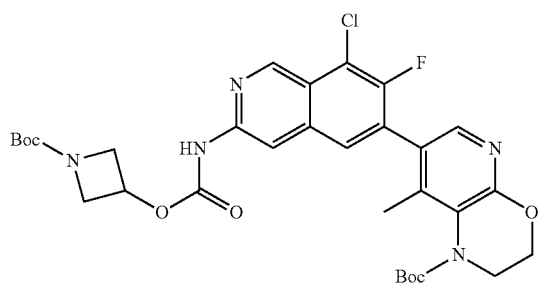 [SMILES: Cc1c(-c2cc3cc(NC(=O)OC4CN(C(=O)OC(C)(C)C)C4)ncc3c(Cl)c2F)cnc2c1N(C(=O)OC(C)(C)C)CCO2]

Under nitrogen, to a solution of tert-butyl 7-(3-amino-8-chloro-7-fluoro-6-isoquinolyl)-8-methyl-2,3-dihydropyrido[2,3-b][1,4]oxazine-1-carboxylate (1.5 g, 3.37 mmol) and 1-boc-3-hydroxyazetidine (3.0 g, 17.32 mmol) in dichloromethane (250 mL) was added DIEA (3.5 g, 27.13 mmol) at room temperature. Then triphosgene (1.4 g, 4.72 mmol) was added and the reaction was stirred at 0° C. for 1 hour. The reaction mixture was washed with water. The organic phase was dried, and concentrated under vacuum and purified by flash chromatography on silica gel eluting with PE/EA (1/1) to afford tert-butyl 7-[3-[(1-tert-butoxycarbonylazetidin-3-yl)oxycarbonylamino]-8-chloro-7-fluoro-6-isoquinolyl]-8-methyl-2,3-dihydropyrido[2,3-b][1,4]oxazine-1-carboxylate (1.1 g, 1.71 mmol, 50.7% yield) as a yellow solid. LCMS (ESI) [M+H]$^+$=644.

Step 2: tert-Butyl 7-[8-(tert-butoxycarbonylamino)-3-[(1-tert-butoxycarbonylazetidin-3-yl)oxycarbonylamino]-7-fluoro-6-isoquinolyl]-8-methyl-2,3-dihydropyrido[2,3-b][1,4]oxazine-1-carboxylate

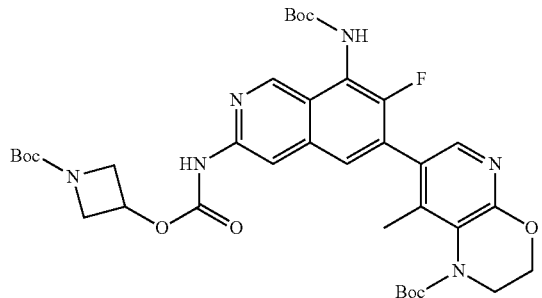 [SMILES: Cc1c(-c2cc3cc(NC(=O)OC4CN(C(=O)OC(C)(C)C)C4)ncc3c(NC(=O)OC(C)(C)C)c2F)cnc2c1N(C(=O)OC(C)(C)C)CCO2]

Under nitrogen, to a mixture of tert-butyl 7-[3-[(1-tert-butoxycarbonylazetidin-3-yl)oxycarbonylamino]-8-chloro-7-fluoro-6-isoquinolyl]-8-methyl-2,3-dihydropyrido[2,3-b][1,4]oxazine-1-carboxylate (700 mg, 1.09 mmol) and NH$_2$-Boc (800 mg, 6.84 mmol) in 1,4-dioxane (20 mL) was added Pd(dba)$_3$CHCl$_3$ (250 mg, 0.24 mmol), Brettphos (250 mg, 0.47 mmol) and Cs$_2$CO$_3$ (1.1 g, 3.37 mmol) at room temperature. The resulting mixture was stirred for 2 h at 90° C. After filtration, the filtrate was concentrated under reduced pressure. The residue was purified by flash chromatography on silica gel eluting with petroleum ether/ethyl acetate (1/4) to afford tert-butyl 7-[8-(tert-butoxycarbonylamino)-3-[(1-

298 tert-butoxycarbonylazetidin-3-yl)oxycarbonylamino]-7-fluoro-6-isoquinolyl]-8-methyl-2,3-dihydropyrido[2,3-b][1,4]oxazine-1-carboxylate (500 mg, 0.69 mmol, 63.5% yield) as a yellow solid. LCMS (ESI) [M+H]$^+$=725.

Step 3: Azetidin-3-yl N-[8-amino-7-fluoro-6-(8-methyl-2,3-dihydro-1H-pyrido[2,3-b][1,4]oxazin-7-yl)-3-isoquinolyl]carbamate

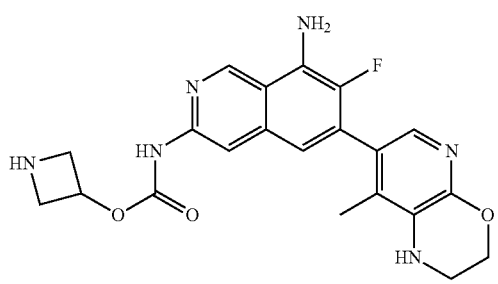 [SMILES: Cc1c(-c2cc3cc(NC(=O)OC4CNC4)ncc3c(N)c2F)cnc2c1NCCO2]

To a solution of tert-butyl 7-[8-(tert-butoxycarbonylamino)-3-[(1-tert-butoxycarbonylazetidin-3-yl)oxycarbonylamino]-7-fluoro-6-isoquinolyl]-8-methyl-2,3-dihydropyrido[2,3-b][1,4]oxazine-1-carboxylate (1.2 g, 1.66 mmol) in dichloromethane (20 mL) was added 2,2,2-trifluoroacetic acid (2 mL) at room temperature. The resulting solution was stirred for 2 h at 25° C. The reaction mixture was adjusted to pH 8 with TEA. The resulting residue was purified by reverse phase chromatography (acetonitrile 0-40/0.1% NH$_4$HCO$_3$ in water) to afford azetidin-3-yl N-[8-amino-7-fluoro-6-(8-methyl-2,3-dihydro-1H-pyrido[2,3-b][1,4]oxazin-7-yl)-3-isoquinolyl]carbamate (250 mg, 0.353 mmol, 21.3% yield) as a yellow solid. LCMS (ESI) [M+H]$^+$= 425.

Step 4: 1-Isopropylazetidin-3-yl (8-amino-7-fluoro-6-(8-methyl-2,3-dihydro-1H-pyrido[2,3-b][1,4]oxazin-7-yl)isoquinolin-3-yl)carbamate

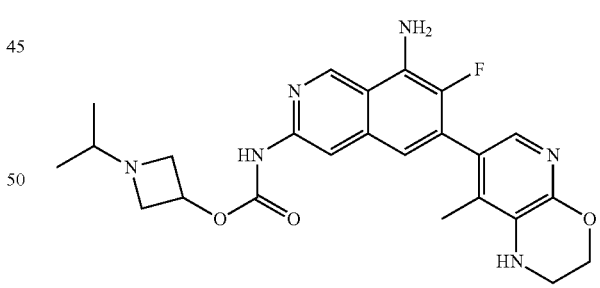

A mixture of azetidin-3-yl N-[8-amino-7-fluoro-6-(8-methyl-2,3-dihydro-1H-pyrido[2,3-b][1,4]oxazin-7-yl)-3-isoquinolyl]carbamate (100 mg, 0.24 mmol), Pd/C (5.0 mg, 0.24 mmol) and acetone (10 mL) in methyl alcohol (20 mL) stirred under a hydrogen atmosphere (1 atm) at room temperature for 3 hours The mixture was then filtered and concentrated. The residue was purified by Prep-HPLC with the following conditions: Column: Sunfire prep C18 column 30*150, 5 μm; Mobile Phase A: Water (0.1% FA), Mobile Phase B: ACN; Flow rate: 60 mL/min; Gradient: 5% B to 18% B in 7 min; 254/220 nm; Rt: 5.92/6.67 min to afford (1-isopropylazetidin-3-yl) N-[8-amino-7-fluoro-6-(8- methyl-2,3-dihydro-1H-pyrido[2,3-b][1,4]oxazin-7-yl)-3-isoquinolyl]carbamate (33.6 mg, 0.072 mmol, 30.6% yield) as a yellow solid. LCMS (ESI) [M+H]⁺=467.2, R$_T$=1.685 min; Method J. ¹H NMR (400 MHz, DMSO-d$_6$) δ10.39 (s, 1H), 9.36 (s, 1H), 7.95 (s, 1H), 7.32 (s, 1H), 6.85 (d, J=6.1 Hz, 1H), 6.24 (s, 2H), 5.69 (d, J=2.8 Hz, 1H), 5.10-5.02 (m, 1H), 4.60-4.25 (m, 3H), 4.09 (d, J=8.9 Hz, 2H), 3.66 (s, 2H), 2.96 (s, 2H), 1.91 (d, J=1.6 Hz, 3H), 1.02 (d, J=6.2 Hz, 6H).

Example 119

1-(2,2,2-Trifluoroethyl)azetidin-3-yl (8-amino-7-fluoro-6-(8-methyl-2,3-dihydro-1H-pyrido[2,3-b][1,4]oxazin-7-yl)isoquinolin-3-yl)carbamate (Compound 420)

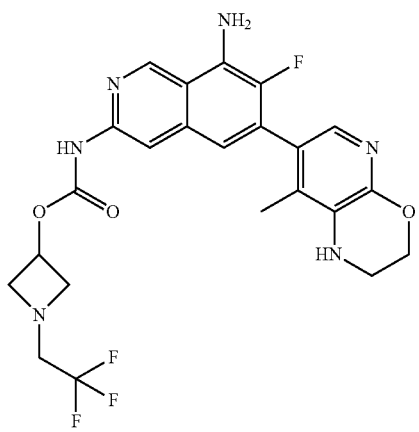 [SMILES: Cc1c(-c2cc3cc(NC(=O)OC4CN(CC(F)(F)F)C4)ncc3c(N)c2F)cnc2c1NCCO2]

To a solution of azetidin-3-yl N-[8-amino-7-fluoro-6-(8-methyl-2,3-dihydro-1H-pyrido[2,3-b][1,4]oxazin-7-yl)-3-isoquinolyl]carbamate (40 mg, 0.09 mmol) and 2,2,2-trifluoroethyltrifluoromethanesulfonate (28 mg, 0.12 mmol) in N,N-dimethylformamide (2 mL) was added DIEA (25 mg, 0.19 mmol) at room temperature. The resulting solution was stirred for 3 h at 25° C. The reaction was quenched by the addition of water and then directly purified by Prep-HPLC (Column: Sunfire prep C18 column 30*150, 5 µm; Mobile Phase A: Water (0.1% FA), Mobile Phase B: ACN; Flow rate: 60 mL/min; Gradient: 13% B to 40% B in 7 min; 254/220 nm; Rt: 6.90 min) to afford [1-(2,2,2-trifluoroethyl)azetidin-3-yl]N-[8-amino-7-fluoro-6-(8-methyl-2,3-dihydro-1H-pyrido[2,3-b][1,4]oxazin-7-yl)-3-isoquinolyl]carbamate (8.1 mg, 0.016 mmol, 17% yield) as a yellow solid. LCMS (ESI) [M+H]⁺=507.2, R$_T$=1.842 min, Method J. ¹H NMR (400 MHz, Methanol-d$_4$) δ9.26 (s, 1H), 8.05 (s, 1H), 7.44 (s, 1H), 6.96 (d, J=6.2 Hz, 1H), 5.18 (t, J=5.8 Hz, 1H), 4.50 (t, J=4.4 Hz, 2H), 3.96-3.88 (m, 2H), 3.55 (s, 4H), 3.26 (t, J=9.6 Hz, 2H), 2.07 (d, J=1.7 Hz, 3H).

Example 120

1-(Oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate (Compound 421)

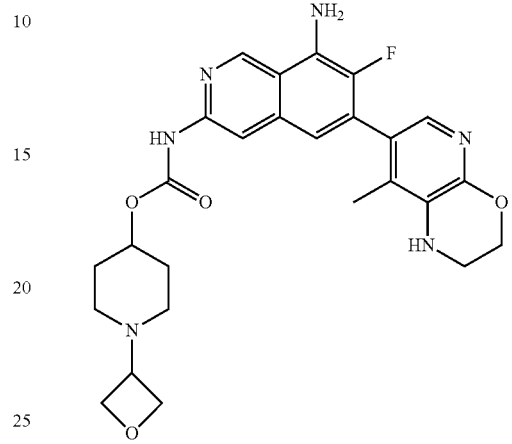

Step 1: tert-Butyl 7-(3-(((((1-(tert-butoxycarbonyl)piperidin-4-yl)oxy)carbonyl)amino)-8-chloro-7-fluoroisoquinolin-6-yl)-8-methyl-2,3-dihydro-1H-pyrido[2,3-b][1,4]oxazine-1-carboxylate

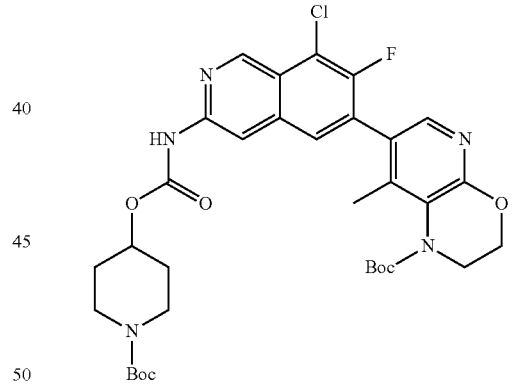

To a solution of tert-butyl 7-(3-amino-8-chloro-7-fluoro-6-isoquinolyl)-8-methyl-2,3-dihydropyrido[2,3-b][1,4]oxazine-1-carboxylate (1.0 g, 2.25 mmol), DIEA (1449.0 mg, 11.23 mmol) and 1-boc-4-hydroxypiperidine (903.0 mg, 4.49 mmol) in dichloromethane (100 mL) was added triphosgene (440.0 mg, 1.48 mmol) at 0° C. The mixture was stirred at 0° C. for 1 hour. The mixture was quenched by water and concentrated under vacuum. The residue was purified by flash chromatography on silica gel eluting with petroleum ether/ethyl acetate (50/50) to afford tert-butyl 7-[3-[(1-tert-butoxycarbonyl-4-piperidyl)oxycarbonylamino]-8-chloro-7-fluoro-6-isoquinolyl]-8-methyl-2,3-dihydropyrido[2,3-b][1,4]oxazine-1-carboxylate (1195 mg, 1.7779 mmol, 79.1% yield) as a brown solid. LCMS (ESI) [M+H]⁺=672.

Step 2: tert-Butyl 7-(8-((tert-butoxycarbonyl)amino)-3-((((1-(tert-butoxycarbonyl)piperidin-4-yl)oxy)carbonyl)amino)-7-fluoroisoquinolin-6-yl)-8-methyl-2,3-dihydro-1H-pyrido[2,3-b][1,4]oxazine-1-carboxylate

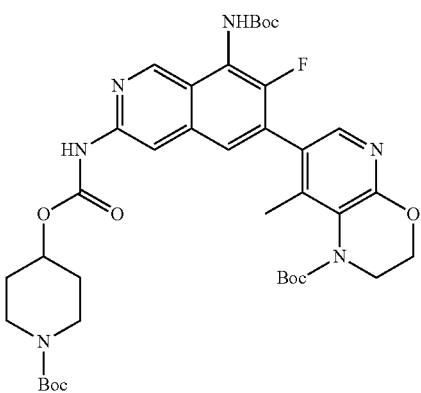 [SMILES: Cc1c(-c2cc3cc(NC(=O)OC4CCN(C(=O)OC(C)(C)C)CC4)ncc3c(NC(=O)OC(C)(C)C)c2F)cnc2c1N(C(=O)OC(C)(C)C)CCO2]

A mixture of tert-butyl 7-[3-[(1-tert-butoxycarbonyl-4-piperidyl)oxycarbonylamino]-8-chloro-7-fluoro-6-isoquinolyl]-8-methyl-2,3-dihydropyrido[2,3-b][1,4]oxazine-1-carboxylate (500.0 mg, 0.74 mmol), NH$_2$Boc (1740.0 mg, 14.87 mmol), Brettphos (159.0 mg, 0.30 mmol), Pd$_2$(dba)$_3$ (153.0 mg, 0.15 mmol) and Cs$_2$CO$_3$ (727.0 mg, 2.23 mmol) in 1,4-dioxane (8 mL) was stirred at 90° C. under N$_2$ for 1 hour. The reaction was concentrated under vacuum and purified by flash chromatography on silica gel eluting with petroleum ether/ethyl acetate (80/20) to afford tert-butyl 7-[8-(tert-butoxycarbonylamino)-3-[(1-tert-butoxycarbonyl-4-piperidyl)oxycarbonylamino]-7-fluoro-5,6-dihydroisoquinolin-6-yl]-8-methyl-2,3-dihydropyrido[2,3-b][1,4]oxazine-1-carboxylate (419 mg, 0.55 mmol, 74% yield) as a brown solid. LCMS (ESI) [M+H]$^+$=753.

Step 3. Piperidin-4-yl (8-amino-7-fluoro-6-(8-methyl-2,3-dihydro-1H-pyrido[2,3-b][1,4]oxazin-7-yl)isoquinolin-3-yl)carbamate

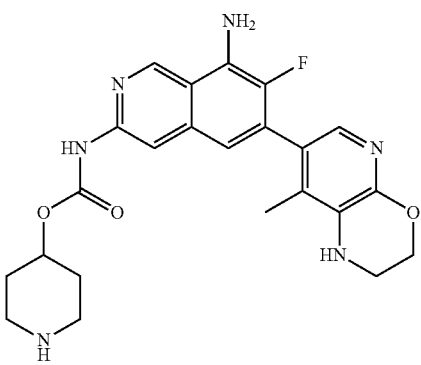 [SMILES: Cc1c(-c2cc3cc(NC(=O)OC4CCNCC4)ncc3c(N)c2F)cnc2c1NCCO2]

A solution of tert-butyl 7-[8-(tert-butoxycarbonylamino)-3-[(1-tert-butoxycarbonyl-4-piperidyl)oxycarbonylamino]-7-fluoro-6-isoquinolyl]-8-methyl-2,3-dihydropyrido[2,3-b][1,4]oxazine-1-carboxylate (400.0 mg, 0.53 mmol) in dichloromethane (5 mL) and TFA (1 mL) was stirred at 25° C. for 1 hour. The reaction mixture was concentrated under vacuum. The residue was adjusted to pH 8 with Et$_3$N and purified by reverse phase chromatography, eluting with water (10 mmol/LNH$_4$HCO$_3$)/ACN (70/30) to afford 4-piperidyl N-[8-amino-7-fluoro-6-(8-methyl-2,3-dihydro-1H-pyrido[2,3-b][1,4]oxazin-7-yl)-3-isoquinolyl]carbamate (89 mg, 0.19 mmol, 37% yield) as a brown solid. LCMS (ESI) [M+H]$^+$=453.

Step 4: 1-(Oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate

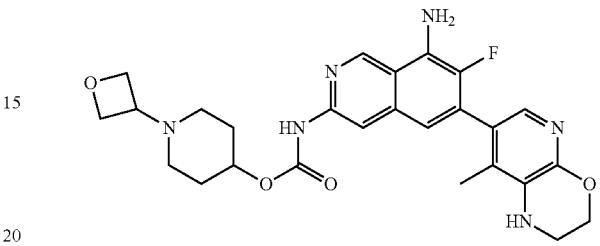

A solution of 4-piperidyl N-[8-amino-7-fluoro-6-(8-methyl-2,3-dihydro-1H-pyrido[2,3-b][1,4]oxazin-7-yl)-3-isoquinolyl]carbamate (50.0 mg, 0.11 mmol), oxetan-3-one (80.0 mg, 1.11 mmol) and titanium tetraisopropanolate (126.0 mg, 0.44 mmol) in methyl alcohol (5 mL) was stirred at 60° C. for 1 hour. Then NaBH$_3$CN (21.0 mg, 0.33 mmol) was added. The reaction was stirred at 25° C. for 1 hour and then concentrated under vacuum. The crude product was purified by Prep-HPLC with following condition (Column: YMC-Actus Triart C18 30*250, 5 μm; Water (10 mmol/L NH$_4$HCO$_3$): ACN=30% B to 40% B in 9 min; 60 mL/min) to give [1-(oxetan-3-yl)-4-piperidyl]N-[8-amino-7-fluoro-6-(8-methyl-2,3-dihydro-1H-pyrido[2,3-b][1,4]oxazin-7-yl)-3-isoquinolyl]carbamate (17.9 mg, 0.035 mmol, 32% yield) as a white solid. LCMS (ESI) [M+H]$^+$=509, R$_T$=1.635 min., Method J. $^1$H NMR (300 MHz, DMSO-d$_6$) δ10.03 (s, 1H), 9.31 (s, 1H), 7.95 (s, 1H), 7.31 (s, 1H), 6.81 (d, J=6.1 Hz, 1H), 6.19 (s, 2H), 5.66 (s, 1H), 4.69-4.60 (m, 1H), 4.60-4.50 (m, 2H), 4.40-4.30 (m, 2H), 4.30-4.20 (m, 2H), 3.51-3.30 (m, 3H), 2.52-2.40 (m, 2H), 2.10-2.05 (m, 2H), 1.90-1.80 (m, 5H), 1.73-1.50 (m, 2H).

Example 121

1-(2,2,2-Trifluoroethyl)piperidin-4-yl (8-amino-7-fluoro-6-(8-methyl-2,3-dihydro-1H-pyrido[2,3-b][1,4]oxazin-7-yl)isoquinolin-3-yl)carbamate (Compound 422)

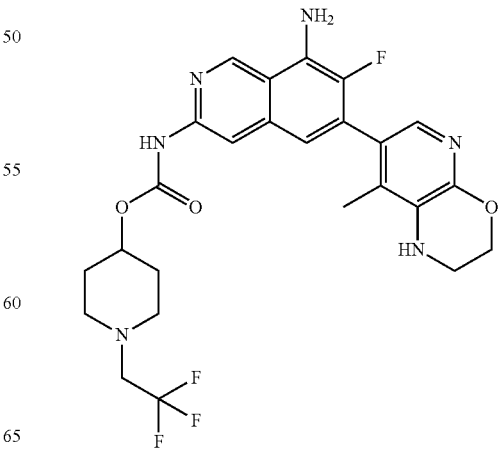

A solution of 4-piperidyl N-[8-amino-7-fluoro-6-(8-methyl-2,3-dihydro-1H-pyrido[2,3-b][1,4]oxazin-7-yl)-3-isoquinolyl]carbamate (50.0 mg, 0.11 mmol), Et₃N (34.0 mg, 0.34 mmol) and 2,2,2-trifluoroethyl trifluoromethanesulfonate (205.0 mg, 0.88 mmol) in tetrahydrofuran (2 mL) was stirred at 25° C. under N₂ for 1 hour. The mixture was concentrated under vacuum. The crude product was purified by Prep-HPLC (Column: YMC-Actus Triart C18 30*250, 5 μm; Water (10 mmol/L NH₄HCO₃): ACN=50% B to 64% B in 7 min; 60 mL/min) to give [1-(2,2,2-trifluoroethyl)-4-piperidyl]N-[8-amino-7-fluoro-6-(8-methyl-2,3-dihydro-1H-pyrido[2,3-b][1,4]oxazin-7-yl)-3-isoquinolyl]carbamate (21.9 mg, 0.041 mmol, 37% yield) as a yellow solid. LCMS (ESI) [M+H]⁺=535, $R_T$=2.101 min, Method J. ¹H NMR (300 MHz, DMSO-d₆) δ 10.03 (s, 1H), 9.31 (s, 1H), 7.95 (s, 1H), 7.31 (s, 1H), 6.81 (d, J=6.2 Hz, 1H), 6.20 (s, 2H), 5.66 (s, 1H), 4.69 (s, 1H), 4.27 (s, 2H), 3.23 (s, 2H), 3.19 (q, J=10.1 Hz, 2H), 2.89-2.84 (m, 2H), 2.55 (d, J=10.4 Hz, 2H), 1.90 (d, J=1.6 Hz, 5H), 1.63 (d, J=9.8 Hz, 2H).

Example 122

(7-Methyl-7-azaspiro[3.5]nonan-2-yl) N-[8-amino-7-fluoro-6-(4-methyl-5,6,7,8-tetrahydro-1,5-naphthyridin-3-yl)-3-isoquinolyl]carbamate (Compound 423)

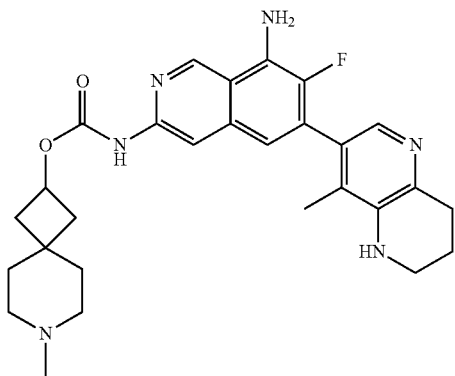 [SMILES: Cc1c(-c2cc3cc(NC(=O)OC4CC5(CCN(C)CC5)C4)ncc3c(N)c2F)cnc2c1NCCC2]

Step 1: tert-Butyl 7-[3-[(7-tert-butoxycarbonyl-7-azaspiro[3.5]nonan-2-yl)oxycarbonylamino]-8-chloro-7-fluoro-6-isoquinolyl]-8-methyl-3,4-dihydro-2H-1,5-naphthyridine-1-carboxylate

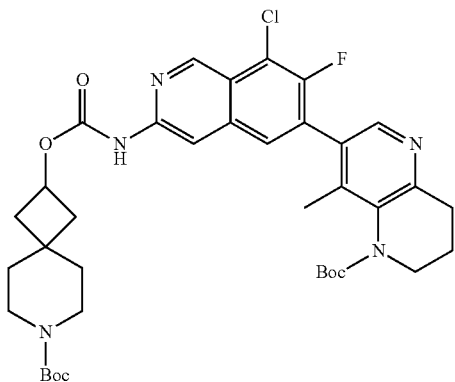 [SMILES: Cc1c(-c2cc3cc(NC(=O)OC4CC5(CCN(C(=O)OC(C)(C)C)CC5)C4)ncc3c(Cl)c2F)cnc2c1N(C(=O)OC(C)(C)C)CCC2]

Under nitrogen, to a solution of tert-butyl 7-(3-amino-8-chloro-7-fluoro-6-isoquinolyl)-8-methyl-3,4-dihydro-2H-1,5-naphthyridine-1-carboxylate (128 mg, 0.29 mmol), tert-butyl 2-hydroxy-7-azaspiro[3.5]nonane-7-carboxylate (204 mg, 0.85 mmol) and DIEA (192 mg, 1.48 mmol) in dichloromethane (20 mL) was added a solution of triphosgene (128 mg, 0.43 mmol) in dichloromethane (1 ml) at 0° C. The reaction was stirred for 2 hours at room temperature. The reaction solution was concentrated under vacuum and purified by flash chromatography on silica gel eluting with petroleum ether/ethyl acetate (2/3) to afford tert-butyl 7-[3-[(7-tert-butoxycarbonyl-7-azaspiro[3.5]nonan-2-yl)oxycarbonylamino]-8-chloro-7-fluoro-6-isoquinolyl]-8-methyl-3,4-dihydro-2H-1,5-naphthyridine-1-carboxylate (164 mg, 0.2309 mmol, 79.9% yield) as a yellow solid. LCMS (ESI) [M+H]⁺=710.

Step 2: tert-Butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-3,4-dihydro-2H-1,5-naphthyridine-1-carboxylate

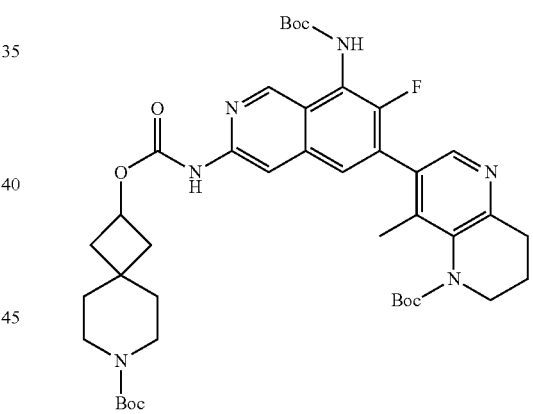

Under nitrogen, a mixture of tert-butyl 7-[3-[(7-tert-butoxycarbonyl-7-azaspiro[3.5]nonan-2-yl)oxycarbonylamino]-8-chloro-7-fluoro-6-isoquinolyl]-8-methyl-3,4-dihydro-2H-1,5-naphthyridine-1-carboxylate (164 mg, 0.23 mmol), NH₂Boc (0.81 g, 6.92 mmol), Pd(dba)₃CHCl₃ (48 mg, 0.050 mmol), Brettphos (49 mg, 0.090 mmol) and Cs₂CO₃ (150 mg, 0.46 mmol) in 1,4-dioxane (10 mL) was stirred at 90° C. for 2 hours. The reaction was concentrated under vacuum and purified by flash chromatography on silica gel eluting with petroleum ether/ethyl acetate (1/4) to afford tert-butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-3,4-dihydro-2H-1,5-naphthyridine-1-carboxylate (140 mg, 0.177 mmol, 76.7% yield) as a yellow solid. LCMS (ESI) [M+H]⁺=791.

Step 3: 7-Azaspiro[3.5]nonan-2-yl N-[8-amino-7-fluoro-6-(4-methyl-5,6,7,8-tetrahydro-1,5-naphthyridin-3-yl)-3-isoquinolyl]carbamate

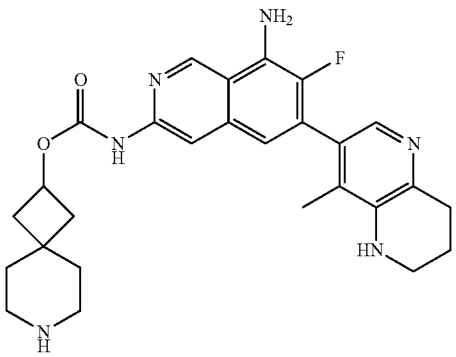 [SMILES: Cc1c(-c2cc3cc(NC(=O)OC4CC5(CCNCC5)C4)ncc3c(N)c2F)cnc2c1NCCC2]

A solution of tert-butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-3,4-dihydro-2H-1,5-naphthyridine-1-carboxylate (140 mg, 0.18 mmol) in dichloromethane (10 mL) and 2,2,2-trifluoroacetic acid (5 mL) was stirred at 30° C. for 1 hour. The reaction was concentrated under vacuum to afford 7-azaspiro[3.5]nonan-2-yl N-[8-amino-7-fluoro-6-(4-methyl-5,6,7,8-tetrahydro-1,5-naphthyridin-3-yl)-3-isoquinolyl]carbamate (80 mg, 0.1631 mmol, 92.1% yield) as a yellow solid. LCMS (ESI) [M+H]$^+$=491.

Step 4: (7-Methyl-7-azaspiro[3.5]nonan-2-yl) N-[8-amino-7-fluoro-6-(4-methyl-5,6,7,8-tetrahydro-1,5-naphthyridin-3-yl)-3-isoquinolyl]carbamate

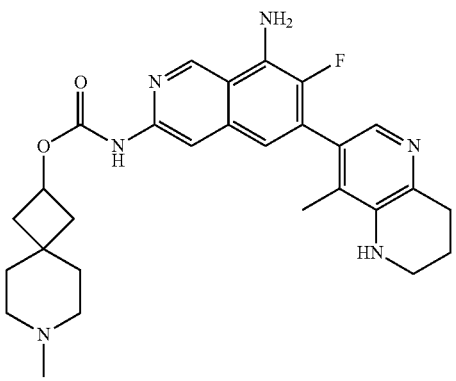

A mixture of 7-azaspiro[3.5]nonan-2-yl N-[8-amino-7-fluoro-6-(4-methyl-5,6,7,8-tetrahydro-1,5-naphthyridin-3-yl)-3-isoquinolyl]carbamate (80 mg, 0.16 mmol) and formaldehyde (35 mg, 0.47 mmol) in methyl alcohol (4 mL) was stirred at 30° C. for 1 hour. Then NaCNBH$_3$ (30 mg, 0.48 mmol) was added. The reaction was stirred at 30° C. for 1 hour. The reaction was concentrated under vacuum and purified by Prep-HPLC (Column: X Bridge Prep OBD C18 Column 30×150 mm 5 μm; Mobile Phase A: Water (10 mmol/L NH$_4$HCO$_3$), Mobile Phase B: ACN; Flow rate: 60 mL/min; Gradient: 18% B to 39% B in 7 min; Rt: 6.67 min) to afford (7-methyl-7-azaspiro[3.5]nonan-2-yl) N-[8-amino-7-fluoro-6-(4-methyl-5,6,7,8-tetrahydro-1,5-naphthyridin-3-yl)-3-isoquinolyl]carbamate (7.7 mg, 0.0153 mmol, 9.4% yield) as a yellow solid. LCMS (ESI) [M+H]$^+$=505.4, Rt=1.987 min., Method J. $^1$H NMR (400 MHz, DMSO-d6) δ10.06 (s, 1H), 9.33 (s, 1H), 7.95 (s, 1H), 7.56 (s, 1H), 6.82 (d, J=6.1 Hz, 1H), 6.22 (s, 2H), 5.43 (t, J=2.6 Hz, 1H), 4.97 (p, J=7.2 Hz, 1H), 3.33-3.30 (m, 3H), 2.84 (t, J=6.4 Hz, 2H), 2.32-2.22 (m, 4H), 2.11 (s, 4H), 1.95-1.89 (m, 2H), 1.88-1.75 (m, 5H), 1.55 (t, J=5.4 Hz, 4H).

Example 123

2-Acetyl-2-azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate (Compound 424)

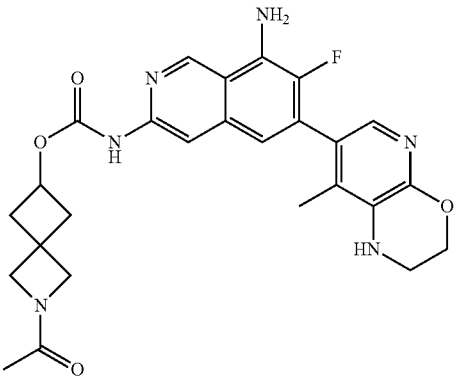 [SMILES: CC(=O)N1CC2(CC(OC(=O)Nc3cc4cc(-c5cnc6c(c5C)NCCO6)c(F)c(N)c4cn3)C2)C1]

Under nitrogen, to a solution of 2-azaspiro[3.3]heptan-6-yl N-[8-amino-7-fluoro-6-(8-methyl-2,3-dihydro-1H-pyrido[2,3-b][1,4]oxazin-7-yl)-3-isoquinolyl]carbamate (40.0 mg, 0.09 mmol) and Et$_3$N (26.0 mg, 0.26 mmol) in dichloromethane (2 mL) was added acetyl anhydride (13.0 mg, 0.1300 mmol) at 0° C. The mixture was stirred at 25° C. for 2 hours. The reaction was quenched by the addition of MeOH (2 mL). The reaction mixture was concentrated under vacuum. The residue was re-dissolved in 3 ml of DMF. The crude product was purified by reversed phase flash chromatography (ACN/water (10 mmol/L NH$_4$HCO$_3$)) to afford (2-acetyl-2-azaspiro[3.3]heptan-6-yl) N-[8-amino-7-fluoro-6-(8-methyl-2,3-dihydro-1H-pyrido[2,3-b][1,4]oxazin-7-yl)-3-isoquinolyl]carbamate (11.5 mg, 0.0227 mmol, 42.2%) as a yellow solid. LCMS (ESI): [M+H]=507.2, R$_T$=1.697 min., Method J. $^1$H NMR (300 MHz, methanol-d$_4$) δ9.23 (s, 1H), 8.05 (s, 1H), 7.38 (s, 1H), 6.94 (d, J=6.2 Hz, 1H), 5.01 (t, J=7.0 Hz, 1H), 4.41 (t, J=4.4 Hz, 2H), 4.26 (d, J=14.8 Hz, 2H), 4.02 (d, J=14.9 Hz, 2H), 3.50 (s, 2H), 2.73 (ddd, J=10.2, 6.9, 3.3 Hz, 2H), 2.44 (d, J=8.0 Hz, 2H), 2.03 (d, J=1.7 Hz, 3H), 1.87 (d, J=3.2 Hz, 3H).

Example 124

2-Methyl-2-azaspiro[3.3]heptan-6-yl (8-amino-7-fluoro-6-(4-methyl-5,6,7,8-tetrahydro-1,5-naphthyridin-3-yl)isoquinolin-3-yl)carbamate (Compound 425)

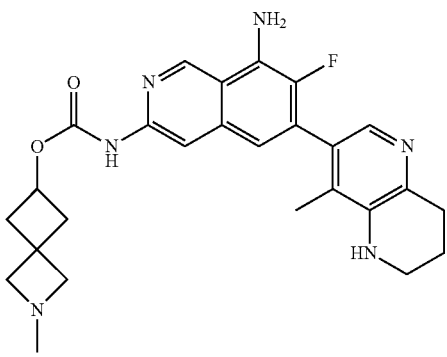 [SMILES: Cc1c(-c2cc3cc(NC(=O)OC4CC5(C4)CN(C)C5)ncc3c(N)c2F)cnc2c1NCCC2]

Step 1: tert-butyl 7-[3-[(2-tert-butoxycarbonyl-2-azaspiro[3.3]heptan-6-yl)oxycarbonylamino]-8-chloro-7-fluoro-6-isoquinolyl]-8-methyl-3,4-dihydro-2H-1,5-naphthyridine-1-carboxylate

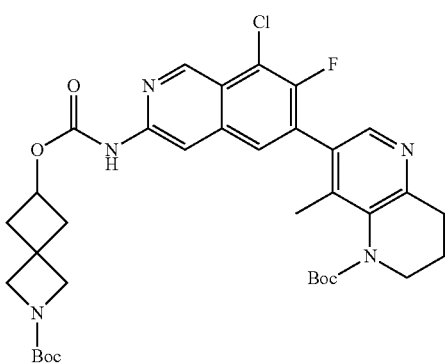 [SMILES: Cc1c(-c2cc3cc(NC(=O)OC4CC5(C4)CN(C(=O)OC(C)(C)C)C5)ncc3c(Cl)c2F)cnc2c1N(C(=O)OC(C)(C)C)CCC2]

To a solution of tert-butyl 6-hydroxy-2-azaspiro[3.3]heptane-2-carboxylate (289 mg, 1.36 mmol), tert-butyl 7-(3-amino-8-chloro-7-fluoro-6-isoquinolyl)-8-methyl-3,4-dihydro-2H-1,5-naphthyridine-1-carboxylate (200 mg, 0.45 mmol) and DIEA (294 mg, 2.26 mmol) in dichloromethane (10 mL) was added triphosgene (202 mg, 0.68 mmol) at 0° C. The reaction was stirred for 1 hour at room temperature and concentrated under vacuum. The residue was purified by flash chromatography on silica gel eluting with petroleum ether/ethyl acetate (1/9) to afford tert-butyl 7-[3-[(2-tert-butoxycarbonyl-2-azaspiro[3.3]heptan-6-yl)oxycarbonylamino]-8-chloro-7-fluoro-6-isoquinolyl]-8-methyl-3,4-dihydro-2H-1,5-naphthyridine-1-carboxylate (150 mg, 0.2199 mmol, 48.7% yield) as a yellow solid. LCMS (ESI) $[M+H]^+=682$.

Step 2: tert-butyl 7-[8-(tert-butoxycarbonyl amino)-3-[(2-tert-butoxycarbonyl-2-azaspiro[3.3]heptan-6-yl)oxycarbonylamino]-7-fluoro-6-isoquinolyl]-8-methyl-3,4-dihydro-2H-1,5-naphthyridine-1-carboxylate

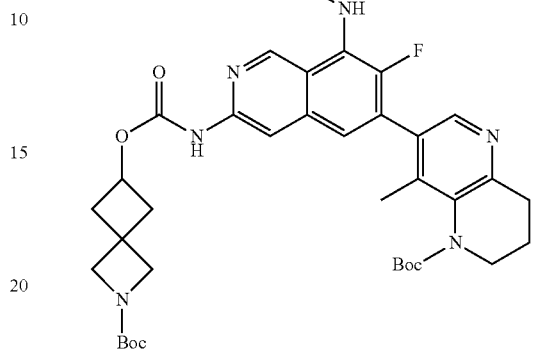

A mixture of tert-butyl 7-[3-[(2-tert-butoxycarbonyl-2-azaspiro[3.3]heptan-6-yl)oxycarbonylamino]-8-chloro-7-fluoro-6-isoquinolyl]-8-methyl-3,4-dihydro-2H-1,5-naphthyridine-1-carboxylate (150 mg, 0.22 mmol), Pd$_2$(dba)$_3$ CHCl$_3$ (46 mg, 0.040 mmol), Brettphos (47 mg, 0.090 mmol), NH$_2$Boc (1.3 g, 11.11 mmol) and Cs$_2$CO$_3$ (143 mg, 0.44 mmol) in 1,4-dioxane (5 mL) was stirred at 90° C. for 1 hour. The reaction mixture was cooled to room temperature, filtrated and concentrated under vacuum. The residue was purified by flash chromatography on silica gel eluting with petroleum ether/ethyl acetate (1/4) to afford tert-butyl 7-[8-(tert-butoxycarbonylamino)-3-[(2-tert-butoxycarbonyl-2-azaspiro[3.3]heptan-6-yl)oxycarbonylamino]-7-fluoro-6-isoquinolyl]-8-methyl-3,4-dihydro-2H-1,5-naphthyridine-1-carboxylate (81 mg, 0.106 mmol, 48.3% yield) as a yellow solid. LCMS (ESI) $[M+H]^+=763$.

Step 3: 2-Azaspiro[3.3]heptan-6-yl N-[8-amino-7-fluoro-6-(4-methyl-5,6,7,8-tetrahydro-1,5-naphthyridin-3-yl)-3-isoquinolyl]carbamate

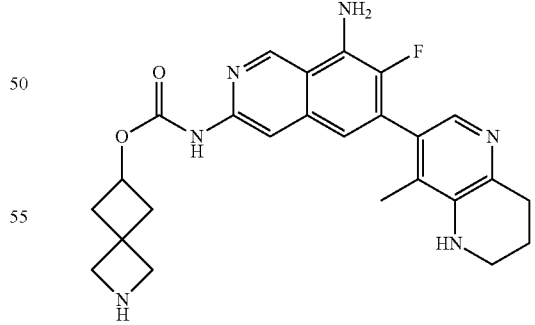

A solution of tert-butyl 7-[8-(tert-butoxycarbonylamino)-3-[(2-tert-butoxycarbonyl-2-azaspiro[3.3]heptan-6-yl)oxycarbonylamino]-7-fluoro-6-isoquinolyl]-8-methyl-3,4-dihydro-2H-1,5-naphthyridine-1-carboxylate (81 mg, 0.106 mmol) in dichloromethane (10 mL) and TFA (5 mL) was stirred at 30° C. for 1 h. The reaction mixture was concentrated under vacuum and purified by reverse phase chromatography (acetonitrile 0-40/0.1% NH₄HCO₃ in water) to afford 2-azaspiro[3.3]heptan-6-yl N-[8-amino-7-fluoro-6-(4-methyl-5,6,7,8-tetrahydro-1,5-naphthyridin-3-yl)-3-isoquinolyl]carbamate (30 mg, 0.0649 mmol, 62.5% yield) as a yellow solid. LCMS (ESI) [M+H]⁺=763.

Step 4: 2-Methyl-2-azaspiro[3.3]heptan-6-yl (8-amino-7-fluoro-6-(4-methyl-5,6,7,8-tetrahydro-1,5-naphthyridin-3-yl)isoquinolin-3-yl)carbamate

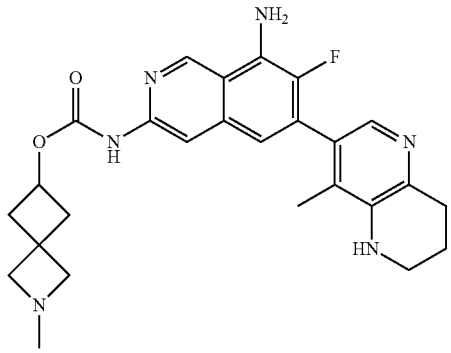 [SMILES: Cc1c(-c2cc3cc(NC(=O)OC4CC5(C4)CN(C)C5)ncc3c(N)c2F)cnc2c1NCCC2]

A solution of 2-azaspiro[3.3]heptan-6-yl N-[8-amino-7-fluoro-6-(4-methyl-5,6,7,8-tetrahydro-1,5-naphthyridin-3-yl)-3-isoquinolyl]carbamate (30 mg, 0.0649 mmol) and formaldehyde (9.7 mg, 0.1298 mmol, 40%) in methyl alcohol (4 mL) was stirred at 30° C. for 1 hour. Then NaBH₃CN (28 mg, 0.44 mmol) was added. The mixture was stirred at 30° C. for 1 hour. The reaction mixture was concentrated under vacuum and purified by Prep-HPLC (Column: X Bridge Prep OBD C18 Column 30×150 mm 5 µm; Mobile Phase A: Water (10 mmol/L NH₄HCO₃), Mobile Phase B: ACN; Flow rate: 60 mL/min; Gradient: 50% B to 57% B in 9 min; 254/220 nm; Rt: 8.87 min) to afford (2-methyl-2-azaspiro[3.3]heptan-6-yl) N-[8-amino-7-fluoro-6-(4-methyl-5,6,7,8-tetrahydro-1,5-naphthyridin-3-yl)-3-isoquinolyl]carbamate (5.5 mg, 0.0115 mmol, 7.6% yield) as a yellow solid. LCMS (ESI) [M+H]⁺=477.2, Rt=1.670 min., Method K. ¹H NMR (400 MHz, DMSO-d₆) δ10.07 (s, 1H), 9.33 (s, 1H), 7.94 (s, 1H), 7.56 (s, 1H), 6.82 (d, J=6.1 Hz, 1H), 6.22 (s, 2H), 5.43 (d, J=2.6 Hz, 1H), 4.83 (p, J=7.2 Hz, 1H), 3.28 (s, 3H), 2.84 (t, J=6.4 Hz, 5H), 2.56-2.46 (m, 2H), 2.20-2.10 (m, 5H), 1.92 (s, 2H), 1.86 (d, J=1.5 Hz, 3H).

Example 125

(1-Acetylazetidin-3-yl) N-[8-amino-7-fluoro-6-(8-methyl-2,3-dihydro-1H-pyrido[2,3-b][1,4]oxazin-7-yl)-3-isoquinolyl]carbamate (Compound 426)

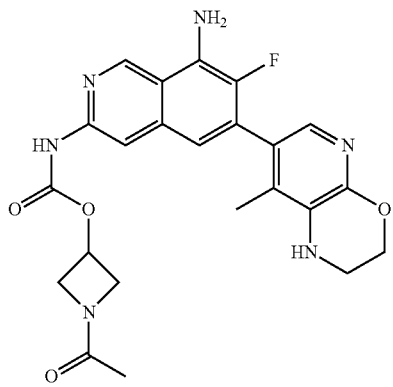

A solution of tert-butyl 7-[3-[(1-acetylazetidin-3-yl)oxycarbonylamino]-8-(tert-butoxycarbonylamino)-7-fluoro-6-isoquinolyl]-8-methyl-2,3-dihydropyrido[2,3-b][1,4]oxazine-1-carboxylate (50 mg, 0.070 mmol) in dichloromethane (4 mL) and 2,2,2-trifluoroacetic acid (1 mL) was stirred at 25° C. for 1 hour. The reaction was concentrated under vacuum. To the residue was added dichloromethane (5 mL) and adjusted to pH 8 with triethylamine. The mixture was concentrated under vacuum and purified by Prep-HPLC (Column: YMC-Actus Triart C18 30*250, 5 µm; Mobile Phase A: Water (10 mmol/L NH₄HCO₃), Mobile Phase B: ACN; Flow rate: 60 mL/min; Gradient: 27% B to 42% B in 7 min; 254/220 nm; Rt: 6.18 min) to afford (1-acetylazetidin-3-yl) N-[8-amino-7-fluoro-6-(8-methyl-2,3-dihydro-1H-pyrido[2,3-b][1,4]oxazin-7-yl)-3-isoquinolyl]carbamate (11.8 mg, 0.0249 mmol, 33.2% yield) as a yellow solid. LCMS (ESI) [M+H]⁺=467.2, Rt=1.751 min., Method J; ¹H NMR (300 MHz, DMSO-d₆) δ10.38 (s, 1H), 9.34 (s, 1H), 7.94 (s, 1H), 7.31 (s, 1H), 6.83 (d, J=6.1 Hz, 1H), 6.22 (s, 2H), 5.67 (s, 1H), 5.19-5.15 (m, 1H), 4.52-4.40 (m, 1H), 4.27 (s, 2H), 4.23-4.06 (m, 2H), 3.78 (d, J=11.2 Hz, 1H), 3.34-3.33 (m, 2H), 1.90 (s, 3H), 1.77 (s, 3H).

Example 126

7-Methyl-7-azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate (Compound 427)

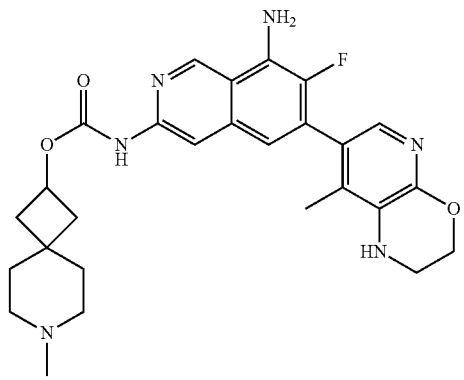 [SMILES: Cc1c(-c2cc3cc(NC(=O)OC4CC5(CCN(C)CC5)C4)ncc3c(N)c2F)cnc2c1NCCO2]

Step 1: tert-Butyl 7-(3-((((7-(tert-butoxycarbonyl)-7-azaspiro[3.5]nonan-2 yl)oxy) carbonyl) amino)-8-chloro-7-fluoroisoquinolin-6-yl)-8-methyl-2,3-dihydro-1H-pyrido[2,3-b][1,4]oxazine-1-carboxylate

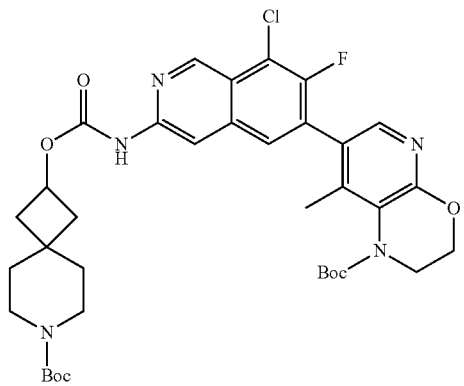 [SMILES: Cc1c(-c2cc3cc(NC(=O)OC4CC5(CCN(C(=O)OC(C)(C)C)CC5)C4)ncc3c(Cl)c2F)cnc2c1N(C(=O)OC(C)(C)C)CCO2]

To a solution of tert-butyl 7-(3-amino-8-chloro-7-fluoro-6-isoquinolyl)-8-methyl-2,3-dihydropyrido[2,3-b][1,4]oxazine-1-carboxylate (300 mg, 0.67 mmol), tert-butyl 2-hydroxy-7-azaspiro[3.5]nonane-7-carboxylate (325.5 mg, 1.35 mmol) and N,N-diisopropylethylamine (435.75 mg, 3.37 mmol) in dichloromethane (4 mL) was added triphosgene (200.1 mg, 0.67 mmol) and the mixture was stirred at 0° C. for 1 hour. The reaction was quenched with water. The resulting mixture was extracted with dichloromethane. The organic layers were combined, dried over anhydrous sodium and concentrated under vacuum. The residue was purified by flash chromatography on silica gel eluting with dichloromethane/methanol (97/3) to afford tert-butyl 7-[3-[(7-tert-butoxycarbonyl-7-azaspiro[3.5]nonan-2-yl)oxycarbonylamino]-8-chloro-7-fluoro-6-isoquinolyl]-8-methyl-2,3-dihydropyrido[2,3-b][1,4]oxazine-1-carboxylate (400 mg, 0.56 mmol, 83.2% yield)] as a yellow solid. LCMS (ESI) [M+H]$^+$=712.4.

Step 2: tert-Butyl 7-(3-((((7-(tert-butoxycarbonyl)-7-azaspiro[3.5]nonan-2-yl)oxy) carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

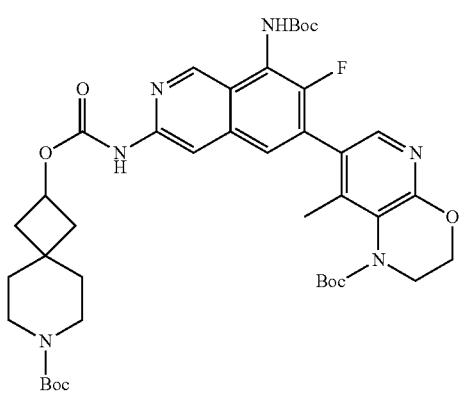 [SMILES: Cc1c(-c2cc3cc(NC(=O)OC4CC5(CCN(C(=O)OC(C)(C)C)CC5)C4)ncc3c(NC(=O)OC(C)(C)C)c2F)cnc2c1N(C(=O)OC(C)(C)C)CCO2]

To a mixture of tert-butyl 7-[3-[(7-tert-butoxycarbonyl-7-azaspiro[3.5]nonan-2-yl)oxycarbonylamino]-8-chloro-7-fluoro-6-isoquinolyl]-8-methyl-2,3-dihydropyrido[2,3-b][1,4]oxazine-1-carboxylate (300.0 mg, 0.42 mmol) and Pd$_2$(dba)$_3$·CHCl$_3$ (87.2 mg, 0.08 mmol), BrettPhos (90.44 mg, 0.17 mmol) and Cs$_2$CO$_3$ (411.73 mg, 1.26 mmol) in 1,4-dioxane (4 mL) was added tert-butyl carbonate (1.23 g, 10.53 mmol) at room temperature and stirred at 90° C. for 1 hour. The reaction mixture was concentrated under vacuum. The residue was purified by flash chromatography on silica gel eluting with dichloromethane/methanol (99/1) to afford tert-butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-2,3-dihydropyrido[2,3-b][1,4]oxazine-1-carboxylate (250 mg, 0.315 mmol, 74.9% yield) as a yellow solid. LCMS (ESI) [M+H]$^+$= 793.4

Step 3: 7-Azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate

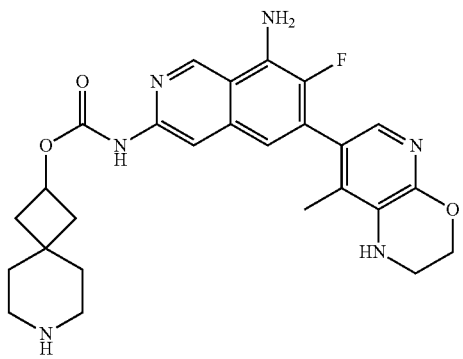 [SMILES: Cc1c(-c2cc3cc(NC(=O)OC4CC5(CCNCC5)C4)ncc3c(N)c2F)cnc2c1NCCO2]

To a solution of tert-butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-2,3-dihydropyrido[2,3-b][1,4]oxazine-1-carboxylate (490.0 mg, 0.62 mmol) in dichloromethane (3 mL) was added trifluoroacetic acid (2 mL). The resulting solution was stirred at room temperature for 1 hour. The reaction was concentrated under vacuum. The residue was re-dissolved in dichloromethane and adjusted to pH 8 with triethylamine. The resulting solution was concentrated under reduce pressure. The residue was purified by reverse phase chromatography (acetonitrile 0-90%/0.1% NH$_4$HCO$_3$ in water) to afford 7-azaspiro[3.5]nonan-2-yl N-[8-amino-7-fluoro-6-(8-methyl-2,3-dihydro-1H-pyrido[2,3-b][1,4]oxazin-7-yl)-3-isoquinolyl]carbamate (100 mg, 0.20 mmol, 32.9% yield)] as a yellow solid. LCMS (ESI) [M+H]$^+$=493.4.

Step 4: 7-Methyl-7-azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate

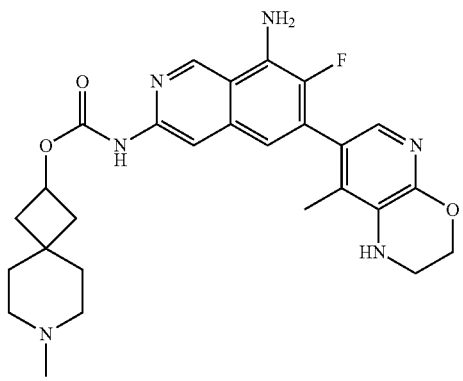 [SMILES: Cc1c(-c2cc3cc(NC(=O)OC4CC5(CCN(C)CC5)C4)ncc3c(N)c2F)cnc2c1NCCO2]

To a solution of 7-azaspiro[3.5]nonan-2-yl N-[8-amino-7-fluoro-6-(8-methyl-2,3-dihydro-1H-pyrido[2,3-b][1,4]oxazin-7-yl)-3-isoquinolyl]carbamate (40 mg, 0.08 mmol) in methyl alcohol (3 mL) was added a formaldehyde aqueous solution (40%, 12.24 mg). The mixture was stirred at room temperature for 2 hours. Then sodium borohydride (6.2 mg, 0.16 mmol) was added and stirred at room temperature for 2 hours. The reaction was quenched with water. The resulting mixture was extracted with dichloromethane. The organic layers were combined and concentrated under vacuum. The residue was purified by Prep-HPLC (Column: X Bridge Prep OBD C18 Column 30×150 mm 5 μm; Mobile Phase A: Water (10 mmol/L $NH_4HCO_3$), Mobile Phase B: ACN; Flow rate: 60 mL/min; Gradient: 14% B to 30% B in 10 min; 254/220 nm; Rt: 9.42 min) to afford (7-methyl-7-azaspiro[3.5]nonan-2-yl) N-[8-amino-7-fluoro-6-(8-methyl-2,3-dihydro-1H-pyrido[2,3-b][1,4]oxazin-7-yl)-3-isoquinolyl]carbamate (16.2 mg, 0.032 mmol, 39.4% yield) as a light yellow solid. LCMS (ESI): [M+H]$^+$=507.3, $R_T$=1.420 min., Method L; $^1$H NMR (300 MHz, DMSO-$d_6$) δ10.04 (s, 1H), 9.31 (s, 1H), 7.93 (s, 1H), 7.31 (s, 1H), 6.81 (d, J=6.2 Hz, 1H), 6.19 (s, 2H), 5.70-5.62 (m, 1H), 4.96 (p, J=7.2 Hz, 1H), 4.27 (t, J=4.3 Hz, 2H), 3.32 (s, 2H), 2.34-2.13 (m, 6H), 2.10 (s, 3H), 1.90 (d, J=1.6 Hz, 3H), 1.78 (dd, J=12.2, 7.3 Hz, 2H), 1.54 (t, J=5.4 Hz, 4H).

Example 127

6-Methyl-6-azaspiro[3.4]octan-2-yl (8-amino-7-fluoro-6-(8-methyl-2,3-dihydro-1H-pyrido[2,3-b][1,4]oxazin-7-yl)isoquinolin-3-yl)carbamate (Compound 428)

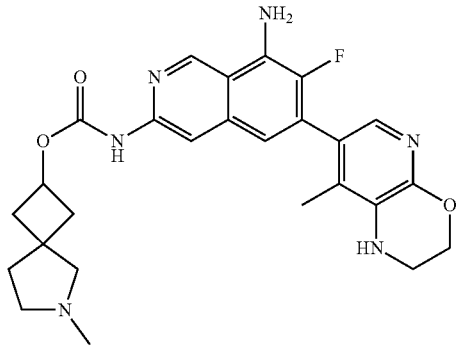 [SMILES: Cc1c(-c2cc3cc(NC(=O)OC4CC5(CCN(C)C5)C4)ncc3c(N)c2F)cnc2c1NCCO2]

Step 1: tert-Butyl 7-(3-(((((6-(tert-butoxycarbonyl)-6-azaspiro[3.4]octan-2-yl)oxy)carbonyl)amino)-8-chloro-7-fluoroisoquinolin-6-yl)-8-methyl-2,3-dihydro-1H-pyrido[2,3-b][1,4]oxazine-1-carboxylate

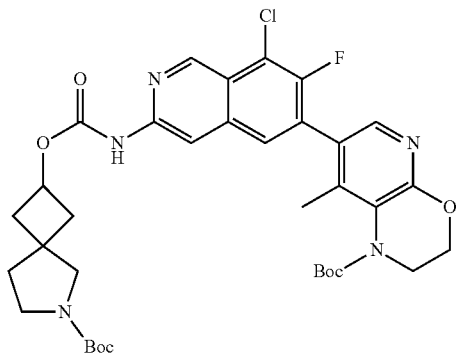 [SMILES: Cc1c(-c2cc3cc(NC(=O)OC4CC5(CCN(C(=O)OC(C)(C)C)C5)C4)ncc3c(Cl)c2F)cnc2c1N(C(=O)OC(C)(C)C)CCO2]

To a solution of tert-butyl 7-(3-amino-8-chloro-7-fluoro-6-isoquinolyl)-8-methyl-2,3-dihydropyrido[2,3-b][1,4]oxazine-1-carboxylate (300.0 mg, 0.67 mmol), DIEA (436.0 mg, 3.38 mmol) and tert-butyl 2-hydroxy-6-azaspiro[3.4]octane-6-carboxylate (307.0 mg, 1.35 mmol) in dichloromethane (10 mL) was added triphosgene (132.0 mg, 0.45 mmol) at 0° C. The mixture was stirred 0° C. for 1 hour. The mixture was quenched by water and extracted with dichloromethane. The organic layer was concentrated under vacuum and purified by flash chromatography on silica gel eluting with EA/PE (70/30) to afford tert-butyl 7-[3-[(6-tert-butoxycarbonyl-6-azaspiro[3.4]octan-2-yl)oxycarbonylamino]-8-chloro-7-fluoro-6-isoquinolyl]-8-methyl-2,3-dihydropyrido[2,3-b][1,4]oxazine-1-carboxylate (430 mg, 0.62 mmol, 91% yield) as a white solid. LCMS (ESI) [M+H]$^+$=698.

Step 2: tert-Butyl 7-(3-(((((6-(tert-butoxycarbonyl)-6-azaspiro[3.4]octan-2-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

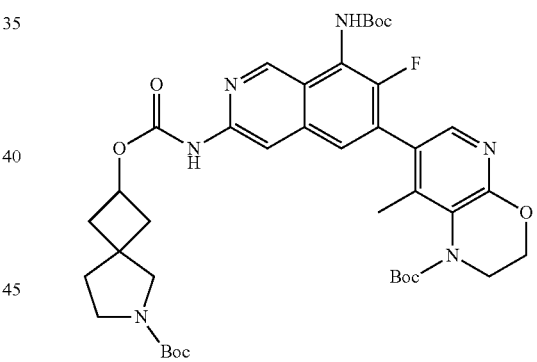

A mixture of tert-butyl 7-[3-[(6-tert-butoxycarbonyl-6-azaspiro[3.4]octan-2-yl)oxycarbonylamino]-8-chloro-7-fluoro-6-isoquinolyl]-8-methyl-2,3-dihydropyrido[2,3-b][1,4]oxazine-1-carboxylate (400.0 mg, 0.57 mmol), $NH_2Boc$ (1343.0 mg, 11.48 mmol), Pd$_2$(dba)$_3$ (119.0 mg, 0.11 mmol), Brettphos (123.0 mg, 0.23 mmol) and Cs$_2$CO$_3$ (561.0 mg, 1.72 mmol) in 1,4-dioxane (6 mL) was stirred at 90° C. for 1 hour. The reaction mixture was concentrated under vacuum and purified by flash chromatography on silica gel eluting with EA/PE (78/22) to afford tert-butyl 7-[8-(tert-butoxycarbonylamino)-3-[(6-tert-butoxycarbonyl-6-azaspiro[3.4]octan-2-yl)oxycarbonylamino]-7-fluoro-6-isoquinolyl]-8-methyl-2,3-dihydropyrido[2,3-b][1,4]oxazine-1-carboxylate (396 mg, 0.51 mmol, 88% yield) as a brown solid. LCMS (ESI) [M+H]$^+$=779.

Step 3. 6-Azaspiro[3.4]octan-2-yl (8-amino-7-fluoro-6-(8-methyl-2,3-dihydro-1H-pyrido[2,3-b][1,4]oxazin-7-yl)isoquinolin-3-yl)carbamate

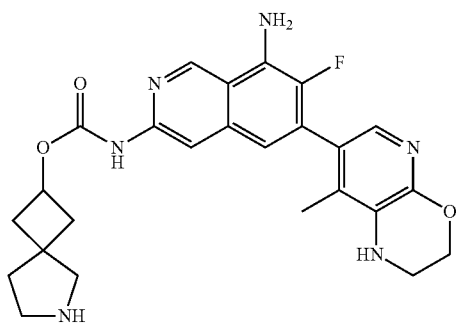 [SMILES: Cc1c(-c2cc3cc(NC(=O)OC4CC5(CCNC5)C4)ncc3c(N)c2F)cnc2c1NCCO2]

To a solution of tert-butyl 7-[8-(tert-butoxycarbonylamino)-3-[(6-tert-butoxycarbonyl-6-azaspiro[3.4]octan-2-yl)oxycarbonylamino]-7-fluoro-6-isoquinolyl]-8-methyl-2,3-dihydropyrido[2,3-b][1,4]oxazine-1-carboxylate (396.0 mg, 0.51 mmol) in dichloromethane (5 mL) was added TFA (2.5 mL) at 25° C. The mixture was stirred at 25° C. for 2 hour and concentrated under vacuum. The residue was adjusted to pH 8 with Et$_3$N and purified by reverse phase chromatography eluting with water (10 mmol/L NH$_4$HCO$_3$)/ACN (65/35) to afford 6-azaspiro[3.4]octan-2-yl N-[8-amino-7-fluoro-6-(8-methyl-2,3-dihydro-1H-pyrido[2,3-b][1,4]oxazin-7-yl)-3-isoquinolyl]carbamate (73 mg, 0.15 mmol, 30% yield) as a brown solid. LCMS (ESI) [M+H]$^+$= 479.

Step 4: 6-Methyl-6-azaspiro[3.4]octan-2-yl (8-amino-7-fluoro-6-(8-methyl-2,3-dihydro-1H-pyrido[2,3-b][1,4]oxazin-7-yl)isoquinolin-3-yl)carbamate

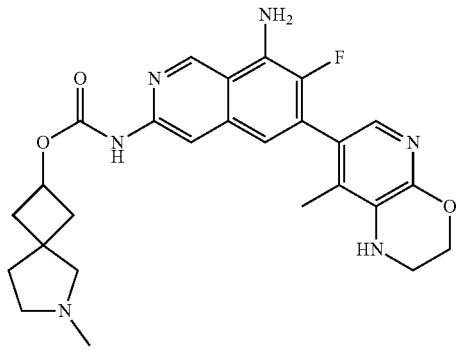 [SMILES: Cc1c(-c2cc3cc(NC(=O)OC4CC5(CCN(C)C5)C4)ncc3c(N)c2F)cnc2c1NCCO2]

A solution of 6-azaspiro[3.4]octan-2-yl N-[8-amino-7-fluoro-6-(8-methyl-2,3-dihydro-1H-pyrido[2,3-b][1,4]oxazin-7-yl)-3-isoquinolyl]carbamate (63.0 mg, 0.13 mmol) and formaldehyde (18.0 mg, 0.60 mmol, 40%) in methyl alcohol (5 mL) was stirred at 25° C. for 1 hour. Then NaBH$_3$CN (23.0 mg, 0.37 mmol) was added. The reaction mixture was stirred at 25° C. for 1 hour. The mixture was concentrated under vacuum and purified by Prep-HPLC (Column: X Bridge Prep OBD C18 Column 30×150 mm 5 µm; water (10 mmol/L NH$_4$HCO$_3$)/ACN) to give (6-methyl-6-azaspiro[3.4]octan-2-yl) N-[8-amino-7-fluoro-6-(8-methyl-2,3-dihydro-1H-pyrido[2,3-b][1,4]oxazin-7-yl)-3-isoquinolyl]carbamate (25 mg, 0.051 mmol, 39% yield) as a yellow solid. LCMS (ESI) [M+H]$^+$=493.4, R$_T$=1.982 min., Method M. $^1$H NMR (300 MHz, DMSO-d$_6$) δ10.06 (s, 1H), 9.31 (s, 1H), 7.94 (s, 1H), 7.31 (s, 1H), 6.81 (d, J=6.2 Hz, 1H), 6.20 (s, 2H), 5.67 (s, 1H), 4.92-4.80 (m, 1H), 4.30-4.20 (m, 2H), 3.40-3.30 (m, 2H), 2.49-2.27 (m, 6H), 2.19 (d, J=9.4 Hz, 3H), 2.14-1.98 (m, 2H), 1.93-1.77 (m, 5H).

Example 128

1-Acetylazetidin-3-yl (8-amino-7-fluoro-6-(4-methyl-5,6,7,8-tetrahydro-1,5-naphthyridin-3-yl)isoquinolin-3-yl)carbamate formic acid (Compound 429)

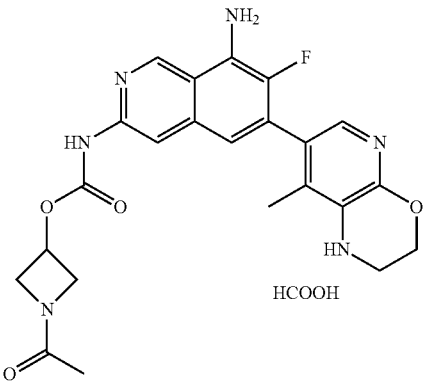 [SMILES: CC(=O)N1CC(OC(=O)Nc2cc3cc(-c4cnc5c(c4C)NCCO5)c(F)c(N)c3cn2)C1 ; "HCOOH"]

Step 1: tert-Butyl 7-[3-[[(1-acetylazetidin-3-yl)oxycarbonylamino]-8-chloro-7-fluoro-6-isoquinolyl]-8-methyl-3,4-dihydro-2H-1,5-naphthyridine-1-carboxylate

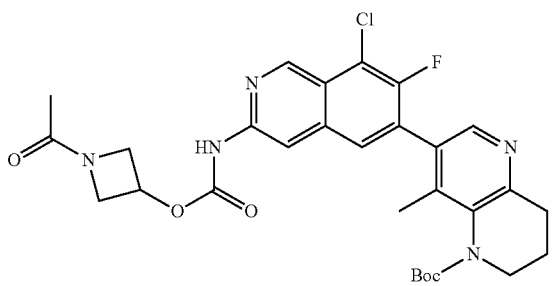 [SMILES: CC(=O)N1CC(OC(=O)Nc2cc3cc(-c4cnc5c(c4C)N(C(=O)OC(C)(C)C)CCC5)c(F)c(Cl)c3cn2)C1]

A solution of tert-butyl 7-(3-amino-8-chloro-7-fluoro-6-isoquinolyl)-8-methyl-3,4-dihydro-2H-1,5-naphthyridine-1-carboxylate (200 mg, 0.45 mmol), 1-(3-hydroxyazetidin-1-yl)ethanone (80 mg, 0.69 mmol) and DIEA (180 mg, 1.40 mmol) in dichloromethane (15 mL) was stirred at 0° C. for 5 min. Then a solution of triphosgene (60 mg, 0.20 mmol) in dichloromethane (1 mL) was added dropwise to the reaction solution at 0° C. The reaction was stirred at room temperature for 1 hour. The resulting solution was extracted with dichloromethane (200 mL). The organic layers were combined, dried over anhydrous sodium sulfate and concentrated under vacuum. The residue was purified by flash chromatography on silica gel eluting with methanol/dichloromethane (7%) to afford tert-butyl 7-[3-[(1-acetylazetidin-3-yl)oxycarbonylamino]-8-chloro-7-fluoro-6-isoquinolyl]-8-methyl-3,4-dihydro-2H-1,5-naphthyridine-1-carboxylate (200 mg, 0.2397 mmol, 53.1% yield) as a yellow solid. LCMS (ESI) [M+H]$^+$=584.0.

Step 2: tert-Butyl 7-[3-[(1-acetylazetidin-3-yl)oxycarbonylamino]-8-(tert-butoxycarbonylamino)-7-fluoro-6-isoquinolyl]-8-methyl-3,4-dihydro-2H-1,5-naphthyridine-1-carboxylate

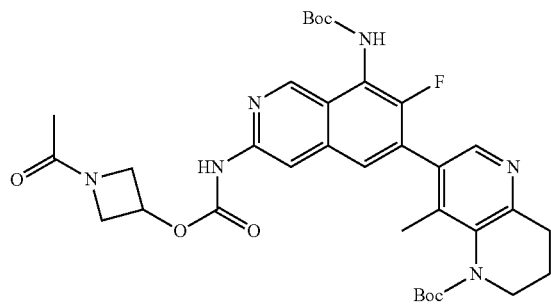 [SMILES: CC(=O)N1CC(OC(=O)Nc2cc3cc(-c4cnc5c(c4C)N(C(=O)OC(C)(C)C)CCC5)c(F)c(NC(=O)OC(C)(C)C)c3cn2)C1]

A mixture of tert-butyl 7-[3-[(1-acetylazetidin-3-yl)oxycarbonylamino]-8-chloro-7-fluoro-6-isoquinolyl]-8-methyl-3,4-dihydro-2H-1,5-naphthyridine-1-carboxylate (200 mg, 0.34 mmol), NH$_2$Boc (280 mg, 2.39 mmol), Brettphos Pd G3 (80 mg, 0.09 mmol) and Cs$_2$CO$_3$ (280 mg, 0.86 mmol) in 1,4-dioxane (10 mL) was stirred for 2 hours at 90° C. The reaction mixture was diluted with water and extracted with ethyl acetate. The organic layer was dried over anhydrous sodium sulfate and concentrated under vacuum. The residue was purified by flash chromatography on silica gel eluting with methanol/dichloromethane (13%) to afford tert-butyl 7-[3-[(1-acetylazetidin-3-yl)oxycarbonyl amino]-8-(tert-butoxycarbonylamino)-7-fluoro-6-isoquinolyl]-8-methyl-3,4-dihydro-2H-1,5-naphthyridine-1-carboxylate (180 mg, 0.1625 mmol, 47.4% yield) as a yellow solid. LCMS (ESI) [M+H]$^+$=665.0.

Step 3: 1-Acetylazetidin-3-yl (8-amino-7-fluoro-6-(4-methyl-5,6,7,8-tetrahydro-1,5-naphthyridin-3-yl)isoquinolin-3-yl)carbamate formic acid

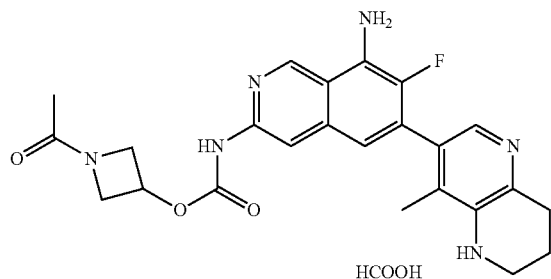 [SMILES: CC(=O)N1CC(OC(=O)Nc2cc3cc(-c4cnc5c(c4C)NCCC5)c(F)c(N)c3cn2)C1 ; "HCOOH"]

A solution of tert-butyl 7-[3-[(1-acetylazetidin-3-yl)oxycarbonylamino]-8-(tert-butoxycarbonylamino)-7-fluoro-6-isoquinolyl]-8-methyl-3,4-dihydro-2H-1,5-naphthyridine-1-carboxylate (180 mg, 0.16 mmol) and TFA (3 mL) in DCM (12 mL) was stirred at room temperature for 2 hours. The reaction mixture was concentrated under vacuum. The residue was purified by Prep-HPLC (Column: X Select CSH Prep C18 OBD Column, 19*250 mm, 5 µm; Mobile Phase A: Water (0.1% FA), Mobile Phase B: MeOH; Flow rate: 25 mL/min; Gradient: 15% B to 36% B in 10 min; 254 nm) to afford (1-acetylazetidin-3-yl) N-[8-amino-7-fluoro-6-(4-methyl-5,6,7,8-tetrahydro-1,5-naphthyridin-3-yl)-3-isoquinolyl]carbamate formic acid (14 mg, 0.0274 mmol, 16.8% yield) as a yellow solid. LCMS (ESI) [M+H]$^+$=465.2, Rt=1.805 min., Method J; $^1$H NMR (300 MHz, Methanol-d$_4$) δ10.44 (s, 1H), 9.39 (s, 1H), 7.99 (s, 1H), 7.75 (s, 1H), 6.90 (d, J=6.0 Hz, 1H), 6.34 (s, 2H), 5.95 (s, 1H), 5.33-5.12 (m, 1H), 4.48 (dd, J=9.8, 6.7 Hz, 1H), 4.27-4.04 (m, 2H), 3.81 (dd, J=10.8, 4.1 Hz, 1H), 2.94 (t, J=6.3 Hz, 2H), 2.55 (s, 2H), 1.95 (d, J=1.5 Hz, 5H), 1.80 (s, 3H).

Example 129

7-(Oxetan-3-yl)-7-azaspiro[3.5]nonan-2-yl (8-amino-7-fluoro-6-(4-methyl-5,6,7,8-tetrahydro-1,5-naphthyridin-3-yl)isoquinolin-3-yl)carbamate (Compound 430)

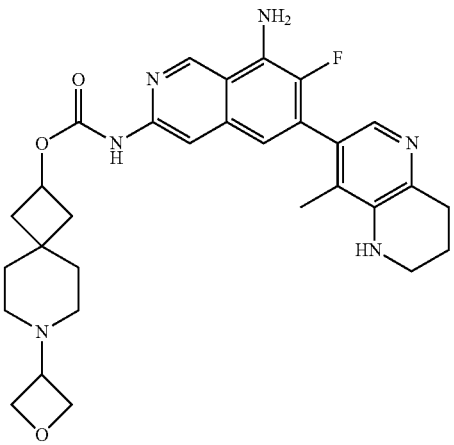 [SMILES: Cc1c(-c2cc3cc(NC(=O)OC4CC5(CCN(C6COC6)CC5)C4)ncc3c(N)c2F)cnc2c1NCCC2]

Step 1: tert-Butyl 7-[3-[(7-tert-butoxycarbonyl-7-azaspiro[3.5]nonan-2-yl)oxycarbonylamino]-8-chloro-7-fluoro-6-isoquinolyl]-8-methyl-3,4-dihydro-2H-1,5-naphthyridine-1-carboxylate

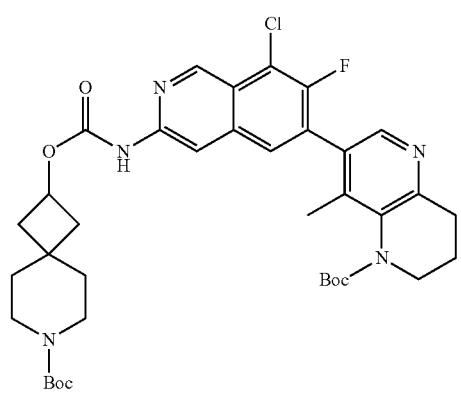 [SMILES: Cc1c(-c2cc3cc(NC(=O)OC4CC5(CCN(C(=O)OC(C)(C)C)CC5)C4)ncc3c(Cl)c2F)cnc2c1N(C(=O)OC(C)(C)C)CCC2]

319

To a solution of tert-butyl 7-(3-amino-8-chloro-7-fluoro-6-isoquinolyl)-8-methyl-3,4-dihydro-2H-1,5-naphthyridine-1-carboxylate (128 mg, 0.29 mmol), tert-butyl 2-hydroxy-7-azaspiro[3.5]nonane-7-carboxylate (204 mg, 0.85 mmol) and DIEA (192 mg, 1.48 mmol) in dichloromethane (20 mL) was added a solution of triphosgene (128 mg, 0.43 mmol) in dichloromethane (1 ml) at 0° C. The resulting solution was stirred for 16 hours at room temperature. The reaction solution was concentrated under vacuum. The residue was purified by flash chromatography on silica gel eluting with petroleum ether/ethyl acetate (2/3) to afford tert-butyl 7-[3-[(7-tert-butoxycarbonyl-7-azaspiro[3.5]nonan-2-yl)oxycarbonylamino]-8-chloro-7-fluoro-6-isoquinolyl]-8-methyl-3,4-dihydro-2H-1,5-naphthyridine-1-carboxylate (164 mg, 0.231 mmol, 79.9% yield) as a yellow solid. LCMS (ESI) [M+H]$^+$=710.

Step 2: Tert-Butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-3,4-dihydro-2H-1,5-naphthyridine-1-carboxylate

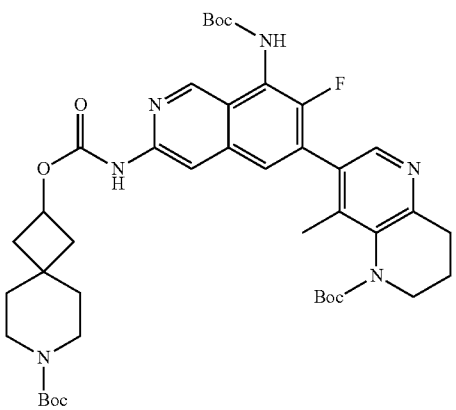 [SMILES: Cc1c(-c2cc3cc(NC(=O)OC4CC5(CCN(C(=O)OC(C)(C)C)CC5)C4)ncc3c(NC(=O)OC(C)(C)C)c2F)cnc2c1N(C(=O)OC(C)(C)C)CCC2]

A mixture of tert-butyl 7-[3-[(7-tert-butoxycarbonyl-7-azaspiro[3.5]nonan-2-yl)oxycarbonylamino]-8-chloro-7-fluoro-6-isoquinolyl]-8-methyl-3,4-dihydro-2H-1,5-naphthyridine-1-carboxylate (164 mg, 0.23 mmol), NH$_2$Boc (0.81 g, 6.92 mmol), Pd(dba)$_3$CHCl$_3$ (48 mg, 0.050 mmol), Brettphos (49 mg, 0.090 mmol) and Cs$_2$CO$_3$ (150 mg, 0.46 mmol) in 1,4-dioxane (10 mL) was stirred at 90° C. for 2 hours. The reaction was was concentrated under vacuum and purified by flash chromatography on silica gel eluting with petroleum ether/ethyl acetate (1/4) to afford tert-butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-3,4-dihydro-2H-1,5-naphthyridine-1-carboxylate (140 mg, 0.177 mmol, 76.7% yield) as a yellow solid. LCMS (ESI) [M+H]$^+$=791.

Step 3: 7-Azaspiro[3.5]nonan-2-yl N-[8-amino-7-fluoro-6-(4-methyl-5,6,7,8-tetrahydro-1,5-naphthyridin-3-yl)-3-isoquinolyl]carbamate

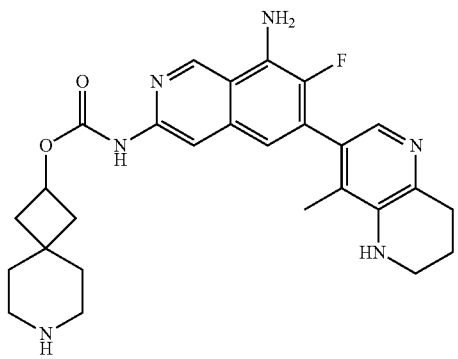 [SMILES: Cc1c(-c2cc3cc(NC(=O)OC4CC5(CCNCC5)C4)ncc3c(N)c2F)cnc2c1NCCC2]

A solution of tert-butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-3,4-dihydro-2H-1,5-naphthyridine-1-carboxylate (140 mg, 0.18 mmol) in dichloromethane (10 mL) and 2,2,2-trifluoroacetic acid (5 mL) was stirred at 30° C. for 1 hour. The reaction was concentrated under vacuum to afford 7-azaspiro[3.5]nonan-2-yl N-[8-amino-7-fluoro-6-(4-methyl-5,6,7,8-tetrahydro-1,5-naphthyridin-3-yl)-3-isoquinolyl]carbamate (50 mg, 0.1018 mmol, 58.1% yield) as a yellow solid. LCMS (ESI) [M+H]$^+$=491.

Step 4: 7-(Oxetan-3-yl)-7-azaspiro[3.5]nonan-2-yl (8-amino-7-fluoro-6-(4-methyl-5,6,7,8-tetrahydro-1,5-naphthyridin-3-yl)isoquinolin-3-yl)carbamate

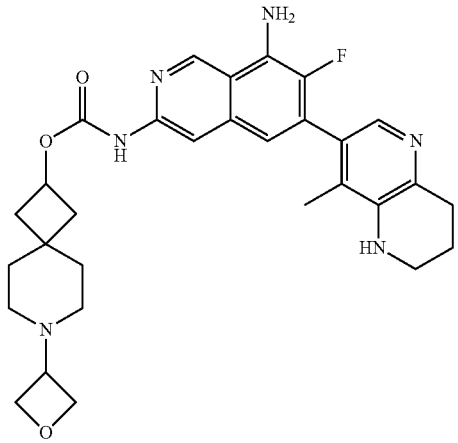 [SMILES: Cc1c(-c2cc3cc(NC(=O)OC4CC5(CCN(C6COC6)CC5)C4)ncc3c(N)c2F)cnc2c1NCCC2]

A solution of 7-azaspiro[3.5]nonan-2-yl N-[8-amino-7-fluoro-6-(4-methyl-5,6,7,8-tetrahydro-1,5-naphthyridin-3-yl)-3-isoquinolyl]carbamate (30 mg, 0.060 mmol), 3-oxetanone (44 mg, 0.61 mmol) and titanium tetraisopropanolate (69 mg, 0.24 mmol) in methyl alcohol (3 mL) was stirred at 60° C. for 1 hour. Then NaBH$_3$CN (12 mg, 0.19 mmol) was added and stirred at room temperature for 1 hour. The reaction mixture was concentrated under vacuum and purified by Prep-HPLC to afford 7-(Oxetan-3-yl)-7-azaspiro[3.5]nonan-2-yl (8-amino-7-fluoro-6-(4-methyl-5,6,7,8-tetrahydro-1,5-naphthyridin-3-yl)isoquinolin-3-yl)carbamate (4.9 mg, 0.009 mmol, 14.7% yield) as a yellow solid. LCMS (ESI) [M+H]⁺=547.3, R$_T$=2.106 min., Method M. ¹H NMR (400 MHz, methanol-d₄) δ9.02 (s, 1H), 8.01 (s, 1H), 7.75 (s, 1H), 6.91 (s, 1H), 5.04 (t, J=4.0 Hz, 1H), 4.67 (t, J=3.9 Hz, 4H), 3.45 (t, J=4.0 Hz, 3H), 2.98 (dd, J=14.2, 3.9 Hz, 2H), 2.45-2.23 (m, 6H), 2.10-1.87 (m, 7H), 1.67-1.65 (m, 4H).

Example 130

(1R,5S,6s)-3-Methyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate (Compound 432a)

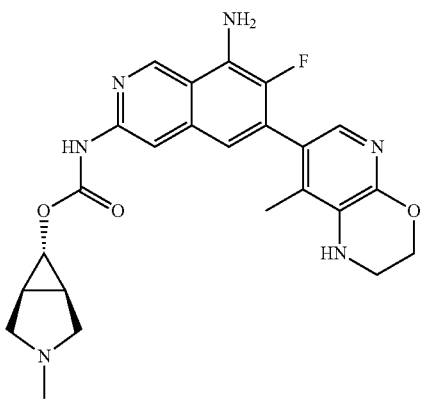 [SMILES: Cc1c(-c2cc3cc(NC(=O)O[C@H]4[C@@H]5CN(C)C[C@@H]54)ncc3c(N)c2F)cnc2c1NCCO2]

Step 1: tert-Butyl 7-(3-(((((1R,5S,6s)-3-(tert-butoxycarbonyl)-3-azabicyclo[3.1.0]hexan-6-yl)oxy)carbonyl)amino)-8-chloro-7-fluoroisoquinolin-6-yl)-8-methyl-2,3-dihydro-1H-pyrido[2,3-b][1,4]oxazine-1-carboxylate

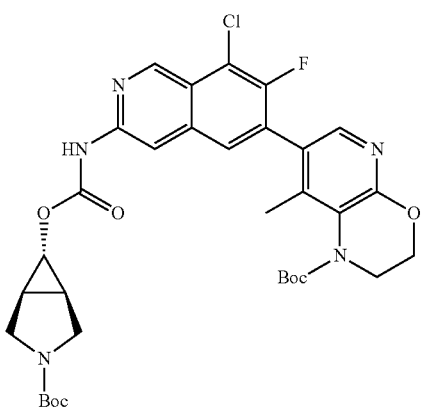 [SMILES: Cc1c(-c2cc3cc(NC(=O)O[C@H]4[C@@H]5CN(C(=O)OC(C)(C)C)C[C@@H]54)ncc3c(Cl)c2F)cnc2c1N(C(=O)OC(C)(C)C)CCO2]

Under nitrogen, a solution of tert-butyl 6-hydroxy-3-azabicyclo[3.1.0]hexane-3-carboxylate (223.0 mg, 1.12 mmol), tert-butyl7-(3-amino-8-chloro-7-fluoro-6-isoquinolyl)-8-methyl-2,3-dihydropyrido[2,3-b][1,4]oxazine-1-carboxylate (200.0 mg, 0.45 mmol) and DIEA (322 mg, 2.5 mmol) in dichloromethane (5 mL) was stirred for 30 min at 0° C. Then triphosgene (103.0 mg, 0.35 mmol) was added and the mixture was stirred at 0° C. for 1 hour. The reaction was concentrated under vacuum and purified by flash chromatography on silica gel eluting with dichloromethane/methanol (5/1) to afford tert-butyl 7-(3-(((((1R,5S,6s)-3-(tert-butoxycarbonyl)-3-azabicyclo[3.1.0]hexan-6-yl)oxy)carbonyl)amino)-8-chloro-7-fluoroisoquinolin-6-yl)-8-methyl-2,3-dihydro-1H-pyrido[2,3-b][1,4]oxazine-1-carboxylate (220 mg, 0.328 mmol, 73% yield) as a yellow solid. LCMS (ESI) [M+H]⁺=670.

Step 2: tert-Butyl 7-(3-(((((1R,5S,6s)-3-(tert-butoxycarbonyl)-3-azabicyclo[3.1.0]hexan-6-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

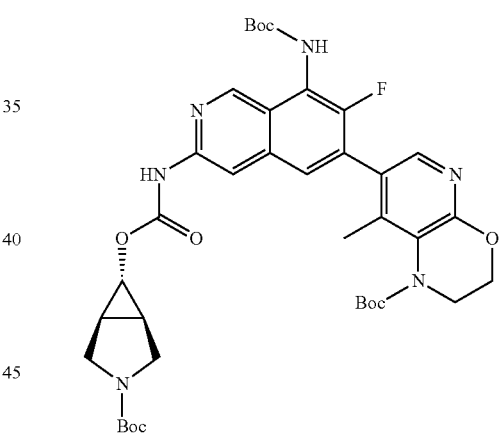

Under nitrogen, a mixture tert-butyl 7-(3-(((((1R,5S,6s)-3-(tert-butoxycarbonyl)-3-azabicyclo[3.1.0]hexan-6-yl)oxy)carbonyl)amino)-8-chloro-7-fluoroisoquinolin-6-yl)-8-methyl-2,3-dihydro-1H-pyrido[2,3-b][1,4]oxazine-1-carboxylate (90.0 mg, 0.13 mmol), Pd₂(dba)₃CHCl₃ (27.0 mg, 0.030 mmol), Brettphos (29.0 mg, 0.05 mmol), Cs₂CO₃ (135.0 mg, 0.41 mmol) and NH₂Boc (405.0 mg, 3.46 mmol) in 1,4-dioxane (9 mL) was stirred for 1 hour at 90° C. After filtration, the solution was collected and concentrated under vacuum. The residue was purified by flash chromatography on silica gel eluting with petroleum ether/ethyl acetate (32/68) to afford tert-butyl 7-(3-(((((1R,5S,6s)-3-(tert-butoxycarbonyl)-3-azabicyclo[3.1.0]hexan-6-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate (80 mg, 0.1066 mmol, 79.3% yield) as a yellow solid. LCMS (ESI) [M+H]⁺=751.

Step 3: (1R,5S,6s)-3-Azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate

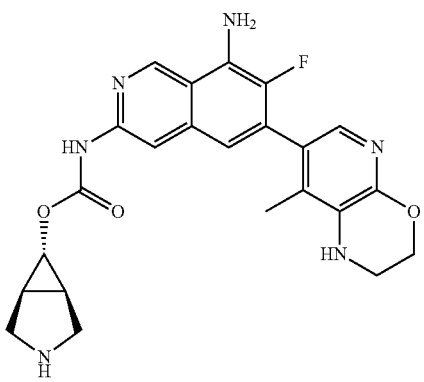 [SMILES: Cc1c(-c2cc3cc(NC(=O)O[C@H]4[C@@H]5CNC[C@@H]54)ncc3c(N)c2F)cnc2c1NCCO2]

A solution of tert-butyl 7-(3-(((((1R,5S,6s)-3-(tert-butoxycarbonyl)-3-azabicyclo[3.1.0]hexan-6-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate (95 mg, 0.13 mmol) in dichloromethane (5 mL) and TFA (1.0 mL, 0.13 mmol) was stirred at room temperature for 1 hour. The reaction mixture was concentrated under vacuum and purified by reverse phase chromatography with MeOH/Water (65/30) to afford (1R,5S,6s)-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate (45 mg, 0.0999 mmol, 79% yield) as a yellow solid. LCMS (ESI) [M+H]$^+$= 451.

Step 4: (1R,5S,6s)-3-Methyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate

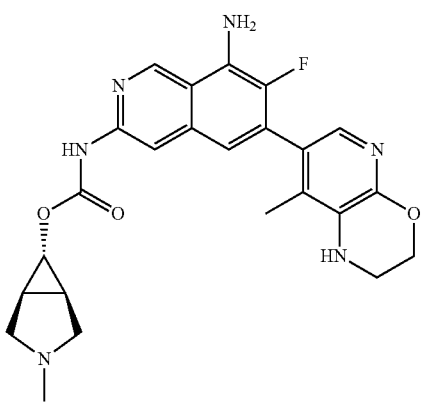 [SMILES: Cc1c(-c2cc3cc(NC(=O)O[C@H]4[C@@H]5CN(C)C[C@@H]54)ncc3c(N)c2F)cnc2c1NCCO2]

A solution of formaldehyde (4.5 mg, 0.15 mmol, 40%) and (1R,5S,6s)-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate (20.0 mg, 0.040 mmol) in dichloromethane (5 mL) was stirred at 0° C. for 30 min. Then NaCNBH$_3$ (14.0 mg, 0.050 mmol) was added and the mixture was stirred at 0° C. for 1 hour. The reaction mixture was concentrated under vacuum. The residue was purified by flash chromatography on silica gel eluting with dichloromethane/methanol (25/75) to (1R,5S,6s)-3-methyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate (10 mg, 0.0215 mmol, 35% yield) as a yellow solid. LCMS (ESI) [M+H]$^+$=465.2, R$_T$ 0.967 min., Method K. $^1$H NMR (300 MHz, DMSO-d$_6$) δ10.15 (s, 1H), 9.33 (s, 1H), 8.15 (s, 1H), 7.98 (s, 1H), 7.33 (s, 1H), 6.87-6.82 (d, J=6 Hz, 1H), 6.23 (s, 2H), 5.69 (s, 1H), 4.29 (s, 2H), 4.11 (s, 1H), 3.34 (s, 1H), 3.10-3.01 (d, J=9 Hz, 2H), 2.43-2.34 (s, J=9 Hz, 1H), 2.25 (s, 4H), 1.96-1.89 (d, J=3 Hz, 3H), 1.74 (s, 2H).

Example 131

[(3S,4R)-3-Fluoro-4-piperidyl]N-[8-amino-7-fluoro-6-(8-methyl-2,3-dihydro-1H-pyrido[2,3-b][1,4]oxazin-7-yl)-3-isoquinolyl]carbamate (Compound 433)

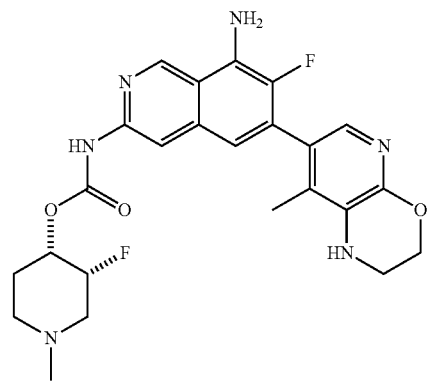

Step 1: tert-Butyl 7-[3-[[[(3S,4R)-1-tert-butoxycarbonyl-3-fluoro-4-piperidyl]oxycarbonylamino]-8-chloro-7-fluoro-6-isoquinolyl]-8-methyl-2,3-dihydropyrido[2,3-b][1,4]oxazine-1-carboxylate

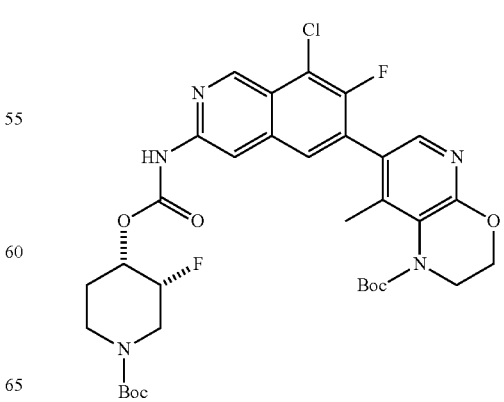

To a solution of tert-butyl 7-(3-amino-8-chloro-7-fluoro-6-isoquinolyl)-8-methyl-2,3-dihydropyrido[2,3-b][1,4]oxazine-1-carboxylate (600 mg, 1.35 mmol), tert-butyl (3S,4R)-3-fluoro-4-hydroxy-piperidine-1-carboxylate (591.5 mg, 2.7 mmol) and DIEA (871.5 mg, 6.74 mmol) in dichloromethane (10 mL) was added triphosgene (280.2 mg, 0.94 mmol). The mixture was stirred at 0° C. for 2 hours. The reaction mixture was concentrated under vacuum and purified by flash chromatography on silica gel eluting with dichloromethane/methanol (20/1) to afford tert-butyl 7-[3-[[(3S,4R)-1-tert-butoxycarbonyl-3-fluoro-4-piperidyl]oxycarbonylamino]-8-chloro-7-fluoro-6-isoquinolyl]-8-methyl-2,3-dihydropyrido[2,3-b][1,4]oxazine-1-carboxylate (800 mg, 1.16 mmol, 86% yield) as a yellow solid. LCMS (ESI) [M+H]⁺=690.2.

Step 2: tert-butyl 7-[8-(tert-butoxycarbonylamino)-3-[[(3S,4R)-1-tert-butoxycarbonyl-3-fluoro-4-piperidyl]oxycarbonylamino]-7-fluoro-6-isoquinolyl]-8-methyl-2,3-dihydropyrido[2,3-b][1,4]oxazine-1-carboxylate

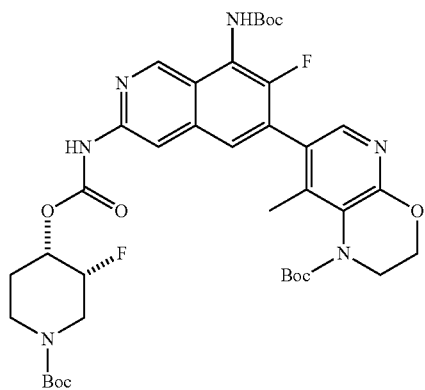

Under nitrogen, a mixture of tert-butyl 7-[3-[[(3S,4R)-1-tert-butoxycarbonyl-3-fluoro-4-piperidyl]oxycarbonylamino]-8-chloro-7-fluoro-6-isoquinolyl]-8-methyl-2,3-dihydropyrido[2,3-b][1,4]oxazine-1-carboxylate (600.0 mg, 0.86 mmol), tert-butyl carbamate (509.2 mg, 4.34 mmol), BrettPhos Pd G3 (157.6 mg, 0.18 mmol) and Cs₂CO₃ (567.0 mg, 1.74 mmol) was stirred at 90° C. for 4 hours. The reaction was concentrated under vacuum and purified by flash chromatography on silica gel eluting with dichloromethane/methanol (20/1) to afford tert-butyl 7-[8-(tert-butoxycarbonylamino)-3-[[(3S,4R)-1-tert-butoxycarbonyl-3-fluoro-4-piperidyl]oxycarbonylamino]-7-fluoro-6-isoquinolyl]-8-methyl-2,3-dihydropyrido[2,3-b][1,4]oxazine-1-carboxylate (410 mg, 0.53 mmol, 62.7% yield) as a yellow solid. LCMS (ESI) [M+H]⁺=771.3.

Step 3: [(3S,4R)-3-fluoro-4-piperidyl]N-[8-amino-7-fluoro-6-(8-methyl-2,3-dihydro-1H-pyrido[2,3-b][1,4]oxazin-7-yl)-3-isoquinolyl]carbamate

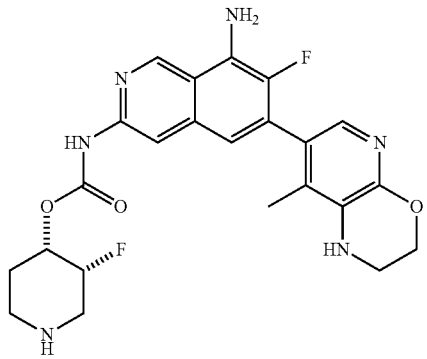

To a solution of tert-butyl 7-[8-(tert-butoxycarbonylamino)-3-[[(3S,4R)-1-tert-butoxycarbonyl-3-fluoro-4-piperidyl]oxycarbonylamino]-7-fluoro-6-isoquinolyl]-8-methyl-2,3-dihydropyrido[2,3-b][1,4]oxazine-1-carboxylate (400.0 mg, 0.52 mmol) in dichloromethane (20 mL) was added 2,2,2-trifluoroacetic acid (10 mL) at 0° C. Then the resulting solution was stirred at room temperature for 0.5 hour. The reaction was was concentrated under vacuum. The residue was diluted with dichloromethane, adjusted to pH 8 with TEA and concentrated under vacuum. The residue was purified by reverse phase chromatography (acetonitrile 1-60%, 0.1% NH₄HCO₃ in water) to afford [(3S,4R)-3-fluoro-4-piperidyl]N-[8-amino-7-fluoro-6-(8-methyl-2,3-dihydro-1H-pyrido[2,3-b][1,4]oxazin-7-yl)-3-isoquinolyl]carbamate (120 mg, 0.256 mmol, 49.2% yield) as a yellow solid. LCMS (ESI) [M+H]⁺=471.2.

Step 4: [(3S,4R)-3-Fluoro-1-methyl-4-piperidyl]N-[8-amino-7-fluoro-6-(8-methyl-2,3-dihydro-1H-pyrido[2,3-b][1,4]oxazin-7-yl)-3-isoquinolyl]carbamate

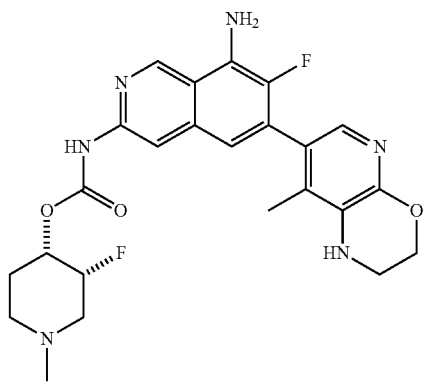

A solution of [(3S,4R)-3-fluoro-4-piperidyl]N-[8-amino-7-fluoro-6-(8-methyl-2,3-dihydro-1H-pyrido[2,3-b][1,4]oxazin-7-yl)-3-isoquinolyl]carbamate (90.0 mg, 0.19 mmol) and formaldehyde (11.5 mg, 0.38 mmol, 40%) in methyl alcohol (5 mL) was stirred at room temperature for 2 hours. Then NaBH₃CN (48.1 mg, 0.77 mmol) was added to the mixture and stirred at room temperature for 1 hour. The reaction was quenched with water. The resulting mixture was extracted with dichloromethane. The organic layers were combined, dried over sodium sulfate and concentrated under vacuum. The residue was purified by Prep-HPLC (Column: X Bridge Prep C18 OBD Column 19×150 mm 5 μm; Mobile Phase A: Water (10 mmol/L NH₄HCO₃), Mobile Phase B: MeOH; Flow rate: 25 mL/min; Gradient: 32% B to 45% B in 10 min) to afford [(3S,4R)-3-fluoro-1-methyl-4-piperidyl]N-[8-amino-7-fluoro-6-(8-methyl-2,3-dihydro-1H-pyrido[2,3-b][1,4]oxazin-7-yl)-3-isoquinolyl]carbamate (9.2 mg, 0.02 mmol, 9.8% yield) as a yellow solid. Absolute stereochemistry was arbitrarily assigned. LCMS (ESI) [M+H]⁺=485.2, $R_T$=1.656 min., Method K. ¹H NMR (300 MHz, DMSO-d₆) δ 10.20 (s, 1H), 9.34 (s, 1H), 7.96 (s, 1H), 7.32 (s, 1H), 6.83 (d, J=6.1 Hz, 1H), 6.23 (s, 2H), 5.68 (s, 1H), 4.92 (s, 1H), 4.85 (s, 1H), 4.28 (s, 2H), 3.38 (s, 2H), 2.72-2.89 (m, 2H), 2.38 (s, 1H), 2.20 (s, 4H), 1.91 (d, J=1.6 Hz, 4H), 1.80 (s, 1H).

Example 132

1-(2,2-Difluoroethyl)azetidin-3-yl (8-amino-7-fluoro-6-(8-methyl-2,3-dihydro-1H-pyrido[2,3-b][1,4]oxazin-7-yl)isoquinolin-3-yl)carbamate (Compound 434)

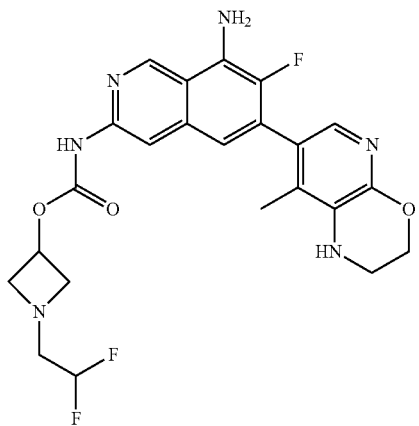 [SMILES: Cc1c(-c2cc3cc(NC(=O)OC4CN(CC(F)F)C4)ncc3c(N)c2F)cnc2c1NCCO2]

A solution of azetidin-3-yl N-[8-amino-7-fluoro-6-(8-methyl-2,3-dihydro-1H-pyrido[2,3-b][1,4]oxazin-7-yl)-3-isoquinolyl]carbamate (50 mg, 0.12 mmol) and 2,2-difluoroethyltrifluoromethanesulfonate (20 mg, 0.09 mmol) in dichloromethane (5 mL) was added TEA (30 mg, 0.30 mmol) at room temperature. The resulting solution was stirred for 1 h at 25° C. The reaction was quenched by adding water and then concentrated under vacuum. The residue was purified by Prep-HPLC (Column: X select CSH OBD Column 30*150 mm 5 μm; Mobile Phase A: Water (10 mmol/L NH₄HCO₃), Mobile Phase B: ACN; Flow rate: 60 mL/min; Gradient: 5% B to 22% B in 10 min) to give [1-(2,2-difluoroethyl)azetidin-3-yl]N-[8-amino-7-fluoro-6-(8-methyl-2,3-dihydro-1H-pyrido[2,3-b][1,4]oxazin-7-yl)-3-isoquinolyl]carbamate (13.1 mg, 0.0268 mmol, 22.8% yield) as a white solid. LCMS (ESI) [M+H]⁺=489.2, $R_T$=1.608 min., Method J. ¹H NMR (300 MHz, DMSO-d₆) δ 10.26 (s, 1H), 9.34 (s, 1H), 7.95 (s, 1H), 7.32 (s, 1H), 6.83 (d, J=6.2 Hz, 1H), 6.23 (s, 2H), 6.15-5.80 (m, 1H), 5.68 (s, 1H), 5.00 (q, J=5.6 Hz, 1H), 4.29-4.27 (m, 2H), 3.76-3.65 (m, 2H), 3.35-3.33 (m, 2H), 3.22 (dd, J=8.4, 5.5 Hz, 2H), 2.87 (td, J=16.1, 4.1 Hz, 2H), 1.91 (d, J=1.6 Hz, 3H).

Example 133

(1,3,3-Trimethyl-4-piperidyl) N-[8-amino-7-fluoro-6-(8-methyl-2,3-dihydro-1H-pyrido[2,3-b][1,4]oxazin-7-yl)-3-isoquinolyl]carbamate (Compound 435)

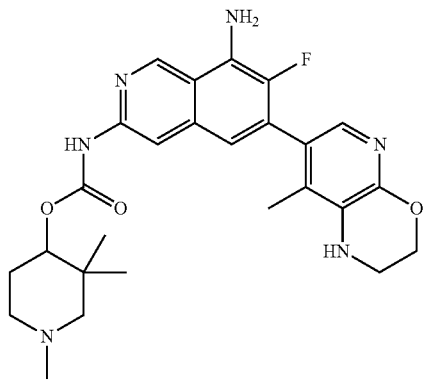 [SMILES: Cc1c(-c2cc3cc(NC(=O)OC4CCN(C)CC4(C)C)ncc3c(N)c2F)cnc2c1NCCO2]

Step 1: tert-Butyl 7-[3-[(1-tert-butoxycarbonyl-3,3-dimethyl-4-piperidyl)oxycarbonylamino]-8-chloro-7-fluoro-6-isoquinolyl]-8-methyl-2,3-dihydropyrido[2,3-b][1,4]oxazine-1-carboxylate

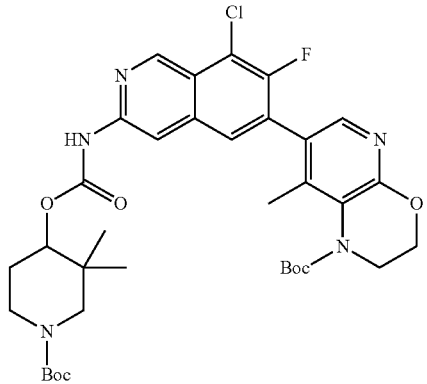 [SMILES: Cc1c(-c2cc3cc(NC(=O)OC4CCN(C(=O)OC(C)(C)C)CC4(C)C)ncc3c(Cl)c2F)cnc2c1N(C(=O)OC(C)(C)C)CCO2]

Under nitrogen, to a solution of tert-butyl 7-(3-amino-8-chloro-7-fluoro-6-isoquinolyl)-8-methyl-2,3-dihydropyrido[2,3-b][1,4]oxazine-1-carboxylate (300.0 mg, 0.67 mmol), tert-butyl 4-hydroxy-3,3-dimethyl-piperidine-1-carboxylate (300.0 mg, 1.31 mmol) and DIEA (435.0 mg, 3.37 mmol) in dichloromethane (6 mL) was added triphosgene (141.0 mg, 0.48 mmol) and stirred at 0° C. for 1 hour. The reaction mixture was concentrated under vacuum and purified by flash chromatography on silica gel eluting with petroleum ether/ethyl acetate (40/60) to afford tert-butyl 7-[3-[(1-tert-butoxycarbonyl-3,3-dimethyl-4-piperidyl)oxycarbonylamino]-8-chloro-7-fluoro-6-isoquinolyl]-8-methyl-2,3-dihydropyrido[2,3-b][1,4]oxazine-1-carboxylate (315 mg, 0.45 mmol, 66.7% yield) as a light yellow solid. LCMS (ESI) [M+H]⁺=700.3.

Step 2: tert-Butyl 7-[8-(tert-butoxycarbonylamino)-3-[(1-tert-butoxycarbonyl-3,3-dimethyl-4-piperidyl)oxycarbonylamino]-7-fluoro-6-isoquinolyl]-8-methyl-2,3-dihydropyrido[2,3-b][1,4]oxazine-1-carboxylate

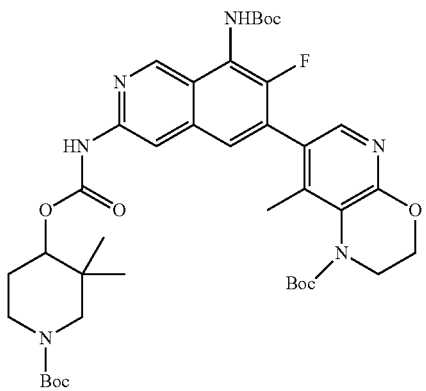 [SMILES: Cc1c(-c2cc3cc(NC(=O)OC4CCN(C(=O)OC(C)(C)C)CC4(C)C)ncc3c(NC(=O)OC(C)(C)C)c2F)cnc2c1N(C(=O)OC(C)(C)C)CCO2]

Under nitrogen, a mixture of tert-butyl 7-[3-[(1-tert-butoxycarbonyl-3,3-dimethyl-4-piperidyl)oxycarbonylamino]-8-chloro-7-fluoro-6-isoquinolyl]-8-methyl-2,3-dihydropyrido[2,3-b][1,4]oxazine-1-carboxylate (300.0 mg, 0.43 mmol), NH$_2$Boc (1254.0 mg, 10.72 mmol), Pd$_2$(dba)$_3$ (90.0 mg, 0.09 mmol), BrettPhos (93.0 mg, 0.17 mmol) and Cs$_2$CO$_3$ (420.0 mg, 1.29 mmol) in 1,4-dioxane (5 mL) was stirred at 90° C. for 1 hour. The reaction mixture was concentrated under vacuum. The residue was purified by flash chromatography silica gel column eluting with petroleum ether/ethyl acetate (37/63) to afford tert-butyl 7-[8-(tert-butoxycarbonylamino)-3-[(1-tert-butoxycarbonyl-3,3-dimethyl-4-piperidyl)oxycarbonylamino]-7-fluoro-6-isoquinolyl]-8-methyl-2,3-dihydropyrido[2,3-b][1,4]oxazine-1-carboxylate (60 mg, 0.077 mmol, 17.9% yield) as a light yellow solid. LCMS (ESI) [M+H]$^+$=781.4.

Step 3: (3,3-Dimethyl-4-piperidyl) N-[8-amino-7-fluoro-6-(8-methyl-2,3-dihydro-1H-pyrido[2,3-b][1,4]oxazin-7-yl)-3-isoquinolyl]carbamate

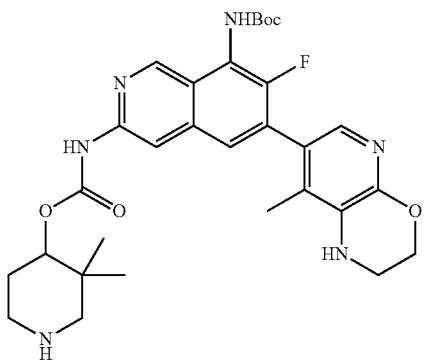 [SMILES: Cc1c(-c2cc3cc(NC(=O)OC4CCNCC4(C)C)ncc3c(NC(=O)OC(C)(C)C)c2F)cnc2c1NCCO2]

A solution of tert-butyl 7-[8-(tert-butoxycarbonylamino)-3-[(1-tert-butoxycarbonyl-3,3-dimethyl-4-piperidyl)oxycarbonylamino]-7-fluoro-6-isoquinolyl]-8-methyl-2,3-dihydropyrido[2,3-b][1,4]oxazine-1-carboxylate (55.0 mg, 0.07 mmol) and TFA (1.0 mL, 0.07 mmol) in dichloromethane (5 mL) was stirred at 25° C. for 1 hour. The reaction mixture was concentrated under vacuum. The residue was purified by reverse phase chromatography eluting with ACN/water (10 mmol/L NH$_4$HCO$_3$) (27/73) to give (3,3-dimethyl-4-piperidyl) N-[8-amino-7-fluoro-6-(8-methyl-2,3-dihydro-1H-pyrido[2,3-b][1,4]oxazin-7-yl)-3-isoquinolyl]carbamate (33.5 mg, 0.069 mmol, 99% yield) as a light yellow solid. LCMS (ESI) [M+H]$^+$=481.2.

Step 4: (1,3,3-Trimethyl-4-piperidyl) N-[8-amino-7-fluoro-6-(8-methyl-2,3-dihydro-1H-pyrido[2,3-b][1,4]oxazin-7-yl)-3-isoquinolyl]carbamate

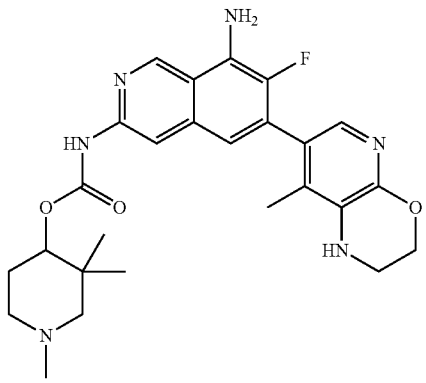 [SMILES: Cc1c(-c2cc3cc(NC(=O)OC4CCN(C)CC4(C)C)ncc3c(N)c2F)cnc2c1NCCO2]

A solution of (3,3-dimethyl-4-piperidyl) N-[8-amino-7-fluoro-6-(8-methyl-2,3-dihydro-1H-pyrido[2,3-b][1,4]oxazin-7-yl)-3-isoquinolyl]carbamate (25.0 mg, 0.05 mmol) and formaldehyde (7.8 mg, 0.26 mmol, 40%) in methyl alcohol (2 mL) was stirred at 25° C. for 1 hour. Then NaBH$_3$CN (10.0 mg, 0.16 mmol) was added and stirred at 25° C. for 1 hour. After concentration, the residue was purified by Prep-HPLC with (Column: X Bridge Prep OBD C18 Column 30×150 mm 5 μm; Water (10 MMOL/L NH$_4$HCO$_3$): ACN=20% B to 43% B in 7 min; 60 mL/min) to afford (1,3,3-trimethyl-4-piperidyl) N-[8-amino-7-fluoro-6-(8-methyl-2,3-dihydro-1H-pyrido[2,3-b][1,4]oxazin-7-yl)-3-isoquinolyl]carbamate (10.5 mg, 0.021 mmol, 40.8% yield) as a light yellow solid. LCMS (ESI) [M+H]$^+$=495.2, R$_T$ 1.696 min; Method K. $^1$H NMR (300 MHz, DMSO-d$_6$) δ 10.02 (s, 1H), 9.35 (s, 1H), 7.96 (s, 1H), 7.32 (s, 1H), 6.82 (d, J=6.1 Hz, 1H), 6.21 (s, 2H), 5.68 (s, 1H), 4.45-4.36 (m, 1H), 4.28-4.20 (m, 2H), 3.40-3.31 (m, 2H), 2.36-2.20 (m, 5H), 2.14 (s, 4H), 1.91-1.60 (m, 7H), 1.03 (s, 3H), 0.92 (s, 3H).

Example 134

(3R,4S)-1-Acetyl-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate and (3S,4R)-1-Acetyl-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate (Compound 437a and Compound 437b)

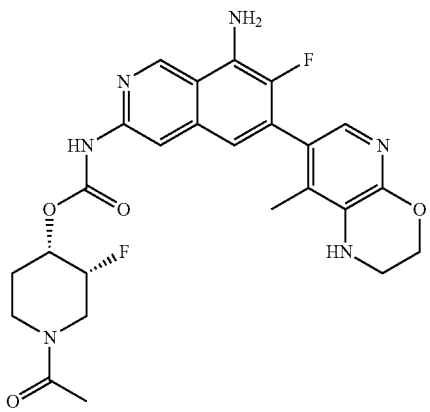

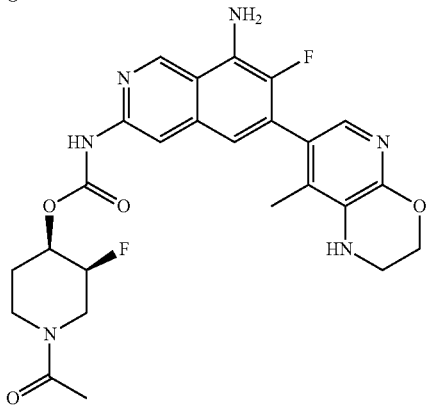

Step 1: tert-Butyl 7-[3-[[(3S,4R)-1-tert-butoxycarbonyl-3-fluoro-4-piperidyl]oxycarbonylamino]-8-chloro-7-fluoro-6-isoquinolyl]-8-methyl-2,3-dihydropyrido[2,3-b][1,4]oxazine-1-carboxylate

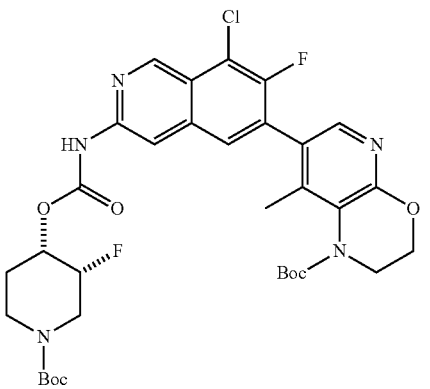

Under nitrogen, to a solution of tert-butyl 7-(3-amino-8-chloro-7-fluoro-6-isoquinolyl)-8-methyl-2,3-dihydropyrido[2,3-b][1,4]oxazine-1-carboxylate (500 mg, 1.12 mmol), (±)-cis-tert-butyl 3-fluoro-4-hydroxy-piperidine-1-carboxylate (492.9 mg, 2.25 mmol) and DIEA (726.3 mg, 5.62 mmol) in dichloromethane (10 mL) was added triphosgene (233.5 mg, 0.79 mmol) at 0° C. The resulting solution was stirred at room temperature for 2 hours. The reaction was quenched by water and extracted with dichloromethan. The organic layers were combined, dried over anhydrous sodium sulfate and concentrated under vacuum. The residue was purified by flash chromatography on silica gel eluting with dichloromethane/methanol (2%) to afford (±)-cis-tert-butyl 7-[3-[[1-tert-butoxycarbonyl-3-fluoro-4-piperidyl]oxycarbonylamino]-8-chloro-7-fluoro-6-isoquinolyl]-8-methyl-2,3-dihydropyrido[2,3-b][1,4]oxazine-1-carboxylate (520 mg, 0.754 mmol, 67% yield) as a yellow solid. LCMS (ESI) [M+H]$^+$=690.2

Step 2: (±)-cis-tert-Butyl 7-[8-(tert-butoxycarbonylamino)-3-[[1-tert-butoxycarbonyl-3-fluoro-4-piperidyl]oxycarbonylamino]-7-fluoro-6-isoquinolyl]-8-methyl-2,3-dihydropyrido[2,3-b][1,4]oxazine-1-carboxylate

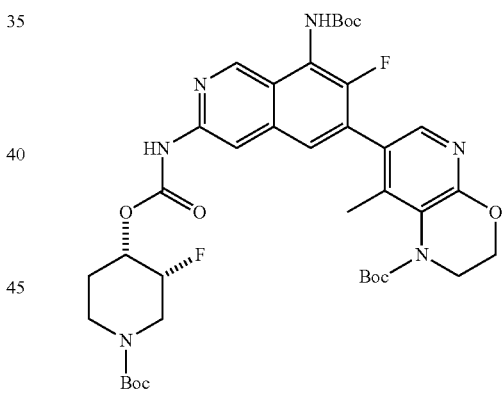

Under nitrogen, a mixture of (±)-cis-tert-butyl 7-[3-[[1-tert-butoxycarbonyl-3-fluoro-4-piperidyl]oxycarbonylamino]-8-chloro-7-fluoro-6-isoquinolyl]-8-methyl-2,3-dihydropyrido[2,3-b][1,4]oxazine-1-carboxylate (500 mg, 0.72 mmol), tert-butyl carbamate (2546.26 mg, 21.74 mmol), BrettPhos Pd G3 (131.4 mg, 0.14 mmol) and Cs$_2$CO$_3$ (472.4 mg, 1.45 mmol) in 1,4-dioxane (15 mL) was stirred at 90° C. for 2 hours. The reaction mixture was concentrated under vacuum and purified by flash chromatography on silica gel eluting with dichloromethane/methanol (4%) to afford (±)-cis-tert-butyl 7-[8-(tert-butoxycarbonylamino)-3-[[1-tert-butoxycarbonyl-3-fluoro-4-piperidyl]oxycarbonylamino]-7-fluoro-6-isoquinolyl]-8-methyl-2,3-dihydropyrido[2,3-b][1,4]oxazine-1-carboxylate (480 mg, 0.4035 mmol, 55.7% yield) as a yellow solid. LCMS (ESI) [M+H]$^+$=771.3

Step 3: (±)-cis-[3-Fluoro-4-piperidyl]N-[8-amino-7-fluoro-6-(8-methyl-2,3-dihydro-1H-pyrido[2,3-b][1,4]oxazin-7-yl)-3-isoquinolyl]carbamate

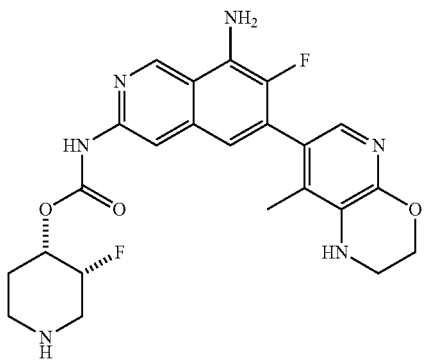

To a solution of (±)-cis-tert-butyl 7-[8-(tert-butoxycarbonylamino)-3-[[1-tert-butoxycarbonyl-3-fluoro-4-piperidyl]oxycarbonylamino]-7-fluoro-6-isoquinolyl]-8-methyl-2,3-dihydropyrido[2,3-b][1,4]oxazine-1-carboxylate (480 mg, 0.622 mmol) in dichloromethane (15 mL) was added TFA (4 mL) at 0° C. The resulting solution was stirred at room temperature for 1.5 hours. The reaction mixture was concentrated under vacuum. The residue was re-dissolved in dichloromethane and adjusted to pH 8 with TEA. The mixture was concentrated under vacuum and purified by reversed phase flash chromatography eluting with $H_2O$/ACN (44%) to afford (±)-[3-fluoro-4-piperidyl]N-[8-amino-7-fluoro-6-(8-methyl-2,3-dihydro-1H-pyrido[2,3-b][1,4]oxazin-7-yl)-3-isoquinolyl]carbamate (110 mg, 0.242 mmol, 40.2% yield) as a yellow solid. LCMS (ESI) [M+H]$^+$= 471.2.

Step 4: (3R,4S)-1-Acetyl-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate and (3S,4R)-1-Acetyl-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate

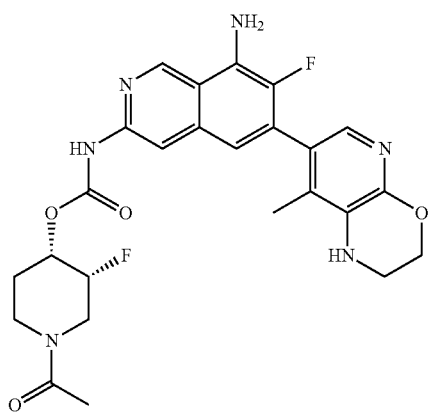

-continued

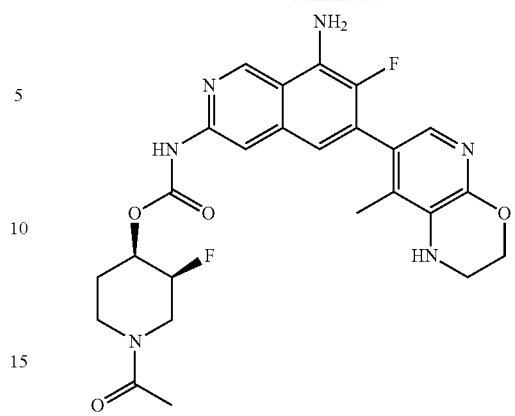

To a solution of (±)-cis[3-fluoro-4-piperidyl]N-[8-amino-7-fluoro-6-(8-methyl-2,3-dihydro-1H-pyrido[2,3-b][1,4]oxazin-7-yl)-3-isoquinolyl]carbamate (100 mg, 0.21 mmol) and TEA (64.6 mg, 0.64 mmol) in dichloromethane (10 mL) was added $Ac_2O$ (32.6 mg, 0.32 mmol) at 0° C. The resulting solution was stirred at room temperature for 4 hours. The reaction was quenched by water and extracted with ethyl acetate. The organic layers were combined, dried over sodium sulfate and concentrated under vacuum. The residue was purified by Prep-HPLC (Column: X Bridge Shield RP18 OBD Column 30*150 mm, 5 μm; Mobile Phase A: Water (10 mmol/L $NH_4HCO_3$), Mobile Phase B: ACN; Flow rate: 60 mL/min; Gradient: 17% B to 42% B in 7 min) to afford the racemic product. The racemic product was separated by chiral-HPLC with the following conditions: Column: CHIRALPAK IG, 5*25 cm, 5 μm; Mobile Phase A: MTBE-HPLC, Mobile Phase B: MeOH; Flow rate: 20 mL/min; Gradient: 50 B to 50 B in 17 min. Relative stereochemistry are as drawn. Absolute stereochemistry was arbitrarily assigned.

Enantiomer 1 (Compound 437a) (8.7 mg, 0.0162 mmol, 7.6% yield); $R_T$ 3.793 min (CHIRALPAK IC-3 0.46*10 cm; 3 μm. (MTBE (0.1% DEA):MeOH=50:50; 1 ml/min). LCMS(ESI) [M+H]$^+$=513.2, 1.603 min., Method K. $^1$H NMR (300 MHz, DMSO-d$_6$) δ 10.27 (d, J=1.4 Hz, 1H), 9.34 (s, 1H), 7.96 (s, 1H), 7.33 (s, 1H), 6.84 (d, J=6.1 Hz, 1H), 6.24 (s, 2H), 5.68 (s, 1H), 4.94 (dd, J=50.8, 21.4 Hz, 2H), 4.46-4.12 (m, 3H), 4.09-3.71 (m, 1H), 3.53 (dd, J=32.6, 14.8 Hz, 1H), 3.26 (s, 2H), 3.21-2.84 (m, 1H), 2.03 (d, J=11.5 Hz, 3H), 1.94-1.65 (m, 5H).

Enantiomer 2 (Compound 437b) (6.5 mg, 0.0125 mmol, 5.9% yield); $R_T$ 3.793 min (CHIRALPAK IC-3 0.46*10 cm; 3 um. MTBE (0.1% DEA):MeOH=50:50; 1 ml/min). LCMS (ESI) [M+H]$^+$=513.2, 1.603 min., Method K. $^1$H NMR (300 MHz, DMSO-d$_6$) δ 10.27 (d, J=1.4 Hz, 1H), 9.34 (s, 1H), 7.96 (s, 1H), 7.33 (s, 1H), 6.84 (d, J=6.1 Hz, 1H), 6.24 (s, 2H), 5.68 (s, 1H), 4.94 (dd, J=50.8, 21.4 Hz, 2H), 4.46-4.12 (m, 3H), 4.09-3.71 (m, 1H), 3.53 (dd, J=32.6, 14.8 Hz, 1H), 3.26 (s, 2H), 3.21-2.84 (m, 1H), 2.03 (d, J=11.5 Hz, 3H), 1.94-1.65 (m, 5H).

Example 135

7-(Oxetan-3-yl)-7-azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate (Compound 438)

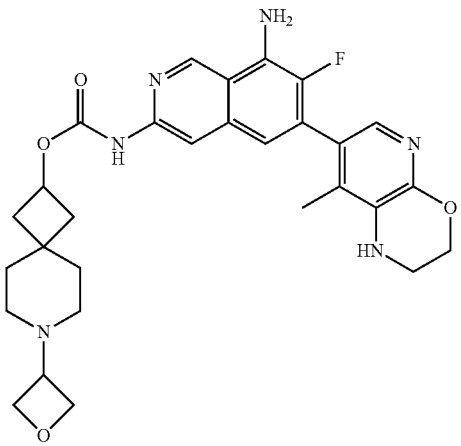 [SMILES: Cc1c(-c2cc3cc(NC(=O)OC4CC5(CCN(C6COC6)CC5)C4)ncc3c(N)c2F)cnc2c1NCCO2]

Step 1: tert-Butyl 7-(3-((((7-(tert-butoxycarbonyl)-7-azaspiro[3.5]nonan-2-yl)oxy)carbonyl)amino)-8-chloro-7-fluoroisoquinolin-6-yl)-8-methyl-2,3-dihydro-1H-pyrido[2,3-b][1,4]oxazine-1-carboxylate

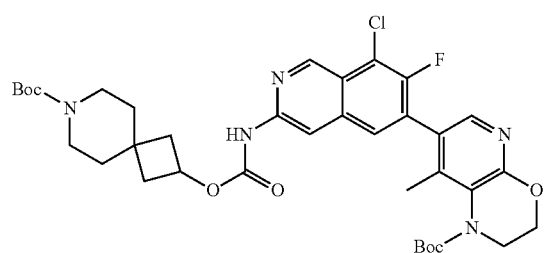 [SMILES: Cc1c(-c2cc3cc(NC(=O)OC4CC5(CCN(C(=O)OC(C)(C)C)CC5)C4)ncc3c(Cl)c2F)cnc2c1N(C(=O)OC(C)(C)C)CCO2]

A solution of tert-butyl 7-(3-amino-8-chloro-7-fluoro-6-isoquinolyl)-8-methyl-2,3-dihydropyrido[2,3-b][1,4]oxazine-1-carboxylate (300.0 mg, 0.67 mmol), tert-butyl 2-hydroxy-7-azaspiro[3.5]nonane-7-carboxylate (325.5 mg, 1.35 mmol) and N,N-diisopropylethylamine (435.8 mg, 3.37 mmol) in dichloromethane (4 mL) was stirred at room temperature for 30 mins. Then triphosgene (200.1 mg, 0.67 mmol) was added and stirred at 0° C. The reaction was stirred at room temperature for 1 hour. The reaction was then quenched with water and extracted with dichloromethane. The organic layers were combined, dried over anhydrous sodium and concentrated under vacuum. The residue was purified by flash chromatography on silica gel eluting with dichloromethane/methanol (97/3) to afford tert-butyl 7-[3-[(7-tert-butoxycarbonyl-7-azaspiro[3.5]nonan-2-yl)oxycarbonylamino]-8-chloro-7-fluoro-6-isoquinolyl]-8-methyl-2,3-dihydropyrido[2,3-b][1,4]oxazine-1-carboxylate (400 mg, 0.562 mmol, 83.2% yield)] as a yellow solid. LCMS (ESI) [M+H]$^+$=712.4.

Step 2: tert-Butyl 7-(3-((((7-(tert-butoxycarbonyl)-7-azaspiro[3.5]nonan-2-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

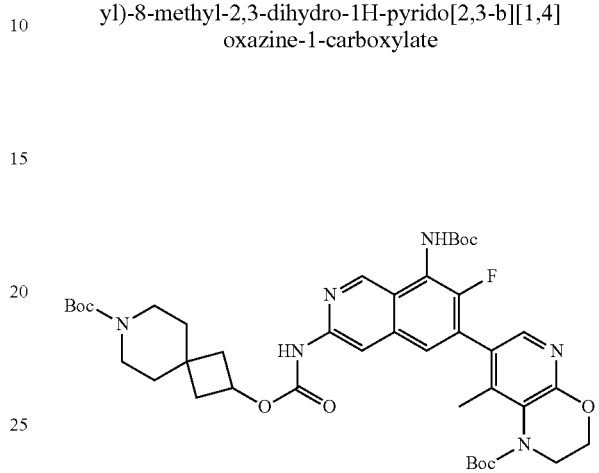

Under nitrogen, to a mixture of tert-butyl 7-[3-[(7-tert-butoxycarbonyl-7-azaspiro[3.5]nonan-2-yl)oxycarbonylamino]-8-chloro-7-fluoro-6-isoquinolyl]-8-methyl-2,3-dihydropyrido[2,3-b][1,4]oxazine-1-carboxylate (300.0 mg, 0.42 mmol) and Pd$_2$(dba)$_3$.CHCl$_3$ (87.2 mg, 0.08 mmol) in 1,4-dioxane (4 mL) was added BrettPhos (90.44 mg, 0.17 mmol), Cs$_2$CO$_3$ (411.73 mg, 1.26 mmol) and tert-butyl carbamate (1.23 g, 10.53 mmol). The reaction was stirred at 90° C. for 1 hour. The resulting mixture was concentrated under vacuum and purified by flash chromatography on silica gel eluting with dichloromethane/methanol (99/1) to afford tert-butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-2,3-dihydropyrido[2,3-b][1,4]oxazine-1-carboxylate (250 mg, 0.315 mmol, 74.9% yield) as a yellow solid. LCMS (ESI) [M+H]$^+$= 793.4.

Step 3: 7-Azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate

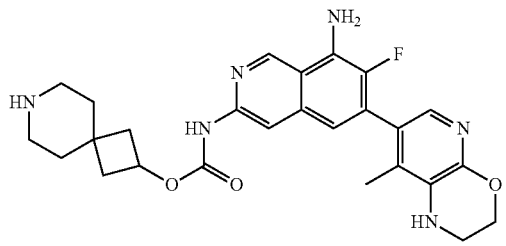 [SMILES: Cc1c(-c2cc3cc(NC(=O)OC4CC5(CCNCC5)C4)ncc3c(N)c2F)cnc2c1NCCO2]

337

To a solution of tert-butyl 7-[8-(tert-butoxycarbonylamino)-3-[[(7-tert-butoxycarbonyl-7-azaspiro[3.5]nonan-2-yl)oxycarbonylamino]-7-fluoro-6-isoquinolyl]-8-methyl-2,3-dihydropyrido[2,3-b][1,4]oxazine-1-carboxylate (490.0 mg, 0.62 mmol) in dichloromethane (5 mL) was added TFA (2 mL). The reaction was stirred at room temperature for 1 hour. The reaction mixture was concentrated under vacuum. The residue was dissolved in dichloromethane and adjusted to pH 8 with triethylamine. The residue was purified by reverse phase chromatography (acetonitrile 0-40, 0.1% NH₄HCO₃ in water) to afford 7-azaspiro[3.5]nonan-2-yl N-[8-amino-7-fluoro-6-(8-methyl-2,3-dihydro-1H-pyrido[2,3-b][1,4]oxazin-7-yl)-3-isoquinolyl]carbamate (100 mg, 0.20 mmol, 32.9% yield)] as a yellow solid. LCMS (ESI) [M+H]⁺=493.4.

Step 4: 7-(Oxetan-3-yl)-7-azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate

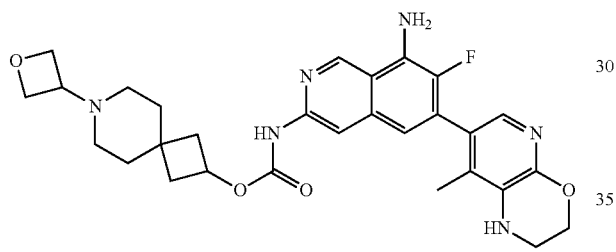

A solution of 7-azaspiro[3.5]nonan-2-yl N-[8-amino-7-fluoro-6-(8-methyl-2,3-dihydro-1H-pyrido[2,3-b][1,4]oxazin-7-yl)-3-isoquinolyl]carbamate (45.0 mg, 0.09 mmol), oxetan-3-one (65.83 mg, 0.91 mmol) and titanium tetraisopropanolate (103.8 mg, 0.37 mmol) in methyl alcohol (4 mL) was stirred at 60° C. for 1 hour. The reaction solution was cooled to room temperature. NaCNBH₃ (17.22 mg, 0.27 mmol) was added and stirred at room temperature for 1 hour. The reaction was quenched with water and extracted with dichloromethane. The organic layers were combined, dried over sodium sulfate and concentrated under vacuum. The residue was purified by Prep-HPLC (Column: X Bridge Prep OBD C18 Column 30×150 mm 5 μm; Mobile Phase A: Water (10 mmol/L NH₄HCO₃), Mobile Phase B: MeOH; Flow rate: 60 mL/min; Gradient: 38% B to 58% B in 7 min) to give [7-(oxetan-3-yl)-7-azaspiro[3.5]nonan-2-yl]N-[8-amino-7-fluoro-6-(8-methyl-2,3-dihydro-1H-pyrido[2,3-b][1,4]oxazin-7-yl)-3-isoquinolyl]carbamate (15.5 mg, 0.0283 mmol, 30.9% yield) as a light yellow solid. LCMS (ESI) [M+H]⁺=549.4, R$_T$=1.752 min., Method J. ¹H NMR (300 MHz, DMSO-d₆) δ 10.07 (s, 1H), 9.33 (s, 1H), 7.95 (s, 1H), 7.33 (s, 1H), 6.83 (d, J=6.2 Hz, 1H), 6.22 (s, 2H), 5.69 (s, 1H), 4.98 (t, J=7.1 Hz, 1H), 4.51 (t, J=6.4 Hz, 2H), 4.41 (d, J=5.9 Hz, 2H), 4.29 (s, 2H), 3.32 (s, 3H), 2.34-2.20 (m, 3H), 2.11 (s, 3H), 1.92 (d, J=1.6 Hz, 3H), 1.81 (s, 2H), 1.60-1.56 (m, 4H).

338

Example 136

[(3S,4S)-1,4-Dimethylpyrrolidin-3-yl]N-[8-amino-7-fluoro-6-(8-methyl-2,3-dihydro-1H-pyrido[2,3-b][1,4]oxazin-7-yl)-3-isoquinolyl]carbamate and [(3R,4R)-1,4-Dimethylpyrrolidin-3-yl]N-[8-amino-7-fluoro-6-(8-methyl-2,3-dihydro-1H-pyrido[2,3-b][1,4]oxazin-7-yl)-3-isoquinolyl]carbamate (Compound 442a and Compound 442b)

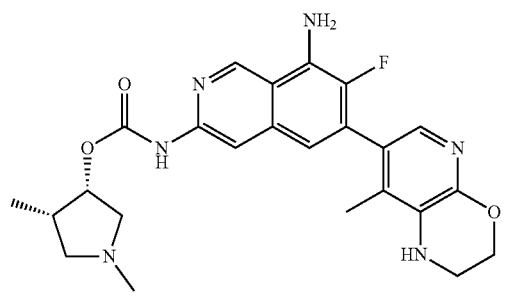

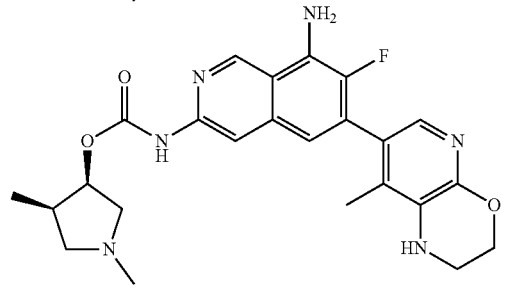

Step 1: (±)-cis-tert-Butyl 7-[3-[[1-tert-butoxycarbonyl-4-methyl-pyrrolidin-3-yl]oxycarbonylamino]-8-chloro-7-fluoro-6-isoquinolyl]-8-methyl-2,3-dihydropyrido[2,3-b][1,4]oxazine-1-carboxylate

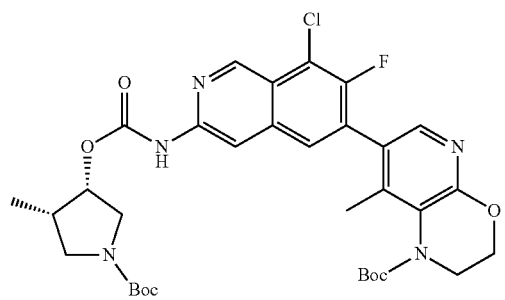

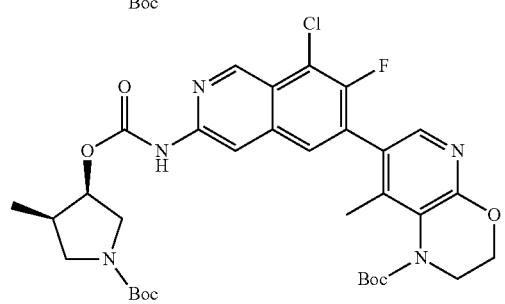

Under nitrogen, to a solution of tert-butyl 7-(3-amino-8-chloro-7-fluoro-6-isoquinolyl)-8-methyl-2,3-dihydropyrido[2,3-b][1,4]oxazine-1-carboxylate (400.0 mg, 0.90 mmol) and tert-butyl (±)-cis-3-hydroxy-4-methyl-pyrrolidine-1-carboxylate (361.0 mg, 1.79 mmol) and DIEA (580.0 mg, 4.5 mmol) in dichloromethane (10 mL) was added triphosgene (186.0 mg, 0.63 mmol). The mixture was stirred at 0° C. for 1 hour. The reaction was then concentrated under vacuum and purified by flash chromatography on silica gel eluting with petroleum ether/ethyl acetate (71/29) to afford (±)-cis-tert-butyl 7-[3-[[1-tert-butoxycarbonyl-4-methyl-pyrrolidin-3-yl]oxycarbonylamino]-8-chloro-7-fluoro-6-isoquinolyl]-8-methyl-2,3-dihydropyrido[2,3-b][1,4]oxazine-1-carboxylate (580 mg, 0.86 mmol, 96% yield) as yellow oil. LCMS (ESI) [M+H]⁺=672.3.

Step 2: (±)-cis-tert-Butyl 7-[8-(tert-butoxycarbonylamino)-3-[[1-tert-butoxycarbonyl-4-methyl-pyrrolidin-3-yl]oxycarbonylamino]-7-fluoro-6-isoquinolyl]-8-methyl-2,3-dihydropyrido[2,3-b][1,4]oxazine-1-carboxylate

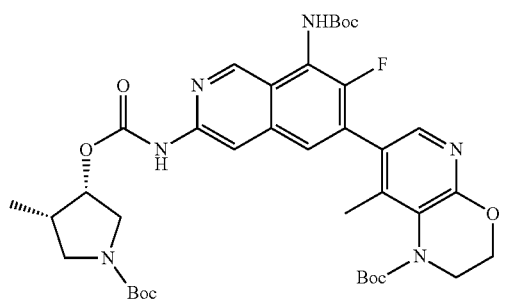

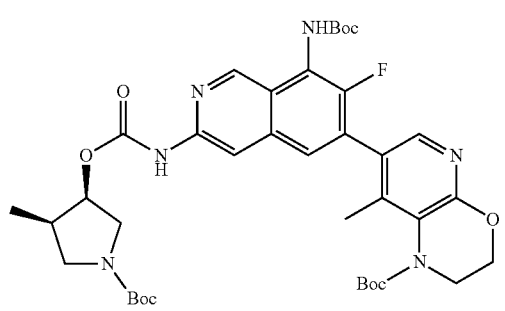 [SMILES: Cc1c(-c2cc3cc(NC(=O)O[C@@H]4CN(C(=O)OC(C)(C)C)C[C@H]4C)ncc3c(NC(=O)OC(C)(C)C)c2F)cnc2c1N(C(=O)OC(C)(C)C)CCO2]

Under nitrogen, a mixture of (±)-cis-tert-butyl 7-[3-[[1-tert-butoxycarbonyl-4-methyl-pyrrolidin-3-yl]oxycarbonylamino]-8-chloro-7-fluoro-6-isoquinolyl]-8-methyl-2,3-dihydropyrido[2,3-b][1,4]oxazine-1-carboxylate (227.0 mg, 0.34 mmol), NH₂Boc (988.0 mg, 8.44 mmol), Pd₂(dba)₃ CHCl₃ (70.0 mg, 0.07 mmol), BrettPhos (72.4 mg, 0.14 mmol) and Cs₂CO₃ (330.0 mg, 1.01 mmol) in 1,4-dioxane (5 mL) was stirred at 90° C. for 1 hour. The mixture was concentrated under vacuum and purified by flash chromatography on silica gel eluting with petroleum ether/ethyl acetate (35/65) to afford (±)-cis-tert-butyl 7-[8-(tert-butoxycarbonylamino)-3-[[1-tert-butoxycarbonyl-4-methyl-pyrrolidin-3-yl]oxycarbonylamino]-7-fluoro-6-isoquinolyl]-8-methyl-2,3-dihydropyrido[2,3-b][1,4]oxazine-1-carboxylate (254 mg, 0.34 mmol, 99% yield) as a yellow solid. LCMS (ESI) [M+H]⁺=753.4.

Step 3: (±)-cis-[4-Methylpyrrolidin-3-yl]N-[8-amino-7-fluoro-6-(8-methyl-2,3-dihydro-1H-pyrido[2,3-b][1,4]oxazin-7-yl)-3-isoquinolyl]carbamate

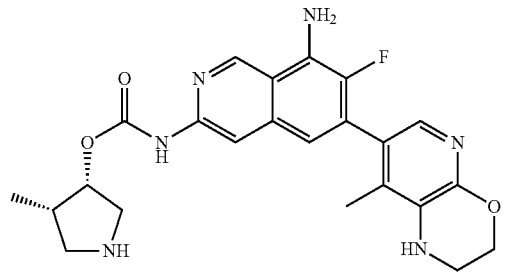

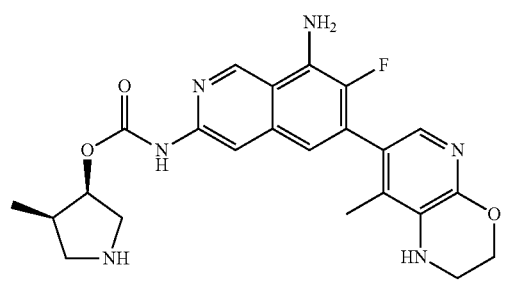 [SMILES: Cc1c(-c2cc3cc(NC(=O)O[C@@H]4CNC[C@H]4C)ncc3c(N)c2F)cnc2c1NCCO2]

A solution of (±)-cis-tert-butyl 7-[8-(tert-butoxycarbonylamino)-3-[[1-tert-butoxycarbonyl-4-methyl-pyrrolidin-3-yl]oxycarbonylamino]-7-fluoro-6-isoquinolyl]-8-methyl-2,3-dihydropyrido[2,3-b][1,4]oxazine-1-carboxylate (250.0 mg, 0.33 mmol) and TFA (1 mL) in dichloromethane (5 mL) was stirred at 25° C. for 1 hour. The reaction was concentrated under vacuum and purified by reverse phase chromatography eluting with ACN/water (10 mmol/L NH₄HCO₃) to afford (±)-cis-[4-methylpyrrolidin-3-yl]N-[8-amino-7-fluoro-6-(8-methyl-2,3-dihydro-1H-pyrido[2,3-b][1,4]oxazin-7-yl)-3-isoquinolyl]carbamate (80 mg, 0.18 mmol, 53% yield) as a light yellow solid. LCMS (ESI) [M+H]⁺= 453.2.

Step 4: [(3S,4S)-1,4-Dimethylpyrrolidin-3-yl]N-[8-amino-7-fluoro-6-(8-methyl-2,3-dihydro-1H-pyrido[2,3-b][1,4]oxazin-7-yl)-3-isoquinolyl]carbamate and [(3R,4R)-1,4-dimethylpyrrolidin-3-yl]N-[8-amino-7-fluoro-6-(8-methyl-2,3-dihydro-1H-pyrido[2,3-b][1,4]oxazin-7-yl)-3-isoquinolyl]carbamate

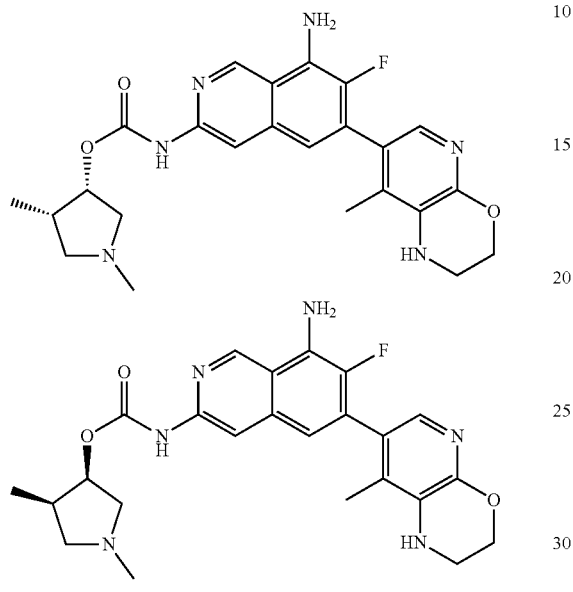

A solution of (±)-cis-[4-methylpyrrolidin-3-yl]N-[8-amino-7-fluoro-6-(8-methyl-2,3-dihydro-1H-pyrido[2,3-b][1,4]oxazin-7-yl)-3-isoquinolyl]carbamate (70.0 mg, 0.15 mmol) and formaldehyde (23.2 mg, 0.31 mmol) in methyl alcohol (5 mL) was stirred at 25° C. for 2 hours. Then NaBH$_4$ (11.7 mg, 0.31 mmol) was added and stirred at 25° C. for 1 hour. After concentration, the residue was purified by Prep-HPLC with (Column)(Bridge Prep OBD C18 Column 30×150 mm 5 μm; Water (10 mmol/L NH$_4$HCO$_3$): ACN=15% B to 26% B in 10 min; 60 mL/min) to give the racemic mixture of products. The racemic product was separated by Chiral-HPLC to afford two enantiomers. Relative stereochemistry as drawn. Absolute stereochemistry arbitrarily assigned.

Enantiomer 1 (Compound 442a) (13.5 mg, 0.029 mmol, 18.7% yield); R$_T$ 3.073 min (CHIRALPAK IG-3 0.46*5 cm; 3 μm; (Hex:DCM=3:1)(0.1% DEA):EtOH=50:50; 1.0 ml/min); LCMS(ESI): [M+H]$^+$=467.2, Rt=1.844 min; Method M. $^1$H NMR (300 MHz, methanol-d$_4$) δ 9.25 (s, 1H), 8.07 (s, 1H), 7.39 (s, 1H), 6.95 (d, J=6.2 Hz, 1H), 5.34-5.25 (m, 1H), 4.52-4.94 (m, 2H), 3.52-3.48 (m, 2H), 3.22-3.19 (m, 1H), 2.96-2.85 (m, 1H), 2.80-2.75 (m, 1H), 2.64-2.34 (m, 5H), 2.03 (s, 3H), 1.12 (d, J=6.7 Hz, 3H).

Enantiomer 2 (Compound 442b) (13.7 mg, 0.0294 mmol, 19% yield); R$_T$ 3.911 min (CHIRALPAK IG-3 0.46*5 cm; 3 μm; (Hex:DCM=3:1 with 0.1% DEA):EtOH=50:50; 1.0 ml/min). LCMS(ESI): [M+H]$^+$=467.2, Rt=1.844 min; Method M. $^1$H NMR (300 MHz, methanol-d$_4$) δ 9.25 (s, 1H), 8.07 (s, 1H), 7.39 (s, 1H), 6.95 (d, J=6.2 Hz, 1H), 5.34-5.25 (m, 1H), 4.52-4.94 (m, 2H), 3.52-3.48 (m, 2H), 3.22-3.19 (m, 1H), 2.96-2.85 (m, 1H), 2.80-2.75 (m, 1H), 2.64-2.34 (m, 5H), 2.03 (s, 3H), 1.12 (d, J=6.7 Hz, 3H).

Example 137

(3S,4R)-1,4-Dimethylpyrrolidin-3-yl (8-amino-7-fluoro-6-(8-methyl-2,3-dihydro-1H-pyrido[2,3-b][1,4]oxazin-7-yl)isoquinolin-3-yl)carbamate and (3R,4S)-1,4-Dimethylpyrrolidin-3-yl (8-amino-7-fluoro-6-(8-methyl-2,3-dihydro-1H-pyrido[2,3-b][1,4]oxazin-7-yl)isoquinolin-3-yl)carbamate (Compound 442c and Compound 442d)

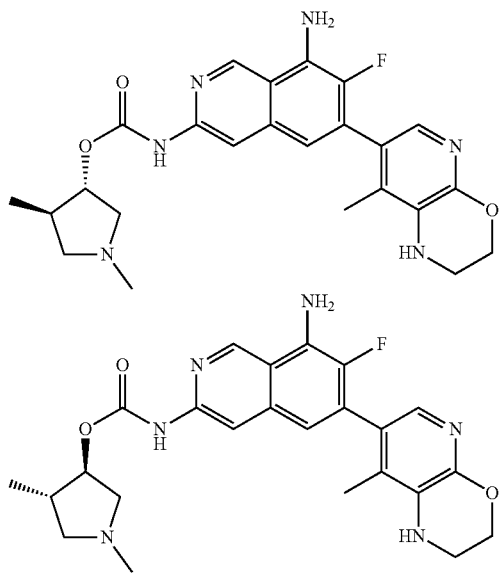

Step 1: (±)-tert-Butyl 7-[8-(tert-butoxycarbonylamino)-3-[[(trans)-1-tert-butoxycarbonyl-4-methyl-pyrrolidin-3-yl]oxycarbonylamino]-7-fluoro-6-isoquinolyl]-8-methyl-2,3-dihydropyrido[2,3-b][1,4]oxazine-1-carboxylate

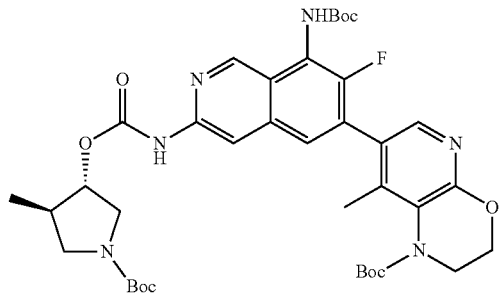

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (200 mg, 0.38 mmol) and trans-tert-butyl 3-hydroxy-4-methyl-pyrrolidine-1-carboxylate (160 mg, 0.79 mmol) in dichloromethane (350 mL) was added DIEA (500 mg, 3.88 mmol) at room temperature. Then triphosgene (67 mg, 0.23 mmol) was added and stirred at 0° C. for 2 hours. The residue was purified by flash chromatography on silica gel eluting with petroleum ether/ethyl acetate (1/1) to afford (±)-tert-butyl 7-[8-(tert-butoxycarbonylamino)-3-[[(trans)-1-tert-butoxycarbonyl-4-methyl-pyrrolidin-3-yl]oxycarbonylamino]-7-fluoro-6-isoquinolyl]-8-methyl-2,3-dihydropyrido[2,3-b][1,4]oxazine-1-carboxylate (160 mg, 0.212 mmol, 55.9% yield) as a yellow solid. LCMS (ESI) [M+H]⁺=753.

Step 2: (±)-[(trans)-4-Methylpyrrolidin-3-yl]N-[8-amino-7-fluoro-6-(8-methyl-2,3-dihydro-1H-pyrido[2,3-b][1,4]oxazin-7-yl)-3-isoquinolyl]carbamate

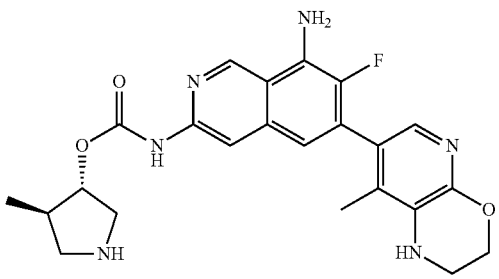

To a solution of (±)-tert-butyl 7-[8-(tert-butoxycarbonylamino)-3-[[(trans)-1-tert-butoxycarbonyl-4-methyl-pyrrolidin-3-yl]oxycarbonylamino]-7-fluoro-6-isoquinolyl]-8-methyl-2,3-dihydropyrido[2,3-b][1,4]oxazine-1-carboxylate (160 mg, 0.21 mmol) in dichloromethane (10 mL) was added 2,2,2-trifluoroacetic acid (2 mL) at room temperature. The reaction was stirred for 2 h at 25° C. The reaction solution was concentrated under vacuum and the crude product would be directly used in the next step without purification. LCMS (ESI) [M+H]⁺=453.

Step 3: (3S,4R)-1,4-Dimethylpyrrolidin-3-yl (8-amino-7-fluoro-6-(8-methyl-2,3-dihydro-1H-pyrido[2,3-b][1,4]oxazin-7-yl)isoquinolin-3-yl)carbamate and (3R,4S)-1,4-Dimethylpyrrolidin-3-yl (8-amino-7-fluoro-6-(8-methyl-2,3-dihydro-1H-pyrido[2,3-b][1,4]oxazin-7-yl)isoquinolin-3-yl)carbamate

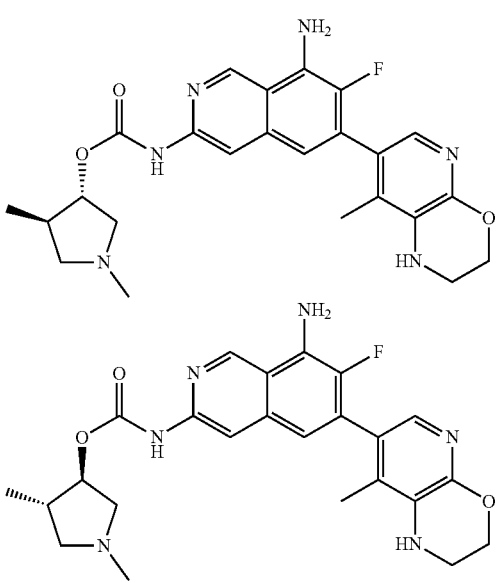

To a solution of (±)-[(trans)-4-methylpyrrolidin-3-yl]N-[8-amino-7-fluoro-6-(8-methyl-2,3-dihydro-1H-pyrido[2,3-b][1,4]oxazin-7-yl)-3-isoquinolyl]carbamate (160 mg, 0.35 mmol) in methyl alcohol (10 mL) was added formaldehyde (80 mg, 1.07 mmol) at 25° C. The reaction was stirred for 1 h at 25° C. Then NaBH₄ (40 mg, 1.05 mmol) was added and stirred at 25° C. for 1 hour. The reaction was quenched with water and then concentrated under vacuum. The residue was purified by Prep-HPLC (Column: X Bridge Prep OBD C18 Column 30×150 mm 5 μm; Mobile Phase A: Water (10 mmol/L NH₄HCO₃), Mobile Phase B: ACN; Flow rate: 60 mL/min; Gradient: 19% B to 22% B in 12 min) to give the racemic mixture of products. The racemic was separated by Chiral-HPLC (Column: CHIRALPAK IG, 2.0 cm I.D*25 cm L (5 μm); Mobile Phase A: Hex:DCM=3:1 (10 mM NH₃-MeOH), Mobile Phase B: EtOH; Flow rate: 20 mL/min; Gradient: 50 B to 50 B in 28 min) to give two enantiomers. Relative stereochemistry are as drawn. Absolute stereochemistry was arbitrarily assigned.

Enantiomer 1 (Compound 442c) (23.1 mg, 0.0495 mmol, 14% yield); R_T 2.590 min (CHIRALPAK IG-3 0.46*5 cm; 3 μm; (Hex:DCM=3:1 with 0.1% DEA): EtOH=50:50; 1 mL/min). LCMS(ESI) [M+H]⁺=467.3, R_T 1.558 min; Method J. ¹H NMR (400 MHz, DMSO-d₆) δ 10.10 (s, 1H), 9.33 (s, 1H), 7.98 (s, 1H), 7.33 (s, 1H), 6.85 (d, J=6.2 Hz, 1H), 6.22 (s, 2H), 5.69 (d, J=3.1 Hz, 1H), 4.69 (dt, J=6.0, 2.9 Hz, 1H), 4.29 (t, J=4.3 Hz, 2H), 3.41-3.30 (m, 2H), 2.95 (t, J=8.1 Hz, 1H), 2.77-2.69 (m, 1H), 2.64 (dd, J=10.9, 6.3 Hz, 1H), 2.24 (s, 3H), 2.28-2.17 (m, 1H), 1.95-1.86 (m, 4H), 1.11 (d, J=7.1 Hz, 3H).

Enantiomer 2 (Compound 442d) (23.8 mg, 0.0510 mmol, 14.4% yield). R_T 5.364 min (CHIRALPAK IG-3 0.46*5 cm; 3 μm. (Hex:DCM=3:1 with 0.1% DEA):EtOH=50:50; 1 mL/min). LCMS(ESI) [M+H]⁺=467.3, R_T 1.885 min., Method J. ¹H NMR (400 MHz, DMSO-d₆) δ 10.10 (s, 1H), 9.33 (s, 1H), 7.98 (s, 1H), 7.33 (s, 1H), 6.85 (d, J=6.2 Hz, 1H), 6.22 (s, 2H), 5.69 (d, J=3.1 Hz, 1H), 4.69 (dt, J=6.0, 2.9 Hz, 1H), 4.29 (t, J=4.3 Hz, 2H), 3.41-3.30 (m, 2H), 2.95 (t, J=8.1 Hz, 1H), 2.77-2.69 (m, 1H), 2.64 (dd, J=10.9, 6.3 Hz, 1H), 2.24 (s, 3H), 2.28-2.17 (m, 1H), 1.95-1.86 (m, 4H), 1.11 (d, J=7.1 Hz, 3H).

Example 138

2-(Oxetan-3-yl)-2-azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate (Compound 443)

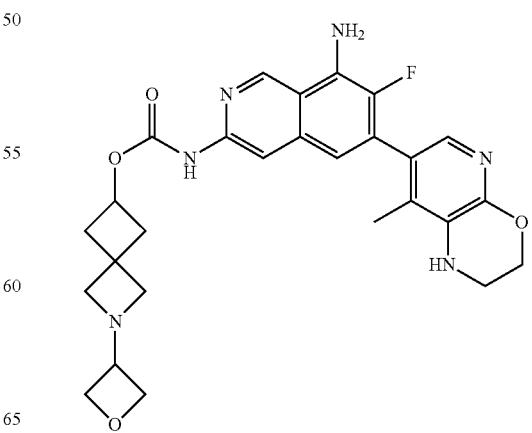

Step 1: tert-Butyl 7-(3-((((2-(tert-butoxycarbonyl)-2-azaspiro[3.3]heptan-6-yl)oxy)carbonyl)amino)-8-chloro-7-fluoroisoquinolin-6-yl)-8-methyl-2,3-dihydro-1H-pyrido[2,3-b][1,4]oxazine-1-carboxylate

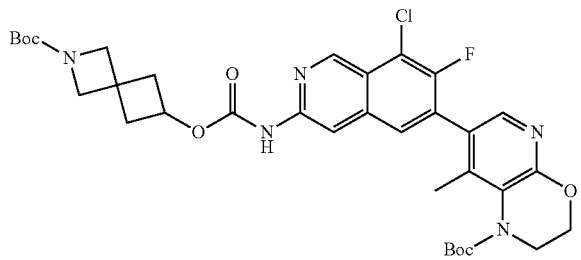 [SMILES: Cc1c(-c2cc3cc(NC(=O)OC4CC5(C4)CN(C(=O)OC(C)(C)C)C5)ncc3c(Cl)c2F)cnc2c1N(C(=O)OC(C)(C)C)CCO2]

Under nitrogen, a solution of tert-butyl 7-(3-amino-8-chloro-7-fluoro-6-isoquinolyl)-8-methyl-2,3-dihydropyrido[2,3-b][1,4]oxazine-1-carboxylate (200.0 mg, 0.45 mmol), tert-butyl 6-hydroxy-2-azaspiro[3.3]heptane-2-carboxylate (195.0 mg, 0.91 mmol) and DIEA (285.0 mg, 2.21 mmol) in dichloromethane (2 mL) was stirred for 10 min at 0° C. Then triphosgene (95 mg, 0.32 mmol) was added. The reaction was stirred at 0° C. for 2 hours. The mixture was concentrated under vacuum and purified by flash chromatography on silica gel eluting with petroleum ether/ethyl acetate (60/40) to afford tert-butyl 7-[3-[(2-tert-butoxycarbonyl-2-azaspiro[3.3]heptan-6-yl)oxycarbonylamino]-8-chloro-7-fluoro-6-isoquinolyl]-8-methyl-2,3-dihydropyrido[2,3-b][1,4]oxazine-1-carboxylate (190 mg, 0.2777 mmol, 61.8% yield) as a yellow solid. LCMS (ESI) [M+H]$^+$=684.

Step 2: tert-Butyl 7-(3-((((2-(tert-butoxycarbonyl)-2-azaspiro[3.3]heptan-6-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

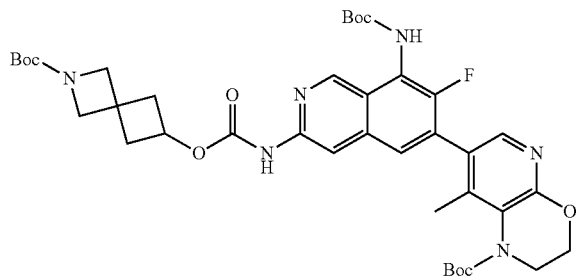 [SMILES: Cc1c(-c2cc3cc(NC(=O)OC4CC5(C4)CN(C(=O)OC(C)(C)C)C5)ncc3c(NC(=O)OC(C)(C)C)c2F)cnc2c1N(C(=O)OC(C)(C)C)CCO2]

A mixture of tert-butyl 7-[3-[(2-tert-butoxycarbonyl-2-azaspiro[3.3]heptan-6-yl)oxycarbonylamino]-8-chloro-7-fluoro-6-isoquinolyl]-8-methyl-2,3-dihydropyrido[2,3-b][1,4]oxazine-1-carboxylate (190.0 mg, 0.28 mmol) in dichloromethane (2 mL) and Pd$_2$(dba)$_3$CHCl$_3$ (1 mL, 0.060 mmol) was stirred at room temperature for 2 hours. The reaction was concentrated under vacuum and purified by flash chromatography on silica gel eluting with petroleum ether/ethyl acetate (20/80) to afford tert-butyl 7-[8-(tert-butoxycarbonylamino)-3-[(2-tert-butoxycarbonyl-2-azaspiro[3.3]heptan-6-yl)oxycarbonylamino]-7-fluoro-6-isoquinolyl]-8-methyl-2,3-dihydropyrido[2,3-b][1,4]oxazine-1-carboxylate (190 mg, 0.248 mmol, 89.5% yield) as a yellow solid. LCMS (ESI) [M+H]$^+$=765.

Step 3: 2-Azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate

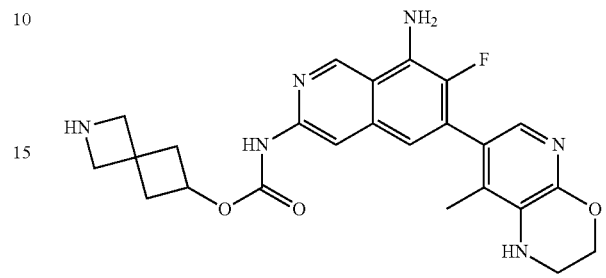

A solution of tert-butyl 7-[8-(tert-butoxycarbonylamino)-3-[(2-tert-butoxycarbonyl-2-azaspiro[3.3]heptan-6-yl)oxycarbonylamino]-7-fluoro-6-isoquinolyl]-8-methyl-2,3-dihydropyrido[2,3-b][1,4]oxazine-1-carboxylate (190.0 mg, 0.25 mmol) in dichloromethane (5 mL) and TFA (5 mL) was stirred at room temperature for 2 hours. The reaction was concentrated under vacuum and purified by reverse phase chromatography with CH$_3$CN/H$_2$O (15/85) to afford 2-azaspiro[3.3]heptan-6-yl N-[8-amino-7-fluoro-6-(8-methyl-2,3-dihydro-1H-pyrido[2,3-b][1,4]oxazin-7-yl)-3-isoquinolyl]carbamate (90 mg, 0.194 mmol, 78% yield) as a yellow solid. LCMS (ESI) [M+H]$^+$=465.

Step 4: 2-(Oxetan-3-yl)-2-azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate

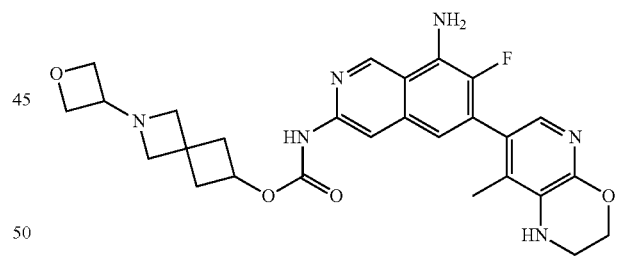

A solution of 2-azaspiro[3.3]heptan-6-yl N-[8-amino-7-fluoro-6-(8-methyl-2,3-dihydro-1H-pyrido[2,3-b][1,4]oxazin-7-yl)-3-isoquinolyl]carbamate (46.0 mg, 0.10 mmol), 3-oxetanone (71.0 mg, 0.99 mmol) and titanium tetraisopropanolate (30.0 mg, 0.11 mmol) in methyl alcohol (2 mL) was stirred at room temperature for 1 hour. Then NaCNBH$_3$ (18.0 mg, 0.29 mmol) was added. The reaction was stirred at room temperature for 1 hour. The resulting mixture was concentrated under vacuum and purified by reverse phase flash chromatography (ACN/water (0.1% FA)) to afford [2-(oxetan-3-yl)-2-azaspiro[3.3]heptan-6-yl] N-[8-amino-7-fluoro-6-(8-methyl-2,3-dihydro-1H-pyrido[2,3-b][1,4]oxazin-7-yl)-3-isoquinolyl]carbamate (40 mg, 0.0768 mmol, 77.6% yield) as a yellow solid. LCMS (ESI) [M+H]$^+$=521.2, R$_T$ 0.887 min., Method L. $^1$H NMR (300

MHz, DMSO-d$_6$) δ 10.08 (s, 1H), 9.32 (s, 1H), 7.95 (s, 1H), 7.32 (s, 1H), 6.83-6.80 (d, J=6.2 Hz, 1H), 6.21 (s, 2H), 5.68 (s, 1H), 4.92-4.80 (m, 1H), 4.55-4.46 (t, J=6 Hz, 2H), 4.34-4.24 (m, 4H), 3.68-3.56 (m, 1H), 3.41-3.46 (m, 2H), 3.25-3.15 (d, J=12 Hz, 4H), 2.61-2.52 (m, 2H), 2.25-2.13 (m, 2H), 1.82 (s, 3H).

Example 139

(R)-1-Methyl-5-oxopyrrolidin-3-yl (8-amino-6-(8-ethyl-2,3-dihydro-1H-pyrido[2,3-b][1,4]oxazin-7-yl)-7-fluoroisoquinolin-3-yl)carbamate and (S)-1-Methyl-5-oxopyrrolidin-3-yl (8-amino-6-(8-ethyl-2,3-dihydro-1H-pyrido[2,3-b][1,4]oxazin-7-yl)-7-fluoroisoquinolin-3-yl)carbamate (Compound 444a and Compound 444b)

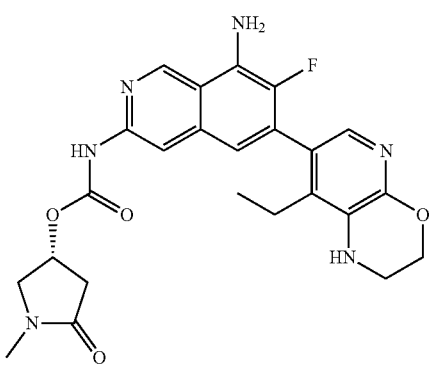

Step 1: 5-Bromo-4-ethyl-pyridin-2-amine

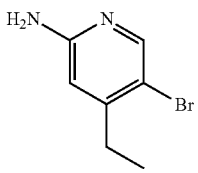

To a solution of 2-amino-4-ethylpyridine (20 g, 163.71 mmol) and NH$_4$OAc (1.3 g, 16.88 mmol) in acetonitrile (500 mL) was added N-bromosuccinimide (30.6 g, 171.91 mmol). The mixture was stirred at 25° C. for 1 hour. The resulting mixture was concentrated under vacuum and diluted with water. The resulting solution was extracted with ethyl acetate. The organic layers were combined, dried over anhydrous sodium sulfate and concentrated under vacuum. The residue was purified by flash chromatography on silica gel eluting with dichloromethane/methanol (98:2) to afford 5-bromo-4-ethyl-pyridin-2-amine (22 g, 109.42 mmol, 66.8% yield) as a yellow solid. LCMS (ESI) [M+H]$^+$=200.9.

Step 2: 5-Bromo-4-ethyl-3-nitro-pyridin-2-ol


A solution of 5-bromo-4-ethyl-pyridin-2-amine (17.5 g, 87.04 mmol) in H$_2$SO$_4$ (200 mL, 87.04 mmol) was stirred at 25° C. for 15 min. HNO$_3$ (9.1 mL, 130.56 mmol) was added at 0° C. The reaction was then stirred at 25° C. for 3 h. The reaction mixture was diluted with ice/water and extracted with ethyl acetate. The organic layers were combined, dried over anhydrous sodium sulfate and concentrated under vacuum. The residue was purified by flash chromatography on silica gel eluting with dichloromethane/methanol (98:2) to afford 5-bromo-4-ethyl-3-nitro-pyridin-2-ol (10.2 g, 41.29 mmol, 47.4% yield) as a yellow solid. LCMS (ESI) [M+H]$^+$=247.1.

Step 3: 3-Amino-5-bromo-4-ethyl-pyridin-2-ol


A mixture of 5-bromo-4-ethyl-3-nitro-pyridin-2-ol (10.2 g, 41.29 mmol), iron (18.5 g, 330.36 mmol) and NH$_4$Cl (17.8 g, 329.63 mmol) in ethanol (160 mL) and water (160 mL) was stirred at 90° C. for 2 hours. The reaction was cooled to room temperature and then filtered. The filtrate was concentrated under vacuum. The residue was washed with water to afford 3-amino-5-bromo-4-ethyl-pyridin-2-ol (8.1 g, 37.32 mmol, 90.4% yield) as a brown solid. LCMS (ESI) [M+H]$^+$=217.1.

Step 4: 7-Bromo-8-ethyl-1H-pyrido[2,3-b][1,4]oxazin-2-one

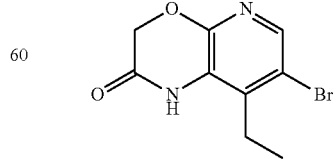

A solution of 3-amino-5-bromo-4-ethyl-pyridin-2-ol (8.1 g, 37.32 mmol) and K$_2$CO$_3$ (15.4 g, 111.59 mmol) in N,N-dimethylformamide (120 mL) was stirred at 25° C. for 15 mins. Then chloroacetyl chloride (5.5 g, 48.7 mmol) was added at 0° C. The reaction was stirred at 25° C. for 1 hour and 90° C. for 2 hours. The solid was removed by filtration. The filtrate was concentrated under vacuum and purified by flash chromatography on silica gel eluting with dichloromethane/methanol (98:2) to afford 7-bromo-8-ethyl-1H-pyrido[2,3-b][1,4]oxazin-2-one (5 g, 19.45 mmol, 52.1% yield) as a light yellow solid. LCMS (ESI) [M+H]$^+$=257.2.

Step 5: 7-Bromo-8-ethyl-2,3-dihydro-1H-pyrido[2,3-b][1,4]oxazine

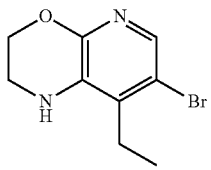

Under nitrogen, to a solution of 7-bromo-8-ethyl-1H-pyrido[2,3-b][1,4]oxazin-2-one (1.4 g, 5.45 mmol) in tetrahydrofuran (50 mL) was added BH$_3$.THF (16.5 mL, 16.34 mmol) at 0° C. The resulting solution was stirred for 1 hour at 60° C. The reaction was quenched with MeOH and adjusted to pH 2 with HCl (1N). The reaction was stirred at 0° C. for 0.5 hour. The reaction mixture was then adjusted to pH 8 with NH$_3$.H$_2$O at 0° C. The solution was diluted with water and extracted with ethyl acetate. The organic layers were combined, dried over anhydrous sodium sulfate and concentrated under vacuum. The residue was purified by flash chromatography on silica gel eluting with dichloromethane/methanol (98:2) to afford 7-bromo-8-ethyl-2,3-dihydro-1H-pyrido[2,3-b][1,4]oxazine (1.1 g, 4.525 mmol, 83.1% yield) as a light yellow solid. LCMS (ESI) [M+H]$^+$=243.2.

Step 6: tert-Butyl 7-bromo-8-ethyl-2,3-dihydropyrido[2,3-b][1,4]oxazine-1-carboxylate

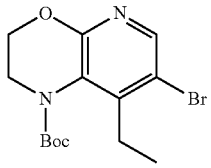

Under nitrogen, to a solution of 7-bromo-8-ethyl-2,3-dihydro-1H-pyrido[2,3-b][1,4]oxazine (1.3 g, 5.35 mmol) in tetrahydrofuran (30 mL) was added NaHMDS (5.6 mL, 10.93 mmol, 2 mol/L in THF) at 0° C. The resulting solution was stirred for 1 hour at 0° C. Then (Boc)$_2$O (1.8 g, 8.26 mmol) was added at 0° C. The mixture was stirred at 25° C. for 3 hours. The reaction was quenched by adding MeOH and concentrated under vacuum. The residue was purified by flash chromatography on silica gel eluting with petroleum ether/ethyl acetate (3/1) to afford tert-butyl 7-bromo-8-ethyl-2,3-dihydropyrido[2,3-b][1,4]oxazine-1-carboxylate (1.6 g, 4.66 mmol, 87.2% yield) as a colorless oil. LCMS (ESI) [M+H]$^+$=343.1.

Step 7: tert-Butyl 8-ethyl-7-(4,4,5,5-tetramethyl-1,3,2-dioxaborolan-2-yl)-2,3-dihydropyrido[2,3-b][1,4]oxazine-1-carboxylate

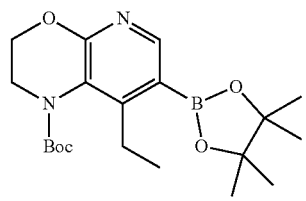 [SMILES: CCc1c(B2OC(C)(C)C(C)(C)O2)cnc2c1N(C(=O)OC(C)(C)C)CCO2]

Under nitrogen, a mixture of bis(pinacolato)diboron (2.3 g, 9.06 mmol), tert-butyl 7-bromo-8-ethyl-2,3-dihydropyrido[2,3-b][1,4]oxazine-1-carboxylate (1.5 g, 4.37 mmol), Pd(dppf)Cl$_2$ (640.0 mg, 0.87 mmol) and KOAc (1.3 g, 13.16 mmol) in 1,4-dioxane (50 mL) was stirred for 2 hours at 90° C. The reaction mixture was filtered and concentrated under vacuum. The residue was purified by flash chromatography on silica gel eluting with petroleum ether/ethyl acetate (4:1) to afford tert-butyl 8-ethyl-7-(4,4,5,5-tetramethyl-1,3,2-dioxaborolan-2-yl)-2,3-dihydropyrido[2,3-b][1,4]oxazine-1-carboxylate (2.6 g, 6.66 mmol) as a yellow oil. LCMS (ESI) [M+H]$^+$=391.3.

Step 8: tert-Butyl 7-(3-amino-8-chloro-7-fluoro-6-isoquinolyl)-8-ethyl-2,3-dihydropyrido[2,3-b][1,4]oxazine-1-carboxylate

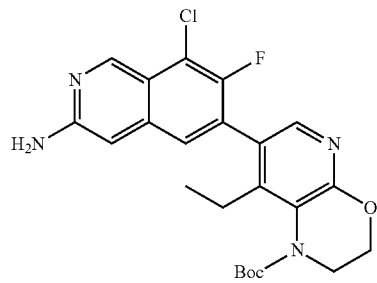 [SMILES: CCc1c(-c2cc3cc(N)ncc3c(Cl)c2F)cnc2c1N(C(=O)OC(C)(C)C)CCO2]

Under nitrogen, a mixture of tert-butyl 8-ethyl-7-(4,4,5,5-tetramethyl-1,3,2-dioxaborolan-2-yl)-2,3-dihydropyrido[2,3-b][1,4]oxazine-1-carboxylate (2.7 g, 6.92 mmol), 8-chloro-7-fluoro-6-iodo-isoquinolin-3-amine (1.1 g, 3.41 mmol), Pd(dppf)Cl$_2$ (499.1 mg, 0.68 mmol) and K$_2$CO$_3$ (1.4 g, 10.14 mmol) in 1,4-dioxane (20 mL) and water (2 mL) was stirred at 60° C. for 16 hours. The reaction was concentrated under vacuum and purified by flash chromatography on silica gel eluting with dichloromethane/methanol (97:3) to afford tert-butyl 7-(3-amino-8-chloro-7-fluoro-6-isoquinolyl)-8-ethyl-2,3-dihydropyrido[2,3-b][1,4]oxazine-1-carboxylate (1 g, 2.18 mmol, 63.9% yield) as a yellow solid. LCMS85 (ESI) [M+H]$^+$=459.3.

Step 9: tert-Butyl 7-[8-chloro-3-(1,3-dioxoisoindolin-2-yl)-7-fluoro-6-isoquinolyl]-8-ethyl-2,3-dihydropyrido[2,3-b][1,4]oxazine-1-carboxylate

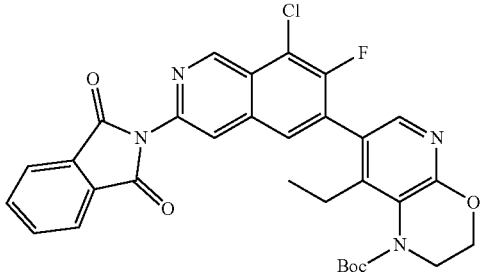 [SMILES: CCc1c(-c2cc3cc(N4C(=O)c5ccccc5C4=O)ncc3c(Cl)c2F)cnc2c1N(C(=O)OC(C)(C)C)CCO2]

Under nitrogen, a solution of tert-butyl 7-(3-amino-8-chloro-7-fluoro-6-isoquinolyl)-8-ethyl-2,3-dihydropyrido[2,3-b][1,4]oxazine-1-carboxylate (1.2 g, 2.61 mmol) and phthalicanhydride (0.6 g, 4.05 mmol) in toluene (20 mL) was stirred for 3 hours at 100° C. The reaction was concentrated under vacuum. The residue was purified by flash chromatography on silica gel eluting with petroleum ether/ethyl acetate (1:1) to afford tert-butyl 7-[8-chloro-3-(1,3-dioxoisoindolin-2-yl)-7-fluoro-6-isoquinolyl]-8-ethyl-2,3-dihydropyrido[2,3-b][1,4]oxazine-1-carboxylate (888 mg, 1.51 mmol, 57.7% yield) as a yellow solid. LCMS (ESI) [M+H]$^+$=589.3.

Step 10: tert-Butyl 7-(8-((tert-butoxycarbonyl)amino)-3-(1,3-dioxoisoindolin-2-yl)-7-fluoroisoquinolin-6-yl)-8-ethyl-2,3-dihydro-1H-pyrido[2,3-b][1,4]oxazine-1-carboxylate

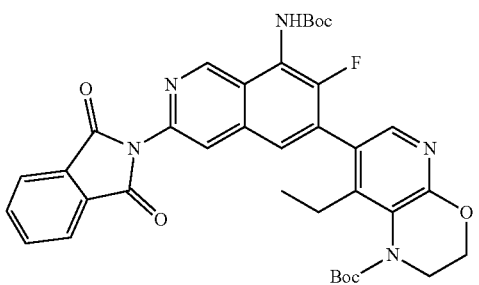 [SMILES: CCc1c(-c2cc3cc(N4C(=O)c5ccccc5C4=O)ncc3c(NC(=O)OC(C)(C)C)c2F)cnc2c1N(C(=O)OC(C)(C)C)CCO2]

Under nitrogen, a mixture of tert-butyl 7-[8-chloro-3-(1,3-dioxoisoindolin-2-yl)-7-fluoro-6-isoquinolyl]-8-ethyl-2,3-dihydropyrido[2,3-b][1,4]oxazine-1-carboxylate (800 mg, 1.36 mmol), NH$_2$Boc (4767.3 mg, 40.74 mmol), Pd$_2$(dba)$_3$·CHCl$_3$ (281.2 mg, 0.28 mmol), Brettphos (291.2 mg, 0.54 mmol) and Cs$_2$CO$_3$ (1328.4 mg, 4.08 mmol) in 1,4-dioxane (52 mL) was stirred for 45 minutes at 90° C. The reaction was concentrated under vacuum to use directly next step without purification. LCMS (ESI) [M+H]$^+$=670.4.

Step 11: tert-Butyl 7-[3-amino-8-(tert-butoxycarbonylamino)-7-fluoro-6-isoquinolyl]-8-ethyl-2,3-dihydropyrido[2,3-b][1,4]oxazine-1-carboxylate

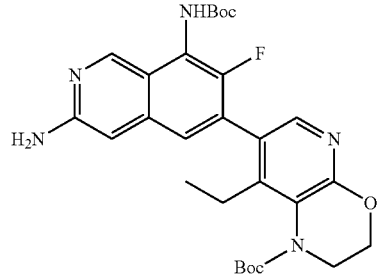

Under nitrogen, to a solution of tert-butyl 7-[8-(tert-butoxycarbonylamino)-3-(1,3-dioxoisoindolin-2-yl)-7-fluoro-6-isoquinolyl]-8-ethyl-2,3-dihydropyrido[2,3-b][1,4]oxazine-1-carboxylate (455.0 mg, 0.68 mmol) in methyl alcohol (30 mL) was added N$_2$H$_4$·H$_2$O (340.2 mg, 6.80 mmol) at 25° C. The resulting solution was stirred for 1 hour at 40° C. and then concentrated under vacuum. The reaction mixture was diluted with water and extracted with ethyl acetate. The organic layers were combined, dried over anhydrous sodium sulfate and concentrated under vacuum. The residue was purified by flash chromatography on silica gel eluting with dichloromethane/methanol (94:6) to afford tert-butyl 7-[3-amino-8-(tert-butoxycarbonylamino)-7-fluoro-6-isoquinolyl]-8-ethyl-2,3-dihydropyrido[2,3-b][1,4]oxazine-1-carboxylate (162 mg, 0.30 mmol, 44.2% yield) as a yellow solid. LCMS (ESI) [M+H]$^+$=540.4.

Step 12: tert-Butyl 7-[8-(tert-butoxycarbonylamino)-7-fluoro-3-[(1-methyl-5-oxo-pyrrolidin-3-yl)oxycarbonylamino]-6-isoquinolyl]-8-ethyl-2,3-dihydropyrido[2,3-b][1,4]oxazine-1-carboxylate

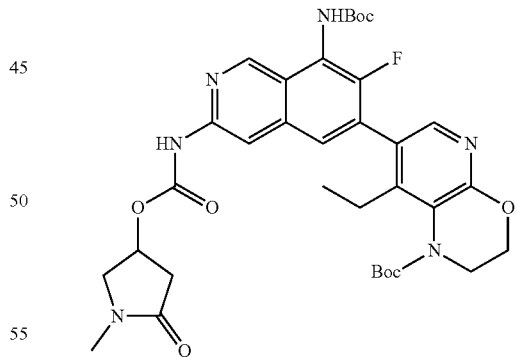

To a solution of 4-hydroxy-1-methyl-pyrrolidin-2-one (405.4 mg, 3.52 mmol) and tert-butyl 7-[3-amino-8-(tert-butoxycarbonylamino)-7-fluoro-6-isoquinolyl]-8-ethyl-2,3-dihydropyrido[2,3-b][1,4]oxazine-1-carboxylate (380 mg, 0.70 mmol) in dichloromethane (16 mL) was added DIEA (910.2 mg, 7.04 mmol) and triphosgene (313.5 mg, 1.06 mmol) at 0° C. The reaction was stirred at 25° C. for 2 hours. The reaction was quenched with water and extracted with dichloromethane. The organic layers were combined, dried over anhydrous sodium sulfate and concentrated under vacuum. The residue was purified by flash chromatography on silica gel eluting with dichloromethane/methanol (96:4) to afford tert-butyl 7-[8-(tert-butoxycarbonylamino)-7-fluoro-3-[(1-methyl-5-oxo-pyrrolidin-3-yl)oxycarbonylamino]-6-isoquinolyl]-8-ethyl-2,3-dihydropyrido[2,3-b][1,4]oxazine-1-carboxylate (230 mg, 0.34 mmol, 48% yield) as a yellow solid. LCMS (ESI) [M+H]$^+$=681.4.

Step 13: (R)-1-Methyl-5-oxopyrrolidin-3-yl (8-amino-6-(8-ethyl-2,3-dihydro-1H-pyrido[2,3-b][1,4]oxazin-7-yl)-7-fluoroisoquinolin-3-yl)carbamate and (S)-1-Methyl-5-oxopyrrolidin-3-yl (8-amino-6-(8-ethyl-2,3-dihydro-1H-pyrido[2,3-b][1,4]oxazin-7-yl)-7-fluoroisoquinolin-3-yl)carbamate

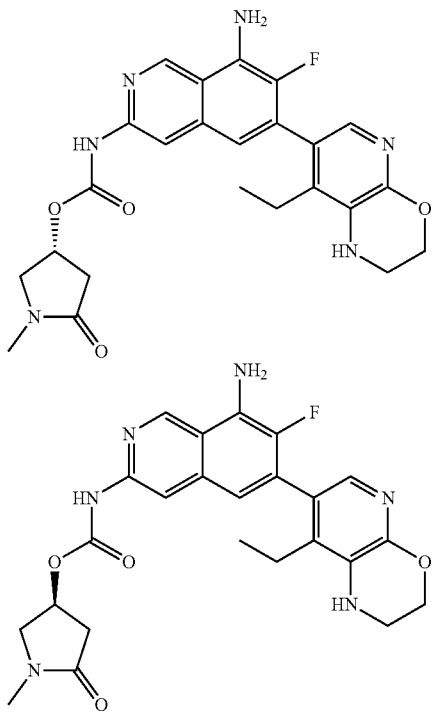

To a solution of tert-butyl 7-[8-(tert-butoxycarbonylamino)-7-fluoro-3-[(1-methyl-5-oxo-pyrrolidin-3-yl)oxycarbonylamino]-6-isoquinolyl]-8-ethyl-2,3-dihydropyrido[2,3-b][1,4]oxazine-1-carboxylate (200 mg, 0.29 mmol) in dichloromethane (6 mL) was added TFA (2 mL, 0.29 mmol). The reaction was stirred for 1 hour at 25° C. and then concentrated under vacuum. The residue was adjusted to pH 8 with TEA and purified by Prep HPLC (X select CSH OBD Column 30*150 mm 5 μm; Mobile Phase A: Water (0.1% FA), Mobile Phase B: ACN; Flow rate: 60 mL/min; Gradient: 7% B to 30% B in 7 min; Rt: 7.38 min) to afford the racemic product. The racemate was separated by chiral HPLC (CHIRALPAK IC, 2*25 cm, 5 μm; Mobile Phase A: MTBE, Mobile Phase B: MeOH; Flow rate: 20 mL/min; Gradient: 30 B to 30 B in 15 min) to afford the two enantiomers (absolute stereochemistry was arbitrarily assigned).

Enantiomer 1 (Compound 444a) (25.1 mg, 0.0522 mmol, 17.8% yield). R$_T$ 3.593 min (CHIRALPAK IC-3, 0.46*5 cm, 3 μm; MTBE (0.1% DEA):MeOH=80:20; 1 mL/min). LCMS (ESI) [M+H]$^+$=481.2, R$_T$ 1.972 min., Method L; $^1$H NMR (400 MHz, DMSO-d$_6$) δ 10.21 (s, 1H), 9.33 (s, 1H), 7.96 (s, 1H), 7.25 (s, 1H), 6.83 (d, J=6.1 Hz, 1H), 6.23 (s, 2H), 5.76 (s, 1H), 5.27 (td, J=5.5, 2.7 Hz, 1H), 4.29 (t, J=4.5 Hz, 2H), 3.78 (dd, J=11.6, 5.7 Hz, 1H), 3.41 (dd, J=11.6, 1.6 Hz, 1H), 3.39-3.33 (m, 2H), 2.83-2.74 (m, 1H), 2.75 (s, 3H), 2.42-2.41 (m, 1H), 2.29-2.27 (m, 2H), 0.91 (t, J=7.4 Hz, 3H).

Enantiomer 1 (Compound 444b) (26.3 mg, 0.0547 mmol, 18.6% yield). R$_T$ 5.240 min (CHIRALPAK IC-3, 0.46*5 cm, 3 μm; MTBE (0.1% DEA):MeOH=80:20; 1 mL/min). LCMS (ESI) [M+H]$^+$=481.2, R$_T$ 1.926 min., Method L; $^1$H NMR (400 MHz, DMSO-d$_6$) δ 10.21 (s, 1H), 9.33 (s, 1H), 7.96 (s, 1H), 7.25 (s, 1H), 6.83 (d, J=6.1 Hz, 1H), 6.23 (s, 2H), 5.76 (s, 1H), 5.27 (td, J=5.5, 2.7 Hz, 1H), 4.29 (t, J=4.5 Hz, 2H), 3.78 (dd, J=11.6, 5.7 Hz, 1H), 3.41 (dd, J=11.6, 1.6 Hz, 1H), 3.39-3.33 (m, 2H), 2.83-2.74 (m, 1H), 2.75 (s, 3H), 2.42-2.41 (m, 1H), 2.29-2.27 (m, 2H), 0.91 (t, J=7.4 Hz, 3H).

Example 140

(±)-cis-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate (Compound 445cd)

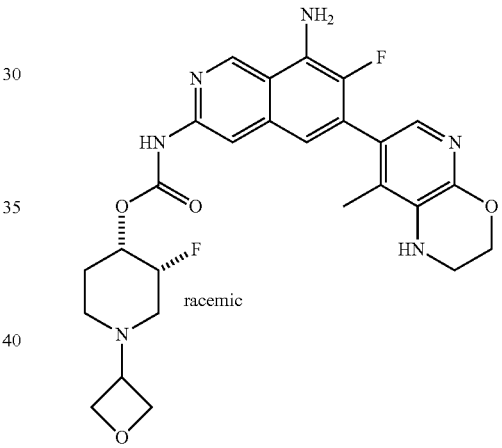

To a solution of (±)-cis-(3-fluoro-4-piperidyl) N-[8-amino-7-fluoro-6-(8-methyl-2,3-dihydro-1H-pyrido[2,3-b][1,4]oxazin-7-yl)-3-isoquinolyl]carbamate (70.0 mg, 0.15 mmol) (from example 137) and 3-oxetanone (107.2 mg, 1.49 mmol) in methyl alcohol (5 mL) was added titanium tetraisopropanolate (169.2 mg, 0.60 mmol) at room temperature. The resulting solution was stirred at 60° C. for 1 hour before allowed to cool to room temperature. NaBH$_3$CN (28 mg, 0.45 mmol) was added. The reaction was then stirred for 2 hours at room temperature. After filtration, the filtrate was concentrated under reduced pressure and purified by Prep-HPLC(Column: X Bridge Prep C18 OBD Column 19×150 mm 5 μm; Mobile Phase A: Water (10 mmol/L NH$_4$HCO$_3$), Mobile Phase B: MeOH; Flow rate: 25 mL/min; Gradient: 40% B to 65% B in 10 min) to give (±)-cis-3-Fluoro-1-(oxetan-3-yl)piperidin-4-yl(8-amino-7-fluoro-6-(8-methyl-2,3-dihydro-1H-pyrido[2,3-b][1,4] oxazin-7-yl)isoquinolin-3-yl)carbamate (14.2 mg, 0.026 mmol, 17.7% yield) as a yellow solid. LCMS (ESI) [M+H]$^+$= 527.3, R$_T$ 1.907 min; Method K. $^1$H NMR (300 MHz, DMSO-d$_6$) δ 10.22 (s, 1H), 9.34 (s, 1H), 7.96 (s, 1H), 7.32 (s, 1H), 6.83 (d, J=6.1 Hz, 1H), 6.22 (s, 2H), 5.68 (s, 1H), 4.79-4.96 (m, 2H), 4.59-4.50 (m, 2H), 4.43 (dt, J=15.7, 6.1 Hz, 2H), 4.28 (s, 2H), 3.58-3.47 (m, 1H), 3.31 (s, 2H), 2.79 (s, 1H), 2.20-2.47 (s, 2H), 1.91 (d, J=1.6 Hz, 3H), 1.85 (s, 2H), 1.23 (s, 1H).

Example 141

S-Tetrahydropyran-4-yl N-[8-amino-7-fluoro-6-(8-methyl-2,3-dihydro-1H-pyrido[2,3-b][1,4]oxazin-7-yl)-3-isoquinolyl]carbamothioate (Compound 601)

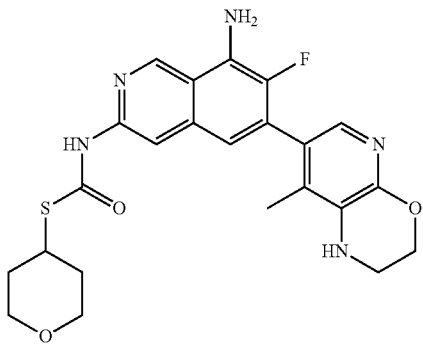 [SMILES: Cc1c(-c2cc3cc(NC(=O)SC4CCOCC4)ncc3c(N)c2F)cnc2c1NCCO2]

Step 1: tert-Butyl 7-[8-(tert-butoxycarbonylamino)-7-fluoro-3-(tetrahydropyran-4-ylsulfanylcarbonylamino)-6-isoquinolyl]-8-methyl-2,3-dihydro-pyrido[2,3-b][1,4]oxazine-1-carboxylate

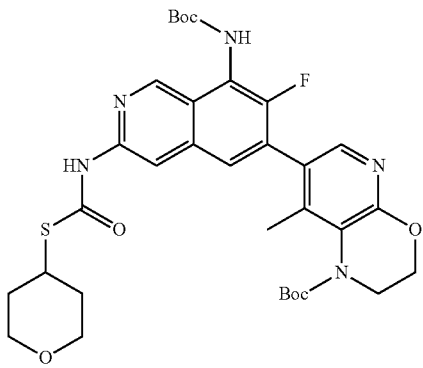 [SMILES: Cc1c(-c2cc3cc(NC(=O)SC4CCOCC4)ncc3c(NC(=O)OC(C)(C)C)c2F)cnc2c1N(C(=O)OC(C)(C)C)CCO2]

Under nitrogen, a solution of tetrahydropyran-4-thiol (17 mg, 0.14 mmol), tert-butyl 7-[3-amino-8-(tert-butoxycarbonylamino)-7-fluoro-6-isoquinolyl]-8-methyl-2,3-dihydro-pyrido[2,3-b][1,4]oxazine-1-carboxylate (60 mg, 0.11 mmol) and DIEA (44 mg, 0.3400 mmol) in dichloromethane (6 mL) was stirred for 5 mins at 0° C. (COCl₂)₃ (13 mg, 0.04 mmol) was added. The reaction was stirred at room temperature for 2 hours. The reaction mixture was quenched with water and then extracted with dichloromethane. The organic layer was dried over anhydrous sodium sulfate and concentrated under vacuum. The residue was purified by flash chromatography on silica gel eluting with petroleum ether/ethyl acetate (70:1) to afford tert-butyl 7-[8-(tert-butoxycarbonylamino)-7-fluoro-3-(tetrahydropyran-4-ylsulfanylcarbonylamino)-6-isoquinolyl]-8-methyl-2,3-dihydro-pyrido[2,3-b][1,4]oxazine-1-carboxylate (20 mg, 0.0284 mmol, 24.8% yield) as a yellow solid. LCMS (ESI) [M+H]⁺= 670.0.

Step 2: S-Tetrahydropyran-4-yl N-[8-amino-7-fluoro-6-(8-methyl-2,3-dihydro-1H-pyrido[2,3-b][1,4]oxazin-7-yl)-3-isoquinolyl]carbamothioate formic acid

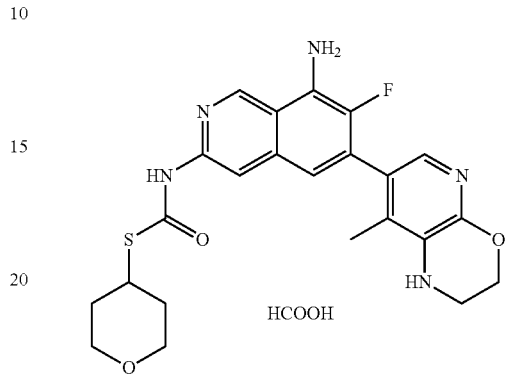

A solution of tert-butyl 7-[8-amino-7-fluoro-3-(tetrahydropyran-4-ylsulfanylcarbonylamino)-6-isoquinolyl]-8-methyl-2,3-dihydropyrido[2,3-b][1,4]oxazine-1-carboxylate (20 mg, 0.040 mmol) in 2,2,2-trifluoroacetic acid (1 mL) and dichloromethane (5 mL) was stirred at room temperature for 1 hour. The reaction mixture was concentrated under vacuum and purified by Prep-HPLC (Column: X Bridge Prep OBD C18 Column 30×150 mm 5 μm; Mobile Phase A: Water (0.1% FA), Mobile Phase B: ACN; Flow rate: 60 mL/min; Gradient: 17% B to 39% B in 7 min; 254 nm; Rt: 6.3 min) to give S-tetrahydropyran-4-yl N-[8-amino-7-fluoro-6-(8-methyl-2,3-dihydro-1H-pyrido[2,3-b][1,4] oxazin-7-yl)-3-isoquinolyl]carbamothioate (5 mg, 0.0095 mmol, 27.1% yield) as a yellow solid. LCMS (ESI): [M+H]⁺= 470.2, $R_T$ 2.061 min., Method J; ¹H NMR (300 MHz, DMSO-d₆) δ 10.90 (s, 1H), 9.36 (s, 1H), 8.09 (s, 1H), 7.40 (s, 1H), 6.88 (d, J=6.2 Hz, 1H), 4.36 (t, J=4.3 Hz, 2H), 3.61 (tt, J=10.7, 4.1 Hz, 1H), 3.48 (dd, J=11.1, 2.4 Hz, 2H), 3.40 (d, J=4.7 Hz, 2H), 3.14 (d, J=1.8 Hz, 2H), 1.95 (d, J=1.7 Hz, 3H), 1.90 (d, J=3.7 Hz, 2H), 1.63 (dtd, J=14.3, 10.7, 4.2 Hz, 2H).

Example 142

1-(8-Amino-7-fluoro-6-(8-methyl-2,3-dihydro-1H-pyrido[2,3-b][1,4]oxazin-7-yl)isoquinolin-3-yl)-3-cyclopropylurea (Compound 702)

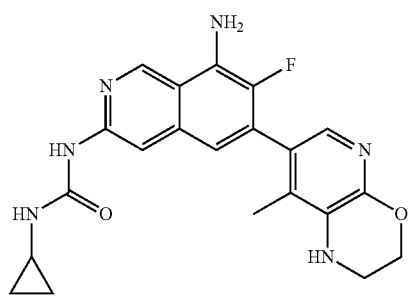 [SMILES: Cc1c(-c2cc3cc(NC(=O)NC4CC4)ncc3c(N)c2F)cnc2c1NCCO2]

Step 1: tert-Butyl 7-(8-chloro-3-(3-cyclopropylureido)-7-fluoroisoquinolin-6-yl)-8-methyl-2,3-dihydro-1H-pyrido[2,3-b][1,4]oxazine-1-carboxylate

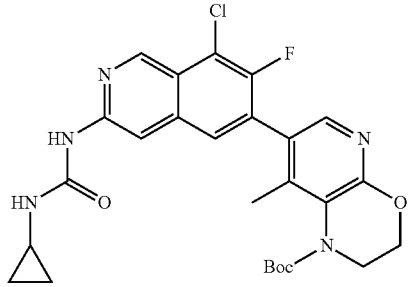 [SMILES: Cc1c(-c2cc3cc(NC(=O)NC4CC4)ncc3c(Cl)c2F)cnc2c1N(C(=O)OC(C)(C)C)CCO2]

A solution of tert-butyl 7-(3-amino-8-chloro-7-fluoro-6-isoquinolyl)-8-methyl-2,3-dihydropyrido[2,3-b][1,4]oxazine-1-carboxylate (200 mg, 0.45 mmol) and isocyanatocyclopropane (523 mg, 6.29 mmol) in dichloromethane (10 mL) was stirred at 25° C. for 3 days. The reaction mixture was concentrated under vacuum and purified by flash chromatography on silica gel eluting with dichloromethane/methanol (94/6) to afford tert-butyl 7-[8-chloro-3-(cyclopropylcarbamoylamino)-7-fluoro-6-isoquinolyl]-8-methyl-2,3-dihydropyrido[2,3-b][1,4]oxazine-1-carboxylate (228 mg, 0.43 mmol, 96% yield) as a brown solid. LCMS (ESI) [M+H]$^+$=528.

Step 2: tert-Butyl 7-(8-(((tert-butoxycarbonyl)amino)-3-(3-cyclopropylureido)-7-fluoroisoquinolin-6-yl)-8-methyl-2,3-dihydro-1H-pyrido[2,3-b][1,4]oxazine-1-carboxylate

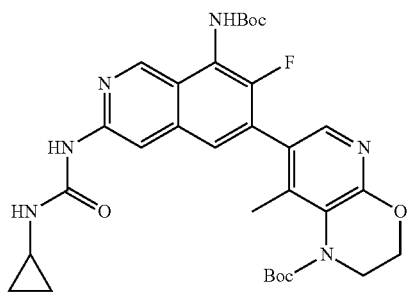 [SMILES: Cc1c(-c2cc3cc(NC(=O)NC4CC4)ncc3c(NC(=O)OC(C)(C)C)c2F)cnc2c1N(C(=O)OC(C)(C)C)CCO2]

A mixture of tert-butyl 7-[8-chloro-3-(cyclopropylcarbamoylamino)-7-fluoro-6-isoquinolyl]-8-methyl-2,3-dihydropyrido[2,3-b][1,4]oxazine-1-carboxylate (250 mg, 0.47 mmol), NH$_2$Boc (1108 mg, 9.47 mmol), Pd$_2$(dba)$_3$ (98 mg, 0.09 mmol), Brettphos (101.0 mg, 0.19 mmol) and Cs$_2$CO$_3$ (463.0 mg, 1.42 mmol) in 1,4-dioxane (5 mL) was stirred at 90° C. for 1 hour. The reaction mixture was concentrated under vacuum and purified by flash chromatography on silica gel eluting with methanol/dichloromethane (5/95) to afford tert-butyl 7-[8-(tert-butoxycarbonylamino)-3-(cyclopropylcarbamoylamino)-7-fluoro-6-isoquinolyl]-8-methyl-2,3-dihydropyrido[2,3-b][1,4]oxazine-1-carboxylate (159 mg, 0.26 mmol, 55% yield) as a brown solid. LCMS (ESI) [M+H]$^+$=609.

Step 3: 1-(8-Amino-7-fluoro-6-(8-methyl-2,3-dihydro-1H-pyrido[2,3-b][1,4]oxazin-7-yl)isoquinolin-3-yl)-3-cyclopropylurea

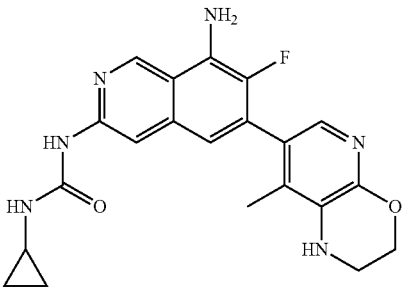 [SMILES: Cc1c(-c2cc3cc(NC(=O)NC4CC4)ncc3c(N)c2F)cnc2c1NCCO2]

A mixture of tert-butyl 7-[8-(tert-butoxycarbonylamino)-3-(cyclopropylcarbamoylamino)-7-fluoro-6-isoquinolyl]-8-methyl-2,3-dihydropyrido[2,3-b][1,4]oxazine-1-carboxylate (75.0 mg, 0.12 mmol) and tert-butyl 7-[3-(cyclopropylcarbamoylamino)-7-fluoro-6-isoquinolyl]-8-methyl-2,3-dihydropyrido[2,3-b][1,4]oxazine-1-carboxylate (75.0 mg, 0.15 mmol) in a mixture of dichloromethane (5 mL) and TFA (1 mL) was stirred at 25° C. for 1 hour. The mixture was concentrated under vacuum. The residue was adjusted to pH 8 with Et$_3$N and purified by Prep-HPLC (Column: X Bridge Prep OBD C18 Column 30×150 mm 5 μm; Water (10 mmol/L NH$_4$HCO$_3$): ACN=17% B to 37% B in 7 min) to give 1-[8-amino-7-fluoro-6-(8-methyl-2,3-dihydro-1H-pyrido[2,3-b][1,4]oxazin-7-yl)-3-isoquinolyl]-3-cyclopropyl-urea (13.6 mg, 0.033 mmol, 14% yield) as a yellow solid. LCMS (ESI) [M+H]$^+$=409. R$_T$ 1.577 min; Method J. $^1$H NMR (300 MHz, DMSO-d$_6$) δ 9.26 (s, 1H), 8.78 (s, 1H), 7.84 (s, 1H), 7.30 (s, 1H), 7.18 (s, 1H), 6.72 (d, J=6.2 Hz, 1H), 6.14 (s, 2H), 5.66 (s, 1H), 4.31-4.27 (m, 2H), 3.40-3.31 (m, 2H), 2.60-2.48 (m, 1H), 1.90 (d, J=1.6 Hz, 3H), 0.70-0.63 (m, 2H), 0.41-0.30 (m, 2H).

Example 143

1-[8-Amino-7-fluoro-6-(4-methyl-5,6,7,8-tetrahydro-1,5-naphthyridin-3-yl)-3-isoquinolyl]-3-methyl-urea (Compound 705)

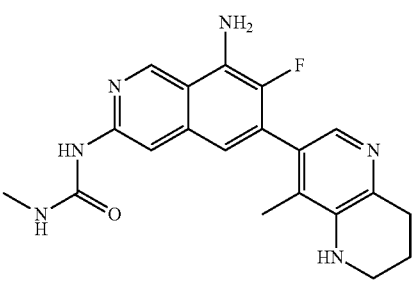 [SMILES: CNC(=O)Nc1cc2cc(-c3cnc4c(c3C)NCCC4)c(F)c(N)c2cn1]

Step 1: tert-Butyl 7-[8-chloro-7-fluoro-3-(methyl-carbamoylamino)-6-isoquinolyl]-8-methyl-3,4-dihydro-2H-1,5-naphthyridine-1-carboxylate

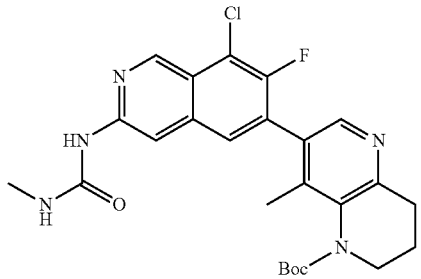 [SMILES: CNC(=O)Nc1cc2cc(-c3cnc4c(c3C)N(C(=O)OC(C)(C)C)CCC4)c(F)c(Cl)c2cn1]

To a solution of phenyl chloroformate (275.7 mg, 1.76 mmol) in dichloromethane (3 mL) was added tert-butyl 7-(3-amino-8-chloro-7-fluoro-6-isoquinolyl)-8-methyl-3,4-dihydro-2H-1,5-naphthyridine-1-carboxylate (156 mg, 0.35 mmol), DMAP (43 mg, 0.35 mmol) and pyridine (3 mL, 0.35 mmol) at 0° C. The reaction mixture was then stirred at 0° C. for 2 hours. Then methyl amine (4 mL, 8.10 mmol) was added and stirred at 60° C. for 2 hours. The reaction was concentrated under vacuum and purified by flash chromatography on silica gel eluting with dichloromethane/methanol (93:7) to afford tert-butyl 7-[8-chloro-7-fluoro-3-(methylcarbamoylamino)-6-isoquinolyl]-8-methyl-3,4-dihydro-2H-1,5-naphthyridine-1-carboxylate (135 mg, 0.27 mmol, 76.7% yield) as a yellow oil. LCMS (ESI) [M+H]$^+$=500.3.

Step 2: tert-Butyl 7-[8-(tert-butoxycarbonylamino)-7-fluoro-3-(methylcarbamoylamino)-6-isoquinolyl]-8-methyl-3,4-dihydro-2H-1,5-naphthyridine-1-carboxylate

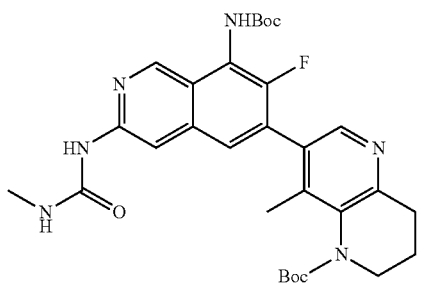 [SMILES: CNC(=O)Nc1cc2cc(-c3cnc4c(c3C)N(C(=O)OC(C)(C)C)CCC4)c(F)c(NC(=O)OC(C)(C)C)c2cn1]

Under nitrogen, a mixture of tert-butyl 7-[8-chloro-7-fluoro-3-(methylcarbamoylamino)-6-isoquinolyl]-8-methyl-3,4-dihydro-2H-1,5-naphthyridine-1-carboxylate (125 mg, 0.25 mmol), NH$_2$Boc (731.3 mg, 6.25 mmol), Pd$_2$(dba)$_3$·CHCl$_3$ (51.8 mg, 0.05 mmol), Brettphos (53.6 mg, 0.10 mmol) and Cs$_2$CO$_3$ (244.5 mg, 0.75 mmol) in 1,4-dioxane (6 mL) was stirred for 40 minutes at 90° C. The reaction mixture was concentrated under vacuum and purified by flash chromatography on silica gel eluting with dichloromethane/methanol (93:7) to afford tert-butyl 7-[8-(tert-butoxycarbonylamino)-7-fluoro-3-(methylcarbamoylamino)-6-isoquinolyl]-8-methyl-3,4-dihydro-2H-1,5-naphthyridine-1-carboxylate (110 mg, 0.19 mmol, 75.8% yield) as a yellow oil. LCMS (ESI) [M+H]$^+$=581.2.

Step 3: 148-Amino-7-fluoro-6-(4-methyl-5,6,7,8-tetrahydro-1,5-naphthyridin-3-yl)-3-isoquinolyl]-3-methyl-urea

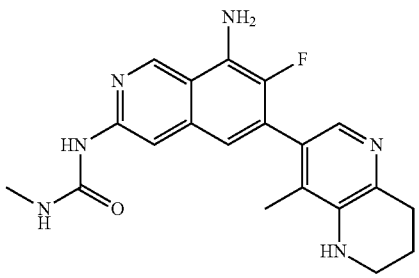 [SMILES: CNC(=O)Nc1cc2cc(-c3cnc4c(c3C)NCCC4)c(F)c(N)c2cn1]

To a solution of tert-butyl 7-[8-(tert-butoxycarbonylamino)-7-fluoro-3-(methylcarbamoylamino)-6-isoquinolyl]-8-methyl-3,4-dihydro-2H-1,5-naphthyridine-1-carboxylate (100 mg, 0.17 mmol) in dichloromethane (5 mL) was added trifluoroacetic acid (1 mL). The mixture was stirred at 25° C. for 1 hour and concentrated under vacuum. The residue was adjusted to pH 9 with TEA and purified by Prep-HPLC (X Bridge Shield RP18 OBD Column 30*150 mm, 5 μm; Mobile Phase A: Water (10 mmol/L NH$_4$HCO$_3$), Mobile Phase B: ACN; Flow rate: 60 mL/min; Gradient: 17% B to 34% B in 10 min; 254/220 nm; Rt: 9.68 min) to give 1-[8-amino-7-fluoro-6-(4-methyl-5,6,7,8-tetrahydro-1,5-naphthyridin-3-yl)-3-isoquinolyl]-3-methyl-urea (23.3 mg, 0.06 mmol, 35.6% yield) as a yellow solid. LCMS (ESI) [M+H]$^+$=381.2, R$_T$ 1.648 min., Method K; $^1$H NMR (300 MHz, DMSO-d$_6$) δ 9.29 (s, 1H), 9.02 (s, 1H), 7.81 (s, 1H), 7.57 (s, 1H), 7.02 (d, J=4.7 Hz, 1H), 6.73 (d, J=6.1 Hz, 1H), 6.17 (s, 2H), 5.43 (s, 1H), 3.33-3.28 (m, 2H), 2.85 (t, J=6.4 Hz, 2H), 2.71 (d, J=4.6 Hz, 3H), 1.95-1.84 (m, 5H).

Example 144

1-(8-Amino-7-fluoro-6-(8-methyl-2,3-dihydro-1H-pyrido[2,3-b][1,4]oxazin-7-yl)isoquinolin-3-yl)-3-cyclopentylurea (Compound 706)

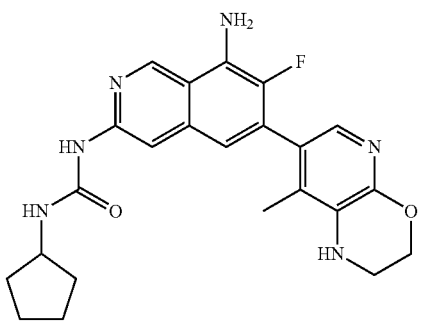 [SMILES: Cc1c(-c2cc3cc(NC(=O)NC4CCCC4)ncc3c(N)c2F)cnc2c1NCCO2]

Step 1: tert-Butyl 7-(8-chloro-3-(3-cyclopentylureido)-7-fluoroisoquinolin-6-yl)-8-methyl-2,3-dihydro-1H-pyrido[2,3-b][1,4]oxazine-1-carboxylate

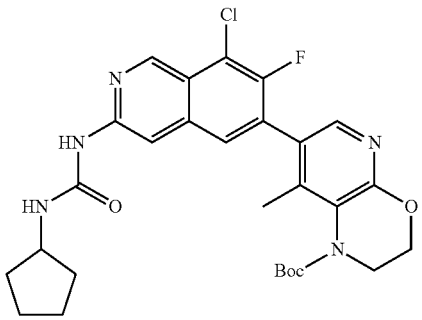 [SMILES: Cc1c(-c2cc3cc(NC(=O)NC4CCCC4)ncc3c(Cl)c2F)cnc2c1N(C(=O)OC(C)(C)C)CCO2]

To a solution of tert-butyl 7-(3-amino-8-chloro-7-fluoro-6-isoquinolyl)-8-methyl-2,3-dihydropyrido[2,3-b][1,4]oxazine-1-carboxylate (214 mg, 0.48 mmol) in dichloromethane (15 mL) was added pyridine (190 mg, 2.41 mmol) and triphosgene (214 mg, 0.72 mmol) in dichloromethane (1 mL). The reaction was stirred at 0° C. for 30 mins, then cyclopentylamine (408 mg, 4.79 mmol) was added. The reaction was stirred at room temperature for 1 hour. The resulting mixture was diluted with dichloromethane and then washed with water. The organic phase was dried over sodium sulfate, concentrated under vacuum and purified by flash chromatography on silica gel eluting with petroleum ether/ethyl acetate (3/7) to afford tert-butyl 7-[8-chloro-3-(cyclopentylcarbamoylamino)-7-fluoro-6-isoquinolyl]-8-methyl-2,3-dihydropyrido[2,3-b][1,4]oxazine-1-carboxylate (254 mg, 0.457 mmol, 95.1% yield) as a yellow solid. LCMS (ESI) [M+H]+=556.

Step 2: tert-Butyl 7-(8-((tert-butoxycarbonyl)amino)-3-(3-cyclopentylureido)-7-fluoroisoquinolin-6-yl)-8-methyl-2,3-dihydro-1H-pyrido[2,3-b][1,4]oxazine-1-carboxylate

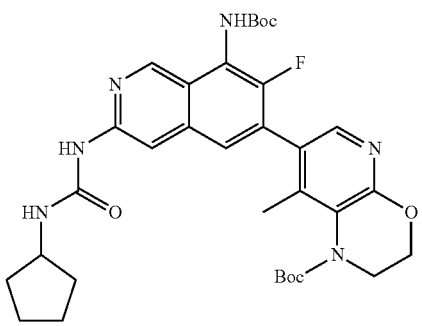 [SMILES: Cc1c(-c2cc3cc(NC(=O)NC4CCCC4)ncc3c(NC(=O)OC(C)(C)C)c2F)cnc2c1N(C(=O)OC(C)(C)C)CCO2]

To a mixture of tert-butyl 7-[8-chloro-3-(cyclopentylcarbamoylamino)-7-fluoro-6-isoquinolyl]-8-methyl-2,3-dihydropyrido[2,3-b][1,4]oxazine-1-carboxylate (260 mg, 0.47 mmol) and tert-butyl carbamate (1666 mg, 14.22 mmol) in 1,4-dioxane (10 mL) was added Pd2(dba)3.CHCl3 (100 mg, 0.10 mmol), BrettPhos (100 mg, 0.19 mmol), cesium carbonate (464 mg, 1.42 mmol). The mixture was stirred at 90° C. for 2 hours. After concentration, the residue was purified by flash chromatography on silica gel eluting with dichloromethane/methanol (96/4) to afford tert-butyl 7-[8-(tert-butoxycarbonylamino)-3-(cyclopentylcarbamoylamino)-7-fluoro-6-isoquinolyl]-8-methyl-2,3-dihydropyrido[2,3-b][1,4]oxazine-1-carboxylate (60 mg, 0.0942 mmol, 20.2% yield) as a yellow solid. LCMS (ESI) [M+H]+=637.

Step 3: 1-(8-Amino-7-fluoro-6-(8-methyl-2,3-dihydro-1H-pyrido[2,3-b][1,4]oxazin-7-yl)isoquinolin-3-yl)-3-cyclopentylurea

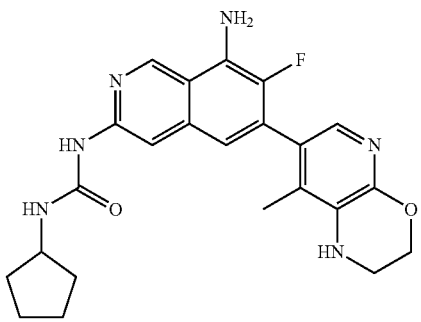 [SMILES: Cc1c(-c2cc3cc(NC(=O)NC4CCCC4)ncc3c(N)c2F)cnc2c1NCCO2]

To a solution of tert-butyl 7-[8-(tert-butoxycarbonylamino)-3-(cyclopentylcarbamoylamino)-7-fluoro-6-isoquinolyl]-8-methyl-2,3-dihydropyrido[2,3-b][1,4]oxazine-1-carboxylate (60 mg, 0.09 mmol) in dichloromethane (5 mL) was added TFA (1 ml). The reaction was stirred at room temperature for 1 hour. After concentration, the residue was diluted with dichloromethane (3 ml) and adjusts to pH 8 with TEA. The resulting solution was concentrated under vacuum. The residue was purified by Prep-HPLC (X Bridge Shield RP18 OBD Column 30*150 mm, 5 μm; Mobile Phase A: Water (10 mmol/L NH4HCO3), Mobile Phase B: ACN; Flow rate: 60 mL/min; Gradient: 27% B to 51% B in 7 min; 254/220 nm; Rt: 6.5 min) to afford 1-[8-amino-7-fluoro-6-(8-methyl-2,3-dihydro-1H-pyrido[2,3-b][1,4]oxazin-7-yl)-3-isoquinolyl]-3-cyclopentyl-urea (14.4 mg, 0.033 mmol, 35% yield) as a yellow solid. LCMS (ESI) [M+H]+=437.2, Rt=1.973 min., Method J. 1H NMR (300 MHz, DMSO-d6) δ 9.28 (s, 1H), 8.79 (s, 1H), 7.85 (s, 1H), 7.33 (s, 1H), 7.13 (d, J=7.2 Hz, 1H), 6.74 (d, J=6.1 Hz, 1H), 6.15 (s, 2H), 5.68 (s, 1H), 4.29 (s, 2H), 3.99 (q, J=6.6 Hz, 1H), 3.37 (s, 2H), 1.95-1.81 (m, 5H), 1.70-1.53 (m, 4H), 1.40 (dd, J=12.3, 6.1 Hz, 2H).

Example 145

1-(8-Amino-7-fluoro-6-(8-methyl-2,3-dihydro-1H-pyrido[2,3-b][1,4]oxazin-7-yl)isoquinolin-3-yl)-3-(2-(2,2,2-trifluoroethyl)-2-azaspiro[3.3]heptan-6-yl)urea (Compound 708)

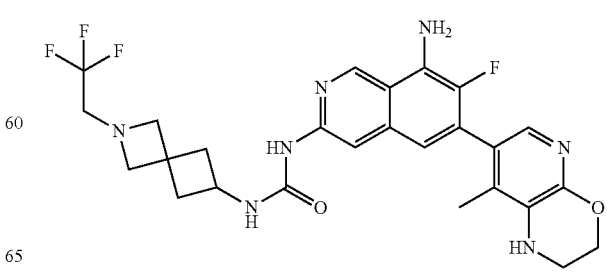

Step 1: tert-Butyl 7-[8-(tert-butoxycarbonylamino)-3-[(2-tert-butoxycarbonyl-2-azaspiro[3.3]heptan-6-yl)carbamoylamino]-7-fluoro-6-isoquinolyl]-8-methyl-3,4-dihydro-2H-1,5-naphthyridine-1-carboxylate

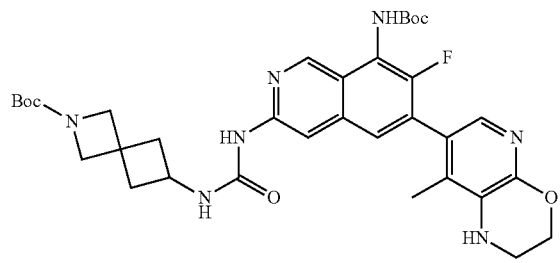 [SMILES: Cc1c(-c2cc3cc(NC(=O)NC4CC5(C4)CN(C(=O)OC(C)(C)C)C5)ncc3c(NC(=O)OC(C)(C)C)c2F)cnc2c1NCCO2]

To a solution of phenyl chloroformate (358 mg, 2.29 mmol) in dichloromethane (7 mL) was added DMAP (69 mg, 0.57 mmol) and tert-butyl 7-[3-amino-8-(tert-butoxycarbonylamino)-7-fluoro-6-isoquinolyl]-8-methyl-3,4-dihydro-2H-1,5-naphthyridine-1-carboxylate (300 mg, 0.57 mmol) in pyridine (4 mL) at 0° C. The reaction was stirred for 2 hours at 0° C. Then tert-butyl 6-amino-2-azaspiro[3.3]heptane-2-carboxylate (608 mg, 2.86 mmol) in dichloromethane (8 mL) was added and stirred for 12 hours at 80° C. The resulting solution was concentrated under vacuum. The residue was purified by flash chromatography on silica gel eluting with dichloromethane/methanol (95/5) to afford tert-butyl 7-[8-(tert-butoxycarbonylamino)-3-[(2-tert-butoxycarbonyl-2-azaspiro[3.3]heptan-6-yl)carbamoylamino]-7-fluoro-6-isoquinolyl]-8-methyl-3,4-dihydro-2H-1,5-naphthyridine-1-carboxylate (400 mg, 0.525 mmol, 91.6% yield) as a yellow solid. LCMS (ESI) [M+H]$^+$=764.

Step 2: 148-Amino-7-fluoro-6-(8-methyl-2,3-dihydro-1H-pyrido[2,3-b][1,4]oxazin-7-yl)-3-isoquinolyl]-3-(2-azaspiro[3.3]heptan-6-yl)urea

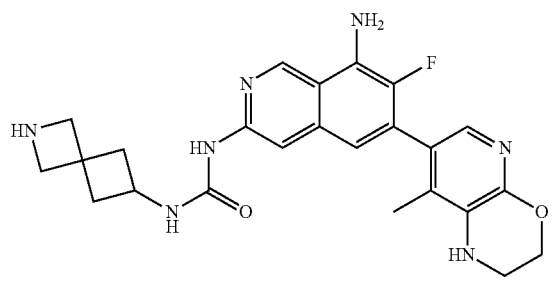 [SMILES: Cc1c(-c2cc3cc(NC(=O)NC4CC5(CNC5)C4)ncc3c(N)c2F)cnc2c1NCCO2]

To a solution of tert-butyl 7-[8-(tert-butoxycarbonylamino)-3-[(2-tert-butoxycarbonyl-2-azaspiro[3.3]heptan-6-yl)carbamoylamino]-7-fluoro-6-isoquinolyl]-8-methyl-2,3-dihydropyrido[2,3-b][1,4]oxazine-1-carboxylate (500 mg, 0.65 mmol) in dichloromethane (20 mL) was added 2,2,2-trifluoroacetic acid (2 mL) at room temperature. The resulting solution was stirred for 3 h at 25° C. The reaction solution was concentrated under vacuum. The residue was purified by reverse phase chromatography (acetonitrile 0-40/0.1% NH$_4$HCO$_3$ in water) to afford 1-[8-amino-7-fluoro-6-(8-methyl-2,3-dihydro-1H-pyrido[2,3-b][1,4]oxazin-7-yl)-3-isoquinolyl]-3-(2-azaspiro[3.3]heptan-6-yl)urea (130 mg, 0.28 mmol, 42.8% yield) as a yellow solid. LCMS (ESI) [M+H]$^+$=464.

Step 3: 1-(8-Amino-7-fluoro-6-(8-methyl-2,3-dihydro-1H-pyrido[2,3-b][1,4]oxazin-7-yl)isoquinolin-3-yl)-3-(2-(2,2,2-trifluoroethyl)-2-azaspiro[3.3]heptan-6-yl)urea

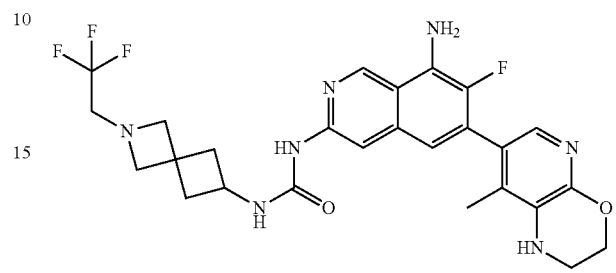

To a solution of 1-[8-amino-7-fluoro-6-(8-methyl-2,3-dihydro-1H-pyrido[2,3-b][1,4]oxazin-7-yl)-3-isoquinolyl]-3-(2-azaspiro[3.3]heptan-6-yl)urea (220 mg, 0.47 mmol) and TEA (500 mg, 4.95 mmol) in N,N-dimethylformamide (8 mL) was added 2,2,2-trifluoroethyltrifluoromethanesulfonate (330 mg, 1.42 mmol) at room temperature. The resulting solution was stirred for 15 min at 25° C. The reaction was quenched by water and then concentrated under vacuum. The residue was purified by reverse phase chromatography (acetonitrile 0-40/0.1% NH$_4$HCO$_3$ in water) to afford 1-[8-amino-7-fluoro-6-(8-methyl-2,3-dihydro-1H-pyrido[2,3-b][1,4]oxazin-7-yl)-3-isoquinolyl]-3-[2-(2,2,2-trifluoroethyl)-2-azaspiro[3.3]heptan-6-yl]urea (201 mg, 0.368 mmol, 77.6% yield) as a yellow solid. LCMS (ESI) [M+H]$^+$=546.2, R$_T$ 2.67 min., Method N. $^1$H NMR (300 MHz, DMSO-d$_6$) δ 9.29 (s, 1H), 8.85 (s, 1H), 7.81 (s, 1H), 7.29 (s, 2H), 6.74 (d, J=6.1 Hz, 1H), 6.15 (s, 2H), 5.67 (s, 1H), 4.29 (s, 2H), 4.03 (q, J=7.8 Hz, 1H), 3.37-3.29 (m, 4H), 3.13 (q, J=10.1 Hz, 2H), 2.55-2.44 (m, 4H), 1.96-1.92 (m, 2H), 1.89 (s, 3H).

Example 146

(S)-1-(8-Amino-7-fluoro-6-(8-methyl-2,3-dihydro-1H-pyrido[2,3-b][1,4]oxazin-7-yl)isoquinolin-3-yl)-3-(tetrahydro-2H-pyran-3-yl)urea and (R)-1-[8-Amino-7-fluoro-6-(8-methyl-2,3-dihydro-1H-pyrido[2,3-b][1,4]oxazin-7-yl)-3-isoquinolyl]-3-[tetrahydropyran-3-yl]urea (Compound 711a and Compound 711b)

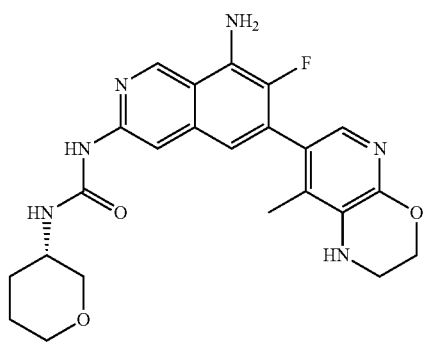

365
-continued

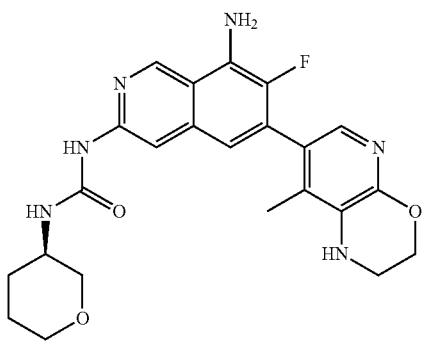

Step 1: tert-Butyl 7-[8-chloro-7-fluoro-3-(tetrahydropyran-3-ylcarbamoylamino)-6-isoquinolyl]-8-methyl-2,3-dihydropyrido[2,3-b][1,4]oxazine-1-carboxylate

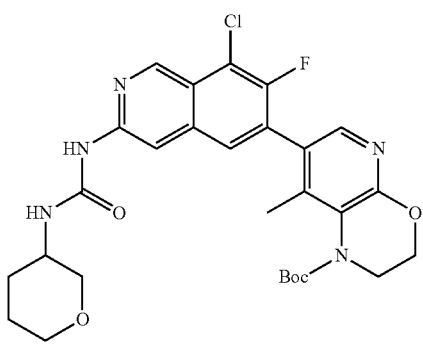 [SMILES: Cc1c(-c2cc3cc(NC(=O)NC4CCCOC4)ncc3c(Cl)c2F)cnc2c1N(C(=O)OC(C)(C)C)CCO2]

To a solution of phenyl chloroformate (527.89 mg, 3.37 mmol) in dichloromethane (7 mL) was added the solution of tert-butyl 7-(3-amino-8-chloro-7-fluoro-6-isoquinolyl)-8-methyl-2,3-dihydropyrido[2,3-b][1,4]oxazine-1-carboxylate (300.0 mg, 0.67 mmol) and DMAP (82.38 mg, 0.67 mmol) in pyridine (7 mL) at 0° C. Then the reaction was stirred for 1 hour at 60° C. Then tetrahydro-2H-pyran-3-amine (682.08 mg, 6.74 mmol) was added and stirred at 60° C. for 12 hours. The reaction was quenched with water. The resulting solution was extracted with dichloromethane and the organic layers were combined. The organic layer was dried over anhydrous sodium sulfate and concentrated under vacuum. The residue was purified by flash chromatography on silica gel eluting with dichloromethane/methanol (10/1) to afford tert-butyl7-[8-chloro-7-fluoro-3-(tetrahydropyran-3-ylcarbamoylamino)-6-isoquinolyl]-8-methyl-2,3-dihydropyrido[2,3-b][1,4]oxazine-1-carboxylate (270 mg, 0.472 mmol, 70% yield) as a yellow solid. LCMS (ESI) [M+H]$^+$= 572.2.

366

Step 2: tert-Butyl 7-[8-(tert-butoxycarbonylamino)-7-fluoro-3-(tetrahydropyran-3-ylcarbamoylamino)-6-isoquinolyl]-8-methyl-2,3-dihydropyrido[2,3-b][1,4]oxazine-1-carboxylate

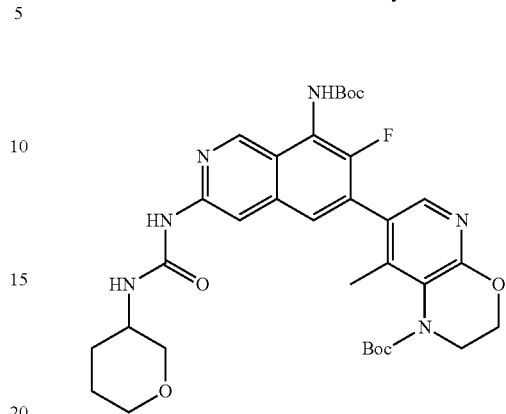

Under nitrogen, a mixture of tert-butyl 7-[8-chloro-7-fluoro-3-(tetrahydropyran-3-ylcarbamoylamino)-6-isoquinolyl]-8-methyl-2,3-dihydropyrido[2,3-b][1,4]oxazine-1-carboxylate (200 mg, 0.35 mmol), tert-butyl carbamate (204.8 mg, 1.75 mmol), Brettphos Pd G3 (63.4 mg, 0.07 mmol) and Cs$_2$CO$_3$ (228 mg, 0.70 mmol) in 1,4-dioxane (8 mL) was stirred at 90° C. for 1 hour. Then the mixture was cooled to room temperature. The reaction mixture was concentrated under vacuum and purified by flash chromatography on silica gel eluting with dichloromethane/methanol (10/1) to afford tert-butyl 7-[8-(tert-butoxycarbonylamino)-7-fluoro-3-(tetrahydropyran-3-ylcarbamoylamino)-6-isoquinolyl]-8-methyl-2,3-dihydropyrido[2,3-b][1,4]oxazine-1-carboxylate (180 mg, 0.27 mmol, 78.9% yield) as a yellow solid. LCMS (ESI) [M+H]$^+$=653.3.

Step 3: (S)-1-(8-Amino-7-fluoro-6-(8-methyl-2,3-dihydro-1H-pyrido[2,3-b][1,4]oxazin-7-yl)isoquinolin-3-yl)-3-(tetrahydro-2H-pyran-3-yl)urea and (R)-1-[8-Amino-7-fluoro-6-(8-methyl-2,3-dihydro-1H-pyrido[2,3-b][1,4]oxazin-7-yl)-3-isoquinolyl]-3-[tetrahydropyran-3-yl]urea

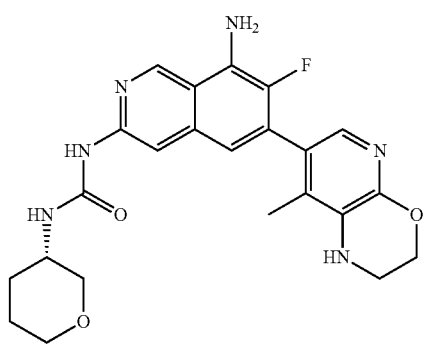

-continued

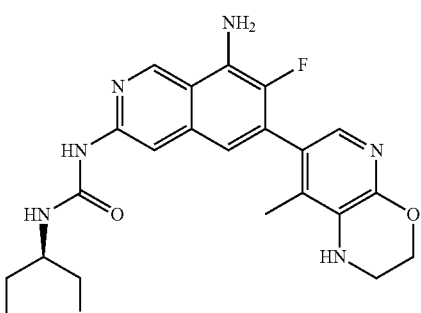

To a solution of tert-butyl 7-[8-(tert-butoxycarbonylamino)-7-fluoro-3-(tetrahydropyran-3-ylcarbamoylamino)-6-isoquinolyl]-8-methyl-2,3-dihydropyrido[2,3-b][1,4]oxazine-1-carboxylate (100.0 mg, 0.15 mmol) in dichloromethane (5 mL) was added 2,2,2-trifluoroacetic acid (2.5 mL). The reaction was stirred at room temperature for 0.5 hour and concentrated under vacuum. The residue was diluted with dichloromethane and adjusted to pH 8 with triethylamine. Then the solution was concentrated under vacuum. The crude product was purified by Prep-HPLC (Column: X Bridge Prep OBD C18 Column 30×150 mm 5 μm; Mobile Phase A: Water (10 mmol/L $NH_4HCO_3$), Mobile Phase B: ACN; Flow rate: 60 mL/min; Gradient: 15% B to 39% B in 7 min) to give the racemic product. Then the racemic product was further separated by pre-chiral-HPLC to afford two enantiomers. Absolute stereochemistry arbitrarily assigned.

Enantiomer 1 (Compound 711a) (8.0 mg, 0.0002 mmol). $R_T$ 1.699 min (CHIRALPAK IG-3 0.46*5 cm; 3 μm. MTBE (0.1% DEA): EtOH=50:50, 1 ml/min). LCMS(ESI) [M+H]⁺= 453.2, $R_T$ 1.965 min.; Method K. ¹H NMR (300 MHz, DMSO-$d_6$) δ 9.29 (s, 1H), 8.95 (s, 1H), 7.84 (s, 1H), 7.33 (s, 2H), 6.75 (d, J=6.1 Hz, 1H), 6.17 (s, 2H), 5.68 (s, 1H), 4.29 (s, 2H), 3.80-3.70 (m, 1H), 3.66 (s, 2H), 3.52 (s, 1H), 3.27 (dd, J=10.6, 6.4 Hz, 3H), 1.92 (d, J=1.7 Hz, 3H), 1.88 (s, 1H), 1.71 (s, 1H), 1.54 (d, J=8.4 Hz, 2H).

Enantiomer 2: (Compound 711b) (6.6 mg, 0.0001 mmol). $R_T$ 2.361 min (CHIRALPAK IG-3 0.46*5 cm; 3 μm. MTBE (0.1% DEA): EtOH=50:50, 1 ml/min). LCMS(ESI) [M+H]⁺= 453.2, $R_T$ 1.971 min; Method K. ¹H NMR (300 MHz, DMSO-$d_6$) δ 9.29 (s, 1H), 8.95 (s, 1H), 7.84 (s, 1H), 7.33 (s, 2H), 6.75 (d, J=6.1 Hz, 1H), 6.17 (s, 2H), 5.68 (s, 1H), 4.29 (s, 2H), 3.80-3.70 (m, 1H), 3.66 (s, 2H), 3.52 (s, 1H), 3.27 (dd, J=10.6, 6.4 Hz, 3H), 1.92 (d, J=1.7 Hz, 3H), 1.88 (s, 1H), 1.71 (s, 1H), 1.54 (d, J=8.4 Hz, 2H).

Example 147

(±)-trans-1-(8-Amino-7-fluoro-6-(8-methyl-2,3-dihydro-1H-pyrido[2,3-b][1,4]oxazin-7-yl)isoquinolin-3-yl)-3-(2-cyanocyclobutyl)urea (Compound 712a)

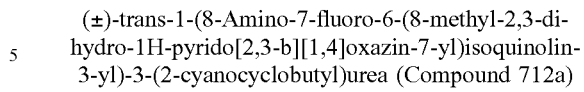
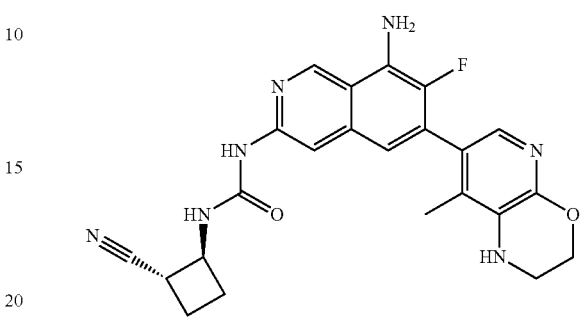

Step 1: (±)-trans-tert-butyl N-(2-carbamoylcyclobutyl) carbamate

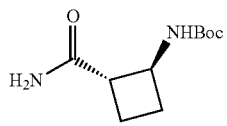

A solution of (±)-trans-2-(tert-butoxycarbonylamino)cyclobutanecarboxylic acid (1.0 g, 4.65 mmol), $NH_4Cl$ (0.7 g, 12.96 mmol), HATU (2.6 g, 6.84 mmol) and DIEA (1.2 g, 9.23 mmol) in N,N-dimethylformamide (5 mL) was stirred at 25° C. for 16 hours. The reaction was quenched by water and extracted with ethyl acetate. The organic layer was dried over anhydrous sodium sulfate and concentrated under vacuum to afford (±)-trans-tert-butyl N-(2-carbamoylcyclobutyl) carbamate (628 mg, 2.931 mmol, 63.1% yield) as a white solid. LCMS (ESI) [M+H]⁺=215.

Step 2: (±)-trans-tert-Butyl N-(2-cyanocyclobutyl) carbamate

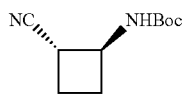 [SMILES: CC(C)(C)OC(=O)N[C@H]1CC[C@@H]1C#N]

A solution of (±)-trans-tert-butyl N-(2-carbamoylcyclobutyl) carbamate (628 mg, 2.93 mmol), 1-propanephosphonic acid cyclic anhydride (3.7 g, 5.82 mmol) and TEA (593 mg, 5.86 mmol) in tetrahydrofuran (10 mL) was stirred at 50° C. for 2 hours. The reaction was quenched by water and extracted with ethyl acetate. The organic layer was dried over anhydrous sodium sulfate and concentrated under vacuum to afford (±)-trans-tert-butyl N-(2-cyanocyclobutyl) carbamate (480 mg, 2.446 mmol, 83.4% yield) as a white solid. LCMS (ESI) [M+H]⁺=197.

Step 3: (±)-trans-2-Aminocyclobutanecarbonitrile

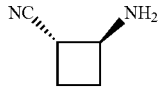

A solution of (±)-trans-tert-butyl N-(2-cyanocyclobutyl) carbamate (480 mg, 2.45 mmol) in 2,2,2-trifluoroacetic acid (2 mL) and dichloromethane (10 mL) was stirred at 25° C. for 1 h. The reaction mixture was concentrated under vacuum to afford (±)-trans-2-aminocyclobutanecarbonitrile (200 mg, crude) as a yellow oil. LCMS (ESI) [M+H]$^+$=97.

Step 4: (±)-trans-tert-Butyl 7-[8-(tert-butoxycarbonylamino)-3-[(2-cyanocyclobutyl)carbamoylamino]-7-fluoro-6-isoquinolyl]-8-methyl-2,3-dihydropyrido[2,3-b][1,4]oxazine-1-carboxylate

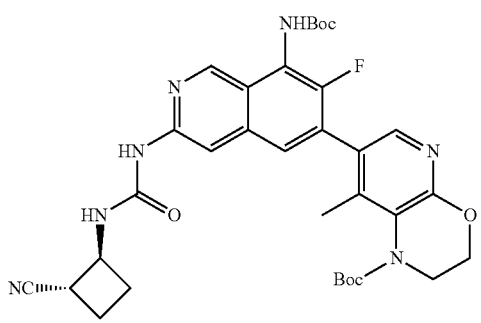 [SMILES: Cc1c(-c2cc3cc(NC(=O)N[C@H]4CC[C@@H]4C#N)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (180 mg, 0.34 mmol) and pyridine (5 mL) in dichloromethane (12 mL) was added triphosgene (50 mg, 0.17 mmol) at 0° C. The reaction was stirred for 1 hour at 0° C. Then (±)-trans-2-aminocyclobutanecarbonitrile (197 mg, 2.05 mmol) was added and stirred at room temperature for 2 hours. The reaction mixture was concentrated under vacuum and purified by reverse phase chromatography (acetonitrile 0-60/0.1% NH$_4$HCO$_3$ in water) to afford (±)-trans-tert-butyl 7-[8-(tert-butoxycarbonylamino)-3-[(2-cyanocyclobutyl)carbamoylamino]-7-fluoro-6-isoquinolyl]-8-methyl-2,3-dihydropyrido[2,3-b][1,4]oxazine-1-carboxylate (80 mg, 0.1235 mmol, 36.1% yield) as a yellow solid. LCMS (ESI) [M+H]$^+$=648.

Step 5: (±)-trans-1-(8-Amino-7-fluoro-6-(8-methyl-2,3-dihydro-1H-pyrido[2,3-b][1,4]oxazin-7-yl)isoquinolin-3-yl)-3-(2-cyanocyclobutyl)urea (Compound 712a)

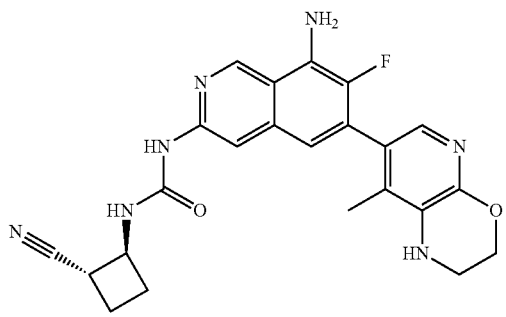 [SMILES: Cc1c(-c2cc3cc(NC(=O)N[C@H]4CC[C@@H]4C#N)ncc3c(N)c2F)cnc2c1NCCO2]

A solution of (±)-trans-tert-butyl 7-[8-(tert-butoxycarbonylamino)-3-[(2-cyanocyclobutyl)carbamoylamino]-7-fluoro-6-isoquinolyl]-8-methyl-2,3-dihydropyrido[2,3-b][1,4]oxazine-1-carboxylate (80 mg, 0.06 mmol) in TFA (4 mL) and dichloromethane (10 mL) was stirred at 25° C. for 1 hour. The reaction mixture was concentrated under vacuum. The crude product was purified by Prep-HPLC (Column: X Bridge Prep Phenyl OBD Column 5 μm, 19*250 mm; Mobile Phase A: Water (0.1% FA), Mobile Phase B: MeOH; Flow rate: 25 mL/min; Gradient: 40% B to 76% B in 21 min; R$_T$ 18 min) to give 1-[8-amino-7-fluoro-6-(8-methyl-2,3-dihydro-1H-pyrido[2,3-b][1,4]oxazin-7-yl)-3-isoquinolyl]-3-[(1S,2S)-2-cyanocyclobutyl]urea (5.2 mg, 0.0116 mmol, 18.8% yield) as a yellow solid. LCMS (ESI) [M+H]$^+$=448.2, R$_T$ 1.999 min., Method M; $^1$H NMR (300 MHz, DMSO-d$_6$) δ 9.30 (s, 1H), 9.05 (s, 1H), 7.88 (s, 1H), 7.52 (d, J=8.0 Hz, 1H), 7.32 (s, 1H), 6.78 (d, J=6.2 Hz, 1H), 6.17 (s, 2H), 5.67 (s, 1H), 4.45 (q, J=8.3 Hz, 1H), 4.28 (t, J=4.3 Hz, 2H), 2.27-2.11 (m, 3H), 2.14-2.12 (m, 1H), 2.11-1.99 (m, 2H), 2.03-1.86 (m, 4H).

Example 148

1-(8-Amino-7-fluoro-6-(8-methyl-2,3-dihydro-1H-pyrido[2,3-b][1,4]oxazin-7-yl)isoquinolin-3-yl)-3-((1R,5S,6r)-3-oxabicyclo[3.1.0]hexan-6-yl)urea (Compound 713a)

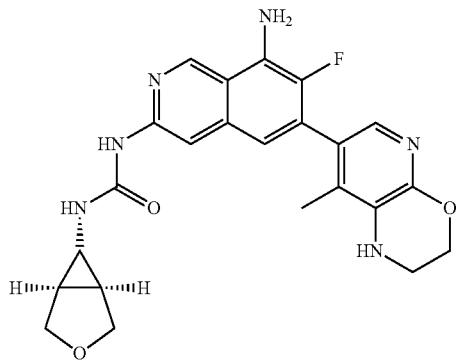

Step 1: tert-Butyl 7-(3-(3-((1R,5S,6r)-3-oxabicyclo[3.1.0]hexan-6-yl)ureido)-8-((tert-butoxycarbonyl)amino)-7-fluoroisoquinolin-6-yl)-8-methyl-2,3-dihydro-1H-pyrido[2,3-b][1,4]oxazine-1-carboxylate

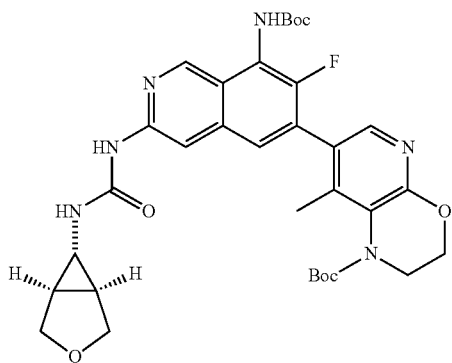

To a solution of phenylcarbonochloridate (445.2 mg, 2.85 mmol) in dichloromethane (5 mL) was added a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (300.0 mg, 0.57 mmol) and 4-dimethylaminopyridine (69.73 mg, 0.57 mmol) in pyridine (2.0 mL) at 0° C. The mixture was stirred for 1 hour at room temperature. Then a solution of (meso-1R,5S,6r)-3-oxabicyclo[3.1.0]Hexan-6-endo-amine hydrochloride (231.26 mg, 1.71 mmol) and triethylamine (231.04 mg, 2.28 mmol) in dichloromethane (4 mL) was added at 0° C. The mixture was stirred at 50° C. for an additional 2 h. The reaction was quenched with water and extracted with dichloromethane. The organic layers were combined, dried over anhydrous sodium sulfate and concentrated under the reduced pressure. The residue was purified by flash chromatography on silica gel eluting with dichloromethane/methanol (10/1) to afford tert-butyl 7-(3-(3-((1R,5S,6r)-3-oxabicyclo[3.1.0]hexan-6-yl)ureido)-8-((tert-butoxycarbonyl)amino)-7-fluoroisoquinolin-6-yl)-8-methyl-2,3-dihydro-1H-pyrido[2,3-b][1,4]oxazine-1-carboxylate (160 mg, 0.25 mmol, 43% yield). LCMS (ESI) [M+H]$^+$=651.3.

Step 2: 1-(8-Amino-7-fluoro-6-(8-methyl-2,3-dihydro-1H-pyrido[2,3-b][1,4]oxazin-7-yl)isoquinolin-3-yl)-3-((1R,5S,6r)-3-oxabicyclo[3.1.0]hexan-6-yl)urea

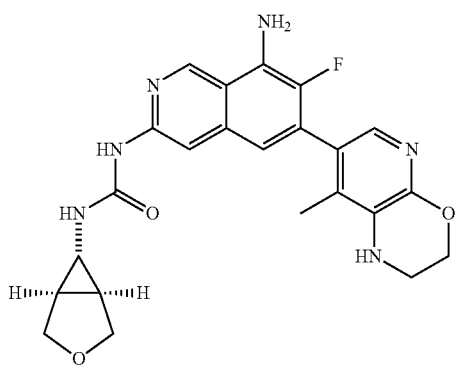

To a solution of tert-butyl 7-(3-(3-((1R,5S,6r)-3-oxabicyclo[3.1.0]hexan-6-yl)ureido)-8-((tert-butoxycarbonyl)amino)-7-fluoroisoquinolin-6-yl)-8-methyl-2,3-dihydro-1H-pyrido[2,3-b][1,4]oxazine-1-carboxylate (150.0 mg, 0.23 mmol) in dichloromethane (4 mL) was added trifluoroacetic acid (2.0 mL). The reaction mixture was stirred at room temperature for 1 hour. The reaction mixture was concentrated under vacuum. The residue was re-dissolved in dichloromethane and adjusted to pH 8 with triethylamine. The resulting mixture was concentrated under vacuum and purified by Prep-HPLC (Column: X Select CSH Prep C18 OBD Column, 5 μm, 19*150 mm; Mobile Phase A: Water (0.1% FA), Mobile Phase B: ACN; Flow rate: 25 mL/min; Gradient: 12% B to 18% B in 15 min) to afford 1-(8-amino-7-fluoro-6-(8-methyl-2,3-dihydro-1H-pyrido[2,3-b][1,4]oxazin-7-yl)isoquinolin-3-yl)-3-((1R,5S,6r)-3-oxabicyclo[3.1.0]hexan-6-yl)urea (31.9 mg, 0.071 mmol, 30.9% yield) as a light yellow solid. LCMS (ESI) [M+H]$^+$=451.3, R$_T$ 1.853 min., Method L; $^1$H NMR (300 MHz, DMSO-d$_6$) δ 9.28 (s, 1H), 8.88 (s, 1H), 7.88 (s, 1H), 7.32 (s, 1H), 7.20 (d, J=2.5 Hz, 1H), 6.74 (d, J=6.1 Hz, 1H), 6.16 (s, 2H), 5.67 (s, 1H), 4.29 (t, J=4.4 Hz, 2H), 3.84 (d, J=8.4 Hz, 2H), 3.62 (d, J=8.1 Hz, 2H), 3.37 (s, 2H), 2.46 (m, 1H), 1.92 (d, J=1.7 Hz, 3H), 1.80 (d, J=2.4 Hz, 2H).

Example 149

1-(8-Amino-7-fluoro-6-(8-methyl-2,3-dihydro-1H-pyrido[2,3-b][1,4]oxazin-7-yl)isoquinolin-3-yl)-3-(3,3-difluorocyclobutyl)urea (Compound 714)

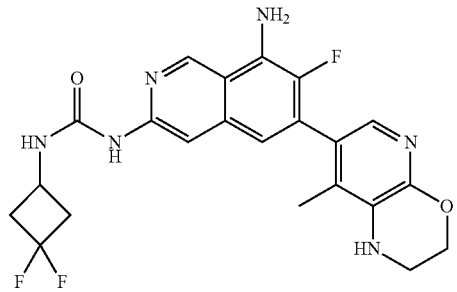 [SMILES: Cc1c(-c2cc3cc(NC(=O)NC4CC(F)(F)C4)ncc3c(N)c2F)cnc2c1NCCO2]

Step 1: tert-Butyl 7-[8-(tert-butoxycarbonylamino)-3-[(3,3-difluorocyclobutyl)carbamoylamino]-7-fluoro-6-isoquinolyl]-8-methyl-2,3-dihydropyrido[2,3-b][1,4]oxazine-1-carboxylate

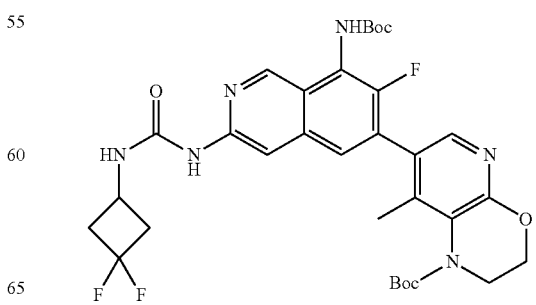

A solution of phenyl chloroformate (298 mg, 1.9 mmol) in dichloromethane (1 mL) was added DMAP (47 mg, 0.39 mmol), pyridine (5 mL, 0.38 mmol) and tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (200 mg, 0.38 mmol) at 0° C. The reaction was stirred for 2 hours at 0° C. Then 3,3-difluorocyclobutan-1-amine (244 mg, 2.28 mmol) in dichloromethane (14 mL) was added. The reaction mixture was stirred for 16 hours at 50° C., diluted with dichloromethane and washed with water. The organic layer was dried over anhydrous sodium sulfate and concentrated under vacuum to afford tert-butyl 7-[8-(tert-butoxycarbonylamino)-3-[(3,3-difluorocyclobutyl)carbamoylamino]-7-fluoro-6-isoquinolyl]-8-methyl-2,3-dihydropyrido[2,3-b][1,4]oxazine-1-carboxylate (150 mg, 0.228 mmol, 59.8% yield) as yellow solid. LCMS (ESI) [M+H]$^+$=659.

Step 2: 1-[8-Amino-7-fluoro-6-(8-methyl-2,3-dihydro-1H-pyrido[2,3-b][1,4]oxazin-7-yl)-3-isoquinolyl]-3-(3,3-difluorocyclobutyl)urea

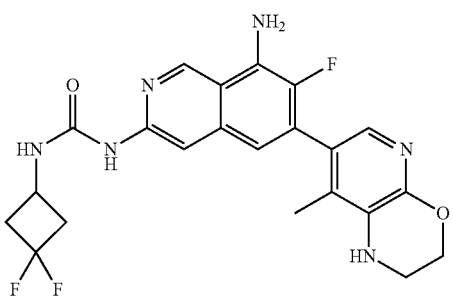 [SMILES: Cc1c(-c2cc3cc(NC(=O)NC4CC(F)(F)C4)ncc3c(N)c2F)cnc2c1NCCO2]

A solution of tert-butyl 7-[8-(tert-butoxycarbonylamino)-3-[(3,3-difluorocyclobutyl)carbamoylamino]-7-fluoro-6-isoquinolyl]-8-methyl-2,3-dihydropyrido[2,3-b][1,4]oxazine-1-carboxylate (150 mg, 0.23 mmol) in TFA (4 mL) and dichloromethane (15 mL) was stirred at 25° C. for 1 hour. The reaction mixture was concentrated under vacuum and purified by Prep-HPLC (Column: X Bridge Prep OBD C18 Column 30×150 mm 5 μm; Mobile Phase A: Water (10 mmol/L NH$_4$HCO$_3$), Mobile Phase B: ACN; Flow rate: 60 mL/min; Gradient: 22% B to 43% B in 7 min; 254/220 nm; R$_T$ 6.87 min) to afford 1-[8-amino-7-fluoro-6-(8-methyl-2,3-dihydro-1H-pyrido[2,3-b][1,4]oxazin-7-yl)-3-isoquinolyl]-3-(3,3-difluorocyclobutyl)urea (56.5 mg, 0.123 mmol, 54.1% yield) as a brown solid. LCMS (ESI) [M+H]$^+$= 459.2, R$_T$ 1.920 min., Method J. $^1$H NMR (300 MHz, DMSO-d$_6$) δ 9.31 (s, 1H), 9.01 (s, 1H), 7.85 (s, 1H), 7.52 (d, J=6.7 Hz, 1H), 7.33 (s, 1H), 6.76 (d, J=6.2 Hz, 1H), 6.18 (s, 2H), 5.68 (s, 1H), 4.29 (s, 2H), 4.07 (s, 1H), 3.34 (s, 2H), 3.06-2.86 (m, 2H), 2.65-2.53 (m, 2H), 1.92 (d, J=1.6 Hz, 3H).

Example 150

Tetrahydro-2H-pyran-4-yl (R)-(8-amino-6-(4,8-dimethyl-5,6,7,8-tetrahydro-1,5-naphthyridin-3-yl)-7-fluoroisoquinolin-3-yl)carbamate and Tetrahydro-2H-pyran-4-yl (S)-(8-amino-6-(4,8-dimethyl-5,6,7,8-tetrahydro-1,5-naphthyridin-3-yl)-7-fluoroisoquinolin-3-yl)carbamate (Compound 461a and Compound 461b)

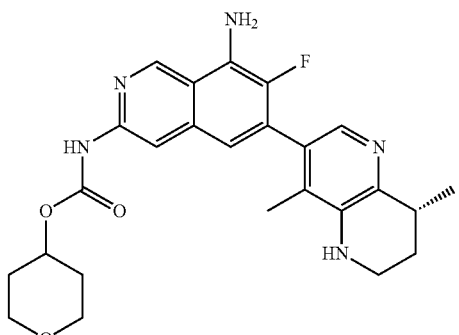

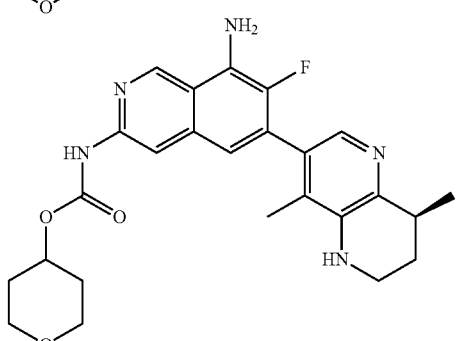

Step 1: tert-Butyl 8-methyl-4-methylene-7-(4,4,5,5-tetramethyl-1,3,2-dioxaborolan-2-yl)-3,4-dihydro-1,5-naphthyridine-1(2H)-carboxylate

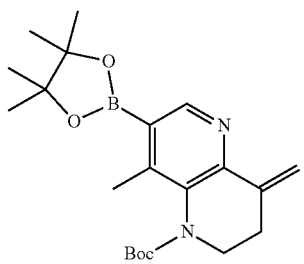

A mixture of tert-butyl 7-bromo-8-methyl-4-methylene-2,3-dihydro-1,5-naphthyridine-1-carboxylate (1.0 g, 2.96 mmol) (from example 113), B$_2$Pin$_2$ (3746.0 mg, 14.81 mmol), Pd(dppf)Cl$_2$ (200.0 mg, 0.27 mmol) and KOAc (867.0 mg, 8.85 mmol) in 1,4-dioxane (15.0 mL) was stirred at 100° C. for 2 hours. The reaction mixture was concentrated under vacuum. The residue was purified by flash chromatography on silica gel eluting with petroleum ether/ethyl acetate (1/10) to afford tert-butyl 8-methyl-4-methylene-7-(4,4,5,5-tetramethyl-1,3,2-dioxaborolan-2-yl)-3,4-dihydro-1,5-naphthyridine-1(2H)-carboxylate (1.1 g, 2.85 mmol, 78.6% yield) as a yellow solid. LCMS (ESI) [M+H]⁺= 387.

Step 2: tert-Butyl 7-(3-amino-8-chloro-7-fluoroisoquinolin-6-yl)-8-methyl-4-methylene-3,4-dihydro-1,5-naphthyridine-1(2H)-carboxylate

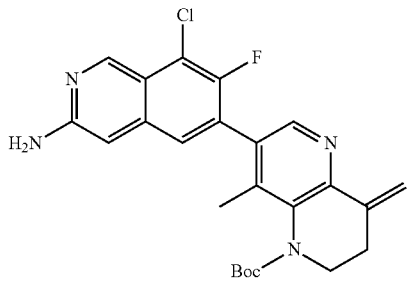 [SMILES: C=C1CCN(C(=O)OC(C)(C)C)c2c1ncc(-c1cc3cc(N)ncc3c(Cl)c1F)c2C]

A mixture of tert-butyl 8-methyl-4-methylene-7-(4,4,5,5-tetramethyl-1,3,2-dioxaborolan-2-yl)-2,3-dihydro-1,5-naphthyridine-1-carboxylate (1.8 g, 4.66 mmol), 8-chloro-7-fluoro-6-iodo-isoquinolin-3-amine (1.5 g, 4.65 mmol), Pd(dppf)Cl₂ (340.0 mg, 0.47 mmol) and K₂CO₃ (2.0 g, 14.49 mmol) in 1,4-dioxane (20.0 mL) and water (2.0 mL) was stirred at 60° C. for 16 hours. The reaction mixture was concentrated under vacuum. The residue was purified by flash chromatography on silica gel eluting with petroleum ether/ethyl acetate (1/1) to afford tert-butyl 7-(3-amino-8-chloro-7-fluoro-6-isoquinolyl)-8-methyl-4-methylene-2,3-dihydro-1,5-naphthyridine-1-carboxylate (700 mg, 1.539 mmol, 33% yield) as a yellow solid. LCMS (ESI) [M+H]⁺= 455.

Step 3: tert-Butyl 7-(3-amino-8-chloro-7-fluoroisoquinolin-6-yl)-4,8-dimethyl-3,4-dihydro-1,5-naphthyridine-1(2H)-carboxylate

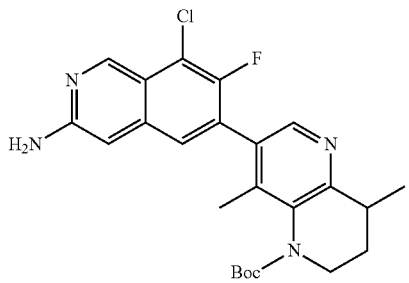 [SMILES: Cc1c(-c2cc3cc(N)ncc3c(Cl)c2F)cnc2c1N(C(=O)OC(C)(C)C)CCC2C]

A mixture of tert-butyl 7-(3-amino-8-chloro-7-fluoro-6-isoquinolyl)-8-methyl-4-methylene-2,3-dihydro-1,5-naphthyridine-1-carboxylate (700.0 mg, 1.54 mmol) and Pd/C (500.0 mg, 1.54 mmol) in methyl alcohol (50.0 mL) was stirred at 25° C. under hydrogen for 4 hours. The reaction mixture was then filtered through celite and concentrated under vacuum. The residue was purified by flash chromatography on silica gel eluting with petroleum ether/ethyl acetate (1:1) to afford tert-butyl 7-(3-amino-8-chloro-7-fluoro-6-isoquinolyl)-4,8-dimethyl-3,4-dihydro-2H-1,5-naphthyridine-1-carboxylate (400 mg, 0.875 mmol, 56.9% yield) as a yellow solid. LCMS (ESI) [M+H]⁺=457.

Step 4: tert-butyl 7-(8-chloro-7-fluoro-3-((((tetrahydro-2H-pyran-4-yl)oxy)carbonyl)amino)isoquinolin-6-yl)-4,8-dimethyl-3,4-dihydro-1,5-naphthyridine-1(2H)-carboxylate

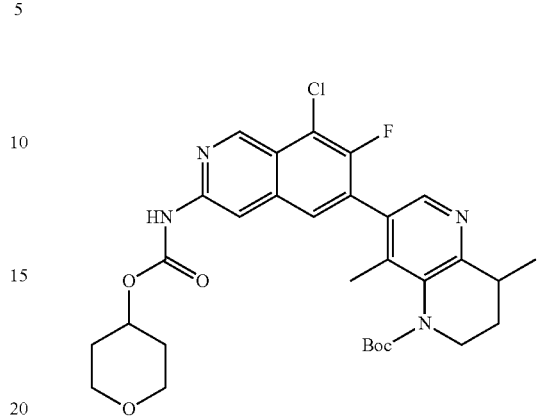

A solution of tert-butyl 7-(3-amino-8-chloro-7-fluoro-6-isoquinolyl)-4,8-dimethyl-3,4-dihydro-2H-1,5-naphthyridine-1-carboxylate (300.0 mg, 0.66 mmol), tetrahydro-2h-pyran-4-ol (342.0 mg, 3.35 mmol) and DIEA (1270 mg, 9.84 mmol) in dichloromethane (15.0 mL) was stirred at 0° C. for 10 min. Then triphosgene (312.0 mg, 1.05 mmol) was added. The reaction was stirred at 0° C. for 1 hour and concentrated under vacuum. The residue was purified by flash chromatography on silica gel eluting with petroleum ether/ethyl acetate (1/2) to afford tert-butyl 7-[8-chloro-7-fluoro-3-(tetrahydropyran-4-yloxycarbonylamino)-6-isoquinolyl]-4,8-dimethyl-3,4-dihydro-2H-1,5-naphthyridine-1-carboxylate (300 mg, 0.513 mmol, 78.1% yield) as a yellow solid. LCMS (ESI) [M+H]⁺=585.

Step 5: tert-Butyl 7-(8-((tert-butoxycarbonyl)amino)-7-fluoro-3-(((((tetrahydro-2H-pyran-4-yl)oxy)carbonyl)amino)isoquinolin-6-yl)-4,8-dimethyl-3,4-dihydro-1,5-naphthyridine-1(2H)-carboxylate

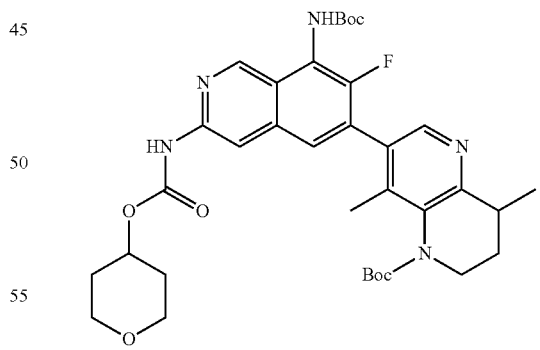

A mixture of tert-butyl 7-[8-chloro-7-fluoro-3-(tetrahydropyran-4-yloxycarbonylamino)-6-isoquinolyl]-4,8-dimethyl-3,4-dihydro-2H-1,5-naphthyridine-1-carboxylate (500 mg, 0.85 mmol), NH₂Boc (1000 mg, 8.55 mmol), Pd₂(dba)₃.CHCl₃ (196 mg, 0.19 mmol), Brettphos (184 mg, 0.34 mmol) and Cs₂CO₃ (836 mg, 2.56 mmol) in 1,4-dioxane (20 mL) was stirred at 90° C. under nitrogen for 2 hours. The reaction mixture was concentrated under vacuum and purified by flash chromatography on silica gel eluting with petroleum ether/ethyl acetate (1:2) to afford tert-butyl 7-[8-(tert-butoxycarbonylamino)-7-fluoro-3-(tetrahydropyran-4-yloxycarbonylamino)-6-isoquinolyl]-4,8-dimethyl-3,4-dihydro-2H-1,5-naphthyridine-1-carboxylate (500 mg, 0.751 mmol, 87.9% yield) as a yellow solid. LCMS (ESI) [M+H]⁺=666.

Step 6: Tetrahydro-2H-pyran-4-yl (R)-(8-amino-6-(4,8-dimethyl-5,6,7,8-tetrahydro-1,5-naphthyridin-3-yl)-7-fluoroisoquinolin-3-yl)carbamate and tetrahydro-2H-pyran-4-yl (S)-(8-amino-6-(4,8-dimethyl-5,6,7,8-tetrahydro-1,5-naphthyridin-3-yl)-7-fluoroisoquinolin-3-yl)carbamate

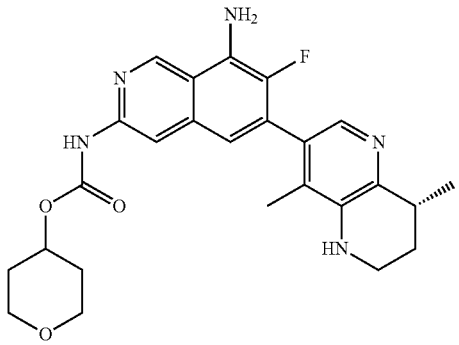

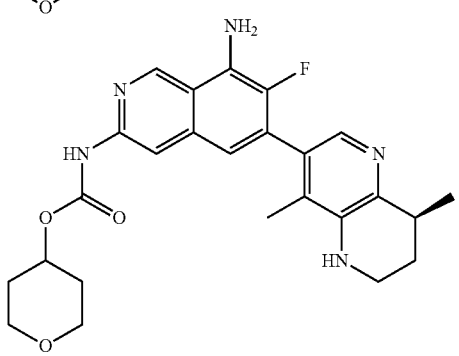

A solution of tert-butyl 7-[8-(tert-butoxycarbonylamino)-7-fluoro-3-(tetrahydropyran-4-yloxycarbonylamino)-6-isoquinolyl]-4,8-dimethyl-3,4-dihydro-2H-1,5-naphthyridine-1-carboxylate (200 mg, 0.30 mmol) and TFA (2.0 mL, 0.30 mmol) in dichloromethane (5.0 mL) was stirred at 25° C. for 1 hour. The reaction was concentrated under vacuum. The residue was purified by Prep-HPLC (Column: X Select CSH Prep C18 OBD Column, 5 μm, 19*150 mm; Mobile Phase A: Water (0.1% FA), Mobile Phase B: MeOH; Flow rate: 25 mL/min; Gradient: 13% B to 43% B in 12.5 min; R_T 10.03 min) and Chiral-HPLC to afford two enantiomers. Absolute stereochemistry was arbitrarily assigned.

Enantiomer 1 (Compound 461a) (19.6 mg, 0.0421 mmol, 14% yield). R_T 2.933 min (CHIRALPAK IF-3 0.46*5 cm; 3 μm. MTBE:EtOH=90:10, 1 ml/min). LCMS (ESI) [M+H]⁺= 466.2, R_T 2.106 min., Method K. ¹H NMR (300 MHz, DMSO-d₆) δ 10.07 (s, 1H), 9.34 (s, 1H), 7.97 (s, 1H), 7.62 (s, 1H), 6.84 (d, J=5.9 Hz, 1H), 6.23 (s, 2H), 5.49 (s, 1H), 4.88 (dt, J=8.9, 4.7 Hz, 1H), 3.85 (dd, J=10.4, 5.9 Hz, 2H), 3.47-3.31 (t, J=9.2 Hz, 4H), 2.96 (q, J=6.5 Hz, 1H), 1.98-1.84 (m, 7H), 1.60 (dtd, J=13.0, 9.3, 4.2 Hz, 2H), 1.31 (d, J=7.0 Hz, 3H).

Enantiomer 2 (Compound 461b) (19.5 mg, 0.0419 mmol, 13.9% yield). R_T 3.662 min (CHIRALPAK IF-3 0.46*5 cm; 3 μm. MTBE:EtOH=90:10, 1 ml/min). LCMS (ESI) [M+H]⁺=466.2, R_T 2.106 min., Method K. ¹H NMR (300 MHz, DMSO-d₆) δ 10.07 (s, 1H), 9.34 (s, 1H), 7.97 (s, 1H), 7.62 (s, 1H), 6.84 (d, J=5.9 Hz, 1H), 6.23 (s, 2H), 5.49 (s, 1H), 4.88 (dt, J=8.9, 4.7 Hz, 1H), 3.85 (dd, J=10.4, 5.9 Hz, 2H), 3.47-3.31 (t, J=9.2 Hz, 4H), 2.96 (q, J=6.5 Hz, 1H), 1.98-1.84 (m, 7H), 1.60 (dtd, J=13.0, 9.3, 4.2 Hz, 2H), 1.31 (d, J=7.0 Hz, 3H).

Example 151

1,4-Dimethyl-1,4-diazepan-6-yl (8-amino-7-fluoro-6-(8-methyl-2,3-dihydro-1H-pyrido[2,3-b][1,4]oxazin-7-yl)isoquinolin-3-yl)carbamate (Compound 465)

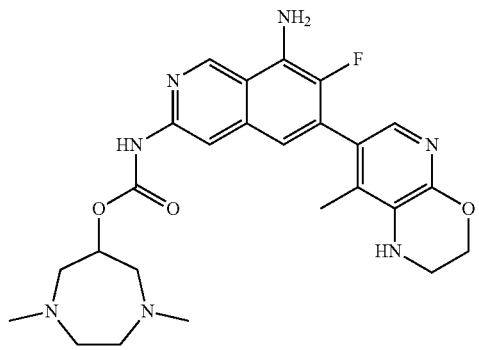 [SMILES: Cc1c(-c2cc3cc(NC(=O)OC4CN(C)CCN(C)C4)ncc3c(N)c2F)cnc2c1NCCO2]

Step 1: di-tert-Butyl 6-(((6-(1-(tert-butoxycarbonyl)-8-methyl-2,3-dihydro-1H-pyrido[2,3-b][1,4]oxazin-7-yl)-8-((tert-butoxycarbonyl)amino)-7-fluoroisoquinolin-3-yl)carbamoyl)oxy)-1,4-diazepane-1,4-dicarboxylate

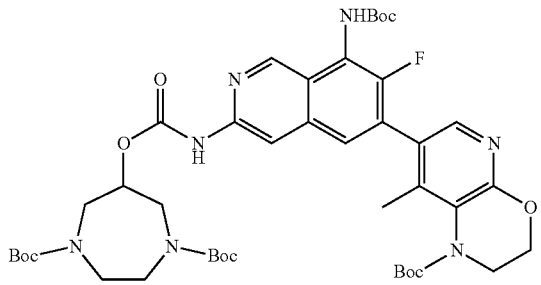 [SMILES: Cc1c(-c2cc3cc(NC(=O)OC4CN(C(=O)OC(C)(C)C)CCN(C(=O)OC(C)(C)C)C4)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (300.0 mg, 0.57 mmol), di-tert-butyl 6-hydroxy-1,4-diazepane-1,4-dicarboxylate (361.0 mg, 1.14 mmol) and DIEA (369.0 mg, 2.86 mmol) in dichloromethane (15 mL) was added triphosgene (112.0 mg, 0.38 mmol) at 0° C. The mixture was stirred at 0° C. for 1 hour. The mixture was quenched with water and concentrated under vacuum. The residue was purified by flash chromatography on silica gel eluting with dichloromethane/methanol (84/16) to afford ditert-butyl 6-[[8-(tert-butoxycarbonylamino)-6-(1-tert-butoxycarbonyl-8-methyl-2,3-dihydropyrido[2,3-b][1,4]oxazin-7-yl)-7-fluoro-3-isoquinolyl]carbamoyloxy]-1,4-diazepane-1,4-

Step 2: 1,4-Diazepan-6-yl (8-amino-7-fluoro-6-(8-methyl-2,3-dihydro-1H-pyrido[2,3-b][1,4]oxazin-7-yl)isoquinolin-3-yl)carbamate

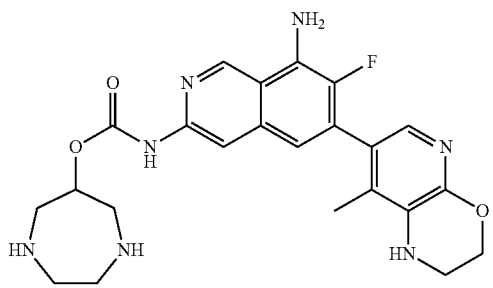 [SMILES: Cc1c(-c2cc3cc(NC(=O)OC4CNCCNC4)ncc3c(N)c2F)cnc2c1NCCO2]

To a solution of di-tert-butyl 6-[[8-(tert-butoxycarbonylamino)-6-(1-tert-butoxycarbonyl-8-methyl-2,3-dihydro-pyrido[2,3-b][1,4]oxazin-7-yl)-7-fluoro-3-isoquinolyl]carbamoyloxy]-1,4-diazepane-1,4-dicarboxylate (398.0 mg, 0.46 mmol) in dichloromethane (5 mL) was added 2,2,2-trifluoroacetic acid (2 mL) at 25° C. The mixture was stirred at 25° C. for 1 hour and concentrated under vacuum. The residue was adjusted to pH 8 with Et₃N and purified by reverse phase chromatography (eluting with water (NH₄HCO₃)/MeOH (66/34)) to afford 1,4-diazepan-6-yl N-[8-amino-7-fluoro-6-(8-methyl-2,3-dihydro-1H-pyrido[2,3-b][1,4]oxazin-7-yl)-3-isoquinolyl]carbamate (52 mg, 0.11 mmol, 24% yield) as a brown solid. LCMS (ESI) [M+H]⁺=468.

Step 3: 1,4-Dimethyl-1,4-diazepan-6-yl (8-amino-7-fluoro-6-(8-methyl-2,3-dihydro-1H-pyrido[2,3-b][1,4]oxazin-7-yl)isoquinolin-3-yl)carbamate

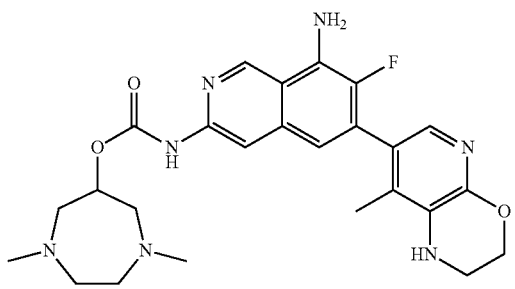 [SMILES: Cc1c(-c2cc3cc(NC(=O)OC4CN(C)CCN(C)C4)ncc3c(N)c2F)cnc2c1NCCO2]

A solution of 1,4-diazepan-6-yl N-[8-amino-7-fluoro-6-(8-methyl-2,3-dihydro-1H-pyrido[2,3-b][1,4]oxazin-7-yl)-3-isoquinolyl]carbamate (80.0 mg, 0.17 mmol) and formaldehyde (40%, 51.0 mg, 1.7 mmol) in methyl alcohol (5 mL) was stirred at 25° C. for 1 hour. Then NaBH₃CN (32.0 mg, 0.51 mmol) was added and stirred at 25° C. for 1 hour. The reaction mixture was concentrated under vacuum and purified by Prep-HPLC (Column: X Bridge Prep OBD C18 Column 30×150 mm 5 μm; Water (10 mmol/L NH₄HCO₃): ACN=12% B to 30% B in 10 min; 60 mL/min) to give (1,4-dimethyl-1,4-diazepan-6-yl) N-[8-amino-7-fluoro-6-(8-methyl-2,3-dihydro-1H-pyrido[2,3-b][1,4]oxazin-7-yl)-3-isoquinolyl]carbamate (12.8 mg, 0.025 mmol, 15% yield) as a yellow solid. LCMS (ESI) [M+H]⁺=496, $R_T$=0.907 min., Method J. ¹H NMR (300 MHz, DMSO-d₆) δ 10.03 (s, 1H), 9.30 (s, 1H), 7.95 (s, 1H), 7.30 (s, 1H), 6.80 (d, J=6.2 Hz, 1H), 6.20 (s, 2H), 5.67 (s, 1H), 4.92-4.86 (m, 1H), 4.31-4.27 (m, 2H), 3.32-3.29 (m, 2H), 2.90-2.85 (m, 2H), 2.75-2.61 (m, 2H), 2.60-2.40 (m, 4H), 2.28 (s, 6H), 1.90 (s, 3H).

Example 152

(R)-1-Ethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate and (S)-1-Ethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate (Compound 478a and Compound 478b)

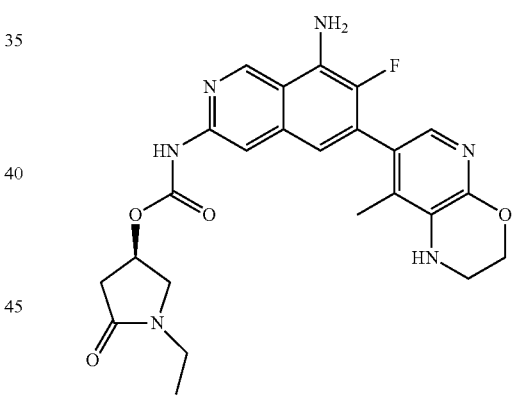

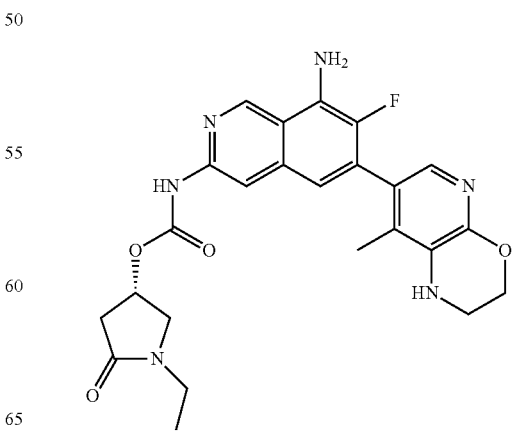

Step 1: tert-Butyl 7-[8-(tert-butoxycarbonyl amino)-3-[(1-ethyl-5-oxo-pyrrolidin-3-yl)oxycarbonylamino]-7-fluoro-6-isoquinolyl]-8-methyl-2,3-dihydropyrido[2,3-b][1,4]oxazine-1-carboxylate

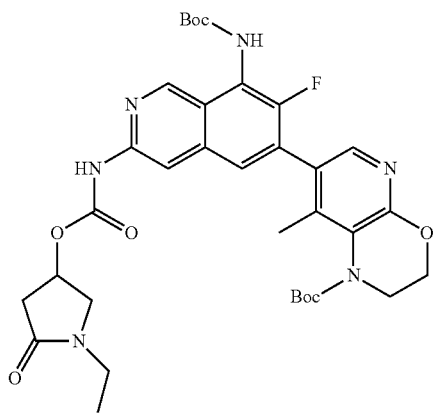 [SMILES: CCN1CC(OC(=O)Nc2cc3cc(-c4cnc5c(c4C)N(C(=O)OC(C)(C)C)CCO5)c(F)c(NC(=O)OC(C)(C)C)c3cn2)CC1=O]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (300 mg, 0.57 mmol) and 1-ethyl-4-hydroxy-pyrrolidin-2-one (300 mg, 2.32 mmol) in dichloromethane (60 mL) was added DIEA (500 mg, 3.88 mmol) at room temperature. Then triphosgene (200 mg, 0.67 mmol) was added. The reaction was stirred at 0° C. for 2 hours before concentrated under vacuum. The residue was purified by flash chromatography on silica gel eluting with dichloromethane/methanol (20/1) to afford tert-butyl 7-[8-(tert-butoxycarbonylamino)-3-[(1-ethyl-5-oxo-pyrrolidin-3-yl)oxycarbonylamino]-7-fluoro-6-isoquinolyl]-8-methyl-2,3-dihydropyrido[2,3-b][1,4]oxazine-1-carboxylate (280 mg, 0.41 mmol, 72.1% yield) as a yellow solid. LCMS (ESI) [M+H]$^+$=681.

Step 2: (R)-1-Ethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate and (S)-1-Ethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate

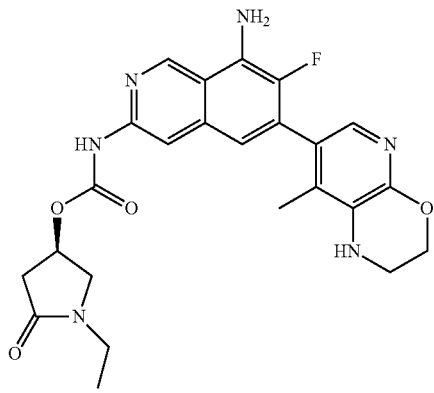

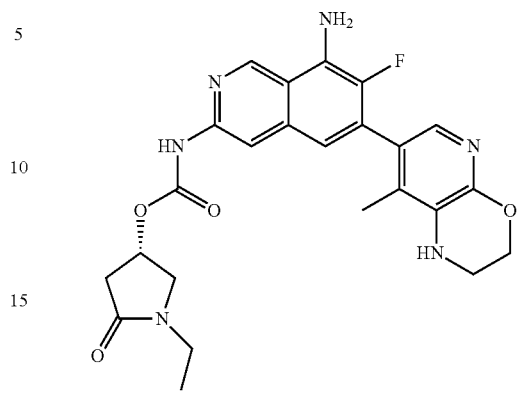

A solution of tert-butyl 7-[8-(tert-butoxycarbonylamino)-3-[(1-ethyl-5-oxo-pyrrolidin-3-yl)oxycarbonylamino]-7-fluoro-6-isoquinolyl]-8-methyl-2,3-dihydropyrido[2,3-b][1,4]oxazine-1-carboxylate (280 mg, 0.41 mmol) and TFA (2 mL) in dichloromethane (10 mL) was stirred for 3 h at 25° C. The reaction was concentrated under vacuum and the residue was purified by Prep-HPLC (Column: X Select CSH Prep C18 OBD Column, 5 μm, 19*150 mm; Mobile Phase A: Water (0.1% FA), Mobile Phase B: ACN; Flow rate: 25 mL/min; Gradient: 7% B to 25% B in 10 min) and chiral-HPLC (Column: CHIRALPAK IC, 2*25 cm, 5 μm; Mobile Phase A: MTBE (0.1% FA), Mobile Phase B: MeOH; Flow rate: 20 mL/min; Gradient: 30 B to 30 B in 8.5 min; 220/254 nm) to afford two enantiomers. Absolute stereochemistry was arbitrarily assigned.

Enantiomer 1 Compound 478a (28.6 mg, 0.0595 mmol, 14.5% yield): R$_T$ 3.418 min (ChIRALPAK 0.46*5 cm, 3 μm; MTBE (0.1% FA):EtOH=50:50 in 8 min; 1 mL/min). LCMS (ESI) [M+H]$^+$=481.3, Rt=1.671 min., Method K; $^1$H NMR (400 MHz, DMSO-d$_6$) δ 10.21 (s, 1H), 9.33 (s, 1H), 7.97 (s, 1H), 7.33 (s, 1H), 6.84 (d, J=6.2 Hz, 1H), 6.23 (s, 2H), 5.70 (s, 1H), 5.32-5.25 (m, 1H), 4.29 (t, J=4.4 Hz, 2H), 3.79 (dd, J=11.6, 5.7 Hz, 1H), 3.41 (dd, J=11.7, 1.5 Hz, 2H), 3.32-3.15 (m, 3H), 2.80 (dd, J=17.6, 7.0 Hz, 1H), 2.30 (dd, J=17.6, 1.9 Hz, 1H), 1.92 (d, J=1.6 Hz, 3H), 1.03 (t, J=7.2 Hz, 3H).

Enantiomer 2 Compound 478b (31.6 mg, 0.0658 mmol, 16% yield): Retention time: 4.48 min (ChIRALPAK IE-3, 0.46*5 cm, 3 μm; MTBE (0.1% FA):EtOH=50:50 in 8 min; 1 mL/min). LCMS (ESI) [M+H]$^+$=481.3, Rt=1.671 min, Method K; $^1$H NMR (400 MHz, DMSO-d$_6$) δ 10.21 (s, 1H), 9.33 (s, 1H), 7.97 (s, 1H), 7.33 (s, 1H), 6.84 (d, J=6.2 Hz, 1H), 6.23 (s, 2H), 5.70 (s, 1H), 5.32-5.25 (m, 1H), 4.29 (t, J=4.4 Hz, 2H), 3.79 (dd, J=11.6, 5.7 Hz, 1H), 3.41 (dd, J=11.7, 1.5 Hz, 2H), 3.32-3.15 (m, 3H), 2.80 (dd, J=17.6, 7.0 Hz, 1H), 2.30 (dd, J=17.6, 1.9 Hz, 1H), 1.92 (d, J=1.6 Hz, 3H), 1.03 (t, J=7.2 Hz, 3H).

Example 153

Cyclobutyl (8-amino-7-fluoro-6-(8-methyl-2,3-dihydro-1H-pyrido[2,3-b][1,4]oxazin-7-yl)isoquinolin-3-yl)carbamate (Compound 487)

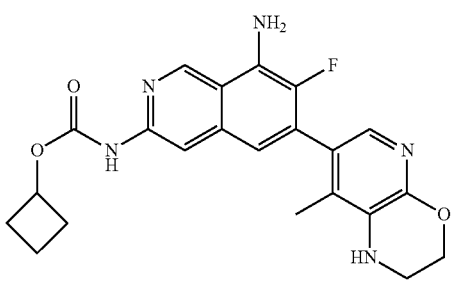 [SMILES: Cc1c(-c2cc3cc(NC(=O)OC4CCC4)ncc3c(N)c2F)cnc2c1NCCO2]

Step 1: tert-Butyl 7-[8-(tert-butoxycarbonylamino)-3-(cyclobutoxycarbonylamino)-7-fluoro-6-isoquinolyl]-8-methyl-2,3-dihydropyrido[2,3-b][1,4]oxazine-1-carboxylate

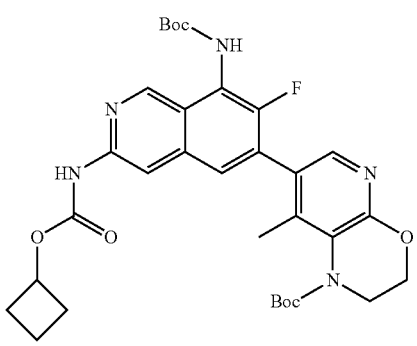 [SMILES: Cc1c(-c2cc3cc(NC(=O)OC4CCC4)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (100 mg, 0.19 mmol) and cyclobutanol (70 mg, 0.97 mmol) in dichloromethane (20 mL) was added DIEA (300 mg, 2.33 mmol) at room temperature. Then triphosgene (75 mg, 0.25 mmol) was added and stirred at 0° C. for 2 hours. The reaction mixture was concentrated under vacuum. The residue was purified by flash chromatography on silica gel eluting with petroleum ether/ethyl acetate (1/1) to afford tert-butyl 7-[8-(tert-butoxycarbonylamino)-3-(cyclobutoxycarbonylamino)-7-fluoro-6-isoquinolyl]-8-methyl-2,3-dihydropyrido[2,3-b][1,4]oxazine-1-carboxylate (100 mg, 0.16 mmol, 84.3% yield) as a yellow solid. LCMS (ESI) [M+H]$^+$= 624.

Step 2: Cyclobutyl (8-amino-7-fluoro-6-(8-methyl-2,3-dihydro-1H-pyrido[2,3-b][1,4]oxazin-7-yl)isoquinolin-3-yl)carbamate

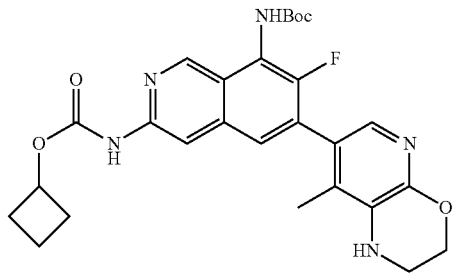 [SMILES: Cc1c(-c2cc3cc(NC(=O)OC4CCC4)ncc3c(NC(=O)OC(C)(C)C)c2F)cnc2c1NCCO2]

To a solution of tert-butyl 7-[8-(tert-butoxycarbonylamino)-3-(cyclobutoxycarbonylamino)-7-fluoro-6-isoquinolyl]-8-methyl-2,3-dihydropyrido[2,3-b][1,4]oxazine-1-carboxylate (120 mg, 0.19 mmol) in dichloromethane (10 mL) was added TFA (1 mL) at 25° C. The resulting solution was stirred for 16 h at 25° C. The reaction mixture was concentrated under vacuum and the residue was purified by Prep-HPLC (Column: X Select CSH Prep C18 OBD Column, 5 μm, 19*150 mm; Mobile Phase A: Water (0.1% FA), Mobile Phase B: MeOH; Flow rate: 25 mL/min; Gradient: 45% B to 60% B in 10 min) to afford cyclobutyl N-[8-amino-7-fluoro-6-(8-methyl-2,3-dihydro-1H-pyrido[2,3-b][1,4]oxazin-7-yl)-3-isoquinolyl]carbamate (17.8 mg, 0.042 mmol, 21.8% yield) as a yellow solid. LCMS (ESI) [M+H]$^+$= 424.2, $R_T$ 0.981 min, Method K. $^1$H NMR (400 MHz, DMSO-$d_6$) δ 10.05 (s, 1H), 9.33 (s, 1H), 7.96 (s, 1H), 7.32 (s, 1H), 6.83 (d, J=6.1 Hz, 1H), 6.21 (s, 2H), 5.68 (t, J=2.8 Hz, 1H), 4.95 (p, J=7.6 Hz, 1H), 4.28 (t, J=4.4 Hz, 2H), 3.41 (t, J=4.4 Hz, 2H), 2.31 (dddt, J=9.8, 7.6, 5.5, 2.5 Hz, 2H), 2.14-2.00 (m, 2H), 1.91 (d, J=1.6 Hz, 3H), 1.76-1.60 (dtd, J=18.6, 10.4, 8.0 Hz, 2H).

Example 154

1-(8-Amino-7-fluoro-6-(8-methyl-2,3-dihydro-1H-pyrido[2,3-b][1,4]oxazin-7-yl)isoquinolin-3-yl)-3-ethylurea (Compound 720)

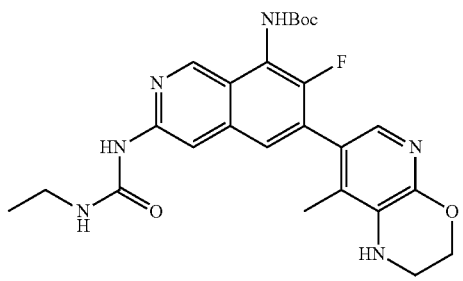 [SMILES: CCNC(=O)Nc1cc2cc(-c3cnc4c(c3C)NCCO4)c(F)c(NC(=O)OC(C)(C)C)c2cn1]

Step 1: tert-Butyl 7-(8-((tert-butoxycarbonyl)amino)-3-(3-ethylureido)-7-fluoroisoquinolin-6-yl)-8-methyl-2,3-dihydro-1H-pyrido[2,3-b][1,4]oxazine-1-carboxylate

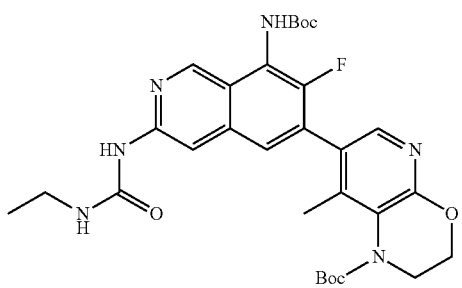 [SMILES: CCNC(=O)Nc1cc2cc(-c3cnc4c(c3C)N(C(=O)OC(C)(C)C)CCO4)c(F)c(NC(=O)OC(C)(C)C)c2cn1]

Under nitrogen, a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (200.0 mg, 0.38 mmol), DMAP (54.0 mg, 0.44 mmol), pyridine (4 mL, 0.38 mmol) and phenyl carbonochloridate (350 mg, 2.24 mmol) in dichloromethane (4 mL) was stirred for 1 h at 0° C. Then ethyl amine (5 mL, 0.38 mmol) was added and stirred at 60° C. for 2 hours. The resulting solution was concentrated under vacuum. The residue was purified by flash chromatography on silica gel eluting with petroleum ether/ethyl acetate (63/27) to afford tert-butyl 7-[8-(tert-butoxycarbonylamino)-3-(ethylcarbamoylamino)-7-fluoro-6-isoquinolyl]-8-methyl-2,3-dihydropyrido[2,3-b][1,4]oxazine-1-carboxylate (150 mg, 0.251 mmol, 66.1% yield) as a yellow solid. LCMS (ESI) [M+H]$^+$=597.

Step 2: 1-(8-Amino-7-fluoro-6-(8-methyl-2,3-dihydro-1H-pyrido[2,3-b][1,4]oxazin-7-yl)isoquinolin-3-yl)-3-ethylurea

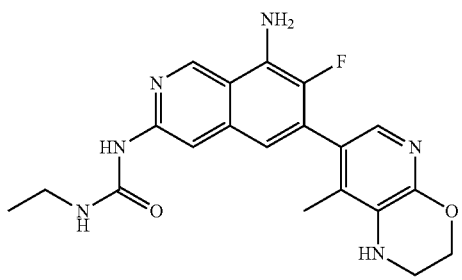 [SMILES: CCNC(=O)Nc1cc2cc(-c3cnc4c(c3C)NCCO4)c(F)c(N)c2cn1]

A solution of tert-butyl 7-[8-(tert-butoxycarbonylamino)-3-(ethylcarbamoylamino)-7-fluoro-6-isoquinolyl]-8-methyl-2,3-dihydropyrido[2,3-b][1,4]oxazine-1-carboxylate (150.0 mg, 0.25 mmol) in dichloromethane (5 mL) and TFA (2 mL) was stirred at room temperature for 2 hours. The solution was concentrated under vacuum. The pH value of the residue was adjusted to alkaline with triethylamine. The mixture was concentrated under vacuum. The residue was purified by Prep-HPLC (Column: X Bridge Prep OBD C18 Column 30×150 mm 5 μm; Mobile phase A: water (10 mmol/L/NH$_4$HCO$_3$), mobile phase B: ACN; Flow rate: 60 mL/min; Gradient: 16% B to 35% B in 7 min) to afford 1-[8-amino-7-fluoro-6-(8-methyl-2,3-dihydro-1H-pyrido[2,3-b][1,4]oxazin-7-yl)-3-isoquinolyl]-3-ethyl-urea (70 mg, 0.177 mmol, 70.2% yield) as a yellow solid. LCMS (ESI) [M+H]$^+$=397.4, R$_T$ 1.696 min., Method K. $^1$H NMR (300 MHz, DMSO-d$_6$) δ 9.26 (s, 1H), 8.91 (s, 1H), 7.81 (s, 1H), 7.30 (s, 1H), 7.05 (d, J=5.9 Hz, 1H), 6.72 (d, J=6.2 Hz, 1H), 6.13 (s, 2H), 5.66 (s, 1H), 4.30-4.24 (m, 2H), 3.32-3.29 (m, 2H), 3.20-3.08 (m, 2H), 1.90 (s, 3H), 1.12-1.02 (t, J=7.5 Hz, 3H).

Example 155

(R)-8-(Oxetan-3-yl)-8-azaspiro[4.5]decan-2-yl (8-amino-7-fluoro-6-(8-methyl-2,3-dihydro-1H-pyrido[2,3-b][1,4]oxazin-7-yl)isoquinolin-3-yl)carbamate and (S)-8-(Oxetan-3-yl)-8-azaspiro[4.5]decan-2-yl (8-amino-7-fluoro-6-(8-methyl-2,3-dihydro-1H-pyrido[2,3-b][1,4]oxazin-7-yl)isoquinolin-3-yl)carbamate (Compound 511a and Compound 511b)

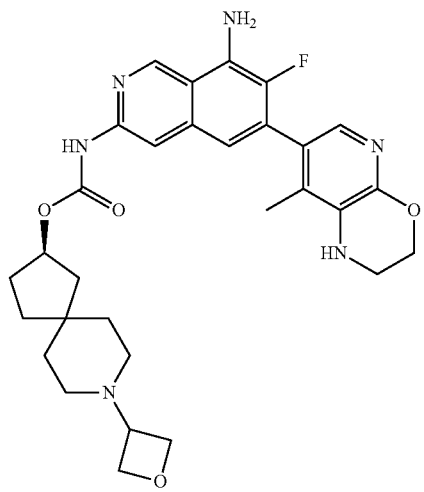

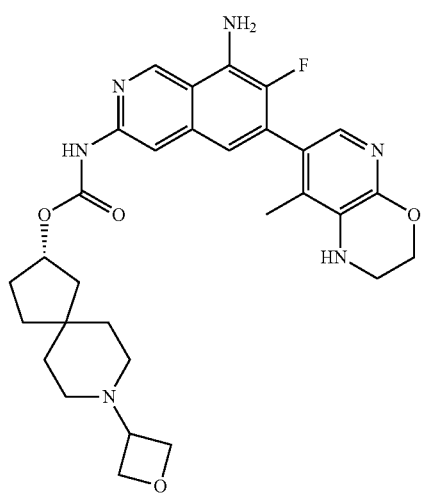

Step 1: tert-Butyl 7-(3-((((8-(tert-butoxycarbonyl)-8-azaspiro[4.5]decan-2-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

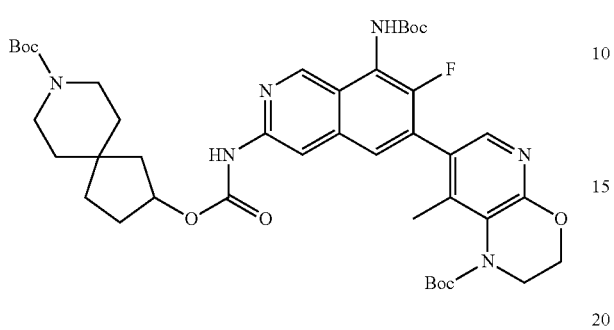

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (200.0 mg, 0.38 mmol), tert-butyl 3-hydroxy-8-azaspiro[4.5]decane-8-carboxylate (194.0 mg, 0.76 mmol) and DIEA (246.0 mg, 1.91 mmol) in dichloromethane (10 mL) was added triphosgene (75.0 mg, 0.25 mmol) at 0° C. The mixture was stirred at 0° C. for 1 hour. The reaction mixture was concentrated under vacuum. The residue was purified by flash chromatography on silica gel eluting with dichloromethane/methanol (93/7) to afford tert-butyl 7-[8-(tert-butoxycarbonylamino)-3-[(8-tert-butoxycarbonyl-8-azaspiro[4.5]decan-3-yl)oxycarbonylamino]-7-fluoro-6-isoquinolyl]-8-methyl-2,3-dihydropyrido[2,3-b][1,4]oxazine-1-carboxylate (279 mg, 0.34 mmol, 90% yield) as a brown solid. LCMS (ESI) [M+H]+=807.

Step 2: 8-Azaspiro[4.5]decan-2-yl (8-amino-7-fluoro-6-(8-methyl-2,3-dihydro-1H-pyrido[2,3-b][1,4]oxazin-7-yl)isoquinolin-3-yl)carbamate

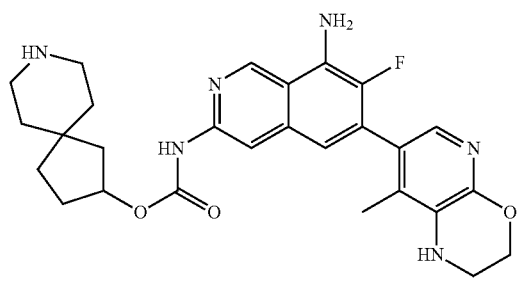 [SMILES: Cc1c(-c2cc3cc(NC(=O)OC4CCC5(CCNCC5)C4)ncc3c(N)c2F)cnc2c1NCCO2]

To a solution of tert-butyl 7-[8-(tert-butoxycarbonylamino)-3-[(8-tert-butoxycarbonyl-8-azaspiro[4.5]decan-3-yl)oxycarbonylamino]-7-fluoro-6-isoquinolyl]-8-methyl-2,3-dihydropyrido[2,3-b][1,4]oxazine-1-carboxylate (200.0 mg, 0.25 mmol) in dichloromethane (5 mL) was added 2,2,2-trifluoroacetic acid (1 mL) at 25° C. and the mixture was stirred at 25° C. for 1 hour. The solvent was concentrated under vacuum. The residue was purified by reverse phase column eluting with water (0.1% NH₄HCO₃)/MeOH (60/40) to afford 8-azaspiro[4.5]decan-3-yl N-[8-amino-7-fluoro-6-(8-methyl-2,3-dihydro-1H-pyrido[2,3-b][1,4]oxazin-7-yl)-3-isoquinolyl]carbamate (50 mg, 0.098 mmol, 39% yield) as a brown solid. LCMS (ESI) [M+H]+=507.

Step 3: (R)-8-(oxetan-3-yl)-8-azaspiro[4.5]decan-2-yl (8-amino-7-fluoro-6-(8-methyl-2,3-dihydro-1H-pyrido[2,3-b][1,4]oxazin-7-yl)isoquinolin-3-yl)carbamate and (S)-8-(oxetan-3-yl)-8-azaspiro[4.5]decan-2-yl (8-amino-7-fluoro-6-(8-methyl-2,3-dihydro-1H-pyrido[2,3-b][1,4]oxazin-7-yl)isoquinolin-3-yl)carbamate

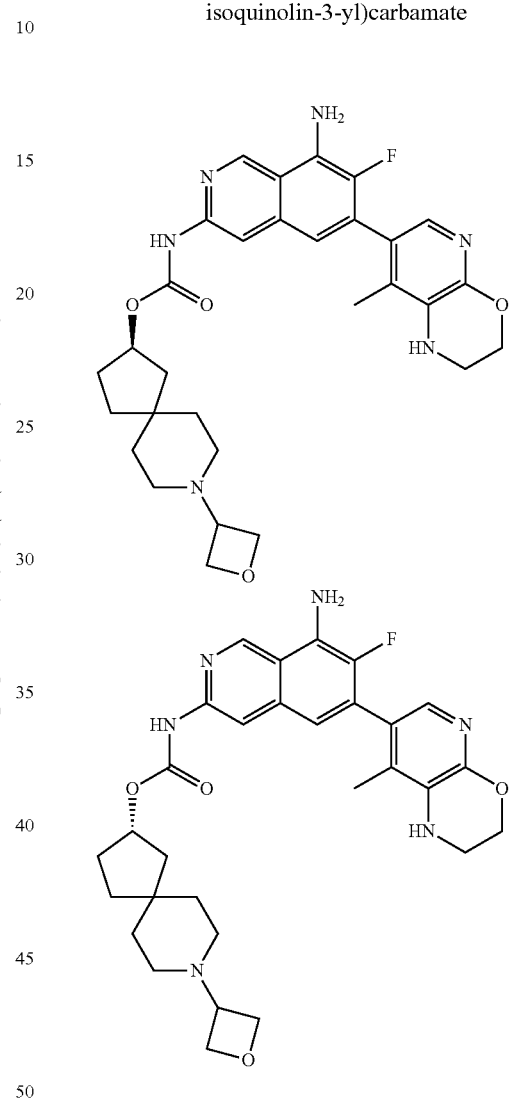

A solution of 8-azaspiro[4.5]decan-3-yl N-[8-amino-7-fluoro-6-(8-methyl-2,3-dihydro-1H-pyrido[2,3-b][1,4]oxazin-7-yl)-3-isoquinolyl]carbamate (100.0 mg, 0.20 mmol), 3-oxetanone (142.0 mg, 1.97 mmol) and titanium tetraisopropanolate (224.0 mg, 0.79 mmol) in methyl alcohol (10 mL) was stirred at 60° C. for 2 hours. Then NaBH₃CN (38.0 mg, 0.60 mmol) was added and stirred at 25° C. for 1 hour. The reaction was concentrated under vacuum and purified by Prep-HPLC with following condition (Column: X Select CSH Prep C18 OBD Column, 5 μm, 19*150 mm; Water (0.1% FA): ACN=7% B to 18% B in 10 min; 25 mL/min) to afford the racemate. Then racemic product was separated by chiral-HPLC (Column: CHIRALPAK IE, 2*25 cm, 5 μm; MTBE (10 mm NH₃-MEOH): EtOH=50% B to 50% B in 17 min; 17 mL/min) to afford two enantiomers. Absolute stereochemistry was arbitrarily assigned.

Enantiomer 1 (Compound 511a) (11.1 mg, 0.019 mmol, 10% yield). R$_T$ 2.666 min (CHIRALPAK IE-3, 0.46*5 cm; 3 μm. MTBE (0.1% DEA):EtOH=50:50, 1 ml/min). LCMS (ESI) [M+H]$^+$=563, R$_T$ 1.587 min, Method J; $^1$H NMR (300 MHz, DMSO-d$_6$) δ 9.95 (s, 1H), 9.31 (s, 1H), 7.94 (s, 1H), 7.30 (s, 1H), 6.80 (d, J=6.2 Hz, 1H), 6.19 (s, 2H), 5.66 (s, 1H), 5.15-5.08 (m, 1H), 4.60-4.28 (m, 6H), 3.40-3.29 (m, 2H), 2.27-1.72 (m, 10H), 1.70-1.40 (m, 8H).

Enantiomer 2 (Compound 511b) (10.7 mg, 0.0190 mmol, 9.6% yield). R$_T$ 2.120 min (CHIRALPAK IE-3, 0.46*5 cm; 3 μm. Mobile phase: MTBE (0.1% DEA):EtOH=50:50, 1 ml/min). LCMS (ESI) [M+H]$^+$=563, R$_T$ 1.589 min., Method J. $^1$H NMR (300 MHz, DMSO-d$_6$) δ 9.95 (s, 1H), 9.31 (s, 1H), 7.94 (s, 1H), 7.30 (s, 1H), 6.80 (d, J=6.2 Hz, 1H), 6.19 (s, 2H), 5.66 (s, 1H), 5.15-5.08 (m, 1H), 4.60-4.28 (m, 6H), 3.40-3.29 (m, 2H), 2.27-1.72 (m, 10H), 1.70-1.40 (m, 8H).

Example 156

(1s,3s)-3-Hydroxycyclobutyl (8-amino-7-fluoro-6-(8-methyl-2,3-dihydro-1H-pyrido[2,3-b][1,4]oxazin-7-yl)isoquinolin-3-yl)carbamate (Compound 485a)

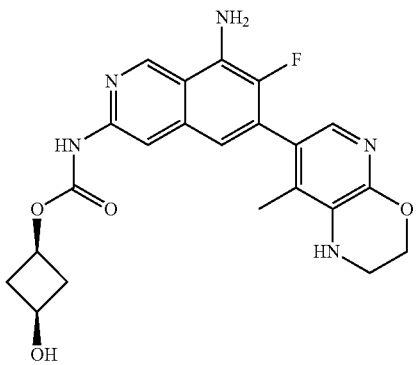 [SMILES: Cc1c(-c2cc3cc(NC(=O)O[C@H]4C[C@@H](O)C4)ncc3c(N)c2F)cnc2c1NCCO2]

Step 1: tert-Butyl 7-(8-((tert-butoxycarbonyl)amino)-7-fluoro-3-((((1s,3s)-3-hydroxycyclobutoxy)carbonyl)amino)isoquinolin-6-yl)-8-methyl-2,3-dihydro-1H-pyrido[2,3-b][1,4]oxazine-1-carboxylate

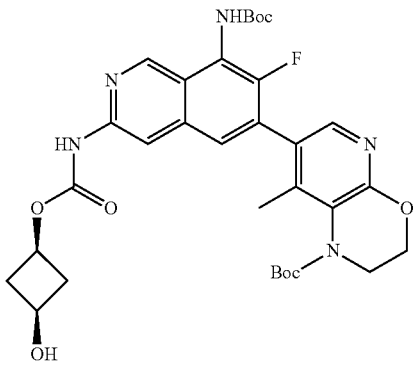 [SMILES: Cc1c(-c2cc3cc(NC(=O)O[C@H]4C[C@@H](O)C4)ncc3c(NC(=O)OC(C)(C)C)c2F)cnc2c1N(C(=O)OC(C)(C)C)CCO2]

A solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (300 mg, 0.57 mmol), (1s,3s)-3-((tert-butyldimethylsilyl)oxy)cyclobutan-1-ol (230 mg, 1.14 mmol) and DIEA (368.86 mg, 2.85 mmol) in dichloromethane (2 mL) was stirred at room temperature for 2 hours. Then triphosgene (169.4 mg, 0.57 mmol) was added. The reaction mixture was then stirred at 0° C. for 1 hour. The reaction mixture was concentrated under vacuum. The residue was purified by reverse phase chromatography (acetonitrile 0-60/0.1% NH$_4$HCO$_3$ in water) to afford tert-butyl 7-[8-(tert-butoxycarbonylamino)-3-[[3-[tert-butyl(dimethyl)silyl]oxycyclobutoxy]carbonylamino]-7-fluoro-6-isoquinolyl]-8-methyl-2,3-dihydropyrido[2,3-b][1,4]oxazine-1-carboxylate (150 mg, 0.23 mmol, 53.7% yield) as a light yellow solid. LC/MS (ESI): [M+H]$^+$=640.3.

Step 2: (1s,3s)-3-Hydroxycyclobutyl (8-amino-7-fluoro-6-(8-methyl-2,3-dihydro-1H-pyrido[2,3-b][1,4]oxazin-7-yl)isoquinolin-3-yl)carbamate

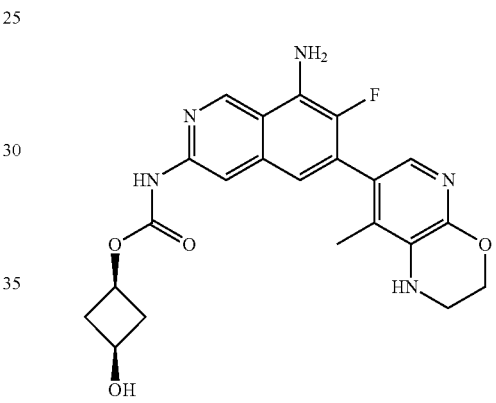

To a solution of tert-butyl 7-[8-(tert-butoxycarbonylamino)-7-fluoro-3-[(3-hydroxycyclobutoxy)carbonylamino]-6-isoquinolyl]-8-methyl-2,3-dihydropyrido[2,3-b][1,4]oxazine-1-carboxylate (150.0 mg, 0.23 mmol) in dichloromethane (8 mL) was added trifluoroacetic acid (1.6 mL). The reaction was stirred at room temperature for 2 hours. The mixture was then concentrated under vacuum. The residue was re-dissolved in dichloromethane and then adjusted to pH 8 with triethylamine. The mixture was concentrated under vacuum and purified by Prep-HPLC (X Select CSH Prep C18 OBD Column, 5 μm, 19*150 mm; Mobile Phase A: Water (0.1% FA), Mobile Phase B: ACN; Flow rate: 25 mL/min; Gradient: 7% B to 33% B in 7 min) to afford (3-hydroxycyclobutyl) N-[8-amino-7-fluoro-6-(8-methyl-2,3-dihydro-1H-pyrido[2,3-b][1,4]oxazin-7-yl)-3-isoquinolyl]carbamate (19.9 mg, 0.045 mmol, 19.3% yield) as a light yellow solid. LCMS (ESI): [M+H]$^+$=440.2, R$_T$ 1.028 min, Method J; $^1$H NMR (300 MHz, DMSO-d$_6$) δ 10.10 (s, 1H), 9.34 (s, 1H), 7.96 (s, 1H), 7.33 (s, 1H), 6.84 (d, J=6.1 Hz, 1H), 6.22 (s, 2H), 5.69 (d, J=2.8 Hz, 1H), 5.22 (d, J=6.5 Hz, 1H), 4.53 (p, J=7.4 Hz, 1H), 4.29 (t, J=4.4 Hz, 2H), 3.84-3.80 (m 1H), 3.38-3.34 (m, 2H), 2.69-2.74 (m, 2H), 2.01-1.86 (m, 5H).

Example 157

1-[8-Amino-7-fluoro-6-(8-methyl-2,3-dihydro-1H-pyrido[2,3-b][1,4]oxazin-7-yl)-3-isoquinolyl]-3-[(1S,2R)-2-fluorocyclopropyl]urea (Compound 734a)

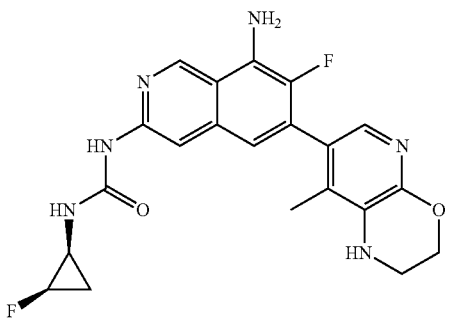 [SMILES: Cc1c(-c2cc3cc(NC(=O)N[C@H]4C[C@H]4F)ncc3c(N)c2F)cnc2c1NCCO2]

Step 1: tert-Butyl 7-[8-chloro-7-fluoro-3-[[(1S,2R)-2-fluorocyclopropyl]carbamoylamino]-6-isoquinolyl]-8-methyl-2,3-dihydropyrido[2,3-b][1,4]oxazine-1-carboxylate

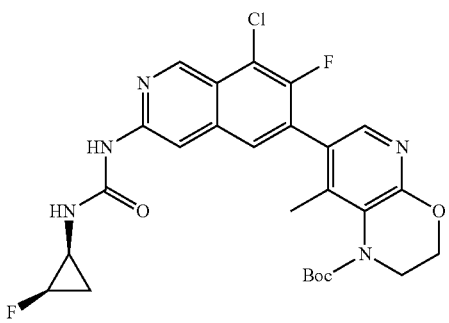 [SMILES: Cc1c(-c2cc3cc(NC(=O)N[C@H]4C[C@H]4F)ncc3c(Cl)c2F)cnc2c1N(C(=O)OC(C)(C)C)CCO2]

To a solution of tert-butyl 7-(3-amino-8-chloro-7-fluoro-6-isoquinolyl)-8-methyl-2,3-dihydropyrido[2,3-b][1,4]oxazine-1-carboxylate (700.0 mg, 1.58 mmol) and pyridine (622.4 mg, 7.86 mmol) in dichloromethane (30 mL) was added triphosgene (700.4 mg, 2.36 mmol). The reaction mixture was stirred at 0° C. for 40 min. Then a solution of [[(1R,2S)-2-fluorocyclopropyl]amino]4-methylbenzenesulfonate (2.32 g, 9.44 mmol) in dichloromethane (5 mL) was added. The solution was stirred at 0° C. for 1.5 h. The reaction was quenched with water and extracted with dichloromethane. The organic layers were combined, dried over anhydrous sodium sulfate and concentrated under vacuum. The residue was purified by flash chromatography on silica gel eluting with dichloromethane/methanol (20/1) to afford tert-butyl 7-[8-chloro-7-fluoro-3-[[(1R,2S)-2-fluorocyclopropyl]carbamoylamino]-6-isoquinolyl]-8-methyl-2,3-dihydropyrido[2,3-b][1,4]oxazine-1-carboxylate (200 mg, 0.37 mmol, 46.6% yield) as a yellow solid. LCMS (ESI) [M+H]⁺= 546.3.

Step 2: tert-Butyl 7-[8-(tert-butoxycarbonylamino)-7-fluoro-3-[[(1S,2R)-2-fluorocyclopropyl]carbamoylamino]-6-isoquinolyl]-8-methyl-2,3-dihydropyrido[2,3-b][1,4]oxazine-1-carboxylate

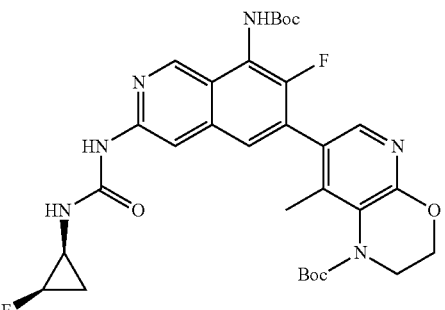

Under nitrogen, a mixture of tert-butyl 7-[8-chloro-7-fluoro-3-[[(1S,2R)-2-fluorocyclopropyl]carbamoylamino]-6-isoquinolyl]-8-methyl-2,3-dihydropyrido[2,3-b][1,4]oxazine-1-carboxylate (200.0 mg, 0.37 mmol), NH₂Boc (2571.6 mg, 21.98 mmol), Brettphos Pd G3 (66.5 mg, 0.07 mmol) and Cs₂CO₃ (238.9 mg, 0.73 mmol) in 1,4-dioxane (8 mL) was stirred for 2 hours at 80° C. The reaction was concentrated under vacuum. The residue was purified by flash chromatography on silica gel eluting with dichloromethane/methanol (20/1) to afford tert-butyl 7-[8-(tert-butoxycarbonylamino)-7-fluoro-3-[[(1S,2R)-2-fluorocyclopropyl]carbamoylamino]-6-isoquinolyl]-8-methyl-2,3-dihydropyrido[2,3-b][1,4]oxazine-1-carboxylate (70 mg, 0.11 mmol, 30.5% yield) as a yellow solid. LCMS (ESI) [M+H]⁺=627.4.

Step 3: 1-[8-Amino-7-fluoro-6-(8-methyl-2,3-dihydro-1H-pyrido[2,3-b][1,4]oxazin-7-yl)-3-isoquinolyl]-3-[(1S,2R)-2-fluorocyclopropyl]urea

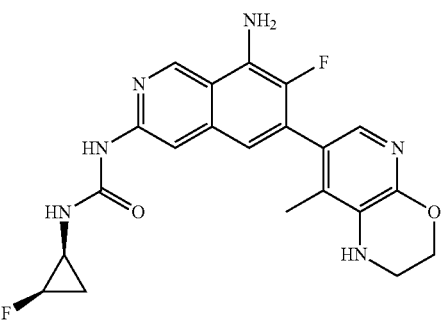 [SMILES: Cc1c(-c2cc3cc(NC(=O)N[C@H]4C[C@H]4F)ncc3c(N)c2F)cnc2c1NCCO2]

To a solution of tert-butyl 7-[8-(tert-butoxycarbonylamino)-7-fluoro-3-[[(1S,2R)-2-fluorocyclopropyl]carbamoylamino]-6-isoquinolyl]-8-methyl-2,3-dihydropyrido[2,3-b][1,4]oxazine-1-carboxylate (64.8 mg, 0.10 mmol) in dichloromethane (5 mL) was added TFA (1 mL). The reaction mixture was stirred at room temperature for 1.5 hours and concentrated under vacuum. The residue was dissolved in dichloromethane, adjusted to pH 8 with TEA and concentrated under vacuum. The residue was purified by prep-HPLC (Column: X Bridge Prep OBD C18 Column 30×150 mm 5 μm; Mobile Phase A: water (10 mmol/L NH$_4$HCO$_3$), Mobile Phase B: ACN; Flow rate: 60 mL/min; Gradient: 14% B to 38% B in 7 min) to afford 1-[8-amino-7-fluoro-6-(8-methyl-2,3-dihydro-1H-pyrido[2,3-b][1,4]oxazin-7-yl)-3-isoquinolyl]-3-[(1R,2S)-2-fluorocyclopropyl]urea (10.04 mg, 0.02 mmol, 22.8% yield) as a yellow solid. LCMS (ESI) [M+H]$^+$=427.2, R$_T$ 1.890 min, Method L; $^1$H NMR (300 MHz, DMSO-d$_6$) δ 9.30 (s, 1H), 9.06 (s, 1H), 7.84 (s, 1H), 7.44 (s, 1H), 7.33 (s, 1H), 6.76 (d, J=6.1 Hz, 1H), 6.18 (s, 2H), 5.68 (s, 1H), 4.89-4.68 (m, 1H), 4.29 (t, J=4.5 Hz, 2H), 3.37-3.35 (m, 2H), 2.70-2.67 (m, 1H), 1.92 (d, J=1.6 Hz, 3H), 1.11-1.09 (m, 1H), 0.83-0.80 (m, 1H).

Example 158

(3R,3aR,6aS)-Hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate and (3S,3aS,6aR)-Hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate (Compound 568a and Compound 568b)

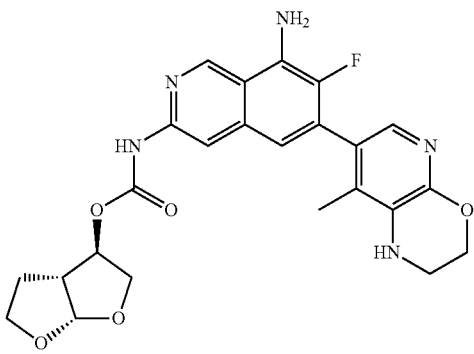

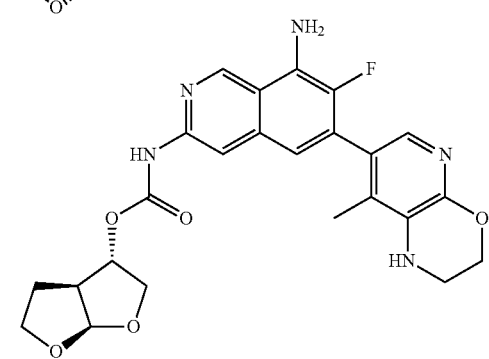

Step 1: 4-methylene-2,3,3a,6a-tetrahydrofuro[2,3-b]furan

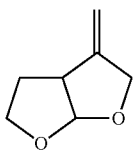

To a solution of Bu$_3$SnH (1700.0 mg, 5.82 mmol) and AIBN (65.0 mg, 0.40 mmol) in toluene (15 mL) was added dropwise a solution of (2R,3S)-3-iodo-2-prop-2-ynoxytetrahydrofuran (1000.0 mg, 3.97 mmol) in toluene (2 mL) at 110° C. The mixture was stirred for 5 hours. The reaction was concentrated under vacuum. The residue was taken up in ACN (100 mL) and washed with petroleum ether. The ACN layer was concentrated under vacuum. The residue was purified by flash chromatography on silica gel eluting with petroleum ether/ethyl acetate (80/20) to afford 4-methylene-2,3,3a,6a-tetrahydrofuro[2,3-b]furan (150 mg, 1.189 mmol, 30% yield) as a light yellow oil. LCMS(ESI): [M+H]$^+$=127.1.

Step 2: (3aR,4S,6aS)-2,3,3a,4,5,6a-Hexahydrofuro[2,3-b]furan-4-ol

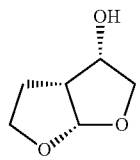

A mixture of 2,3,3a,6a-tetrahydrofuro[2,3-b]furan-4-one (247.0 mg, 1.93 mmol) and NaBH$_4$ (147.0 mg, 3.87 mmol) in ethanol (5 mL) was stirred at 25° C. for 2 hours. The reaction was concentrated under vacuum. The residue was purified by flash chromatography on silica gel eluting with dichloromethane/methanol (92/8) to afford (3aR,4S,6a5)-2,3,3a,4,5,6a-hexahydrofuro[2,3-b]furan-4-ol (160 mg, 1.229 mmol, 63.8% yield) as a colorless oil. LCMS(ESI) [M+H]$^+$= 131.1

Step 3: (3R,3aR,6aS)-Hexahydrofuro[2,3-b]furan-3-yl 4-nitrobenzoate

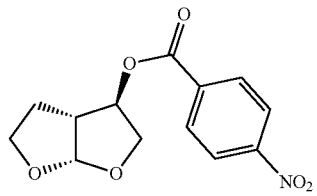 [SMILES: O=C(O[C@H]1CO[C@@H]2OCC[C@@H]21)c1ccc([N+](=O)[O-])cc1]

To a solution of PPh$_3$ (705.0 mg, 2.69 mmol) in tetrahydrofuran (30 mL) was added DIAD (540.0 mg, 2.67 mmol) and the mixture was stirred at 25° C. for 1 hour. Then a solution of 4-nitrobenzoic acid (465.0 mg, 2.78 mmol) and (3aR,4S,6aS)-2,3,3a,4,5,6a-hexahydrofuro[2,3-b]furan-4-ol (300.0 mg, 2.31 mmol) in THF was added. The mixture was stirred at 25° C. for 3 hours. The mixture was concentrated under vacuum. The residue was purified by flash chromatography on silica gel eluting with petroleum ether/ethyl acetate (50/50) to afford (3R,3aR,6aS)-hexahydrofuro[2,3-b]furan-3-yl 4-nitrobenzoate (360 mg, 1.2892 mmol, 55.9% yield).

Step 2: (3R,3aR,6aS)-hexahydrofuro[2,3-b]furan-3-ol

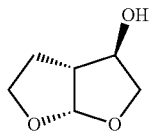

A mixture of (3R,3aR,6aS)-hexahydrofuro[2,3-b]furan-3-yl 4-nitrobenzoate (360 mg, 1.28 mmol) and K$_2$CO$_3$ (883 mg, 6.4 mmol) in methyl alcohol (1 mL) was stirred at 25° C. for 12 hours. After concentration under vacuum the residue was purified by flash chromatography on silica gel eluting with petroleum ether/ethyl acetate (1/1) to afford (3R,3aR,6aS)-hexahydrofuro[2,3-b]furan-3-ol (120 mg, 0.92 mmol) as a colorless oil. $^1$H NMR (300 MHz, CDCl$_3$) δ 5.89 (d, J=4.9 Hz, 1H), 4.23 (d, J=3.2 Hz, 1H), 3.99 (dd, J=10.3, 3.2 Hz, 1H), 3.94-3.77 (m, 3H), 2.88-2.75 (m, 1H), 2.17 (ddt, J=13.1, 10.6, 8.4 Hz, 1H), 1.71 (ddt, J=13.1, 6.6, 4.3 Hz, 1H).

Step 3: (3R,3aR,6aS)-Hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate and tert-Butyl 7-(8-((tert-butoxycarbonyl)amino)-7-fluoro-3-(((((3S,3aS,6aR)-hexahydrofuro[2,3-b]furan-3-yl)oxy)carbonyl)amino)isoquinolin-6-yl)-8-methyl-2,3-dihydro-1H-pyrido[2,3-b][1,4]oxazine-1-carboxylate

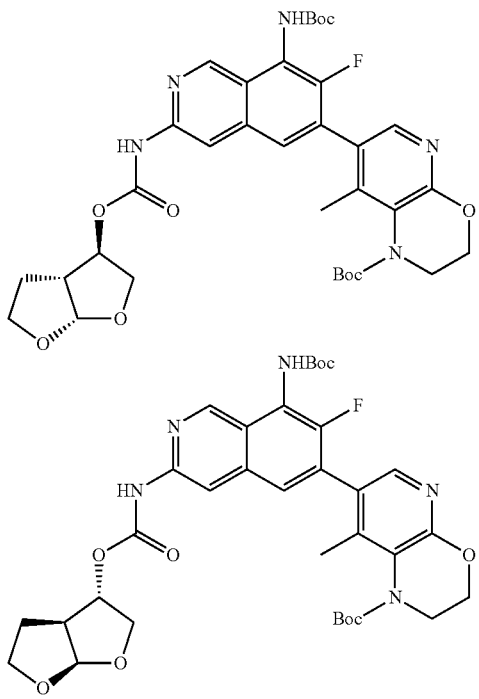

To a mixture of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (380.0 mg, 0.72 mmol), 2,3,3a,4,5,6a-hexahydrofuro[2,3-b]furan-4-ol (188.0 mg, 1.44 mmol) and DIEA (466.0 mg, 3.61 mmol) in dichloromethane (40 mL) was added triphosgene (128.0 mg, 0.43 mmol) at 0° C. The mixture was stirred at 0° C. for 2 hours and concentrated under vacuum. The residue was purified by flash chromatography on silica gel eluting with dichloromethane/methanol (10/1) to afford the racemic product (300 mg). The racemate was separated by chiral HPLC (Column: CHIRALPAK IC, 2*25 cm, 5 μm; Mobile Phase A: MTBE (10 mm NH$_3$ in MeOH), Mobile Phase B:MeOH; Flow rate: 20 mL/min; Gradient: 20% B to 20% B in 12 min) to afford (3R,3aR,6aS)-hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate (92 mg, 0.135 mmol, 18.7% yield) and tert-butyl 7-(8-((tert-butoxycarbonyl)amino)-7-fluoro-3-(((((3S,3aS,6aR)-hexahydrofuro[2,3-b]furan-3-yl)oxy)carbonyl)amino)isoquinolin-6-yl)-8-methyl-2,3-dihydro-1H-pyrido[2,3-b][1,4]oxazine-1-carboxylate (94 mg, 0.1379 mmol, 19.1% yield) as yellow solid. LCMS (ESI) [M+H]$^+$=682.

Step 4: (3R,3aR,6aS)-Hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate and (3S,3aS,6aR)-Hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate

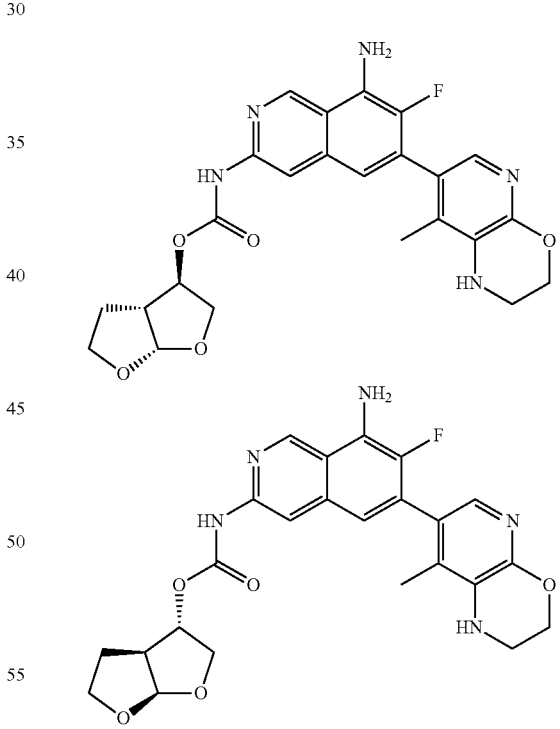

To a solution of (3R,3aR,6aS)-hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate (92.0 mg, 0.13 mmol) in dichloromethane (4 mL) was added 2,2,2-trifluoroacetic acid (2 mL). The mixture was stirred at room temperature for 2 hours and concentrated under vacuum. The residue was purified by Prep-HPLC (Column: X select CSH OBD Column 30*150 mm, 5 μm; Mobile Phase A: Water (0.1% FA), Mobile Phase B: ACN; Flow rate: 60 mL/min) to afford (3R,3aR,6aS)-hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate (Compound 568a) (38.1 mg, 0.0791 mmol, 58.6% yield) as a yellow solid (Relative stereochemistry as drawn. Absolute stereochemistry arbitrarily assigned): $R_T$ 1.229 min (CHIRALPAK IE-3, 0.46*5 cm; 3 μm; MTBE (0.1% DEA): MeOH=50:50, 1 ml/min). LCMS (ESI) [M+H]$^+$=482, $R_T$ 1.861 min, Method J; $^1$H NMR (300 MHz, DMSO-d$_6$) δ 10.18 (s, 1H), 9.34 (s, 1H), 7.98 (s, 1H), 7.33 (s, 1H), 6.85 (d, J=6.1 Hz, 1H), 6.22 (s, 2H), 5.77 (d, J=5.0 Hz, 1H), 5.67 (s, 1H), 5.12 (d, J=3.4 Hz, 1H), 4.29 (t, J=4.4 Hz, 2H), 4.02 (dd, J=10.9, 3.6 Hz, 1H), 3.92 (d, J=10.9 Hz, 1H), 3.87-3.68 (m, 2H), 3.45-3.35 (s, 2H), 2.92 (dt, J=9.8, 4.1 Hz, 1H), 2.21-2.02 (m, 1H), 1.93-1.89 (m, 4H).

(3S,3aS,6aR)-hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate (Compound 568b) was prepared in a similar fashion (37.2 mg, 0.0773 mmol, 57.3% yield) as a yellow solid (Relative stereochemistry as drawn. Absolute stereochemistry arbitrarily assigned): RT 1.600 min (CHIRALPAK IE-3, 0.46*5 cm; 3 μm; MTBE (0.1% DEA):MeOH=50:50, 1 ml/min). LCMS (ESI) [M+H]$^+$=482, $R_T$ 1.861 min, Method J, $^1$H NMR (300 MHz, DMSO-d$_6$) δ 10.18 (s, 1H), 9.34 (s, 1H), 7.98 (s, 1H), 7.33 (s, 1H), 6.85 (d, J=6.1 Hz, 1H), 6.22 (s, 2H), 5.77 (d, J=5.0 Hz, 1H), 5.67 (s, 1H), 5.12 (d, J=3.4 Hz, 1H), 4.29 (t, J=4.4 Hz, 2H), 4.02 (dd, J=10.9, 3.6 Hz, 1H), 3.92 (d, J=10.9 Hz, 1H), 3.87-3.68 (m, 2H), 3.45-3.35 (s, 2H), 2.92 (dt, J=9.8, 4.1 Hz, 1H), 2.21-2.02 (m, 1H), 1.93-1.89 (m, 4H).

Example 159

1-[8-Amino-7-fluoro-6-(8-methyl-2,3-dihydro-1H-pyrido[2,3-b][1,4]oxazin-7-yl)-3-isoquinolyl]-3-(3-methoxycyclobutyl)urea (Compound 733a)

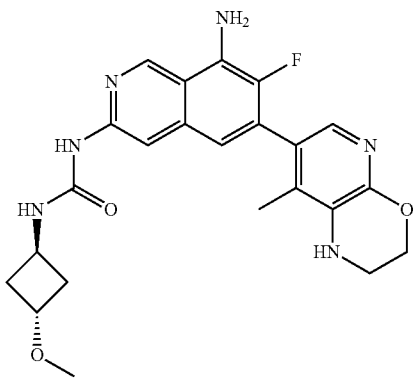 [SMILES: CO[C@H]1C[C@H](NC(=O)Nc2cc3cc(-c4cnc5c(c4C)NCCO5)c(F)c(N)c3cn2)C1]

Step 1: tert-Butyl 7-[8-(tert-butoxycarbonylamino)-7-fluoro-3-[(3-methoxycyclobutyl)carbamoylamino]-6-isoquinolyl]-8-methyl-2,3-dihydropyrido[2,3-b][1,4]oxazine-1-carboxylate

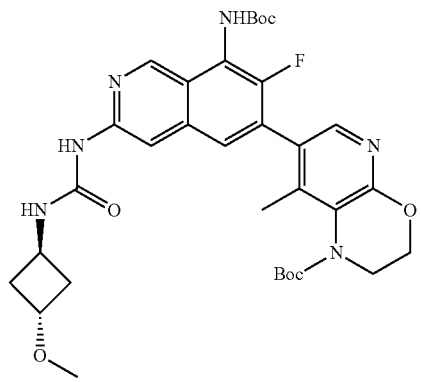 [SMILES: CO[C@H]1C[C@H](NC(=O)Nc2cc3cc(-c4cnc5c(c4C)N(C(=O)OC(C)(C)C)CCO5)c(F)c(NC(=O)OC(C)(C)C)c3cn2)C1]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (200.0 mg, 0.31 mmol) and DMAP (37.8 mg, 0.31 mmol) in dichloromethane (10 mL) was added (1r,3r)-3-methoxycyclobutan-1-amine (127.4 mg, 1.26 mmol) and the mixture was stirred at 60° C. for 5 hours. The reaction mixture was concentrated under vacuum and purified by flash chromatography on silica gel eluting with dichloromethane/methanol (91/9) to afford tert-butyl 7-[8-(tert-butoxycarbonylamino)-7-fluoro-3-[(3-methoxycyclobutyl)carbamoylamino]-6-isoquinolyl]-8-methyl-2,3-dihydropyrido[2,3-b][1,4]oxazine-1-carboxylate (186 mg, 0.28 mmol, 92% yield) as white solid. LCMS (ESI) [M+H]$^+$= 653.3.

Step 2: 1-[8-Amino-7-fluoro-6-(8-methyl-2,3-dihydro-1H-pyrido[2,3-b][1,4]oxazin-7-yl)-3-isoquinolyl]-3-(3-methoxycyclobutyl)urea

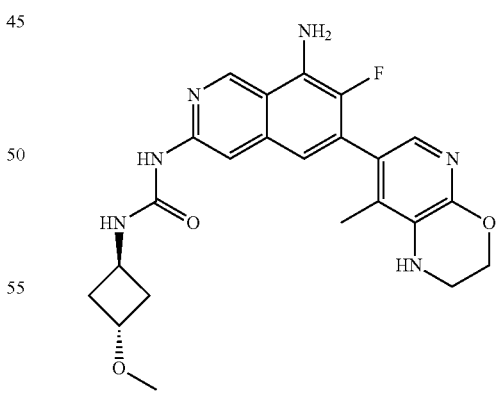

A solution of tert-butyl 7-[8-(tert-butoxycarbonylamino)-7-fluoro-3-[(3-methoxycyclobutyl)carbamoylamino]-6-isoquinolyl]-8-methyl-2,3-dihydropyrido[2,3-b][1,4]oxazine-1-carboxylate (180.0 mg, 0.28 mmol) and TFA (1.0 mL, 0.28 mmol) in dichloromethane (5 mL) was stirred at 25° C. for 1 hour. After concentration, the residue was purified by Prep-HPLC (Column: X Bridge Shield RP18 OBD Column 30*150 mm, 5 µm; Water (10 mmol/L NH₄HCO₃): ACN=19% B to 34% B in 10 min; 60 mL/min) to afford 1-[8-amino-7-fluoro-6-(8-methyl-2,3-dihydro-1H-pyrido[2,3-b][1,4]oxazin-7-yl)-3-isoquinolyl]-3-(3-methoxycyclobutyl)urea (82.1 mg, 0.18 mmol, 65.8% yield) as a yellow solid. LCMS (ESI): [M+H]=453.3; R$_T$ 1.105 min.; Method M; ¹H NMR (300 MHz, DMSO-d₆) δ 9.27 (s, 1H), 8.83 (s, 1H), 7.82 (s, 1H), 7.49-7.20 (m, 2H), 6.72 (d, J=6.2 Hz, 1H), 6.14 (s, 2H), 5.66 (s, 1H), 4.46-4.20 (m, 3H), 4.10-3.95 (m, 1H), 3.40-3.30 (m, 2H), 3.26 (s, 3H), 2.24-2.07 (m, 4H), 1.90 (s, 3H).

Example 160

1-(8-Amino-7-fluoro-6-(8-methyl-2,3-dihydro-1H-pyrido[2,3-b][1,4]oxazin-7-yl)isoquinolin-3-yl)-3-isopropylurea (Compound 746)

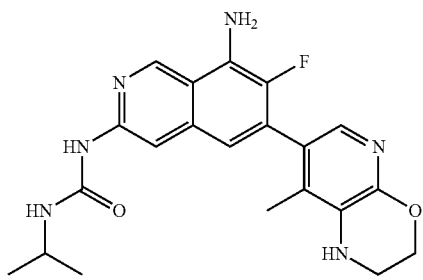 [SMILES: Cc1c(-c2cc3cc(NC(=O)NC(C)C)ncc3c(N)c2F)cnc2c1NCCO2]

Step 1: tert-Butyl 7-[8-chloro-7-fluoro-3-(isopropylcarbamoylamino)-6-isoquinolyl]-8-methyl-2,3-dihydropyrido[2,3-b][1,4]oxazine-1-carboxylate

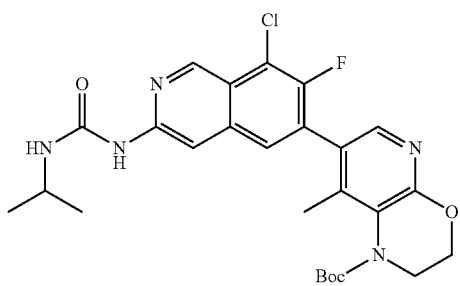 [SMILES: Cc1c(-c2cc3cc(NC(=O)NC(C)C)ncc3c(Cl)c2F)cnc2c1N(C(=O)OC(C)(C)C)CCO2]

Under nitrogen, to a solution of tert-butyl 7-(3-amino-8-chloro-7-fluoro-6-isoquinolyl)-8-methyl-2,3-dihydropyrido[2,3-b][1,4]oxazine-1-carboxylate (500 mg, 1.12 mmol) and pyridine (2 mL) in dichloromethane (20 mL) was added triphosgene (167 mg, 0.56 mmol) at 0° C. The mixture was stirred for 1 hour at 0° C. Then isopropylamine (664 mg, 11.23 mmol) was added and then the mixture was stirred at room temperature for 2 hours. The reaction mixture was concentrated under vacuum. The residue was purified by flash chromatography on silica gel eluting with petroleum ether/ethyl acetate (24/76) to afford tert-butyl 7-[8-chloro-7-fluoro-3-(isopropylcarbamoylamino)-6-isoquinolyl]-8-methyl-2,3-dihydropyrido[2,3-b][1,4]oxazine-1-carboxylate (230 mg, 0.434 mmol, 38.6% yield) as a yellow solid. LCMS (ESI) [M+H]⁺=530.

Step 2: tert-Butyl 7-[8-(tert-butoxycarbonylamino)-7-fluoro-3-(isopropylcarbamoylamino)-6-isoquinolyl]-8-methyl-2,3-dihydropyrido[2,3-b][1,4]oxazine-1-carboxylate

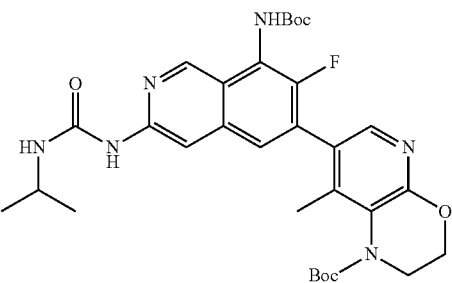 [SMILES: Cc1c(-c2cc3cc(NC(=O)NC(C)C)ncc3c(NC(=O)OC(C)(C)C)c2F)cnc2c1N(C(=O)OC(C)(C)C)CCO2]

Under nitrogen, a mixture of tert-butyl 7-[8-chloro-7-fluoro-3-(isopropylcarbamoylamino)-6-isoquinolyl]-8-methyl-2,3-dihydropyrido[2,3-b][1,4]oxazine-1-carboxylate (220 mg, 0.42 mmol), NH₂Boc (2.5 g, 21.37 mmol), Cs₂CO₃ (270 mg, 0.83 mmol), Brettphos (89 mg, 0.17 mmol) and Pd₂(dba)₃CHCl₃ (86 mg, 0.080 mmol) in 1,4-dioxane (6 mL) was stirred at 90° C. for 2 hours. After filtration, the filtrate was concentrated under vacuum and purified by flash chromatography on silica gel eluting with methanol/dichloromethane (1/9) to afford tert-butyl 7-[8-(tert-butoxycarbonylamino)-7-fluoro-3-(isopropylcarbamoylamino)-6-isoquinolyl]-8-methyl-2,3-dihydropyrido[2,3-b][1,4]oxazine-1-carboxylate (191 mg, 0.235 mmol, 56.5% yield) as a brown oil. LCMS (ESI) [M+H]⁺=611.

Step 3: 1-[8-Amino-7-fluoro-6-(8-methyl-2,3-dihydro-1H-pyrido[2,3-b][1,4]oxazin-7-yl)-3-isoquinolyl]-3-isopropyl-urea

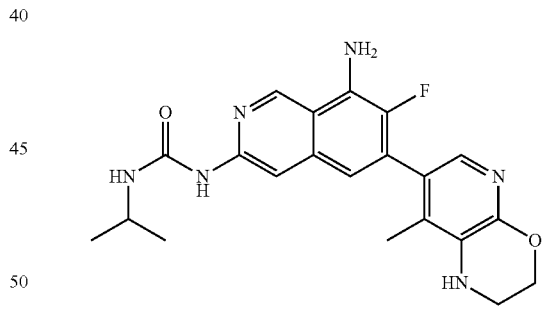

A solution of tert-butyl 7-[8-(tert-butoxycarbonylamino)-7-fluoro-3-(isopropylcarbamoylamino)-6-isoquinolyl]-8-methyl-2,3-dihydropyrido[2,3-b][1,4]oxazine-1-carboxylate (190 mg, 0.31 mmol) in 2,2,2-trifluoroacetic acid (4 mL) and dichloromethane (10 mL) was stirred at room temperature for 2 hours. The reaction mixture was concentrated under vacuum. The residue was adjusted to pH 9 with TEA and concentrated under vacuum. The crude product was purified by Prep-HPLC (Column: X Bridge Prep OBD C18 Column, 30×150 mm 5 µm; Mobile Phase A: water (10 mmol/L NH₄HCO₃), Mobile Phase B: ACN; Flow rate: 60 mL/min; Gradient: 21 B to 39 B in 7 min) to afford 1-[8-amino-7-fluoro-6-(8-methyl-2,3-dihydro-1H-pyrido[2,3-b][1,4]oxazin-7-yl)-3-isoquinolyl]-3-isopropyl-urea (16.3 mg, 0.0397 mmol, 12.8% yield) as a yellow solid. LCMS (ESI) [M+H]$^+$=411.2, R$_T$ 2.153 min, Method M; $^1$H NMR (300 MHz, DMSO-d$_6$) δ 9.28 (s, 1H), 8.81 (s, 1H), 7.84 (s, 1H), 7.32 (s, 1H), 6.98 (d, J=7.5 Hz, 1H), 6.73 (d, J=6.2 Hz, 1H), 6.14 (s, 2H), 5.67 (s, 1H), 4.29 (d, J=4.5 Hz, 2H), 3.82-3.80 (m, 1H), 3.40-3.38 (m, 2H), 1.92 (d, J=1.6 Hz, 3H), 1.13 (d, J=6.5 Hz, 6H).

Example 161

(R)-1-(8-Amino-7-fluoro-6-(8-methyl-2,3-dihydro-1H-pyrido[2,3-b][1,4]oxazin-7-yl)isoquinolin-3-yl)-3-(tetrahydrofuran-3-yl)urea and (S)-1-(8-Amino-7-fluoro-6-(8-methyl-2,3-dihydro-1H-pyrido[2,3-b][1,4]oxazin-7-yl)isoquinolin-3-yl)-3-(tetrahydrofuran-3-yl)urea (Compound 722a and Compound 722b)

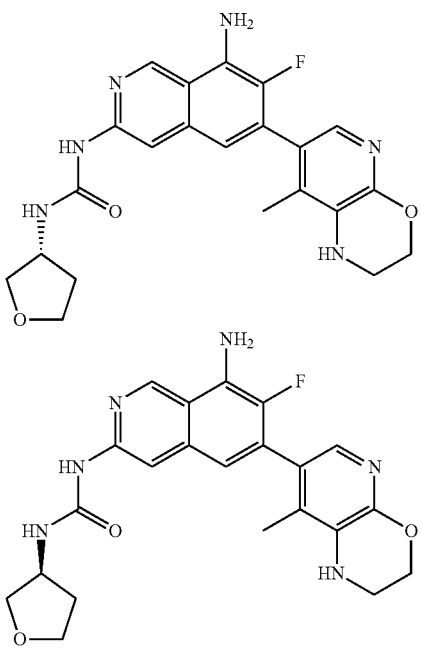

Step 1: tert-Butyl 7-[8-(tert-butoxycarbonylamino)-7-fluoro-3-(tetrahydrofuran-3-ylcarbamoylamino)-6-isoquinolyl]-8-methyl-2,3-dihydropyrido[2,3-b][1,4]oxazine-1-carboxylate

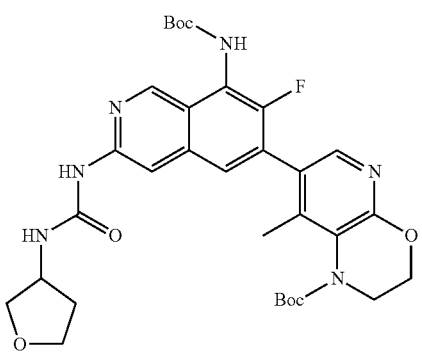 [SMILES: Cc1c(-c2cc3cc(NC(=O)NC4CCOC4)ncc3c(NC(=O)OC(C)(C)C)c2F)cnc2c1N(C(=O)OC(C)(C)C)CCO2]

Under nitrogen, a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300 mg, 0.46 mmol) and tetrahydro-3-furanylamine (200 mg, 2.30 mmol) in dichloromethane (20 mL) was added pyridine (80 mg, 1.01 mmol) at room temperature. The resulting solution was stirred for 16 h at 60° C. The residue was purified by flash chromatography on silica gel eluting with dichloromethane/methanol (10/1) to afford tert-butyl 7-[8-(tert-butoxycarbonylamino)-7-fluoro-3-(tetrahydrofuran-3-ylcarbamoylamino)-6-isoquinolyl]-8-methyl-2,3-dihydropyrido[2,3-b][1,4]oxazine-1-carboxylate (250 mg, 0.3914 mmol, 84.2% yield) as a yellow solid. LCMS (ESI) [M+H]$^+$=639.

Step 2: (R)-1-(8-Amino-7-fluoro-6-(8-methyl-2,3-dihydro-1H-pyrido[2,3-b][1,4]oxazin-7-yl)isoquinolin-3-yl)-3-(tetrahydrofuran-3-yl)urea (Compound 722a) and (S)-1-(8-Amino-7-fluoro-6-(8-methyl-2,3-dihydro-1H-pyrido[2,3-b][1,4]oxazin-7-yl)isoquinolin-3-yl)-3-(tetrahydrofuran-3-yl)urea (Compound 722b)

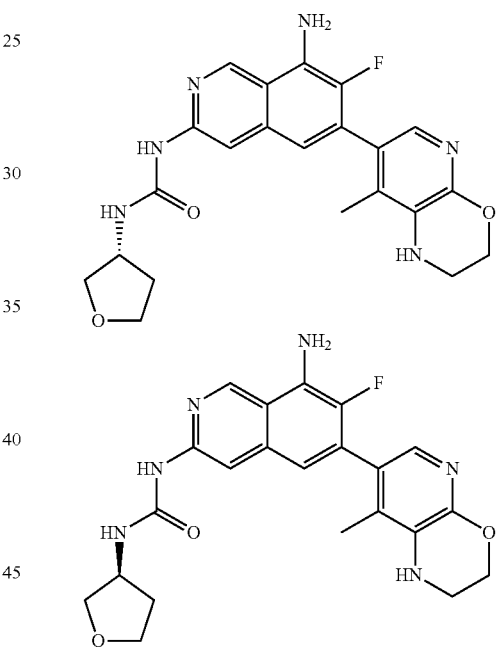

A solution of tert-butyl 7-[8-(tert-butoxycarbonylamino)-7-fluoro-3-(tetrahydrofuran-3-ylcarbamoylamino)-6-isoquinolyl]-8-methyl-2,3-dihydropyrido[2,3-b][1,4]oxazine-1-carboxylate (250 mg, 0.39 mmol) in dichloromethane (10 mL) was added TFA (2 mL) at room temperature. The resulting solution was stirred for 3 h at 25° C. and concentrated under vacuum. The crude product was purified by Prep-HPLC (Column: X Select CSH Prep C18 OBD Column, 5 μm, 19*150 mm; Mobile Phase A: water (0.1% FA), Mobile Phase B: ACN; Flow rate: 20 mL/min; Gradient: 5% B to 35% B in 7 min; 254/220 nm; R$_T$ 6.80 min) and chiral-HPLC (Column: CHIRALPAK IG, 20*250 mm, 5 μm; Mobile Phase A: MTBE, Mobile Phase B: MeOH; Flow rate: 20 mL/min) to afford two enantiomers. Absolute stereochemistry arbitrarily assigned.

Enantiomer 1 Compound 722a (32.1 mg, 0.0732 mmol, 18.7% yield). RT 1.617 min (CHIRALPAK IG-3, 46*5 cm, 3 μm; MTBE (0.1% DEA):MeOH=60:40 in 5 min; 1 mL/min). LCMS (ESI) [M+H]⁺=439.1, $R_T$ 0.915 min, Method L; ¹H NMR (400 MHz, DMSO-d₆) δ 9.28 (s, 1H), 8.86 (s, 1H), 7.85 (s, 1H), 7.36 (d, J=6.4 Hz, 1H), 7.32 (s, 1H), 6.74 (d, J=6.0 Hz, 1H), 6.15 (s, 2H), 5.67 (s, 1H), 4.32-4.20 (m, 3H), 3.87-3.67 (m, 3H), 3.52 (dd, J=9.0, 3.4 Hz, 1H), 3.33 (s, 2H), 2.16 (dq, J=13.4, 7.5 Hz, 1H), 1.92 (s, 3H), 1.73 (ddt, J=12.6, 8.2, 4.6 Hz, 1H).

Enantiomer 2 Compound 722b (30.9 mg, 0.0705 mmol, 18% yield). $R_T$ 2.441 min (CHIRALPAK IG-3, 46*5 cm, 3 μm; MTBE (0.1% DEA):MeOH=60:40 in 5 min; 1 mL/min). LCMS (ESI) [M+H]⁺=439.1, $R_T$ 0.915 min, Method L; ¹H NMR (400 MHz, DMSO-d₆) δ 9.28 (s, 1H), 8.86 (s, 1H), 7.85 (s, 1H), 7.36 (d, J=6.4 Hz, 1H), 7.32 (s, 1H), 6.74 (d, J=6.0 Hz, 1H), 6.15 (s, 2H), 5.67 (s, 1H), 4.32-4.20 (m, 3H), 3.87-3.67 (m, 3H), 3.52 (dd, J=9.0, 3.4 Hz, 1H), 3.33 (s, 2H), 2.16 (dq, J=13.4, 7.5 Hz, 1H), 1.92 (s, 3H), 1.73 (ddt, J=12.6, 8.2, 4.6 Hz, 1H).

Example 162

(3S,5S)-7-Methyl-1-oxa-7-azaspiro[4.4]nonan-3-yl (8-amino-7-fluoro-6-(8-methyl-2,3-dihydro-1H-pyrido[2,3-b][1,4]oxazin-7-yl)isoquinolin-3-yl)carbamate, (3R,5R)-7-Methyl-1-oxa-7-azaspiro[4.4]nonan-3-yl(8-amino-7-fluoro-6-(8-methyl-2,3-dihydro-1H-pyrido[2,3-b][1,4]oxazin-7-yl)isoquinolin-3-yl)carbamate, (3S,5R)-7-Methyl-1-oxa-7-azaspiro[4.4]nonan-3-yl (8-amino-7-fluoro-6-(8-methyl-2,3-dihydro-1H-pyrido[2,3-b][1,4]oxazin-7-yl)isoquinolin-3-yl)carbamate and (3R,5S)-7-Methyl-1-oxa-7-azaspiro[4.4]nonan-3-yl(8-amino-7-fluoro-6-(8-methyl-2,3-dihydro-1H-pyrido[2,3-b][1,4]oxazin-7-yl)isoquinolin-3-yl)carbamate (Compound 467a, Compound 467b, Compound 467c and Compound 467d)

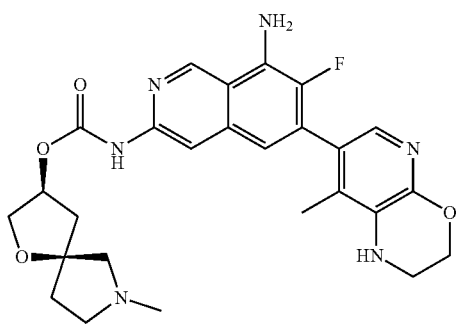

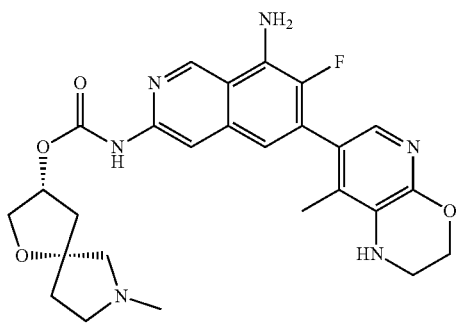

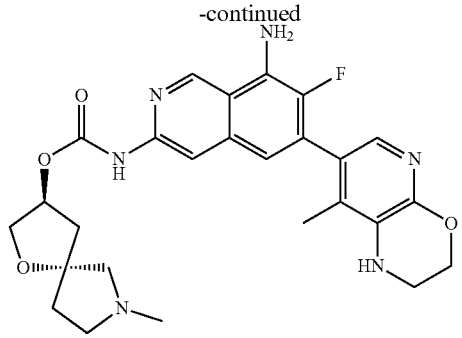

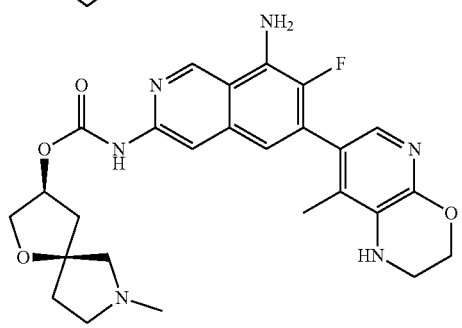

Step 1: tert-Butyl-7-[8-(tert-butoxycarbonylamino)-3-[(7-tert-butoxycarbonyl-1-oxa-7-azaspiro[4.4]nonan-3-yl)oxycarbonylamino]-7-fluoro-6-isoquinolyl]-8-methyl-2,3-dihydropyrido[2,3-b][1,4]oxazine-1-carboxylate

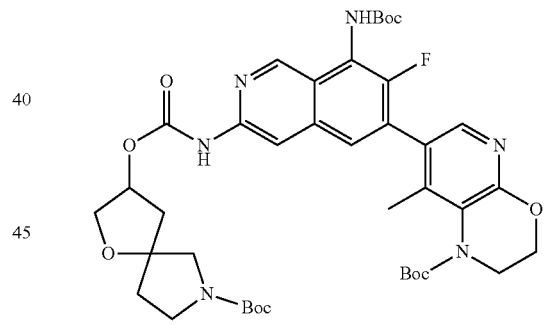

To a solution of tert-butyl-7-[3-amino-8-(tert-butoxycarbonylamino)-7-fluoro-6-isoquinolyl]-8-methyl-2,3-dihydropyrido[2,3-b][1,4]oxazine-1-carboxylate (180 mg, 0.34 mmol), tert-butyl 3-hydroxy-1-oxa-7-azaspiro[4.4]nonane-7-carboxylate (162 mg, 0.67 mmol) and DIEA (630 mg, 4.88 mmol) in dichloromethane (18 mL) was added a solution of triphosgene (198 mg, 0.67 mmol) in dichloromethane (1 mL). The mixture was stirred for 2 hours at 0° C. The reaction solution was diluted with dichloromethane and the resulting solution was washed with water. The organic layer was dried over anhydrous sodium sulfate and concentrated under vacuum. The residue was purified by flash chromatography on silica gel eluting with petroleum ether/ethyl acetate (4:1) to afford tert-butyl-7-[8-(tert-butoxycarbonylamino)-3-[(7-tert-butoxycarbonyl-1-oxa-7-azaspiro[4.4]nonan-3-yl)oxycarbonylamino]-7-fluoro-6-isoquinolyl]-8-methyl-2,3-dihydropyrido[2,3-b][1,4]oxazine-1- carboxylate (158 mg, 0.0018 mmol, 50% yield) as a reddish brown solid. LCMS (ESI) [M+H]⁺=795.3.

Step 2: 1-Oxa-7-azaspiro[4.4]nonan-3-yl-N-[8-amino-7-fluoro-6-(8-methyl-2,3-dihydro-1H-pyrido[2,3-b][1,4]oxazin-7-yl)-3-isoquinolyl]carbamate

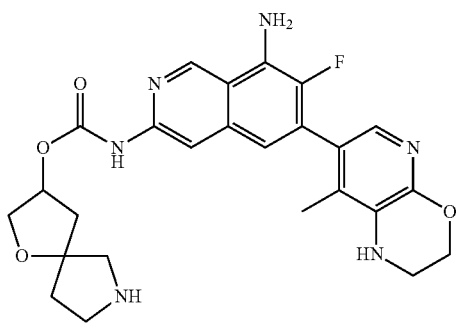 [SMILES: Cc1c(-c2cc3cc(NC(=O)OC4COC5(CCNC5)C4)ncc3c(N)c2F)cnc2c1NCCO2]

A solution of tert-butyl-7-[8-(tert-butoxycarbonylamino)-3-[(7-tert-butoxycarbonyl-1-oxa-7-azaspiro[4.4]nonan-3-yl)oxycarbonylamino]-7-fluoro-6-isoquinolyl]-8-methyl-2,3-dihydropyrido[2,3-b][1,4]oxazine-1-carboxylate (150 mg, 0.19 mmol) in 2,2,2-trifluoroacetic acid (3 mL) and dichloromethane (12 mL) was stirred at 25° C. for 1 hour. The reaction mixture was concentrated under vacuum. The residue was re-dissolved in dichloromethane (10 mL), adjusted to pH 8 with trimethylamine and concentrated under vacuum. The crude product would be directly used in the next step without purification.

Step 3: (3S,5S)-7-Methyl-1-oxa-7-azaspiro[4.4]nonan-3-yl (8-amino-7-fluoro-6-(8-methyl-2,3-dihydro-1H-pyrido[2,3-b][1,4]oxazin-7-yl)isoquinolin-3-yl)carbamate, (3R,5R)-7-Methyl-1-oxa-7-azaspiro[4.4]nonan-3-yl (8-amino-7-fluoro-6-(8-methyl-2,3-dihydro-1H-pyrido[2,3-b][1,4]oxazin-7-yl)isoquinolin-3-yl)carbamate, (3S,5R)-7-Methyl-1-oxa-7-azaspiro[4.4]nonan-3-yl (8-amino-7-fluoro-6-(8-methyl-2,3-dihydro-1H-pyrido[2,3-b][1,4]oxazin-7-yl)isoquinolin-3-yl)carbamate and (3R,5S)-7-Methyl-1-oxa-7-azaspiro[4.4]nonan-3-yl (8-amino-7-fluoro-6-(8-methyl-2,3-dihydro-1H-pyrido[2,3-b][1,4]oxazin-7-yl)isoquinolin-3-yl)carbamate

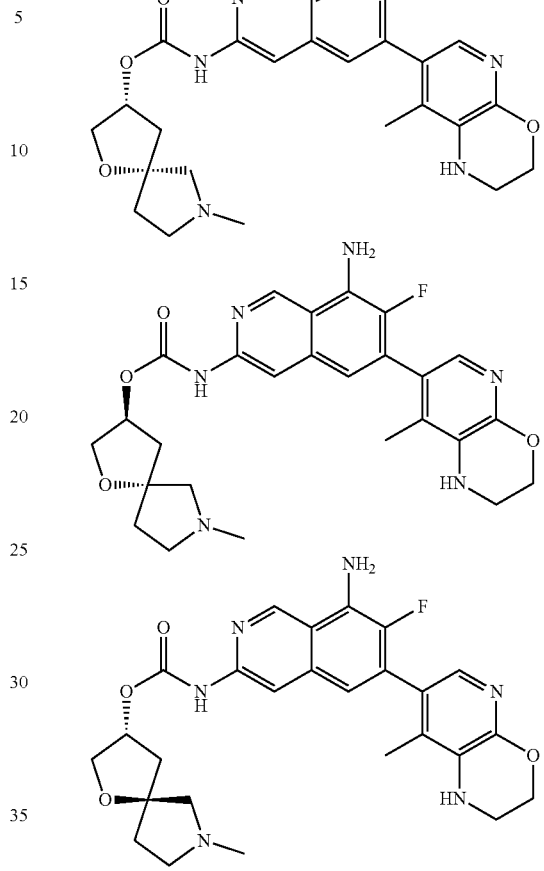

A solution of 1-oxa-7-azaspiro[4.4]nonan-3-yl N-[8-amino-7-fluoro-6-(8-methyl-2,3-dihydro-1H-pyrido[2,3-b][1,4]oxazin-7-yl)-3-isoquinolyl]carbamate (140 mg, 0.28 mmol) and formaldehyde (15.0 mg, 0.38 mmol) in methyl alcohol (14 mL) was stirred at 25° C. for 1 hour. Then sodium borohydride (27 mg, 0.71 mmol) was added. The reaction was stirred at 25° C. for 1 hour. The reaction was then quenched by adding water and concentrated under vacuum. The residue was purified by reverse phase chromatography (acetonitrile 5-50/0.1% NH₄HCO₃ in water) to afford two pairs of racemic products. These two racemates was separated individually by Chiral-HPLC to afford two enantiomers. Relative stereochemistry are as drawn. Absolute stereochemistry was arbitrarily assigned.

Isomer 1 Compound 467a (11.5 mg, 0.0221 mmol, 7.8% yield). $R_T$ 2.818 min (CHIRALPAK IF-3, 0.46*5 cm; 3 μm. MTBE (0.2% IPA):MeOH=50:50 in 5 min, 1.0 mL/min). LCMS (ESI) [M+H]=509.4, $R_T$ 1.584 min, Method J; ¹H NMR (300 MHz, DMSO-d₆) δ 10.14 (s, 1H), 9.33 (s, 1H), 7.94 (s, 1H), 7.30 (s, 1H), 6.82 (d, J=6.1 Hz, 1H), 6.21 (s, 2H), 5.67 (s, 1H), 5.24 (s, 1H), 4.27 (s, 2H), 4.05-3.92 (m, 1H), 3.72 (d, J=10.4 Hz, 1H), 2.80-2.55 (m, 3H), 2.46-2.36 (m, 1H), 2.35-2.05 (m, 6H), 1.98-1.78 (m, 6H).

Isomer 2 Compound 467b (10.3 mg, 0.0197 mmol, 7% yield). $R_T$ 2.000 min (CHIRALPAK IF-3, 0.46*5 cm; 3 μm. Mobile phase: MTBE (0.2% IPA):MeOH=50:50 in 5 min, 1.0 mL/min). LCMS (ESI) [M+H]=509.4, $R_T$ 1.580 min., Method J; ¹H NMR (300 MHz, DMSO-d₆) δ 10.14 (s, 1H), 9.33 (s, 1H), 7.94 (s, 1H), 7.30 (s, 1H), 6.82 (d, J=6.1 Hz, 1H), 6.21 (s, 2H), 5.67 (s, 1H), 5.24 (s, 1H), 4.27 (s, 2H), 4.05-3.92 (m, 1H), 3.72 (d, J=10.4 Hz, 1H), 2.80-2.55 (m, 3H), 2.46-2.36 (m, 1H), 2.35-2.05 (m, 6H), 1.98-1.78 (m, 6H).

Isomer 3 Compound 467c (10.3 mg, 0.0197 mmol, 7% yield). $R_T$ 2.404 min (CHIRALPAK IE-3, 0.46*5 cm; 3 μm. Mobile phase: MTBE (0.2% IPA):EtOH=50:50 in 5 min, 1.0 mL/min). LCMS (ESI) [M+H]=509.4, $R_T$ 1.610 min, Method K; $^1$H NMR (300 MHz, DMSO-$d_6$) δ 10.12 (s, 1H), 9.32 (s, 1H), 7.94 (s, 1H), 7.31 (s, 1H), 6.81 (d, J=6.2 Hz, 1H), 6.20 (s, 2H), 5.67 (s, 1H), 5.26-5.17 (m, 1H), 4.27 (t, J=4.3 Hz, 2H), 4.02-3.92 (m, 1H), 3.76 (d, J=10.3, 2.1 Hz, 1H), 2.70-2.58 (m, 2H), 2.48-2.35 (m, 3H), 2.32-2.13 (m, 5H), 2.1-1.92 (m, 3H), 1.95-1.88 (m, 3H).

Isomer 4 Compound 467d (19.0 mg, 0.0358 mmol, 12.7% yield). $R_T$ 3.773 min (CHIRALPAK IE-3, 0.46*5 cm; 3 μm. Mobile phase: MTBE (0.2% IPA):EtOH=50:50 in 5 min, 1.0 mL/min). LCMS (ESI) [M+H]=509.4, $R_T$ 1.610 min, Method K; $^1$H NMR (300 MHz, DMSO-$d_6$) δ 10.12 (s, 1H), 9.32 (s, 1H), 7.94 (s, 1H), 7.31 (s, 1H), 6.81 (d, J=6.2 Hz, 1H), 6.20 (s, 2H), 5.67 (s, 1H), 5.26-5.17 (m, 1H), 4.27 (t, J=4.3 Hz, 2H), 4.02-3.92 (m, 1H), 3.76 (d, J=10.3, 2.1 Hz, 1H), 2.70-2.58 (m, 2H), 2.48-2.35 (m, 3H), 2.32-2.13 (m, 5H), 2.1-1.92 (m, 3H), 1.95-1.88 (m, 3H).

Example 163

(S)-1,4,4-Trimethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate and (R)-1,4,4-Trimethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate (Compound 480a and Compound 480b)

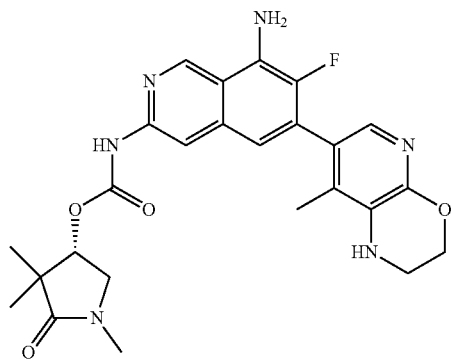

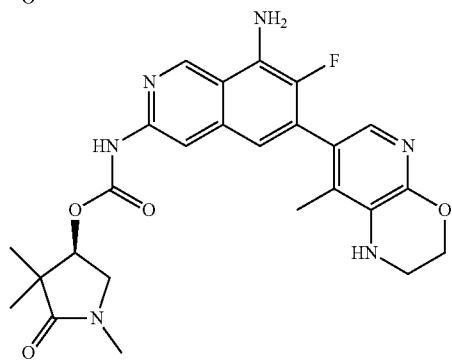

Step 1: Ethyl 4-bromo-2,2-dimethyl-3-oxobutanoate

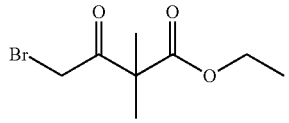

To a solution of ethyl 2,2-dimethyl-3-oxobutanoate (3.50 g, 22.13 mmol) in ethanol (40.0 mL) was added Br$_2$ (3.85 g, 24.34 mmol). The reaction was stirred for 4 hours at room temperature. The mixture was concentrated under vacuum to afford the titled product (4.80 g). The crude product was used directly for the next step without purification.

Step 2: 1,3,3-trimethylpyrrolidine-2,4-dione

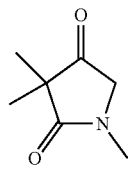

To a solution of ethyl 4-bromo-2,2-dimethyl-3-oxo-butanoate (4.80 g, 20.25 mmol) in ethanol (10 0 mL) was added methylamine (628.82 mg, 20.25 mmol). The reaction was stirred at RT for 2 hours and then concentrated under vacuum. The residue was purified by flash chromatography on silica gel eluting with dichloromethane/methanol (10/1) to afford 1,3,3-trimethylpyrrolidine-2,4-dione (1.70 g, 12.05 mmol, 59.5% yield) as a light-yellow solid. LCMS (ESI) [M+H]$^+$=142.

Step 3: 4-hydroxy-1,3,3-trimethyl-pyrrolidin-2-one

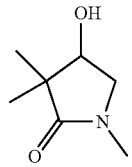

To a solution of 1,3,3-trimethylpyrrolidine-2,4-dione (1.50 g, 10.63 mmol) in methyl alcohol (30 mL) was added sodium borohydride (803.92 mg, 21.25 mmol and stirred at RT for 2 hours. The reaction was quenched with water and extracted with dichloromethane. The organic layer was combined, concentrated under vacuum and purified by flash chromatography on silica gel eluting with dichloromethane/methanol (10/1) to afford 4-hydroxy-1,3,3-trimethyl-pyrrolidin-2-one (1.0 g, 6.99 mmol, 66.7% yield) as a white solid. LCMS (ESI) [M+H]$^+$=144; $^1$H NMR (300 MHz, DMSO-$d_6$) δ 5.16 (s, 1H), 3.82 (s, 1H), 3.44 (dd, J=10.1, 6.2 Hz, 1H), 2.97 (dd, J=10.0, 4.7 Hz, 1H), 2.67 (s, 3H), 0.93 (s, 3H), 0.88 (s, 3H).

Step 4: tert-Butyl 7-[8-(tert-butoxycarbonylamino)-7-fluoro-3-[(1,4,4-trimethyl-5-oxo-pyrrolidin-3-yl)oxycarbonylamino]-6-isoquinolyl]-8-methyl-2,3-dihydropyrido[2,3-b][1,4]oxazine-1-carboxylate

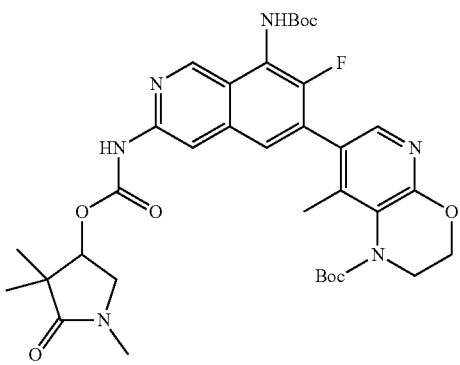 [SMILES: Cc1c(-c2cc3cc(NC(=O)OC4CN(C)C(=O)C4(C)C)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (300.0 mg, 0.57 mmol), DIEA (368.86 mg, 2.85 mmol) and 4-hydroxy-1,3,3-trimethyl-pyrrolidin-2-one (163.46 mg, 1.14 mmol) in dichloromethane (25 mL) was added triphosgene (169.39 mg, 0.5700 mmol) at 0° C. The mixture was stirred at RT for 2 hours. The reaction was quenched with water and extracted with dichloromethane. The organic layers were combined, dried over sodium sulfate and concentrated under vacuum. The residue was purified by flash chromatography on silica gel eluting with DCM/MeOH (10/1) to afford tert-butyl 7-[8-(tert-butoxycarbonylamino)-7-fluoro-3-[(1,4,4-trimethyl-5-oxo-pyrrolidin-3-yl)oxycarbonylamino]-6-isoquinolyl]-8-methyl-2,3-dihydropyrido[2,3-b][1,4]oxazine-1-carboxylate (150 mg, 0.22 mmol, 37.9% yield). LCMS (ESI) [M+H]$^+$=695.

Step 5: (S)-1,4,4-Trimethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate and (R)-1,4,4-Trimethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate

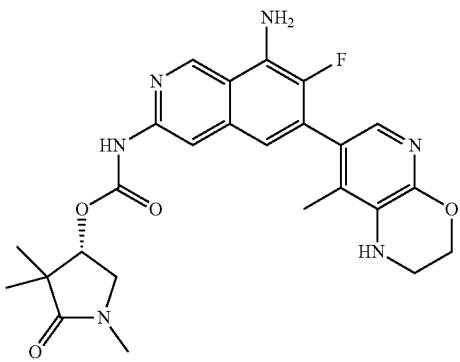

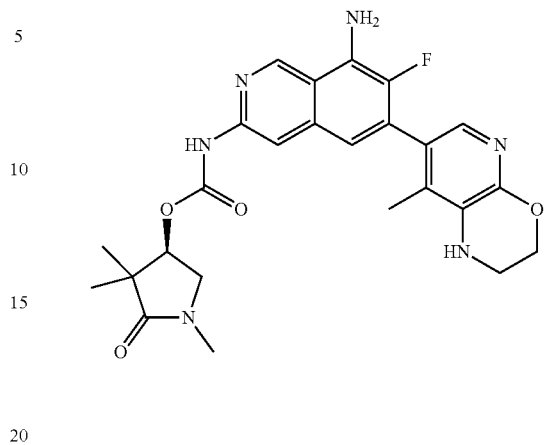

To a solution of tert-butyl 7-[8-(tert-butoxycarbonylamino)-7-fluoro-3-[(1,4,4-trimethyl-5-oxo-pyrrolidin-3-yl)oxycarbonylamino]-6-isoquinolyl]-8-methyl-2,3-dihydropyrido[2,3-b][1,4]oxazine-1-carboxylate (150.0 mg, 0.22 mmol) in dichloromethane (10 mL) was added trifluoroacetic acid (10 mL). The reaction was stirred at room temperature for 30 min and then concentrated under reduce pressure. The residue was purified by Prep-HPLC (Column: X Select CSH Prep C18 OBD Column, 5 μm, 19*150 mm; Mobile Phase A: Water (0.1% FA), Mobile Phase B: ACN; Flow rate: 25 mL/min; Gradient: 8% B to 32% B in 10 min; 254/220 nm; $R_T$ 10.20 min) to afford the racemic product. The racemic product was further separated by Chiral-Prep-HPLC to afford two enantiomers. Absolute stereochemistry was arbitrarily assigned.

Enantiomer 1: (Compound 480a) (26.0 mg, 0.053 mmol, 24.3% yield). $R_T$ 2.681 min (CHIRALPAK IE-3, 0.46*5 cm; 3 μm. Mobile phase: MTBE:EtOH=70:30, 1 ml/min). LCMS (ESI): [M+H]$^+$=495.2, $R_T$ 2.126 min; Method K. $^1$H NMR (400 MHz, DMSO-d$_6$) δ 10.24 (s, 1H), 9.35 (s, 1H), 7.97 (s, 1H), 7.33 (s, 1H), 6.85 (d, J=6.2 Hz, 1H), 6.22 (s, 2H), 5.68 (s, 1H), 4.98 (dd, J=5.5, 2.3 Hz, 1H), 4.29 (t, J=4.4 Hz, 2H), 3.79 (dd, J=11.5, 5.5 Hz, 1H), 3.30 (dd, J=11.4, 2.3 Hz, 3H), 2.75 (s, 3H), 1.92 (d, J=1.7 Hz, 3H), 1.08 (d, J=6.5 Hz, 6H).

Enantiomer 2: (Compound 480b) (21.1 mg, 0.053 mmol, 19.7% yield). $R_T$ 4.892 min (CHIRALPAK IE-3, 0.46*5 cm; 3 μm. Mobile phase: MTBE:EtOH=70:30, 1 ml/min). LCMS (ESI): [M+H]$^+$=495.2, $R_T$ 2.126 min; Method K. $^1$H NMR (400 MHz, DMSO-d$_6$) δ 10.24 (s, 1H), 9.35 (s, 1H), 7.97 (s, 1H), 7.33 (s, 1H), 6.85 (d, J=6.2 Hz, 1H), 6.22 (s, 2H), 5.68 (s, 1H), 4.98 (dd, J=5.5, 2.3 Hz, 1H), 4.29 (t, J=4.4 Hz, 2H), 3.79 (dd, J=11.5, 5.5 Hz, 1H), 3.30 (dd, J=11.4, 2.3 Hz, 3H), 2.75 (s, 3H), 1.92 (d, J=1.7 Hz, 3H), 1.08 (d, J=6.5 Hz, 6H).

Example 164

(1S,2R)-2-Cyanocyclopentyl (8-amino-7-fluoro-6-(8-methyl-2,3-dihydro-1H-pyrido[2,3-b][1,4]oxazin-7-yl)isoquinolin-3-yl)carbamate and (1R,2S)-2-Cyanocyclopentyl (8-amino-7-fluoro-6-(8-methyl-2,3-dihydro-1H-pyrido[2,3-b][1,4]oxazin-7-yl)isoquinolin-3-yl)carbamate (Compound 482b and Compound 482a)

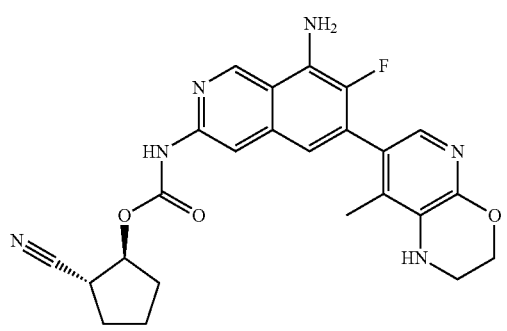

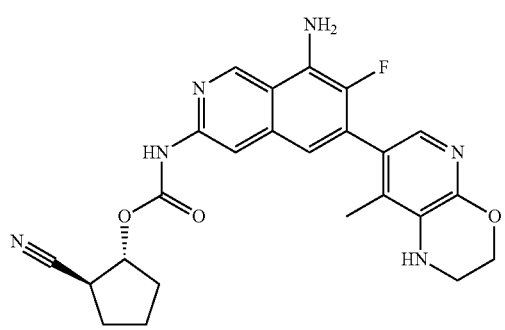

Step 1: (±)-trans-tert-Butyl 7-[8-(tert-butoxycarbonylamino)-3-[(2-cyanocyclopentoxy)carbonylamino]-7-fluoro-6-isoquinolyl]-8-methyl-2,3-dihydropyrido[2,3-b][1,4]oxazine-1-carboxylate

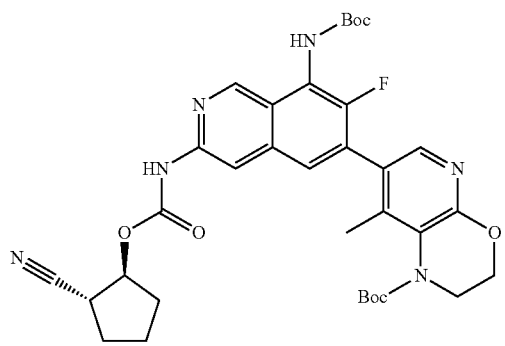

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (300 mg, 0.57 mmol) and (±)-trans-2-hydroxycyclopentanecarbonitrile (300 mg, 2.7 mmol) in dichloromethane (60 mL) was added DIEA (500 mg, 3.88 mmol) at room temperature. Then triphosgene (200 mg, 0.67 mmol) was added. The reaction was stirred at 0° C. for 2 hours. The reaction mixture was concentrated under vacuum and purified by flash chromatography on silica gel eluting with petroleum ether/ethyl acetate (1/1) to afford (±)-trans-tert-butyl 7-[8-(tert-butoxycarbonylamino)-3-[(2-cyanocyclopentoxy)carbonylamino]-7-fluoro-6-isoquinolyl]-8-methyl-2,3-dihydropyrido[2,3-b][1,4]oxazine-1-carboxylate (220 mg, 0.332 mmol, 58.2% yield) as a yellow solid. LCMS (ESI) [M+H]$^+$=663.

Step 2: (1S,2R)-2-cyanocyclopentyl (8-amino-7-fluoro-6-(8-methyl-2,3-dihydro-1H-pyrido[2,3-b][1,4]oxazin-7-yl)isoquinolin-3-yl)carbamate and (1R,2S)-2-cyanocyclopentyl (8-amino-7-fluoro-6-(8-methyl-2,3-dihydro-1H-pyrido[2,3-b][1,4]oxazin-7-yl)isoquinolin-3-yl)carbamate To a solution of (±)-trans-tert-butyl 7-[8-(tert-butoxycarbonylamino)-3-[(2-cyanocyclopentoxy)carbonylamino]-7- fluoro-6-isoquinolyl]-8-methyl-2,3-dihydropyrido[2,3-b][1,4]oxazine-1-carboxylate (220 mg, 0.33 mmol) in dichloromethane (10 mL) was added TFA (2 mL) at room temperature. The resulting solution was stirred for 3 h at 25° C. The reaction mixture was concentrated under vacuum and purified by Prep-HPLC (Column: X Bridge Prep OBD C18 Column, 30×150 mm, 5 µm; Mobile Phase A: Water (10 mmol/L NH$_4$HCO$_3$), Mobile Phase B: ACN; Flow rate: 60 mL/min; Gradient: 10% B to 37% B in 10 min, then hold at 37% B for 2 min) and chiral-HPLC (Column: CHIRALPAK IG, 20*250 mm, 5 µm; Mobile Phase A: MTBE, Mobile Phase B: MeOH; Flow rate: 20 mL/min; Gradient: 30 B to 30 B in 15 min) to afford two enantiomers.

Enantiomer 1: Compound 482a (1R,2S)-2-cyanocyclopentyl (8-amino-7-fluoro-6-(8-methyl-2,3-dihydro-1H-pyrido[2,3-b][1,4]oxazin-7-yl)isoquinolin-3-yl)carbamate (27.1 mg, 0.062 mmol, 22.8% yield). R$_T$ 1.726 min (CHIRALPAK Ig-3, 0.46*5 cm, 3 µm; MTBE (0.1% DEA): MeOH=70:30 in 5 min; 1 mL/min). LCMS (ESI) [M+H]$^+$= 463.2, R$_T$ 0.996 min, Method L; $^1$H NMR (400 MHz, DMSO-d$_6$) δ 10.22 (s, 1H), 9.34 (s, 1H), 7.98 (s, 1H), 7.33 (s, 1H), 6.87 (d, J=6.1 Hz, 1H), 6.23 (s, 2H), 5.68 (s, 1H), 5.26-5.18 (m, 1H), 4.29 (t, J=4.4 Hz, 2H), 3.35 (t, J=4.4 Hz, 2H) 3.17 (dd, J=7.6, 4.9 Hz, 1H), 2.13 (m, 2H), 1.92 (d, J=1.7 Hz, 3H), 1.84-1.76 (m, 4H).

Enantiomer 2: Compound 482b (1S,2R)-2-cyanocyclopentyl (8-amino-7-fluoro-6-(8-methyl-2,3-dihydro-1H-pyrido[2,3-b][1,4]oxazin-7-yl)isoquinolin-3-yl)carbamate (25.9 mg, 0.059 mmol, 21.8% yield). R$_T$ 2.428 min (CHIRALPAK Ig-3, 0.46*5 cm, 3 µm; MTBE (0.1% DEA): MeOH=70:30 in 5 min; 1 mL/min). LCMS (ESI) [M+H]$^+$= 463.2, R$_T$ 1.05 min, Method L; $^1$H NMR (400 MHz, DMSO-d$_6$) δ 10.22 (s, 1H), 9.34 (s, 1H), 7.98 (s, 1H), 7.33 (s, 1H), 6.87 (d, J=6.1 Hz, 1H), 6.23 (s, 2H), 5.68 (s, 1H), 5.26-5.18 (m, 1H), 4.29 (t, J=4.4 Hz, 2H), 3.35 (t, J=4.4 Hz, 2H) 3.17 (dd, J=7.6, 4.9 Hz, 1H), 2.13 (m, 2H), 1.92 (d, J=1.7 Hz, 3H), 1.84-1.76 (m, 4H).

Example 165

1-(8-Amino-7-fluoro-6-(8-methyl-2,3-dihydro-1H-pyrido[2,3-b][1,4]oxazin-7-yl)isoquinolin-3-yl)-3-((1S,2R)-2-methylcyclopropyl)urea and 1-(8-Amino-7-fluoro-6-(8-methyl-2,3-dihydro-1H-pyrido[2,3-b][1,4]oxazin-7-yl)isoquinolin-3-yl)-3-((1R,2S)-2-methylcyclopropyl)urea (Compound 736a and Compound 736b)

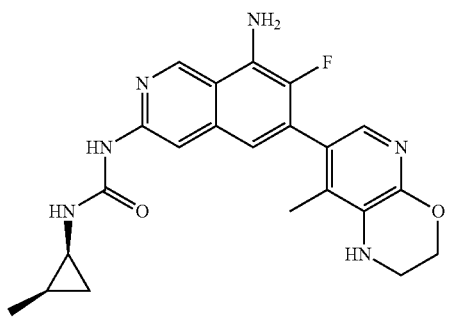

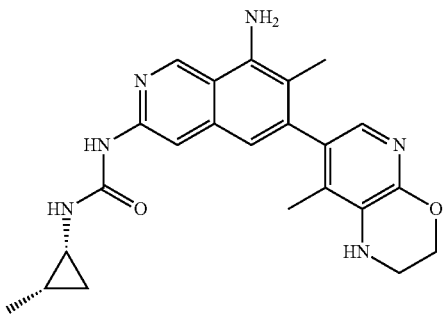

Step 1: (±)-cis-tert-Butyl 7-(8-((tert-butoxycarbonyl)amino)-7-fluoro-3-(3-(2-methylcyclopropyl)ureido)isoquinolin-6-yl)-8-methyl-2,3-dihydro-1H-pyrido[2,3-b][1,4]oxazine-1-carboxylate

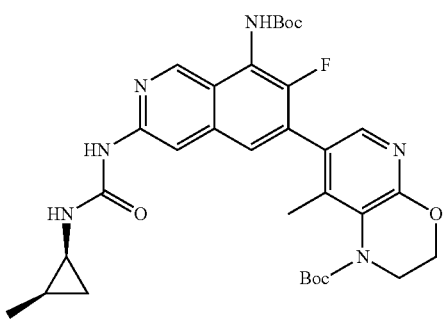 [SMILES: Cc1c(-c2cc3cc(NC(=O)N[C@H]4C[C@H]4C)ncc3c(NC(=O)OC(C)(C)C)c2F)cnc2c1N(C(=O)OC(C)(C)C)CCO2]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300 mg, 0.46 mmol) and 4-dimethylaminopyridine (57 mg, 0.47 mmol) in dichloromethane (15 mL) was added dropwise a solution of (±)-cis-2-methylcyclopropanamine hydrochloride (108 mg, 1 mmol) and triethylamine (1.0 mL, 7.21 mmol) in dichloromethane (5 mL) at 0° C. Then the reaction was stirred at 0° C. for 2 hours. The resulting solution was diluted with dichloromethane. The organic layer was washed with water, dried over anhydrous sodium sulfate and concentrated under vacuum. The residue was purified by flash chromatography on silica gel eluting with petroleum ether/ethyl acetate (4:1) to afford (±)-cis-tert-butyl 7-(8-((tert-butoxycarbonyl)amino)-7-fluoro-3-(3-(2-methylcyclopropyl)ureido)isoquinolin-6-yl)-8-methyl-2,3-dihydro-1H-pyrido[2,3-b][1,4]oxazine-1-carboxylate (250 mg, 0.361 mmol, 77.8% yield) as a yellow solid. LCMS (ESI) [M+H]$^+$=623.2.

Step 2: 1-(8-Amino-7-fluoro-6-(8-methyl-2,3-di-hydro-1H-pyrido[2,3-b][1,4]oxazin-7-yl)isoquinolin-3-yl)-3-((1S,2R)-2-methylcyclopropyl)urea and 1-(8-Amino-7-fluoro-6-(8-methyl-2,3-dihydro-1H-pyrido[2,3-b][1,4]oxazin-7-yl)isoquinolin-3-yl)-3-((1R,2S)-2-methylcyclopropyl)urea

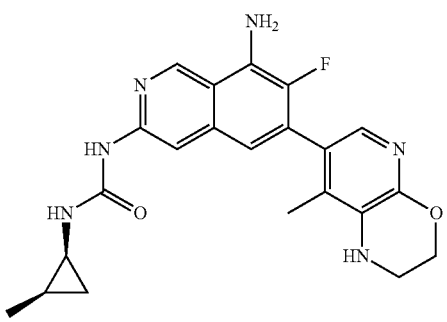

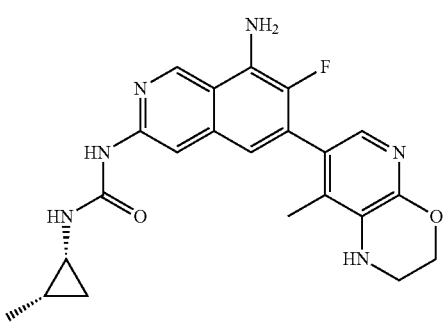

A solution of (±)-cis-tert-butyl 7-(8-((tert-butoxycarbonyl)amino)-7-fluoro-3-(3-(2-methylcyclopropyl)ureido)isoquinolin-6-yl)-8-methyl-2,3-dihydro-1H-pyrido[2,3-b][1,4]oxazine-1-carboxylate (250 mg, 0.40 mmol) in dichloromethane (20 mL) and 2,2,2-trifluoroacetic acid (5 mL) was stirred at 25° C. for 1 hour. The reaction mixture was concentrated under vacuum. The residue was added dichloromethane (5 mL) and adjusted to pH 8 with triethylamine. The reaction mixture was concentrated under vacuum and purified by Prep-HPLC (Column:)(Bridge Prep OBD C18 Column 30×150 mm 5 μm; Mobile Phase A: water (10 mmol/L NH$_4$HCO$_3$), Mobile Phase B: ACN; Flow rate: 60 mL/min; Gradient: 19% B to 33% B in 10 min) to afford a racemic product as a yellow solid. The racemic product was separated by Chiral-HPLC to afford two enantiomers. Relative stereochemistry are as drawn. Absolute stereochemistry was arbitrarily assigned.

Enantiomer 1 Compound 736a (34.5 mg, 0.0807 mmol, 20.1% yield). R$_T$ 4.285 min (Lux 5μ Cellulose-4, 2.12*25 cm, 5 μm. Hex (0.1% DEA): EtOH=60:40 in 8 min, 1.0 mL/min). LCMS (ESI) [M+H]=432.2, R$_T$ 2.226 min, Method J; $^1$H NMR (300 MHz, DMSO-d$_6$) δ 9.25 (s, 1H), 8.76 (s, 1H), 7.86 (s, 1H), 7.30 (s, 1H), 7.13 (s, 1H), 6.73 (d, J=6.1 Hz, 1H), 6.13 (s, 2H), 5.66 (s, 1H), 4.26 (d, J=4.7 Hz, 2H), 3.30-3.26 (m, 2H), 2.26 (d, J=7.0 Hz, 1H), 1.90 (d, J=1.7 Hz, 3H), 1.02 (d, J=6.1 Hz, 3H), 0.91-0.72 (m, 1H), 0.57-0.43 (m, 2H).

Enantiomer 1 Compound 736b (35.6 mg, 0.0819 mmol, 20.4% yield): Retention time: 5.542 min (Lux 5μ Cellulose-4, 2.12*25 cm, 5 μm. Hex (0.1% DEA): EtOH=60:40 in 8 min, 1.0 mL/min). LCMS (ESI) [M+H]=432.2, R$_T$ 2.226 min, Method J; $^1$H NMR (300 MHz, DMSO-d$_6$) δ 9.25 (s, 1H), 8.76 (s, 1H), 7.86 (s, 1H), 7.30 (s, 1H), 7.13 (s, 1H), 6.73 (d, J=6.1 Hz, 1H), 6.13 (s, 2H), 5.66 (s, 1H), 4.26 (d, J=4.7 Hz, 2H), 3.30-3.26 (m, 2H), 2.26 (d, J=7.0 Hz, 1H), 1.90 (d, J=1.7 Hz, 3H), 1.02 (d, J=6.1 Hz, 3H), 0.91-0.72 (m, 1H), 0.57-0.43 (m, 2H).

Example 166

(R)-1-(Dimethylamino)propan-2-yl (8-amino-7-fluoro-6-(8-methyl-2,3-dihydro-1H-pyrido[2,3-b][1,4]oxazin-7-yl)isoquinolin-3-yl)carbamate and (S)-1-(Dimethylamino)propan-2-yl (8-amino-7-fluoro-6-(8-methyl-2,3-dihydro-1H-pyrido[2,3-b][1,4]oxazin-7-yl)isoquinolin-3-yl)carbamate (Compound 523a and Compound 523b)

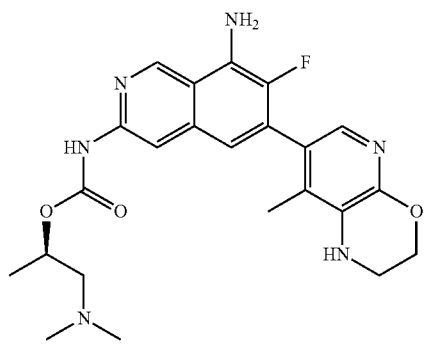

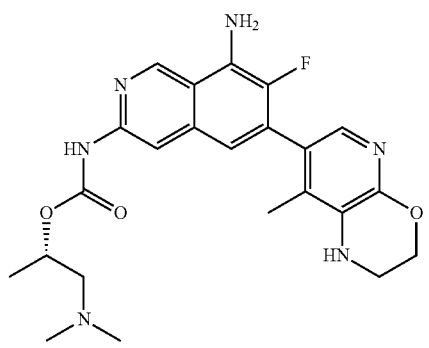

Step 1: tert-Butyl 7-(8-((tert-butoxycarbonyl)amino)-3-((((1-((tert-butoxycarbonyl)amino)propan-2-yl)oxy)carbonyl)amino)-7-fluoroisoquinolin-6-yl)-8-methyl-2,3-dihydro-1H-pyrido[2,3-b][1,4]oxazine-1-carboxylate

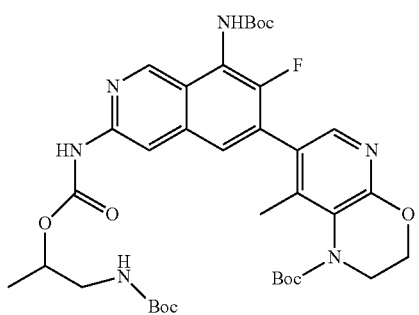 [SMILES: Cc1c(-c2cc3cc(NC(=O)OC(C)CNC(=O)OC(C)(C)C)ncc3c(NC(=O)OC(C)(C)C)c2F)cnc2c1N(C(=O)OC(C)(C)C)CCO2]

To a mixture of tert-butyl 7-[3-amino-8-(tert-butoxycarbonylamino)-7-fluoro-6-isoquinolyl]-2,3-dihydropyrido[2,3-b][1,4]oxazine-1-carboxylate (300 mg, 0.59 mmol) and N-boc-1-amino-2-propanol (300 mg, 1.71 mmol) in dichloromethane (10 mL) was added DIEA (370 mg, 2.87 mmol) and triphosgene (120 mg, 0.40 mmol). The mixture was stirred at 0° C. for 2 hours. The resulting solution was diluted with dichloromethane and then washed with water. The organic phase was concentrated under vacuum. The residue was purified by flash chromatography with reverse phase HPLC (0.1% formic acid)/ACN (45/55) to afford tert-butyl 7-[8-(tert-butoxycarbonylamino)-3-[[2-(tert-butoxycarbonylamino)-1-methyl-ethoxy]carbonylamino]-7-fluoro-6-isoquinolyl]-2,3-dihydropyrido[2,3-b][1,4]oxazine-1-carboxylate (106 mg, 0.149 mmol, 25.4% yield) as a yellow solid. LCMS (ESI) [M+H]$^+$=727.

Step 2: 1-Aminopropan-2-yl (8-amino-7-fluoro-6-(8-methyl-2,3-dihydro-1H-pyrido[2,3-b][1,4]oxazin-7-yl)isoquinolin-3-yl)carbamate

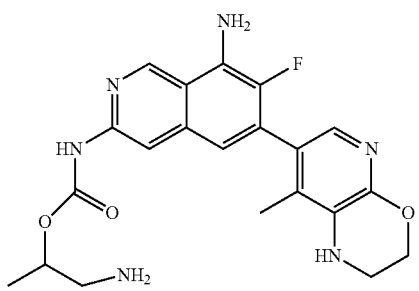 [SMILES: Cc1c(-c2cc3cc(NC(=O)OC(C)CN)ncc3c(N)c2F)cnc2c1NCCO2]

To a solution of tert-butyl 7-[8-(tert-butoxycarbonylamino)-3-[[2-(tert-butoxycarbonylamino)-1-methyl-ethoxy]carbonylamino]-7-fluoro-6-isoquinolyl]-8-methyl-2,3-dihydropyrido[2,3-b][1,4]oxazine-1-carboxylate (400 mg, 0.55 mmol) in dichloromethane (10 mL) was added TFA (2 mL, 0.55 mmol). The mixture was stirred at room temperature for 1 hour. After concentration, the residue was purified by reverse phase chromatography (water (0.1% formic acid)/MeOH (80/20)) to afford (2-amino-1-methyl-ethyl) N-[8-amino-7-fluoro-6-(8-methyl-2,3-dihydro-1H-pyrido[2,3-b][1,4]oxazin-7-yl)-3-isoquinolyl]carbamate (106 mg, 0.249 mmol, 45.2% yield) as a yellow solid. LCMS (ESI) [M+H]$^+$=427.

Step 3: (R)-1-(Dimethylamino)propan-2-yl (8-amino-7-fluoro-6-(8-methyl-2,3-dihydro-1H-pyrido[2,3-b][1,4]oxazin-7-yl)isoquinolin-3-yl)carbamate and (S)-1-(Dimethylamino)propan-2-yl (8-amino-7-fluoro-6-(8-methyl-2,3-dihydro-1H-pyrido[2,3-b][1,4]oxazin-7-yl)isoquinolin-3-yl)carbamate

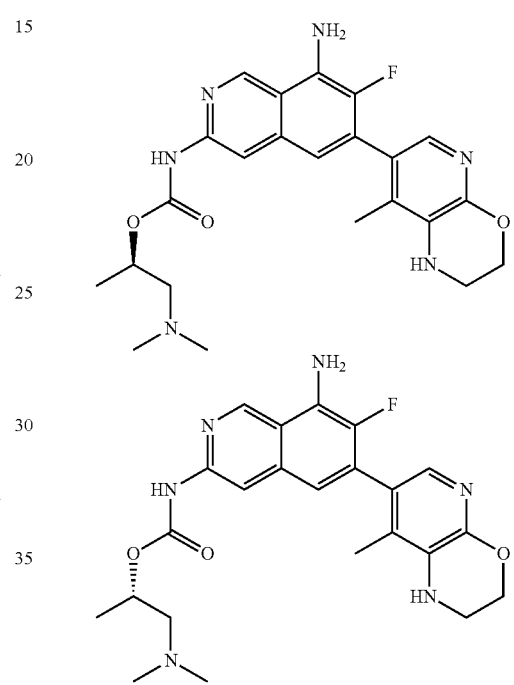

To a solution of (2-amino-1-methyl-ethyl) N-[8-amino-7-fluoro-6-(8-methyl-2,3-dihydro-1H-pyrido[2,3-b][1,4]oxazin-7-yl)-3-isoquinolyl]carbamate (100 mg, 0.23 mmol) in dichloromethane (5 mL) was added a solution of formaldehyde (29 mg, 0.97 mmol). The mixture was stirred at room temperature for 1 hour. before sodium cyanoborohydride (56 mg, 0.89 mmol) was added. The mixture was stirred at room temperature for 2 hours. After concentration, the residue was purified by Prep-HPLC (X Select CSH Prep C18 OBD Column, 5 μm, 19*150 mm; Mobile Phase A: Water (0.1% FA), Mobile Phase B: ACN; Flow rate: 25 mL/min; Gradient: 5% B to 19% B in 7 min) to afford the racemic product. The racemate was separated by chiral-HPLC to afford two enantiomers. Absolute stereochemistry was arbitrarily assigned.

Enantiomer 1 (Compound 523a) (13.6 mg, 0.0299 mmol, 12.8% yield). RT 6.077 min (CHIRALPAK IE-3, 0.46*5 cm; 3 μm. MTBE (0.1% DEA): EtOH=60:40, 1 mL/min). LCMS (ESI) [M+H]$^+$=455.2, R$_T$ 1.583 min.; Method K. $^1$H NMR (400 MHz, DMSO-d$_6$) δ 9.98 (s, 1H), 9.33 (s, 1H), 7.98 (s, 1H), 7.33 (s, 1H), 6.83 (d, J=6.2 Hz, 1H), 6.21 (s, 2H), 5.67 (d, J=3.3 Hz, 1H), 5.03-4.92 (m, 1H), 4.29 (t, J=4.3 Hz, 2H), 3.41-3.52 (m, 2H), 2.47 (d, J=7.3 Hz, 1H), 2.28 (dd, J=12.7, 5.1 Hz, 1H), 2.19 (s, 6H), 1.92 (d, J=1.6 Hz, 3H), 1.23 (d, J=6.3 Hz, 3H).

Enantiomer 2 (Compound 523b) (11.7 mg, 0.0257 mmol, 11% yield). R$_T$ 7.841 min (CHIRALPAK IE-3, 0.46*5 cm; 3 μm. MTBE (0.1% DEA): EtOH=60:40, 1 mL/min). LCMS (ESI) [M+H]$^+$=455.2, R$_T$ 1.583 min.; Method K. $^1$H NMR (400 MHz, DMSO-d$_6$) δ 9.98 (s, 1H), 9.33 (s, 1H), 7.98 (s, 1H), 7.33 (s, 1H), 6.83 (d, J=6.2 Hz, 1H), 6.21 (s, 2H), 5.67 (d, J=3.3 Hz, 1H), 5.03-4.92 (m, 1H), 4.29 (t, J=4.3 Hz, 2H), 3.41-3.52 (m, 2H), 2.47 (d, J=7.3 Hz, 1H), 2.28 (dd, J=12.7, 5.1 Hz, 1H), 2.19 (s, 6H), 1.92 (d, J=1.6 Hz, 3H), 1.23 (d, J=6.3 Hz, 3H).

Example 167

1-[8-Amino-7-fluoro-6-(8-methyl-2,3-dihydro-1H-pyrido[2,3-b][1,4]oxazin-7-yl)-3-isoquinolyl]-3-[(1S,2R)-2-hydroxycyclopentyl]urea (Compound 728a)

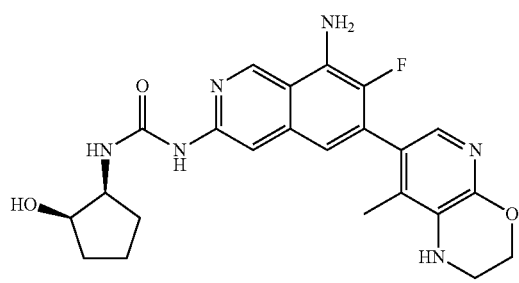 [SMILES: Cc1c(-c2cc3cc(NC(=O)N[C@H]4CCC[C@H]4O)ncc3c(N)c2F)cnc2c1NCCO2]

Step 1: tert-Butyl 7-[8-(tert-butoxycarbonylamino)-7-fluoro-3-[[(1S,2R)-2-hydroxycyclopentyl]carbamoylamino]-6-isoquinolyl]-8-methyl-2,3-dihydropyrido[2,3-b][1,4]oxazine-1-carboxylate

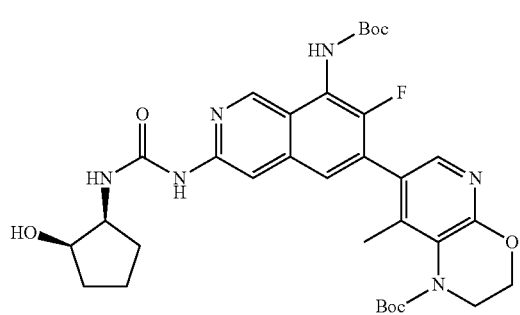 [SMILES: Cc1c(-c2cc3cc(NC(=O)N[C@H]4CCC[C@H]4O)ncc3c(NC(=O)OC(C)(C)C)c2F)cnc2c1N(C(=O)OC(C)(C)C)CCO2]

A solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (200.0 mg, 0.31 mmol) and DMAP (37.9 mg, 0.31 mmol) in dichloromethane (10 mL) was stirred at room temperature for 15 min. Then a solution of cis-2-aminocyclopentanol (128.8 mg, 0.93 mmol) and TEA (93.93 mg, 0.93 mol) in dichloromethane (2 mL) was added. The mixture was stirred at 55° C. for 1 hour and then concentrated under vacuum. The residue was purified by flash chromatography on silica gel eluting with dichloromethane/methanol (95/5) to afford tert-butyl 7-[8-(tert-butoxycarbonylamino)-7-fluoro-3-[[(1R,2S)-2-hydroxycyclopentyl]carbamoylamino]-6-isoquinolyl]-8-methyl-2,3-dihydropyrido[2,3-b][1,4]oxazine-1-carboxylate (150 mg, 0.23 mmol, 74.2% yield) as a light yellow solid. LCMS (ESI) [M+H]$^+$= 653.3.

Step 2: 1-[8-Amino-7-fluoro-6-(8-methyl-2,3-dihydro-1H-pyrido[2,3-b][1,4]oxazin-7-yl)-3-isoquinolyl]-3-[(1S,2R)-2-hydroxycyclopentyl]urea

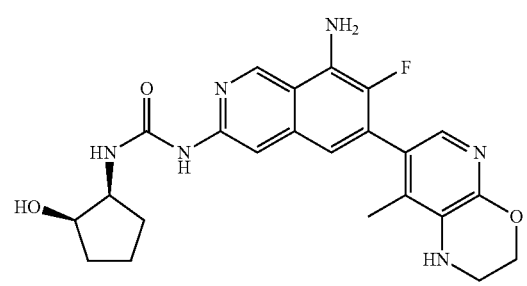

To a solution of tert-butyl 7-[8-(tert-butoxycarbonylamino)-7-fluoro-3-[[(1S,2R)-2-hydroxycyclopentyl]carbamoylamino]-6-isoquinolyl]-8-methyl-2,3-dihydropyrido[2,3-b][1,4]oxazine-1-carboxylate (140.0 mg, 0.21 mmol) in dichloromethane (10 mL) was added TFA (2 mL) was added. The mixture was stirred at room temperature for 1.5 hours and then concentrated under vacuum. The residue was re-dissolved in dichloromethane and adjusted to pH 8 with TEA. The mixture was concentrated under vacuum and purified by pre-HPLC (Column: X Bridge Prep OBD C18 Column 30×150 mm 5 μm; Mobile Phase A: Water (10 mmol/L NH$_4$HCO$_3$), Mobile Phase B: ACN; Flow rate: 60 mL/min; Gradient: 13% B to 35% B in 7 min) to afford 1-[8-amino-7-fluoro-6-(8-methyl-2,3-dihydro-1H-pyrido[2,3-b][1,4]oxazin-7-yl)-3-isoquinolyl]-3-[(1S,2R)-2-hydroxycyclopentyl]urea (53.8 mg, 0.12 mmol, 55.4% yield) as a yellow solid. LCMS (ESI) [M+H]$^+$=453.2, R$_T$ 1.908 min, Method L; $^1$H NMR (300 MHz, DMSO-d$_6$) δ 9.28 (s, 1H), 9.10 (s, 1H), 7.84 (s, 1H), 7.33 (s, 1H), 7.22 (d, J=7.6 Hz, 1H), 6.73 (d, J=6.1 Hz, 1H), 6.15 (s, 2H), 5.67 (d, J=3.0 Hz, 1H), 4.88 (d, J=4.1 Hz, 1H), 4.29 (t, J=4.4 Hz, 2H), 3.94-3.97 (m, 1H), 3.85 (d, J=8.6 Hz, 1H), 3.33-3.31 (m, 2H), 1.92 (d, J=1.7 Hz, 3H), 1.89-1.38 (m, 6H).

Example 168

(S)-1-Isopropyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate and (R)-1-Isopropyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate (Compound 479a and Compound 479b)

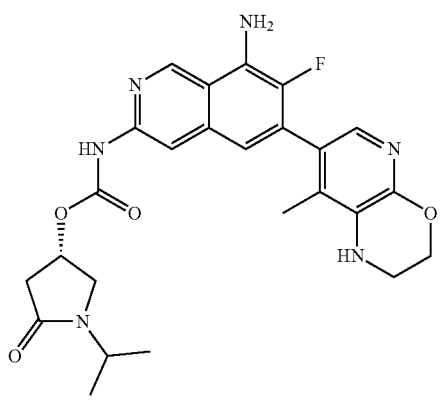

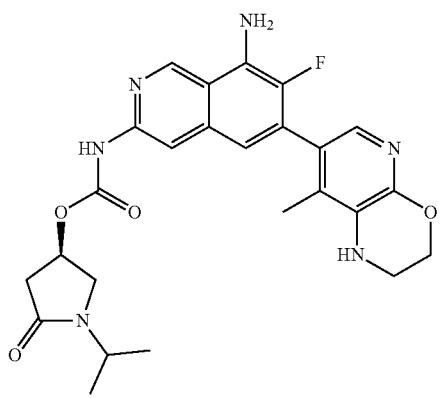

Step 1: 1-Isopropyl-3-methoxy-2H-pyrrol-5-one

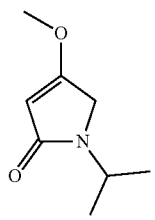

Under nitrogen, to a solution of methyl (Z)-4-chloro-3-methoxy-but-2-enoate (5.0 g, 30.3 mmol) in acetonitrile (80 mL) was added dropwise a solution of isopropylamine (2.3 g, 38.98 mmol) and triethylamine (3.97 g, 39.31 mmol) in acetonitrile (20 mL). The mixture was stirred at reflux for 4 hours. The reaction mixture was concentrated under vacuum. The residue was diluted with water and then extracted with dichloromethane. The organic layer was washed with 1N HCl. The organic layer was dried over anhydrous sodium sulfate and concentrated under vacuum. The residue was purified by flash chromatography on silica gel eluting with dichloromethane/methanol (10/1) to afford 1-isopropyl-3-methoxy-2H-pyrrol-5-one (2.26 g, 13.543 mmol, 44.7% yield) as a colorless oil. LCMS (ESI) $[M+H]^+= 156.1$.

Step 2: 1-Isopropylpyrrolidine-2, 4-dione

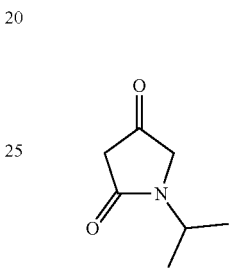

A solution of 1-isopropyl-3-methoxy-2H-pyrrol-5-one (2.26 g, 14.58 mmol) in 1N HCl (88 mL) and acetonitrile (44 mL) was stirred at 65° C. for 4 hours. The reaction mixture was concentrated under vacuum to afford crude product (1.6 g). The crude product would be directly used in the next step without purification. LCMS (ESI) $[M+H]^+=142.1$.

Step 3: 4-Hydroxy-1-isopropyl-pyrrolidin-2-one

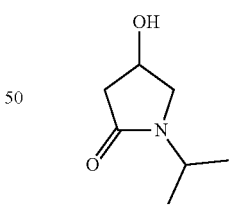

A solution of 1-isopropylpyrrolidine-2,4-dione (1.6 g, 11.35 mmol) and sodium borohydride (1.29 g, 33.95 mmol) in ethanol (50 mL) was stirred at room temperature for 2 hours. The resulting solution was concentrated under vacuum. The residue was diluted with water and extracted with ethyl acetate. The organic layers were combined, dried over sodium sulfate and concentrated under vacuum. The residue was purified by flash chromatography on silica gel eluting with dichloromethane/methanol (9/1) to afford 4-hydroxy-1-isopropyl-pyrrolidin-2-one (700 mg, 4.498 mmol, 39.6% yield) as brown oil. LCMS (ESI) $[M+H]^+=144.1$.

Step 4: tert-Butyl-7-[8-(tert-butoxycarbonyl amino)-7-fluoro-3-[(1-isopropyl-5-oxo-pyrrolidin-3-yl)oxycarbonylamino]-6-isoquinolyl]-8-methyl-2,3-dihydropyrido[2,3-b][1,4]oxazine-1-carboxylate

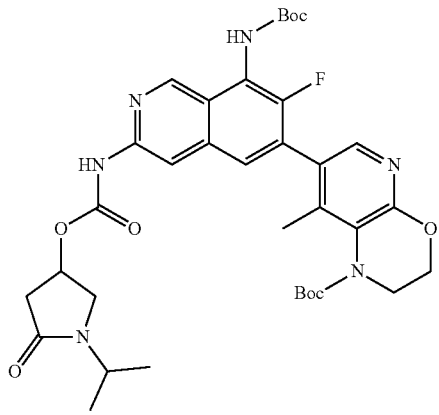 [SMILES: Cc1c(-c2cc3cc(NC(=O)OC4CC(=O)N(C(C)C)C4)ncc3c(NC(=O)OC(C)(C)C)c2F)cnc2c1N(C(=O)OC(C)(C)C)CCO2]

Under nitrogen, a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (300 mg, 0.57 mmol), 4-hydroxy-1-isopropyl-pyrrolidin-2-one (245 mg, 1.71 mmol) and N,N-diisopropylethylamine (736 mg, 5.71 mmol) in dichloromethane (28 mL) was stirred for 10 mins at 0° C. Then a solution of triphosgene (240 mg, 0.81 mmol) in dichloromethane (2 mL) was added dropwise. The mixture was stirred at 0° C. for 2 hours. The resulting solution was diluted with dichloromethane and extracted with DCM. The organic layer was washed with water, dried over anhydrous sodium sulfate and concentrated under vacuum. The residue was purified by flash chromatography on silica gel eluting with dichloromethane/methanol (19/1) to afford tert-butyl-7-[8-(tert-butoxycarbonylamino)-7-fluoro-3-[(1-isopropyl-5-oxo-pyrrolidin-3-yl)oxycarbonylamino]-6-isoquinolyl]-8-methyl-2,3-dihydropyrido[2,3-b][1,4]oxazine-1-carboxylate (180 mg, 0.246 mmol, 43.2% yield) as a brown solid. LCMS (ESI) [M+H]$^+$=695.3.

Step 5: (S)-1-Isopropyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate and (R)-1-Isopropyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate

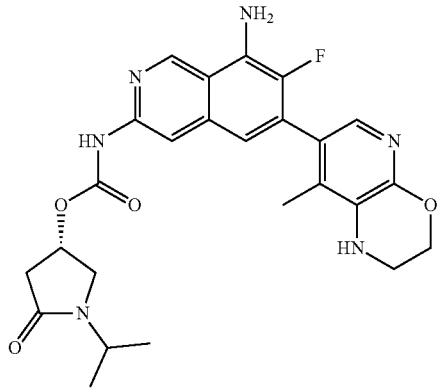

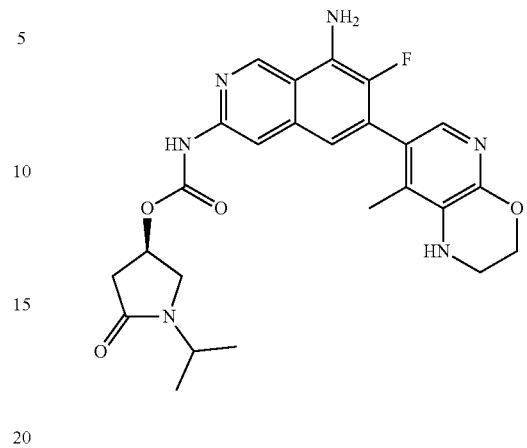

A solution of tert-butyl-7-[8-(tert-butoxycarbonylamino)-7-fluoro-3-[(1-isopropyl-5-oxo-pyrrolidin-3-yl)oxycarbonylamino]-6-isoquinolyl]-8-methyl-2,3-dihydropyrido[2,3-b][1,4]oxazine-1-carboxylate (180 mg, 0.26 mmol) in dichloromethane (20 mL) and TFA (5 mL) was stirred at 25° C. for 1 hour. The reaction was concentrated under vacuum. The residue was re-dissolved in dichloromethane and adjusted to pH 8 with triethylamine. The mixture was concentrated under vacuum and purified by Prep-HPLC (Column: X-Bridge Prep OBD C18 Column 30×150 mm 5 μm; Mobile Phase A: Water (10 mmol/L NH$_4$HCO$_3$), Mobile Phase B: ACN; Flow rate: 60 mL/min; Gradient: 17% B to 36% B in 7 min) to give the racemic product. The racemate was separated by chiral-HPLC to afford two enantiomers. Absolute stereochemistry was arbitrarily assigned.

Enantiomer 1: Compound 479a (21.6 mg, 0.0433 mmol, 16.7% yield). R$_T$ 2.014 min (CHIRALPAK IG-3, 0.46*5 cm; 3 μm. MTBE:EtOH=50:50 in 5 min, 1.0 mL/min). LCMS (ESI) [M+H]$^+$=495.2, R$_T$ 1.857 min, Method J; $^1$H NMR (300 MHz, DMSO-d$_6$) δ 10.19 (s, 1H), 9.32 (s, 1H), 7.95 (s, 1H), 7.31 (s, 1H), 6.82 (d, J=6.2 Hz, 1H), 6.21 (s, 2H), 5.67 (s, 1H), 5.27 (s, 1H), 4.28 (d, J=4.3 Hz, 2H), 4.16 (p, J=6.7 Hz, 1H), 3.88-3.69 (m, 1H), 3.41-3.38 (m, 2H), 2.89-2.75 (m, 1H), 2.31-2.25 (m, 2H), 1.90 (d, J=1.6 Hz, 3H), 1.06 (t, J=6.5 Hz, 6H).

Enantiomer 2: Compound 479b (22.1 mg, 0.044 mmol, 17% yield). R$_T$ 3.049 min (CHIRALPAK IG-3, 0.46*5 cm; 3 μm. MTBE:EtOH=50:50 in 5 min, 1.0 mL/min). LCMS (ESI) [M+H]$^+$=495.2, R$_T$ 1.857 min, Method J; $^1$H NMR (300 MHz, DMSO-d$_6$) δ 10.19 (s, 1H), 9.32 (s, 1H), 7.95 (s, 1H), 7.31 (s, 1H), 6.82 (d, J=6.2 Hz, 1H), 6.21 (s, 2H), 5.67 (s, 1H), 5.27 (s, 1H), 4.28 (d, J=4.3 Hz, 2H), 4.16 (p, J=6.7 Hz, 1H), 3.88-3.69 (m, 1H), 3.41-3.38 (m, 2H), 2.89-2.75 (m, 1H), 2.31-2.25 (m, 2H), 1.90 (d, J=1.6 Hz, 3H), 1.06 (t, J=6.5 Hz, 6H).

Example 169

(S)-1-Methyl-5-oxopyrrolidin-3-yl (8-amino-7-fluoro-6-(4-methyl-5,6,7,8-tetrahydro-1,5-naphthyridin-3-yl)isoquinolin-3-yl)carbamate and (R)-1-Methyl-5-oxopyrrolidin-3-yl (8-amino-7-fluoro-6-(4-methyl-5,6,7,8-tetrahydro-1,5-naphthyridin-3-yl)isoquinolin-3-yl)carbamate (Compound 481a and Compound 481b)

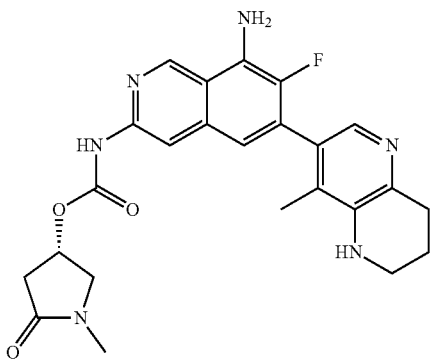

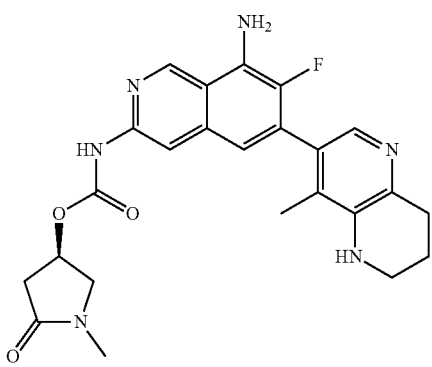

Step 1: tert-Butyl 7-[8-(tert-butoxycarbonylamino)-7-fluoro-3-[(1-methyl-5-oxo-pyrrolidin-3-yl)oxycarbonylamino]-6-isoquinolyl]-8-methyl-3,4-dihydro-2H-1,5-naphthyridine-1-carboxylate

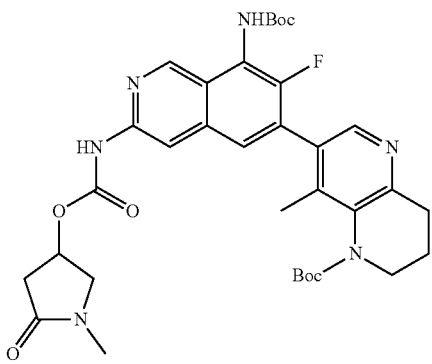 [SMILES: Cc1c(-c2cc3cc(NC(=O)OC4CC(=O)N(C)C4)ncc3c(NC(=O)OC(C)(C)C)c2F)cnc2c1N(C(=O)OC(C)(C)C)CCC2]

To a solution of tert-butyl 7-[3-amino-8-(tert-butoxycarbonylamino)-7-fluoro-6-isoquinolyl]-8-methyl-3,4-dihydro-2H-1,5-naphthyridine-1-carboxylate (400.0 mg, 0.76 mmol), DIEA (493.7 mg, 3.82 mmol) and 4-hydroxy-1-methyl-pyrrolidin-2-one (176.0 mg, 1.53 mmol) in dichloromethane (14 mL) was added triphosgene (226.7 mg, 0.76 mmol) and stirred at 0° C. for 1.5 h. The reaction was quenched with water. The resulting solution was extracted with dichloromethane. The organic layers were combined, dried over anhydrous sodium sulfate and concentrated under vacuum. The residue was purified by flash chromatography on silica gel eluting with dichloromethane/methanol (95/5) to afford tert-butyl 7-[8-(tert-butoxycarbonylamino)-7-fluoro-3-[(1-methyl-5-oxo-pyrrolidin-3-yl)oxycarbonylamino]-6-isoquinolyl]-8-methyl-3,4-dihydro-2H-1,5-naphthyridine-1-carboxylate (250 mg, 0.38 mmol, 49.2% yield) as a yellow solid. LCMS (ESI) $[M+H]^+=665$.

Step 2: (S)-1-methyl-5-oxopyrrolidin-3-yl (8-amino-7-fluoro-6-(4-methyl-5,6,7,8-tetrahydro-1,5-naphthyridin-3-yl)isoquinolin-3-yl)carbamate and (R)-1-methyl-5-oxopyrrolidin-3-yl (8-amino-7-fluoro-6-(4-methyl-5,6,7,8-tetrahydro-1,5-naphthyridin-3-yl)isoquinolin-3-yl)carbamate

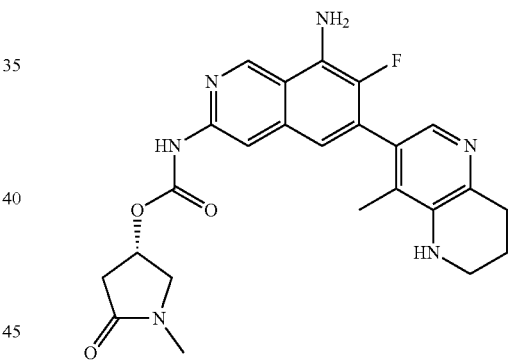

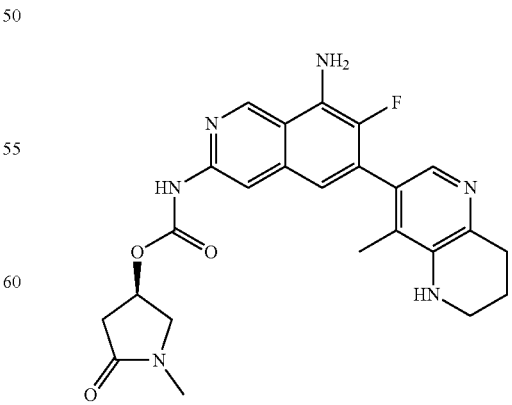

To a solution of tert-butyl 7-[8-(tert-butoxycarbonylamino)-7-fluoro-3-[(1-methyl-5-oxo-pyrrolidin-3-yl)oxycarbonylamino]-6-isoquinolyl]-8-methyl-3,4-dihydro-2H-1,5-naphthyridine-1-carboxylate (250.0 mg, 0.38 mmol) in dichloromethane (10 mL) was added TFA (2 mL). The mixture was then stirred at room temperature for 1.5 hours. The reaction was concentrated under vacuum. The residue was dissolved in dichloromethane and adjusted to pH 8 with TEA and concentrated under vacuum. The residue was purified by prep-HPLC (Column: X Select CSH Prep C18 OBD Column, 5 μm, 19*150 mm; Mobile Phase A: Water (0.1% FA), Mobile Phase B: ACN; Flow rate: 25 mL/min; Gradient: 5% B to 24% B in 7 min) and separated by chiral HPLC (Column: CHIRALPAK IE, 2*25 cm, 5 μm; Mobile Phase A: MTBE, Mobile Phase B: MeOH; Flow rate: 20 mL/min; Gradient: 30 B to 30 B in 16 min) afford two enantiomers. Absolute stereochemistry was arbitrarily assigned.

Enantiomer 1: (Compound 481a) (35.2 mg, 0.069 mmol, 18.3% yield). $R_T$ 2.164 min (CHIRALPAK IE-3, 0.46*5 cm; 3 μm, Mobile phase: MTBE: MeOH=70:30, 1 ml/min). LCMS (ESI): [M+H]$^+$=465.3, $R_T$ 1.939 min; Method L. $^1$H NMR (300 MHz, DMSO-d$_6$) δ 10.24 (s, 1H), 9.35 (s, 1H), 7.98 (s, 1H), 7.64 (s, 1H), 6.86 (d, J=6.1 Hz, 1H), 6.27 (s, 2H), 5.63 (s, 1H), 5.33-5.23 (m, 1H), 3.78 (dd, J=11.6, 5.7 Hz, 1H), 3.42 (m, 3H), 2.94-2.74 (m, 3H), 2.76 (s, 3H), 2.29 (d, J=17.6 Hz, 1H), 1.92-1.90 (m, 5H).

Enantiomer 2: (Compound 481b) (35.2 mg, 0.069 mmol, 18.3% yield). $R_T$ 3.101 min (CHIRALPAK IE-3, 0.46*5 cm; 3 μm, Mobile phase: MTBE: MeOH=70:30, 1 ml/min). LCMS (ESI): [M+H]$^+$=465.3, $R_T$ 1.939 min; Method L. $^1$H NMR (300 MHz, DMSO-d$_6$) δ 10.24 (s, 1H), 9.35 (s, 1H), 7.98 (s, 1H), 7.64 (s, 1H), 6.86 (d, J=6.1 Hz, 1H), 6.27 (s, 2H), 5.63 (s, 1H), 5.33-5.23 (m, 1H), 3.78 (dd, J=11.6, 5.7 Hz, 1H), 3.42 (m, 3H), 2.94-2.74 (m, 3H), 2.76 (s, 3H), 2.29 (d, J=17.6 Hz, 1H), 1.92-1.90 (m, 5H).

Example 170

(1s,3s)-3-Cyanocyclobutyl (8-amino-7-fluoro-6-(4-methyl-5,6,7,8-tetrahydro-1,5-naphthyridin-3-yl)isoquinolin-3-yl)carbamate (Compound 483a)

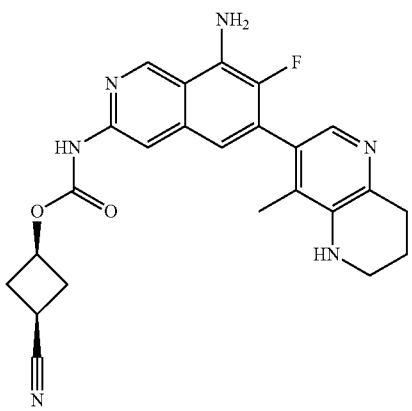 [SMILES: Cc1c(-c2cc3cc(NC(=O)O[C@H]4C[C@@H](C#N)C4)ncc3c(N)c2F)cnc2c1NCCC2]

Step 1: tert-Butyl 7-(8-((tert-butoxycarbonyl)amino)-3-((((1s,3s)-3-cyanocyclobutoxy)carbonyl)amino)-7-fluoroisoquinolin-6-yl)-8-methyl-3,4-dihydro-1,5-naphthyridine-1(2H)-carboxylate

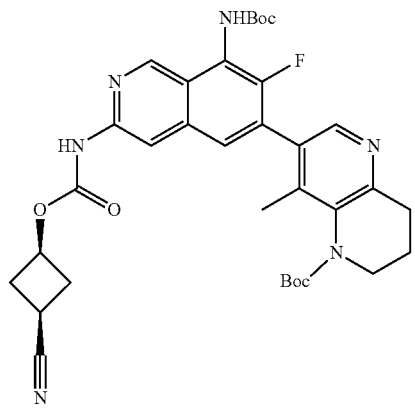 [SMILES: Cc1c(-c2cc3cc(NC(=O)O[C@H]4C[C@@H](C#N)C4)ncc3c(NC(=O)OC(C)(C)C)c2F)cnc2c1N(C(=O)OC(C)(C)C)CCC2]

Under nitrogen, to a solution of tert-butyl 7-[3-amino-8-(tert-butoxycarbonylamino)-7-fluoro-6-isoquinolyl]-8-methyl-3,4-dihydro-2H-1,5-naphthyridine-1-carboxylate (150.0 mg, 0.29 mmol), cis-3-hydroxycyclobutanecarbonitrile (55.6 mg, 0.57 mmol) and DIEA (185.0 mg, 1.43 mmol) in dichloromethane (15 mL) was added tirphosgene (59.5 mg, 0.20 mmol) at 0° C. and the mixture was stirred for 1 hour. The reaction mixture was concentrated under vacuum. The residue was purified by flash chromatography on silica gel eluting with PE/EA(22/78) to afford tert-butyl 7-(8-((tert-butoxycarbonyl)amino)-3-((((1s,3s)-3-cyanocyclobutoxy)carbonyl)amino)-7-fluoroisoquinolin-6-yl)-8-methyl-3,4-dihydro-1,5-naphthyridine-1(2H)-carboxylate (100 mg, 0.15 mmol, 54% yield) as a white solid. LCMS (ESI): [M+H]+=647.3.

Step 2: (1s,3s)-3-Cyanocyclobutyl (8-amino-7-fluoro-6-(4-methyl-5,6,7,8-tetrahydro-1,5-naphthyridin-3-yl)isoquinolin-3-yl)carbamate

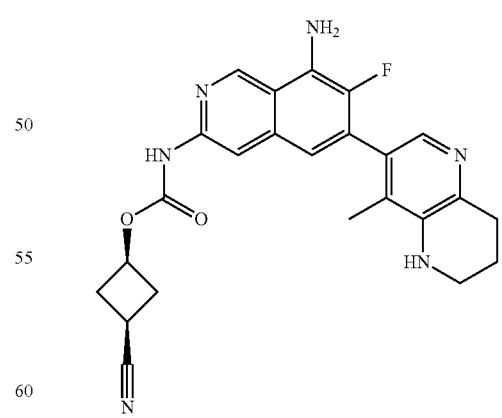

A solution of tert-butyl 7-(8-((tert-butoxycarbonyl)amino)-3-((((1s,3s)-3-cyanocyclobutoxy)carbonyl)amino)-7-fluoroisoquinolin-6-yl)-8-methyl-3,4-dihydro-1,5-naphthyridine-1(2H)-carboxylate (95.0 mg, 0.15 mmol) and TFA (1.0 mL, 0.15 mmol) in dichloromethane (5 mL) was stirred at 25° C. for 1 hour. After concentration, the residue was purified by Prep-HPLC (Column: XSelect CSH Prep C18 OBD Column, 5 μm, 19*150 mm; Water (0.1% FA): ACN=5% B to 29% B in 7 min; 25 mL/min) to afford (1s,3s)-3-cyanocyclobutyl (8-amino-7-fluoro-6-(4-methyl-5,6,7,8-tetrahydro-1,5-naphthyridin-3-yl)isoquinolin-3-yl) carbamate (24 mg, 0.054 mmol, 36.6% yield) as a pale yellow solid. LCMS (ESI) [M+H]$^+$=447.3; R$_T$ 1.163 min; Method J; $^1$H NMR (300 MHz, DMSO-d$_6$) δ 10.22 (s, 1H), 9.33 (s, 1H), 7.93 (s, 1H), 7.56 (s, 1H), 6.82 (d, J=6.1 Hz, 1H), 6.23 (s, 2H), 5.47 (s, 1H), 5.00-4.92 (m, 1H), 3.50-3.23 (m, 2H), 3.20-3.10 (m, 1H), 2.83-2.70 (m, 4H), 2.42-2.20 (m, 2H), 1.98-1.69 (m, 5H).

Example 171

1-(8-Amino-7-fluoro-6-(8-methyl-2,3-dihydro-1H-pyrido[2,3-b][1,4]oxazin-7-yl)isoquinolin-3-yl)-3-((3S,4S)-4-methoxytetrahydrofuran-3-yl)urea and 1-(8-Amino-7-fluoro-6-(8-methyl-2,3-dihydro-1H-pyrido[2,3-b][1,4]oxazin-7-yl)isoquinolin-3-yl)-3-((3R,4R)-4-methoxytetrahydrofuran-3-yl)urea (Compound 723a and Compound 723b)

Step 1: (±)-cis-tert-Butyl 7-(8-((tert-butoxycarbonyl)amino)-7-fluoro-3-(3-(4-methoxytetrahydrofuran-3-yl)ureido)isoquinolin-6-yl)-8-methyl-2,3-dihydro-1H-pyrido[2,3-b][1,4]oxazine-1-carboxylate To a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (200.0 mg, 0.31 mmol), (±)-cis-4-methoxytetrahydrofuran-3-amine hydrochloride (143.0 mg, 0.93 mmol) and DMAP (38.0 mg, 0.31 mmol) in dichloromethane (5 mL) was added DIEA (200 mg, 1.55 mmol) at 25° C. The mixture was stirred at 55° C. for 24 hours and concentrated under vacuum. The residue was purified by flash chromatography on silica gel eluting with dichloromethane/methanol (88/12) to afford (±)-cis-tert-butyl 7-(8-((tert-butoxycarbonyl)amino)-7-fluoro-3-(3-(4-methoxytetrahydrofuran-3-yl)ureido)isoquinolin-6-yl)-8-methyl-2,3-dihydro-1H-pyrido[2,3-b][1,4]oxazine-1-carboxylate (182 mg, 0.27 mmol, 87% yield) as a white solid. LCMS (ESI) [M+H]$^+$=669.

Step 2: 1-(8-Amino-7-fluoro-6-(8-methyl-2,3-dihydro-1H-pyrido[2,3-b][1,4]oxazin-7-yl)isoquinolin-3-yl)-3-((3S,4S)-4-m ethoxytetrahydrofuran-3-yl) urea and 1-(8-Amino-7-fluoro-6-(8-methyl-2,3-dihydro-1H-pyrido[2,3-b][1,4]oxazin-7-yl) isoquinolin-3-yl)-3-((3R,4R)-4-methoxytetrahydrofuran-3-yl)urea

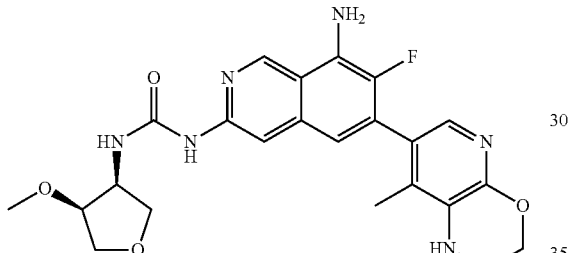

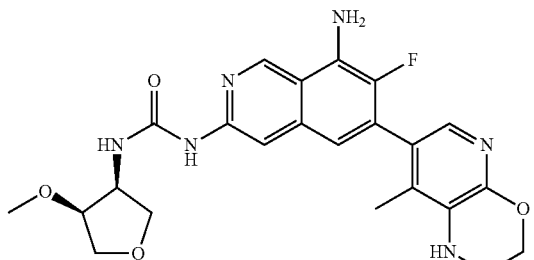

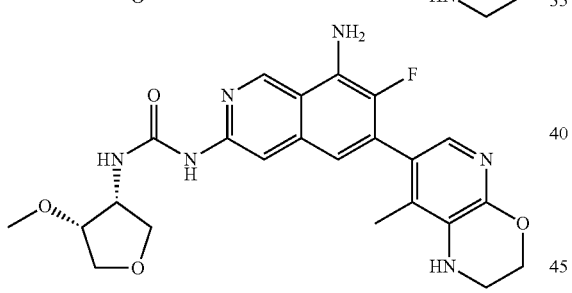

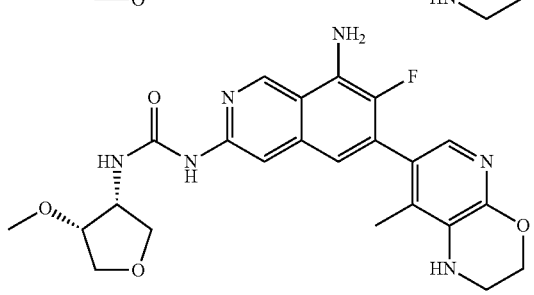

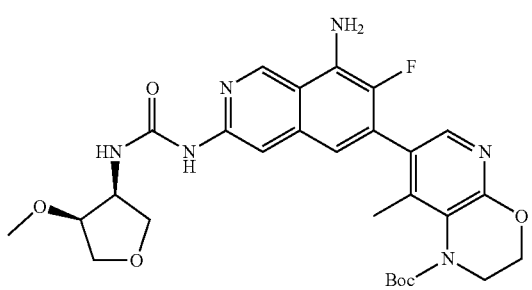 [SMILES: CO[C@@H]1COC[C@@H]1NC(=O)Nc1cc2cc(-c3cnc4c(c3C)N(C(=O)OC(C)(C)C)CCO4)c(F)c(N)c2cn1]

To a solution of (±)-cis-tert-butyl 7-(8-((tert-butoxycarbonyl)amino)-7-fluoro-3-(3-(4-methoxytetrahydrofuran-3-yl)ureido)isoquinolin-6-yl)-8-methyl-2,3-dihydro-1H-pyrido[2,3-b][1,4]oxazine-1-carboxylate (172.0 mg, 0.26 mmol) in dichloromethane (4 mL) was added 2,2,2-trifluoroacetic acid (1 mL). The mixture was stirred at 25° C. for 1 hour and then concentrated under vacuum. The residue was adjusted to pH 8 with Et$_3$N. The crude product was purified by Prep-HPLC with following condition (Column: X Bridge BEH130 Prep C18 OBD Column 19×150 mm 5 μm 13 nm; Water (10 mm NH$_4$HCO$_3$): MeOH=35% B to 45% B in 7 min, 25 mL/min) to afford the racemic product. The mixture was separated by chiral-HPLC to give two enantiomers. Relative stereochemistry are as drawn. Absolute stereochemistry was arbitrarily assigned.

Enantiomer 1 (Compound 723a) (29.5 mg, 0.06 mmol, 24% yield). R$_T$ 1.241 min (CHIRALPAK IE-3, 0.46*5 cm; 3 μm. MTBE (0.1% DEA):EtOH=50:50, 1 mL/min). LCMS (ESI) [M+H]$^+$=469, R$_T$ 1.781 min, Method J; $^1$H NMR (300 MHz, DMSO-d$_6$) δ 9.28 (s, 1H), 9.22 (s, 1H), 7.77 (s, 1H), 7.58 (s, 1H), 7.30 (s, 1H), 6.73 (d, J=6.1 Hz, 1H), 6.16 (s, 2H), 5.66 (s, 1H), 4.38-4.22 (m, 3H), 3.97-3.70 (m, 4H), 3.40-3.31 (m, 6H), 1.90 (d, J=1.6 Hz, 3H).

Enantiomer 2 (Compound 723b) (28.9 mg, 0.062 mmol, 24% yield). R$_T$ 1.805 min (CHIRALPAK IE-3, 0.46*5 cm; 3 μm. MTBE (0.1% DEA):EtOH=50:50, 1 mL/min). LCMS (ESI) [M+H]$^+$=469, R$_T$ 1.781 min, Method J; $^1$H NMR (300 MHz, DMSO-d$_6$) δ 9.28 (s, 1H), 9.22 (s, 1H), 7.77 (s, 1H), 7.58 (s, 1H), 7.30 (s, 1H), 6.73 (d, J=6.1 Hz, 1H), 6.16 (s, 2H), 5.66 (s, 1H), 4.38-4.22 (m, 3H), 3.97-3.70 (m, 4H), 3.40-3.31 (m, 6H), 1.90 (d, J=1.6 Hz, 3H).

Example 172

2-(2,2-Di fluoroethyl)-2-azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate (Compound 494)

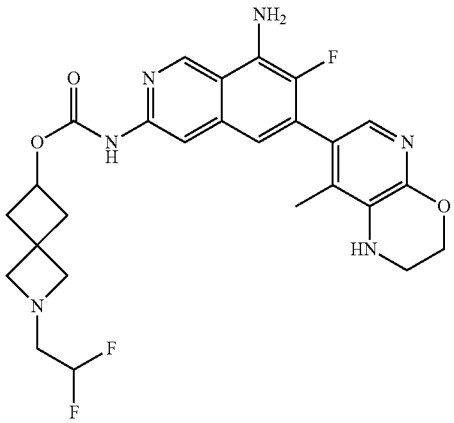 [SMILES: Cc1c(-c2cc3cc(NC(=O)OC4CC5(C4)CN(CC(F)F)C5)ncc3c(N)c2F)cnc2c1NCCO2]

Step 1: tert-Butyl 7-(3-((((2-(tert-butoxycarbonyl)-2-azaspiro[3.3]heptan-6-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

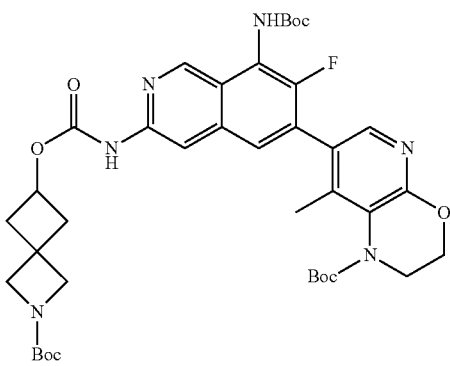 [SMILES: Cc1c(-c2cc3cc(NC(=O)OC4CC5(C4)CN(C(=O)OC(C)(C)C)C5)ncc3c(NC(=O)OC(C)(C)C)c2F)cnc2c1N(C(=O)OC(C)(C)C)CCO2]

A solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (200 mg, 0.38 mmol), tert-butyl 6-hydroxy-2-azaspiro[3.3]heptane-2-carboxylate (164 mg, 0.77 mmol) and DIEA (245 mg, 1.9 mmol) in dichloromethane (5 mL) was stirred at 0° C. for 1 hour. Then triphosgene (80 mg, 0.27 mmol) was added. The mixture was stirred at 0° C. for 1 hour and concentrated under vacuum. The residue was purified by reversed phase chromatography (C18 column with ACN/water (20/80)) to afford tert-butyl 7-[8-(tert-butoxycarbonylamino)-3-[(2-tert-butoxycarbonyl-2-azaspiro[3.3]heptan-6-yl)oxycarbonylamino]-7-fluoro-6-isoquinolyl]-8-methyl-2,3-dihydropyrido[2,3-b][1,4]oxazine-1-carboxylate (220 mg, 0.288 mmol, 75.6% yield) as a yellow solid. LCMS (ESI) [M+H]$^+$= 764.

Step 2: 2-Azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate

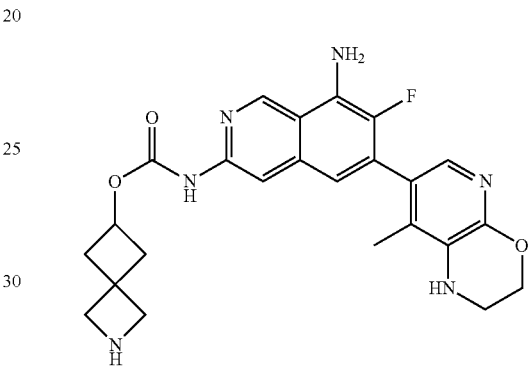

A solution of tert-butyl 7-[8-(tert-butoxycarbonylamino)-3-[(2-tert-butoxycarbonyl-2-azaspiro[3.3]heptan-6-yl)oxycarbonylamino]-7-fluoro-6-isoquinolyl]-8-methyl-2,3-dihydropyrido[2,3-b][1,4]oxazine-1-carboxylate (200.0 mg, 0.26 mmol) in TFA (2 mL) and dichloromethane (5 mL) was stirred at room temperature for 1 hour. The reaction mixture was then concentrated under vacuum and purified by reversed phase chromatograph (C18 column with ACN/water (18/82)) to afford 2-azaspiro[3.3]heptan-6-yl N-[8-amino-7-fluoro-6-(8-methyl-2,3-dihydro-1H-pyrido[2,3-b][1,4]oxazin-7-yl)-3-isoquinolyl]carbamate (90 mg, 0.194 mmol, 74.1% yield) as a yellow solid. LCMS (ESI) [M+H]$^+$= 465.

Step 3: 2-(2,2-Difluoroethyl)-2-azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate

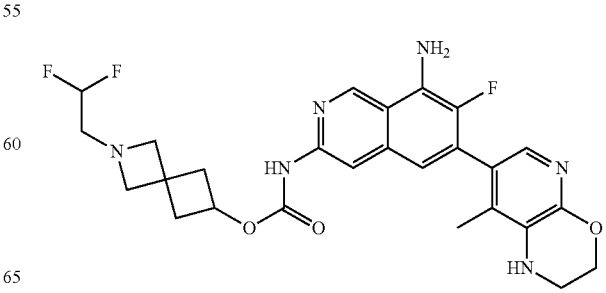

A solution of 2-azaspiro[3.3]heptan-6-yl N-[8-amino-7-fluoro-6-(8-methyl-2,3-dihydro-1H-pyrido[2,3-b][1,4]oxazin-7-yl)-3-isoquinolyl]carbamate (66.0 mg, 0.14 mmol) and Et₃N (72 mg, 0.14 mmol) in tetrahydrofuran (6.6 mL) was stirred at room temperature for 5 min. Then 2,2-difluoroethyltrifluoromethanesulfonate (45 mg, 0.21 mmol) was added and stirred at room temperature for 1 hour. The reaction mixture was concentrated under vacuum and purified by Prep-HPLC (X Select CSH PreC18 OBD Column, 5 µm, 19×150 nm); Mobile phase A: water (0.1% FA), Mobile phase B: ACN; Flow rate 25 mL/min; Gradient: 5% B to 25% to in 7 min) to afford [2-(2,2-difluoroethyl)-2-azaspiro[3.3]heptan-6-yl]N-[8-amino-7-fluoro-6-(8-methyl-2,3-dihydro-1H-pyrido[2,3-b][1,4]oxazin-7-yl)-3-isoquinolyl]carbamate (15 mg, 0.0284 mmol, 20% yield) as a yellow solid. LCMS (ESI) [M+H]⁺=529.3, $R_T$ 6.230 min, Method M. ¹H NMR (400 MHz, DMSO-$d_6$) δ 10.51 (s, 1H), 10.12 (s, 1H), 9.34 (s, 1H), 7.94 (s, 1H), 7.33 (s, 1H), 6.85-6.82 (d, J=6 Hz, 1H), 6.34-6.20 (m, 2H), 5.71 (s, 1H), 4.31-4.13 (m, 6H), 3.84-3.67 (m, 2H), 3.46-3.30 (m, 2H), 2.77 (s, 1H), 2.69 (s, 1H), 2.24-26 (m, 2H), 2.63 (s, 1H), 1.92 (s, 3H).

Example 173

(R)-(3-Fluoro-1-methylpyrrolidin-3-yl)methyl (8-amino-7-fluoro-6-(8-methyl-2,3-dihydro-1H-pyrido[2,3-b][1,4]oxazin-7-yl)isoquinolin-3-yl)carbamate and (S)-(3-Fluoro-1-methylpyrrolidin-3-yl)methyl (8-amino-7-fluoro-6-(8-methyl-2,3-dihydro-1H-pyrido[2,3-b][1,4]oxazin-7-yl)isoquinolin-3-yl)carbamate (Compound 451a and Compound 451b)

Step 1: tert-Butyl 7-[8-(tert-butoxycarbonylamino)-3-[(1-tert-butoxycarbonyl-3-fluoro-pyrrolidin-3-yl)methoxycarbonylamino]-7-fluoro-6-isoquinolyl]-8-methyl-2,3-dihydropyrido[2,3-b][1,4]oxazine-1-carboxylate

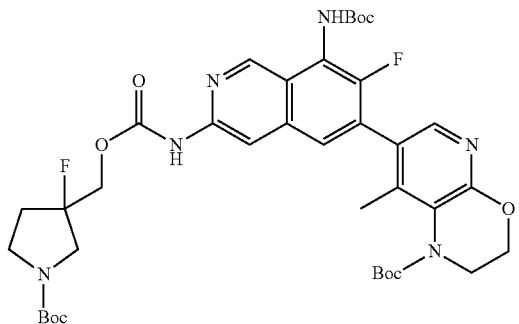 [SMILES: Cc1c(-c2cc3cc(NC(=O)OCC4(F)CCN(C(=O)OC(C)(C)C)C4)ncc3c(NC(=O)OC(C)(C)C)c2F)cnc2c1N(C(=O)OC(C)(C)C)CCO2]

A solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (370 mg, 0.70 mmol), tert-butyl 3-fluoro-3-(hydroxymethyl)pyrrolidine-1-carboxylate (680 mg, 3.1 mmol) and DIEA (0.90 g, 6.92 mmol) in dichloromethane (8 mL) was added a solution of triphosgene (208 mg, 0.70 mmol) in dichloromethane (4 mL) at 0° C. The reaction was stirred for 2 hours at room temperature. The mixture was concentrated under vacuum and purified by flash chromatography on silica gel eluting with petroleum ether/ethyl acetate (1/7) to afford tert-butyl 7-[8-(tert-butoxycarbonylamino)-3-[(1-tert-butoxycarbonyl-3-fluoro-pyrrolidin-3-yl)methoxycarbonylamino]-7-fluoro-6-isoquinolyl]-8-methyl-2,3-dihydropyrido[2,3-b][1,4]oxazine-1-carboxylate (200 mg, 0.259 mmol, 36.9% yield) as a yellow solid. LCMS (ESI) [M+H]⁺=771.

Step 2: (3-Fluoropyrrolidin-3-yl)methyl N-[8-amino-7-fluoro-6-(8-methyl-2,3-dihydro-1H-pyrido[2,3-b][1,4]oxazin-7-yl)-3-isoquinolyl]carbamate

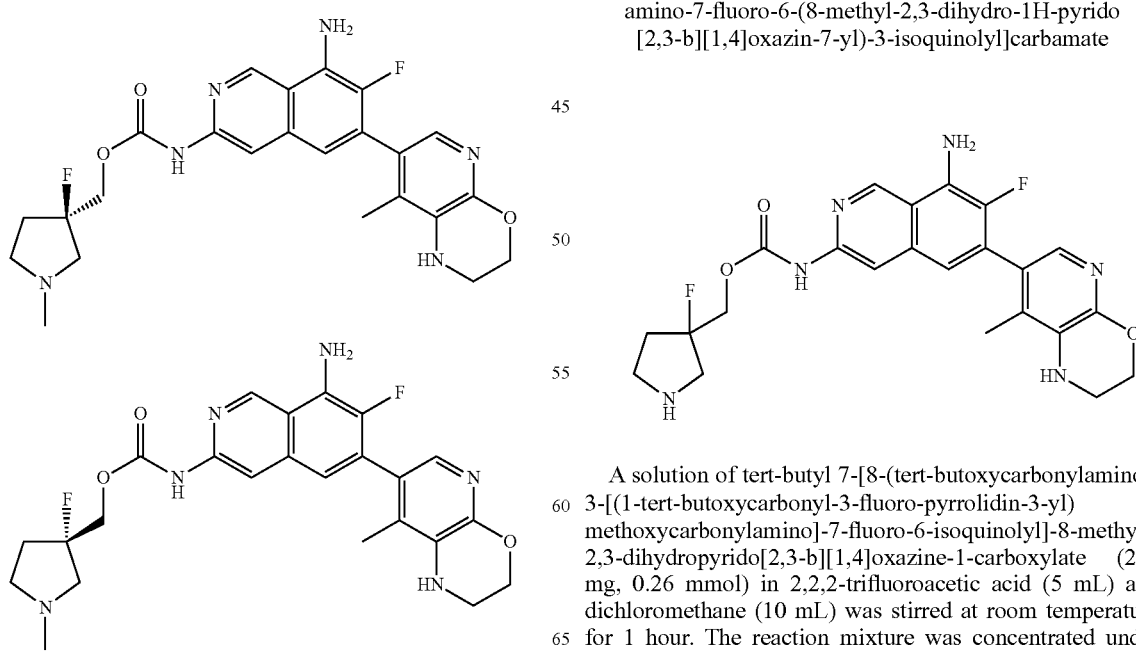

A solution of tert-butyl 7-[8-(tert-butoxycarbonylamino)-3-[(1-tert-butoxycarbonyl-3-fluoro-pyrrolidin-3-yl)methoxycarbonylamino]-7-fluoro-6-isoquinolyl]-8-methyl-2,3-dihydropyrido[2,3-b][1,4]oxazine-1-carboxylate (200 mg, 0.26 mmol) in 2,2,2-trifluoroacetic acid (5 mL) and dichloromethane (10 mL) was stirred at room temperature for 1 hour. The reaction mixture was concentrated under vacuum to afford (3-fluoropyrrolidin-3-yl)methyl N-[8-amino-7-fluoro-6-(8-methyl-2,3-dihydro-1H-pyrido[2,3-b]

[1,4]oxazin-7-yl)-3-isoquinolyl]carbamate (120 mg, 0.2551 mmol, 98.3% yield) as a yellow oil. LCMS (ESI) [M+H]+= 471.

Step 3: (R)-(3-Fluoro-1-methylpyrrolidin-3-yl)methyl (8-amino-7-fluoro-6-(8-methyl-2,3-dihydro-1H-pyrido[2,3-b][1,4]oxazin-7-yl)isoquinolin-3-yl)carbamate and (S)-(3-Fluoro-1-methylpyrrolidin-3-yl)methyl (8-amino-7-fluoro-6-(8-methyl-2,3-dihydro-1H-pyrido[2,3-b][1,4]oxazin-7-yl)isoquinolin-3-yl)carbamate

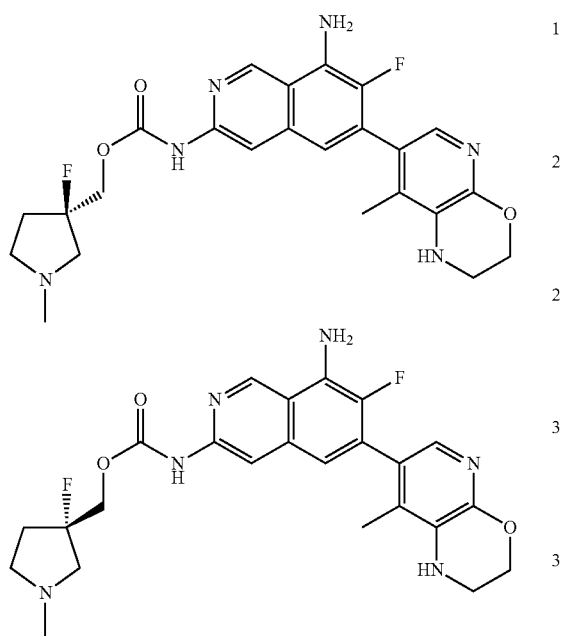

A solution of (3-fluoropyrrolidin-3-yl)methyl N-[8-amino-7-fluoro-6-(8-methyl-2,3-dihydro-1H-pyrido[2,3-b][1,4]oxazin-7-yl)-3-isoquinolyl]carbamate (120 mg, 0.26 mmol) and formaldehyde (40%, 38 mg, 0.51 mmol) in methyl alcohol (10 mL) was stirred at 25° C. for 2 hours. Then NaBH₄ (28 mg, 0.76 mmol) was added and the mixture was stirred at 25° C. for 1 h. The reaction mixture was concentrated under vacuum and purified by Prep-HPLC (Column: X Select CSH Prep C18 OBD Column, 5 μm, 19*150 mm; Mobile Phase A: Water (0.1% FA), Mobile Phase B: ACN; Flow rate: 25 mL/min; Gradient: 5% B to 21% B in 7 min; 254/220 nm; Rt: 6 min.) to give the racemic mixture of products. The racemic mixture was separated by chiral-HPLC to afford two enantiomers. Absolute stereochemistry was arbitrarily assigned.

Enantiomer 1 (Compound 451a) (22.2 mg, 0.0458 mmol, 18% yield). R$_T$ 10.715 min (CHIRALPAK IG, 2.0 cm I.D*25 cm L (5 μm); Mobile Phase A: Hex:DCM=1:1 (10 mm NH3-MEOH), Mobile Phase B: EtOH; Flow rate: 20 mL/min; Gradient: 50 B to 50 B in 18 min). LCMS (ESI) [M+H]+=485, R$_T$ 2.158 min., Method M. ¹H NMR (300 MHz, DMSO-d₆) δ 10.23 (s, 1H), 9.35 (s, 1H), 7.96 (s, 1H), 7.33 (s, 1H), 6.85 (d, J=6.1 Hz, 1H), 6.23 (s, 2H), 5.67 (d, J=3.2 Hz, 1H), 4.28 (d, J=6.0 Hz, 4H), 3.34-3.32 (m, 2H), 2.83-2.42 (m, 4H), 2.26 (s, 3H), 2.16-1.98 (m, 2H), 1.92 (d, J=1.6 Hz, 3H).

Enantiomer 2 (Compound 451ab) (20.2 mg, 0.0417 mmol, 16.3% yield). Retention time: 15.235 min (CHIRAL-PAK IG, 2.0 cm I.D*25 cm L (5 μm); Mobile Phase A: Hex:DCM=1:1 (10 mm NH3-MEOH), Mobile Phase B: EtOH-HPLC; Flow rate: 20 mL/min; Gradient: 50 B to 50 B in 18 min). LCMS (ESI) [M+H]+=485, R$_T$ 2.158 min., Method M. ¹H NMR (300 MHz, DMSO-d₆) δ 10.23 (s, 1H), 9.35 (s, 1H), 7.96 (s, 1H), 7.33 (s, 1H), 6.85 (d, J=6.1 Hz, 1H), 6.23 (s, 2H), 5.67 (d, J=3.2 Hz, 1H), 4.28 (d, J=6.0 Hz, 4H), 3.34-3.32 (m, 2H), 2.83-2.42 (m, 4H), 2.26 (s, 3H), 2.16-1.98 (m, 2H), 1.92 (d, J=1.6 Hz, 3H).

Example 174

1-(8-Amino-7-fluoro-6-(4-methyl-5,6,7,8-tetrahydro-1,5-naphthyridin-3-yl)isoquinolin-3-yl)-3-(2-(2,2-difluoroethyl)-2-azaspiro[3.3]heptan-6-yl)urea (Compound 739)

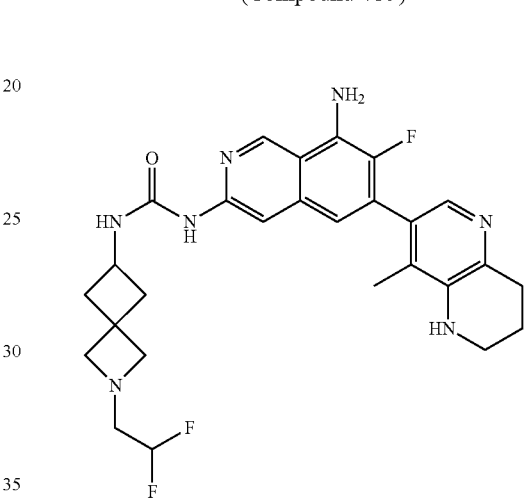

Step 1: tert-Butyl 7-[8-(tert-butoxycarbonylamino)-3-[(2-tert-butoxycarbonyl-2-azaspiro[3.3]heptan-6-yl)carbamoylamino]-7-fluoro-6-isoquinolyl]-8-methyl-3,4-dihydro-2H-1,5-naphthyridine-1-carboxylate

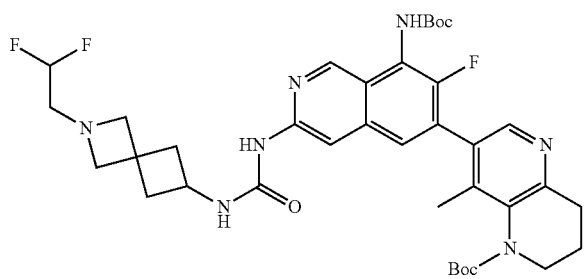 [SMILES: Cc1c(-c2cc3cc(NC(=O)NC4CC5(C4)CN(CC(F)F)C5)ncc3c(NC(=O)OC(C)(C)C)c2F)cnc2c1N(C(=O)OC(C)(C)C)CCC2]

A solution of phenyl chloroformate (358 mg, 2.29 mmol) in dichloromethane (7 mL) was added DMAP (69 mg, 0.57 mmol) and tert-butyl 7-[3-amino-8-(tert-butoxycarbonylamino)-7-fluoro-6-isoquinolyl]-8-methyl-3,4-dihydro-2H-1,5-naphthyridine-1-carboxylate (300 mg, 0.57 mmol) in pyridine (4 mL) at 0° C. The reaction was stirred for 2 hours at 0° C. Then tert-butyl 6-amino-2-azaspiro[3.3]heptane-2-carboxylate (608 mg, 2.86 mmol) in dichloromethane (8 mL) was added. The reaction was stirred for 16 hours at 80° C. and then concentrated under vacuum. The residue was purified by flash chromatography on silica gel eluting with dichloromethane/methanol (95/5) to afford tert-butyl 7-[8-(tert-butoxycarbonylamino)-3-[(2-tert-butoxycarbonyl-2-azaspiro[3.3]heptan-6-yl)carbamoylamino]-7-fluoro-6-isoquinolyl]-8-methyl-3,4-dihydro-2H-1,5-naphthyridine-1-carboxylate (400 mg, 0.525 mmol, 91.6% yield) as a yellow solid. LCMS (ESI) [M+H]⁺=762.

Step 2: 1-[8-Amino-7-fluoro-6-(4-methyl-5,6,7,8-tetrahydro-1,5-naphthyridin-3-yl)-3-isoquinolyl]-3-(2-azaspiro[3.3]heptan-6-yl)urea

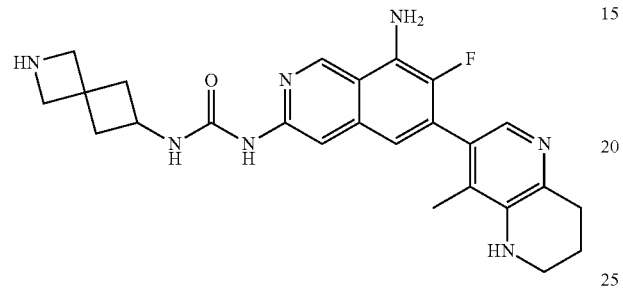

A solution of tert-butyl 7-[8-(tert-butoxycarbonylamino)-3-[(2-tert-butoxycarbonyl-2-azaspiro[3.3]heptan-6-yl)carbamoylamino]-7-fluoro-6-isoquinolyl]-8-methyl-3,4-dihydro-2H-1,5-naphthyridine-1-carboxylate (400 mg, 0.53 mmol) in 2,2,2-trifluoroacetic acid (4 mL) and dichloromethane (10 mL) was stirred at 25° C. for 1 hour. The reaction was concentrated under vacuum to afford 1-[8-amino-7-fluoro-6-(4-methyl-5,6,7,8-tetrahydro-1,5-naphthyridin-3-yl)-3-isoquinolyl]-3-(2-azaspiro[3.3]heptan-6-yl)urea (200 mg, 0.4333 mmol, 82.5% yield). LCMS (ESI) [M+H]⁺=462.

Step 3: 1-(8-amino-7-fluoro-6-(4-methyl-5,6,7,8-tetrahydro-1,5-naphthyridin-3-yl)isoquinolin-3-yl)-3-(2-(2,2-difluoroethyl)-2-azaspiro[3.3]heptan-6-yl)urea

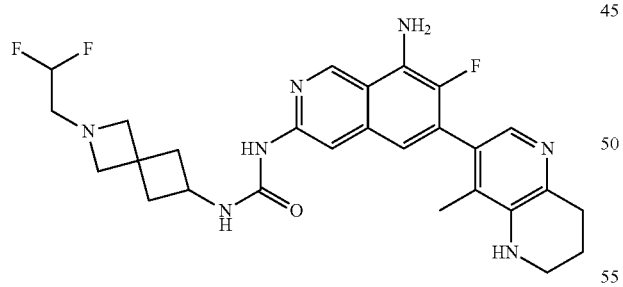

A solution of 1-[8-amino-7-fluoro-6-(4-methyl-5,6,7,8-tetrahydro-1,5-naphthyridin-3-yl)-3-isoquinolyl]-3-(2-azaspiro[3.3]heptan-6-yl)urea (200 mg, 0.43 mmol), 2,2-difluoroethyltrifluoromethanesulfonate (186 mg, 0.87 mmol) and TEA (87.7 mg, 0.87 mmol) in dichloromethane (15 mL) was stirred at 25° C. for 1 hour. The reaction was concentrated under vacuum and purified by Prep-HPLC to afford 1-(8-amino-7-fluoro-6-(4-methyl-5,6,7,8-tetrahydro-1,5-naphthyridin-3-yl)isoquinolin-3-yl)-3-(2-(2,2-difluoroethyl)-2-azaspiro[3.3]heptan-6-yl)urea (40 mg, 0.076 mol, 27.8% yield) as a yellow solid. LCMS (ESI) [M+H]⁺=526, R_T 2.262 min, method=M. ¹H NMR (300 MHz, DMSO-d₆) δ 9.29 (s, 1H), 8.86 (s, 1H), 7.82 (s, 1H), 7.56 (s, 1H), 7.30 (d, J=7.6 Hz, 1H), 6.73 (d, J=6.1 Hz, 1H), 6.17 (s, 2H), 6.14-5.72 (tt, J=4.2 Hz, 54 Hz, 1H), 5.43 (s, 1H), 4.02 (q, J=7.9 Hz, 1H), 3.88-3.39 (m, 4H), 3.21 (s, 2H), 2.91-2.64 (m, 4H), 2.44 (t, J=10.0 Hz, 2H), 2.05-1.89 (m, 4H), 1.87 (s, 3H).

Example 175

1-(8-amino-7-fluoro-6-(4-methyl-5,6,7,8-tetrahydro-1,5-naphthyridin-3-yl)isoquinolin-3-yl)-3-((1r,3r)-3-fluorocyclobutyl)urea (Compound 732a)

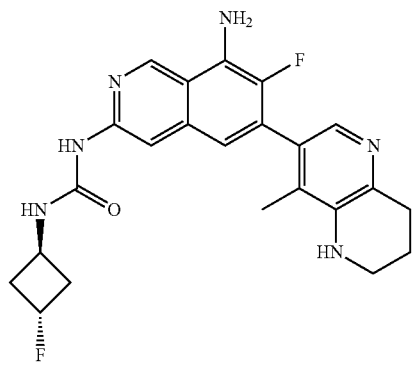 [SMILES: Cc1c(-c2cc3cc(NC(=O)N[C@H]4C[C@H](F)C4)ncc3c(N)c2F)cnc2c1NCCC2]

Step 1: tert-Butyl 7-[8-(tert-butoxycarbonylamino)-7-fluoro-3-[(3-fluorocyclobutyl)carbamoylamino]-6-isoquinolyl]-8-methyl-3,4-dihydro-2H-1,5-naphthyridine-1-carboxylate

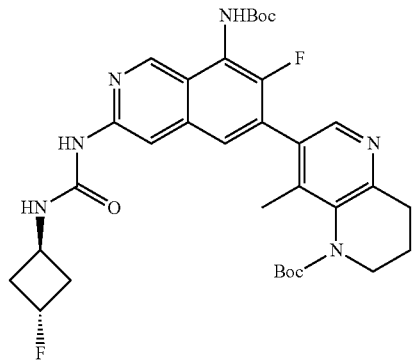 [SMILES: Cc1c(-c2cc3cc(NC(=O)N[C@H]4C[C@H](F)C4)ncc3c(NC(=O)OC(C)(C)C)c2F)cnc2c1N(C(=O)OC(C)(C)C)CCC2]

To a solution of phenyl chloroformate (299 mg, 1.91 mmol) in dichloromethane (3 mL) was added tert-butyl 7-[3-amino-8-(tert-butoxycarbonylamino)-7-fluoro-6-isoquinolyl]-8-methyl-3,4-dihydro-2H-1,5-naphthyridine-1-carboxylate (200 mg, 0.38 mmol) and DMAP (47 mg, 0.39 mmol) in pyridine (4 mL) at 0° C. 3-Fluorocyclobutanamine (204 mg, 2.29 mmol) in dichloromethane (12 mL) was added. The mixture was stirred at 50° C. for 16 hours. The reaction was concentrated under vacuum and purified by flash chromatography on silica gel eluting with ethyl acetate (100%) to afford tert-butyl 7-[8-(tert-butoxycarbonylamino)-7-fluoro-3-[(3-fluorocyclobutyl)carbamoylamino]-6-isoquinolyl]-8-methyl-3,4-dihydro-2H-1,5-naphthyridine-1-carboxylate (200 mg, 0.313 mmol, 82% yield) as a yellow solid. LCMS (ESI) [M+H]⁺=639.

Step 2: 1-(8-Amino-7-fluoro-6-(4-methyl-5,6,7,8-tetrahydro-1,5-naphthyridin-3-yl)isoquinolin-3-yl)-3-((1r,3r)-3-fluorocyclobutyl)urea

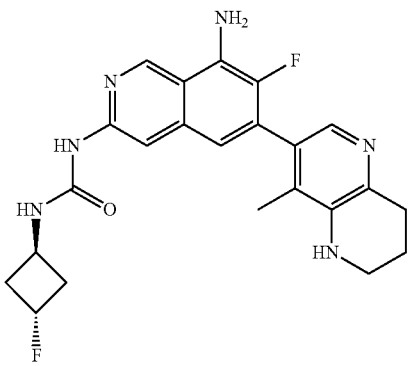

A solution of tert-butyl 7-[8-(tert-butoxycarbonylamino)-7-fluoro-3-[(3-fluorocyclobutyl)carbamoylamino]-6-isoquinolyl]-8-methyl-3,4-dihydro-2H-1,5-naphthyridine-1-carboxylate (120 mg, 0.19 mmol) in TFA (4 mL) and dichloromethane (10 mL) was stirred at 25° C. for 1 hour. The reaction mixture was concentrated under vacuum and purified by Prep-HPLC (Column: X Select CSH Prep C18 OBD Column, 5 μm, 19*150 mm; Mobile Phase A: Water (0.1% FA), Mobile Phase B: ACN; Flow rate: 25 mL/min; Gradient: 10% B to 33% B in 7 min) to afford 1-(8-amino-7-fluoro-6-(4-methyl-5,6,7,8-tetrahydro-1,5-naphthyridin-3-yl)isoquinolin-3-yl)-3-((1r,3r)-3-fluorocyclobutyl)urea (56.2 mg, 0.116 mmol, 61.7% yield) as a yellow solid. LCMS (ESI) [M+H]⁺=439.2, $R_T$ 1.271 min, Method M. ¹H NMR (400 MHz, DMSO-d₆) δ 9.30 (s, 1H), 8.90 (s, 1H), 7.86 (s, 1H), 7.58 (s, 1H), 7.38 (d, J=6.7 Hz, 1H), 6.75 (d, J=6.0 Hz, 1H), 6.18 (s, 2H), 5.48 (s, 2H), 4.35 (dq, J=6.4, 3.1 Hz, 1H), 3.34 (dq, J=6.5, 3.6 Hz, 4H), 2.86 (t, J=6.4 Hz, 2H), 2.44 (s, 2H), 1.93 (s, 2H), 1.88 (d, J=1.5 Hz, 3H).

Example 176

(R)-1-Hydroxypropan-2-yl (8-amino-7-fluoro-6-(8-methyl-2,3-dihydro-1H-pyrido[2,3-b][1,4]oxazin-7-yl)isoquinolin-3-yl)carbamate and (S)-1-Hydroxypropan-2-yl (8-amino-7-fluoro-6-(8-methyl-2,3-dihydro-1H-pyrido[2,3-b][1,4]oxazin-7-yl)isoquinolin-3-yl)carbamate (Compound 530a and Compound 530b)

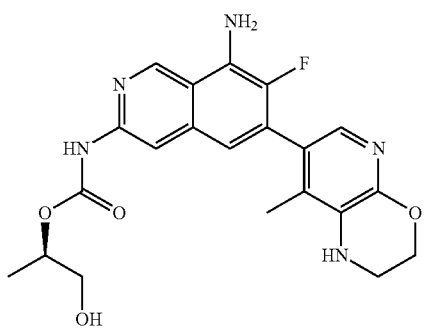

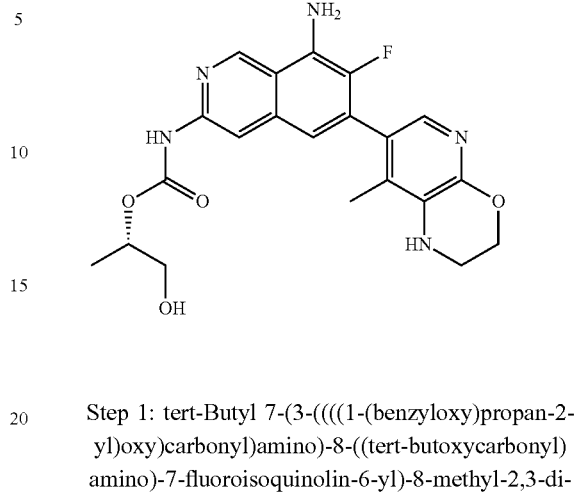

Step 1: tert-Butyl 7-(3-((((1-(benzyloxy)propan-2-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

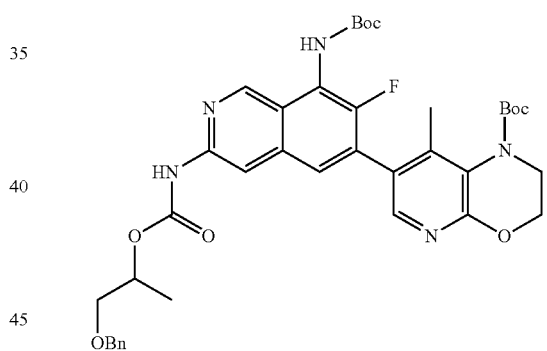

A solution of 1-benzyloxy-2-propanol (126.0 mg, 0.76 mmol), tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (200 mg, 0.38 mmol) and DIEA (246 mg, 0.38 mmol) in dichloromethane (5 mL) was stirred at 0° C. for 1 hour. Then triphosgene (80 mg, 0.27 mmol) was added. The mixture was stirred at 0° C. for 1 hour and concentrated under vacuum. The residue was purified by reversed phase chromatography (C18) with ACN/water (18/82) to afford tert-butyl 7-[3-[(2-benzyloxy-1-methyl-ethoxy)carbonylamino]-8-(tert-butoxycarbonylamino)-7-fluoro-6-isoquinolyl]-8-methyl-2,3-dihydropyrido[2,3-b][1,4]oxazine-1-carboxylate (210 mg, 0.293 mmol, 76.9% yield) as a yellow solid. LCMS (ESI) [M+H]⁺= 718.3.

Step 2: 1-(Benzyloxy)propan-2-yl (8-amino-7-fluoro-6-(8-methyl-2,3-dihydro-1H-pyrido[2,3-b][1,4]oxazin-7-yl)isoquinolin-3-yl)carbamate

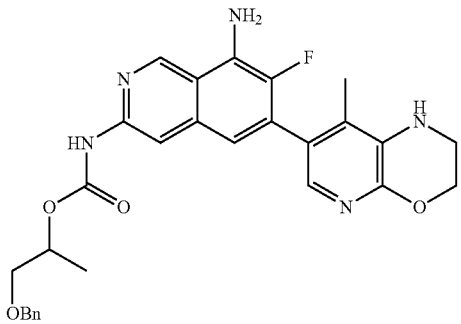 [SMILES: Cc1c(-c2cc3cc(NC(=O)OC(C)COCc4ccccc4)ncc3c(N)c2F)cnc2c1NCCO2]

A solution of tert-butyl 7-[3-[(2-benzyloxy-1-methyl-ethoxy)carbonylamino]-8-(tert-butoxycarbonylamino)-7-fluoro-6-isoquinolyl]-8-methyl-2,3-dihydropyrido[2,3-b][1,4]oxazine-1-carboxylate (200.0 mg, 0.28 mmol) in dichloromethane (5 mL) and TFA (2 mL) was stirred at room temperature for 1 hour. The reaction was concentrated under vacuum and purified by reversed phase chromatography (C18) with ACN/water (20/80) to afford (2-benzyloxy-1-methyl-ethyl) N-[8-amino-7-fluoro-6-(8-methyl-2,3-dihydro-1H-pyrido[2,3-b][1,4]oxazin-7-yl)-3-isoquinolyl]carbamate (130 mg, 0.251 mmol, 90.1% yield) as a yellow solid. LCMS (ESI) [M+H]$^+$=517.2

Step 3: (R)-1-hydroxypropan-2-yl (8-amino-7-fluoro-6-(8-methyl-2,3-dihydro-1H-pyrido[2,3-b][1,4]oxazin-7-yl)isoquinolin-3-yl)carbamate and (S)-1-hydroxypropan-2-yl (8-amino-7-fluoro-6-(8-methyl-2,3-dihydro-1H-pyrido[2,3-b][1,4]oxazin-7-yl)isoquinolin-3-yl)carbamate

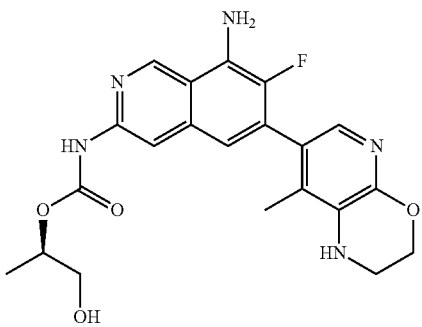

Under hydrogen (1 atm), a mixture of (2-benzyloxy-1-methyl-ethyl) N-[8-amino-7-fluoro-6-(8-methyl-2,3-dihydro-1H-pyrido[2,3-b][1,4]oxazin-7-yl)-3-isoquinolyl]carbamate (140.0 mg, 0.27 mmol) and Pd/C (80 mg, 0.27 mmol) in methyl alcohol (2 mL) was stirred at room temperature for 3 hours. After filtration, the filtrate was concentrated under vacuum and purified by Prep-HPLC (Colum: X Select CSH PreC18 OBD Column, 5 µm, 19×150 nm; Mobile phase A: water (0.1% FA), Mobile phase B: ACN; Flow rate 25 ML/min; Gradient: 6% B to 36% to in 7 min) to give the racemic mixture of products. The racemic mixture was separated by chiral-HPLC to afford two enantiomers. Absolute stereochemistry was arbitrarily assigned.

Enantiomer 1 (Compound 530a) (4.4 mg, 0.0103 mmol, 3.8% yield). R$_T$ 1.208 min (CHIRALPAK IG-3 0.46*5 cm; 3 µm; MTBE (0.1% DEA):EtOH=50:50, 1 mL/min). LCMS (ESI) [M+H]$^+$=428.2, R$_T$ 2.081 min, Method M. $^1$H NMR (300 MHz, DMSO-d$_6$) δ 9.94 (s, 1H), 9.33 (s, 1H), 7.98 (s, 1H), 7.33 (s, 1H), 6.84-6.80 (d, J=6.2 Hz, 1H), 6.22 (s, 2H), 5.69 (s, 1H), 4.95-4.78 (m, 2H), 4.32-4.26 (m, 2H), 3.53-3.42 (m, 4H), 1.92 (s, 3H), 1.26-1.18 (d, J=6 Hz, 3H).

Enantiomer 2 (Compound 530b) (4.5 mg, 0.0105 mmol, 3.9% yield). R$_T$ 2.402 min (CHIRALPAK IG-3 0.46*5 cm; 3 µm; MTBE (0.1% DEA): EtOH=50:50, 1 mL/min). LCMS (ESI) [M+H]$^+$=428.2, R$_T$ 2.081 min, Method M. $^1$H NMR (300 MHz, DMSO-d$_6$) δ 9.94 (s, 1H), 9.33 (s, 1H), 7.98 (s, 1H), 7.33 (s, 1H), 6.84-6.80 (d, J=6.2 Hz, 1H), 6.22 (s, 2H), 5.69 (s, 1H), 4.95-4.78 (m, 2H), 4.32-4.26 (m, 2H), 3.53-3.42 (m, 4H), 1.92 (s, 3H), 1.26-1.18 (d, J=6 Hz, 3H).

Example 177

(R)-1-(8-Amino-7-fluoro-6-(4-methyl-5,6,7,8-tetrahydro-1,5-naphthyridin-3-yl)isoquinolin-3-yl)-3-(tetrahydrofuran-3-yl)urea (Compound 719a)

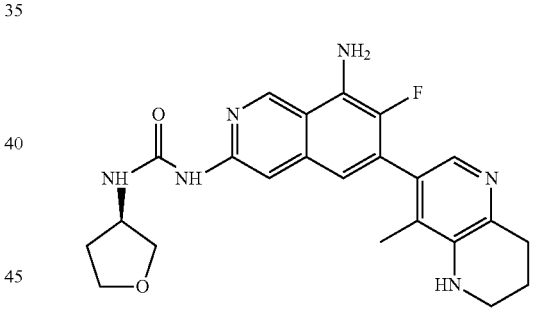

Step 1: tert-Butyl (R)-7-(8-((tert-butoxycarbonyl)amino)-7-fluoro-3-(3-(tetrahydrofuran-3-yl)ureido)isoquin-olin-6-yl)-8-methyl-3,4-dihydro-1,5-naphthyridine-1(2H)-carboxylate

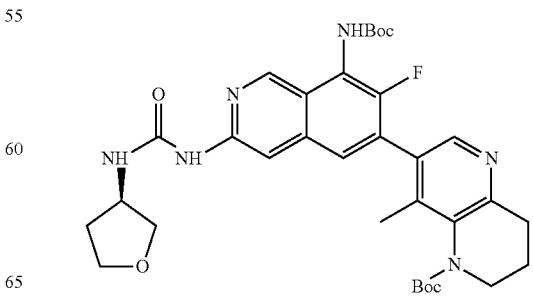

To a solution of phenyl chloroformate (149.5 mg, 0.95 mmol) in dichloromethane (3 mL) was added the solution of tetrahydro-3-furanylamine (249.6 mg, 2.87 mmol) and 4-dimethylaminopyridine (23.3 mg, 0.19 mmol) in pyridine (1 mL) at 0° C. The mixture was stirred at room temperature for 1 hour. Then a solution of tetrahydro-3-furanylamine (249.6 mg, 2.87 mmol) in dichloromethane (3 mL) was added and the mixture was stirred at 60° C. for 2 hours. The reaction was quenched with water and extracted with dichloromethane. The organic layers were combined and concentrated under vacuum. The residue was purified by flash chromatography on silica gel eluting with dichloromethane/methanol (10/1) to afford tert-butyl 7-[8-(tert-butoxycarbonylamino)-7-fluoro-3-(tetrahydrofuran-3-ylcarbamoylamino)-6-isoquinolyl]-8-methyl-3,4-dihydro-2H-1,5-naphthyridine-1-carboxylate (90 mg, 0.141 mmol, 74% yield) as a yellow solid. LCMS (ESI) [M+H]$^+$=637.

Step 2: (R)-1-(8-Amino-7-fluoro-6-(4-methyl-5,6,7,8-tetrahydro-1,5-naphthyridin-3-yl)isoquinolin-3-yl)-3-(tetrahydrofuran-3-yl)urea

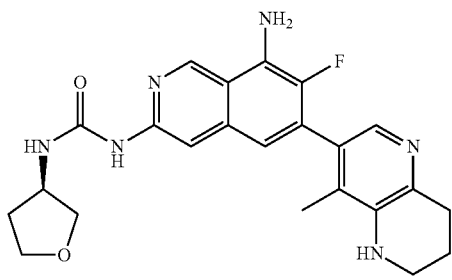 [SMILES: Cc1c(-c2cc3cc(NC(=O)N[C@@H]4CCOC4)ncc3c(N)c2F)cnc2c1NCCC2]

To a solution of tert-butyl 7-[8-(tert-butoxycarbonylamino)-7-fluoro-3-[[(3S)-tetrahydrofuran-3-yl]carbamoylamino]-6-isoquinolyl]-8-methyl-3,4-dihydro-2H-1,5-naphthyridine-1-carboxylate (90.0 mg, 0.14 mmol) in dichloromethane (10 mL) was added trifluoroacetic acid (3.0 mL). The mixture was stirred at room temperature for 2 hours. The reaction was concentrated under vacuum, re-dissolved in dichloromethane and adjusted to pH 8 with triethylamine. The mixture was concentrated under reduced pressure and purified by Prep-HPLC (Column: X Bridge Shield RP18 OBD Column 30*150 mm, 5 μm; Mobile Phase A: Water (10 mmol/L NH$_4$HCO$_3$), Mobile Phase B: ACN; Flow rate: 60 mL/min; Gradient: 18% B to 48% B in 8 min; 2) to afford 1-[8-amino-7-fluoro-6-(4-methyl-5,6,7,8-tetrahydro-1,5-naphthyridin-3-yl)-3-isoquinolyl]-3-[(3S)-tetrahydrofuran-3-yl]urea (38 mg, 0.0871 mmol, 61.6% yield) as a light yellow solid. LCMS(ESI) [M+H]$^+$=437.3, R$_T$ 1.876 min., Method L; $^1$H NMR $^1$H NMR (300 MHz, DMSO-d$_6$) δ 9.29 (s, 1H), 8.86 (s, 1H), 7.85 (s, 1H), 7.56 (s, 1H), 7.35 (d, J=6.8 Hz, 1H), 6.74 (d, J=6.1 Hz, 1H), 6.17 (s, 2H), 5.42 (d, J=2.7 Hz, 1H), 4.23-4.26 (m, 1H), 3.88-3.65 (m, 3H), 3.52 (dd, J=8.9, 3.4 Hz, 1H), 3.29 (m, 2H), 2.84 (t, J=6.4 Hz, 2H), 2.14-2.17 (m, 1H), 1.96-1.83 (m, 6H).

Example 178

1-(8-Amino-7-fluoro-6-(8-methyl-2,3-dihydro-1H-pyrido[2,3-b][1,4]oxazin-7-yl)isoquinolin-3-yl)-3-((1S,2R)-2-methoxycyclopentyl)urea and 1-(8-Amino-7-fluoro-6-(8-methyl-2,3-dihydro-1H-pyrido[2,3-b][1,4]oxazin-7-yl)isoquinolin-3-yl)-3-((1R,2S)-2-methoxycyclopentyl)urea (Compound 729a and Compound 729b)

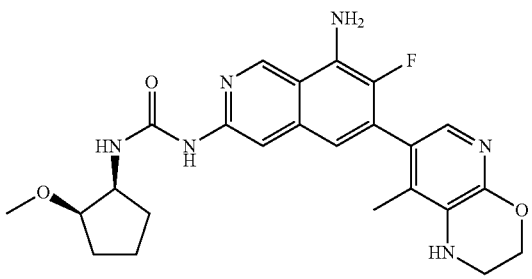

Step 1: tert-Butyl 7-(8-((tert-butoxycarbonyl)amino)-7-fluoro-3-(3-(2-methoxycyclopentyl)ureido)isoquinolin-6-yl)-8-methyl-2,3-dihydro-1H-pyrido[2,3-b][1,4]oxazine-1-carboxylate

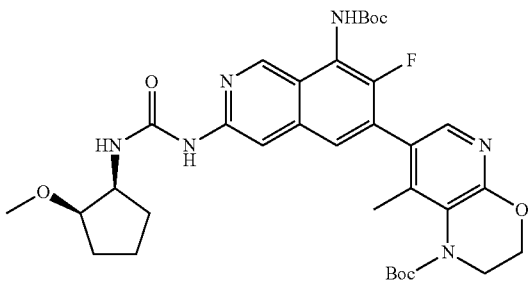 [SMILES: CO[C@@H]1CCC[C@@H]1NC(=O)Nc1cc2cc(-c3cnc4c(c3C)N(C(=O)OC(C)(C)C)CCO4)c(F)c(NC(=O)OC(C)(C)C)c2cn1]

To a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (150.0 mg, 0.23 mmol) and 4-dimethylaminopyridine (28.5 mg, 0.23 mmol) in dichloromethane (10 mL) was added 2-methoxycyclopentanamine (54.0 mg, 0.47 mmol) at room temperature. The reaction mixture was stirred at 55° C. for 5 hours and then concentrated under vacuum. The residue was purified by flash chromatography on silica gel eluting with dichloromethane/methanol (15:1) to afford tert-butyl 7-[8-(tert-butoxycarbonylamino)-7-fluoro-3-[(2-methoxycyclopentyl)carbamoylamino]-6-isoquinolyl]-8-methyl-2,3-dihydropyrido[2,3-b]

[1,4]oxazine-1-carboxylate (150 mg, 0.21 mmol, 90.1% yield) as a yellow solid. LCMS (ESI) [M+H]+=667.1.

Step 2: 1-(8-Amino-7-fluoro-6-(8-methyl-2,3-dihydro-1H-pyrido[2,3-b][1,4]oxazin-7-yl)isoquinolin-3-yl)-3-((1S,2R)-2-methoxycyclopentyl)urea and 1-(8-Amino-7-fluoro-6-(8-methyl-2,3-dihydro-1H-pyrido[2,3-b][1,4]oxazin-7-yl)isoquinolin-3-yl)-3-((1R,2S)-2-methoxycyclopentyl)urea

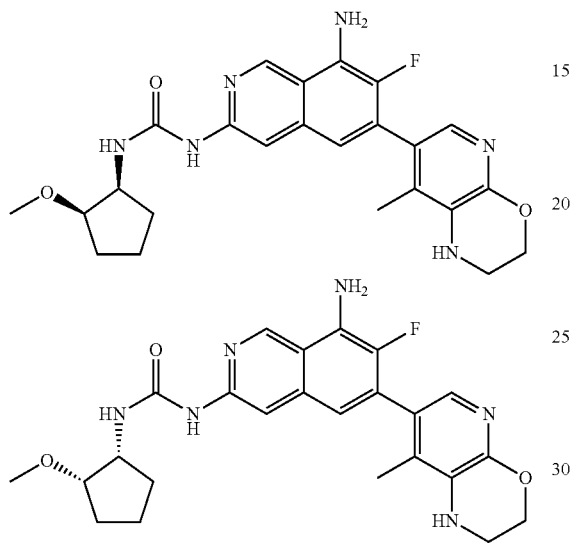

To a solution of tert-butyl 7-[8-(tert-butoxycarbonylamino)-7-fluoro-3-[(2-methoxycyclopentyl)carbamoylamino]-6-isoquinolyl]-8-methyl-2,3-dihydropyrido[2,3-b][1,4]oxazine-1-carboxylate (150.0 mg, 0.21 mmol) in dichloromethane (15 mL) was added trifluoroacetic acid (5.6 mL, 72.69 mmol). The reaction was stirred at room temperature for 1 hour and then concentrated under vacuum. The crude product was purified by Prep-HPLC (Column: X Bridge Prep OBD C18 Column 30×150 mm 5 μm; Mobile Phase A: Water (10 mmol/L NH4HCO3), Mobile Phase B: ACN; Flow rate: 60 mL/min; Gradient: 22% B to 40% B in 7 min) to afford the racemic product. The racemic product was separated by chiral-Prep-HPLC to afford two enantiomers. Relative stereochemistry are as drawn. Absolute stereochemistry was arbitrarily assigned.

Enantiomer 1: (Compound 729a) (19.6 mg, 0.0417 mmol, 19.9% yield) as a yellow. $R_T$ 2.097 min (Column: CHIRALPAK IE, 2*25 cm, 5 μm; Mobile phase: (Hex:DCM=3:1)(0.1% DEA):EtOH=50:50, 1 ml/min). LCMS (ESI) [M+H]= 467.2, $R_T$ 1.183 min, Method J; $^1$H NMR (400 MHz, DMSO-$d_6$) δ 9.28 (s, 1H), 9.09 (s, 1H), 7.81 (s, 1H), 7.35 (s, 1H), 7.32 (s, 1H), 6.73 (d, J=6.0 Hz, 1H), 6.15 (s, 2H), 5.67 (s, 1H), 4.28 (t, J=4.0 Hz, 2H), 4.01-3.97 (m, 1H), 3.65-3.62 (m, 1H), 3.37 (s, 2H), 3.28 (s, 3H), 1.92 (s, 3H), 1.92-1.85 (m, 1H), 1.76-1.65 (m, 3H), 1.56-1.42 (m, 2H).

Enantiomer 2: (Compound 729b) (20.2 mg, 0.0431 mmol, 20.5% yield) as a yellow solid. $R_T$ 2.802 min (Column: CHIRALPAK IE, 2*25 cm, 5 μm; Mobile phase: (Hex:DCM=3:1)(0.1% DEA):EtOH=50:50, 1 ml/min). LCMS (ESI) [M+H]+=467.2, $R_T$ 1.183 min, Method J; $^1$H NMR (400 MHz, DMSO-$d_6$) δ 9.28 (s, 1H), 9.09 (s, 1H), 7.81 (s, 1H), 7.35 (s, 1H), 7.32 (s, 1H), 6.73 (d, J=6.0 Hz, 1H), 6.15 (s, 2H), 5.67 (s, 1H), 4.28 (t, J=4.0 Hz, 2H), 4.01-3.97 (m, 1H), 3.65-3.3.62 (m, 1H), 3.37 (s, 2H), 3.28 (s, 3H), 1.92 (s, 3H), 1.92-1.85 (m, 1H), 1.76-1.65 (m, 3H), 1.56-1.42 (m, 2H).

Example 179

1-[8-Amino-7-fluoro-6-(8-methyl-2,3-dihydro-1H-pyrido[2,3-b][1,4]oxazin-7-yl)-3-isoquinolyl]-3-[(1R,2S)-2-fluorocyclopentyl]urea and 1-[8-Amino-7-fluoro-6-(8-methyl-2,3-dihydro-1H-pyrido[2,3-b][1,4]oxazin-7-yl)-3-isoquinolyl]-3-[(1S,2R)-2-fluorocyclopentyl]urea (Compound 727a and Compound 727b)

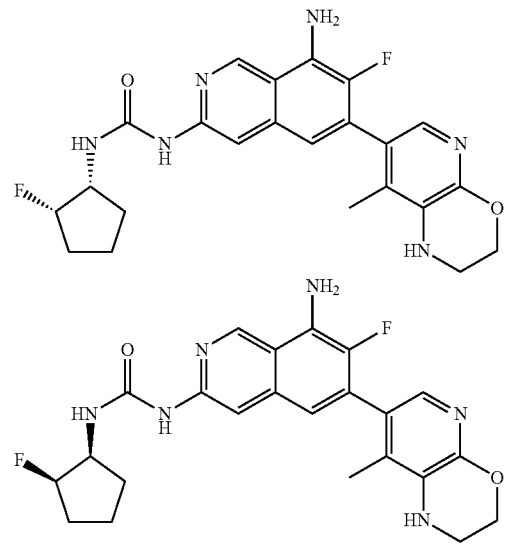

Step 1: tert-butyl 7-[8-(tert-butoxycarbonylamino)-7-fluoro-3-[(2-fluorocyclopentyl)carbamoylamino]-6-isoquinolyl]-8-methyl-2,3-dihydropyrido[2,3-b][1,4]oxazine-1-carboxylate

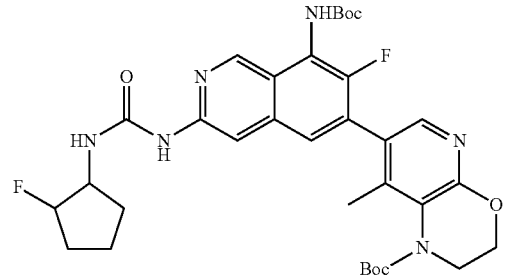 [SMILES: Cc1c(-c2cc3cc(NC(=O)NC4CCCC4F)ncc3c(NC(=O)OC(C)(C)C)c2F)cnc2c1N(C(=O)OC(C)(C)C)CCO2]

To a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300.0 mg, 0.46 mmol) and DMAP (56.7 mg, 0.46 mmol) in dichloromethane (20 mL) was added a solution of 2-fluorocyclopentanamine hydrochloride (194.6 mg, 1.39 mmol) in dichloromethane at room temperature. Then the reaction was stirred at 55° C. for 6 hours. The reaction mixture was concentrated under vacuum and purified by flash chromatography on silica gel eluting with dichloromethane/methanol (10/1) to afford tert-butyl 7-[8-(tert-butoxycarbonylamino)-7-fluoro-3-[(2-fluorocyclopentyl)carbamoylamino]-6-isoquinolyl]-8-methyl-2,3-dihydropyrido[2,3-b][1,4]oxazine-1-carboxylate (290 mg, 0.443 mmol, 95.3% yield) as a yellow solid. LCMS (ESI) [M+H]⁺= 655.3.

Step 2: 148-Amino-7-fluoro-6-(8-methyl-2,3-dihydro-1H-pyrido[2,3-b][1,4]oxazin-7-yl)-3-isoquinolyl]-3-[(1R,2S)-2-fluorocyclopentyl]urea and 1-[8-Amino-7-fluoro-6-(8-methyl-2,3-dihydro-1H-pyrido[2,3-b][1,4]oxazin-7-yl)-3-isoquinolyl]-3-[(1S,2R)-2-fluorocyclopentyl]urea

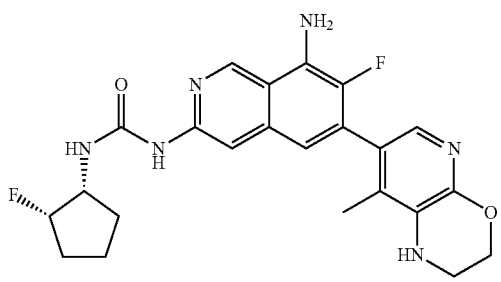

To a solution of tert-butyl7-[8-(tert-butoxycarbonylamino)-7-fluoro-3-[(2-fluorocyclopentyl)carbamoylamino]-6-isoquinolyl]-8-methyl-2,3-dihydropyrido[2,3-b][1,4]oxazine-1-carboxylate (450.0 mg, 0.69 mmol) in dichloromethane (10 mL) was added 2,2,2-trifluoroacetic acid (3 mL) at 0° C. The resulting solution was stirred at room temperature for 3 hours. The mixture was concentrated under vacuum, re-dissolved with dichloromethane and adjusted to pH 8 with triethylamine. The mixture was concentrated under vacuum and purified by Prep-HPLC (Column:)(Bridge Prep C18 OBD Column 19×150 mm 5 µm; Mobile Phase A: Water (10 mmol/L NH₄HCO₃), Mobile Phase B: MeOH; Flow rate: 25 mL/min; Gradient: 41% B to 54% B in 11 min) to afford the racemic product. The racemic product was separated by chiral-HPLC to afford two enantiomers. Relative stereochemistry are as drawn. Absolute stereochemistry was arbitrarily assigned.

Enantiomer 1: (Compound 727a) (71.5 mg, 0.1573 mmol, 22.9% yield). R$_T$ 2.828 min (CHIRALPAK IG-3 0.46*5 cm; 3 µm. Mobile phase: (Hex:DCM=3:1)(0.1% DEA): EtOH=50:50). LCMS(ESI) [M+H]⁺=455.2, R$_T$ 2.100 min; Method K. ¹H NMR (300 MHz, DMSO-d₆) δ 9.27 (s, 1H), 9.04 (s, 1H), 7.81 (s, 1H), 7.40 (d, J=8.0 Hz, 1H), 7.31 (s, 1H), 6.73 (d, J=6.2 Hz, 1H), 6.15 (s, 2H), 5.66 (s, 1H), 5.04 (d, J=3.9 Hz, 1H), 4.27 (t, J=4.5 Hz, 2H), 4.01 (s, 1H), 3.31 (s, 2H), 1.75-1.96 (m, 7H), 1.53-1.72 (m, 2H).

Enantiomer 2: (Compound 727b) (74.2 mg, 0.163 mmol, 23.8% yield). R$_T$ 4.162 min (CHIRALPAK IG-3 0.46*5 cm; 3 µm. Mobile phase: (Hex:DCM=3:1)(0.1% DEA): EtOH=50:50). LCMS(ESI): [M+H]⁺=455.2, R$_T$ 2.100 min; Method K. ¹H NMR (300 MHz, DMSO-d₆) δ 9.27 (s, 1H), 9.04 (s, 1H), 7.81 (s, 1H), 7.40 (d, J=8.0 Hz, 1H), 7.31 (s, 1H), 6.73 (d, J=6.2 Hz, 1H), 6.15 (s, 2H), 5.66 (s, 1H), 5.04 (d, J=3.9 Hz, 1H), 4.27 (t, J=4.5 Hz, 2H), 4.01 (s, 1H), 3.31 (s, 2H), 1.75-1.96 (m, 7H), 1.53-1.72 (m, 2H).

Example 180

1-((1R,2S)-2-fluorocyclopropane-1-carbonyl)azetidin-3-yl (8-amino-7-fluoro-6-(4-methyl-5,6,7,8-tetrahydro-1,5-naphthyridin-3-yl)isoquinolin-3-yl)carbamate and 14(1S,2R)-2-fluorocyclopropane-1-carbonyl)azetidin-3-yl (8-amino-7-fluoro-6-(4-methyl-5,6,7,8-tetrahydro-1,5-naphthyridin-3-yl)isoquinolin-3-yl)carbamate (Compound 531a and Compound 531b)

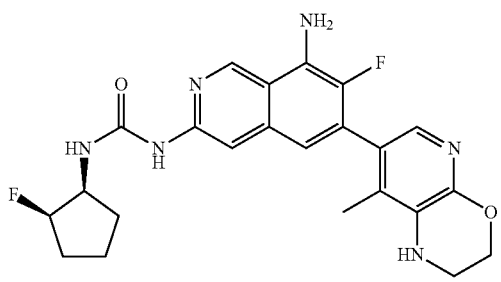

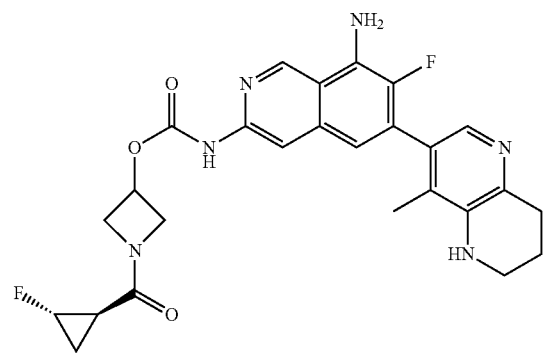

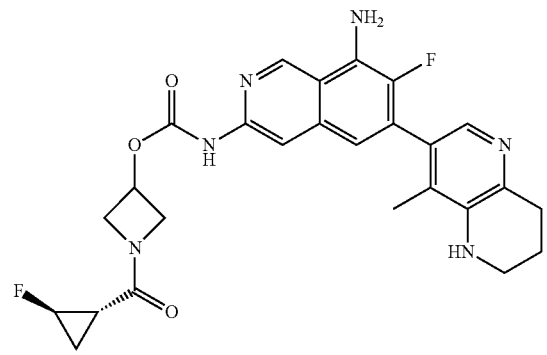

To a solution of azetidin-3-yl N-[8-amino-7-fluoro-6-(4-methyl-5,6,7,8-tetrahydro-1,5-naphthyridin-3-yl)-3-isoquinolyl]carbamate (100 mg, 0.24 mmol) and (±)-trans-2-fluorocyclopropanecarboxylic acid (35 mg, 0.34 mmol) in N,N-dimethylformamide (5 mL) was added HATU (100 mg, 0.26 mmol) and DIEA (100 mg, 0.78 mmol) at room temperature. The resulting mixture was stirred for 2 h at 25° C. and then concentrated under vacuum. The residue was purified by Prep-HPLC (Column: XSelect CSH Prep C18 OBD Column, 5 μm, 19*150 mm; Mobile Phase A: Water (0.1% FA), Mobile Phase B: ACN; Flow rate: 25 mL/min; Gradient: 5% B to 29% B in 8 min; 254/220 nm; Rt: 7.83 min) and chiral-HPLC to afford two enantiomers. Relative stereochemistry as drawn. Absolute stereochemistry was arbitrarily assigned.

Enantiomer 1 (Compound 531a) (21.9 mg, 0.0431 mmol, 18.2% yield). $R_T$ 2.539 min (ChIRALPAK IG-3, 0.46*5 cm, 3 μm; MTBE (0.1% DEA):MeOH=70:30 in 5 min; 1 mL/min). LCMS (ESI) $[M+H]^+$=509.3, $R_T$ 0.91 min., Method K; $^1$H NMR (400 MHz, DMSO-$d_6$) δ 10.40 (s, 1H), 9.36 (s, 1H), 7.97 (s, 1H), 7.56 (s, 1H), 6.84 (d, J=6.1 Hz, 1H), 6.24 (s, 2H), 5.43 (s, 1H), 5.24 (dd, J=7.2, 3.4 Hz, 1H), 4.85-4.62 (m, 2H), 4.31-4.18 (m, 2H), 3.84 (td, J=10.8, 4.0 Hz, 1H), 3.38 (t, J=6.3 Hz, 2H), 2.84 (t, J=6.3 Hz, 2H), 2.17 (dt, J=18.0, 8.8 Hz, 1H), 1.92 (s, 2H), 1.86 (d, J=1.5 Hz, 3H), 1.41 (ddd, J=12.8, 6.6, 2.7 Hz, 1H), 1.11 (ddd, J=12.8, 6.6, 2.7 Hz, 1H).

Enantiomer 2 (Compound 531b) (20.9 mg, 0.0411 mmol, 17.4% yield). $R_T$ 3.613 min (ChIRALPAK IG-3, 46*5 cm, 3 μm; MTBE (0.1% DEA):MeOH=70:30 in 5 min; 1 mL/min). LCMS (ESI) $[M+H]^+$=509.3, $R_T$ 0.911 min., Method K; $^1$H NMR (400 MHz, DMSO-$d_6$) δ 10.40 (s, 1H), 9.36 (s, 1H), 7.97 (s, 1H), 7.56 (s, 1H), 6.84 (d, J=6.1 Hz, 1H), 6.24 (s, 2H), 5.43 (s, 1H), 5.24 (dd, J=7.2, 3.4 Hz, 1H), 4.85-4.62 (m, 2H), 4.31-4.18 (m, 2H), 3.84 (td, J=10.8, 4.0 Hz, 1H), 3.38 (t, J=6.3 Hz, 2H), 2.84 (t, J=6.3 Hz, 2H), 2.17 (dt, J=18.0, 8.8 Hz, 1H), 1.92 (s, 2H), 1.86 (d, J=1.5 Hz, 3H), 1.41 (ddd, J=12.8, 6.6, 2.7 Hz, 1H), 1.11 (ddd, J=12.8, 6.6, 2.7 Hz, 1H).

Example 181

2-(2,2-Difluoroethyl)-2-azaspiro[3.3]heptan-6-yl (8-amino-7-fluoro-6-(4-methyl-5,6,7,8-tetrahydro-1,5-naphthyridin-3-yl)isoquinolin-3-yl)carbamate (Compound 532)

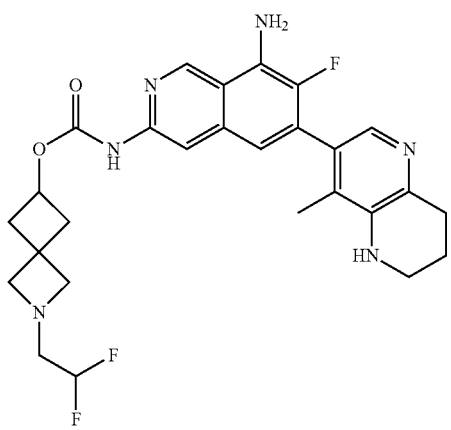 [SMILES: Cc1c(-c2cc3cc(NC(=O)OC4CC5(C4)CN(CC(F)F)C5)ncc3c(N)c2F)cnc2c1NCCC2]

Step 1: tert-Butyl-7-[8-(tert-butoxycarbonylamino)-3-[(2-tert-butoxycarbonyl-2-azaspiro[3.3]heptan-6-yl)oxycarbonylamino]-7-fluoro-6-isoquinolyl]-8-methyl-3,4-dihydro-2H-1,5-naphthyridine-1-carboxylate

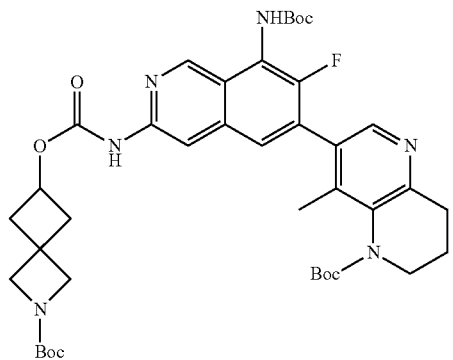 [SMILES: Cc1c(-c2cc3cc(NC(=O)OC4CC5(C4)CN(C(=O)OC(C)(C)C)C5)ncc3c(NC(=O)OC(C)(C)C)c2F)cnc2c1N(C(=O)OC(C)(C)C)CCC2]

Under nitrogen, a solution of tert-butyl-7-[3-amino-8-(tert-butoxycarbonylamino)-7-fluoro-6-isoquinolyl]-8-methyl-3,4-dihydro-2H-1,5-naphthyridine-1-carboxylate (200 mg, 0.38 mmol), tert-butyl 6-hydroxy-2-azaspiro[3.3]heptane-2-carboxylate (160 mg, 0.75 mmol) and N,N-diisopropylethylamine (490 mg, 3.8 mmol) in dichloromethane (12 mL) was stirred at 0° C. Then a solution of triphosgene (110 mg, 0.37 mmol) in dichloromethane (2 mL) was added dropwise. The reaction was stirred at 0° C. for 2 hours. The resulting solution was diluted with dichloromethane and washed with water. The organic layer was dried over anhydrous sodium sulfate, concentrated under vacuum and purified by flash chromatography on silica gel eluting with dichloromethane/methanol (19/1) to afford tert-butyl-7-[8-(tert-butoxycarbonylamino)-3-[(2-tert-butoxycarbonyl-2-azaspiro[3.3]heptan-6-yl)oxycarbonylamino]-7-fluoro-6-isoquinolyl]-8-methyl-3,4-dihydro-2H-1,5-naphthyridine-1-carboxylate (250 mg, 0.302 mmol, 79% yield) as a brown solid. LCMS (ESI) $[M+H]^+$=763.

Step 2: 2-Azaspiro-[3.3]heptan-6-yl-N-[8-amino-7-fluoro-6-(4-methyl-5,6,7,8-tetrahydro-1,5-naphthyridin-3-yl)-3-isoquinolyl]carbamate

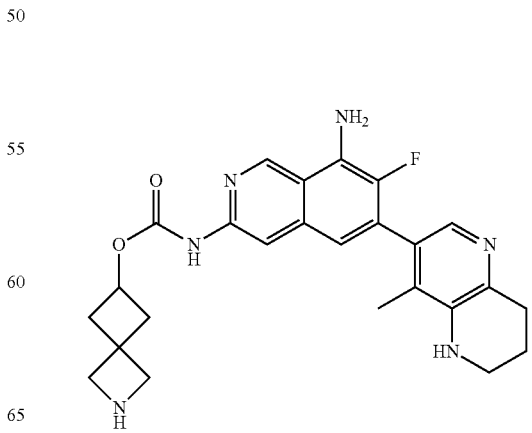

A solution of tert-butyl 7-[8-(tert-butoxycarbonylamino)-3-[(2-tert-butoxycarbonyl-2-azaspiro[3.3]heptan-6-yl)oxycarbonylamino]-7-fluoro-6-isoquinolyl]-8-methyl-3,4-dihydro-2H-1,5-naphthyridine-1-carboxylate (250 mg, 0.33 mmol) in 2 N HCl in 1,4-dioxane (20 mL) was stirred at room temperature for 1 hours. The reaction mixture was concentrated under vacuum. The crude product would be directly used in the next step without purification.

Step 3: [2-(2,2-Difluoroethyl)-2-azaspiro[3.3]heptan-6-yl]N-[8-amino-7-fluoro-6-(4-methyl-5,6,7,8-tetrahydro-1,5-naphthyridin-3-yl)-3-isoquinolyl] carbamate

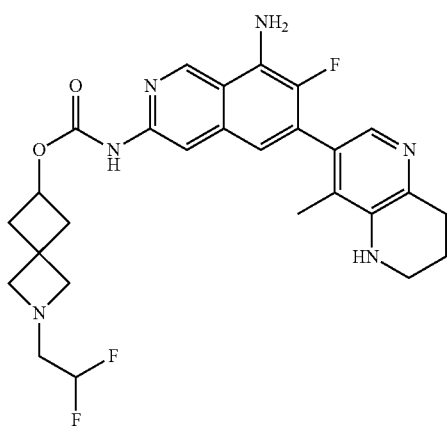 [SMILES: Cc1c(-c2cc3cc(NC(=O)OC4CC5(C4)CN(CC(F)F)C5)ncc3c(N)c2F)cnc2c1NCCC2]

A solution of 2-azaspiro[3.3]heptan-6-yl N-[8-amino-7-fluoro-6-(4-methyl-5,6,7,8-tetrahydro-1,5-naphthyridin-3-yl)-3-isoquinolyl]carbamate (200 mg, 0.43 mmol) and triethylamine (2.01 mL, 14.46 mmol) in tetrahydrofuran (20 mL) was stirred at room temperature for 5 mins. Then 2,2-difluoroethyltrifluoromethanesulfonate (90 mg, 0.42 mmol) was added. The mixture was stirred at room temperature for 2 hours. The mixture was then concentrated under vacuum and purified by reverse phase chromatography (acetonitrile 5-50/water) to afford 2-(2,2-difluoroethyl)-2-azaspiro[3.3]heptan-6-yl (8-amino-7-fluoro-6-(4-methyl-5,6,7,8-tetrahydro-1,5-naphthyridin-3-yl)isoquinolin-3-yl) carbamate (19.5 mg, 0.0332 mmol, 7.7% yield) as a light yellow solid. LCMS(ESI) [M+H]$^+$=527.2, R$_T$ 0.876 min; Method L; $^1$H NMR (400 MHz, DMSO-d$_6$) δ 10.09 (s, 1H), 9.34 (s, 1H), 7.96 (s, 1H), 7.57 (s, 1H), 6.83 (d, J=6.1 Hz, 1H), 6.23 (s, 2H), 6.08-5.77 (m, 1H), 5.44 (s, 1H), 4.98-4.76 (m, 1H), 3.32-3.14 (m, 6H), 2.90 (t, J=10.3, 2H), 2.85-2.65 (m, 2H), 2.61 (s, 2H), 2.25-2.10 (m, 2H), 1.98-1.82 (m, 2H), 1.86 (s, 3H).

Example 182

1-(8-Amino-6-(5-amino-4-methylpyridin-3-yl)-7-fluoroisoquinolin-3-yl)-3-cyclopentylurea (Compound 749)

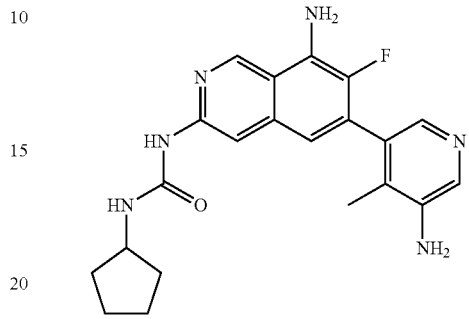

Step 1: tert-Butyl N-tert-butoxycarbonyl-N-[5-[8-chloro-3-(cyclopentylcarbamoylamino)-7-fluoro-6-isoquinolyl]-4-methyl-3-pyridyl]carbamate

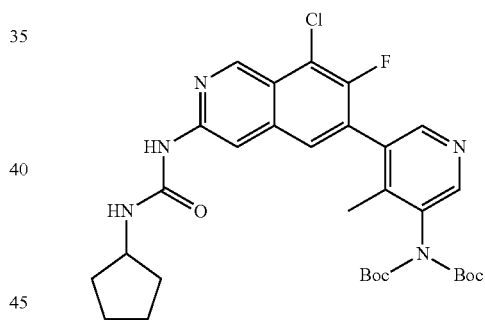

A solution of phenyl chloroformate (933.8 mg, 5.96 mmol) in dichloromethane (20 mL) was stirred at 0° C. for 5 min. Then tert-butyl N-[5-(3-amino-8-chloro-7-fluoro-6-isoquinolyl)-4-methyl-3-pyridyl]-N-tert-butoxycarbonyl-carbamate (600.0 mg, 1.19 mmol) and 4-dimethylaminopyridine (729.4 mg, 5.97 mmol) in pyridine (20 mL) was added. The reaction was stirred at 0° C. for 1 hour at room temperature. Then cyclopentylamine (1.01 g, 11.93 mmol) was added to the reaction mixture. The resulting solution was stirred at room temperature for 12 hours at 55° C. The reaction was quenched with water and extracted with dichloromethane. The organic layers were combined, dried over anhydrous sodium sulfate and concentrated under vacuum. The residue was purified by flash chromatography on silica gel eluting with dichloromethane/methanol (50/1) to afford tert-butyl N-tert-butoxycarbonyl-N-[5-[8-chloro-3-(cyclopentylcarbamoylamino)-7-fluoro-6-isoquinolyl]-4-methyl-3-pyridyl]carbamate (600 mg, 0.84 mmol, 70.4% yield) as a yellow solid. LCMS (ESI) [M+H]$^+$=614.2.

Step 2: tert-Butyl (tert-butoxycarbonyl)(5-(8-((tert-butoxycarbonyl)amino)-3-(3-cyclopentylureido)-7-fluoroisoquinolin-6-yl)-4-methylpyridin-3-yl)carbamate

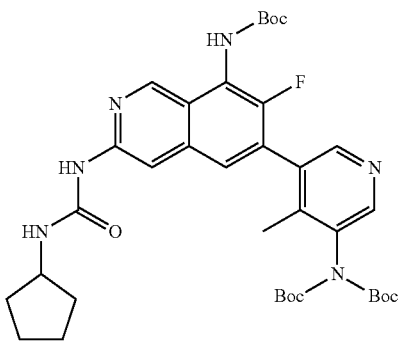 [SMILES: Cc1c(-c2cc3cc(NC(=O)NC4CCCC4)ncc3c(NC(=O)OC(C)(C)C)c2F)cncc1N(C(=O)OC(C)(C)C)C(=O)OC(C)(C)C]

Under nitrogen, to a mixture of tert-butyl N-tert-butoxycarbonyl-N-[5-[8-chloro-3-(cyclopentylcarbamoylamino)-7-fluoro-6-isoquinolyl]-4-methyl-3-pyridyl]carbamate (600.0 mg, 0.98 mmol), tert-butyl carbamate (2.30 g, 19.62 mmol), tris(dibenzylideneacetone)dipalladium chloroform adduct (204.0 mg, 0.20 mmol) and 2-(dicyclohexylphosphino)3,6-dimethoxy-2',4',6'-triisopropyl-1,1'-biphenyl (210.0 mg, 0.39 mmol) in 1,4-dioxane (45 ml) was added cesium carbonate (966.0 mg, 2.95 mmol) at room temperature. The resulting mixture was stirred at 90° C. for 2 hours and then concentrated under vacuum. The residue was purified by flash chromatography on silica gel eluting with dichloromethane/methanol (10/1) to afford tert-butyl N-tert-butoxycarbonyl-N-[5-[8-(tert-butoxycarbonylamino)-3-(cyclopentylcarbamoylamino)-7-fluoro-6-isoquinolyl]-4-methyl-3-pyridyl]carbamate (800 mg, 0.81 mmol, 82.5% yield) as a brown solid. LCMS (ESI) [M+H]⁺=695.3.

Step 3: 1-(8-Amino-6-(5-amino-4-methylpyridin-3-yl)-7-fluoroisoquinolin-3-yl)-3-cyclopentylurea

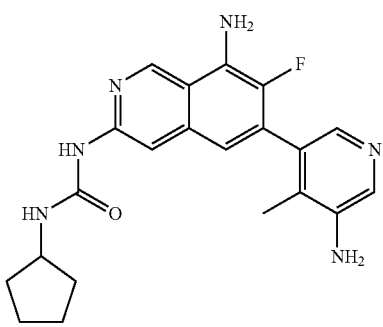 [SMILES: Cc1c(N)cncc1-c1cc2cc(NC(=O)NC3CCCC3)ncc2c(N)c1F]

To a solution of tert-butyl N-tert-butoxycarbonyl-N-[5-[8-(tert-butoxycarbonylamino)-3-(cyclopentylcarbamoylamino)-7-fluoro-6-isoquinolyl]-4-methyl-3-pyridyl]carbamate (800.0 mg, 0.81 mmol) in dichloromethane (30 mL) was added trifluoroacetic acid (10.0 mL, 129.8 mmol). The reaction was stirred at room temperature for 1 hour and then concentrated under vacuum. The residue was diluted with dichloromethane and adjusted to pH 7 with triethylamine. Then the mixture was concentrated under vacuum and purified by prep-HPLC (X Bridge Shield RP18 OBD Column 30*150 mm, 5 μm; Mobile Phase A: Water (10 mmol/L NH₄HCO₃), Mobile Phase B: ACN; Flow rate: 60 mL/min; Gradient: 26% B to 45% B in 8 min) to give 1-[8-amino-6-(5-amino-4-methyl-3-pyridyl)-7-fluoro-3-isoquinolyl]-3-cyclopentyl-urea (100.2 mg, 0.254 mmol, 31.5% yield) as a yellow solid. LCMS (ESI) [M+H]=395.2, $R_T$ 1.943 min, Method K; ¹H NMR (400 MHz, DMSO-d₆) δ 9.29 (s, 1H), 8.79 (s, 1H), 7.98 (s, 1H), 7.85 (s, 1H), 7.65 (s, 1H), 7.12 (d, J=7.2 Hz, 1H), 6.75 (d, J=6 Hz, 1H), 6.17 (s, 2H), 5.24 (s, 2H), 4.01-3.96 (m, 1H), 1.91 (s, 3H), 1.91-1.83 (m, 2H), 1.68-1.62 (m, 2H), 1.60-1.55 (m, 2H), 1.43-1.35 (m, 2H).

Example 183

1-(8-Amino-7-fluoro-6-(8-methyl-2,3-dihydro-1H-pyrido[2,3-b][1,4]oxazin-7-yl)isoquinolin-3-yl)-3-((3R,4R)-3-methoxytetrahydro-2H-pyran-4-yl)urea and 1-(8-Amino-7-fluoro-6-(8-methyl-2,3-dihydro-1H-pyrido[2,3-b][1,4]oxazin-7-yl)isoquinolin-3-yl)-3-((3S,4S)-3-methoxytetrahydro-2H-pyran-4-yl)urea (Compound 750b and Compound 750a)

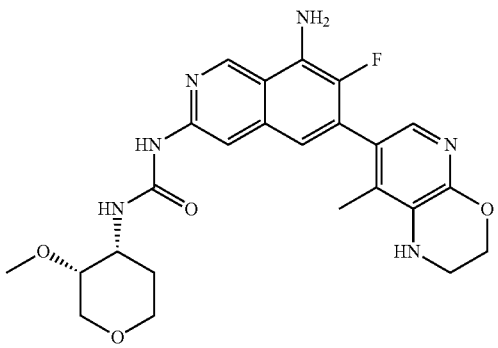

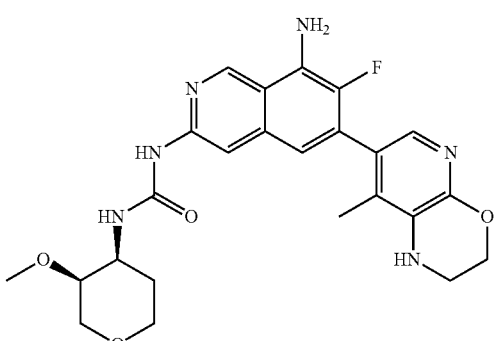

Step 1: tert-Butyl 7-[8-(tert-butoxycarbonylamino)-7-fluoro-3-[3-methoxytetrahydropyran-4-yl]carbamoylamino]-6-isoquinolyl]-8-methyl-2,3-dihydropyrido[2,3-b][1,4]oxazine-1-carboxylate

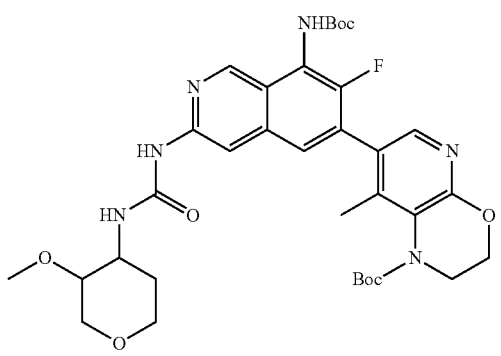 [SMILES: COC1COCCC1NC(=O)Nc1cc2cc(-c3cnc4c(c3C)N(C(=O)OC(C)(C)C)CCO4)c(F)c(NC(=O)OC(C)(C)C)c2cn1]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (200.0 mg, 0.31 mmol) and DMAP (38.1 mg, 0.31 mmol) in dichloromethane (7.5 mL) was added a solution of 3-methoxytetrahydropyran-4-amine (81.2 mg, 0.61 mmol) and DIEA (2.0 mL, 0.31 mmol) in dichloromethane at room temperature. The resulting solution was stirred at 55° C. for 3 hours. The reaction was concentrated under vacuum and purified by flash chromatography on silica gel eluting with dichloromethane/methanol (20/1) to afford tert-butyl 7-[8-(tert-butoxycarbonylamino)-7-fluoro-3-[3-methoxytetrahydropyran-4-yl]carbamoylamino]-6-isoquinolyl]-8-methyl-2,3-dihydropyrido[2,3-b][1,4]oxazine-1-carboxylate (200 mg, 0.29 mmol, 94.6% yield) as a yellow solid. LCMS (ESI) [M+H]⁺=683.3.

Step 2: 1-(8-Amino-7-fluoro-6-(8-methyl-2,3-dihydro-1H-pyrido[2,3-b][1,4]oxazin-7-yl)isoquinolin-3-yl)-3-((3R,4R)-3-methoxytetrahydro-2H-pyran-4-yl)urea and 1-(8-Amino-7-fluoro-6-(8-methyl-2,3-dihydro-1H-pyrido[2,3-b][1,4]oxazin-7-yl)isoquinolin-3-yl)-3-((3S,4S)-3-methoxytetrahydro-2H-pyran-4-yl)urea

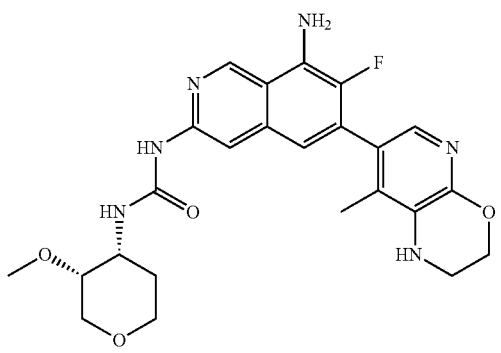

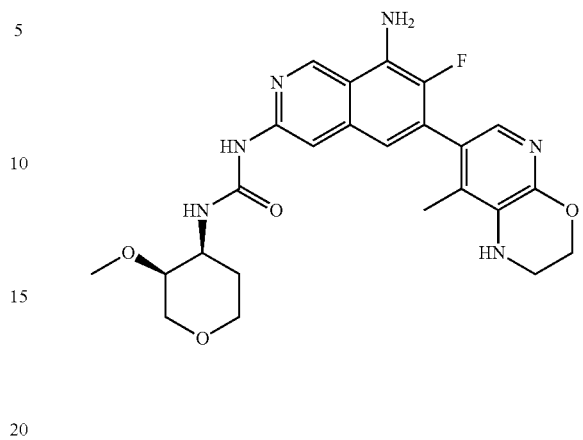

To a solution of tert-butyl 7-[8-(tert-butoxycarbonylamino)-7-fluoro-3-[(3-methoxytetrahydropyran-4-yl)carbamoylamino]-6-isoquinolyl]-8-methyl-2,3-dihydropyrido[2,3-b][1,4]oxazine-1-carboxylate (200.0 mg, 0.29 mmol) in dichloromethane (15 mL) was added 2,2,2-trifluoroacetic acid (5 mL) at 0° C. The resulting solution was stirred at room temperature for 1.5 hours. The reaction mixture was concentrated under vacuum. The residue was diluted with DCM, adjusted to pH 8 with TEA and concentrated under vacuum. The residue was purified by Prep-HPLC (Column:)(Bridge Shield RP18 OBD Column 30*150 mm, 5 μm; Mobile Phase A: Water (10 mmol/L NH₄HCO₃), Mobile Phase B: ACN; Flow rate: 60 mL/min; Gradient: 17% B to 38% B in 7 min) to give a racemate product. The racemic product was further separated by Chiral-HPLC to afford two enantiomers.

Enantiomer 1: (Compound 750b) (29.9 mg, 0.062 mmol, 21.2% yield), R$_T$ 2.205 min (column: CHIRALPAK IG-3 0.46*5 cm; 3 μm. Mobile phase: (Hex:DCM=3:1)(0.1% DEA): EtOH=50:50). LCMS(ESI): [M+H]⁺=483.2, R$_T$ 1.790 min; Method J. ¹H NMR (400 MHz, DMSO-d₆) δ 9.29 (s, 1H), 9.11 (s, 1H), 7.79 (s, 1H), 7.51 (s, 1H), 7.32 (s, 1H), 6.73 (d, J=6.1 Hz, 1H), 6.17 (s, 2H), 5.67 (d, J=2.7 Hz, 1H), 4.28 (t, J=4.4 Hz, 2H), 3.91-3.95 (m, 2H), 3.76 (d, J=11.6 Hz, 1H), 3.48-3.32 (m, 7H), 3.29 (s, 1H), 1.91 (d, J=1.6 Hz, 3H), 1.80-1.53 (m, 2H).

Enantiomer 2: (Compound 750a) (28.7 mg, 0.0595 mmol, 20.3% yield). R$_T$ 2.782 min (column: CHIRALPAK IG-3 0.46*5 cm; 3 μm. Mobile phase: (Hex:DCM=3:1)(0.1% DEA): EtOH=50:50). LCMS(ESI): [M+H]⁺=483.2, R$_T$ 1.790 min., Method J. ¹H NMR (400 MHz, DMSO-d₆) δ 9.29 (s, 1H), 9.11 (s, 1H), 7.79 (s, 1H), 7.51 (s, 1H), 7.32 (s, 1H), 6.73 (d, J=6.1 Hz, 1H), 6.17 (s, 2H), 5.67 (d, J=2.7 Hz, 1H), 4.28 (t, J=4.4 Hz, 2H), 3.91-3.95 (m, 2H), 3.76 (d, J=11.6 Hz, 1H), 3.48-3.32 (m, 7H), 3.29 (s, 1H), 1.91 (d, J=1.6 Hz, 3H), 1.80-1.53 (m, 2H).

Example 184

(1s,3s)-3-Cyanocyclobutyl (8-amino-7-fluoro-6-(8-methyl-2,3-dihydro-1H-pyrido[2,3-b][1,4]oxazin-7-yl)isoquinolin-3-yl)carbamate (Compound 484a)

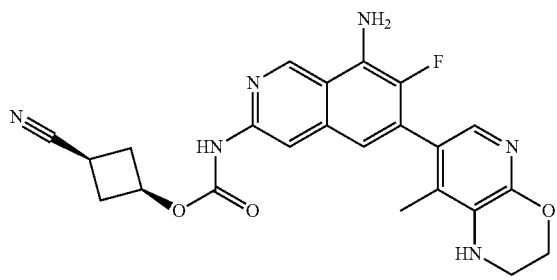 [SMILES: Cc1c(-c2cc3cc(NC(=O)O[C@H]4C[C@@H](C#N)C4)ncc3c(N)c2F)cnc2c1NCCO2]

Step 1: tert-Butyl 7-(8-((tert-butoxycarbonyl)amino)-3-(((((1s,3s)-3-cyanocyclobutoxy)carbonyl)amino)-7-fluoroisoquinolin-6-yl)-8-methyl-2,3-dihydro-1H-pyrido[2,3-b][1,4]oxazine-1-carboxylate

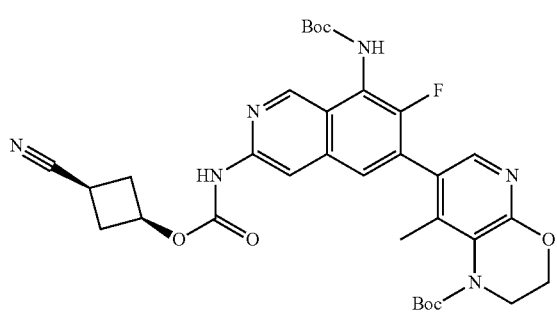 [SMILES: Cc1c(-c2cc3cc(NC(=O)O[C@H]4C[C@@H](C#N)C4)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-3,4-dihydro-2H-1,5-naphthyridine-1-carboxylate (180 mg, 0.34 mmol), (1s,3s)-3-hydroxycyclobutane-1-carbonitrile (40 mg, 0.41 mmol) and DIEA (132 mg, 1.02 mmol) in dichloromethane (18 mL) was added triphosgene (150 mg, 0.51 mmol) at 0° C. The reaction was stirred for 2 hours at 0° C. The reaction solution was concentrated under vacuum and purified by flash chromatography on silica gel eluting with MeOH/DCM (7%) to afford (1s,3s)-3-cyanocyclobutyl (8-amino-7-fluoro-6-(8-methyl-2,3-dihydro-1H-pyrido[2,3-b][1,4]oxazin-7-yl)isoquinolin-3-yl)carbamate (200 mg, 0.308 mmol, 90.0% yield) as a yellow solid. LCMS (ESI) [M+H]⁺=650.0

Step 2: (1s,3s)-3-Cyanocyclobutyl (8-amino-7-fluoro-6-(8-methyl-2,3-dihydro-1H-pyrido[2,3-b][1,4]oxazin-7-yl)isoquinolin-3-yl)carbamate Compound 484a

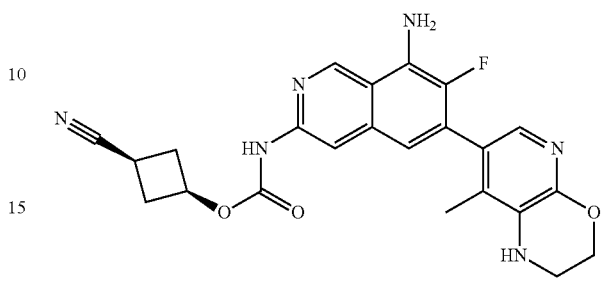

A solution of (1s,3s)-3-cyanocyclobutyl (8-amino-7-fluoro-6-(8-methyl-2,3-dihydro-1H-pyrido[2,3-b][1,4]oxazin-7-yl)isoquinolin-3-yl)carbamate (81 mg, 0.12 mmol) in 2,2,2-trifluoroacetic acid (2 mL) and dichloromethane (8 mL) was stirred at room temperature for 2 hours. The reaction was concentrated under vacuum and purified by Prep-HPLC (Column: X Select CSH Prep C18 OBD Column, 5 μm, 19*150 mm; Mobile Phase A: Water (0.1% FA), Mobile Phase B: MeOH; Flow rate: 25 mL/min; Gradient: 29% B to 50% B in 7 min) to afford (1s,3s)-3-cyanocyclobutyl (8-amino-7-fluoro-6-(8-methyl-2,3-dihydro-1H-pyrido[2,3-b][1,4]oxazin-7-yl)isoquinolin-3-yl)carbamate (27 mg, 0.0542 mmol, 44.5% yield) as a yellow solid. LCMS (ESI) [M+H]⁺=449.2, $R_T$ 1.837 min, method=J; ¹H NMR (300 MHz, DMSO-$d_6$) δ 10.23 (s, 1H), 9.35 (s, 1H), 7.95 (s, 1H), 7.33 (s, 1H), 6.85 (d, J=6.2 Hz, 1H), 6.24 (s, 2H), 5.69 (s, 1H), 4.94 (t, J=7.4 Hz, 1H), 4.29 (t, J=4.4 Hz, 2H), 3.34-3.33 (m, 2H), 3.12 (tt, J=9.6, 8.0 Hz, 1H), 2.89-2.71 (m, 2H), 2.39 (tdd, J=9.8, 7.7, 2.6 Hz, 2H), 1.92 (d, J=1.7 Hz, 3H).

Example 185

(1s,3s)-3-hydroxycyclobutyl (8-amino-7-fluoro-6-(4-methyl-5,6,7,8-tetrahydro-1,5-naphthyridin-3-yl)isoquinolin-3-yl)carbamate (Compound 553a)

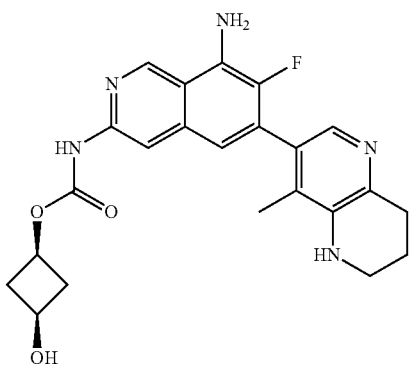 [SMILES: Cc1c(-c2cc3cc(NC(=O)O[C@H]4C[C@@H](O)C4)ncc3c(N)c2F)cnc2c1NCCC2]

Step 1: tert-Butyl 7-(8-((tert-butoxycarbonyl)amino)-3-((((1s,3s)-3-((tert-butyldimethylsilyl)oxy)cyclobutoxy)carbonyl)amino)-7-fluoroisoquinolin-6-yl)-8-methyl-3,4-dihydro-1,5-naphthyridine-1(2H)-carboxylate

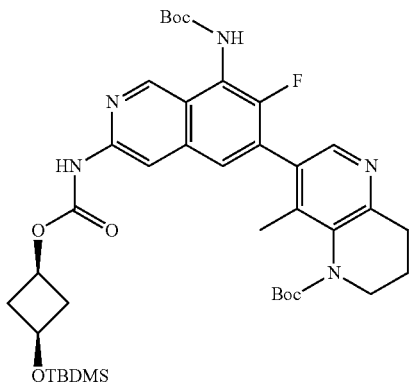 [SMILES: Cc1c(-c2cc3cc(NC(=O)O[C@H]4C[C@@H](O[Si](C)(C)C(C)(C)C)C4)ncc3c(NC(=O)OC(C)(C)C)c2F)cnc2c1N(C(=O)OC(C)(C)C)CCC2]

To a solution of tert-butyl 7-[3-amino-8-(tert-butoxycarbonylamino)-7-fluoro-6-isoquinolyl]-8-methyl-3,4-dihydro-2H-1,5-naphthyridine-1-carboxylate (180 mg, 0.34 mmol), (1s,3s)-3-((tert-butyldimethylsilyl)oxy)cyclobutan-1-ol (130 mg, 0.64 mmol) and DIEA (132 mg, 1.02 mmol) in dichloromethane (18 mL) was added triphosgene (150 mg, 0.51 mmol) at 0° C. The resulting solution was stirred for 2 hours at 0° C. The reaction solution was concentrated under vacuum. The residue was purified by flash chromatography on silica gel eluting with methanol/dichloromethane (7%) to afford tert-butyl 7-(8-((tert-butoxycarbonyl)amino)-3-((((1s,3s)-3-((tert-butyldimethylsilyl)oxy)cyclobutoxy)carbonyl)amino)-7-fluoroisoquinolin-6-yl)-8-methyl-3,4-dihydro-1,5-naphthyridine-1(2H)-carboxylate (200 mg, 0.239 mmol, 69.6% yield) as a yellow solid. LCMS (ESI) [M+H]$^+$=752.0.

Step 2: tert-Butyl 7-(8-((tert-butoxycarbonyl)amino)-7-fluoro-3-((((1s,3s)-3-hydroxycyclobutoxy)carbonyl)amino)isoquinolin-6-yl)-8-methyl-3,4-dihydro-1,5-naphthyridine-1(2H)-carboxylate

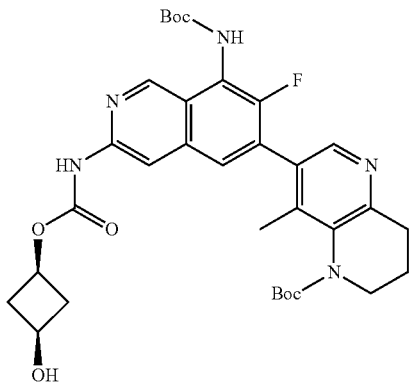 [SMILES: Cc1c(-c2cc3cc(NC(=O)O[C@H]4C[C@@H](O)C4)ncc3c(NC(=O)OC(C)(C)C)c2F)cnc2c1N(C(=O)OC(C)(C)C)CCC2]

To a solution of tert-butyl 7-(8-((tert-butoxycarbonyl)amino)-3-((((1s,3s)-3-((tert-butyldimethylsilyl)oxy)cyclobutoxy)carbonyl)amino)-7-fluoroisoquinolin-6-yl)-8-methyl-3,4-dihydro-1,5-naphthyridine-1(2H)-carboxylate (200 mg, 0.27 mmol) in tetrahydrofuran (20 mL) was added TBAF (130 mg, 0.50 mmol). The mixture was stirred at room temperature for 1 hour. The mixture was then concentrated under vacuum to afford tert-butyl 7-(8-((tert-butoxycarbonyl)amino)-7-fluoro-3-((((1s,3s)-3-hydroxycyclobutoxy)carbonyl)amino)isoquinolin-6-yl)-8-methyl-3,4-dihydro-1,5-naphthyridine-1(2H)-carboxylate (150 mg, 0.165 mmol, 61.9% yield) as a yellow solid. LCMS (ESI) [M+H]$^+$=638.0.

Step 3: (1s,3s)-3-Hydroxycyclobutyl (8-amino-7-fluoro-6-(4-methyl-5,6,7,8-tetrahydro-1,5-naphthyridin-3-yl)isoquinolin-3-yl)carbamate

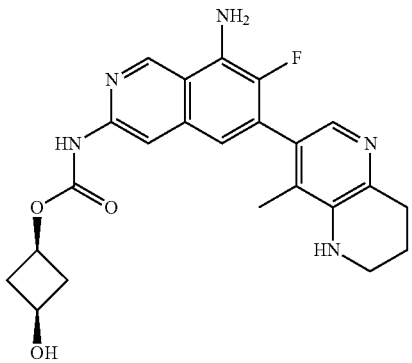 [SMILES: Cc1c(-c2cc3cc(NC(=O)O[C@H]4C[C@@H](O)C4)ncc3c(N)c2F)cnc2c1NCCC2]

A solution of tert-butyl 7-(8-((tert-butoxycarbonyl)amino)-7-fluoro-3-((((1s,3s)-3-hydroxycyclobutoxy)carbonyl)amino)isoquinolin-6-yl)-8-methyl-3,4-dihydro-1,5-naphthyridine-1(2H)-carboxylate (96 mg, 0.15 mmol) in dichloromethane (10 mL) and TFA (2 mL) was stirred at room temperature for 1.5 hours. The reaction mixture was concentrated under vacuum. The residue was purified by Prep-HPLC (Column: X Select CSH Prep C18 OBD Column, 5 μm, 19*150 mm; Mobile Phase A: Water (0.1% FA), Mobile Phase B: ACN; Flow rate: 25 mL/min; Gradient: 5% B to 21% B in 7 min) to afford (1s,3s)-3-hydroxycyclobutyl (8-amino-7-fluoro-6-(4-methyl-5,6,7,8-tetrahydro-1,5-naphthyridin-3-yl)isoquinolin-3-yl)carbamate (60 mg, 0.123 mmol, 81.6% yield) as a yellow solid. LCMS (ESI) [M+H]$^+$= 438.2, R$_T$ 1.645 min, method=J; $^1$H NMR (400 MHz, DMSO-d$_6$) δ 10.08 (s, 1H), 9.33 (s, 1H), 7.96 (s, 1H), 7.56 (s, 1H), 6.82 (d, J=6.1 Hz, 1H), 6.22 (s, 2H), 5.43 (s, 1H), 5.20 (s, 1H), 4.52 (p, J=7.3 Hz, 1H), 3.81 (p, J=7.1 Hz, 1H), 3.34-3.33 (m, 2H), 2.84 (t, J=6.4 Hz, 2H), 2.75-2.64 (m, 2H), 1.97-1.88 (m, 4H), 1.86 (d, J=1.5 Hz, 3H).

Example 186

(R)-6,7-Dihydro-5H-pyrrolo[1,2-c]imidazol-6-yl (8-amino-7-fluoro-6-(8-methyl-2,3-dihydro-1H-pyrido[2,3-b][1,4]oxazin-7-yl)isoquinolin-3-yl)carbamate and (S)-6,7-Dihydro-5H-pyrrolo[1,2-a]imidazol-6-yl (8-amino-7-fluoro-6-(8-methyl-2,3-dihydro-1H-pyrido[2,3-b][1,4]oxazin-7-yl)isoquinolin-3-yl)carbamate (Compound 504a and Compound 504b)

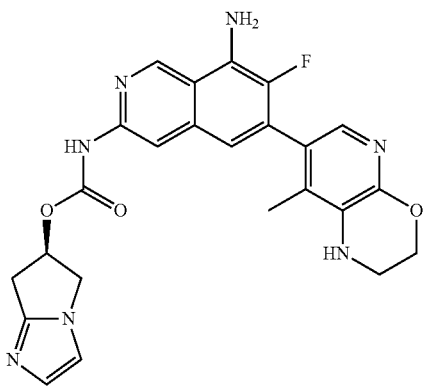

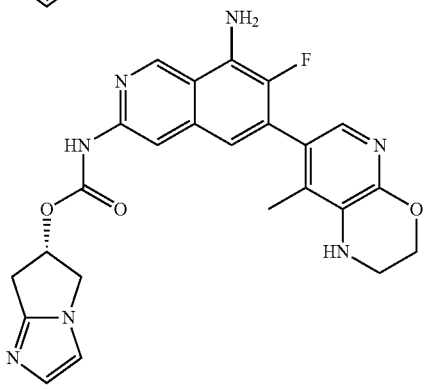

Step 1: tert-Butyl 7-[8-(tert-butoxycarbonylamino)-3-(6,7-dihydro-5H-pyrrolo[1,2-a]imidazol-6-yloxycarbonylamino)-7-fluoro-6-isoquinolyl]-8-methyl-2,3-dihydropyrido[2,3-b][1,4]oxazine-1-carboxylate

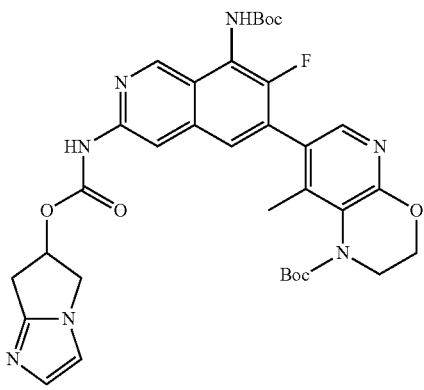 [SMILES: Cc1c(-c2cc3cc(NC(=O)OC4Cc5nccn5C4)ncc3c(NC(=O)OC(C)(C)C)c2F)cnc2c1N(C(=O)OC(C)(C)C)CCO2]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300.0 mg, 0.46 mmol) and DMAP (56.7 mg, 0.46 mmol) in 1,4-dioxane (10 mL) was added a solution of 6,7-dihydro-5H-pyrrolo[1,2-a]imidazol-6-ol (173.0 mg, 1.39 mmol) in 1,4-dioxane (5 mL) at 25° C. The resulting solution was stirred for 1 hour at 90° C. The reaction mixture was concentrated under vacuum. The residue was purified by flash chromatography on silica gel eluting with dichloromethane/methanol (71/29) to afford tert-butyl 7-[8-(tert-butoxycarbonylamino)-3-(6,7-dihydro-5H-pyrrolo[1,2-a]imidazol-6-yloxycarbonylamino)-7-fluoro-6-isoquinolyl]-8-methyl-2,3-dihydropyrido[2,3-b][1,4]oxazine-1-carboxylate (247 mg, 0.36 mmol, 78% yield) as a pale yellow solid. LCMS (ESI) [M+H]$^+$=676.3.

Step 2: (R)-6,7-Dihydro-5H-pyrrolo[1,2-a]imidazol-6-yl (8-amino-7-fluoro-6-(8-methyl-2,3-dihydro-1H-pyrido[2,3-b][1,4]oxazin-7-yl)isoquinolin-3-yl)carbamate and (S)-6,7-Dihydro-5H-pyrrolo[1,2-a]imidazol-6-yl (8-amino-7-fluoro-6-(8-methyl-2,3-dihydro-1H-pyrido[2,3-b][1,4]oxazin-7-yl)isoquinolin-3-yl)carbamate A solution of tert-butyl 7-[8-(tert-butoxycarbonylamino)-3-(6,7-dihydro-5H-pyrrolo[1,2-a]imidazol-6-yloxycarbonylamino)-7-fluoro-6-isoquinolyl]-8-methyl-2,3-dihydropyrido[2,3-b][1,4]oxazine-1-carboxylate (237.0 mg, 0.35 mmol) and TFA (2.5 mL, 0.35 mmol) in dichloromethane (5 mL) was stirred at 25° C. for 30 minutes. After concentration, the residue was purified by Prep-HPLC (Column: X Select CSH Prep C18 OBD Column, 5 μm, 19*150 mm; Water (0.1% FA): ACN=5% B to 21% B in 7 min; 25 mL/min) to afford the racemic product. The racemic product was separated by chiral-HPLC to afford two enantiomers. Absolute stereochemistry was arbitrarily assigned.

Enantiomer 1 (Compound 504a) (21.9 mg, 0.046 mmol, 13% yield). $R_T$ 1.952 min (CHIRAL Cellulose-SB 0.46*10 cm; 3 μm; MTBE (0.1% DEA):EtOH=50:50; 1.0 ml/min). LCMS (ESI) [M+H]$^+$=476.2, $R_T$ 1.084 min, Method M; $^1$H NMR (300 MHz, DMSO-d$_6$) δ 10.22 (s, 1H), 9.34 (s, 1H), 8.02 (s, 1H), 7.34 (s, 1H), 7.24 (d, J=1.2 Hz, 1H), 7.06 (d, J=1.2 Hz, 1H), 6.87 (d, J=6.2 Hz, 1H), 6.24 (s, 2H), 6.01-5.98 (m, 1H), 5.72-5.69 (m, 1H), 4.30-4.20 (m, 2H), 4.20-3.97 (m, 2H), 3.37-3.33 (m, 2H), 3.15-3.00 (m, 1H), 2.60 (s, 1H), 1.93 (s, 3H).

Enantiomer 2 (Compound 504b) (10.5 mg, 0.0221 mmol, 6.3% yield) $R_T$ 2.419 min (CHIRAL Cellulose-SB 0.46*10 cm; 3 μm; MTBE (0.1% DEA):EtOH=50:50; 1.0 ml/min). LCMS (ESI) [M+H]$^+$=476.2, $R_T$ 1.084 min., Method M; $^1$H NMR (300 MHz, DMSO-d$_6$) δ 10.22 (s, 1H), 9.34 (s, 1H), 8.02 (s, 1H), 7.34 (s, 1H), 7.24 (d, J=1.2 Hz, 1H), 7.06 (d, J=1.2 Hz, 1H), 6.87 (d, J=6.2 Hz, 1H), 6.24 (s, 2H), 6.01-5.98 (m, 1H), 5.72-5.69 (m, 1H), 4.30-4.20 (m, 2H), 4.20-3.97 (m, 2H), 3.37-3.33 (m, 2H), 3.15-3.00 (m, 1H), 2.60 (s, 1H), 1.93 (s, 3H).

Example 187

1-(8-Amino-7-fluoro-6-(4-methyl-5,6,7,8-tetrahydro-1,5-naphthyridin-3-yl)isoquinolin-3-yl)-3-((2s,4s)-6-oxaspiro[3.4]octan-2-yl)urea and 1-(8-Amino-7-fluoro-6-(4-methyl-5,6,7,8-tetrahydro-1,5-naphthyridin-3-yl)isoquinolin-3-yl)-3-((2r,4r)-6-oxaspiro[3.4]octan-2-yl)urea (Compound 740a) (Compound 740b)

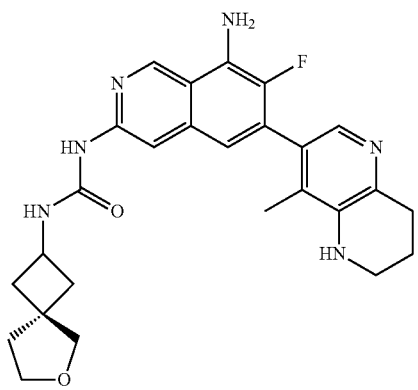

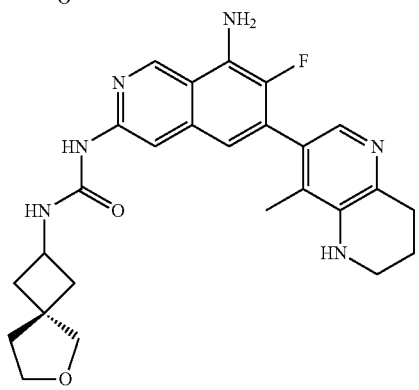

Step 1: tert-Butyl 7-(3-(3-(6-oxaspiro[3.4]octan-2-yl)ureido)-8-((tert-butoxycarbonyl)amino)-7-fluoroisoquinolin-6-yl)-8-methyl-3,4-dihydro-1,5-naphthyridine-1(2H)-carboxylate

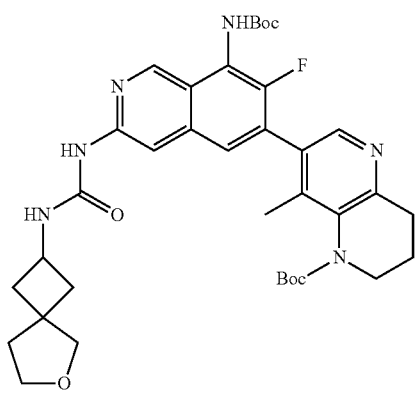 [SMILES: Cc1c(-c2cc3cc(NC(=O)NC4CC5(CCOC5)C4)ncc3c(NC(=O)OC(C)(C)C)c2F)cnc2c1N(C(=O)OC(C)(C)C)CCC2]

To a solution of phenyl chloroformate (270 mg, 1.72 mmol) in pyridine (3 mL) was added a solution of tert-butyl 7-[3-amino-8-(tert-butoxycarbonylamino)-7-fluoro-6-isoquinolyl]-8-methyl-3,4-dihydro-2H-1,5-naphthyridine-1-carboxylate (150 mg, 0.29 mmol) in dichloromethane (3 mL) and DMAP (35 mg, 0.29 mmol). The mixture was stirred at 0° C. for 1 hour. Then 6-oxaspiro[3.4]octan-2-amine (220 mg, 1.73 mmol) was added. The mixture was stirred at 60° C. for 12 hours. After concentration, the residue was purified by flash chromatography on silica gel eluting with dichloromethane/methanol (96/4) to afford tert-butyl 7-[8-(tert-butoxycarbonylamino)-7-fluoro-3-(6-oxaspiro[3.4]octan-2-ylcarbamoylamino)-6-isoquinolyl]-8-methyl-3,4-dihydro-2H-1,5-naphthyridine-1-carboxylate (120 mg, 0.177 mmol, 61.9% yield) as a yellow solid. LCMS (ESI) [M+H]$^+$=677.

Step 2: 1-(8-Amino-7-fluoro-6-(4-methyl-5,6,7,8-tetrahydro-1,5-naphthyridin-3-yl)isoquinolin-3-yl)-3-(6-oxaspiro[3.4]octan-2-yl)urea and 1-(8-Amino-7-fluoro-6-(4-methyl-5,6,7,8-tetrahydro-1,5-naphthyridin-3-yl)isoquinolin-3-yl)-3-(6-oxaspiro[3.4]octan-2-yl)urea

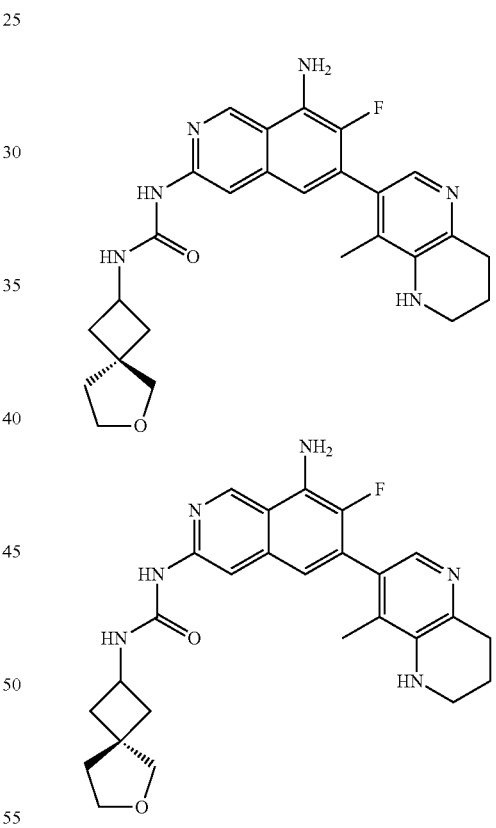

To a solution of tert-butyl 7-[8-(tert-butoxycarbonylamino)-7-fluoro-3-(6-oxaspiro[3.4]octan-2-ylcarbamoylamino)-6-isoquinolyl]-8-methyl-3,4-dihydro-2H-1,5-naphthyridine-1-carboxylate (128 mg, 0.19 mmol) in dichloromethane (5 mL) was added TFA (1 ml). The mixture was stirred at room temperature for 1 hour. After concentration, the residue was purified by Prep-HPLC (X Bridge Shield RP18 OBD Column 30*150 mm, 5 μm; Mobile Phase A: Water (10 mmol/L NH$_4$HCO$_3$), Mobile Phase B: ACN; Flow rate: 60 mL/min; Gradient: 25% B to 44% B in 7 min) to afford the racemic product. The racemate was separated by chiral-HPLC to afford two enantiomers. Absolute stereochemistry was arbitrarily assigned.

Enantiomer 1 (Compound 740a) (13.5 mg, 0.0289 mmol, 18.7% yield). $R_T$ 2.196 min (CHIRALPAK IG-3 0.46*5 cm; 3 μm. Mobile phase: MTBE (0.1% DEA):EtOH=70:30, 1 mL/min). LCMS (ESI) [M+H]$^+$=477.2, $R_T$ 2.108 min, Method K. $^1$H NMR (300 MHz, DMSO-d$_6$) δ 9.29 (s, 1H), 8.86 (s, 1H), 7.82 (s, 1H), 7.56 (s, 1H), 7.37 (d, J=7.5 Hz, 1H), 6.73 (d, J=6.1 Hz, 1H), 6.16 (s, 2H), 5.42 (s, 1H), 4.09 (q, J=7.9 Hz, 1H), 3.70-3.60 (m, 4H), 3.25-3.35 (m, 2H), 2.84 (t, J=6.4 Hz, 2H), 2.33 (s, 2H), 2.01-1.83 (m, 9H).

Enantiomer 2 (Compound 740b) (28.3 mg, 0.0594 mmol, 31.4% yield). $R_T$ 3.188 min (CHIRALPAK IG-3 0.46*5 cm; 3 μm. Mobile phase: MTBE (0.1% DEA):EtOH=70:30, 1 mL/min). LCMS (ESI) [M+H]$^+$=477.2, $R_T$ 2.108 min, Method K. $^1$H NMR (300 MHz, DMSO-d$_6$) δ 9.29 (s, 1H), 8.86 (s, 1H), 7.82 (s, 1H), 7.56 (s, 1H), 7.37 (d, J=7.5 Hz, 1H), 6.73 (d, J=6.1 Hz, 1H), 6.16 (s, 2H), 5.42 (s, 1H), 4.09 (q, J=7.9 Hz, 1H), 3.70-3.60 (m, 4H), 3.25-3.35 (m, 2H), 2.84 (t, J=6.4 Hz, 2H), 2.33 (s, 2H), 2.01-1.83 (m, 9H).

Example 188

(3-Hydroxy-3-methyl-cyclobutyl) N-[8-amino-7-fluoro-6-(8-methyl-2,3-dihydro-1H-pyrido[2,3-b][1,4]oxazin-7-yl)-3-isoquinolyl]carbamate (Compound 486)

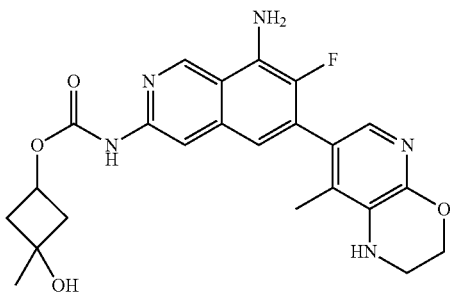 [SMILES: Cc1c(-c2cc3cc(NC(=O)OC4CC(C)(O)C4)ncc3c(N)c2F)cnc2c1NCCO2]

Step 1: 3-Benzyloxy-1-methyl-cyclobutanol

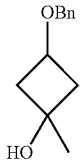

Under nitrogen, to a solution of 3-(benzyloxy)cyclobutanone (4.0 g, 22.7 mmol) in tetrahydrofuran (40 mL) was added methylmagnesium (5.03 mL, 68.19 mmol) at −78° C. The resulting solution was stirred at room temperature for 2 hours. The reaction was quenched by adding MeOH. The resulting solution was concentrated under vacuum and purified by flash chromatography on silica gel eluting with dichloromethane/methanol (20/1) to afford 3-benzyloxy-1-methyl-cyclobutanol (3.7 g, 19.25 mmol, 84.8% yield) as a yellow oil.

Step 2: (3-Benzyloxy-1-methyl-cyclobutoxy)-tert-butyl-dimethyl-silane

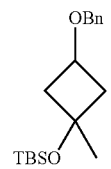

To a solution of 3-benzyloxy-1-methyl-cyclobutanol (2.4 g, 12.48 mmol) and imidazole (4.26 g, 62.57 mmol) in dichloromethane (30 mL) was added tert-butyldimethylchlorosilane (5.64 g, 37.42 mmol) at 0° C. The resulting solution was stirred at room temperature for 5 hours. The resulting solution was concentrated under vacuum and purified by flash chromatography on silica gel eluting with petroleum ether/dichloromethane (1/1) to afford (3-benzyloxy-1-methyl-cyclobutoxy)-tert-butyl-dimethyl-silane (3 g, 9.79 mmol, 78.4% yield) as a colorless oil.

Step 3: 7-Bromo-1H-1,6-naphthyridin-2-one

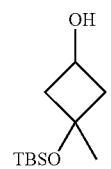

To a solution of (3-benzyloxy-1-methyl-cyclobutoxy)-tert-butyl-dimethyl-silane (800.0 mg, 2.61 mmol) in methyl alcohol (10 mL) was added Pd/C (10%, 160.0 mg, 0.15 mmol) at room temperature. The resulting solution was stirred at room temperature under hydrogen for 16 hours. After filtration, the filtrate was concentration under reduced pressure. The residue was purified by flash chromatography on silica gel eluting with dichloromethane/methanol (20/1) to afford 3-[tert-butyl(dimethyl)silyl]oxy-3-methyl-cyclobutanol (500 mg, 2.31 mmol, 88.5% yield) as a yellow oil. $^1$H NMR (400 MHz, DMSO-d$_6$) δ 4.96 (s, 1H), 3.70 (t, J=7.1 Hz, 1H), 2.25-2.31 (m, 2H), 1.88-1.93 (m, 2H), 1.21 (s, 3H), 0.84 (s, 9H), 0.05 (s, 6H).

Step 4: tert-Butyl7-[8-(tert-butoxycarbonylamino)-3-[[3-[tert-butyl (dimethyl)silyl]oxy-3-methyl-cyclobutoxy]carbonylamino]-7-fluoro-6-isoquinolyl]-8-methyl-2,3-dihydropyrido[2,3-b][1,4]oxazine-1-carboxylate

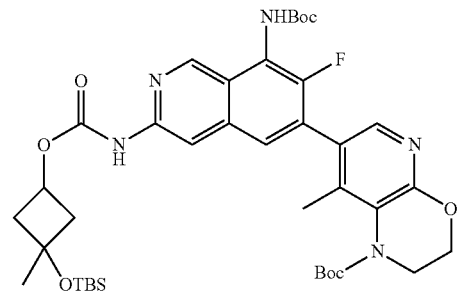 [SMILES: Cc1c(-c2cc3cc(NC(=O)OC4CC(C)(O[Si](C)(C)C(C)(C)C)C4)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (155.3 mg, 0.3 mmol), 3-[tert-butyl(dimethyl)silyl]oxy-3-methyl-cyclobutanol (127.5 mg, 0.59 mmol) and N,N-diisopropylethylamine (0.15 mL, 0.88 mmol) in dichloromethane (15 mL) was added triphosgene (87.0 mg, 0.29 mmol) at 0° C. The resulting solution was stirred at room temperature for 2 hours. The resulting mixture was concentrated under vacuum and purified by flash chromatography on silica gel eluting with dichloromethane/methanol (10/1) to afford tert-butyl 7-[8-(tert-butoxycarbonylamino)-3-[[3-[tert-butyl(dimethyl)silyl]oxy-3-methyl-cyclobutoxy]carbonylamino]-7-fluoro-6-isoquinolyl]-8-methyl-2,3-dihydropyrido[2,3-b][1,4]oxazine-1-carboxylate (130 mg, 0.17 mmol, 57.3% yield). LCMS (ESI) [M+H]$^+$=768.4.

Step 5: [7-(tert-butoxycarbonylamino)-1,6-naphthyridin-2-yl]trifluoromethanesulfonate

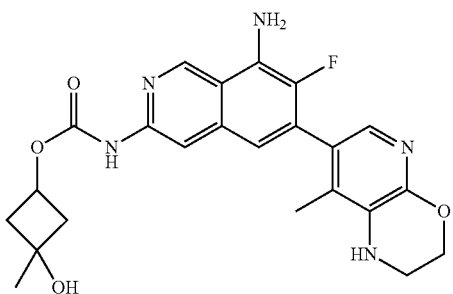 [SMILES: Cc1c(-c2cc3cc(NC(=O)OC4CC(C)(O)C4)ncc3c(N)c2F)cnc2c1NCCO2]

To a solution of tert-butyl 7-[8-(tert-butoxycarbonylamino)-3-[[3-[tert-butyl(dimethyl)silyl]oxy-3-methyl-cyclobutoxy]carbonylamino]-7-fluoro-6-isoquinolyl]-8-methyl-2,3-dihydropyrido[2,3-b][1,4]oxazine-1-carboxylate (110.0 mg, 0.14 mmol) in dichloromethane (6 mL) was added trifluoroacetic acid (3 mL) at 0° C. The resulting solution was stirred at room temperature for 1 hour. The resulting solution was concentrated under vacuum, dissolved in dichloromethane and adjusted to pH 8 with triethylamine. Then the mixture was concentrated under vacuum and purified by prep-HPLC (Column: Xselect CSH OBD Column 30*150 mm 5 μm; Mobile Phase A: Water (0.1% FA), Mobile Phase B: ACN; Flow rate: 60 mL/min; Gradient: 7% B to 37% B in 7 min) to afford (3-hydroxy-3-methyl-cyclobutyl) N-[8-amino-7-fluoro-6-(8-methyl-2,3-dihydro-1H-pyrido[2,3-b][1,4]oxazin-7-yl)-3-isoquinolyl]carbamate (18 mg, 0.037 mmol, 25.8% yield) as an off-white solid. LCMS (ESI) [M+H]$^+$=454.2, $R_T$ 1.724 min, Method J. $^1$H NMR (400 MHz, DMSO-d$_6$) δ 10.08 (s, 1H), 9.33 (s, 1H), 7.95 (s, 1H), 7.32 (s, 1H), 6.83 (d, J=6.1 Hz, 1H), 6.21 (s, 2H), 5.68 (d, J=2.7 Hz, 1H), 5.16 (s, 1H), 4.58-4.65 (m, J=7.3 Hz, 1H), 4.28 (t, J=4.4 Hz, 2H), 3.37 (t, J=4.0 Hz, 2H), 2.49-2.44 (m, 2H), 2.21-2.07 (m, 2H), 1.91 (d, J=1.6 Hz, 3H), 1.23 (s, 3H).

Example 189

1-(8-amino-7-fluoro-6-(8-methyl-2,3-dihydro-1H-pyrido[2,3-b][1,4]oxazin-7-yl)isoquinolin-3-yl)-3-((1R,3R)-3-methoxycyclopentyl)urea, 1-(8-amino-7-fluoro-6-(8-methyl-2,3-dihydro-1H-pyrido[2,3-b][1,4]oxazin-7-yl)isoquinolin-3-yl)-3-((1S,3S)-3-methoxycyclopentyl)urea, 1-(8-amino-7-fluoro-6-(8-methyl-2,3-dihydro-1H-pyrido[2,3-b][1,4]oxazin-7-yl)isoquinolin-3-yl)-3-((1R,3S)-3-methoxycyclopentyl)urea and 1-(8-amino-7-fluoro-6-(8-methyl-2,3-dihydro-1H-pyrido[2,3-b][1,4]oxazin-7-yl)isoquinolin-3-yl)-3-((1S,3R)-3-methoxycyclopentyl)urea (Compound 730a, Compound 730b; Compound 730c and Compound 730d)

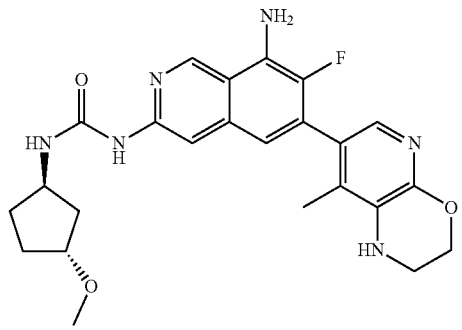

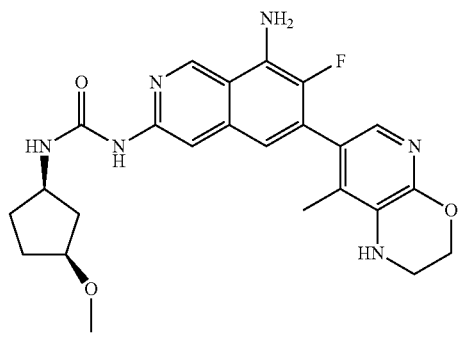

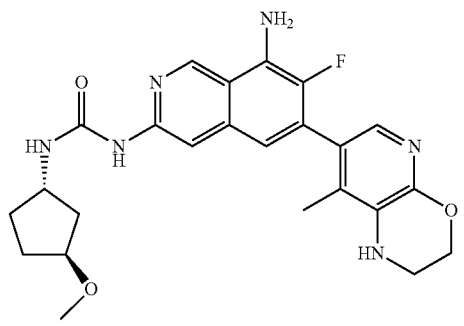

-continued

Step 1: tert-Butyl 7-(8-((tert-butoxycarbonyl) amino)-7-fluoro-3-(3-(3-methoxycyclopentyl)ureido) isoquinolin-6-yl)-8-methyl-2,3-dihydro-1H-pyrido[2, 3-b][1,4]oxazine-1-carboxylate

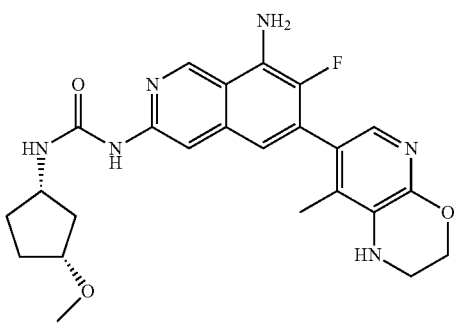

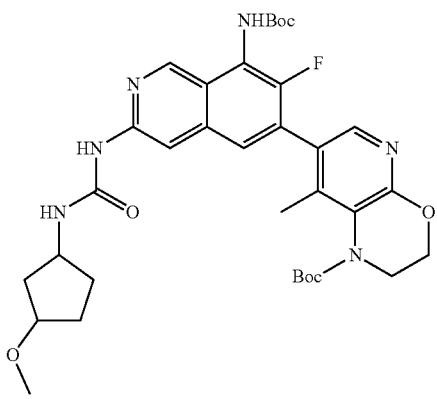 [SMILES: COC1CCC(NC(=O)Nc2cc3cc(-c4cnc5c(c4C)N(C(=O)OC(C)(C)C)CCO5)c(F)c(NC(=O)OC(C)(C)C)c3cn2)C1]

To a mixture of tert-butyl 6-[8-(tert-butoxycarbonylamino)-7-fluoro-3-(phenoxycarbonylamino)-6-isoquinolyl]-5-methyl-2,3-dihydro-1,4-benzoxazine-4-carboxylate (400 mg, 0.62 mmol) and DIEA (0.5 ml) in dichloromethane (16 mL) was added a mixture of 3-methoxycyclopentanamine hydrochloride (94 mg, 0.62 mmol) and DIEA (0.5 ml) in dichloromethane (1 ml). The mixture was stirred at 60° C. for 12 hours. After concentration, the residue was purified by flash chromatography on silica gel eluting with dichloromethane/methanol (96/4) to afford tert-butyl 6-[8-(tert-butoxycarbonylamino)-7-fluoro-3-[(3-methoxycyclopentyl)carbamoylamino]-6-isoquinolyl]-5-methyl-2,3-dihydro-1,4-benzoxazine-4-carboxylate (300 mg, 0.451 mmol, 72.6% yield) as a yellow solid. LC/MS (ESI) [M+H]$^+$=667.

Step 2: 1-(8-Amino-7-fluoro-6-(8-methyl-2,3-dihydro-1H-pyrido[2,3-b][1,4]oxazin-7-yl)isoquinolin-3-yl)-3-((1R,3R)-3-methoxycyclopentyl)urea (Compound 730a), 1-(8-Amino-7-fluoro-6-(8-methyl-2,3-dihydro-1H-pyrido[2,3-b][1,4]oxazin-7-yl) isoquinolin-3-yl)-3-((1R,3S)-3-methoxycyclopentyl) urea (Compound 730b), 1-(8-Amino-7-fluoro-6-(8-methyl-2,3-dihydro-1H-pyrido[2,3-b][1,4]oxazin-7-yl)isoquinolin-3-yl)-3-((1S,3S)-3-methoxycyclopentyl)urea (Compound 730c) and 1-(8-Amino-7-fluoro-6-(8-methyl-2,3-dihydro-1H-pyrido[2,3-b][1,4]oxazin-7-yl)isoquinolin-3-yl)-3-((1S,3R)-3-methoxycyclopentyl)urea (Compound 730d)

To a solution of tert-butyl 6-[8-(tert-butoxycarbonylamino)-7-fluoro-3-[(3-methoxycyclopentyl)carbamoylamino]-6-isoquinolyl]-5-methyl-2,3-dihydro-1,4-benzoxazine-4-carboxylate (400 mg, 0.60 mmol) in dichloromethane (10 mL) was added TFA (2 mL). The mixture was stirred at room temperature for 2 hours. After concentration, the residue was purified by Prep-HPLC (Column: X Bridge Shield RP18 OBD Column 30*150 mm, 5 μm; Mobile Phase A: Water (10 mmol/L NH$_4$HCO$_3$), Mobile Phase B: ACN; Flow rate: 60 mL/min; Gradient: 22% B to 43% B in 7 min) to afford a mixture of products. The mixture was separated by chiral-HPLC to afford four isomers. Relative stereochemistry are as drawn. Absolute stereochemistry was arbitrarily assigned.

Enantiomer 1 (Compound 730a) (41.3 mg, 0.0887 mmol, 14.8% yield). R$_T$ 1.733 min (CHIRALPAK IE-3, 0.46*5 cm; 3 μm. MTBE (0.1% DEA): EtOH=60:50, 1 mL/min). LCMS (ESI) [M+H]$^+$=455.2, R$_T$ 2.093 min, Method K. $^1$H NMR (300 MHz, DMSO-d$_6$) δ 9.27 (s, 1H), 8.79 (s, 1H), 7.85 (s, 1H), 7.32 (s, 1H), 7.11 (d, J=7.0 Hz, 1H), 6.74 (d, J=6.1 Hz, 1H), 6.14 (s, 2H), 5.67 (s, 1H), 4.28 (s, 2H), 4.08 (q, J=7.2 Hz, 1H), 3.85 (dd, J=6.1, 3.2 Hz, 1H), 3.32-3.36 (m, 2H), 3.17 (s, 3H), 1.97 (s, 2H), 2.06-1.84 (m, 4H), 1.62-1.51 (m, 2H), 1.38 (dt, J=11.4, 7.5 Hz, 1H).

Enantiomer 2 (Compound 730c) (24.1 mg, 0.0518 mmol, 8.6% yield). R$_T$ 2.900 min (CHIRALPAK IE-3, 0.46*5 cm; 3 μm. MTBE (0.1% DEA): EtOH=50:50, 1 mL/min). LCMS (ESI) [M+H]$^+$=455.2, R$_T$ 2.125 min, Method K. $^1$H NMR (300 MHz, DMSO-d$_6$) δ 9.27 (s, 1H), 8.93 (s, 1H), 7.79 (s, 1H), 7.32 (s, 1H), 7.29 (s, 1H), 6.72 (d, J=6.2 Hz, 1H), 6.15 (s, 2H), 5.67 (s, 1H), 4.28 (s, 2H), 4.06 (q, J=6.7 Hz, 1H), 3.78 (tt, J=6.2, 3.5 Hz, 1H), 3.41-3.31 (m, 2H), 3.22 (s, 3H), 2.19-2.03 (m, 1H), 1.91 (d, J=1.6 Hz, 4H), 1.79-1.60 (m, 2H), 1.58-1.43 (m, 2H).

Enantiomer 3 (Compound 730b) (18.3 mg, 0.0393 mmol, 6.5% yield), R$_T$ 2.264 min (CHIRALPAK IE-3, 0.46*5 cm; 3 μm. MTBE (0.1% DEA): EtOH=60:50, 1 mL/min). LCMS (ESI) [M+H]$^+$=455.2, R$_T$ 2.093 min., Method K. $^1$H NMR (300 MHz, DMSO-d$_6$) δ 9.27 (s, 1H), 8.79 (s, 1H), 7.85 (s, 1H), 7.32 (s, 1H), 7.11 (d, J=7.0 Hz, 1H), 6.74 (d, J=6.1 Hz, 1H), 6.14 (s, 2H), 5.67 (s, 1H), 4.28 (s, 2H), 4.08 (q, J=7.2 Hz, 1H), 3.85 (dd, J=6.1, 3.2 Hz, 1H), 3.32-3.36 (m, 2H), 3.17 (s, 3H), 1.97 (s, 2H), 2.06-1.84 (m, 4H), 1.62-1.51 (m, 2H), 1.38 (dt, J=11.4, 7.5 Hz, 1H).

Enantiomer 4 (Compound 730d) (33.8 mg, 0.0726 mmol, 12.1% yield). R$_T$ 4.378 min (CHIRALPAK IE-3, 0.46*5 cm; 3 μm. MTBE (0.1% DEA): EtOH=50:50, 1 mL/min). LCMS (ESI) [M+H]$^+$=455.2, R$_T$ 2.125 min, Method K. $^1$H NMR (300 MHz, DMSO-d$_6$) δ 9.27 (s, 1H), 8.93 (s, 1H), 7.79 (s, 1H), 7.32 (s, 1H), 7.29 (s, 1H), 6.72 (d, J=6.2 Hz, 1H), 6.15 (s, 2H), 5.67 (s, 1H), 4.28 (s, 2H), 4.06 (q, J=6.7 Hz, 1H), 3.78 (tt, J=6.2, 3.5 Hz, 1H), 3.41-3.31 (m, 2H), 3.22 (s, 3H), 2.19-2.03 (m, 1H), 1.91 (d, J=1.6 Hz, 4H), 1.79-1.60 (m, 2H), 1.58-1.43 (m, 2H).

Example 190

1-(Methylsulfonyl)azetidin-3-yl (8-amino-7-fluoro-6-(4-methyl-5,6,7,8-tetrahydro-1,5-naphthyridin-3-yl)isoquinolin-3-yl)carbamate (Compound 493)

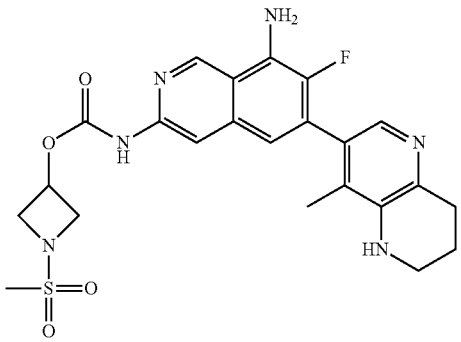 [SMILES: Cc1c(-c2cc3cc(NC(=O)OC4CN(S(C)(=O)=O)C4)ncc3c(N)c2F)cnc2c1NCCC2]

Step 1: tert-Butyl 7-[8-(tert-butoxycarbonylamino)-7-fluoro-3-[(1-methylsulfonylazetidin-3-yl)oxycarbonylamino]-6-isoquinolyl]-8-methyl-3,4-dihydro-2H-1,5-naphthyridine-1-carboxylate

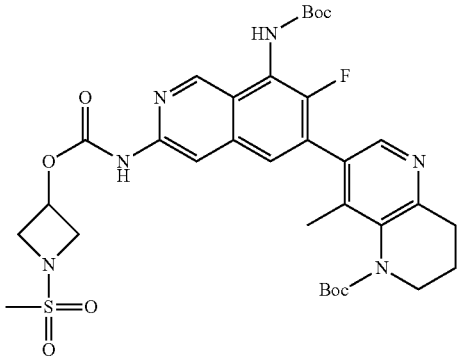 [SMILES: Cc1c(-c2cc3cc(NC(=O)OC4CN(S(C)(=O)=O)C4)ncc3c(NC(=O)OC(C)(C)C)c2F)cnc2c1N(C(=O)OC(C)(C)C)CCC2]

To a solution of tert-butyl 7-[3-amino-8-(tert-butoxycarbonylamino)-7-fluoro-6-isoquinolyl]-8-methyl-3,4-dihydro-2H-1,5-naphthyridine-1-carboxylate (150 mg, 0.29 mmol) and 1-methylsulfonylazetidin-3-ol (220 mg, 1.46 mmol) in dichloromethane (30 mL) was added DIEA (200 mg, 1.55 mmol) at room temperature. Then triphosgene (250 mg, 0.84 mmol) was added. The mixture was stirred at 0° C. for 1 hour and then concentrated. The residue was purified by flash chromatography on silica gel eluting with petroleum ether/ethyl acetate (1/1) to afford tert-butyl 7-[8-(tert-butoxycarbonylamino)-7-fluoro-3-[(1-methylsulfonylazetidin-3-yl)oxycarbonylamino]-6-isoquinolyl]-8-methyl-3,4-dihydro-2H-1,5-naphthyridine-1-carboxylate (120 mg, 0.171 mmol, 59.8% yield) as a yellow solid. LCMS (ESI) [M+H]$^+$= 701.

Step 2: 1-(methylsulfonyl)azetidin-3-yl (8-amino-7-fluoro-6-(4-methyl-5,6,7,8-tetrahydro-1,5-naphthyridin-3-yl)isoquinolin-3-yl)carbamate

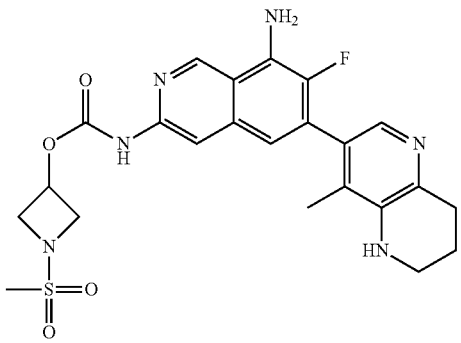 [SMILES: Cc1c(-c2cc3cc(NC(=O)OC4CN(S(C)(=O)=O)C4)ncc3c(N)c2F)cnc2c1NCCC2]

To a solution of tert-butyl 7-[8-(tert-butoxycarbonylamino)-7-fluoro-3-[(1-methylsulfonylazetidin-3-yl)oxycarbonylamino]-6-isoquinolyl]-8-methyl-3,4-dihydro-2H-1,5-naphthyridine-1-carboxylate (120 mg, 0.17 mmol) in dichloromethane (10 mL) was added TFA (1 mL) at room temperature. The resulting solution was stirred for 1 h at 25° C. The reaction solution was concentrated under vacuum and purified by Prep-HPLC to afford (1-methylsulfonylazetidin-3-yl) N-[8-amino-7-fluoro-6-(4-methyl-5,6,7,8-tetrahydro-1,5-naphthyridin-3-yl)-3-isoquinolyl]carbamate (38.1 mg, 0.0761 mmol, 44.5% yield) as a yellow solid. LCMS (ESI) [M+H]$^+$=501.2, Rt=1.941 min, Method M. $^1$H NMR (400 MHz, DMSO-d$_6$) δ 10.47 (s, 1H), 9.40 (s, 1H), 7.99 (s, 1H), 7.81 (s, 1H), 6.92 (d, J=6.0 Hz, 1H), 6.35 (s, 2H), 6.12 (s, 1H), 5.21 (tt, J=6.7, 4.8 Hz, 1H), 4.24 (dd, J=9.6, 6.7 Hz, 2H), 3.94 (dd, J=9.7, 4.7 Hz, 2H), 3.38 (s, 2H), 3.08 (s, 3H), 2.98 (t, J=6.5 Hz, 2H), 1.98 (d, J=1.4 Hz, 5H).

Example 191

(±)-trans-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate (Compound 441ab)

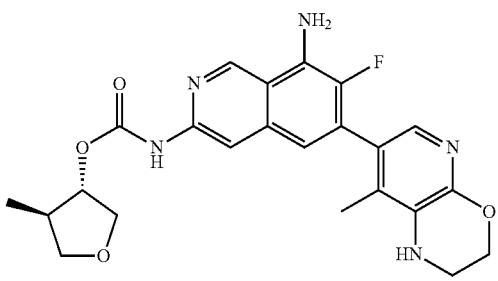

and

-continued

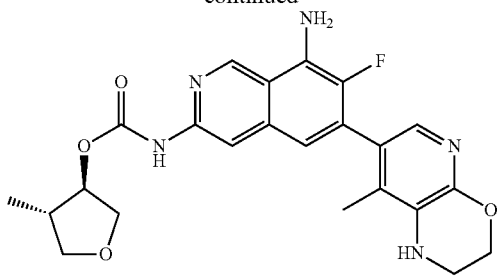

Step 1: (±)-trans-tert-Butyl 7-(8-((tert-butoxycarbonyl)amino)-7-fluoro-3-((((4-methyltetrahydrofuran-3-yl)oxy)carbonyl)amino)isoquinolin-6-yl)-8-methyl-2,3-dihydro-1H-pyrido[2,3-b][1,4]oxazine-1-carboxylate

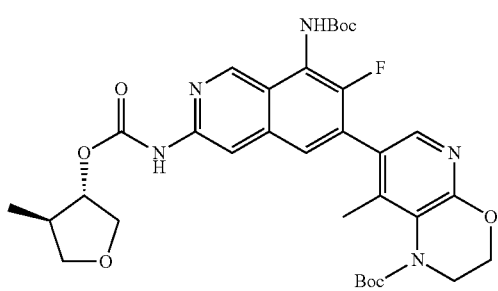

and

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (1.19 g, 2.26 mmol), DIEA (5 mL, 2.26 mmol) and (±)-trans-4-methyl-tetrahydrofuran-3-ol (578 mg, 5.66 mmol) in dichloromethane (30 mL) was added triphosgene (537 mg, 1.81 mmol) in dichloromethane (10 mL) at 0° C. The reaction was stirred for 1 h at room temperature. The reaction mixture was concentrated under vacuum. The residue was purified by flash chromatography on silica gel eluting with petroleum ether/ethyl acetate (22/78) to afford (±)-trans-tert-butyl 7-(8-((tert-butoxycarbonyl)amino)-7-fluoro-3-((((4-methyltetrahydrofuran-3-yl)oxy)carbonyl)amino)isoquinolin-6-yl)-8-methyl-2,3-dihydro-1H-pyrido[2,3-b][1,4]oxazine-1-carboxylate (900 mg, 1.377 mmol, 60.8% yield) as a yellow solid. LCMS (ESI) [M+H]$^+$=654.

Step 2: (±)-trans-(4-Methyltetrahydrofuran-3-yl) N-[8-amino-7-fluoro-6-(8-methyl-2,3-dihydro-1H-pyrido[2,3-b][1,4]oxazin-7-yl)-3-isoquinolyl]carbamate

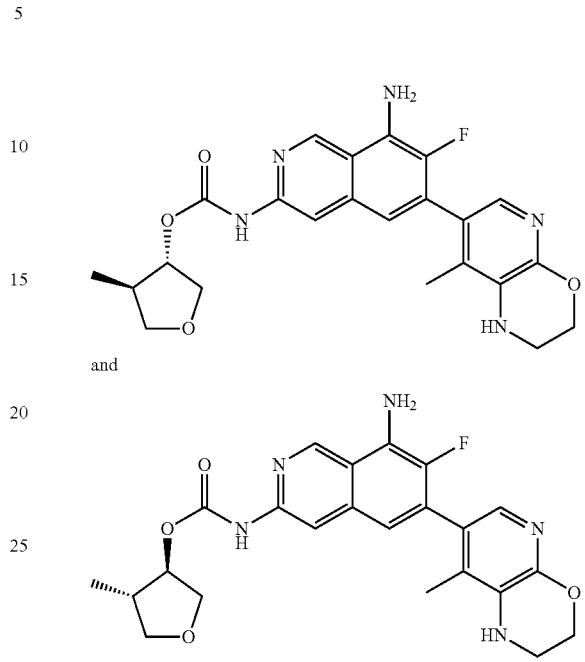

and

A solution of (±)-trans-tert-butyl 7-[8-(tert-butoxycarbonylamino)-7-fluoro-3-[[4-methyltetrahydrofuran-3-yl]oxycarbonylamino]-6-isoquinolyl]-8-methyl-2,3-dihydropyrido[2,3-b][1,4]oxazine-1-carboxylate (900 mg, 1.38 mmol) and TFA (2 mL) in dichloromethane (10 mL) was stirred at 25° C. for 1 h. The reaction was concentrated under vacuum. The residue was purified by reverse phase chromatography (acetonitrile 0-50/0.1% FA in water) to afford (±)-trans-(4-methyltetrahydrofuran-3-yl) N-[8-amino-7-fluoro-6-(8-methyl-2,3-dihydro-1H-pyrido[2,3-b][1,4]oxazin-7-yl)-3-isoquinolyl]carbamate, formate salt (271 mg, 0.543 mmol, 39.4% yield) as a yellow solid. LCMS (ESI) [M+H]$^+$=454.2, $R_T$ 2.307, method=M. $^1$H NMR (400 MHz, DMSO-$d_6$) δ 10.15 (s, 1H), 9.34 (s, 1H), 7.96 (s, 1H), 7.32 (s, 1H), 6.83 (d, J=6.0 Hz, 1H), 6.22 (s, 2H), 5.70 (s, 1H), 4.85 (s, 1H), 4.28 (s, 2H), 3.97 (q, J=7.4, 6.8 Hz, 2H), 3.75 (d, J=10.6 Hz, 2H), 3.36 (s, 2H), 3.33 (dd, J=8.2, 4.9 Hz, 1H), 1.92 (s, 3H), 1.05 (s, 3H). The racemic mixture was further purified by chiral SFC (Chiralpak IC, 150×30 mm×5 μM; Isocratic 45% methanol with 0.1% NH$_4$OH) to give the two single enantiomers:

Enantiomer 1: (3S,4R)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate (Compound 441a) (86 mg): $R_T$=1.204 min (CHIRALPAK IC; isocratic 50% MeOH with 0.1% NH$_4$OH, 2.5 min run time). LCMS (ESI) [M+H]$^+$=454.2, $R_T$=3.57 min, Method N. $^1$H NMR (400 MHz, DMSO-$d_6$) δ 10.13 (s, 1H), 9.34 (s, 1H), 7.97 (s, 1H), 7.34 (s, 1H), 6.85 (d, J=6.2 Hz, 1H), 6.20 (s, 2H), 5.70 (s, 1H), 4.85 (dt, J=4.6, 2.1 Hz, 1H), 4.34-4.26 (m, 2H), 4.03-3.91 (m, 2H), 3.75 (m, 1H), 2.34-2.32 (m, 1H), 1.93 (s, 3H), 1.06 (d, J=7.2 Hz, 3H).

Enantiomer 2: (3R,4S)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate (Compound 441b) (80 mg): $R_T$=1.777 min (CHIRALPAK IC; isocratic 50% MeOH with 0.1% NH₄OH, 2.5 min run time). LCMS (ESI) [M+H]⁺=454.2, R_T=3.56 min, Method N. ¹H NMR (400 MHz, DMSO-d₆) δ 10.12 (s, 1H), 9.33 (s, 1H), 7.97 (s, 1H), 7.33 (s, 1H), 6.85 (d, J=6.2 Hz, 1H), 6.20 (s, 2H), 5.66 (s, 1H), 4.85 (dt, J=4.6, 2.1 Hz, 1H), 4.34-4.26 (m, 2H), 4.03-3.91 (m, 2H), 3.75 (m, 1H), 3.37-3.34 (m, 3H), 2.36-2.31 (m, 1H), 1.93 (s, 3H), 1.06 (d, J=7.2 Hz, 3H).

Example 192

1-[8-Amino-7-fluoro-6-(8-methyl-2,3-dihydro-1H-pyrido[2,3-b][1,4]oxazin-7-yl)-3-isoquinolyl]-3-[(cis)-3-cyanocyclopentyl]urea (Compound 726)

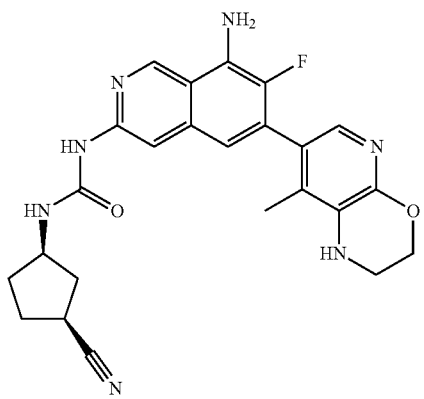 [SMILES: Cc1c(-c2cc3cc(NC(=O)N[C@@H]4CC[C@H](C#N)C4)ncc3c(N)c2F)cnc2c1NCCO2]

Step 1: tert-Butyl 7-[8-(tert-butoxycarbonylamino)-3-[[(cis)-3-cyanocyclopentyl]carbamoylamino]-7-fluoro-6-isoquinolyl]-8-methyl-2,3-dihydropyrido[2,3-b][1,4]oxazine-1-carboxylate

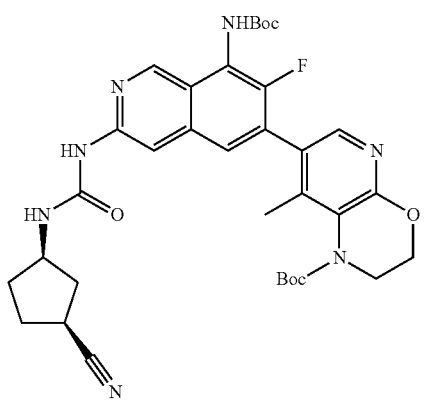 [SMILES: Cc1c(-c2cc3cc(NC(=O)N[C@@H]4CC[C@H](C#N)C4)ncc3c(NC(=O)OC(C)(C)C)c2F)cnc2c1N(C(=O)OC(C)(C)C)CCO2]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (200.0 mg, 0.31 mmol) and DMAP (37.8 mg, 0.31 mmol) in dichloromethane (10 mL) was added a solution of (cis)-3-aminocyclopentanecarbonitrile (135.8 mg, 0.93 mmol) in dichloromethane (2 mL) at 25° C. The resulting solution was stirred for 4 hours at 60° C. The resulting mixture was concentrated under vacuum and purified by flash chromatography on silica gel eluting with dichloromethane/methanol (94/6) to afford tert-butyl 7-[8-(tert-butoxycarbonylamino)-3-[[(cis)-3-cyanocyclopentyl]carbamoylamino]-7-fluoro-6-isoquinolyl]-8-methyl-2,3-dihydropyrido[2,3-b][1,4]oxazine-1-carboxylate (175 mg, 0.26 mmol, 85% yield) as a pale yellow solid. LC/MS (ESI) [M+H]⁺=662.3.

Step 2: 1-[8-Amino-7-fluoro-6-(8-methyl-2,3-dihydro-1H-pyrido[2,3-b][1,4]oxazin-7-yl)-3-isoquinolyl]-3-[(cis)-3-cyanocyclopentyl]urea

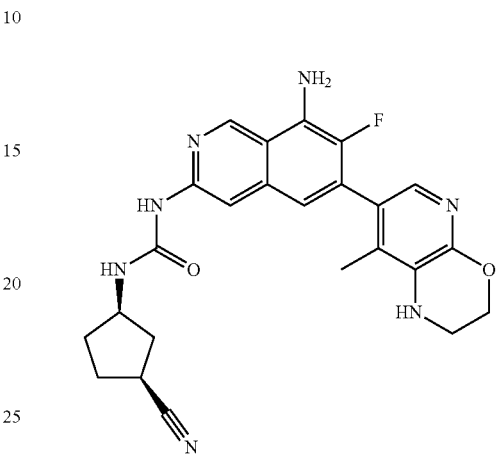

A solution of tert-butyl 7-[8-(tert-butoxycarbonylamino)-3-[[(cis)-3-cyanocyclopentyl]carbamoylamino]-7-fluoro-6-isoquinolyl]-8-methyl-2,3-dihydropyrido[2,3-b][1,4]oxazine-1-carboxylate (170.0 mg, 0.26 mmol) and TFA (1.0 mL, 0.26 mmol) in dichloromethane (5 mL) was stirred at 25° C. for 2 hours. After concentration, the residue was purified by Prep-HPLC (Column: X Bridge Prep OBD C18 Column 30×150 mm 5 μm; Water (10 mmol/L NH₄HCO₃): ACN=17% B to 39% B in 7 min; 60 mL/min) to afford 1-[8-amino-7-fluoro-6-(8-methyl-2,3-dihydro-1H-pyrido[2,3-b][1,4]oxazin-7-yl)-3-isoquinolyl]-3-[(cis)-3-cyanocyclopentyl]urea (65 mg, 0.14 mmol, 55% yield) as a white solid. LCMS (ESI) [M+H]⁺=462.2; R_T 1.839 min; Method K; ¹H NMR (400 MHz, DMSO-d₆) δ 9.29 (s, 1H), 8.87 (s, 1H), 7.86 (s, 1H), 7.35-7.20 (m, 2H), 6.75 (d, J=6.2 Hz, 1H), 6.15 (s, 2H), 5.67 (s, 1H), 4.32-4.20 (m, 2H), 4.10-4.01 (m, 1H), 3.50-3.30 (m, 2H), 3.10-3.00 (m, 1H), 2.50-2.26 (m, 2H), 2.10-1.85 (m, 5H), 1.70-1.50 (m, 2H).

Example 193

1-Propionylazetidin-3-yl (8-amino-7-fluoro-6-(4-methyl-5,6,7,8-tetrahydro-1,5-naphthyridin-3-yl)isoquinolin-3-yl)carbamate (Compound 492)

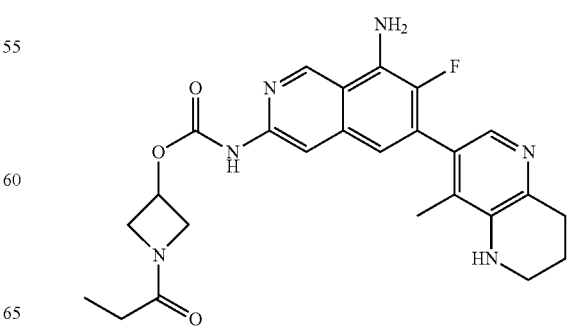

Step 1: tert-Butyl 7-[8-(tert-butoxycarbonylamino)-3-[(1-tert-butoxycarbonylazetidin-3-yl)oxycarbonylamino]-7-fluoro-6-isoquinolyl]-8-methyl-3,4-dihydro-2H-1,5-naphthyridine-1-carboxylate

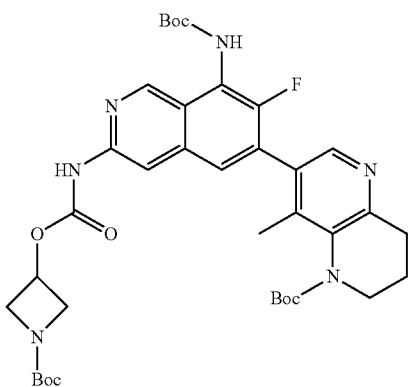 [SMILES: Cc1c(-c2cc3cc(NC(=O)OC4CN(C(=O)OC(C)(C)C)C4)ncc3c(NC(=O)OC(C)(C)C)c2F)cnc2c1N(C(=O)OC(C)(C)C)CCC2]

To a solution of tert-butyl 7-[3-amino-8-(tert-butoxycarbonylamino)-7-fluoro-6-isoquinolyl]-8-methyl-3,4-dihydro-2H-1,5-naphthyridine-1-carboxylate (300 mg, 0.57 mmol) and 1-boc-3-hydroxyazetidine (500 mg, 2.89 mmol) in dichloromethane (50 mL) was added DIEA (200 mg, 1.55 mmol) at room temperature. Then triphosgene (250 mg, 0.84 mmol) was added and the mixture was stirred at 0° C. for 1 hour. The reaction solution was concentrated under vacuum and the residue was purified by flash chromatography on silica gel eluting with petroleum ether/ethyl acetate (1/1) to afford tert-butyl 7-[8-(tert-butoxycarbonylamino)-3-[(1-tert-butoxycarbonylazetidin-3-yl)oxycarbonylamino]-7-fluoro-6-isoquinolyl]-8-methyl-3,4-dihydro-2H-1,5-naphthyridine-1-carboxylate (220 mg, 0.304 mmol, 53.1% yield) as a yellow solid. LCMS (ESI) [M+H]$^+$=723.

Step 2: Azetidin-3-yl N-[8-amino-7-fluoro-6-(4-methyl-5,6,7,8-tetrahydro-1,5-naphthyridin-3-yl)-3-isoquinolyl]carbamate

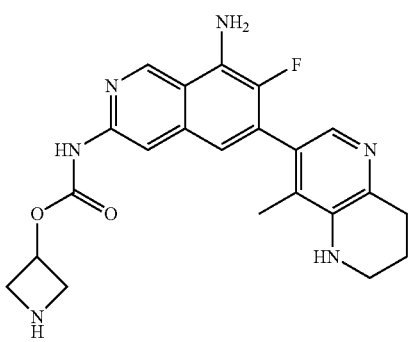 [SMILES: Cc1c(-c2cc3cc(NC(=O)OC4CNC4)ncc3c(N)c2F)cnc2c1NCCC2]

To a solution of tert-butyl 7-[8-(tert-butoxycarbonylamino)-3-[(1-tert-butoxycarbonylazetidin-3-yl)oxycarbonylamino]-7-fluoro-6-isoquinolyl]-8-methyl-3,4-dihydro-2H-1,5-naphthyridine-1-carboxylate (220 mg, 0.30 mmol) in dichloromethane (10 mL) was added HCl/dioxane (2 mL, 3 mol/L) at room temperature. The resulting solution was stirred for 1 h at 25° C. and then concentrated under vacuum. The crude product was used directly in the next step without purification. LCMS (ESI) [M+H]$^+$=423.

Step 3: 1-Propionylazetidin-3-yl (8-amino-7-fluoro-6-(4-methyl-5,6,7,8-tetrahydro-1,5-naphthyridin-3-yl)isoquinolin-3-yl)carbamate

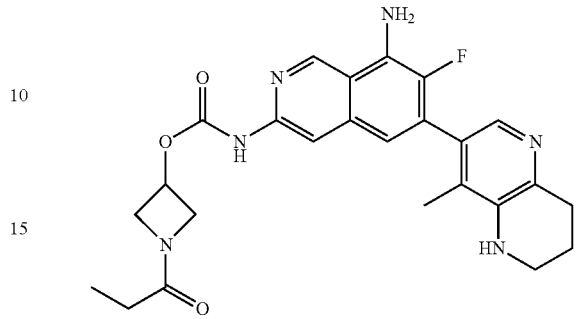

To a solution of azetidin-3-yl N-[8-amino-7-fluoro-6-(4-methyl-5,6,7,8-tetrahydro-1,5-naphthyridin-3-yl)-3-isoquinolyl]carbamate (50 mg, 0.12 mmol) and propionic anhydride (20 mg, 0.15 mmol) in dichloromethane (5 mL) was added TEA (20 mg, 0.20 mmol) at room temperature. The reaction was stirred for 1 h at 25° C. and concentrated under vacuum. The crude product was purified by Prep-HPLC (Column: X Bridge Shield RP18 OBD Column 19*250 mm, 10 μm; Mobile Phase A: Water (0.1% FA), Mobile Phase B: MeOH; Flow rate: 25 mL/min; Gradient: 25% B to 37% B in 10 min) to afford (1-propanoylazetidin-3-yl) N-[8-amino-7-fluoro-6-(4-methyl-5,6,7,8-tetrahydro-1,5-naphthyridin-3-yl)-3-isoquinolyl]carbamate (22.6 mg, 0.0472 mmol, 39.9% yield) as a yellow solid. LCMS (ESI) [M+H]$^+$=479.2, R$_T$ 1.765 min; Method J. $^1$H NMR (400 MHz, DMSO-d$_6$) δ 10.36 (s, 1H), 9.36 (s, 1H), 7.96 (s, 1H), 7.57 (s, 1H), 6.84 (d, J=6.1 Hz, 1H), 6.23 (s, 2H), 5.45-5.39 (m, 1H), 5.20 (td, J=6.8, 3.5 Hz, 1H), 4.52-4.43 (m, 1H), 4.20 (dd, J=10.7, 6.8 Hz, 1H), 4.11 (dd, J=9.8, 4.0 Hz, 1H), 3.81 (dd, J=10.7, 4.0 Hz, 1H), 3.35 (t, J=6.5 Hz, 2H), 2.85 (t, J=6.5 Hz, 2H), 2.09 (qd, J=7.4, 1.6 Hz, 2H), 1.92 (s, 2H), 1.86 (d, J=1.5 Hz, 3H), 0.96 (t, J=7.5 Hz, 3H).

Example 194

(3-Fluoro-1-methyl-azetidin-3-yl)methyl N-[8-amino-7-fluoro-6-(8-methyl-2,3-dihydro-1H-pyrido[2,3-b][1,4]oxazin-7-yl)-3-isoquinolyl]carbamate (Compound 450)

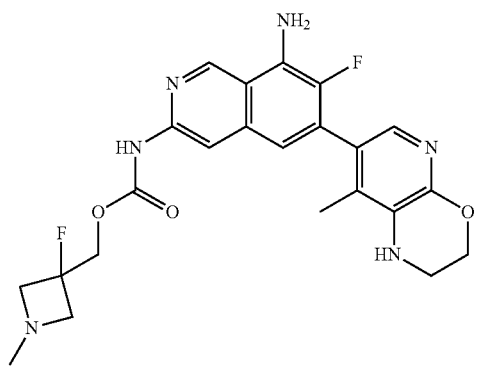 [SMILES: Cc1c(-c2cc3cc(NC(=O)OCC4(F)CN(C)C4)ncc3c(N)c2F)cnc2c1NCCO2]

Step 1: tert-Butyl 7-[8-(tert-butoxycarbonylamino)-3-[(1-tert-butoxycarbonyl-3-fluoro-azetidin-3-yl)methoxycarbonylamino]-7-fluoro-6-isoquinolyl]-8-methyl-2,3-dihydropyrido[2,3-b][1,4]oxazine-1-carboxylate

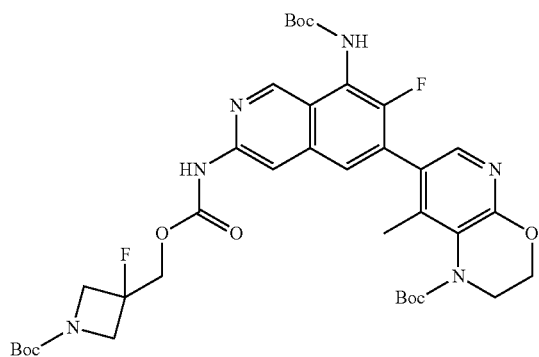 [SMILES: Cc1c(-c2cc3cc(NC(=O)OCC4(F)CN(C(=O)OC(C)(C)C)C4)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (150 mg, 0.29 mmol), tert-butyl 3-fluoro-3-(hydroxymethyl)azetidine-1-carboxylate (116 mg, 0.57 mmol) and DIEA (108 mg, 0.84 mmol) in dichloromethane (15 mL) was added triphosgene (120 mg, 0.40 mmol) at 0° C. The reaction was stirred for 2 hours at 0° C. The reaction mixture was concentrated under vacuum. The residue was purified by flash chromatography on silica gel eluting with methanol/dichloromethane (15%) to afford tert-butyl 7-[8-(tert-butoxycarbonylamino)-3-[(1-tert-butoxycarbonyl-3-fluoro-azetidin-3-yl)methoxycarbonylamino]-7-fluoro-6-isoquinolyl]-8-methyl-2,3-dihydropyrido[2,3-b][1,4]oxazine-1-carboxylate (85 mg, 0.101 mmol, 35.4% yield) as a yellow solid. LCMS (ESI) [M+H]$^+$=757.0.

Step 2: (3-Fluoroazetidin-3-yl)methyl N-[8-amino-7-fluoro-6-(8-methyl-2,3-dihydro-1H-pyrido[2,3-b][1,4]oxazin-7-yl)-3-isoquinolyl]carbamate

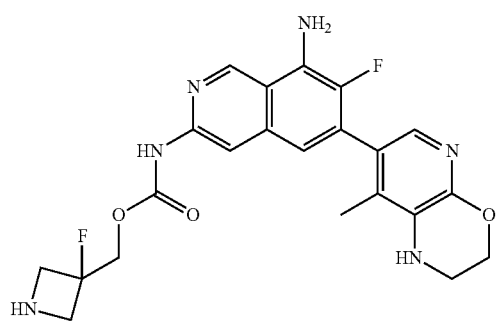 [SMILES: Cc1c(-c2cc3cc(NC(=O)OCC4(F)CNC4)ncc3c(N)c2F)cnc2c1NCCO2]

A solution of tert-butyl 7-[8-(tert-butoxycarbonylamino)-3-[(1-tert-butoxycarbonyl-3-fluoro-azetidin-3-yl)methoxycarbonylamino]-7-fluoro-6-isoquinolyl]-8-methyl-2,3-dihydropyrido[2,3-b][1,4]oxazine-1-carboxylate (160 mg, 0.19 mmol) in dichloromethane (16 mL) and TFA (4 mL) was stirred at room temperature for 2 hours. The reaction mixture was concentrated under vacuum to afford (3-fluoroazetidin-3-yl)methyl N-[8-amino-7-fluoro-6-(8-methyl-2,3-dihydro-1H-pyrido[2,3-b][1,4]oxazin-7-yl)-3-isoquinolyl]carbamate (85 mg, 0.149 mmol, 78.3% yield) as a yellow solid. LCMS (ESI) [M+H]$^+$=456.0.

Step 3: (3-Fluoro-1-methyl-azetidin-3-yl)methyl N-[8-amino-7-fluoro-6-(8-methyl-2,3-dihydro-1H-pyrido[2,3-b][1,4]oxazin-7-yl)-3-isoquinolyl]carbamate

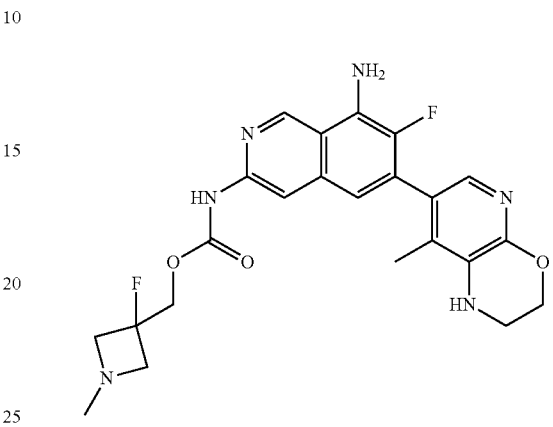

A solution of (3-fluoroazetidin-3-yl)methyl N-[8-amino-7-fluoro-6-(8-methyl-2,3-dihydro-1H-pyrido[2,3-b][1,4]oxazin-7-yl)-3-isoquinolyl]carbamate (85 mg, 0.17 mmol) in methyl alcohol (10 mL) and formaldehyde (40%, 15 mg, 0.47 mmol) was stirred at room temperature for 1 hour. Then NaBH$_4$ (18 mg, 0.46 mmol) was added. The mixture was stirred at room temperature for 1 hour and then concentrated under vacuum. The residue was purified by Prep-HPLC to afford (3-fluoro-1-methyl-azetidin-3-yl)methyl N-[8-amino-7-fluoro-6-(8-methyl-2,3-dihydro-1H-pyrido[2,3-b][1,4]oxazin-7-yl)-3-isoquinolyl]carbamate (7.8 mg, 0.015 mmol, 8.9% yield) as a white solid. LCMS (ESI) [M+H]$^+$=471.2, R$_T$ 2.204 min, Method M; $^1$H NMR (400 MHz, DMSO-d$_6$) δ 10.24 (s, 1H), 9.35 (s, 1H), 7.96 (s, 1H), 7.33 (s, 1H), 6.85 (d, J=6.2 Hz, 1H), 6.21 (s, 2H), 5.67 (s, 1H), 4.48 (s, 1H), 4.42 (s, 1H), 4.29 (d, J=4.8 Hz, 2H), 3.51 (dd, J=12.5, 8.8 Hz, 2H), 3.36 (s, 2H), 3.11 (dd, J=21.6, 8.4 Hz, 2H), 2.32 (s, 3H), 1.92 (d, J=1.6 Hz, 3H).

Example 195

(1r,3r)-3-Methoxycyclobutyl (8-amino-7-fluoro-6-(8-methyl-2,3-dihydro-1H-pyrido[2,3-b][1,4]oxazin-7-yl)isoquinolin-3-yl)carbamate (Compound 576a)

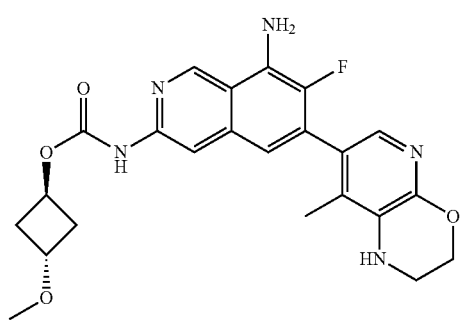 [SMILES: CO[C@H]1C[C@H](OC(=O)Nc2cc3cc(-c4cnc5c(c4C)NCCO5)c(F)c(N)c3cn2)C1]

Step 1: tert-Butyl 7-(8-((tert-butoxycarbonyl)amino)-7-fluoro-3-((((1r,3r)-3-methoxycyclobutoxy)carbonyl)amino)isoquinolin-6-yl)-8-methyl-3,4-dihydro-1,5-naphthyridine-1(2H)-carboxylate

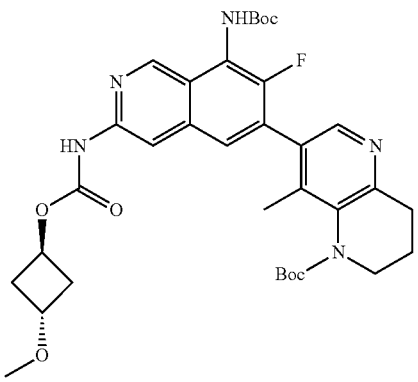 [SMILES: CO[C@H]1C[C@H](OC(=O)Nc2cc3cc(-c4cnc5c(c4C)N(C(=O)OC(C)(C)C)CCC5)c(F)c(NC(=O)OC(C)(C)C)c3cn2)C1]

To a solution of tert-butyl 7-[3-amino-8-(tert-butoxycarbonylamino)-7-chloro-6-isoquinolyl]-8-methyl-2,3-dihydropyrido[2,3-b][1,4]oxazine-1-carboxylate (200.0 mg, 0.37 mmol), N,N-diisopropylethylamine (0.32 mL, 1.84 mmol) and trans-3-methoxycyclobutanol (76.0 mg, 0.74 mmol) in dichloromethane (20 mL) was added triphosgene (76.0 mg, 0.26 mmol). The mixture was stirred at 0° C. for 30 min. The reaction was quenched with water and extracted with dichloromethane. The organic layers were combined, dried over anhydrous sodium sulfate and concentrated under vacuum. The residue was purified by flash chromatography on silica gel eluting with dichloromethane/methanol (50/1) to afford tert-butyl 7-(8-((tert-butoxycarbonyl)amino)-7-fluoro-3-((((1r,3r)-3-methoxycyclobutoxy)carbonyl)amino)isoquinolin-6-yl)-8-methyl-3,4-dihydro-1,5-naphthyridine-1(2H)-carboxylate (200 mg, 0.298 mmol, 80.9% yield) as a yellow solid. LCMS (ESI) [M+H]$^+$=652.3.

Step 2: (1r,3r)-3-Methoxycyclobutyl (8-amino-7-fluoro-6-(8-methyl-2,3-dihydro-1H-pyrido[2,3-b][1,4]oxazin-7-yl)isoquinolin-3-yl)carbamate

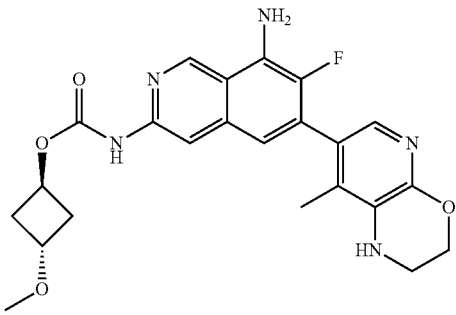 [SMILES: CO[C@H]1C[C@H](OC(=O)Nc2cc3cc(-c4cnc5c(c4C)NCCO5)c(F)c(N)c3cn2)C1]

To a solution of tert-butyl 7-[8-(tert-butoxycarbonylamino)-7-fluoro-3-[(3-methoxycyclobutoxy)carbonylamino]-6-isoquinolyl]-8-methyl-2,3-dihydropyrido[2,3-b][1,4]oxazine-1-carboxylate (200 mg, 0.30 mmol) in dichloromethane (18 mL) was added trifluoroacetic acid (6 mL). The mixture was stirred at room temperature for 30 min. The reaction mixture was concentrated under vacuum. The residue was purified by Prep-HPLC (Column: X select CSH OBD Column 30*150 m, 5 μm mobile Phase A: Water (0.1% FA), Mobile Phase B: ACN; Flow rate: 60 mL/min; Gradient: 11% B to 32% B in 10 min) to afford (1r,3r)-3-methoxycyclobutyl (8-amino-7-fluoro-6-(8-methyl-2,3-dihydro-1H-pyrido[2,3-b][1,4]oxazin-7-yl)isoquinolin-3-yl)carbamate (23.8 mg, 0.053 mmol, 18% yield) as a white solid. Stereochemistry arbitrarily assigned. LCMS (ESI) [M+H]=454.2, $R_T$ 2.031 min, Method K; $^1$H NMR (400 MHz, DMSO-d$_6$) δ 9.22 (s, 1H), 8.04 (s, 1H), 7.38 (s, 1H), 6.93 (d, J=6.4 Hz, 1H), 4.79-4.72 (m, 1H), 4.41 (t, J=4.4 Hz, 2H), 3.71-3.65 (m, 1H), 3.51-3.48 (m, 2H), 3.15 (s, 3H), 2.87-2.81 (m, 2H), 2.11-2.02 (m, 2H), 2.02 (s, 3H).

Example 196

(1s,3s)-3-(difluoromethyl)cyclobutyl (8-amino-7-fluoro-6-(8-methyl-2,3-dihydro-1H-pyrido[2,3-b][1,4]oxazin-7-yl)isoquinolin-3-yl)carbamate and (1r,3r)-3-(difluoromethyl)cyclobutyl (8-amino-7-fluoro-6-(8-methyl-2,3-dihydro-1H-pyrido[2,3-b][1,4]oxazin-7-yl)isoquinolin-3-yl)carbamate (Compound 577a and Compound 577b)

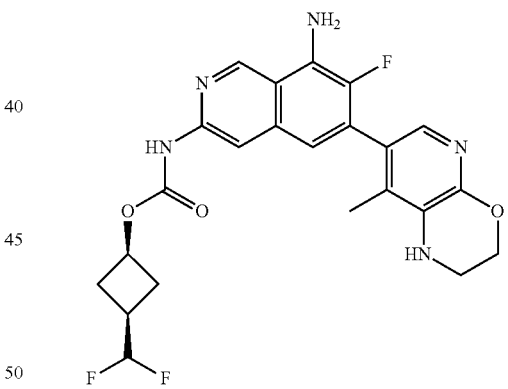

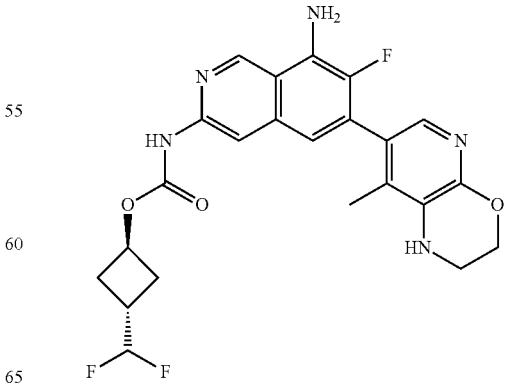

Step 1: tert-Butyl 7-[8-(tert-butoxycarbonylamino)-3-[[3-(difluoromethyl)cyclobutoxy]carbonylamino]-7-fluoro-6-isoquinolyl]-8-methyl-2,3-dihydropyrido[2,3-b][1,4]oxazine-1-carboxylate

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (380 mg, 0.72 mmol) and 3-(difluoromethyl)cyclobutanol (180 mg, 1.47 mmol) in dichloromethane (20 mL) and DIEA (300 mg, 2.33 mmol) was added triphosgene (300 mg, 1.01 mmol) at 0° C. The reaction was stirred for 1 hour at 0° C. The reaction mixture was concentrated under vacuum. The residue was purified by flash chromatography on silica gel eluting with dichloromethane/methanol (7%) to afford tert-butyl 7-[8-(tert-butoxycarbonylamino)-3-[[3-(difluoromethyl)cyclobutoxy]carbonylamino]-7-fluoro-6-isoquinolyl]-8-methyl-2,3-dihydropyrido[2,3-b][1,4]oxazine-1-carboxylate (200 mg, 0.297 mmol, 41.1% yield) as a yellow solid. LCMS (ESI) [M+H]$^+$=674.0.

Step 2: (1s,3s)-3-(Difluoromethyl)cyclobutyl (8-amino-7-fluoro-6-(8-methyl-2,3-dihydro-1H-pyrido[2,3-b][1,4]oxazin-7-yl)isoquinolin-3-yl)carbamate and (1r,3r)-3-(Difluoromethyl)cyclobutyl (8-amino-7-fluoro-6-(8-methyl-2,3-dihydro-1H-pyrido[2,3-b][1,4]oxazin-7-yl)isoquinolin-3-yl)carbamate

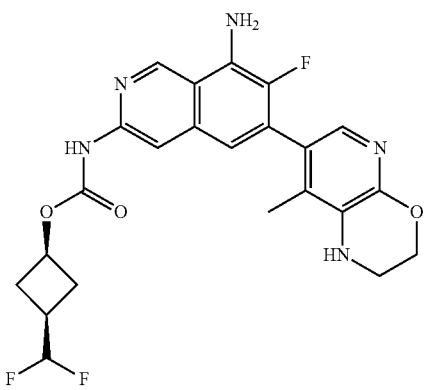

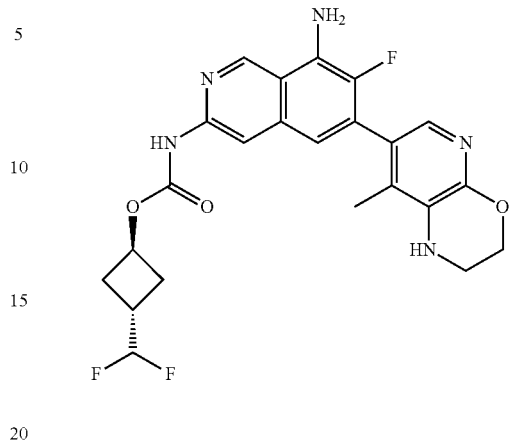

A solution of tert-butyl 7-[8-(tert-butoxycarbonylamino)-3-[[3-(difluoromethyl)cyclobutoxy]carbonylamino]-7-fluoro-6-isoquinolyl]-8-methyl-2,3-dihydropyrido[2,3-b][1,4]oxazine-1-carboxylate (120 mg, 0.18 mmol) in dichloromethane (10 mL) and 2,2,2-trifluoroacetic acid (2 mL) was stirred at room temperature for 2 hours. The reaction was concentrated under vacuum. The residue was purified by Prep-HPLC (Column: X select CSH OBD Column 30*150 mm 5 μm; Mobile Phase A: Water (0.1% FA), Mobile Phase B: ACN; Flow rate: 60 mL/min; Gradient: 20% B to 43% B in 10 min). Chiral-HPLC resolution afforded two enantiomers. Stereochemistry was arbitrarily assigned.

Enantiomer 1: (Compound 577a) (40 mg, 0.0827 mmol, 46.4% yield). $R_T$ 10.917 min (CHIRALPAK IA, 2*25 cm, 5 μm; Mobile Phase A: Hex:DCM=3:1 (10 mm NH$_3$-MEOH), Mobile Phase B: EtOH; Flow rate: 18 mL/min; Gradient: 50 B to 50 B in 15 min). LCMS (ESI) [M+H]$^+$=474.2, $R_T$ 1.321 min, Method J. $^1$H NMR (400 MHz, DMSO-d$_6$) δ 10.13 (s, 1H), 9.34 (s, 1H), 7.95 (s, 1H), 7.32 (s, 1H), 6.84 (d, J=6.1 Hz, 1H), 6.20 (s, 3H), 5.67 (d, J=2.8 Hz, 1H), 5.05 (p, J=7.2 Hz, 1H), 4.29 (t, J=4.4 Hz, 2H), 3.36 (t, J=4.4 Hz, 2H), 2.73 (dtt, J=11.9, 7.5, 4.0 Hz, 1H), 2.42 (td, J=7.7, 3.6 Hz, 2H), 2.36-2.25 (m, 2H), 1.92 (d, J=1.6 Hz, 3H).

Enantiomer 2: (Compound 577b) (8.6 mg, 0.0181 mmol, 10.2% yield). $R_T$ 14.166 min (CHIRALPAK IA, 2*25 cm, 5 μm; Mobile Phase A: Hex:DCM=3:1 (10 mm NH$_3$-MEOH), Mobile Phase B: EtOH; Flow rate: 18 mL/min; Gradient: 50 B to 50 B in 15 min). LCMS (ESI) [M+H]$^+$=474.2, $R_T$ 1.321 min, Method J; $^1$H NMR (400 MHz, DMSO-d$_6$) δ 10.13 (s, 1H), 9.34 (s, 1H), 7.95 (s, 1H), 7.32 (s, 1H), 6.84 (d, J=6.1 Hz, 1H), 6.20 (s, 3H), 5.67 (d, J=2.8 Hz, 1H), 5.05 (p, J=7.2 Hz, 1H), 4.29 (t, J=4.4 Hz, 2H), 3.36 (t, J=4.4 Hz, 2H), 2.73 (dtt, J=11.9, 7.5, 4.0 Hz, 1H), 2.42 (td, J=7.7, 3.6 Hz, 2H), 2.36-2.25 (m, 2H), 1.92 (d, J=1.6 Hz, 3H).

Example 197

[(6R)-6,7-Dihydro-5H-pyrrolo[1,2-b][1,2,4]triazol-6-yl]N-[8-amino-7-fluoro-6-(8-methyl-2,3-dihydro-1H-pyrido[2,3-b][1,4]oxazin-7-yl)-3-isoquinolyl]carbamate and [(6S)-6,7-Dihydro-5H-pyrrolo[1,2-b][1,2,4]triazol-6-yl]N-[8-amino-7-fluoro-6-(8-methyl-2,3-dihydro-1H-pyrido[2,3-b][1,4]oxazin-7-yl)-3-isoquinolyl]carbamate (Compound 578a and Compound 578b)

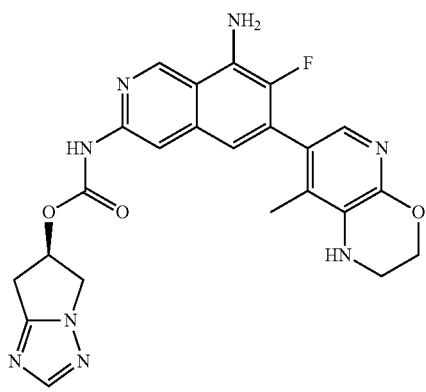

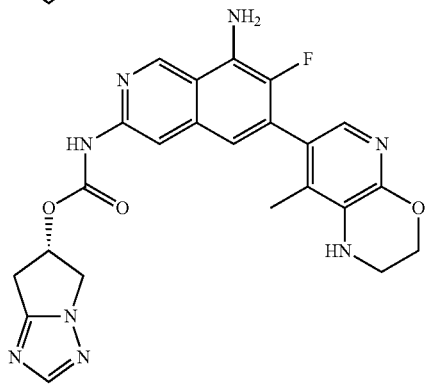

Step 1: tert-Butyl 7-[8-(tert-butoxycarbonylamino)-3-(6,7-dihydro-5H-pyrrolo[1,2-b][1,2,4]triazol-6-yloxycarbonylamino)-7-fluoro-6-isoquinolyl]-8-methyl-2,3-dihydropyrido[2,3-b][1,4]oxazine-1-carboxylate

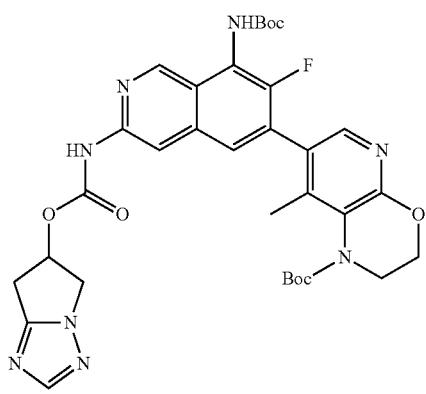

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (154.8 mg, 0.24 mmol) and DMAP (29.3 mg, 0.24 mmol) in 1,4-dioxane (5 mL) was added a solution of 6,7-dihydro-5H-pyrrolo[1,2-b][1,2,4]triazol-6-ol (90.0 mg, 0.72 mmol) in 1,4-dioxane (1 mL) at 25° C. The reaction was stirred for 3 hours at 90° C. The reaction mixture was concentrated under vacuum. The residue was purified by flash chromatography on silica gel eluting with dichloromethane/methanol (92/8) to afford tert-butyl 7-[8-(tert-butoxycarbonylamino)-3-(6,7-dihydro-5H-pyrrolo[1,2-b][1,2,4]triazol-6-yloxycarbonylamino)-7-fluoro-6-isoquinolyl]-8-methyl-2,3-dihydropyrido[2,3-b][1,4]oxazine-1-carboxylate (123 mg, 0.18 mmol, 76% yield) as a pale yellow solid. LCMS (ESI) $[M+H]^+=677.3$ Step 2: [(6R)-6,7-Dihydro-5H-pyrrolo[1,2-b][1,2,4]triazol-6-yl]N-[8-amino-7-fluoro-6-(8-methyl-2,3-dihydro-1H-pyrido[2,3-b][1,4]oxazin-7-yl)-3-isoquinolyl]carbamate and [(6S)-6,7-Dihydro-5H-pyrrolo[1,2-b][1,2,4]triazol-6-yl]N-[8-amino-7-fluoro-6-(8-methyl-2,3-dihydro-1H-pyrido[2,3-b][1,4]oxazin-7-yl)-3-isoquinolyl]carbamate

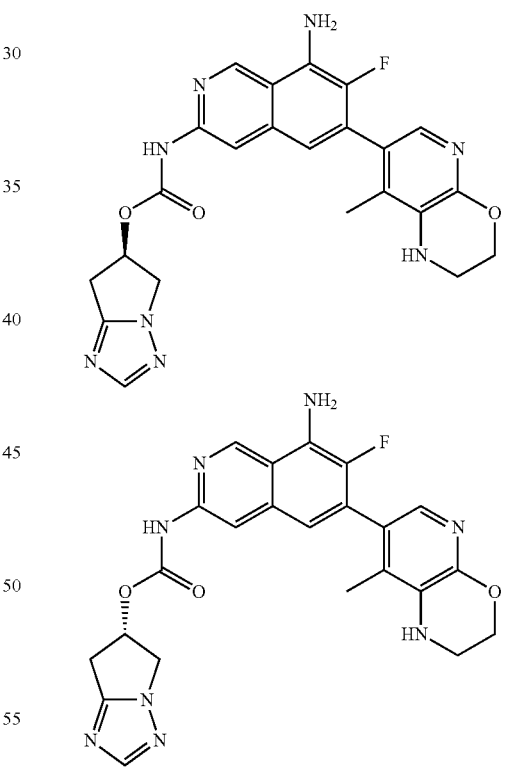

A solution of tert-butyl 7-[8-(tert-butoxycarbonylamino)-3-(6,7-dihydro-5H-pyrrolo[1,2-b][1,2,4]triazol-6-yloxycarbonylamino)-7-fluoro-6-isoquinolyl]-8-methyl-2,3-dihydropyrido[2,3-b][1,4]oxazine-1-carboxylate (120.0 mg, 0.18 mmol) and TFA (2.5 mL) in dichloromethane (5 mL) was stirred at 25° C. for 30 minutes. After concentration, the residue was purified by Prep-HPLC (Column: X select CSH OBD Column 30*150 mm, 5 μm; Water (0.1% FA): ACN=5% B to 31% B in 7 min; 60 mL/min) to afford a racemate. The racemic product was separated by chiral-HPLC to afford two enantiomers. Absolute stereochemistry was arbitrarily assigned.

Enantiomer 1 (Compound 578a, 11.2 mg, 0.024 mmol, 13% yield). $R_T$ 2.251 min (CHIRALPAK ID-3 0.46*5 cm; 3 μm; MTBE (0.1% DEA):MeOH=50:50; 1.0 ml/min). LCMS (ESI) [M+H]$^+$=476.2, $R_T$ 1.873 min, Method M. $^1$H NMR (300 MHz, DMSO-d$_6$) δ 10.29 (s, 1H), 9.34 (s, 1H), 8.00 (s, 2H), 7.34 (s, 1H), 6.87 (d, J=6.2 Hz, 1H), 6.23 (s, 2H), 5.92 (t, J=6.3 Hz, 1H), 5.68 (s, 1H), 4.60-4.51 (m, 1H), 4.35-4.20 (m, 3H), 3.44-3.30 (m, 4H), 1.93 (s, 3H).

Enantiomer 2 (Compound 578b, 10.9 mg, 0.023 mmol, 13% yield). $R_T$ 3.276 min (CHIRALPAK ID-3 0.46*5 cm; 3 μm; MTBE (0.1% DEA):MeOH=50:50; 1.0 ml/min). LCMS (ESI) [M+H]$^+$=476.2, $R_T$ 1.873 min, Method M; $^1$H NMR (300 MHz, DMSO-d$_6$) δ 10.29 (s, 1H), 9.34 (s, 1H), 8.00 (s, 2H), 7.34 (s, 1H), 6.87 (d, J=6.2 Hz, 1H), 6.23 (s, 2H), 5.92 (t, J=6.3 Hz, 1H), 5.68 (s, 1H), 4.60-4.51 (m, 1H), 4.35-4.20 (m, 3H), 3.44-3.30 (m, 4H), 1.93 (s, 3H).

Example 198

1,1-Dioxidotetrahydro-2H-thiopyran-4-yl (8-amino-7-fluoro-6-(4-methyl-5,6,7,8-tetrahydro-1,5-naphthyridin-3-yl)isoquinolin-3-yl)carbamate (Compound 579)

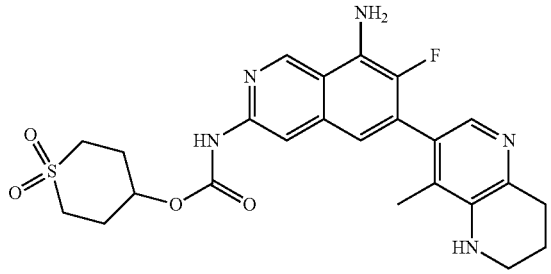 [SMILES: Cc1c(-c2cc3cc(NC(=O)OC4CCS(=O)(=O)CC4)ncc3c(N)c2F)cnc2c1NCCC2]

Step 1: tert-Butyl 7-(8-((tert-butoxycarbonyl)amino)-3-((((1,1-dioxidotetrahydro-2H-thiopyran-4-yl)oxy)carbonyl)amino)-7-fluoroisoquinolin-6-yl)-8-methyl-3,4-dihydro-1,5-naphthyridine-1(2H)-carboxylate

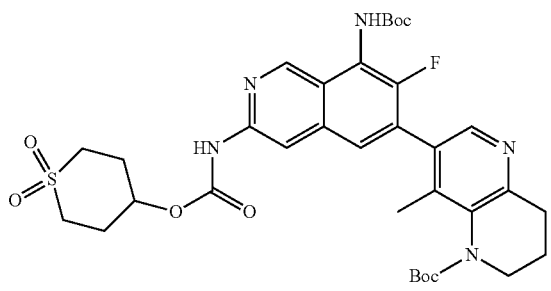 [SMILES: Cc1c(-c2cc3cc(NC(=O)OC4CCS(=O)(=O)CC4)ncc3c(NC(=O)OC(C)(C)C)c2F)cnc2c1N(C(=O)OC(C)(C)C)CCC2]

To a solution of tert-butyl 7-[3-amino-8-(tert-butoxycarbonylamino)-7-fluoro-6-isoquinolyl]-8-methyl-3,4-dihydro-2H-1,5-naphthyridin-5-ium-1-carboxylate (100.0 mg, 0.19 mmol), tetrahydro-2H-thiopyran-4-ol 1,1-dioxide (57.26 mg, 0.38 mmol) and N,N-diisopropylethylamine (122.95 mg, 0.95 mmol) in dichloromethane (4 mL) was added triphosgene (56.57 mg, 0.19 mmol) at 0° C. The mixture was stirred at room temperature for 2 hours. The reaction was quenched with water. The reaction mixture was extracted with dichloromethane. The organic layers were combined, concentrated under vacuum and purified by flash chromatography on silica gel eluting with dichloromethane/methanol (10/1) to afford tert-butyl 7-[8-(tert-butoxycarbonylamino)-3-[(1,1-dioxothian-4-yl)oxycarbonylamino]-7-fluoro-6-isoquinolyl]-8-methyl-3,4-dihydro-2H-1,5-naphthyridine-1-carboxylate (100 mg, 0.143 mmol, 75% yield) as a yellow solid. LCMS (ESI) [M+H]$^+$=700.3.

Step 2: 1,1-Dioxidotetrahydro-2H-thiopyran-4-yl (8-amino-7-fluoro-6-(4-methyl-5,6,7,8-tetrahydro-1,5-naphthyridin-3-yl)isoquinolin-3-yl)carbamate

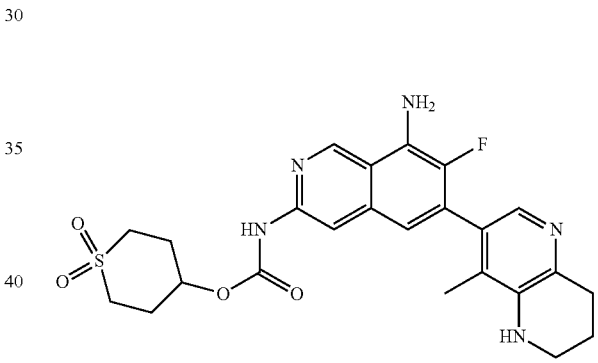

To a solution of tert-butyl 7-[8-(tert-butoxycarbonylamino)-3-[(1,1-dioxothian-4-yl)oxycarbonylamino]-7-fluoro-6-isoquinolyl]-8-methyl-3,4-dihydro-2H-1,5-naphthyridine-1-carboxylate (90.0 mg, 0.13 mmol) in dichloromethane (2 mL) was added trifluoroacetic acid (1.0 mL). The reaction mixture was stirred at room temperature for 2 hours. The resulting solution was concentrated under vacuum. The residue was dissolved in dichloromethane and adjusted to pH 8 with triethylamine. The mixture was concentrated under vacuum. The residue was purified by Pre-HPLC (Column: X select CSH OBD Column 30*150 mm, 5 μm; Mobile Phase A: Water (0.1% FA), Mobile Phase B: ACN; Flow rate: 60 mL/min; Gradient: 5% B to 17% B in 10 min) to afford (1,1-dioxothian-4-yl) N-[8-amino-7-fluoro-6-(4-methyl-5,6,7,8-tetrahydro-1,5-naphthyridin-3-yl)-3-isoquinolyl]carbamate (32.1 mg, 0.064 mmol, 50% yield) as a yellow solid. LCMS (ESI) [M+H]$^+$=500.2, $R_T$ 2.194 min; Method M. $^1$H NMR (300 MHz, DMSO-d$_6$) δ 10.17 (s, 1H), 9.38 (s, 1H), 7.98 (s, 1H), 7.64 (s, 1H), 6.87 (d, J=6.1 Hz, 1H), 6.26 (s, 2H), 5.62 (s, 1H), 4.99-5.02 (m, 1H), 3.28-3.16 (m, 6H), 2.89 (t, J=6.4 Hz, 2H), 2.21 (q, J=5.5, 4.8 Hz, 4H), 1.98-1.87 (m, 5H)

Example 199

7-Azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate (Compound 580)

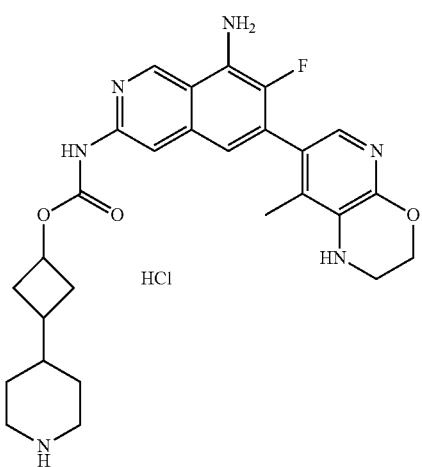 [SMILES: Cc1c(-c2cc3cc(NC(=O)OC4CC(C5CCNCC5)C4)ncc3c(N)c2F)cnc2c1NCCO2 ; Cl]

Step 1: tert-Butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-2,3-dihydropyrido[2,3-b][1,4]oxazine-1-carboxylate

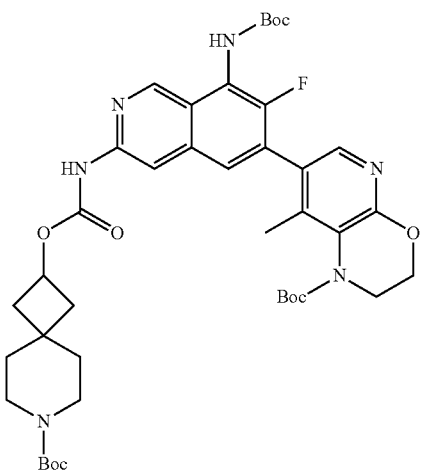 [SMILES: Cc1c(-c2cc3cc(NC(=O)OC4CC5(CCN(C(=O)OC(C)(C)C)CC5)C4)ncc3c(NC(=O)OC(C)(C)C)c2F)cnc2c1N(C(=O)OC(C)(C)C)CCO2]

To a solution of tert-butyl 2-hydroxy-7-azaspiro[3.5]nonane-7-carboxylate (920 mg, 3.81 mmol) and DIEA (490 mg, 3.8 mmol) in dichloromethane (50 mL) was added triphosgene (300 mg, 1.01 mmol) at 0° C. The reaction was stirred for 30 min at 0° C. Then tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (1000 mg, 1.9 mmol) and DIEA (490 mg, 3.8 mmol) in dichloromethane (10 mL) was added. The mixture was stirred at 0° C. for 1 hour. The reaction was quenched by water and then concentrated under vacuum. The residue was purified by flash chromatography on silica gel eluting with petroleum ether/ethyl acetate (1/2) to afford tert-butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-2,3-dihydropyrido[2,3-b][1,4]oxazine-1-carboxylate (600 mg, 0.757 mmol, 39.8% yield) as a yellow solid. LCMS (ESI) [M+H]$^+$=793.

Step 2: 7-Azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate

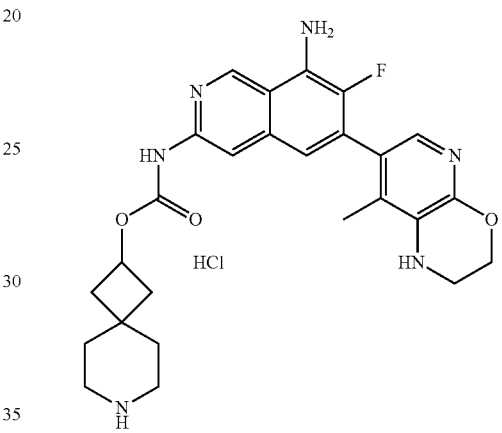

To a solution of tert-butyl 7-[8-(tert-butoxycarbonylamino)-3-[(7-tert-butoxycarbonyl-7-azaspiro[3.5]nonan-2-yl)oxycarbonylamino]-7-fluoro-6-isoquinolyl]-8-methyl-2,3-dihydropyrido[2,3-b][1,4]oxazine-1-carboxylate (600 mg, 0.76 mmol) in dichloromethane (20 mL) was added TFA (4 mL) at room temperature. The reaction was stirred for 1 h at 25° C. and then concentrated under vacuum. The residue was purified by Prep-HPLC (Column: X Bridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 5 B to 43 B in 7 min) to afford 7-azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate. The product dissolved in methanol (50 mL) was treated with a 1,4-dioxane solution of HCl (0.04 M) to afford 7-azaspiro[3.5]nonan-2-yl N-[8-amino-7-fluoro-6-(8-methyl-2,3-dihydro-1H-pyrido[2,3-b][1,4]oxazin-7-yl)-3-isoquinolyl]carbamate hydrochloride (270.5 mg, 0.5113 mmol, 67.6% yield) as a red solid. LCMS (ESI) [M+H]$^+$= 493.3, R$_T$ 0.635 min; Method L; $^1$H NMR (400 MHz, DMSO-d$_6$) δ 10.17 (s, 1H), 9.41 (s, 1H), 8.87 (s, 2H), 7.97 (s, 1H), 7.52 (s, 1H), 6.90 (d, J=6.0 Hz, 1H), 5.80 (bs, 2H), 4.99 (p, J=7.1 Hz, 1H), 4.47 (t, J=4.5 Hz, 2H), 3.47 (t, J=4.4 Hz, 2H), 2.99 (s, 2H), 2.94 (s, 2H), 2.43-2.34 (m, 2H), 2.01 (d, J=1.6 Hz, 3H), 1.96-1.86 (m, 2H), 1.81-1.73 (m, 4H).

Example 200

(R)-Tetrahydrofuran-3-yl (8-amino-7-fluoro-6-(7-(hydroxymethyl)-4-methyl-5,6,7,8-tetrahydro-1,5-naphthyridin-3-yl)isoquinolin-3-yl)carbamate (Compound 581a)

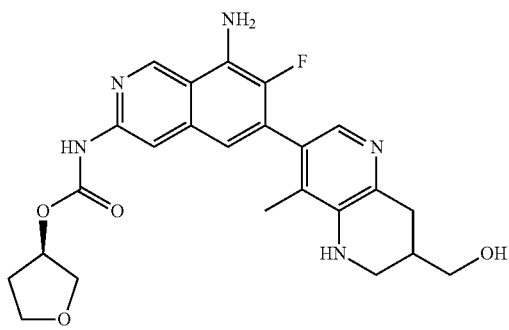 [SMILES: Cc1c(-c2cc3cc(NC(=O)O[C@@H]4CCOC4)ncc3c(N)c2F)cnc2c1NCC(CO)C2]

Step 1: Ethyl 2-(((5-bromo-2-iodo-4-methylpyridin-3-yl)(tert-butoxycarbonyl)amino)methyl)acrylate

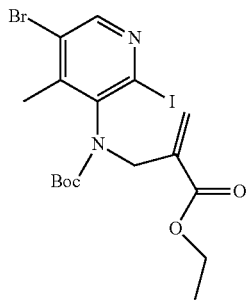 [SMILES: C=C(CN(C(=O)OC(C)(C)C)c1c(I)ncc(Br)c1C)C(=O)OCC]

To a solution of tert-butyl N-(5-bromo-2-iodo-4-methyl-3-pyridyl)carbamate (8.0 g, 19.37 mmol) in N,N-dimethylformamide (80 mL) was added NaH (1.55 g, 38.75 mmol, 60% purity). The mixture was stirred at 0° C. for 30 mins. Ethyl 2-(bromomethyl)acrylate (6.0 g, 31.08 mmol) was added and the mixture was stirred at 0° C. for 2 hours. The resulting solution was diluted with ethyl acetate and then washed by water. The organic layer was dried over anhydrous sodium sulfate and concentrated under vacuum. The residue was purified by reversed phase flash chromatography with water (0.01% NH$_4$HCO$_3$)/ACN (50/50) to afford ethyl 2-[[(5-bromo-2-iodo-4-methyl-3-pyridyl)-tert-butoxycarbonyl-amino]methyl]prop-2-enoate (3.3 g, 6.284 mmol, 32.4% yield) as a yellow oil. LCMS (ESI) [M+H]$^+$=525.

Step 2: 1-(tert-Butyl) 3-ethyl 7-bromo-8-methyl-1,5-naphthyridine-1,3(2H)-dicarboxylate

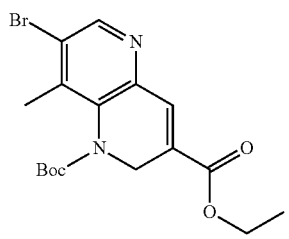 [SMILES: CCOC(=O)C1=Cc2ncc(Br)c(C)c2N(C(=O)OC(C)(C)C)C1]

To a solution of ethyl 2-[[(5-bromo-2-iodo-4-methyl-3-pyridyl)-tert-butoxycarbonyl-amino]methyl]prop-2-enoate (3.3 g, 6.28 mmol) in N,N-dimethylformamide (100 mL) was added palladium acetate (2.0 g, 8.93 mmol), TBAB (2.0 g, 6.21 mmol) and sodium bicarbonate (1.6 g, 19.05 mmol). The mixture was stirred at 90° C. for 4 hours. After concentration, the residue was purified by flash chromatography on Al$_2$O$_3$ gel eluting with petroleum ether/ethyl acetate (90/10) to afford 1-(tert-butyl) 3-ethyl 7-bromo-8-methyl-1,5-naphthyridine-1,3(2H)-dicarboxylate (800 mg, 2 mmol, 32% yield) as yellow oil. LCMS (ESI) [M+H]$^+$=397.

Step 3: tert-Butyl 7-bromo-3-(hydroxymethyl)-8-methyl-3,4-dihydro-1,5-naphthyridine-1(2H)-carboxylate

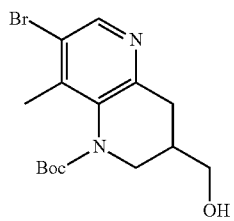 [SMILES: Cc1c(Br)cnc2c1N(C(=O)OC(C)(C)C)CC(CO)C2]

To a solution of 1-(tert-butyl) 3-ethyl 7-bromo-8-methyl-1,5-naphthyridine-1,3(2H)-dicarboxylate (800 mg, 2.02 mmol) in ethanol (20 mL) was added NaBH$_4$ (230 mg, 9.58 mmol). The mixture was stirred at 0° C. for 2 hours. After concentration, the residue was purified by flash chromatography on silica gel eluting with dichloromethane/methanol (92/8) to afford tert-butyl 7-bromo-3-(hydroxymethyl)-8-methyl-tetralin-1-carboxylate (539 mg, 1.517 mmol, 75.2% yield) as a yellow solid. LCMS (ESI) [M+H]$^+$=357.

Step 4: (5-(tert-Butoxycarbonyl)-7-(hydroxymethyl)-4-methyl-5,6,7,8-tetrahydro-1,5-naphthyridin-3-yl)boronic acid

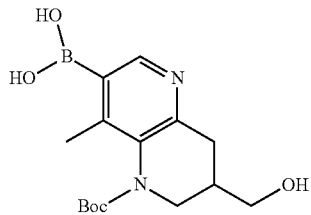

To a mixture of tert-butyl 7-bromo-3-(hydroxymethyl)-8-methyl-3,4-dihydro-2H-1,5-naphthyridine-1-carboxylate (530 mg, 1.48 mmol) and B$_2$Pin$_2$ (1890 mg, 7.47 mmol) in 1,4-dioxane (15 mL) was added Pd(dppf)Cl2 (220 mg, 0.30 mmol) and potassium acetate (440 mg, 4.49 mmol). The mixture was stirred at 90° C. for 3 hours. After concentration, the residue was purified by flash reversed phase chromatography eluting with water (0.01% NH$_4$HCO$_3$)/ACN (80/20) to afford (5-(tert-butoxycarbonyl)-7-(hydroxymethyl)-4-methyl-5,6,7,8-tetrahydro-1,5-naphthyridin-3-yl)boronic acid (400 mg, 1.242 mmol, 83.7% yield) as a brown solid. LCMS (ESI) [M+H]$^+$=323.

Step 5: tert-Butyl 7-(3-amino-8-chloro-7-fluoroisoquinolin-6-yl)-3-(hydroxymethyl)-8-methyl-3,4-dihydro-1,5-naphthyridine-1(2H)-carboxylate

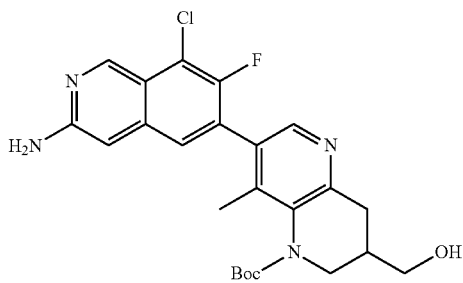 [SMILES: Cc1c(-c2cc3cc(N)ncc3c(Cl)c2F)cnc2c1N(C(=O)OC(C)(C)C)CC(CO)C2]

To a mixture of 8-chloro-7-fluoro-6-iodo-isoquinolin-3-amine (480.0 mg, 1.49 mmol) and (5-(tert-butoxycarbonyl)-7-(hydroxymethyl)-4-methyl-5,6,7,8-tetrahydro-1,5-naphthyridin-3-yl)boronic acid (480 mg, 1.49 mmol) in 1,4-dioxane (15 mL) and water (1.5 mL) was added Pd(dppf)Cl$_2$ (220 mg, 0.30 mmol), potassium carbonate (615 mg, 4.46 mmol). The mixture was stirred at 90° C. for 3 hours. After concentration the residue was purified by flash chromatography on silica gel eluting with dichloromethane/methanol (96/4) to afford tert-butyl 7-(3-amino-8-chloro-7-fluoroisoquinolin-6-yl)-3-(hydroxymethyl)-8-methyl-3,4-dihydro-1,5-naphthyridine-1(2H)-carboxylate (400 mg, 0.848 mmol, 57% yield) as a yellow solid. LCMS (ESI) [M+H]$^+$=473.

Step 6: tert-Butyl 7-(3-amino-8-chloro-7-fluoro-8-methyl-8l5-isoquinolin-6-yl)-3-(((tert-butyldimethylsilyl)oxy)methyl)-8-methyl-3,4-dihydro-1,5-naphthyridine-1(2H)-carboxylate

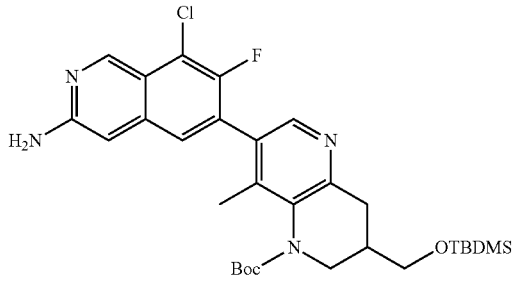 [SMILES: Cc1c(-c2cc3cc(N)ncc3c(Cl)c2F)cnc2c1N(C(=O)OC(C)(C)C)CC(CO[Si](C)(C)C(C)(C)C)C2]

To a mixture of tert-butyl 7-(3-amino-8-chloro-7-fluoro-6-isoquinolyl)-3-(hydroxymethyl)-8-methyl-3,4-dihydro-2H-1,5-naphthyridine-1-carboxylate (190 mg, 0.40 mmol) and tert-butyldimethylchlorosilane (76 mg, 0.50 mmol) in dichloromethane (5 mL) was added imidazole (114 mg, 1.67 mmol). The mixture was stirred at room temperature for 2 hours. After concentration, the residue was purified by flash chromatography on silica gel eluting with dichloromethane/methanol (96/4) to afford tert-butyl 7-(3-amino-8-chloro-7-fluoro-6-isoquinolyl)-3-[[tert-butyl (dimethyl)silyl]oxymethyl]-8-methyl-3,4-dihydro-2H-1,5-naphthyridine-1-carboxylate (150 mg, 0.255 mmol, 63.6% yield) as a yellow solid. LCMS (ESI) [M+H]$^+$=602.

Step 7: tert-Butyl 3-(((tert-butyldimethylsilyl)oxy)methyl)-7-(8-chloro-7-fluoro-3-(((((R)-tetrahydrofuran-3-yl)oxy)carbonyl)amino)isoquinolin-6-yl)-8-methyl-3,4-dihydro-1,5-naphthyridine-1(2H)-carboxylate

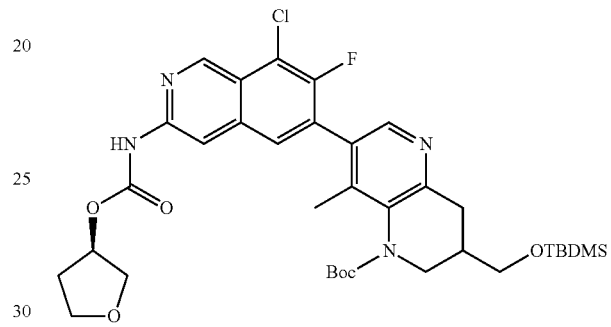

To a mixture of tert-butyl 8-amino-7-(3-amino-8-chloro-7-fluoro-6-isoquinolyl)-3-[[tert-butyl(dimethyl)silyl]oxymethyl]-3,4-dihydro-2H-1,5-naphthyridine-1-carboxylate (100 mg, 0.17 mmol) and 3-hydroxytetrahydrofuran (80 mg, 0.91 mmol) in dichloromethane (6 mL) was added triphosgene (40 mg, 0.13 mmol) and DIEA (120 mg, 0.93 mmol) at 0° C. The mixture was stirred at room temperature for 1 hour. After concentration, the residue was purified by flash chromatography on silica gel eluting with dichloromethane/methanol (96/4) to tert-butyl 8-amino-3-[[tert-butyl(dimethyl)silyl]oxymethyl]-7-[8-chloro-7-fluoro-3-(tetrahydrofuran-3-yloxycarbonylamino)-6-isoquinolyl]-3,4-dihydro-2H-1,5-naphthyridine-1-carboxylate (100 mg, 0.142 mmol, 83.8% yield) as a yellow solid. LCMS (ESI) [M+H]$^+$=701.

Step 8: tert-Butyl ((R)-tetrahydrofuran-3-yl) (6-(7-(((tert-butyldimethylsilyl)oxy)methyl)-4-methyl-5,6,7,8-tetrahydro-1,5-naphthyridin-3-yl)-7-fluoroisoquinoline-3,8-diyl)dicarbamate

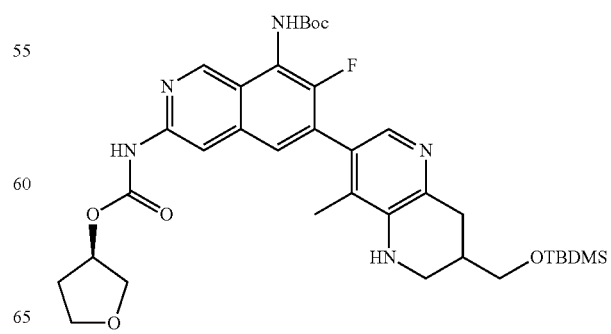

To a mixture of tert-butyl 3-[[tert-butyl(dimethyl)silyl]oxymethyl]-7-[8-chloro-7-fluoro-3-(tetrahydrofuran-3-yloxycarbonylamino)-6-isoquinolyl]-8-methyl-3,4-dihydro-2H-1,5-naphthyridine-1-carboxylate (120 mg, 0.17 mmol) and tert-butyl carbamate (599 mg, 5.11 mmol) in 1,4-dioxane (4 mL) was added Pd₂(dba)₃ (48 mg, 0.050 mmol), cesium carbonate (168 mg, 0.52 mmol) and BrettPhos (48 mg, 0.090 mmol). The mixture was stirred at 70° C. for 1 hour. After concentration, The residue was purified by flash chromatography on silica gel eluting with dichloromethane/methanol (96/4) to afford tert-butyl 7-[8-(tert-butoxycarbonylamino)-7-fluoro-3-(tetrahydrofuran-3-yloxycarbonylamino)-6-isoquinolyl]-3-[[tert-butyl(dimethyl)silyl]oxymethyl]-8-methyl-3,4-dihydro-2H-1,5-naphthyridine-1-carboxylate (95 mg, 0.1215 mmol, 71% yield) as yellow solid. LCMS (ESI) [M+H]⁺=682.

Step 9: tert-Butyl ((R)-tetrahydrofuran-3-yl) (7-fluoro-6-(7-(hydroxymethyl)-4-methyl-5,6,7,8-tetrahydro-1,5-naphthyridin-3-yl)isoquinoline-3,8-diyl)dicarbamate

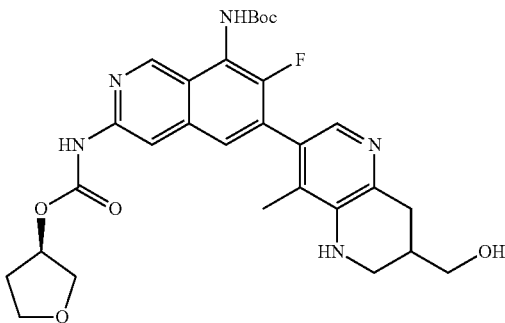

To a solution of tert-butyl 7-[8-(tert-butoxycarbonylamino)-7-fluoro-3-(tetrahydrofuran-3-yloxycarbonylamino)-6-isoquinolyl]-3-[[tert-butyl(dimethyl)silyl]oxymethyl]-8-methyl-3,4-dihydro-2H-quinoline-1-carboxylate (90 mg, 0.12 mmol) in tetrahydrofuran (5 mL) was added TBAF.3H₂O (108 mg, 0.34 mmol). The mixture was stirred at room temperature for 2 hours. After concentration, the residue was purified by flash chromatography on silica gel eluting with dichloromethane/methanol (96/4) to afford tert-butyl 7-[8-(tert-butoxycarbonylamino)-7-fluoro-3-(tetrahydrofuran-3-yloxycarbonylamino)-6-isoquinolyl]-3-(hydroxymethyl)-8-methyl-3,4-dihydro-2H-quinoline-1-carboxylate (50 mg, 0.075 mmol, 65.1% yield) as a yellow solid. LCMS (ESI) [M+H]⁺=568.

Step 10: (R)-Tetrahydrofuran-3-yl (8-amino-7-fluoro-6-(7-(hydroxymethyl)-4-methyl-5,6,7,8-tetrahydro-1,5-naphthyridin-3-yl)isoquinolin-3-yl)carbamate

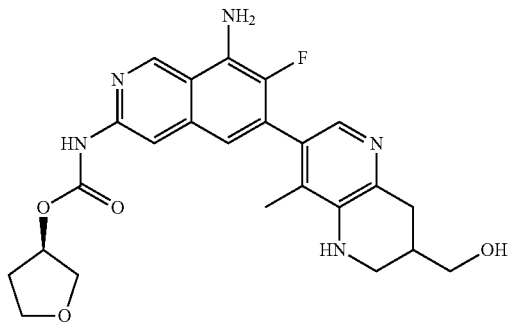 [SMILES: Cc1c(-c2cc3cc(NC(=O)O[C@@H]4CCOC4)ncc3c(N)c2F)cnc2c1NCC(CO)C2]

To a solution of tert-butyl 7-[8-(tert-butoxycarbonylamino)-7-fluoro-3-[[(3R)-tetrahydrofuran-3-yl]oxycarbonylamino]-6-isoquinolyl]-3-(hydroxymethyl)-8-methyl-3,4-dihydro-2H-1,5-naphthyridine-1-carboxylate (30 mg, 0.040 mmol) in dichloromethane (5 mL) was added TFA (1 mL). The mixture was stirred at room temperature for 1 hour. After concentration the residue was purified by prep-HPLC (Column: X Bridge Prep Phenyl OBD Column 5 μm, 19*250 mm; Mobile Phase A: Water (0.1% FA); Mobile Phase B: ACN; Flow rate: 25 mL/min; Gradient: 7% B to 20% B in 12 min) to afford (R)-tetrahydrofuran-3-yl (8-amino-7-fluoro-6-(7-(hydroxymethyl)-4-methyl-5,6,7,8-tetrahydro-1,5-naphthyridin-3-yl)isoquinolin-3-yl)carbamate (2.7 mg, 0.0053 mmol, 11.7% yield) as a yellow solid. Mixture of diastereomers. LCMS (ESI) [M+H]⁺=478, $R_T$ 1.382 min, Method J. ¹H NMR (300 MHz, DMSO-d₆) δ 10.13 (s, 1H), 9.34 (s, 1H), 7.98 (s, 1H), 7.59 (s, 1H), 6.84 (d, J=6.1 Hz, 1H), 6.23 (s, 2H), 5.46 (s, 1H), 5.28 (tt, J=4.4, 2.1 Hz, 1H), 4.69 (s, 1H), 3.92-3.67 (m, 4H), 3.41-3.52 (m, 3H), 2.96 (t, J=10.4 Hz, 1H), 2.86 (dd, J=16.7, 5.0 Hz, 1H), 2.66-2.52 (m, 1H), 2.27-2.11 (m, 1H), 2.02 (s, 2H), 1.88 (d, J=1.6 Hz, 3H).

Example 201

(1S,3R)-3-Hydroxycyclopentyl (8-amino-7-fluoro-6-(8-methyl-2,3-dihydro-1H-pyrido[2,3-b][1,4]oxazin-7-yl)isoquinolin-3-yl)carbamate and (1R,3S)-3-hydroxycyclopentyl (8-amino-7-fluoro-6-(8-methyl-2,3-dihydro-1H-pyrido[2,3-b][1,4]oxazin-7-yl) isoquinolin-3-yl)carbamate (Compound 582a and Compound 582b3)

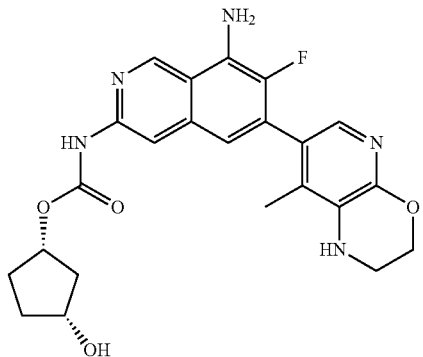

-continued

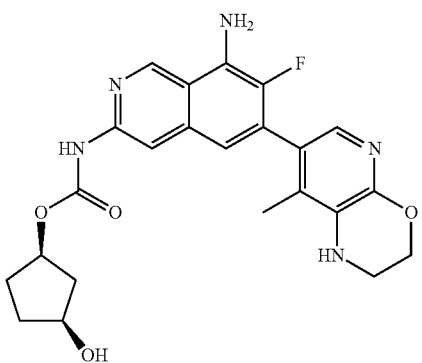

Step 1: tert-Butyl 7-[8-(tert-butoxycarbonylamino)-7-fluoro-3-[[(1S,3R)-3-hydroxycyclopentoxy]carbonylamino]-6-isoquinolyl]-8-methyl-2,3-dihydropyrido[2,3-b][1,4]oxazine-1-carboxylate

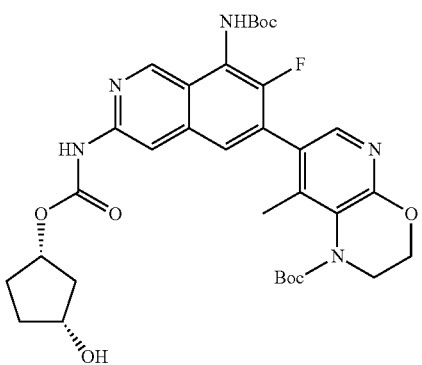 [SMILES: Cc1c(-c2cc3cc(NC(=O)O[C@H]4CC[C@@H](O)C4)ncc3c(NC(=O)OC(C)(C)C)c2F)cnc2c1N(C(=O)OC(C)(C)C)CCO2]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (150.0 mg, 0.23 mmol) and DMAP (28.5 mg, 0.23 mmol) in 1,4-dioxane (15 mL) was added a solution of (±)-cis-cyclopentane-1,3-diol (48.0 mg, 0.47 mmol) in 1,4-dioxane (1 mL) at 25° C. The resulting solution was stirred for 3 hours at 90° C. The mixture was concentrated under vacuum. The residue was purified by flash chromatography on silica gel eluting with dichloromethane/methanol (95/5) to afford (±)-cis-tert-butyl 7-[8-(tert-butoxycarbonylamino)-7-fluoro-3-[[3-hydroxycyclopentoxy]carbonylamino]-6-isoquinolyl]-8-methyl-2,3-dihydropyrido[2,3-b][1,4]oxazine-1-carboxylate (150 mg, 0.23 mmol, 98% yield) as a white solid. LCMS (ESI) [M+H]$^+$=654.3

Step 2: (1S,3R)-3-Hydroxycyclopentyl (8-amino-7-fluoro-6-(8-methyl-2,3-dihydro-1H-pyrido[2,3-b][1,4]oxazin-7-yl)isoquinolin-3-yl)carbamate and (1R,3S)-3-hydroxycyclopentyl (8-amino-7-fluoro-6-(8-methyl-2,3-dihydro-1H-pyrido[2,3-b][1,4]oxazin-7-yl)isoquinolin-3-yl)carbamate

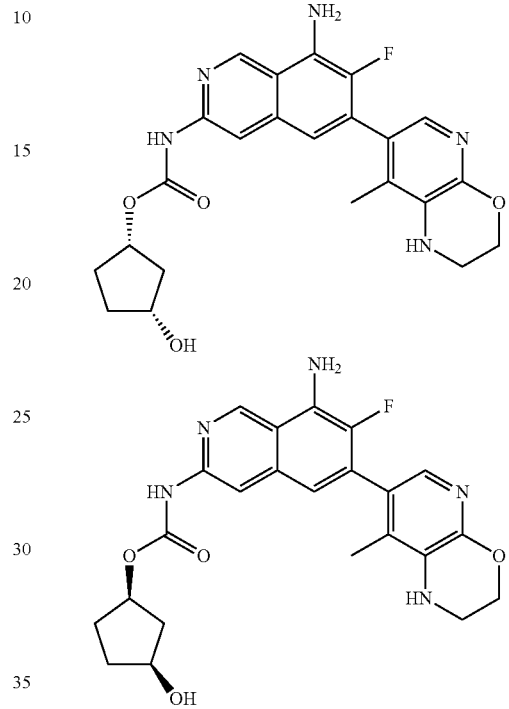

A solution of tert-butyl 7-[8-(tert-butoxycarbonylamino)-7-fluoro-3-[[(1S,3R)-3-hydroxycyclopentoxy]carbonylamino]-6-isoquinolyl]-8-methyl-2,3-dihydropyrido[2,3-b][1,4]oxazine-1-carboxylate (210.0 mg, 0.32 mmol) and TFA (2.5 mL) in dichloromethane (5 mL) was stirred at 25° C. for 30 minutes. After concentration, the residue was purified by Prep-HPLC (Column: X Bridge Prep OBD C18 Column 30×150 mm, 5 μm; Water (10 mmol/L NH$_4$HCO$_3$): ACN=14% B to 35% B in 7 min; 60 mL/min) to afford a racemate. The racemic product was separated by chiral-HPLC to afford two enantiomers. Relative stereochemistry are as drawn. Absolute stereochemistry was arbitrarily assigned.

Enantiomer 1 (Compound 582a, 13.1 mg, 0.029 mmol, 18% yield). R$_T$ 1.855 min (CHIRALPAK IC-3 0.46*5 cm; 3 μm; MTBE (0.1% DEA):EtOH=70:30; 1.0 ml/min). LCMS (ESI) [M+H]$^+$=454.2, R$_T$ 1.980 min., Method K; $^1$H NMR (300 MHz, DMSO-d$_6$) δ 9.95 (s, 1H), 9.33 (s, 1H), 7.99 (s, 1H), 7.33 (s, 1H), 6.83 (d, J=6.2 Hz, 1H), 6.20 (s, 2H), 5.68 (s, 1H), 5.13-4.94 (m, 1H), 4.63 (d, J=4.5 Hz, 1H), 4.35-4.25 (m, 2H), 4.14-4.00 (m, 1H), 3.41-3.37 (m, 2H), 2.37-2.21 (m, 1H), 1.92 (s, 3H), 1.87-1.69 (m, 3H), 1.65-1.47 (m, 2H).

Enantiomer 2 (Compound 582b, 12.2 mg, 0.027 mmol, 17% yield): Retention time: 3.647 min (CHIRALPAK IC-3 0.46*5 cm; 3 μm; MTBE (0.1% DEA):EtOH=70:30; 1.0 ml/min). LCMS (ESI) [M+H]$^+$=454.2, R$_T$ 1.973 min, Method K; $^1$H NMR (300 MHz, DMSO-d$_6$) δ 9.95 (s, 1H), 9.33 (s, 1H), 7.99 (s, 1H), 7.33 (s, 1H), 6.83 (d, J=6.2 Hz, 1H), 6.20 (s, 2H), 5.68 (s, 1H), 5.13-4.94 (m, 1H), 4.63 (d, J=4.5 Hz, 1H), 4.35-4.25 (m, 2H), 4.14-4.00 (m, 1H), 3.41-3.37 (m, 2H), 2.37-2.21 (m, 1H), 1.92 (s, 3H), 1.87-1.69 (m, 3H), 1.65-1.47 (m, 2H).

Example 202

1-(8-Amino-7-fluoro-6-(8-methyl-2,3-dihydro-1H-pyrido[2,3-b][1,4]oxazin-7-yl)isoquinolin-3-yl)-3-((1s,3s)-3-fluorocyclobutyl)urea and 1-(8-Amino-7-fluoro-6-(8-methyl-2,3-dihydro-1H-pyrido[2,3-b][1,4]oxazin-7-yl)isoquinolin-3-yl)-3-((1r,3r)-3-fluorocyclobutyl)urea (Compound 748a and Compound 748b)

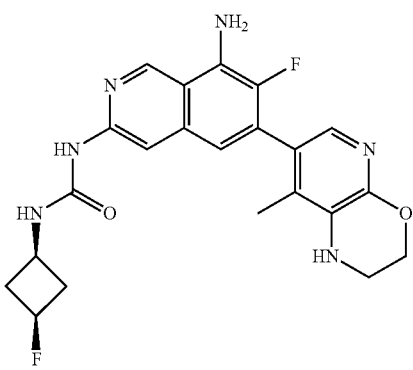

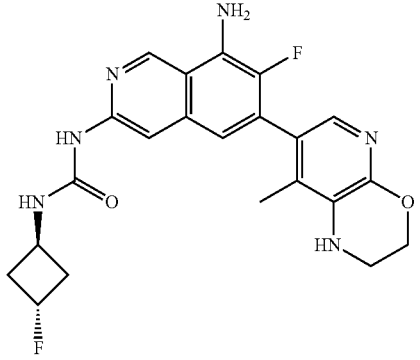

Step 1: tert-Butyl 7-[8-(tert-butoxycarbonylamino)-7-fluoro-3-[(3-fluorocyclobutyl)carbamoylamino]-6-isoquinolyl]-8-methyl-2,3-dihydropyrido[2,3-b][1,4]oxazine-1-carboxylate

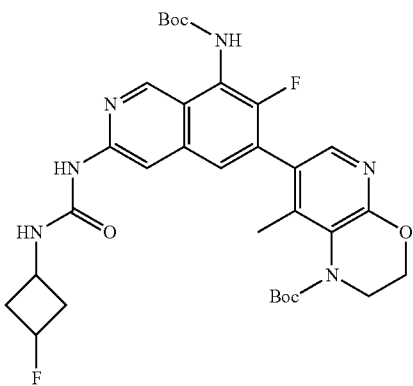 [SMILES: Cc1c(-c2cc3cc(NC(=O)NC4CC(F)C4)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (380 mg, 0.72 mmol), DMAP (88 mg, 0.72 mmol) and pyridine (5 mL) in dichloromethane (20 mL) was added phenyl chloroformate (566 mg, 3.61 mmol) at room temperature. The resulting solution was stirred for 1 hour at room temperature. Then 3-fluorocyclobutanamine hydrochloride (363 mg, 2.89 mmol) was added. The mixture was stirred for 16 hours at 50° C. The reaction mixture was concentrated under vacuum and purified by flash chromatography on silica gel eluting with dichloromethane/methanol (10%) to afford tert-butyl 7-[8-(tert-butoxycarbonylamino)-7-fluoro-3-[(3-fluorocyclobutyl)carbamoylamino]-6-isoquinolyl]-8-methyl-2,3-dihydropyrido[2,3-b][1,4]oxazine-1-carboxylate (200 mg, 0.306 mmol, 42.3% yield) as a yellow solid. LCMS (ESI) $[M+H]^+=641.0$.

Step 2: 1-(8-Amino-7-fluoro-6-(8-methyl-2,3-dihydro-1H-pyrido[2,3-b][1,4]oxazin-7-yl)isoquinolin-3-yl)-3-((1s,3s)-3-fluorocyclobutyl)urea and 1-(8-Amino-7-fluoro-6-(8-methyl-2,3-dihydro-1H-pyrido[2,3-b][1,4]oxazin-7-yl)isoquinolin-3-yl)-3-((1r,3r)-3-fluorocyclobutyl)urea

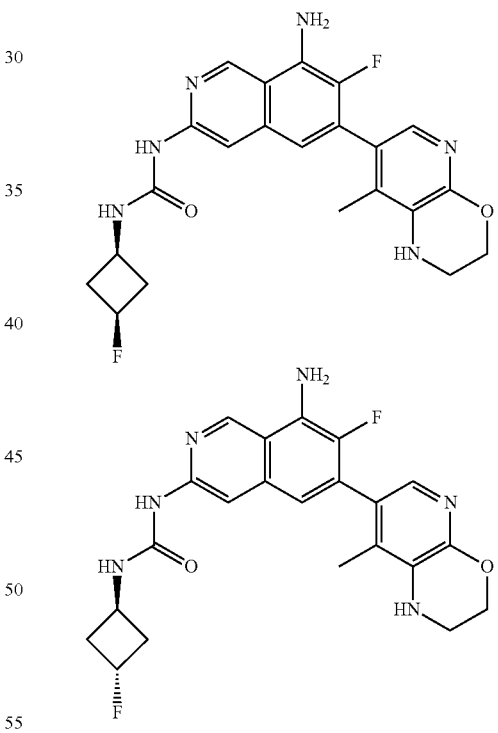

A solution of tert-butyl 7-[8-(tert-butoxycarbonylamino)-7-fluoro-3-[(3-fluorocyclobutyl)carbamoylamino]-6-isoquinolyl]-8-methyl-2,3-dihydropyrido[2,3-b][1,4]oxazine-1-carboxylate (300 mg, 0.47 mmol) in dichloromethane (10 mL) and 2,2,2-trifluoroacetic acid (2 mL) was stirred at room temperature for 1 hour. The reaction mixture was concentrated under vacuum. The residue was purified by SFC to afford two isomers. Stereochemistry was arbitrarily assigned.

Isomer 1: (Compound 748a) (10 mg, 0.0227 mmol, 4.8% yield) as yellow sold. RT 6.70 min (Column: Ultimate XB-NH2, 21.2*250 mm; 5 µm; Mobile Phase A: CO₂, Mobile Phase B: MeOH: ACN=2:8 (0.1% NH₃.H₂O); Flow rate: 50 mL/min). LCMS (ESI) [M+H]⁺=441.2, $R_T$ 2.370 min., Method M; ¹H NMR (400 MHz, DMSO-d₆) δ 9.29 (s, 1H), 8.86 (s, 1H), 7.84 (s, 1H), 7.36 (d, J=6.7 Hz, 1H), 7.34 (s, 1H), 6.75 (d, J=6.2 Hz, 1H), 6.14 (s, 2H), 5.65 (s, 1H), 4.94-4.76 (m, 1H), 4.28 (t, J=4.4 Hz, 2H), 3.78-3.72 (m, 1H), 3.38-3.36 (m, 2H), 2.80-2.72 (m, 2H), 2.13-2.09 (m, 2H), 1.93 (d, J=1.7 Hz, 3H).

Isomer 2: (Compound 748b) (27 mg, 0.0613 mmol, 13.1% yield) as yellow solid. RT 7.57 (Column: Ultimate XB-NH2, 21.2*250 mm; 5 µm; Mobile Phase A: CO₂, Mobile Phase B: MeOH: ACN=2:8 (0.1% NH₃.H₂O); Flow rate: 50 mL/min). LCMS (ESI): [M+H]⁺=441.2, $R_T$ 2.370 min., Method M; ¹H NMR (400 MHz, DMSO-d₆) δ 9.30 (s, 1H), 8.90 (s, 1H), 7.86 (s, 1H), 7.38 (d, J=6.7 Hz, 1H), 7.34 (s, 1H), 6.76 (d, J=6.2 Hz, 1H), 6.16 (s, 1H), 5.70 (s, 1H), 5.33-5.18 (m, 1H), 4.30 (t, J=4.4 Hz, 3H), 3.38 (d, J=4.4 Hz, 3H), 2.55 (s, 2H), 2.42-2.23 (m, 2H), 1.93 (d, J=1.7 Hz, 3H).

Example 203

(3S,4S)-3-Methoxytetrahydro-2H-pyran-4-yl 8-amino-7-fluoro-6-(8-methyl-2,3-dihydro-1H-pyrido[2,3-b][1,4]oxazin-7-yl)isoquinolin-3-yl)carbamate; (3S,4R)-3-Methoxytetrahydro-2H-pyran-4-yl (8-amino-7-fluoro-6-(8-methyl-2,3-dihydro-1H-pyrido[2,3-b][1,4]oxazin-7-yl)isoquinolin-3-yl) carbamate; (3R,4S)-3-Methoxytetrahydro-2H-pyran-4-yl (8-amino-7-fluoro-6-(8-methyl-2,3-dihydro-1H-pyrido[2,3-b][1,4]oxazin-7-yl)isoquinolin-3-yl) carbamate; and (3R,4R)-3-Methoxytetrahydro-2H-pyran-4-yl (8-amino-7-fluoro-6-(8-methyl-2,3-dihydro-1H-pyrido[2,3-b][1,4]oxazin-7-yl) isoquinolin-3-yl)carbamate (Compound 583a, Compound 583b, Compound 583c and Compound 583d)

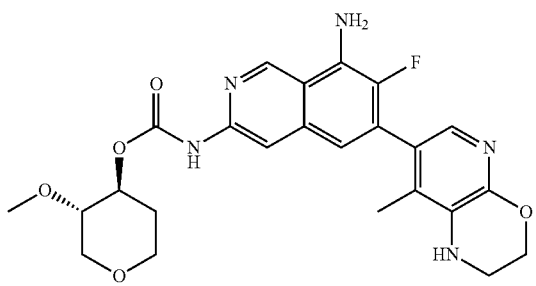

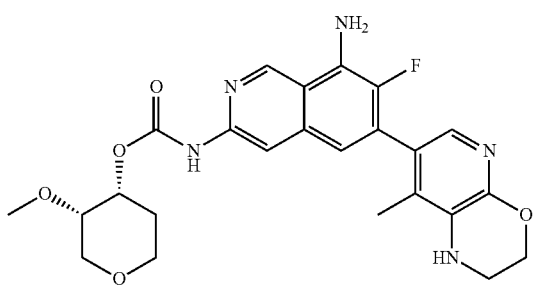

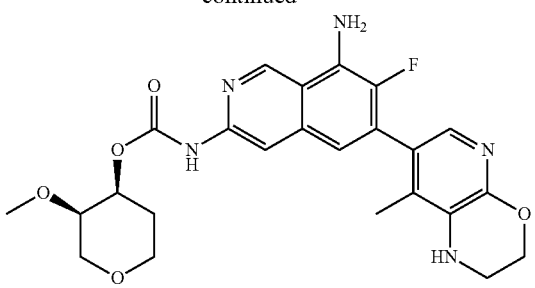

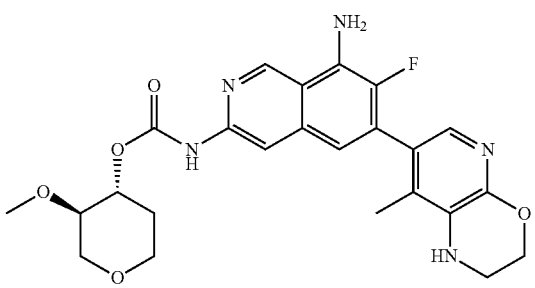

Step 1: tert-Butyl 7-[8-(tert-butoxycarbonylamino)-7-fluoro-3-[(3-methoxytetrahydropyran-4-yl)oxycarbonylamino]-6-isoquinolyl]-8-methyl-2,3-dihydro-pyrido[2,3-b][1,4]oxazine-1-carboxylate

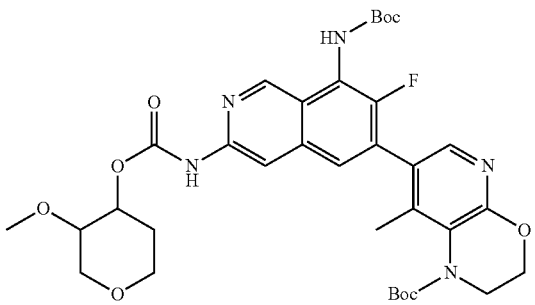 [SMILES: COC1COCCC1OC(=O)Nc1cc2cc(-c3cnc4c(c3C)N(C(=O)OC(C)(C)C)CCO4)c(F)c(NC(=O)OC(C)(C)C)c2cn1]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (500.0 mg, 0.95 mmol), DIEA (614.8 mg, 4.76 mmol) and 3-methoxytetrahydropyran-4-ol (251.5 mg, 1.9 mmol) in dichloromethane (40 mL) was added triphosgene (282.4 mg, 0.95 mmol). The mixture was stirred at 0° C. for 1.5 hours. The reaction was quenched with water and extracted with dichloromethane. The organic layers were combined, dried over anhydrous sodium sulfate and concentrated under vacuum. The residue was purified by flash chromatography on silica gel eluting with dichloromethane/methanol (98/2) to afford tert-butyl 7-[8-(tert-butoxycarbonylamino)-7-fluoro-3-[(3-methoxytetrahydropyran-4-yl)oxycarbonylamino]-6-isoquinolyl]-8-methyl-2,3-dihydropyrido[2,3-b][1,4]oxazine-1-carboxylate (380 mg, 0.55 mmol, 58.4% yield) as a yellow solid. LCMS (ESI) [M+H]⁺=684.

Step 2: (3S,4S)-3-Methoxytetrahydro-2H-pyran-4-yl (8-amino-7-fluoro-6-(8-methyl-2,3-dihydro-1H-pyrido[2,3-b][1,4]oxazin-7-yl)isoquinolin-3-yl)carbamate (3S,4R)-3-Methoxytetrahydro-2H-pyran-4-yl (8-amino-7-fluoro-6-(8-methyl-2,3-dihydro-1H-pyrido[2,3-b][1,4]oxazin-7-yl)isoquinolin-3-yl)carbamate (3R,4S)-3-Methoxytetrahydro-2H-pyran-4-yl (8-amino-7-fluoro-6-(8-methyl-2,3-dihydro-1H-pyrido[2,3-b][1,4]oxazin-7-yl)isoquinolin-3-yl)carbamate and (3R,4R)-3-Methoxytetrahydro-2H-pyran-4-yl (8-amino-7-fluoro-6-(8-methyl-2,3-dihydro-1H-pyrido[2,3-b][1,4]oxazin-7-yl)isoquinolin-3-yl)carbamate

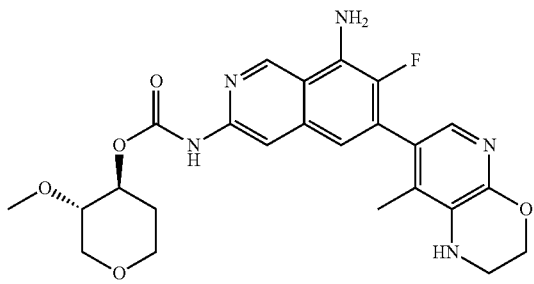

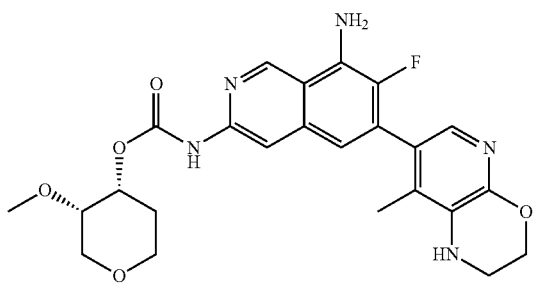

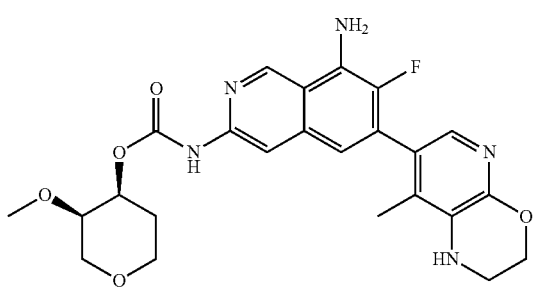

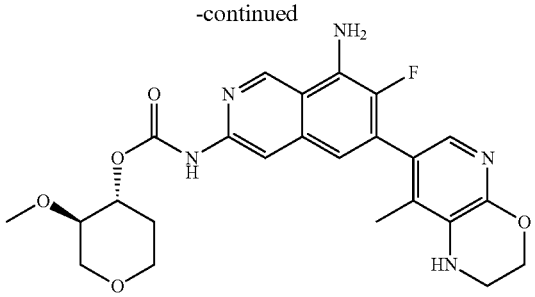

-continued

To solution of tert-butyl 7-[8-(tert-butoxycarbonylamino)-7-fluoro-3-[(3-methoxytetrahydropyran-4-yl)oxycarbonylamino]-6-isoquinolyl]-8-methyl-2,3-dihydropyrido[2,3-b][1,4]oxazine-1-carboxylate (380.0 mg, 0.56 mmol) in dichloromethane (5 mL) was added TFA (2 mL). The mixture was stirred at room temperature for 2 hours. The reaction mixture was concentrated under vacuum. The residue was dissolved in dichloromethane and adjusted to pH 8 with TEA. The mixture was concentrated under vacuum. The residue was purified by pre-HPLC with the following condition (Column: Xselect CSH OBD Column 30*150 mm, 5 μm; Mobile Phase A: Water (0.1% FA), Mobile Phase B: ACN; Flow rate: 60 mL/min; Gradient: 7% B to 37% B in 7 min) to afford the isomeric mixture of products. The racemic product was further separated by chiral-HPLC to afford four isomers. Stereochemistry was arbitrarily assigned.

Isomer 1: (Compound 583a) (23.7 mg, 0.05 mmol, 8.8% yield). $R_T$ 1.686 min (column: CHIRALPAK ID-3 0.46*5 cm; 3 μm, Mobile phase: MTBE (0.1% DEA):EtOH=60:40, 1 ml/min). LCMS (ESI): [M+H]$^+$=484.2, $R_T$ 2.156 min., Method L. $^1$H NMR (300 MHz, DMSO-d$_6$) δ 10.12 (s, 1H), 9.36 (s, 1H), 7.98 (s, 1H), 7.34 (s, 1H), 6.84 (d, J=6.2 Hz, 1H), 6.22 (s, 2H), 5.68 (d, J=2.6 Hz, 1H), 5.14-5.18 (m, 1H), 4.34-4.25 (m, 2H), 3.70-3.75 (m, 2H), 3.61-3.53 (m, 3H), 3.37 (m, 5H), 1.93 (d, J=1.6 Hz, 4H), 1.83-1.70 (m, 1H).

Isomer 2: (Compound 583b) (2.5 mg, 0.005 mmol, 0.9% yield). $R_T$ 2.489 min (column: CHIRALPAK ID-3 0.46*5 cm; 3 μm, Mobile phase: MTBE (0.1% DEA):EtOH=60:40, 1 ml/min). LCMS (ESI): [M+H]$^+$=484.2, $R_T$ 2.092 min.; Method L. $^1$H NMR (300 MHz, DMSO-d$_6$) δ 10.14 (s, 1H), 9.35 (s, 1H), 7.98 (s, 1H), 7.34 (s, 1H), 6.85 (d, J=6.2 Hz, 1H), 6.22 (s, 2H), 5.68 (d, J=2.6 Hz, 1H), 4.80 (s, 1H), 4.34-4.25 (m, 2H), 3.98 (dd, J=9.6, 6.1 Hz, 1H), 3.76-3.80 (m, 1H), 3.51-3.34 (m, 3H), 3.38 (s, 3H), 3.31-3.22 (m, 2H), 2.11-1.99 (m, 1H), 1.93 (d, J=1.6 Hz, 3H), 1.60 (m, 1H).

Isomer 3: (Compound 583c) (5.1 mg, 0.01 mmol, 1.9% yield). $R_T$ 2.109 min (column: CHIRALPAK IE-3 0.46*5 cm; 3 μm; Mobile phase: MTBE (0.1% DEA):EtOH=60:40, 1 ml/min). LCMS (ESI): [M+H]$^+$=484.2, $R_T$ 2.092 min., Method L. $^1$H NMR (300 MHz, DMSO-d$_6$) δ10.14 (s, 1H), 9.35 (s, 1H), 7.98 (s, 1H), 7.34 (s, 1H), 6.85 (d, J=6.2 Hz, 1H), 6.22 (s, 2H), 5.68 (d, J=2.6 Hz, 1H), 4.80 (s, 1H), 4.34-4.25 (m, 2H), 3.98 (dd, J=9.6, 6.1 Hz, 1H), 3.76-3.80 (m, 1H), 3.51-3.34 (m, 3H), 3.38 (s, 3H), 3.31-3.22 (m, 2H), 2.11-1.99 (m, 1H), 1.93 (d, J=1.6 Hz, 3H), 1.60 (m, 1H).

Isomer 4: (Compound 583d) (47.8 mg, 0.09 mmol, 17.8% yield). $R_T$ 3.113 min (column: CHIRALPAK IE-3 0.46*5 cm; 3 μm; Mobile phase: MTBE (0.1% DEA):EtOH=60:40, 1 ml/min). LCMS (ESI): [M+H]$^+$=484.2, $R_T$ 2.156 min., Method L. $^1$H NMR (300 MHz, DMSO-d$_6$) δ10.12 (s, 1H), 9.36 (s, 1H), 7.98 (s, 1H), 7.34 (s, 1H), 6.84 (d, J=6.2 Hz, 1H), 6.22 (s, 2H), 5.68 (d, J=2.6 Hz, 1H), 5.14-5.18 (m, 1H), 4.34-4.25 (m, 2H), 3.70-3.75 (m, 2H), 3.61-3.53 (m, 3H), 3.37 (m, 5H), 1.93 (d, J=1.6 Hz, 4H), 1.83-1.70 (m, 1H).

Example 204

(1s,3s)-3-Morpholinocyclobutyl (8-amino-7-fluoro-6-(8-methyl-2,3-dihydro-1H-pyrido[2,3-b][1,4]oxazin-7-yl)isoquinolin-3-yl)carbamate (Compound 550b)

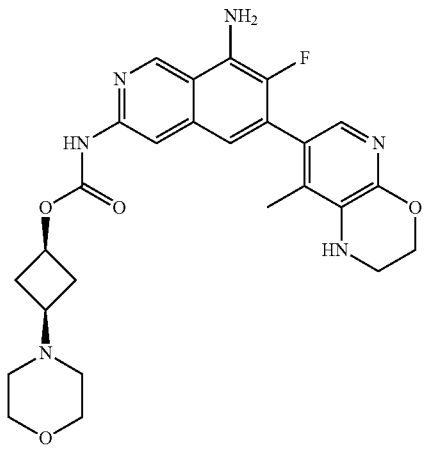 [SMILES: Cc1c(-c2cc3cc(NC(=O)O[C@H]4C[C@@H](N5CCOCC5)C4)ncc3c(N)c2F)cnc2c1NCCO2]

Step 1: 4-((1s,3s)-3-(Benzyloxy)cyclobutyl)morpholine

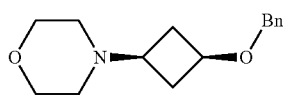 [SMILES: c1ccc(CO[C@H]2C[C@@H](N3CCOCC3)C2)cc1]

A solution of 3-(benzyloxy)cyclobutan-1-one (1.0 g, 5.68 mmol) and morpholine (988.8 mg, 11.35 mmol) in methyl alcohol (18 mL) was stirred at 22° C. for 1 hour. Then NaBH$_4$ (644.06 mg, 17.03 mmol) was added and the mixture was stirred at room temperature for 2 hours. The reaction mixture was concentrated under vacuum and purified by flash chromatography on silica gel eluting with dichloromethane/methanol (10/1) to afford 4-(3-benzyloxycyclobutyl)morpholine (920 mg, 3.7197 mmol, 65.5% yield) as a colorless oil. LCMS (ESI) [M+H]$^+$=248.1.

Step 2: (1s,3s)-3-morpholinocyclobutan-1-ol

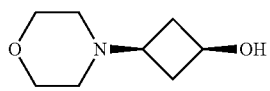 [SMILES: O[C@H]1C[C@@H](N2CCOCC2)C1]

A mixture of 4-(3-benzyloxycyclobutyl)morpholine (740.0 mg, 2.99 mmol) and Pd/C (10%, 150 mg) in methyl alcohol (15 mL) was stirred under hydrogen (1 atm) at room temperature for 24 hours. The reaction mixture was filtered and concentrated under vacuum. The residue was purified by flash chromatography on silica gel eluting with dichloromethane/methanol (10/1) to afford 3-morpholinocyclobutanol (100 mg, 0.64 mmol, 21.3% yield) as a colorless oil. LCMS (ESI) [M+H]$^+$=158.1. $^1$H NMR (400 MHz, DMSO-d$_6$) δ 4.92 (d, J=6.9 Hz, 1H), 3.76-3.80 (m, 1H), 3.54 (t, J=4.7 Hz, 4H), 2.30 (qd, J=7.8, 4.7 Hz, 2H), 2.19 (q, J=6.3, 5.5 Hz, 4H), 2.18-2.07 (m, 1H), 1.58 (qd, J=8.7, 2.3 Hz, 2H).

Step 3: tert-Butyl 7-(8-((tert-butoxycarbonyl)amino)-7-fluoro-3-((((1s,3s)-3-morpholinocyclobutoxy)carbonyl)amino)isoquinolin-6-yl)-8-methyl-2,3-dihydro-1H-pyrido[2,3-b][1,4]oxazine-1-carboxylate

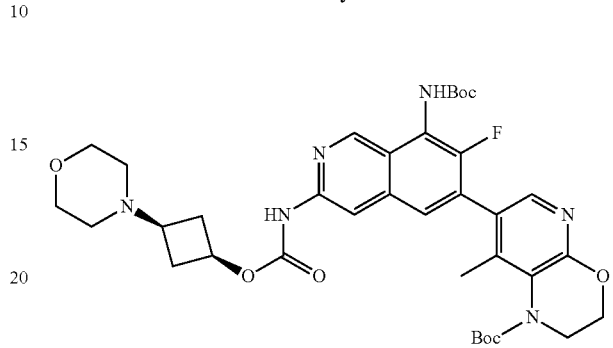

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (120.0 mg, 0.23 mmol), N,N-diisopropylethylamine (0.12 mL, 0.69 mmol) and 3-morpholinocyclobutanol (72.0 mg, 0.4600 mmol) in dichloromethane (12 mL) was added triphosgene (48.0 mg, 0.1600 mmol). The mixture was stirred at 0° C. for 1 hour. The reaction was diluted with water. The organic layer was dried over anhydrous sodium sulfate, filtered and concentrated under vacuum. The residue was purified by flash chromatography on silica gel eluting with dichloromethane/methanol (10/1) to afford tert-butyl 7-[8-(tert-butoxycarbonylamino)-7-fluoro-3-[(3-morpholinocyclobutoxy)carbonylamino]-6-isoquinolyl]-8-methyl-2,3-dihydropyrido[2,3-b][1,4]oxazine-1-carboxylate (150 mg, 0.21 mmol, 92.7% yield) as a yellow solid. LCMS (ESI) [M+H]$^+$=709.3.

Step 4: (1s,3s)-3-Morpholinocyclobutyl (8-amino-7-fluoro-6-(8-methyl-2,3-dihydro-1H-pyrido[2,3-b][1,4]oxazin-7-yl)isoquinolin-3-yl)carbamate

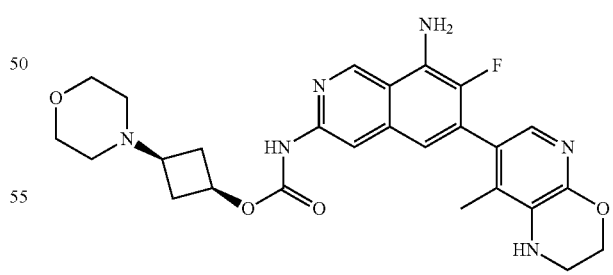

To a solution of tert-butyl 7-[8-(tert-butoxycarbonylamino)-7-fluoro-3-[(3-morpholinocyclobutoxy)carbonylamino]-6-isoquinolyl]-8-methyl-2,3-dihydropyrido[2,3-b][1,4]oxazine-1-carboxylate (150.0 mg, 0.21 mmol) in dichloromethane (10 mL) was added TFA (5 mL). The mixture was stirred at room temperature for 2 hours and concentrated under vacuum. The residue was diluted with acetonitrile (2 mL). The reaction mixture was adjusted to pH 8 with NaHCO₃. After filtration, the solid was collected to afford the crude product. The crude product was purified by Prep-HPLC (Column: Xselect CSH OBD Column 30*150 mm, 5 μm; Mobile Phase A: Water (0.1% FA), Mobile Phase B: ACN; Flow rate: 60 mL/min) to afford (3-morpholinocyclobutyl) N-[8-amino-7-fluoro-6-(8-methyl-2,3-dihydro-1H-pyrido[2,3-b][1,4]oxazin-7-yl)-3-isoquinolyl]carbamate (62.6 mg, 0.1221 mmol, 57.7% yield) as a red solid. LCMS (ESI) [M+H]⁺=509.3, $R_T$ 1.434 min, Method J; ¹H NMR (300 MHz, DMSO-$d_6$) δ 11.87 (s, 1H), 10.35 (s, 1H), 9.43 (s, 1H), 7.99 (s, 1H), 7.56 (s, 1H), 6.96 (d, J=6.0 Hz, 1H), 4.86-4.77 (m, 1H), 4.50 (s, 2H), 3.99-3.80 (m, 4H), 3.49-3.31 (m, 5H), 2.98-2.91 (m, 2H), 2.75-2.72 (m, 2H), 2.60-2.50 (m, 1H), 2.00 (s, 3H).

Example 205

(1s,3R)-3-Hydroxycyclobutyl (8-amino-7-fluoro-6-((6aR,7aS)-4-methyl-6,6a,7,7a-tetrahydro-5h-cyclopropa[c][1,5]naphthyridin-3-yl)isoquinolin-3-yl)carbamate and (1s,3S)-3-Hydroxycyclobutyl (8-amino-7-fluoro-6-((6aS,7aR)-4-methyl-6,6a,7,7a-tetrahydro-5H-cyclopropa[c][1,5]naphthyridin-3-yl)isoquinolin-3-yl)carbamate (Compound 584a and Compound 584b)

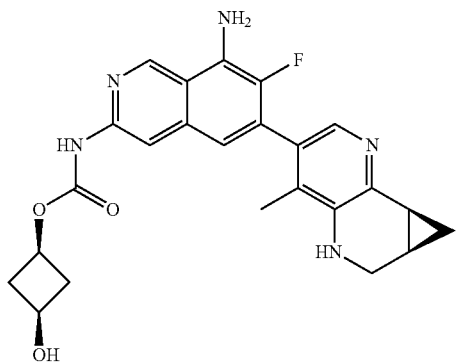

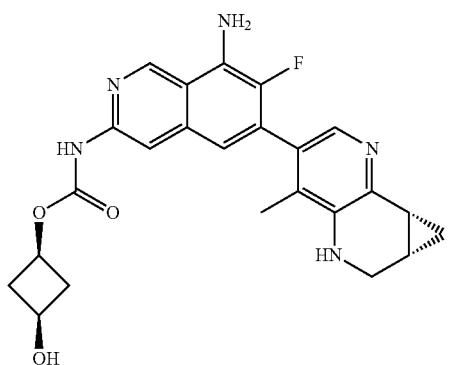

Step 1: tert-Butyl N-(5-bromo-4-methyl-2-vinyl-3-pyridyl)carbamate

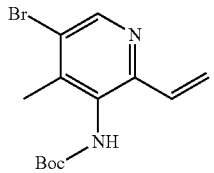 [SMILES: C=Cc1ncc(Br)c(C)c1NC(=O)OC(C)(C)C]

Under nitrogen, to a solution of tert-butyl N-(5-bromo-2-iodo-4-methyl-3-pyridyl)carbamate (5.0 g, 12.11 mmol) and 4,4,5,5-tetramethyl-2-vinyl-1,3,2-dioxaborolane (2.8 g, 18.18 mmol) in 1,4-dioxane (50 mL) and water (5 mL) was added Pd(dppf)Cl₂ (0.85 g, 1.16 mmol) and K₂CO₃ (5.0 g, 36.23 mmol) at room temperature. The resulting solution was stirred for 2 h at 60° C. After filtration, the filtrate was concentrated under reduced pressure. The residue was purified by flash chromatography on silica gel eluting with petroleum ether/ethyl acetate (5/1) to afford tert-butyl N-(5-bromo-4-methyl-2-vinyl-3-pyridyl)carbamate (3.5 g, 11.175 mmol, 92.3% yield) as a yellow solid. LCMS (ESI) [M+H]⁺= 313.

Step 2: tert-Butyl N-allyl-N-(5-bromo-4-methyl-2-vinyl-3-pyridyl)carbamate

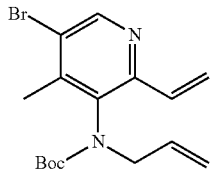 [SMILES: C=CCN(C(=O)OC(C)(C)C)c1c(C=C)ncc(Br)c1C]

A solution of tert-butyl N-(5-bromo-4-methyl-2-vinyl-3-pyridyl)carbamate (1000 mg, 3.19 mmol) and NaHMDS (4 mL, 8 mmol, 2 mol/L in THF) in tetrahydrofuran (20 mL) was stirred at room temperature under nitrogen for 30 min. Then NaI (1198 mg, 7.99 mmol) and allyl bromide (966 mg, 7.98 mmol) was added. The mixture was stirred at room temperature for 1 hour and then concentrated under vacuum. The residue was purified by flash chromatography on silica gel eluting with petroleum ether/ethyl acetate (1:2) to afford tert-butyl N-allyl-N-(5-bromo-4-methyl-2-vinyl-3-pyridyl)carbamate (670 mg, 1.897 mmol, 59.4% yield) as a yellow oil. LCMS (ESI) [M+H]⁺=353.

Step 3: tert-Butyl 7-bromo-8-methyl-2H-1,5-naphthyridine-1-carboxylate

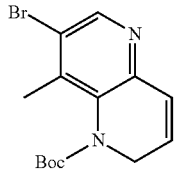 [SMILES: Cc1c(Br)cnc2c1N(C(=O)OC(C)(C)C)CC=C2]

A solution of tert-butyl N-allyl-N-(5-bromo-4-methyl-2-vinyl-3-pyridyl)carbamate (4.0 g, 11.32 mmol) and Grubbs catalyst 2nd generation (2.0 g, 2.36 mmol) in dichloromethane (200 mL) was stirred at 40° C. under nitrogen for 2 hours. The reaction solution was washed with water. The organic phase was concentrated under vacuum. The residue was purified by flash chromatography on silica gel eluting with petroleum ether/ethyl acetate (5/1) to afford tert-butyl 7-bromo-8-methyl-2H-1,5-naphthyridine-1-carboxylate (2.68 g, 8.241 mmol, 72.8% yield) as a yellow oil. LCMS (ESI) [M+H]$^+$=325.

Step 4: tert-Butyl 5-bromo-4-methyl-1,1a,2,7b-tetrahydrocyclopropa[c][1,5]naphthyridine-3-carboxylate

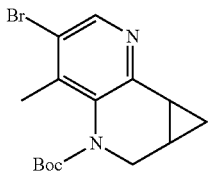 [SMILES: Cc1c(Br)cnc2c1N(C(=O)OC(C)(C)C)CC1CC21]

A solution of trimethylsulfoxonium iodide (8.1 g, 36.81 mmol) and t-BuOK (3.3 g, 29.46 mmol) in DMSO (100 mL) was stirred at room temperature for 2 hours. Then tert-butyl 7-bromo-8-methyl-2H-1,5-naphthyridine-1-carboxylate (2.4 g, 7.38 mmol) was added and the mixture was stirred at 50° C. for 16 hours. The reaction mixture was diluted with ethyl acetate, washed with sodium carbonate (aq.) and brine. The organic phase was dried, filtered and concentrated under vacuum. The residue was purified by flash chromatography on silica gel eluting with petroleum ether/ethyl acetate (3/1) to afford tert-butyl 5-bromo-4-methyl-1,1a,2,7b-tetrahydrocyclopropa[c][1,5]naphthyridine-3-carboxylate (1500 mg, 4.422 mmol, 59.9% yield) as a yellow solid. LCMS (ESI) [M+H]$^+$=339.

Step 5: tert-Butyl 4-methyl-5-(4,4,5,5-tetramethyl-1,3,2-dioxaborolan-2-yl)-1,1a,2,7b-tetrahydrocyclopropa[c][1,5]naphthyridine-3-carboxylate

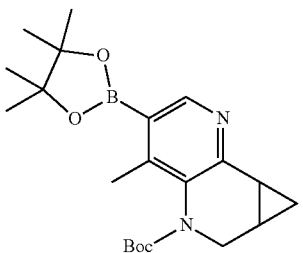 [SMILES: Cc1c(B2OC(C)(C)C(C)(C)O2)cnc2c1N(C(=O)OC(C)(C)C)CC1CC21]

A solution of tert-butyl 5-bromo-4-methyl-1,1a,2,7b-tetrahydrocyclopropa[c][1,5]naphthyridine-3-carboxylate (1500 mg, 4.42 mmol), bis(pinacolato)diboron (5600 mg, 22.05 mmol), Pd(dppf)Cl$_2$ (323 mg, 0.44 mmol) and KOAc (1300 mg, 13.27 mmol) in 1,4-dioxane (60 mL) and water (6 mL) was stirred at 60° C. for 16 hours. The reaction mixture was concentrated under vacuum. The residue was purified by flash chromatography on silica gel eluting with petroleum ether/ethyl acetate (1/10) to afford tert-butyl 4-methyl-5-(4,4,5,5-tetramethyl-1,3,2-dioxaborolan-2-yl)-1,1a,2,7b-tetrahydrocyclopropa[c][1,5]naphthyridine-3-carboxylate (1500 mg, 3.88 mmol, 87.8% yield) as a yellow solid. LCMS (ESI) [M+H]$^+$=387.

Step 6: tert-Butyl 5-(3-amino-8-chloro-7-fluoro-6-isoquinolyl)-4-methyl-1,1a,2,7b-tetrahydrocyclopropa[c][1,5]naphthyridine-3-carboxylate

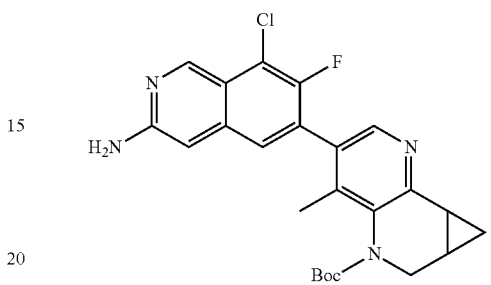

A mixture of tert-butyl 4-methyl-5-(4,4,5,5-tetramethyl-1,3,2-dioxaborolan-2-yl)-1,1a,2,7b-tetrahydrocyclopropa[c][1,5]naphthyridine-3-carboxylate (1.5 g, 3.90 mmol), 8-chloro-7-fluoro-6-iodo-isoquinolin-3-amine (1.35 g, 4.2 mmol), Pd(dppf)Cl$_2$ (300 mg, 0.30 mmol) and K$_2$CO$_3$ (1650 mg, 1.20 mmol) in 1,4-dioxane (150 mL) and water (3 mL) was stirred at 60° C. for 2 hours. The reaction mixture was concentrated under vacuum and purified by flash chromatography on silica gel eluting with petroleum ether/ethyl acetate (1/1) to afford tert-butyl 5-(3-amino-8-chloro-7-fluoro-6-isoquinolyl)-4-methyl-1,1a,2,7b-tetrahydrocyclopropa[c][1,5]naphthyridine-3-carboxylate (1200 mg, 2.637 mmol, 67.9% yield) as a yellow solid. LCMS (ESI) [M+H]$^+$= 455.

Step 7: tert-Butyl 5-[8-chloro-3-(1,3-dioxoisoindolin-2-yl)-7-fluoro-6-isoquinolyl]-4-methyl-1,1a,2,7b-tetrahydrocyclopropa[c][1,5]naphthyridine-3-carboxylate

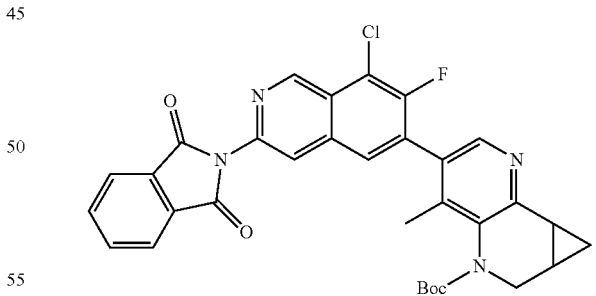

To a solution of tert-butyl 5-(3-amino-8-chloro-7-fluoro-6-isoquinolyl)-4-methyl-1,1a,2,7b-tetrahydrocyclopropa[c][1,5]naphthyridine-3-carboxylate (1.0 g, 2.2 mmol) in toluene (100 mL) was added phthalicanhydride (700 mg, 4.73 mmol) at room temperature. The resulting solution was stirred for 16 h at 100° C. and concentrated under vacuum. The residue was purified by flash chromatography on silica gel eluting with petroleum ether/ethyl acetate (1/3) to afford tert-butyl 5-[8-chloro-3-(1,3-dioxoisoindolin-2-yl)-7-fluoro-6-isoquinolyl]-4-methyl-1,1a,2,7b-tetrahydrocyclopropa[c][1,5]naphthyridine-3-carboxylate (700 mg, 1.197 mmol, 54.4% yield) as a brown solid. LCMS (ESI) [M+H]⁺= 585.

Step 8: tert-Butyl 5-[8-(tert-butoxycarbonylamino)-3-(1,3-dioxoisoindolin-2-yl)-7-fluoro-6-isoquinolyl]-4-methyl-1,1a,2,7b-tetrahydrocyclopropa[c][1,5]naphthyridine-3-carboxylate

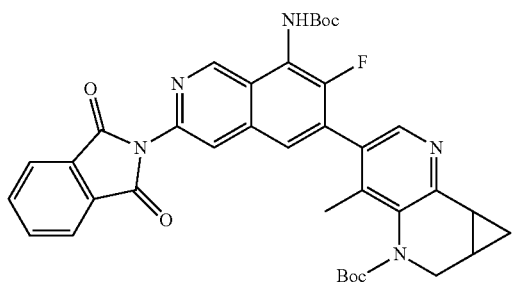 [SMILES: Cc1c(-c2cc3cc(N4C(=O)c5ccccc5C4=O)ncc3c(NC(=O)OC(C)(C)C)c2F)cnc2c1N(C(=O)OC(C)(C)C)CC1CC21]

Under nitrogen, to a solution of tert-butyl 5-[8-chloro-3-(1,3-dioxoisoindolin-2-yl)-7-fluoro-6-isoquinolyl]-4-methyl-1,1a,2,7b-tetrahydrocyclopropa[c][1,5]naphthyridine-3-carboxylate (640 mg, 1.09 mmol) and NH₂Boc (2.6 g, 22.22 mmol) in 1,4-dioxane (30 mL) was added Brettphos Pd G3 (200 mg, 0.22 mmol) and K₂CO₃ (450 mg, 3.26 mmol) at room temperature. The resulting mixture was stirred for 2 h at 90° C. After filtration, the filtrate was concentrated under reduced pressure. The crude product was used in the next step without purification. LCMS (ESI) [M+H]⁺=666.

Step 9: tert-Butyl 5-[3-amino-8-(tert-butoxycarbonylamino)-7-fluoro-6-isoquinolyl]-4-methyl-1,1a,2,7b-tetrahydrocyclopropa[c][1,5]naphthyridine-3-carboxylate

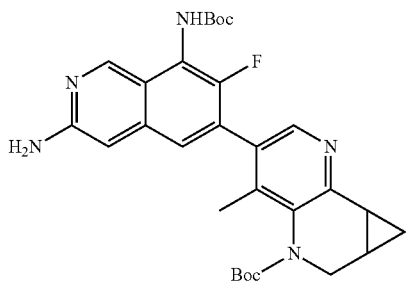 [SMILES: Cc1c(-c2cc3cc(N)ncc3c(NC(=O)OC(C)(C)C)c2F)cnc2c1N(C(=O)OC(C)(C)C)CC1CC21]

Under nitrogen, to a solution of tert-butyl 5-[8-(tert-butoxycarbonylamino)-3-(1,3-dioxoisoindolin-2-yl)-7-fluoro-6-isoquinolyl]-4-methyl-1,1a,2,7b-tetrahydrocyclopropa[c][1,5]naphthyridine-3-carboxylate (600 mg, 0.90 mmol) in methyl alcohol (10 mL) was added N₂H₄·H₂O (600 mg, 9.6 mmol) at room temperature. The resulting solution was stirred for 2 h at 40° C. The residue was purified by flash chromatography on silica gel eluting with dichloromethane/methanol (92/8) to afford tert-butyl 5-[3-amino-8-(tert-butoxycarbonylamino)-7-fluoro-6-isoquinolyl]-4-methyl-1,1a,2,7b-tetrahydrocyclopropa[c][1,5]naphthyridine-3-carboxylate (400 mg, 0.7468 mmol, 82.9% yield) as a brown solid. LCMS (ESI) [M+H]⁺=536.

Step 10: tert-Butyl 5-[8-(tert-butoxycarbonylamino)-3-[[3-[tert-butyl(dimethyl)silyl]oxycyclobutoxy]carbonylamino]-7-fluoro-6-isoquinolyl]-4-methyl-1,1a,2,7b-tetrahydrocyclopropa[c][1,5]naphthyridine-3-carboxylate

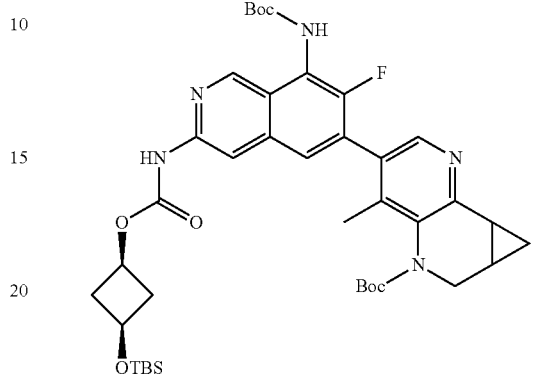

To a solution of tert-butyl 5-[3-amino-8-(tert-butoxycarbonylamino)-7-fluoro-6-isoquinolyl]-4-methyl-1,1a,2,7b-tetrahydrocyclopropa[c][1,5]naphthyridine-3-carboxylate (300 mg, 0.56 mmol) and 3-[tert-butyl(dimethyl)silyl]oxycyclobutanol (250 mg, 1.24 mmol) in dichloromethane (30 mL) was added DIEA (730 mg, 5.66 mmol) at room temperature. Then triphosgene (140 mg, 0.47 mmol) was added. The mixture was stirred at 0° C. for 1 hour. The residue was purified by flash chromatography on silica gel eluting with petroleum ether/ethyl acetate (1/1) to afford tert-butyl 5-[8-(tert-butoxycarbonylamino)-3-[[3-[tert-butyl(dimethyl)silyl]oxycyclobutoxy]carbonylamino]-7-fluoro-6-isoquinolyl]-4-methyl-1,1a,2,7b-tetrahydrocyclopropa[c][1,5]naphthyridine-3-carboxylate (220 mg, 0.288 mmol, 51.4% yield) as a yellow solid. LCMS (ESI) [M+H]⁺=764.

Step 11: (1s,3r)-3-hydroxycyclobutyl (8-amino-7-fluoro-6-((6ar,7as)-4-methyl-6,6a,7,7a-tetrahydro-5H-cyclopropa[c][1,5]naphthyridin-3-yl)isoquinolin-3-yl)carbamate and (1s,3s)-3-Hydroxycyclobutyl (8-amino-7-fluoro-6-((6as,7ar)-4-methyl-6,6a,7,7a-tetrahydro-5H-cyclopropa[c][1,5]naphthyridin-3-yl)isoquinolin-3-yl)carbamate

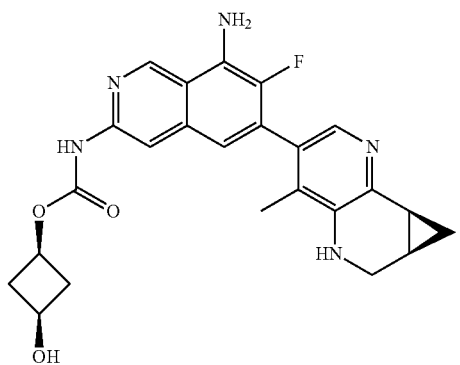

513
-continued

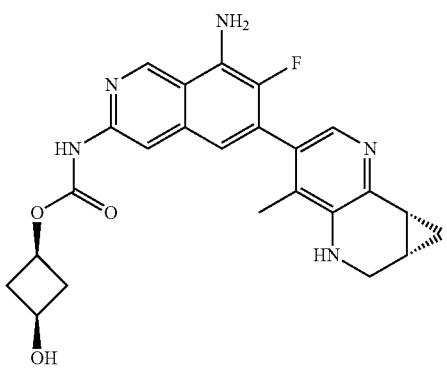

To a solution of tert-butyl 5-[8-(tert-butoxycarbonylamino)-3-[[3-[tert-butyl(dimethyl)silyl]oxycyclobutoxy]carbonylamino]-7-fluoro-6-isoquinolyl]-4-methyl-1,1a,2,7b-tetrahydrocyclopropa[c][1,5]naphthyridine-3-carboxylate (220 mg, 0.29 mmol) in dichloromethane (6 mL) was added TFA (3 mL) at room temperature. The reaction was concentrated under vacuum and purified by reverse phase chromatography (acetonitrile 0-40/0.1% NH$_4$HCO$_3$ in water) to afford a mixture of stereoisomers. The mixture was separated by chiral-Prep-HPLC (Column: CHIRALPAK IF, 2*25 cm, 5 μm; Mobile Phase A: MTBE (10 mm NH$_3$-MeOH), Mobile Phase B: EtOH; Flow rate: 13 mL/min; Gradient: 15 B to 15 B in 38 min) to afford two enantiomers. Relative stereochemistry on cyclobutyl is as drawn. Absolute stereochemistry was arbitrarily assigned.

Enantiomer 1 (Compound 584a) (27.1 mg, 0.062 mmol, 22.8% yield). R$_T$ 3.018 min (CHIRALPAK IF-3, 0.46*5 cm, 3 μm; MTBE (0.1% DEA):EtOH=85:15 in 8 min; 1 mL/min). LCMS (ESI) [M+H]$^+$=450.2, R$_T$ 1.057 min, Method J; $^1$H NMR (300 MHz, DMSO-d$_6$) δ 10.08 (s, 1H), 9.34 (s, 1H), 7.96 (s, 1H), 7.59 (s, 1H), 6.84 (d, J=6.2 Hz, 1H), 6.21 (s, 2H), 5.20 (d, J=6.6 Hz, 1H), 5.14 (s, 1H), 4.53 (p, J=7.4 Hz, 1H), 3.81 (p, J=7.1 Hz, 1H), 3.46-3.36 (m, 1H), 3.25-3.14 (m, 1H), 2.78-2.63 (m, 2H), 2.09 (td, J=8.5, 4.3 Hz, 1H), 2.01-1.85 (m, 6H), 1.30-1.28 (m, 1H), 0.95 (dt, J=8.4, 4.2 Hz, 1H).

Enantiomer 2 (Compound 584b) (25.9 mg, 0.059 mmol, 21.8% yield). R$_T$ 4.381 min (CHIRALPAK IF-3, 46*5 cm, 3 μm; MTBE (0.1% DEA):EtOH=85:15 in 8 min; 1 mL/min). LCMS (ESI) [M+H]$^+$=450.2, R$_T$ 1.057 min, Method J; $^1$H NMR (300 MHz, DMSO-d$_6$) δ 10.08 (s, 1H), 9.34 (s, 1H), 7.96 (s, 1H), 7.59 (s, 1H), 6.84 (d, J=6.2 Hz, 1H), 6.21 (s, 2H), 5.20 (d, J=6.6 Hz, 1H), 5.14 (s, 1H), 4.53 (p, J=7.4 Hz, 1H), 3.81 (p, J=7.1 Hz, 1H), 3.46-3.36 (m, 1H), 3.25-3.14 (m, 1H), 2.78-2.63 (m, 2H), 2.09 (td, J=8.5, 4.3 Hz, 1H), 2.01-1.85 (m, 6H), 1.30-1.28 (m, 1H), 0.95 (dt, J=8.4, 4.2 Hz, 1H).

514

Example 206

(1s,3s)-3-Hydroxycyclobutyl (8-amino-6-((S)-4,7-dimethyl-5,6,7,8-tetrahydro-1,5-naphthyridin-3-yl)-7-fluoroisoquinolin-3-yl)carbamate and (1s,3s)-3-Hydroxycyclobutyl (8-amino-6-((R)-4,7-dimethyl-5,6,7,8-tetrahydro-1,5-naphthyridin-3-yl)-7-fluoroisoquinolin-3-yl)carbamate (Compound 560a and Compound 560b)

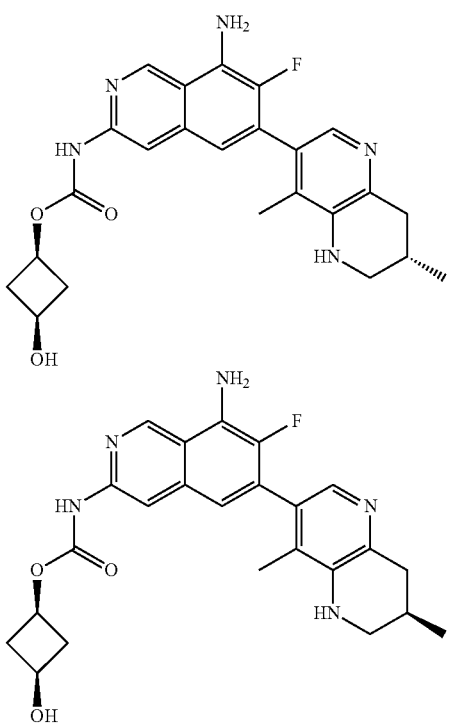

Step 1: tert-Butyl N-(5-bromo-2-iodo-4-methyl-3-pyridyl)-N-(3-bromo-2-methyl-propyl)carbamate

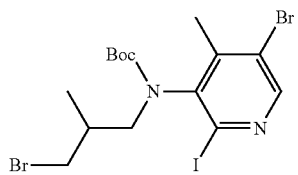 [SMILES: Cc1c(Br)cnc(I)c1N(CC(C)CBr)C(=O)OC(C)(C)C]

Under nitrogen, a solution of tert-butyl N-(5-bromo-2-iodo-4-methyl-3-pyridyl)carbamate (4.40 g, 10.65 mmol), 3-bromo-2-methyl-1-propanol (3.20 g, 20.91 mmol) and PPh$_3$ (5.60 mg, 21.37 mmol) in tetrahydrofuran (50 mL) was stirred at 0° C. Then DIAD (4.30 g, 21.29 mmol) was added dropwise. The mixture was stirred at 25° C. for 2 hours. The reaction mixture was concentrated under vacuum. The residue was purified by flash chromatography on silica gel eluting with ethyl acetate/petroleum ether (1/4) to afford tert-butyl N-(5-bromo-2-iodo-4-methyl-3-pyridyl)-N-(3-bromo-2-methyl-propyl)carbamate (5.20 g, 9.488 mmol, 89.1% yield) as a white solid. LCMS (ESI) [M+H]$^+$=547.

Step 2: tert-Butyl 7-bromo-3,8-dimethyl-3,4-di-hydro-2H-1,5-naphthyridine-1-carboxylate

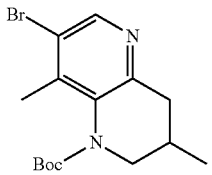

A solution of zinc (2.86 g, 43.74 mmol), nickel chloride (1.9 g, 14.62 mmol) and methyl acrylate (3.77 g, 43.84 mmol) in pyridine (40 mL) was stirred at room temperature and then heated to 55° C. for 20 min. Then a solution of tert-butyl N-(5-bromo-2-iodo-4-methyl-3-pyridyl)-N-(3-bromo-2-methyl-propyl)carbamate (4.0 g, 7.3 mmol) in N,N-dimethylformamide (160 mL) was added dropwise. The mixture was stirred at 0° C. for 1 hour. The reaction was quenched with water. After filtration, the filtrate was collected and diluted with water. The resulting solution was extracted with ethyl acetate. The organic layers were combined, dried over anhydrous sodium sulfate and concentrated under vacuum. The residue was purified by flash chromatography on silica gel eluting with ethyl acetate/petroleum ether (1/10) to afford tert-butyl 7-bromo-3,8-dimethyl-3,4-dihydro-2H-1,5-naphthyridine-1-carboxylate (1 g, 2.784 mmol, 38.1% yield) as a brown color solid. LCMS (ESI) $[M+H]^+=341$.

Step 3: tert-Butyl 3,8-dimethyl-7-(4,4,5,5-tetramethyl-1,3,2-dioxaborolan-2-yl)-3,4-dihydro-2H-1,5-naphthyridine-1-carboxylate

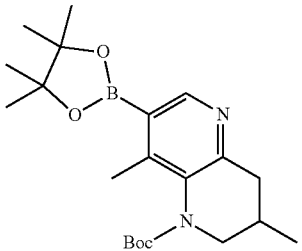

A mixture of tert-butyl 7-bromo-3,8-dimethyl-3,4-dihydro-2H-1,5-naphthyridine-1-carboxylate (1.0 g, 2.94 mmol), bis(pinacolato)diboron (7.47 g, 29.42 mmol), 1,1'-bis(diphenylphosphino) ferrocene-palladium(II)dichloride dichloromethane complex (0.48 g, 0.59 mmol) and potassium acetate (0.86 g, 8.78 mmol) in 1,4-dioxane (50 mL) was stirred at 0° C. for 16 hours. After filtration, the filtrate was collected and concentrated under vacuum. The resulting residue was purified by reverse phase chromatography (acetonitrile 0-50/0.1% NH$_4$OH in water) to afford tert-butyl 3,8-dimethyl-7-(4,4,5,5-tetramethyl-1,3,2-dioxaborolan-2-yl)-3,4-dihydro-2H-1,5-naphthyridine-1-carboxylate (0.72 g, 1.762 mmol, 59.9% yield) as a black solid. LCMS (ESI) $[M+H]^+=341$.

Step 4: tert-Butyl 7-(3-amino-8-chloro-7-fluoro-6-isoquinolyl)-3,8-dimethyl-3,4-dihydro-2H-1,5-naphthyridine-1-carboxylate

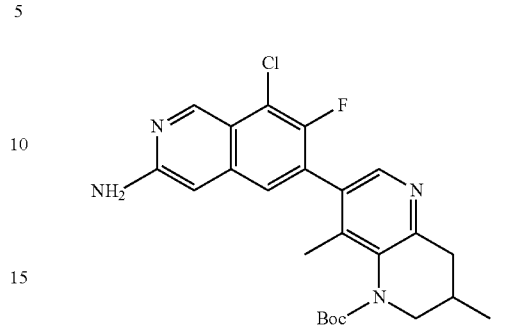

A mixture of tert-butyl 3,8-dimethyl-7-(4,4,5,5-tetramethyl-1,3,2-dioxaborolan-2-yl)-3,4-dihydro-2H-1,5-naphthyridine-1-carboxylate (700.0 mg, 1.8 mmol), 8-chloro-7-fluoro-6-iodo-isoquinolin-3-amine (698 mg, 2.16 mmol), 1,1'-bis(diphenylphosphino)ferrocene-palladium(II)dichloride dichloromethane complex (372 mg, 0.46 mmol) and potassium carbonate (746.0 mg, 5.41 mmol) in 1,4-dioxane (30 mL) and water (3 mL) was stirred for 12 hours at 60° C. The reaction mixture was diluted with ethyl acetate and dried over anhydrous sodium sulfate, filtered and concentrated under vacuum. The residue was purified by flash chromatography on silica gel eluting with petroleum ether/ethyl acetate (1:1) to afford tert-butyl 7-(3-amino-8-chloro-7-fluoro-6-isoquinolyl)-3,8-dimethyl-3,4-dihydro-2H-1,5-naphthyridine-1-carboxylate (680 mg, 1.369 mmol, 75.9% yield) as a brown solid.

Step 5: tert-Butyl-7-[8-chloro-3-(1,3-dioxoisoindolin-2-yl)-7-fluoro-6-isoquinolyl]-3,8-dimethyl-3,4-dihydro-2H-1,5-naphthyridine-1-carboxylate

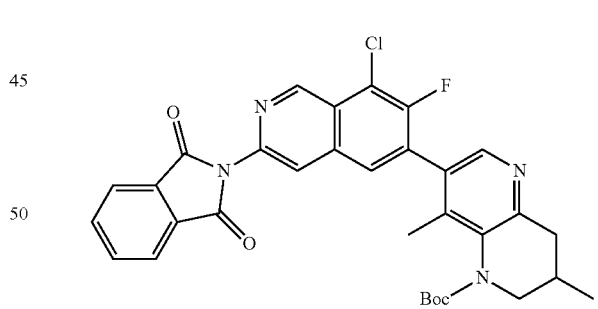

A solution of tert-butyl 7-(3-amino-8-chloro-7-fluoro-6-isoquinolyl)-3,8-dimethyl-3,4-dihydro-2H-1,5-naphthyridine-1-carboxylate (660 mg, 1.44 mmol) and phthalicanhydride (427 mg, 2.89 mmol) in toluene (40 mL) was stirred at 100° C. for 2 hours. The reaction mixture was concentrated under vacuum. The residue was purified by flash chromatography on silica gel eluting with ethyl acetate/petroleum (60:40) to afford tert-butyl-7-[8-chloro-3-(1,3-dioxoisoindolin-2-yl)-7-fluoro-6-isoquinolyl]-3,8-dimethyl-3,4-dihydro-2H-1,5-naphthyridine-1-carboxylate (450 mg, 0.728 mmol, 50.4% yield) as a brown solid. LCMS (ESI) $[M+H]^+=587$.

Step 6: tert-Butyl-7-[8-(tert-butoxycarbonylamino)-3-(1,3-dioxoisoindolin-2-yl)-7-fluoro-6-isoquinolyl]-3,8-dimethyl-3,4-dihydro-2H-1,5-naphthyridine-1-carboxylate

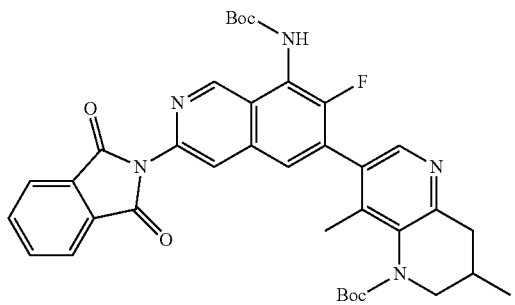 [SMILES: Cc1c(-c2cc3cc(N4C(=O)c5ccccc5C4=O)ncc3c(NC(=O)OC(C)(C)C)c2F)cnc2c1N(C(=O)OC(C)(C)C)CC(C)C2]

A mixture of tert-butyl 7-[8-chloro-3-(1,3-dioxoisoindolin-2-yl)-7-fluoro-6-isoquinolyl]-3,8-dimethyl-3,4-dihydro-2H-1,5-naphthyridine-1-carboxylate (450 mg, 0.77 mmol), tert-butyl carbamate (1.79 g, 15.3 mmol), Brettphpos Pd G3 (132 mg, 0.15 mmol) and potassium carbonate (198 mg, 1.43 mmol) in 1,4-dioxane (30 mL) was stirred at 90° C. for 3 hours. After filtration, the filtrate was concentrated under reduced pressure to afford crude product as a brown solid. The crude product would be directly used in the next step without purification. LCMS (ESI) [M+H]⁺=668. LCMS (ESI) [M+H]⁺=668.

Step 7: tert-Butyl 7-[3-amino-8-(tert-butoxycarbonylamino)-7-fluoro-6-isoquinolyl]-3,8-dimethyl-3,4-dihydro-2H-1,5-naphthyridine-1-carboxylate

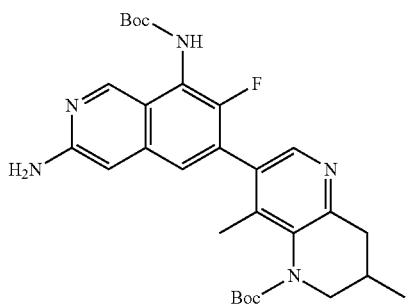 [SMILES: Cc1c(-c2cc3cc(N)ncc3c(NC(=O)OC(C)(C)C)c2F)cnc2c1N(C(=O)OC(C)(C)C)CC(C)C2]

A solution of tert-butyl 7-[8-(tert-butoxycarbonylamino)-3-(1,3-dioxoisoindolin-2-yl)-7-fluoro-6-isoquinolyl]-3,8-dimethyl-3,4-dihydro-2H-1,5-naphthyridine-1-carboxylate (400 mg, crude) and hydrazine hydrate (299 mg, 5.98 mmol) in methyl alcohol (26 mL) was stirred at room temperature for 2 hours. The reaction mixture was concentrated under vacuum. The residue was purified by flash chromatography on silica gel eluting with ethyl acetate/petroleum (60/40) to afford tert-butyl 7-[3-amino-8-(tert-butoxycarbonylamino)-7-fluoro-6-isoquinolyl]-3,8-dimethyl-3,4-dihydro-2H-1,5-naphthyridine-1-carboxylate (240 mg, 0.429 mmol, 71.6% yield) as a brown solid. LCMS (ESI) [M+H]⁺=538.

Step 8: tert-Butyl-7-[8-(tert-butoxycarbonyl amino)-3-[[3-[tert-butyl (dimethyl)silyl]oxycyclobutoxy]-carbonylamino]-7-fluoro-6-isoquinolyl]-3,8-dimethyl-3,4-dihydro-2H-1,5-naphthyridine-1-carboxylate

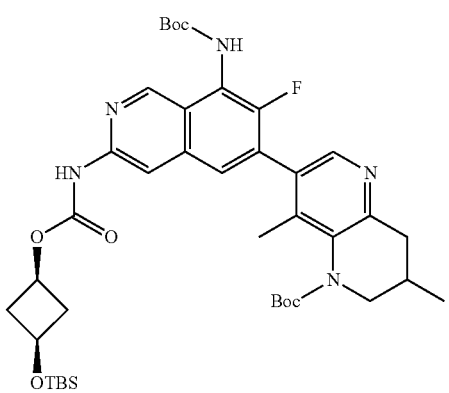 [SMILES: Cc1c(-c2cc3cc(NC(=O)O[C@H]4C[C@@H](O[Si](C)(C)C(C)(C)C)C4)ncc3c(NC(=O)OC(C)(C)C)c2F)cnc2c1N(C(=O)OC(C)(C)C)CC(C)C2]

A solution of tert-butyl 7-[3-amino-8-(tert-butoxycarbonylamino)-7-fluoro-6-isoquinolyl]-3,8-dimethyl-3,4-dihydro-2H-1,5-naphthyridine-1-carboxylate (240 mg, 0.45 mmol), cis-3-[tert-butyl(dimethyl)silyl]oxycyclobutanol (180 mg, 0.89 mmol) and N,N-diisopropylethylamine (575 mg, 4.46 mmol) in dichloromethane (18 mL) was stirred at 0° C. Then a solution of triphosgene (132 mg, 0.44 mmol) in dichloromethane (2 mL) was added dropwise. The mixture was stirred at 0° C. for 2 hours. The resulting mixture was diluted with dichloromethane and washed with water. The organic layer was dried over anhydrous sodium sulfate and concentrated under vacuum. The residue was purified by flash chromatography on silica gel eluting with dichloromethane/methanol (19:1) to afford cis-tert-butyl-7-[8-(tert-butoxycarbonylamino)-3-[[3-[tert-butyl(dimethyl)silyl]oxycyclobutoxy]carbonylamino]-7-fluoro-6-isoquinolyl]-3,8-dimethyl-3,4-dihydro-2H-1,5-naphthyridine-1-carboxylate (300 mg, 0.372 mmol, 83.4% yield) as a brown solid. LCMS (ESI) [M+H]⁺=766.

Step 9: (1s,3s)-3-Hydroxycyclobutyl (8-amino-6-((S)-4,7-dimethyl-5,6,7,8-tetrahydro-1,5-naphthyridin-3-yl)-7-fluoroisoquinolin-3-yl)carbamate and (1s,3s)-3-Hydroxycyclobutyl (8-amino-6-((R)-4,7-dimethyl-5,6,7,8-tetrahydro-1,5-naphthyridin-3-yl)-7-fluoroisoquinolin-3-yl)carbamate

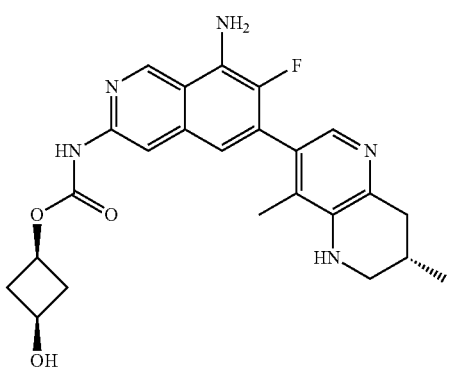

519
-continued

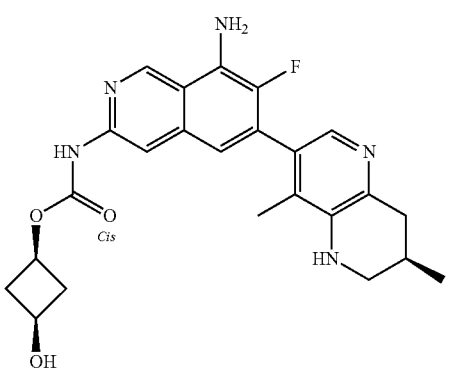

To a solution of tert-butyl-7-[8-(tert-butoxycarbonylamino)-3-[[3-[tert-butyl(dimethyl)silyl]oxycyclobutoxy]carbonylamino]-7-fluoro-6-isoquinolyl]-3,8-dimethyl-3,4-dihydro-2H-1,5-naphthyridine-1-carboxylate (260 mg, 0.34 mmol) in dichloromethane (15 mL) was added TFA (20 mL). The mixture was stirred at room temperature for 1 hour. The reaction mixture was concentrated under vacuum. The crude product was purified by Prep-HPLC (Column: X-Bridge Prep Phenyl OBD Column 5 μm, 19*250 mm; Mobile Phase A: water (0.1% FA), Mobile Phase B: ACN; Flow rate: 25 mL/min; Gradient: 5% B to 33% B in 8 min) to afford a mixture of stereoisomers. The mixture was separated by Chiral-HPLC to afford two isomers. Relative stereochemistry on cyclobutyl are as drawn. Absolute stereochemistry was arbitrarily assigned.

Isomer 1 (Compound 560a) (20.4 mg, 0.044 mmol, 13% yield). $R_T$ 1.984 min (CHIRALPAK IF-3, 2*25 cm, 5 μm; (Hex:DCM=3:1)(0.1% DEA): EtOH=50:50 in 6 min, 1.0 mL/min). LCMS (ESI) [M+H]=452.3, $R_T$ 2.263 min, Method M; $^1$H NMR (400 MHz, DMSO-$d_6$) δ 10.08 (s, 1H), 9.34 (s, 1H), 7.96 (s, 1H), 7.59 (s, 1H), 6.84 (d, J=6.1 Hz, 1H), 6.22 (s, 2H), 5.50 (s, 1H), 5.21 (d, J=6.6 Hz, 1H), 4.53 (p, J=7.3 Hz, 1H), 3.81 (p, J=7.1 Hz, 1H), 2.89 (d, J=11.5 Hz, 2H), 2.76-2.67 (m, 2H), 2.59-2.52 (m, 2H), 2.00-1.86 (m, 6H), 1.06 (d, J=6.6 Hz, 3H).

Isomer 2 (Compound 560b) (20.9 mg, 0.0457 mmol, 13.5% yield). $R_T$ 3.275 min (CHIRALPAK IF-3, 2*25 cm, 5 μm; (Hex:DCM=3:1) (0.1% DEA): EtOH=50:50 in 6 min, 1.0 mL/min). LCMS (ESI) [M+H]=452.3, $R_T$ 2.263 min, Method M; $^1$H NMR (400 MHz, DMSO-$d_6$) δ 10.08 (s, 1H), 9.34 (s, 1H), 7.96 (s, 1H), 7.59 (s, 1H), 6.84 (d, J=6.1 Hz, 1H), 6.22 (s, 2H), 5.50 (s, 1H), 5.21 (d, J=6.6 Hz, 1H), 4.53 (p, J=7.3 Hz, 1H), 3.81 (p, J=7.1 Hz, 1H), 2.89 (d, J=11.5 Hz, 2H), 2.76-2.67 (m, 2H), 2.59-2.52 (m, 2H), 2.00-1.86 (m, 6H), 1.06 (d, J=6.6 Hz, 3H).

520

Example 207

(R)-Tetrahydrofuran-3-yl (8-amino-6-(4-cyano-5-methyl-3,4-dihydro-2H-pyrano[2,3-b]pyridin-6-yl)-7-fluoroisoquinolin-3-yl)carbamate (Compound 562a)

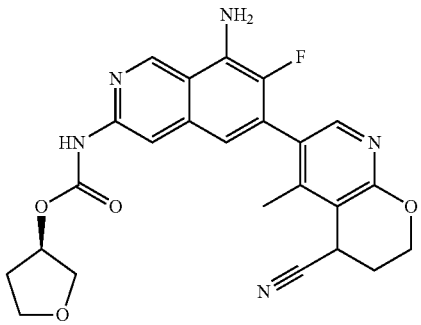 [SMILES: Cc1c(-c2cc3cc(NC(=O)O[C@@H]4CCOC4)ncc3c(N)c2F)cnc2c1C(C#N)CCO2]

Step 1: 3,5-Dibromo-2-methoxy-4-methylpyridine

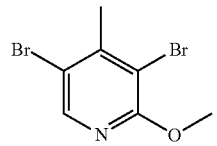

To a suspension of sodium acetate (11.6 mL, 215.05 mmol) and 2-methoxy-4-methylpyridine (8.83 g, 71.69 mmol) in acetic acid (70 mL) was added bromine (34.4 g, 215.06 mmol). The resulting solution was heated at 80° C. for 12 hours. The reaction was cooled to room temperature and concentrated under reduced pressure. The residue was then treated with a 10% sodium hydroxide solution and saturated sodium sulfite solution. The resulting mixture was extracted with diethyl ether. The combined organic layers were dried with anhydrous magnesium sulfate, filtered, and concentrated. The residue was purified by flash chromatography on silica gel eluting with petroleum ether/ethyl acetate (10/1) to afford 3,5-dibromo-2-methoxy-4-methyl-pyridine (18.54 g, 65.64 mmol, 91.6% yield) as a white solid. LCMS (ESI) [M+H]$^+$=280.0.

Step 2: 1-(5-Bromo-2-methoxy-4-methylpyridin-3-yl)prop-2-en-1-ol

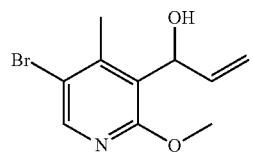

A solution of 3,5-dibromo-2-methoxy-4-methyl-pyridine (18.54 g, 65.64 mmol) in diethyl ether (250 mL) was cooled to −65° C. under nitrogen. N-butyl lithium (5.06 g, 79.12 mmol) was added dropwise with stirring while maintaining the temperature at −65° C. The reaction was cooled to −70°

C. and stirred for 1 hour under nitrogen. Acrolein (4.43 g, 79.12 mmol) was added dropwise at −65° C. Then the reaction was warmed to room temperature overnight. The reaction was quenched with saturated sodium bicarbonate solution and extracted with dichloromethane. The combined extracts were dried with magnesium sulfate and filtered. The filtrate was concentrated to afford 1-(5-bromo-2-methoxy-4-methyl-3-pyridyl)prop-2-en-1-ol (16.84 g, 65.48 mmol) as a clear oil which was used directly in the next step without further purification. LCMS (ESI) [M+H]$^+$=258.0.

Step 3: 1-(5-Bromo-2-methoxy-4-methylpyridin-3-yl)prop-2-en-1-one

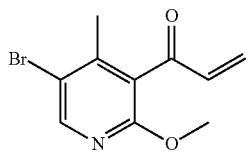

To a solution of 1-(3-bromo-6-methoxy-2-methyl-phenyl)prop-2-en-1-ol (16.84 g, 65.48 mmol) in dichloromethane (150 mL) was added Dess-Martin periodinane (41.7 g, 98.21 mmol) at room temperature. The reaction was stirred at room temperature overnight, then quenched by addition of a saturated sodium bicarbonate solution. The organic layer was collected. The aqueous layer was extracted with dichloromethane. The combined organic layers were dried with magnesium sulfate, filtered, and concentrated to afford a yellow oil that was purified by flash chromatography on silica gel eluting with PE/EtOAc (8/1) to afford 1-(3-bromo-6-methoxy-2-methyl-phenyl)prop-2-en-1-one (4.81 g, 18.78 mmol, 28.6% yield in two step) as a clear oil. LC/MS (ESI): (M+H)$^+$=256.0.

Step 4: 6-Bromo-5-methyl-2,3-dihydro-4H-pyrano[2,3-b]pyridin-4-one

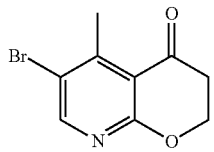

To a solution of 1-(5-bromo-2-methoxy-4-methyl-3-pyridyl)prop-2-en-1-one (4.81 g, 18.78 mmol) in acetic acid (80 mL) was added hydrobromicacid (9.5 g, 56.35 mmol). The reaction was heated to 100° C. for 45 min, then cooled to room temperature and extracted with ether. The combined organic layers were washed with saturated sodium bicarbonate solution. The organic layer was collected, dried with magnesium sulfate, filtered, and concentrated under vacuum. The residue was purified by flash chromatography on silica gel eluting with petroleum ether/ethyl acetate (4/1) to afford 6-bromo-5-methyl-2,3-dihydropyrano[2,3-b]pyridin-4-one (1803.9 mg, 7.45 mmol, 39.7% yield) as a white solid. LCMS (ESI) [M+H]$^+$=242.1.

Step 5: 6-Bromo-5-methyl-3,4-dihydro-2H-pyrano[2,3-b]pyridin-4-ol

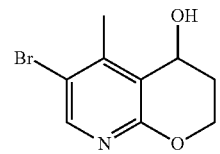

To a solution of 6-bromo-5-methyl-2,3-dihydropyrano[2,3-b]pyridin-4-one (1.81 mg, 7.45 mmol) in methyl alcohol (50 ml) was added sodium borohydride (657 mg, 17.35 mmol). The mixture was stirred for 12 hours at room temperature. The reaction was quenched water and then the mixture was extracted with ethyl acetate. The combined organic layers was then dried with magnesium sulfate, filtered, and concentrated to give 6-bromo-5-methyl-3,4-dihydro-2H-pyrano[2,3-b]pyridin-4-ol (1771.4 mg, 7.26 mmol) as a white solid, which was used directly in the next step without further purification. LCMS (ESI) [M+H]$^+$=244.1.

Step 6: 6-Bromo-4-chloro-5-methyl-3,4-dihydro-2H-pyrano[2,3-b]pyridine

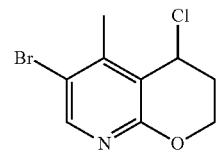

A solution of 6-bromo-5-methyl-3,4-dihydro-2H-pyrano[2,3-b]pyridin-4-ol (1.77 g, 7.26 mmol) and triethylamine (3.03 ml, 21.77 mmol) in dichloromethane (50 ml) was stirred at 0° C. for 5 min. Then methanesulfonyl chloride (0.84 ml, 10.88 mmol) was added. The mixture was stirred at 0° C. for 2 hours. The reaction was quenched with water and extracted with DCM. The organic layers were combined, dried over anhydrous sodium sulfate and concentrated under vacuum to give 6-bromo-4-chloro-5-methyl-3,4-dihydro-2H-pyrano[2,3-b]pyridine (2.28 g, 8.71 mmol) as a red oil, which was used directly in the next step without further purification. LCMS (ESI) [M+H]$^+$=262.1.

Step 7: 6-Bromo-5-methyl-3,4-dihydro-2H-pyrano[2,3-b]pyridine-4-carbonitrile

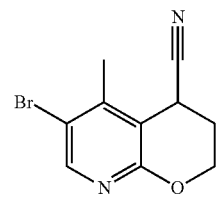

A solution of 6-bromo-4-chloro-5-methyl-3,4-dihydro-2H-pyrano[2,3-b]pyridine (2.29 mg, 8.71 mmol) and tetraethylammonium cyanide (4.08 g, 26.11 mmol) in toluene (90 ml) was stirred at 70° C. for 3 hours. The reaction mixture was diluted with water and extracted with ethyl acetate. The organic layers were combined, dried over anhydrous sodium sulfate and concentrated under vacuum. The residue was purified by flash chromatography on silica gel eluting with petroleum ether/ethyl acetate (1/1) to afford 6-bromo-5-methyl-3,4-dihydro-2H-pyrano[2,3-b]pyridine-4-carbonitrile (800.0 mg, 3.16 mmol, 42.42% yield in two step) as a yellow solid. LCMS (ESI) [M+H]⁺=253.1.

Step 8: 5-Methyl-6-(4,4,5,5-tetramethyl-1,3,2-dioxaborolan-2-yl)-3,4-dihydro-2H-pyrano[2,3-b]pyridine-4-carbonitrile

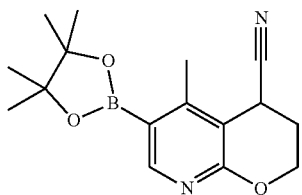 [SMILES: Cc1c(B2OC(C)(C)C(C)(C)O2)cnc2c1C(C#N)CCO2]

Under nitrogen, to a solution of 6-bromo-5-methyl-3,4-dihydro-2H-pyrano[2,3-b]pyridine-4-carbonitrile (800.0 mg, 3.16 mmol), bis(pinacolato)diboron (1.60 g, 6.32 mmol) and [1,1'-bis(diphenylphosphino)ferrocene]dichloropalladium(II) (468.9 mg, 0.63 mmol) in 1,4-dioxane (60 mL) was added potassium acetate (0.59 mL, 9.48 mmol) at room temperature. The resulting solution was stirred at 90° C. for 2 hours and concentrated under reduce pressure. The reaction mixture was used in the next step without purification. LCMS (ESI) [M+H]⁺=301.2.

Step 9: (R)-Tetrahydrofuran-3-yl (8-chloro-7-fluoro-6-iodoisoquinolin-3-yl)carbamate

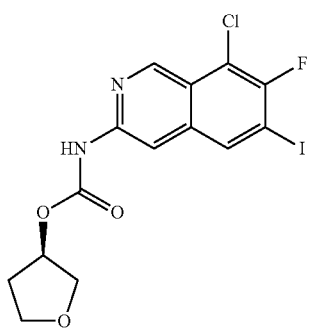 [SMILES: O=C(Nc1cc2cc(I)c(F)c(Cl)c2cn1)O[C@@H]1CCOC1]

To a solution of 8-chloro-7-fluoro-6-iodo-isoquinolin-3-amine (2.0 g, 6.2 mmol) and (R)-3-hydroxytetrahydrofuran (1.09 g, 12.42 mmol) in dichloromethane (60 ml) was added N,N-diisopropylethylamine (5.4 ml, 31.01 mmol) at 0° C. Then triphosgene (1.29 g, 4.34 mmol) dissolved in dichloromethane was added. The mixture was stirred at 0° C. for 0.5 hours. Then the resulting solution was stirred at room temperature for 12 hours. The reaction was quenched with water and extracted with dichloromethane. The organic layers were combined, dried over anhydrous sodium sulfate and concentrated under vacuum. The residue was purified by flash chromatography on silica gel eluting with dichloromethane/methanol (10/1) to afford [(3R)-tetrahydrofuran-3-yl]N-(8-chloro-7-fluoro-6-iodo-3-isoquinolyl)carbamate (1.5 g, 3.4 mmol, 55.4% yield) as a brown solid. LCMS (ESI) [M+H]⁺=436.9.

Step 10: (R)-Tetrahydrofuran-3-yl (8-chloro-6-(4-cyano-5-methyl-3,4-dihydro-2H-pyrano[2,3-b]pyridin-6-yl)-7-fluoroisoquinolin-3-yl)carbamate

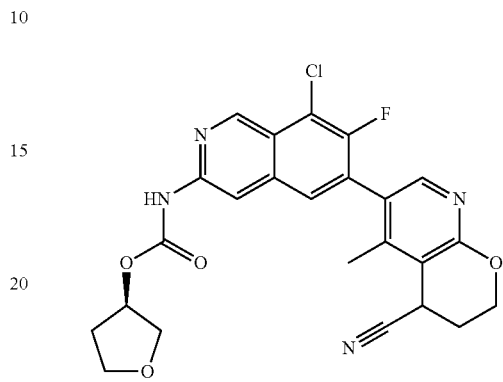

Under nitrogen, to a mixture of 5-methyl-6-(4,4,5,5-tetramethyl-1,3,2-dioxaborolan-2-yl)-3,4-dihydro-2H-pyrano[2,3-b]pyridine-4-carbonitrile (944.0 mg, 3.14 mmol), [(3R)-tetrahydrofuran-3-yl]N-(8-chloro-7-fluoro-6-iodo-3-isoquinolyl)carbamate (1.51 g, 3.46 mmol) and [1,1'-bis(diphenylphosphino)ferrocene]dichloropalladium(II) (466.6 mg, 0.63 mmol) in 1,4-dioxane (60 ml) and water (6 ml) was added K₂CO₃ (1.30 g, 9.43 mmol) at room temperature. The resulting solution was stirred at 70° C. for 2 hours. The reaction mixture was concentrated under vacuum. The residue was purified by flash chromatography on silica gel eluting with dichloromethane/ethyl acetate (1/1) to afford [(3R)-tetrahydrofuran-3-yl]N-[8-chloro-6-(4-cyano-5-methyl-3,4-dihydro-2H-pyrano[2,3-b]pyridin-6-yl)-7-fluoro-3-isoquinolyl]carbamate (600.0 mg, 1.24 mmol, 39.2% yield in two step) as a brown solid. LCMS (ESI) [M+H]⁺=483.1.

Step 11: tert-Butyl ((R)-tetrahydrofuran-3-yl) (6-(4-cyano-5-methyl-3,4-dihydro-2H-pyrano[2,3-b]pyridin-6-yl)-7-fluoroisoquinoline-3,8-diyl)dicarbamate

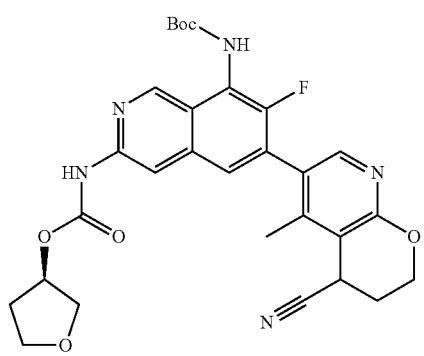 [SMILES: Cc1c(-c2cc3cc(NC(=O)O[C@@H]4CCOC4)ncc3c(NC(=O)OC(C)(C)C)c2F)cnc2c1C(C#N)CCO2]

Under nitrogen, to a mixture of [(3R)-tetrahydrofuran-3-yl]N-[8-chloro-6-(4-cyano-5-methyl-3,4-dihydro-2H-pyrano[2,3-b]pyridin-6-yl)-7-fluoro-3-isoquinolyl]carbamate (600.0 mg, 1.24 mmol), tert-butyl carbamate (8.73 g, 74.55 mmol) and BrettPhos Pd G3 (225.3 mg, 0.25 mmol) in 1,4-dioxane (60 mL) was added K$_2$CO$_3$ (515.2 mg, 3.73 mmol) at room temperature. The resulting solution was stirred at 90° C. for 2 hours. The reaction mixture was concentrated under vacuum. The residue was purified by flash chromatography on silica gel eluting with dichloromethane/ethyl acetate (1/1) to afford [(3R)-tetrahydrofuran-3-yl]N-[8-(tert-butoxycarbonylamino)-6-(4-cyano-5-methyl-3,4-dihydro-2H-pyrano[2,3-b]pyridin-6-yl)-7-fluoro-3-isoquinolyl]carbamate (250 mg, 0.44 mmol, 35.7% yield) as a yellow solid. LCMS (ESI) [M+H]$^+$=564.2.

Step 12: (R)-Tetrahydrofuran-3-yl (8-amino-6-(4-cyano-5-methyl-3,4-dihydro-2H-pyrano[2,3-b]pyridin-6-yl)-7-fluoroisoquinolin-3-yl)carbamate

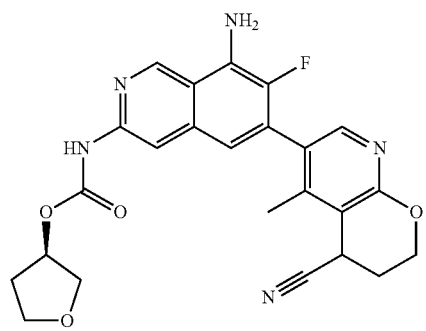 [SMILES: Cc1c(-c2cc3cc(NC(=O)O[C@@H]4CCOC4)ncc3c(N)c2F)cnc2c1C(C#N)CCO2]

To a solution of [(3R)-tetrahydrofuran-3-yl]N-[8-(tert-butoxycarbonylamino)-6-(4-cyano-5-methyl-3,4-dihydro-2H-pyrano[2,3-b]pyridin-6-yl)-7-fluoro-3-isoquinolyl]carbamate (250.0 mg, 0.4436 mmol) in dichloromethane (15 mL) was added trifluoroacetic acid (5.0 mL, 64.9 mmol) at RT. The mixture was stirred for 1 h and then concentrated under vacuum. The residue was diluted with dichloromethane and adjusted pH to 7 with triethylamine. Then the mixture was concentrated and purified by Prep-HPLC (Column: X select CSH OBD Column 30*150 mm 5 µm; Mobile Phase A: Water (0.1% FA), Mobile Phase B: ACN; Flow rate: 60 mL/min; Gradient: 12% B to 47% B in 7 min) to afford [(3R)-tetrahydrofuran-3-yl]N-[8-amino-6-(4-cyano-5-methyl-3,4-dihydro-2H-pyrano[2,3-b]pyridin-6-yl)-7-fluoro-3-isoquinolyl]carbamate (58.4 mg, 0.1255 mmol, 28.3% yield) as a yellow solid (Mixture of distereomers). LCMS (ESI) [M+H]$^+$=464.2, R$_T$ 1.325 min, Method J; $^1$H NMR (400 MHz, DMSO-d$_6$) δ 10.14 (s, 1H), 9.36 (s, 1H), 8.09 (s, 1H), 8.00 (s, 1H), 6.91 (s, 1H), 6.29 (s, 2H), 5.29-5.27 (m, 1H), 4.57 (d, J=14.0 Hz, 2H), 4.30-4.24 (m, 1H), 3.87-3.72 (m, 4H), 2.39 (d, J=2.0 Hz, 1H), 2.23-2.15 (m, 5H), 2.01-1.97 (m, 1H).

Example 208

(3S,4S)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate and (3R,4R)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate (Compound 452a and Compound 452b)

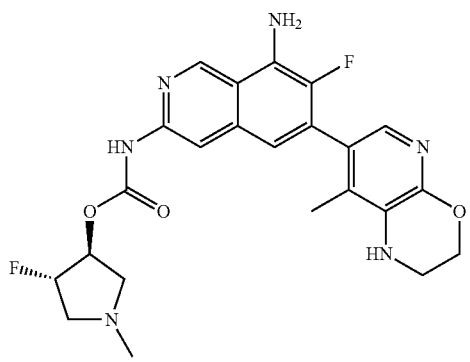

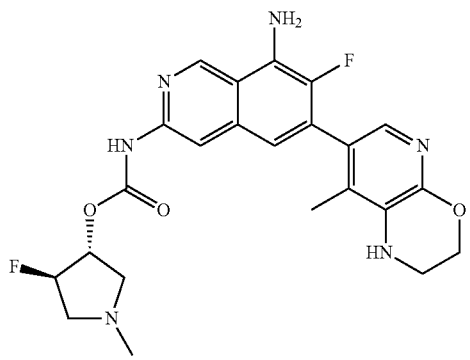

Step 1: (3S,4S)-4-fluoropyrrolidin-3-ol

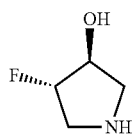

To a solution of tert-butyl-3-fluoro-4-hydroxy-pyrrolidine-1-carboxylate (500.0 mg, 2.44 mmol) in dichloromethane (2 mL) was added trifluoroacetic acid (2.0 mL). The mixture was stirred for 2 hours and concentrated under vacuum. The crude product was used directly for the next step without purification.

Step 2: (±)-trans-4-Fluoro-1-methyl-pyrrolidin-3-ol

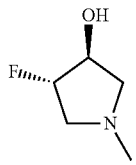

To a solution of 4-fluoropyrrolidin-3-ol (512.0 mg, 4.88 mmol) and acetic acid (585.0 mg, 9.74 mmol) in methyl alcohol (3.0 mL) was added an aqueous formaldehyde solution (7.2 g, 40%). The mixture was stirred for 2 hours at room temperature. Sodium borohydride (2.21 g, 58.46 mmol) was added. The reaction was stirred for 2 hours at room temperature and then concentrated under vacuum. The residue was purified by flash chromatography on silica gel eluting with dichloromethane/methanol (10/1) to afford (±)-trans-4-fluoro-1-methyl-pyrrolidin-3-ol (250 mg, 2.10 mmol, 43.0% yield) as a yellow solid. LCMS (ESI) [M+H]$^+$= 120.

Step 3: (±)-trans-tert-Butyl 7-[8-(tert-butoxycarbonylamino)-7-fluoro-3-[[4-fluoro-1-methyl-pyrrolidin-3-yl]oxycarbonylamino]-6-isoquinolyl]-8-methyl-2,3-dihydropyrido[2,3-b][1,4]oxazine-1-carboxylate

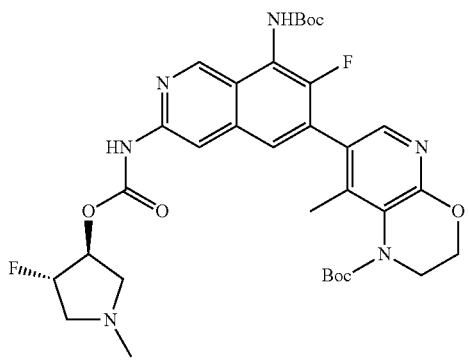 [SMILES: Cc1c(-c2cc3cc(NC(=O)O[C@H]4CN(C)C[C@@H]4F)ncc3c(NC(=O)OC(C)(C)C)c2F)cnc2c1N(C(=O)OC(C)(C)C)CCO2]

A solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (250.0 mg, 0.39 mmol), (±)-trans-4-fluoro-1-methyl-pyrrolidin-3-ol (230.7 mg, 1.94 mmol) and DMAP (47.3 mg, 0.39 mmol) in 1,4-dioxane (5 mL) was stirred at 90° C. for 2 hours. The reaction was quenched with water and extracted with dichloromethane. The organic layers were combined and concentrated under vacuum. The residue was purified by flash chromatography on silica gel eluting with dichloromethane/methanol (10/1) to afford (±)-trans-tert-butyl 7-[8-(tert-butoxycarbonylamino)-7-fluoro-3-[[4-fluoro-1-methyl-pyrrolidin-3-yl]oxycarbonylamino]-6-isoquinolyl]-8-methyl-2,3-dihydropyrido[2,3-b][1,4]oxazine-1-carboxylate (110 mg, 0.164 mmol, 42.4% yield) as a yellow solid. LCMS (ESI) [M+H]$^+$=120.

Step 4: (3S,4S)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate and (3R,4R)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl) carbamate

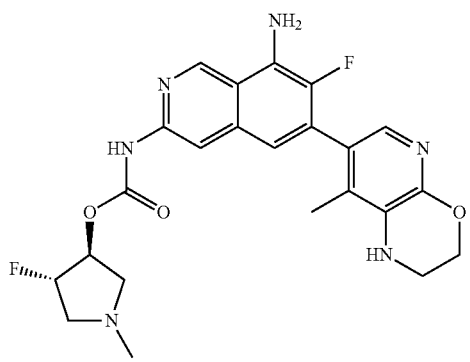

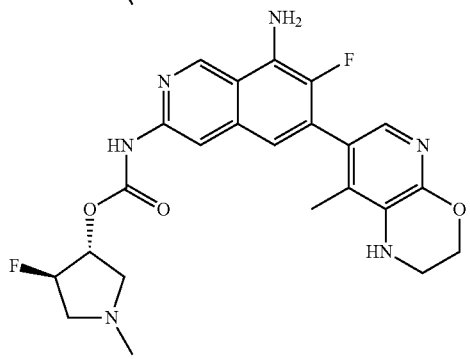

To a solution of (±)-trans-tert-butyl 7-[8-(tert-butoxycarbonylamino)-7-fluoro-3-[[4-fluoro-1-methyl-pyrrolidin-3-yl]oxycarbonylamino]-6-isoquinolyl]-8-methyl-2,3-dihydropyrido[2,3-b][1,4]oxazine-1-carboxylate (110.0 mg, 0.16 mmol) in dichloromethane (5 mL) was added TFA (1 mL). The mixture was stirred at room temperature for 2 hours. The resulting solution was concentrated under vacuum. The residue was purified by prep-HPLC (Column: X select CSH OBD Column 30*150 mm, 5 μm; Mobile Phase A: Water (0.1% FA), Mobile Phase B: ACN; Flow rate: 60 mL/min; Gradient: 5% B to 20% B in 7 min) to afford the racemic product. The racemic product was separated by chiral-prep-HPLC to afford two enantiomers. Relative stereochemistry are as drawn. Absolute stereochemistry was arbitrarily assigned.

Enantiomer 1: (Compound 452a) (10.5 mg, 0.022 mmol, 13.4% yield). $R_T$ 1.274 min (column: CHIRALPAK IA-3 0.46*5 cm; 3 μm. Mobile phase: MTBE:EtOH=50:50, 1 ml/min). LCMS (ESI): [M+H]$^+$=471.2, $R_T$ 1.524 min, Method K. $^1$H NMR (300 MHz, DMSO-d$_6$) δ 10.31 (s, 1H), 9.35 (s, 1H), 7.97 (s, 1H), 7.33 (s, 1H), 6.86 (d, J=6.1 Hz, 1H), 6.23 (s, 2H), 5.67 (s, 1H), 5.31-5.21 (m, 1H), 5.15 (s, 1H), 4.29 (t, J=4.4 Hz, 2H), 3.60 (s, 2H), 3.10 (s, 1H), 3.01 (s, 1H), 2.73 (s, 1H), 2.5 (s, 4H), 1.92 (d, J=1.6 Hz, 3H).

Enantiomer 2: (Compound 452b) (8.5 mg, 0.018 mmol, 11% yield). $R_T$ 2.616 min (column: CHIRALPAK IA-3 0.46*5 cm; 3 μm; Mobile phase: MTBE:EtOH=50:50, 1 ml/min). LCMS (ESI) [M+H]$^+$=471.2, $R_T$ 1.520 min., Method K. $^1$H NMR (300 MHz, DMSO-d$_6$) δ 10.31 (s, 1H), 9.35 (s, 1H), 7.97 (s, 1H), 7.33 (s, 1H), 6.86 (d, J=6.1 Hz, 1H), 6.23 (s, 2H), 5.67 (s, 1H), 5.31-5.21 (m, 1H), 5.15 (s, 1H), 4.29 (t, J=4.4 Hz, 2H), 3.60 (s, 2H), 3.10 (s, 1H), 3.01 (s, 1H), 2.73 (s, 1H), 2.5 (s, 4H), 1.92 (d, J=1.6 Hz, 3H).

Example 209

(1S,3s)-3-((R)-1-Hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate; (1S,3r)-3-((S)-1-Hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate; (1R,3r)-3-((R)-1-Hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate; and (1R,3s)-3-((5)-1-hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate (Compound 573a, Compound 573b, Compound 573c, and Compound 573d)

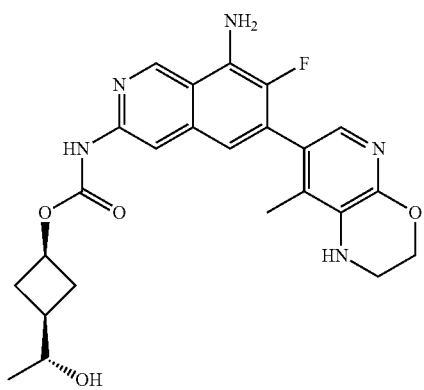

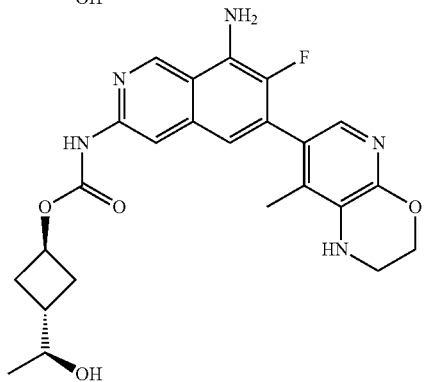

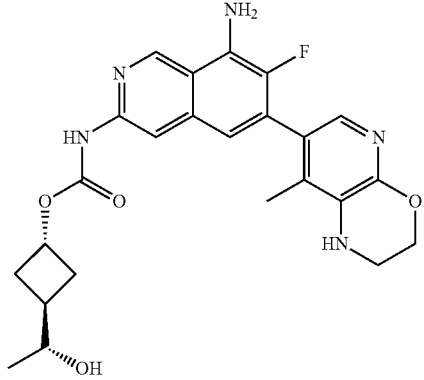

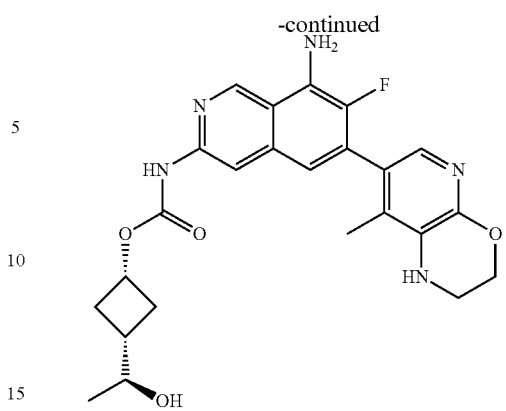

Step 1: 3-(Benzyloxy)-N-methoxy-N-methylcyclobutane-1-carboxamide

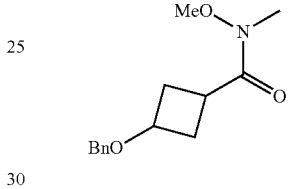

A solution of 3-benzyloxy-cyclobutanecarboxylicacid (1000 mg, 4.85 mmol), N-methoxy-N-methyl-methanamine hydrochloride (815 mg, 7.3 mmol) and DIEA (2505 mg, 19.42 mmol) in DMF (10 mL) was stirred at room temperature for 5 min. Then HATU (2766 mg, 7.27 mmol) was added. The reaction was stirred at room temperature for 2 hours. The reaction was quenched by methanol and then the mixture was diluted with ethyl acetate. The resulting solution was washed with water. The organic layer was dried over anhydrous sodium sulfate and concentrated under vacuum to afford 3-benzyloxy-N-methoxy-N-methyl-cyclobutanecarboxamide (1102 mg, 4.42 mmol, 91.2% yield) as a colorless oil. LCMS (ESI) [M+H]$^+$=250.

Step 2: 1-(3-(benzyloxy)cyclobutyl)ethan-1-one

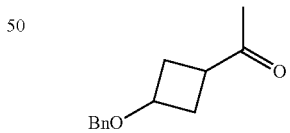

To a solution of tert-butyl 3-(benzyloxy)-N-methoxy-N-methylcyclobutane-1-carboxamide (1050 mg, 4.22 mmol) in THF (5 mL) was added methyl magnesium bromide (5.6 mL, 5.6 mmol/L, 1 mol/L in THF). The mixture was stirred at 0° C. for 2 hours. The reaction was quenched by methanol. The mixture was diluted with ethyl acetate and then the resulting solution was washed with water. The organic layer was concentrated under vacuum. The residue was purified by flash chromatography on silica gel eluting with petroleum ether/ethyl acetate (30/70) to afford 1-(3-(benzyloxy)cyclobutyl)ethan-1-one (1028 mg, 4.42 mmol, 90% yield) as a colorless oil. LCMS (ESI) [M+H]$^+$=204.

Step 3: 1-(3-(benzyloxy)cyclobutyl)ethan-1-ol

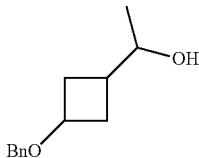

A solution of 1-(3-benzyloxycyclobutyl)ethanone (1028 mg, 5.03 mmol) and NaBH₄ (385 mg, 10.13 mmol) in methyl alcohol (10 mL) was stirred at room temperature for 2 hours. The reaction was quenched by adding aqueous sodium thiosulfate. The residue was diluted with water, then adjusted to pH 6-7 with sodium bicarbonate. The resulting solution was extracted with dichloromethane. The organic layers were combined, dried over anhydrous sodium sulfate and concentrated under vacuum to afford 1-(3-benzyloxycyclobutyl)ethanol (816 mg, 3.956 mmol, 78.6% yield) as a colorless oil. LCMS (ESI) [M+H]⁺=206.

Step 4: (1-(3-(Benzyloxy)cyclobutyl)ethoxy)(tert-butyl)dimethylsilane

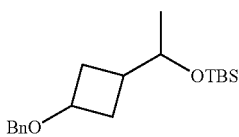

Under nitrogen, a solution of 1-(3-benzyloxycyclobutyl)ethanol (816 mg, 3.961 mmol), tert-butylchlorodimethylsilane (1188 mg, 7.952 mmol) and imidazole (108 mg, 15 mmol) in dichloromethane (15 mL) was stirred for 2 hours at room temperature. The reaction was quenched by water and extracted with dichloromethane. The organic layer was dried over anhydrous sodium sulfate and concentrated under vacuum. The residue was purified by flash chromatography on silica gel eluting with petroleum ether/ethyl acetate (10/90) to afford (1-(3-(benzyloxy)cyclobutyl)ethoxy)(tert-butyl)dimethylsilane (900 mg, 3.956 mmol, 78.6% yield) as a colorless oil. LCMS (ESI) [M+H]⁺=321.

Step 5: 3-(1-((tert-Butyldimethylsilyl)oxy)ethyl)cyclobutan-1-ol

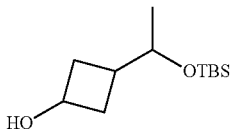

A mixture of 1-(3-benzyloxycyclobutyl)ethoxy-tert-butyl-dimethyl-silane (600 mg, 1.87 mmol) and Pd/C (10%, 420 mg, 1.87 mmol in methanol was stirred under hydrogen (1 atm) for 2 hours at 40° C. The mixture was then filtered and concentrated under vacuum. The residue was purified by flash chromatography on silica gel eluting with petroleum ether/ethyl acetate (18/82) to afford 3-[1-[tert-butyl(dimethyl)silyl]oxyethyl]cyclobutanol (400 mg, 1.736 mmol, 92.7% yield) as a colorless oil. LCMS (ESI) [M+H]⁺=231.

Step 6: tert-Butyl 7-(8-((tert-butoxycarbonyl)amino)-3-(((3-(1-((tert-butyldimethylsilyl)oxy)ethyl)cyclobutoxy)carbonyl)amino)-7-fluoroisoquinolin-6-yl)-8-methyl-2,3-dihydro-1H-pyrido[2,3-b][1,4]oxazine-1-carboxylate

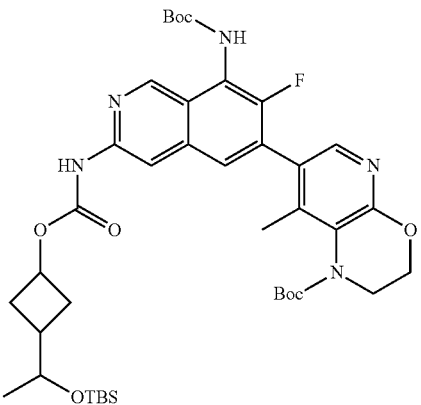 [SMILES: Cc1c(-c2cc3cc(NC(=O)OC4CC(C(C)O[Si](C)(C)C(C)(C)C)C4)ncc3c(NC(=O)OC(C)(C)C)c2F)cnc2c1N(C(=O)OC(C)(C)C)CCO2]

A solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (460 mg, 0.71 mmol), 3-[1-[tert-butyl(dimethyl)silyl]oxyethyl]cyclobutanol (328 mg, 1.42 mmol), DIEA (90 mg, 0.70 mmol) and DMAP (88 mg, 0.72 mmol) in 1,4-dioxane (5 mL) was stirred for 2 h at 90° C. The reaction was concentrated under vacuum. The residue was purified by flash chromatography on silica gel eluting with petroleum ether/ethyl acetate (38/62) to afford tert-butyl 7-[8-(tert-butoxycarbonylamino)-3-[[3-[1-[tert-butyl(dimethyl)silyl]oxyethyl]cyclobutoxy]carbonylamino]-7-fluoro-6-isoquinolyl]-8-methyl-2,3-dihydropyrido[2,3-b][1,4]oxazine-1-carboxylate (500 mg, 0.639 mmol, 89.7% yield) as a yellow solid. LCMS (ESI) [M+H]⁺=782.

Step 7: tert-Butyl 7-(8-((tert-butoxycarbonyl)amino)-7-fluoro-3-(((3-(1-hydroxyethyl)cyclobutoxy)carbonyl)amino)isoquinolin-6-yl)-8-methyl-2,3-dihydro-1H-pyrido[2,3-b][1,4]oxazine-1-carboxylate

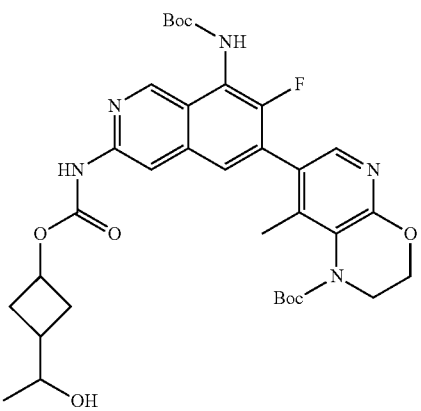 [SMILES: Cc1c(-c2cc3cc(NC(=O)OC4CC(C(C)O)C4)ncc3c(NC(=O)OC(C)(C)C)c2F)cnc2c1N(C(=O)OC(C)(C)C)CCO2]

A solution of tert-butyl 7-[8-(tert-butoxycarbonylamino)-3-[[3-[1-[tert-butyl(dimethyl)silyl]oxyethyl]cyclobutoxy]carbonylamino]-7-fluoro-6-isoquinolyl]-8-methyl-2,3-dihydropyrido[2,3-b][1,4]oxazine-1-carboxylate (300 mg, 0.38 mmol) and TBAF (277 mg, 0.88 mmol) in tetrahydrofuran (5 mL) was stirred at room temperature for 2 hours. The reaction solution was concentrated under vacuum. The residue was purified by flash chromatography on silica gel eluting with petroleum ether/ethyl acetate (35/65) to afford tert-butyl 7-[8-(tert-butoxycarbonylamino)-7-fluoro-3-[[3-(1-hydroxyethyl)cyclobutoxy]carbonylamino]-6-isoquinolyl]-8-methyl-2,3-dihydropyrido[2,3-b][1,4]oxazine-1-carboxylate (200 mg, 0.299 mmol, 78.1% yield) as a yellow solid. LCMS (ESI) [M+H]$^+$=782.

Step 8: (1S,3s)-3-((R)-1-hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate, (1S,3r)-3-((S)-1-Hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate, (1R,3r)-3-((R)-1-Hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate and (1R,3s)-3-((S)-1-Hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate

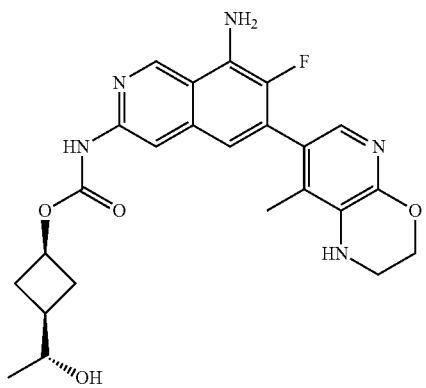

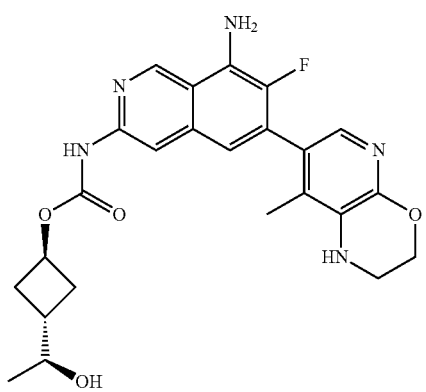

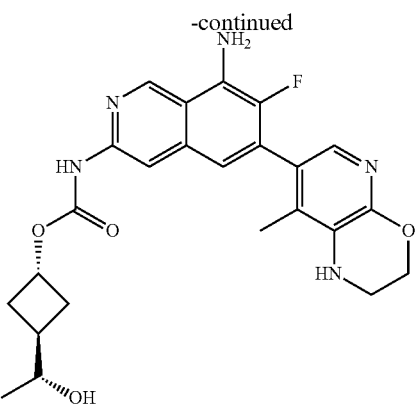

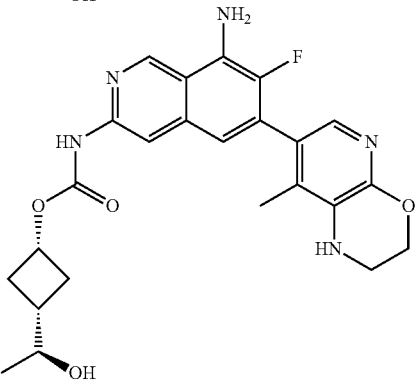

A solution of tert-butyl 7-[8-(tert-butoxycarbonylamino)-7-fluoro-3-[[3-(1-hydroxyethyl)cyclobutoxy]carbonylamino]-6-isoquinolyl]-8-methyl-2,3-dihydropyrido[2,3-b][1,4]oxazine-1-carboxylate (180 mg, 0.27 mmol) in dichloromethane (5 mL) and TFA (2 mL) was stirred at room temperature for 1 hour. The reaction mixture was concentrated under vacuum. The residue was purified by Prep-HPLC (X Bridge CSH OBD C18 Column 30×150 mm, 5 μm; Mobile Phase A: Water (0.1% FA), Mobile Phase B: ACN; Flow rate: 60 mL/min; Gradient: 9 B to 41 B in 7 min) to afford a mixture of isomeric products. The mixture was separated by chiral-HPLC to afford four isomers. Relative stereochemistry are as drawn. Absolute stereochemistry was arbitrarily assigned.

Enantiomer 1 (Compound 573a) (12.2 mg, 0.021 mmol, 9.7% yield). $R_T$ 1.526 min (CHIRALPAK IA-3 0.46*5 cm; 3 μm; MTBE:EtOH=80:20, 1 mL/min). LCMS (ESI) [M+H]$^+$=468.2, $R_T$ 1.845 min, Method J; $^1$H NMR (300 MHz, DMSO-d$_6$) δ 10.00 (s, 1H), 9.31 (s, 1H), 7.94 (s, 1H), 7.31 (s, 1H), 6.81 (d, J=6.2 Hz, 1H), 6.18 (s, 2H), 5.65 (s, 1H), 4.56-4.47 (d, J=6 Hz, 1H), 4.27 (s, 1H), 3.57-3.44 (m, 2H), 3.50 (q, J=5.5 Hz, 1H), 3.56-3.44 (m, 2H), 2.32-2.24 (m, 2H), 1.94-1.81 (m, 6H), 1.03-0.92 (m, 3H).

Enantiomer 2 (Compound 573b) (2.4 mg, 0.005 mmol, 1.9% yield). $R_T$ 2.059 min (CHIRALPAK IA-3 0.46*5 cm; 3 μm; MTBE:EtOH=85:15, 1 mL/min). LCMS(ESI) [M+H]$^+$=468.2, $R_T$ 2.059 min, Method J. $^1$H NMR (300 MHz, DMSO-d$_6$) δ 10.00 (s, 1H), 9.31 (s, 1H), 7.94 (s, 1H), 7.31 (s, 1H), 6.81 (d, J=6.2 Hz, 1H), 6.18 (s, 2H), 5.65 (s, 1H), 5.00-4.71 (m, 1H), 4.59-4.57 (m, 1H), 4.26 (s, 2H), 3.67-3.58 (m, 1H), 3.36-3.32 (m, 2H), 3.26-2.50 (m, 1H), 2.38-2.35 (m, 4H), 2.34-2.31 (m, 3H), 1.12 (d, J=6.3 Hz, 3H).

Enantiomer 3 (Compound 573c) (3 mg, 0.006 mmol, 2.4% yield). $R_T$ 3.911 min (CHIRALPAK IA-3 0.46*5 cm; 3 um; MTBE:EtOH=85:15, 1 mL/min). LCMS(ESI)

[M+H]⁺=468.2, $R_T$ 2.059 min, Method J. ¹H NMR (300 MHz, DMSO-d₆) δ 10.00 (s, 1H), 9.31 (s, 1H), 7.94 (s, 1H), 7.31 (s, 1H), 6.81 (d, J=6.2 Hz, 1H), 6.18 (s, 2H), 5.65 (s, 1H), 5.00-4.71 (m, 1H), 4.59-4.57 (m, 1H), 4.26 (s, 2H), 3.67-3.58 (m, 1H), 3.36-3.32 (m, 2H), 3.26-2.50 (m, 1H), 2.38-2.35 (m, 4H), 2.34-2.31 (m, 3H), 1.12 (d, J=6.3 Hz, 3H).

Enantiomer 4 (Compound 573b) (13.6 mg, 0.029 mmol, 10.8% yield). $R_T$ 3.911 min (CHIRALPAK IA-3 0.46*5 cm; 3 μm; MTBE:EtOH=80:20, 1 mL/min). LCMS (ESI) [M+H]⁺=468.2, $R_T$ 1.845 min, Method J; ¹H NMR (300 MHz, DMSO-d₆) δ 10.00 (s, 1H), 9.31 (s, 1H), 7.94 (s, 1H), 7.31 (s, 1H), 6.81 (d, J=6.2 Hz, 1H), 6.18 (s, 2H), 5.65 (s, 1H), 4.56-4.47 (d, J=6 Hz, 1H), 4.27 (s, 1H), 3.57-3.44 (m, 2H), 3.50 (q, J=5.5 Hz, 1H), 3.56-3.44 (m, 2H), 2.32-2.24 (m, 2H), 1.94-1.81 (m, 6H), 1.03-0.92 (m, 3H).

Example 210

(1r,3r)-3-(2-Hydroxypropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate and (1s,3s)-3-(2-hydroxypropan-2-yl)cyclobutyl (8-amino-7-fluoro-6-(8-methyl-2,3-dihydro-1H-pyrido[2,3-b][1,4]oxazin-7-yl) isoquinolin-3-yl)carbamate (Compound 574a and Compound 574b)

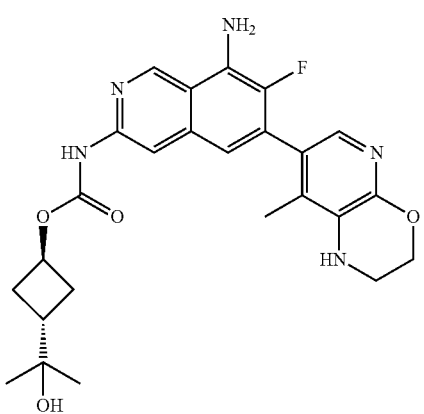

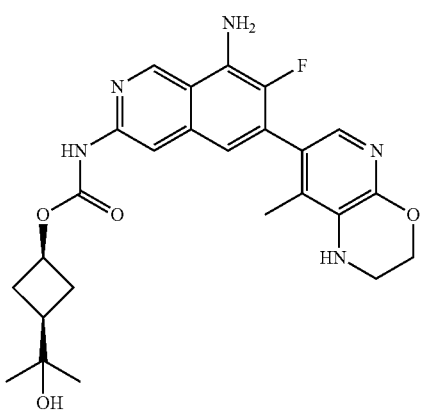

Step 1: Methyl 3-(benzyloxy)cyclobutane-1-carboxylate

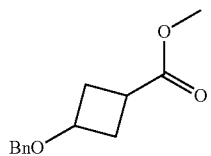

To a solution of 3-benzyloxy-cyclobutanecarboxylicacid (1000 mg, 4.85 mmol), N-methoxy-N-methyl-methanamine hydrochloride (815.0 mg, 7.3 mmol) and DIEA (2505 mg, 19.42 mmol) in DMF (10 mL) was added HATU (2766 mg, 7.27 mmol). The mixture was stirred at room temperature for 2 hours. The reaction was diluted with methanol and ethyl acetate. The resulting solution was washed with water, dried over anhydrous sodium sulfate and concentrated under vacuum to afford 3-benzyloxy-N-methoxy-N-methyl-cyclobutanecarboxamide (1102 mg, 4.420 mmol, 91.2% yield) as a colorless oil. LCMS (ESI) [M+H]⁺=220.

Step 2: 2-(3-(benzyloxy)cyclobutyl)propan-2-ol

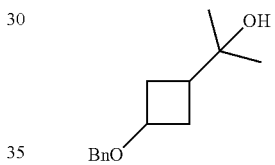

Under nitrogen, a solution of methyl 3-benzyloxycyclobutanecarboxylate (1200 mg, 5.45 mmol) and MeMgCl (7 mL, 21 mmol, 3 mol/L) in tetrahydrofuran (2 mL) was stirred for 2 h at room temperature. The reaction was quenched by adding methanol and then concentrated under vacuum. The residue was purified by flash chromatography on silica gel eluting with petroleum ether/ethyl acetate (35/65) to afford 2-(3-benzyloxycyclobutyl)propan-2-ol (1000 mg, 4.539 mmol, 83.3% yield) as a colorless solid. LCMS (ESI) [M+H]⁺=220.

Step 3: 3-(2-Hydroxypropan-2-yl)cyclobutan-1-ol

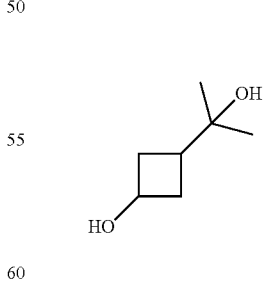

Under hydrogen (1 atm), a mixture of 2-(3-benzyloxycyclobutyl)propan-2-ol (1000 mg, 4.54 mmol) and Pd/C (210 mg, 4.54 mmol) in methyl alcohol (2 mL) was stirred for 12 hours at 40° C. After filtration, the filtrate was concentrated under vacuum to afford 3-(1-hydroxy-1-methyl-ethyl)cyclobutanol (500 mg, 3.84 mmol, 84.6% yield) as a colorless oil. LCMS (ESI) [M+H]⁺=130.

Step 4: tert-Butyl 7-(8-((tert-butoxycarbonyl)amino)-7-fluoro-3-(((3-(2-hydroxypropan-2-yl)cyclobutoxy)carbonyl)amino)isoquinolin-6-yl)-8-methyl-2,3-dihydro-1H-pyrido[2,3-b][1,4]oxazine-1-carboxylate

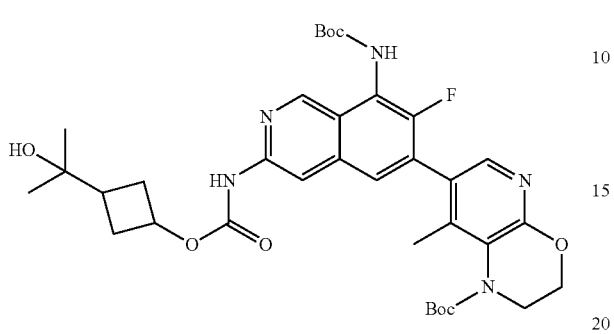

Under nitrogen, a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300.0 mg, 0.46 mmol), 3-(1-hydroxy-1-methyl-ethyl)cyclobutanol (120 mg, 0.92 mmol), DIEA (299 mg, 2.32 mmol) and DMAP (57 mg, 0.47 mmol) in 1,4-dioxane (3 mL) was stirred for 2 h at 90° C. The reaction solution was concentrated under vacuum. The residue was purified by flash chromatography on silica gel eluting with petroleum ether/ethyl acetate (38/62) to afford tert-butyl 7-[8-(tert-butoxycarbonylamino)-3-[[3-[1-[tert-butyl(dimethyl)silyl]oxyethyl]cyclobutoxy]carbonylamino]-7-fluoro-6-isoquinolyl]-8-methyl-2,3-dihydropyrido[2,3-b][1,4]oxazine-1-carboxylate (280 mg, 0.358 mmol, 77.1% yield) as a yellow solid. LCMS (ESI) [M+H]$^+$=681.

Step 5: (1r,3r)-3-(2-Hydroxypropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate and (1s,3s)-3-(2-Hydroxypropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate

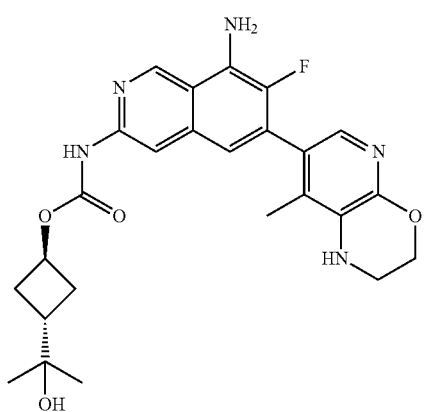

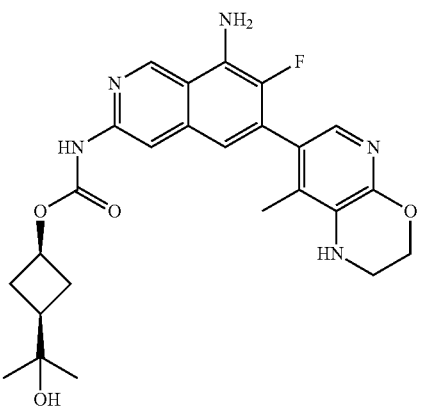

A solution of tert-butyl 7-[8-(tert-butoxycarbonylamino)-7-fluoro-3-[[3-(1-hydroxy-1-methyl-ethyl)cyclobutoxy]carbonylamino]-6-isoquinolyl]-8-methyl-2,3-dihydropyrido[2,3-b][1,4]oxazine-1-carboxylate (280 mg, 0.417 mmol) in TFA (1 mL) and dichloromethane (5 mL) was stirred at room temperature for 2 hours. The mixture was concentrated under vacuum. The residue was purified by Prep-HPLC (Column: X Bridge Prep OBD C18 Column 30×150 mm, 5 μm; Mobile Phase A: Water (10 mmol/L NH$_4$HCO$_3$), Mobile Phase B: ACN; Flow rate: 60 mL/min; Gradient: 15% B to 26% B in 10 min) to afford a racemic mixture. The mixture was separated by chiral-HPLC to afford two isomers. Stereochemistry was arbitrarily assigned.

Isomer 1 (Compound 574a) ((27.2 mg, 0.0565 mmol, 77% yield). R$_T$ 7.921 min (CHIRALPAK IC 2*25 cm, 5 μm, Mobile phase A: MTBE; water (0.1% FA), Mobile phase B: EtOH). LCMS (ESI) [M+H]$^+$=482.5, R$_T$ 2.197 min, Method K. $^1$H NMR (300 MHz, DMSO-d$_6$) δ 9.99 (s, 1H), 9.31 (s, 1H), 7.94 (s, 1H), 7.31 (s, 1H), 6.80 (d, J=6.2 Hz, 1H), 6.18 (s, 2H), 5.65 (s, 1H), 4.93 (t, J=6.6 Hz, 1H), 4.40-4.20 (m, 3H), 3.50-3.30 (m, 2H), 2.50-2.28 (m, 3H), 2.20-2.05 (m, 2H), 1.92 (s, 3H), 1.03 (s, 6H).

Isomer 2 (Compound 574b) (3.1 mg, 0.0064 mmol, 8.8% yield). R$_T$ 10.454 min (CHIRALPAK IC 2*25 cm, 5 μm, Mobile phase A: MTBE; water (0.1% FA), Mobile phase B: EtOH). LCMS(ESI) [M+H]$^+$=482.5, R$_T$ 1.209 min., Method J. $^1$H NMR (300 MHz, DMSO-d$_6$) δ 10.00 (s, 1H), 9.31 (s, 1H), 7.94 (s, 1H), 7.31 (s, 1H), 6.81 (d, J=6.0 Hz, 1H), 6.18 (s, 2H), 5.65 (s, 1H), 4.75 (t, J=7.7 Hz, 1H), 4.29-4.24 (m, 3H), 3.40-3.20 (m, 2H), 2.30-2.10 (m, 2H), 2.04-1.95 (m, 2H), 1.90 (s, 3H), 1.88-1.78 (m, 1H), 0.98 (s, 6H).

Example 211

(3S,3aR,6aR)-Hexahydrofuro[3,4-b]furan-3-yl (8-amino-7-fluoro-6-(8-methyl-2,3-dihydro-1H-pyrido[2,3-b][1,4]oxazin-7-yl)isoquinolin-3-yl)carbamate and (3R,3aR,6aR)-Hexahydrofuro[3,4-b]furan-3-yl (8-amino-7-fluoro-6-(8-methyl-2,3-dihydro-1H-pyrido[2,3-b][1,4]oxazin-7-yl)isoquinolin-3-yl)carbamate (Compound 563a and Compound 563b)

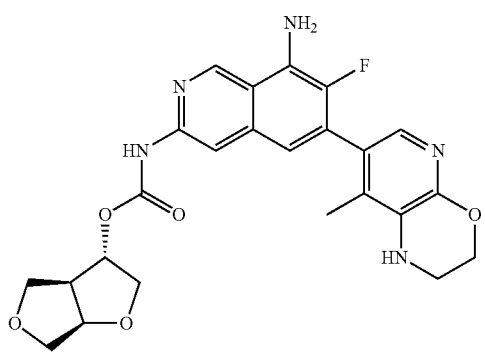

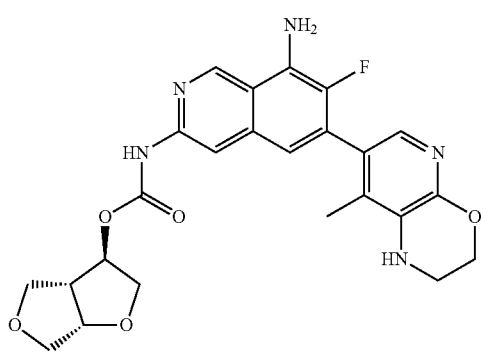

Step 1: (±)-trans-4-Prop-2-ynoxytetrahydrofuran-3-ol

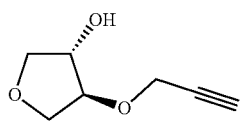

To a solution of 3,4-epoxytetrahydrofuran (30.0 g, 348.5 mmol) and propargyl alcohol (19.8 g, 353.2 mmol) in dichloromethane (1.8 L) was added boron trifluoride diethyl etherate (4.42 mL, 34.88 mmol) at 0° C. The resulting solution was stirred at room temperature for 16 hours. The resulting mixture was concentrated under vacuum and purified by flash chromatography on silica gel eluting with petroleum ether/ethyl acetate (1/5) to afford (±)-trans-4-prop-2-ynoxytetrahydrofuran-3-ol (10 g, 70.35 mmol, 20.2% yield) as a yellow oil.

Step 2: O-[(3S,4S)-4-Prop-2-ynoxytetrahydrofuran-3-yl]methylsulfanylmethanethioate

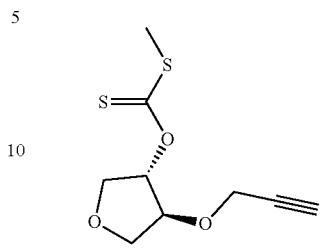

Under a $N_2$ atmosphere, to a solution of (±)-trans-4-prop-2-ynoxytetrahydrofuran-3-ol (7.0 g, 49.24 mmol) in tetrahydrofuran (140 mL) was added NaH (3.53 g, 147 mmol, 60% purity) at 0° C. The mixture was stirred at room temperature for 30 min. Carbon disulfide (4.42 mL, 73.6 mmol) was added at 0° C. and the mixture was stirred at room temperature for 30 min. Iodomethane (10.5 g, 73.97 mmol) was added at 0° C. and the mixture was stirred at room temperature for 2 hours. The reaction mixture was quenched with aqueous $NH_4Cl$ solution and extracted with ethyl acetate. The organic layer was dried ($Na_2SO_4$) and concentrated under vacuum. The residue was purified by flash chromatography on silica gel eluting with petroleum ether/ethyl acetate (10/1) to afforded O-[(3S,4S)-4-prop-2-ynoxytetrahydrofuran-3-yl]methylsulfanylmethanethioate (6.8 g, 29.3 mmol, 59.4% yield) as a yellow oil.

Step 3: 3-Methylene-3a,4,6,6a-tetrahydrofuro[3,4-b]furan

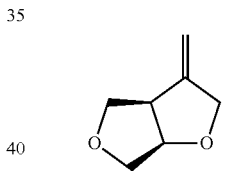

Under $N_2$ atmosphere, to a solution of O-[(1S,2S)-2-prop-2-ynoxycyclopentyl]methyl sulfanylmethanethioate (6.0 g, 26.04 mmol) in toluene (420 ml) was added tri-n-butyltin hydride (13.86 mL, 51.6 mmol) at room temperature. The mixture was heated at reflux for 30 min. A catalytic amount of AIBN (216 mg, 1.32 mmol) was added at reflux and the mixture was continued to reflux for 4 h. The reaction mixture was cooled to room temperature and concentrated. The residue was purified by flash chromatography on silica gel eluting with petroleum ether/ethyl acetate (5/1) to afford 3-methylene-3a,4,6,6a-tetrahydrofuro[3,4-b]furan (1.8 g, 14.4 mmol, 54.78% yield) as colorless oil.

Step 4: (3R,3aS,6aR)-2,3,3a,4,6,6a-Hexahydrofuro[3,4-b]furan-3-ol

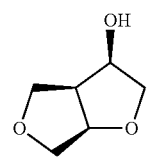

To a solution of 3-methylene-3a,4,6,6a-tetrahydrofuro[3,4-b]furan (1.26 g, 9.99 mmol) and RuCl₃ (620.55 mg, 3 mmol) in carbon tetrachloride (10 mL), acetonitrile (10 mL) and water (10 mL) was added NaIO₄ (5.34 g, 24.95 mmol) at 0° C. The resulting solution was stirred at room temperature for 2 hours. The reaction was quenched by aq. NaHCO₃ and aq. Na₂S₂O₃. The resulting mixture was extracted with ethyl acetate. The organic layers were combined, dried over anhydrous sodium sulfate, filtered and concentration under vacuum. The residue was dissolved in ethanol (10 mL) and NaBH₄ (468.8 mg, 12.34 mmol) was added at room temperature. The resulting solution was stirred at room temperature for 3 hours. The mixture was concentrated under reduced pressure. The residue was purified by flash chromatography on silica gel eluting with dichloromethane/methanol (20/1) to afford (3R,3aS,6aR)-2,3,3a,4,6,6a-hexahydrofuro[3,4-b]furan-3-ol (450 mg, 3.46 mmol, 39.9% yield) as a yellow oil. ¹H-NMR (300 MHz, CDCl₃) δ 4.60-4.50 (m, 1H), 4.40-4.30 (m, 2H), 4.02-4.07 (m, 1H), 3.90 (d, 1H), 3.60 (dd, J=2.1, 8.8 Hz, 1H), 3.46-3.40 (m, 2H), 2.90-2.75 (m, 1H), 2.20 (bs, 1H).

Step 5: [(3S,3aR,6aR)-2,3,3a,4,6,6a-Hexahydrofuro[3,4-b]furan-3-yl]4-nitrobenzoate

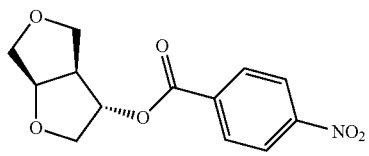 [SMILES: O=C(O[C@@H]1CO[C@H]2COC[C@H]21)c1ccc([N+](=O)[O-])cc1]

To a solution of (3R,3aS,6aR)-2,3,3a,4,6,6a-hexahydrofuro[3,4-b]furan-3-ol (420.0 mg, 3.23 mmol), 4-nitrobenzoic acid (808.5 mg, 4.84 mmol) and PPh₃ (1.27 g, 4.84 mmol) in tetrahydrofuran (20 mL) was added DIAD (978.6 mg, 4.84 mmol) at 0° C. The resulting solution was stirred at room temperature for 16 hours. The mixture was concentrated under vacuum. The residue was purified by flash chromatography on silica gel eluting with petroleum ether/ethyl acetate (5/1) to afford [(3S,3aR,6aR)-2,3,3a,4,6,6a-hexahydrofuro[3,4-b]furan-3-yl]4-nitrobenzoate (700 mg, 2.5 mmol, 77.7% yield) as a white solid.

Step 6: (3S,3aS,6aR)-2,3,3a,4,6,6a-Hexahydrofuro[3,4-b]furan-3-ol

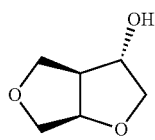

A mixture of [(3S,3aR,6aR)-2,3,3a,4,6,6a-hexahydrofuro[3,4-b]furan-3-yl]4-nitrobenzoate (700.0 mg, 2.51 mmol) in methyl alcohol (35 mL) and K₂CO₃ (1.73 g, 12.53 mmol) was stirred at room temperature for 4 hours. The resulting solution was concentrated under vacuum. The residue was purified by flash chromatography on silica gel eluting with dichloromethane/methanol (20/1) to afford (3S,3aS,6aR)-2,3,3a,4,6,6a-hexahydrofuro[3,4-b]furan-3-ol (200 mg, 1.54 mmol, 57.3% yield) as a yellow oil. ¹H NMR (300 MHz, Chloroform-d) δ 4.86 (dd, J=6.7, 3.7 Hz, 1H), 4.25 (dt, J=3.1, 1.4 Hz, 1H), 4.03 (d, J=10.4 Hz, 1H), 3.92 (dd, J=9.8, 3.4 Hz, 1H), 3.86-3.71 (m, 3H), 3.56 (dd, J=10.4, 3.8 Hz, 1H), 2.85 (qd, J=7.0, 6.1, 3.5 Hz, 1H), 1.88 (s, 1H).

Step 7: tert-Butyl 7-(8-((tert-butoxycarbonyl)amino)-7-fluoro-3-(((((3S,3aR,6aR)-hexahydrofuro[3,4-b]furan-3-yl)oxy)carbonyl)amino)isoquinolin-6-yl)-8-methyl-2,3-dihydro-1H-pyrido[2,3-b][1,4]oxazine-1-carboxylate and tert-butyl 7-(8-((tert-butoxycarbonyl)amino)-7-fluoro-3-(((((3R,3aS,6aS)-hexahydrofuro[3,4-b]furan-3-yl)oxy)carbonyl)amino)isoquinolin-6-yl)-8-methyl-2,3-dihydro-1H-pyrido[2,3-b][1,4]oxazine-1-carboxylate

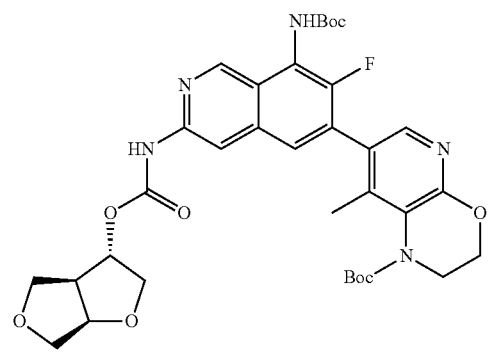

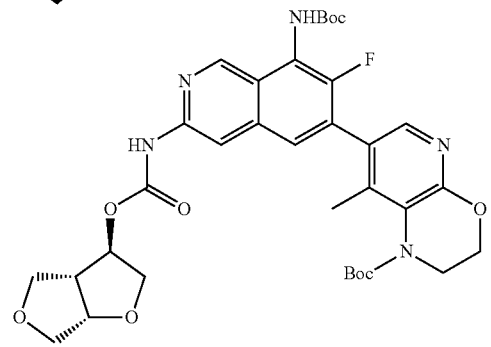

To a solution of (3S,3aS,6aR)-2,3,3a,4,6,6a-hexahydrofuro[3,4-b]furan-3-ol (198.09 mg, 1.52 mmol), tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (400.0 mg, 0.76 mmol) and DIEA (294.54 mg, 2.28 mmol) in dichloromethane (40 mL) was added triphosgene (158.09 mg, 0.53 mmol) at 0° C. The resulting solution was stirred at 0° C. for 30 min and then concentrated under vacuum. The residue was purified by flash chromatography on silica gel eluting with petroleum ether/ethyl acetate (1/4) to afford a racemic product. The racemic product was further separated by chiral-HPLC (Column: CHIRALPAK IC, 3*25 cm, 5 μm; Mobile Phase A: Hexane: DCM=3:1 (0.1% DEA), Mobile Phase B: EtOH; Flow rate: 40 mL/min; Gradient: 50% B to 50% B in 20 min) to afford two enantiomers. Relative stereochemistry are as drawn. Absolute stereochemistry was arbitrarily assigned.

Enantiomer 1 (intermediate of Compound 563a): (150 mg, 0.22 mmol, 28.9% yield). R$_T$ 1.621 min (CHIRALPAK IC-3, 0.46*5 cm; 3 μm; Mobile phase: (Hex:DCM=3:1) (0.1% DEA):EtOH=50:50, 1 ml/min). LCMS (ESI) [M+H]⁺= 682.3.

Enantiomer 2 (intermediate of Compound 563b): (145 mg, 0.22 mmol, 27.9% yield). $R_T$ 2.772 min (CHIRALPAK IC-3, 0.46*5 cm; 3 μm; Mobile phase: (Hex:DCM=3:1) (0.1% DEA):EtOH=50:50, 1 ml/min). LCMS (ESI) [M+H]$^+$= 682.3.

Step 8: (3S,3aR,6aR)-Hexahydrofuro[3,4-b]furan-3-yl (8-amino-7-fluoro-6-(8-methyl-2,3-dihydro-1H-pyrido[2,3-b][1,4]oxazin-7-yl)isoquinolin-3-yl)carbamate and (3R,3aR,6aR)-Hexahydrofuro[3,4-b]furan-3-yl (8-amino-7-fluoro-6-(8-methyl-2,3-dihydro-1H-pyrido[2,3-b][1,4]oxazin-7-yl) isoquinolin-3-yl)carbamate

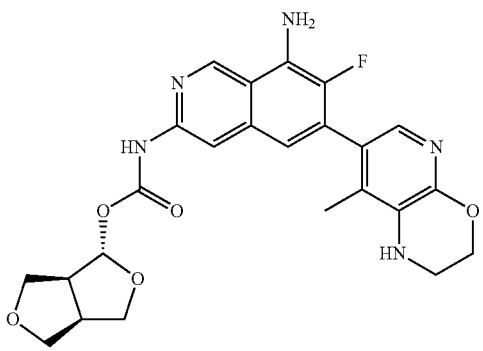

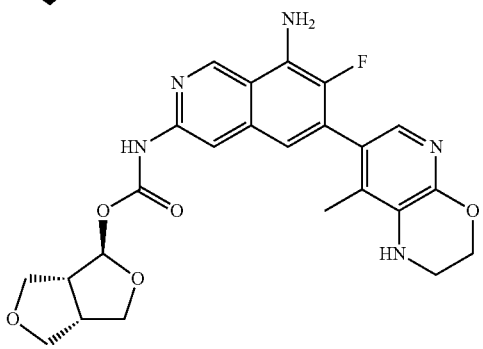

A mixture of tert-butyl 7-(8-((tert-butoxycarbonyl) amino)-7-fluoro-3-(((((3S,3aR,6aR)-hexahydrofuro[3,4-b]furan-3-yl)oxy)carbonyl)amino)isoquinolin-6-yl)-8-methyl-2,3-dihydro-1H-pyrido[2,3-b][1,4]oxazine-1-carboxylate (150 mg, 0.22 mmol) in dichloromethane (2 ml) and trifluoroacetic acid (2 ml) was stirred at room temperature for 2 hours. Then the resulting solution was concentrated under vacuum. The residue was dissolved in acetonitrile and adjusted to pH 8 with aqueous NaHCO$_3$ solution. The solid was collected by filtration and washed with water to give Enantiomer 1 (Compound 563a) (Relative stereochemistry are as drawn. Absolute stereochemistry was arbitrarily assigned) (49 mg, 0.102 mmol, 46.2% yield): $R_T$ 4.377 min (CHIRALPAK IA-U 3.0*50 mm 1.6 μm; Mobile Phase A: CO$_2$, Mobile Phase B: IPA (20 mm NH$_3$), 10%-50%, 6.5 min; 2 ml/min). LCMS (ESI): [M+H]$^+$=482.2, $R_T$ 2.137 min., Method J; $^1$H NMR (400 MHz, DMSO-d$_6$) δ 10.18 (s, 1H), 9.33 (s, 1H), 7.97 (s, 1H), 7.33 (s, 1H), 6.84 (d, J=6.2 Hz, 1H), 6.21 (s, 2H), 5.66 (d, J=3.4 Hz, 1H), 5.23-5.00 (m, 1H), 4.77 (dd, J=6.7, 3.6 Hz, 1H), 4.29 (t, J=4.3 Hz, 2H), 3.96-3.78 (m, 4H), 3.68 (dd, J=9.5, 8.0 Hz, 1H), 3.46 (dd, J=10.2, 3.7 Hz, 1H), 3.16-3.20 (m, 2H) 3.04-2.90 (m, 1H), 1.92 (d, J=1.6 Hz, 3H).

Similarly, tert-butyl 7-(8-((tert-butoxycarbonyl)amino)-7-fluoro-3-(((((3R,3aS,6aS)-hexahydrofuro[3,4-b]furan-3-yl)oxy)carbonyl)amino)isoquinolin-6-yl)-8-methyl-2,3-dihydro-1H-pyrido[2,3-b][1,4]oxazine-1-carboxylate was used to afford Enantiomer 2 (Compound 563b) (Relative stereochemistry as drawn. Absolute stereochemistry arbitrarily assigned) (49.5 mg, 0.102 mmol, 46.5% yield): $R_T$ 4.856 min CHIRALPAK IA-U 3.0*50 mm 1.6 μm; Mobile Phase A: CO$_2$, Mobile Phase B: IPA (20 mm NH$_3$), 10%-50%, 6.5 min; 2 ml/min). LCMS (ESI): [M+H]$^+$=482.2, $R_T$ 2.137 min., Method J; $^1$H NMR (400 MHz, DMSO-d$_6$) δ 10.18 (s, 1H), 9.33 (s, 1H), 7.97 (s, 1H), 7.33 (s, 1H), 6.84 (d, J=6.2 Hz, 1H), 6.21 (s, 2H), 5.66 (d, J=3.4 Hz, 1H), 5.23-5.00 (m, 1H), 4.77 (dd, J=6.7, 3.6 Hz, 1H), 4.29 (t, J=4.3 Hz, 2H), 3.96-3.78 (m, 4H), 3.68 (dd, J=9.5, 8.0 Hz, 1H), 3.46 (dd, J=10.2, 3.7 Hz, 1H), 3.16-3.20 (m, 2H) 3.04-2.90 (m, 1H), 1.92 (d, J=1.6 Hz, 3H).

Example 212

(3R,4R)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3S,4S)-4-Fluorotetrahydrofuran-3-yl (8-amino-7-fluoro-6-(8-methyl-2,3-dihydro-1H-pyrido[2,3-b][1,4] oxazin-7-yl)isoquinolin-3-yl)carbamate (Compound 477a and Compound 477b)

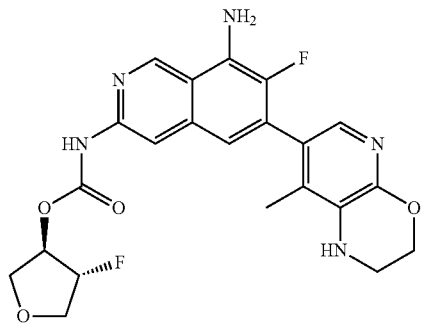

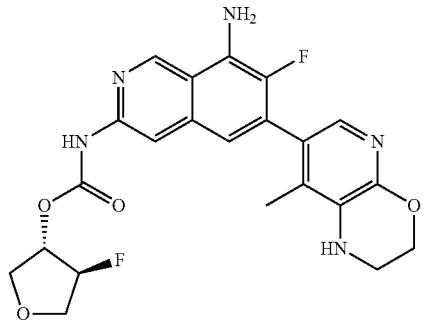

Step 1: 4-Fluorotetrahydrofuran-3-ol

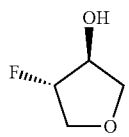

545

A mixture of 3,4-epoxytetrahydrofuran (2.7 g, 31.40 mmol) and triethylamine trihydrofluoride (7.68 mL, 47.1 mmol) was stirred at 120° C. for 12 hours. The mixture was cooled to room temperature and then quenched with saturated sodium bicarbonate solution. The resulting solution was extracted with dichloromethane/2-propanol (5/1) and concentrated under vacuum. The residue was purified by flash chromatography on silica gel eluting with petroleum ether/ethyl acetate (4:1) to afford 4-fluorotetrahydrofuran-3-ol (2.02 g, 19.04 mmol, 60.9% yield) as yellow oil.

Step 2: tert-Butyl 7-(8-((tert-butoxycarbonyl)amino)-7-fluoro-3-((((4-fluorotetrahydrofuran-3-yl)oxy)carbonyl)amino)isoquinolin-6-yl)-8-methyl-2,3-dihydro-1H-pyrido[2,3-b][1,4]oxazine-1-carboxylate

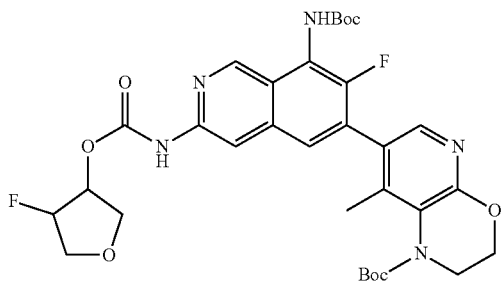 [SMILES: Cc1c(-c2cc3cc(NC(=O)OC4COCC4F)ncc3c(NC(=O)OC(C)(C)C)c2F)cnc2c1N(C(=O)OC(C)(C)C)CCO2]

A solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (200.0 mg, 0.38 mmol), N,N-diisopropylethylamine (0.33 mL, 1.92 mmol) and 4-fluorotetrahydrofuran-3-ol (2.02 g, 19.04 mmol) in dichloromethane (20 mL) was stirred at 0° C. for 5 min. Then triphosgene (80.0 mg, 0.27 mmol) in dichloromethane was added and the reaction was stirred at 0° C. for 0.5 hours. The reaction mixture was quenched with water and extracted with dichloromethane. The organic layers were combined, dried over anhydrous sodium sulfate, filtered and concentrated under vacuum. The residue was purified by flash chromatography on silica gel eluting with dichloromethane/methanol (30/1) to afford tert-butyl 7-[8-(tert-butoxycarbonylamino)-7-fluoro-3-[(4-fluorotetrahydrofuran-3-yl)oxycarbonylamino]-6-isoquinolyl]-8-methyl-2,3-dihydropyrido[2,3-b][1,4]oxazine-1-carboxylate (190.0 mg, 0.29 mmol, 76.3% yield) as yellow solid. LCMS (ESI) [M+H]⁺=658.3.

Step 3: (3R,4R)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3S,4S)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate

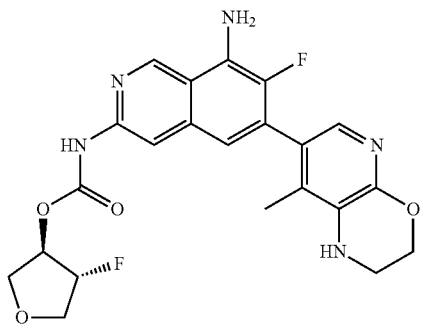

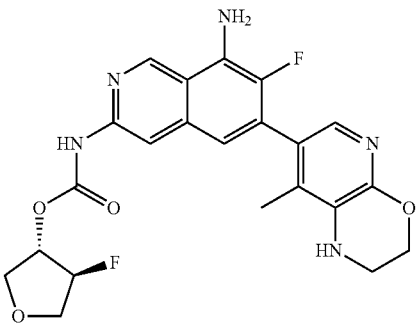

To a solution of tert-butyl 7-[8-(tert-butoxycarbonylamino)-7-fluoro-3-[(4-fluorotetrahydrofuran-3-yl)oxycarbonyl amino]-6-isoquinolyl]-8-methyl-2,3-dihydropyrido[2,3-b][1,4]oxazine-1-carboxylate (190.0 mg, 0.29 mmol) in dichloromethane (18 mL) was added trifluoroacetic acid (6 mL). The mixture was stirred at room temperature for 1 hour and then concentrated under vacuum. The residue was diluted with dichloromethane and adjusted to pH 8 with triethylamine. The mixture was concentrated under vacuum and purified by Prep-HPLC (Column: X select CSH OBD Column 30*150 mm, 5 μm; Mobile Phase A: Water (0.1% FA), Mobile Phase B: ACN; Flow rate: 60 mL/min; Gradient: 11% B to 34% B in 10 min) to give a racemic mixture. The racemic product was separated by chiral Prep-HPLC to afford two enantiomers. Relative stereochemistry are as drawn. Absolute stereochemistry was arbitrarily assigned.

Enantiomer 1: Compound 477a (12.3 mg, 0.0264 mmol, 9.1% yield) as yellow solid. $R_T$ 1.349 min (CHIRALPAK IE-3, 0.46*5 cm; 3 μm; Mobile phase: MTBE (0.1% DEA):EtOH=75:25, 1 ml/min); LCMS (ESI): [M+H]⁺=458.2, $R_T$ 1.843 min, Method J; ¹H NMR (400 MHz, DMSO-d₆) δ 10.32 (s, 1H), 9.35 (s, 1H), 7.97 (s, 1H), 7.33 (s, 1H), 6.86 (d, J=6.0 Hz, 1H), 6.22 (s, 2H), 5.67 (s, 1H), 5.40 (s, 1H), 5.27-5.24 (m, 1H), 4.29 (t, J=4.4 Hz, 2H), 4.14-4.10 (m, 1H), 3.99 (d, J=2.0 Hz, 1H), 3.99-3.87 (m, 1H), 3.83-3.79 (m, 1H), 3.37 (s, 2H), 1.92 (s, 3H).

Enantiomer 2: Compound 477b (9 mg, 0.0195 mmol, 6.8% yield) as a yellow solid. $R_T$ 2.474 min (CHIRALPAK IE-3, 0.46*5 cm; 3 μm; Mobile phase: MTBE (0.1% DEA):EtOH=75:25, 1 ml/min); LCMS (ESI): [M+H]⁺=458.2, $R_T$ 1.843 min, Method J; ¹H NMR (400 MHz, DMSO-d₆) δ 10.32 (s, 1H), 9.35 (s, 1H), 7.97 (s, 1H), 7.33 (s, 1H), 6.86 (d, J=6.0 Hz, 1H), 6.22 (s, 2H), 5.67 (s, 1H), 5.40 (s, 1H), 5.27-5.24 (m, 1H), 4.29 (t, J=4.4 Hz, 2H), 4.14-4.10 (m, 1H), 3.99 (d, J=2.0 Hz, 1H), 3.99-3.87 (m, 1H), 3.83-3.79 (m, 1H), 3.37 (s, 2H), 1.92 (s, 3H).

Example 213

1-(8-Amino-7-fluoro-6-(8-methyl-2,3-dihydro-1H-pyrido[2,3-b][1,4]oxazin-7-yl)isoquinolin-3-yl)-3-((3S,4S)-4-fluorotetrahydrofuran-3-yl)urea and 1-(8-Amino-7-fluoro-6-(8-methyl-2,3-dihydro-1H-pyrido[2,3-b][1,4]oxazin-7-yl)isoquinolin-3-yl)-3-((3R,4R)-4-fluorotetrahydrofuran-3-yl)urea (Compound 724a and Compound 724b)

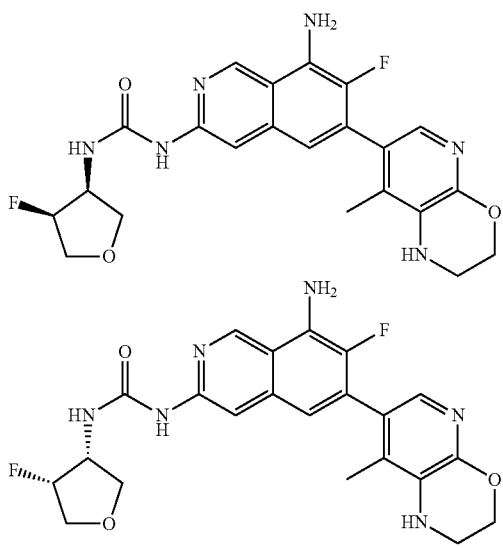

Step 1: (±)-cis-N,N-Dibenzyl-4-fluorotetrahydrofuran-3-amine

To a solution of (±)-cis-4-(dibenzylamino)tetrahydrofuran-3-ol (620 mg, 2.19 mmol) in dichloromethane (10 mL) was added DAST (700 mg, 4.35 mmol) at −78° C. The mixture was stirred at −78° C. for 2 hours. The mixture was concentrated under vacuum. The residue was purified by flash chromatography on silica gel eluting with petroleum ether/ethyl acetate (88/12) to afford (±)-cis-N,N-dibenzyl-4-fluorotetrahydrofuran-3-amine (300 mg, 1.051 mmol, 48% yield) as a colorless oil. LCMS (ESI) [M+H]⁺=286.

Step 2: (±)-cis-4-Fluorotetrahydrofuran-3-amine

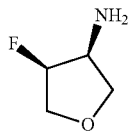

A mixture of (±)-cis-N,N-dibenzyl-4-fluoro-tetrahydrofuran-3-amine (340 mg, 1.19 mmol) and Pd/C (10%, 120 mg, 1.19 mmol) in 1,4-dioxane (1 mL) and methyl alcohol (4 mL) was stirred at 40° C. for 3 hours. After filtration, the filtrate was concentrated under vacuum to afford (±)-cis-4-fluorotetrahydrofuran-3-amine (120 mg, 1.142 mmol, 95.8% yield) as a yellow solid. GCMS=106.

Step 3: (±)-cis-tert-Butyl 7-(8-((tert-butoxycarbonyl)amino)-7-fluoro-3-(3-(4-fluorotetrahydrofuran-3-yl)ureido)isoquinolin-6-yl)-8-methyl-2,3-dihydro-1H-pyrido[2,3-b][1,4]oxazine-1-carboxylate

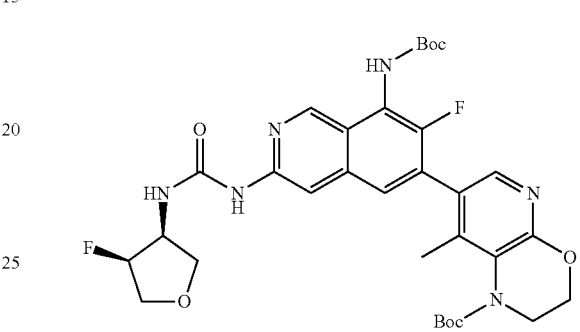

A solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300 mg, 0.46 mmol), DMAP (56 mg, 0.46 mmol) and (±)-cis-4-fluorotetrahydrofuran-3-amine (98 mg, 0.93 mmol) in 1,4-dioxane (10 mL) was stirred for 2 hours at 90° C. The reaction mixture was concentrated under vacuum. The residue was purified by flash chromatography on silica gel eluting with petroleum ether/ethyl acetate (43/57) to afford (±)-cis-tert-butyl 7-(8-((tert-butoxycarbonyl)amino)-7-fluoro-3-(3-(4-fluorotetrahydrofuran-3-yl)ureido)isoquinolin-6-yl)-8-methyl-2,3-dihydro-1H-pyrido[2,3-b][1,4]oxazine-1-carboxylate (280 mg, 0.426 mmol, 91.8% yield) as a yellow solid. LCMS (ESI) [M+H]⁺=657.

Step 4: 1-(8-Amino-7-fluoro-6-(8-methyl-2,3-dihydro-1H-pyrido[2,3-b][1,4]oxazin-7-yl)isoquinolin-3-yl)-3-((3S,4S)-4-fluorotetrahydrofuran-3-yl)urea and 1-(8-Amino-7-fluoro-6-(8-methyl-2,3-dihydro-1H-pyrido[2,3-b][1,4]oxazin-7-yl)isoquinolin-3-yl)-3-((3R,4R)-4-fluorotetrahydrofuran-3-yl)urea

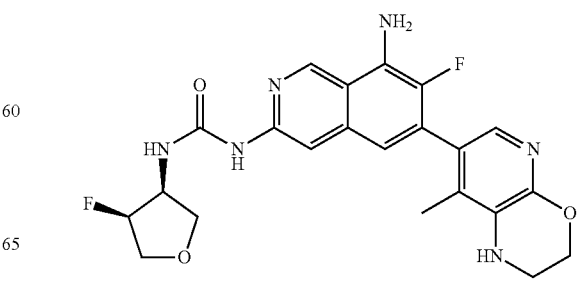

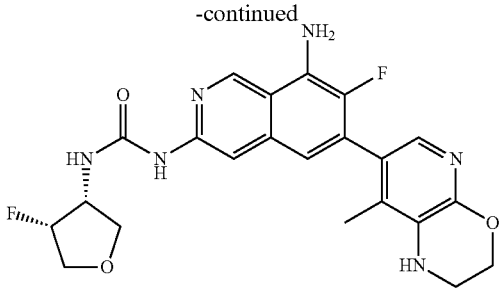

A solution of (±)-cis-tert-butyl 7-(8-(((tert-butoxycarbonyl)amino)-7-fluoro-3-(3-(4-fluorotetrahydrofuran-3-yl)ureido)isoquinolin-6-yl)-8-methyl-2,3-dihydro-1H-pyrido[2,3-b][1,4]oxazine-1-carboxylate (130 mg, 0.20 mmol) in dichloromethane (5 mL) and 2,2,2-trifluoroacetic acid (2 mL) was stirred at room temperature for 1 hour. The reaction solution was concentrated under vacuum. The residue was purified by Prep-HPLC (Column: X Bridge Prep OBD C18 Column 30×150 mm, 5 μm; Mobile Phase A: Water (10 mmol/L NH$_4$HCO$_3$), Mobile Phase B: ACN; Flow rate: 60 mL/min; Gradient: 15% B to 26% B in 10 min) to afford a racemate. The racemic product was separated by chiral-HPLC to afford two enantiomers. Relative stereochemistry are as drawn. Absolute stereochemistry was arbitrarily assigned.

Enantiomer 1 (Compound 724a) (54.2 mg, 0.119 mmol, 60% yield). R$_T$ 1.216 min (CHIRALPAK IG-3 0.46*5 cm; 3 μm; MTBE (0.1% DEA):MeOH=50:50). LCMS(ESI) [M+H]$^+$=467.2, R$_T$ 1.892 min, Method K. $^1$H NMR (300 MHz, DMSO-d$_6$) δ 9.28 (s, 1H), 8.94 (s, 1H), 7.85 (s, 1H), 7.45-7.38 (d, J=6 Hz, 1H), 7.31 (s, 1H), 6.75-6.73 (s, J=6 Hz, 1H), 5.65 (s, 2H), 5.28-5.04 (m, 1H), 5.07 (s, 1H), 4.31-4.23 (m, 3H), 4.08-3.81 (m, 3H), 3.68-3.36 (m, 1H), 3.43-3.32 (m, 2H). 1.93 (s, 3H).

Enantiomer 2 (Compound 724b) (52.7 mg, 0.116 mmol, 58.3% yield). R$_T$ 1.861 min (CHIRALPAK IG-3 0.46*5 cm; 3 μm; (MTBE (0.1% DEA):MeOH=50:50). LCMS(ESI) [M+H]$^+$=467.2, R$_T$ 1.892 min, Method K. $^1$H NMR (300 MHz, DMSO-d$_6$) δ 9.28 (s, 1H), 8.94 (s, 1H), 7.85 (s, 1H), 7.45-7.38 (d, J=6 Hz, 1H), 7.31 (s, 1H), 6.75-6.73 (s, J=6 Hz, 1H), 5.65 (s, 2H), 5.28-5.04 (m, 1H), 5.07 (s, 1H), 4.31-4.23 (m, 3H), 4.08-3.81 (m, 3H), 3.68-3.36 (m, 1H), 3.43-3.32 (m, 2H). 1.93 (s, 3H).

Example 214

(3S,4R)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate and (3R,4S)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate (Compound 452c and Compound 452d)

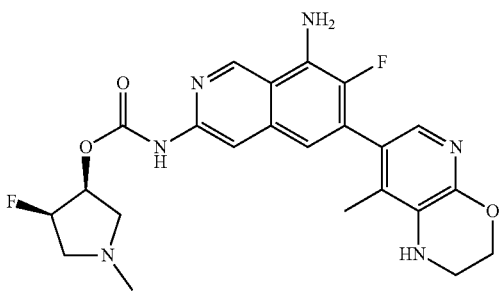

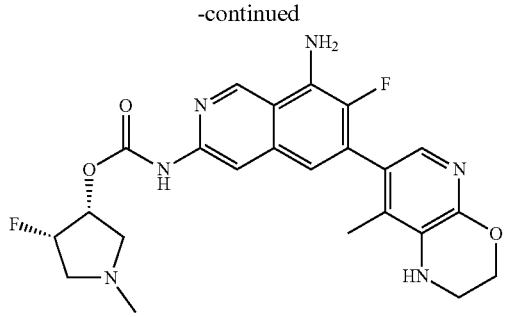

Step 1: (3S,4R)-4-Fluoropyrrolidin-3-ol

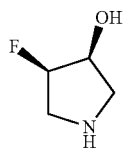

To a solution of tert-butyl 3-fluoro-4-hydroxy-pyrrolidine-1-carboxylate (500.0 mg, 2.44 mmol) in dichloromethane (2 mL) and trifluoroacetic acid (2.0 mL) was stirred for 2 hours at room temperature. The reaction mixture was concentrated under vacuum. The crude product was used directly for the next step without purification.

Step 2: 4-Fluoro-1-methyl-pyrrolidin-3-ol

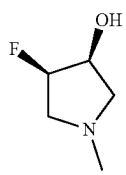

A solution of 4-fluoropyrrolidin-3-ol (510.0 mg, 4.86 mmol) and acetic acid (585.0 mg, 9.74 mmol) in methyl alcohol (3.0 mL) and formaldehyde aqueous solution (7.2 g, 40%) was stirred for 2 hours at room temperature. Sodium borohydride (2.21 g, 58.46 mmol) was added and the mixture was stirred for 2 hours at room temperature. The mixture was concentrated under vacuum and purified by flash chromatography on silica gel eluting with dichloromethane/methanol (10/1) to afford 4-fluoro-1-methyl-pyrrolidin-3-ol (310 mg, 2.60 mmol, 53.2% yield) as a yellow solid. LCMS (ESI) [M+H]$^+$=120.

551

Step 3: tert-Butyl 7-[8-(tert-butoxycarbonylamino)-7-fluoro-3-[[(3S,4S)-4-fluoro-1-methyl-pyrrolidin-3-yl]oxycarbonylamino]-6-isoquinolyl]-8-methyl-2,3-dihydropyrido[2,3-b][1,4]oxazine-1-carboxylate

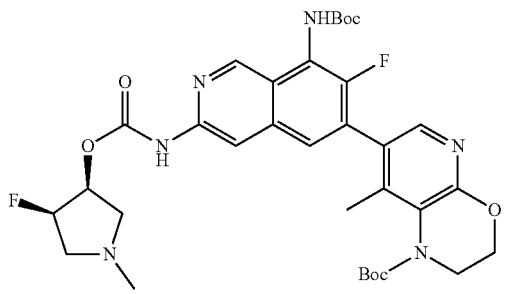 [SMILES: Cc1c(-c2cc3cc(NC(=O)O[C@H]4CN(C)C[C@H]4F)ncc3c(NC(=O)OC(C)(C)C)c2F)cnc2c1N(C(=O)OC(C)(C)C)CCO2]

A solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (310.0 mg, 0.484 mmol), 4-fluoro-1-methyl-pyrrolidin-3-ol (286.1 mg, 2.41 mmol) and DMAP (58.7 mg, 0.484 mmol) in 1,4-dioxane (5 mL) was stirred at 90° C. for 2 hours. The reaction was quenched with water and extracted with dichloromethane. The organic layers were combined and concentrated under vacuum. The residue was purified by flash chromatography on silica gel eluting with dichloromethane/methanol (10/1) to afford tert-butyl 7-[8-(tert-butoxycarbonylamino)-7-fluoro-3-[[(3S,4S)-4-fluoro-1-methyl-pyrrolidin-3-yl]oxycarbonylamino]-6-isoquinolyl]-8-methyl-2,3-dihydropyrido[2,3-b][1,4]oxazine-1-carboxylate (80 mg, 0.119 mmol, 30.8% yield) as a yellow solid. LCMS (ESI) [M+H]⁺=671.3.

Step 4: (3S,4R)-4-fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate and (3R,4S)-4-fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate

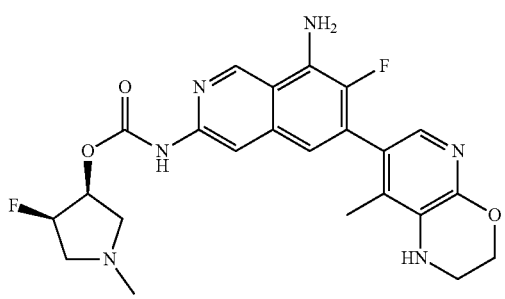

552

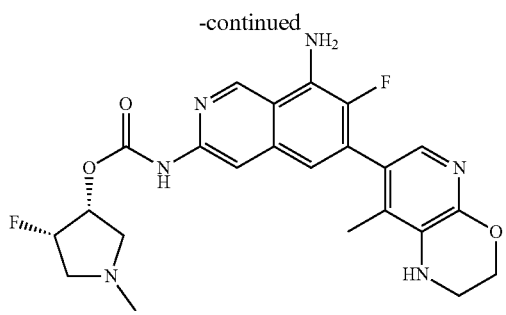

A solution of tert-butyl 7-[8-(tert-butoxycarbonylamino)-7-fluoro-3-[(4-fluoro-1-methyl-pyrrolidin-3-yl)oxycarbonylamino]-6-isoquinolyl]-8-methyl-2,3-dihydropyrido[2,3-b][1,4]oxazine-1-carboxylate (80.0 mg, 0.119 mmol) in dichloromethane (5 mL), and TFA (1 mL) was stirred at RT for 2 hours. The resulting solution was concentrated under vacuum. The residue was dissolved in DCM and adjusted to pH 8 with triethylamine. The resulting solution was concentrated under vacuum. The residue was purified by Prep-HPLC (Column: X select CSH OBD Column 30*150 mm 5 μm; Mobile Phase A: Water (0.1% FA), Mobile Phase B: ACN; Flow rate: 60 mL/min; Gradient: 5% B to 20% B in 7 min) to afford a racemic product. The racemic product was further separated by chair-Prep-HPLC to obtain two enantiomers. Relative stereochemistry are as drawn. Absolute stereochemistry was arbitrarily assigned.

Enantiomer 1: Compound 452c (5.9 mg, 0.017 mmol, 10.4% yield). R$_T$ 1.203 min (CHIRALPAK IC-3 0.46*5 cm; 3 μm. Mobile phase: MTBE:EtOH=50:50, 1 ml/min). LCMS (ESI): [M+H]⁺=471.3, R$_T$ 1.692 min, Method L; ¹H NMR (300 MHz, DMSO-d₆) δ10.23 (s, 1H), 9.32 (s, 1H), 7.95 (s, 1H), 7.31 (s, 1H), 6.83 (d, J=6.2 Hz, 1H), 6.20 (s, 2H), 5.65 (s, 1H), 5.27-5.09 (m, 2H), 4.27 (s, 2H), 3.37 (s, 2H), 2.79-2.72 (m, 4H), 2.28 (s, 3H), 1.90 (s, 3H).

Enantiomer 2: Compound 452d (8.3 mg, 0.0196 mmol, 12% yield). R$_T$ 2.607 min (CHIRALPAK IC-3 0.46*5 cm; 3 μm. Mobile phase: MTBE:EtOH=50:50, 1 ml/min). LCMS (ESI): [M+H]⁺=471.3, R$_T$ 1.692 min, Method L; ¹H NMR (300 MHz, DMSO-d₆) δ 10.23 (s, 1H), 9.32 (s, 1H), 7.95 (s, 1H), 7.31 (s, 1H), 6.83 (d, J=6.2 Hz, 1H), 6.20 (s, 2H), 5.65 (s, 1H), 5.27-5.09 (m, 2H), 4.27 (s, 2H), 3.37 (s, 2H), 2.79-2.72 (m, 4H), 2.28 (s, 3H), 1.90 (s, 3H).

Example 215

(1r,3r)-3-(Hydroxymethyl)cyclobutyl (8-amino-7-fluoro-6-(8-methyl-2,3-dihydro-1H-pyrido[2,3-b][1,4]oxazin-7-yl)isoquinolin-3-yl)carbamate and (1s,3s)-3-(Hydroxymethyl)cyclobutyl (8-amino-7-fluoro-6-(8-methyl-2,3-dihydro-1H-pyrido[2,3-b][1,4]oxazin-7-yl)isoquinolin-3-yl)carbamate (Compound 571a and Compound 571b)

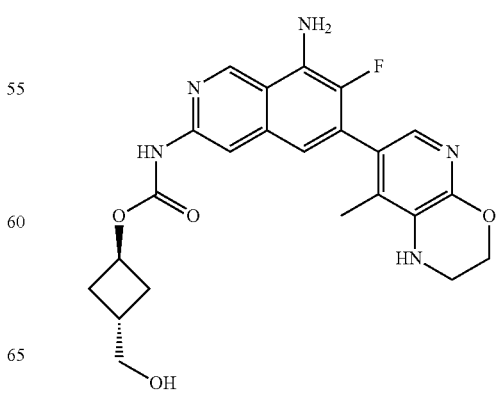

-continued

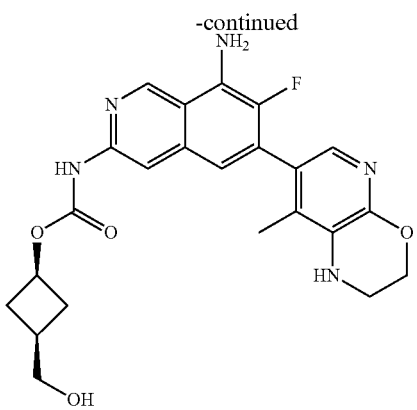

Step 1: (3-(Benzyloxy)cyclobutyl)methanol

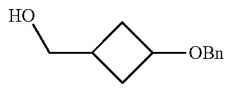 [SMILES: OCC1CC(OCc2ccccc2)C1]

A solution of 3-benzyloxy-cyclobutanecarboxylicacid (3.0 g, 14.55 mmol) and $B_2H_6$ (44 mL, 46.15 mmol) in tetrahydrofuran (50 mL) was stirred at 25° C. for 1 hour. The reaction was quenched with methanol. The reaction was concentrated under vacuum. The crude product will be used for next step. LCMS (ESI) [M+H]$^+$=192.

Step 2: ((3-(Benzyloxy)cyclobutyl)methoxy)(tert-butyl)dimethylsilane

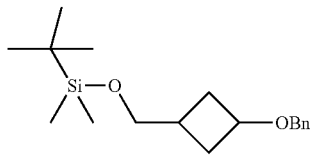 [SMILES: CC(C)(C)[Si](C)(C)OCC1CC(OCc2ccccc2)C1]

A solution of (3-benzyloxycyclobutyl)methanol (500 mg, 2.6 mmol), TBDMSCl (777 mg, 5.18 mmol) and imidazole (704 mg, 10.34 mmol) in dichloromethane (10 mL) was stirred at 25° C. for 1 hour. The reaction mixture was concentrated under vacuum. The residue was purified by flash chromatography on silica gel eluting with petroleum ether/ethyl acetate (77/23) to afford (3-benzyloxycyclobutyl)methoxy-tert-butyl-dimethyl-silane (770 mg, 2.512 mmol, 96.6% yield) as a colorless oil. LCMS (ESI) [M+H]$^+$= 307.

Step 3: 3-(((tert-Butyldimethylsilyl)oxy)methyl)cyclobutan-1-ol

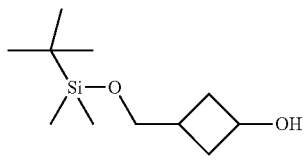

A mixture of (3-benzyloxycyclobutyl)methoxy-tert-butyl-dimethyl-silane (840 mg, 2.74 mmol) and Pd/C (800 mg, 6.78 mmol) in methyl alcohol (30 mL) was stirred at 40° C. for 2 days under hydrogen (1 atm). After filtration, the reaction mixture was concentrated under vacuum. The crude product (800 mg) was used for next step. LCMS (ESI) [M+H]$^+$=216.

Step 4: tert-Butyl 7-(8-(((tert-butoxycarbonyl)amino)-3-(((3-(((tert-butyldimethylsilyl)oxy)methyl)cyclobutoxy)carbonyl)amino)-7-fluoroisoquinolin-6-yl)-8-methyl-2,3-dihydro-1H-pyrido[2,3-b][1,4]oxazine-1-carboxylat

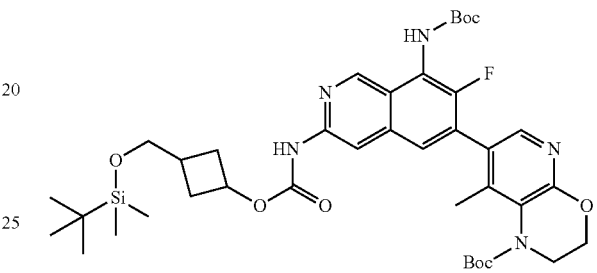

A solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (609 mg, 1.16 mmol), 3-[[tert-butyl(dimethyl)silyl]oxymethyl]cyclobutanol (587 mg, 2.71 mmol), triphosgene (265 mg, 0.89 mmol) and DIEA (868 mg, 6.73 mmol) in dichloromethane (20 mL) was stirred at 0° C. for 2 hours. The reaction was quenched with water and extracted with dichloromethane. The organic layer was dried over anhydrous sodium sulfate, filtered and concentrated under vacuum. The residue was purified by flash chromatography on silica gel eluting with dichloromethane (96/4) to afford tert-butyl 7-[8-(tert-butoxycarbonylamino)-3-[[3-[[tert-butyl(dimethyl)silyl]oxymethyl]cyclobutoxy]carbonylamino]-7-fluoro-6-isoquinolyl]-8-methyl-2,3-dihydropyrido[2,3-b][1,4]oxazine-1-carboxylate (850 mg, 1.1068 mmol, 95.5% yield) as a brown solid. LCMS (ESI) [M+H]$^+$=768.

Step 5: tert-Butyl 7-(8-((tert-butoxycarbonyl)amino)-7-fluoro-3-(((3-(hydroxymethyl)cyclobutoxy)carbonyl)amino)isoquinolin-6-yl)-8-methyl-2,3-dihydro-1H-pyrido[2,3-b][1,4]oxazine-1-carboxylate

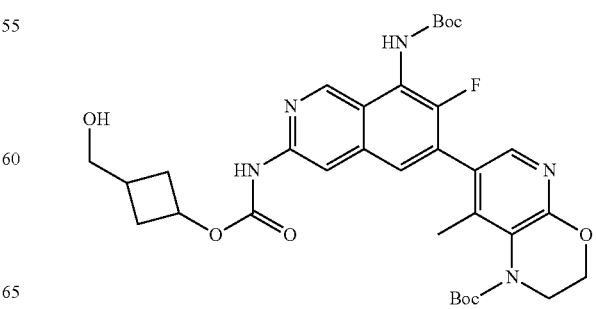

A solution of tert-butyl 7-[8-(tert-butoxycarbonylamino)-3-[[3-[[tert-butyl (dimethyl)silyl]oxymethyl]cyclobutoxy]carbonylamino]-7-fluoro-6-isoquinolyl]-8-methyl-2,3-dihydropyrido[2,3-b][1,4]oxazine-1-carboxylate (889 mg, 1.16 mmol) and TBAF (1460 mg, 4.63 mmol) in tetrahydrofuran (10 mL) was stirred at 25° C. for 4 hours. The reaction mixture was concentrated under vacuum. The residue was purified by flash chromatography on silica gel eluting with dichloromethane/methanol (94/6) to afford tert-butyl 7-[8-(tert-butoxycarbonylamino)-7-fluoro-3-[[3-(hydroxymethyl)cyclobutoxy]carbonylamino]-6-isoquinolyl]-8-methyl-2,3-dihydropyrido[2,3-b][1,4]oxazine-1-carboxylate (416 mg, 0.636 mmol, 55% yield) as a yellow solid. LCMS (ESI) [M+H]⁺=654.

Step 6: (1r,3r)-3-(Hydroxymethyl)cyclobutyl (8-amino-7-fluoro-6-(8-methyl-2,3-dihydro-1H-pyrido[2,3-b][1,4]oxazin-7-yl)isoquinolin-3-yl)carbamate and (1s,3s)-3-(hydroxymethyl)cyclobutyl (8-amino-7-fluoro-6-(8-methyl-2,3-dihydro-1H-pyrido[2,3-b][1,4]oxazin-7-yl)isoquinolin-3-yl)carbamate

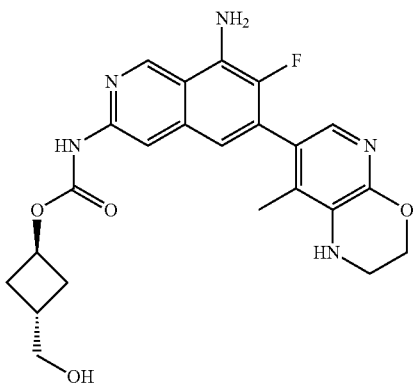

A solution of tert-butyl 7-[8-(tert-butoxycarbonylamino)-7-fluoro-3-[[3-(hydroxymethyl)cyclobutoxy]carbonylamino]-6-isoquinolyl]-8-methyl-2,3-dihydropyrido[2,3-b][1,4]oxazine-1-carboxylate (120 mg, 0.18 mmol) in dichloromethane (5 mL) and TFA (2 mL) was stirred at room temperature for 1 hour. The solution was concentrated under vacuum. The residue was purified by Prep-HPLC (Column: X Bridge Prep OBD C18 Column 30×150 mm, 5 μm; Mobile Phase A: Water (10 mm NH₄HCO₃), Mobile Phase B: ACN; Flow rate: 60 mL/min; Gradient: 15% B to 26% B in 10 min) to afford a mixture of stereoisomers. The mixture was separated by chiral-HPLC to afford two stereoisomers. Stereochemistry was arbitrarily assigned.

Isomer 1 (Compound 571a) (26.9 mg, 0.0593 mmol, 32.3% yield). R$_T$ 12.514 min (CHIRALPAK IA 2×25 cm; 5 μm. Mobile phase A: (Hex:DCM=3:1) (10 M NH₃-MeOH); Mobile phase B: EtOH). LCMS(ESI) [M+H]⁺=454.2, R$_T$ 1.864 min; Method J. ¹H NMR (300 MHz, DMSO-d₆) δ 10.02 (s, 1H), 9.30 (s, 1H), 7.94 (s, 1H), 7.30 (s, 1H), 6.85-6.78 (d, J=6 Hz, 1H), 6.17 (s, 2H), 5.66 (s, 1H), 5.10-4.93 (m, 1H), 4.71-4.63 (m, 1H), 4.27 (s, 2H), 3.48-3.40 (d, J=4.5 Hz, 2H), 3.37-3.31 (m, 2H), 2.38-2.15 (m, 2H), 2.16-2.05 (m, 3H), 1.90 (s, 3H).

Isomer 2 (Compound 571b) (20.7 mg, 0.0456 mmol, 24.9% yield): Retention time: 13.339 min (CHIRALPAK IA 2*25 cm; 5 μm. Mobile phase A: (Hex:DCM=3:1) (10 M NH₃-MeOH); Mobile phase B: EtOH). LCMS(ESI) [M+H]⁺= 454.2, R$_T$ 1.771 min; Method K. ¹H NMR (300 MHz, DMSO-d₆) δ 10.02 (s, 1H), 9.36 (s, 1H), 7.95 (s, 1H), 7.31 (s, 1H), 6.83-6.78 (d, J=6 Hz, 1H), 6.18 (s, 2H), 5.68 (s, 1H), 4.91-4.74 (m, 1H), 4.62-4.52 (m, 1H), 2.28 (s, 2H), 3.40-3.32 (m, 4H), 2.40-2.28 (m, 2H), 2.05-1.98 (m, 1H), 1.98-1.77 (m, 5H).

Example 216

(1s,3s)-3-(Methylsulfonyl)cyclobutyl (8-amino-7-fluoro-6-(8-methyl-2,3-dihydro-1H-pyrido[2,3-b][1,4]oxazin-7-yl)isoquinolin-3-yl)carbamate (Compound 572a)

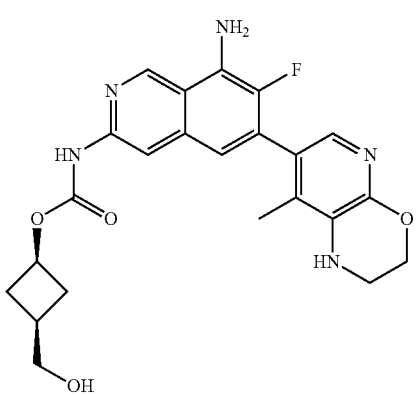

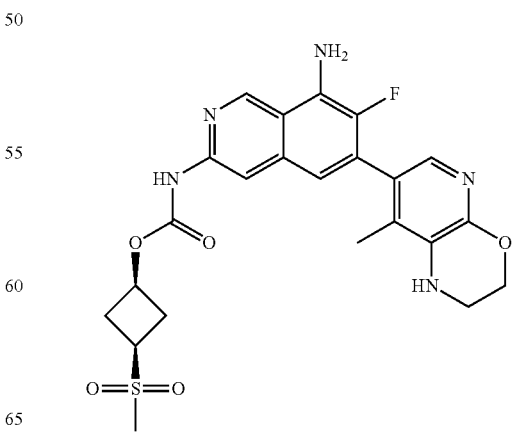

Step 1: tert-Butyl 7-(8-((tert-butoxycarbonyl)amino)-7-fluoro-3-((((1s,3s)-3-(methylsulfonyl)cyclobutoxy)carbonyl)amino)isoquinolin-6-yl)-8-methyl-2,3-dihydro-1H-pyrido[2,3-b][1,4]oxazine-1-carboxylate

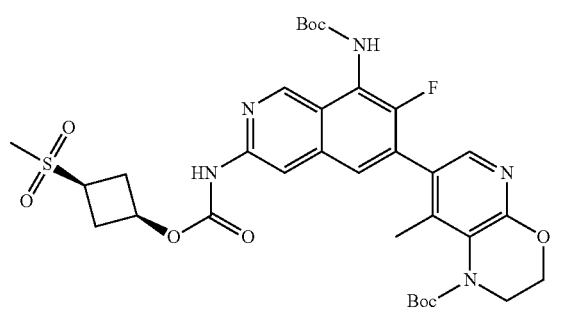 [SMILES: Cc1c(-c2cc3cc(NC(=O)O[C@H]4C[C@@H](S(C)(=O)=O)C4)ncc3c(NC(=O)OC(C)(C)C)c2F)cnc2c1N(C(=O)OC(C)(C)C)CCO2]

Under nitrogen, to a solution of cis-3-methylsulfonylcyclobutanol (150 mg, 1 mmol) and tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (150 mg, 0.23 mmol) in dichloromethane (25 mL) was added TEA (250 mg, 2.48 mmol) at room temperature. Then triphosgene (90 mg, 0.30 mmol) was added and the mixture was stirred at 0° C. for 1 hour. The residue was purified by flash chromatography on silica gel eluting with petroleum ether/ethyl acetate (1/9) to afford tert-butyl 7-(8-((tert-butoxycarbonyl)amino)-7-fluoro-3-((((1s,3s)-3-(methylsulfonyl)cyclobutoxy)carbonyl)amino)isoquinolin- 6-yl)-8-methyl-2,3-dihydro-1H-pyrido[2,3-b][1,4]oxazine-1-carboxylate (100 mg, 0.143 mmol, 61.3% yield) as a yellow solid. LCMS (ESI) [M+H]$^+$= 702.

Step 2: (1s,3s)-3-(Methylsulfonyl)cyclobutyl (8-amino-7-fluoro-6-(8-methyl-2,3-dihydro-1H-pyrido[2,3-b][1,4]oxazin-7-yl)isoquinolin-3-yl)carbamate

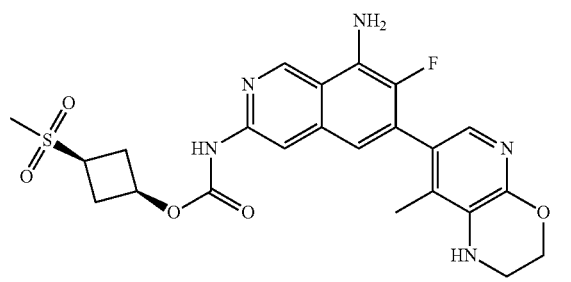 [SMILES: Cc1c(-c2cc3cc(NC(=O)O[C@H]4C[C@@H](S(C)(=O)=O)C4)ncc3c(N)c2F)cnc2c1NCCO2]

To a solution of tert-butyl 7-(8-((tert-butoxycarbonyl)amino)-7-fluoro-3-((((1s,3s)-3-(methylsulfonyl)cyclobutoxy)carbonyl)amino)isoquinolin-6-yl)-8-methyl-2,3-dihydro-1H-pyrido[2,3-b][1,4]oxazine-1-carboxylate (100 mg, 0.14 mmol) in dichloromethane (8 mL) was added 2,2,2-trifluoroacetic acid (2 mL) at 25° C. The resulting solution was stirred for 2 h at 25° C. The crude product was purified by Prep-HPLC (Column: X select CSH OBD Column 30*150 mm, 5 μm; Mobile Phase A: Water (0.1% FA), Mobile Phase B: ACN; Flow rate: 60 mL/min; Gradient: 9% B to 34% B in 7 min) to afford (3-methylsulfonylcyclobutyl) N-[8-amino-7-fluoro-6-(8-methyl-2,3-dihydro-1H-pyrido[2,3-b][1,4]oxazin-7-yl)-3-isoquinolyl]carbamate (58.3 mg, 0.106 mmol, 74.7% yield) as a yellow solid. LCMS (ESI) [M+H]$^+$=502.1, R$_T$ 1.931 min; Method K. $^1$H NMR (400 MHz, DMSO-d$_6$) δ 10.23 (s, 1H), 9.35 (s, 1H), 7.96 (s, 1H), 7.33 (s, 1H), 6.85 (d, J=6.2 Hz, 1H), 6.22 (s, 2H), 5.67 (d, J=3.2 Hz, 1H), 4.99 (p, J=7.6 Hz, 1H), 4.29 (t, J=4.4 Hz, 2H), 3.82-3.69 (m, 1H), 3.33 (s, 2H), 2.93 (s, 3H), 2.76-2.64 (m, 2H), 2.39 (ddd, J=12.4, 6.3, 2.4 Hz, 2H), 1.92 (d, J=1.6 Hz, 3H).

Example 217

(1r,3r)-(3-Cyanocyclobutyl) N-[8-amino-7-fluoro-6-(8-methyl-2,3-dihydro-1H-pyrido[2,3-b][1,4]oxazin-7-yl)-3-isoquinolyl]carbamate (Compound 484b)

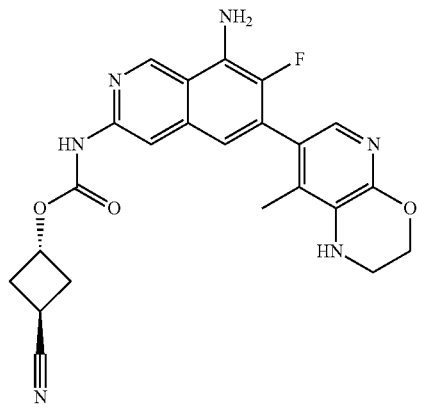 [SMILES: Cc1c(-c2cc3cc(NC(=O)O[C@H]4C[C@H](C#N)C4)ncc3c(N)c2F)cnc2c1NCCO2]

Step 1: tert-Butyl 7-[8-(tert-butoxycarbonylamino)-3-[(3-cyanocyclobutoxy)carbonylamino]-7-fluoro-6-isoquinolyl]-8-methyl-2,3-dihydropyrido[2,3-b][1,4]oxazine-1-carboxylate

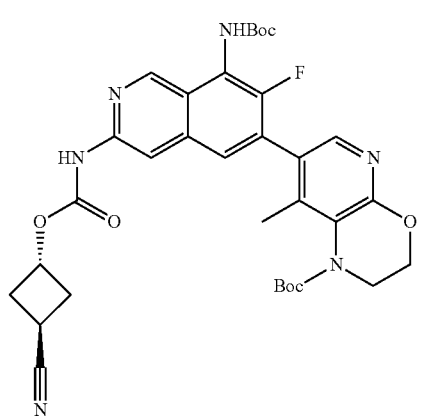 [SMILES: Cc1c(-c2cc3cc(NC(=O)O[C@H]4C[C@H](C#N)C4)ncc3c(NC(=O)OC(C)(C)C)c2F)cnc2c1N(C(=O)OC(C)(C)C)CCO2]

559

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300.0 mg, 0.46 mmol) and DMAP (56.7 mg, 0.46 mmol) in 1,4-dioxane (10 mL) was added 3-hydroxycyclobutanecarbonitrile (135.0 mg, 1.39 mmol) at 25° C. The resulting solution was stirred for 3 hours at 90° C. The reaction was concentrated under vacuum. The residue was purified by flash chromatography on silica gel eluting with dichloromethane/methanol (96/4) to afford tert-butyl 7-[8-(tert-butoxycarbonylamino)-3-[(3-cyanocyclobutoxy)carbonylamino]-7-fluoro-6-isoquinolyl]-8-methyl-2,3-dihydropyrido[2,3-b][1,4]oxazine-1-carboxylate (290 mg, 0.45 mmol, 96% yield) as a yellow oil. LCMS (ESI) [M+H]+=649.3

Step 2: (3-Cyanocyclobutyl) N-[8-amino-7-fluoro-6-(8-methyl-2,3-dihydro-1H-pyrido[2,3-b][1,4]oxazin-7-yl)-3-isoquinolyl]carbamate

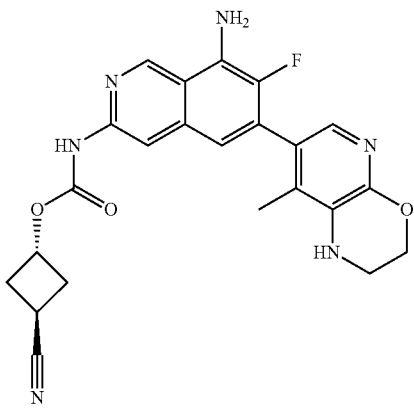 [SMILES: Cc1c(-c2cc3cc(NC(=O)O[C@H]4C[C@H](C#N)C4)ncc3c(N)c2F)cnc2c1NCCO2]

A solution of tert-butyl 7-[8-(tert-butoxycarbonylamino)-3-[(3-cyanocyclobutoxy)carbonylamino]-7-fluoro-6-isoquinolyl]-8-methyl-2,3-dihydropyrido[2,3-b][1,4]oxazine-1-carboxylate (290.0 mg, 0.45 mmol) and TFA (3.0 mL, 0.45 mmol) in dichloromethane (9 mL) was stirred at 25° C. for 2 hours. After concentration the residue was purified by Prep-HPLC (Column: X Bridge Shield RP18 OBD Column 19*250 mm, 10 μm; Water (0.1% FA): ACN=14% B to 30% B in 15 min; 25 mL/min) to afford (3-cyanocyclobutyl) N-[8-amino-7-fluoro-6-(8-methyl-2,3-dihydro-1H-pyrido[2,3-b][1,4]oxazin-7-yl)-3-isoquinolyl]carbamate (37 mg, 0.08 mmol, 19% yield) as a pale yellow solid. LCMS (ESI): [M+H]=449.2; $R_T$ 1.973 min.; Method K. $^1$H NMR (400 MHz, DMSO-$d_6$) δ 10.22 (s, 1H), 9.35 (s, 1H), 7.96 (s, 1H), 7.33 (s, 1H), 6.85 (d, J=6.2 Hz, 1H), 6.22 (s, 2H), 5.68 (d, J=2.7 Hz, 1H), 5.22-5.10 (m, 1H), 4.32-4.20 (m, 2H), 3.47-3.37 (m, 3H), 2.70-2.60 (m, 2H), 2.61-2.53 (m, 2H), 1.92 (s, 3H).

560

Example 218

(3S,4R)-1-(2,2-Difluoroethyl)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate and (3R,4S)-1-(2,2-Difluoroethyl)-3-fluoropiperidn-4-yl (8-amino-7-fluoro-6-(8-methyl-2,3-dihydro-1H-pyrido[2,3-b][1,4]oxazin-7-yl) isoquinolin-3-yl)carbamate (Compound 566a and Compound 566b)

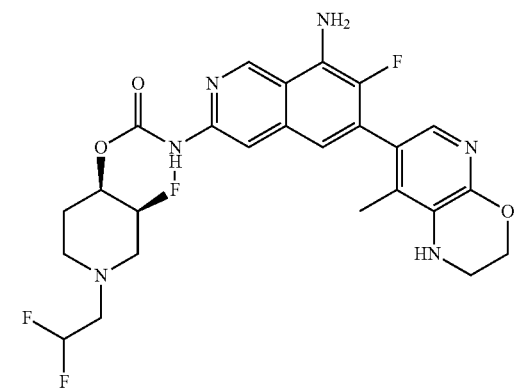

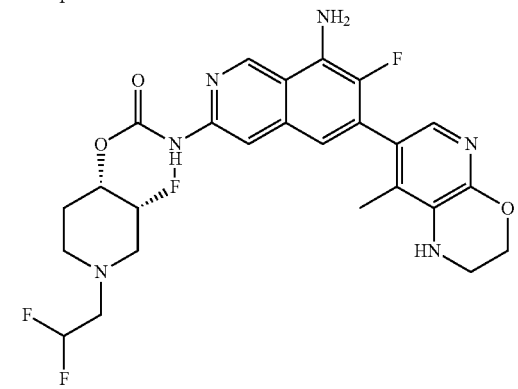

Step 1: (±)-cis-tert-Butyl 7-[8-(tert-butoxycarbonyl amino)-3-[(1-tert-butoxycarbonyl-3-fluoro-4-piperidyl)oxycarbonylamino]-7-fluoro-6-isoquinolyl]-8-methyl-2,3-dihydropyrido[2,3-b][1,4]oxazine-1-carboxylate

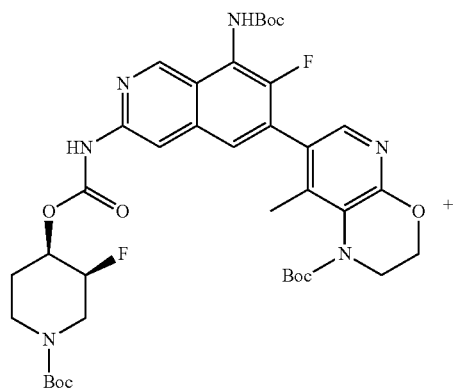

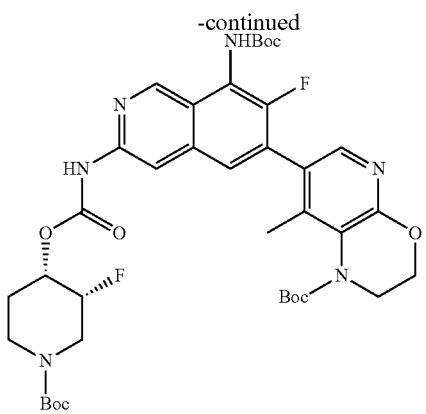

Under nitrogen, to a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (3000.0 mg, 5.71 mmol), tert-butyl 3-fluoro-4-hydroxypiperidine-1-carboxylate (1880.0 mg, 8.57 mmol) and DIEA (3680.0 mg, 28.53 mmol) in dichloromethane (50 mL) was added triphosgene (1185.0 mg, 3.99 mmol) at 0° C. The resulting solution was stirred for 2 hours at 0° C. The organic layer was concentrated under vacuum. The residue was purified by flash chromatography on silica gel eluting with petroleum ether/ethyl acetate (62/38) to afford a pair of enantiomers (2400 mg, 3.1136 mmol, 54.5% yield) as a white solid. LCMS (ESI) [M+H]⁺=771.

The enantiomers were separated by chiral-HPLC to afford a pair of enantiomers: tert-butyl 7-[8-(tert-butoxycarbonylamino)-3-[[(3S,4R)-1-tert-butoxycarbonyl-3-fluoro-4-piperidyl]oxycarbonylamino]-7-fluoro-6-isoquinolyl]-8-methyl-2,3-dihydropyrido[2,3-b][1,4]oxazine-1-carboxylate (1100 mg, 1.4271 mmol, 45.8% yield) and tert-butyl 7-[8-(tert-butoxycarbonylamino)-3-[[(3R,4S)-1-tert-butoxycarbonyl-3-fluoro-4-piperidyl]oxycarbonylamino]-7-fluoro-6-isoquinolyl]-8-methyl-2,3-dihydropyrido[2,3-b][1,4]oxazine-1-carboxylate (800 mg, 1.0379 mmol, 33.3% yield). (Absolute stereochemistry was arbitrarily assigned.)

Step 2: (3S,4R)-3-Fluoropiperidin-4-yl (8-amino-7-fluoro-6-(8-methyl-2,3-dihydro-1H-pyrido[2,3-b][1,4]oxazin-7-yl)isoquinolin-3-yl)carbamate

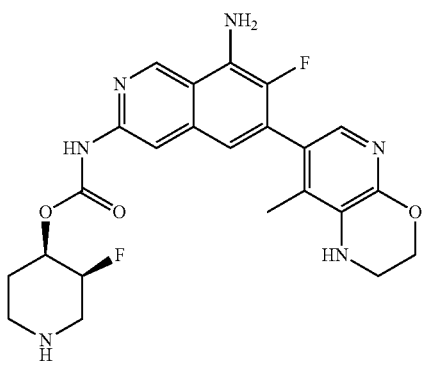 [SMILES: Cc1c(-c2cc3cc(NC(=O)O[C@@H]4CCNC[C@@H]4F)ncc3c(N)c2F)cnc2c1NCCO2]

A solution of tert-butyl 7-[8-(tert-butoxycarbonylamino)-3-[[(3S,4R)-1-tert-butoxycarbonyl-3-fluoro-4-piperidyl]oxycarbonylamino]-7-fluoro-6-isoquinolyl]-8-methyl-2,3-dihydropyrido[2,3-b][1,4]oxazine-1-carboxylate (100 mg, 0.13 mmol) in HCl (5 mL, 2 mol/L in MeOH) was stirred at room temperature for 2 hours. The reaction mixture was concentrated under vacuum to afford (3S,4R)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate (50 mg, 0.1063 mmol, 81.9% yield) as a red solid. LCMS (ESI) [M+H]⁺=471.

Step 3: (3S,4R)-1-(2,2-Difluoroethyl)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate (Compound 566a)

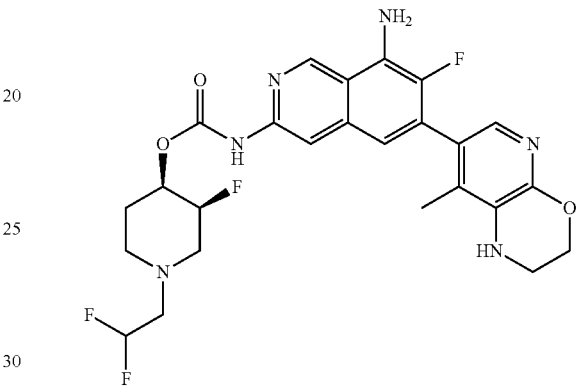

A solution of (3S,4R)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate (70.0 mg, 0.148 mmol) and 2,2-difluoroethyltrifluoromethanesulfonate (25 mg) in dichloromethane (5 mL) and TFA (5 mL) was stirred at room temperature for 2 hours. The solution was concentrated under vacuum. The resulting residue was purified by reverse phase chromatography with water (0.1% FA)/ACN (30/70) to afford (3S,4R)-1-(2,2-difluoroethyl)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate (Compound 566a) (Relative stereochemistry as drawn. Absolute stereochemistry arbitrarily assigned) (28 mg, 0.0524 mmol, 8.2% yield): $R_T$ 4.235 min (CHIRALPAK IC, 3.0*100 mm, 3 μm; $CO_2$: MeOH (0.1% DEA) Gradient (B%): 10% to 50% in 4.0 min, hold 2.0 min at 50%. Back Pressure (psi): 1500.000, Flow rate: 2 ml/min). LCMS(ESI) [M+H]⁺=535.3, $R_T$ 1.905 min., Method J; ¹H NMR (300 MHz, methanol-$d_4$) δ 9.60 (s, 1H), 7.93 (s, 1H), 7.65 (s, 1H), 7.18 (d, J=5.9 Hz, 1H), 6.75-6.31 (m, 1H), 5.45-5.24 (m, 2H), 4.76-4.67 (t, J=4.5 Hz, 2H), 4.06-3.98 (m, 1H), 3.90-3.75 (m, 7H), 3.72-3.65 (m, 1H), 2.52-2.36 (m, 2H), 2.23-2.28 (d, J=3 Hz, 3H).

Using a same procedure, (3R,4S)-1-(2,2-difluoroethyl)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate (Compound 566b) (Relative stereochemistry as drawn. Absolute stereochemistry arbitrarily assigned) was prepared from tert-butyl 7-(3-(((((3R,4S)-1-(tert-butoxycarbonyl)-3-fluoropiperidin-4-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate: $R_T$ 4.771 min (CHIRALPAK IC, 3.0*100 mm, 3 μm; $CO_2$: MeOH (0.1% DEA) Gradient (B %): 10% to 50% in 4.0 min, hold 2.0 min at 50%. Back Pressure (psi):

1500.000, Flow rate: 2 ml/min). LCMS(ESI) [M+H]$^+$= 535.3, $R_T$ 1.905 min; Method J. $^1$H NMR (300 MHz, Methanol-d$_4$) δ 9.60 (s, 1H), 7.93 (s, 1H), 7.65 (s, 1H), 7.18 (d, J=5.9 Hz, 1H), 6.75-6.31 (m, 1H), 5.45-5.24 (m, 2H), 4.76-4.67 (t, J=4.5 Hz, 2H), 4.06-3.98 (m, 1H), 3.90-3.75 (m, 7H), 3.72-3.65 (m, 1H), 2.52-2.36 (m, 2H), 2.23-2.28 (d, J=3 Hz, 3H).

Example 219

[(1R,3R)-3-Hydroxy-3-methyl-cyclopentyl]N-[8-amino-7-fluoro-6-(8-methyl-2,3-dihydro-1H-pyrido[2,3-b][1,4]oxazin-7-yl)-3-isoquinolyl]carbamate hydrochloride, [(1S,3S)-3-Hydroxy-3-methyl-cyclopentyl]N-[8-amino-7-fluoro-6-(8-methyl-2,3-dihydro-1H-pyrido[2,3-b][1,4]oxazin-7-yl)-3-isoquinolyl]carbamate hydrochloride, [(1S,3R)-3-Hydroxy-3-methyl-cyclopentyl]N-[8-amino-7-fluoro-6-(8-methyl-2,3-dihydro-1H-pyrido[2,3-b][1,4]oxazin-7-yl)-3-isoquinolyl]carbamate hydrochloride and [(1R,3S)-3-Hydroxy-3-methyl-cyclopentyl]N-[8-amino-7-fluoro-6-(8-methyl-2,3-dihydro-1H-pyrido[2,3-b][1,4]oxazin-7-yl)-3-isoquinolyl]carbamate hydrochloride (Compound 533a, Compound 533b, Compound 533c and Compound 533d)

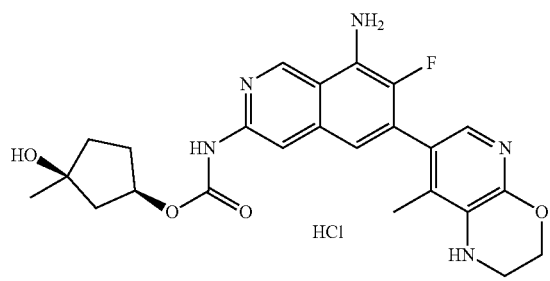

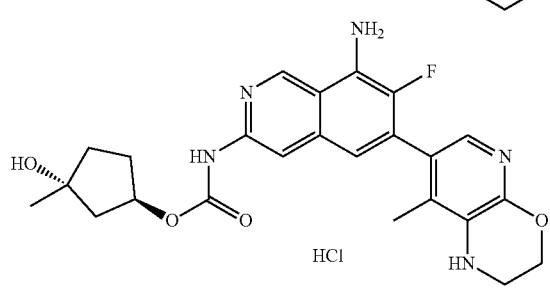

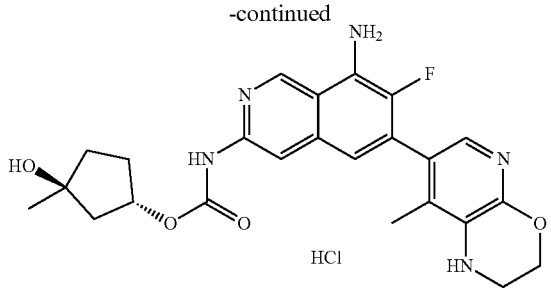

Step 1: 3-[tert-butyl(diphenyl)silyl]oxycyclopentanone

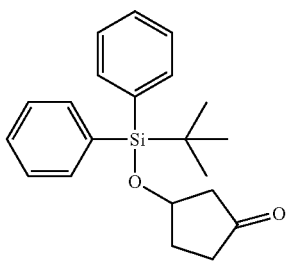 [SMILES: CC(C)(C)[Si](OC1CCC(=O)C1)(c1ccccc1)c1ccccc1]

To a solution of 3-hydroxycyclopentanone (1000.0 mg, 9.99 mmol) in dichloromethane (40 mL) was added tert-butyldiphenylchlorosilane (4110.0 mg, 14.95 mmol) and imidazole (2720.0 mg, 40 mmol). The mixture was stirred at 25° C. for 1 hour. The reaction mixture was concentrated under vacuum. The residue was purified by flash chromatography on silica gel eluting with petroleum ether/ethyl acetate (92/8) to afford 3-[tert-butyl(diphenyl)silyl]oxycyclopentanone (3350 mg, 9.89 mmol, 99% yield) as a clarity oil. LCMS (ESI) [M+H]$^+$=339.2.

Step 2: 3-[tert-Butyl(diphenyl)silyl]oxy-1-methyl-cyclopentanol

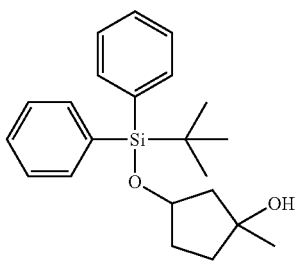 [SMILES: CC1(O)CCC(O[Si](c2ccccc2)(c2ccccc2)C(C)(C)C)C1]

Under nitrogen, to a solution of 3-[tert-butyl(diphenyl)silyl]oxycyclopentanone (3900.0 mg, 11.52 mmol) in tetrachloroethylene (50 mL) was added methyl magnesium chloride (15.4 mL, 46.2 mmol) at 0° C. The resulting solution was stirred for 1 hour at 25° C. The reaction was quenched with water and extracted with ethyl acetate. The organic layers were combined, dried over anhydrous sodium sulfate, filtered and concentrated under vacuum to afford 3-[tert-butyl(diphenyl)silyl]oxy-1-methyl-cyclopentanol (4000 mg, 11.28 mmol, 97% yield) as a clarity oil. LCMS (ESI) [M+H]$^+$=355.2

Step 3: (1S,3R)-1-Methylcyclopentane-1,3-diol and (1S,3S)-1-methylcyclopentane-1,3-diol

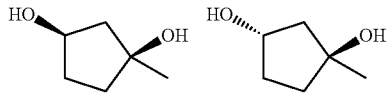

A solution of 3-[tert-butyl(diphenyl)silyl]oxy-1-methylcyclopentanol (4000.0 mg, 11.28 mmol) and TBAF (9000.0 mg, 28.57 mmol) in tetrahydrofuran (40 mL) was stirred at 25° C. for 1 hour. The reaction mixture was concentrated under vacuum. The residue was purified by flash chromatography on silica gel eluting with petroleum ether/ethyl acetate to afford (1S,3R)-1-methylcyclopentane-1,3-diol (500 mg, 4.30 mmol, 38% yield) as a yellow oil. $^1$H NMR (300 MHz, DMSO-$d_6$) δ 4.48 (d, J=5.0 Hz, 1H), 4.31 (s, 1H), 4.12-3.89 (m, 1H), 1.88-1.23 (m, 6H), 1.13 (s, 3H). And (1S,3S)-1-methylcyclopentane-1,3-diol (200 mg, 1.72 mmol, 15% yield) as a yellow oil. $^1$H NMR (400 MHz, DMSO-$d_6$) δ 4.38 (d, J=4.2 Hz, 1H), 4.29-4.16 (m, 1H), 4.14 (s, 1H), 1.98-1.81 (m, 2H), 1.72-1.34 (m, 4H), 1.24 (s, 3H).

Step 4: (+/−)-tert-Butyl 7-[8-(tert-butoxycarbonylamino)-7-fluoro-3-[[(1R,3S)-3-hydroxy-3-methyl-cyclopentoxy]carbonylamino]-6-isoquinolyl]-8-methyl-2,3-dihydropyrido[2,3-b][1,4]oxazine-1-carboxylate

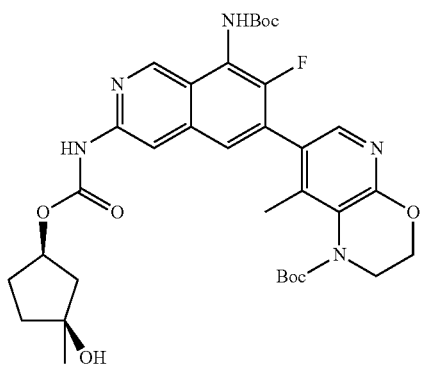 [SMILES: Cc1c(-c2cc3cc(NC(=O)O[C@@H]4CC[C@](C)(O)C4)ncc3c(NC(=O)OC(C)(C)C)c2F)cnc2c1N(C(=O)OC(C)(C)C)CCO2]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300.0 mg, 0.46 mmol) and DMAP (56.7 mg, 0.46 mmol) in 1,4-dioxane (10 mL) was added (1S,3R)-1-methylcyclopentane-1,3-diol (108.0 mg, 0.93 mmol) at 25° C. The resulting solution was stirred for 3 hours at 90° C. The mixture was concentrated under vacuum. The residue was purified by flash chromatography on silica gel eluting with dichloromethane/methanol (97/3) to afford tert-butyl 7-[8-(tert-butoxycarbonylamino)-7-fluoro-3-[[(1R,3S)-3-hydroxy-3-methyl-cyclopentoxy]carbonylamino]-6-isoquinolyl]-8-methyl-2,3-dihydropyrido[2,3-b][1,4]oxazine-1-carboxylate (300 mg, 0.45 mmol, 96% yield) as a pale yellow solid. LCMS (ESI) [M+H]$^+$=668.3.

(+/−)-tert-Butyl 7-[8-(tert-butoxycarbonylamino)-7-fluoro-3-[[(1S,3S)-3-hydroxy-3-methyl-cyclopentoxy]carbonylamino]-6-isoquinolyl]-8-methyl-2,3-dihydropyrido[2,3-b][1,4]oxazine-1-carboxylate

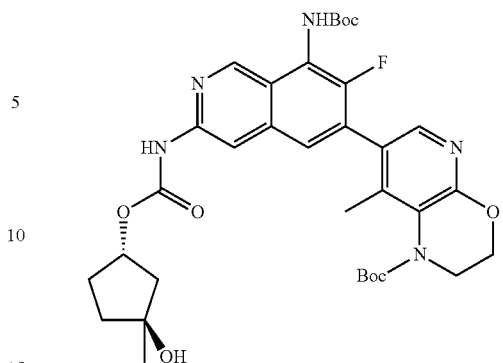

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300.0 mg, 0.46 mmol) and DMAP (56.7 mg, 0.46 mmol) in 1,4-dioxane (10 mL) was added (1S,3S)-1-methylcyclopentane-1,3-diol (108.0 mg, 0.93 mmol) at 25° C. The resulting solution was stirred for 3 hours at 90° C. The reaction mixture was concentrated under vacuum. The residue was purified by flash chromatography on silica gel eluting with dichloromethane/methanol (96/4) to afford tert-butyl 7-[8-(tert-butoxycarbonylamino)-7-fluoro-3-[[(1S,3S)-3-hydroxy-3-methyl-cyclopentoxy]carbonylamino]-6-isoquinolyl]-8-methyl-2,3-dihydropyrido[2,3-b][1,4]oxazine-1-carboxylate (200 mg, 0.299 mmol, 64% yield) as a pale yellow solid. LCMS (ESI) [M+H]$^+$=668.3.

Step 5: [(1R,3R)-3-Hydroxy-3-methyl-cyclopentyl] N-[8-amino-7-fluoro-6-(8-methyl-2,3-dihydro-1H-pyrido[2,3-b][1,4]oxazin-7-yl)-3-isoquinolyl]carbamate hydrochloride and [(1S,3S)-3-Hydroxy-3-methyl-cyclopentyl]N-[8-amino-7-fluoro-6-(8-methyl-2,3-dihydro-1H-pyrido[2,3-b][1,4]oxazin-7-yl)-3-isoquinolyl]carbamate hydrochloride

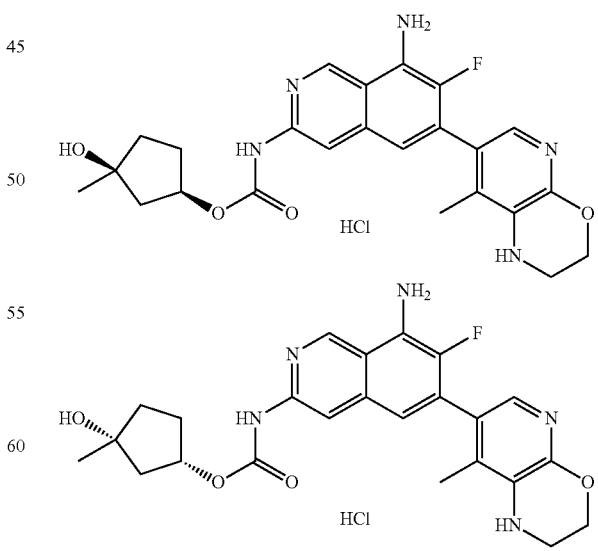

A solution of tert-butyl 7-[8-(tert-butoxycarbonylamino)-7-fluoro-3-[[(1R,3S)-3-hydroxy-3-methyl-cyclopentoxy]

carbonylamino]-6-isoquinolyl]-8-methyl-2,3-dihydropyrido[2,3-b][1,4]oxazine-1-carboxylate (295.0 mg, 0.44 mmol) and TFA (3.0 mL) in dichloromethane (9 mL) was stirred at 25° C. for 2 hours. After concentration, the residue was purified by Prep-HPLC (Column: X select CSH OBD Column 30*150 mm, 5 µm; Water (0.1% FA):CAN=9% B to 41% B in 7 min; 60 mL/min) to afford a racemate. The racemic product was separated by Chiral-HPLC to afford two enantiomers. Stereochemistry was arbitrarily assigned.

Enantiomer 1 (Compound 533a) (22.8 mg, 0.045 mmol, 10% yield). $R_T$ 2.162 min (CHIRALPAK IC-3 0.46*5 cm; 3 nm; MTBE (0.1% DEA):EtOH=70:30; 1.0 ml/min). LCMS (ESI) $[M+H]^+$=468.2, $R_T$ 2.019 min., Method J; $^1$H NMR (400 MHz, DMSO-$d_6$) δ 10.04 (s, 1H), 9.37 (s, 1H), 7.99 (s, 1H), 7.49 (s, 1H), 6.88 (d, J=6.1 Hz, 1H), 5.07-4.99 (m, 1H), 4.70-4.20 (m, 6H), 3.50-3.44 (m, 2H), 2.12-1.95 (m, 5H), 1.94-1.82 (m, 1H), 1.81-1.70 (m, 2H), 1.61-1.53 (m, 1H), 1.23 (s, 3H).

Enantiomer 2 (Compound 533b) (24.8 mg, 0.049 mmol, 11% yield). $R_T$ 3.594 min (CHIRALPAK IC-3 0.46*5 cm; 3 nm; MTBE (0.1% DEA):EtOH=70:30; 1.0 ml/min). LCMS (ESI) $[M+H]^+$=468.2, $R_T$ 2.019 min, Method J; $^1$H NMR (400 MHz, DMSO-$d_6$) δ 10.04 (s, 1H), 9.37 (s, 1H), 7.99 (s, 1H), 7.49 (s, 1H), 6.88 (d, J=6.1 Hz, 1H), 5.07-4.99 (m, 1H), 4.70-4.20 (m, 6H), 3.50-3.44 (m, 2H), 2.12-1.95 (m, 5H), 1.94-1.82 (m, 1H), 1.81-1.70 (m, 2H), 1.61-1.53 (m, 1H), 1.23 (s, 3H).

[(1S,3R)-3-Hydroxy-3-methyl-cyclopentyl]N-[8-amino-7-fluoro-6-(8-methyl-2,3-dihydro-1H-pyrido[2,3-b][1,4]oxazin-7-yl)-3-isoquinolyl]carbamate hydrochloride and [(1R,3S)-3-Hydroxy-3-methyl-cyclopentyl]N-[8-amino-7-fluoro-6-(8-methyl-2,3-dihydro-1H-pyrido[2,3-b][1,4]oxazin-7-yl)-3-isoquinolyl]carbamate hydrochloride

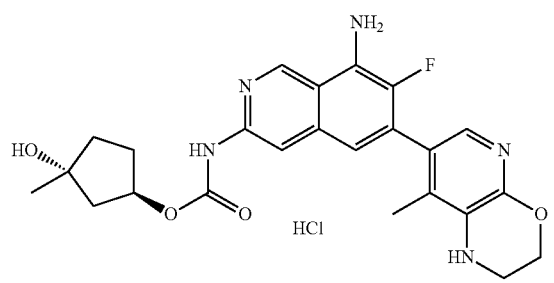

A solution of tert-butyl 7-[8-(tert-butoxycarbonylamino)-7-fluoro-3-[[(1S,3S)-3-hydroxy-3-methyl-cyclopentoxy]carbonylamino]-6-isoquinolyl]-8-methyl-2,3-dihydropyrido[2,3-b][1,4]oxazine-1-carboxylate (200.0 mg, 0.30 mmol) and TFA (3.0 mL) in dichloromethane (10 mL) was stirred at 25° C. for 2 hours. After concentration, the residue was purified by Prep-HPLC (Column: X Bridge Prep OBD C18 Column, 30×150 mm, 5 nm; Water (10 mmol/L NH$_4$HCO$_3$):ACN=18% B to 35% B in 7 min; 60 mL/min) to afford a racemate. The racemic product was separated by chiral-HPLC (Column: CHIRALPAK ID-03, 2.0 cm I.D*25 cm L (5 nm); MTBE (10 M NH$_3$-MEOH):IPA=30% B to 30% B in 20 min; Flow rate 15 mL/min) to afford two enantiomers. Stereochemistry was arbitrarily assigned.

Enantiomer 3 (Compound 533c) (21.5 mg, 0.042 mmol, 14% yield). $R_T$ 2.380 min (CHIRALPAK ID-3 Size: 0.46*5 cm; 3 nm; MTBE (0.1% DEA):IPA=70:30; 1.0 ml/min). LCMS (ESI) $[M+H]^+$=468.2, $R_T$ 2.077 min; Method K; $^1$H NMR (300 MHz, DMSO-$d_6$) δ 10.00 (s, 1H), 9.35 (s, 1H), 7.98 (s, 1H), 7.44 (s, 1H), 6.87 (d, J=6.1 Hz, 1H), 5.25-5.10 (m, 1H), 4.41-4.38 (m, 2H), 4.20-3.61 (m, 4H), 3.43-3.30 (m, 2H), 2.39-2.14 (m, 2H), 1.97 (s, 3H), 1.78-1.49 (m, 4H), 1.31 (s, 3H).

Enantiomer 4 (Compound 533d) (13.3 mg, 0.026 mmol, 9% yield). $R_T$ 3.737 min (CHIRALPAK ID-3 Size: 0.46*5 cm; 3 µm; MTBE (0.1% DEA):IPA=70:30; 1.0 ml/min). LCMS (ESI): $[M+H]^+$=468.2, $R_T$ 2.077 min., Method K; $^1$H NMR (300 MHz, DMSO-$d_6$) δ 10.00 (s, 1H), 9.35 (s, 1H), 7.98 (s, 1H), 7.44 (s, 1H), 6.87 (d, J=6.1 Hz, 1H), 5.25-5.10 (m, 1H), 4.41-4.38 (m, 2H), 4.20-3.61 (m, 4H), 3.43-3.30 (m, 2H), 2.39-2.14 (m, 2H), 1.97 (s, 3H), 1.78-1.49 (m, 4H), 1.31 (s, 3H).

Example 220

(1s,3s)-3-Cyanocyclobutyl (8-amino-6-(5-amino-4-methylpyridin-3-yl)-7-fluoroisoquinolin-3-yl)carbamate (Compound 534a)

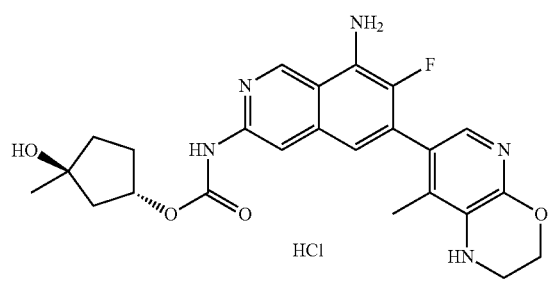

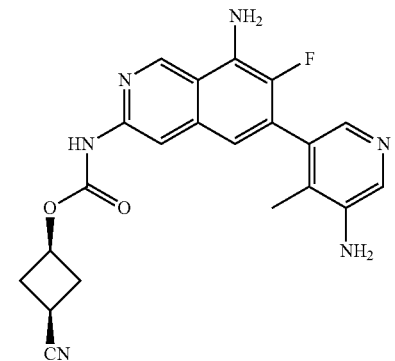 [SMILES: Cc1c(N)cncc1-c1cc2cc(NC(=O)O[C@H]3C[C@@H](C#N)C3)ncc2c(N)c1F]

Step 1: tert-Butyl N-tert-butoxycarbonyl-N-[5-[8-(tert-butoxycarbonylamino)-3-[(3-cyanocyclobutoxy)carbonylamino]-7-fluoro-6-isoquinolyl]-4-methyl-3-pyridyl]carbamate

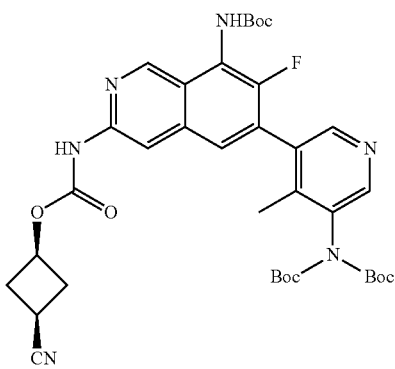 [SMILES: Cc1c(-c2cc3cc(NC(=O)O[C@H]4C[C@@H](C#N)C4)ncc3c(NC(=O)OC(C)(C)C)c2F)cncc1N(C(=O)OC(C)(C)C)C(=O)OC(C)(C)C]

To a solution of tert-butyl N-[5-[3-amino-8-(tert-butoxycarbonylamino)-7-fluoro-6-isoquinolyl]-4-methyl-3-pyridyl]-N-tert-butoxycarbonyl-carbamate (196.5 mg, 0.33 mmol), 3-hydroxycyclobutanecarbonitrile (163.5 mg, 1.68 mmol) and DIEA (435.1 mg, 3.36 mmol) in dichloromethane (10 mL) was added triphosgene (99.9 mg, 0.33 mmol). The mixture was stirred at 0° C. for 1 hour. The reaction was quenched with water and extracted with dichloromethane. The organic layers were combined, dried over anhydrous sodium sulfate, filtered and concentrated under vacuum. The residue was purified by flash chromatography on silica gel eluting with dichloromethane/methanol (97/3) to afford tert-butyl N-tert-butoxycarbonyl-N-[5-[8-(tert-butoxycarbonylamino)-3-[(3-cyanocyclobutoxy)carbonylamino]-7-fluoro-6-isoquinolyl]-4-methyl-3-pyridyl]carbamate (200 mg, 0.28 mmol, 84.1% yield) as a yellow oil. LCMS (ESI) [M+H]$^+$=707.4.

Step 2: (1s,3s)-3-Cyanocyclobutyl (8-amino-6-(5-amino-4-methylpyridin-3-yl)-7-fluoroisoquinolin-3-yl)carbamate

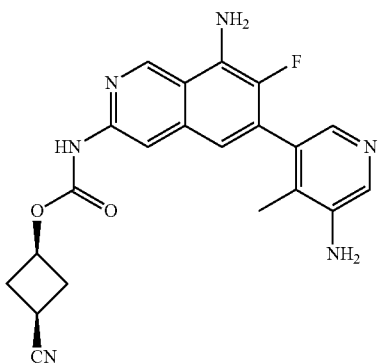 [SMILES: Cc1c(N)cncc1-c1cc2cc(NC(=O)O[C@H]3C[C@@H](C#N)C3)ncc2c(N)c1F]

To a solution of tert-butyl N-[5-[(Z)-3-(tert-butoxycarbonylamino)-3-[6-[(3-cyanocyclobutoxy)carbonylamino]-4-methyl-3-pyridyl]-2-fluoro-allyl]-4-methyl-3-pyridyl]-N-(hydroxymethyl)carbamate; isobutane (250.0 mg, 0.36 mmol) in dichloromethane (4 mL) was added TFA (4 mL, 0.36 mmol). The mixture was stirred at room temperature for 2 hours and concentrated under vacuum. The residue was re-dissolved in dichloromethane and adjusted to pH 8 with TEA. The mixture was concentrated under vacuum and purified by prep-HPLC (Column: X select CSH OBD Column 30*150 mm, 5 μm; Mobile Phase A: Water (0.1% FA), Mobile Phase B: ACN; Flow rate: 60 mL/min; Gradient: 7% B to 35% B in 7 min) to afford (3-cyanocyclobutyl) N-[8-amino-6-(5-amino-4-methyl-3-pyridyl)-7-fluoro-3-isoquinolyl]carbamate (26.1 mg, 0.064 mmol, 18% yield) as a light yellow solid. LCMS (ESI) [M+H]$^+$=407.1, R$_T$ 1.942 min., Method K; $^1$H NMR (300 MHz, DMSO-d$_6$) δ 10.23 (s, 1H), 9.37 (s, 1H), 7.99 (d, J=11.3 Hz, 2H), 7.73 (s, 1H), 6.89 (d, J=6.1 Hz, 1H), 6.28 (s, 2H), 5.44 (s, 2H), 4.95 (m, 1H), 3.12 (m, 1H), 2.90-2.73 (m, 2H), 2.40 (m, 2H), 1.95 (d, J=1.5 Hz, 3H).

Example 221

(1S,2S)-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate hydrochloride and (1R,2R)-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate hydrochloride (Compound 542c and Compound 542d)

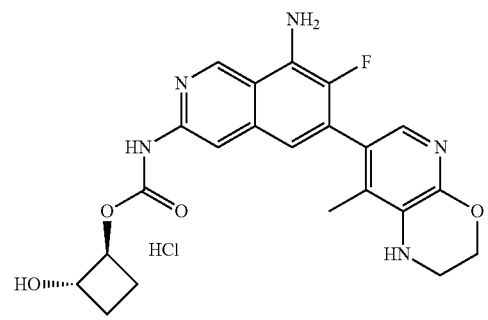

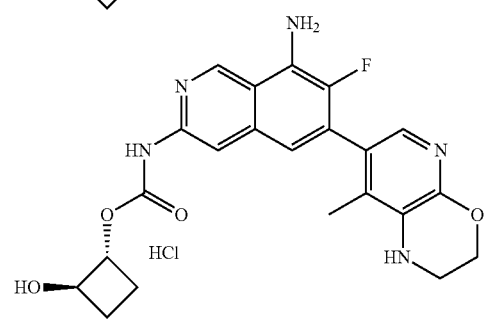

Step 1: trans-2-(Benzyloxylcyclobutan-1-ol

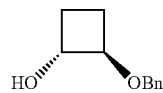

A mixture of benzyl alcohol (3850 mg, 35.65 mmol) and sodium (250.0 mg, 10.87 mmol) was stirred at 90° C. for 0.5 hour. 5-oxabicyclo[2.1.0]pentane (250.0 mg, 3.57 mmol) was added and the mixture was stirred at 90° C. for 12 hours.

The reaction was quenched by acetic acid. After filtration and concentrated under vacuum, the crude was purified by reverse phase flash chromatography eluted by 60% of water (0.01% NH$_4$HCO$_3$) and 40% of ACN to afford trans-2-benzyloxycyclobutanol (280 mg, 1.571 mmol, 44% yield) as a yellow oil.

Step 2: trans-cyclobutane-1,2-diol

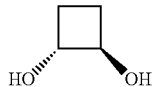

A mixture of trans-2-benzyloxycyclobutanol (300.0 mg, 1.68 mmol) and Pd/C (10 wt %, 150 mg) in methyl alcohol (5 mL) was stirred under hydrogen at 40° C. for 8 hours. The mixture was then filtered and concentrated to afforded trans-cyclobutane-1,2-diol (234 mg, 2.65 mmol) as colorless oil. $^1$H NMR (300 MHz, CDCl$_3$) δ 4.00 (t, J=6.3 Hz, 1H), 3.51 (s, 1H), 2.08 (q, J=6.2 Hz, 3H), 1.56-1.19 (m, 1H).

Step 3: tert-Butyl 7-(8-((tert-butoxycarbonyl)amino)-7-fluoro-3-(((((1S,2S)-2-hydroxycyclobutoxy)carbonyl)amino)isoquinolin-6-yl)-8-methyl-2,3-dihydro-1H-pyrido[2,3-b][1,4]oxazine-1-carboxylate

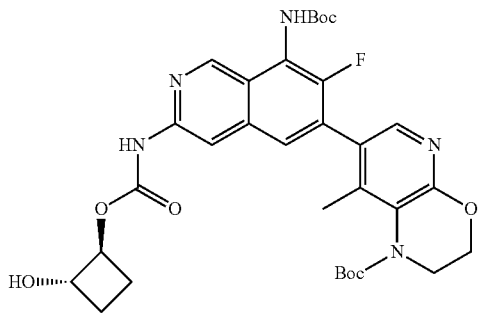

To a mixture of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (234.0 mg, 0.36 mmol) and trans-cyclobutane-1,2-diol (160.0 mg, 1.82 mmol) in dichloromethane (10 mL) was added DMAP (44.0 mg, 0.36 mmol). The mixture was stirred at 60° C. for 12 hours. After concentration, the residue was purified by flash chromatography on silica gel eluting with dichloromethane/methanol (95/5) to afford tert-butyl 7-[8-(tert-butoxycarbonylamino)-7-fluoro-3-[[(1S,2S)-2-hydroxycyclobutoxy]carbonylamino]-6-isoquinolyl]-8-methyl-2,3-dihydropyrido[2,3-b][1,4]oxazine-1-carboxylate (140 mg, 0.2189 mmol, 60.4% yield) as a yellow solid. LCMS (ESI) [M+H]$^+$=640.

Step 4: (1S,2S)-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate hydrochloride and (1R,2R)-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate hydrochloride

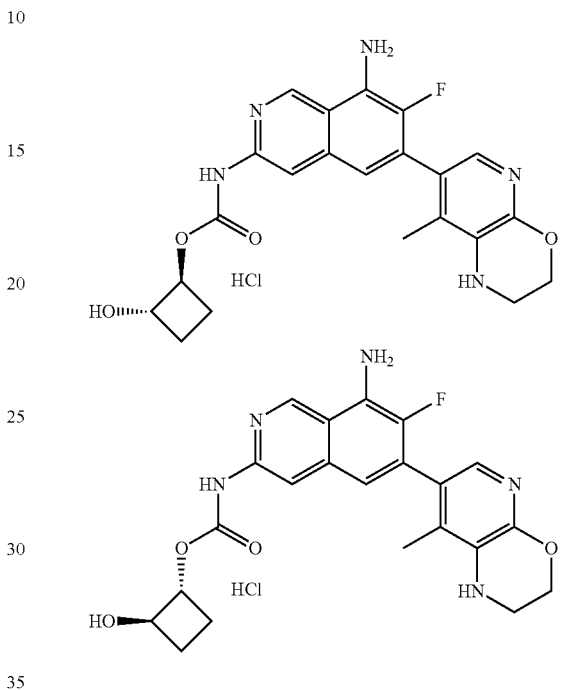

To a solution of tert-butyl 7-[8-(tert-butoxycarbonylamino)-7-fluoro-3-[(2-hydroxycyclobutoxy)carbonylamino]-6-isoquinolyl]-8-methyl-2,3-dihydropyrido[2,3-b][1,4]oxazine-1-carboxylate (160.0 mg, 0.25 mmol) in dichloromethane (5 mL) was added TFA (1 mL). The mixture was stirred at room temperature for 2 hours. After concentration, the residue was purified by HPLC (X select CSH OBD Column 30*150 mm, 5 μm, 19*150 mm; Mobile Phase A: Water (10 mmol/L NH$_4$HCO$_3$), Mobile Phase B: ACN; Flow rate: 25 mL/min; Gradient: 20% B to 40% B in 7 min) to afford a racemic product. The racemate was separated by chiral HPLC to afford two enantiomers. Relative stereochemistry are as drawn. Absolute stereochemistry was arbitrarily assigned.

Enantiomer 1: Compound 542c (25.7 mg, 0.0540 mmol, 21.6% yield). R$_T$ 0.975 min (CHIRALPAK IC-3 0.46*5 cm; 3 μm; MTBE (0.1% DEA):MeOH=50:50). LCMS (ESI) [M+H]$^+$=440.2, R$_T$ 1.819 min; Method J. $^1$H NMR (300 MHz, DMSO-d$_6$) δ 10.15 (s, 1H), 9.36 (s, 1H), 7.97 (s, 1H), 7.48 (s, 1H), 6.88 (d, J=6.1 Hz, 1H), 4.70 (d, J=7.8 Hz, 1H), 4.42 (s, 2H), 3.99 (q, J=7.9 Hz, 1H), 3.43 (s, 2H), 2.08-1.94 (m, 5H), 1.38-1.21 (m, 2H).

Enantiomer 2: Compound 542d (27.2 mg, 0.0572 mmol, 22.9% yield). R$_T$ 2.281 min (CHIRALPAK IC-3 0.46*5 cm; 3 μm; MTBE (0.1% DEA):MeOH=50:50). LCMS (ESI) [M+H]$^+$=440.2, R$_T$ 1.819 min; Method J. $^1$H NMR (300 MHz, DMSO-d$_6$) δ 10.15 (s, 1H), 9.36 (s, 1H), 7.97 (s, 1H), 7.48 (s, 1H), 6.88 (d, J=6.1 Hz, 1H), 4.70 (d, J=7.8 Hz, 1H), 4.42 (s, 2H), 3.99 (q, J=7.9 Hz, 1H), 3.43 (s, 2H), 2.08-1.94 (m, 5H), 1.38-1.21 (m, 2H).

Example 222

(1S,2R)-2-Cyanocyclobutyl (8-amino-7-fluoro-6-(8-methyl-2,3-dihydro-1H-pyrido[2,3-b][1,4]oxazin-7-yl)isoquinolin-3-yl)carbamate and (1R,2S)-2-Cyanocyclobutyl (8-amino-7-fluoro-6-(8-methyl-2,3-dihydro-1H-pyrido[2,3-b][1,4]oxazin-7-yl)isoquinolin-3-yl)carbamate (Compound 535a and Compound 535b)

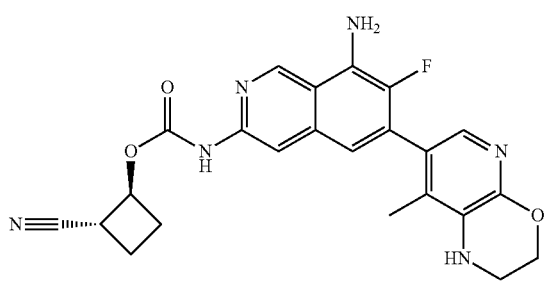

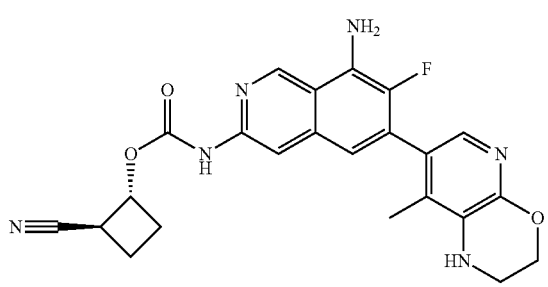

Step 1: trans-2-Hydroxycyclobutane-1-carbonitrile

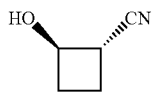

A solution of diethylaluminum cyanide (5.7 mL, 2.85 mmol) and 5-oxabicyclo[2.1.0]pentane (200.0 mg, 2.85 mmol) in toluene (8 mL) was stirred at 25° C. for 6 hours. The reaction mixture was quenched with aq. NaHCO₃ and extracted with ethyl acetate. The organic layer was concentrated under vacuum. The residue was purified by flash chromatography on silica gel eluting with petroleum ether/ethyl acetate (0% to 100%). The product was used directly to the next step. $^1$H NMR (300 MHz, DMSO-$d_6$) δ 5.93 (d, J=9.0 Hz, 1H), 4.25-4.09 (m, 1H), 2.99-2.84 (m, 1H), 2.18-2.03 (m, 1H), 2.02-1.84 (m, 1H), 1.87-1.71 (m, 1H), 1.71-1.52 (m, 1H).

Step 2: tert-Butyl 7-(8-((tert-butoxycarbonyl)amino)-3-((((1S,2R)-2-cyanocyclobutoxy)carbonyl)amino)-7-fluoroisoquinolin-6-yl)-8-methyl-2,3-dihydro-1H-pyrido[2,3-b][1,4]oxazine-1-carboxylate

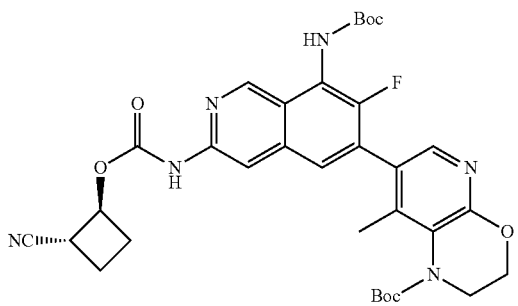 [SMILES: Cc1c(-c2cc3cc(NC(=O)O[C@H]4CC[C@@H]4C#N)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (464.0 mg, 0.88 mmol), trans-2-hydroxycyclobutanecarbonitrile (171.0 mg, 1.76 mmol) and DIEA (569.0 mg, 4.41 mmol) in dichloromethane (10 mL) was added triphosgene (175 mg, 0.59 mmol) at 0° C. The mixture was stirred at 25° C. for 1 hour. The reaction was quenched with water and extracted with dichloromethane. The organic layer was concentrated under vacuum. The residue was purified by flash chromatography on silica gel eluting with dichloromethane/methanol (95/5) to afford tert-butyl 7-[8-(tert-butoxycarbonylamino)-3-[[(trans)-2-cyanocyclobutoxy]carbonylamino]-7-fluoro-6-isoquinolyl]-8-methyl-2,3-dihydropyrido[2,3-b][1,4]oxazine-1-carboxylate (366 mg, 0.56 mmol, 64% yield) as a brown solid. LCMS (ESI) [M+H]$^+$=649.

Step 3: (1S,2R)-2-Cyanocyclobutyl (8-amino-7-fluoro-6-(8-methyl-2,3-dihydro-1H-pyrido[2,3-b][1,4]oxazin-7-yl)isoquinolin-3-yl)carbamate and (1R,2S)-2-Cyanocyclobutyl (8-amino-7-fluoro-6-(8-methyl-2,3-dihydro-1H-pyrido[2,3-b][1,4]oxazin-7-yl)isoquinolin-3-yl)carbamate

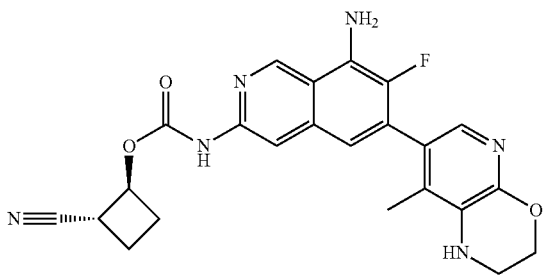

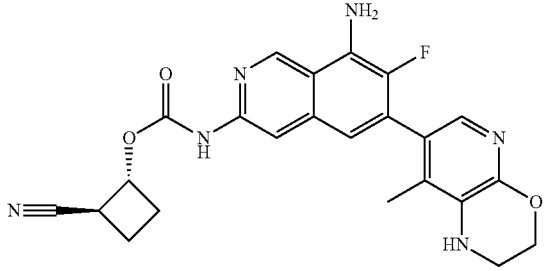

A solution of tert-butyl 7-[8-(tert-butoxycarbonylamino)-3-[[(1S,2R)-2-cyanocyclobutoxy]carbonylamino]-7-fluoro-6-isoquinolyl]-8-methyl-2,3-dihydropyrido[2,3-b][1,4]oxazine-1-carboxylate (356.0 mg, 0.44 mmol) in dichloromethane (2 mL) and TFA (1.5 mL) was stirred at 25° C. for 1 hour. The reaction mixture was adjusted to pH 8 with triethylamine and concentrated under vacuum. The crude product was purified by Prep-HPLC (Column: X select CSH OBD Column 30*150 mm, 5 µm; Water (0.1% FA):ACN=10% B to 35% B in 10 min; 60 mL/min) to afford a racemic product. The racemic product was separated by chiral Prep-HPLC to give two enantiomers. Relative stereochemistry as drawn. Absolute stereochemistry arbitrarily assigned.

Enantiomer 1: Compound 535a (8.9 mg, 0.02 mmol, 5% yield). $R_T$ 1.604 min (CHIRALPAK IG-3 0.46*5 cm; 3 µm. MTBE:EtOH=70:30, 1 ml/min). LCMS (ESI) [M+H]$^+$=449, $R_T$ 2.035 min; Method K. $^1$H NMR (300 MHz, DMSO-d$_6$) δ 10.27 (s, 1H), 9.33 (s, 1H), 7.95 (s, 1H), 7.31 (s, 1H), 6.87 (d, J=6.2 Hz, 1H), 6.20 (s, 2H), 5.65 (s, 1H), 5.22-5.13 (m, 1H), 4.35-4.27 (m, 2H), 3.52-3.41 (m, 3H), 2.41-2.10 (m, 3H), 2.02-1.87 (m, 4H).

Enantiomer 2: Compound 533b (9.1 mg, 0.020 mmol, 5% yield). $R_T$ 2.656 min (CHIRALPAK IG-3 0.46*5 cm; 3 µm. MTBE:EtOH=70:30, 1 ml/min). LCMS (ESI) [M+H]$^+$=449, $R_T$ 2.035 min; Method K. $^1$H NMR (300 MHz, DMSO-d$_6$) δ 10.27 (s, 1H), 9.33 (s, 1H), 7.95 (s, 1H), 7.31 (s, 1H), 6.87 (d, J=6.2 Hz, 1H), 6.20 (s, 2H), 5.65 (s, 1H), 5.22-5.13 (m, 1H), 4.35-4.27 (m, 2H), 3.52-3.41 (m, 3H), 2.41-2.10 (m, 3H), 2.02-1.87 (m, 4H).

Example 223

(1r,3s)-3-(Cyanomethyl)cyclobutyl (8-amino-7-fluoro-6-(8-methyl-2,3-dihydro-1H-pyrido[2,3-b][1,4]oxazin-7-yl)isoquinolin-3-yl)carbamate and (1s,3r)-3-(Cyanomethyl)cyclobutyl (8-amino-7-fluoro-6-(8-methyl-2,3-dihydro-1H-pyrido[2,3-b][1,4]oxazin-7-yl)isoquinolin-3-yl)carbamate (Compound 536a and Compound 536b)

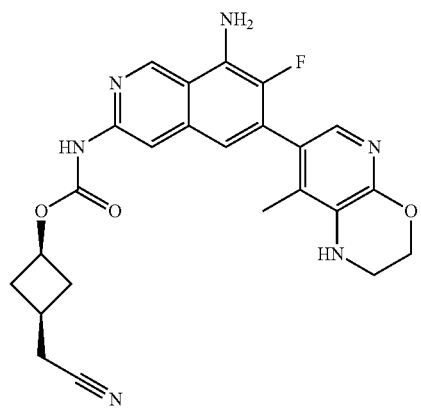

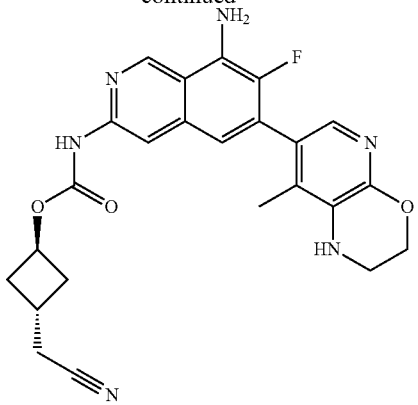

-continued

Step 1: Ethyl 3-[tert-butyl(diphenyl)silyl]oxycyclobutanecarboxylate

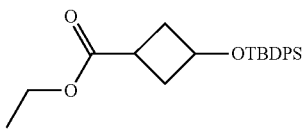

A solution of ethyl 3-hydroxycyclobutanecarboxylate (10 g, 69.36 mmol) and imidazole (4.8 g, 70.51 mmol) in dichloromethane (300 mL) was added tert-butylchlorodiphenylsilane (21.0 g, 76.64 mmol) at room temperature. The resulting solution was stirred for 2 h at 25° C. The reaction was quenched by methanol and then concentrated under vacuum. The residue was purified by flash chromatography on silica gel eluting with petroleum ether/ethyl acetate (10/1) to afford ethyl 3-[tert-butyl(diphenyl)silyl]oxycyclobutanecarboxylate (25 g, 65.348 mmol, 94.2% yield) as a colorless oil. LCMS (ESI) [M+H]$^+$=383.

Step 2: [3-[tert-Butyl(diphenyl)silyl]oxycyclobutyl]methanol

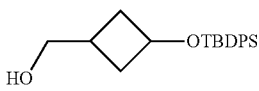

To a solution of ethyl 3-[tert-butyl(diphenyl)silyl]oxycyclobutanecarboxylate (5.0 g, 13.07 mmol) in diphenyl ether (300 mL) was added LiAlH$_4$ (13 mL, 13.07 mmol, 1 mol/L) at 0° C. The resulting mixture was stirred for 2 h at 0° C. The reaction was quenched by water, extracted with ethyl acetate, filtrated and concentrated under vacuum. The residue was purified by flash chromatography on silica gel eluting with petroleum ether/ethyl acetate (1/1) to afford [3-[tert-butyl(diphenyl)silyl]oxycyclobutyl]methanol (1.1 g, 3.23 mmol, 24.7% yield) as a colorless oil. LCMS (ESI) [M+H]$^+$=341.

Step 3: [3-[tert-butyl(diphenyl)silyl]oxycyclobutyl]methyl methanesulfonate

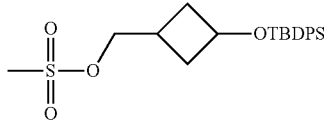

To a solution of [3-[tert-butyl(diphenyl)silyl]oxycyclobutyl]methanol (5.0 g, 14.68 mmol) and TEA (5.0 g, 49.5 mmol) in dichloromethane (300 mL) was added methanesulfonyl chloride (5.0 g, 43.86 mmol) at 0° C. The reaction was stirred for 2 h at 0° C. and then quenched by water. The resulting solution was extracted with ethyl acetate and concentrated under vacuum. The residue was purified by flash chromatography on silica gel eluting with petroleum ether/ethyl acetate (10/1) to afford [3-[tert-butyl(diphenyl)silyl]oxycyclobutyl]methyl methanesulfonate (5.3 g, 12.661 mmol, 86.2% yield) as a colorless solid. LCMS (ESI) [M+H]$^+$=419.

Step 4: 2-[3-[tert-Butyl(diphenyl)silyl]oxycyclobutyl]acetonitrile

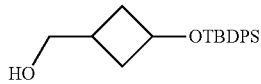

To a solution of [3-[tert-butyl(diphenyl)silyl]oxycyclobutyl]methyl methanesulfonate (5.3 g, 12.66 mmol) in DMSO (50 mL) was added KCN (2.65 g, 40.77 mmol) at room temperature. The resulting solution was stirred for 2 h at 110° C. The reaction was quenched by water and then extracted with ethyl acetate. The organic layers were dried, filtrated and concentrated under vacuum. The residue was purified by flash chromatography on silica gel eluting with petroleum ether/ethyl acetate (5/1) to afford 2-[3-[tert-butyl(diphenyl)silyl]oxycyclobutyl]acetonitrile (4 g, 11.444 mmol, 90.4% yield) as a colorless oil. LCMS (ESI) [M+H]$^+$= 350.

Step 5: 2-(3-Hydroxycyclobutyl)acetonitrile

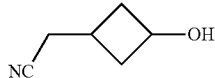

A solution of 2-[3-[tert-butyl(diphenyl)silyl]oxycyclobutyl]acetonitrile (2.0 g, 5.72 mmol) in tetrahydrofuran (5 mL) and TBAF (2.98 g, 11.44 mmol) was stirred for 16 h at 25° C. and then concentrated under vacuum. The residue was purified by flash chromatography on silica gel eluting with petroleum ether/ethyl acetate (1/1) to afford 2-(3-hydroxycyclobutyl)acetonitrile (200 mg, 1.799 mmol, 31.5% yield) as colorless oil. LCMS (ESI) [M+H]$^+$=112.

Step 6: tert-Butyl 7-[8-(tert-butoxycarbonylamino)-3-[[3-(cyanomethyl)cyclobutoxy]carbonylamino]-7-fluoro-6-isoquinolyl]-8-methyl-2,3-dihydropyrido[2,3-b][1,4]oxazine-1-carboxylate

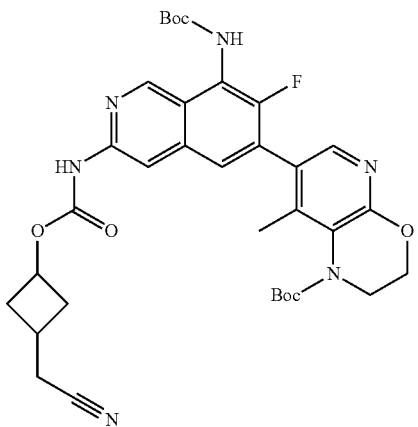 [SMILES: Cc1c(-c2cc3cc(NC(=O)OC4CC(CC#N)C4)ncc3c(NC(=O)OC(C)(C)C)c2F)cnc2c1N(C(=O)OC(C)(C)C)CCO2]

A solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (300 mg, 0.57 mmol) and 2-(3-hydroxycyclobutyl)acetonitrile (200 mg, 1.8 mmol) in dichloromethane (30 mL) was added DIEA (800 mg, 6.2 mmol) at room temperature. Then triphosgene (200 mg, 0.67 mmol) was added. The mixture was stirred at 0° C. for 1 hour. The residue was purified by flash chromatography on silica gel eluting with petroleum ether/ethyl acetate (1/2) to afford tert-butyl 7-[8-(tert-butoxycarbonylamino)-3-[[3-(cyanomethyl)cyclobutoxy]carbonylamino]-7-fluoro-6-isoquinolyl]-8-methyl-2,3-dihydropyrido[2,3-b][1,4]oxazine-1-carboxylate (250 mg, 0.3772 mmol, 66.1% yield) as a yellow solid. LCMS (ESI) [M+H]$^+$= 663.

Step 7: (1r,3s)-3-(Cyanomethyl)cyclobutyl (8-amino-7-fluoro-6-(8-methyl-2,3-dihydro-1H-pyrido[2,3-b][1,4]oxazin-7-yl)isoquinolin-3-yl)carbamate and (1s,3r)-3-(Cyanomethyl)cyclobutyl (8-amino-7-fluoro-6-(8-methyl-2,3-dihydro-1H-pyrido[2,3-b][1,4]oxazin-7-yl)isoquinolin-3-yl)carbamate

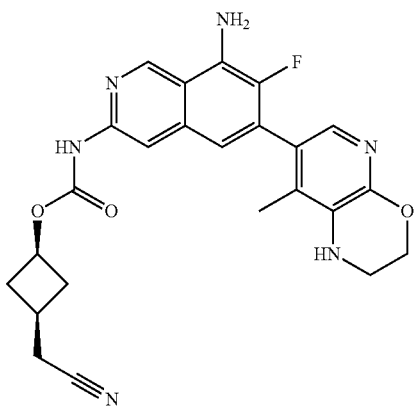

-continued

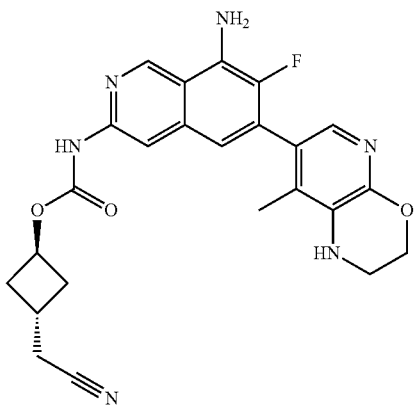

To a solution of tert-butyl 7-[8-(tert-butoxycarbonylamino)-3-[[3-(cyanomethyl)cyclobutoxy]carbonylamino]-7-fluoro-6-isoquinolyl]-8-methyl-2,3-dihydropyrido[2,3-b][1,4]oxazine-1-carboxylate (250 mg, 0.38 mmol) in dichloromethane (8 mL) was added TFA (2 mL) at room temperature. The resulting solution was stirred for 1 h and then concentrated under vacuum. The crude product was purified by Prep-HPLC (Column: X select CSH OBD Column 30*150 mm, 5 μm; Mobile Phase A: Water (0.1% FA), Mobile Phase B: ACN; Flow rate: 60 mL/min; Gradient: 12 B to 40 B in 9 min) to afford a racemic mixture. The racemate was separated by chiral-HPLC (Column (CHIRALPAK IA-3, 4.6*50 mm, 3 μm; Mobile Phase A: (Hex: DCM=3:1) (0.1% DEA): EtOH=50:50; Flow rate: 1 mL/min) to give two enantiomers. Stereochemistry was arbitrarily assigned.

Enantiomer 1 (Compound 536a) (23.4 mg, 0.0506 mmol, 13.4% yield). $R_T$ 3.696 min (CHIRALPAK IA-3, 0.46*5 cm, 3 μm; Hex:DCM=3:1)(0.1% DEA):EtOH=50:50 in 8 min; 1 mL/min). LCMS (ESI) [M+H]$^+$=463.2, $R_T$ 0.677 min., Method K; $^1$H NMR (400 MHz, DMSO-d$_6$) δ 10.10 (s, 1H), 9.33 (s, 1H), 7.95 (s, 1H), 7.32 (s, 1H), 6.83 (d, J=6.1 Hz, 1H), 6.20 (s, 2H), 5.66 (t, J=2.7 Hz, 1H), 5.15 (p, J=6.7 Hz, 1H), 4.28 (t, J=4.4 Hz, 2H), 3.41 (t, J=4.4 Hz, 2H), 2.75 (d, J=7.4 Hz, 2H), 2.63 (d, J=6.1 Hz, 1H), 2.38-2.16 (m, 4H), 1.92 (d, J=1.6 Hz, 3H).

Enantiomer 2 (Compound 536b) (60.7 mg, 0.1312 mmol, 34.8% yield). $R_T$ 4.659 min (CHIRALPAK IA-3, 46*5 cm, 3 μm; Hex:DCM=3:1)(0.1% DEA):EtOH=50:50 in 8 min; 1 mL/min). LCMS (ESI) [M+H]$^+$=463.2, $R_T$ 0.677 min, Method K; $^1$H NMR ((400 MHz, DMSO-d$_6$) δ 10.10 (s, 1H), 9.33 (s, 1H), 7.95 (s, 1H), 7.32 (s, 1H), 6.83 (d, J=6.1 Hz, 1H), 6.20 (s, 2H), 5.66 (t, J=2.7 Hz, 1H), 5.15 (p, J=6.7 Hz, 1H), 4.28 (t, J=4.4 Hz, 2H), 3.41 (t, J=4.4 Hz, 2H), 2.75 (d, J=7.4 Hz, 2H), 2.63 (d, J=6.1 Hz, 1H), 2.38-2.16 (m, 4H), 1.92 (d, J=1.6 Hz, 3H).

Example 224

(1s,3s)-3-Cyano-3-methylcyclobutyl (8-amino-7-fluoro-6-(8-methyl-2,3-dihydro-1H-pyrido[2,3-b][1,4]oxazin-7-yl)isoquinolin-3-yl)carbamate and (1r,3r)-3-Cyano-3-methylcyclobutyl (8-amino-7-fluoro-6-(8-methyl-2,3-dihydro-1H-pyrido[2,3-b][1,4]oxazin-7-yl)isoquinolin-3-yl)carbamate (Compound 537a and Compound 537b)

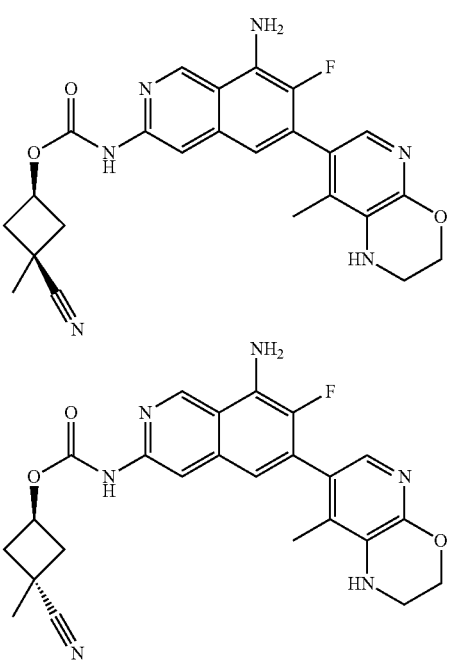

Step 1: 3-[tert-butyl(dimethyl)silyl]oxycyclobutanecarbonitrile

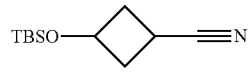

A solution of 3-hydroxycyclobutanecarbonitrile (800.0 mg, 8.24 mmol), 1H-imidazole (2.80 mg, 41.19 mmol) in dichloromethane (40 mL), and TBDMSCl (3.72 g, 24.71 mmol) was stirred for 4 hours at room temperature. The reaction mixture was concentrated under vacuum. The residue was purified by flash chromatography on silica gel eluting with petroleum ether/ethyl acetate (90/10) to afford 3-[tert-butyl(dimethyl)silyl]oxycyclobutanecarbonitrile (1.6 g, 7.57 mmol, 91.9% yield) as brown oil.

Step 2: 3-[tert-Butyl(dimethyl)silyl]oxy-1-methylcyclobutanecarbonitrile

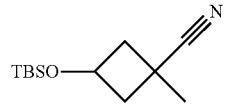

Under nitrogen, to a solution of 3-[tert-butyl(dimethyl)silyl]oxycyclobutanecarbonitrile (1.20 mg, 5.68 mmol) in tetrahydrofuran (30 mL) was added lithium diisopropylamide (1.8 g, 17.03 mmol). The mixture was stirred at −78° C. for 1 hour. Then iodomethane (1.61 g, 11.35 mmol) was added at −78° C. and the mixture was stirred for 2 hours at room temperature. The reaction was quenched with water and extracted with dichloromethane. The organic layers were combined and concentrated under vacuum. The residue was purified by flash chromatography on silica gel eluting with dichloromethane/methanol (10/1) to afford 3-[tert-butyl(dimethyl)silyl]oxy-1-methyl-cyclobutanecarbonitrile (600 mg, 2.66 mmol, 46.9% yield) as a yellow solid.

Step 3: 3-Hydroxy-1-methyl-cyclobutanecarbonitrile

To a solution of 3-[tert-butyl(dimethyl)silyl]oxy-1-methyl-cyclobutanecarbonitrile (1.0 g, 4.44 mmol) in tetrahydrofuran (20 mL) was added tetrabutylammonium fluoride trihydrate (2.80 g, 8.87 mmol). The mixture was stirred at room temperature for 2 hours. The reaction mixture was concentrated under vacuum. The residue was purified by flash chromatography on silica gel eluting with petroleum ether/ethyl acetate (10/1) to afford 3-hydroxy-1-methyl-cyclobutanecarbonitrile (770 mg, 6.93 mmol, 64.1% yield) as a yellow oil.

Step 4: tert-Butyl 7-[8-(tert-butoxycarbonylamino)-3-[(3-cyano-3-methyl-cyclobutoxy)carbonylamino]-7-fluoro-6-isoquinolyl]-8-methyl-2,3-dihydropyrido[2,3-b][1,4]oxazine-1-carboxylate

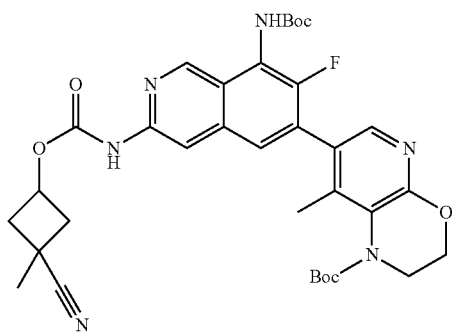 [SMILES: Cc1c(-c2cc3cc(NC(=O)OC4CC(C)(C#N)C4)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (600.0 mg, 1.14 mmol), 3-hydroxy-1-methyl-cyclobutanecarbonitrile (253.8 mg, 2.28 mmol) and N,N-diisopropylethylamine (737.7 mg, 5.71 mmol) in dichloromethane (12 mL) was added triphosgene (338.8 mg, 1.14 mmol). The mixture was stirred at 0° C. for 2 hours. The reaction was quenched with water and extracted with dichloromethane. The organic layers were combined and concentrated under vacuum. The residue was purified by reverse phase chromatography (acetonitrile 0-60/0.1% NH$_4$HCO$_3$ in water) to afford tert-butyl 7-[8-(tert-butoxycarbonylamino)-3-[(3-cyano-3-methyl-cyclobutoxy)carbonylamino]-7-fluoro-6-isoquinolyl]-8-methyl-2,3-dihydropyrido[2,3-b][1,4]oxazine-1-carboxylate (600 mg, 0.91 mmol, 79.3% yield) as a yellow solid. LCMS (ESI) [M+H]$^+$=663.3.

Step 5: (1s,3s)-3-Cyano-3-methylcyclobutyl (8-amino-7-fluoro-6-(8-methyl-2,3-dihydro-1H-pyrido[2,3-b][1,4]oxazin-7-yl)isoquinolin-3-yl)carbamate and (1r,3r)-3-Cyano-3-methylcyclobutyl (8-amino-7-fluoro-6-(8-methyl-2,3-dihydro-1H-pyrido[2,3-b][1,4]oxazin-7-yl)isoquinolin-3-yl)carbamate

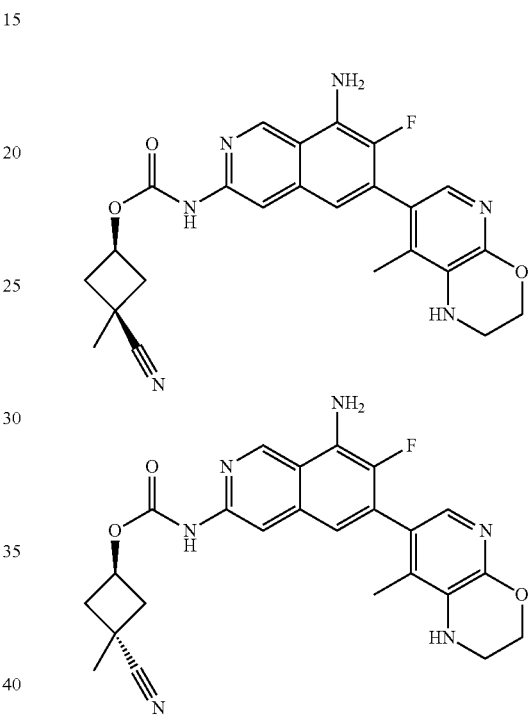

To a solution of tert-butyl 7-[8-(tert-butoxycarbonylamino)-3-[(3-cyano-3-methyl-cyclobutoxy)carbonylamino]-7-fluoro-6-isoquinolyl]-8-methyl-2,3-dihydropyrido[2,3-b][1,4]oxazine-1-carboxylate (590.0 mg, 0.89 mmol) in dichloromethane (14 mL) was added trifluoroacetic acid (7.0 mL). The mixture was stirred at RT for 2 hours. The reaction was quenched with water and extracted with dichloromethane. The organic layers were combined and concentrated under vacuum. The residue was purified by Prep-HPLC (Column: CHIRALPAK IA, 2*25 cm, 5 μm; Mobile Phase A: MTBE, Mobile Phase B: EtOH; Flow rate: 16 mL/min; Gradient: 50 B to 50 B in 16 min) to afford a racemic mixture. The mixture was further separated by chiral Prep-HPLC to afford two isomers. Stereochemistry was arbitrarily assigned.

Isomer 1: Compound 537a (43.5 mg, 0.094 mmol, 10.6% yield). $R_T$ 1.187 min (CHIRALPAK IA-3 0.46*5 cm; 3 μm. Mobile phase: MTBE:EtOH=50:50, 1 ml/min). [M+H]$^+$= 463.1, $R_T$ 2.176 min, Method K; $^1$H NMR (300 MHz, DMSO-d$_6$) δ 10.21 (s, 1H), 9.35 (s, 1H), 7.96 (s, 1H), 7.33 (s, 1H), 6.85 (d, J=6.2 Hz, 1H), 6.22 (s, 2H), 5.69 (s, 1H), 5.08 (p, J=7.2 Hz, 1H), 4.30 (t, J=4.4 Hz, 2H), 3.35 (s, 2H), 3.00-2.87 (m, 2H), 2.33-2.20 (m, 2H), 1.92 (d, J=1.6 Hz, 3H), 1.55 (s, 3H).

Isomer 2: Compound 537b (36.6 mg, 0.080 mmol, 8.9% yield). $R_T$ 1.874 min (CHIRALPAK IA-3 0.46*5 cm; 3 μm. Mobile phase: MTBE:EtOH=50:50, 1 ml/min). [M+H]$^+$= 463.1, $R_T$ 2.176 min., Method K; $^1$H NMR (300 MHz, DMSO-$d_6$) δ 10.21 (s, 1H), 9.35 (s, 1H), 7.96 (s, 1H), 7.33 (s, 1H), 6.85 (d, J=6.2 Hz, 1H), 6.22 (s, 2H), 5.69 (s, 1H), 5.08 (p, J=7.2 Hz, 1H), 4.30 (t, J=4.4 Hz, 2H), 3.35 (s, 2H), 3.00-2.87 (m, 2H), 2.33-2.20 (m, 2H), 1.92 (d, J=1.6 Hz, 3H), 1.55 (s, 3H).

Example 225

(3S,4R)-4-Cyanotetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3R,4S)-4-Cyanotetrahydrofuran-3-yl (8-amino-7-fluoro-6-(8-methyl-2,3-dihydro-1H-pyrido[2,3-b][1,4]oxazin-7-yl)isoquinolin-3-yl)carbamate (Compound 538a and Compound 538b)

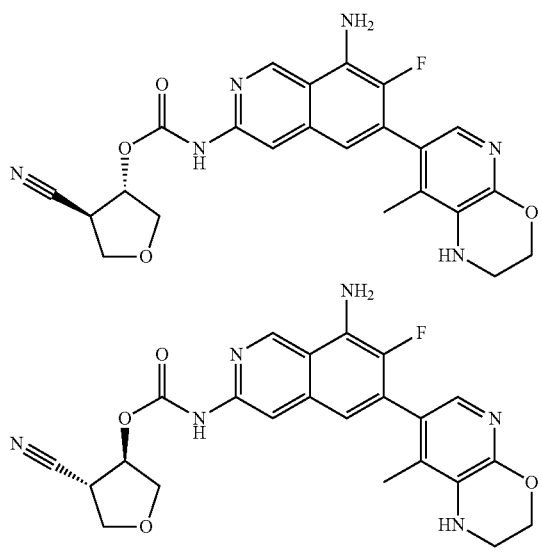

Step 1:
trans-4-hydroxytetrahydrofuran-3-carbonitrile

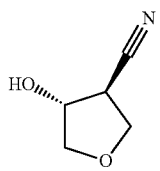

A solution of diethylaluminum cyanide (2.58 g, 23.24 mmol) in toluene was added slowly to a solution of 3,4-epoxytetrahydrofuran (1.0 g, 11.62 mmol) in toluene (40 mL) at room temperature. After stirring overnight, the reaction mixture was quenched carefully (caution: exothermic) by a slow addition of 1.0 N NaOH solution and then diluted with water. The aqueous mixture was extracted with ethyl acetate. The combined organics were washed with water and brine, dried (MgSO$_4$), filtered and concentrated under reduced pressure. The residue was purified by flash chromatography on silica gel eluting with petroleum ether/ethyl acetate (1/1) to afford trans-4-hydroxytetrahydrofuran-3-carbonitrile (1 g, 8.841 mmol, 76.1% yield) as colorless oil. $^1$H NMR (400 MHz, DMSO-$d_6$) δ 5.80-5.76 (m, 1H), 4.53-4.49 (m, 1H), 4.01-3.97 (m, 1H), 3.94-3.91 (m, 1H), 3.87-3.83 (m, 1H), 3.52-3.49 (m, 1H), 3.15-3.14 (m, 1H).

Step 2: (±)-trans-tert-Butyl 7-(8-((tert-butoxycarbonyl)amino)-3-((((4-cyanotetrahydrofuran-3-yl)oxy)carbonyl)amino)-7-fluoroisoquinolin-6-yl)-8-methyl-2,3-dihydro-1H-pyrido[2,3-b][1,4]oxazine-1-carboxylate

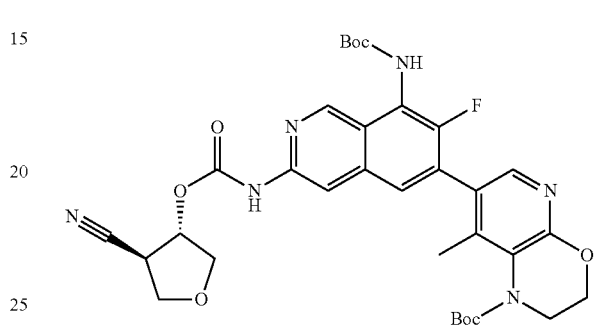

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (300.0 mg, 0.57 mmol) and trans-4-hydroxytetrahydrofuran-3-carbonitrile (129.0 mg, 1.14 mmol) in dichloromethane (30 mL) was added N,N-diisopropylethylamine (0.5 mL, 2.86 mmol) at 0° C. Then triphosgene (120.0 mg, 0.40 mmol) was added. The mixture was stirred at 0° C. for 1 hour followed by at room temperature for 2 hours. The reaction was quenched with water and extracted with dichloromethane. The organic layers were combined, dried over anhydrous sodium sulfate and concentrated under vacuum. The residue was purified by flash chromatography on silica gel eluting with dichloromethane/methanol (50:1) to afford (±)-trans-tert-butyl 7-(8-((tert-butoxycarbonyl)amino)-3-((((4-cyanotetrahydrofuran-3-yl)oxy)carbonyl)amino)-7-fluoroisoquinolin-6-yl)-8-methyl-2,3-dihydro-1H-pyrido[2,3-b][1,4]oxazine-1-carboxylate (230 mg, 0.346 mmol, 60.6% yield) as a yellow solid. LCMS (ESI) [M+H]$^+$=665.

Step 3: (3S,4R)-4-Cyanotetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3R,4S)-4-Cyanotetrahydrofuran-3-yl (8-amino-7-fluoro-6-(8-methyl-2,3-dihydro-1H-pyrido[2,3-b][1,4]oxazin-7-yl)isoquinolin-3-yl)carbamate

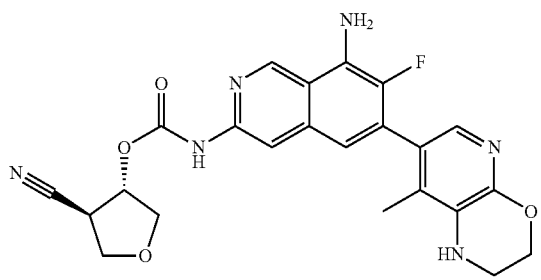

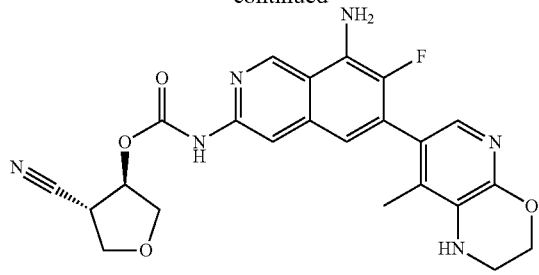

To a solution of tert-butyl 7-[8-(tert-butoxycarbonylamino)-3-[(4-cyanotetrahydrofuran-3-yl)oxycarbonylamino]-7-fluoro-6-isoquinolyl]-8-methyl-2,3-dihydropyrido[2,3-b][1,4]oxazine-1-carboxylate (200.0 mg, 0.30 mmol) in dichloromethane (20 mL) was added trifluoroacetic acid (8.0 mL). The mixture was stirred at room temperature for 2 hours. The reaction mixture was concentrated under vacuum. The residue was diluted with dichloromethane and the pH of the solution was adjusted to pH 8 with triethylamine. The mixture was then concentrated under vacuum. The residue was purified by Prep-HPLC (X select CSH OBD Column 30*150 mm 5 μm; Mobile Phase A: Water (0.1% FA), Mobile Phase B: ACN; Flow rate 60 mL/min; Gradient: 13 B to 43 B in 7 min) to afford a racemic product. The racemic product was further separated by chiral Prep-HPLC to afford two enantiomers. Relative stereochemistry are as drawn. Absolute stereochemistry was arbitrarily assigned.

Enantiomer 1: (Compound 538a) (7.9 mg, 0.0170 mmol, 5.6% yield) as a yellow solid. $R_T$ 1.349 min (CHIRALPAK IC-3, 0.46*5 cm; 3 μm; Mobile phase: MTBE:EtOH=70:30; 1 ml/min); LCMS (ESI): [M+H]=465.2, $R_T$ 1.886 min., Method K; $^1$H NMR (300 MHz, DMSO-$d_6$) δ 10.36 (s, 1H), 9.35 (s, 1H), 7.99 (s, 1H), 7.33 (s, 1H), 6.88 (d, J=6.6 Hz, 1H), 6.23 (s, 2H), 5.67 (s, 1H), 5.44-5.41 (m, 1H), 4.29 (s, 2H), 4.16-4.06 (m, 2H), 3.89 (t, J=7.35 Hz, 2H), 3.62-3.57 (m, 1H), 3.36 (s, 2H), 1.92 (s, 3H).

Enantiomer 2: (Compound 538b) (12.8 mg, 0.0274 mmol, 9.1% yield) as a yellow solid. $R_T$ 2.474 min (CHIRALPAK IC-3, 0.46*5 cm; 3 μm; Mobile phase: MTBE:EtOH=70:30; 1 ml/min); LCMS (ESI): [M+H]=465.2, $R_T$ 1.886 min, Method K; $^1$H NMR (300 MHz, DMSO-$d_6$) δ 10.36 (s, 1H), 9.35 (s, 1H), 7.99 (s, 1H), 7.33 (s, 1H), 6.88 (d, J=6.6 Hz, 1H), 6.23 (s, 2H), 5.67 (s, 1H), 5.44-5.41 (m, 1H), 4.29 (s, 2H), 4.16-4.06 (m, 2H), 3.89 (t, J=7.35 Hz, 2H), 3.62-3.57 (m, 1H), 3.36 (s, 2H), 1.92 (s, 3H).

Example 226

(1r,3r)-3-(Methylamino)cyclobutyl (8-amino-7-fluoro-6-(8-methyl-2,3-dihydro-1H-pyrido[2,3-b][1,4]oxazin-7-yl)isoquinolin-3-yl)carbamate (Compound 539a)

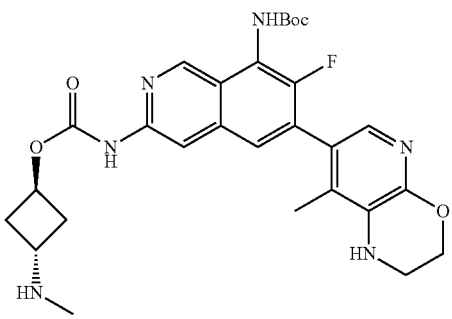 [SMILES: CN[C@H]1C[C@H](OC(=O)Nc2cc3cc(-c4cnc5c(c4C)NCCO5)c(F)c(NC(=O)OC(C)(C)C)c3cn2)C1]

Step 1: tert-Butyl 7-(3-((((1r,3r)-3-((tert-butoxycarbonyl)(methyl)amino)cyclobutoxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

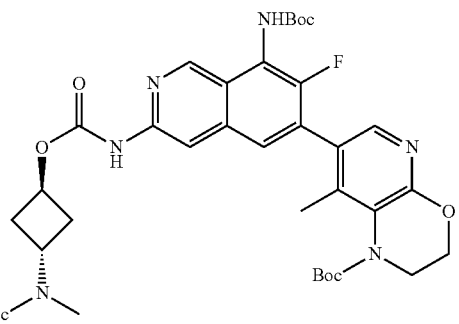

A solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (300 mg, 0.57 mmol), tert-butyl N-(3-hydroxycyclobutyl)-N-methyl-carbamate (229 mg, 1.14 mmol) and N,N'-diisopropylethylamine (736 mg, 5.71 mmol) in dichloromethane (18 mL) was stirred for 5 min at 0° C. Then a solution of triphosgene (169 mg, 0.57 mmol) in dichloromethane (2 mL) was added dropwise. The mixture was stirred at 0° C. for 1 hour. The mixture was concentrated under vacuum and purified by flash chromatography on silica gel eluting with ethyl acetate/petroleum ether (4:1) to afford tert-butyl 7-[8-(tert-butoxycarbonylamino)-3-[[3-[tert-butoxycarbonyl(methyl)amino]cyclobutoxy]carbonylamino]-7-fluoro-6-isoquinolyl]-8-methyl-2,3-dihydropyrido[2,3-b][1,4]oxazine-1-carboxylate (300 mg, 0.398 mmol, 69.9% yield) as a pale yellow solid. LCMS (ESI) [M+H]$^+$=753.

Step 2: (1r,3r)-3-(Methylamino)cyclobutyl (8-amino-7-fluoro-6-(8-methyl-2,3-dihydro-1H-pyrido[2,3-b][1,4]oxazin-7-yl)isoquinolin-3-yl)carbamate

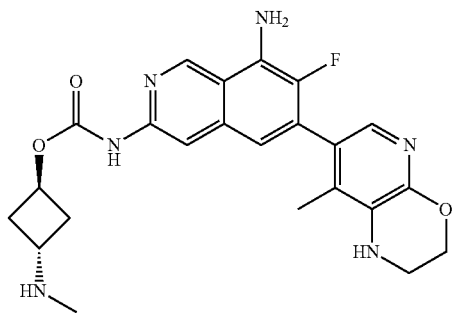 [SMILES: CN[C@H]1C[C@H](OC(=O)Nc2cc3cc(-c4cnc5c(c4C)NCCO5)c(F)c(N)c3cn2)C1]

A solution of tert-butyl 7-[8-(tert-butoxycarbonylamino)-3-[[3-[tert-butoxycarbonyl(methyl)amino]cyclobutoxy]carbonylamino]-7-fluoro-6-isoquinolyl]-8-methyl-2,3-dihydropyrido[2,3-b][1,4]oxazine-1-carboxylate (50 mg, 0.070 mmol) and TFA (1 mL) in dichloromethane (4 mL) was stirred at room temperature for 1 hour. The reaction mixture was concentrated under vacuum. The crude product was purified by Prep-HPLC (X-Bridge Prep OBD C18 Column, 30×150 mm 5 μm; Mobile Phase A: Water (10 mmol/L NH$_4$HCO$_3$), Mobile Phase B: ACN; Flow rate: 60 mL/min; Gradient: 11% B to 31% B in 7 min) to afford (1r,3r)-3-(methylamino)cyclobutyl (8-amino-7-fluoro-6-(8-methyl-2,3-dihydro-1H-pyrido[2,3-b][1,4]oxazin-7-yl)isoquinolin-3-yl)carbamate (17.2 mg, 0.0377 mmol, 56.7% yield) as a light yellow solid. LCMS (ESI) [M+H]$^+$=453.2, R$_T$ 1.421 min, Method J; $^1$H NMR (300 MHz, DMSO-d$_6$) δ 10.05 (s, 1H), 9.33 (s, 1H), 7.96 (s, 1H), 7.33 (s, 1H), 6.84 (d, J=6.2 Hz, 1H), 6.20 (s, 2H), 5.67 (s, 1H), 5.08 (p, J=6.2 Hz, 1H), 4.29 (s, 2H), 3.45-3.3.5 (m, 2H), 3.28-3.15 (m, 1H), 2.32-2.09 (m, 7H), 2.11-1.92 (m, 4H).

Example 227

(1s,3s)-3-Fluorocyclobutyl (8-amino-7-fluoro-6-(8-methyl-2,3-dihydro-1H-pyrido[2,3-b][1,4]oxazin-7-yl)isoquinolin-3-yl)carbamate hydrochloride (Compound 541a)

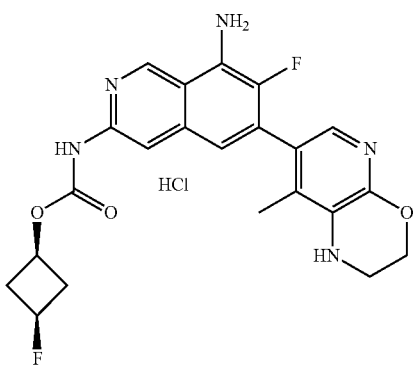 [SMILES: Cc1c(-c2cc3cc(NC(=O)O[C@H]4C[C@@H](F)C4)ncc3c(N)c2F)cnc2c1NCCO2 ; Cl]

Step 1: tert-Butyl 7-[8-(tert-butoxycarbonylamino)-7-fluoro-3-[(3-fluorocyclobutoxy)carbonylamino]-6-isoquinolyl]-8-methyl-2,3-dihydropyrido[2,3-b][1,4]oxazine-1-carboxylate

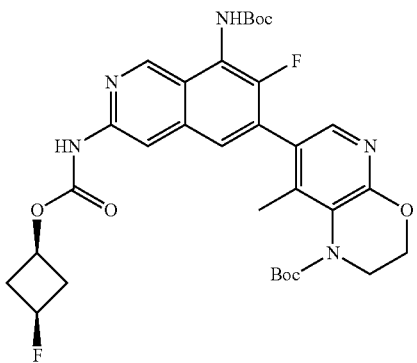 [SMILES: Cc1c(-c2cc3cc(NC(=O)O[C@H]4C[C@@H](F)C4)ncc3c(NC(=O)OC(C)(C)C)c2F)cnc2c1N(C(=O)OC(C)(C)C)CCO2]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (400.0 mg, 0.62 mmol) and DMAP (75.6 mg, 0.62 mmol) in 1,4-dioxane (20 mL) was added 3-fluorocyclobutanol (111.6 mg, 1.24 mmol) at room temperature. The resulting solution was stirred for 5 hours at 90° C. and concentrated under vacuum. The residue was purified by flash chromatography on silica gel eluting with dichloromethane/methanol (10/1) to afford tert-butyl 7-[8-(tert-butoxycarbonylamino)-7-fluoro-3-[(3-fluorocyclobutoxy)carbonylamino]-6-isoquinolyl]-8-methyl-2,3-dihydropyrido[2,3-b][1,4]oxazine-1-carboxylate (310 mg, 0.483 mmol, 78% yield) as a yellow solid. LCMS (ESI) [M+H]$^+$= 642.3.

Step 2: (1s,3s)-3-Fluorocyclobutyl (8-amino-7-fluoro-6-(8-methyl-2,3-dihydro-1H-pyrido[2,3-b][1,4]oxazin-7-yl)isoquinolin-3-yl)carbamate hydrochloride

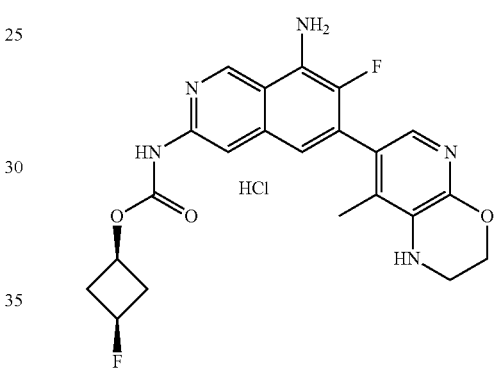

To a solution of tert-butyl 7-[8-(tert-butoxycarbonylamino)-7-fluoro-3-[(3-fluorocyclobutoxy)carbonylamino]-6-isoquinolyl]-8-methyl-2,3-dihydropyrido[2,3-b][1,4]oxazine-1-carboxylate (300.0 mg, 0.47 mmol) in dichloromethane (10 mL) was added TFA (2 mL) at 0° C. The resulting solution was stirred at room temperature for 1.5 hours. The reaction mixture was concentrated under vacuum. The residue was re-dissolved in dichloromethane and the pH value of the solution was adjusted to pH 8 with TEA. The mixture was concentrated under vacuum and purified by Prep-HPLC (Column:)(Bridge Shield RP18 OBD Column 30*150 mm, 5 μm; Mobile Phase A: Water (10 mmol/L NH$_4$HCO$_3$), Mobile Phase B: ACN; Flow rate: 60 mL/min; Gradient: 17% B to 38% B in 7 min) to afford the free base form of the product. Then the free base was dissolved in methanol and treated with HCl (0.04 mL, 1 M in dioxane) for 20 minutes. The mixture was concentrated under vacuum to afford (1s,3s)-3-fluorocyclobutyl (8-amino-7-fluoro-6-(8-methyl-2,3-dihydro-1H-pyrido[2,3-b][1,4]oxazin-7-yl)isoquinolin-3-yl)carbamate hydrochloride (32.8 mg, 0.068 mmol, 14.6% yield) as an orange solid. LCMS (ESI) [M+H]$^+$=442.2. R$_T$ 2.019 min; Method J. $^1$H NMR $^1$H NMR (400 MHz, DMSO-d$_6$) δ 10.27 (s, 1H), 9.40 (s, 1H), 7.98 (s, 1H), 7.55 (s, 1H), 6.92 (d, J=6.1 Hz, 1H), 4.78-4.82 (m, 1H), 4.58-4.62 (m, 1H), 4.48 (t, J=4.4 Hz, 2H), 3.48 (t, J=4.4 Hz, 2H), 2.97-2.86 (m, 2H), 2.22-2.33 (m, 2H), 2.02 (d, J=1.5 Hz, 3H).

Example 228

(1S,2R)-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate and (1R,2S)-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate (Compound 542a and Compound 542b)

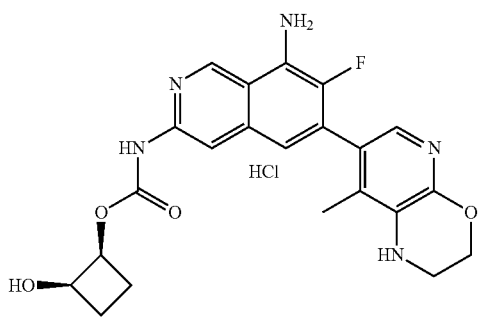

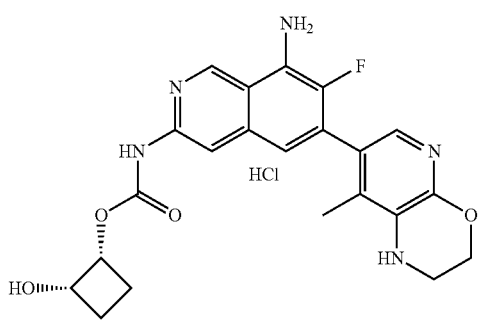

Step 1: cis-Cyclobutane-1,2-diol

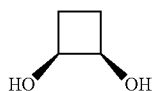

To a solution of 1,2-(trimethylsilyloxy)cyclobutene (3.0 g, 13.02 mmol) in tetrahydrofuran (100 mL) was added Pd/C (10%, 800.0 mg, 6.35 mmol). The mixture was stirred at under hydrogen at room temperature for 12 hours. After filtration, the filtrate was concentrated under vacuum. The residue was purified by flash chromatography on silica gel eluting with ethyl acetate/petroleum ether (2/1) to afford cis-cyclobutane-1,2-diol (300 mg, 3.40 mmol, 26.2% yield) as a colorless oil. $^1$H NMR (300 MHz, CDCl$_3$) δ 4.59 (s, 2H), 4.19 (q, J=3.7 Hz, 2H), 2.17-1.69 (m, 4H).

Step 2: (±)-cis-tert-Butyl 7-[8-(tert-butoxycarbonylamino)-7-fluoro-3-[[2-hydroxycyclobutoxy]carbonylamino]-6-isoquinolyl]-8-methyl-2,3-dihydropyrido[2,3-b][1,4]oxazine-1-carboxylate

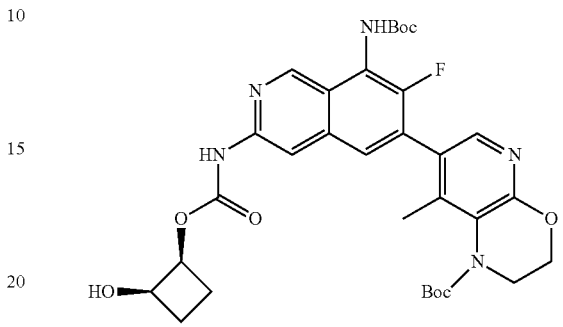

A solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (200.0 mg, 0.31 mmol), cis-cyclobutane-1,2-diol (54.6 mg, 0.62 mmol) and 4-dimethylaminopyridine (37.8 mg, 0.31 mmol) in 1,4-dioxane (4 mL) was stirred at 90° C. for 2 hours. The reaction was quenched with water and extracted with ethyl acetate. The organic layers were combined, dried over anhydrous sodium sulfate, filtered and concentrated under vacuum. The residue was purified by reverse phase chromatography (acetonitrile 0-65/0.1% FA in water) to afford (±)-cis-tert-butyl 7-[8-(tert-butoxycarbonylamino)-7-fluoro-3-[[2-hydroxycyclobutoxy]carbonylamino]-6-isoquinolyl]-8-methyl-2,3-dihydropyrido[2,3-b][1,4]oxazine-1-carboxylate (90 mg, 0.141 mmol, 45.4% yield) as a yellow solid. LCMS (ESI) [M+H]$^+$=640.3.

Step 3: (1S,2R)-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate and (1R,2S)-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate

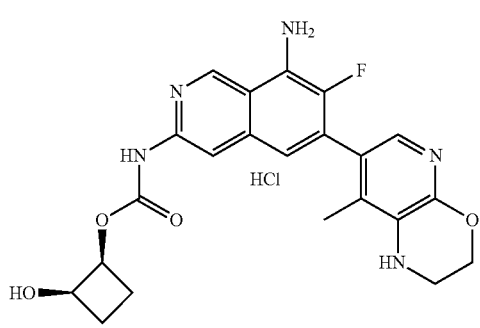

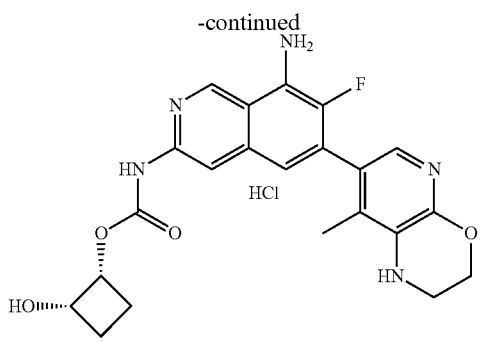

To a solution of tert-butyl 7-[8-(tert-butoxycarbonylamino)-7-fluoro-3-[(2-hydroxycyclobutoxy)carbonylamino]-6-isoquinolyl]-8-methyl-2,3-dihydropyrido[2,3-b][1,4]oxazine-1-carboxylate (84.0 mg, 0.13 mmol) in dichloromethane (5 mL) was added TFA (2.5 mL). The mixture was stirred at room temperature for 2 hours. The reaction mixture was concentrated under vacuum. The residue was purified by Prep-HPLC (CHIRALPAK IC, 2*25 cm, 5 μm; Mobile Phase A: MTBE, Mobile Phase B: MeOH; Flow rate: 35 mL/min; Gradient: 50% B to 50% B in 30 min) to afford a racemic product. The racemic product was further separated by chiral-Prep-HPLC to afford two enantiomers. Relative stereochemistry are as drawn. Absolute stereochemistry was arbitrarily assigned.

Enantiomer 1: Compound 542a (7 mg, 0.016 mmol, 11.8% yield). $R_T$ 0.906 min (CHIRALPAK IC-3 0.46*5 cm; 3 μm; MTBE (0.1% DEA): MeOH=50:50). LCMS (ESI): [M+H]$^+$=440.2, $R_T$ 1.942 min. Method K; $^1$H NMR (300 MHz, DMSO-d$_6$) δ 10.07 (s, 1H), 9.40 (s, 1H), 8.00 (s, 1H), 7.53 (s, 1H), 6.89 (d, J=6.1 Hz, 1H), 5.03-4.90 (m, 1H), 4.46 (t, J=4.2 Hz, 2H), 4.30-4.32 (m, 1H), 3.47 (t, J=4.3 Hz, 2H), 2.15-1.98 (m, 6H), 1.85-1.89 (m, 1H).

Enantiomer 2: Compound 542b (12 mg, 0.027 mmol, 19.6% yield). $R_T$ 1.829 min (CHIRALPAK IC-3 0.46*5 cm; 3 μm; MTBE (0.1% DEA): MeOH=50:50). LCMS (ESI): [M+H]$^+$=440.2, $R_T$ 1.942 min. Method K.; $^1$H NMR (300 MHz, DMSO-d$_6$) δ 10.07 (s, 1H), 9.40 (s, 1H), 8.00 (s, 1H), 7.53 (s, 1H), 6.89 (d, J=6.1 Hz, 1H), 5.03-4.90 (m, 1H), 4.46 (t, J=4.2 Hz, 2H), 4.30-4.32 (m, 1H), 3.47 (t, J=4.3 Hz, 2H), 2.15-1.98 (m, 6H), 1.85-1.89 (m, 1H).

Example 229

(1R,5S,6s)-3-oxabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate and (1R,5S,6r)-3-oxabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate (Compound 543a and Compound 543b)

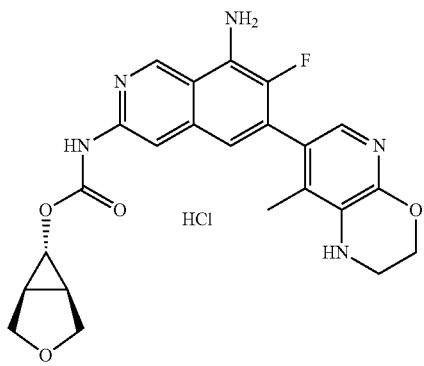

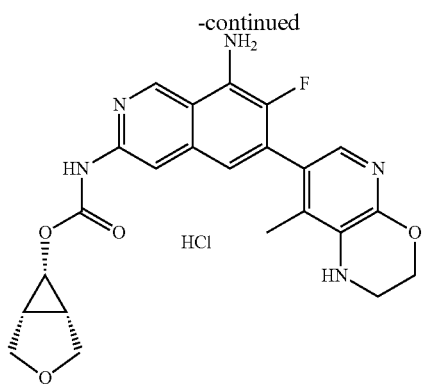

Step 1: 2-(Diiodomethyl)-4,4,5,5-tetramethyl-1,3,2-dioxaborolane

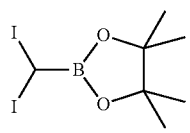

Under nitrogen, to a solution of trimethylborate (19 mL, 157 mmol) in tetrahydrofuran (250 mL) was added n-butyllithium (60 mL, 142 mmol, 2.5 M in n-hexane) at −100° C. The resulting solution was stirred for 40 minutes at −100° C. Then dichloromethane (10 mL, 157 mmol) was added. The mixture was stirred at −100° C. for 30 minutes. The reaction was quenched with HCl (30 mL, 5 N in water). The reaction mixture was diluted with water and extracted with Et$_2$O. The organic layers were combined, dried over anhydrous sodium sulfate, filtered and concentrated under vacuum.

The residue was dissolved in toluene (300 mL) and then pinacol (1.67 g, 141.3 mmol) was added. The solution was stirred at 110° C. for 18 hours. The solution was concentrated under vacuum. The residue was re-dissolved in acetone (400 mL) and sodium iodide (5.4 g, 361.1 mmol) was added. The solution was stirred at room temperature for 24 hours. The solution was concentrated under vacuum, diluted with water and extracted with Et$_2$O. The organic layers were combined, dried over anhydrous sodium sulfate, filtered and concentrated under vacuum. The residue was then suspended in hexane. The mixture was decanted to remove the black insoluble solid followed by recrystallization with hexane afforded 2-(diiodomethyl)-4,4,5,5-tetramethyl-1,3,2-dioxaborolane (8 g, 20.32 mmol, 12.9% yield) as a yellow solid.

Step 2: 4,4,5,5-Tetramethyl-2-[3-oxabicyclo[3.1.0]hexan-6-yl]-1,3,2-dioxaborolan

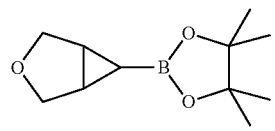

Under nitrogen, a solution of CrCl$_2$ (5.5 g, 44.71 mmol) and TMEDA (5.2 g, 44.71 mmol) in tetrahydrofuran (85 mL) was stirred for 1 hour at room temperature. Then 2-(diiodomethyl)-4,4,5,5-tetramethyl-1,3,2-dioxaborolane (4.4 g, 11.18 mmol) was added. The mixture was stirred at room temperature for 1 hour. 2,5-dihydrofuran (522.3 mg, 7.45 mmol) was added and the mixture was stirred at 50° C. for additional 20 hours. The reaction was quenched with water and extracted with ethyl acetate. The organic layers were combined, dried over anhydrous sodium sulfate, filtered and concentrated under vacuum. The residue was purified by flash chromatography on silica gel eluting with dichloromethane/methanol (10/1) to afford 4,4,5,5-tetramethyl-2-[3-oxabicyclo[3.1.0]hexan-6-yl]-1,3,2-dioxaborolane (1.2 g, 5.57 mmol, 74.7% yield) as light yellow oil.

Step 3: 3-Oxabicyclo[3.1.0]hexan-6-ol

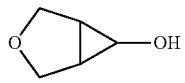

A solution of 4,4,5,5-tetramethyl-2-[3-oxabicyclo[3.1.0]hexan-6-yl]-1,3,2-dioxaborolane (1.15.0 g, 5.45 mmol) in tetrahydrofuran (26 mL) and water (26 mL) was stirred at 0° C. for 15 min. Then NaBO$_3$.4H$_2$O (2.52 g, 16.35 mmol) was added. The mixture was stirred at 0° C. for 4 hours. The reaction mixture was filtered and diluted with water. The resulting solution was extracted with ethyl acetate. The organic layers were combined, dried over anhydrous sodium sulfate, filtered and concentrated under vacuum. The residue was purified by flash chromatography on silica gel eluting with dichloromethane/methanol (97/3) to afford 3-oxabicyclo[3.1.0]hexan-6-ol (400 mg, 4.0 mmol, 73.3% yield) as colorless oil. $^1$H NMR (300 MHz, DMSO-d$_6$) δ 5.29 (s, 1H), 3.94 (s, 1H), 3.73 (d, J=8.3 Hz, 2H), 3.60-3.46 (m, 2H), 1.64 (q, J=1.8 Hz, 2H)

Step 4. tert-Butyl 7-[8-(tert-butoxycarbonylamino)-7-fluoro-3-(3-oxabicyclo[3.1.0]hexan-6-yloxycarbonylamino)-6-isoquinolyl]-8-methyl-2,3-dihydropyrido[2,3-b][1,4]oxazine-1-carboxylate

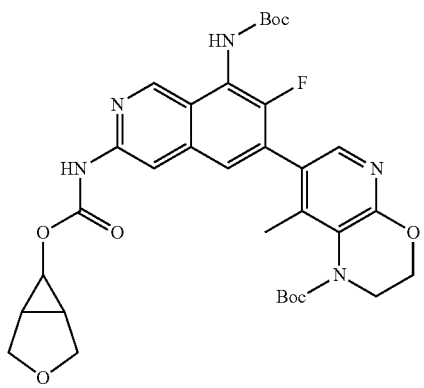 [SMILES: Cc1c(-c2cc3cc(NC(=O)OC4C5COCC54)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (210.0 mg, 0.40 mmol), DIEA (516.4 mg, 4 mmol) and 3-oxabicyclo[3.1.0]hexan-6-ol (80.1 mg, 0.80 mmol) in dichloromethane (25 mL) was added triphosgene (83.0 mg, 0.28 mmol). The mixture was stirred at 0° C. for 1 hour. The reaction mixture was quenched with water and extracted with dichloromethane. The organic layers were combined, dried over anhydrous sodium sulfate, filtered and concentrated under vacuum. The residue was purified by flash chromatography on silica gel eluting with dichloromethane/methanol (98/2) to afford tert-butyl 7-[8-(tert-butoxycarbonylamino)-7-fluoro-3-(3-oxabicyclo[3.1.0]hexan-6-yloxycarbonylamino)-6-isoquinolyl]-8-methyl-2,3-dihydropyrido[2,3-b][1,4]oxazine-1-carboxylate (112 mg, 0.17 mmol, 43% yield) as a yellow solid.

Step 5: (1R,5S,6s)-3-oxabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate (Compound 543a) and (1R,5S,6r)-3-oxabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate (Compound 543b)

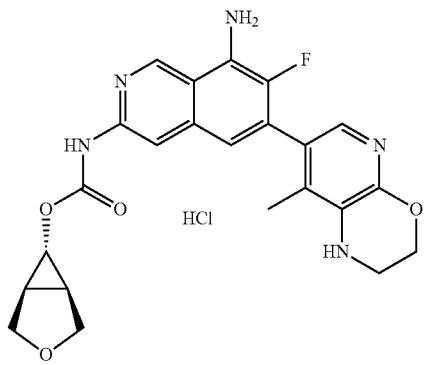

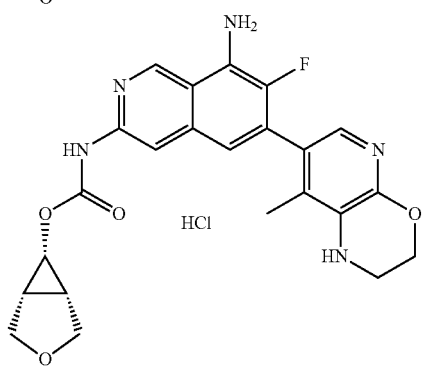

To a solution of tert-butyl 7-[8-(tert-butoxycarbonylamino)-7-fluoro-3-(3-oxabicyclo[3.1.0]hexan-6-yloxycarbonylamino)-6-isoquinolyl]-8-methyl-2,3-dihydropyrido[2,3-b][1,4]oxazine-1-carboxylate (250.0 mg, 0.38 mmol) in dichloromethane (6 mL) was added TFA (2 mL). The mixture was stirred at room temperature for 3 hours and concentrated under vacuum. The residue was re-dissolved in dichloromethane and the pH of solution was adjusted to 8 with TEA. The mixture was concentrated under vacuum and purified by prep-HPLC (Column: X select CSH OBD Column 30*150 mm, 5 μm; Mobile Phase A: Water (0.1% FA), Mobile Phase B: ACN; Flow rate: 60 mL/min; Gradient: 10% B to 32% B in 10 min) to afford a mixture of stereoisomers. The mixture was further separated by chiral-HPLC to afford two isomers.

Isomer 1: Compound 543a (54.6 mg, 0.12 mmol, 31.5% yield). $R_T$ 2.331 min (CHIRALPAK IC-3 0.46*5 cm; 3 μm; Mobile phase: (Hex:DCM=3:1) (0.1% DEA):EtOH=50:50). LCMS (ESI) [M+H]$^+$=452.1, $R_T$ 2.132 min; Method K. $^1$H NMR (300 MHz, DMSO-d$_6$) δ 10.36 (s, 1H), 9.46 (s, 1H), 8.03 (s, 1H), 7.60 (s, 1H), 6.96 (d, J=6.0 Hz, 1H), 4.55 (t, J=4.4 Hz, 2H), 3.90 (d, J=8.5 Hz, 2H), 3.72 (t, J=1.7 Hz, 1H), 3.60-3.66 (m, 2H), 3.52 (t, J=4.3 Hz, 2H), 2. 27-2.01 (m, 5H).

Isomer 2: Compound 543b (12 mg, 0.027 mmol, 6.9% yield). $R_T$ 3.307 min (CHIRALPAK IC-3 0.46*5 cm; 3 μm; Mobile phase: (Hex:DCM=3:1) (0.1% DEA): EtOH=50: 50). LCMS (ESI) [M+H]$^+$=452.1, $R_T$ 2.132 min; Method K. $^1$H NMR (300 MHz, DMSO-d$_6$) δ 10.36 (s, 1H), 9.46 (s, 1H), 8.03 (s, 1H), 7.60 (s, 1H), 6.96 (d, J=6.0 Hz, 1H), 4.55 (t, J=4.4 Hz, 2H), 3.90 (d, J=8.5 Hz, 2H), 3.72 (t, J=1.7 Hz, 1H), 3.60-3.66 (m, 2H), 3.52 (t, J=4.3 Hz, 2H), 2.12-2.03 (m, 5H).

Example 230

(3R,4S)-4-Methyltetrahydrofuran-3-yl (8-amino-6-(5-amino-4-methylpyridin-3-yl)-7-fluoroisoquinolin-3-yl)carbamate and (3S,4R)-4-Methyltetrahydrofuran-3-yl (8-amino-6-(5-amino-4-methylpyridin-3-yl)-7-fluoroisoquinolin-3-yl)carbamate (Compound 544a and Compound 544b)

Step 1: (±)-trans-(4-Methyltetrahydrofuran-3-yl) N-[8-(tert-butoxycarbonylamino)-6-[5-(tert-butoxycarbonylamino)-4-methyl-3-pyridyl]-7-fluoro-3-isoquinolyl]carbamate

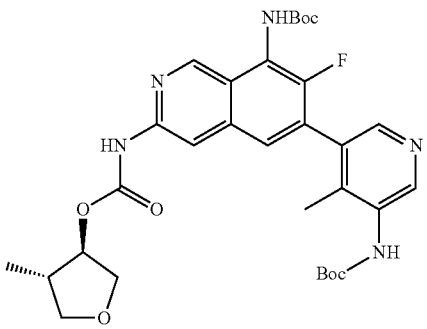 [SMILES: Cc1c(NC(=O)OC(C)(C)C)cncc1-c1cc2cc(NC(=O)O[C@H]3COC[C@@H]3C)ncc2c(NC(=O)OC(C)(C)C)c1F]

To a solution of tert-butyl N-[5-[3-amino-8-(tert-butoxycarbonylamino)-7-fluoro-6-isoquinolyl]-4-methyl-3-pyridyl]carbamate (300.0 mg, 0.62 mmol), DIEA (801.9 mg, 6.20 mmol) and trans-4-methyltetrahydrofuran-3-ol (316.9 mg, 3.10 mmol) in dichloromethane (20 mL) was added triphosgene (184.2 mg, 0.62 mmol). The mixture was stirred at 0° C. for 1 hour. The reaction mixture was quenched with water and extracted with dichloromethane. The organic layers were combined, dried over anhydrous sodium sulfate, filtered and concentrated under vacuum. The residue was purified by flash chromatography on silica gel eluting with dichloromethane/methanol (97/3) to afford (4-methyltetrahydrofuran-3-yl) N-[8-(tert-butoxycarbonylamino)-6-[5-(tert-butoxycarbonylamino)-4-methyl-3-pyridyl]-7-fluoro-3-isoquinolyl]carbamate (200 mg, 0.33 mmol, 52.7% yield) as yellow oil.

Step 2: (3R,4S)-4-Methyltetrahydrofuran-3-yl (8-amino-6-(5-amino-4-methylpyridin-3-yl)-7-fluoroisoquinolin-3-yl)carbamate and (3S,4R)-4-Methyltetrahydrofuran-3-yl (8-amino-6-(5-amino-4-methylpyridin-3-yl)-7-fluoroisoquinolin-3-yl)carbamate

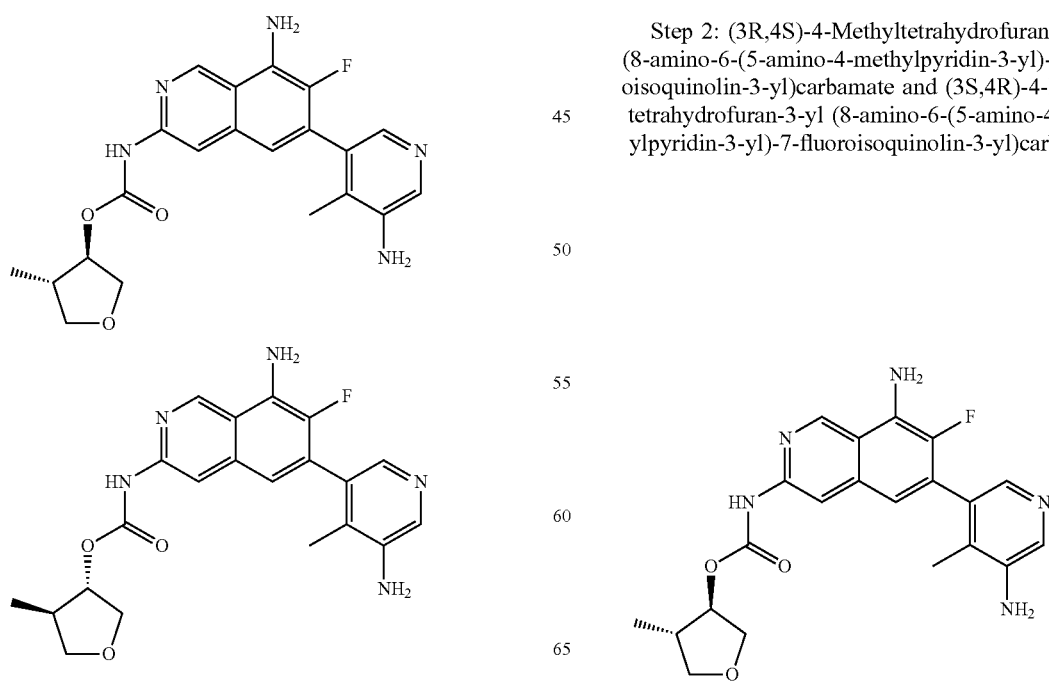

-continued

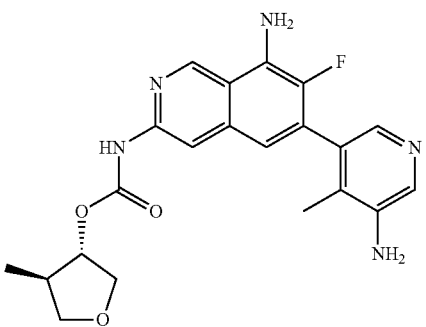

To a solution of (4-methyltetrahydrofuran-3-yl) N-[8-(tert-butoxycarbonylamino)-6-[5-(tert-butoxycarbonylamino)-4-methyl-3-pyridyl]-7-fluoro-3-isoquinolyl]carbamate (200.0 mg, 0.33 mmol) in dichloromethane (3 mL) was added TFA (1 mL). The mixture was stirred at 0° C. for 1.5 hours. The reaction mixture was concentrated under vacuum, re-dissolved in DCM and the pH of the mixture was adjusted to pH 8 with TEA. The reaction mixture was concentrated under vacuum and purified by prep-HPLC (Column: X select CSH OBD Column 30*150 mm, 5 μm; Mobile Phase A: Water (0.1% FA), Mobile Phase B: ACN; Flow rate: 60 mL/min; Gradient: 5 B to 28 B in 7 min) to afford a racemic product. The racemic product was further separated by chiral HPLC to afford two enantiomers. Relative stereochemistry are as drawn. Absolute stereochemistry was arbitrarily assigned.

Enantiomer 1: Compound 544a (9.7 mg, 0.024 mmol, 7.2% yield). $R_T$ 2.031 min (CHIRALPAK IA-3 0.46*5 cm; 3 μm; (Hex:DCM=3:1) (0.1% DEA): EtOH=50:50). LCMS (ESI) [M+H]$^+$=412.1, $R_T$ 0.963 min, Method L; $^1$H NMR (300 MHz, DMSO-d$_6$) δ 10.15 (s, 1H), 9.35 (s, 1H), 7.99 (d, J=1.9 Hz, 2H), 7.66 (s, 1H), 6.87 (d, J=6.1 Hz, 1H), 6.24 (s, 2H), 5.25 (s, 2H), 4.84-4.87 (m, 1H), 4.04-3.91 (m, 2H), 3.76 (dd, J=10.5, 1.9 Hz, 1H), 3.34 (dd, J=8.4, 4.7 Hz, 1H), 2.30-2.37 (m, 1H), 1.92 (d, J=1.5 Hz, 3H), 1.07 (d, J=7.1 Hz, 3H).

Enantiomer 2: Compound 544b (5.1 mg, 0.012 mmol, 3.8% yield). $R_T$ 2.527 min (CHIRALPAK IA-3 0.46*5 cm; 3 μm; (Hex:DCM=3:1)(0.1% DEA): EtOH=50:50). LCMS (ESI) [M+H]$^+$=412.1, $R_T$ 0.963 min, Method L; $^1$H NMR (300 MHz, DMSO-d$_6$) δ 10.15 (s, 1H), 9.35 (s, 1H), 7.99 (d, J=1.9 Hz, 2H), 7.66 (s, 1H), 6.87 (d, J=6.1 Hz, 1H), 6.24 (s, 2H), 5.25 (s, 2H), 4.84-4.87 (m, 1H), 4.04-3.91 (m, 2H), 3.76 (dd, J=10.5, 1.9 Hz, 1H), 3.34 (dd, J=8.4, 4.7 Hz, 1H), 2.30-2.37 (m, 1H), 1.92 (d, J=1.5 Hz, 3H), 1.07 (d, J=7.1 Hz, 3H).

Example 231

(1r,3r)-3-(Dimethylamino)cyclobutyl (8-amino-7-fluoro-6-(8-methyl-2,3-dihydro-1H-pyrido[2,3-b][1,4]oxazin-7-yl)isoquinolin-3-yl)carbamate hydrochloride (Compound 447a)

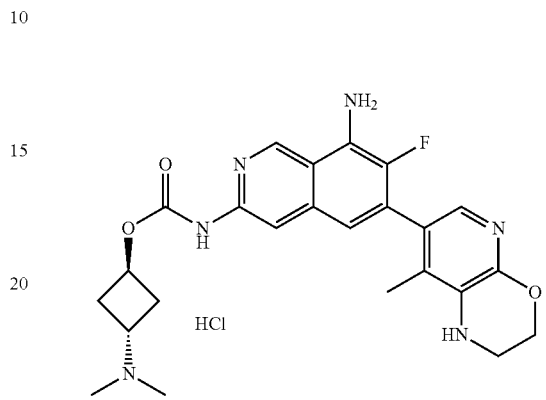

A solution of [3-(methylamino)cyclobutyl]N-[8-amino-7-fluoro-6-(8-methyl-2,3-dihydro-1H-pyrido[2,3-b][1,4]oxazin-7-yl)-3-isoquinolyl]carbamate (90 mg, 0.20 mmol) and formaldehyde (40%, 9.0 mg, 0.22 mmol) in methyl alcohol (8 mL) was stirred at 25° C. for 1 hour. Then sodium borohydride (18 mg, 0.47 mmol) was added and the mixture was stirred at 25° C. for 1 hour. The reaction was quenched by water and concentrated under vacuum. The residue was purified by Prep-HPLC (X Bridge Prep OBD C18 Column, 30×150 mm, 5 μm; Mobile Phase A: Water (10 mmol/L NH$_4$HCO$_3$); Mobile Phase B:MeOH; Flow rate: 60 mL/min; Gradient: 29% B to 63% B in 7 min) to afford (1R,3R)-3-(dimethylamino)cyclobutyl (8-amino-7-fluoro-6-(8-methyl-2,3-dihydro-1H-pyrido[2,3-b][1,4]oxazin-7-yl)isoquinolin-3-yl)carbamate. Then to a solution of (1R,3R)-3-(dimethylamino)cyclobutyl (8-amino-7-fluoro-6-(8-methyl-2,3-dihydro-1H-pyrido[2,3-b][1,4]oxazin-7-yl)isoquinolin-3-yl)carbamate in methanol (10 mL) was added 1,4-dioxane solution of HCl (2 ml, 1 N). The mixture was stirred for 30 mins at room temperature. The reaction was concentrated under vacuum to afford (1r,3r)-3-(dimethylamino)cyclobutyl (8-amino-7-fluoro-6-(8-methyl-2,3-dihydro-1H-pyrido[2,3-b][1,4]oxazin-7-yl)isoquinolin-3-yl)carbamate hydrochloride (50.7 mg, 0.101 mmol, 50.6% yield) as a red solid. LCMS (ESI) [M+H]$^+$=467.2, $R_T$ 1.469 min, Method J; $^1$H NMR (300 MHz, DMSO-d$_6$) δ 10. 80 (s, 1H), 10.29 (s, 1H), 9.40 (s, 1H), 7.98 (s, 1H), 7.49 (s, 1H), 6.90 (d, J=6.1 Hz, 1H), 5.20 (bs, 3H), 5.08 (d, J=3.8 Hz, 1H), 4.43 (s, 2H), 3.90-3.70 (m, 1H), 3.60-3.40 (m, 2H), 2.90-2.65 (m, 8H), 2.43 (d, J=10.3 Hz, 2H), 1.99 (d, J=1.6 Hz, 3H).

Example 232

(+1-)-trans-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate (Compound 445ab)

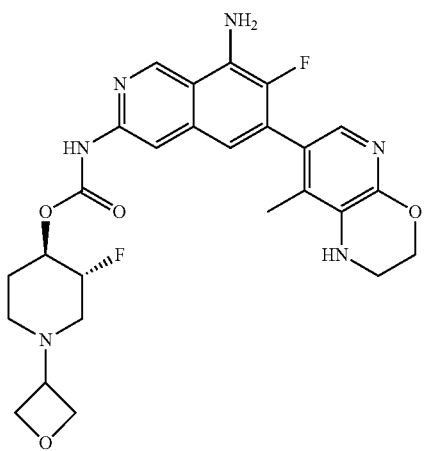

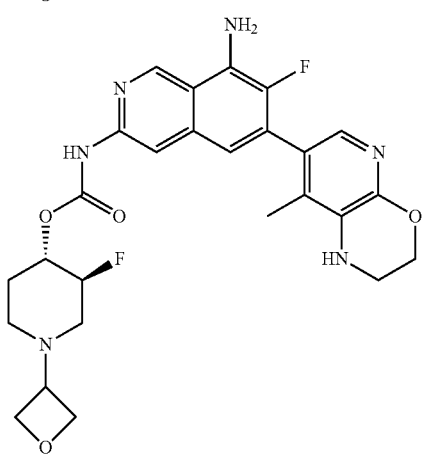

Step 1: (+/−)-trans-tert-Butyl 7-(3-(((((1-(tert-butoxycarbonyl)-3-fluoropiperidin-4-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

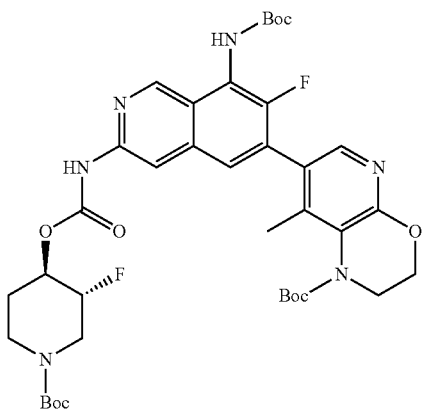

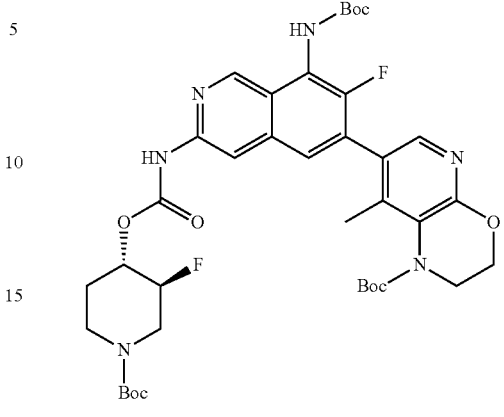

A solution of tert-butyl 7-[3-amino-8-(tert-butoxycarbonylamino)-7-fluoro-6-isoquinolyl]-8-methyl-2,3-dihydro-pyrido[2,3-b][1,4]oxazine-1-carboxylate (500 mg, 0.95 mmol), (+/−)-trans-tert-butyl 3-fluoro-4-hydroxy-piperidine-1-carboxylate (416 mg, 1.9 mmol) and DIEA (613 mg, 4.75 mmol) in dichloromethane (5 mL) was stirred at 0° C. for 0.5 hour. Then triphosgene (146 mg, 0.49 mmol) was added. The mixture was stirred at 0° C. for 2 hours and concentrated under vacuum. The residue was purified by flash chromatography on silica gel eluting with petroleum ether/ethyl acetate (65/35) to afford (+/−)-trans-tert-butyl 7-(3-(((((1-(tert-butoxycarbonyl)-3-fluoropiperidin-4-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate (600 mg, 0.778 mmol, 81.8% yield) as a yellow solid. LCMS (ESI) [M+H]$^+$=771.

Step 2: (+/−)-trans-3-Fluoropiperidin-4-yl (8-amino-7-fluoro-6-(8-methyl-2,3-dihydro-1H-pyrido[2,3-b][1,4]oxazin-7-yl)isoquinolin-3-yl)carbamate

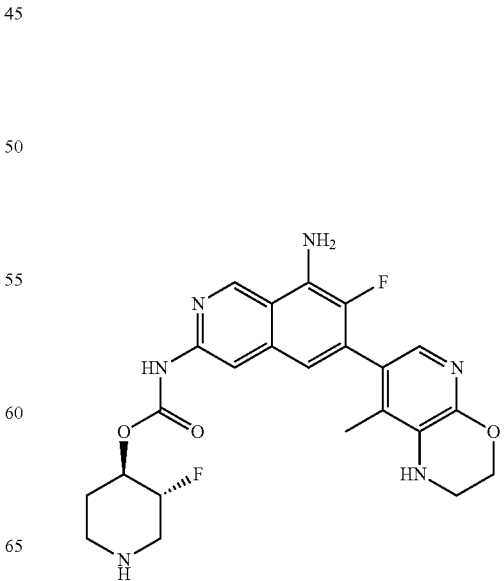

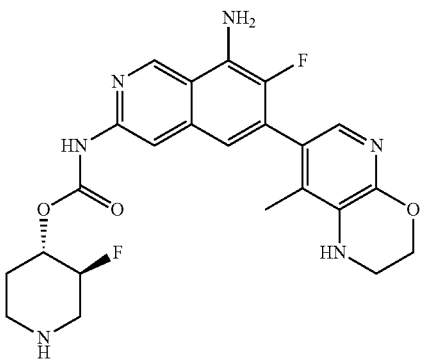

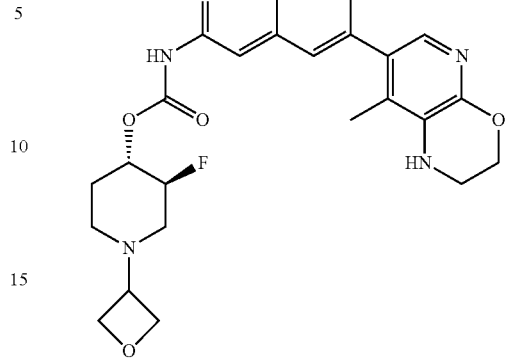

A solution of (+/−)-trans-tert-butyl 7-[8-(tert-butoxycarbonylamino)-3-[[1-tert-butoxycarbonyl-3-fluoro-4-piperidyl]oxycarbonylamino]-7-fluoro-6-isoquinolyl]-8-methyl-2,3-dihydropyrido[2,3-b][1,4]oxazine-1-carboxylate (800 mg, 1.04 mmol) in dichloromethane (5 mL) and TFA (4 m) was stirred at 25° C. for 2 hours. The reaction mixture was concentrated under vacuum and purified by reverse phase chromatography with MeOH/water (44/56) to afford (+/−)-trans-tert-butyl 7-[8-amino-7-fluoro-3-[[3-fluoro-4-piperidyl]oxycarbonylamino]-6-isoquinolyl]-8-methyl-2,3-dihydropyrido[2,3-b][1,4]oxazine-1-carboxylate (580 mg, 1.0165 mmol, 97.9% yield) as a yellow solid. GCMS (ESI) [M+H]+=471.

Step 3: (+/−)-trans-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate A solution of 3-oxetanone (534.82 mg, 7.42 mmol) and (+/−)-trans-tert-butyl 7-[8-amino-7-fluoro-3-[[3-fluoro-4-piperidyl]oxycarbonylamino]-6-isoquinolyl]-8-methyl-2,3-dihydropyrido[2,3-b][1,4]oxazine-1-carboxylate (350 mg, 0.74 mmol) in methyl alcohol (15 mL) was stirred at room temperature for 10 min. Then titanium tetraisopropanolate (849.82 mg, 2.99 mmol) was added. The mixture was stirred at 60° C. for 2 hours. Then NaCNBH₃ (140.0 mg, 2.22 mmol) was added. The mixture was stirred at room temperature for an additional 1 hour. The reaction mixture was concentrated under vacuum and purified by flash chromatography on silica gel eluting with [MeOH]/[water](66/34) to afford (+/−)-trans-3-fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate (3.2 mg, 0.0061 mmol, 0.8000% yield) as a yellow solid. LCMS (ESI) [M+H]⁺=495.2, $R_T$ 1.522 min; Method J. ¹H NMR (300 MHz, DMSO-d₆) δ 10.19 (s, 1H), 9.33 (s, 1H), 7.94 (s, 1H), 7.31 (s, 1H), 6.83-6.78 (d, J=6.2 Hz, 1H), 6.20 (s, 2H), 5.65 (s, 1H), 4.48-4.67 (m, 2H), 4.58-4.46 (m, 2H), 4.45-4.37 (m, 2H), 4.27 (s, 2H), 3.60-3.49 (m, 1H), 3.39-3.32 (m, 2H), 3.04-2.95 (m, 1H), 2.69-2.57 (m, 1H), 2.21-1.99 (m, 3H), 1.90 (s, 3H), 1.70-1.52 (m, 1H).

Example 233

1-((1R,2S)-2-Fluorocyclopropane-1-carbonyl)azetidin-3-yl (8-amino-7-fluoro-6-(8-methyl-2,3-dihydro-1H-pyrido[2,3-b][1,4]oxazin-7-yl)isoquinolin-3-yl)carbamate and 1-((1S,2R)-2-Fluorocyclopropane-1-carbonyl)azetidin-3-yl (8-amino-7-fluoro-6-(8-methyl-2,3-dihydro-1H-pyrido[2,3-b][1,4]oxazin-7-yl)isoquinolin-3-yl)carbamate (Compound 545a and Compound 545b)

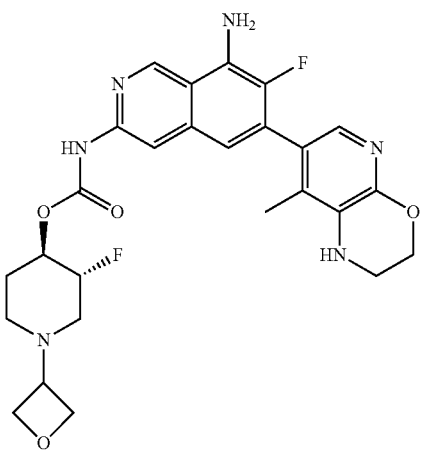

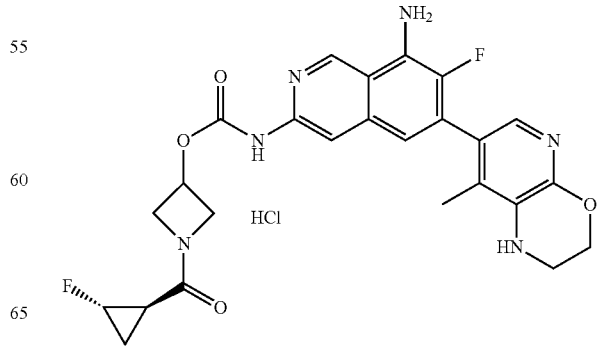

603
-continued

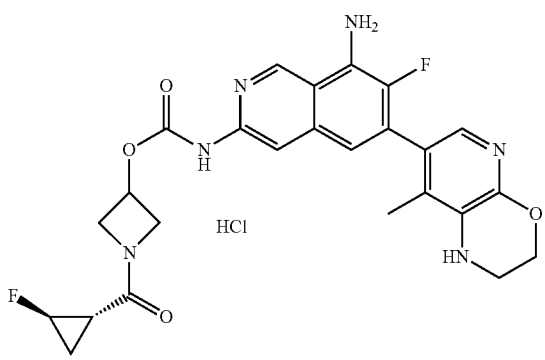

Step 1: tert-Butyl 7-[8-(tert-butoxycarbonylamino)-3-[(1-tert-butoxycarbonylazetidin-3-yl)oxycarbonylamino]-7-fluoro-6-isoquinolyl]-8-methyl-2,3-dihydropyrido[2,3-b][1,4]oxazine-1-carboxylate

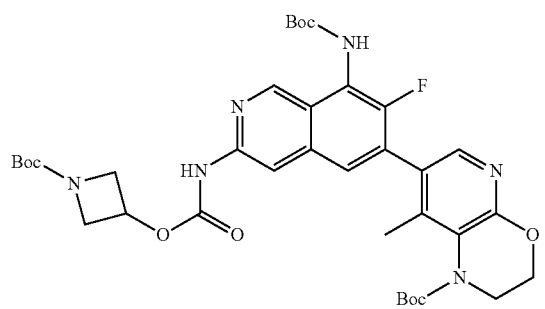 [SMILES: Cc1c(-c2cc3cc(NC(=O)OC4CN(C(=O)OC(C)(C)C)C4)ncc3c(NC(=O)OC(C)(C)C)c2F)cnc2c1N(C(=O)OC(C)(C)C)CCO2]

To a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300 mg, 0.46 mmol) and 1-boc-3-hydroxyazetidine (350 mg, 2.02 mmol) in dichloromethane (15 mL) was added DMAP (60 mg, 0.49 mmol) at room temperature. The reaction was stirred for 16 h at 60° C. The resulting solution was concentrated under vacuum. The residue was purified by flash chromatography on silica gel eluting with petroleum ether/ethyl acetate (1/2) to afford tert-butyl 7-[8-(tert-butoxycarbonylamino)-3-[(1-tert-butoxycarbonylazetidin-3-yl)oxycarbonylamino]-7-fluoro-6-isoquinolyl]-8-methyl-2,3-dihydropyrido[2,3-b][1,4]oxazine-1-carboxylate (200 mg, 0.276 mmol, 59.4% yield) as a yellow solid. LCMS (ESI) [M+H]$^+$=725.

604

Step 2: Azetidin-3-yl N-[8-amino-7-fluoro-6-(8-methyl-2,3-dihydro-1H-pyrido[2,3-b][1,4]oxazin-7-yl)-3-isoquinolyl]carbamate

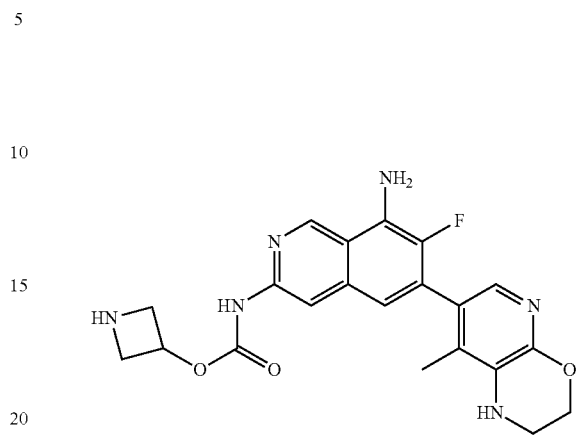

A solution of tert-butyl 7-[8-(tert-butoxycarbonylamino)-3-[(1-tert-butoxycarbonylazetidin-3-yl)oxycarbonylamino]-7-fluoro-6-isoquinolyl]-8-methyl-2,3-dihydropyrido[2,3-b][1,4]oxazine-1-carboxylate (200 mg, 0.28 mmol) in dichloromethane (8 mL) and TFA (2 mL) was stirred for 1 h at 25° C. The reaction mixture was then concentrated under vacuum. The residue was purified by reverse phase chromatography (acetonitrile 0-40/0.1% NH$_4$HCO$_3$ in water) to afford azetidin-3-yl N-[8-amino-7-fluoro-6-(8-methyl-2,3-dihydro-1H-pyrido[2,3-b][1,4]oxazin-7-yl)-3-isoquinolyl]carbamate (80 mg, 0.1885 mmol, 68.3% yield) as a yellow solid. LCMS (ESI) [M+H]$^+$=425.

Step 3: 1-((1R,2S)-2-fluorocyclopropane-1-carbonyl)azetidin-3-yl (8-amino-7-fluoro-6-(8-methyl-2,3-dihydro-1H-pyrido[2,3-b][1,4]oxazin-7-yl)isoquinolin-3-yl)carbamate and 1-((1S,2R)-2-fluorocyclopropane-1-carbonyl)azetidin-3-yl (8-amino-7-fluoro-6-(8-methyl-2,3-dihydro-1H-pyrido[2,3-b][1,4]oxazin-7-yl)isoquinolin-3-yl)carbamate

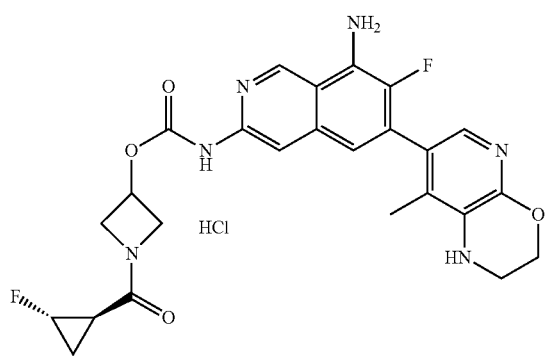

605
-continued

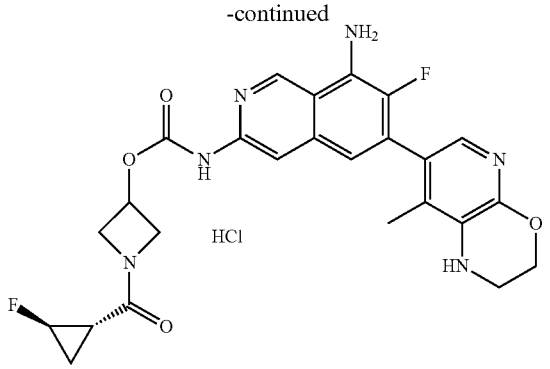

HCl

To a solution of azetidin-3-yl N-[8-amino-7-fluoro-6-(8-methyl-2,3-dihydro-1H-pyrido[2,3-b][1,4]oxazin-7-yl)-3-isoquinolyl]carbamate (80 mg, 0.19 mmol) in DMF (5 mL) was added trans-2-fluorocyclopropanecarboxylic acid (30 mg, 0.29 mmol), DIEA (100 mg, 0.78 mmol) and HATU (80 mg, 0.21 mmol) at 25° C. The reaction was stirred at 25° C. for 1 hour and then concentrated under vacuum. The residue was purified by Prep-HPLC and chiral HPLC to afford two enantiomers. The two enantiomers were treated with 1,4-dioxane solution of HCl (0.04 M) to afford their HCl salts. Relative stereochemistry are as drawn. Absolute stereochemistry was arbitrarily assigned.

Enantiomer 1: Compound 545a (21.3 mg, 0.0389 mmol, 20.7% yield). $R_T$ 2.853 min (CHIRALPAK IG-3, 0.46*5 cm, 3 μm; MTBE (0.1% DEA):MeOH=70:30 in 8 min; 1 mL/min). LCMS (ESI) [M+H]$^+$=511.2, $R_T$ 1.943 min, Method K; $^1$H NMR (300 MHz, DMSO-d$_6$) δ 10.45 (s, 1H), 9.40 (s, 1H), 7.99 (s, 1H), 7.52 (s, 1H), 6.91 (d, J=6.1 Hz, 1H), 5.62 (bs, 1H), 5.31-5.19 (m, 2H), 4.89 (s, 1H), 4.69-4.67 (m, 2H), 4.45-4.43 (m, 2H), 4.28-4.26 (m, 2H), 3.88-3.85 (m, 1H), 3.47-3.46 (m, 2H), 2.18 (dt, J=17.6, 8.9 Hz, 1H), 2.00 (d, J=1.6 Hz, 3H), 1.50-1.36 (m, 1H), 1.13 (tt, J=12.3, 5.5 Hz, 1H).

Enantiomer 2: Compound 545b (20.8 mg, 0.038 mmol, 20.2% yield). $R_T$ 4.366 min (CHIRALPAK IG-3, 0.46*5 cm, 3 μm; MTBE (0.1% DEA):MeOH=70:30 in 8 min; 1 mL/min). LCMS (ESI) [M+H]$^+$=511.2, $R_T$ 1.943 min, Method K; $^1$H NMR (300 MHz, DMSO-d$_6$) δ 10.45 (s, 1H), 9.40 (s, 1H), 7.99 (s, 1H), 7.52 (s, 1H), 6.91 (d, J=6.1 Hz, 1H), 5.62 (bs, 1H), 5.31-5.19 (m, 2H), 4.89 (s, 1H), 4.69-4.67 (m, 2H), 4.45-4.43 (m, 2H), 4.28-4.26 (m, 2H), 3.88-3.85 (m, 1H), 3.47-3.46 (m, 2H), 2.18 (dt, J=17.6, 8.9 Hz, 1H), 2.00 (d, J=1.6 Hz, 3H), 1.50-1.36 (m, 1H), 1.13 (tt, J=12.3, 5.5 Hz, 1H).

Example 234

(3S,4S)-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3R,4R)-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate (Compound 546a and Compound 546b)

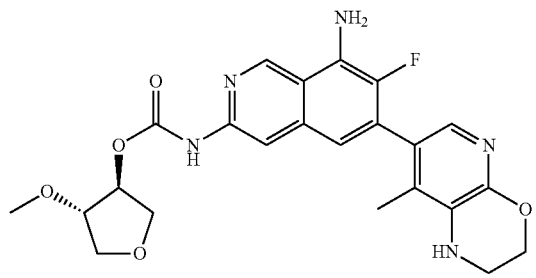

606
-continued

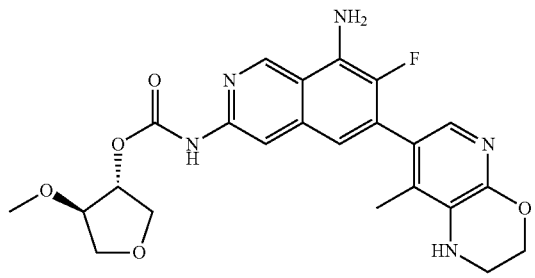

Step 1: (±)-trans-tert-Butyl 7-(8-((tert-butoxycarbonyl)amino)-7-fluoro-3-((((4-methoxytetrahydrofuran-3-yl)oxy)carbonyl)amino)isoquinolin-6-yl)-8-methyl-2,3-dihydro-1H-pyrido[2,3-b][1,4]oxazine-1-carboxylate

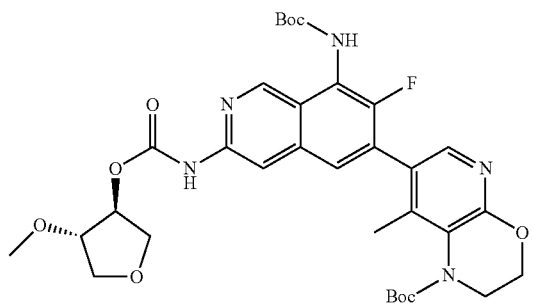 [SMILES: CO[C@H]1COC[C@@H]1OC(=O)Nc1cc2cc(-c3cnc4c(c3C)N(C(=O)OC(C)(C)C)CCO4)c(F)c(NC(=O)OC(C)(C)C)c2cn1]

To a solution of tert-butyl 7-[3-amino-8-(tert-butoxycarbonylamino)-7-fluoro-6-isoquinolyl]-8-methyl-2,3-dihydropyrido[2,3-b][1,4 chromatography]oxazine-1-carboxylate (3000.0 mg, 5.71 mmol) and trans-4-methoxytetrahydrofuran-3-ol (2040.0 mg, 17.27 mmol) in dichloromethane (300 mL) was added DIEA (3690.0 mg, 28.6 mmol) at room temperature. Then triphosgene (1800.0 mg, 6.07 mmol) was added and purified by the mixture was stirred at 0° C. for 2 hours. The reaction mixture was concentrated under vacuum. The residue was purified by flash chromatography on silica gel eluting with petroleum ether/ethyl acetate (1:1) to afford (±)-trans-tert-butyl 7-(8-((tert-butoxycarbonyl)amino)-7-fluoro-3-((((4-methoxytetrahydrofuran-3-yl)oxy)carbonyl)amino)isoquinolin-6-yl)-8-methyl-2,3-dihydro-1H-pyrido[2,3-b][1,4]oxazine-1-carboxylate (2100 mg, 3.1357 mmol, 54.9% yield) as a yellow solid. LCMS (ESI) [M+H]$^+$=670.

Step 2: (±)-trans-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate

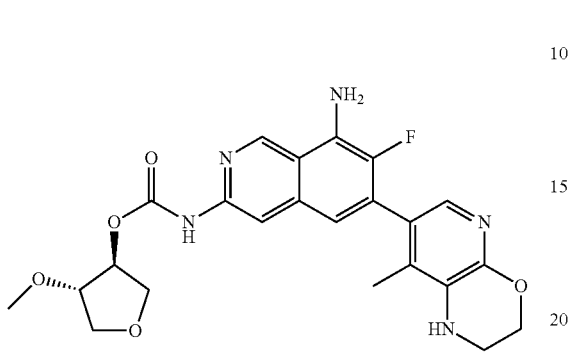

A solution of (±)-trans-tert-butyl 7-(8-((tert-butoxycarbonyl)amino)-7-fluoro-3-((((4-methoxytetrahydrofuran-3-yl)oxy)carbonyl)amino)isoquinolin-6-yl)-8-methyl-2,3-dihydro-1H-pyrido[2,3-b][1,4]oxazine-1-carboxylate (1500.0 mg, 2.24 mmol) in dichloromethane (10 mL) and TFA (10 mL) was stirred for 1 h at room temperature. The solvent was concentrated under vacuum. The residue was diluted with CH$_3$CN. The reaction mixture was adjusted to pH 8 with NaHCO$_3$. After filtration the solids were collected and washed by MeOH (50 mL) to afford (±)-trans-4-methoxytetrahydrofuran-3-yl (8-amino-7-fluoro-6-(8-methyl-2,3-dihydro-1H-pyrido[2,3-b][1,4]oxazin-7-yl)isoquinolin-3-yl) carbamate (602.8 mg, 1.252 mmol, 55.9% yield) as a yellow solid. LCMS (ESI) [M+H]$^+$=470.2, R$_T$ 2.543 min, Method K; $^1$H NMR (400 MHz, DMSO-d$_6$) δ 10.21 (s, 1H), 9.34 (s, 1H), 7.98 (s, 1H), 7.33 (s, 1H), 6.86 (d, J=6.4 Hz, 1H), 6.21 (s, 2H), 5.66 (s, 1H), 5.15 (d, J=4.8 Hz, 1H), 4.30-4.27 (m, 2H), 3.99-3.91 (m, 3H), 3.79 (d, J=10.4 Hz, 1H), 3.69-3.36 (m, 1H), 3.37 (s, 5H), 1.92 (s, 3H).

The racemic mixture was further purified by chiral SFC (Chiralcel OX; isocratic 50% MeOH with 0.1% NH$_4$OH) to give the two single enantiomers. Relative stereochemistry are as drawn. Absolute stereochemistry was arbitrarily assigned.

Enantiomer 1 (Compound 546a) (39 mg): R$_T$ 0.707 min (Chiralcel OX; isocratic 50% MeOH with 0.1% NH$_4$OH, 2.5 min run time). LCMS (ESI) [M+H]$^+$=470.2, R$_T$ 3.35, method=N. 1H-NMR (400 MHz, DMSO-d$_6$) δ 10.21 (s, 1H), 9.35 (s, 1H), 7.97 (s, 1H), 7.33 (s, 1H), 6.86 (d, J=6.1 Hz, 1H), 6.21 (s, 2H), 5.66 (s, 1H), 5.15 (d, J=4.2 Hz, 1H), 4.29 (t, J=4.4 Hz, 2H), 4.02-3.89 (m, 3H), 3.79 (m 1H), 3.68 (m, 1H), 3.37 (s, 5H), 1.92 (d, J=1.6 Hz, 3H).

Enantiomer 2 (Compound 546b) (19 mg): R$_T$ 0.901 min (Chiralcel OX; isocratic 50% MeOH with 0.1% NH$_4$OH, 2.5 min run time). LCMS (ESI) [M+H]$^+$=470.2, R$_T$ 3.36, method=N. $^1$H-NMR (400 MHz, DMSO-d$_6$) δ 10.21 (s, 1H), 9.34 (s, 1H), 7.97 (s, 1H), 7.33 (s, 1H), 6.86 (d, J=6.1 Hz, 1H), 6.21 (s, 2H), 5.66 (s, 1H), 5.15 (d, J=4.2 Hz, 1H), 4.29 (t, J=4.4 Hz, 2H), 4.02-3.89 (m, 3H), 3.79 (m, 1H), 3.68 (m, 1H), 3.37 (s, 5H), 1.92 (d, J=1.6 Hz, 3H).

Example 235

(R)-Tetrahydrofuran-3-yl (8-amino-6-(7-cyano-4-methyl-5,6,7,8-tetrahydro-1,5-naphthyridin-3-yl)-7-fluoroisoquinolin-3-yl)carbamate (Compound 547a)

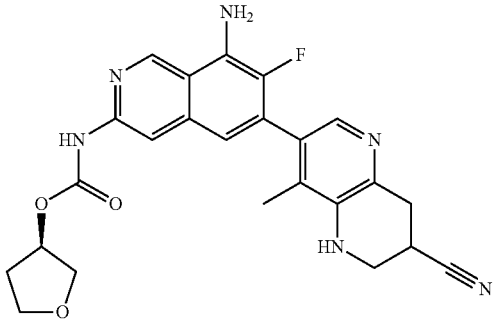 [SMILES: Cc1c(-c2cc3cc(NC(=O)O[C@@H]4CCOC4)ncc3c(N)c2F)cnc2c1NCC(C#N)C2]

Step 1: tert-Butyl N-(5-bromo-2-iodo-4-methyl-3-pyridyl)-N-(2-cyanoallyl)carbamate

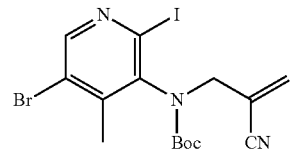 [SMILES: C=C(C#N)CN(C(=O)OC(C)(C)C)c1c(I)ncc(Br)c1C]

To a solution of tert-butyl N-(5-bromo-2-iodo-4-methyl-3-pyridyl)carbamate (3.2 g, 7.75 mmol) in DMF (80 mL) was added sodium hydride (0.22 g, 9.17 mmol) at 0° C. The reaction was stirred for 30 min at 0° C. Then a solution of 2-(bromomethyl)prop-2-enenitrile (1.5 g, 10.27 mmol) in DMF (5 ml) was added dropwise. The resulting mixture was stirred at 0° C. for 1 hour. The reaction was quenched with water and extracted with ethyl acetate. The organic layers were combined, washed with water, dried over anhydrous sodium sulfate, filtered and concentrated under vacuum. The residue was purified by flash chromatography on silica gel eluting with petroleum ether/ethyl acetate (4/1) to afford tert-butyl N-(5-bromo-2-iodo-4-methyl-3-pyridyl)-N-(2-cyanoallyl)carbamate (3.3 g, 6.419 mmol, 82.8% yield) as a white solid. LCMS (ESI) [M+H]$^+$=478.

Step 2: tert-Butyl 7-bromo-3-cyano-8-methyl-3,4-dihydro-2H-1,5-naphthyridine-1-carboxylate

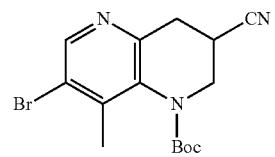 [SMILES: Cc1c(Br)cnc2c1N(C(=O)OC(C)(C)C)CC(C#N)C2]

A solution of indium chloride (416.0 mg, 1.88 mmol) and sodium methanolate (101.0 mg, 1.87 mmol) in THF (30 mL) was stirred at 25° C. for 30 min. Diphenylsilane (800 mg, 4.35 mmol) was added and the mixture was stirred at 25° C.

for 30 min. Then a solution of tert-butyl N-(5-bromo-2-iodo-4-methyl-3-pyridyl)-N-(2-cyanoallyl)carbamate (900 mg, 1.88 mmol) in THF (30 mL) and triethylborane (185 mg, 1.888 mmol) were added. The mixture was stirred at 0° C. for 4 hour. The reaction mixture was concentrated under vacuum. The residue was purified by flash chromatography on silica gel eluting with ethyl acetate/petroleum ether (1/1) to afford tert-butyl 7-bromo-3-cyano-8-methyl-3,4-dihydro-2H-1,5-naphthyridine-1-carboxylate (325 mg, 0.924 mmol, 49.1% yield) as pale yellow oil. LCMS (ESI) [M+H]$^+$=325.

Step 3: tert-Butyl-3-cyano-8-methyl-7-(4,4,5,5-tetramethyl-1,3,2-dioxaborolan-2-yl)-3,4-dihydro-2H-1,5-naphthyridine-1-carboxylate

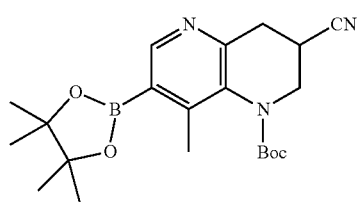 [SMILES: Cc1c(B2OC(C)(C)C(C)(C)O2)cnc2c1N(C(=O)OC(C)(C)C)CC(C#N)C2]

Under nitrogen, a mixture of tert-butyl 7-bromo-3-cyano-8-methyl-3,4-dihydro-2H-1,5-naphthyridine-1-carboxylate (200 mg, 0.57 mmol), bis(pinacolato)diboron (1.44 g, 5.67 mmol), 1,1'-bis(diphenylphosphino)ferrocene-palladium(II) dichloride dichloromethane complex (92 mg, 0.11 mmol) and potassium acetate (111 mg, 1.13 mmol) in 1,4-dioxane (15 mL) was stirred at 100° C. for 2 hours. The reaction mixture was diluted with ethyl acetate (10 mL) and filtered. The filtrate was concentrated under reduced pressure and purified by flash chromatography on silica gel eluting with ethyl acetate/petroleum ether (1:1) to afford tert-butyl 3-cyano-8-methyl-7-(4,4,5,5-tetramethyl-1,3,2-dioxaborolan-2-yl)-3,4-dihydro-2H-1,5-naphthyridine-1-carboxylate (124 mg, 0.2888 mmol, 50.8% yield) as a brown solid. LCMS (ESI) [M+H]$^+$=400.

Step 4: [(3R)-Tetrahydrofuran-3-yl]N-(8-chloro-7-fluoro-6-iodo-3-isoquinolyl)carbamate

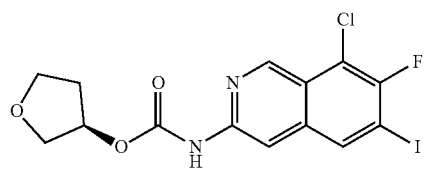 [SMILES: O=C(Nc1cc2cc(I)c(F)c(Cl)c2cn1)O[C@@H]1CCOC1]

Under nitrogen, a mixture of 8-chloro-7-fluoro-6-iodo-isoquinolin-3-amine (1.2 g, 3.72 mmol), (R)-3-hydroxytetrahydrofuran (0.65 g, 7.39 mmol) and N,N-diisopropylethylamine (6.83 g, 37.12 mmol) in dichloromethane (55 ml) was added triphosgene (1.1 g, 3.7 mmol) in dichloromethane (5 ml). The mixture was stirred at 0° C. for 1 hour. The reaction mixture was concentrated under vacuum. The residue was purified by flash chromatography on silica gel eluting with dichloromethane/methanol (97/3) to afford [(3R)-tetrahydrofuran-3-yl]N-(8-chloro-7-fluoro-6-iodo-3-isoquinolyl)carbamate (900 mg, 2.061 mmol, 55.5% yield) as a brown solid. LCMS (ESI) [M+H]$^+$=437.

Step 5: tert-Butyl 7-[8-chloro-7-fluoro-3-[[(3R)-tetrahydrofuran-3-yl]oxycarbonylamino]-6-isoquinolyl]-3-cyano-8-methyl-3,4-dihydro-2H-1,5-naphthyridine-1-carboxylate

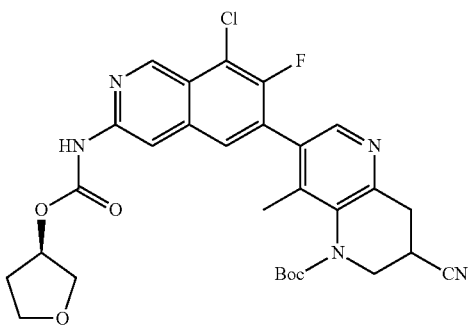 [SMILES: Cc1c(-c2cc3cc(NC(=O)O[C@@H]4CCOC4)ncc3c(Cl)c2F)cnc2c1N(C(=O)OC(C)(C)C)CC(C#N)C2]

Under nitrogen, to a mixture of tert-butyl 3-cyano-8-methyl-7-(4,4,5,5-tetramethyl-1,3,2-dioxaborolan-2-yl)-3,4-dihydro-2H-1,5-naphthyridine-1-carboxylate (100 mg, 0.25 mmol), [(3R)-tetrahydrofuran-3-yl]N-(8-chloro-7-fluoro-6-iodo-3-isoquinolyl)carbamate (131 mg, 0.30 mmol), 1,1'-bis(diphenylphosphino)ferrocene-palladium(II) dichloride dichloromethane complex (40.9 mg, 0.050 mmol) and potassium carbonate (34.59 mg, 0.25 mmol) in 1,4-dioxane (10 mL) was added water (1 mL) at room temperature. Then reaction mixture was stirred at 90° C. for 2 hours. The reaction mixture was diluted with ethyl acetate and filtered. The filtrate was concentrated under reduced pressure. The residue was purified by flash chromatography on silica gel eluting with ethyl acetate/petroleum ether (1/4) to afford tert-butyl 7-[8-chloro-7-fluoro-3-[[(3R)-tetrahydrofuran-3-yl]oxycarbonylamino]-6-isoquinolyl]-3-cyano-8-methyl-3,4-dihydro-2H-1,5-naphthyridine-1-carboxylate (75 mg, 0.122 mmol, 48.8% yield) as a brown solid. LCMS (ESI) [M+H]$^+$=582.

Step 6: tert-Butyl 7-[8-chloro-7-fluoro-3-[[(3R)-tetrahydrofuran-3-yl]oxycarbonylamino]-6-isoquinolyl]-3-cyano-8-methyl-3,4-dihydro-2H-1,5-naphthyridine-1-carboxylate

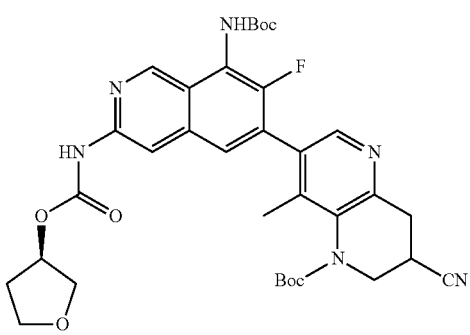 [SMILES: Cc1c(-c2cc3cc(NC(=O)O[C@@H]4CCOC4)ncc3c(NC(=O)OC(C)(C)C)c2F)cnc2c1N(C(=O)OC(C)(C)C)CC(C#N)C2]

Under nitrogen, a suspension of tert-butyl 7-[8-chloro-7-fluoro-3-[[(3R)-tetrahydrofuran-3-yl]oxycarbonylamino]-6-isoquinolyl]-3-cyano-8-methyl-3,4-dihydro-2H-1,5-naphthyridine-1-carboxylate (70 mg, 0.12 mmol), tert-butyl carbamate (140 mg, 1.20 mmol), Brettphos Pd G3 (22 mg, 0.020 mmol) and potassium carbonate (34 mg, 0.25 mmol) in 1,4-dioxane (3 ml) was stirred at 90° C. for 2 hours. After filtration, the filtrate was concentrated under reduced pressure. The residue was purified by flash chromatography on silica gel eluting with ethyl acetate/petroleum ether (1/4) to afford tert-butyl 7-[8-chloro-7-fluoro-3-[[(3R)-tetrahydrofuran-3-yl]oxycarbonylamino]-6-isoquinolyl]-3-cyano-8-methyl-3,4-dihydro-2H-1,5-naphthyridine-1-carboxylate (70 mg, 0.12 mmol) as a brown solid. LCMS (ESI) [M+H]$^+$=663.

Step 7: (R)-Tetrahydrofuran-3-yl (8-amino-6-(7-cyano-4-methyl-5,6,7,8-tetrahydro-1,5-naphthyridin-3-yl)-7-fluoroisoquinolin-3-yl)carbamate

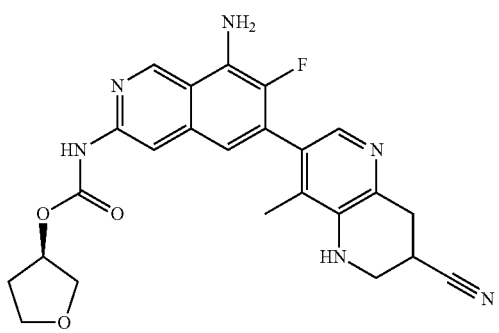 [SMILES: Cc1c(-c2cc3cc(NC(=O)O[C@@H]4CCOC4)ncc3c(N)c2F)cnc2c1NCC(C#N)C2]

A solution of tert-butyl 7-[8-(tert-butoxycarbonylamino)-7-fluoro-3-[[(3R)-tetrahydrofuran-3-yl]oxycarbonylamino]-6-isoquinolyl]-3-cyano-8-methyl-3,4-dihydro-2H-1,5-naphthyridine-1-carboxylate (45 mg, 0.070 mmol) in dichloromethane (2.5 mL) and TFA (0.60 mL) was stirred at 25° C. for 2 hours. The reaction mixture was concentrated under vacuum and purified by Prep-HPLC (X select CSH OBD Column 30*150 mm, 5 μm, n; Mobile Phase A: Water (0.1% FA), Mobile Phase B: ACN; Flow rate: 60 mL/min; Gradient: 5% B to 25% B in 7 min) to afford [(3R)-tetrahydrofuran-3-yl]N-[8-amino-6-(7-cyano-4-methyl-5,6,7,8-tetrahydro-1,5-naphthyridin-3-yl)-7-fluoro-3-isoquinolyl]carbamate (15.3 mg, 0.0321 mmol, 47.3% yield) as a yellow solid (Mixture of diastereomers). LCMS (ESI) [M+H]$^+$=463.2, $R_T$ 4.045 min., Method J; $^1$H NMR (300 MHz, DMSO-d$_6$) δ 10.20 (s, 1H), 9.39 (s, 1H), 8.01 (s, 2H), 6.96 (s, 1H), 6.52-6.37 (m, 2H), 5.33-5.24 (m, 1H), 3.92-3.69 (m, 4H), 3.57 (dd, J=24.2, 10.7 Hz, 3H), 3.48-3.35 (m, 2H), 2.28-2.12 (m, 2H), 2.09-1.94 (m, 4H).

Example 236

(R)-tetrahydrofuran-3-yl (8-amino-7-fluoro-6-((S)-5-hydroxy-4-methyl-6,7-dihydro-5H-cyclopenta[b]pyridin-3-yl)isoquinolin-3-yl)carbamate and (R)-tetrahydrofuran-3-yl (8-amino-7-fluoro-6-((R)-5-hydroxy-4-methyl-6,7-dihydro-5H-cyclopenta[b]pyridin-3-yl)isoquinolin-3-yl)carbamate (Compound 548a and Compound 548b)

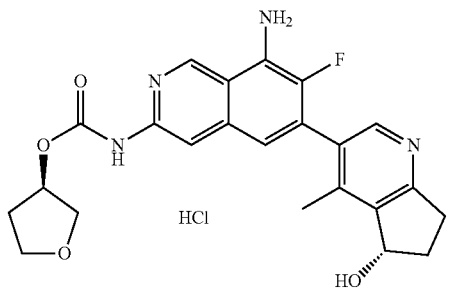

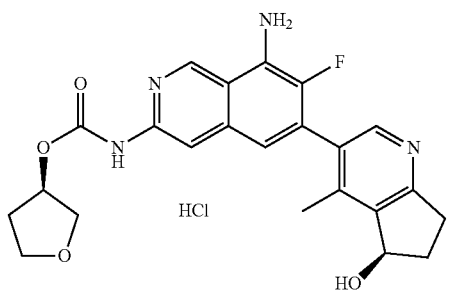

Step 1: Methyl 5-bromo-4-methyl-1-oxido-pyridin-1-ium-3-carboxylate

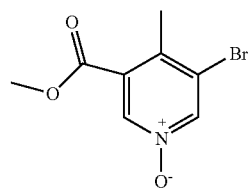

A solution of methyl 5-bromo-4-methyl-pyridine-3-carboxylate (2500.0 mg, 10.87 mmol) and m-CPBA (3756.0 mg, 21.84 mmol) in dichloromethane (20 mL) was stirred at room temperature for 2 hours. The reaction was quenched by aq. sodium thiosulfate. The pH of the solution was adjusted to pH 7-8 with a saturated aqueous NaHCO$_3$ solution. The resulting solution was extracted with dichloromethane. The organic layers were combined and concentrated under vacuum to afford methyl 5-bromo-4-methyl-1-oxido-pyridin-1-ium-3-carboxylate (2400 mg, 9.75 mmol, 89% yield) as a white solid. LCMS (ESI) [M+H]$^+$=246.0.

Step 2: Methyl 2,5-dibromo-4-methyl-pyridine-3-carboxylate

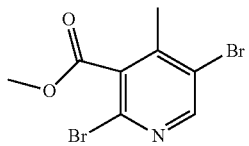

To a solution of methyl 5-bromo-4-methyl-1-oxido-pyridin-1-ium-3-carboxylate (1000.0 mg, 4.06 mmol) in dichloromethane (20 mL) was added POBr$_3$ (1161.0 mg, 4.07 mmol) at room temperature. The mixture was stirred at 65° C. for 2 hours. The reaction was quenched with water and neutralized with aq. NaHCO$_3$. The mixture was extracted with ethyl acetate. The organic layers were combined, dried over anhydrous sodium sulfate, filtered and concentrated under vacuum. The residue was purified by flash chromatography on silica gel eluting with petroleum ether/ethyl acetate (1:1) to afford methyl 2,5-dibromo-4-methyl-pyridine-3-carboxylate (500 mg, 1.62 mmol, 40% yield) as a colorless oil. LCMS (ESI) [M+H]$^+$=307.9.

Step 3: Methyl 5-bromo-2-(3-methoxy-3-oxo-propyl)-4-methyl-pyridine-3-carboxylate

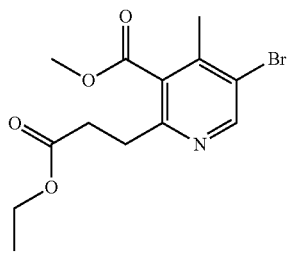 [SMILES: CCOC(=O)CCc1ncc(Br)c(C)c1C(=O)OC]

A suspension of Zn (2.96 g, 45.54 mmol) and I$_2$ (771.0 mg, 3.04 mmol) in N,N-dimethylacetamide (20 mL) was stirred at room temperature for 10 minutes. Then methyl 3-iodopropanoate (6.9 g, 32.24 mmol) was added. The mixture was stirred at room temperature for 2 hours and filtered. The filtrate was transferred to a mixture of methyl 2,5-dibromo-4-methyl-pyridine-3-carboxylate (2.33 g, 7.54 mmol) and Pd(PPh$_3$)$_4$ (2.36 g, 1.52 mmol) in N,N-dimethylacetamide (20 mL). The mixture was stirred at 70° C. for 2 hours and then diluted with ethyl acetate. The resulting solution was washed with water. The organic layer was concentrated under vacuum and purified by reverse phase chromatography eluting with ACN/water (NH$_4$HCO$_3$ 10 mmol/L) to afford methyl 5-bromo-2-(3-methoxy-3-oxo-propyl)-4-methyl-pyridine-3-carboxylate (1070 mg, 3.38 mmol, 45% yield) as a yellow solid. LCMS (ESI) [M+H]$^+$=330.0.

Step 4: Methyl 3-bromo-4-methyl-5-oxo-6,7-dihydrocyclopenta[b]pyridine-6-carboxylate

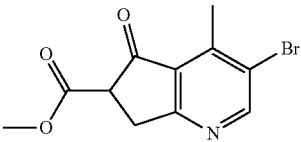 [SMILES: COC(=O)C1Cc2ncc(Br)c(C)c2C1=O]

To a solution of methyl 5-bromo-2-(3-ethoxy-3-oxo-propyl)-4-methyl-pyridine-3-carboxylate (1070.0 mg, 3.24 mmol) in tetrahydrofuran (30 mL) was added NaOMe (1.2 mL, 6.48 mmol). The mixture was stirred at 25° C. for 1 hour. After concentration, the residue was purified by reverse phase chromatography eluting with ACN/water (10 mmol/L NH$_4$HCO$_3$) to give methyl 3-bromo-4-methyl-5-oxo-6,7-dihydrocyclopenta[b]pyridine-6-carboxylate (372 mg, 1.31 mmol, 40% yield) as a white solid. LCMS (ESI) [M+H]$^+$=284.0.

Step 5: 3-Bromo-4-methyl-6,7-dihydrocyclopenta[b]pyridin-5-one

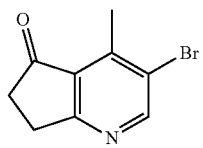

A solution of methyl 3-bromo-4-methyl-5-oxo-6,7-dihydrocyclopenta[b]pyridine-6-carboxylate (367.0 mg, 1.29 mmol) and LiCl (271.0 mg, 6.45 mmol) in DMSO (10 mL) and water (0.5 mL) was stirred at 100° C. for 1 hour. The residue was purified by reverse phase chromatography eluting with ACN/water (10 mmol/L NH$_4$HCO$_3$) to afford 3-bromo-4-methyl-6,7-dihydrocyclopenta[b]pyridin-5-one (234 mg, 1.035 mmol, 80% yield) as a white solid. LCMS (ESI) [M+H]$^+$=226.0.

Step 6: 3-Bromo-4-methyl-6,7-dihydro-5H-cyclopenta[b]pyridin-5-ol

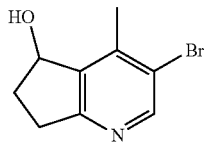

A solution of 3-bromo-4-methyl-6,7-dihydrocyclopenta[b]pyridin-5-one (568.0 mg, 2.51 mmol) and NaBH$_4$ (191.0 mg, 5.03 mmol) in methyl alcohol (10 mL) was stirred at 25° C. for 30 min. After concentration, the residue was purified by reverse phase chromatography eluting with ACN/water (10 mmol/L) to afford 3-bromo-4-methyl-6,7-dihydro-5H-cyclopenta[b]pyridin-5-ol (535 mg, 2.34 mmol, 93% yield) as a yellow solid. LCMS (ESI) [M+H]$^+$=228.0.

Step 7: (3-Bromo-4-methyl-6,7-dihydro-5H-cyclopenta[b]pyridin-5-yl)oxy-tert-butyl-dimethyl-silane

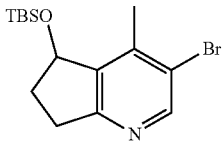 [SMILES: Cc1c(Br)cnc2c1C(O[Si](C)(C)C(C)(C)C)CC2]

A solution of 3-bromo-4-methyl-6,7-dihydro-5H-cyclopenta[b]pyridin-5-ol (630.0 mg, 2.76 mmol), imidazole (1134.0 mg, 16.66 mmol) and tert-butylchlorodimethylsilane (1660.0 mg, 11.07 mmol) in dichloromethane (15 mL) was stirred at 25° C. for 2 hours. The mixture was concentrated under vacuum. The residues were purified by flash chromatography on silica gel eluting with petroleum ether/ethyl acetate (80/20) to give (3-bromo-4-methyl-6,7-dihydro-5H-cyclopenta[b]pyridin-5-yl)oxy-tert-butyl-dimethyl-silane (850 mg, 2.48 mmol, 89% yield) as a white solid. LCMS (ESI) [M+H]$^+$=342.1.

Step 8: [5-[tert-Butyl(dimethyl)silyl]oxy-4-methyl-6,7-dihydro-5H-cyclopenta[b]pyridin-3-yl]boronic acid

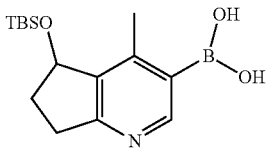 [SMILES: Cc1c(B(O)O)cnc2c1C(O[Si](C)(C)C(C)(C)C)CC2]

A mixture of (3-bromo-4-methyl-6,7-dihydro-5H-cyclopenta[b]pyridin-5-yl)oxy-tert-butyl-dimethyl-silane (800.0 mg, 2.34 mmol), Pd(dppf)Cl$_2$ (382.0 mg, 0.52 mmol), B$_2$Pin$_2$ (4750.0 mg, 18.7 mmol) and KOAc (688.0 mg, 7.02 mmol) in DMSO (10 mL) was stirred at 100° C. for 2 hours. The residue was purified by reverse phase chromatography eluting with ACN/water (10 mmol/L NH$_4$HCO$_3$) 5% to 100% in 30 min, then eluting with 100% MeOH to give [5-[tert-butyl(dimethyl)silyl]oxy-4-methyl-6,7-dihydro-5H-cyclopenta[b]pyridin-3-yl]boronic acid (510 mg, 1.66 mmol, 71% yield) as a brown solid. LCMS (ESI) [M+H]$^+$=308.2.

Step 9: [(3R)-Tetrahydrofuran-3-yl]N-[6-[5-[tert-butyl(dimethyl)silyl]oxy-4-methyl-6,7-dihydro-5H-cyclopenta[b]pyridin-3-yl]-8-chloro-7-fluoro-3-isoquinolyl]carbamate

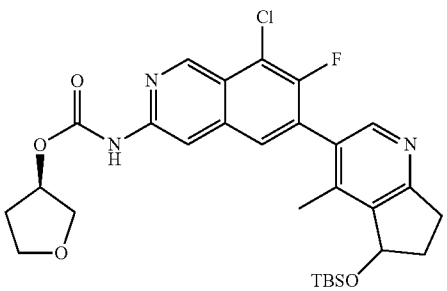 [SMILES: Cc1c(-c2cc3cc(NC(=O)O[C@@H]4CCOC4)ncc3c(Cl)c2F)cnc2c1C(O[Si](C)(C)C(C)(C)C)CC2]

A mixture of [(3R)-tetrahydrofuran-3-yl]N-(8-chloro-7-fluoro-6-iodo-3-isoquinolyl)carbamate (476.0 mg, 1.09 mmol), [5-[tert-butyl(dimethyl)silyl]oxy-4-methyl-6,7-dihydro-5H-cyclopenta[b]pyridin-3-yl]boronic acid (510.0 mg, 1.66 mmol), Pd(dppf)Cl$_2$ (178.0 mg, 0.24 mmol) and K$_2$CO$_3$ (451.0 mg, 3.27 mmol) in 1,4-dioxane (10 mL) and water (2 mL) was stirred at 70° C. for 3 hours. The mixture was concentrated under vacuum. The residue was purified by flash chromatography on silica gel eluting with petroleum ether/ethyl acetate (40/60) to give [(3R)-tetrahydrofuran-3-yl]N-[6-[5-[tert-butyl(dimethyl)silyl]oxy-4-methyl-6,7-dihydro-5H-cyclopenta[b]pyridin-3-yl]-8-chloro-7-fluoro-3-isoquinolyl]carbamate (300 mg, 0.52 mmol, 48% yield) as a light yellow solid. LCMS (ESI) [M+H]$^+$=572.2.

Step 10: [(3R)-Tetrahydrofuran-3-yl]N-[8-(tert-butoxycarbonylamino)-6-[5-[tert-butyl(dimethyl)silyl]oxy-4-methyl-6,7-dihydro-5H-cyclopenta[b]pyridin-3-yl]-7-fluoro-3-isoquinolyl]carbamate

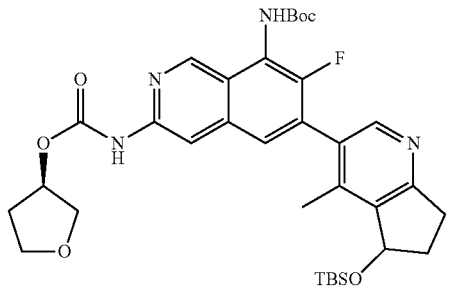 [SMILES: Cc1c(-c2cc3cc(NC(=O)O[C@@H]4CCOC4)ncc3c(NC(=O)OC(C)(C)C)c2F)cnc2c1C(O[Si](C)(C)C(C)(C)C)CC2]

A mixture of [(3R)-tetrahydrofuran-3-yl]N-[6-[5-[tert-butyl(dimethyl)silyl]oxy-4-methyl-6,7-dihydro-5H-cyclopenta[b]pyridin-3-yl]-8-chloro-7-fluoro-3-isoquinolyl]carbamate (400.0 mg, 0.70 mmol), tert-butyl carbamate (2040.0 mg, 17.41 mmol), Pd$_2$(dba)$_3$CHCl$_3$ (142.0 mg, 0.14 mmol), Brettphos (147.0 mg, 0.27 mmol) and Cs$_2$CO$_3$ (680.0 mg, 2.09 mmol) in 1,4-dioxane (5 mL) was stirred at 100° C. for 3 hours. The mixture was concentrated under vacuum and purified by flash chromatography on silica gel eluting with petroleum ether/ethyl acetate (20/80) to give [(3R)-tetrahydrofuran-3-yl]N-[8-(tert-butoxycarbonylamino)-6-[5-[tert-butyl (dimethyl)silyl]oxy-4-methyl-6,7-dihydro-5H-cyclopenta[b]pyridin-3-yl]-7-fluoro-3-isoquinolyl]carbamate (270 mg, 0.413 mmol, 59% yield) as a light yellow solid. LCMS (ESI) [M+H]$^+$=653.3.

Step 11: [(3R)-Tetrahydrofuran-3-yl]N-[8-(tert-butoxycarbonylamino)-7-fluoro-6-(5-hydroxy-4-methyl-6,7-dihydro-5H-cyclopenta[b]pyridin-3-yl)-3-isoquinolyl]carbamate

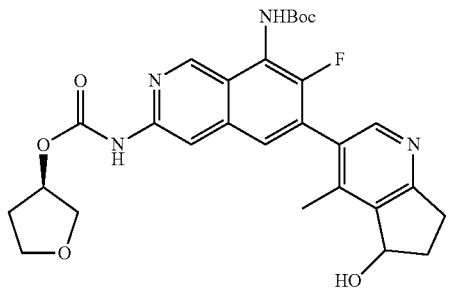 [SMILES: Cc1c(-c2cc3cc(NC(=O)O[C@@H]4CCOC4)ncc3c(NC(=O)OC(C)(C)C)c2F)cnc2c1C(O)CC2]

A mixture of [(3R)-tetrahydrofuran-3-yl]N-[8-(tert-butoxycarbonylamino)-6-[5-[tert-butyl(dimethyl)silyl]oxy-4-methyl-6,7-dihydro-5H-cyclopenta[b]pyridin-3-yl]-7-fluoro-3-isoquinolyl]carbamate (240.0 mg, 0.37 mmol) and TBAF (233.0 mg, 0.74 mmol) in tetrahydrofuran (4 mL) was stirred at 25° C. for 2 hours. The mixture was concentrated under vacuum and purified by reverse phase chromatography eluting with ACN/water (10 mmol/L NH$_4$HCO$_3$) to give[(3R)-tetrahydrofuran-3-yl]N-[8-(tert-butoxycarbonylamino)-7-fluoro-6-(5-hydroxy-4-methyl-6,7-dihydro-5H-cyclopenta[b]pyridin-3-yl)-3-isoquinolyl]carbamate (190 mg, 0.35 mmol, 96% yield) as a light yellow solid. LCMS (ESI) [M+H]$^+$=539.2.

Step 12: (R)-Tetrahydrofuran-3-yl (8-amino-7-fluoro-6-((S)-5-hydroxy-4-methyl-6,7-dihydro-5H-cyclopenta[b]pyridin-3-yl)isoquinolin-3-yl)carbamate and (R)-Tetrahydrofuran-3-yl (8-amino-7-fluoro-6-((R)-5-hydroxy-4-methyl-6,7-dihydro-5H-cyclopenta[b]pyridin-3-yl)isoquinolin-3-yl)carbamate

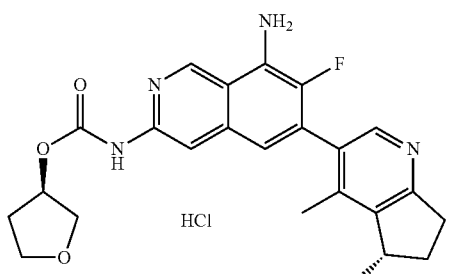

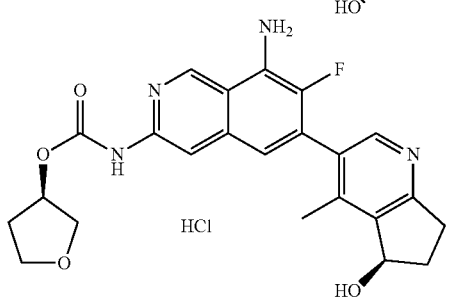

A solution of [(3R)-tetrahydrofuran-3-yl]N-[8-(tert-butoxycarbonylamino)-7-fluoro-6-[(5S)-5-hydroxy-4-methyl-6,7-dihydro-5H-cyclopenta[b]pyridin-3-yl]-3-isoquinolyl]carbamate (150.0 mg, 0.28 mmol) and TFA (2.0 mL) in dichloromethane (10 mL) was stirred at 25° C. for 1 hour. After concentration, the residue was purified by Prep-HPLC to afford a mixture of stereoisomers. The mixture was separated by chiral HPLC to afford two stereoisomers. Absolute stereochemistry of alcohol was arbitrarily assigned.

Isomer 1 (Compound 548a) (16.7 mg, 0.038 mmol, 14% yield); R$_T$ 1.297 min (CHIRALPAK IC-3 0.46*5 cm; 3 μm; MTBE (0.1% DEA):MeOH=90:10; 1.0 ml/min). LCMS (ESI) [M+H]$^+$=539.2, R$_T$ 1.761 min., Method K; $^1$H NMR (300 MHz, DMSO-d$_6$) δ 10.23 (s, 1H), 9.42 (s, 1H), 8.72 (s, 1H), 8.03 (s, 1H), 6.99 (d, J=6.0 Hz, 1H), 5.82-4.86 (m, 5H), 3.90-3.70 (m, 4H), 3.42-3.30 (m, 1H), 3.19-2.96 (m, 1H), 2.51-2.42 (m, 4H), 2.32-1.87 (m, 3H).

Isomer 2 (Compound 548b) (14.5 mg, 0.0331 mmol, 11.9% yield); R$_T$ 2.128 min (CHIRALPAK IC-3 0.46*5 cm;

3 μm; MTBE (0.1% DEA):MeOH=90:10; 1.0 ml/min). LCMS (ESI) [M+H]$^+$=539.2, R$_T$ 1.761 min., Method K; $^1$H NMR (300 MHz, DMSO-d$_6$) δ 10.23 (s, 1H), 9.42 (s, 1H), 8.72 (s, 1H), 8.03 (s, 1H), 6.99 (d, J=6.0 Hz, 1H), 5.82-4.86 (m, 5H), 3.90-3.70 (m, 4H), 3.42-3.30 (m, 1H), 3.19-2.96 (m, 1H), 2.51-2.42 (m, 4H), 2.32-1.87 (m, 3H).

Example 237

(1s,3s)-3-(2-Cyanopropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate and (1r,3r)-3-(2-Cyanopropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate (Compound 549a and Compound 549b)

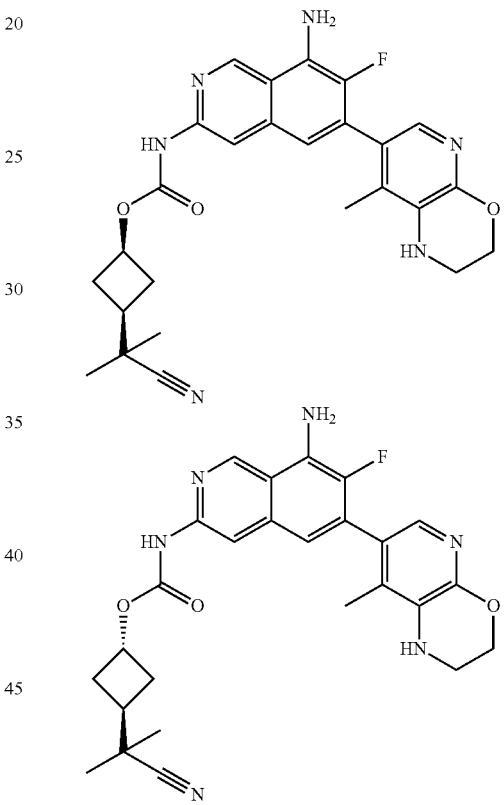

Step 1: 2-[3-[tert-Butyl(diphenyl)silyl]oxycyclobutyl]-2-methyl-propanenitrile

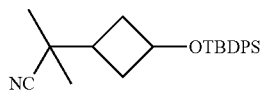

Under nitrogen, to a solution of 2-[3-[tert-butyl(diphenyl)silyl]oxycyclobutyl]acetonitrile (2600 mg, 7.44 mmol) in tetrahydrofuran (130 mL) was added LDA (24 mL, 44.63 mmol) at 0° C. The resulting solution was stirred for 1 h at 0° C. Then iodomethane (5200 mg, 36.62 mmol) was added at 0° C. and the mixture was stirred at room temperature for 3 hours. The reaction was quenched by an aqueous NH₄Cl solution. The resulting mixture was extracted with ethyl acetate, filtrated and concentrated under vacuum. The residue was purified by flash chromatography on silica gel eluting with petroleum ether/dichloromethane (2/1) to afford 2-[3-[tert-butyl(diphenyl)silyl]oxycyclobutyl]-2-methyl-propanenitrile (1.6 g, 4.237 mmol, 57% yield) as a colorless oil. LCMS (ESI) [M+H]⁺=378.

Step 2:
2-(3-Hydroxycyclobutyl)-2-methyl-propanenitrile

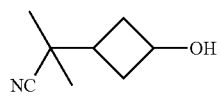

To a solution of 2-[3-[tert-butyl(diphenyl)silyl]oxycyclobutyl]-2-methyl-propanenitrile (1.6 g, 4.24 mmol) in THF (6 mL) was added TBAF (3.317 g, 12.71 mmol) at room temperature. The resulting mixture was stirred for 16 h at 25° C. The residue was purified by flash chromatography on silica gel eluting with petroleum ether/ethyl acetate (4/1) to afford 2-(3-hydroxycyclobutyl)-2-methyl-propanenitrile (450 mg, 3.233 mmol, 76.3% yield) as a colorless oil. LCMS (ESI) [M+H]⁺=140.

Step 3: tert-Butyl 7-[8-(tert-butoxycarbonyl amino)-3-[[3-(1-cyano-1-methyl-ethyl)cyclobutoxy]carbonylamino]-7-fluoro-6-isoquinolyl]-8-methyl-2,3-dihydropyrido[2,3-b][1,4]oxazine-1-carboxylate

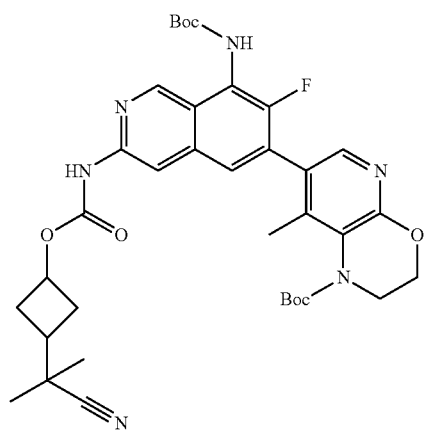 [SMILES: Cc1c(-c2cc3cc(NC(=O)OC4CC(C(C)(C)C#N)C4)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (300 mg, 0.57 mmol) and 2-(3-hydroxycyclobutyl)-2-methyl-propanenitrile (300 mg, 2.16 mmol) in dichloromethane (30 mL) was added DIEA (800 mg, 6.20 mmol) at room temperature. Then triphosgene (200 mg, 0.6700 mmol) was added and the mixture was stirred at 0° C. for 1 hour. The residue was purified by flash chromatography on silica gel eluting with petroleum ether/ethyl acetate (1/2) to afford tert-butyl 7-[8-(tert-butoxycarbonylamino)-3-[[3-(1-cyano-1-methyl-ethyl)cyclobutoxy]carbonylamino]-7-fluoro-6-isoquinolyl]-8-methyl-2,3-dihydropyrido[2,3-b][1,4]oxazine-1-carboxylate (260 mg, 0.376 mmol, 65.9% yield) as a yellow solid. LCMS (ESI) [M+H]⁺=691.

Step 4: (1s,3s)-3-(2-Cyanopropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate and (1r,3r)-3-(2-Cyanopropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate

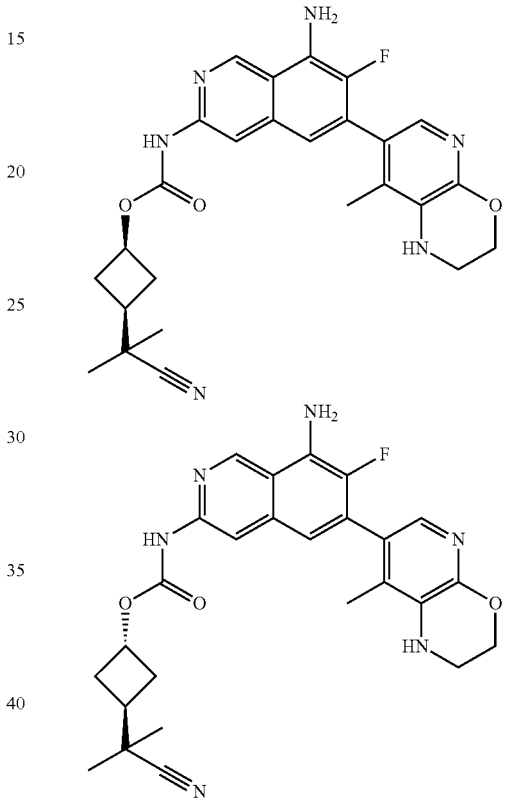

To a solution of tert-butyl 7-[8-(tert-butoxycarbonylamino)-3-[[3-(1-cyano-1-methyl-ethyl)cyclobutoxy]carbonylamino]-7-fluoro-6-isoquinolyl]-8-methyl-2,3-dihydropyrido[2,3-b][1,4]oxazine-1-carboxylate (260 mg, 0.38 mmol) in dichloromethane (8 mL) was added trifluoroacetic acid (2 mL, 0.38 mmol) at room temperature. The resulting solution was stirred for 1 h at 25° C. and then concentrated under vacuum. The crude product was purified by prep-HPLC and chiral-HPLC to afford two enantiomers. Stereochemistry was arbitrarily assigned.

Enantiomer 1 (Compound 549a) (2.4 mg, 0.0049 mmol, 1.3% yield). $R_T$ 2.064 min (CHIRALPAK IC-3, 0.46*5 cm, 3 μm; (Hex:DCM=3:1)(0.1% DEA):EtOH=50:50 in 5 min; 1 mL/min). LCMS (ESI) [M+H]⁺=491.2, $R_T$ 1.334 min, Method K; ¹H NMR (300 MHz, DMSO-d₆) δ 10.14 (s, 1H), 9.34 (s, 1H), 7.97 (s, 1H), 7.33 (s, 1H), 6.84 (d, J=6.2 Hz, 1H), 6.21 (s, 2H), 5.67 (s, 1H), 5.04 (p, J=6.7 Hz, 1H), 4.29-4.28 (m, 2H), 3.40-3.38 (m, 2H), 2.60-2.58 (m, 1H), 2.44-2.21 (m, 4H), 1.92 (d, J=1.6 Hz, 3H), 1.26 (s, 6H).

Enantiomer 2 (Compound 549b) (47.3 mg, 0.0964 mmol, 25.6% yield). $R_T$ 2.987 min (CHIRALPAK IC-3, 46*5 cm, 3 μm; (Hex:DCM=3:1)(0.1% DEA):EtOH=50:50; 1 mL/min). LCMS (ESI) [M+H]$^+$=491.2, R$_T$ 1.343 min., Method K; $^1$H NMR (300 MHz, DMSO-d$_6$) δ 10.14 (s, 1H), 9.34 (s, 1H), 7.97 (s, 1H), 7.33 (s, 1H), 6.84 (d, J=6.2 Hz, 1H), 6.21 (s, 2H), 5.67 (s, 1H), 5.04 (p, J=6.7 Hz, 1H), 4.29-4.28 (m, 2H), 3.40-3.38 (m, 2H), 2.60-2.58 (m, 1H), 2.44-2.21 (m, 4H), 1.92 (d, J=1.6 Hz, 3H), 1.26 (s, 6H).

Example 238

(1r,3r)-3-Morpholinocyclobutyl (8-amino-7-fluoro-6-(8-methyl-2,3-dihydro-1H-pyrido[2,3-b][1,4]oxazin-7-yl)isoquinolin-3-yl)carbamate (Compound 550a)

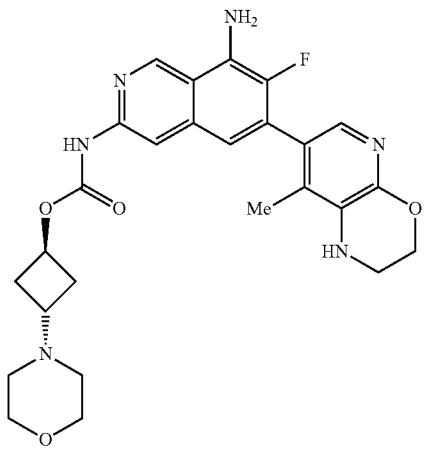

Step 1: trans-4-(3-Benzyloxycyclobutyl)morpholine

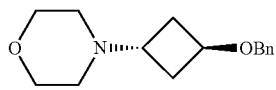

Under nitrogen, a solution of (3-benzyloxycyclobutyl)methanesulfonate (400.0 mg, 1.56 mmol) in morpholine (2.5 mL, 1.56 mmol) was stirred for 10 hours at 100° C. The reaction was concentrated under vacuum. The residue was purified by reverse phase chromatography eluting with ACN/water (10 mmol/L NH$_4$HCO$_3$) (60/40) to afford trans-4-(3-benzyloxycyclobutyl)morpholine (270 mg, 1.09 mmol, 70% yield) as a pale yellow oil. LC/MS (ESI) [M+H]$^+$= 248.2.

Step 2: trans-3-Morpholinocyclobutanol

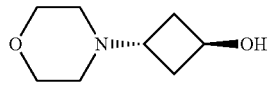 [SMILES: O[C@H]1C[C@H](N2CCOCC2)C1]

Under hydrogen, a mixture of trans-4-(3-benzyloxycyclobutyl)morpholine (260.0 mg, 1.05 mmol) and Pd/C (10%, 130.0 mg) in methyl alcohol (10 mL) was stirred at 40° C. for 24 hours. The reaction mixture was filtered and concentrated under vacuum. The residue was purified by flash chromatography on silica gel eluting with dichloromethane/methanol (10/1) to afford trans-3-morpholinocyclobutanol (165 mg, 1.05 mmol, 99% yield) as a yellow oil. LCMS (ESI) [M+H]$^+$=158.1. $^1$H NMR (400 MHz, DMSO-d$_6$) δ 4.92 (d, J=5.2 Hz, 1H), 4.19-4.07 (m, 1H), 3.56 (t, J=4.6 Hz, 4H), 2.79-2.65 (m, 1H), 2.23 (s, 4H), 2.09 (m, 2H), 1.83 (m, 2H).

Step 3: trans-tert-Butyl 7-[8-(tert-butoxycarbonylamino)-7-fluoro-3-[(3-morpholinocyclobutoxy)carbonylamino]-6-isoquinolyl]-8-methyl-2,3-dihydropyrido[2,3-b][1,4]oxazine-1-carboxylate

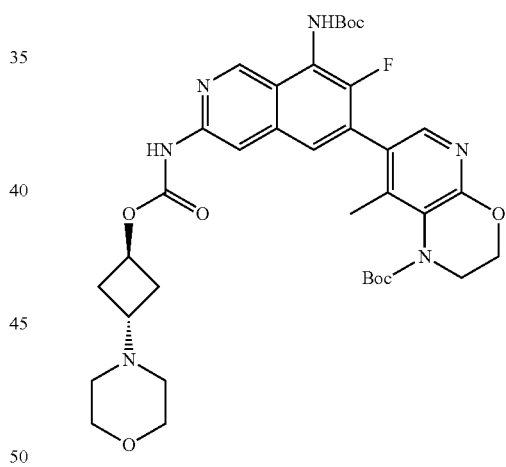

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (233.0 mg, 0.36 mmol) and DMAP (44.0 mg, 0.36 mmol) in DMF (5 mL) was added trans-3-morpholin-4-ylcyclobutanol (170.0 mg, 1.08 mmol) at 90° C. The mixture was stirred for 1 hour and concentrated under vacuum. The residue was purified by reverse phase chromatography eluting with ACN/water (10 mmol/L NH$_4$HCO$_3$) (42/58) to afford trans-tert-butyl 7-[8-(tert-butoxycarbonylamino)-7-fluoro-3-[(3-morpholinocyclobutoxy)carbonylamino]-6-isoquinolyl]-8-methyl-2,3-dihydropyrido[2,3-b][1,4]oxazine-1-carboxylate (110 mg, 0.15 mmol, 43% yield) as a white solid. LCMS (ESI) [M+H]$^+$= 709.3.

Step 4: (1r,3r)-3-morpholinocyclobutyl (8-amino-7-fluoro-6-(8-methyl-2,3-dihydro-1H-pyrido[2,3-b][1,4]oxazin-7-yl)isoquinolin-3-yl)carbamate (Compound 550a)

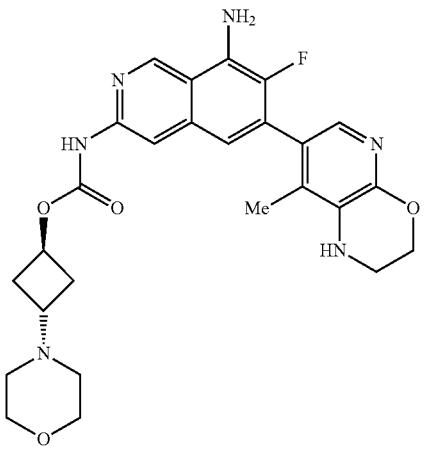

A solution of tert-butyl 7-[8-(tert-butoxycarbonylamino)-7-fluoro-3-[(3-morpholinocyclobutoxy)carbonylamino]-6-isoquinolyl]-8-methyl-2,3-dihydropyrido[2,3-b][1,4]oxazine-1-carboxylate (100.0 mg, 0.14 mmol) and TFA (2.0 mL) in dichloromethane (10 mL) was stirred at 25° C. for 3 hours. After concentration, the residue was purified by Prep-HPLC (Column: X select CSH OBD Column 30*150 mm, 5 μm; Water (0.1% FA):ACN=5% B to 21% B in 7 min; 60 mL/min) to afford (3-morpholinocyclobutyl) N-[8-amino-7-fluoro-6-(8-methyl-2,3-dihydro-1H-pyrido[2,3-b][1,4]oxazin-7-yl)-3-isoquinolyl]carbamate (42 mg, 0.083 mmol, 58% yield) as a pale yellow solid. LCMS (ESI) [M+H]⁺=509.2; $R_T$ 1.063 min, Method M; ¹H NMR (300 MHz, DMSO-d₆) δ 10.25 (s, 1H), 10.07 (s, 1H), 9.36 (s, 1H), 7.96 (s, 1H), 7.35 (s, 1H), 6.85 (d, J=6.2 Hz, 1H), 6.84-5.07 (m, 3H), 5.22-5.10 (m, 1H), 4.35-4.30 (m, 2H), 4.14-3.90 (m, 4H), 3.71-3.64 (m, 2H), 3.50-3.32 (m, 3H), 3.10-2.90 (m, 2H), 2.80-2.64 (m, 2H), 2.56-2.40 (m, 2H), 1.93 (s, J=1.7 Hz, 3H).

Example 239

(3-Cyclopropyl-3-hydroxy-cyclobutyl) N-[8-amino-7-fluoro-6-(8-methyl-2,3-dihydro-1H-pyrido[2,3-b][1,4]oxazin-7-yl)-3-isoquinolyl]carbamate (Compound 551a)

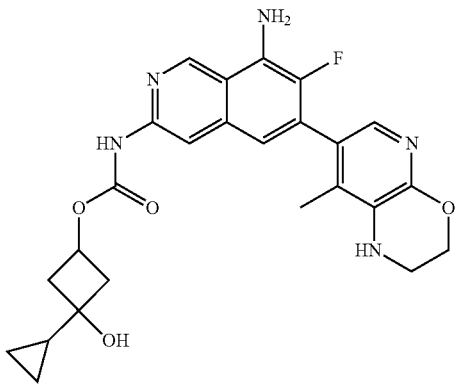 [SMILES: Cc1c(-c2cc3cc(NC(=O)OC4CC(O)(C5CC5)C4)ncc3c(N)c2F)cnc2c1NCCO2]

Step 1: 3-Benzyloxy-1-cyclopropyl-cyclobutanol

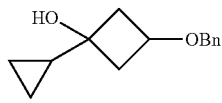 [SMILES: OC1(C2CC2)CC(OCc2ccccc2)C1]

Under nitrogen, to a solution of 3-(benzyloxy)cyclobutanone (500.0 mg, 2.84 mmol) in tetrahydrofuran (10 mL) was added cyclopropyl magnesium bromide (11 mL, 1 M, 11 mmol) at 0° C. The resulting solution was stirred for 1 hour at 25° C. The reaction was quenched by water and extracted with ethyl acetate. The organic layers were combined, dried over anhydrous sodium sulfate, filtered and concentrated under vacuum to afford 3-benzyloxy-1-cyclopropyl-cyclobutanol (600 mg, 2.75 mmol, 96% yield) as a yellow oil. LCMS (ESI) [M+H]⁺=219.1.

Step 2: 1-Cyclopropylcyclobutane-1,3-diol

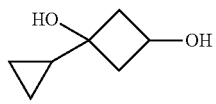

Under hydrogen (1 atm), a suspension of 3-benzyloxy-1-cyclopropyl-cyclobutanol (750.0 mg, 3.44 mmol) and Pd/C (10%, 400.0 mg, 3.44 mmol) in methyl alcohol (20 mL) was stirred for 24 hours at 40° C. After filtration, the filtrate was concentrated under vacuum. The residue was purified by flash chromatography on silica gel eluting with dichloromethane/methanol (10/1) to afford 1-cyclopropylcyclobutane-1,3-diol (200 mg, 1.56 mmol, 45% yield) as a yellow oil. LCMS (ESI) [M+H]⁺=129.1. ¹H NMR (300 MHz, DMSO-d₆) δ 4.86 (d, J=5.8 Hz, 1H), 3.17 (d, J=5.3 Hz, 2H), 2.18 (m, 2H), 1.88-1.75 (m, 2H), 0.98-0.81 (m, 1H), 0.34-0.23 (m, 2H), 0.18 (m, 2H).

Step 3: tert-Butyl 7-[8-(tert-butoxycarbonylamino)-3-[(3-cyclopropyl-3-hydroxy-cyclobutoxy)carbonylamino]-7-fluoro-6-isoquinolyl]-8-methyl-2,3-dihydropyrido[2,3-b][1,4]oxazine-1-carboxylate

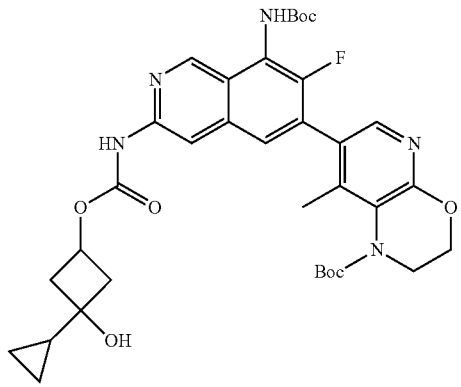 [SMILES: Cc1c(-c2cc3cc(NC(=O)OC4CC(O)(C5CC5)C4)ncc3c(NC(=O)OC(C)(C)C)c2F)cnc2c1N(C(=O)OC(C)(C)C)CCO2]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (200.0 mg, 0.310 mmol) and DMAP (38.0 mg, 0.31 mmol) in dichloromethane (5 mL) was added 1-cyclopropylcyclobutane-1,3-diol (119.0 mg, 0.93 mmol) at 25° C. The resulting solution was stirred for 24 hours at 60° C. The reaction mixture was concentrated under vacuum and purified by flash chromatography on silica gel eluting with dichloromethane/methanol (95/5) to afford tert-butyl 7-[8-(tert-butoxycarbonylamino)-3-[(3-cyclopropyl-3-hydroxy-cyclobutoxy)carbonylamino]-7-fluoro-6-isoquinolyl]-8-methyl-2,3-dihydropyrido[2,3-b][1,4]oxazine-1-carboxylate (140 mg, 0.20 mmol, 66% yield) as a light yellow solid. LCMS (ESI) [M+H]$^+$=680.1.

Step 4: (3-Cyclopropyl-3-hydroxy-cyclobutyl) N-[8-amino-7-fluoro-6-(8-methyl-2,3-dihydro-1H-pyrido[2,3-b][1,4]oxazin-7-yl)-3-isoquinolyl]carbamate

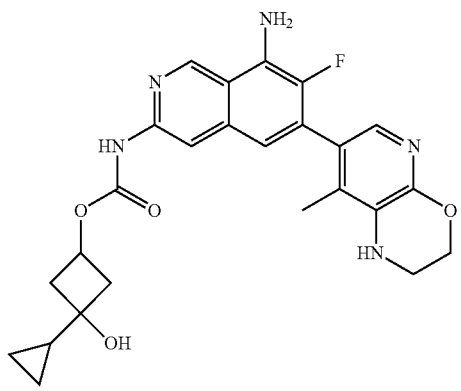 [SMILES: Cc1c(-c2cc3cc(NC(=O)OC4CC(O)(C5CC5)C4)ncc3c(N)c2F)cnc2c1NCCO2]

A solution of tert-butyl 7-[8-(tert-butoxycarbonylamino)-3-[(3-cyclopropyl-3-hydroxy-cyclobutoxy)carbonylamino]-7-fluoro-6-isoquinolyl]-8-methyl-2,3-dihydropyrido[2,3-b][1,4]oxazine-1-carboxylate (100.0 mg, 0.15 mmol) and HCl (1.0 mL, 4M, 4 mmol) in dichloromethane (10 mL) was stirred at 25° C. for 1 hour. After concentration the residue was purified by prep-HPLC (Column: X Bridge Prep OBD C18 Column, 30×150 mm, 5 μm; Water (10 mmol/L NH$_4$HCO$_3$): ACN=19% B to 40% B in 7 min; 60 mL/min) to afford (3-cyclopropyl-3-hydroxy-cyclobutyl) N-[8-amino-7-fluoro-6-(8-methyl-2,3-dihydro-1H-pyrido[2,3-b][1,4]oxazin-7-yl)-3-isoquinolyl]carbamate (4.2 mg, 0.0088 mmol, 6% yield) as a pale yellow solid (mixture of stereoisomers). LCMS (ESI) [M+H]$^+$=480.1, R$_T$ 4.468 min, Method M; $^1$H NMR (400 MHz, DMSO-d$_6$) δ 10.04 (s, 1H), 9.33 (s, 1H), 7.95 (s, 1H), 7.32 (s, 1H), 6.83 (s, 1H), 6.19 (s, 2H), 5.66 (s, 1H), 5.15-5.03 (m, 1H), 4.84 (s, 1H), 4.35-4.25 (m, 2H), 3.42-3.35 (m, 2H), 2.35-2.19 (m, 2H), 2.01-1.88 (m, 5H), 1.10-0.99 (m, 1H), 0.41-0.32 (m, 2H), 0.31-0.28 (m, 2H).

Example 240

1-(Methylsulfonyl)azetidin-3-yl (8-amino-7-fluoro-6-(8-methyl-2,3-dihydro-1H-pyrido[2,3-b][1,4]oxazin-7-yl)isoquinolin-3-yl)carbamate (Compound 552)

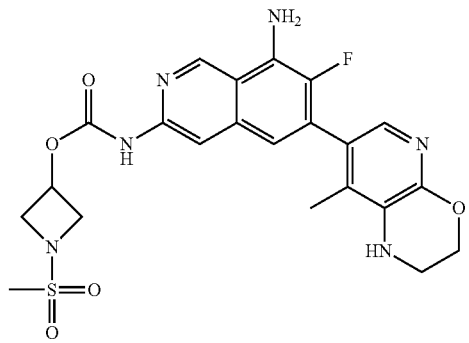 [SMILES: Cc1c(-c2cc3cc(NC(=O)OC4CN(S(C)(=O)=O)C4)ncc3c(N)c2F)cnc2c1NCCO2]

Step 1: tert-Butyl 7-[8-(tert-butoxycarbonylamino)-7-fluoro-3-[(1-methylsulfonylazetidin-3-yl)oxycarbonylamino]-6-isoquinolyl]-8-methyl-2,3-dihydropyrido[2,3-b][1,4]oxazine-1-carboxylate

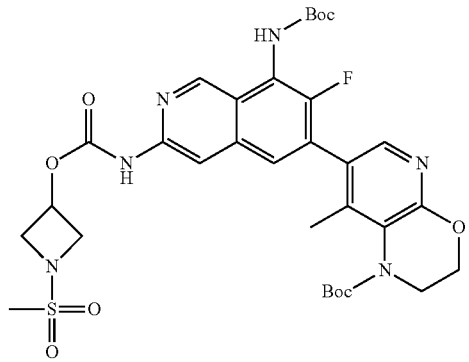 [SMILES: Cc1c(-c2cc3cc(NC(=O)OC4CN(S(C)(=O)=O)C4)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (150 mg, 0.29 mmol) and 1-methylsulfonylazetidin-3-ol (150 mg, 0.99 mmol) in dichloromethane (20 mL) was added DIEA (350 mg, 2.71 mmol) at room temperature. Then triphosgene (90 mg, 0.30 mmol) was added and the mixture was stirred at 0° C. for 1 h. The reaction was concentrated under vacuum. The residue was purified by flash chromatography on silica gel eluting with petroleum ether/ethyl acetate (1/5) to afford tert-butyl 7-[8-(tert-butoxycarbonylamino)-7-fluoro-3-[(1-methylsulfonylazetidin-3-yl)oxycarbonylamino]-6-isoquinolyl]-8-methyl-2,3-dihydropyrido[2,3-b][1,4]oxazine-1-carboxylate (120 mg, 0.1708 mmol, 59.8% yield) as a yellow solid. LCMS (ESI) [M+H]$^+$=703.

627

Step 2: 1-(Methylsulfonyl)azetidin-3-yl (8-amino-7-fluoro-6-(8-methyl-2,3-dihydro-1H-pyrido[2,3-b][1,4]oxazin-7-yl)isoquinolin-3-yl)carbamate

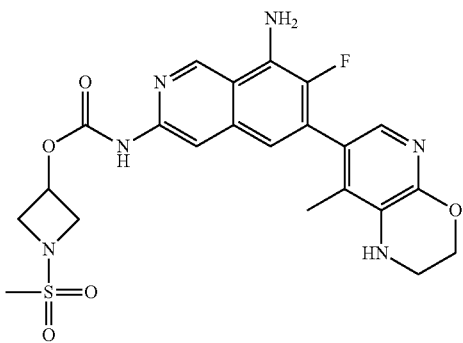

To a solution of tert-butyl 7-[8-(tert-butoxycarbonylamino)-7-fluoro-3-[(1-methylsulfonylazetidin-3-yl)oxycarbonylamino]-6-isoquinolyl]-8-methyl-2,3-dihydropyrido[2,3-b][1,4]oxazine-1-carboxylate (120 mg, 0.17 mmol) in dichloromethane (8 mL) was added TFA (2 mL) at 25° C. The reaction was stirred for 1 h at 25° C. and then concentrated under vacuum. The residue was purified by Prep-HPLC to afford (1-methylsulfonylazetidin-3-yl) N-[8-amino-7-fluoro-6-(8-methyl-2,3-dihydro-1H-pyrido[2,3-b][1,4]oxazin-7-yl)-3-isoquinolyl]carbamate (49.8 mg, 0.0991 mmol, 58% yield) as a yellow solid. LCMS (ESI) [M+H]$^+$= 503.2, $R_T$ 0.961 min, Method K. $^1$H NMR (400 MHz, DMSO-$d_6$) δ 10.42 (s, 1H), 9.37 (s, 1H), 7.96 (s, 1H), 7.37 (s, 1H), 6.87 (d, J=6.1 Hz, 1H), 6.26 (s, 2H), 5.77 (s, 1H), 5.21 (tt, J=6.7, 4.7 Hz, 1H), 4.32 (t, J=4.4 Hz, 2H), 4.24 (dd, J=9.5, 6.7 Hz, 2H), 3.94 (dd, J=9.7, 4.7 Hz, 2H), 3.39 (d, J=8.9 Hz, 2H), 3.08 (s, 3H), 1.94 (d, J=1.6 Hz, 3H).

Example 241

(3S,4R)-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate and (3R,4S)-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate (Compound 445c and Compound 445d)

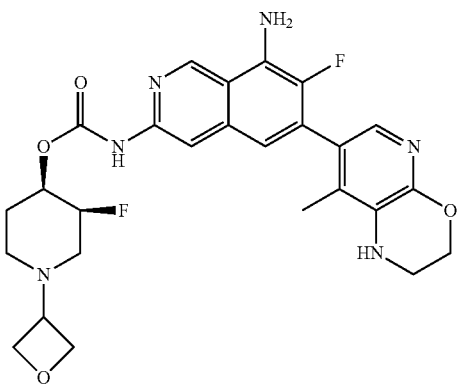

628

-continued

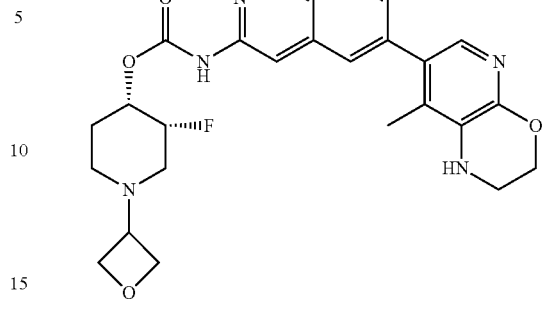

Step 1: (±)-cis-tert-Butyl 7-(3-((((1-(tert-butoxycarbonyl)-3-fluoropiperidin-4-yl)oxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

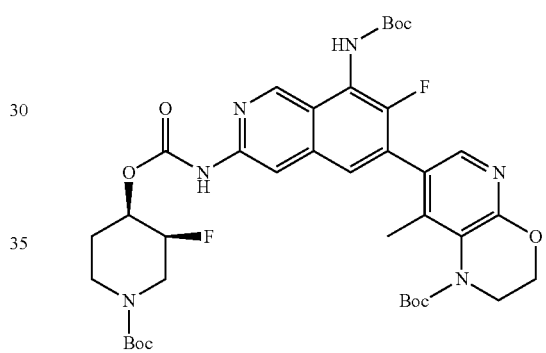

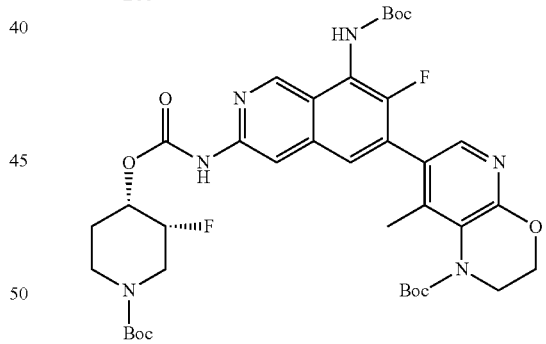

A solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (1000 mg, 1.9 mmol), tert-butyl (±)-cis-3-fluoro-4-hydroxy-piperidine-1-carboxylate (833 mg, 3.8 mmol), triphosgene (373 mg, 1.26 mmol) and DIEA (1226.0 mg, 9.5 mmol) in dichloromethane (30 mL) was stirred at 0° C. for 1 hour. The reaction was quenched with water and extracted with dichloromethane. The organic layer was concentrated under vacuum and purified by flash chromatography on silica gel eluting with petroleum ether/ethyl acetate (80/20) to afford (±)-cis-tert-butyl 7-(3-((((1-(tert-butoxycarbonyl)-3-fluoropiperidin-4-yl)oxy)carbonyl)amino)-8-((tert-butoxycarbonyl)amino)-7-fluoroisoquinolin-6-yl)-8-methyl-2,3-dihydro-1H-pyrido[2, 3-b][1,4]oxazine-1-carboxylate (1126 mg, 1.461 mmol, 76.8% yield) as a white solid. LCMS (ESI) [M+H]⁺=771.

Step 2: (±)-cis-3-Fluoropiperidin-4-yl (8-amino-7-fluoro-6-(8-methyl-2,3-dihydro-1H-pyrido[2,3-b][1,4]oxazin-7-yl)isoquinolin-3-yl)carbamate

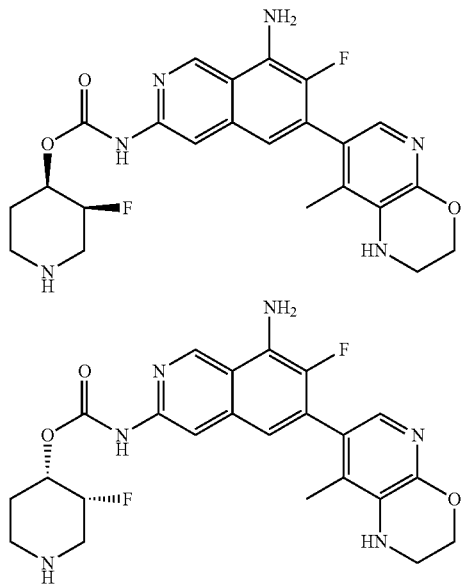

A solution of (±)-cis-tert-butyl 7-[8-(tert-butoxycarbonylamino)-3-[[1-tert-butoxycarbonyl-3-fluoro-4-piperidyl]oxycarbonylamino]-7-fluoro-6-isoquinolyl]-8-methyl-2,3-dihydropyrido[2,3-b][1,4]oxazine-1-carboxylate (1116.0 mg, 1.45 mmol) in dichloromethane (6 mL) and TFA (3 mL) was stirred at 25° C. for 6 hours. The reaction mixture was concentrated under vacuum and purified by reverse phase chromatography (water (NH₄HCO₃)/MeOH (56/44)) to afford (±)-cis-(3-fluoro-4-piperidyl) N-[8-amino-7-fluoro-6-(8-methyl-2,3-dihydro-1H-pyrido[2,3-b][1,4]oxazin-7-yl)-3-isoquinolyl]carbamate (436 mg, 0.927 mmol, 64% yield) as a yellow solid. LCMS (ESI) [M+H]⁺=471.

Step 3: (±)-cis-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate A solution of (±)-cis-(3-fluoro-4-piperidyl) N-[8-amino-7-fluoro-6-(8-methyl-2,3-dihydro-1H-pyrido[2,3-b][1,4]oxazin-7-yl)-3-isoquinolyl]carbamate (426.0 mg, 0.91 mmol), 3-oxetanone (651.0 mg, 9.03 mmol) and titanium tetraisopropanolate (1027.0 mg, 3.62 mmol) in methyl alcohol (15 mL) was stirred at 60° C. for 2 hours. Then NaCNBH₃ (171.0 mg, 2.71 mmol) was added and the mixture was stirred at 25° C. for 2 hours. The reaction mixture was concentrated under vacuum. The resulting residue was purified by reverse phase chromatography (water (NH₄HCO₃)/ACN (35/65)) to afford (±)-cis-3-fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate (170 mg, 0.3229 mmol, 35.7% yield) as a yellow solid. LCMS (ESI) [M+H]⁺=526.

Step 4: (3S,4R)-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate and (3R,4S)-3-Fluoro-1-(oxetan-3-yl) piperidin-4-yl (8-amino-7-fluoro-6-(8-methyl-2,3-dihydro-1H-pyrido[2,3-b][1,4]oxazin-7-yl)isoquinolin-3-yl)carbamate

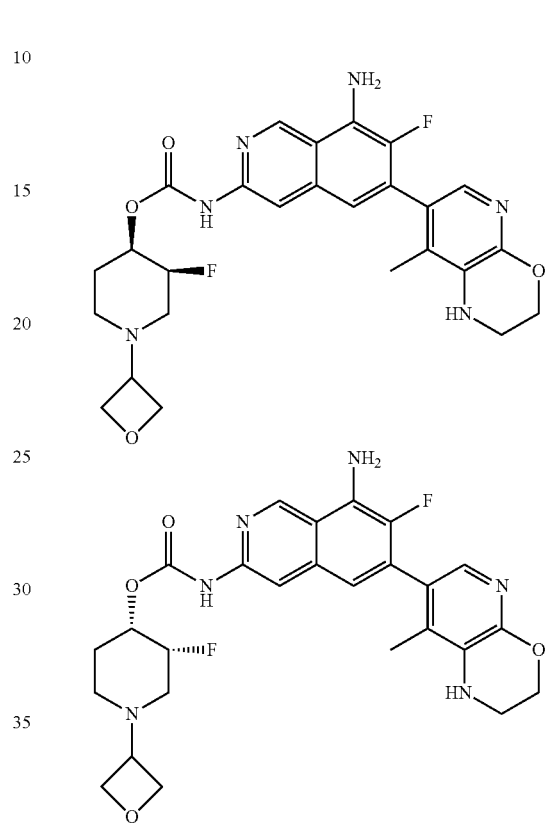

A solution of (±)-cis-3-fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate (420 mg, 0.89 mmol) and 3-oxetanone (651.0 mg, 9.03 mmol) in methyl alcohol (15 mL) was stirred at room temperature for 10 min. Then titanium tetraisopropanolate (1027 mg, 3.62 mmol) was added and the mixture was stirred at 60° C. for 1 hour. NaCNBH₃ (172.0 mg, 2.73 mmol) was then added and the mixture was stirred at room temperature for 1 hour. The reaction mixture was concentrated under vacuum and purified by Prep-HPLC (X Bridge Prep OBD C18 Column 30×150 mm, 5 μm; Mobile Phase A: Water (10 mmol/L NH₄HCO₃), Mobile Phase B: ACN; Flow rate: 60 mL/min; Gradient: 15% B to 26% B in 10 min) to afford a racemate product. The racemic product was separated by Chiral HPLC to afford two enantiomers. Relative stereochemistry are as drawn. Absolute stereochemistry was arbitrarily assigned.

Enantiomer 1 (Compound 445c) (48 mg, 0.0912 mmol, 2.5% yield). $R_T$ 2.267 min (CHIRALPAK IC-3 0.46*5 cm; 3 μm; (Hex:DCM=3:1):MeOH=50:50, 1 ml/min). LCMS (ESI) [M+H]⁺=527.2, $R_T$ 1.444 min; Method J. ¹H NMR (300 MHz, DMSO-d₆) δ 10.19 (s, 1H), 9.33 (s, 1H), 7.94 (s, 1H), 7.31 (s, 1H), 6.81 (d, J=6.1 Hz, 1H), 6.20 (s, 2H), 5.65 (s, 1H), 4.94-4.78 (m, 2H), 4.53-4.26 (m, 6H), 3.51 (p, J=6.4 Hz, 1H), 3.33 (s, 2H), 2.78 (s, 1H), 2.51 (s, 1H), 2.45-2.18 (m, 2H), 1.90-1.83 (m, 5H).

Enantiomer 2 (Compound 445d) (25 mg, 0.0475 mmol, 1.3% yield). $R_T$ 3.911 min (CHIRALPAK IC-3 0.46*5 cm; 3 μm; (Hex:DCM=3:1):MeOH=50:50, 1 ml/min). LCMS (ESI) [M+H]$^+$=527.2, Rt=1.444 min; Method J. $^1$H NMR (300 MHz, DMSO-d$_6$) δ 10.19 (s, 1H), 9.33 (s, 1H), 7.94 (s, 1H), 7.31 (s, 1H), 6.81 (d, J=6.1 Hz, 1H), 6.20 (s, 2H), 5.65 (s, 1H), 4.94-4.78 (m, 2H), 4.53-4.26 (m, 6H), 3.51 (p, J=6.4 Hz, 1H), 3.33 (s, 2H), 2.78 (s, 1H), 2.51 (s, 1H), 2.45-2.18 (m, 2H), 1.90-1.83 (m, 5H).

Example 242

(3R,4R)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3S,4S)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate (Compound 441c and Compound 441d)

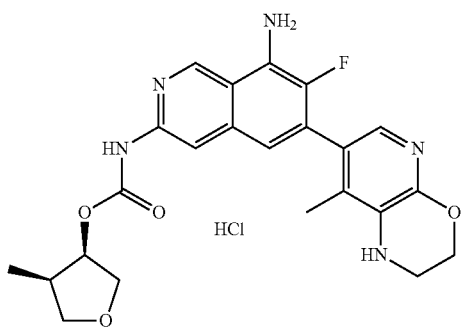

Step 1: (±)-trans-4-Methyltetrahydrofuran-3-ol

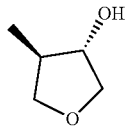

Under nitrogen, to a solution of CuI (16.6 g, 87.16 mmol) in THF (750 mL) was added methyl magnesium chloride (289.7 mL, 869.1 mmol, 3 M in THF) at −60° C. The resulting solution was stirred for 30 min at −60° C. Then 3,4-epoxytetrahydrofuran (50.0 g, 580.8 mmol) was added and stirred at −60° C. for 3 h. The reaction was quenched with an aqueous ammonium chloride solution. The reaction mixture was diluted with water and extracted with ethyl acetate. The organic layers were combined and dried over anhydrous sodium sulfate, filtered and concentrated under reduce pressure. The residue was purified by flash chromatography on silica gel eluting with dichloromethane/methanol (10/1) to afford (±)-trans-4-methyltetrahydrofuran-3-ol (31 g, 303.53 mmol, 52.3% yield) as a yellow oil.

Step 2: (±)-cis-(4-Methyltetrahydrofuran-3-yl) 4-nitrobenzoate

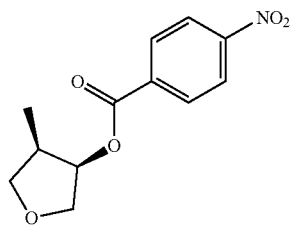 [SMILES: C[C@@H]1COC[C@@H]1OC(=O)c1ccc([N+](=O)[O-])cc1]

To a solution of (±)-trans-4-methyltetrahydrofuran-3-ol (1.0 g, 9.79 mmol), 4-nitrobenzoic acid (3.27 g, 19.58 mmol) and PPh$_3$ (6.42 g, 24.48 mmol) in tetrahydrofuran (20 mL) was added diisopropylazodicarboxylate (4.82 mL, 24.48 mmol) at 0° C. The resulting solution was stirred at room temperature for 4 hours. The resulting mixture was concentrated under vacuum and purified by flash chromatography on silica gel eluting with petroleum ether/ethyl acetate (1/1) to afford (±)-cis-(4-methyltetrahydrofuran-3-yl) 4-nitrobenzoate (1.5 g, 5.98 mmol, 61% yield) as a yellow solid.

Step 3: (±)-cis-(3R,4R)-4-Methyltetrahydrofuran-3-ol

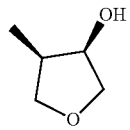

To a solution of (±)-cis-(4-methyltetrahydrofuran-3-yl) 4-nitrobenzoate (1.5 g, 5.98 mmol) in water (5 mL) and tetrahydrofuran (15 mL) was added lithium hydroxide (430.56 mg, 17.94 mmol) at room temperature. The resulting mixture was stirred at room temperature for 3 hours. The reaction was diluted by water and extracted with ethyl acetate. The organic layers were combined, dried over anhydrous sodium sulfate, filtered and concentrated under reduce pressure. The residue was purified by flash chromatography on silica gel eluting with dichloromethane/methanol (10/1) to afford (±)-cis-4-methyltetrahydrofuran-3-ol (330 mg, 3.23 mmol, 32.5% yield) as a yellow oil. $^1$H NMR (400 MHz, DMSO-d$_6$) δ 4.71 (d, J=4.5 Hz, 1H), 4.04 (qd, J=4.6, 1.8 Hz, 1H), 3.83-3.72 (m, 2H), 3.52 (dd, J=9.2, 1.8 Hz, 1H), 3.25 (dd, J=10.1, 7.5 Hz, 1H), 0.93 (d, J=6.8 Hz, 3H).

Step 4: (±)-cis-tert-Butyl 7-[8-(tert-butoxycarbonylamino)-7-fluoro-3-[[(3R,4R)-4-methyltetrahydrofuran-3-yl]oxycarbonylamino]-6-isoquinolyl]-8-methyl-2,3-dihydropyrido[2,3-b][1,4]oxazine-1-carboxylate

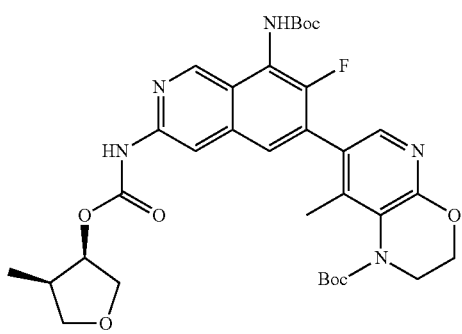 [SMILES: Cc1c(-c2cc3cc(NC(=O)O[C@H]4COC[C@H]4C)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (310.63 mg, 0.59 mmol), (±)-cis-(3R,4R)-4-methyltetrahydrofuran-3-ol (120.0 mg, 1.17 mmol) and N,N-diisopropylethylamine (0.31 mL, 1.76 mmol) in dichloromethane (30 mL) was added triphosgene (123.0 mg, 0.41 mmol) at 0° C. The resulting solution was stirred at room temperature for 30 min and concentrated under vacuum. The residue was purified by flash column chromatography on silica gel eluting with petroleum ether/ethyl acetate (4/3) to afford (±)-cis-tert-butyl 7-[8-(tert-butoxycarbonylamino)-7-fluoro-3-[[4-methyltetrahydrofuran-3-yl]oxycarbonylamino]-6-isoquinolyl]-8-methyl-2,3-dihydropyrido[2,3-b][1,4]oxazine-1-carboxylate (320 mg, 0.49 mmol, 82.8% yield) as a yellow solid. LCMS (ESI) [M+H]$^+$=654.3.

Step 5: (3R,4R)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3S,4S)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate

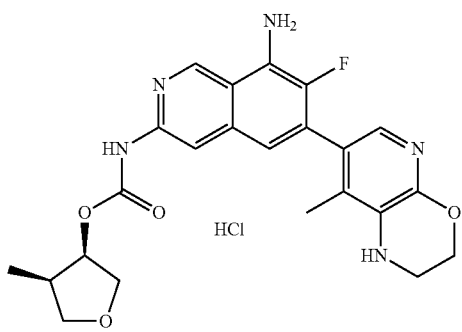

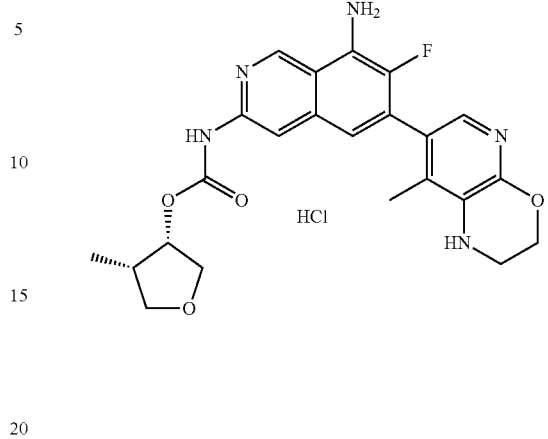

To a solution of tert-butyl 7-[8-(tert-butoxycarbonylamino)-7-fluoro-3-[[(cis)-4-methyltetrahydrofuran-3-yl]oxycarbonylamino]-6-isoquinolyl]-8-methyl-2,3-dihydropyrido[2,3-b][1,4]oxazine-1-carboxylate (200.0 mg, 0.31 mmol) in dichloromethane (10 mL) was added trifluoroacetic acid (5.0 mL, 64.9 mmol) at 0° C. The resulting solution was stirred at RT for 30 min and concentrated under vacuum. Then the resulting solution was diluted by acetonitrile and adjusted to pH 8 with an aqueous solution of sodium bicarbonate. After filtration, the solid was collected and washed by water. The solid was dissolved in methanol and treated with HCl (0.2 mL, 1 M in dioxane). Then the resulting mixture was concentrated under vacuum to give the racemic product. The racemic product was further isolated by chiral-HPLC to afford two enantiomers. Relative stereochemistry are as drawn. Absolute stereochemistry was arbitrarily assigned.

Enantiomer 1: Compound 441c (32.9 mg, 0.0618 mmol, 23.4% yield) as a yellow solid. R$_T$ 1.493 min (CHIRALPAK IA-3, 4.6*50 mm 3 μm; (Hex:DCM=3:1) (0.1% FA): EtOH=50:50; 1 mL/min). LCMS (ESI) [M+H]$^+$=454.2, R$_T$ 1.870 min, Method K; $^1$H NMR (300 MHz, DMSO-d$_6$) δ10.24 (s, 1H), 9.40 (s, 1H), 7.99 (s, 1H), 7.51 (s, 1H), 6.90 (d, J=6.1 Hz, 1H), 5.26-5.16 (m, 1H), 4.45 (s, 2H), 4.08-3.87 (m, 2H), 3.84-3.71 (m, 1H), 3.57-3.30 (m, 3H), 2.49-2.33 (m, 1H), 2.00 (d, J=1.6 Hz, 3H), 1.03 (d, J=6.8 Hz, 3H).

Enantiomer 2: Compound 441d (31 mg, 0.0618 mmol, 22.3% yield) as a yellow solid. R$_T$ 3.114 min (CHIRALPAK IA-3, 4.6*50 mm 3 μm; (Hex:DCM=3:1) (0.1% FA): EtOH=50:50; 1 mL/min). LCMS (ESI) [M+H]$^+$=454.2, R$_T$ 1.870 min, Method K; $^1$H NMR (300 MHz, DMSO-d$_6$) δ10.24 (s, 1H), 9.40 (s, 1H), 7.99 (s, 1H), 7.51 (s, 1H), 6.90 (d, J=6.1 Hz, 1H), 5.26-5.16 (m, 1H), 4.45 (s, 2H), 4.08-3.87 (m, 2H), 3.84-3.71 (m, 1H), 3.57-3.30 (m, 3H), 2.49-2.33 (m, 1H), 2.00 (d, J=1.6 Hz, 3H), 1.03 (d, J=6.8 Hz, 3H).

Example 243

(1s,3r)-3-Ethyl-3-hydroxycyclobutyl (8-amino-7-fluoro-6-(8-methyl-2,3-dihydro-1H-pyrido[2,3-b][1,4]oxazin-7-yl)isoquinolin-3-yl)carbamate and (1r,3s)-3-Ethyl-3-hydroxycyclobutyl (8-amino-7-fluoro-6-(8-methyl-2,3-dihydro-1H-pyrido[2,3-b][1,4]oxazin-7-yl)isoquinolin-3-yl)carbamate hydrochloride (Compound 512a and Compound 512b)

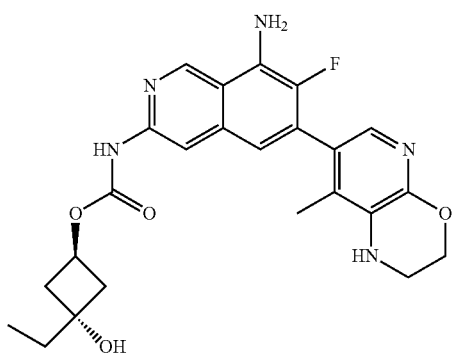

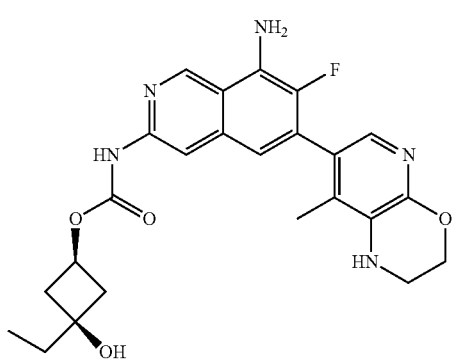

Step 1: 3-(Benzyloxy)-1-ethylcyclobutan-1-ol

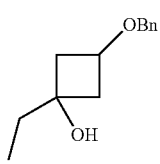

To a solution of 3-(benzyloxy)cyclobutanone (1.0 g, 5.68 mmol) in tetrahydrofuran (20 mL) was added ethyl magnesium chloride (8.51 mL, 17.03 mmol, 2 mol/L) at 0° C. The mixture was stirred at room temperature for 2 hours and then quenched by MeOH. After concentration, the residue was purified by flash chromatography on silica gel eluting with petroleum ether/ethyl acetate (10/90) to afford 3-benzyloxy-1-ethyl-cyclobutanol (300 mg, 1.454 mmol, 25.6% yield) as a colorless oil. $^1$H NMR (300 MHz, DMSO-$d_6$) δ 7.60-6.93 (m, 5H), 4.34 (s, 2H), 3.61 (p, J=7.1 Hz, 1H), 2.31 (m, 1H), 1.88 (m 2H), 1.54-1.21 (m, 2H), 1.04-0.57 (m, 3H).

Step 2: 1-Ethylcyclobutane-1,3-diol

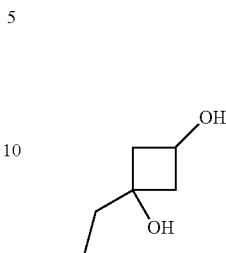

To a solution of 3-benzyloxy-1-ethyl-cyclobutanol (300 mg, 1.45 mmol) in methyl alcohol (6 mL) was added Pd/C (150 mg, 20%). The mixture was stirred at 40° C. for 8 hours under hydrogen (1 atm). After filtration, the filtrate was concentrated under vacuum. The residue was purified by flash chromatography on silica gel eluting with dichloromethane/methanol (10/1) to afford 1-ethylcyclobutane-1,3-diol (100 mg, 0.861 mmol, 59.2% yield) as colorless oil.

Step 3: tert-Butyl 7-(8-((tert-butoxycarbonyl)amino)-3-(((3-ethyl-3-hydroxycyclobutoxy)carbonyl)amino)-7-fluoroisoquinolin-6-yl)-8-methyl-2,3-dihydro-1H-pyrido[2,3-b][1,4]oxazine-1-carboxylate

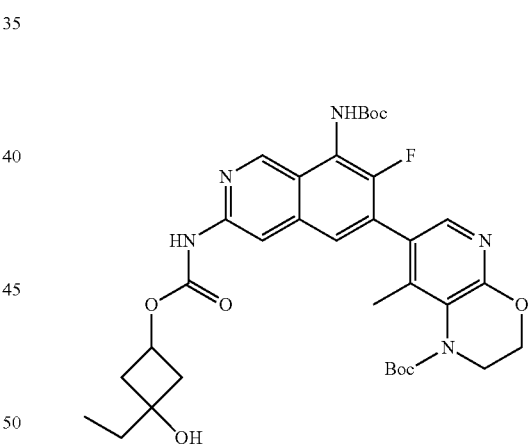

To a mixture of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (170 mg, 0.26 mmol) and 1-ethylcyclobutane-1,3-diol (90 mg, 0.77 mmol) in dichloromethane (6 mL) was added DMAP (32 mg, 0.26 mmol). The mixture was stirred at 60° C. for 12 hours. After concentration, the residue was purified by flash chromatography on silica gel eluting with dichloromethane/methanol (10/1) to afford tert-butyl 7-[8-(tert-butoxycarbonylamino)-3-[(3-ethyl-3-hydroxy-cyclobutoxy)carbonylamino]-7-fluoro-6-isoquinolyl]-8-methyl-2,3-dihydropyrido[2,3-b][1,4]oxazine-1-carboxylate (150 mg, 0.225 mmol, 85.3% yield) as a yellow solid. LCMS (ESI) [M+H]$^+$=668.

Step 4: (1s,3r)-3-Ethyl-3-hydroxycyclobutyl (8-amino-7-fluoro-6-(8-methyl-2,3-dihydro-1H-pyrido[2,3-b][1,4]oxazin-7-yl)isoquinolin-3-yl)carbamate hydrochloride and (1r,3s)-3-Ethyl-3-hydroxycyclobutyl (8-amino-7-fluoro-6-(8-methyl-2,3-dihydro-1H-pyrido[2,3-b][1,4]oxazin-7-yl)isoquinolin-3-yl)carbamate hydrochloride

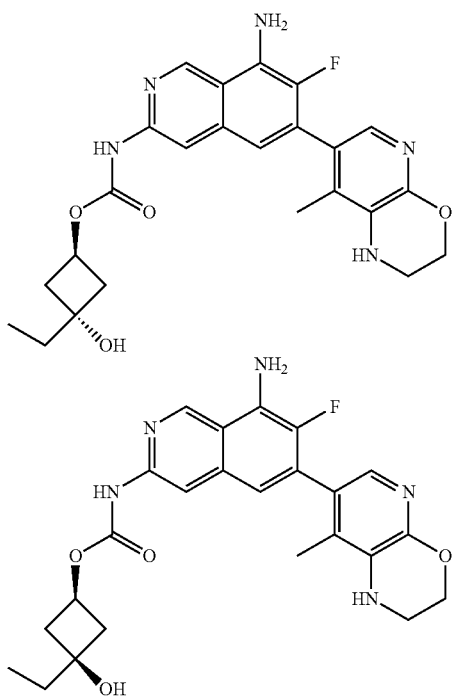

To a solution of tert-butyl 7-[8-(tert-butoxycarbonylamino)-3-[(3-ethyl-3-hydroxy-cyclobutoxy)carbonylamino]-7-fluoro-6-isoquinolyl]-8-methyl-2,3-dihydro-pyrido[2,3-b][1,4]oxazine-1-carboxylate (145.0 mg, 0.22 mmol) in dichloromethane (5 mL) was added TFA (1 mL). The mixture was stirred at room temperature for 3 hours. After concentration, the residue was purified by prep-HPLC (X select CSH OBD Column 30*150 mm, 5 µm; Mobile Phase A: Water (0.1% FA), Mobile Phase B: ACN; Flow rate: 60 mL/min; Gradient: 10% B to 32% B in 10 min) to afford to two isomers. The individual isomers were treated with 2 eq. of HCl in dioxane (4M) at room temperature for 30 min. After concentration, each of the isomers were lyophilized. Stereochemistry was arbitrarily assigned.

Isomer 1: Compound 512a (3.5 mg, 0.0069 mmol, 3.2% yield), LCMS (ESI) [M+H]$^+$=468, R$_T$=2.635 min, Method J; $^1$H NMR (300 MHz, DMSO-d$_6$) δ 10.10 (s, 1H), 9.35 (s, 1H), 7.95 (s, 1H), 7.47 (s, 1H), 6.87 (d, J=6.1 Hz, 1H), 5.39-4.51 (t, J=6.7 Hz, 5H), 4.41 (d, J=4.1 Hz, 2H), 3.44 (m, 2H), 2.31 (dd, J=13.1, 7.4 Hz, 2H), 2.07-1.94 (m, 5H), 1.55 (q, J=7.4 Hz, 2H), 0.82 (t, J=7.3 Hz, 3H).

Isomer 2: Compound 512b (27.8 mg, 0.0552 mmol, 25.4% yield). LCMS (ESI) [M+H]$^+$=468, R$_T$=1.732 min, Method M; $^1$H NMR (300 MHz, DMSO-d$_6$) δ 10.15 (s, 1H), 9.37 (s, 1H), 7.96 (s, 1H), 7.50 (s, 1H), 6.87 (d, J=6.1 Hz, 1H), 5.55-4.96 (m, 4H), 4.53 (q, J=7.2 Hz, 1H), 4.43 (s, 2H), 3.44 (s, 2H), 2.44 (dd, J=6.9, 2.9 Hz, 2H), 2.12-2.04 (m, 2H), 1.98 (d, J=1.6 Hz, 3H), 1.44 (q, J=7.2 Hz, 2H), 0.84 (t, J=7.2 Hz, 3H).

Example 244

(3S,4R)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3R,4S)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate (Compound 477c and Compound 477d)

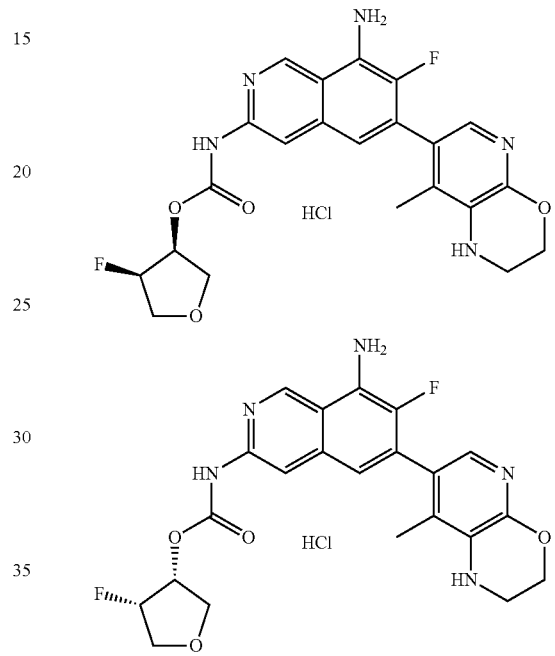

Step 1: cis-4-Fluorotetrahydrofuran-3-yl 4-nitrobenzoate

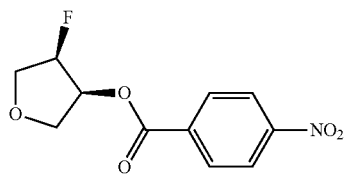 [SMILES: O=C(O[C@H]1COC[C@H]1F)c1ccc([N+](=O)[O-])cc1]

Under nitrogen, a solution of PPh$_3$ (3.21 g, 12.25 mmol) in THF (40 mL) was added diisopropylazodicarboxylate (2.41 mL, 12.25 mmol) at room temperature. The resulting solution was stirred at room temperature for 1 hour. Then trans-4-fluorotetrahydrofuran-3-ol (1.0 g, 9.43 mmol) and 4-nitrobenzoic acid (1.58 g, 9.43 mmol) in THF was added and the mixture was stirred for 16 hours at RT. The reaction mixture was concentrated under vacuum and purified by flash chromatography on silica gel eluting with petroleum ether/ethyl acetate (4/1) to afford cis-4-fluorotetrahydrofuran-3-yl 4-nitrobenzoate (3.5 g, 52% purity) as a white solid. LCMS (ESI) [M+H]$^+$=256.1.

Step 2: cis-4-Fluorotetrahydrofuran-3-ol

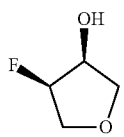

To a solution of cis-(4-fluorotetrahydrofuran-3-yl) 4-nitrobenzoate (3.5 g, 13.67 mmol) in methyl alcohol (180 mL) was added K$_2$CO$_3$ (9.45 g, 68.35 mmol) and the mixture was stirred at room temperature for 1.5 hours. After filtration the filtrate was concentrated under reduced pressure. The residue was purified by flash chromatography on silica gel eluting with petroleum ether/ethyl acetate (1/1) to afford 4-fluorotetrahydrofuran-3-ol (500 mg, 4.71 mmol, 50% yield) as yellowish oil. $^1$H NMR (400 MHz, DMSO-d$_6$) δ 5.26 (d, J=6.0 Hz, 1H), 5.02-4.56 (m, 1H), 4.26-4.14 (m, 1H), 3.98-3.78 (m, 3H), 3.43-3.38 (m, 1H).

Step 3: (±)-cis-tert-butyl 7-(8-((tert-butoxycarbonyl)amino)-7-fluoro-3-((((4-fluorotetrahydrofuran-3-yl)oxy)carbonyl)amino)isoquinolin-6-yl)-8-methyl-2,3-dihydro-1H-pyrido[2,3-b][1,4]oxazine-1-carboxylate

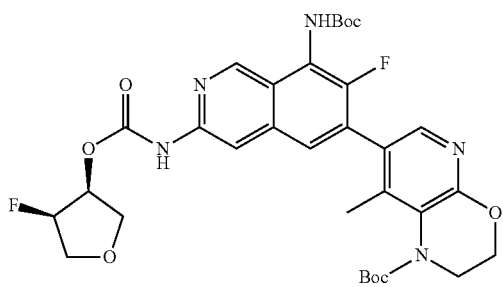 [SMILES: Cc1c(-c2cc3cc(NC(=O)O[C@H]4COC[C@H]4F)ncc3c(NC(=O)OC(C)(C)C)c2F)cnc2c1N(C(=O)OC(C)(C)C)CCO2]

A solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300.0 mg, 0.46 mmol), 4-dimethylaminopyridine (60.0 mg, 0.49 mmol) and cis-4-fluorotetrahydrofuran-3-ol (249.0 mg, 2.35 mmol) in dichloromethane (30 mL) was stirred at 60° C. for overnight. The reaction mixture was concentrated under vacuum. The residue was purified by flash chromatography on silica gel eluting with dichloromethane/methanol (50/1) to afford (±)-cis-tert-butyl 7-(8-((tert-butoxycarbonyl)amino)-7-fluoro-3-((((4-fluorotetrahydrofuran-3-yl)oxy)carbonyl)amino)isoquinolin-6-yl)-8-methyl-2,3-dihydro-1H-pyrido[2,3-b][1,4]oxazine-1-carboxylate (270 mg, 0.41 mmol, 88.4% yield) as a white solid. LCMS (ESI) [M+H]$^+$=658.

Step 4: (3S,4R)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3R,4S)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate

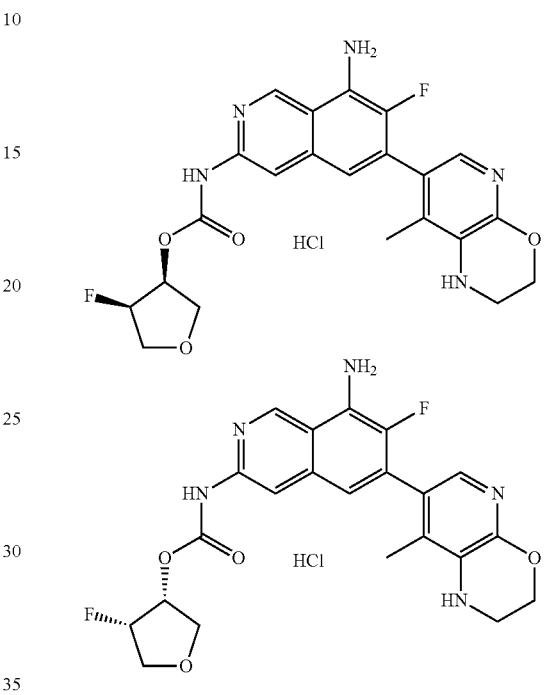

To a solution of tert-butyl 7-[8-(tert-butoxycarbonylamino)-7-fluoro-3-[(4-fluorotetrahydrofuran-3-yl)oxycarbonylamino]-6-isoquinolyl]-8-methyl-2,3-dihydropyrido[2,3-b][1,4]oxazine-1-carboxylate (260.0 mg, 0.40 mmol) in dichloromethane (10 mL) was added trifluoroacetic acid (4.0 mL, 51.92 mmol). The mixture was stirred at room temperature for 2 hours. The reaction mixture was concentrated under vacuum. The mixture was diluted with dichloromethane and the pH adjusted to pH 8 with triethylamine. The reaction mixture was concentrated under vacuum and purified by Prep-HPLC (Column: X select CSH OBD Column 30*150 mm, 5 μm; Mobile Phase A: Water (0.1% FA), Mobile Phase B: ACN; Flow rate: 60 mL/min; Gradient: 12 B to 38 B in 7 min) to afford a racemic product. The racemic product was separated by chiral-Prep-HPLC to afford two enantiomers. Relative stereochemistry are as drawn. Absolute stereochemistry was arbitrarily assigned, Enantiomer 1: Compound 477c (39.2 mg, 0.084 mmol, 21.2% yield). R$_T$ 1.726 min (CHIRALPAK IC-3, 0.46*5 cm; 3 μm; (Hex:DCM=3:1)(0.1% DEA): EtOH=50:50. 1 ml/min); LCMS (ESI): [M+H]+458.2, R$_T$ 1.727 min, Method J; $^1$H NMR (400 MHz, DMSO-d$_6$) δ 10.43 (s, 1H), 9.40 (s, 1H), 7.99 (s, 1H), 7.53 (s, 1H), 6.92 (d, J=6.0 Hz, 1H), 5.43-5.18 (m, 2H), 4.47 (t, J=4.0 Hz, 2H), 4.07-4.03 (m, 2H), 4.01-3.92 (m, 1H), 3.78-3.74 (m, 1H), 3.47 (s, 2H), 2.01 (s, 3H).

Enantiomer 2: Compound 477d (41 mg, 0.0873 mmol, 22.1% yield). R$_T$ 2.403 min (CHIRALPAK IC-3, 0.46*5 cm; 3 μm; (Hex:DCM=3:1)(0.1% DEA): EtOH=50:50. 1 ml/min); LCMS (ESI): [M+H]+458.2, R$_T$ 1.727 min, Method J; $^1$H NMR (400 MHz, DMSO-d$_6$) δ 10.43 (s, 1H), 9.40 (s, 1H), 7.99 (s, 1H), 7.53 (s, 1H), 6.92 (d, J=6.0 Hz, 1H), 5.43-5.18 (m, 2H), 4.47 (t, J=4.0 Hz, 2H), 4.07-4.03 (m, 2H), 4.01-3.92 (m, 1H), 3.78-3.74 (m, 1H), 3.47 (s, 2H), 2.01 (s, 3H).

Example 245

(1s, 3s)-3-(3,3-Difluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate (Compound 513a)

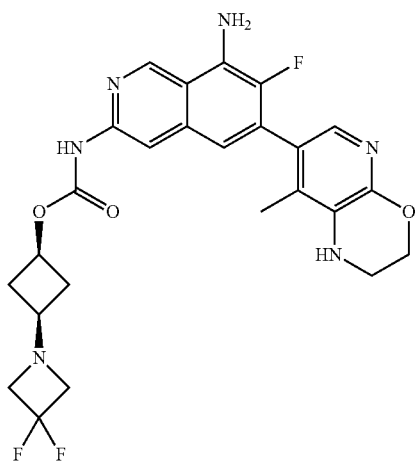 [SMILES: Cc1c(-c2cc3cc(NC(=O)O[C@H]4C[C@@H](N5CC(F)(F)C5)C4)ncc3c(N)c2F)cnc2c1NCCO2]

Step 1: 1-((1s,3s)-3-(Benzyloxy)cyclobutyl)-3,3-difluoroazetidine

A solution of 3,3-difluoroazetidine hydrochloride (3.7 g, 28.38 mmol) in methyl alcohol (20 mL) was stirred at room temperature for 5 min. Then N,N-diisopropylethylamine (3.7 g, 28.38 mmol), 3-(benzyloxy)cyclobutanone (1.0 g, 5.68 mmol) and titanium tetraisopropanolate (4.8 g, 17.03 mmol) were added at room temperature and the mixture was stirred at 60° C. for 2 hours. Sodium cyanoborohydride (1.07 g, 17.03 mmol) was added and the mixture was stirred at room temperature for 2 hours. The reaction mixture was concentrated under vacuum. The residue was purified by flash chromatography on silica gel eluting with petroleum ether/ethyl acetate (2/1) to afford 1-(3-benzyloxycyclobutyl)-3,3-difluoro-azetidine (415 mg, 1.6 mmol, 28.9% yield) as a yellow oil. LCMS (ESI) [M+H]$^+$=254.

Step 2: (1s,3s)-3-(3,3-Difluoroazetidin-1-yl)cyclobutan-1-ol

Under hydrogen, a suspension of 1-(3-benzyloxycyclobutyl)-3,3-difluoro-azetidine (360 mg, 1.42 mmol) and Pd/C (10%, 180 mg) in methyl alcohol (8 mL) was stirred at room temperature for 4 hours. After filtration, the filtrate was concentrated under vacuum and purified by flash chromatography on silica gel eluting with dichloromethane/methanol (10/1) to afford (1s,3s)-3-(3,3-difluoroazetidin-1-yl)cyclobutan-1-ol (150 mg, 0.91 mmol, 64.5% yield) as a yellow oil. LCMS (ESI) [M+H]$^+$=164. $^1$H NMR (300 MHz, DMSO-d$_6$) δ 5.01-4.93 (m, 1H), 4.20-4.24 (m, 1H), 3.74-3.78 (m, 1H), 3.47-3.51 (m, 4H), 2.34-2.19 (m, 1H), 1.95-1.99 (m, 1H), 1.88-1.74 (m, 1H), 1.67-1.52 (m, 1H).

Step 3: tert-Butyl 7-(8-((tert-butoxycarbonyl)amino)-3-((((1s,3s)-3-(3,3-difluoroazetidin-1-yl)cyclobutoxy)carbonyl)amino)-7-fluoroisoquinolin-6-yl)-8-methyl-2,3-dihydro-1H-pyrido[2,3-b][1,4]oxazine-1-carboxylate

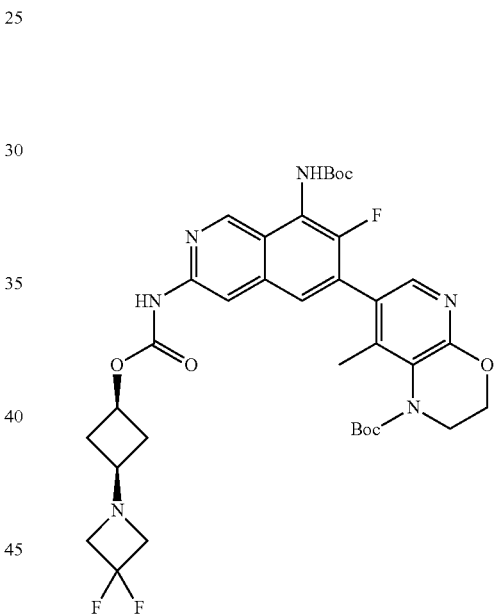

A solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (317.0 mg, 0.49 mmol), (1s,3s)-3-(3,3-difluoroazetidin-1-yl)cyclobutan-1-ol (120.0 mg, 0.74 mmol) and 4-dimethylaminopyridine (60.0 mg, 0.49 mmol) in dichloromethane (5 mL) was stirred at 60° C. for 2 hours. The reaction was concentrated under vacuum and purified by flash chromatography on silica gel eluting with dichloromethane/methanol (10/1) to afford tert-butyl 7-[8-(tert-butoxycarbonylamino)-3-[[3-(3,3-difluoroazetidin-1-yl)cyclobutoxy]carbonylamino]-7-fluoro-6-isoquinolyl]-8-methyl-2,3-dihydropyrido[2,3-b][1,4]oxazine-1-carboxylate (186 mg, 0.26 mmol, 53% yield) as a yellow solid. LCMS (ESI) [M+H]$^+$=715.

Step 4: (1s,3s)-3-(3,3-Difluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate

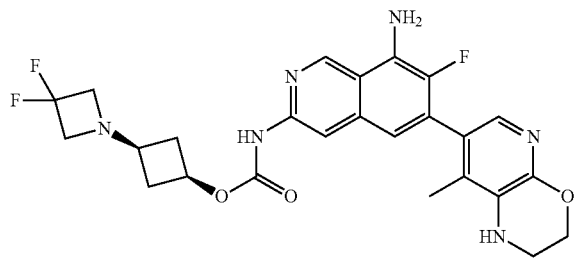 [SMILES: Cc1c(-c2cc3cc(NC(=O)O[C@H]4C[C@@H](N5CC(F)(F)C5)C4)ncc3c(N)c2F)cnc2c1NCCO2]

To a solution of tert-butyl 7-[8-(tert-butoxycarbonylamino)-3-[[3-(3,3-difluoroazetidin-1-yl)cyclobutoxy]carbonylamino]-7-fluoro-6-isoquinolyl]-8-methyl-2,3-dihydropyrido[2,3-b][1,4]oxazine-1-carboxylate (170.0 mg, 0.24 mmol) in dichloromethane (2 mL) was added TFA (1.0 mL). The mixture was stirred at room temperature for 2 hours. The reaction mixture was concentrated under vacuum. The residue was re-dissolved in DCM and adjusted to pH 8 with TEA. The resulting mixture was concentrated under vacuum. The residue was purified by Prep-HPLC (Column: X Bridge Shield RP18 OBD Column, 30*150 mm, 5 μm; Mobile Phase A: Water (10 mmol/L NH$_4$HCO$_3$), Mobile Phase B:ACN; Flow rate: 60 mL/min; Gradient: 27 B % to 45% B in 8 min) to afford[3-(3,3-difluoroazetidin-1-yl)cyclobutyl]N-[8-amino-7-fluoro-6-(8-methyl-2,3-dihydro-1H-pyrido[2,3-b][1,4]oxazin-7-yl)-3-isoquinolyl]carbamate (31.7 mg, 0.062 mmol, 25.9% yield) as a yellow solid. LCMS (ESI): [M+H]$^+$=515.2, R$_T$ 1.666 min, Method K; $^1$H NMR (300 MHz, DMSO-d$_6$) δ 10.09 (s, 1H), 9.34 (s, 1H), 7.96 (s, 1H), 7.33 (s, 1H), 6.84 (d, J=6.2 Hz, 1H), 6.21 (s, 2H), 5.67 (s, 1H), 4.69-4.74 (m, 1H), 4.29 (t, J=4.3 Hz, 2H), 3.57 (t, J=12.6 Hz, 4H), 3.38 (s, 2H), 2.99-3.04 (m, 1H), 2.55 (s, 2H), 1.96-1.80 (m, 5H).

Example 246

(1r,3r)-3-(1H-Imidazol-1-yl)cyclobutyl (8-amino-7-fluoro-6-(8-methyl-2,3-dihydro-1H-pyrido[2,3-b][1,4]oxazin-7-yl)isoquinolin-3-yl)carbamate hydrochloride (Compound 514a)

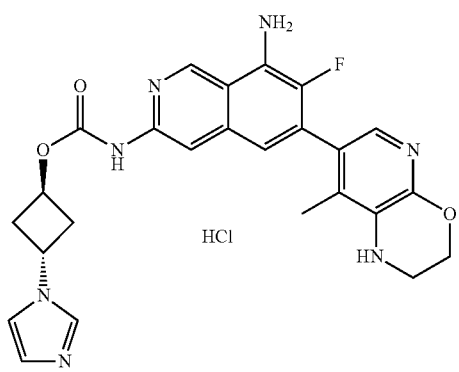 [SMILES: Cc1c(-c2cc3cc(NC(=O)O[C@H]4C[C@H](n5ccnc5)C4)ncc3c(N)c2F)cnc2c1NCCO2 ; Cl]

Step 1: (1s,3s)-3-(Benzyloxy)cyclobutyl methanesulfonate

To a mixture of 3-benzyloxycyclobutanol (200.0 mg, 1.12 mmol) and TEA (350.0 mg, 3.47 mmol) in dichloromethane (5 mL) was added methyl sulfonyl chloride (200.0 mg, 1.75 mmol). The mixture was stirred at 0° C. for 1 hour. The reaction was quenched with water and extract with ethyl acetate. The organic layer was dried over anhydrous sodium sulfate, filtered and concentrated under vacuum to afford (3-benzyloxycyclobutyl) methanesulfonate (220 mg, 0.858 mmol, 76.5% yield) as a colorless oil. LCMS (ESI) [M+H]$^+$= 257.

Step 2: 1-((1r,3r)-3-(Benzyloxy)cyclobutyl)-1H-imidazole

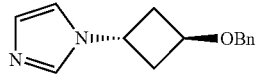 [SMILES: c1ccc(CO[C@H]2C[C@H](n3ccnc3)C2)cc1]

To a mixture of (1s,3s)-3-(benzyloxy)cyclobutyl methanesulfonate (750 mg, 2.93 mmol) and imidazole (796 mg, 11.69 mmol) in DMF (15 mL) was added cesium carbonate (4775 mg, 14.65 mmol). The mixture was stirred at 80° C. for 12 hours. After concentration, the resulting residue was purified by reverse phase chromatography (acetonitrile 0-60/0.1% NH$_4$OH in water) to afford 1-((1r,3r)-3-(benzyloxy)cyclobutyl)-1H-imidazole (356 mg, 1.559 mmol, 53.3% yield) as a colorless oil. LCMS (ESI) [M+H]$^+$=227.

Step 3: (1r,3r)-3-(1H-imidazol-1-yl)cyclobutan-1-ol

To a solution of 1-(3-benzyloxycyclobutyl)imidazole (358 mg, 1.57 mmol) in methyl alcohol (5 mL) was added Pd/C (800 mg, 10%). The mixture was stirred under hydrogen (1 atm) at 40° C. for 8 hours. After filtration,n the filtrate was concentrated under vacuum. The residue was purified by flash chromatography on silica gel eluting with dichloromethane/methanol (10/1) to afford 3-imidazol-1-ylcyclobutanol (170 mg, 1.23 mmol, 78.5% yield) as a colorless oil. LCMS (ESI) [M+H]$^+$=139.

Step 4: tert-Butyl 7-(3-((((1r,3r)-3-(1H-imidazol-1-yl)cyclobutoxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

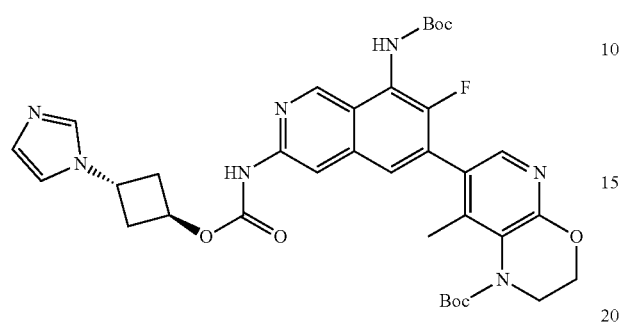

To a mixture of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (250 mg, 0.39 mmol) and 3-imidazol-1-ylcyclobutanol (245 mg, 1.77 mmol) in dichloromethane (10 mL) was added DMAP (50 mg, 0.41 mmol). The mixture was stirred at 60° C. for 12 hours. After concentration, the residue was purified by flash chromatography on silica gel eluting with dichloromethane/methanol (90/10) to afford tert-butyl 7-[8-(tert-butoxycarbonylamino)-7-fluoro-3-[(3-imidazol-1-ylcyclobutoxy)carbonylamino]-6-isoquinolyl]-8-methyl-2,3-dihydropyrido[2,3-b][1,4]oxazine-1-carboxylate (140 mg, 0.203 mmol, 52.4% yield) as a yellow solid. LCMS (ESI) [M+H]$^+$=690.

Step 5: (1r,3r)-3-(1H-Imidazol-1-yl)cyclobutyl (8-amino-7-fluoro-6-(8-methyl-2,3-dihydro-1H-pyrido[2,3-b][1,4]oxazin-7-yl)isoquinolin-3-yl)carbamate hydrochloride

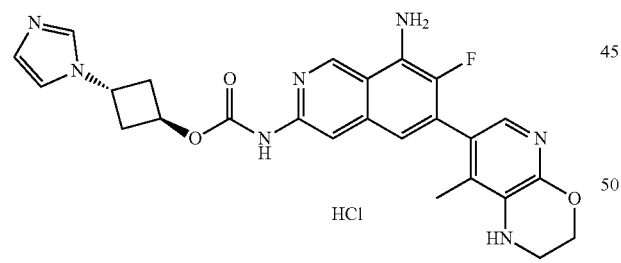

To a solution of tert-butyl 7-[8-(tert-butoxycarbonylamino)-7-fluoro-3-[(3-imidazol-1-ylcyclobutoxy)carbonylamino]-6-isoquinolyl]-8-methyl-2,3-dihydropyrido[2,3-b][1,4]oxazine-1-carboxylate (140 mg, 0.20 mmol) in dichloromethane (5 mL) was added TFA (1 mL). The mixture was stirred at room temperature for 1 hour. After concentration, the residue was purified by prep-HPLC (X Bridge Prep Phenyl OBD Column, 5 μm, 19*250 mm; Mobile Phase A: Water (0.1% FA), Mobile Phase B: ACN; Flow rate: 25 mL/min; Gradient: 29% B to 45% B in 9 min) to afford the desired product. The free base material was treated with HCl in dioxane (5 ml, 3 mol/L) and stirred 30 min at room temperature. The resulting solution was concentrated under vacuum to afford (1r,3r)-3-(1H-imidazol-1-yl)cyclobutyl (8-amino-7-fluoro-6-(8-methyl-2,3-dihydro-1H-pyrido[2,3-b][1,4]oxazin-7-yl)isoquinolin-3-yl) carbamate hydrochloride (55.2 mg, 0.105 mmol, 51.7% yield) as an orange solid. LCMS (ESI) [M+H]$^+$=490.3, R$_T$ 1.560 min, Method J; $^1$H NMR (400 MHz, DMSO-d$_6$) δ 10.33 (s, 1H), 9.41 (s, 1H), 9.34 (t, J=1.5 Hz, 1H), 8.00 (dd, J=3.6, 1.8 Hz, 2H), 7.77 (t, J=1.7 Hz, 1H), 7.47 (s, 1H), 6.89 (d, J=6.1 Hz, 1H), 6.17-5.71 (m, 3H), 5.21 (d, J=7.3 Hz, 2H), 4.42 (s, 2H), 3.44 (s, 2H), 2.96 (dt, J=13.9, 7.0 Hz, 2H), 2.76 (ddd, J=14.3, 8.5, 3.6 Hz, 2H), 1.99 (d, J=1.7 Hz, 3H).

Example 247

(3S,4R)-4-Ethyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3R,4S)-4-Ethyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate ((Compound 515a and Compound 515b

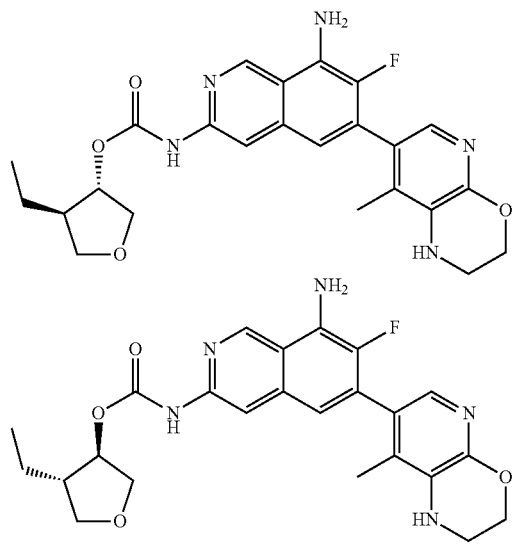

Step 1: (±)-trans-4-Ethyltetrahydrofuran-3-ol

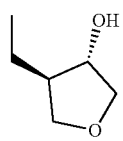

To a mixture of CuI (331.0 mg, 1.74 mmol) in THF (50 mL) was added ethyl magnesium chloride (8.7 mL, 17.4 mmol, 2 mol/L). The mixture was stirred at −40° C. for 30 minutes. Then 3,4-epoxytetrahydrofuran (1000 mg, 11.62 mmol) was added and the mixture was stirred at −40° C. for 2 hours. The reaction was quenched with water and extracted with ethyl acetate. The organic layers were combined, dried over anhydrous sodium sulfate, filtered and concentrated under vacuum to afford 4-ethyltetrahydrofuran-3-ol (1100 mg, 9.469 mmol, 81.5% yield) as a yellow oil. LCMS (ESI) [M+H]⁺=117.1. ¹H NMR (400 MHz, DMSO-d₆) δ 4.87 (d, J=3.6 Hz, 1H), 3.94-3.84 (m, 2H), 3.72 (m, 1H), 3.43 (m, 1H), 3.32 (m, 1H), 1.83 (m, 1H), 1.44-1.31 (m, 1H), 1.28-1.12 (m, 1H), 0.89 (t, J=7.4 Hz, 3H).

Step 2: (±)-trans-tert-Butyl 7-[8-(tert-butoxycarbonylamino)-3-[[(3S,4R)-4-ethyltetrahydrofuran-3-yl]oxycarbonylamino]-7-fluoro-6-isoquinolyl]-8-methyl-2,3-dihydropyrido[2,3-b][1,4]oxazine-1-carboxylate

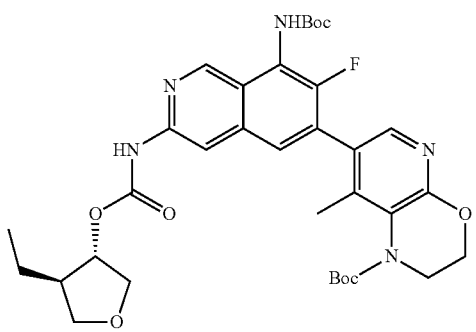 [SMILES: CC[C@@H]1COC[C@H]1OC(=O)Nc1cc2cc(-c3cnc4c(c3C)N(C(=O)OC(C)(C)C)CCO4)c(F)c(NC(=O)OC(C)(C)C)c2cn1]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300.0 mg, 0.46 mmol) and DMAP (57.0 mg, 0.47 mmol) in dichloromethane (10 mL) was added 4-ethyltetrahydrofuran-3-ol (161.0 mg, 1.39 mmol) at 60° C. The mixture was stirred for 12 hours and concentrated under vacuum. The residue was purified by flash chromatography on silica gel eluting with dichloromethane/methanol (96/4) to afford (±)-trans-tert-butyl 7-[8-(tert-butoxycarbonylamino)-3-[[4-ethyltetrahydrofuran-3-yl]oxycarbonylamino]-7-fluoro-6-isoquinolyl]-8-methyl-2,3-dihydropyrido[2,3-b][1,4]oxazine-1-carboxylate (300 mg, 0.4493 mmol, 96.7% yield) as a yellow oil. LCMS (ESI) [M+H]⁺=668.3.

Step 3: (3S,4R)-4-Ethyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3R,4S)-4-Ethyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate

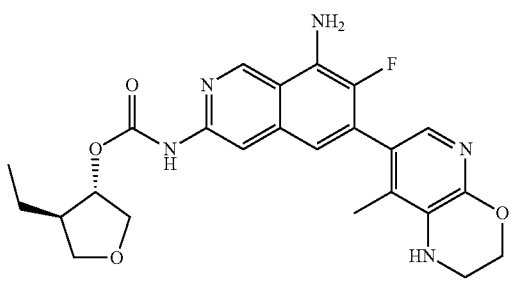

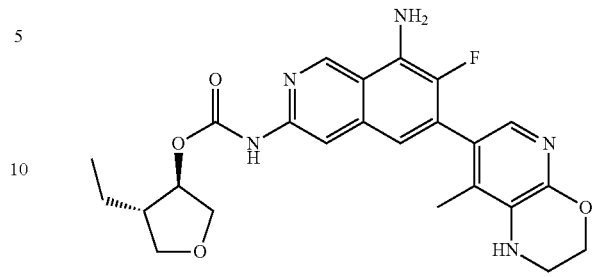

A solution of tert-butyl 7-[8-(tert-butoxycarbonylamino)-3-[(4-ethyltetrahydrofuran-3-yl)oxycarbonylamino]-7-fluoro-6-isoquinolyl]-8-methyl-2,3-dihydropyrido[2,3-b][1,4]oxazine-1-carboxylate (300 mg, 0.45 mmol) and TFA (2.0 mL, 0.45 mmol) in dichloromethane (10 mL) was stirred at 25° C. for 3 hours. After concentration, the residue was purified by Prep-HPLC (Column: X select CSH OBD Column 30*150 mm 5 μm; Mobile Phase A: Water (0.1% FA), Mobile Phase B: ACN; Flow rate: 60 mL/min; Gradient: 17% B to 41% B in 10 min) to afford a racemate. The racemic product was separated by chiral-HPLC to afford two enantiomers. Relative stereochemistry are as drawn. Absolute stereochemistry was arbitrarily assigned.

Enantiomer 1 (Compound 515a) (27.4 mg, 0.0586 mmol, 13% yield): RT 1.775 min (CHIRALPAK IC-3 0.46*5 cm; 3 μm; (Hex:DCM=3:1)(0.1% DEA):EtOH=50:50; 1.0 ml/min). LCMS (ESI) [M+H]⁺=468.2, R_T 2.279 min.; Method K; ¹H NMR (400 MHz, DMSO-d₆) δ 10.08 (s, 1H), 9.30 (s, 1H), 7.95 (s, 1H), 7.32 (s, 1H), 6.86 (d, J=6.1 Hz, 1H), 4.94 (dt, J=4.4, 2.1 Hz, 1H), 4.30 (t, J=4.3 Hz, 2H), 3.98 (dd, J=8.7, 6.8 Hz, 1H), 3.91-3.84 (m, 5H), 3.37 (d, J=4.1 Hz, 3H), 2.18-2.08 (m, 1H), 1.91 (d, J=1.6 Hz, 3H), 1.49 (dd, J=14.1, 7.0 Hz, 1H), 1.41-1.29 (m, 1H), 0.91 (t, J=7.4 Hz, 3H).

Enantiomer 2 (Compound 515b) (24.4 mg, 0.0522 mmol, 11.6% yield): R_T 2.996 min (CHIRALPAK IC-3 0.46*5 cm; 3 μm; (Hex:DCM=3:1)(0.1% DEA):EtOH=50:50; 1.0 ml/min). LCMS (ESI) [M+H]⁺=468.2, R_T 2.279 min; Method K; ¹H NMR (400 MHz, DMSO-d₆) δ 10.08 (s, 1H), 9.30 (s, 1H), 7.95 (s, 1H), 7.32 (s, 1H), 6.86 (d, J=6.1 Hz, 1H), 4.94 (dt, J=4.4, 2.1 Hz, 1H), 4.30 (t, J=4.3 Hz, 2H), 3.98 (dd, J=8.7, 6.8 Hz, 1H), 3.91-3.84 (m, 5H), 3.37 (d, J=4.1 Hz, 3H), 2.18-2.08 (m, 1H), 1.91 (d, J=1.6 Hz, 3H), 1.49 (dd, J=14.1, 7.0 Hz, 1H), 1.41-1.29 (m, 1H), 0.91 (t, J=7.4 Hz, 3H).

Example 248

(3R,4S)-4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3S,4R)-4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl) carbamate (Compound 516a and Compound 516b)

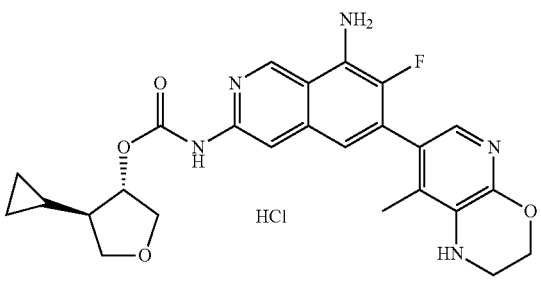

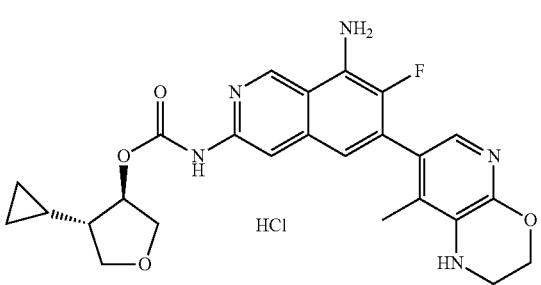

Step 1: (±)-trans-4-Cyclopropyltetrahydrofuran-3-ol

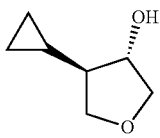

To a solution of 3,4-epoxytetrahydrofuran (1000 mg, 11.62 mmol) in THF (10 mL) was added dropwise cyclopropyl magnesium bromide (17.4 mL, 1M in THF, 17.4 mmol) and then the mixture was stirred at −40° C. for 2 hours. The reaction was quenched by saturated aqueous NH4Cl solution and extracted with ethyl acetate. After concentration, the residue was purified by flash chromatography on silica gel eluting with petroleum ether/ethyl acetate (1/1) to afford (±)-trans-4-cyclopropyltetrahydrofuran-3-ol (1300 mg, 10.143 mmol, 87.3% yield) as a colorless oil.

Step 2: (±)-trans-tert-Butyl 7-(8-((tert-butoxycarbonyl)amino)-3-((((4-cyclopropyltetrahydrofuran-3-yl)oxy)carbonyl)amino)-7-fluoroisoquinolin-6-yl)-8-methyl-2,3-dihydro-1H-pyrido[2,3-b][1,4]oxazine-1-carboxylate

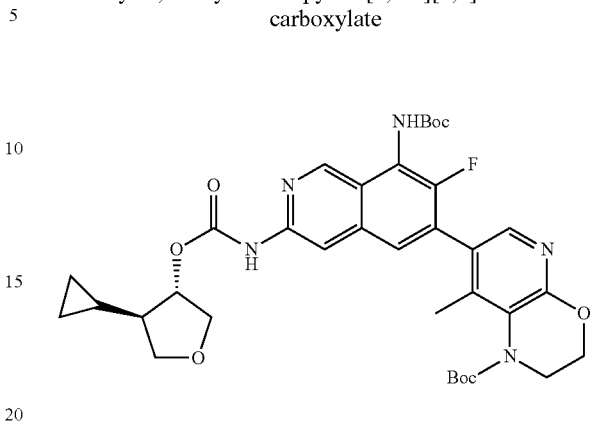

To a mixture of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (300 mg, 0.46 mmol) and (±)-trans-4-cyclopropyltetrahydrofuran-3-ol (300 mg, 2.34 mmol) in dichloromethane (10 mL) was added DMAP (57.0 mg, 0.47 mmol). The mixture was stirred at 60° C. for 12 hours. After concentration, the residue was purified by flash chromatography on silica gel eluting with dichloromethane/methanol (10/1) to afford tert-butyl 7-[8-(tert-butoxycarbonylamino)-3-[(4-cyclopropyltetrahydrofuran-3-yl)oxycarbonylamino]-7-fluoro-6-isoquinolyl]-8-methyl-2,3-dihydropyrido[2,3-b][1,4]oxazine-1-carboxylate (140 mg, 0.206 mmol, 44.3% yield) as a yellow solid. LCMS (ESI) [M+H]$^+$=680.

Step 3: (3R,4S)-4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (3S,4R)-4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl) carbamate

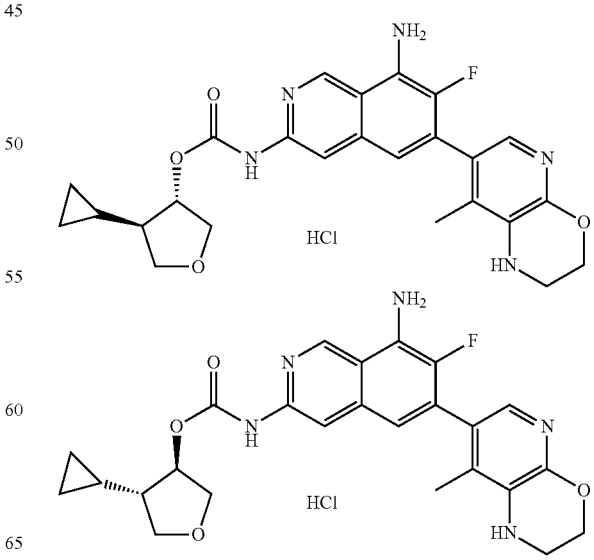

To a solution of tert-butyl 7-[8-(tert-butoxycarbonylamino)-3-[(4-cyclopropyltetrahydrofuran-3-yl)oxycarbonylamino]-7-fluoro-6-isoquinolyl]-8-methyl-2,3-dihydropyrido[2,3-b][1,4]oxazine-1-carboxylate (150 mg, 0.22 mmol) in dichloromethane (5 mL) was added TFA (1 mL). The mixture was stirred at room temperature for 2 hours. After concentration, the residue was purified by Prep-HPLC (X select CSH OBD Column 30*150 mm, 5 µm; Mobile Phase A: Water (10 mmol/L NH$_4$HCO$_3$), Mobile Phase B: ACN; Flow rate: 60 mL/min; Gradient: 27% B to 43% B in 7 min) to afford a racemic product. The racemate was separated by chiral-HPLC to afford two enantiomers. Relative stereochemistry are as drawn. Absolute stereochemistry was arbitrarily assigned.

Enantiomer 1: Compound 516a (13.1 mg, 0.0254 mmol, 11.5% yield). R$_T$ 1.826 min (CHIRALPAK IC-3 0.46*5 cm; 3 µm. Mobile phase: (Hex: DCM=3:1)(0.1% DEA): EtOH=50:50, 1 ml/min). LCMS (ESI) [M+H]$^+$=480.2, R$_T$ 2.507 min; Method L; $^1$H NMR (300 MHz, DMSO-d$_6$) δ 10.19 (s, 1H), 9.35 (s, 1H), 7.96 (s, 1H), 7.49 (s, 1H), 6.89 (d, J=6.2 Hz, 1H), 5.07 (dd, J=4.7, 2.3 Hz, 1H), 4.51-4.42 (m, 4H), 4.16-3.96 (m, 3H), 3.75 (d, J=10.7 Hz, 1H), 3.52 (dd, J=8.5, 4.6 Hz, 1H), 3.49-3.39 (m, 2H), 1.98 (s, 3H), 1.70 (s, 1H), 0.81-0.72 (m, 1H), 0.53-0.42 (m, 2H), 0.29 (s, 1H), 0.20 (s, 1H).

Enantiomer 2: Compound 516b (12.5 mg, 0.0242 mmol, 11% yield) as yellow solid. R$_T$ 3.068 min (CHIRALPAK IC-3 0.46*5 cm; 3 µm. Mobile phase: (Hex:DCM=3:1) (0.1% DEA):EtOH=50:50, 1 ml/min). LCMS (ESI) [M+H]$^+$= 480.2, R$_T$ 2.507 min; Method L; $^1$H NMR (300 MHz, DMSO-d$_6$) δ 10.19 (s, 1H), 9.35 (s, 1H), 7.96 (s, 1H), 7.49 (s, 1H), 6.89 (d, J=6.2 Hz, 1H), 5.07 (dd, J=4.7, 2.3 Hz, 1H), 4.51-4.42 (m, 4H), 4.16-3.96 (m, 3H), 3.75 (d, J=10.7 Hz, 1H), 3.52 (dd, J=8.5, 4.6 Hz, 1H), 3.49-3.39 (m, 2H), 1.98 (s, 3H), 1.70 (s, 1H), 0.81-0.72 (m, 1H), 0.53-0.42 (m, 2H), 0.29 (s, 1H), 0.20 (s, 1H).

Example 249

(1s,3s)-3-(Azetidine-1-carbonyl)cyclobutyl (8-amino-7-fluoro-6-(8-methyl-2,3-dihydro-1H-pyrido[2,3-b][1,4]oxazin-7-yl)isoquinolin-3-yl)carbamate (Compound 517a)

Step 1. Azetidin-1-yl((1s,3s)-3-hydroxycyclobutyl)methanone

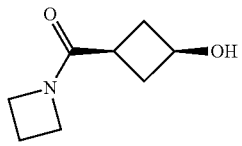 [SMILES: O=C([C@H]1C[C@@H](O)C1)N1CCC1]

To a solution of cis-3-hydroxycyclobutanecarboxylic acid (300.0 mg, 2.58 mmol), azetidine (221.4 mg, 3.88 mmol) and DIEA (1.0 g, 7.74 mmol) in dichloromethane (10 mL) was added HATU (1.47 g, 3.87 mmol). The mixture was stirred at room temperature for 3 hours. The resulting solution was concentrated under vacuum. The residue was purified by flash chromatography on silica gel eluting with dichloromethane/methanol (10/1) to afford azetidin-1-yl ((1s,3s)-3-hydroxycyclobutyl)methanone (230 mg, 1.60 mmol, 62.2% yield) as an off-white solid.

Step 2: tert-Butyl 7-(3-((((1s,3s)-3-(azetidine-1-carbonyl)cyclobutoxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

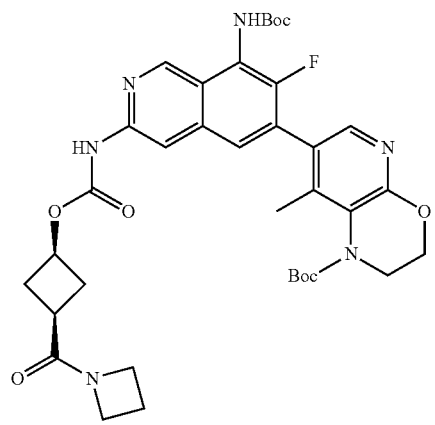 [SMILES: Cc1c(-c2cc3cc(NC(=O)O[C@H]4C[C@@H](C(=O)N5CCC5)C4)ncc3c(NC(=O)OC(C)(C)C)c2F)cnc2c1N(C(=O)OC(C)(C)C)CCO2]

To a solution of tert-butyl 7-[3-amino-7-fluoro-8-(isopropoxycarbonylamino)-6-isoquinolyl]-8-methyl-2,3-dihydropyrido[2,3-b][1,4]oxazine-1-carboxylate (150 mg, 0.29 mmol), azetidin-1-yl-(3-hydroxycyclobutyl)methanone (91.5 mg, 0.59 mmol) and DIEA (111.0 mg, 0.86 mmol) in DCM (15 mL) was added triphosgene (61.5 mg, 0.21 mmol) at 0° C. The mixture was stirred at room temperature for 30 min. The resulting solution was concentrated under vacuum. The residue was purified by flash chromatography on silica gel eluting with petroleum ether/ethyl acetate (4/3) to afford tert-butyl 7-(3-((((1s,3s)-3-(azetidine-1-carbonyl)cyclobutoxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate (150 mg, 0.21 mmol, 72.4% yield) as a yellow solid. LCMS (ESI) [M+H]$^+$=707.3.

Step 4: (1s,3s)-3-(Azetidine-1-carbonyl)cyclobutyl (8-amino-7-fluoro-6-(8-methyl-2,3-dihydro-1H-pyrido[2,3-b][1,4]oxazin-7-yl)isoquinolin-3-yl)carbamate (Compound 517a)

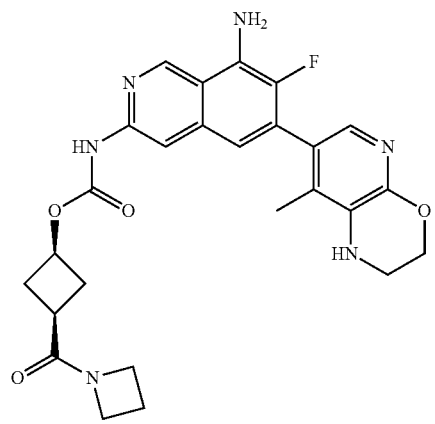 [SMILES: Cc1c(-c2cc3cc(NC(=O)O[C@H]4C[C@@H](C(=O)N5CCC5)C4)ncc3c(N)c2F)cnc2c1NCCO2]

To a solution of tert-butyl 7-(3-((((1s,3s)-3-(azetidine-1-carbonyl)cyclobutoxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate (150.0 mg, 0.21 mmol) in dichloromethane (6 mL) was added trifluoroacetic acid (3.0 mL). The mixture was stirred at room temperature for 30 min. The resulting solution was concentrated under vacuum. The residue was re-dissolved in dichloromethane and adjusted to pH 8 with TEA. The residue was purified by Prep-HPLC (Column: Xselect CSH OBD Column 30*150 mm, 5 μm; Mobile Phase A: Water (0.1% FA), Mobile Phase B: ACN; Flow rate: 60 mL/min; Gradient: 9% B to 39% B in 7 min) to afford [3-(azetidine-1-carbonyl)cyclobutyl]N-[8-amino-7-fluoro-6-(8-methyl-2,3-dihydro-1H-pyrido[2,3-b][1,4]oxazin-7-yl)-3-isoquinolyl]carbamate (27.4 mg, 0.053 mmol, 25.4% yield) as a yellow solid. LCMS (ESI) [M+H]$^+$=507.2, R$_T$ 1.724 min, Method J. $^1$H NMR (400 MHz, DMSO-d$_6$) δ 10.09 (s, 1H), 9.33 (s, 1H), 7.95 (s, 1H), 7.32 (s, 1H), 6.83 (d, J=6.2 Hz, 1H), 6.20 (s, 2H), 5.67 (d, J=2.7 Hz, 1H), 4.87-4.94 (m, 1H), 4.28 (t, J=4.3 Hz, 2H), 4.07 (t, J=7.6 Hz, 2H), 3.83 (t, J=7.7 Hz, 2H), 3.31-3.37 (m, 2H), 2.77-2.63 (m, 1H), 2.46 (dd, J=7.4, 2.8 Hz, 2H), 2.24-2.09 (m, 4H), 1.92 (d, J=1.6 Hz, 3H).

Example 250

(R)-Tetrahydrofuran-3-yl (8-amino-7-fluoro-6-((R)-3-fluoro-8-methyl-2,3-dihydro-1H-pyrido[2,3-b][1,4]oxazin-7-yl)isoquinolin-3-yl)carbamate and (R)-Tetrahydrofuran-3-yl (8-amino-7-fluoro-6-((S)-3-fluoro-8-methyl-2,3-dihydro-1H-pyrido[2,3-b][1,4]oxazin-7-yl)isoquinolin-3-yl)carbamate (Compound 518a and Compound 518b)

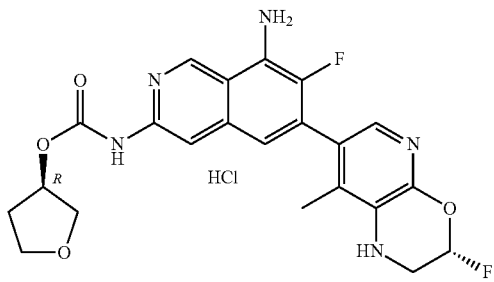

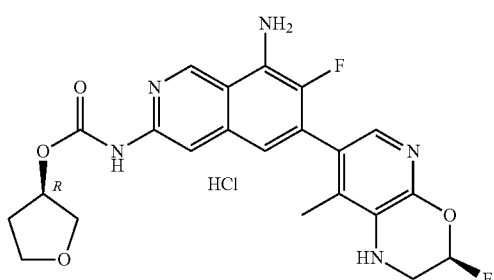

Step 1: 7-Bromo-3-fluoro-8-methyl-1H-pyrido[2,3-b][1,4]oxazin-2-one

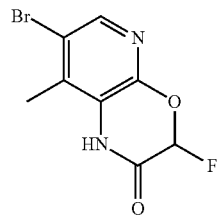

Under nitrogen, to a solution of 3-amino-5-bromo-4-methyl-pyridin-2-ol (6.0 mg, 29.55 mmol) and KF (6.87 g, 118.2 mmol) in N,N-dimethylformamide (60 mL) was added ethyl bromofluoroacetate (1.09 g, 59.1 mmol) at room temperature. The resulting solution was stirred at 80° C. for 5 hours. The reaction mixture was diluted with water and extracted with ethyl acetate. The organic layers were combined, dried over anhydrous sodium sulfate and concentrated under vacuum. The residue was purified by flash chromatography on silica gel eluting with petroleum ether/ethyl acetate (5/1) to afford 7-bromo-3-fluoro-8-methyl-1H-pyrido[2,3-b][1,4]oxazin-2-one (1.4 g, 5.363 mmol, 24.1% yield) as a yellow solid. LCMS (ESI) [M+H]$^+$=261.1.

Step 2: 7-Bromo-3-fluoro-8-methyl-2,3-dihydro-1H-pyrido[2,3-b][1,4]oxazine

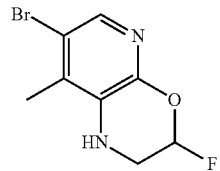

Under nitrogen, to a solution of 7-bromo-3-fluoro-8-methyl-1H-pyrido[2,3-b][1,4]oxazin-2-one (1.4 g, 5.36 mmol) in tetrahydrofuran (25 mL) was added BH$_3$ (16.1 mL, 16.1 mmol, 1 M in THF) at 0° C. The resulting solution was stirred at 0° C. for 0.5 h and at 60° C. for 2 h. The reaction was quenched with MeOH at 0° C. Then HCl (3 ml, 6 M in water) was added and the mixture was stirred for 0.5 h. The mixture was then adjusted to pH 8 with NH$_3$H$_2$O and extracted with dichloromethane. The organic layers were combined, dried over anhydrous sodium sulfate, filtered and concentrated under vacuum. The residue was purified by flash chromatography on silica gel eluting with petroleum ether/ethyl acetate (3/1) to afford 7-bromo-3-fluoro-8-methyl-2,3-dihydro-1H-pyrido[2,3-b][1,4]oxazine (800 mg, 3.24 mmol, 60.4% yield) as a yellow solid. LCMS (ESI) [M+H]$^+$=247.1.

Step 3: tert-Butyl 7-bromo-3-fluoro-8-methyl-2,3-dihydropyrido[2,3-b][1,4]oxazine-1-carboxylate

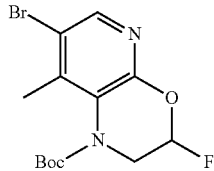 [SMILES: Cc1c(Br)cnc2c1N(C(=O)OC(C)(C)C)CC(F)O2]

Under nitrogen, to a solution of 7-bromo-3-fluoro-8-methyl-2,3-dihydro-1H-pyrido[2,3-b][1,4]oxazine (800.0 mg, 3.24 mmol) in THF (25 mL) was added NaHMDS (4.8 ml, 9.71 mmol, 2 M in THF) at 0° C. The resulting solution was stirred for 0.5 h at 0° C. Then (Boc)₂O (2.12 g, 9.71 mmol) was added and the mixture was stirred at 0° C. for 1.5 h. The reaction was quenched with MeOH and concentrated under vacuum. The residue was purified by flash chromatography on silica gel eluting with petroleum ether/ethyl acetate (5/1) to afford tert-butyl 7-bromo-3-fluoro-8-methyl-2,3-dihydropyrido[2,3-b][1,4]oxazine-1-carboxylate (500 mg, 1.44 mmol, 44.5% yield) as a white solid. LCMS (ESI) [M+H]⁺=347.2.

Step 4: tert-Butyl 3-fluoro-8-methyl-7-(4,4,5,5-tetramethyl-1,3,2-dioxaborolan-2-yl)-2,3-dihydropyrido[2,3-b][1,4]oxazine-1-carboxylate

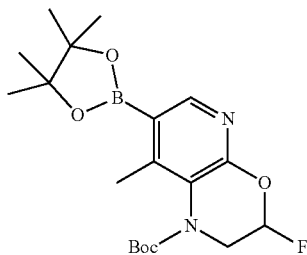 [SMILES: Cc1c(B2OC(C)(C)C(C)(C)O2)cnc2c1N(C(=O)OC(C)(C)C)CC(F)O2]

Under nitrogen, a mixture of tert-butyl 7-bromo-3-fluoro-8-methyl-2,3-dihydropyrido[2,3-b][1,4]oxazine-1-carboxylate (500.0 mg, 1.44 mmol), B₂Pin₂ (1.83 g, 7.2 mmol), Pd(dppf)Cl₂ (235.2 mg, 0.29 mmol) and KOAc (424.0 mg, 4.32 mmol) in 1,4-dioxane (20 mL) was stirred at 100° C. for 3 h. The reaction mixture was concentrated under vacuum. The residue was purified by flash chromatography on silica gel eluting with petroleum ether/ethyl acetate (3/1) to afford tert-butyl 3-fluoro-8-methyl-7-(4,4,5,5-tetramethyl-1,3,2-dioxaborolan-2-yl)-2,3-dihydropyrido[2,3-b][1,4]oxazine-1-carboxylate (500 mg, 1.27 mmol, 88.1% yield) as a yellow solid. LCMS (ESI) [M+H]⁺=394.3.

Step 5: tert-Butyl 7-[8-chloro-7-fluoro-3-[[(3R)-tetrahydrofuran-3-yl]oxycarbonylamino]-6-isoquinolyl]-3-fluoro-8-methyl-2,3-dihydropyrido[2,3-b][1,4]oxazine-1-carboxylate

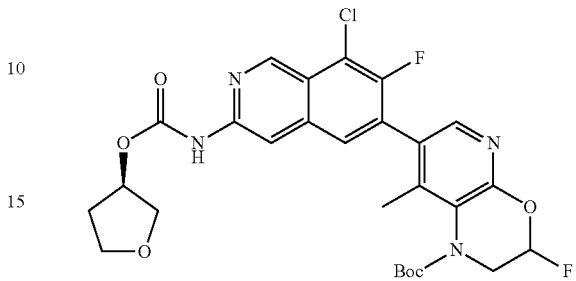

Under nitrogen, a mixture of [(3R)-tetrahydrofuran-3-yl] N-(8-chloro-7-fluoro-6-iodo-3-isoquinolyl)carbamate (500.0 mg, 1.15 mmol), tert-butyl 3-fluoro-8-methyl-7-(4,4,5,5-tetramethyl-1,3,2-dioxaborolan-2-yl)-2,3-dihydropyrido[2,3-b][1,4]oxazine-1-carboxylate (541.8 mg, 1.37 mmol), Pd(dppf)Cl₂ (186.9 mg, 0.23 mmol) and K₂CO₃ (474.1 mg, 3.44 mmol) in 1,4-dioxane (15 mL) and water (1.5 mL) was stirred at 90° C. for 3 hours. The resulting mixture was concentrated under vacuum. The residue was purified by flash chromatography on silica gel eluting with dichloromethane/methanol (20/1) to afford tert-butyl 7-[8-chloro-7-fluoro-3-[[(3R)-tetrahydrofuran-3-yl]oxycarbonylamino]-6-isoquinolyl]-3-fluoro-8-methyl-2,3-dihydropyrido[2,3-b][1,4]oxazine-1-carboxylate (380 mg, 0.66 mmol, 57.5% yield) as a yellow solid. LCMS (ESI) [M+H]⁺= 577.0.

Step 6: tert-Butyl 7-[8-(tert-butoxycarbonylamino)-7-fluoro-3-[[(3R)-tetrahydrofuran-3-yl]oxycarbonylamino]-6-isoquinolyl]-3-fluoro-8-methyl-2,3-dihydropyrido[2,3-b][1,4]oxazine-1-carboxylate

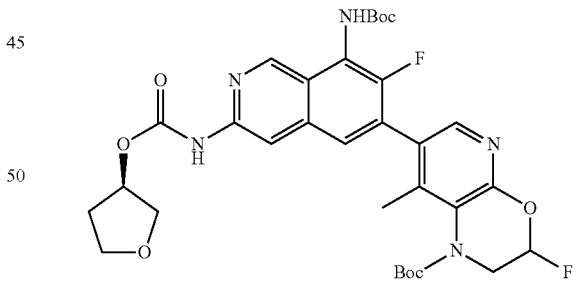

Under nitrogen, a mixture of tert-butyl 7-[8-chloro-7-fluoro-3-[[(3R)-tetrahydrofuran-3yl]oxycarbonylamino]-6-isoquinolyl]-3-fluoro-8-methyl-2,3-dihydropyrido[2,3-b][1,4]oxazine-1-carboxylate (380.0 mg, 0.66 mmol), NH₂Boc (3.82 g, 32.93 mmol), Brettphos Pd G3 (119.4 mg, 0.13 mmol) and Cs₂CO₃ (428.1 mg, 1.32 mmol) in 1,4-dioxane (8 mL) was stirred at 90° C. for 3 h. The reaction was concentrated under vacuum and purified by flash chromatography on silica gel eluting with dichloromethane/methanol (20/1) to afford tert-butyl 7 48-(tert-butoxycarbonylamino)-7-fluoro-3-[[(3R)-tetrahydrofuran-3-yl]oxycarbonylamino]-6-isoquinolyl]-3-fluoro-8-methyl-2,3- dihydropyrido[2,3-b][1,4]oxazine-1-carboxylate (270 mg, 0.41 mmol, 62.3% yield) as a yellow solid. LCMS (ESI) [M+H]$^+$=657.7.

Step 7: (R)-Tetrahydrofuran-3-yl (8-amino-7-fluoro-6-((R)-3-fluoro-8-methyl-2,3-dihydro-1H-pyrido[2,3-b][1,4]oxazin-7-yl)isoquinolin-3-yl)carbamate and (R)-Tetrahydrofuran-3-yl (8-amino-7-fluoro-6-((S)-3-fluoro-8-methyl-2,3-dihydro-1H-pyrido[2,3-b][1,4]oxazin-7-yl)isoquinolin-3-yl)carbamate

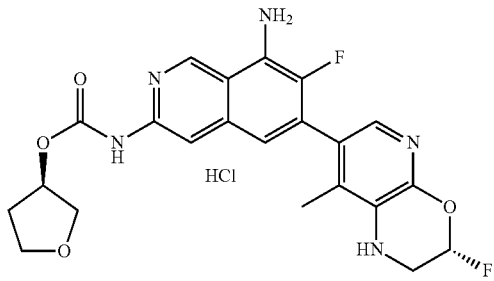

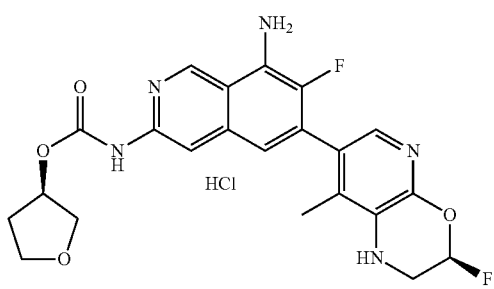

To a solution of tert-butyl 7-[8-(tert-butoxycarbonylamino)-7-fluoro-3-[[(3R)-tetrahydrofuran-3-yl]oxycarbonylamino]-6-isoquinolyl]-3-fluoro-8-methyl-2,3-dihydropyrido[2,3-b][1,4]oxazine-1-carboxylate (270 mg, 0.41 mmol) in dichloromethane (8 mL) was added TFA (3.6 mL). The mixture was stirred at room temperature for 3 hours. The mixture was concentrated under vacuum and the residue was purified by Prep-HPLC (Column: X Bridge Prep OBD C18 Column, 30×150 mm, 5 µm; Mobile Phase A: Water (10 mmol/L NH$_4$HCO$_3$), Mobile Phase B: ACN) to afford a mixture of stereoisomers. The mixture was separated by chiral HPLC to afford two stereoisomers. Then the two isomers were dissolved in methanol, treated with HCl (0.1 ml, 1 M in dioxane) and concentrated to afford their HCl salts. Absolute stereochemistry at oxazin was arbitrarily assigned.

Isomer 1: (Compound 518a) (8 mg, 0.016 mmol, 6.7% yield). R$_T$ 1.306 min (CHIRALPAK IC-3 0.46*5 cm; 3 µm. Mobile phase: (MTBE (0.3% IPAmine):EtOH=60:40). LCMS(ESI): [M+H]$^+$=457.4, R$_T$ 2.070 min; Method J. $^1$H NMR (400 MHz, methanol-d$_4$) δ 9.42 (s, 1H), 7.86 (s, 1H), 7.57 (s, 1H), 7.08 (d, J=6.0 Hz, 1H), 6.34 (d, J=53.4 Hz, 1H), 5.52-5.36 (m, 1H), 4.02-3.94 (m, 3H), 3.90 (td, J=8.4, 4.4 Hz, 1H), 3.72 (dd, J=13.2, 4.2 Hz, 1H), 3.53-3.38 (m, 1H), 2.31 (dtd, J=14.5, 8.5, 6.2 Hz, 1H), 2.24-1.98 (m, 4H).

Isomer 2 (Compound 518b) (6.1 mg, 0.0124 mmol, 5.1% yield). R$_T$ 1.2660 min (CHIRALPAK IC-3 0.46*5 cm; 3 µm. Mobile phase: (MTBE (0.3% IPA):EtOH=60:40). LCMS (ESI): [M+H]$^+$=457.4, R$_T$ 2.070 min; Method J. $^1$H NMR (400 MHz, Methanol-d$_4$) δ 9.42 (s, 1H), 7.86 (s, 1H), 7.57 (s, 1H), 7.08 (d, J=6.0 Hz, 1H), 6.34 (d, J=53.4 Hz, 1H), 5.52-5.36 (m, 1H), 4.02-3.94 (m, 3H), 3.90 (td, J=8.4, 4.4 Hz, 1H), 3.72 (dd, J=13.2, 4.2 Hz, 1H), 3.53-3.38 (m, 1H), 2.31 (dtd, J=14.5, 8.5, 6.2 Hz, 1H), 2.24-1.98 (m, 4H).

Example 251

(1s,3s)-3-(Dimethylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate (Compound 519a)

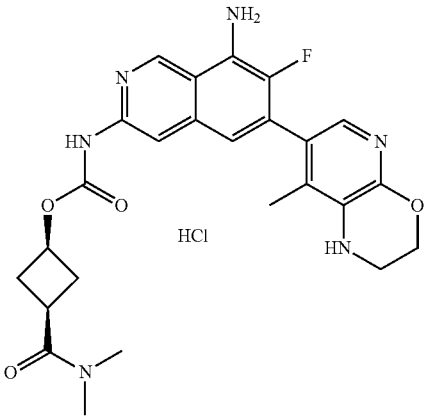 [SMILES: Cc1c(-c2cc3cc(NC(=O)O[C@H]4C[C@@H](C(=O)N(C)C)C4)ncc3c(N)c2F)cnc2c1NCCO2 ; Cl]

Step 1: (1s,3s)-3-Hydroxy-N,N-dimethylcyclobutane-1-carboxamide

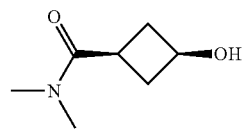

To a solution of 3-hydroxycyclobutanecarboxylic acid (300.0 mg, 2.58 mmol), N,N-dimethylamine (174.8 mg, 3.88 mmol) and DIEA (1.0 g, 7.74 mmol) in dichloromethane (20 mL) was added HATU (1.47 g, 3.88 mmol) at room temperature. The resulting solution was stirred at room temperature for 3 hours. Then the resulting solution was concentrated under vacuum. The residue was purified by flash chromatography on silica gel eluting with dichloromethane/methanol (10/1) to afford (1s,3s)-3-hydroxy-N,N-dimethylcyclobutane-1-carboxamide (230 mg, 1.60 mmol, 62.2% yield) as an off-white solid.

Step 2: tert-Butyl 7-(8-((tert-butoxy carbonyl)amino)-3-((((1s,3s)-3-(dimethylcarbamoyl)cyclobutoxy)carbonyl)amino)-7-fluoroisoquinolin-6-yl)-8-methyl-2,3-dihydro-1H-pyrido[2,3-b][1,4]oxazine-1-carboxylate

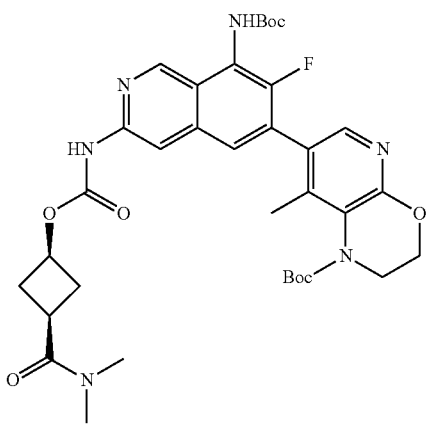 [SMILES: Cc1c(-c2cc3cc(NC(=O)O[C@H]4C[C@@H](C(=O)N(C)C)C4)ncc3c(NC(=O)OC(C)(C)C)c2F)cnc2c1N(C(=O)OC(C)(C)C)CCO2]

To a solution of tert-butyl 7-[3-amino-7-fluoro-8-(isopropoxycarbonylamino)-6-isoquinolyl]-8-methyl-2,3-dihydropyrido[2,3-b][1,4]oxazine-1-carboxylate (150.0 mg, 0.29 mmol), 3-hydroxy-N,N-dimethyl-cyclobutanecarboxamide (81.7 mg, 0.57 mmol) and DIEA (110.7 mg, 0.86 mmol) in 1,2-dichloroethane (15 mL) was added triphosgene (59.3 mg, 0.20 mmol) at 0° C. The resulting solution was stirred at room temperature for 30 min and concentrated under vacuum. The residue was purified by flash chromatography on silica gel eluting with petroleum ether/ethyl acetate (4/3) to afford tert-butyl 7-(8-((tert-butoxycarbonyl)amino)-3-(((((1s,3s)-3-(dimethylcarbamoyl)cyclobutoxy)carbonyl)amino)-7-fluoroisoquinolin-6-yl)-8-methyl-2,3-dihydro-1H-pyrido[2,3-b][1,4]oxazine-1-carboxylate (160 mg, 0.23 mmol, 80.7% yield) as a yellow solid. LCMS (ESI) [M+H]$^+$=695.3.

Step 3: (1s,3s)-3-(Dimethylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate

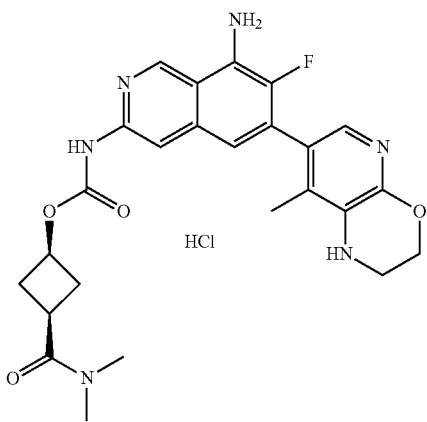 [SMILES: Cc1c(-c2cc3cc(NC(=O)O[C@H]4C[C@@H](C(=O)N(C)C)C4)ncc3c(N)c2F)cnc2c1NCCO2 ; Cl]

To a solution of tert-butyl 7-(8-((tert-butoxycarbonyl)amino)-3-((((1s,3s)-3-(dimethylcarbamoyl)cyclobutoxy)carbonyl)amino)-7-fluoroisoquinolin-6-yl)-8-methyl-2,3-dihydro-1H-pyrido[2,3-b][1,4]oxazine-1-carboxylate (150.0 mg, 0.22 mmol) in dichloromethane (6 mL) was added trifluoroacetic acid (3.0 mL). The mixture was stirred at room temperature for 30 min. Then the resulting solution was concentrated under vacuum. The pH of the residue was adjusted to pH 8 with TEA. The resulting residue was purified by Prep-HPLC (Column: X select CSH OBD Column 30*150 mm, 5 μm; Mobile Phase A: Water (0.1% FA), Mobile Phase B: ACN; Flow rate: 60 mL/min; Gradient: 9% B to 36% B in 7 min). The purified product was dissolved in methanol, treated with HCl (0.2 ml, 1 M in dioxane) and concentrated to afford [3-(dimethylcarbamoyl)cyclobutyl] N-[8-amino-7-fluoro-6-(8-methyl-2,3-dihydro-1H-pyrido[2,3-b][1,4]oxazin-7-yl)-3-isoquinolyl]carbamate hydrochloride (55.1 mg, 0.10 mmol, 46.4% yield) as a white solid. LCMS (ESI) [M+H]$^+$=495.2, R$_T$ 1.786 min, Method J. $^1$H NMR (400 MHz, DMSO-d$_6$) δ 10.27 (s, 1H), 9.45 (s, 1H), 7.98 (s, 1H), 7.59 (s, 1H), 6.95 (d, J=6.0 Hz, 1H), 4.89-4.97 (m, 1H), 4.53 (t, J=4.5 Hz, 2H), 3.51 (d, J=4.5 Hz, 2H), 3.00-3.07 (m, 1H), 2.91 (s, 3H), 2.82 (s, 3H), 2.59-2.54 (m, 2H), 2.30-2.14 (m, 2H), 2.05 (d, J=1.5 Hz, 3H).

Example 252

(1s,3s)-3-(Methylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate hydrochloride (Compound 520a)

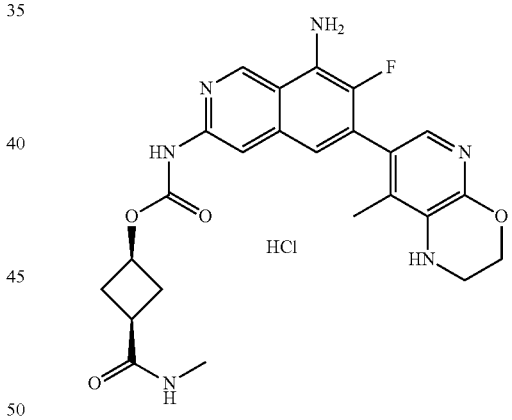

Step 1:
3-Hydroxy-N-methyl-cyclobutanecarboxamide

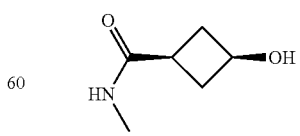

To a solution of cis-3-hydroxycyclobutanecarboxylic acid (300.0 mg, 2.58 mmol), methanamine (120.4 mg, 3.88 mmol) and DIEA (1.0 g, 7.74 mmol) in dichloromethane (10 mL) was added HATU (1.47 g, 3.87 mmol) at room temperature. The resulting mixture was stirred at room temperature for 3 hours. Then the resulting solution was concentrated under vacuum. The residue was purified by flash chromatography on silica gel eluting with dichloromethane/methanol (10/1) to afford (1s,3s)-3-hydroxy-N-methylcyclobutane-1-carboxamide (230 mg, 1.78 mmol, 68.9% yield) as an off-white solid.

Step 2: tert-Butyl 7-(8-((tert-butoxycarbonyl)amino)-7-fluoro-3-(((((1s,3s)-3-(methylcarbamoyl)cyclobutoxy)carbonyl)amino)isoquinolin-6-yl)-8-methyl-2,3-dihydro-1H-pyrido[2,3-b][1,4]oxazine-1-carboxylate

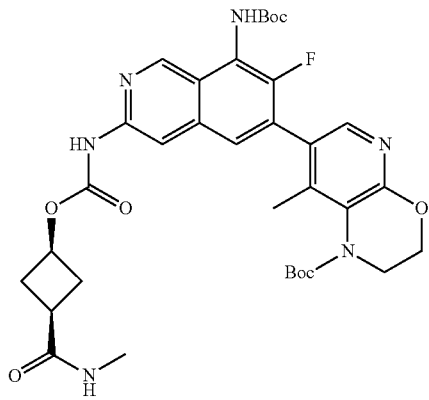 [SMILES: CNC(=O)[C@H]1C[C@@H](OC(=O)Nc2cc3cc(-c4cnc5c(c4C)N(C(=O)OC(C)(C)C)CCO5)c(F)c(NC(=O)OC(C)(C)C)c3cn2)C1]

To a solution of tert-butyl7-[3-amino-8-(tert-butoxycarbonylamino)-7-fluoro-6-isoquinolyl]-8-methyl-2,3-dihydropyrido[2,3-b][1,4]oxazine-1-carboxylate (150.0 mg, 0.29 mmol), 3-hydroxy-N-methyl-cyclobutanecarboxamide (73.7 mg, 0.57 mmol) and DIEA (110.7 mg, 0.86 mmol) in dichloromethane (15 mL) was added triphosgene (59.3 mg, 0.20 mmol) at 0° C. The resulting solution was stirred at room temperature for 30 min and concentrated under vacuum. The residue was purified by flash on silica gel eluting with petroleum ether/ethyl acetate (4/3) to afford tert-butyl 7-(8-((tert-butoxycarbonyl)amino)-7-fluoro-3-(((((1s,3s)-3-(methylcarbamoyl)cyclobutoxy)carbonyl)amino)isoquinolin-6-yl)-8-methyl-2,3-dihydro-1H-pyrido[2,3-b][1,4]oxazine-1-carboxylate (120 mg, 0.18 mmol, 61.8% yield) as a yellow solid. LCMS (ESI) [M+H]$^+$=681.

Step 3: (1s,3s)-3-(Methylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate hydrochloride

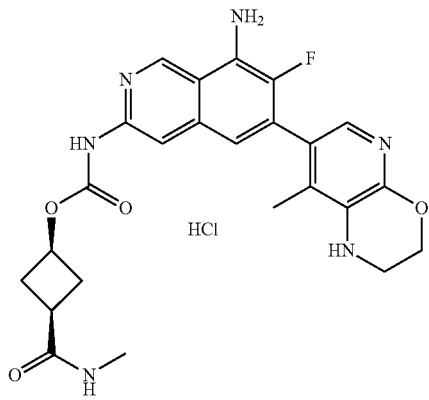 [SMILES: CNC(=O)[C@H]1C[C@@H](OC(=O)Nc2cc3cc(-c4cnc5c(c4C)NCCO5)c(F)c(N)c3cn2)C1 ; Cl]

To a solution of tert-butyl7-[8-(tert-butoxycarbonylamino)-7-fluoro-3-[[3-(methylcarbamoyl)cyclobutoxy]carbonylamino]-6-isoquinolyl]-8-methyl-2,3-dihydropyrido[2,3-b][1,4]oxazine-1-carboxylate (150.0 mg, 0.22 mmol) in dichloromethane (4 mL) was added trifluoroacetic acid (2.0 mL, 25.96 mmol) at 0° C. The resulting solution was stirred at room temperature for 30 min. The pH of the reaction mixture was adjusted to pH 8 with TEA. The crude product was purified by Prep-HPLC (Column: X select CSH OBD Column 30*150 mm, 5 μm; Mobile Phase A: Water (0.1% FA), Mobile Phase B:ACN; Flow rate: 60 mL/min; Gradient: 5% B to 33% B in 7 min). The purified product was dissolved in methanol and treated with HCl (0.2 ml, 1 M in dioxane) and concentrated under vacuum to afford [3-(methylcarbamoyl)cyclobutyl]N-[8-amino-7-fluoro-6-(8-methyl-2,3-dihydro-1H-pyrido[2,3-b][1,4]oxazin-7-yl)-3-isoquinolyl]carbamate hydrochloride (67.9 mg, 0.13 mmol, 58.4% yield) as an orange solid. LCMS (ESI) [M+H]$^+$= 481.2, R$_T$ 1.771 min, Method J. $^1$H NMR (400 MHz, DMSO-d$_6$) δ10.26 (s, 1H), 9.44 (s, 1H), 7.98 (s, 1H), 7.84 (d, J=5.2 Hz, 1H), 7.59 (s, 1H), 6.94 (d, J=6.0 Hz, 1H), 4.86-4.93 (m, 1H), 4.53 (d, J=4.7 Hz, 2H), 3.50 (t, J=4.5 Hz, 2H), 2.69-2.58 (m, 4H), 2.42-2.46 (m, 2H), 2.16-2.24 (m, 2H), 2.04 (d, J=1.6 Hz, 3H).

Example 253

(3S,4R)-3-Fluoro-1-((S)-tetrahydrofuran-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; (3S,4R)-3-fluoro-1-((R)-tetrahydrofuran-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; (3R,4S)-3-fluoro-1-((S)-tetrahydrofuran-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; and (3R,4S)-3-fluoro-1-((R)-tetrahydrofuran-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate (Compound 569a, Compound 569b, Compound 569c. and Compound 569d)

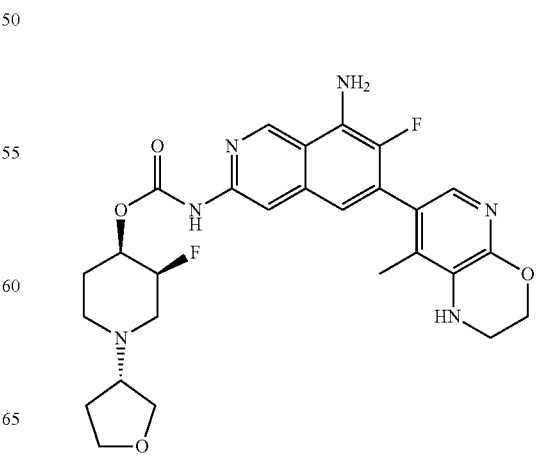

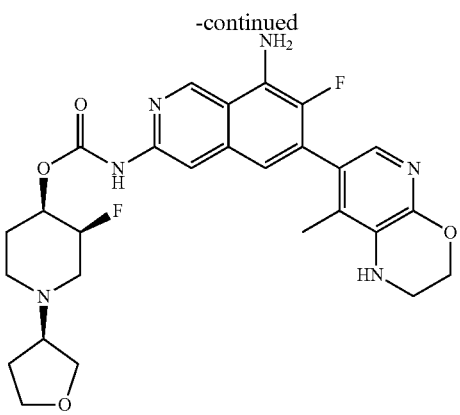

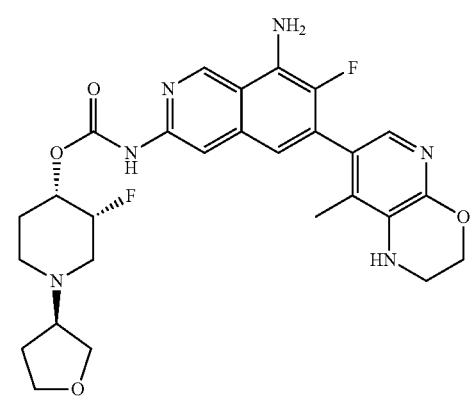

A solution of ((3S,4R)-3-fluoro-4-piperidyl) N-[8-amino-7-fluoro-6-(8-methyl-2,3-dihydro-1H-pyrido[2,3-b][1,4]oxazin-7-yl)-3-isoquinolyl]carbamate (300.0 mg, 1.28 mmol) and 3-oxotetrahydrofuran (164 mg, 1.92 mmol) in methyl alcohol (10 mL) was stirred at 25° C. for 5 min. Then titanium tetraisopropanolate (362.0 mg, 1.27 mmol) was added. The mixture was stirred at 60° C. for 1 hour. After cooling to room temperature, NaCNBH$_3$ (120.0 mg, 1.62 mmol) was added and the mixture was stirred at 25° C. for 1 hour. The reaction mixture was concentrated under vacuum and purified by Prep-HPLC (Column: X Bridge Prep OBD C18 Column 30×150 mm, 5 μm; Mobile Phase A: Water (10 mmol, NH$_4$HCO$_3$), Mobile Phase B: ACN; Flow rate: 60 mL/min; Gradient: 23% B to 40% B in 10 min) to afford a racemate product. The racemic product was separated by chiral-HPLC (CHIRALPAK IA-3 2*25 cm, 5 μm. Mobile phase A: MeOH (8 mmol/L NH$_3$ in MeOH), Mobile phase B: MDCM; Flow rate 20 ml/L, Gradient: 30% B to 30% B in 17.4 min) to afford two enantiomers. Relative stereochemistry are as drawn. Absolute stereochemistry was arbitrarily assigned.

Isomer 1: Compound 569a (22 mg, 0.0407 mmol, 3.2% yield): R$_T$ 2.412 min (CHIRALPAK IE-3, 0.46*5 cm; 3 μm; MeOH: DCM (0.1% DEA)=70:30; 1 ml/min). LCMS (ESI) [M+H]$^+$=541.3, R$_T$ 0.939 min, Method J. $^1$H NMR (300 MHz, DMSO-d$_6$) δ 10.19 (s, 1H), 9.35 (s, 1H), 7.96 (s, 1H), 7.33 (s, 1H), 6.83 (d, J=6.1 Hz, 1H), 6.21 (s, 2H), 5.66 (s, 1H), 4.92 (s, 2H), 4.76 (s, 2H), 4.28 (s, 2H), 3.80 (s, 1H), 3.72 (t, J=7.8 Hz, 1H), 3.62 (q, J=7.9 Hz, 3H), 3.12-2.92 (m, 2H), 2.75-2.54 (m, 1H), 2.40-2.19 (m, 1H), 1.91 (s, 5H), 1.84-1.70 (m, 2H).

Isomer 2: Compound 569b (23 mg, 0.0425 mmol, 3.9% yield): R$_T$ 2.986 min (CHIRALPAK IE-3, 0.46*5 cm; 3 μm; MeOH: DCM (0.1% DEA)=70:30; 1 ml/min). LCMS (ESI) [M+H]$^+$=541.3, R$_T$ 0.939 min, Method J. $^1$H NMR (300 MHz, DMSO-d$_6$) δ 10.19 (s, 1H), 9.35 (s, 1H), 7.96 (s, 1H), 7.33 (s, 1H), 6.83 (d, J=6.1 Hz, 1H), 6.21 (s, 2H), 5.66 (s, 1H), 4.92 (s, 2H), 4.76 (s, 2H), 4.28 (s, 2H), 3.80 (s, 1H), 3.72 (t, J=7.8 Hz, 1H), 3.62 (q, J=7.9 Hz, 3H), 3.12-2.92 (m, 2H), 2.75-2.54 (m, 1H), 2.40-2.19 (m, 1H), 1.91 (s, 5H), 1.84-1.70 (m, 2H).

The other 2 isomers were prepared using a similar procedure using ((3R,4S)-3-fluoro-4-piperidyl) N-[8-amino-7-fluoro-6-(8-methyl-2,3-dihydro-1H-pyrido[2,3-b][1,4]oxazin-7-yl)-3-isoquinolyl]carbamate as the starting material. Relative stereochemistry are as drawn. Absolute stereochemistry was arbitrarily assigned.

Isomer 3: Compound 569c (13.8 mg, 0.0255 mmol, 2% yield): R$_T$ 4.903 min (CHIRALPAK IG-3 0.46*5 cm; 3 μm; (Hex:DCM=1:1)(0.1% DEA):MeOH=40:60); 1 ml/min). LCMS (ESI) [M+H]$^+$=541.3, R$_T$ 1.882 min, Method K; $^1$H NMR (300 MHz, DMSO-d$_6$) δ 10.18 (s, 1H), 9.35 (s, 1H), 7.96 (s, 1H), 7.33 (s, 1H), 6.83 (d, J=6.2 Hz, 1H), 6.20 (s, 2H), 5.66 (s, 1H), 4.90 (s, 2H), 4.74 (s, 2H), 3.85-3.77 (m, 1H), 3.76-3.68 (m, 1H), 3.65-3.58 (m, 1H), 3.56-3.48 (m, 1H), 3.31 (s, 3H), 3.11-2.94 (m, 1H), 2.94-2.79 (m, 1H), 2.89-2.74 (m, 1H), 2.76-2.54 (m, 1H), 1.93-1.88 (m, 5H), 1.84-1.74 (m, 2H)

Isomer 4: Compound 569d (10.7 mg, 0.0198 mmol, 1.6% yield): R$_T$ 6.596 min(CHIRALPAK IG-3 0.46*5 cm; 3 μm; (Hex:DCM=1:1)(0.1% DEA):MeOH=40:60); 1 ml/min). LCMS (ESI) [M+H]$^+$=541.3, R$_T$ 1.882 min, Method K; $^1$H NMR (300 MHz, DMSO-d$_6$) δ 10.18 (s, 1H), 9.35 (s, 1H), 7.96 (s, 1H), 7.33 (s, 1H), 6.83 (d, J=6.2 Hz, 1H), 6.20 (s, 2H), 5.66 (s, 1H), 4.90 (s, 2H), 4.74 (s, 2H), 3.85-3.77 (m, 1H), 3.76-3.68 (m, 1H), 3.65-3.58 (m, 1H), 3.56-3.48 (m, 1H), 3.31 (s, 3H), 3.11-2.94 (m, 1H), 2.94-2.79 (m, 1H), 2.89-2.74 (m, 1H), 2.76-2.54 (m, 1H), 1.93-1.88 (m, 5H), 1.84-1.74 (m, 2H).

Example 254

(1r,3r)-3-Hydroxy-3-methylcyclobutyl (8-amino-7-fluoro-6-(4-methyl-5-(methylamino)pyridin-3-yl)isoquinolin-3-yl)carbamate and (1s,3s)-3-Hydroxy-3-methylcyclobutyl (8-amino-7-fluoro-6-(4-methyl-5-(methylamino)pyridin-3-yl)isoquinolin-3-yl)carbamate (Compound 527a and Compound 527b)

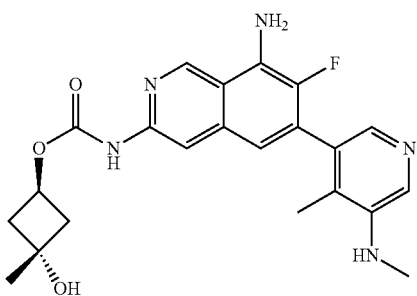

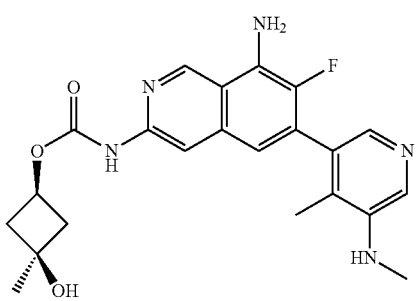

Step 1: tert-butyl N-(5-bromo-4-methyl-3-pyridyl)carbamate

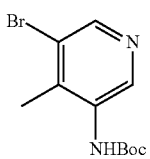

A solution of 5-bromo-4-methyl-pyridin-3-amine (8000.0 mg, 42.77 mmol) in THF (400 mL) was added dropwise NaHMDS (45 mL, 45 mmol, 1 mol/L in THF) at −78° C. The reaction was stirred for 1 hour at −78° C. Then (Boc)$_2$O (11.60 g, 53.21 mmol) was added. The mixture was stirred at −78° C. for 2 hours. The reaction was quenched with methanol and concentrated under vacuum. The residue was purified by flash chromatography on silica gel eluting with petroleum ether/ethyl acetate (46/54) to afford tert-butyl N-(5-bromo-4-methyl-3-pyridyl)carbamate (10 g, 34.825 mmol, 81.4% yield) as a white solid. LCMS (ESI) [M+H]$^+$= 288.

Step 2: tert-butyl N-(5-bromo-4-methyl-3-pyridyl)-N-methyl-carbamate

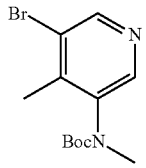 [SMILES: Cc1c(Br)cncc1N(C)C(=O)OC(C)(C)C]

To a solution of tert-butyl N-(5-bromo-4-methyl-3-pyridyl)carbamate (8000.0 mg, 27.86 mmol) and t-BuOK (4683.0 mg, 41.81 mmol) in THF (150 mL) was added iodomethane (5937.0 mg, 41.81 mmol) at room temperature. The reaction was stirred for 2 hours at room temperature. After filtration, the filtrate was concentrated under vacuum and purified by flash chromatography on silica gel eluting with petroleum ether/ethyl acetate (30/70) to afford tert-butyl N-(5-bromo-4-methyl-3-pyridyl)-N-methyl-carbamate (7900 mg, 26.23 mmol, 94.1% yield) as a colorless oil. LCMS (ESI) [M+H]$^+$=303.

Step 3: tert-butyl N-methyl-N-[4-methyl-5-(4,4,5,5-tetramethyl-1,3,2-dioxaborolan-2-yl)-3-pyridyl]carbamate

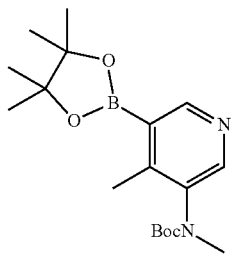

A mixture of tert-butyl N-(5-bromo-4-methyl-3-pyridyl)-N-methyl-carbamate (7900.0 mg, 26.23 mmol), B$_2$Pin$_2$ (33.754 g, 132.89 mmol), Pd(dppf)Cl$_2$ (3800.0 mg, 5.2 mmol) and KOAc (7800.0 mg, 79.59 mmol) in 1,4-dioxane (150 mL) was stirred at 90° C. for 2 hours. The reaction was concentrated under vacuum and purified by flash chromatography on silica gel eluting with petroleum ether/ethyl acetate (35/65) to afford tert-butyl N-methyl-N-[4-methyl-5-(4,4,5,5-tetramethyl-1,3,2-dioxaborolan-2-yl)-3-pyridyl]carbamate (8000 mg, 22.973 mmol, 87.6% yield) as a yellow oil. LCMS (ESI) [M+H]$^+$=349.

Step 4: tert-Butyl N-[5-(3-amino-8-chloro-7-fluoro-6-isoquinolyl)-4-methyl-3-pyridyl]-N-methyl-carbamate

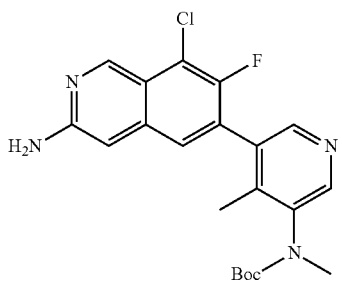 [SMILES: Cc1c(-c2cc3cc(N)ncc3c(Cl)c2F)cncc1N(C)C(=O)OC(C)(C)C]

A mixture of tert-butyl N-methyl-N-[4-methyl-5-(4,4,5,5-tetramethyl-1,3,2-dioxaborolan-2-yl)-3-pyridyl]carbamate (13 g, 37.33 mmol), 8-chloro-7-fluoro-6-iodo-isoquinolin-3-amine (10 g, 31.01 mmol), Pd(dppf)Cl₂ (4.5 g, 6.16 mmol) and K₂CO₃ (12 g, 86.96 mmol) in 1,4-dioxane (150 mL) and water (15 mL) was stirred at 70° C. for 2 hours. After filtration, the filtrate was concentrated under vacuum and purified by flash chromatography on silica gel eluting with petroleum ether/ethyl acetate (10/90) to afford tert-butyl N-[5-(3-amino-8-chloro-7-fluoro-6-isoquinolyl)-4-methyl-3-pyridyl]-N-methyl-carbamate (9000 mg, 21.589 mmol, 57.8% yield) as a yellow solid. LCMS (ESI) [M+H]⁺=417.

Step 5: tert-butyl (5-(3-(((3-((tert-butyldimethylsilyl)oxy)-3-methylcyclobutoxy)carbonyl)amino)-8-chloro-7-fluoroisoquinolin-6-yl)-4-methylpyridin-3-yl)(methyl)carbamate

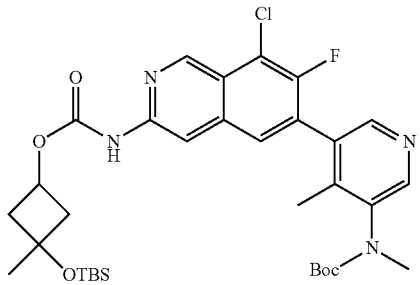 [SMILES: Cc1c(-c2cc3cc(NC(=O)OC4CC(C)(O[Si](C)(C)C(C)(C)C)C4)ncc3c(Cl)c2F)cncc1N(C)C(=O)OC(C)(C)C]

A solution of 3-[tert-butyl(dimethyl)silyl]oxy-3-methyl-cyclobutanol (1061.0 mg, 4.90 mmol), tert-butylN-[5-(3-amino-8-chloro-7-fluoro-6-isoquinolyl)-4-methyl-3-pyridyl]-N-methyl-carbamate (1025.0 mg, 2.46 mmol) and DIEA (1585.0 mg, 12.29 mmol) in dichloromethane (20 mL) was stirred for 30 min at 0° C. Then triphosgene (509.0 mg, 1.72 mmol) was added. The mixture was stirred at 0° C. for 1 hour. The reaction was concentrated under vacuum and purified by flash chromatography on silica gel eluting with petroleum ether/ethyl acetate (35/65) to afford tert-butyl (5-(3-(((3-((tert-butyldimethyl silyl)oxy)-3-methylcyclobutoxy)carbonyl)amino)-8-chloro-7-fluoroisoquinolin-6-yl)-4-methylpyridin-3-yl)(methyl)carbamate (1.375 g, 2.091 mmol, 85% yield) as yellow solid. LCMS (ESI) [M+H]⁺= 660.

Step 6: tert-butyl N-[5-[8-(tert-butoxycarbonylamino)-3-[[3-[tert-butyl (dimethyl)silyl]oxy-3-methyl-cyclobutoxy]carbonylamino]-7-fluoro-6-isoquinolyl]-4-methyl-3-pyridyl]-N-methyl-carbamate

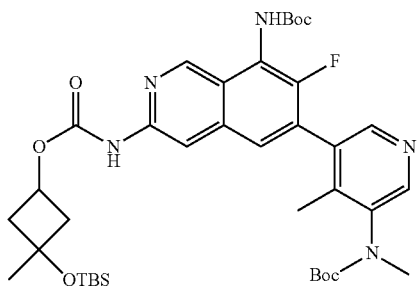 [SMILES: Cc1c(-c2cc3cc(NC(=O)OC4CC(C)(O[Si](C)(C)C(C)(C)C)C4)ncc3c(NC(=O)OC(C)(C)C)c2F)cncc1N(C)C(=O)OC(C)(C)C]

A mixture of tert-butyl N-[5-[3-[[3-[tert-butyl(dimethyl)silyl]oxy-3-methyl-cyclobutoxy]carbonylamino]-8-chloro-7-fluoro-6-isoquinolyl]-4-methyl-3-pyridyl]-N-methyl-carbamate (5700.0 mg, 8.65 mmol), NH₂Boc (20.1 g, 171.79 mmol), Brettphos-Pd-G3 (1500.0 mg, 1.66 mmol) and K₂CO₃ (1193.16 mg, 8.65 mmol) in 1,4-dioxane (100 mL) was stirred at 90° C. for 2 hours. After filtration, the filtrate was concentrated under vacuum. The residue was purified by flash chromatography on silica gel eluting with petroleum ether/ethyl acetate (44/56) to afford tert-butyl N-[5-[8-(tert-butoxycarbonylamino)-3-[[3-[tert-butyl(dimethyl)silyl]oxy-3-methyl-cyclobutoxy]carbonylamino]-7-fluoro-6-isoquinolyl]-4-methyl-3-pyridyl]-N-methyl-carbamate (5000 mg, 6.757 mmol, 78.2% yield) as a yellow solid. LCMS (ESI) [M+H]⁺=740.

Step 7: (1r,3r)-3-Hydroxy-3-methylcyclobutyl (8-amino-7-fluoro-6-(4-methyl-5-(methylamino)pyridin-3-yl)isoquinolin-3-yl)carbamate and (1s,3s)-3-Hydroxy-3-methylcyclobutyl (8-amino-7-fluoro-6-(4-methyl-5-(methylamino)pyridin-3-yl)isoquinolin-3-yl)carbamate

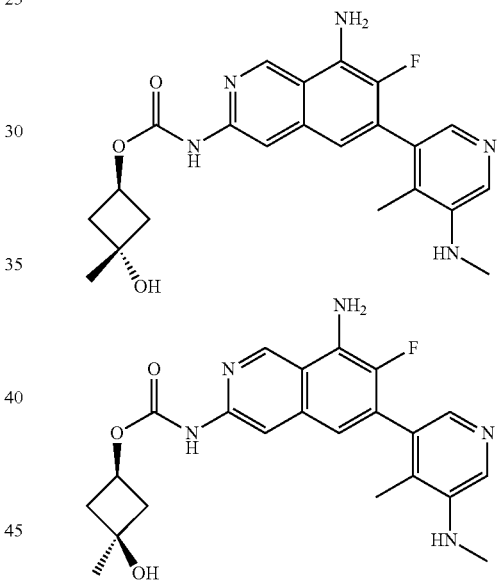

A solution of tert-butyl N-[5-[8-(tert-butoxycarbonylamino)-3-[[3-[tert-butyl(dimethyl)silyl]oxy-3-methyl-cyclobutoxy]carbonylamino]-7-fluoro-6-isoquinolyl]-4-methyl-3-pyridyl]-N-methyl-carbamate (2000.0 mg, 2.7 mmol) in dichloromethane (5 mL) and TFA (5 mL) was stirred at room temperature for 2 hours. The mixture was concentrated under vacuum. The pH of the residue was adjusted to 8 with Et₃N. The mixture was then concentrated and purified by flash chromatography on silica gel eluting with water/ACN (47/53) to afford 3-hydroxy-3-methylcyclobutyl (8-amino-7-fluoro-6-(4-methyl-5-(methylamino)pyridin-3-yl)isoquinolin-3-yl)carbamate (550 mg). The mixture was separated by SFC to afford two isomers. Stereochemistry was arbitrarily assigned.

Isomer 1 (Compound 527a) (154 mg, 0.365 mmol, 18% yield). LCMS (ESI) [M+H]⁺=425.2, R$_T$ 1.086 min, Method K. ¹H NMR (300 MHz, DMSO-d₆) δ 10.27 (s, 1H), 9.40 (s, 1H), 7.98 (s, 1H), 7.48 (s, 1H), 6.92 (d, J=6.1 Hz, 1H), 6.49 (s, 1H), 6.24 (s, 2H), 5.45-5.36 (m, 1H), 5.12-5.01 (m, 1H), 4.98 (s, 1H), 2.89 (s, 3H), 2.49-2.30 (m, 2H), 2.17-1.99 (m, 2H), 1.93 (s, 3H), 1.32 (s, 3H).

Isomer 2 (Compound 527b) (37 mg, 0.087 mmol, 3% yield). LCMS (ESI) [M+H]⁺=425.2, R$_T$ 1.106 min, Method K. ¹H NMR (300 MHz, DMSO-d₆) δ 10.30 (s, 1H), 9.42 (s, 1H), 7.98 (s, 1H), 7.89 (s, 1H), 7.77 (s, 1H), 6.93 (d, J=6.1 Hz, 1H), 6.49 (s, 1H), 5.46-4.39 (m, 1H), 5.16 (s, 1H), 4.69-4.59 (m, 1H), 2.94 (s, 3H), 2.51-2.37 (m, 2H), 2.20-2.09 (m, 2H), 1.94 (d, J=1.6 Hz, 3H), 1.11-1.02 (d, J=7.2 Hz, 3H).

Example 255

(1s,3s)-3-(3-Fluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate and (1r,3r)-3-(3-Fluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate ((Compound 525a and Compound 525b)

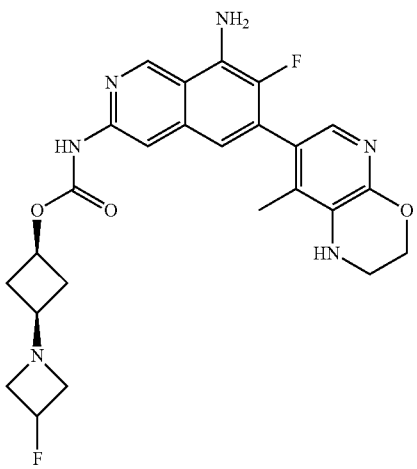

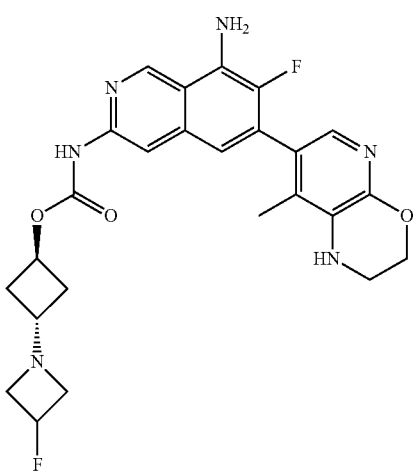

Step 1: 1-(3-Benzyloxycyclobutyl)-3-fluoro-azetidine

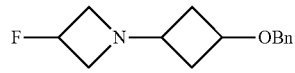 [SMILES: FC1CN(C2CC(OCc3ccccc3)C2)C1]

A solution of 3-(benzyloxy)cyclobutanone (550.0 mg, 3.12 mmol), 3-fluoroazetidinehydrochloride (1050 mg, 9.41 mmol), titanium tetraisopropanolate (1775.0 mg, 6.25 mmol) and DIEA (1209.0 mg, 9.37 mmol) in methyl alcohol (5 mL) was stirred for 2 h at 60° C. Then NaCNBH₃ (200.0 mg, 3.17 mmol) was added. The mixture was stirred at room temperature for 2 hours. The reaction was quenched by MeOH and filtered. The filtrate was concentrated under vacuum. The residue was purified by reverse phase chromatography with water/CH₃CN (34/66) to afford 1-(3-benzyloxycyclobutyl)-3-fluoro-azetidine (620 mg, 2.635 mmol, 84.4% yield) as a colorless oil. LCMS (ESI) [M+H]⁺=236.

Step 2: (1s,3s)-3-(3-Fluoroazetidin-1-yl)cyclobutan-1-ol

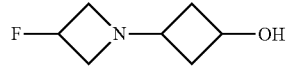

Under hydrogen (1 atm), a suspension of 1-(3-benzyloxycyclobutyl)-3-fluoro-azetidine (330.0 mg, 1.4 mmol) and Pd/C (100.0 mg, 1.4 mmol) in methyl alcohol (3 mL) was stirred for 24 h at 40° C. After filtration, the filtrate was concentrated under vacuum to afford 3-(3-fluoroazetidin-1-yl)cyclobutanol (180 mg, 1.24 mmol, 88.4% yield) as a colorless oil. LCMS (ESI) [M+H]⁺=146.

Step 3: tert-Butyl 7-(8-((tert-butoxycarbonyl)amino)-7-fluoro-3-((((1s,3s)-3-(3-fluoroazetidin-1-yl)cyclobutoxy)carbonyl)amino)isoquinolin-6-yl)-8-methyl-2,3-dihydro-1H-pyrido[2,3-b][1,4]oxazine-1-carboxylate

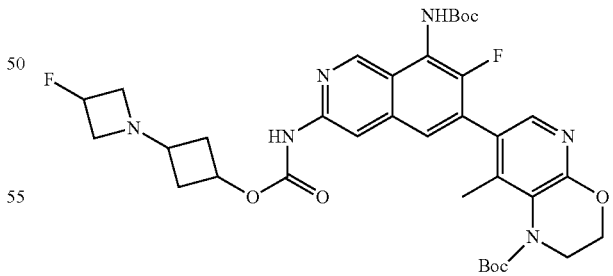

A solution of 3-(3-fluoroazetidin-1-yl)cyclobutanol (149.0 mg, 1.03 mmol), tert-butyl 7-[8-(tert-butoxycarbonyl amino)-7-fluoro-3-(phenoxycarbonylamino)-6-isoquinolyl]-8-methyl-2,3-dihydropyrido[2,3-b][1,4]oxazine-1-carboxylate (331 mg, 0.51 mmol) and DMAP (65.0 mg, 0.53 mmol) in dichloromethane (5 mL) was stirred for 2 h at 60° C. The reaction was concentrated under vacuum. The resulting residue was purified by reverse phase chromatography with water/ACN (26/74) to afford tert-butyl 7-[8-(tert-butoxycarbonylamino)-7-fluoro-3-[[3-(3-fluoroazetidin-1-yl)cyclobutoxy]carbonylamino]-6-isoquinolyl]-8-methyl-2,3-dihydropyrido[2,3-b][1,4]oxazine-1-carboxylate (280 mg, 0.402 mmol, 39.2% yield) as a yellow solid. LCMS (ESI) [M+H]⁺=697.

Step 4: (1s,3s)-3-(3-Fluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate (1r,3r)-3-(3-fluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate

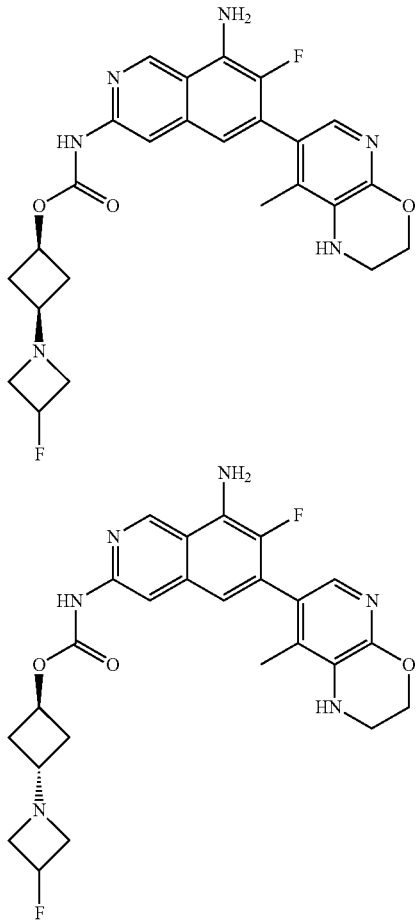

A solution of tert-butyl 7-[8-(tert-butoxycarbonylamino)-7-fluoro-3-[[3-(3-fluoroazetidin-1-yl)cyclobutoxy]carbonylamino]-6-isoquinolyl]-8-methyl-2,3-dihydropyrido[2,3-b][1,4]oxazine-1-carboxylate (275.51 mg, 0.40 mmol) in dichloromethane (5 mL) and TFA (1 mL) was stirred at room temperature for 3 hours. The reaction was concentrated under vacuum and purified by Prep-HPLC (X Select CSH PreC18 OBD Column, 30*150 mm, 5 μm, Mobile phase A: water (0.1% FA), Mobile phase B: ACN; Flow rate 60 mL/min; Gradient: 7% B to 16% in 7 min) to afford a mixture of isomers. The mixture was separated by chiral HPLC to afford two isomers. Stereochemistry was arbitrarily assigned.

Isomer 1 (Compound 525a) (2.5 mg, 0.0054 mmol, 1.7% yield). R$_T$ 3.073 min (CHIRALPAK IG-3 0.46*5 cm; 3 μm; (Hex:DCM=3:1)(0.1% DEA):EtOH=50:50, 1 mL/min). LCMS (ESI) [M+H]⁺=497.3, R$_T$ 1.237 min., Method M; ¹H NMR (300 MHz, DMSO-d$_6$) δ 10.05 (s, 1H), 9.31 (s, 1H), 7.93 (s, 1H), 7.31 (s, 1H), 6.86-6.78 (d, J=6.2 Hz, 1H), 6.18 (s, 2H), 5.65 (s, 1H), 5.30-4.95 (m, 2H), 4.29 (s, 2H), 3.60-3.44 (m, 2H), 3.19-3.03 (m, 2H), 3.09-2.89 (m, 3H), 2.15-2.02 (m, 4H), 1.92-1.89 (m, 3H).

Isomer 2 (Compound 525b) (17 mg, 0.0323 mmol, 9.5% yield). R$_T$ 3.911 min (CHIRALPAK IG-3 0.46*5 cm; 3 μm; (Hex:DCM=3:1)(0.1% DEA):EtOH=50:50, 1 mL/min). LCMS(ESI) [M+H]⁺=497.3, R$_T$ 1.589 min, Method K. ¹H NMR (300 MHz, DMSO-d$_6$) δ 10.05 (s, 1H), 9.31 (s, 1H), 7.93 (s, 1H), 7.31 (s, 1H), 6.86-6.78 (d, J=6.2 Hz, 1H), 6.18 (s, 2H), 5.65 (s, 1H), 5.30-4.95 (m, 2H), 4.29 (s, 2H), 3.60-3.44 (m, 2H), 3.19-3.03 (m, 2H), 3.09-2.89 (m, 3H), 2.15-2.02 (m, 4H), 1.92-1.89 (m, 3H).

Example 256

(1R,2R,3S)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate and (1S,2S,3R)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate ((Compound 526a and Compound 526b)

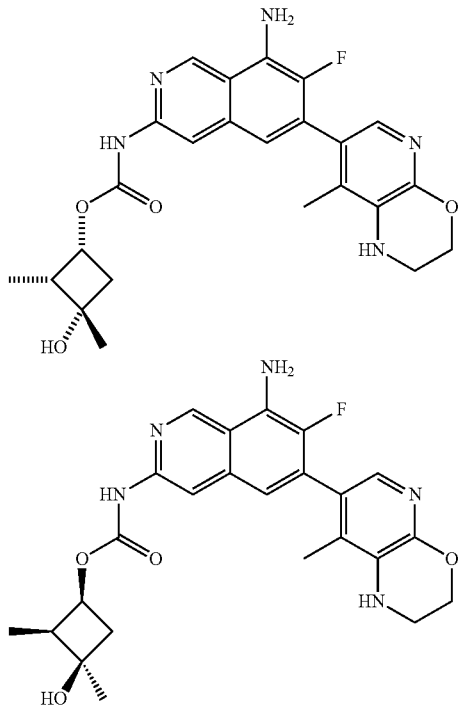

Step 1: (Z)-prop-1-enoxy]methylbenzene

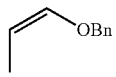

A solution of allyl benzyl ether (1.0 g, 6.75 mmol) and t-BuOK (113 mg, 1.01 mmol) in dimethyl sulfoxide (10 mL) was stirred at 37° C. for 72 hours. The reaction was diluted with ethyl acetate, washed with water and brine, dried over sodium anhydrous sulfate, filtered and concentrated under vacuum. The residue was purified by flash chromatography on silica gel eluting with ethyl acetate/petroleum ether (1:10) to afford (Z)-prop-1-enoxy]methylbenzene (900 mg, 6.073 mmol, 90% yield) as a colorless oil.

Step 2: (±)-cis-3-(Benzyloxy)-2-methylcyclobutan-1-one

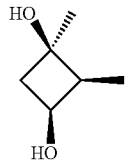

To a mixture of (Z)-prop-1-enoxy]methylbenzene (8.0 g, 53.98 mmol) and Zn/Cu (53.0 g, 815.38 mmol) in diethyl ether (250 mL) was added dropwise trichloroacetylchloride (19.5 g, 107.73 mmol). The mixture was stirred at 20° C. for 30 min. A saturated solution of NH$_4$Cl (44.0 g, 814.81 mmol) in methyl alcohol (200 mL) was added and the resulting mixture was refluxed for 10 min. The resulting solution was filtrated and concentrated under vacuum. The residue was purified by flash chromatography on silica gel to afford (±)-cis-3-(benzyloxy)-2-methylcyclobutan-1-one (3.4 g, 17.872 mmol, 33.1% yield) as a colorless oil.

Step 3: (±)-(1R,2S,3S)-3-Benzyloxy-1,2-dimethyl-cyclobutanol

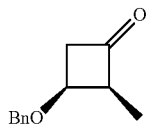

Methyl magnesium chloride (0.2 mL, 0.60 mmol) was added dropwise to a solution of (±)-cis-3-benzyloxy-2-methyl-cyclobutanone (100 mg, 0.53 mmol) in tetrahydrofuran (1 mL) at −78° C. The mixture was stirred at −78° C. for 1 hour. The reaction was quenched by water and extracted with ethyl acetate. The organic phase was dried over Na$_2$SO$_4$, filtered and concentrated under vacuum. The residue was purified by flash chromatography on silica gel eluting with ethyl acetate/petroleum ether (1/1) to afford (±)-(1R,2S,3S)-3-benzyloxy-1,2-dimethyl-cyclobutanol (60 mg, 0.291 mmol, 55.3% yield) as colorless oil. LCMS (ESI) [M+H]$^+$=207.

Step 4: (±)-(1R,2S,3S)-1,2-Dimethylcyclobutane-1,3-diol

A mixture of (±)-(1R,2S,3SI)-3-benzyloxy-1,2-dimethyl-cyclobutanol (1.0 g, 4.85 mmol) and Pd/C (10%, 300.0 mg, 4.85 mmol) in methyl alcohol (40 mL) was stirred under hydrogen for 3 h at 25° C. After filtration, the filtrate was concentrated under vacuum. The residue was purified by flash chromatography on silica gel eluting with PE/EA (1/2) to afford (±)-(1R,2S,3S)-1,2-dimethylcyclobutane-1,3-diol (400 mg, 3.44 mmol, 71% yield) as a colorless oil. LCMS (ESI) [M+H]$^+$=116. $^1$H NMR (300 MHz, DMSO-d$_6$) 4.75 (d, J=6 Hz, 1H), 4.27 (s, 1H), 3.72-3.63 (m, 1H), 2.12-2.06 (m, 1H), 1.82-1.73 (m, 1H), 1.64-1.58 (m, 1H), 1.17 (s, 3H), (d, J=6 Hz, 1H).

Step 5: (±)-tert-Butyl 7-[8-(tert-butoxycarbonylamino)-7-fluoro-3-[[(1S,2S,3R)-3-hydroxy-2,3-dimethyl-cyclobutoxy]carbonylamino]-6-isoquinolyl]-8-methyl-2,3-dihydropyrido[2,3-b][1,4]oxazine-1-carboxylate

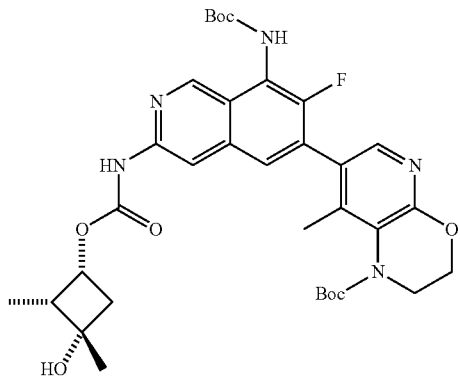

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (250 mg, 0.48 mmol) and (±)-(1R,2S,3S)-1,2-dimethylcyclobutane-1,3-diol (200.0 mg, 1.72 mmol) in dichloromethane (50 mL) was added DIEA (600.0 mg, 4.65 mmol) at room temperature. Then triphosgene (150.0 mg, 0.51 mmol) was added and the mixture was stirred at 0° C. for 1 hour. The residue was purified by flash chromatography on silica gel eluting with PE/EA (1/1) to afford (±)-tert-butyl 7-[8-(tert-butoxycarbonylamino)-7-fluoro-3-[[(1S,2S,3R)-3-hydroxy-2,3-dimethyl-cyclobutoxy]carbonylamino]-6-isoquinolyl]-8-methyl-2,3-dihydropyrido[2,3-b][1,4]oxazine-1-carboxylate (250 mg, 0.3744 mmol, 78.7% yield) as a yellow solid. LCMS (ESI) [M+H]$^+$=668.

Step 6: (1r,2r,3s)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate and (1s,2s,3s)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate

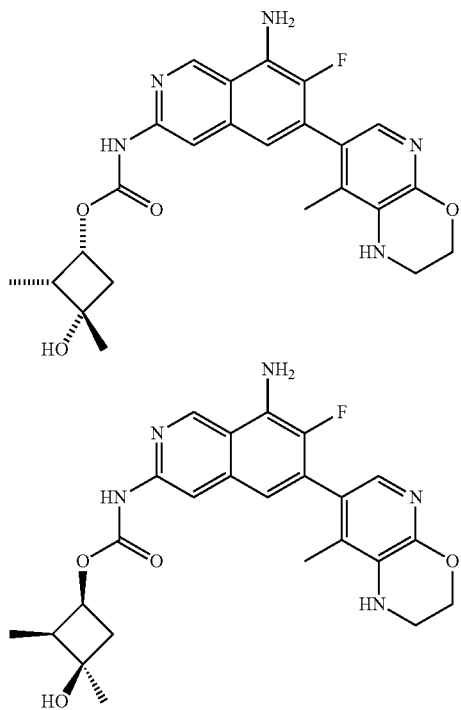

To a solution of (±)-tert-butyl 7-[8-(tert-butoxycarbonylamino)-7-fluoro-3-[[(1R,2R,3S)-3-hydroxy-2,3-dimethyl-cyclobutoxy]carbonylamino]-6-isoquinolyl]-8-methyl-2,3-dihydropyrido[2,3-b][1,4]oxazine-1-carboxylate (250.0 mg, 0.37 mmol) in dichloromethane (10 mL) was added TFA (2 mL) at room temperature. The resulting solution was stirred for 1 h at 25° C. and concentrated. The crude product was purified by Prep-HPLC (Column: X select CSH OBD Column 30*150 mm, 5 μm; Mobile Phase A: Water (0.1% FA), Mobile Phase B: ACN; Flow rate: 60 mL/min; Gradient: 10% B to 40% B in 7 min) and chiral-HPLC (Column: CHIRALPAK IE, 2*25 cm, 5 μm; Mobile Phase A: MeOH (8 mmol/L NH$_3$.MeOH), Mobile Phase B: DCM; Flow rate 18 mL/min) to afford the single enantiomers. Relative stereochemistry are as drawn. Absolute stereochemistry was arbitrarily assigned.

Enantiomer 1: Compound 526a (1R,2R,3S)-3-hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate in methanol (10 mL) was treated with HCl (4 mol/L, 2 eq) in 1,4-dioxane and stirred for 30 mins at room temperature. The resulting solution was concentrated under vacuum and freeze-dried to afford (1R,2R,3S)-3-hydroxy-2,3-dimethyl-cyclobutyl]N-[8-amino-7-fluoro-6-(8-methyl-2,3-dihydro-1H-pyrido[2,3-b][1,4]oxazin-7-yl)-3-isoquinolyl]carbamate hydrochloride (21.1 mg, 0.0419 mmol, 11.2% yield) as a red solid. R$_T$ 1.183 min (CHIRALPAK IE-3, 0.46*5 cm, 3 μm; DCM (0.1% DEA): MeOH=50:50 in 3 min; 1 mL/min). LCMS (ESI) [M+H]$^+$=468.2, R$_T$ 1.940 min, Method J; $^1$H NMR (300 MHz, DMSO-d$_6$) δ 10.22 (s, 1H), 9.44 (s, 1H), 7.97 (s, 1H), 7.55 (s, 1H), 6.91 (d, J=5.9 Hz, 1H), 6.50-5.90 (bs, 4H), 4.75-4.70 (m, 1H), 4.50 (s, 2H), 3.48 (s, 2H), 2.33-2.31 (m, 1H), 2.23-2.03 (m, 2H), 2.03 (s, 3H), 1.25 (s, 3H), 0.96 (d, J=7.3 Hz, 3H).

Enantiomer 2: Compound 526b (1S,2S,3R)-3-hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate in methanol (5 mL) was treated with HCl (4 mol/L, 2 eq) in 1,4-dioxane for 30 mins at room temperature. The resulting solution was concentrated under vacuum and freeze-dried to afford [(1S,2S,3R)-3-hydroxy-2,3-dimethyl-cyclobutyl]N-[8-amino-7-fluoro-6-(8-methyl-2,3-dihydro-1H-pyrido[2,3-b][1,4]oxazin-7-yl)-3-isoquinolyl]carbamate hydrochloride (20.2 mg, 0.0401 mmol, 10.7% yield) as a red solid. R$_T$ 1.840 min (CHIRALPAK IE-3, 0.46*5 cm, 3 μm; DCM (0.1% DEA):MeOH=50:50 in 3 min; 1 mL/min). LCMS (ESI) [M+H]$^+$=468.2, R$_T$ 1.141 min., Method K; $^1$H NMR (300 MHz, DMSO-d$_6$) δ 10.22 (s, 1H), 9.44 (s, 1H), 7.97 (s, 1H), 7.55 (s, 1H), 6.91 (d, J=5.9 Hz, 1H), 6.50-5.90 (bs, 4H), 4.75-4.70 (m, 1H), 4.50 (s, 2H), 3.48 (s, 2H), 2.33-2.31 (m, 1H), 2.23-2.03 (m, 2H), 2.03 (s, 3H), 1.25 (s, 3H), 0.96 (d, J=7.3 Hz, 3H).

Example 257

(1S,2R,3S)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate and (1R,2S,3R)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate (Compound 526c and Compound 526d)

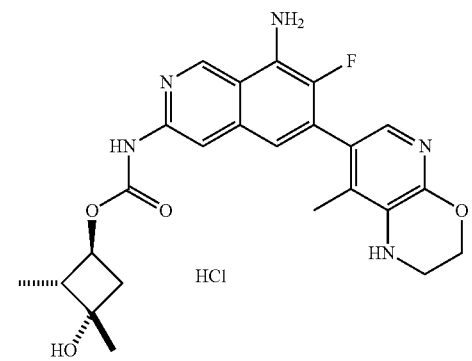

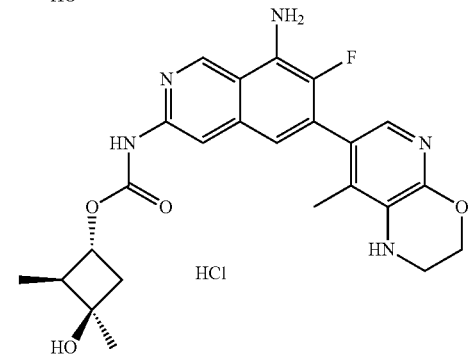

Step 1: (±)-(2r,3s)-3-Benzyloxy-2-methyl-cyclobutanone

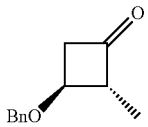

To a solution of (±)-(2S,3S)-3-benzyloxy-2-methyl-cyclobutanone (4.8 g, 25.23 mmol) in dichloromethane (150 mL) was added DBU (1.2 g, 7.89 mmol) at 25° C. The resulting solution was stirred for 16 hours at 25° C. The residue was purified by flash chromatography on silica gel eluting with petroleum ether/ethyl acetate (10/1) to afford (±)-(2R,3S)-3-benzyloxy-2-methyl-cyclobutanone (1.7 g, 8.94 mmol, 35.4% yield) as a colorless oil. LCMS (ESI) [M+H]$^+$=191.

Step 2: (±)-(1S,2R,3S)-3-Benzyloxy-1,2-dimethyl-cyclobutanol

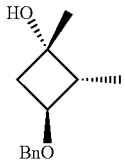

A solution of (±)-(2R,3S)-3-benzyloxy-2-methyl-cyclobutanone (1.7 g, 8.94 mmol) in THF (20 mL) was added methyl magnesium bromide (4.5 mL, 9 mmol) at −78° C. The resulting solution was stirred for 1 hour at room temperature. The reaction was quenched by saturated ammonium chloride (20 mL). The residue was purified by flash chromatography on silica gel eluting with petroleum ether/ethyl acetate (10/1) to afford (±)-(1S,2R,3S)-3-benzyloxy-1,2-dimethyl-cyclobutanol (1.3 g, 6.302 mmol, 70.5% yield) as a colorless oil. LCMS (ESI) [M+H]$^+$=207.

Step 3: (±)-(1S,2R,3S)-1,2-Dimethylcyclobutane-1,3-diol

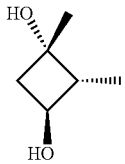

A mixture of (±)-(1S,2R,3S)-3-benzyloxy-1,2-dimethyl-cyclobutanol (1.0 g, 4.85 mmol) and Pd/C (10%, 300 mg, 4.85 mmol) in methyl alcohol (20 mL) was stirred under hydrogen (1 atm) for 3 h at 25° C. After filtration, the filtrate was concentrated under reduced pressure. The residue was purified by flash chromatography on silica gel eluting with petroleum ether/ethyl acetate (1/2) to afford (±)-(1S,2R,3S)-1,2-dimethylcyclobutane-1,3-diol (330 mg, 2.84 mmol, 58.6% yield) as colorless oil. LCMS (ESI) [M+H]$^+$=116. $^1$H NMR (300 MHz, DMSO-d$_6$) δ 4.75 (d, J=6.0 Hz, 1H), 4.27 (s, 1H), 3.72-3.63 (m, 1H), 2.12-2.06 (m, 1H), 1.82-11.72 (m, 1H), 1.64-1.58 (m, 1H), 1.17 (s, 3H), 0.89 (d, J=6.0 Hz, 3H).

Step 4: (±)-tert-Butyl 7-[8-(tert-butoxycarbonylamino)-7-fluoro-3-[[(1S,2R,3S)-3-hydroxy-2,3-dimethyl-cyclobutoxy]carbonylamino]-6-isoquinolyl]-8-methyl-2,3-dihydropyrido[2,3-b][1,4]oxazine-1-carboxylate

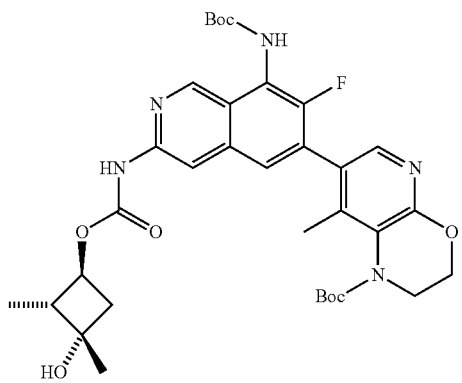 [SMILES: Cc1c(-c2cc3cc(NC(=O)O[C@H]4C[C@](C)(O)[C@@H]4C)ncc3c(NC(=O)OC(C)(C)C)c2F)cnc2c1N(C(=O)OC(C)(C)C)CCO2]

Under nitrogen, to a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (260 mg, 0.49 mmol) and (±)-(1S,2R,3S)-1,2-dimethylcyclobutane-1,3-diol (120 mg, 1.03 mmol) in dichloromethane (30 mL) was added DIEA (700 mg, 5.43 mmol) at room temperature. Then triphosgene (80 mg, 0.27 mmol) was added and the mixture was stirred at 0° C. for 1 hour. The residue was purified by flash chromatography on silica gel eluting with petroleum ether/ethyl acetate (2/1) to afford (±)-tert-butyl 7-[8-(tert-butoxycarbonylamino)-7-fluoro-3-[[(1S,2R,3S)-3-hydroxy-2,3-dimethyl-cyclobutoxy]carbonylamino]-6-isoquinolyl]-8-methyl-2,3-dihydropyrido[2,3-b][1,4]oxazine-1-carboxylate (260 mg, 0.389 mmol, 78.7% yield) as a yellow solid. LCMS (ESI) [M+H]$^+$= 668.

Step 5: (1s,2r,3s)-3-hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate and (1r,2s,3r)-3-hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate

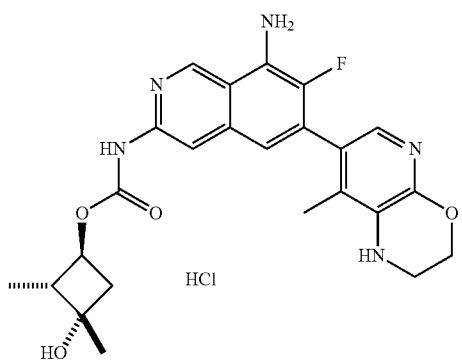

-continued

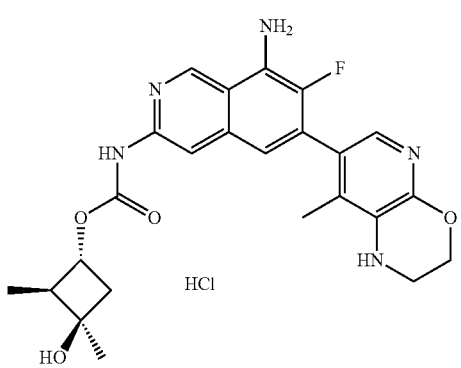

To a solution of tert-butyl 7-[8-(tert-butoxycarbonylamino)-7-fluoro-3-[[(1S,2R,3S)-3-hydroxy-2,3-dimethyl-cyclobutoxy]carbonylamino]-6-isoquinolyl]-8-methyl-2,3-dihydropyrido[2,3-b][1,4]oxazine-1-carboxylate (260 mg, 0.39 mmol) in dichloromethane (10 mL) was added TFA (2 mL) at room temperature. The resulting solution was stirred for 1 h at 25° C. The crude product was purified by Prep-HPLC (Column: X select CSH OBD Column 30*150 mm, 5 μm; Mobile Phase A: Water (0.1% FA), Mobile Phase B: ACN; Flow rate: 60 mL/min; Gradient: 12% B to 37% B in 7 min) and chiral-HPLC to afford two enantiomers. Each enantiomer was dissolved in methanol and treated with HCl/1,4-dioxane (0.04 M, 2 eq) for 30 min at room temperature and concentrated to afford the corresponding hydrochloride salt. Relative stereochemistry as drawn. Absolute stereochemistry arbitrarily assigned.

Enantiomer 1 (Compound 526c) (28.4 mg, 0.0564 mmol, 14.5% yield). $R_T$ 2.040 min (CHIRALPAK IC-3, 0.46*5 cm, 3 m; (Hex:DCM=1:1)(0.1% DEA):IPA=60:40 in 4 min; 1 mL/min). LCMS (ESI) [M+H]$^+$=468.2, $R_T$ 1.151 min, Method K; $^1$H NMR (300 MHz, DMSO-d$_6$) δ 10.16 (s, 1H), 9.41 (s, 1H), 7.97 (s, 1H), 7.54 (s, 1H), 6.92 (d, J=6.0 Hz, 1H), 4.66 (q, J=7.3 Hz, 1H), 4.49 (s, 2H), 3.48 (d, J=5.3 Hz, 2H), 2.30 (dd, J=12.0, 7.6 Hz, 1H), 2.13 (t, J=6.9 Hz, 1H), 2.02 (s, 3H), 1.91 (dd, J=12.1, 7.1 Hz, 1H), 1.24 (s, 3H), 1.01 (d, J=7.0 Hz, 3H).

Enantiomer 2 (Compound 526d) (25.9 mg, 0.0514 mmol, 13.2% yield). $R_T$ 2.857 min (ChIRALPAK IC-3, 46*5 cm, 3 μm; (Hex:DCM=1:1)(0.1% DEA):IPA=60:40 in 4 min; 1 mL/min). LCMS (ESI) [M+H]$^+$=468.2, $R_T$ 1.154 min., Method K; $^1$H NMR (300 MHz, DMSO-d$_6$) δ 10.15 (s, 1H), 9.40 (s, 1H), 7.97 (s, 1H), 7.54 (s, 1H), 6.92 (d, J=6.0 Hz, 1H), 4.66 (q, J=7.2 Hz, 1H), 4.48 (s, 2H), 3.47 (s, 2H), 2.30 (dd, J=12.1, 7.7 Hz, 1H), 2.13 (t, J=7.1 Hz, 1H), 2.02 (s, 3H), 1.91 (dd, J=12.0, 7.3 Hz, 1H), 1.24 (s, 3H), 1.01 (d, J=6.9 Hz, 3H).

Example 258

(1-Cyclopropylsulfonylazetidin-3-yl)-N-[8-amino-7-fluoro-6-(8-methyl-2,3-dihydro-1H-pyrido[2,3-b][1,4]oxazin-7-yl)-3-isoquinolyl]-carbamate hydrochloride (Compound 524)

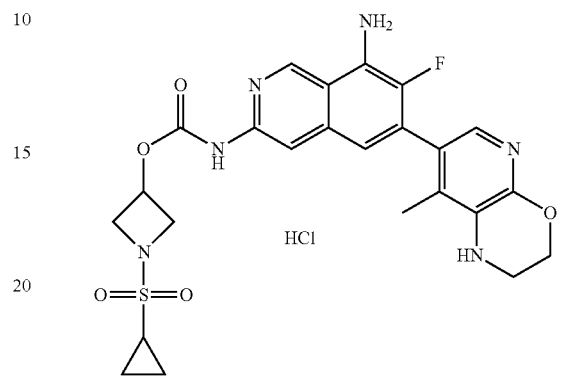

Step 1:
3-Benzyloxy-1-cyclopropylsulfonyl-azetidine

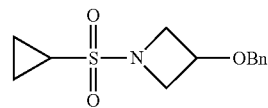 [SMILES: O=S(=O)(C1CC1)N1CC(OCc2ccccc2)C1]

To a solution of 3-benzyloxyazetidine (1.0 g, 6.13 mmol), triethylamine (3.1 g, 30.69 mmol) and 4-dimethylaminopyridine (224 mg, 1.83 mmol) in dichloromethane (30 mL) was added cyclopropanesulfonyl chloride (2.6 g, 18.42 mmol). The mixture was stirred at 0° C. for 2 hours. The reaction solution was washed with water and concentrated under reduced pressure. The residue was purified by flash chromatography on silica gel eluting with petroleum ether/ethyl acetate (4/1) to afford 3-benzyloxy-1-cyclopropylsulfonyl-azetidine (900 mg, 3.37 mmol, 54.9% yield) as a white solid. LCMS (ESI) [M+H]$^+$=268.

Step 2: 1-cyclopropylsulfonylazetidin-3-ol

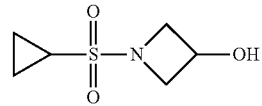 [SMILES: O=S(=O)(C1CC1)N1CC(O)C1]

To a solution of 3-benzyloxy-1-cyclopropylsulfonyl-azetidine (500 mg, 1.87 mmol) in methyl alcohol (20 mL) was added Pd(OH)$_2$/C (800 mg, 1.87 mmol). The reaction was stirred for 2 days at 45° C. After filtration, the filtrate was concentrated under reduced pressure. The residue was purified by flash chromatography on silica gel eluting with ethyl acetate to afford 1-cyclopropylsulfonylazetidin-3-ol (160 mg, 0.903 mmol, 48.3% yield) as a colorless oil. LCMS (ESI) [M+H]$^+$=178.

Step 3: tert-Butyl-7-[8-(tert-butoxycarbonyl amino)-3-[(1-cyclopropylsulfonylazetidin-3-yl)-oxycarbonylamino]-7-fluoro-6-isoquinolyl]-8-methyl-2,3-dihydropyrido[2,3-b][1,4]oxazine-1-carboxylate

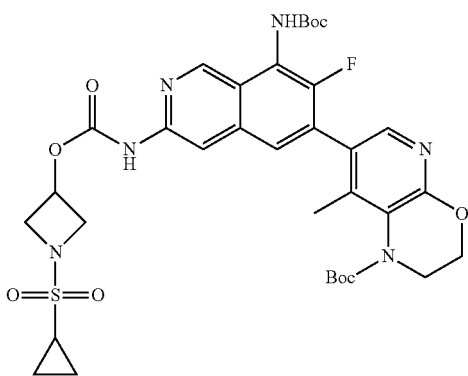 [SMILES: Cc1c(-c2cc3cc(NC(=O)OC4CN(S(=O)(=O)C5CC5)C4)ncc3c(NC(=O)OC(C)(C)C)c2F)cnc2c1N(C(=O)OC(C)(C)C)CCO2]

To a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (200 mg, 0.38 mmol), 1-cyclopropylsulfonylazetidin-3-ol (100.0 mg, 0.56 mmol) and N,N-diisopropylethylamine (490.0 mg, 3.8 mmol) in dichloromethane (15 mL) was added a solution of triphosgene (112 mg, 0.38 mmol) in dichloromethane (1 mL). The mixture was stirred for at 0° C. for 2 hours and concentrated under vacuum. The residue was purified by flash chromatography on silica gel eluting with ethyl acetate/petroleum ether (1/4) to afford tert-butyl 7-[8-(tert-butoxycarbonylamino)-3-[(1-cyclopropylsulfonylazetidin-3-yl)oxycarbonyl amino]-7-fluoro-6-isoquinolyl]-8-methyl-2,3-dihydropyrido-[2,3-b][1,4]oxazine-1-carboxylate (168 mg, 0.2075 mmol, 54.6% yield) as a faint yellow solid. LCMS (ESI) [M+H]=729.

Step 4: (1-Cyclopropylsulfonylazetidin-3-yl)-N-[8-amino-7-fluoro-6-(8-methyl-2,3-dihydro-1H-pyrido[2,3-b][1,4]oxazin-7-yl)-3-isoquinolyl]carbamate hydrochloride

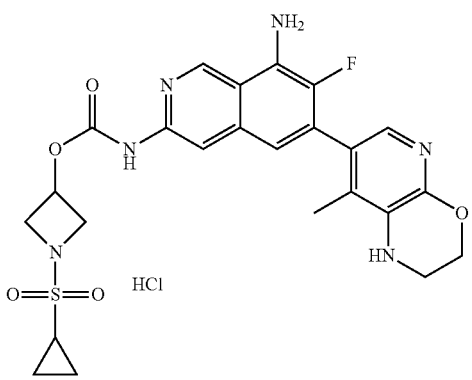 [SMILES: Cc1c(-c2cc3cc(NC(=O)OC4CN(S(=O)(=O)C5CC5)C4)ncc3c(N)c2F)cnc2c1NCCO2 ; Cl]

To a solution of tert-butyl 7-[8-(tert-butoxycarbonylamino)-3-[(1-cyclopropylsulfonylazetidin-3-yl)oxycarbonylamino]-7-fluoro-6-isoquinolyl]-8-methyl-2,3-dihydropyrido[2,3-b][1,4]oxazine-1-carboxylate (160 mg, 0.22 mmol) in dichloromethane (10 mL) was added TFA (2 mL). The mixture was stirred at 25° C. for 1 hour and concentrated under vacuum. The residue was purified by Prep-HPLC (X-select CSH OBD Column 30*150 mm, 5 μm; Mobile Phase A: Water (0.1% FA), Mobile Phase B: ACN; Flow rate: 60 mL/min; Gradient: 15% B to 39% B in 7 min) to afford 1-(cyclopropylsulfonyl)azetidin-3-yl (8-amino-7-fluoro-6-(8-methyl-2,3-dihydro-1H-pyrido[2,3-b][1,4]oxazin-7-yl)isoquinolin-3-yl)carbamate (60 mg) as a yellow solid. Then to a solution of the purified product in methanol (8 mL) was added 0.4 M HCl in methanol (0.5 mL) and the solution was stirred at 25° C. for 0.5 hour. The solution was concentrated under vacuum to afford (1-cyclopropylsulfonylazetidin-3-yl)-N-[8-amino-7-fluoro-6-(8-methyl-2,3-dihydro-1H-pyrido[2,3-b][1,4]oxazin-7-yl)-3-isoquinolyl]-carbamate hydrochloride (56.1 mg, 0.0989 mmol, 45% yield) a red solid. LCMS (ESI) [M+H]$^+$=529.1, R$_T$ 0.995 min, Method L; $^1$H NMR (300 MHz, DMSO-d$_6$) δ 10.47 (s, 1H), 9.39 (s, 1H), 7.98 (s, 1H), 7.49 (s, 1H), 6.90 (d, J=6.1 Hz, 1H), 5.24 (t, J=5.5 Hz, 1H), 4.48-4.35 (m, 4H), 4.32-4.21 (m, 3H), 3.98 (dd, J=9.5, 4.8 Hz, 2H), 3.52-3.40 (m, 2H), 2.90-2.70 (m, 1H), 1.99 (d, J=1.6 Hz, 3H), 1.11-0.93 (m, 4H).

Example 259

(1s,3s)-3-Methoxy-3-methyl cyclobutyl (8-amino-7-fluoro-6-(8-methyl-2,3-dihydro-1H-pyrido[2,3-b][1,4]oxazin-7-yl)isoquinolin-3-yl)carbamate (Compound 528a)

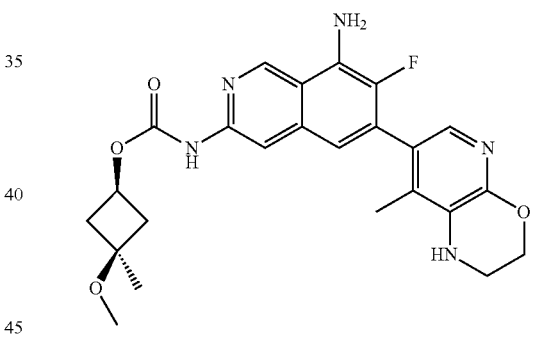

Step 1:
(3-Methoxy-3-methyl-cyclobutoxy)methylbenzene

To a solution of 3-benzyloxy-1-methyl-cyclobutanol (500.0 mg, 2.6 mmol) in tetrahydrofuran (10 mL) was added NaH (150.0 mg, 3.91 mmol) at 0° C. The mixture was stirred for 15 minutes. Then a solution of iodomethane (1110.0 mg, 7.82 mmol) in THF (1 mL) was added and the mixture was stirred at 0° C. for 3 hours. The reaction was diluted with methanol and concentrated under vacuum. The residue was purified by flash chromatography on silica gel eluting with petroleum ether/ethyl acetate (79/21) to afford (3-methoxy-3-methyl-cyclobutoxy)methylbenzene (420 mg, 2.04 mmol, 78% yield) as a clarity oil. LCMS (ESI) [M+H]$^+$=267.

Step 2: 3-Methoxy-3-methyl-cyclobutanol

A mixture of (3-methoxy-3-methyl-cyclobutoxy)methylbenzene (400 mg, 1.94 mmol) and Pd/C (10%, 200 mg, 1.94 mmol) in methyl alcohol (10 mL) was stirred under hydrogen (1 atm) for 24 hours at 40° C. The reaction was filtered, and the filtrate was concentrated to afford 3-methoxy-3-methyl-cyclobutanol (372 mg, 1.92 mmol, 99% yield) as a clarity oil. LCMS (ESI) [M+H]$^+$=117.1.

Step 3: tert-Butyl 7-[8-(tert-butoxycarbonylamino)-7-fluoro-3-[(3-methoxy-3-methyl-cyclobutoxy)carbonylamino]-6-isoquinolyl]-8-methyl-2,3-dihydropyrido[2,3-b][1,4]oxazine-1-carboxylate

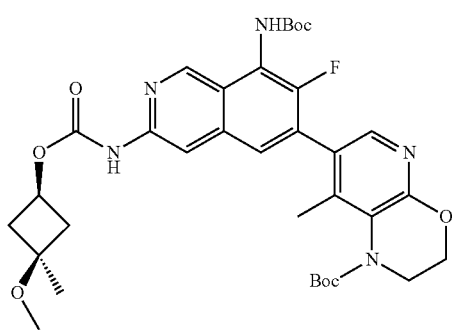 [SMILES: CO[C@]1(C)C[C@H](OC(=O)Nc2cc3cc(-c4cnc5c(c4C)N(C(=O)OC(C)(C)C)CCO5)c(F)c(NC(=O)OC(C)(C)C)c3cn2)C1]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (600.0 mg, 0.93 mmol) and DMAP (114.0 mg, 0.93 mmol) in dichloromethane (10 mL) was added 3-methoxy-3-methyl-cyclobutanol (322.0 mg, 2.77 mmol) at 25° C. The resulting solution was stirred for 24 hours at 60° C. and concentrated under vacuum. The residue was purified by flash chromatography on silica gel eluting with dichloromethane/methanol (96/4) to afford tert-butyl 7-[8-(tert-butoxycarbonylamino)-7-fluoro-3-[(3-methoxy-3-methyl-cyclobutoxy)carbonylamino]-6-isoquinolyl]-8-methyl-2,3-dihydropyrido[2,3-b][1,4]oxazine-1-carboxylate (450 mg, 0.67 mmol, 73% yield) as a pale yellow solid. LCMS (ESI) [M+H]$^+$=668.3

Step 4: (1s,3s)-3-Methoxy-3-methylcyclobutyl (8-amino-7-fluoro-6-(8-methyl-2,3-dihydro-1H-pyrido[2,3-b][1,4]oxazin-7-yl)isoquinolin-3-yl)carbamate

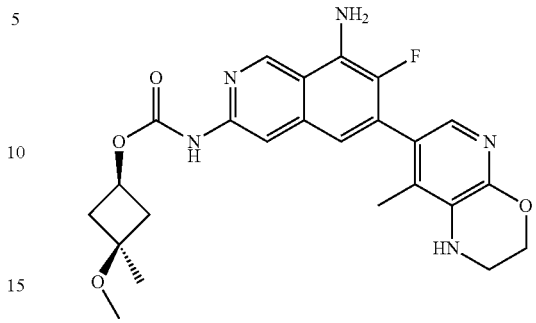

A solution of tert-butyl 7-[8-(tert-butoxycarbonylamino)-7-fluoro-3-[(3-methoxy-3-methyl-cyclobutoxy)carbonylamino]-6-isoquinolyl]-8-methyl-2,3-dihydropyrido[2,3-b][1,4]oxazine-1-carboxylate (450.0 mg, 0.67 mmol) and TFA (2.0 mL) in dichloromethane (10 mL) was stirred at 25° C. for 2 hours. After concentration, the residue was purified by Prep-HPLC (X select CSH OBD Column 30*150 mm, 5 μm; ACN: Water (0.1% FA)=Gradient: 19% B to 40% B in 7 min; 60 mL/min) to afford (1s,3s)-3-methoxy-3-methylcyclobutyl (8-amino-7-fluoro-6-(8-methyl-2,3-dihydro-1H-pyrido[2,3-b][1,4]oxazin-7-yl)isoquinolin-3-yl)carbamate.

A solution of (1s,3s)-3-methoxy-3-methylcyclobutyl (8-amino-7-fluoro-6-(8-methyl-2,3-dihydro-1H-pyrido[2,3-b][1,4]oxazin-7-yl)isoquinolin-3-yl)carbamate and HCl in dioxane (0.4 mL, 4M, 1.6 mmol) in MeOH (5 mL) was stirred at room temperature for 10 minutes. The mixture was concentrated under vacuum to afford (1s,3s)-3-methoxy-3-methylcyclobutyl (8-amino-7-fluoro-6-(8-methyl-2,3-dihydro-1H-pyrido[2,3-b][1,4]oxazin-7-yl)isoquinolin-3-yl) carbamate HCl salt (52.9 mg, 0.11 mmol, 17% yield) as an orange solid. LCMS (ESI) [M+H]$^+$=468.2, R$_T$ 2.053 min, Method J; $^1$H NMR (300 MHz, DMSO-d$_6$) δ 10.16 (s, 1H), 9.37 (s, 1H), 7.97 (s, 1H), 7.48 (s, 1H), 6.88 (d, J=6.0 Hz, 1H), 4.74 (q, J=7.2 Hz, 1H), 4.56-4.00 (m, 5H), 3.44-3.45 (m, 2H), 3.09 (s, 3H), 2.44-2.26 (m, 2H), 2.13-2.20 (m, 2H), 1.98 (d, J=1.6 Hz, 3H), 1.27 (s, 3H).

Example 260

(1r,3r)-3-(((8-Amino-7-fluoro-6-(8-methyl-2,3-dihydro-1H-pyrido[2,3-b][1,4]oxazin-7-yl)isoquinolin-3-yl)carbamoyl)oxy)-1-methylcyclobutyl acetate and (1s,3s)-3-(((8-Amino-7-fluoro-6-(8-methyl-2,3-dihydro-1H-pyrido[2,3-b][1,4]oxazin-7-yl)isoquinolin-3-yl)carbamoyl)oxy)-1-methylcyclobutyl acetate (Compound 529a and Compound 529b)

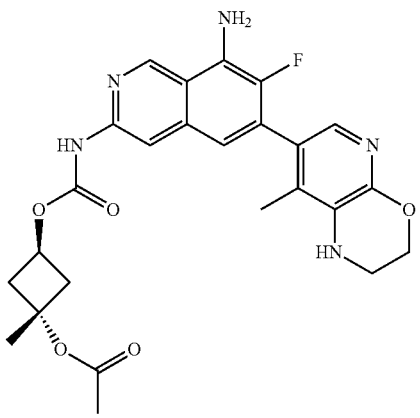

-continued

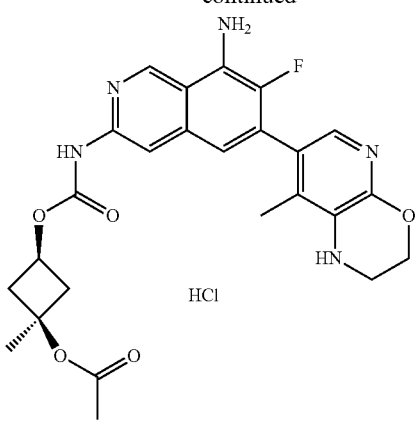

Step 1: 3-(Benzyloxy)-1-methylcyclobutyl acetate

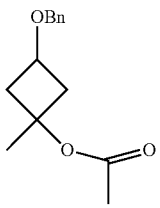 [SMILES: CC(=O)OC1(C)CC(OCc2ccccc2)C1]

To a solution of 3-(benzyloxy)cyclobutanone (1.0 g, 5.68 mmol) in THF (20 mL) was added ethyl magnesium chloride (8.51 mL, 17.03 mmol) at 0° C. The mixture was stirred at room temperature for 2 hours. The reaction was diluted by methanol, concentrated and purified by flash chromatography on silica gel eluting with petroleum ether/ethyl acetate (10/90) to afford 3-benzyloxy-1-ethyl-cyclobutanol (300 mg, 1.454 mmol, 25.6% yield) as colorless oil.

Step 2: 3-Hydroxy-1-methylcyclobutyl acetate

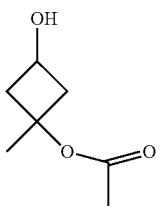

A mixture of (3-benzyloxy-1-methyl-cyclobutyl) acetate (500 mg, 2.13 mmol) and Pd/C (200 mg, 10 wt %) in methyl alcohol (10 ml) was stirred under hydrogen at 40° C. for 8 hours. The mixture was then filtered and concentrated under vacuum to afford 3-hydroxy-1-methylcyclobutyl acetate (170 mg, 1.18 mmol) as a colorless oil.

Step 3: tert-Butyl 7-(3-(((3-acetoxy-3-methylcyclobutoxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate

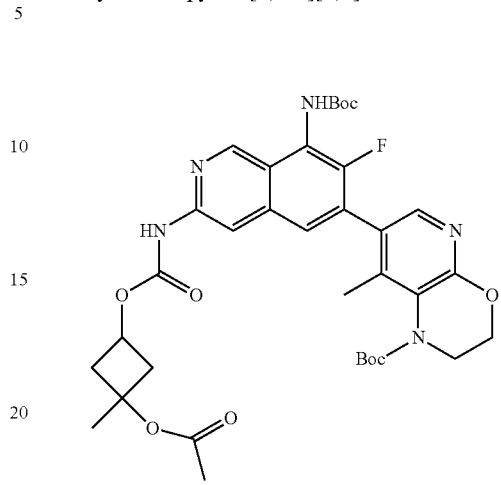

To a mixture of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (250 mg, 0.39 mmol) and (3-hydroxy-1-methylcyclobutyl) acetate (170 mg, 1.18 mmol) in dichloromethane (50 mL) was added DMAP (50 mg, 0.41 mmol). The mixture was stirred at 60° C. for 12 hours. After concentration, the residue was purified by flash chromatography on a silica gel eluting with dichloromethane/methanol (10/1) to afford tert-butyl 7-(3-(((3-acetoxy-3-methylcyclobutoxy)carbonyl)amino)-8-((tert-butoxycarbonyl)amino)-7-fluoroisoquinolin-6-yl)-8-methyl-2,3-dihydro-1H-pyrido[2,3-b][1,4]oxazine-1-carboxylate as a yellow solid. LCMS (ESI) [M+H]⁺=696.3.

Step 4: (1r,3r)-3-((8-Amino-7-fluoro-6-(8-methyl-2,3-dihydro-1H-pyrido[2,3-b][1,4]oxazin-7-yl)isoquinolin-3-yl)carbamoyl)oxy)-1-methylcyclobutyl acetate and (1s,3s)-3-(((8-Amino-7-fluoro-6-(8-methyl-2,3-dihydro-1H-pyrido[2,3-b][1,4]oxazin-7-yl)isoquinolin-3-yl)carbamoyl)oxy)-1-methylcyclobutyl acetate hydrochloride

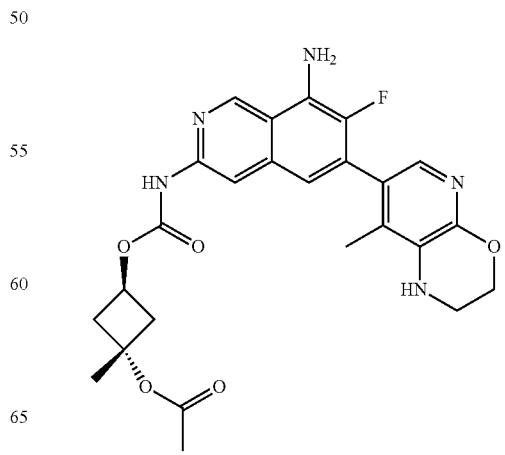

687

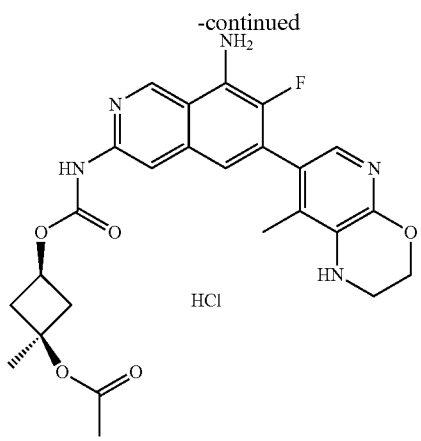

To a solution of tert-butyl 7-[3-[(3-acetoxy-3-methyl-cyclobutoxy)carbonylamino]-8-(tert-butoxycarbonylamino)-7-fluoro-6-isoquinolyl]-8-methyl-2,3-dihydro-pyrido[2,3-b][1,4]oxazine-1-carboxylate (200 mg, 0.29 mmol) in dichloromethane (2 mL) was added TFA (2 mL). The mixture was stirred at room temperature for 1 hour. After concentration, the residue was purified by prep-HPLC (X Bridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 27% B to 57% B in 7 min) to afford two isomers. Stereochemistry was arbitrarily assigned.

Diastereomer 1: Compound 529a (3.4 mg, 0.0069 mmol, 2.4% yield) as a yellow solid. LCMS (ESI) $[M+H]^+$=496.2, 1.287 min., Method J, $^1$H NMR (300 MHz, DMSO-$d_6$) δ 10.14 (s, 1H), 9.33 (s, 1H), 7.94 (s, 1H), 7.31 (s, 1H), 6.82 (d, J=6.1 Hz, 1H), 6.19 (s, 2H), 5.65 (s, 1H), 5.08-4.97 (m, 1H), 4.27 (s, 2H), 3.41-3.33 (m, 2H), 2.74 (dd, J=13.8, 7.4 Hz, 2H), 2.23 (dd, J=14.0, 4.3 Hz, 2H), 1.97 (s, 3H), 1.90 (d, J=1.6 Hz, 3H), 1.58 (s, 3H).

Diastereomer 2: Compound 529b (40.1 mg, 0.0754 mmol, 26.2% yield) (after making HCl salt) as an orange solid. LCMS (ESI) $[M+H]^+$=496.2, 1.284 min., Method J, $^1$H NMR (300 MHz, DMSO-$d_6$) δ 10.19 (s, 1H), 9.36 (s, 1H), 7.95 (s, 1H), 7.49 (s, 1H), 6.88 (d, J=6.1 Hz, 1H), 4.85-4.79 (m, 2H), 4.40-4.35 (m, 4H), 3.44 (s, 2H), 2.67 (td, J=7.8, 7.0, 4.3 Hz, 2H), 2.37-2.23 (m, 2H), 1.97 (d, J=5.8 Hz, 6H), 1.47 (s, 3H).

Example 261

(3R,4S)-4-Methyltetrahydrofuran-3-yl (8-amino-7-fluoro-6-((S)-3-fluoro-8-methyl-2,3-dihydro-1H-pyrido[2,3-b][1,4]oxazin-7-yl)isoquinolin-3-yl)carbamate and (3R,4S)-4-Methyltetrahydrofuran-3-yl (8-amino-7-fluoro-6-((R)-3-fluoro-8-methyl-2,3-dihydro-1H-pyrido[2,3-b][1,4]oxazin-7-yl)isoquinolin-3-yl)carbamate (Compound 567a and Compound 567b)

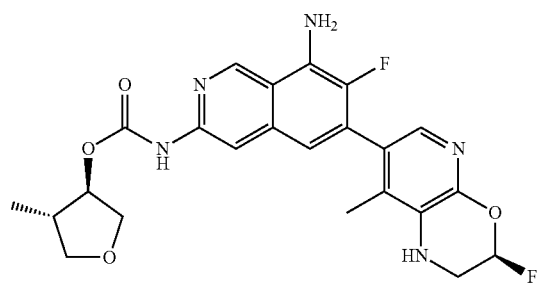

688

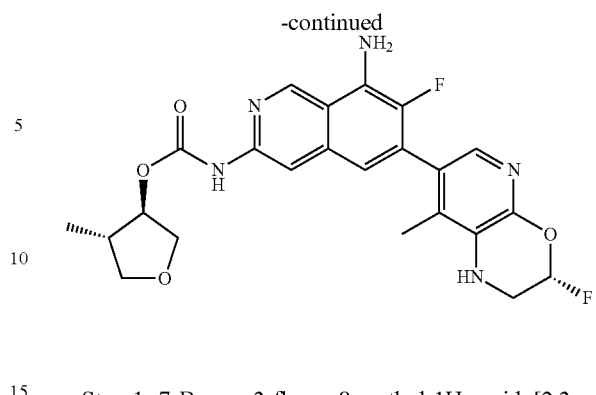

Step 1: 7-Bromo-3-fluoro-8-methyl-1H-pyrido[2,3-b][1,4]oxazin-2-one

Under nitrogen, to a solution of 3-amino-5-bromo-4-methyl-pyridin-2-ol (5 g, 24.63 mmol) and $K_2CO_3$ (10.195 g, 73.88 mmol) in N,N-dimethylformamide (50 mL) was added 2-chloro-2-fluoro-acetyl chloride (4191.51 mg, 32.01 mmol) at 0° C. The resulting mixture was stirred at room temperature for 1 hour and at 90° C. for 1 hour. The reaction was quenched with water and extracted with ethyl acetate. The organic layer was dried over anhydrous sodium sulfate, filtered and concentrated under vacuum. The residue was purified by flash chromatography on silica gel eluting with petroleum ether/ethyl acetate (45/55) to afford 7-bromo-3-fluoro-8-methyl-1H-pyrido[2,3-b][1,4]oxazin-2-one (2500 mg, 9.576 mmol, 38.9% yield) as a yellow solid. LCMS (ESI) $[M+H]^+$=261.05.

Step 2: 7-Bromo-3-fluoro-8-methyl-2,3-dihydro-1H-pyrido[2,3-b][1,4]oxazine

Under nitrogen, to a solution of 7-bromo-3-fluoro-8-methyl-1H-pyrido[2,3-b][1,4]oxazin-2-one (2500.0 mg, 9.58 mmol) in tetrahydrofuran (50 mL) was added $BH_3$·THF (28.73 mL, 28.73 mmol) at 0° C. The solution was stirred at 0° C. for 0.5 hour and at 60° C. for 1 hour. The reaction was quenched with methanol at 0° C. To the reaction mixture was added 1N HCl (10 ml) solution. The mixture was then stirred at room temperature for 30 min and adjusted to pH 8 with ammonium hydroxide. The resulting solution was extracted with dichloromethane. The organic layers were combined and concentrated under vacuum. The residue was purified by flash chromatography on silica gel eluting with petroleum ether/ethyl acetate (26/74) to afford 7-bromo-3-fluoro-8- methyl-2,3-dihydro-1H-pyrido[2,3-b][1,4]oxazine (1100 mg, 4.452 mmol, 46.5% yield) as a yellow solid. LCMS (ESI) [M+H]$^+$=246.

Step 3: tert-Butyl 7-bromo-3-fluoro-8-methyl-2,3-dihydropyrido[2,3-b][1,4]oxazine-1-carboxylate

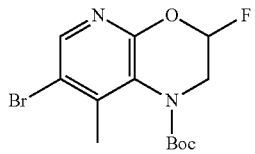 [SMILES: Cc1c(Br)cnc2c1N(C(=O)OC(C)(C)C)CC(F)O2]

Under nitrogen, to a solution of 7-bromo-3-fluoro-8-methyl-2,3-dihydro-1H-pyrido[2,3-b][1,4]oxazine (1100.0 mg, 4.45 mmol) in tetrahydrofuran (50 mL) was added NaHMDS (2449.29 mg, 13.36 mmol) at −78° C. The resulting solution was stirred at −78° C. for 0.5 hour. Then (Boc)$_2$O (2923.2 mg, 13.36 mmol) was added and stirred at −78° C. for 1 hour. The reaction was quenched with MeOH and concentrated under vacuum. The residue was purified by flash chromatography on silica gel eluting with petroleum ether/ethyl acetate (14/86) to afford tert-butyl 7-bromo-3-fluoro-8-methyl-2,3-dihydropyrido[2,3-b][1,4]oxazine-1-carboxylate (850 mg, 2.448 mmol, 55% yield) as a white solid. LCMS (ESI) [M+H]$^+$=347.2.

Step 4: tert-Butyl 3-fluoro-8-methyl-7-(4,4,5,5-tetramethyl-1,3,2-dioxaborolan-2-yl)-2,3-dihydropyrido[2,3-b][1,4]oxazine-1-carboxylate

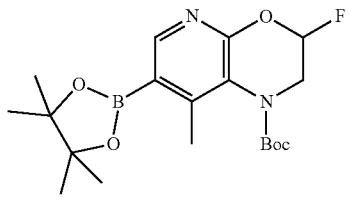 [SMILES: Cc1c(B2OC(C)(C)C(C)(C)O2)cnc2c1N(C(=O)OC(C)(C)C)CC(F)O2]

A mixture of [tert-butyl 7-bromo-3-fluoro-8-methyl-2,3-dihydropyrido[2,3-b][1,4]oxazine-1-carboxylate (50.0 mg, 0.140 mmol), KOAc (57.0 mg, 0.58 mmol), B$_2$pin$_2$ (110.0 mg, 0.43 mmol) and Pd(dppf)Cl$_2$ (21.0 mg, 0.030 mmol)] in 1,4-dioxane (2 mL) was stirred at 100° C. for 16 hours. After filtration, the filtrate was concentrated under reduced pressure. The residue was purified by flash chromatography on silica gel eluting with petroleum ether/ethyl acetate (70/30) to afford tert-butyl 3-fluoro-8-methyl-7-(4,4,5,5-tetramethyl-1,3,2-dioxaborolan-2-yl)-2,3-dihydropyrido[2,3-b][1,4]oxazine-1-carboxylate (50 mg, 0.127 mmol, 88.1% yield) as light yellow oil. LCMS (ESI) [M+H]$^+$=395.

Step 5: (3R,4S)-4-Methyltetrahydrofuran-3-yl N-(8-chloro-7-fluoro-6-iodo-3-isoquinolyl)carbamate

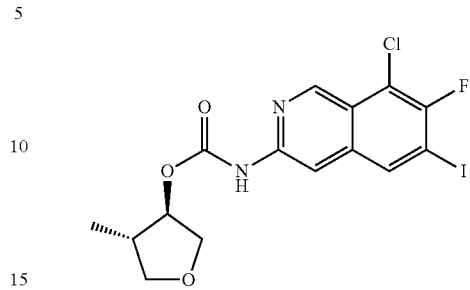

Under nitrogen, to a solution of 8-chloro-7-fluoro-6-iodo-isoquinolin-3-amine (800.0 mg, 2.48 mmol), DIEA (1.6 g, 12.38 mmol) and (3S,4R)-4-methyltetrahydrofuran-3-ol (507.0 mg, 4.96 mmol) in dichloromethane (20 mL) was added triphosgene (514.0 mg, 1.74 mmol) at 0° C. The reaction was stirred for 0.5 hour at 0° C. The resulting solution was concentrated under vacuum. The residue was purified by flash chromatography on silica gel eluting with dichloromethane/methanol (98/2) to afford (3R,4S)-4-methyltetrahydrofuran-3-yl N-(8-chloro-7-fluoro-6-iodo-3-isoquinolyl)carbamate (720 mg, 1.598 mmol, 64.4% yield)] as a brown solid. LCMS (ESI) [M+H]$^+$=451.

Step 6: tert-Butyl 7-[8-chloro-7-fluoro-3-[[(3R,4S)-4-methyltetrahydrofuran-3-yl]oxycarbonylamino]-6-isoquinolyl]-3-fluoro-8-methyl-2,3-dihydropyrido[2,3-b][1,4]oxazine-1-carboxylate

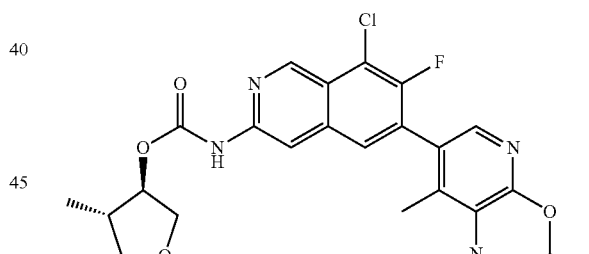

Under nitrogen, to a solution of (4-methyltetrahydrofuran-3-yl) N-(8-chloro-7-fluoro-6-iodo-3-isoquinolyl)carbamate (100.0 mg, 0.22 mmol), Pd(dppf)Cl$_2$ (24.0 mg, 0.030 mmol), K$_2$CO$_3$ (93.0 mg, 0.67 mmol) and tert-butyl 3-fluoro-8-methyl-7-(4,4,5,5-tetramethyl-1,3,2-dioxaborolan-2-yl)-2,3-dihydropyrido[2,3-b][1,4]oxazine-1-carboxylate (96.0 mg, 0.24 mmol) in 1,4-dioxane (1.8 mL) and water (0.20 mL) was stirred for 3.5 hours at 100° C. The reaction was concentrated under vacuum. The residue was purified by flash chromatography on silica gel eluting with petroleum ether/ethyl acetate (35/65) to afford tert-butyl 7-[8-chloro-7-fluoro-3-[[(3R,4S)-4-methyltetrahydrofuran-3-yl]oxycarbonyl amino]-6-isoquinolyl]-3-fluoro-8-methyl-2,3-dihydropyrido[2,3-b][1,4]oxazine-1-carboxylate (70 mg, 0.1184 mmol, 53.4% yield)] as a light yellow solid. LCMS (ESI) [M+H]$^+$=592.

Step 7: tert-Butyl 7-[8-(tert-butoxycarbonylamino)-7-fluoro-3-[[(3R,4S)-4-methyltetrahydrofuran-3-yl]oxycarbonylamino]-6-isoquinolyl]-3-fluoro-8-methyl-2,3-dihydropyrido[2,3-b][1,4]oxazine-1-carboxylate

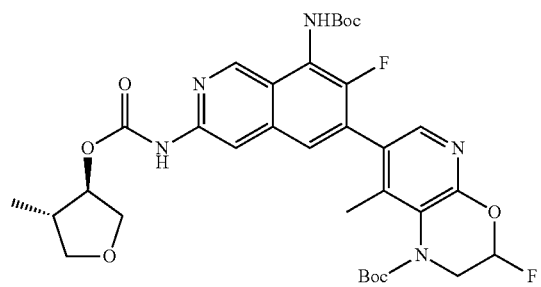 [SMILES: Cc1c(-c2cc3cc(NC(=O)O[C@H]4COC[C@@H]4C)ncc3c(NC(=O)OC(C)(C)C)c2F)cnc2c1N(C(=O)OC(C)(C)C)CC(F)O2]

Under nitrogen, a mixture of tert-butyl 7-[8-chloro-7-fluoro-3-[(4-methyltetrahydrofuran-3-yl)oxycarbonylamino]-6-isoquinolyl]-3-fluoro-8-methyl-2,3-dihydropyrido[2,3-b][1,4]oxazine-1-carboxylate (350.0 mg, 0.59 mmol), BrettphosPd G3 (109.0 mg, 0.12 mmol), $K_2CO_3$ (247.0 mg, 1.78 mmol) and $NH_2Boc$ (1.7 g, 14.66 mmol) in 1,4-dioxane (3 mL) was stirred for 2 hours at 90° C. The reaction was concentrated under vacuum. The residue was purified by flash chromatography on silica gel eluting with petroleum ether/ethyl acetate (25/75) to afford tert-butyl 7-[8-(tert-butoxycarbonylamino)-7-fluoro-3-[[(3R,4S)-4-methyltetrahydrofuran-3-yl]oxycarbonylamino]-6-isoquinolyl]-3-fluoro-8-methyl-2,3-dihydropyrido[2,3-b][1,4]oxazine-1-carboxylate (320 mg, 0.4764 mmol, 80.4% yield) as a brown solid. LCMS (ESI) $[M+H]^+$=671.

Step 8: (3R,4S)-4-Methyltetrahydrofuran-3-yl (8-amino-7-fluoro-6-((S)-3-fluoro-8-methyl-2,3-dihydro-1H-pyrido[2,3-b][1,4]oxazin-7-yl)isoquinolin-3-yl)carbamate and (3R,4S)-4-Methyltetrahydrofuran-3-yl (8-amino-7-fluoro-6-((R)-3-fluoro-8-methyl-2,3-dihydro-1H-pyrido[2,3-b][1,4]oxazin-7-yl)isoquinolin-3-yl)carbamate A solution of tert-butyl 7-[8-(tert-butoxycarbonylamino)-7-fluoro-3-[[(3R,4S)-4-methyltetrahydrofuran-3-yl]oxycarbonylamino]-6-isoquinolyl]-3-fluoro-8-methyl-2,3-dihydropyrido[2,3-b][1,4]oxazine-1-carboxylate (300.0 mg, 0.45 mmol) in TFA (5 mL) and dichloromethane (5 mL) was stirred at room temperature for 2 hours. The reaction solution was concentrated under vacuum. The residue was purified by Prep-HPLC (Column: X Bridge Prep OBD C18 Column 30×150 mm, 5 μm; Mobile Phase A: Water (0.1% TFA), Mobile Phase B: ACN; Flow rate: 60 mL/min; Gradient: 23% B to 46% B in 10 min) to afford a racemate product. The racemic product was separated by chiral-HPLC (CHIRAL ART Cellulose-SB, 2*25 cm, 5 μm; Mobile Phase A: hexane, Mobile Phase B: EtOH; Flow rate: 20 mL/min; Gradient: 30% B to 30% B in 10 min) to afford two enantiomers. Absolute stereochemistry at oxazin was arbitrarily assigned.

Enantiomer 1 (Compound 567a) (42.9 mg, 0.0845 mmol, 18.9% yield): $R_T$ 4.768 (CHIRAL Cellulose-SB4.6*100 mm 3 μm. Mobile phase:Mobile phase::Hex (0.1% DEA): EtOH=70:30; 1 ml/min) LCMS(ESI) $[M+H]^+$=472.2, $R_T$ 6.081 min, Method J; $^1$H NMR (300 MHz, DMSO-$d_6$) δ 10.27 (s, 1H), 9.40 (s, 1H), 7.98 (s, 1H), 7.48 (s, 1H), 6.92 (d, J=6.1 Hz, 1H), 6.49 (s, 1H), 4.91-4.83 (m, 1H), 4.05-3.91 (m, 2H), 3.82-3.71 (m, 1H), 3.64-3.53 (m, 1H), 3.65-3.54 (m, 2H), 2.43-2.26 (m, 1H), 1.98 (d, J=1.6 Hz, 3H), 1.12-1.02 (d, J=7.2 Hz, 3H).

Enantiomer 2 (Compound 567b) (50 mg, 0.0984 mmol, 22% yield): $R_T$ 5.717 (CHIRAL Cellulose-SB4.6*100 mm 3 μm. Mobile phase:Mobile phase:Hex (0.1% DEA): EtOH=70:30; 1 ml/min) LCMS(ESI) $[M+H]^+$=472.2, $R_T$ 6.081 min, Method J; $^1$H NMR (300 MHz, DMSO-$d_6$) δ 10.27 (s, 1H), 9.40 (s, 1H), 7.98 (s, 1H), 7.48 (s, 1H), 6.92 (d, J=6.1 Hz, 1H), 6.49 (s, 1H), 4.91-4.83 (m, 1H), 4.05-3.91 (m, 2H), 3.82-3.71 (m, 1H), 3.64-3.53 (m, 1H), 3.65-3.54 (m, 2H), 2.43-2.26 (m, 1H), 1.98 (d, J=1.6 Hz, 3H), 1.12-1.02 (d, J=7.2 Hz, 3H).

Example 262

(1r,3r)-3-Hydroxy-3-methylcyclobutyl (8-amino-7-fluoro-6-(8-methyl-2,3-dihydro-1H-pyrido[2,3-b][1,4]oxazin-7-yl)isoquinolin-3-yl)carbamate (Compound 486b) and (1s,3s)-3-Hydroxy-1-methylcyclobutyl (8-amino-7-fluoro-6-(8-methyl-2,3-dihydro-1H-pyrido[2,3-b][1,4]oxazin-7-yl)isoquinolin-3-yl)carbamate (Compound 554a)

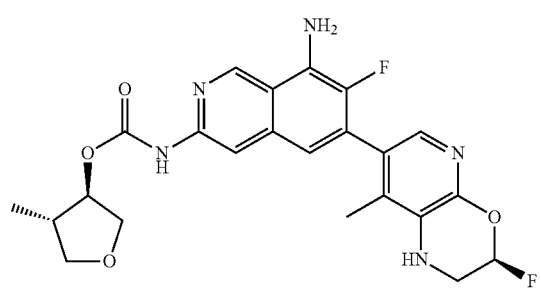

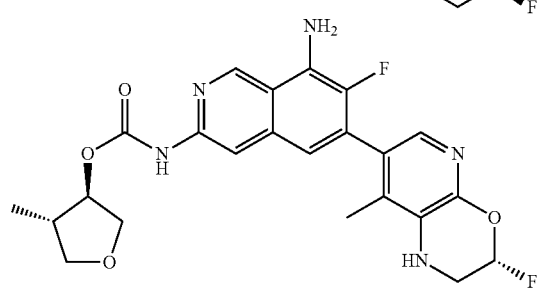

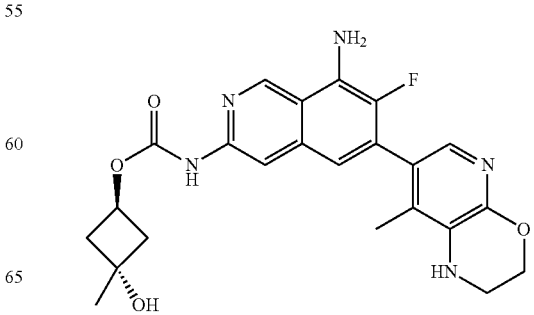

-continued

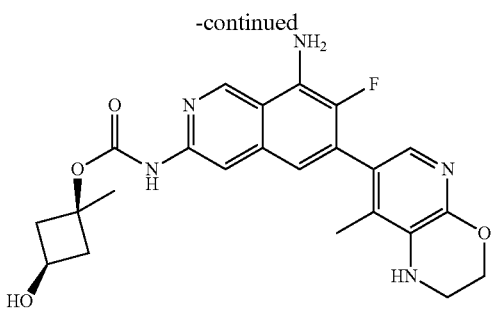

Step 1: 3-Benzyloxy-1-methyl-cyclobutanol

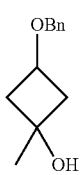

To a solution of 3-(benzyloxy)cyclobutanone (5000.0 mg, 28.38 mmol) in tetrahydrofuran (50 mL) was added dropwise methyl magnesium chloride (28.4 mL, 85.13 mmol, 3 mol/L in THF) at −78° C. The resulting solution was stirred at −78° C. for 2 hours. The reaction was quenched with MeOH and concentrated under vacuum. The residue was purified by flash chromatography on silica gel eluting with petroleum ether/ethyl acetate to afford 3-benzyloxy-1-methyl-cyclobutanol (4300 mg, 22.367 mmol, 78.8% yield) as a yellow oil. LCMS (ESI) [M+H]⁺=193.1.

Step 2: 1-Methylcyclobutane-1,3-diol

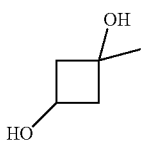

A mixture of 3-benzyloxy-1-methyl-cyclobutanol (2000.0 mg, 10.4 mmol) and Pd/C (10 wt %, 400 mg, 0.52 mmol) in methyl alcohol (30 mL) was stirred under hydrogen (1 atm) at room temperature for 16 hours. The mixture was then filtered and concentrated under reduced pressure. The residue was purified by flash chromatography on silica gel eluting with dichloromethane/methanol to afford 1-methyl-cyclobutane-1,3-diol (1100 mg, 10.232 mmol, 98.4% yield) as a yellow oil. LCMS (ESI) [M+H]⁺=103.1.

Step 3: tert-Butyl 7-(8-((tert-butoxycarbonyl)amino)-7-fluoro-3-(((3-hydroxy-3-methylcyclobutoxy)carbonyl)amino)isoquinolin-6-yl)-8-methyl-2,3-dihydro-1H-pyrido[2,3-b][1,4]oxazine-1-carboxylate

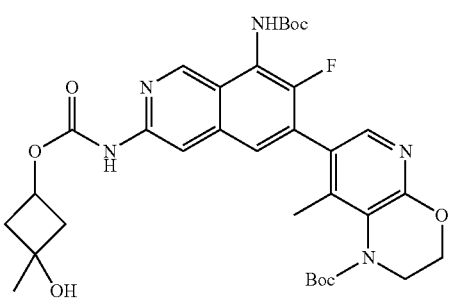 [SMILES: Cc1c(-c2cc3cc(NC(=O)OC4CC(C)(O)C4)ncc3c(NC(=O)OC(C)(C)C)c2F)cnc2c1N(C(=O)OC(C)(C)C)CCO2]

Under nitrogen, to a solution of tert-butyl 7-[3-amino-8-(tert-butoxycarbonylamino)-7-fluoro-6-isoquinolyl]-8-methyl-2,3-dihydropyrido[2,3-b][1,4]oxazine-1-carboxylate (1000.0 mg, 1.9 mmol), 1-methylcyclobutane-1,3-diol (388.6 mg, 3.8 mmol) and DIEA (1229.52 mg, 9.51 mmol) in dichloromethane (25 mL) was added triphosgene (282.3 mg, 0.95 mmol) at 0° C. The resulting solution was stirred at 0° C. for 0.5 hour. The reaction was quenched with water and extracted with dichloromethane. The organic layers were combined, dried over anhydrous sodium sulfate and concentrated under vacuum. The residue was purified by flash chromatography on silica gel eluting with dichloromethane/methanol (5%) to afford tert-butyl 7-[8-(tert-butoxycarbonylamino)-7-fluoro-3-[(3-hydroxy-3-methyl-cyclobutoxy)carbonylamino]-6-isoquinolyl]-8-methyl-2,3-dihydropyrido[2,3-b][1,4]oxazine-1-carboxylate (1100 mg, 1.6827 mmol, 88.4% yield) as a yellow solid. LCMS (ESI) [M+H]⁺=654.3.

Step 4: (1r,3r)-3-Hydroxy-3-methylcyclobutyl (8-amino-7-fluoro-6-(8-methyl-2,3-dihydro-1H-pyrido[2,3-b][1,4]oxazin-7-yl)isoquinolin-3-yl)carbamate (Compound 486b) and (1s,3s)-3-Hydroxy-1-methylcyclobutyl (8-amino-7-fluoro-6-(8-methyl-2,3-dihydro-1H-pyrido[2,3-b][1,4]oxazin-7-yl)isoquinolin-3-yl)carbamate (Compound 554b)

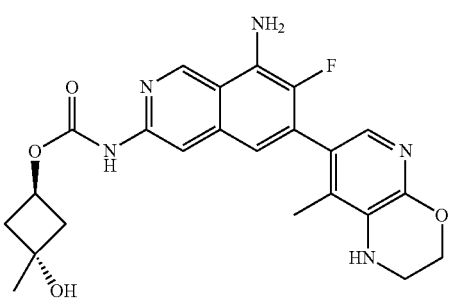

-continued

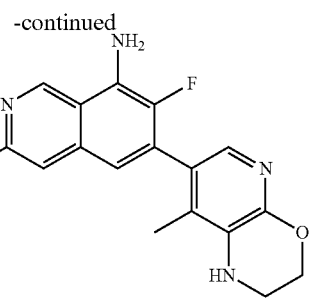

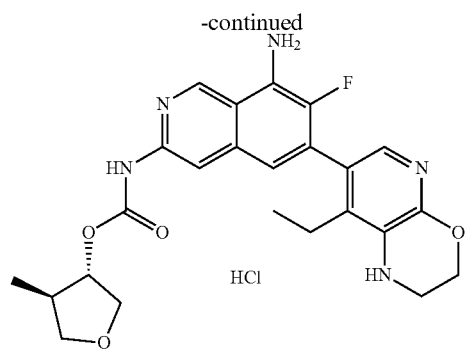

To a solution of tert-butyl 7-[8-(tert-butoxycarbonylamino)-7-fluoro-3-[(3-hydroxy-3-methyl-cyclobutoxy)carbonylamino]-6-isoquinolyl]-8-methyl-2,3-dihydropyrido[2,3-b][1,4]oxazine-1-carboxylate (1100.0 mg, 1.68 mmol) in dichloromethane (25 mL) was added TFA (10 mL) at 0° C. The resulting solution was stirred at room temperature for 3 hours. The mixture was concentrated under vacuum and purified by Prep-HPLC (Column: X select CSH OBD Column 30*150 mm 5 μm, n; Mobile Phase A: Water (0.1% FA), Mobile Phase B: ACN; Flow rate: 60 mL/min; Gradient: 16% B to 46% B in 7 min; 254 nm) to afford two isomers.

Isomer 1 (Compound 486b) (277.9 mg, 0.5672 mmol, 33.7% yield). LCMS (ESI) [M+H]$^+$=454.2, $R_T$ 1.053 min; Method J. $^1$H NMR (400 MHz, DMSO-d$_6$) δ 10.16 (s, 1H), 9.40 (s, 1H), 7.98 (s, 1H), 7.53 (s, 1H), 6.91 (d, J=6.1 Hz, 1H), 5.06 (tt, J=7.4, 5.6 Hz, 1H), 4.47 (t, J=4.5 Hz, 2H), 3.48 (d, J=4.6 Hz, 2H), 2.45-2.26 (m, 2H), 2.11-2.03 (m, 2H), 2.01 (d, J=1.5 Hz, 3H), 1.34 (s, 3H).

Isomer 2 (Compound 554a) (10.4 mg, 0.0208 mmol, 1.2% yield). LCMS (ESI) [M+H]$^+$=454.2, $R_T$ 1.710 min., Method J. $^1$H NMR (400 MHz, DMSO-d$_6$) δ 9.91 (s, 1H), 9.32 (s, 1H), 7.97 (s, 1H), 7.34 (s, 1H), 6.84 (d, J=6.2 Hz, 1H), 5.72 (s, 2H), 4.31 (t, J=4.3 Hz, 2H), 3.90 (p, J=7.2 Hz, 1H), 3.47 (d, J=4.6 Hz, 2H), 2.56-2.52 (m, 2H), 2.14 (t, J=9.7 Hz, 2H), 1.93 (d, J=1.5 Hz, 3H), 1.47 (s, 3H).

Example 263

(3R,4S)-4-Methyltetrahydrofuran-3-yl (8-amino-6-(8-ethyl-2,3-dihydro-1H-pyrido[2,3-b][1,4]oxazin-7-yl)-7-fluoroisoquinolin-3-yl)carbamate hydrochloride and (3S,4R)-4-Methyltetrahydrofuran-3-yl (8-amino-6-(8-ethyl-2,3-dihydro-1H-pyrido[2,3-b][1,4]oxazin-7-yl)-7-fluoroisoquinolin-3-yl)carbamate hydrochloride (Compound 555a and Compound 555b)

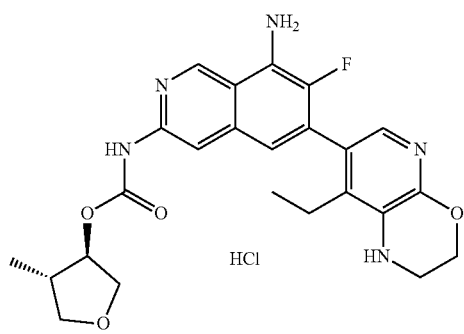

Step 1: tert-Butyl 8-ethyl-7-(4,4,5,5-tetramethyl-1,3,2-dioxaborolan-2-yl)-2,3-dihydro-1H-pyrido[2,3-b][1,4]oxazine-1-carboxylate

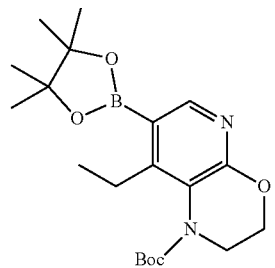 [SMILES: CCc1c(B2OC(C)(C)C(C)(C)O2)cnc2c1N(C(=O)OC(C)(C)C)CCO2]

To a mixture of tert-butyl 7-bromo-8-ethyl-2,3-dihydropyrido[2,3-b][1,4]oxazine-1-carboxylate (500 mg, 1.46 mmol) and B$_2$pin$_2$ (1851 mg, 7.29 mmol) in 1,4-dioxane (10 mL) was added KOAc (428 mg, 4.37 mmol), Pd(dppf)Cl$_2$ (213 mg, 0.29 mmol). The mixture was stirred at 90° C. for 3 hours. After concentration, the residue was purified by flash chromatography on silica gel eluting with petroleum ether/ethyl acetate (1/1) to afford tert-butyl 8-ethyl-7-(4,4,5,5-tetramethyl-1,3,2-dioxaborolan-2-yl)-2,3-dihydropyrido[2,3-b][1,4]oxazine-1-carboxylate (400 mg, 1.0249 mmol, 70.4% yield) as a yellow oil. LCMS (ESI) [M+H]$^+$=391.2.

Step 2: tert-Butyl 7-(3-amino-8-chloro-7-fluoroisoquinolin-6-yl)-8-ethyl-2,3-dihydro-1H-pyrido[2,3-b][1,4]oxazine-1-carboxylate

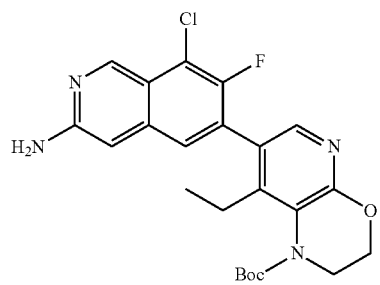 [SMILES: CCc1c(-c2cc3cc(N)ncc3c(Cl)c2F)cnc2c1N(C(=O)OC(C)(C)C)CCO2]

To a mixture of 8-chloro-7-fluoro-6-iodo-isoquinolin-3-amine (483 mg, 1.5 mmol) and tert-butyl 8-ethyl-7-(4,4,5,5-tetramethyl-1,3,2-dioxaborolan-2-yl)-2,3-dihydropyrido[2,3-b][1,4]oxazine-1-carboxylate (758 mg, 1.94 mmol) in 1,4-dioxane (10 mL) and water (2 mL) was added Pd(dppf)Cl$_2$ (220 mg, 0.30 mmol), K$_2$CO$_3$ (620 mg, 4.49 mmol). The mixture was stirred at 90° C. for 3 hours. After concentration, the residue was purified by flash chromatography on silica gel eluting with dichloromethane/methanol (10/1) to afford tert-butyl 7-(3-amino-8-chloro-7-fluoro-6-isoquinolyl)-8-ethyl-2,3-dihydropyrido[2,3-b][1,4]oxazine-1-carboxylate (320 mg, 0.697 mmol, 46.6% yield) as a yellow solid. LCMS (ESI) [M+H]$^+$=459.1.

Step 3: tert-Butyl 7-(8-chloro-7-fluoro-3-(((((3R,4S)-4-methyltetrahydrofuran-3-yl)oxy)carbonyl)amino)isoquinolin-6-yl)-8-ethyl-2,3-dihydro-1H-pyrido[2,3-b][1,4]oxazine-1-carboxylate

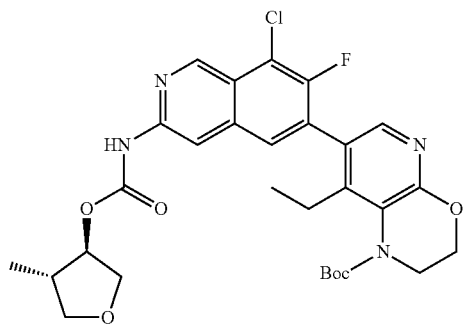 [SMILES: CCc1c(-c2cc3cc(NC(=O)O[C@H]4COC[C@@H]4C)ncc3c(Cl)c2F)cnc2c1N(C(=O)OC(C)(C)C)CCO2]

To a mixture of tert-butyl 7-(3-amino-8-chloro-7-fluoro-6-isoquinolyl)-8-ethyl-2,3-dihydropyrido[2,3-b][1,4]oxazine-1-carboxylate (320 mg, 0.70 mmol) and 4-methyltetrahydrofuran-3-ol (214 mg, 2.1 mmol) in dichloromethane (10 mL) was added triphosgene (103 mg, 0.35 mmol), DIEA (450 mg, 3.49 mmol) and then the mixture was stirred at 0° C. for 2 hours. After concentration, the residue was purified by flash chromatography on silica gel eluting with dichloromethane/methanol (10/1) to afford tert-butyl 7-[8-chloro-7-fluoro-3-[(4-methyltetrahydrofuran-3-yl)oxycarbonylamino]-6-isoquinolyl]-8-ethyl-2,3-dihydropyrido[2,3-b][1,4]oxazine-1-carboxylate (320 mg, 0.545 mmol, 78.2% yield) as a yellow solid. LCMS (ESI) [M+H]$^+$=587.2.

Step 4: tert-Butyl 7-(8-((tert-butoxycarbonyl)amino)-7-fluoro-3-(((((3R,4S)-4-methyltetrahydrofuran-3-yl)oxy)carbonyl)amino)isoquinolin-6-yl)-8-ethyl-2,3-dihydro-1H-pyrido[2,3-b][1,4]oxazine-1-carboxylate

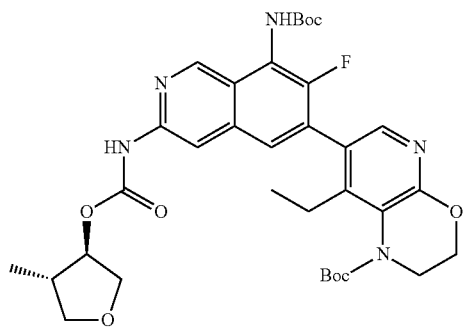 [SMILES: CCc1c(-c2cc3cc(NC(=O)O[C@H]4COC[C@@H]4C)ncc3c(NC(=O)OC(C)(C)C)c2F)cnc2c1N(C(=O)OC(C)(C)C)CCO2]

To a mixture of tert-butyl 7-[8-chloro-7-fluoro-3-[(4-methyltetrahydrofuran-3-yl)oxycarbonylamino]-6-isoquinolyl]-8-methyl-2,3-dihydropyrido[2,3-b][1,4]oxazine-1-carboxylate (320 mg, 0.56 mmol) and tert-butyl carbamate (1913 mg, 16.33 mmol) in 1,4-dioxane (5 mL) was added Pd$_2$(dba)$_3$ CHCl$_3$ (85 mg, 0.080 mmol), BrettPhos (116 mg, 0.22 mmol), cesium carbonate (533 mg, 1.63 mmol). The mixture was stirred at 90° C. for 2 hours. After concentration, the residue was purified by flash chromatography on silica gel eluting with dichloromethane/methanol (10/1) to afford tert-butyl 7-[8-(tert-butoxycarbonylamino)-7-fluoro-3-[(4-methyltetrahydrofuran-3-yl)oxycarbonylamino]-6-isoquinolyl]-8-methyl-2,3-dihydropyrido[2,3-b][1,4]oxazine-1-carboxylate (260 mg, 0.397 mmol, 71.2% yield) as a yellow solid. LCMS (ESI) [M+H]$^+$=668.3.

Step 5: (3R,4S)-4-Methyltetrahydrofuran-3-yl (8-amino-6-(8-ethyl-2,3-dihydro-1H-pyrido[2,3-b][1,4]oxazin-7-yl)-7-fluoroisoquinolin-3-yl)carbamate hydrochloride and (3S,4R)-4-methyltetrahydrofuran-3-yl (8-amino-6-(8-ethyl-2,3-dihydro-1H-pyrido[2,3-b][1,4]oxazin-7-yl)-7-fluoroisoquinolin-3-yl)carbamate hydrochloride

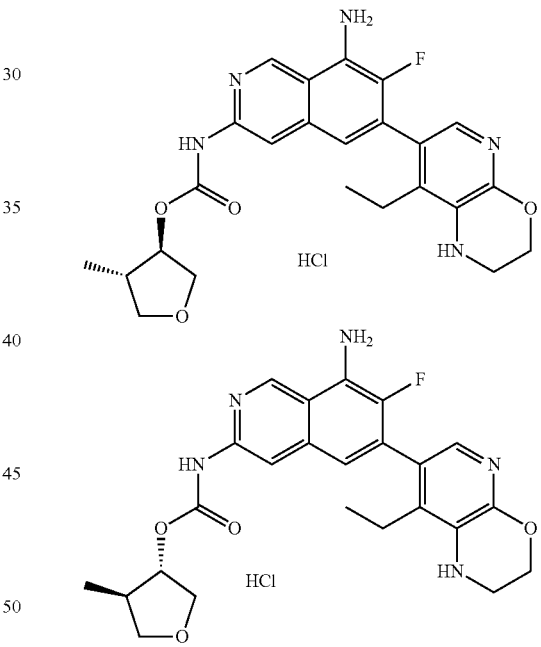

To a solution of tert-butyl 7-[8-(tert-butoxycarbonylamino)-7-fluoro-3-[(4-methyltetrahydrofuran-3-yl)oxycarbonylamino]-6-isoquinolyl]-8-ethyl-2,3-dihydropyrido[2,3-b][1,4]oxazine-1-carboxylate (200 mg, 0.30 mmol) in dichloromethane (4 mL) was added TFA (2 mL) and then the mixture was stirred at room temperature for 1 hour. After concentration, the residue was purified by Prep-HPLC (X select CSH OBD Column 30*150 mm, 5 μm; Mobile Phase A: Water (0.1% FA), Mobile Phase B: ACN; Flow rate: 60 mL/min; Gradient: 15% B to 45% B in 7 min) to afford a racemic product. The racemate was separated by chiral HPLC to afford two enantiomers. Relative stereochemistry are as drawn. Absolute stereochemistry was arbitrarily assigned.

Enantiomer 1 (Compound 555a) (17 mg, 0.0337 mmol, 11.3% yield). $R_T$ 1.080 min (CHIRALPAK IE-3, 0.46*5 cm; 3 μm. MTBE (0.1% DEA):EtOH=50:50, 1 mL/min). LCMS (ESI) [M+H]$^P$=468.2, $R_T$ 2.030 min, Method J; $^1$H NMR (300 MHz, DMSO-d$_6$) δ 10.17 (s, 1H), 9.34 (s, 1H), 7.96 (s, 1H), 7.36 (s, 1H), 6.85 (d, J=6.2 Hz, 1H), 4.93-4.73 (m, 1H), 4.37 (s, 2H), 4.03-3.77 (m, 4H), 3.79-3.71 (m, 2H), 3.46-3.17 (m, 3H), 2.43-2.16 (m, 3H), 1.04 (d, J=7.2 Hz, 3H), 0.91 (t, J=7.4 Hz, 3H).

Enantiomer 1 (Compound 555b) (25 mg, 0.0496 mmol, 16.6% yield). $R_T$ 1.735 min (CHIRALPAK IE-3, 0.46*5 cm; 3 μm; MTBE (0.1% DEA): EtOH=50:50, 1 mL/min). LCMS (ESI) [M+H]$^+$=468.2, $R_T$ 2.031 min., Method J. $^1$H NMR (300 MHz, DMSO-d$_6$) δ 10.22 (s, 1H), 9.37 (s, 1H), 7.97 (s, 1H), 7.46 (s, 1H), 6.88 (d, J=6.1 Hz, 1H), 5.20 (bs, 3H), 4.93-4.73 (m, 1H), 4.46 (s, 2H), 4.03-3.84 (m, 2H), 3.79-3.70 (m, 1H), 3.44 (s, 2H), 3.32 (dd, J=8.4, 4.8 Hz, 1H), 2.42-2.22 (m, 3H), 1.04 (d, J=7.2 Hz, 3H), 0.92 (t, J=7.3 Hz, 3H).

Example 264

(3R,4S)-4-Methyltetrahydrofuran-3-yl (8-amino-6-(8-methyl-2,3-dihydro-1H-pyrido[2,3-b][1,4]oxazin-7-yl)isoquinolin-3-yl)carbamate hydrochloride and (3S,4R)-4-Methyltetrahydrofuran-3-yl (8-amino-6-(8-methyl-2,3-dihydro-1H-pyrido[2,3-b][1,4]oxazin-7-yl)isoquinolin-3-yl)carbamate hydrochloride (Compound 556a and Compound 556b)

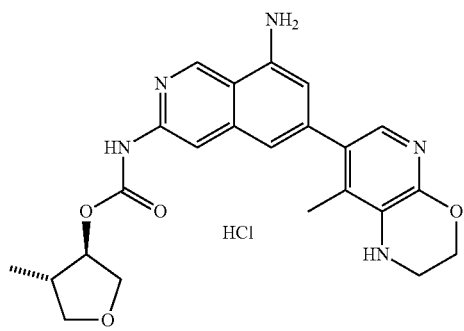

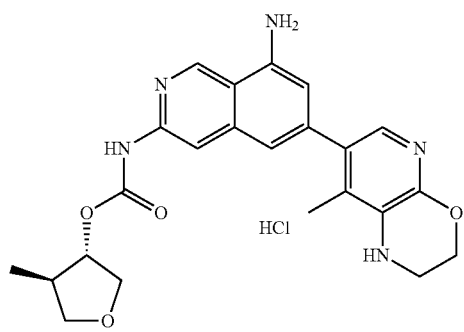

Step 1: tert-Butyl 7-(3-amino-8-chloro-6-isoquinolyl)-8-methyl-2,3-dihydropyrido[2,3-b][1,4]oxazine-1-carboxylate

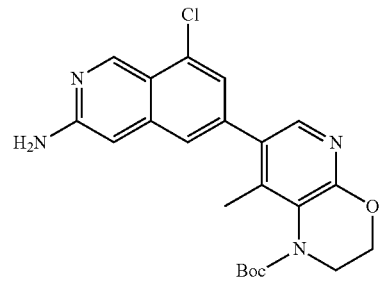 [SMILES: Cc1c(-c2cc(Cl)c3cnc(N)cc3c2)cnc2c1N(C(=O)OC(C)(C)C)CCO2]

Under nitrogen, a solution of 8-chloro-6-iodo-isoquinolin-3-amine (3.5 g, 11.49 mmol), tert-butyl 8-methyl-7-(4,4,5,5-tetramethyl-1,3,2-dioxaborolan-2-yl)-2,3-dihydropyrido[2,3-b][1,4]oxazine-1-carboxylate (4.76 g, 12.64 mmol), Pd(dppf)Cl$_2$ (1.88 g, 2.3 mmol) and Na$_2$CO$_3$ (3.66 g, 34.48 mmol) in 1,4-dioxane (30 mL) and water (3 mL) was stirred for 2 h at 90° C. for 4 hours. The reaction was concentrated under vacuum. The residue was purified by flash chromatography on silica gel eluting with dichloromethane/methanol (20/1) to afford tert-butyl 7-(3-amino-8-chloro-6-isoquinolyl)-8-methyl-2,3-dihydropyrido[2,3-b][1,4]oxazine-1-carboxylate (3 g, 7.02 mmol, 61.1% yield) as a yellow solid. LCMS (ESI) [M+H]$^+$=426.9.

Step 2: tert-Butyl 7-[8-chloro-3-[[(3S,4R)-4-methyltetrahydrofuran-3-yl]oxycarbonylamino]-6-isoquinolyl]-8-methyl-2,3-dihydropyrido[2,3-b][1,4]oxazine-1-carboxylate

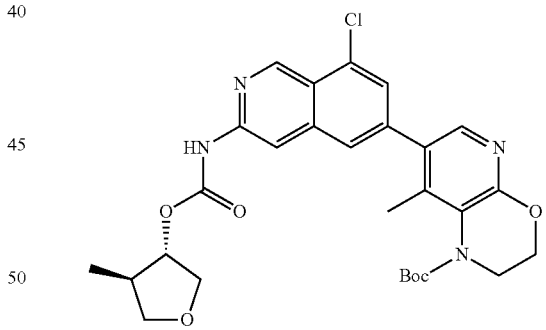

Under nitrogen, to a solution of tert-butyl 7-(3-amino-8-chloro-6-isoquinolyl)-8-methyl-2,3-dihydropyrido[2,3-b][1,4]oxazine-1-carboxylate (400.0 mg, 0.94 mmol), trans-4-methyltetrahydrofuran-3-ol (191.2 mg, 1.87 mmol) and DIEA (605.5 mg, 4.69 mmol) in DCM (20 mL) was added triphosgene (139.0 mg, 0.47 mmol) at 0° C. The resulting solution was stirred at 0° C. for 1 h. The reaction mixture was concentrated under vacuum. The residue was purified by flash chromatography on silica gel eluting with dichloromethane/methanol (20/1) to afford tert-butyl 7-[8-chloro-3-[[(trans)-4-methyltetrahydrofuran-3-yl]oxycarbonylamino]-6-isoquinolyl]-8-methyl-2,3-dihydropyrido[2,3-b][1,4]oxazine-1-carboxylate (530 mg, 0.88 mmol, 93.8% yield) as a yellow solid. LCMS (ESI) [M+H]$^+$=555.0.

Step 3: tert-Butyl 7-[8-(tert-butoxycarbonylamino)-3-[[(3R,4R)-4-methyltetrahydrofuran-3-yl]oxycarbonylamino]-6-isoquinolyl]-8-methyl-2,3-dihydropyrido[2,3-b][1,4]oxazine-1-carboxylate

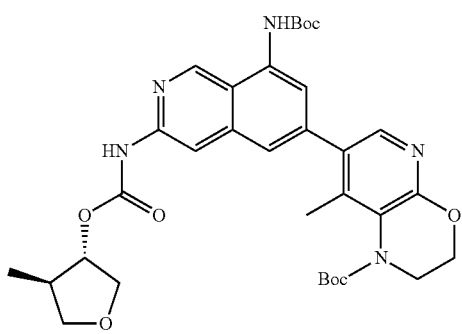 [SMILES: Cc1c(-c2cc(NC(=O)OC(C)(C)C)c3cnc(NC(=O)O[C@@H]4COC[C@H]4C)cc3c2)cnc2c1N(C(=O)OC(C)(C)C)CCO2]

Under nitrogen, a mixture of tert-butyl 7-[8-chloro-3-[[(trans)-4-methyltetrahydrofuran-3-yl]oxycarbonylamino]-6-isoquinolyl]-8-methyl-2,3-dihydropyrido[2,3-b][1,4]oxazine-1-carboxylate (500.0 mg, 0.90 mmol), NH$_2$Boc (5.25 g, 45.04 mmol), Brettphos Pd G3 (163.3 mg, 0.18 mmol) and Cs$_2$CO$_3$ (587.4 mg, 1.8 mmol) in 1,4-dioxane (30 mL) was stirred at 90° C. for 3 hours. The reaction mixture was concentrated under vacuum. The residue was purified by flash chromatography on silica gel eluting with dichloromethane/methanol (20/1) to afford tert-butyl 7-[8-(tert-butoxycarbonylamino)-3-[[(trans)-4-methyltetrahydrofuran-3-yl]oxycarbonylamino]-6-isoquinolyl]-8-methyl-2,3-dihydropyrido[2,3-b][1,4]oxazine-1-carboxylate (400 mg, 0.56 mmol, 62.6% yield) as a yellow solid. LCMS (ESI) [M+H]$^+$=635.7.

Step 4: (3R,4S)-4-Methyltetrahydrofuran-3-yl (8-amino-6-(8-methyl-2,3-dihydro-1H-pyrido[2,3-b][1,4]oxazin-7-yl)isoquinolin-3-yl)carbamate hydrochloride and (3S,4R)-4-Methyltetrahydrofuran-3-yl (8-amino-6-(8-methyl-2,3-dihydro-1H-pyrido[2,3-b][1,4]oxazin-7-yl)isoquinolin-3-yl)carbamate hydrochloride

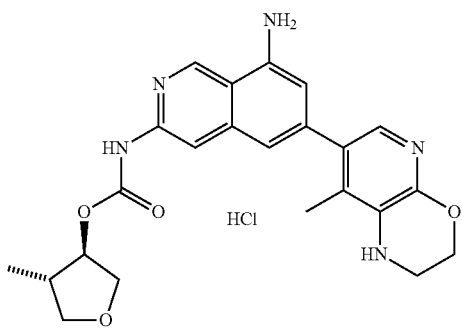

To a solution of tert-butyl 7-[8-(tert-butoxycarbonylamino)-3-[[(trans)-4-methyltetrahydrofuran-3-yl]oxycarbonylamino]-6-isoquinolyl]-8-methyl-2,3-dihydropyrido[2,3-b][1,4]oxazine-1-carboxylate (400.0 mg, 0.63 mmol) in dichloromethane (15 mL) was added TFA (5 mL) at 0° C. Then the solution was stirred at room temperature for 2 hours. The reaction mixture was concentrated under vacuum. The residue was re-dissolved in acetonitrile. The pH of the mixture was adjusted to pH 8 with NaHCO$_3$ aqueous solution. The resulting solution was concentrated under vacuum and purified by Prep-HPLC (Column: X select CSH OBD Column 30*150 mm, 5 μm; Mobile Phase A: Water (0.1% FA), Mobile Phase B: ACN; Flow rate: 60 mL/min; Gradient: 6% B to 36% B in 7 min) to afford a racemic product. The racemic product was separated by chiral HPLC to afford two enantiomers. Then each enantiomer was dissolved in methanol, treated with HCl (0.1 ml, 1 M in dioxane) and concentrated to afford an HCl salt. Relative stereochemistry are as drawn. Absolute stereochemistry was arbitrarily assigned.

Enantiomer 1: Compound 556a (36.7 mg, 0.0764 mmol, 16.2% yield). R$_T$ 1.746 min (CHIRALPAK IC-3 0.46*5 cm; 3 μm; (MTBE (0.1% DEA): EtOH=70:30). LCMS(ESI) [M+H]$^+$=435.5, R$_T$ 1.092 min; Method J. $^1$H NMR (400 MHz, DMSO-d$_6$) δ 10.31 (s, 1H), 9.32 (s, 1H), 7.95 (s, 1H), 7.50 (s, 1H), 6.93 (s, 1H), 6.55 (d, J=1.5 Hz, 1H), 4.86 (dt, J=4.5, 2.1 Hz, 1H), 4.47 (t, J=4.4 Hz, 2H), 4.08-3.92 (m, 2H), 3.78-3.68 (m, 1H), 3.47 (t, J=4.4 Hz, 2H), 3.35 (dd, J=8.5, 4.8 Hz, 1H), 2.43-2.26 (m, 1H), 2.11 (s, 3H), 1.07 (d, J=7.2 Hz, 3H).

Enantiomer 2: Compound 556b (36.2 mg, 0.0759 mmol, 16.1% yield). R$_T$ 1.746 min (CHIRALPAK IC-3 0.46*5 cm; 3 μm; (MTBE (0.1% DEA): EtOH=70:30). LCMS(ESI) [M+H]$^+$=435.5, R$_T$=1.092 min; Method J. $^1$H NMR (400 MHz, DMSO-d$_6$) δ 10.31 (s, 1H), 9.32 (s, 1H), 7.95 (s, 1H), 7.50 (s, 1H), 6.93 (s, 1H), 6.55 (d, J=1.5 Hz, 1H), 4.86 (dt, J=4.5, 2.1 Hz, 1H), 4.47 (t, J=4.4 Hz, 2H), 4.08-3.92 (m, 2H), 3.78-3.68 (m, 1H), 3.47 (t, J=4.4 Hz, 2H), 3.35 (dd, J=8.5, 4.8 Hz, 1H), 2.43-2.26 (m, 1H), 2.11 (s, 3H), 1.07 (d, J=7.2 Hz, 3H).

Example 265

(1s,3s)-3-Cyanocyclobutyl (8-amino-6-(8-methyl-2,3-dihydro-1H-pyrido[2,3-b][1,4]oxazin-7-yl)isoquinolin-3-yl)carbamate hydrochloride (Compound 557a)

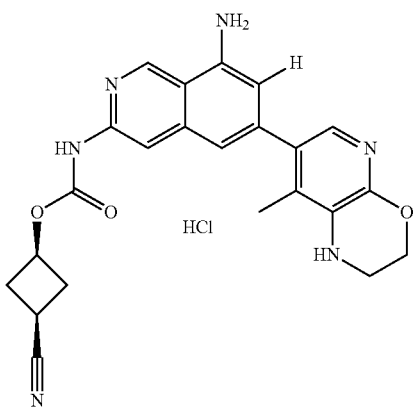 [SMILES: Cc1c(-c2cc(N)c3cnc(NC(=O)O[C@H]4C[C@@H](C#N)C4)cc3c2)cnc2c1NCCO2 ; Cl]

Step 1: tert-Butyl 7-(8-chloro-3-((((1s,3s)-3-cyanocyclobutoxy)carbonyl)amino)isoquinolin-6-yl)-8-methyl-2,3-dihydro-1H-pyrido[2,3-b][1,4]oxazine-1-carboxylate

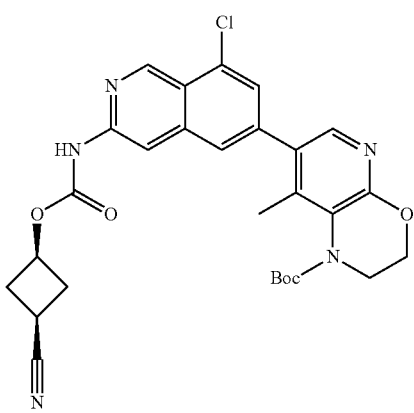 [SMILES: Cc1c(-c2cc(Cl)c3cnc(NC(=O)O[C@H]4C[C@@H](C#N)C4)cc3c2)cnc2c1N(C(=O)OC(C)(C)C)CCO2]

Under nitrogen, to a solution of tert-butyl 7-(3-amino-8-chloro-6-isoquinolyl)-8-methyl-2,3-dihydropyrido[2,3-b][1,4]oxazine-1-carboxylate (300.0 mg, 0.70 mmol), 3-hydroxycyclobutanecarbonitrile (136.5 mg, 1.41 mmol) and DIEA (454.1 mg, 3.51 mmol) in dichloromethane (10 mL) was added triphosgene (104.3 mg, 0.35 mmol) at 0° C. The resulting solution was stirred at 0° C. for 3 hours. The reaction mixture was concentrated under vacuum and purified by flash chromatography on silica gel eluting with dichloromethane/methanol (21/1) to afford tert-butyl 7-(8-chloro-3-((((1s,3s)-3-cyanocyclobutoxy)carbonyl)amino)isoquinolin-6-yl)-8-methyl-2,3-dihydro-1H-pyrido[2,3-b][1,4]oxazine-1-carboxylate (434 mg, 0.62 mmol, 88.7% yield) as a yellow solid. LCMS (ESI) [M+H]$^+$=550.2.

Step 2: tert-Butyl 7-(8-((tert-butoxycarbonyl)amino)-3-((((1s,3s)-3-cyanocyclobutoxy)carbonyl)amino)isoquinolin-6-yl)-8-methyl-2,3-dihydro-1H-pyrido[2,3-b][1,4]oxazine-1-carboxylate

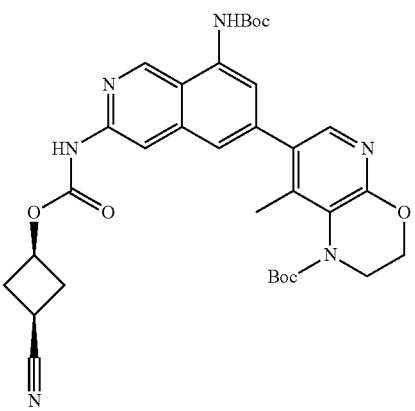 [SMILES: Cc1c(-c2cc(NC(=O)OC(C)(C)C)c3cnc(NC(=O)O[C@H]4C[C@@H](C#N)C4)cc3c2)cnc2c1N(C(=O)OC(C)(C)C)CCO2]

Under nitrogen, a mixture of tert-butyl 7-(8-chloro-3-((((1s,3s)-3-cyanocyclobutoxy)carbonyl)amino)isoquinolin-6-yl)-8-methyl-2,3-dihydro-1H-pyrido[2,3-b][1,4]oxazine-1-carboxylate (420.0 mg, 0.76 mmol), NH$_2$Boc (4.43 mg, 38.18 mmol), Brettphos Pd G3 (138.4 mg, 0.15 mmol) and Cs$_2$CO$_3$ (497.9 mg, 1.53 mmol) in 1,4-dioxane (15 mL) was stirred at 90° C. for 3 hours. The reaction was concentrated under vacuum and purified by flash chromatography on silica gel eluting with dichloromethane/methanol (20/1) to afford tert-butyl 7-(8-((tert-butoxycarbonyl)amino)-3-((((1s,3s)-3-cyanocyclobutoxy)carbonyl)amino)isoquinolin-6-yl)-8-methyl-2,3-dihydro-1H-pyrido[2,3-b][1,4]oxazine-1-carboxylate (400 mg, 0.63 mmol, 83.1% yield) as a yellow solid. LCMS (ESI): [M+H]$^+$=631.3

Step 3: (1s,3s)-3-Cyanocyclobutyl (8-amino-6-(8-methyl-2,3-dihydro-1H-pyrido[2,3-b][1,4]oxazin-7-yl)isoquinolin-3-yl)carbamate hydrochloride (Compound 557a)

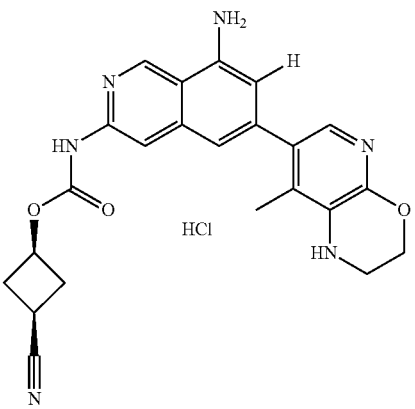 [SMILES: Cc1c(-c2cc(N)c3cnc(NC(=O)O[C@H]4C[C@@H](C#N)C4)cc3c2)cnc2c1NCCO2 ; Cl]

To a solution of tert-butyl 7-[8-(tert-butoxycarbonylamino)-3-[(3-cyanocyclobutoxy)carbonylamino]-6-isoquinolyl]-8-methyl-2,3-dihydropyrido[2,3-b][1,4]oxazine-1-carboxylate (390 mg, 0.62 mmol) in dichloromethane (10 mL) was added TFA (3 mL) at 0° C. Then the solution was stirred at room temperature for 2.5 hours. The reaction was concentrated under vacuum. The residue was diluted with acetonitrile and pH adjusted to 8 with NaHCO₃ aqueous solution. The resulting mixture was concentrated under vacuum and purified by Prep-HPLC (Column: X Bridge Prep OBD C18 Column 30×150 mm, 5 μm; Mobile Phase A: Water (10 mmol/L NH₄HCO₃), Mobile Phase B: ACN; Flow rate: 60 mL/min; Gradient: 20% B to 43% B in 7 min) to afford (1s,3s)-3-cyanocyclobutyl (8-amino-6-(8-methyl-2,3-dihydro-1H-pyrido[2,3-b][1,4]oxazin-7-yl)isoquinolin-3-yl) carbamate. Then, the product was dissolved in methanol and treated with HCl (0.1 ml, 1 M in dioxane) and concentrated to afford (3-cyanocyclobutyl) N-[8-amino-6-(8-methyl-2,3-dihydro-1H-pyrido[2,3-b][1,4]oxazin-7-yl)-3-isoquinolyl] carbamate hydrochloride (33.7 mg, 0.072 mmol, 22.6% yield) as an orange solid. LCMS (ESI) [M+H]⁺=431.2, $R_T$ 1.067 min, Method J. ¹H NMR (400 MHz, DMSO-d₆) δ 10.28 (s, 1H), 9.29 (s, 1H), 7.92 (s, 1H), 7.46 (s, 1H), 6.88 (d, J=1.4 Hz, 1H), 6.51 (d, J=1.5 Hz, 1H), 4.95 (p, J=7.5 Hz, 1H), 4.43 (t, J=4.4 Hz, 2H), 3.45 (t, J=4.4 Hz, 2H), 3.10-3.14 (m, 1H), 2.78-2.85 (m, 2H), 2.46-2.30 (m, 2H), 2.09 (s, 3H).

Example 266

(3R,4S)-4-Methyltetrahydrofuran-3-yl (8-amino-7-fluoro-6-(8-methyl-2-oxo-2,3-dihydro-1H-pyrido[2,3-b][1,4]oxazin-7-yl)isoquinolin-3-yl)carbamate hydrochloride and (3S,4R)-4-Methyltetrahydrofuran-3-yl (8-amino-7-fluoro-6-(8-methyl-2-oxo-2,3-dihydro-1H-pyrido[2,3-b][1,4]oxazin-7-yl)isoquinolin-3-yl)carbamate hydrochloride (Compound 558a and Compound 558b)

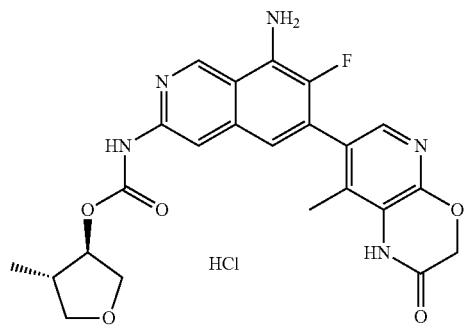

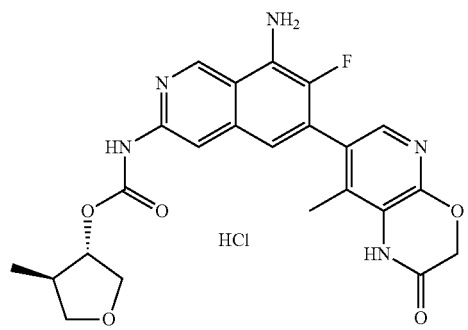

Step 1: 8-Methyl-7-(4,4,5,5-tetramethyl-1,3,2-dioxaborolan-2-yl)-1H-pyrido[2,3-b][1,4]oxazin-2(3H)-one

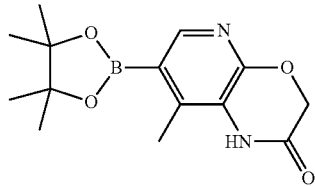 [SMILES: Cc1c(B2OC(C)(C)C(C)(C)O2)cnc2c1NC(=O)CO2]

A mixture of 7-bromo-8-methyl-1H-pyrido[2,3-b][1,4]oxazin-2-one (3 g, 12.34 mmol), bis(pinacolato)diboron (31.34 g, 123.43 mmol), [1,1'-bis(diphenylphosphino)ferrocene]dichloropalladium(II) (1.86 g, 2.51 mmol) and potassium acetate (2.33 g, 37.29 mmol) in 1,4-dioxane (60 mL) was stirred at 90° C. for 3 hours. The reaction mixture was concentrated under vacuum and purified by flash chromatography on silica gel eluting with petroleum ether/ethyl acetate (70%) to afford 8-methyl-7-(4,4,5,5-tetramethyl-1,3,2-dioxaborolan-2-yl)-1H-pyrido[2,3-b][1,4]oxazin-2-one (1778 mg, 6.128 mmol, 49.7% yield) as a brown solid. LCMS (ESI) [M+H]⁺=291.2.

Step 2: 7-(3-Amino-8-chloro-7-fluoroisoquinolin-6-yl)-8-methyl-1H-pyrido[2,3-b][1,4]oxazin-2(3H)-one

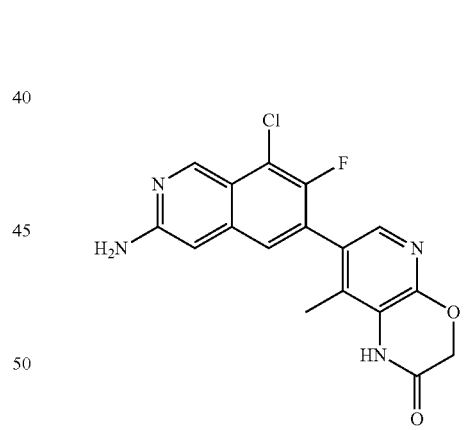

Under nitrogen, a mixture of 8-chloro-7-fluoro-6-iodo-isoquinolin-3-amine (2955.9 mg, 9.17 mmol), 8-methyl-7-(4,4,5,5-tetramethyl-1,3,2-dioxaborolan-2-yl)-1H-pyrido[2,3-b][1,4]oxazin-2-one (1770 mg, 6.1 mmol), [1,1'-bis(diphenylphosphino)ferrocene]dichloropalladium(II) (920.4 mg, 1.24 mmol) and K₂CO₃ (2531.1 mg, 18.31 mmol) in 1,4-dioxane (20 mL) and water (2 mL) was stirred at 70° C. for 3 hours. The reaction mixture was concentrated under vacuum and purified by flash chromatography on silica gel eluting with dichloromethane/methanol (10:1) to afford 7-(3-amino-8-chloro-7-fluoro-6-isoquinolyl)-8-methyl-1H-pyrido[2,3-b][1,4]oxazin-2-one (450 mg, 1.254 mmol, 20.6% yield) as a yellow solid. LCMS (ESI) [M+H]⁺=359.1.

Step 3: (±)-trans-4-Methyltetrahydrofuran-3-yl (8-chloro-7-fluoro-6-(8-methyl-2-oxo-2,3-dihydro-1H-pyrido[2,3-b][1,4]oxazin-7-yl)isoquinolin-3-yl) carbamate

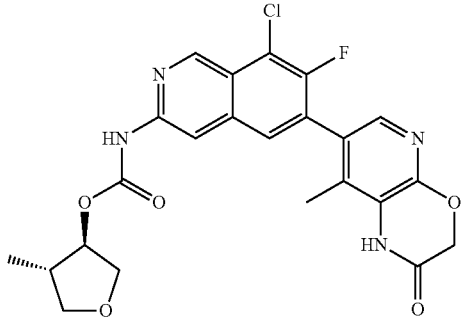 [SMILES: Cc1c(-c2cc3cc(NC(=O)O[C@H]4COC[C@@H]4C)ncc3c(Cl)c2F)cnc2c1NC(=O)CO2]

To a solution of 7-(3-amino-8-chloro-7-fluoro-6-isoquinolyl)-8-methyl-1H-pyrido[2,3-b][1,4]oxazin-2-one (300 mg, 0.84 mmol) and 4-methyltetrahydrofuran-3-ol (171 mg, 1.67 mmol) in dichloromethane (30 mL) was added N,N-diisopropylethylamine (0.73 mL, 4.2 mmol). The mixture was stirred at 0° C. for 5 min. Triphosgene (174 mg, 0.59 mmol) was then added and the mixture was stirred at 0° C. for 1 hour. The reaction was quenched with water and concentrated under vacuum. The residue was purified by reverse phase chromatography (acetonitrile 5-55/0.1% NH₄HCO₃ in water) to afford to afford (±)-trans-4-methyltetrahydrofuran-3-yl (8-chloro-7-fluoro-6-(8-methyl-2-oxo-2,3-dihydro-1H-pyrido[2,3-b][1,4]oxazin-7-yl)isoquinolin-3-yl)carbamate (100 mg, 0.205 mmol, 24.6% yield) as a yellow solid. LCMS (ESI) [M+H]⁺=487.2.

Step 4: tert-Butyl ((3R,4S)-4-methyltetrahydrofuran-3-yl) (7-fluoro-6-(8-methyl-2-oxo-2,3-dihydro-1H-pyrido[2,3-b][1,4]oxazin-7-yl)isoquinoline-3,8-diyl)dicarbamate and tert-Butyl ((3S,4R)-4-methyltetrahydrofuran-3-yl) (7-fluoro-6-(8-methyl-2-oxo-2,3-dihydro-1H-pyrido[2,3-b][1,4]oxazin-7-yl)isoquinoline-3,8-diyl)dicarbamate

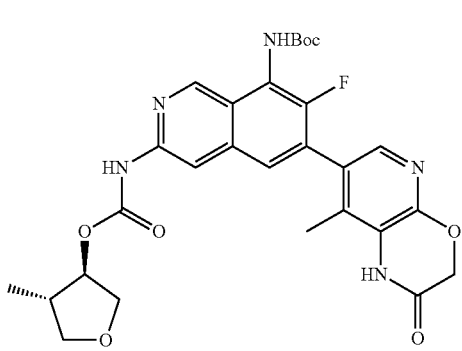

-continued

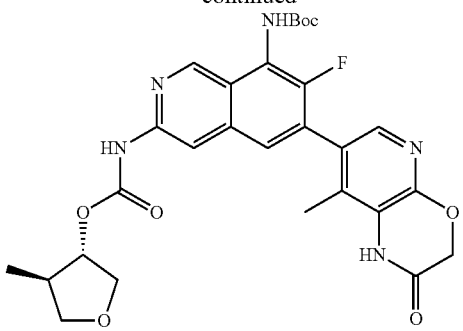

To a mixture of (±)-trans-4-methyltetrahydrofuran-3-yl (8-chloro-7-fluoro-6-(8-methyl-2-oxo-2,3-dihydro-1H-pyrido[2,3-b][1,4]oxazin-7-yl)isoquinolin-3-yl)carbamate (268 mg, 0.55 mmol) and tert-butyl carbamate (1913 mg, 16.33 mmol) in 1,4-dioxane (5 mL) was added Brettphos Pd G3 (50 mg, 0.060 mmol), potassium carbonate (230 mg, 1.67 mmol). The mixture was stirred at 90° C. for 2 hours. After concentration, the residue was purified by flash chromatography on silica gel eluting with dichloromethane/methanol (10/1) to afford (4-methyltetrahydrofuran-3-yl) N-[8-(tert-butoxycarbonylamino)-7-fluoro-6-(8-methyl-2-oxo-1H-pyrido[2,3-b][1,4]oxazin-7-yl)-3-isoquinolyl]carbamate (200 mg, 0.352 mmol, 64% yield) as a yellow solid. Then the mixture of the enantiomers was separated by chiral-HPLC (CHIRALPAK IC, 2*25 cm, 5 μm; Mobile Phase A: MTBE (10 mm NH₃), Mobile Phase B: EtOH; Flow rate: 20 mL/min; Gradient: 0% B to 20% B in 15 min; 220/254 nm; $R_T$ 1:7.454 min; $R_T$ 2:12.621 min) to afford the two enantiomers (enantiomer 1: 41 mg, 0.07 mmol; enantiomer 2: 40 mg, 0.07 mmol) as yellow solids.

Step 5: (3R,4S)-4-Methyltetrahydrofuran-3-yl (8-amino-7-fluoro-6-(8-methyl-2-oxo-2,3-dihydro-1H-pyrido[2,3-b][1,4]oxazin-7-yl)isoquinolin-3-yl) carbamate hydrochloride and (3S,4R)-4-Methyltetrahydrofuran-3-yl (8-amino-7-fluoro-6-(8-methyl-2-oxo-2,3-dihydro-1H-pyrido[2,3-b][1,4]oxazin-7-yl) isoquinolin-3-yl)carbamate hydrochloride

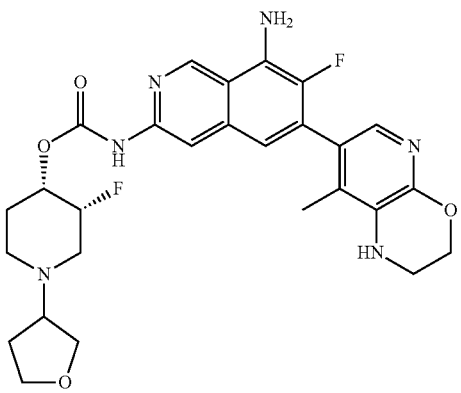

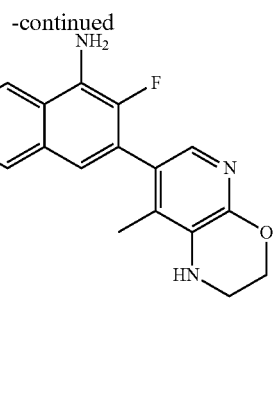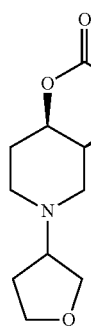

To a solution of [(3R,4S)-4-methyltetrahydrofuran-3-yl] N-[8-(tert-butoxycarbonylamino)-7-fluoro-6-(8-methyl-2-oxo-1H-pyrido[2,3-b][1,4]oxazin-7-yl)-3-isoquinolyl]carbamate (50 mg, 0.090 mmol) in dichloromethane (1 mL) was added TFA (1 mL) and the mixture was stirred at room temperature for 1 hour. After concentration the residue was purified by Prep-HPLC (X select CSH OBD Column 30*150 mm 5 μm; Mobile Phase A: Water (0.1% FA), Mobile Phase B: ACN; Flow rate: 60 mL/min; Gradient: 18% B to 43% B in 7 min). The product was then dissolved in MeOH. 1 equiv. of HCl (4M HCl in 1,4-dioxane) was added. The mixture was then concentrated to give [(3R,4S)-4-methyltetrahydrofuran-3-yl]N-[8-amino-7-fluoro-6-(8-methyl-2-oxo-1H-pyrido[2,3-b][1,4]oxazin-7-yl)-3-isoquinolyl]carbamate hydrochloride (Compound 558a) (24.9 mg, 0.0494 mmol, 18.7% yield) as an orange solid. Relative stereochemistry are as drawn. Absolute stereochemistry was arbitrarily assigned. $R_T$ 1.354 min (CHIRALPAK IE-3 0.46*5 cm; 3 μm. Mobile phase: MTBE (0.1% DEA): EtOH=80:20, 1 ml/min). LCMS (ESI) [M+H]$^+$=468.2. $R_T$ 1.282 min, Method J; $^1$H NMR (300 MHz, DMSO-d$_6$) δ 10.57 (s, 1H), 10.24 (s, 1H), 9.39 (s, 1H), 7.98 (s, 1H), 7.74 (s, 1H), 6.92-6.90 (dd, 1H), 5.10 (brs, 3H), 4.91-4.85 (m, 1H), 4.85-4.78 (m, 2H), 4.03-3.95 (m, 2H), 3.80-3.75 (m, 1H), 3.35-3.30 (m, 1H), 2.45-2.21 (m, 1H), 2.12-2.07 (m, 3H), 1.09-1.03 (s, 3H).

To a solution of [(3S,4R)-4-methyltetrahydrofuran-3-yl] N-[8-(tert-butoxycarbonylamino)-7-fluoro-6-(8-methyl-2-oxo-1H-pyrido[2,3-b][1,4]oxazin-7-yl)-3-isoquinolyl]carbamate (50.0 mg, 0.090 mmol) in dichloromethane (1 mL) was added TFA (1 mL) and the mixture was stirred at room temperature for 1 hour. After concentration, the residue was purified by Prep-HPLC (X select CSH OBD Column 30*150 mm 5 μm, n; Mobile Phase A: Water (0.1% FA), Mobile Phase B:ACN; Flow rate: 60 mL/min; Gradient: 18% B to 43% B in 7 min). The product was then dissolved in MeOH. 1 equiv. of HCl (4M HCl in 1,4-dioxane) was added. The mixture was then concentrated to give[(3S,4R)-4-methyltetrahydrofuran-3-yl]N-[8-amino-7-fluoro-6-(8-methyl-2-oxo-1H-pyrido[2,3-b][1,4]oxazin-7-yl)-3-isoquinolyl]carbamate hydrochloride (Compound 558b) (21.2 mg, 0.0421 mmol, 15.9% yield) as an orange solid. Relative stereochemistry are as drawn. Absolute stereochemistry was arbitrarily assigned. RT 2.020 min (CHIRALPAK IE-3, 0.46*5 cm; 3 μm. Mobile phase: MTBE (0.1% DEA): EtOH=80:20, 1 ml/min). LCMS (ESI) [M+H]$^+$=468.2. $R_T$ 1.282 min, Method J; $^1$H NMR (300 MHz, DMSO-d$_6$) δ 10.57 (s, 1H), 10.24 (s, 1H), 9.39 (s, 1H), 7.98 (s, 1H), 7.74 (s, 1H), 6.92-6.90 (dd, 1H), 5.10 (brs, 3H), 4.91-4.85 (m, 1H), 4.85-4.78 (m, 2H), 4.03-3.95 (m, 2H), 3.80-3.75 (m, 1H), 3.35-3.30 (m, 1H), 2.45-2.21 (m, 1H), 2.12-2.07 (m, 3H), 1.09-1.03 (s, 3H).

Example 267

(1R,2S)-2-Methylcyclobutyl (8-amino-7-fluoro-6-(8-methyl-2,3-dihydro-1H-pyrido[2,3-b][1,4]oxazin-7-yl)isoquinolin-3-yl)carbamate, (1S,2R)-2-Methylcyclobutyl (8-amino-7-fluoro-6-(8-methyl-2,3-dihydro-1H-pyrido[2,3-b][1,4]oxazin-7-yl) isoquinolin-3-yl)carbamate, (1R,2R)-2-Methyl cyclobutyl (8-amino-7-fluoro-6-(8-methyl-2,3-dihydro-1H-pyrido[2,3-b][1,4]oxazin-7-yl)isoquinolin-3-yl)carbamate and (1S,2S)-2-Methyl cyclobutyl (8-amino-7-fluoro-6-(8-methyl-2,3-dihydro-1H-pyrido[2,3-b][1,4]oxazin-7-yl)isoquinolin-3-yl)carbamate (Compound 559a, Compound 559b, Compound 559c, and Compound 559d)

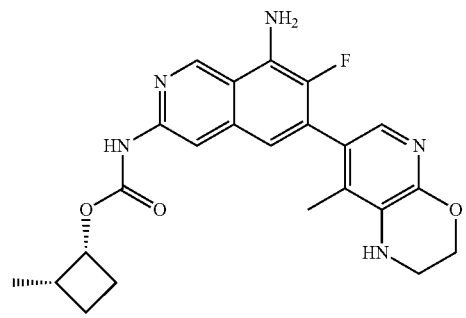

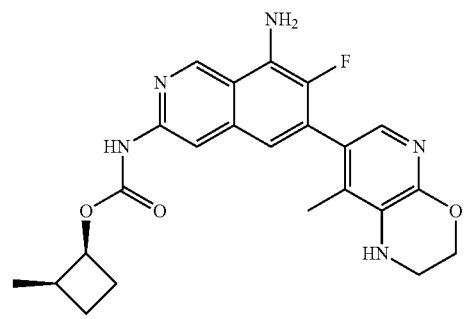

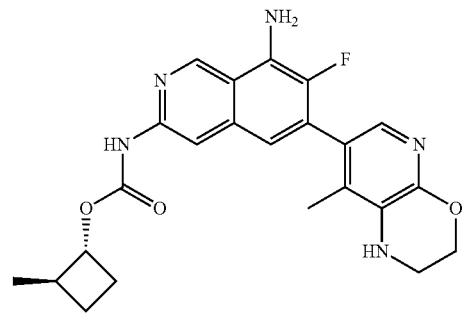

-continued

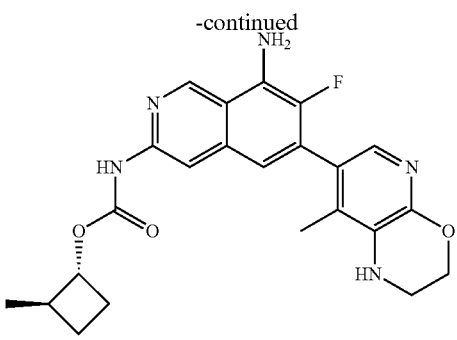

Step 1: tert-Butyl 7-(8-((tert-butoxycarbonyl)amino)-7-fluoro-3-(((2-methylcyclobutoxy)carbonyl)amino)isoquinolin-6-yl)-8-methyl-2,3-dihydro-1H-pyrido[2,3-b][1,4]oxazine-1-carboxylate

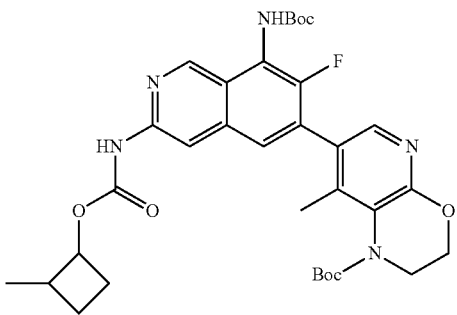 [SMILES: Cc1c(-c2cc3cc(NC(=O)OC4CCC4C)ncc3c(NC(=O)OC(C)(C)C)c2F)cnc2c1N(C(=O)OC(C)(C)C)CCO2]

Under nitrogen, to a solution of tert-butyl 7-[8-(tert-butoxycarbonylamino)-7-fluoro-3-(phenoxycarbonylamino)-6-isoquinolyl]-8-methyl-2,3-dihydropyrido[2,3-b][1,4]oxazine-1-carboxylate (600.0 mg, 0.93 mmol) and DMAP (120.0 mg, 0.98 mmol) in dichloromethane (10 mL) was added 2-methylcyclobutanol (240.0 mg, 2.79 mmol) at room temperature. The solution was stirred for 24 hours at 60° C. The reaction was concentrated under vacuum. The residue was purified by flash chromatography on silica gel eluting with dichloromethane/methanol (94/6) to afford tert-butyl 7-[8-(tert-butoxycarbonylamino)-7-fluoro-3-[(2-methylcyclobutoxy)carbonylamino]-6-isoquinolyl]-8-methyl-2,3-dihydropyrido[2,3-b][1,4]oxazine-1-carboxylate (500 mg, 0.78 mmol, 84% yield) as a pale yellow solid. LC/MS (ESI) [M+H]$^+$=638.3.

Step 2: (1R,2S)-2-Methylcyclobutyl (8-amino-7-fluoro-6-(8-methyl-2,3-dihydro-1H-pyrido[2,3-b][1,4]oxazin-7-yl)isoquinolin-3-yl)carbamate, (1S,2R)-2-Methyl cyclobutyl (8-amino-7-fluoro-6-(8-methyl-2,3-dihydro-1H-pyrido[2,3-b][1,4]oxazin-7-yl)isoquinolin-3-yl)carbamate, (1R,2R)-2-Methylcyclobutyl (8-amino-7-fluoro-6-(8-methyl-2,3-dihydro-1H-pyrido[2,3-b][1,4]oxazin-7-yl)isoquinolin-3-yl)carbamate and (1S,2S)-2-Methylcyclobutyl (8-amino-7-fluoro-6-(8-methyl-2,3-dihydro-1H-pyrido[2,3-b][1,4]oxazin-7-yl)isoquinolin-3-yl)carbamate A solution of tert-butyl 7-[8-(tert-butoxycarbonylamino)-7-fluoro-3-[(2-methylcyclobutoxy)carbonylamino]-6-isoquinolyl]-8-methyl-2,3-dihydropyrido[2,3-b][1,4]oxazine-1-carboxylate (500.0 mg, 0.78 mmol) and TFA (2.0 mL) in dichloromethane (10 mL) was stirred at 25° C. for 2 hours. After concentration, the residue was purified by Prep-HPLC (Column: Xselect CSH OBD Column 30*150 mm, 5 μm; Water (0.1% FA): ACN=25% B to 55 B % in 7 min; 60 mL/min) to afford 2-methylcyclobutyl (8-amino-7-fluoro-6-(8-methyl-2,3-dihydro-1H-pyrido[2,3-b][1,4]oxazin-7-yl)isoquinolin-3-yl)carbamate. The racemic product was separated by chiral-HPLC to afford four isomers. Relative stereochemistry are as drawn. Absolute stereochemistry was arbitrarily assigned.

Isomer 1 (Compound 559a): $R_T$ 2.721 min (CHIRALPAK AS-H, 4.6*100 cm, 3 μm; CO$_2$/MeOH (0.1% DEA)=10%-50% in 4 min; 4 mL/min) to afford (1R,2S)-2-methylcyclobutyl (8-amino-7-fluoro-6-(8-methyl-2,3-dihydro-1H-pyrido[2,3-b][1,4]oxazin-7-yl)isoquinolin-3-yl)carbamate (58.7 mg, 0.1342 mmol, 17.1% yield) as an orange solid, LCMS (ESI): [M+H]$^+$=438.2, $R_T$ 1.428 min., Method K; $^1$H NMR (300 MHz, DMSO-d$_6$) δ 10.13 (s, 1H), 9.37 (s, 1H), 7.96 (s, 1H), 7.50 (s, 1H), 6.87 (d, J=6.1 Hz, 1H), 5.20-5.80 (m, 3H), 4.98 (q, J=7.5 Hz, 1H), 4.44 (d, J=4.7 Hz, 2H), 3.44 (s, 2H), 2.74-2.61 (m, 1H), 2.35-2.14 (m, 2H), 1.98 (s, 3H), 1.91-1.76 (m, 1H), 1.40 (t, J=10.5 Hz, 1H), 1.06 (d, J=7.2 Hz, 3H).

Isomer 2 (Compound 559b): $R_T$ 2.951 min (CHIRALPAK AS-H, 4.6*100 cm, 3 μm; CO$_2$/MeOH (0.1% DEA)=10%-50% in 4 min; 4 mL/min) to afford [(1S,2S)-2-methylcyclobutyl]N-[8-amino-7-fluoro-6-(8-methyl-2,3-dihydro-1H-pyrido[2,3-b][1,4]oxazin-7-yl)-3-isoquinolyl]carbamate (62.5 mg, 0.1429 mmol, 18.2% yield) as an orange solid, LCMS (ESI) [M+H]$^+$=438.2; $R_T$ 1.428 min., Method K; $^1$H NMR (300 MHz, DMSO-d$_6$) δ 10.13 (s, 1H), 9.37 (s, 1H), 7.96 (s, 1H), 7.50 (s, 1H), 6.87 (d, J=6.1 Hz, 1H), 5.20-5.80 (m, 3H), 4.98 (q, J=7.5 Hz, 1H), 4.44 (d, J=4.7 Hz, 2H), 3.44 (s, 2H), 2.74-2.61 (m, 1H), 2.35-2.14 (m, 2H), 1.98 (s, 3H), 1.91-1.76 (m, 1H), 1.40 (t, J=10.5 Hz, 1H), 1.06 (d, J=7.2 Hz, 3H).

Isomer 3 (Compound 559c): $R_T$ 3.001 min, (CHIRALPAK AS-H, 4.6*100 cm, 3 μm; CO$_2$/MeOH (0.1% DEA)= 10%-50% in 4 min; 4 mL/min) to afford [(1R,2S)-2-methylcyclobutyl]N-[8-amino-7-fluoro-6-(8-methyl-2,3-dihydro-1H-pyrido[2,3-b][1,4]oxazin-7-yl)-3-isoquinolyl]carbamate (25.7 mg, 0.0587 mmol, 7.5% yield) as an orange solid LCMS (ESI) [M+H]$^+$=438.2, $R_T$ 1.453 min., Method K; $^1$H NMR (300 MHz, DMSO-d$_6$) δ10.13 (s, 1H), 9.38 (s, 1H), 7.98 (s, 1H), 7.52 (s, 1H), 6.92 (s, 1H), 4.60-4.57 (m, 1H), 4.55-4.46 (m, 2H), 3.46-3.50 (m, 2H), 2.74-2.52 (m, 1H), 2.51-2.19 (m, 1H), 2.01-1.83 (m, 5H), 1.27-1.12 (m, 4H).

Isomer 4 (Compound 559d): $R_T$:3.336 min, (CHIRALPAK AS-H, 4.6*100 cm, 3 μm; CO$_2$/MEOH (0.1% DEA)= 10%-50% in 4 min; 4 mL/min) to afford [(1S,2R)-2-methylcyclobutyl]N-[8-amino-7-fluoro-6-(8-methyl-2,3-dihydro-1H-pyrido[2,3-b][1,4]oxazin-7-yl)-3-isoquinolyl]carbamate (21.9 mg, 0.050 1 mmol, 6.4% yield) as an orange solid. LCMS (ESI) [M+H]$^+$=438.2, $R_T$ 1.453 min., Method K; $^1$H NMR (300 MHz, DMSO-d$_6$) δ10.13 (s, 1H), 9.38 (s, 1H), 7.98 (s, 1H), 7.52 (s, 1H), 6.92 (s, 1H), 4.60-4.57 (m, 1H), 4.55-4.46 (m, 2H), 3.46-3.50 (m, 2H), 2.74-2.52 (m, 1H), 2.51-2.19 (m, 1H), 2.01-1.83 (m, 5H), 1.27-1.12 (m, 4H).

Example 268

(3R,4S)-4-Methyltetrahydrofuran-3-yl (8-amino-7-cyano-6-(8-methyl-2,3-dihydro-1H-pyrido[2,3-b][1,4]oxazin-7-yl)isoquinolin-3-yl)carbamate (Compound 561a)

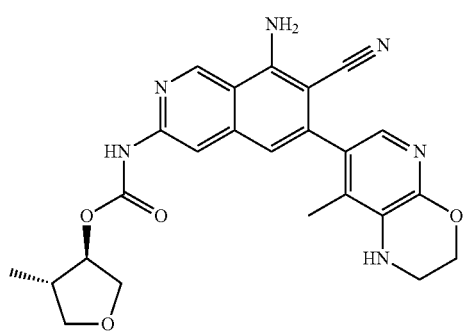 [SMILES: Cc1c(-c2cc3cc(NC(=O)O[C@H]4COC[C@@H]4C)ncc3c(N)c2C#N)cnc2c1NCCO2]

Step 1: tert-butyl N-[5-(3-amino-8-chloro-7-fluoro-6-isoquinolyl)-4-methyl-3-pyridyl]-N-methyl-carbamate

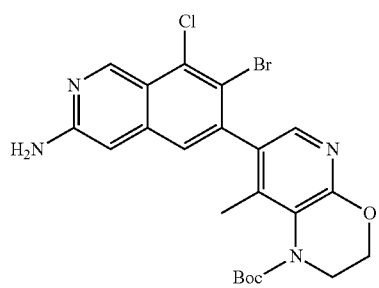 [SMILES: Cc1c(-c2cc3cc(N)ncc3c(Cl)c2Br)cnc2c1N(C(=O)OC(C)(C)C)CCO2]

Under nitrogen, a mixture of tert-butyl N-methyl-N-[4-methyl-5-(4,4,5,5-tetramethyl-1,3,2-dioxaborolan-2-yl)-3-pyridyl]carbamate (13 g, 37.33 mmol), 8-chloro-7-fluoro-6-iodo-isoquinolin-3-amine (10 g, 31.01 mmol), Pd(dppf)Cl$_2$ (4.5 g, 6.16 mmol) and K$_2$CO$_3$ (12 g, 86.96 mmol) in 1,4-dioxane (150 mL) and water (15 mL) was stirred at 70° C. for 2 hours. After filtration, the filtrate was concentrated under vacuum and purified by flash chromatography on silica gel eluting with petroleum ether/ethyl acetate (10/90) to afford tert-butyl N-[5-(3-amino-8-chloro-7-fluoro-6-isoquinolyl)-4-methyl-3-pyridyl]-N-methyl-carbamate (9 g, 21.589 mmol, 57.8% yield) as a yellow solid. LCMS (ESI) [M+H]$^+$=505.

Step 2: tert-Butyl 7-(3-amino-8-chloro-7-cyano-6-isoquinolyl)-8-methyl-2,3-dihydropyrido[2,3-b][1,4]oxazine-1-carboxylate

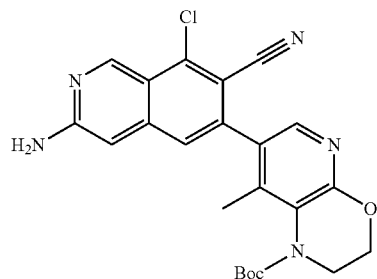 [SMILES: Cc1c(-c2cc3cc(N)ncc3c(Cl)c2C#N)cnc2c1N(C(=O)OC(C)(C)C)CCO2]

Under nitrogen, a mixture of tert-butyl 7-(3-amino-7-bromo-8-chloro-6-isoquinolyl)-8-methyl-2,3-dihydropyrido[2,3-b][1,4]oxazine-1-carboxylate (200.0 mg, 0.40 mmol), Pd(PPh$_3$)$_4$ (92.0 mg, 0.060 mmol) and Zn(CN)$_2$ (25.0 mg, 0.22 mmol) in N,N-dimethylacetamide (5 mL) was stirred at 100° C. for 16 hours. The reaction mixture was concentrated under vacuum. The resulting residue was purified by reverse phase chromatography with water/ACN (47/53) to afford tert-butyl 7-(3-amino-8-chloro-7-cyano-6-isoquinolyl)-8-methyl-2,3-dihydropyrido[2,3-b][1,4]oxazine-1-carboxylate (100 mg, 0.221 mmol, 56% yield) as a yellow solid. LCMS (ESI) [M+H]$^+$=452.

Step 3: tert-Butyl 7-(8-chloro-7-cyano-3-(((((3R,4S)-4-methyltetrahydrofuran-3-yl)oxy)carbonyl)amino)isoquinolin-6-yl)-8-methyl-2,3-dihydro-1H-pyrido[2,3-b][1,4]oxazine-1-carboxylate

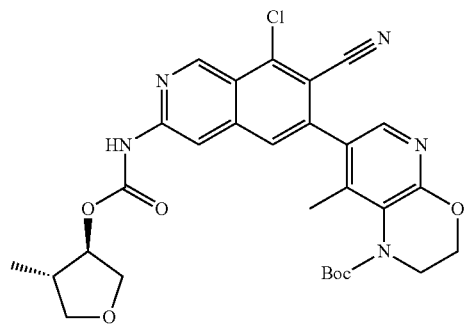 [SMILES: Cc1c(-c2cc3cc(NC(=O)O[C@H]4COC[C@@H]4C)ncc3c(Cl)c2C#N)cnc2c1N(C(=O)OC(C)(C)C)CCO2]

A solution of tert-butyl 7-(3-amino-8-chloro-7-cyano-6-isoquinolyl)-8-methyl-2,3-dihydropyrido[2,3-b][1,4]oxazine-1-carboxylate (80.0 mg, 0.18 mmol), (3S,4R)-4-methyltetrahydrofuran-3-ol (36.0 mg, 0.35 mmol) and DIEA (114.0 mg, 0.88 mmol) in dichloromethane (1 mL) was stirred at 0° C. for 2 hours. The reaction mixture was concentrated under vacuum and purified by flash chromatography on silica gel eluting with petroleum ether/ethyl acetate (60/40) to afford (87.2 mg, 85% yield) as a yellow solid. LCMS (ESI) [M+H]$^+$=580.

Step 4: tert-Butyl 7-(7-cyano-8-((diphenylmethylene)amino)-3-(((((3R,4S)-4-methyltetrahydrofuran-3-yl)oxy)carbonyl)amino)isoquinolin-6-yl)-8-methyl-2,3-dihydro-1H-pyrido[2,3-b][1,4]oxazine-1-carboxylate

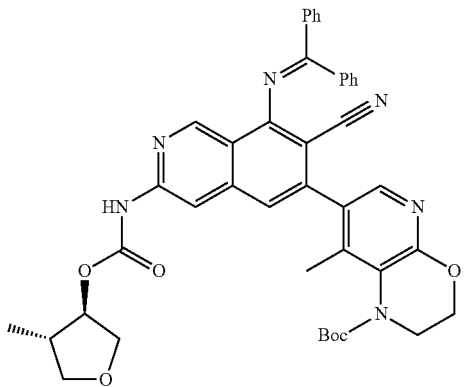 [SMILES: Cc1c(-c2cc3cc(NC(=O)O[C@H]4COC[C@@H]4C)ncc3c(N=C(c3ccccc3)c3ccccc3)c2C#N)cnc2c1N(C(=O)OC(C)(C)C)CCO2]

Under nitrogen, a mixture of tert-butyl 7-[8-chloro-7-cyano-3-[[(3R,4S)-4-methyltetrahydrofuran-3-yl]oxycarbonyl amino]-6-isoquinolyl]-8-methyl-2,3-dihydropyrido[2,3-b][1,4]oxazine-1-carboxylate (70.0 mg, 0.12 mmol), Pd(OAc)$_2$ (6.0 mg, 0.030 mmol), Xantphos (28.0 mg, 0.050 mmol), Cs$_2$CO$_3$ (118.0 mg, 0.36 mmol) and benzophenone imine (66.0 mg, 0.36 mmol) in N,N-dimethylformamide (1 mL) and toluene (1 mL) was stirred for 3 hours at 100° C. After filtration, the filtrate was concentrated under vacuum. The residue was purified by reverse phase chromatography with water/ACN (35/65) to afford tert-butyl 7-(7-cyano-8-((diphenylmethylene)amino)-3-(((((3R,4S)-4-methyltetrahydrofuran-3-yl)oxy)carbonyl)amino)isoquinolin-6-yl)-8-methyl-2,3-dihydro-1H-pyrido[2,3-b][1,4]oxazine-1-carboxylate (50 mg, 0.0701 mmol, 58.1% yield) as a yellow solid. LCMS (ESI) [M+H]$^+$=712.

Step 5: (3R,4S)-4-Methyltetrahydrofuran-3-yl (8-amino-7-cyano-6-(8-methyl-2,3-dihydro-1H-pyrido[2,3-b][1,4]oxazin-7-yl)isoquinolin-3-yl)carbamate (Compound 561a)

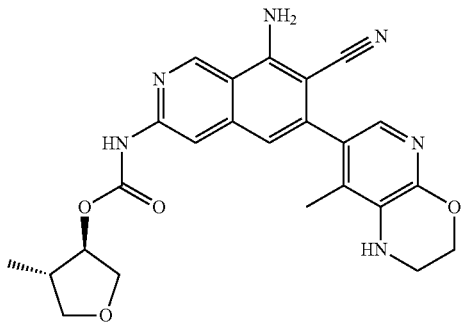 [SMILES: Cc1c(-c2cc3cc(NC(=O)O[C@H]4COC[C@@H]4C)ncc3c(N)c2C#N)cnc2c1NCCO2]

A solution of tert-butyl tert-butyl 7-(7-cyano-8-((diphenylmethylene)amino)-3-(((((3S,4R)-4-methyltetrahydrofuran-3-yl)oxy)carbonyl)amino)isoquinolin-6-yl)-8-methyl-2,3-dihydro-1H-pyrido[2,3-b][1,4]oxazine-1-carboxylate (40.0 mg, 0.060 mmol) in dichloromethane (0.5 mL) and TFA (1 mL) was stirred at room temperature for 2 hours. The reaction mixture was concentrated under vacuum. The resulting residue was purified by reverse phase chromatography with water/ACN (46/54) to afford (3R,4S)-4-methyltetrahydrofuran-3-yl (8-amino-7-cyano-6-(8-methyl-2,3-dihydro-1H-pyrido[2,3-b][1,4]oxazin-7-yl)isoquinolin-3-yl) carbamate (40.0 mg, 0.060 mmol) as a yellow solid. LCMS (ESI) [M+H]$^+$=461.2, R$_T$ 1.844, Method K $^1$H NMR (300 MHz, DMSO-d$_6$) δ 10.40 (s, 1H), 9.44 (s, 1H), 7.98 (s, 1H), 7.30 (s, 3H), 6.81 (s, 1H), 5.71 (s, 1H), 4.86 (s, 1H), 4.29 (s, 2H), 4.04-3.90 (m, 2H), 3.76 (d, J=10.6 Hz, 1H), 3.41-3.42 (m, 2H), 3.31-3.27 (m, 1H), 2.24-2.28 (m, 1H), 1.93 (s, 3H), 1.10-1.02 (d, J=6 Hz, 3H).

Example 269

1-(8-Amino-7-fluoro-6-(8-methyl-2,3-dihydro-1H-pyrido[2,3-b][1,4]oxazin-7-yl)isoquinolin-3-yl)-3-((1R,3S)-3-cyanocyclopentyl)urea and 1-(8-Amino-7-fluoro-6-(8-methyl-2,3-dihydro-1H-pyrido[2,3-b][1,4]oxazin-7-yl)isoquinolin-3-yl)-3-((1S,3R)-3-cyanocyclopentyl)urea (Compound 726a and Compound 726b)

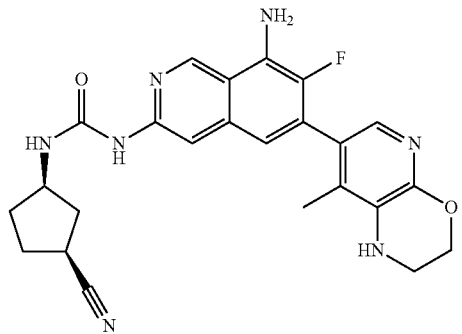

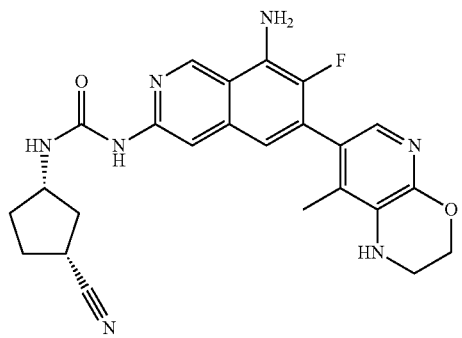

Synthesized following procedures similar to those described above according to the general synthetic methods. Relative stereochemistry are as drawn. Absolute stereochemistry was arbitrarily assigned.

Isomer 1: Compound 726a LCMS (ESI) [M+H]⁺=462.2, $R_T$=3.306 min, Method N; ¹H NMR (400 MHz, DMSO-d₆) δ 9.29 (s, 1H), 8.87 (s, 1H), 7.86 (s, 1H), 7.35-7.20 (m, 2H), 6.75 (d, J=6.2 Hz, 1H), 6.15 (s, 2H), 5.67 (s, 1H), 4.32-4.20 (m, 2H), 4.10-4.01 (m, 1H), 3.50-3.30 (m, 2H), 3.10-3.00 (m, 1H), 2.50-2.26 (m, 2H), 2.10-1.85 (m, 5H), 1.70-1.50 (m, 2H).

Isomer 2: Compound 726b LCMS (ESI) [M+H]⁺=462.2, $R_T$=3.308 min, Method N; ¹H NMR (400 MHz, DMSO-d₆) δ 9.29 (s, 1H), 8.87 (s, 1H), 7.86 (s, 1H), 7.35-7.20 (m, 2H), 6.75 (d, J=6.2 Hz, 1H), 6.15 (s, 2H), 5.67 (s, 1H), 4.32-4.20 (m, 2H), 4.10-4.01 (m, 1H), 3.50-3.30 (m, 2H), 3.10-3.00 (m, 1H), 2.50-2.26 (m, 2H), 2.10-1.85 (m, 5H), 1.70-1.50 (m, 2H).

Example 270

(2S,3R)-2-methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate, (2R,3S)-2-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate, (2S,3S)-2-methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate and (2R,3R)-2-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate (Compound 510a, Compound 510b, Compound 510c and Compound 510d)

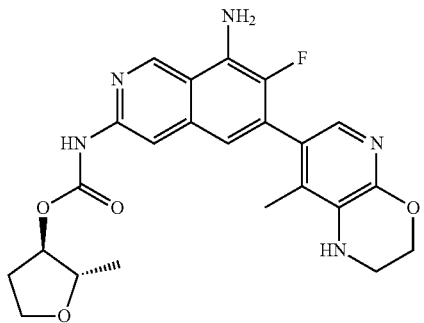

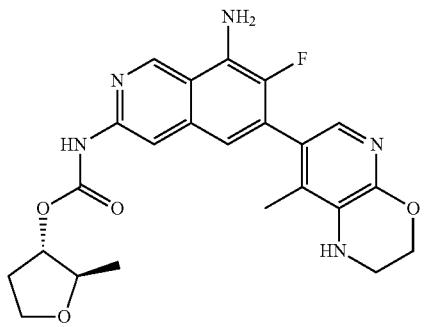

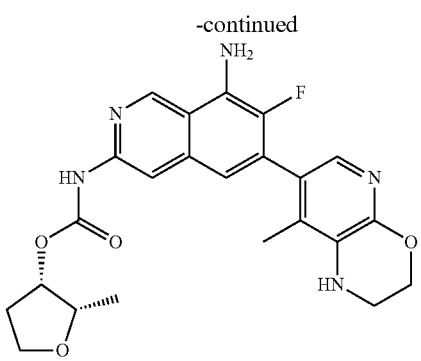

-continued

Synthesized following procedures similar to those described herein and methods known in the art. Relative stereochemistry and absolute stereochemistry were arbitrarily assigned.

Isomer 1: Compound 510a LCMS (ESI) [M+H]⁺=454.2, $R_T$ 3.413 min, Method N; ¹H NMR (400 MHz, DMSO-d₆) δ 10.10 (s, 1H), 9.34 (d, J=0.9 Hz, 1H), 7.97 (d, J=0.9 Hz, 1H), 7.33 (s, 1H), 6.83 (d, J=6.1 Hz, 1H), 6.20 (s, 2H), 5.70-5.62 (m, 1H), 5.20 (ddd, J=6.1, 3.9, 2.0 Hz, 1H), 4.29 (t, J=4.4 Hz, 2H), 3.97-3.82 (m, 2H), 3.64 (td, J=8.6, 5.8 Hz, 1H), 2.41-2.26 (m, 1H), 2.06-1.89 (m, 4H), 1.27-1.15 (m, 5H).

Isomer 2: Compound 510b LCMS (ESI) [M+H]⁺=454.2, $R_T$ 3.418 min, Method N; ¹H NMR (400 MHz, DMSO-d₆) δ 10.10 (s, 1H), 9.34 (d, J=0.9 Hz, 1H), 7.97 (d, J=0.8 Hz, 1H), 7.33 (s, 1H), 6.84 (d, J=6.1 Hz, 1H), 6.20 (s, 2H), 5.66 (t, J=2.8 Hz, 1H), 5.20 (ddd, J=6.1, 3.9, 2.0 Hz, 1H), 4.33-4.25 (m, 2H), 3.97-3.82 (m, 2H), 3.64 (td, J=8.6, 5.8 Hz, 1H), 3.37 (d, J=4.8 Hz, 1H), 2.33 (ddt, J=12.8, 8.8, 6.5 Hz, 1H), 2.06-1.89 (m, 4H), 1.27-1.15 (m, 4H).

Isomer 3: Compound 510c LCMS (ESI) [M+H]⁺=454.2, $R_T$ 3.498 min, Method N.

Isomer 4: Compound 510d LCMS (ESI) [M+H]⁺=454.2, $R_T$ 3.503 min, Method N; ¹H NMR (400 MHz, DMSO-d₆) δ 10.11 (s, 1H), 9.33 (d, J=1.0 Hz, 1H), 8.00-7.94 (m, 1H), 7.33 (s, 1H), 6.85 (d, J=6.1 Hz, 1H), 6.20 (s, 2H), 5.66 (t, J=2.7 Hz, 1H), 4.85 (dt, J=6.5, 2.3 Hz, 1H), 4.29 (t, J=4.4 Hz, 2H), 4.03-3.86 (m, 2H), 3.78 (ddd, J=9.5, 8.5, 6.5 Hz, 1H), 3.41-3.33 (m, 2H), 2.24 (dddd, J=13.6, 9.5, 8.3, 6.4 Hz, 1H), 2.01-1.89 (m, 4H), 1.18 (d, J=6.5 Hz, 3H).

Example 271

(1R,5S,9s)-7-(Oxetan-3-yl)-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate (Compound 575a)

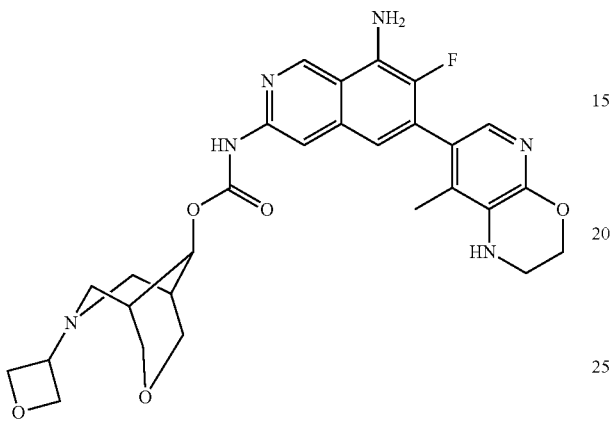

Synthesized following procedures similar to those described herein and methods known in the art. Stereochemistry was arbitrarily assigned. LCMS (ESI) [M+H]$^+$=551.3, R$_T$ 2.427 min, Method N. $^1$H NMR (400 MHz, DMSO-d$_6$) δ 10.22 (s, 1H), 9.37 (s, 1H), 7.98 (s, 1H), 7.33 (s, 1H), 6.83 (d, J=6.1 Hz, 1H), 6.20 (s, 2H), 5.70-5.62 (m, 1H), 4.75 (t, J=3.7 Hz, 1H), 4.51 (p, J=6.3 Hz, 4H), 4.29 (t, J=4.4 Hz, 2H), 4.00 (d, J=11.1 Hz, 2H), 3.67 (d, J=11.0 Hz, 2H), 3.00-2.90 (m, 2H), 2.24 (d, J=11.0 Hz, 2H), 1.92 (d, J=1.6 Hz, 4H), 1.86 (d, J=3.7 Hz, 3H), 1.65 (s, 1H).

Example 272

Additional compounds were synthesized using methods and procedures similar to those described above and methods known in the art. The LC/MS analytical data is provided in Table A1.

TABLE A1

| No. | Structure | Name | LCMS Rt (min) m/z Method |
|---|---|---|---|
| 403a | 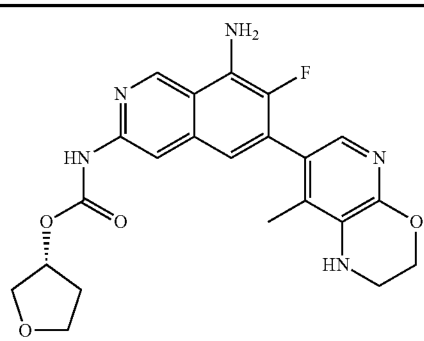 | (R)-Tetrahydrofuran-3-yl (8-amino-7-fluoro-6-(8-methyl-2,3-dihydro-1H-pyrido[2,3-b][1,4]oxazin-7-yl)isoquinolin-3-yl)carbamate | 2.126 440.0 M |

TABLE A1-continued

| No. | Structure | Name | LCMS Rt (min) m/z Method |
|---|---|---|---|
| 403b | 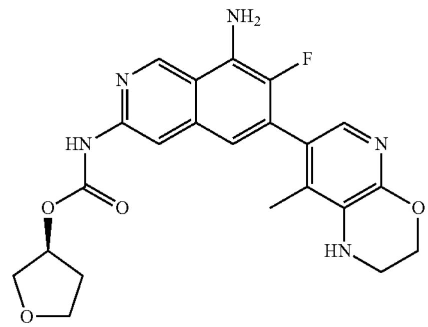 [SMILES: Cc1c(-c2cc3cc(NC(=O)O[C@H]4CCOC4)ncc3c(N)c2F)cnc2c1NCCO2] | (S)-Tetrahydrofuran-3-yl (8-amino-7-fluoro-6-(8-methyl-2,3-dihydro-1H-pyrido[2,3-b][1,4]oxazin-7-yl)isoquinolin-3-yl)carbamate | 3.252 440.2 N |
| 418a | 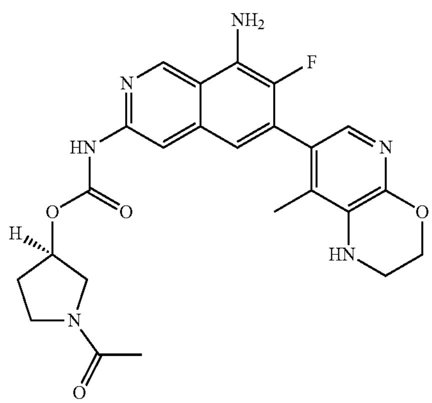 [SMILES: CC(=O)N1CC[C@@H](OC(=O)Nc2cc3cc(-c4cnc5c(c4C)NCCO5)c(F)c(N)c3cn2)C1] | (R)-1-Acetylpyrrolidin-3-yl (8-amino-7-fluoro-6-(8-methyl-2,3-dihydro-1H-pyrido[2,3-b][1,4]oxazin-7-yl)isoquinolin-3-yl)carbamate (Absolute stereochemistry arbitrarily assigned) | 3.104 481.2 N |
| 431 | 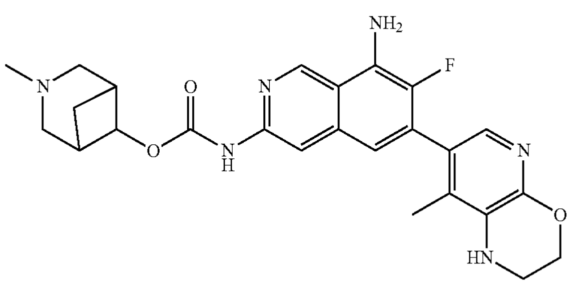 [SMILES: Cc1c(-c2cc3cc(NC(=O)OC4C5CC4CN(C)C5)ncc3c(N)c2F)cnc2c1NCCO2] | 3-Methyl-3-azabicyclo[3.1.1]heptan-6-yl (8-amino-7-fluoro-6-(8-methyl-2,3-dihydro-1H-pyrido[2,3-b][1,4]oxazin-7-yl)isoquinolin-3-yl)carbamate | 2.59 479.2 N |
| 436 | 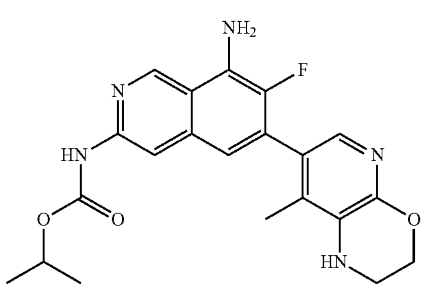 | Isopropyl (8-amino-7-fluoro-6-(8-methyl-2,3-dihydro-1H-pyrido[2,3-b][1,4]oxazin-7-yl)isoquinolin-3-yl)carbamate | 3.78 412.2 N |

TABLE A1-continued

| No. | Structure | Name | LCMS Rt (min) m/z Method |
|---|---|---|---|
| 439a | 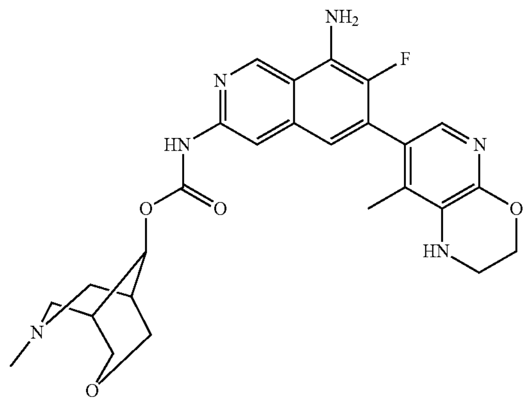 [SMILES: Cc1c(-c2cc3cc(NC(=O)OC4C5COCC4CN(C)C5)ncc3c(N)c2F)cnc2c1NCCO2] | (1R,5S,9s)-7-Methyl-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate (Absolute stereochemistry arbitrarily assigned) | 2.416 509.2 N |
| 439b | 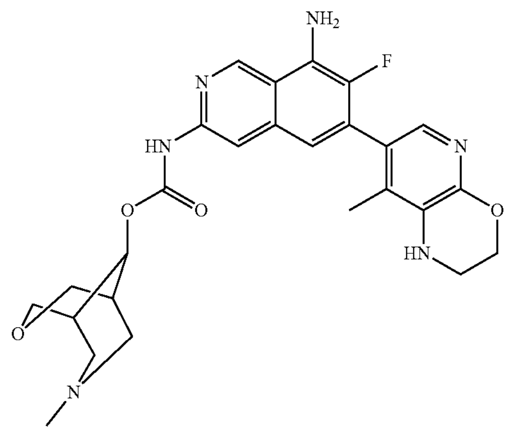 [SMILES: Cc1c(-c2cc3cc(NC(=O)OC4C5COCC4CN(C)C5)ncc3c(N)c2F)cnc2c1NCCO2] | (1R,5S,9r)-7-Methyl-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate (Absolute stereochemistry arbitrarily assigned) | 2.516 509.2 N |
| 440a | 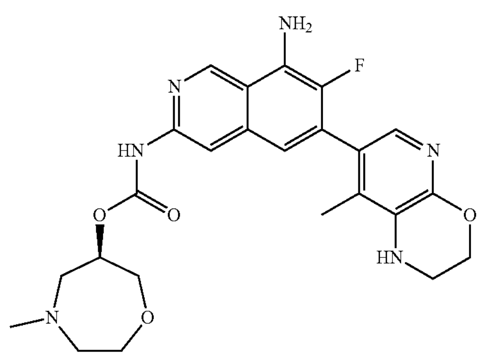 [SMILES: Cc1c(-c2cc3cc(NC(=O)O[C@H]4COCCN(C)C4)ncc3c(N)c2F)cnc2c1NCCO2] | (R)-4-Methyl-1,4-oxazepan-6-yl (8-amino-7-fluoro-6-(8-methyl-2,3-dihydro-1H-pyrido[2,3-b][1,4]oxazin-7-yl)isoquinolin-3-yl)carbamate (Absolute stereochemistry arbitrarily assigned) | 2.39 483.2 N |
| 440b | 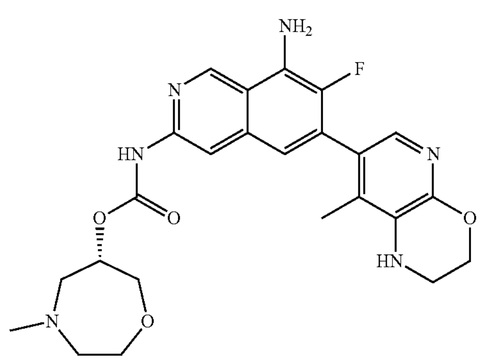 [SMILES: Cc1c(-c2cc3cc(NC(=O)O[C@@H]4COCCN(C)C4)ncc3c(N)c2F)cnc2c1NCCO2] | (R)-4-Methyl-1,4-oxazepan-6-yl (8-amino-7-fluoro-6-(8-methyl-2,3-dihydro-1H-pyrido[2,3-b][1,4]oxazin-7-yl)isoquinolin-3-yl)carbamate (Absolute stereochemistry arbitrarily assigned) | 2.41 583.2 N |

TABLE A1-continued

| No. | Structure | Name | LCMS Rt (min) m/z Method |
|---|---|---|---|
| 474 | 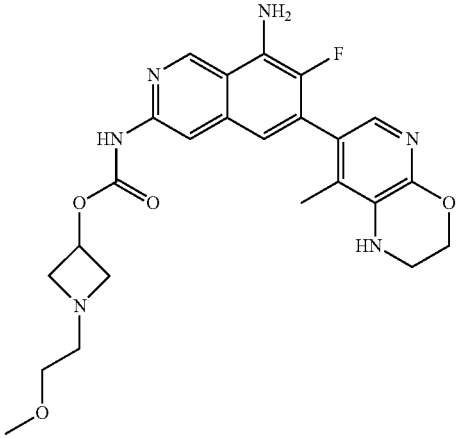 [SMILES: COCCN1CC(OC(=O)Nc2cc3cc(-c4cnc5c(c4C)NCCO5)c(F)c(N)c3cn2)C1] | 1-(2-Methoxyethyl)azetidin-3-yl (8-amino-7-fluoro-6-(8-methyl-2,3-dihydro-1H-pyrido[2,3-b][1,4]oxazin-7-yl)isoquinolin-3-yl)carbamate | 2.426 483.2 N |
| 485b | 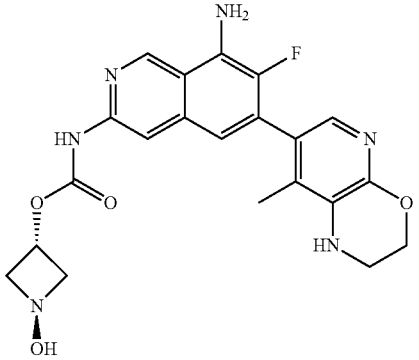 | (1r,3r)-3-Hydroxycyclobutyl (8-amino-7-fluoro-6-(8-methyl-2,3-dihydro-1H-pyrido[2,3-b][1,4]oxazin-7-yl)isoquinolin-3-yl)carbamate | 2.968 440.2 N |
| 499a | 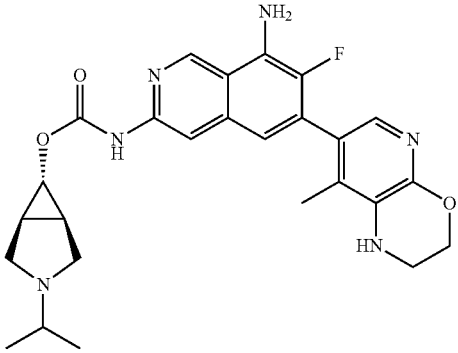 [SMILES: Cc1c(-c2cc3cc(NC(=O)O[C@H]4[C@@H]5CN(C(C)C)C[C@@H]54)ncc3c(N)c2F)cnc2c1NCCO2] | (1R,5S,6s)-3-Isopropyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate | 2.527 493.3 N |

TABLE A1-continued

| No. | Structure | Name | LCMS Rt (min) m/z Method |
|---|---|---|---|
| 502a | 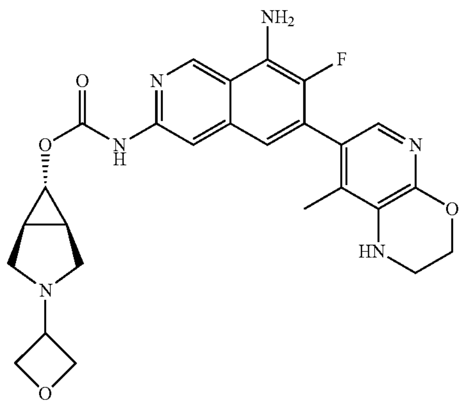 [SMILES: Cc1c(-c2cc3cc(NC(=O)O[C@H]4[C@@H]5CN(C6COC6)C[C@@H]54)ncc3c(N)c2F)cnc2c1NCCO2] | (1R,5S,6s)-3-(Oxetan-3-yl)-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate | 2.42 508.2 N |
| 506a | 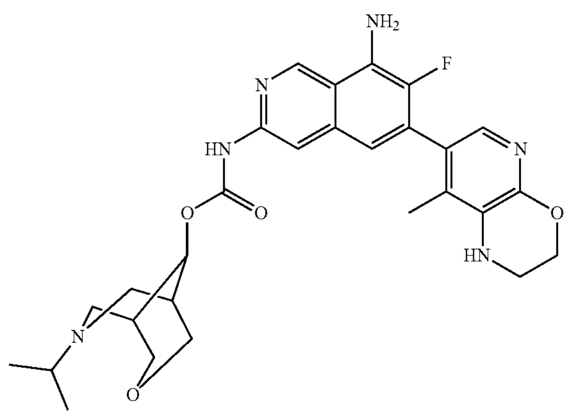 [SMILES: Cc1c(-c2cc3cc(NC(=O)OC4C5COCC4CN(C(C)C)C5)ncc3c(N)c2F)cnc2c1NCCO2] | (1R,5S,9s)-7-Isopropyl-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate (Stereochemistry arbitrarily assigned) | 2.588 537.3 N |
| 507a | 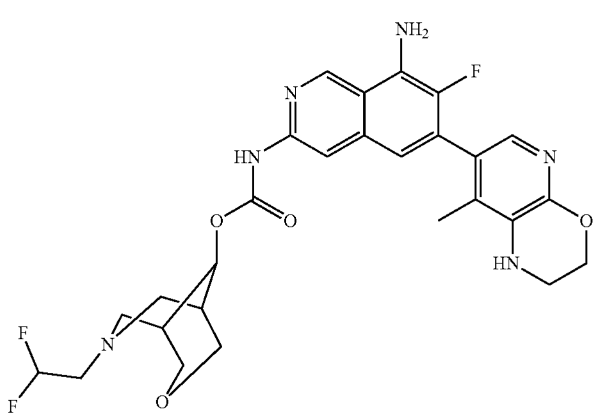 [SMILES: Cc1c(-c2cc3cc(NC(=O)OC4C5COCC4CN(CC(F)F)C5)ncc3c(N)c2F)cnc2c1NCCO2] | (1R,5S,9s)-7-(2,2-Difluoroethyl)-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate (Stereochemistry arbitrarily assigned) | 2.61 280.2, 559.3 N |

TABLE A1-continued

| No. | Structure | Name | LCMS Rt (min) m/z Method |
|---|---|---|---|
| 521 | 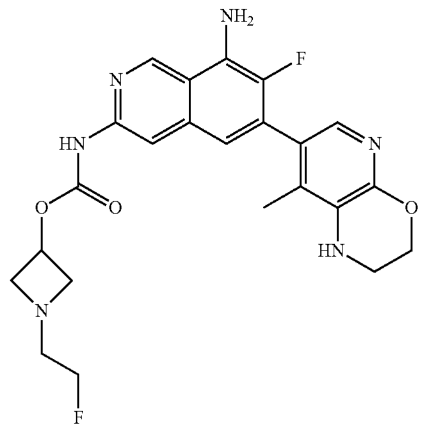 [SMILES: Cc1c(-c2cc3cc(NC(=O)OC4CN(CCF)C4)ncc3c(N)c2F)cnc2c1NCCO2] | 1-(2-Fluoroethyl)azetidin-3-yl (8-amino-7-fluoro-6-(8-methyl-2,3-dihydro-1H-pyrido[2,3-b][1,4]oxazin-7-yl)isoquinolin-3-yl)carbamate | 2.340 471.2 N |
| 522a | 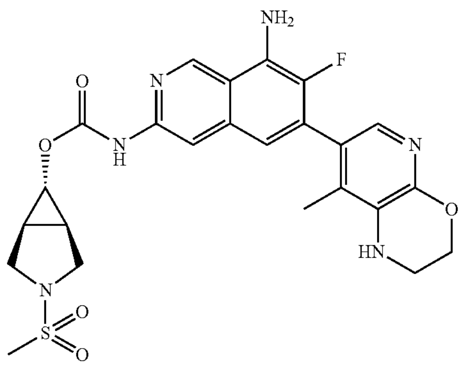 [SMILES: Cc1c(-c2cc3cc(NC(=O)O[C@H]4[C@@H]5CN(S(C)(=O)=O)C[C@@H]54)ncc3c(N)c2F)cnc2c1NCCO2] | (1R,5S,6s)-3-(Methylsulfonyl)-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate | 3.386 529.2 N |
| 540 | 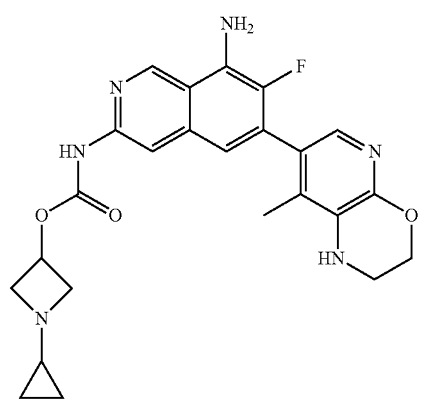 [SMILES: Cc1c(-c2cc3cc(NC(=O)OC4CN(C5CC5)C4)ncc3c(N)c2F)cnc2c1NCCO2] | 1-Cyclopropylazetidin-3-yl (8-amino-7-fluoro-6-(8-methyl-2,3-dihydro-1H-pyrido[2,3-b][1,4]oxazin-7-yl)isoquinolin-3-yl)carbamate | 2.426 465.2 N |
| 703a | 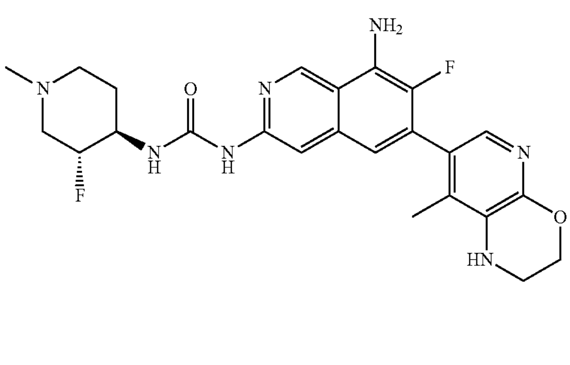 [SMILES: Cc1c(-c2cc3cc(NC(=O)N[C@@H]4CCN(C)C[C@H]4F)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-((3R,4R)-3-fluoro-1-methylpiperidin-4-yl)urea (Relative stereochemistry as drawn. Absolute stereochemistry arbitrarily assigned) | 2.63 484.2 N |

TABLE A1-continued

| No. | Structure | Name | LCMS Rt (min) m/z Method |
|---|---|---|---|
| 703b | 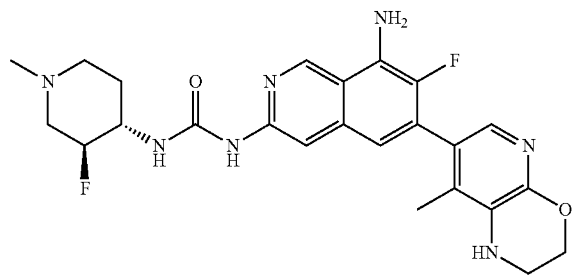 [SMILES: Cc1c(-c2cc3cc(NC(=O)N[C@H]4CCN(C)C[C@@H]4F)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-((3S,4S)-3-fluoro-1-methylpiperidin-4-yl)urea (Relative stereochemistry as drawn. Absolute stereochemistry arbitrarily assigned) | 2.32 484.2 N |
| 703c | 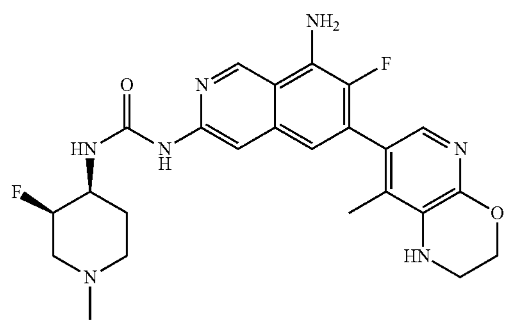 [SMILES: Cc1c(-c2cc3cc(NC(=O)N[C@H]4CCN(C)C[C@H]4F)ncc3c(N)c2F)cnc2c1NCCO2] | (±)-1-(8-Amino-7-fluoro-6-(8-methyl-2,3-dihydro-1H-pyrido[2,3-b][1,4]oxazin-7-yl)isoquinolin-3-yl)-3-((cis)-3-fluoro-1-methylpiperidin-4-yl)urea (Absolute stereochemistry arbitrarily assigned) | 2.30 484.3 N |
| 704 | 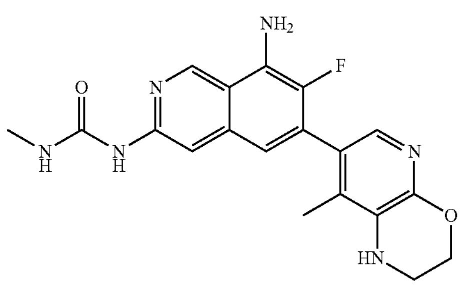 [SMILES: CNC(=O)Nc1cc2cc(-c3cnc4c(c3C)NCCO4)c(F)c(N)c2cn1] | 1-(8-Amino-7-fluoro-6-(8-methyl-2,3-dihydro-1H-pyrido[2,3-b][1,4]oxazin-7-yl)isoquinolin-3-yl)-3-methylurea | 2.711 383.2 N |
| 707 | 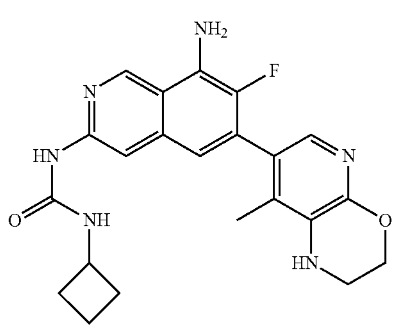 [SMILES: Cc1c(-c2cc3cc(NC(=O)NC4CCC4)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-cyclobutylurea | 3.45 423.2 N |

TABLE A1-continued

| No. | Structure | Name | LCMS Rt (min) m/z Method |
|---|---|---|---|
| 709 | 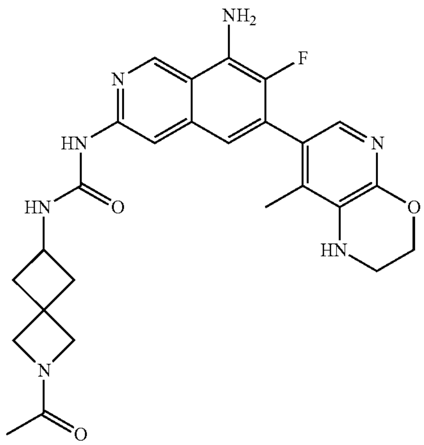 [SMILES: CC(=O)N1CC2(CC(NC(=O)Nc3cc4cc(-c5cnc6c(c5C)NCCO6)c(F)c(N)c4cn3)C2)C1] | 1-(2-Acetyl-2-azaspiro[3.3]heptan-6-yl)-3-(8-amino-7-fluoro-6-(8-methyl-2,3-dihydro-1H-pyrido[2,3-b][1,4]oxazin-7-yl)isoquinolin-3-yl)urea | 3.05 506.2 N |
| 710a | 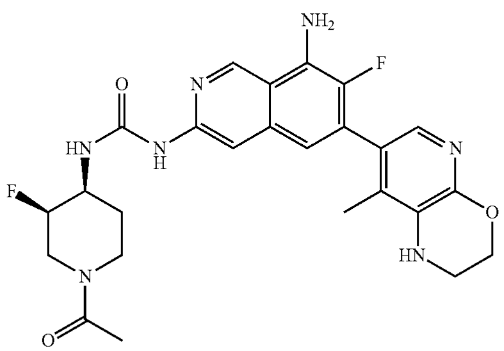 [SMILES: CC(=O)N1CC[C@H](NC(=O)Nc2cc3cc(-c4cnc5c(c4C)NCCO5)c(F)c(N)c3cn2)[C@H](F)C1] | (±)-1-((cis)-1-Acetyl-3-fluoropiperidin-4-yl)-3-(8-amino-7-fluoro-6-(8-methyl-2,3-dihydro-1H-pyrido[2,3-b][1,4]oxazin-7-yl)isoquinolin-3-yl)urea (Absolute stereochemistry arbitrarily assigned) | 3.05 512.3 N |
| 721 | 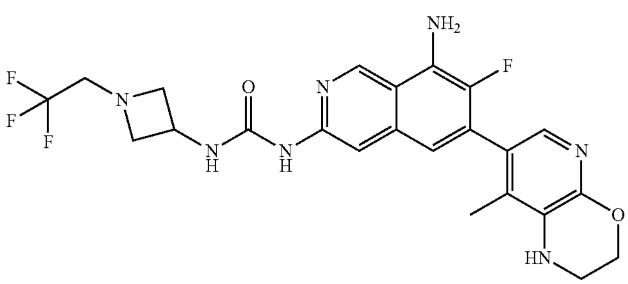 [SMILES: Cc1c(-c2cc3cc(NC(=O)NC4CN(CC(F)(F)F)C4)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-(1-(2,2,2-trifluoroethyl)azetidin-3-yl)urea | 2.880 506.2 N |
| 742 | 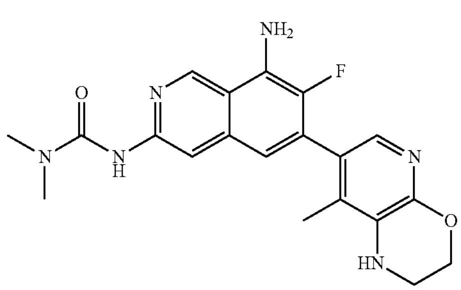 [SMILES: Cc1c(-c2cc3cc(NC(=O)N(C)C)ncc3c(N)c2F)cnc2c1NCCO2] | 3-(8-Amino-7-fluoro-6-(8-methyl-2,3-dihydro-1H-pyrido[2,3-b][1,4]oxazin-7-yl)isoquinolin-3-yl)-1,1-dimethylurea | 2.693 397.2 N |

TABLE A1-continued

| No. | Structure | Name | LCMS Rt (min) m/z Method |
|---|---|---|---|
| 745 | 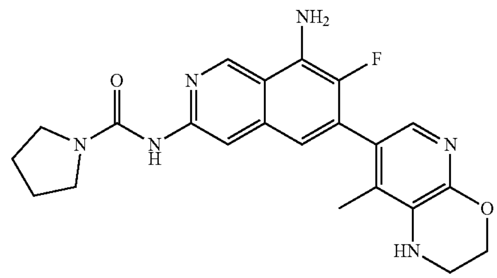 [SMILES: Cc1c(-c2cc3cc(NC(=O)N4CCCC4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)pyrrolidine-1-carboxamide | 2.977 423.2 N |
| 747a | 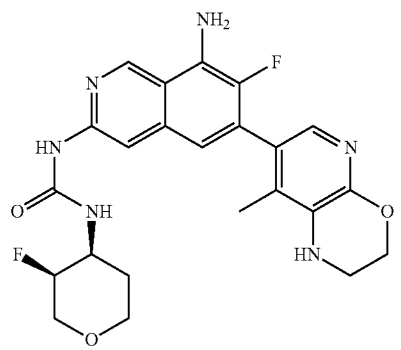 [SMILES: Cc1c(-c2cc3cc(NC(=O)N[C@H]4CCOC[C@H]4F)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-((3S,4S)-3-fluorotetrahydro-2H-pyran-4-yl)urea (Relative stereochemistry as drawn. Absolute stereochemistry arbitrarily assigned) | 3.124 471.2 N |
| 747b | 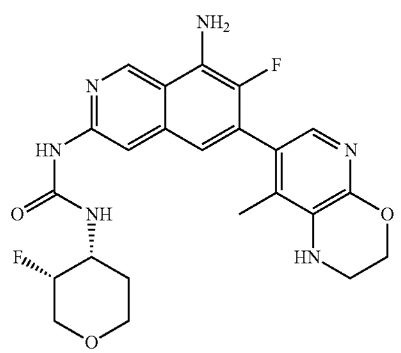 [SMILES: Cc1c(-c2cc3cc(NC(=O)N[C@@H]4CCOC[C@@H]4F)ncc3c(N)c2F)cnc2c1NCCO2] | 1-(8-Amino-7-fluoro-6-(8-methyl-2,3-dihydro-1H-pyrido[2,3-b][1,4]oxazin-7-yl)isoquinolin-3-yl)-3-((3R,4R)-3-fluorotetrahydro-2H-pyran-4-yl)urea (Relative stereochemistry as drawn. Absolute stereochemistry arbitrarily assigned) | 3.124 471.2 N |
| 751 | 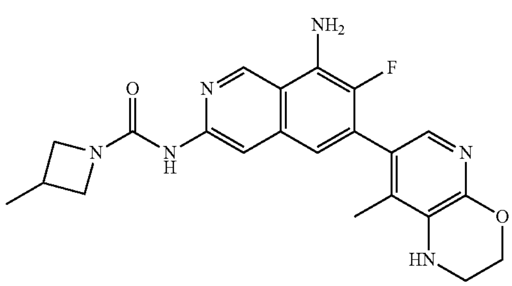 [SMILES: Cc1c(-c2cc3cc(NC(=O)N4CC(C)C4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)-3-methylazetidine-1-carboxamide | 1.591 423.2 J |
| 752 | 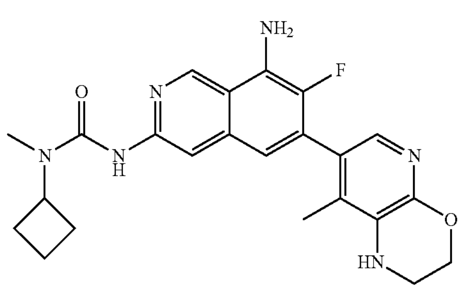 [SMILES: Cc1c(-c2cc3cc(NC(=O)N(C)C4CCC4)ncc3c(N)c2F)cnc2c1NCCO2] | 3-(8-Amino-7-fluoro-6-(8-methyl-2,3-dihydro-1H-pyrido[2,3-b][1,4]oxazin-7-yl)isoquinolin-3-yl)-1-cyclobutyl-1-methylurea | 3.453 437.2 N |

TABLE A1-continued

| No. | Structure | Name | LCMS Rt (min) m/z Method |
|---|---|---|---|
| 753 | 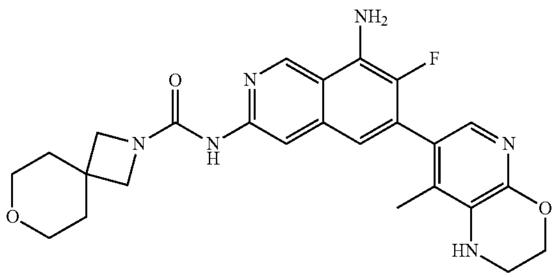 [SMILES: Cc1c(-c2cc3cc(NC(=O)N4CC5(CCOCC5)C4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)-7-oxa-2-azaspiro[3.5]nonane-2-carboxamide | 2.996 479.2 N |
| 754 | 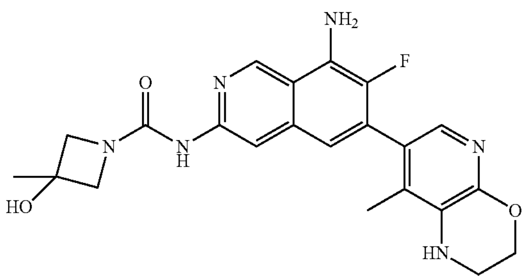 [SMILES: Cc1c(-c2cc3cc(NC(=O)N4CC(C)(O)C4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)-7-oxa-2-azaspiro[3.5]nonane-2-carboxamide | 2.648 439.2 N |
| 755 | 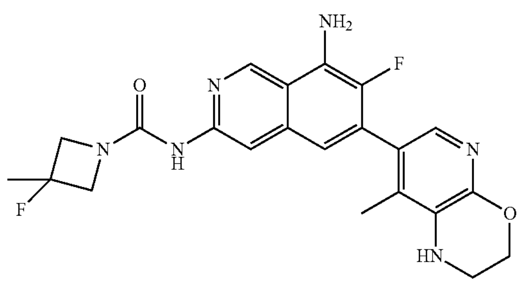 [SMILES: Cc1c(-c2cc3cc(NC(=O)N4CC(C)(F)C4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)-3-fluoro-3-methylazetidine-1-carboxamide | 3.133 441.2 N |
| 756 | 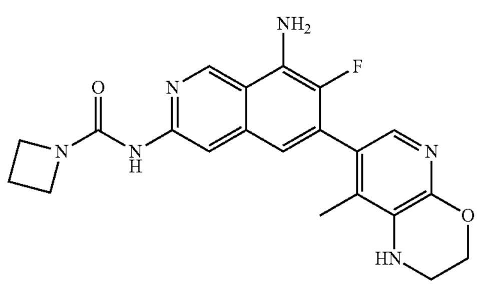 [SMILES: Cc1c(-c2cc3cc(NC(=O)N4CCC4)ncc3c(N)c2F)cnc2c1NCCO2] | N-(8-Amino-7-fluoro-6-(8-methyl-2,3-dihydro-1H-pyrido[2,3-b][1,4]oxazin-7-yl)isoquinolin-3-yl)azetidine-1-carboxamide | 2.787 409.2 N |

BIOLOGICAL EXAMPLES

Exemplary compounds of Formula (I) were tested to assess compound inhibition of HPK-1.

Example B1: HPK1-FL HTRF Enzymatic Assay ("HTRF")

Assay Principle: HPK-FL enzyme phosphorylates Biotin-SLP-76 substrate in the presence of ATP at 1 mm and varying concentrations of test compound. Product is detected by FRET using Eu-anti-pSLP76 Ab and SA-XL665. Also see www.cisbio.com/HTRF for additional HTRF technology information.

Instrumentation: Echo555 compound dispenser; Agilent Bravo; Perkin Elmer Envision.

Final Assay Conditions:
HPK full length, T165E S171E: 0.125 nM
Biotin-SLP76: 100 nM
ATP: 1 mm (ATP Km=20 µM)
Eu-anti-pSLP76: 2 nM
SA-XL665: 8.3 nM
Preincubation time: 30 min
Kinase reaction time: 60 min
Temperature: ambient
Total volume: 12 µl
$ATP^{app}$ Km: 17.7 µM
Materials:
Assay plate: White ProxiPlate 384 F (PerkinElmer cat #6008289)
Kinase: HPK full length double mutant Substrate: Biotin-SLP76
ATP: 100 mm ATP
BSG: 2% BSG
DMSO: DMSO (Sigma cat #34869-100ML)
Reaction Buffer: H₂O/50 mm HEPES, pH 7.5/10 mm MgCl₂/2 mm TCEP/0.01% Brij-35/0.01% BSG
Detection mix:Eu-anti-pSLP76/SA-XL665 (Cisbio, #610SAXAC)

Assay Procedure Ki Determination:

To a 384 well Proxiplate with 80 nL compound or DMSO spotted on was added 4 μl/well kinase mix. The mixture was preincubated for 30 minutes and then 4 μl/well substrate mix was added. The solution was incubated for 60 min and then 4 μl/well detection mix was added. The solution was incubated for another 60 min. The plates were then loaded onto a Perkin Elmer Envision and the TR-FRET signal was measured at 615 and 665 nm. A ratio of 665/620 was used to calculate the % activity at each concentration of compound.

Example B2: HPK1 Lantha Binding Assay ("Lanth")

Materials:

| Reagent | Vender-Cat# |
| --- | --- |
| white ProxiPlate 384 F(assay plate) | PerkinElmer-6008289 |
| 384-well Microplate(compound plate) | Labcyte-LP-0200 |
| HPK1 enzyme | Signalchem-M23-11G |
| Tracer-222 | Invitrogen-PV6121 |
| Eu-Anti-GST Ab | Invitrogen-PV5594 |
| Assay Buffer | 2 mM DTT(Sigma-43815), 0.01% BRIJ-35(Sigma-B4184), 10 mM MgCl₂, 50 mM HEPES(Invitrogen-15630130) |

Procedure:

I. Compound Dilution:

The compounds to be tested were diluted by preparing 12.5 μL/well of 5 mm compound (100×) in columns 2 and 13 and 10 μL/well of DMSO in columns 3-12, 14-23, and wells A1-H1 and I24-P24 of the compound plate using a Bravo liquid handling platform. For the reference compound, the top concentration was 1 mm. To the plate was added 10 μL 2 mm staurosporine in wells J1-P1 and A24-H24. A 11 point 5-fold compound serial dilution was performed using the Bravo liquid handling platform. From the plate were transferred 2.5 μL of the solutions from column 2 and column 13 to the 10 μL of DMSO in columns 3 and 14 & so on. The compound plate was centrifuged at 2500 rpm for 1 min. From the compound plate was transferred 80 nl of the compounds into an assay plate using the Echo liquid handler system. One compound plate makes two assay plates. Each assay plate is sealed and stored in an N₂ cabinet.

II. Assay Condition:

The following assay concentrations and times were used: 2 nM HPK1, 2 nM Eu-Anti-GST Ab, and 15 nM Tracer222, with 60 min incubation time.

III. HPK1 Lantha Binding Assay:

For the binding assay, 4 μL 2× HPK1 and Eu-anti-GST antibody were added to each well of the assay plate using a Multidrop reagent dispenser. The solutions were incubated in a 23 C incubator for 1 h. To each well of the assay plate was added 4 μL 2× Tracer-222 using a Multidrop reagent dispenser. The solutions were again incubated in a 23° C. incubator for 1 h. The results of the assay were read using an Envision plate reader with the following parameters: TR_FRET, 340ex/615 and 665em; 100 μsec Delay; and 200 μsec integration.

IV. Analysis:

Compound Ki was analyzed using Morrison ki fit model in XL-fit a. fit=(1−((((E+x)±(Ki*(1±(S/Kd))))−(((((E+x)+(Ki*(1+(S/Kd))))^2)−((4*E)*x))^0.5)/(2*E)))
   res=(y-fit)

b. Parameters:
   E=enzyme concentration
   S=Tracer222 concentration, Kd=Tracer222 Kd
   All measurements are reported using the same units (nM).

Exemplary compounds were tested in the HTRF binding assays. The Ki values determined are listed in Table B1.

TABLE B1

| Compound No. | HPK1 Ki (nM) |
| --- | --- |
| 401 | 0.019 |
| 402 | 0.11 |
| 403 | 0.023 |
| 403a | <0.013 |
| 403b | 0.064 |
| 404 | 0.030 |
| 405a | 0.138 |
| 405b | 0.158 |
| 406 | 0.40 |
| 407 | 0.030 |
| 408a | 0.089 |
| 408b | 0.069 |
| 409a | 0.053 |
| 409b | 0.048 |
| 410a | 0.167 |
| 410b | 0.029 |
| 411a | 0.25 |
| 411b | 0.20 |
| 412a | 41 |
| 412b | 0.29 |
| 413 | 0.65 |
| 414a | 0.59 |
| 414b | 21 |
| 415a | 3 |
| 415b | 16 |
| 416a | 0.075 |
| 416b | 0.075 |
| 417 | <0.013 |
| 418a | <0.013 |
| 419 | 0.061 |
| 420 | <0.013 |
| 421 | <0.013 |
| 422 | 0.023 |
| 423 | <0.013 |
| 424 | <0.013 |
| 425 | <0.013 |
| 426 | <0.013 |
| 427 | <0.013 |
| 428 | <0.013 |
| 429 | 0.028 |
| 430 | <0.013 |
| 431 | 2.3 |
| 432a | <0.013 |
| 433 | <0.013 |
| 434 | <0.013 |
| 435 | 0.187 |
| 436 | 0.014 |
| 437a | <0.013 |
| 437b | 0.054 |
| 439a | <0.013 |
| 439b | 0.48 |
| 440a | 0.084 |
| 440b | 0.277 |

TABLE B1-continued

| Compound No. | HPK1 Ki (nM) |
|---|---|
| 441a | <0.013 |
| 441b | <0.013 |
| 441ab | 0.037 |
| 441c | 0.16 |
| 441d | 0.32 |
| 442b | 0.201 |
| 442c | 0.154 |
| 442d | 0.046 |
| 443 | <0.013 |
| 444a | <0.013 |
| 444b | <0.013 |
| 445ab | <0.013 |
| 445c | 0.015 |
| 445d | <0.013 |
| 447a | <0.013 |
| 450 | 0.13 |
| 451a | 0.14 |
| 451b | <0.013 |
| 452a | 0.030 |
| 452b | 0.036 |
| 452c | 0.17 |
| 452d | <0.013 |
| 461a | 0.891 |
| 461b | 1.01 |
| 465 | 0.46 |
| 467a | 0.031 |
| 467b | 0.064 |
| 467c | 0.027 |
| 467d | <0.013 |
| 474 | 0.060 |
| 477a | 0.034 |
| 477b | 0.017 |
| 477c | 0.15 |
| 477d | 0.020 |
| 478a | 0.25 |
| 478b | <0.013 |
| 479a | 0.021 |
| 479b | <0.013 |
| 480a | 0.034 |
| 480b | 0.28 |
| 481a | 0.184 |
| 481b | 0.018 |
| 482a | <0.013 |
| 482b | <0.013 |
| 483a | <0.013 |
| 484a | <0.013 |
| 484b | 0.015 |
| 485a | <0.013 |
| 485b | <0.013 |
| 486 | <0.013 |
| 486b | 0.018 |
| 487 | <0.013 |
| 492 | 0.055 |
| 493 | 0.064 |
| 494 | <0.013 |
| 499a | <0.013 |
| 502a | <0.013 |
| 504a | <0.013 |
| 504b | 0.76 |
| 506a | <0.013 |
| 507a | <0.013 |
| 510a | 0.395 |
| 510b | 0.308 |
| 510c | <0.013 |
| 510d | 0.016 |
| 511a | <0.013 |
| 511b | 0.017 |
| 512a | 0.015 |
| 512b | <0.013 |
| 513a | 0.022 |
| 514a | <0.013 |
| 515a | 0.105 |
| 515b | 0.017 |
| 516a | 0.031 |
| 516b | <0.013 |
| 517a | <0.013 |
| 518a | 0.069 |
| 518b | 0.044 |
| 519a | <0.013 |
| 520a | <0.013 |
| 521 | 0.11 |
| 522a | <0.013 |
| 523a | 0.85 |
| 523b | 8.75 |
| 524 | 0.020 |
| 525a | <0.013 |
| 526a | 0.015 |
| 526b | 0.016 |
| 526c | 0.015 |
| 526d | 0.018 |
| 527a | 0.538 |
| 527b | 0.216 |
| 528a | <0.013 |
| 529b | 0.019 |
| 530a | 0.26 |
| 530b | 0.11 |
| 531a | 0.055 |
| 531b | 0.152 |
| 532 | 0.014 |
| 533a | 0.035 |
| 533b | 0.059 |
| 533c | 0.014 |
| 533d | 0.015 |
| 534a | 0.14 |
| 535a | <0.013 |
| 535b | 0.029 |
| 536a | <0.013 |
| 536b | <0.013 |
| 537a | 0.015 |
| 537b | <0.013 |
| 538a | 0.058 |
| 538b | 0.016 |
| 539a | <0.013 |
| 540 | 0.021 |
| 541a | 0.014 |
| 542a | 0.33 |
| 542b | 0.078 |
| 542c | 0.021 |
| 542d | 0.014 |
| 543a | <0.013 |
| 543b | 0.083 |
| 544a | 0.138 |
| 544b | 2.7 |
| 545a | 0.021 |
| 545b | 0.018 |
| 546a | <0.013 |
| 546b | 0.051 |
| 548a | 1.7 |
| 548b | 93 |
| 549a | <0.013 |
| 549b | <0.013 |
| 550a | <0.013 |
| 550b | 0.054 |
| 551a | <0.013 |
| 552 | 0.014 |
| 553a | <0.013 |
| 554a | 0.253 |
| 555a | <0.013 |
| 555b | <0.013 |
| 556a | 0.032 |
| 556b | <0.013 |
| 557a | <0.013 |
| 558a | 0.90 |
| 558b | 3.75 |
| 559a | 0.025 |
| 559b | 0.14 |
| 559c | <0.013 |
| 559d | <0.013 |
| 560a | 0.019 |
| 560b | 0.32 |
| 562a | 0.068 |
| 563a | 0.219 |
| 563b | 0.025 |
| 566a | 0.293 |
| 566b | 0.149 |
| 567a | 0.330 |

TABLE B1-continued

| Compound No. | HPK1 Ki (nM) |
| --- | --- |
| 567b | 0.119 |
| 568a | 0.185 |
| 568b | 0.018 |
| 569a | 0.277 |
| 569b | 0.254 |
| 569c | 0.029 |
| 569d | 0.031 |
| 571a | 0.014 |
| 571b | <0.013 |
| 572a | <0.013 |
| 573a | 0.015 |
| 573b | 0.019 |
| 573c | 0.017 |
| 573d | <0.013 |
| 574a | 0.020 |
| 574b | <0.013 |
| 575a | <0.013 |
| 576a | <0.013 |
| 577a | 0.015 |
| 577b | <0.013 |
| 578a | 0.028 |
| 578b | 0.15 |
| 579 | 0.85 |
| 580 | <0.013 |
| 581a | 0.43 |
| 582a | 0.020 |
| 582b | 0.020 |
| 583a | 0.12 |
| 583b | 0.021 |
| 583c | 0.099 |
| 583d | 0.72 |
| 584a | 0.14 |
| 584b | 2.1 |
| 601 | <0.013 |
| 701 | <0.013 |
| 702 | <0.013 |
| 703a | 0.022 |
| 703b | <0.013 |
| 703c | 0.030 |
| 704 | <0.013 |
| 705 | 0.15 |
| 706 | <0.013 |
| 707 | <0.013 |
| 708 | <0.013 |
| 709 | <0.013 |
| 710a | <0.013 |
| 711a | <0.013 |
| 711b | <0.013 |
| 712ab | <0.013 |
| 713a | <0.013 |
| 714 | <0.013 |
| 719a | 0.016 |
| 720 | <0.013 |
| 721 | <0.013 |
| 722a | <0.013 |
| 722b | <0.013 |
| 723a | 0.469 |
| 723b | 0.029 |
| 724a | 0.019 |
| 724b | 0.019 |
| 726a | <0.013 |
| 726b | 0.016 |
| 727a | <0.013 |
| 727b | <0.013 |
| 728a | <0.013 |
| 729a | 1.37 |
| 729b | 0.015 |
| 730a | <0.013 |
| 730b | <0.013 |
| 730c | <0.013 |
| 730d | <0.013 |
| 732a | <0.013 |
| 733a | <0.013 |
| 734a | <0.013 |
| 736a | <0.013 |
| 736b | <0.013 |
| 739 | <0.013 |
| 740a | <0.013 |
| 740b | <0.013 |
| 742 | 1.12 |
| 745 | 0.29 |
| 746 | <0.013 |
| 747a | <0.013 |
| 747b | <0.013 |
| 748a | <0.013 |
| 748b | 0.018 |
| 749 | 0.102 |
| 750a | 0.96 |
| 750b | <0.013 |
| 751 | 0.044 |
| 752 | 0.52 |
| 753 | 0.039 |
| 754 | 0.205 |
| 755 | 0.090 |
| 756 | 0.020 |

Example B3: Human T-cell IL2 Induction Assay

Assay Principle: Anti-CD3 and anti-CD28 activates TCR signaling in primary human pan T cells leading to IL-2 promoter induction. Secreted IL-2 in cell culture supernatant is detected by electrochemiluminescence using a capture antibody against IL-2 and an anti-IL-2 antibody labeled with SULFO-tag. Also see www.mesoscale.com for additional electrochemiluminescence technology information.

Assay Procedure: Incubate primary human pan T cells with varying concentrations of test compounds for 30 minutes in a humidified incubator at 37° C. and 5% $CO_2$. Transfer cells to a plate pre-coated with a fixed concentration of anti-human CD3 (determined separately for each donor lot) and add soluble anti-human CD28 (final concentration=1 µg/ml). Stimulate cells in a humidified incubator at 37° C. and 5% $CO_2$ for 4 hours. Transfer 25 µl of supernatant to a MSD single spot plate pre-coated with an anti-human IL-2 antibody. Incubate MSD plate overnight at 4° C. with gentle shaking. Wash MSD plate 4× with wash buffer. Add SULFO-tagged detection antibody at a 1:50 dilution and incubate at room temperature shaking for 2 hours. Wash MSD plate 4× with wash buffer and add 150 µl 2×MSD read buffer. Read on an MSD instrument. Normalize data to stimulated/untreated controls to calculate % activity at each concentration of compound.

Materials:

Frozen Primary Human Pan-T Cells (StemCell Technologies #70024)

anti-human CD3 (OKT3 clone) (eBioscience #16-0037-81)

anti-human CD28 (CD28.2 clone) (BD #555725)

96-well Human IL-2 tissue culture kit (MSD #K151AHB-4)

Instrumentation:

Biomek FX for liquid handling (Beckman Coulter)

MSD SECTOR S 600 (Meso Scale Discovery)

Exemplary compounds of Formula (I) were tested in the human T-cell IL-2 induction assays. The % increase measured for IL-2 in cells treated by the test compounds relative to untreated cells are provided in Table B2 for certain compounds.

TABLE B2

| Compound No. | % IL-2 increase relative to untreated cells | Assayed concentration (µM) |
|---|---|---|
| 409b | 2838% | 2.778 |
| 411a | 2119% | 2.778 |
| 416a | 2989% | 2.778 |
| 441b | 1158% | 2.778 |
| 445b | 1436% | 2.778 |
| 477b | 1494% | 5.469 |
| 477d | 1745% | 8.33 |
| 482a | 737% | 2.778 |
| 482b | 1719% | 2.778 |
| 484b | 1782% | 2.778 |
| 486 | 1400% | 2.778 |
| 510c | 700% | 2.778 |
| 512b | 2613% | 2.778 |
| 526b | 970% | 2.778 |
| 526c | 1677% | 2.778 |
| 527 | 738% | 2.778 |
| 535a | 831% | 2.778 |
| 536b | 2280% | 8.333 |
| 546a | 914% | 8.33 |
| 550a | 1059% | 2.778 |
| 574a | 1634% | 1.196 |
| 701 | 4163% | 2.778 |
| 727b | 938% | 0.926 |
| 751 | 1363% | 2.778 |
| 755 | 1061% | 2.778 |

Example B4: pSLP76 Assay

Assay Principle: Anti-CD3 activates TCR signaling in human Jurkat cells leading to phosphorylation of SLP-76 at the 5376 reside by HPK-1. Phospho-SLP76 (S376) is detected by sandwich ELISA using an anti-pSLP76(S376) capture antibody and a biotinylated anti-SLP76 detection antibody.

Materials:
Jurkat, clone E6-1 (ATCC Cat #TIB-152)
anti-CD3 DynaBeads (Invitrogen, Cat #111.51D)
anti-pSLP76 (S376) rabbit monoclonal (Genentech)
Biotinylated anti-SLP76 rabbit polyclonal
(Thermo, biotin conjugation performed in-house)
Streptavidin—Horseradish Peroxidase (GE, Cat #RPN4401V)
TMB Substrate (Cell Signaling, Cat #7004)
STOP Solution (Cell Signaling, Cat #7002)

Assay Procedure:

Incubate Jurkat cells with varying concentrations of test compounds for 30 minutes in a humidified incubator at 37° C. and 5% $CO_2$. Add anti-CD3 DynaBeads at a 4:1 bead:cell ratio. Stimulate cells in a humidified incubator at 37° C. and 5% $CO_2$ for 10 minutes. Add cold lysis buffer and incubate on a shaker at 4° C. for 30 minutes. Transfer cell lysates to a pre-blocked ELISA plate coated with capture antibody. Incubate at room temperature shaking for 2 hours. Wash ELISA plate 5× with wash buffer and add 25 µl of biotinylated detection antibody at a final concentration of 0.5 µg/ml. Incubate at room temperature shaking for 1 hour. Wash ELISA plate 5× with wash buffer and add 25 µl of streptavidin enzyme conjugate at a final dilution of 1:8000. Incubate at room temperature shaking for 20 minutes. Wash ELISA plate 5× with wash buffer and add 25 µl of TMB substrate solution. Incubate at room temperature in the dark shaking for 20 minutes. Add 25 µl of STOP solution and read on SoftMax Pro for absorbance at 450 nm.

Exemplary compounds of Formula (I) were tested in pSLP76 assays. The $IC_{50}$ values measured are provided in Table B3 for certain compounds.

TABLE B3

| Compound No. | pSLP76 $IC_{50}$ (µM) | HHep Clearance (mL/min/kg) | MDCK AB $P_{app}$ (×$10^{-6}$ cm/s) |
|---|---|---|---|
| 401 | 0.097 | 9.2 | 18 |
| 403a | 0.048 | 7.7 | 10 |
| 441b | 0.036 | 6.9 | 15 |
| 477d | 0.066 | 5.7 | 16 |
| 482a | 0.038 | 11 | 15 |
| 484b | 0.026 | 7.9 | 19 |
| 510c | 0.062 | 8.7 | 20 |
| 527 | 0.064 | 11 | 13 |
| 546a | 0.062 | 6.5 | 10 |
| 555b | 0.024 | 13 | 15 |
| 574a | 0.032 | 8.3 | 12 |
| 751 | 0.041 | <6.2 | 11 |
| 755 | 0.046 | 6.8 | 10 |

Example B5: Permeability Assay

Cell permeability of compounds of interest was assessed in the gMDCKI cell line, which is a modified MDCKI (Madin-Darby canine kidney) originally acquired from American Type Culture Collection (Manassa, Va.) and generated at Genentech. The cells were seeded on 24-well Millicell plates (Millipore, Billerca, Mass.) 4 days prior to use (polyethylene terephtalate membrane, 1 mm pore size) at a seeding density of 2.5×$10^5$ cells/mL at 37° C. with 5% $CO_2$ and 95% humidity. Test article was tested at 10 µM in the apical-to-basolateral (A-B) and basolateral-to-apical (B-A) directions. Test compound was dissolved in transport buffer consisting of Hank's balanced salt solution and 10 mm HEPES (Invitrogen Corporation, Grand Island, N.Y.). Transepithelial electrical resistance (TEER) and lucifer yellow (LY) permeability were used to monitor monolayer integrity at the beginning and the end of the experiments, respectively. Test articles were analyzed by LC-MS/MS.

The apparent permeability ($P_{app}$), in the apical to A-B and B-A directions, is calculated after a 2-hour incubation as:

$$P_{app}=(dQ/dt)(1/AC_0)$$

where: dQ/dt=rate of compound appearance in the receiver compartment; A=Surface area of the insert; $C_0$=Initial substrate concentration at $T_0$. The efflux ratio (ER) is calculated as ($P_{app}$, B–A/$P_{app}$, A–B).

Cell permeability were assessed for exemplary compounds of Formula (I). The MDCK AB $P_{app}$ values are listed in Table B3 for certain compounds.

Example B6: Hepatocyte Stability Assay

Metabolic stability of compounds are assessed using a hepatocyte stability assay. Cryopreserved human hepatocytes from a 10 donor pool are quickly thawed at 37° C., suspended in prewarmed In VitroGRO™ HT Medium, and then centrifuged at 100×g at room temperature for 10 min. The supernatants are discarded, and cells are resuspended in 5 mL Dulbecco's Modified Eagle Medium (DMEM) medium. Cell viability in suspension is counted on a Hepatometer® Vision (Lonza, N.C.), and viable cells are then adjusted to 1.0×$10^{16}$ cells/mL in DMEM. Compounds are first diluted to 2 µM with DMEM medium, and then aliquots of 125 µL of drug-containing medium are transferred to 96-well non-coated plates. Incubation is initiated by the addition of 125 µL of hepatocyte suspension to yield a total incubation volume of 250 µL. Final concentration of each compound is 1 µM, and final cell density is $0.5 \times 10^6$ cells/mL. Incubations are conducted in a humidified incubator at 37° C. Aliquots of 50 µL incubation medium are taken out at different time intervals (0, 60, 120 and 180 min), and immediately mixed with 100 µL of ice-cold acetonitrile containing 50 nM propranolol (internal standard). Samples are then centrifuged at 10,000×g for 10 min, and 80 µL of supernatant is taken out and diluted with 160 µL of water prior to LC/MS-MS analysis. The in vitro intrinsic clearance and scaled hepatic clearance were determined as described in Obach et al. *J. Pharmacol. Exp. Ther.* 283:46-58 (1997).

Human hepatocyte stability was assessed for exemplary compounds of Formula (I) according to the above procedures. The human hepatic clearance (HHep) values are listed in Table B3 for certain compounds.

Example B7: Pharmacokinetics (PK) Studies

Pharmacokinetic Study in Rat: Male Sprague Dawley rats obtained from Lingchang/Vital River Laboratory Animal Technology Co., Ltd., (Shanghai/Beijing, P.R. China) with body weight ranging between 200 g to 300 g were use in the PK studies. Group of 3 rats were given a 1 mg/kg intravenous bolus (IV) dose of the test article in solution formulation, and another group of 3 rats were given a 2 or 5 mg/kg oral (PO) dose of test article as a 0.5% methylcellulose with 0.2% Tween 80 (MCT) suspension or as a solution. Blood samples (250 µL, per time point) were collected serially via the catheter in femoral artery at 0.033, 0.083, 0.25, 0.5, 1, 2, 4, 6, and 8 hours after IV or PO administration from each of the rat. Blood samples were collected into pre-chilled tubes containing Potassium (K2) EDTA and centrifuged at 3,200 g for 10 minutes at 2 to 8° C. within 1 hour of collection to harvest plasma. Plasma samples were stored at −70° C. until LC/MS/MS analysis. Concentration in each plasma sample was determined by a non-validated LC/MS/MS. Data is acquired using multiple reaction monitoring (MRM) with specific transitions monitored for each compound.

Pharmacokinetic Analysis: Pharmacokinetic parameters were calculated by non-compartmental methods as described in Gibaldi and Perrier (Gibaldi and Perrier, 1982) using Phoenix® WinNonlin® version 6.4 (Certara L. P.). Following PO administration, percent bioavailability (% F) was determined for each animal by dividing the dose normalized area under the plasma concentration-time curve, extrapolated to infinity ($AUC_{inf}$) obtained following each PO dose by the mean dose normalized $AUC_{inf}$ of the animals dosed by IV injection. All PK parameters are presented as mean±standard deviation (SD).

Pharmacokinetic studies were conducted in rat for exemplary compounds of Formula (I). The percent bioavailability (% F) values determined are listed in Table B4 for certain compounds, together with the dosage, vehicle and form used in the studies.

TABLE B4

| Compound No. | % F | Dose (mg/kg) | Vehicle | Form |
|---|---|---|---|---|
| 401 | 16% | 5 | MCT | Suspension |
| 403a | 4% | 5 | 10/90 DMSO/MCT | Suspension |
| 441b | 30% | 2 | 10/90 DMSO/MCT | Solution |
| 477d | 43% | 2 | 10% DMSO/60% PEG400/ 30% Water | Solution |
| 482a | 41% | 5 | MCT, pH = 2.5 | Suspension |
| 484b | 16% | 5 | 10% DMSO/60% PEG400/ 30% Water | Solution |
| 510c | 28% | 2 | MCT | Suspension |
| 527 | 12% | 2 | MCT | Suspension |
| 546a | 22% | 5 | 10% DMSO/35% PEG400/ 55% Water | Solution |
| 555b | 34% | 2 | 10% DMSO/60% PEG400/ 30% Water | Solution |
| 574a | 16% | 2 | 10% DMSO/60% PEG400/ 30% Water | Solution |
| 751 | 9.4% | 2 | 10% DMSO/60% PEG400/ 30% Water | Solution |
| 755 | 4% | 5 | 10% DMSO/60% PEG400/ 30% Water | Solution |

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed within the invention. The upper and lower limits of these small ranges which may independently be included in the smaller rangers is also encompassed within the invention, subject to any specifically excluded limit in the stated range. Where the stated range includes one or both of the limits, ranges excluding either or both of those included limits are also included in the invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:
1. A compound of formula (IA):

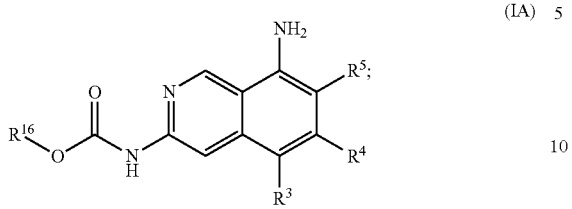

or a pharmaceutically acceptable salt thereof, wherein:
$R^{16}$ is $C_{1-6}$ alkyl, $C_{3-10}$ cycloalkyl, 7- to 14-membered heteroaryl, or 3- to 14-membered heterocyclyl; wherein the $C_{1-6}$ alkyl, $C_{3-10}$ cycloalkyl, 7- to 14-membered heteroaryl and 3- to 14-membered heterocyclyl of $R^{16}$ are each optionally substituted with 1, 2, 3, 4 or 5 substituents independently selected from $R^{10}$;
$R^3$ is hydrogen, halogen, cyano, $C_{1-6}$ alkyl, $C_{3-8}$ cycloalkyl, 3- to 14-membered heterocyclyl, or —$OR^7$; wherein the $C_{1-6}$ alkyl, $C_{3-8}$ cycloalkyl and 3- to 14-membered heterocyclyl of $R^3$ are each optionally substituted with 1, 2, 3, 4 or 5 substituents independently selected from $R^{10}$;
$R^4$ is 5- to 14-membered heteroaryl optionally substituted with 1, 2, 3, 4 or 5 substituents independently selected from $R^{10}$;
$R^5$ is hydrogen, halogen, cyano, $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl, 3- to 14-membered heterocyclyl, —$C(O)R^6$, —$C(O)OR^7$, —$C(O)NR^{8a}R^{8b}$, —$OR^7$, —$OC(O)R^6$, —$OC(O)NR^{8a}R^{8b}$, —$SR^7$, —$S(O)R^9$, —$S(O)_2R^9$, —$S(O)_2NR^{8a}R^{8b}$, —$P(O)R^{9a}R^{9b}$, —$NR^{8a}R^{8b}$, —$N(R^8)C(O)OR^6$, —$N(R^8)C(O)OR^7$, —$N(R^8)C(O)NR^{8a}R^{8b}$, —$N(R^8)S(O)_2R^9$, or —$N(R^8)S(O)_2NR^{8a}R^{8b}$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^5$ are each optionally substituted with 1, 2, 3, 4 or 5 substituents independently selected from $R^{10}$;
each $R^6$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 14-membered heteroaryl and 3- to 12-membered heterocyclyl of $R^6$ are each optionally substituted with 1, 2, 3, 4 or 5 substituents independently selected from $R^{10}$;
each $R^7$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^7$ are each optionally substituted with 1, 2, 3, 4 or 5 substituents independently selected from $R^{10}$;
each $R^8$ is independently hydrogen or $C_{1-6}$ alkyl;
each $R^{8a}$ and $R^{8b}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{8a}$ and $R^{8b}$ are each optionally substituted with 1, 2, 3, 4 or 5 substituents independently selected from $R^{10}$;
or $R^{8a}$ and $R^{8b}$ are taken together with the nitrogen atom to which they are attached to form a 4- to 12-membered heterocyclyl optionally substituted with 1, 2, 3, 4 or 5 substituents independently selected from $R^{10}$;
each $R^9$ is independently $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^9$ are each optionally substituted with 1, 2, 3, 4 or 5 substituents independently selected from $R^{10}$;
each $R^{9a}$ and $R^{9b}$ is independently $C_{1-6}$ alkyl, $C_{3-8}$ cycloalkyl, $C_{6-10}$ aryl, 5- to 14-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{9a}$ and $R^{9b}$ are each optionally substituted with 1, 2, 3, 4 or 5 substituents independently selected from $R^{10}$;
or $R^{9a}$ and $R^{9b}$ are taken together with the phosphorus atom to which they are attached to form a 4- to 12-membered heterocyclyl optionally substituted with 1, 2, 3, 4 or 5 substituents independently selected from $R^{10}$;
each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —$C(O)R^a$, —$C(O)OR^b$, —$C(O)NR^cR^d$, —$OR^b$, —$OC(O)R^a$, —$OC(O)NR^cR^d$, —$SR^b$, —$S(O)R^e$, —$S(O)_2R^e$, —$S(O)(=NH)R^e$, —$S(O)_2NR^cR^d$, —$NR^cR^d$, —$N(R^f)C(O)R^a$, —$N(R^f)C(O)OR^b$, —$N(R^f)C(O)NR^cR^d$, —$N(R^f)S(O)_2R^e$, —$N(R^f)S(O)_2NR^cR^d$, or —$P(O)R^gR^h$; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^{10}$ are each optionally substituted with 1, 2, 3 or 4 substituents independently selected from $R^{11}$;
each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^a$ are each optionally substituted with 1, 2, 3 or 4 substituents independently selected from $R^{11}$;
each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$;
each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$;
or $R^c$ and $R^d$ are taken together with the nitrogen atom to which they are attached to form a 4- to 12-membered heterocyclyl optionally substituted with 1, 2, 3 or 4 substituents independently selected from $R^{11}$;
each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$;

each $R^f$ is independently hydrogen or $C_{1-6}$ alkyl;

each $R^g$ and $R^h$ is independently $C_{1-6}$ alkyl, $C_{3-8}$ cycloalkyl, $C_{6-10}$ aryl, 5- to 10-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^g$ and $R^h$ are each optionally substituted with 1, 2, 3 or 4 substituents independently selected from $R^{11}$;

or $R^g$ and $R^h$ are taken together with the phosphorus atom to which they are attached to form a 4- to 12-membered heterocyclyl optionally substituted with 1, 2, 3 or 4 substituents independently selected from $R^{11}$;

each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)$R^{a1}$, —C(O)O$R^{b1}$, —C(O)NR$^{c1}R^{d1}$, —O$R^{b1}$, —OC(O)$R^{a1}$, —OC(O)NR$^{c1}R^{d1}$, —S$R^{b1}$, —S(O)$R^{e1}$, —S(O)$_2R^{e1}$, —S(O)$_2$NR$^{c1}R^{d1}$, —NR$^{c1}R^{d1}$, —N($R^{f1}$)C(O)$R^{a1}$, —N($R^{f1}$)C(O)O$R^{b1}$, —N($R^{f1}$)C(O)NR$^{c1}R^{d1}$, —N($R^{f1}$)S(O)$_2R^{e1}$, —N($R^{f1}$)S(O)$_2$NR$^{c1}R^{d1}$, or —P(O)$R^{g1}R^{h1}$; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)NR$^{c2}R^{d2}$, —O$R^{b2}$, —OC(O)$R^{a2}$, —OC(O)NR$^{c2}R^{d2}$, —S(O)$_2R^{e2}$, —S(O)$_2$NR$^{c2}R^{d2}$, —NR$^{c2}R^{d2}$, —N($R^{f2}$)C(O)$R^{a2}$, —N($R^{f2}$)C(O)O$R^{b2}$, —N($R^{f2}$)C(O)NR$^{c2}R^{d2}$, —N($R^{f2}$)S(O)$_2R^{e2}$, —N($R^{f2}$)S(O)$_2$NR$^{c2}R^{d2}$, or —P(O)$R^{g2}R^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{a2}$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_{1-6}$ alkyl, $C_{3-6}$ cycloalkyl, and 3- to 8-membered heterocyclyl of $R^{g2}$ and $R^{h2}$ are each optionally substituted with 1, 2, 3 or 4 substituents independently selected from $R^{13}$;

or $R^{g2}$ and $R^{h2}$ are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl.

2. The compound of claim 1, or a pharmaceutically acceptable salt thereof, wherein $R^3$ is hydrogen.

3. The compound of claim 1, or a pharmaceutically acceptable salt thereof, wherein $R^5$ is hydrogen, fluoro or chloro.

4. The compound of claim 1, or a pharmaceutically acceptable salt thereof, wherein $R^5$ is halogen.

5. The compound of claim 3, or a pharmaceutically acceptable salt thereof, wherein $R^5$ is fluoro.

6. The compound of claim 1, or a pharmaceutically acceptable salt thereof, wherein $R^4$ is

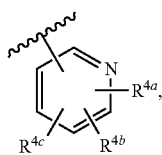

wherein the wavy line represents the point of attachment, $R^{4a}$, $R^{4b}$ and $R^{4c}$ are each independently hydrogen or $R^{10}$, or two vicinal $R^{4(a-c)}$ are taken together with the atoms to which they are attached form a fused 5- to 10-membered heterocyclyl optionally substituted with 1, 2, 3 or 4 substituents independently selected from $R^{10}$ or a fused $C_{5-8}$ cycloalkyl optionally substituted with 1, 2, 3 or 4 substituents independently selected from $R^{10}$.

7. The compound of claim 6, or a pharmaceutically acceptable salt thereof, wherein $R^4$ is

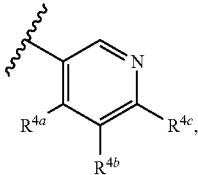

wherein $R^{4a}$ is $C_{1-6}$ alkyl, and $R^{4b}$ and $R^{4c}$ are taken together with the atoms to which they are attached form a fused 5- to 10-membered heterocyclyl optionally substituted with 1, 2, 3 or 4 substituents independently selected from the group consisting of $C_{1-6}$ alkyl, hydroxyl, halogen and cyano, or a fused $C_{5-8}$ cycloalkyl optionally substituted with 1, 2, 3 or 4 substituents independently selected from the group consisting of $C_{1-6}$ alkyl, hydroxyl, halogen and cyano.

8. The compound of claim 7, or a pharmaceutically acceptable salt thereof, wherein $R^4$ is

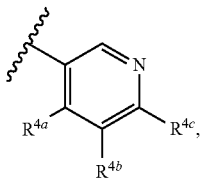

wherein $R^{4a}$ is $C_{1-6}$ alkyl, and $R^{4b}$ and $R^{4c}$ are taken together with the atoms to which they are attached form a fused 5- to 10-membered heterocyclyl.

9. The compound of claim 1, or a pharmaceutically acceptable salt thereof, wherein $R^4$ is selected from the group consisting of:

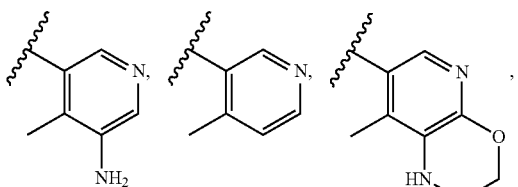

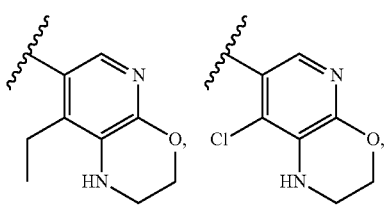

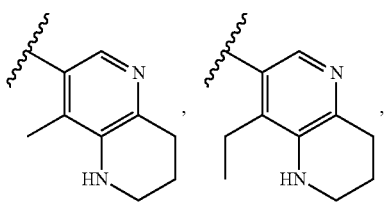

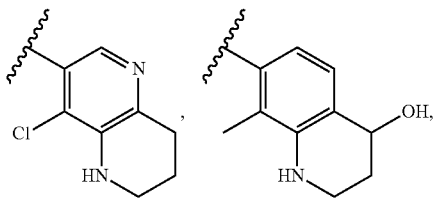

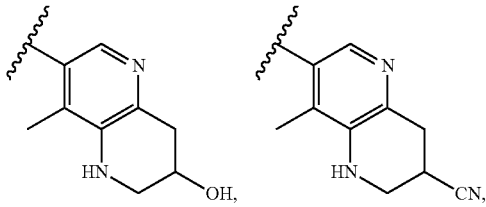

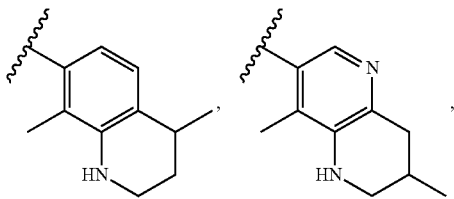

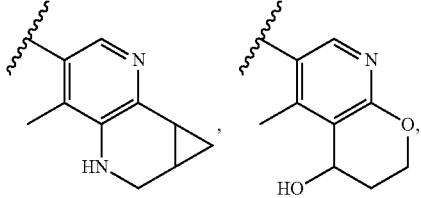

-continued

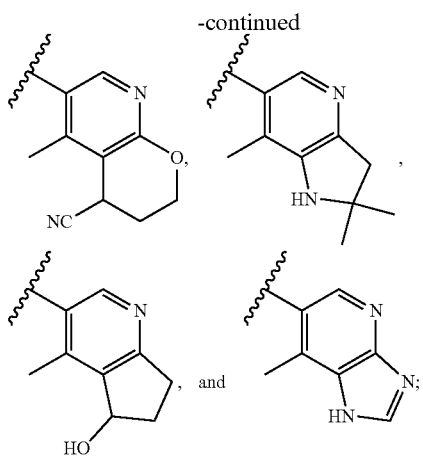

wherein the wavy line represents the point of attachment.

10. The compound of claim 1, or a pharmaceutically acceptable salt thereof, wherein $R^4$ is selected from the group consisting of:

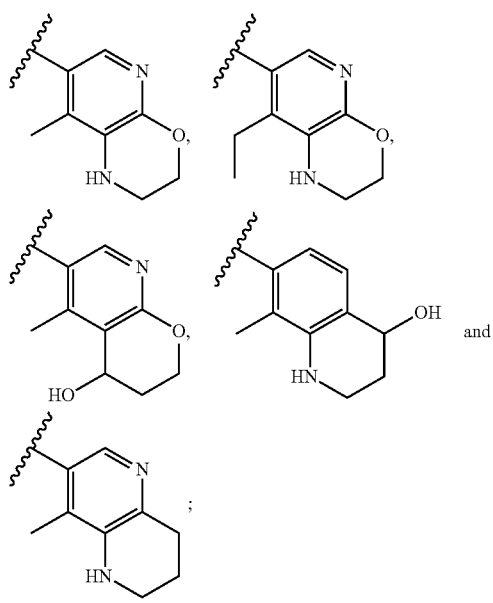

wherein the wavy line represents the point of attachment.

11. The compound of claim 1, or a pharmaceutically acceptable salt thereof, wherein $R^4$ is

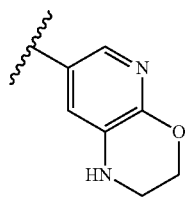 [SMILES: *c1cnc2c(c1)NCCO2]

substituted with 1 substituent selected from $R^{10}$.

12. The compound of claim 11, or a pharmaceutically acceptable salt thereof, wherein $R^4$ is

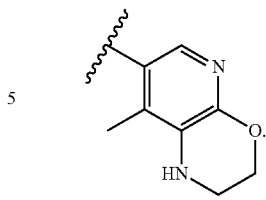

13. The compound of claim 1, or a pharmaceutically acceptable salt thereof, wherein $R^{16}$ is 3- to 14-membered heterocyclyl optionally substituted with 1, 2, 3, 4 or 5 substituents independently selected from $R^{10}$.

14. The compound of claim 13, or a pharmaceutically acceptable salt thereof, wherein $R^{16}$ is a 4- to 10-membered heterocyclyl having 1 or 2 heteroatoms independently selected from the group consisting of N, O and S, and optionally substituted with 1, 2, 3, 4 or 5 substituents independently selected from $R^{10}$.

15. The compound of claim 13, or a pharmaceutically acceptable salt thereof, wherein $R^{16}$ is a 4- to 10-membered heterocyclyl having 1 or 2 heteroatoms independently selected from the group consisting of N, O and S, and substituted with 1 substituent selected from $R^{10}$.

16. The compound of claim 1, or a pharmaceutically acceptable salt thereof, wherein $R^{16}$ is $C_{3-8}$ cycloalkyl optionally substituted with 1, 2, 3, 4 or 5 substituents independently selected from $R^{10}$.

17. The compound of claim 16, or a pharmaceutically acceptable salt thereof, wherein $R^{16}$ is $C_{3-8}$ cycloalkyl substituted with 1 substituent independently selected from $R^{10}$.

18. The compound of claim 1, or a pharmaceutically acceptable salt thereof, wherein $R^{16}$ is selected from the group consisting of:

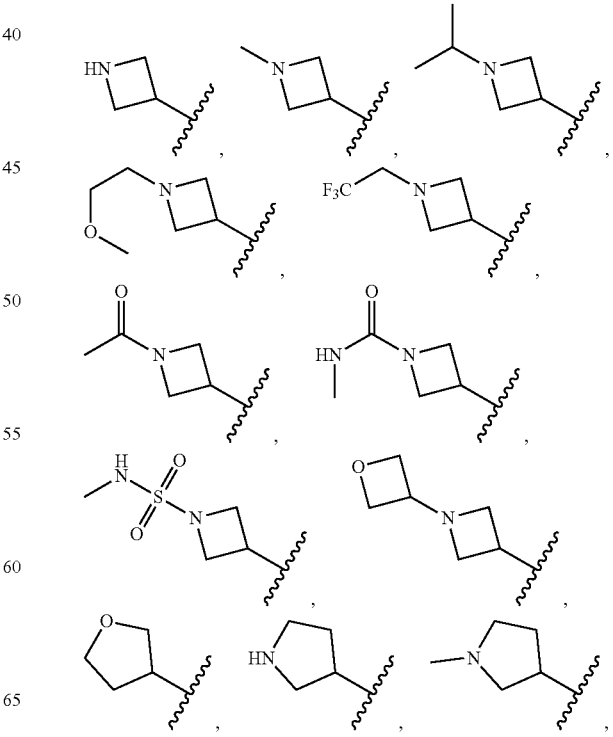

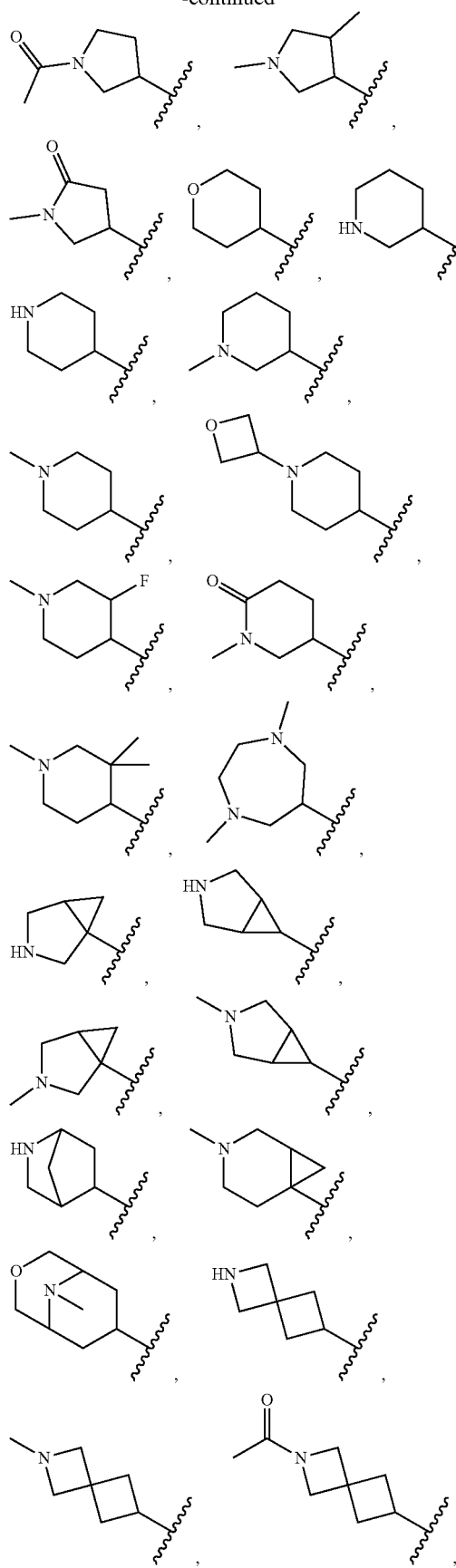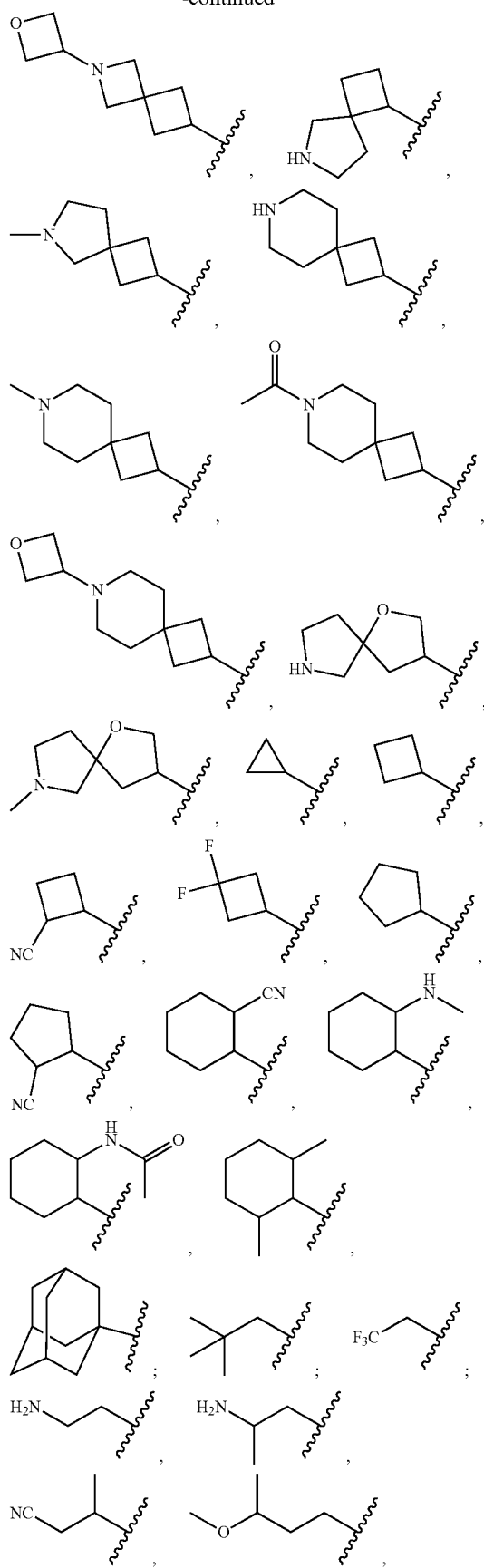

759
-continued
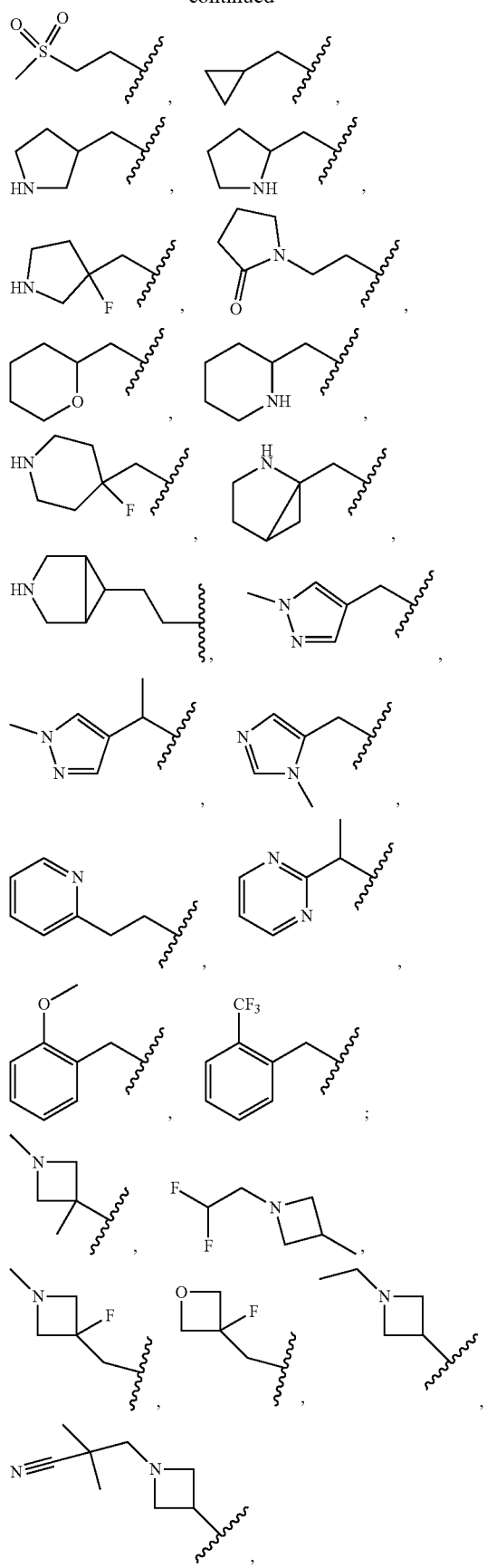
760
-continued
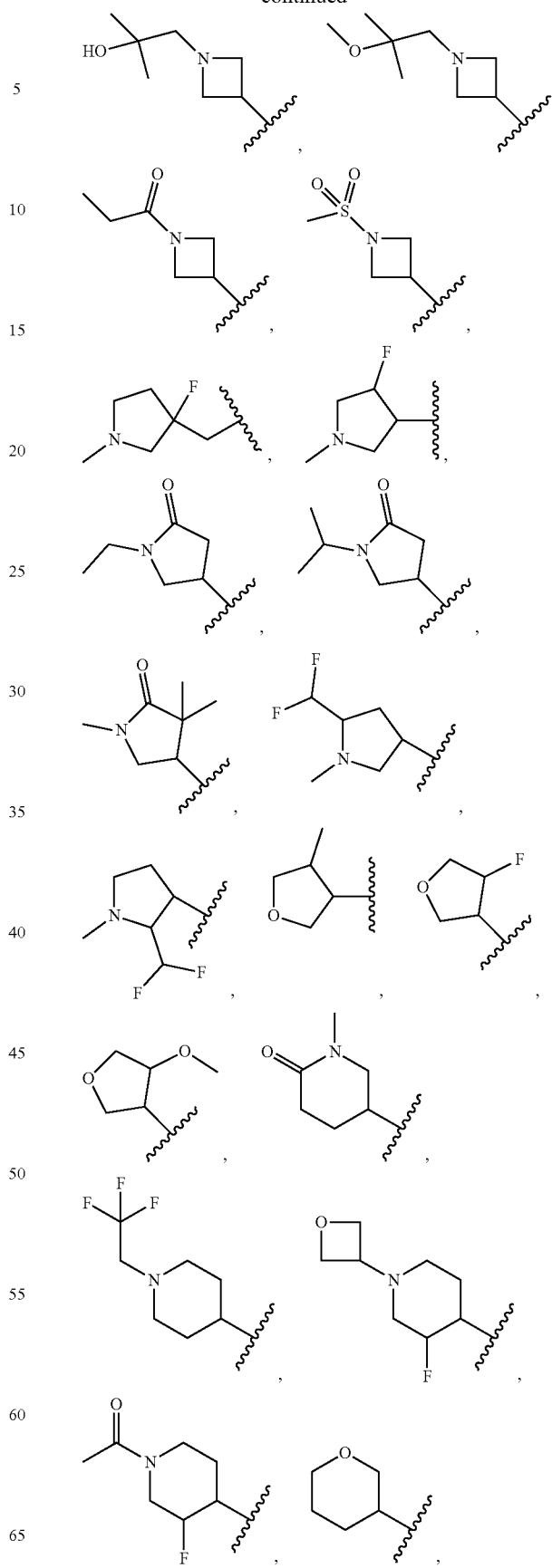

761
-continued

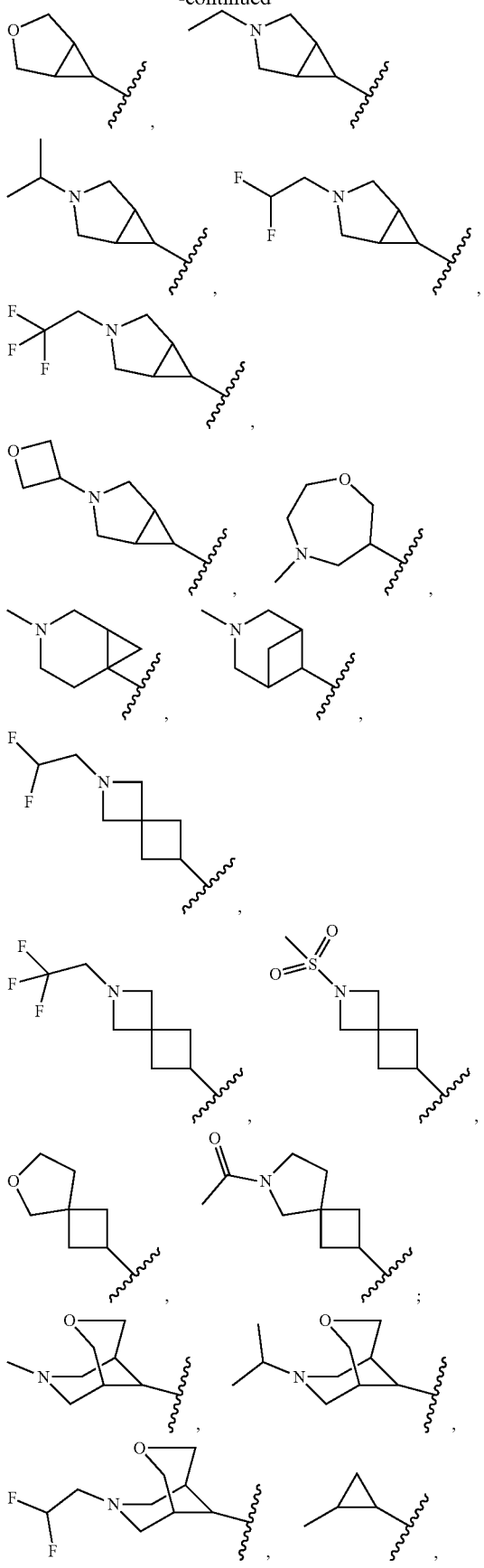

762
-continued

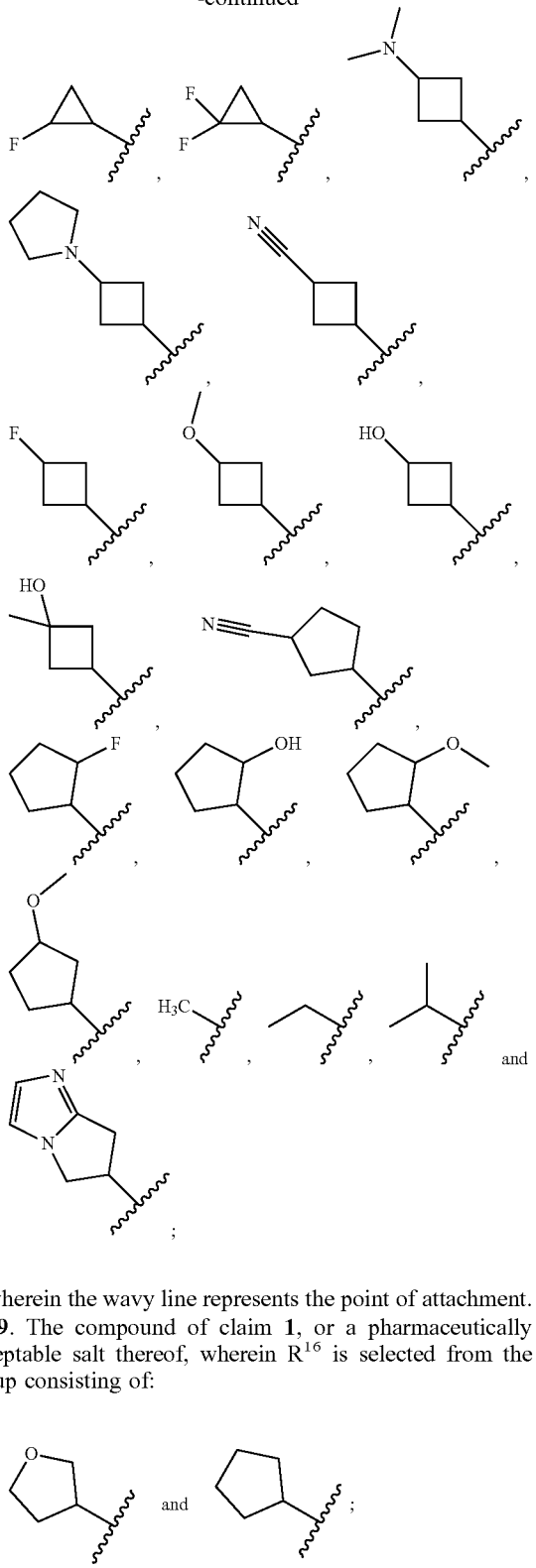

wherein the wavy line represents the point of attachment.

19. The compound of claim 1, or a pharmaceutically acceptable salt thereof, wherein $R^{16}$ is selected from the group consisting of:

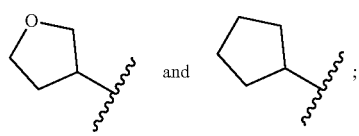 [SMILES: *C1CCOC1 ; *C1CCCC1]

each independently optionally substituted with 1, 2, 3, 4 or 5 substituents independently selected from $R^{10}$.

20. The compound of claim 1, or a pharmaceutically acceptable salt thereof, wherein $R^{10}$ is independently $C_{1-6}$ alkyl or cyano.

21. The compound of claim 20, or a pharmaceutically acceptable salt thereof, wherein $R^{10}$ is independently methyl or cyano.

22. The compound of claim 20, or a pharmaceutically acceptable salt thereof, wherein $R^{10}$ is independently methyl.

23. The compound of claim 1, or a pharmaceutically acceptable salt thereof, wherein:

$R^3$ is hydrogen;

$R^4$ is

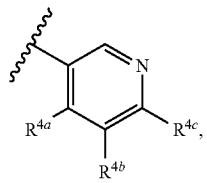

wherein $R^{4a}$ is $C_{1-6}$ alkyl, and $R^{4b}$ and $R^{4c}$ are taken together with the atoms to which they are attached form a fused 5- to 10-membered heterocyclyl;

$R^5$ is halogen;

$R^{16}$ is a 4- to 10-membered heterocyclyl having 1 or 2 heteroatoms independently selected from the group consisting of N, O and S, or $C_{3-8}$ cycloalkyl, wherein said 4- to 10-membered heterocyclyl and $C_{3-8}$ cycloalkyl are substituted with 1 substituent selected from $R^{10}$; and $R^{10}$ is $C_{1-6}$ alkyl or cyano.

24. The compound of claim 1, or a pharmaceutically acceptable salt thereof, wherein:

$R^3$ is hydrogen;

$R^4$ is

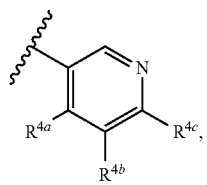

wherein $R^{4a}$ is methyl, and $R^{4b}$ and $R^{4c}$ are taken together with the atoms to which they are attached to form a morpholine ring;

$R^5$ is fluoro;

$R^{16}$ is selected from the group consisting of

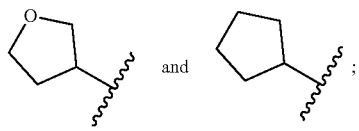

wherein $R^{16}$ is substituted with 1 substituent selected from $R^{10}$; and $R^{10}$ is methyl or cyano.

25. The compound of claim 1, wherein the compound is of the formula (IA-1):

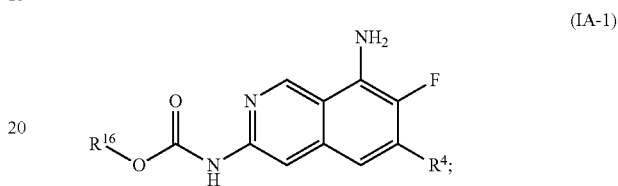

(IA-1)

or a pharmaceutically acceptable salt thereof.

26. The compound of claim 1, wherein the compound is of the formula (IA-2):

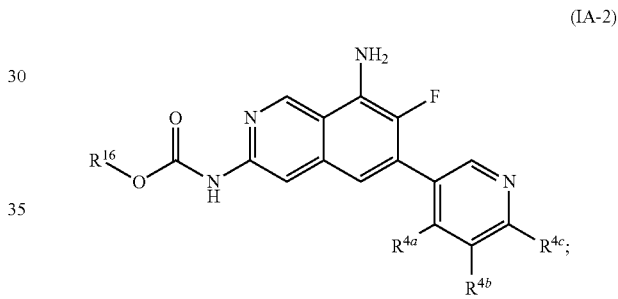

(IA-2)

or a pharmaceutically acceptable salt thereof, wherein $R^{4a}$ is $C_{1-6}$ alkyl; $R^{4b}$ and $R^{4c}$ are independently hydrogen or $R^{10}$, or $R^{4b}$ and $R^{4c}$ are taken together with the atoms to which they are attached form a fused 5- to 10-membered heterocyclyl optionally substituted with 1, 2, 3 or 4 substituents independently selected from the group consisting of $C_{1-6}$ alkyl, hydroxyl, halogen and cyano, or a fused $C_{5-8}$ cycloalkyl optionally substituted with 1, 2, 3 or 4 substituents independently selected from the group consisting of $C_{1-6}$ alkyl, hydroxyl, halogen and cyano.

27. The compound of claim 1, or a pharmaceutically acceptable salt thereof, wherein the compound is selected from the group consisting of:

| No. | Structure | Name |
|---|---|---|
| 401 | 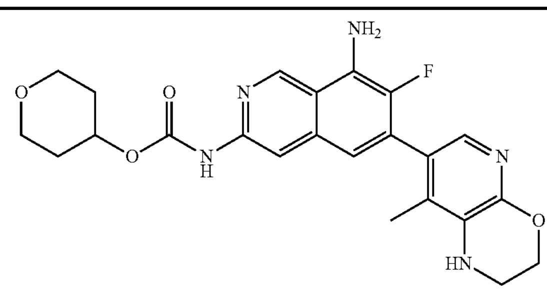 | Tetrahydro-2H-pyran-4-yl(8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 402 | 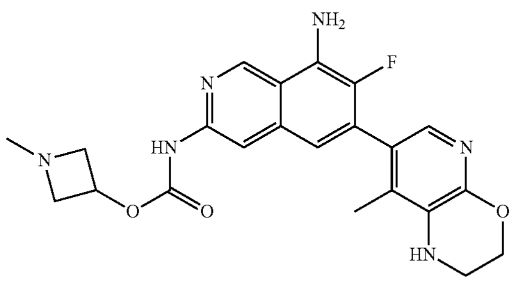 [SMILES: Cc1c(-c2cc3cc(NC(=O)OC4CN(C)C4)ncc3c(N)c2F)cnc2c1NCCO2] | 1-Methylazetidin-3-yl (8-amino-7-fluoro-6-(8-methyl-2,3-dihydro-1H-pyrido[2,3-b][1,4]oxazin-7-yl)isoquinolin-3-yl)carbamate; |
| 403 | 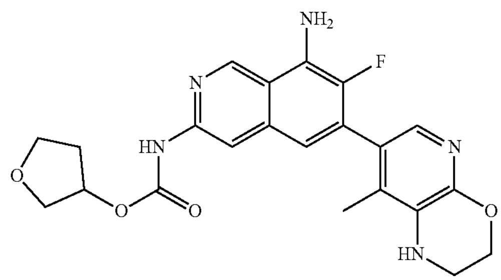 [SMILES: Cc1c(-c2cc3cc(NC(=O)OC4CCOC4)ncc3c(N)c2F)cnc2c1NCCO2] | Tetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 403a 403b | | (R)-Tetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (S)-Tetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 404 | 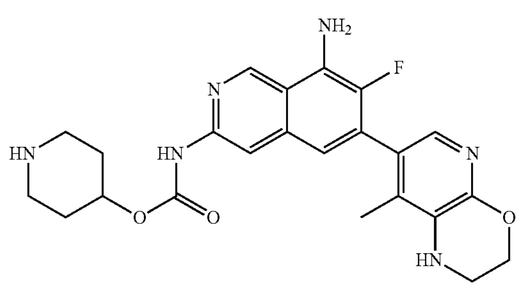 [SMILES: Cc1c(-c2cc3cc(NC(=O)OC4CCNCC4)ncc3c(N)c2F)cnc2c1NCCO2] | Piperidin-4-yl (8-amino-7-fluoro-6-(8-methyl-2,3-dihydro-1H-pyrido[2,3-b][1,4]oxazin-7-yl)isoquinolin-3-yl)carbamate; |
| 405 | 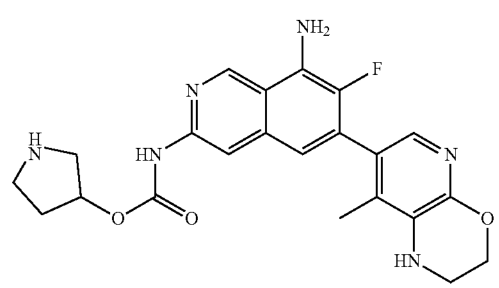 [SMILES: Cc1c(-c2cc3cc(NC(=O)OC4CCNC4)ncc3c(N)c2F)cnc2c1NCCO2] | Pyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 405a 405b | | (S)-Pyrrolidin-3-yl (8-amino-7-fluoro-6-(8-methyl-2,3-dihydro-1H-pyrido[2,3-b][1,4]oxazin-7-yl)isoquinolin-3-yl)carbamate; (R)-Pyrrolidin-3-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 406 | 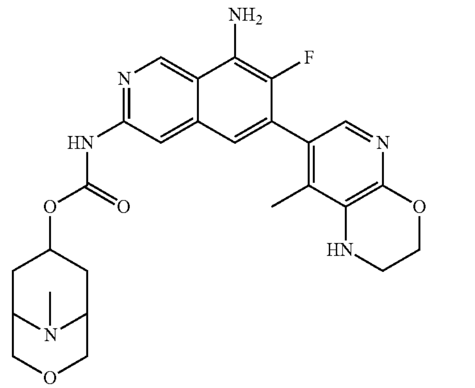 [SMILES: Cc1c(-c2cc3cc(NC(=O)OC4CC5COCC(C4)N5C)ncc3c(N)c2F)cnc2c1NCCO2] | 9-Methyl-3-oxa-9-azabicyclo[3.3.1]nonan-7-yl (8-amino-7-fluoro-6-(8-methyl-2,3-dihydro-1H-pyrido[2,3-b][1,4]oxazin-7-yl)isoquinolin-3-yl)carbamate; |
| 407 | 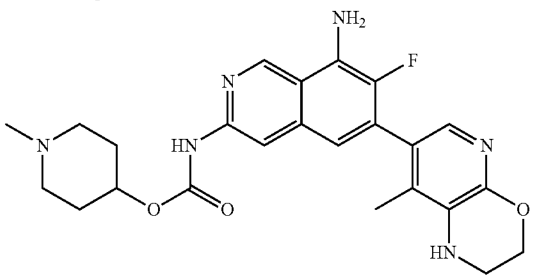 [SMILES: Cc1c(-c2cc3cc(NC(=O)OC4CCN(C)CC4)ncc3c(N)c2F)cnc2c1NCCO2] | 1-Methylpiperidin-4-yl (8-amino-7-fluoro-6-(8-methyl-2,3-dihydro-1H-pyrido[2,3-b][1,4]oxazin-7-yl)isoquinolin-3-yl)carbamate; |
| 408 | 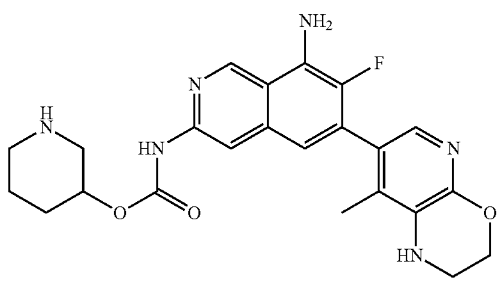 [SMILES: Cc1c(-c2cc3cc(NC(=O)OC4CCCNC4)ncc3c(N)c2F)cnc2c1NCCO2] | Piperidin-3-yl (8-amino-7-fluoro-6-(8-methyl-2,3-dihydro-1H-pyridor2,3-b][1,4]oxazin-7-yl)isoquinolin-3-yl)carbamate; |
| 408a 408b | | (R)-Piperidin-3-yl (8-amino-7-fluoro-6-(8-methyl-2,3-dihydro-1H-pyrido[2,3-b][1,4]oxazin-7-yl)isoquinolin-3-yl)carbamate; (S)-Piperidin-3-yl (8-amino-7-fluoro-6-(8-methyl-2,3-dihydro-1H-pyrido[2,3-b][1,4]oxazin-7-yl)isoquinolin-3-yl)carbamate; |
| 409 | 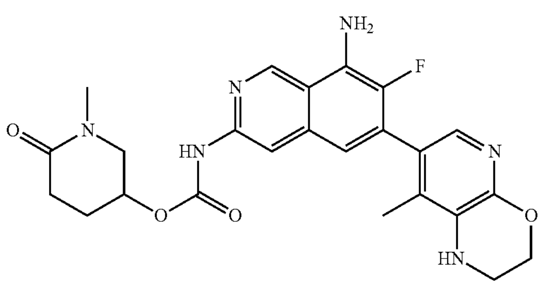 [SMILES: Cc1c(-c2cc3cc(NC(=O)OC4CCC(=O)N(C)C4)ncc3c(N)c2F)cnc2c1NCCO2] | 1-Methyl-6-oxopiperidin-3-yl (8-amino-7-fluoro-6-(8-methyl-2,3-dihydro-1H-pyrido[2,3-b][1,4]oxazin-7-yl)isoquinolin-3-yl)carbamate; |
| 409a 409b | | (R)-1-Methyl-6-oxopiperidin-3-yl (8-amino-7-fluoro-6-(8-methyl-2,3-dihydro-1H-pyrido[2,3-b][1,4]oxazin-7-yl)isoquinolin-3-yl)carbamate; (S)-1-Methyl-6-oxopiperidin-3-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
| --- | --- | --- |
| 410 | 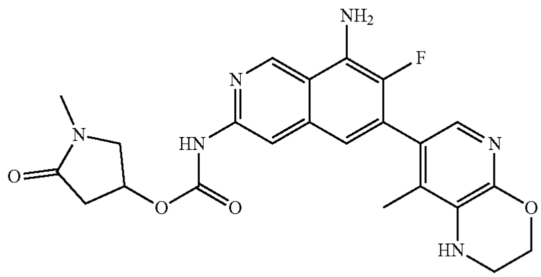 [SMILES: Cc1c(-c2cc3cc(NC(=O)OC4CC(=O)N(C)C4)ncc3c(N)c2F)cnc2c1NCCO2] | 1-Methyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 410a<br>410b | | (R)-1-Methyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate;<br>(S)-1-Methyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 411 | 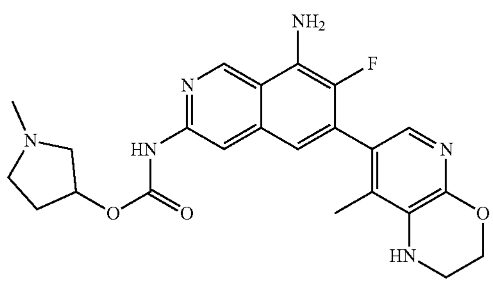 [SMILES: Cc1c(-c2cc3cc(NC(=O)OC4CCN(C)C4)ncc3c(N)c2F)cnc2c1NCCO2] | 1-Methylpyrrolidin-3-yl (8-amino-7-fluoro-6-(8-methyl-2,3-dihydro-1H-yl)isoquinolin-3-yl)carbamate; pyrido[2,3-b][1,4]oxazin-7- |
| 411a<br>411b | | (R)-1-Methylpyrrolidin-3-yl (8-amino-7-fluoro-6-(8-methyl-2,3-dihydro-1H-pyrido[2,3-b][1,4]oxazin-7-yl)isoquinolin-3-yl)carbamate;<br>(S)-1-Methylpyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 412 | 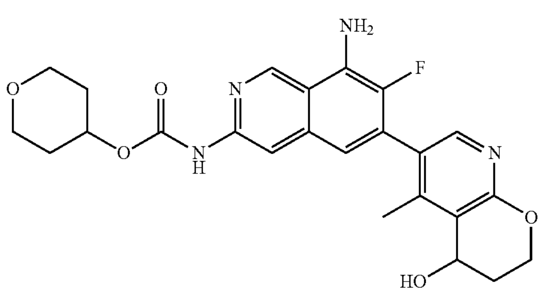 | Tetrahydro-2H-pyran-4-yl (8-amino-7-fluoro-6-(4-hydroxy-5-methyl-3,4-dihydro-2H-pyrano[2,3-b]pyridin-6-yl)isoquinolin-3-yl)carbamate; |
| 412a<br>412b | | Tetrahydro-2H-pyran-4-yl (R)-(8-amino-7-fluoro-6-(4-hydroxy-5-methyl-3,4-dihydro-2H-pyrano[2,3-b]pyridin-6-yl)isoquinolin-3-yl)carbamate;<br>Tetrahydro-2H-pyran-4-yl (S)-(8-amino-7-fluoro-6-(4-hydroxy-5-methyl-3,4-dihydro-2H-pyrano[2,3-b]pyridin-6-yl)isoquinolin-3-yl)carbamate; |

| No. | Structure | Name |
| --- | --- | --- |
| 413 | 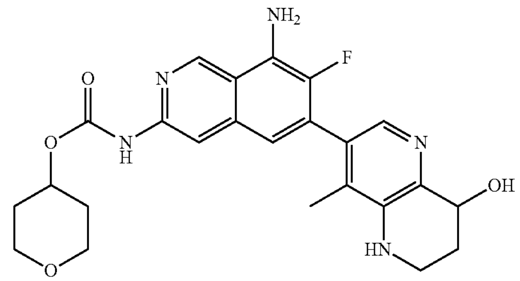 [SMILES: Cc1c(-c2cc3cc(NC(=O)OC4CCOCC4)ncc3c(N)c2F)cnc2c1NCCC2O] | Tetrahydro-2H-pyran-4-yl (8-amino-7-fluoro-6-(8-hydroxy-4-methyl-5,6,7,8-tetrahydro-1,5-naphthyridin-3-yl)isoquinolin-3-yl)carbamate; |
| 414 | 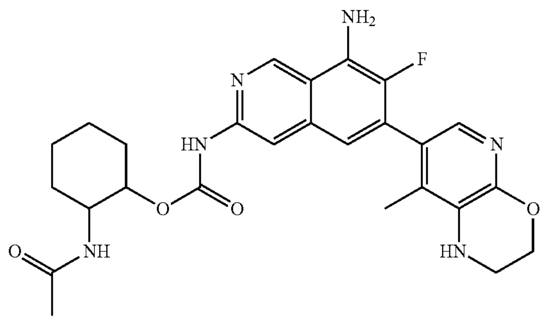 [SMILES: CC(=O)NC1CCCCC1OC(=O)Nc1cc2cc(-c3cnc4c(c3C)NCCO4)c(F)c(N)c2cn1] | (trans)-2-Acetamidocyclohexyl (8-amino-7-fluoro-6-(8-methyl-2,3-dihydro-1H-pyrido[2,3-b][1,4]oxazin-7-yl)isoquinolin-3-yl)carbamate; |
| 414a 414b | | (1S,2S)-2-Acetamidocyclohexyl (8-amino-7-fluoro-6-(8-methyl-2,3-dihydro-1H-pyrido[2,3-b][1,4]oxazin-7-yl)isoquinolin-3-yl)carbamate; (1R,2R)-2-Acetamidocyclohexyl (8-amino-7-fluoro-6-(8-methyl-2,3-dihydro-1H-pyrido[2,3-b][1,4]oxazin-7-yl)isoquinolin-3-yl)carbamate; |
| 415 | 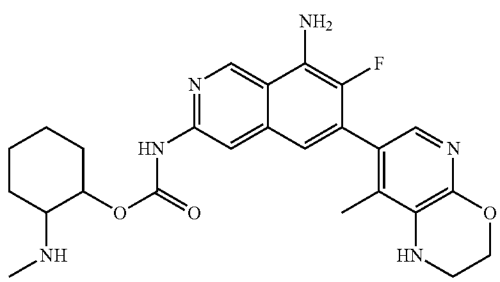 [SMILES: CNC1CCCCC1OC(=O)Nc1cc2cc(-c3cnc4c(c3C)NCCO4)c(F)c(N)c2cn1] | (trans)-2-(Methylamino)cyclohexyl (8-amino-7-fluoro-6-(8-methyl-2,3-dihydro-1H-pyrido[2,3-b][1,4]oxazin-7-yl)isoquinolin-3-yl)carbamate; |
| 415a 415b | | (1S,2S)-2-(Methylamino)cyclohexyl (8-amino-7-fluoro-6-(8-methyl-2,3-dihydro-1H-pyrido[2,3-b][1,4]oxazin-7-yl)isoquinolin-3-yl)carbamate; (1R,2R)-2-(Methylamino)cyclohexyl (8-amino-7-fluoro-6-(8-methyl-2,3-dihydro-1H-pyrido[2,3-b][1,4]oxazin-7-yl)isoquinolin-3-yl)carbamate; |
| 416 | 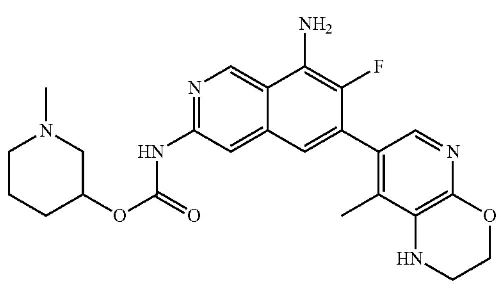 [SMILES: Cc1c(-c2cc3cc(NC(=O)OC4CCCN(C)C4)ncc3c(N)c2F)cnc2c1NCCO2] | 1-Methylpiperidin-3-yl (8-amino-7-fluoro-6-(8-methyl-2,3-dihydro-1H-pyrido[2,3-b][1,4]oxazin-7-yl)isoquinolin-3-yl)carbamate; |
| 416a 416b | | (R)-1-Methylpiperidin-3-yl (8-amino-7-fluoro-6-(8-methyl-2,3-dihydro-1H-pyrido[2,3-b][1,4]oxazin-7-yl)isoquinolin-3-yl)carbamate; (S)-1-Methylpiperidin-3-yl (8-amino-7- |

-continued

| No. | Structure | Name |
|---|---|---|
|  |  | fluoro-6-(8-methyl-2,3-dihydro-1H-pyrido[2,3-b][1,4]oxazin-7-yl)isoquinolin-3-yl)carbamate; |
| 417 | 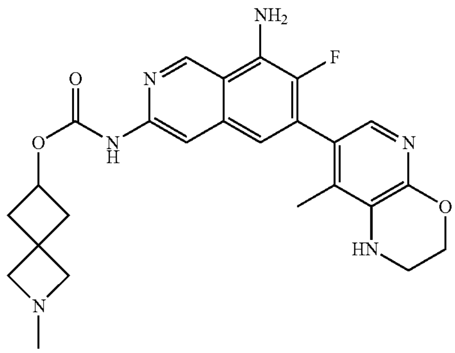 [SMILES: Cc1c(-c2cc3cc(NC(=O)OC4CC5(C4)CN(C)C5)ncc3c(N)c2F)cnc2c1NCCO2] | 2-Methyl-2-azaspiro[3,3]heptan-6-yl (8-amino-7-fluoro-6-(8-methyl-2,3-dihydro-1H-pyrido[2,3-b][1,4]oxazin-7-yl)isoquinolin-3-yl)carbamate; |
| 418 | 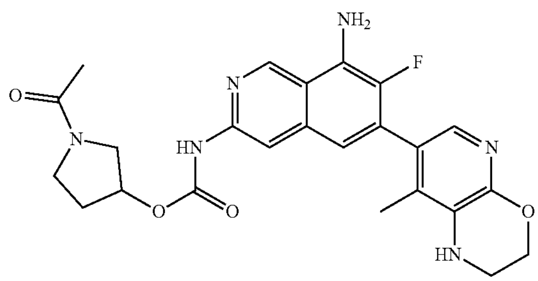 [SMILES: CC(=O)N1CCC(OC(=O)Nc2cc3cc(-c4cnc5c(c4C)NCCO5)c(F)c(N)c3cn2)C1] | 1-Acetylpyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 418a |  | (R)-1-Acetylpyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 418b |  | (S)-1-Acetylpyrrolidin-3-yl(8-amino-7-fluoro-6-(8-methyl-2,3-dihydro-1H-pyrido[2,3-b][1,4]oxazin-7-yl)isoquinolin-3-yl)carbamate; |
| 419 | 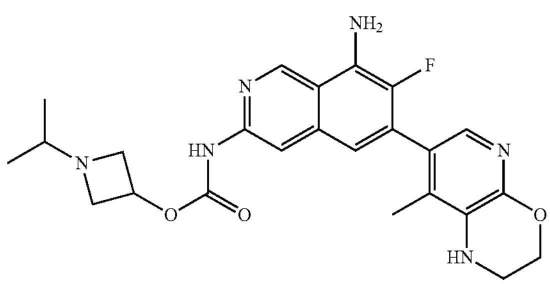 [SMILES: Cc1c(-c2cc3cc(NC(=O)OC4CN(C(C)C)C4)ncc3c(N)c2F)cnc2c1NCCO2] | 1-Isopropylazetidin-3-yl (8-amino-7-fluoro-6-(8-methyl-2,3-dihydro-1H-pyrido[2,3-b][1,4]oxazin-7-yl)isoquinolin-3-yl)carbamate; |
| 420 | 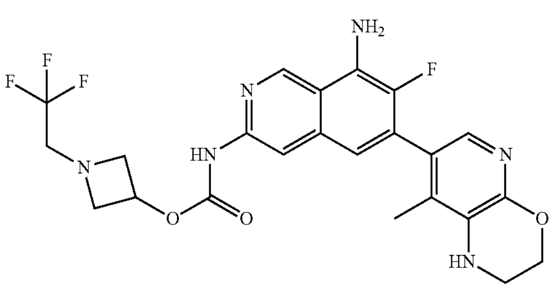 [SMILES: Cc1c(-c2cc3cc(NC(=O)OC4CN(CC(F)(F)F)C4)ncc3c(N)c2F)cnc2c1NCCO2] | 1-(2,2,2-Trifluoroethyl)azetidin-3-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 421 | 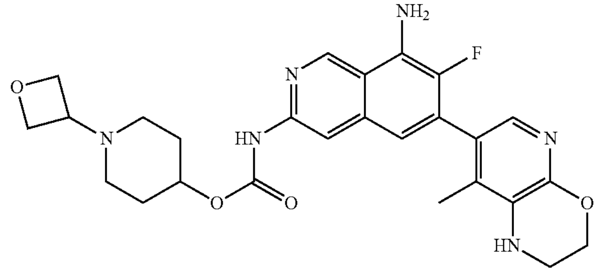 [SMILES: Cc1c(-c2cc3cc(NC(=O)OC4CCN(C5COC5)CC4)ncc3c(N)c2F)cnc2c1NCCO2] | 1-(Oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; |
| 422 | 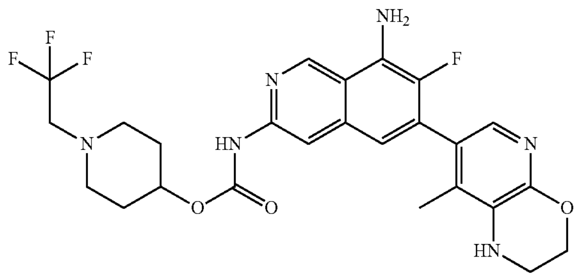 [SMILES: Cc1c(-c2cc3cc(NC(=O)OC4CCN(CC(F)(F)F)CC4)ncc3c(N)c2F)cnc2c1NCCO2] | 1-(2,2,2-Trifluoroethyl)piperidin-4-yl (8-amino-7-fluoro-6-(8-methyl-2,3-dihydro-1H-pyrido[2,3-b][1,4]oxazin-7-yl)isoquinolin-3-yl)carbamate; |
| 423 | 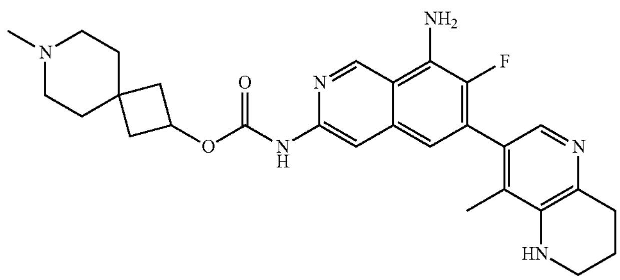 [SMILES: Cc1c(-c2cc3cc(NC(=O)OC4CC5(CCN(C)CC5)C4)ncc3c(N)c2F)cnc2c1NCCC2] | 7-Methyl-7-azaspiro[3.5]nonan-2-yl (8-amino-7-fluoro-6-(4-methyl-5,6,7,8-tetrahydro-1,5-naphthyridin-3-yl)isoquinolin-3-yl)carbamate; |
| 424 | 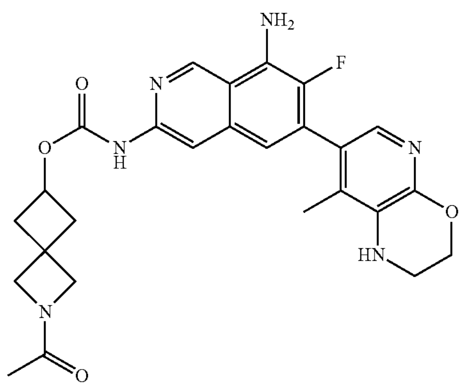 [SMILES: CC(=O)N1CC2(CC(OC(=O)Nc3cc4cc(-c5cnc6c(c5C)NCCO6)c(F)c(N)c4cn3)C2)C1] | 2-Acetyl-2-azaspiro[3,3]heptan-6-yl (8-amino-7-fluoro-6-(8-methyl-2,3-dihydro-1H-pyrido[2,3-b][1,4]oxazin-7-yl)isoquinolin-3-yl)carbamate; |
| 425 | 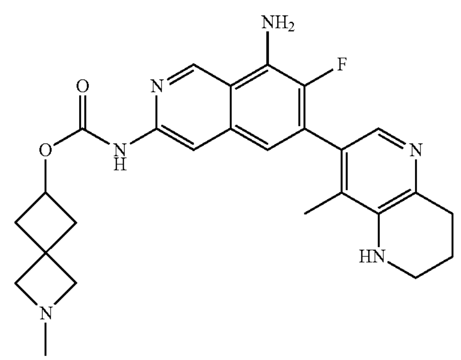 [SMILES: Cc1c(-c2cc3cc(NC(=O)OC4CC5(C4)CN(C)C5)ncc3c(N)c2F)cnc2c1NCCC2] | 2-Methyl-2-azaspiro[3,3]heptan-6-yl (8-amino-7-fluoro-6-(4-methyl-5,6,7,8-tetrahydro-1,5-naphthyridin-3-yl)isoquinolin-3-yl)carbamate; |

| No. | Structure | Name |
|-----|-----------|------|
| 426 | 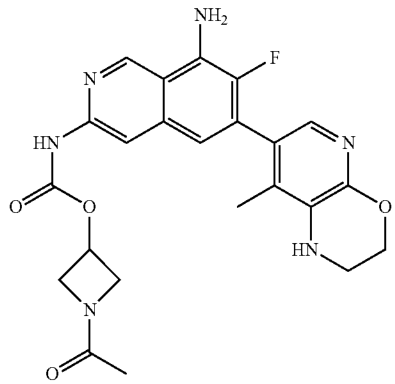 [SMILES: CC(=O)N1CC(OC(=O)Nc2cc3cc(-c4cnc5c(c4C)NCCO5)c(F)c(N)c3cn2)C1] | 1-Acetylazetidin-3-yl (8-amino-7-fluoro-6-(8-methyl-2,3-dihydro-1H-pyrido[2,3-b][1,4]oxazin-7-yl)isoquinolin-3-yl)carbamate; |
| 427 | 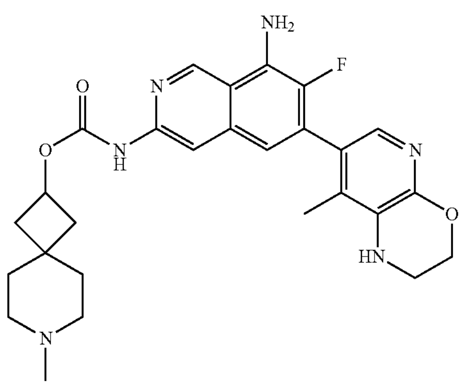 [SMILES: Cc1c(-c2cc3cc(NC(=O)OC4CC5(CCN(C)CC5)C4)ncc3c(N)c2F)cnc2c1NCCO2] | 7-Methyl-7-azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate; |
| 428 | 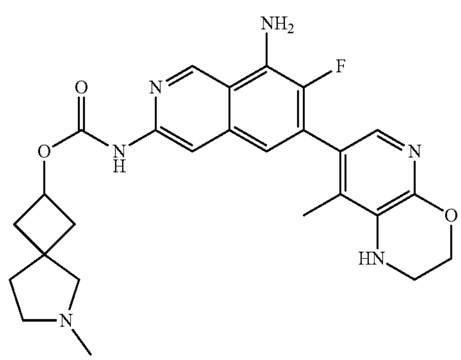 [SMILES: Cc1c(-c2cc3cc(NC(=O)OC4CC5(CCN(C)C5)C4)ncc3c(N)c2F)cnc2c1NCCO2] | 6-Methyl-6-azaspiro[3.4]octan-2-yl (8-amino-7-fluoro-6-(8-methyl-2,3-dihydro-1H-pyrido[2,3-b][1,4]oxazin-7-yl)isoquinolin-3-yl)carbamate; |
| 429 | 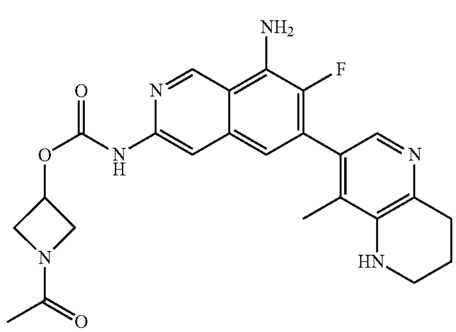 [SMILES: CC(=O)N1CC(OC(=O)Nc2cc3cc(-c4cnc5c(c4C)NCCC5)c(F)c(N)c3cn2)C1] | 1-Acetylazetidin-3-yl (8-amino-7-fluoro-6-(4-methyl-5,6,7,8-tetrahydro-1,5-naphthyridin-3-yl)isoquinolin-3-yl)carbamate; |

| No. | Structure | Name |
|---|---|---|
| 430 | 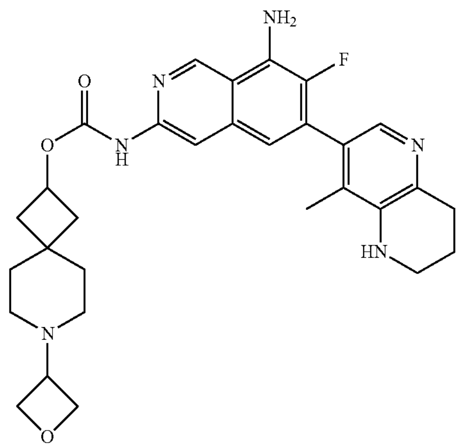 [SMILES: Cc1c(-c2cc3cc(NC(=O)OC4CC5(CCN(C6COC6)CC5)C4)ncc3c(N)c2F)cnc2c1NCCC2] | 7-(Oxetan-3-yl)-7-azaspiro[3.5]nonan-2-yl (8-amino-7-fluoro-6-(4-methyl-5,6,7,8-tetrahydro-1,5-naphthyridin-3-yl)isoquinolin-3-yl)carbamate; |
| 431 | 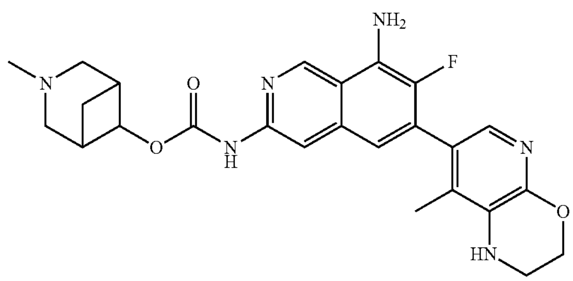 [SMILES: Cc1c(-c2cc3cc(NC(=O)OC4C5CC4CN(C)C5)ncc3c(N)c2F)cnc2c1NCCO2] | 3-Methyl-3-azabicyclo[3.1.1]heptan-6-yl (8-amino-7-fluoro-6-(8-methyl-2,3-dihydro-1H-pyrido[2,3-b][1,4]oxazin-7-yl)isoquinolin-3-yl)carbamate; |
| 432 | 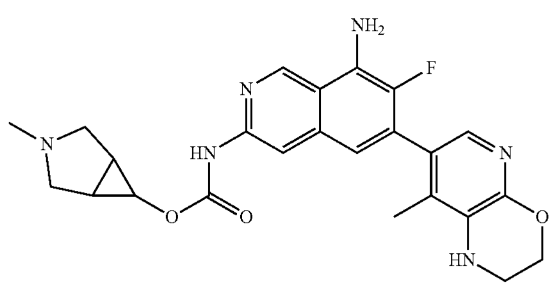 [SMILES: Cc1c(-c2cc3cc(NC(=O)OC4C5CN(C)CC54)ncc3c(N)c2F)cnc2c1NCCO2] | 3-Methyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |
| 432a 432b | | (1R,5S,6r)-3-Methyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; (1R,5S,6s)-3-Methyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |
| 433 | 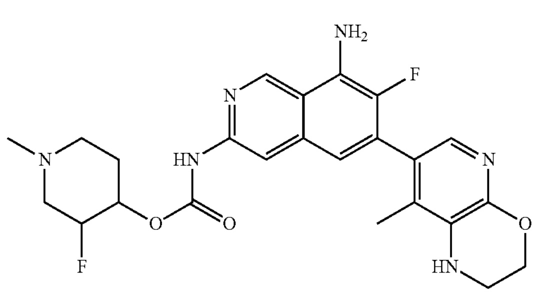 [SMILES: Cc1c(-c2cc3cc(NC(=O)OC4CCN(C)CC4F)ncc3c(N)c2F)cnc2c1NCCO2] | (cis)-3-Fluoro-1-methylpiperidin-4-yl (8-amino-7-fluoro-6-(8-methyl-2,3-dihydro-1H-pyrido[2,3-b][1,4]oxazin-7-yl)isoquinolin-3-yl)carbamate; |
| 433a 433b | | (3R,4S)-3-Fluoro-1-methylpiperidin-4-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| | | (3S,4R)-3-Fluoro-1-methylpiperidin-4-yl (8-amino-7-fluoro-6-(8-methyl-2,3-dihydro-1H-pyrido[2,3-b][1,4]oxazin-7-yl)isoquinolin-3-yl)carbamate; |
| 434 | 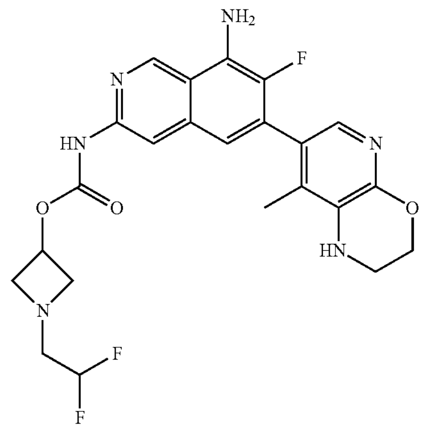 [SMILES: Cc1c(-c2cc3cc(NC(=O)OC4CN(CC(F)F)C4)ncc3c(N)c2F)cnc2c1NCCO2] | 1-(2,2-Difluoroethyl)azetidin-3-yl (8-amino-7-fluoro-6-(8-methyl-2,3-dihydro-1H-pyrido[2,3-b][1,4]oxazin-7-yl)isoquinolin-3-yl)carbamate; |
| 435 | 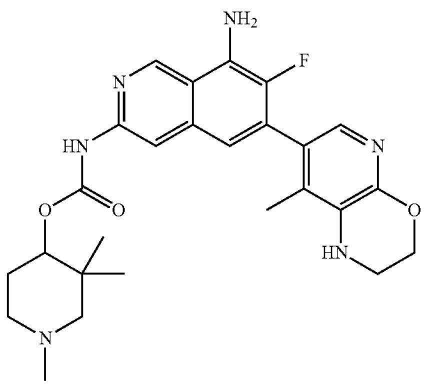 [SMILES: Cc1c(-c2cc3cc(NC(=O)OC4CCN(C)CC4(C)C)ncc3c(N)c2F)cnc2c1NCCO2] | 1,3,3-Trimethylpiperidin-4-yl (8-amino-7-fluoro-6-(8-methyl-2,3-dihydro-1H-pyrido[2,3-b][1,4]oxazin-7-yl)isoquinolin-3-yl)carbamate; |
| 436 | 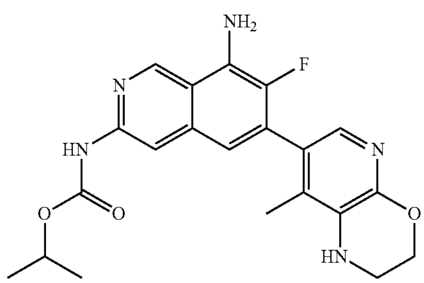 [SMILES: Cc1c(-c2cc3cc(NC(=O)OC(C)C)ncc3c(N)c2F)cnc2c1NCCO2] | Isopropyl (8-amino-7-fluoro-6-(8-methyl-2,3-dihydro-1H-pyrido[2,3-b][1,4]oxazin-7-yl)isoquinolin-3-yl)carbamate; |
| 437 | 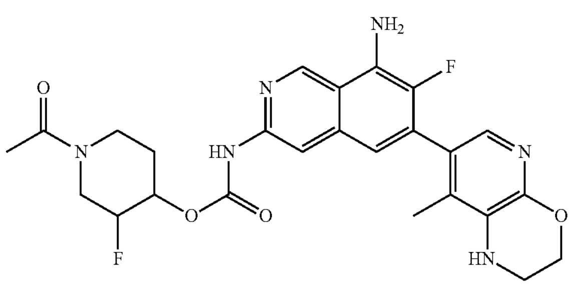 [SMILES: CC(=O)N1CCC(OC(=O)Nc2cc3cc(-c4cnc5c(c4C)NCCO5)c(F)c(N)c3cn2)C(F)C1] | (cis)-1-Acetyl-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate; |
| 437a 437b | | (3S,4R)-1-Acetyl-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate; (3RAS)-1-Acetyl-3-fluoropiperidin-4-yl |

| No. | Structure | Name |
|---|---|---|
| | | (8-amino-7-fluoro-6-(8-methyl-2,3-dihydro-1H-pyrido[2,3-b][1,4]oxazin-7-yl)isoquinolin-3-yl)carbamate; |
| 438 | 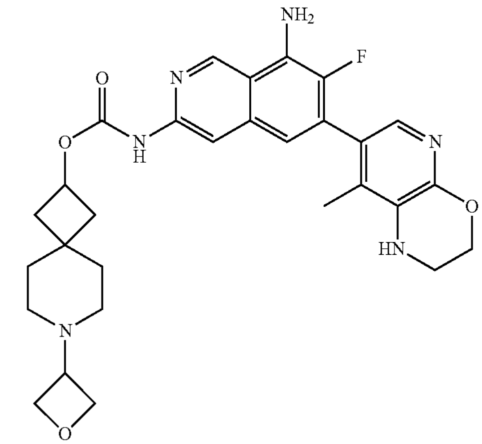 [SMILES: Cc1c(-c2cc3cc(NC(=O)OC4CC5(CCN(C6COC6)CC5)C4)ncc3c(N)c2F)cnc2c1NCCO2] | 7-(Oxetan-3-yl)-7-azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate; |
| 439 | 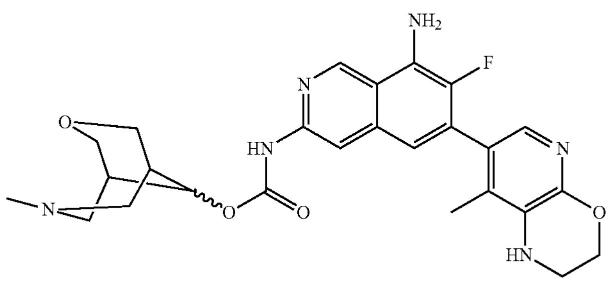 [SMILES: Cc1c(-c2cc3cc(NC(=O)OC4C5COCC4CN(C)C5)ncc3c(N)c2F)cnc2c1NCCO2] | 7-Methyl-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; |
| 439a | | (1R,5S,9s)-7-Methyl-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; |
| 439b | | (1R,5S,9r)-7-Methyl-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; |
| 440 | 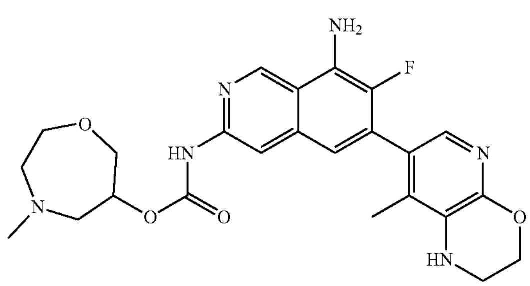 [SMILES: Cc1c(-c2cc3cc(NC(=O)OC4COCCN(C)C4)ncc3c(N)c2F)cnc2c1NCCO2] | 4-Methyl-1,4-oxazepan-6-yl (8-amino-7-fluoro-6-(8-methyl-2,3-dihydro-1/7-pyrido[2,3-b][1,4]oxazin-7-yl)isoquinolin-3-yl)carbamate; |
| 440a | | (R)-4-Methyl-1,4-oxazepan-6-yl (8-amino-7-fluoro-6-(8-methyl-2,3-dihydro-1H-pyrido[2,3-b][1,4]oxazin-7-yl)isoquinolin-3-yl)carbamate; (S)-4-Methyl-1,4-oxazepan-6-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 440b | | |
| 441 | | 4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 441a 441b | | (trans)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4S)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3S,4R)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 441c 441d | | (cis)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4R)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3S,4S)-4-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 442 | | 1,4-Dimethylpyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 442a 442b | | (cis)-1,4-Dimethylpyrrolidin-3-yl (8-amino-7-fluoro-6-(8-methyl-2,3-dihydro-1H-pyrido[2,3-b][1,4]oxazin-7-yl)isoquinolin-3-yl)carbamate; [(3S,4S)-1,4-Dimethylpyrrolidin-3-yl] N-[8-amino-7-fluoro-6-(8-methyl-2,3-dihydro-1H-pyrido[2,3-b][1,4]oxazin-7-yl)-3-isoquinolyl]carbamate; [(3R,4R)-1,4-Dimethylpyrrolidin-3-yl] N-[8-amino-7-fluoro-6-(8-methyl-2,3-dihydro-1H-pyrido[2,3-b][1,4]oxazin-7-yl)-3-isoquinolyl]carbamate; |
| 442c 442d | | (trans)-1,4-Dimethylpyrrolidin-3-yl (8-amino-7-fluoro-6-(8-methyl-2,3-dihydro-1H-pyrido[2,3-b][1,4]oxazin-7-yl)isoquinolin-3-yl)carbamate; (3S,4R)-1,4-Dimethylpyrrolidin-3-yl (8-amino-7-fluoro-6-(8-methyl-2,3-dihydro-1H-pyrido[2,3-b][1,4]oxazin-7-yl)isoquinolin-3-yl)carbamate; (3R,4S)-1,4-dimethylpyrrolidin-3-yl (8- |

| No. | Structure | Name |
|---|---|---|
| | | amino-7-fluoro-6-(8-methyl-2,3-dihydro-1H-pyrido[2,3-b][1,4]oxazin-7-yl)isoquinolin-3-yl)carbamate; |
| 443 | 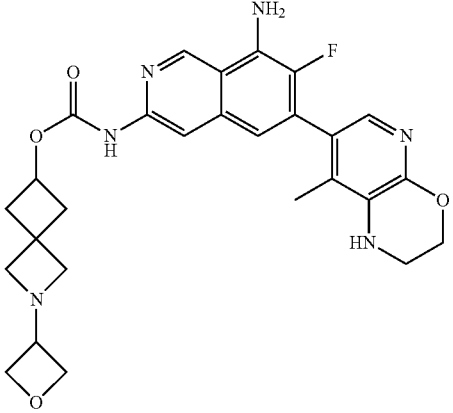 [SMILES: Cc1c(-c2cc3cc(NC(=O)OC4CC5(C4)CN(C4COC4)C5)ncc3c(N)c2F)cnc2c1NCCO2] | 2-(Oxetan-3-yl)-2-azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate; |
| 444 | 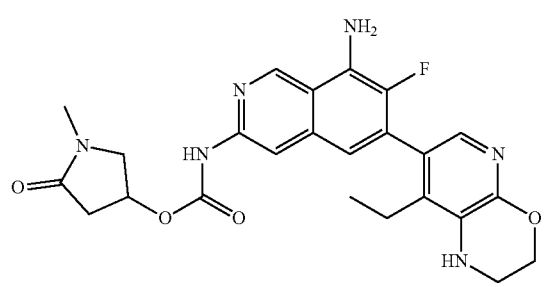 [SMILES: CCc1c(-c2cc3cc(NC(=O)OC4CC(=O)N(C)C4)ncc3c(N)c2F)cnc2c1NCCO2] | 1-Methyl-5-oxopyrrolidin-3-yl (8-amino-6-(8-ethyl-2,3-dihydro-1H-pyrido[2,3-b][1,4]oxazin-7-yl)-7-fluoroisoquinolin-3-yl)carbamate; |
| 444a 444b | | (S)-1-Methyl-5-oxopyrrolidin-3-yl (8-amino-6-(8-ethyl-2,3-dihydro-1H-pyrido[2,3-b][1,4]oxazin-7-yl)-7-fluoroisoquinolin-3-yl)carbamate; (R)-1-Methyl-5-oxopyrrolidin-3-yl (8-amino-6-(8-ethyl-2,3-dihydro-1H-pyrido[2,3-b][1,4]oxazin-7-yl)-7-fluoroisoquinolin-3-yl)carbamate; |
| 445 | 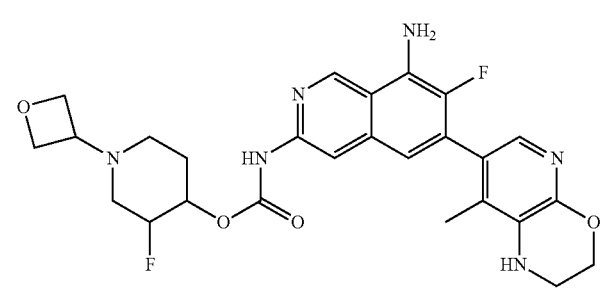 [SMILES: Cc1c(-c2cc3cc(NC(=O)OC4CCN(C5COC5)CC4F)ncc3c(N)c2F)cnc2c1NCCO2] | 3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; |
| 445a 445b | | trans-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; (3S,4S)-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; (3R,4R)-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 445c | | cis-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; (3S,4R)-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; (3R,4S)-3-Fluoro-1-(oxetan-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; |
| 445d | | |
| 446 | 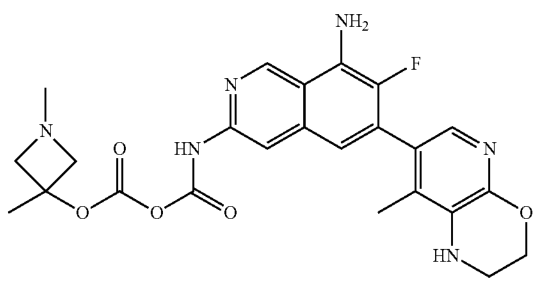 [SMILES: Cc1c(-c2cc3cc(NC(=O)OC(=O)OC4(C)CN(C)C4)ncc3c(N)c2F)cnc2c1NCCO2] | 1,3-Dimethylazetidin-3-yl (8-amino-7-fluoro-6-(8-methyl-2,3-dihydro-1H-pyrido[2,3-b][1,4]oxazin-7-yl)isoquinolin-3-yl)carbamate; |
| 447 | 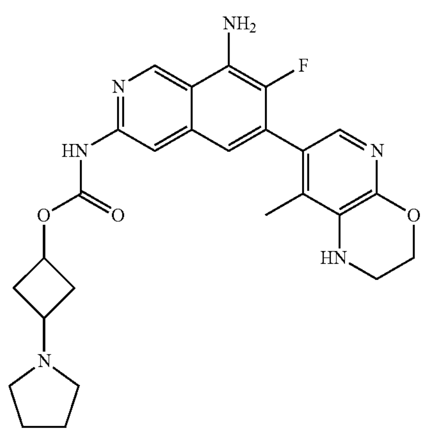 [SMILES: Cc1c(-c2cc3cc(NC(=O)OC4CC(N5CCCC5)C4)ncc3c(N)c2F)cnc2c1NCCO2] | 3-(Dimethylamino)cyclobutyl (8-amino-7-fluoro-6-(8-methyl-2,3-dihydro-1H-pyrido[2,3-b][1,4]oxazin-7-yl)isoquinolin-3-yl)carbamate; |
| 447a | | (1r,3r)-3-(Dimethylamino)cyclobutyl(8-amino-7-fluoro-6-(8-methyl-2,3-dihydro-1H-pyrido[2,3-b][1,4]oxazin-7-yl)isoquinolin-3-yl)carbamate; |
| 447b | | (1s,3s)-3-(Dimethylamino)cyclobutyl(8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 448 | 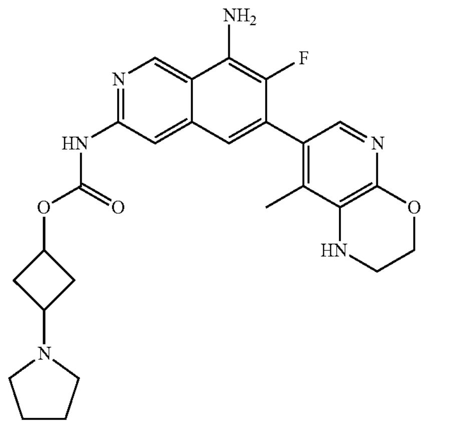 [SMILES: Cc1c(-c2cc3cc(NC(=O)OC4CC(N5CCCC5)C4)ncc3c(N)c2F)cnc2c1NCCO2] | 3-(Pyrrolidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate; |
| 449 | 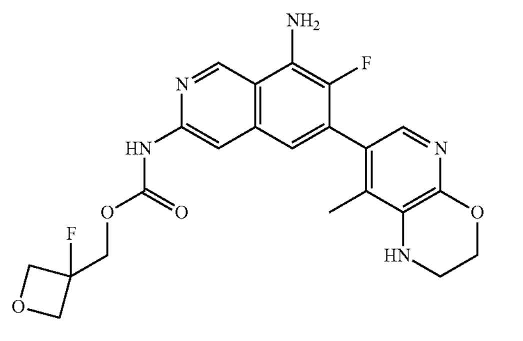 [SMILES: Cc1c(-c2cc3cc(NC(=O)OCC4(F)COC4)ncc3c(N)c2F)cnc2c1NCCO2] | (3-Fluorooxetan-3-yl)methyl (8-amino-7-fluoro-6-(8-methyl-2,3-dihydro-1H-pyrido[2,3-b][1,4]oxazin-7-yl)isoquinolin-3-yl)carbamate; |
| 450 | 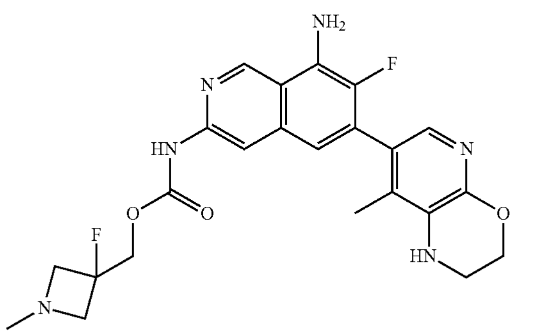 [SMILES: Cc1c(-c2cc3cc(NC(=O)OCC4(F)CN(C)C4)ncc3c(N)c2F)cnc2c1NCCO2] | (3-Fluoro-1-methylazetidin-3-yl)methyl (8-amino-7-fluoro-6-(8-methyl-2,3-dihydro-1H-pyrido[2,3-b][1,4]oxazin-7-yl)isoquinolin-3-yl)carbamate; |
| 451 | 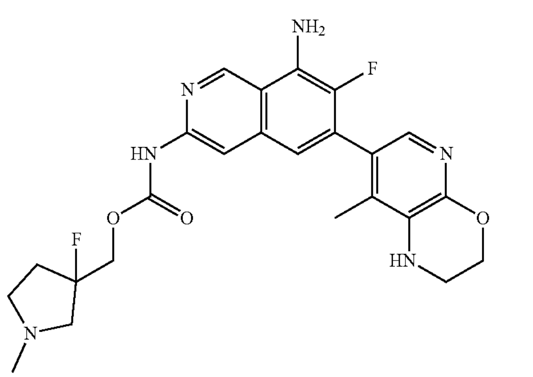 [SMILES: Cc1c(-c2cc3cc(NC(=O)OCC4(F)CCN(C)C4)ncc3c(N)c2F)cnc2c1NCCO2] | (3-Fluoro-1-methylpyrrolidin-3-yl)methyl (8-amino-7-fluoro-6-(8-methyl-2,3-dihydro-1H-pyrido[2,3-b][1,4]oxazin-7-yl)isoquinolin-3-yl)carbamate; |
| 451a 451b | | (R)-(3-Fluoro-1-methylpyrrolidin-3-yl)methyl (8-amino-7-fluoro-6-(8-methyl-2,3-dihydro-1H-pyrido[2,3-b][1,4]oxazin-7-yl)isoquinolin-3-yl)carbamate; (S)-(3-Fluoro-1-methylpyrrolidin-3-yl)methyl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 452 | 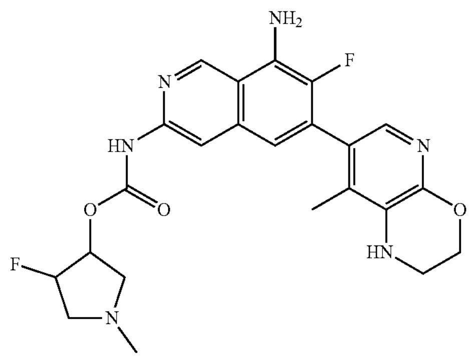 [SMILES: Cc1c(-c2cc3cc(NC(=O)OC4CN(C)CC4F)ncc3c(N)c2F)cnc2c1NCCO2] | 4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 452a | | trans-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate; (3S,4S)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate; (3R,4R)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 452b | | |
| 452c | | cis-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate; (3S,4R)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate; (3R,4S)-4-Fluoro-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 452d | | |
| 453 | 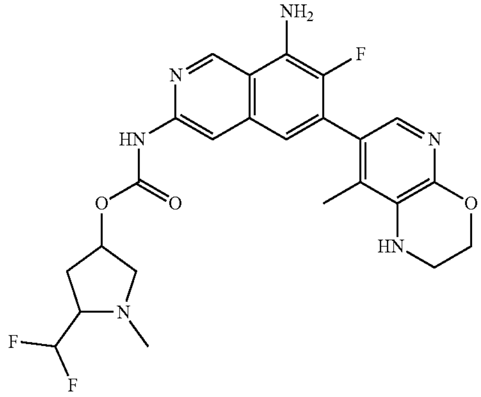 [SMILES: Cc1c(-c2cc3cc(NC(=O)OC4CC(C(F)F)N(C)C4)ncc3c(N)c2F)cnc2c1NCCO2] | 5-(Difluoromethyl)-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 454 | 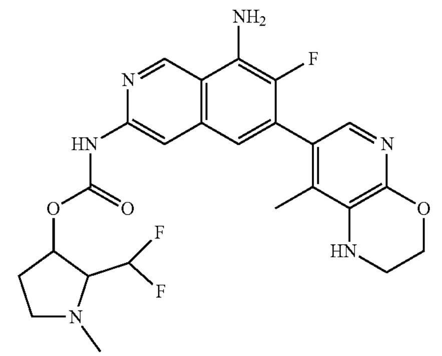 [SMILES: Cc1c(-c2cc3cc(NC(=O)OC4CCN(C)C4C(F)F)ncc3c(N)c2F)cnc2c1NCCO2] | 2-(Difluoromethyl)-1-methylpyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 455 | 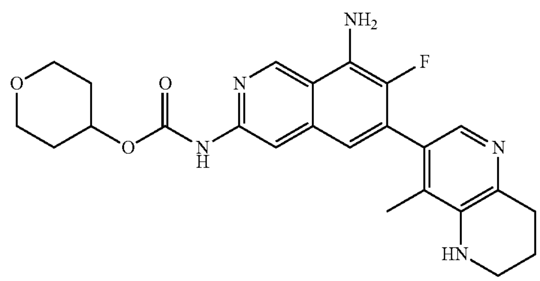 [SMILES: Cc1c(-c2cc3cc(NC(=O)OC4CCOCC4)ncc3c(N)c2F)cnc2c1NCCC2] | Tetrahydro-2H-pyran-4-yl(8-amino-7-fluoro-6-(4-methyl-5,6,7,8-tetrahydro-1,5-naphthyridin-3-yl)isoquinolin-3-yl)carbamate; |
| 456 | 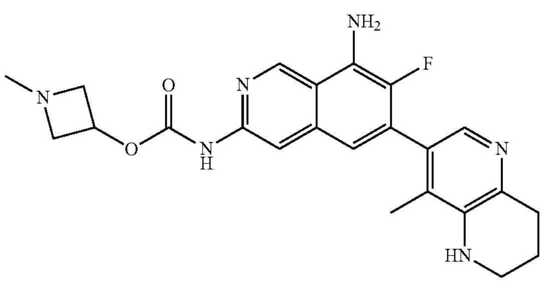 [SMILES: Cc1c(-c2cc3cc(NC(=O)OC4CN(C)C4)ncc3c(N)c2F)cnc2c1NCCC2] | 1-Methylazetidin-3-yl (8-amino-7-fluoro-6-(4-methyl-5,6,7,8-tetrahydro-1,5-naphthyridin-3-yl)isoquinolin-3-yl)carbamate; |
| 457 | 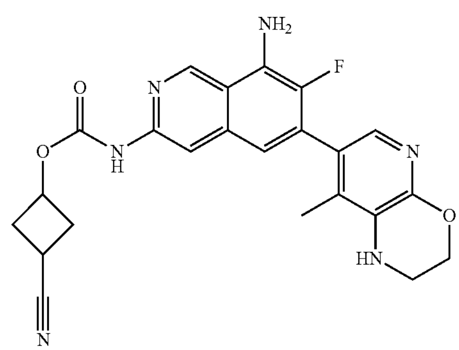 [SMILES: Cc1c(-c2cc3cc(NC(=O)OC4CC(C#N)C4)ncc3c(N)c2F)cnc2c1NCCO2] | 3-Cyanocyclobutyl (8-amino-7-cyano-6-(8-methyl-2,3-dihydro-1H-pyrido[2,3-b][1,4]oxazin-7-yl)isoquinolin-3-yl)carbamate; |
| 458 | 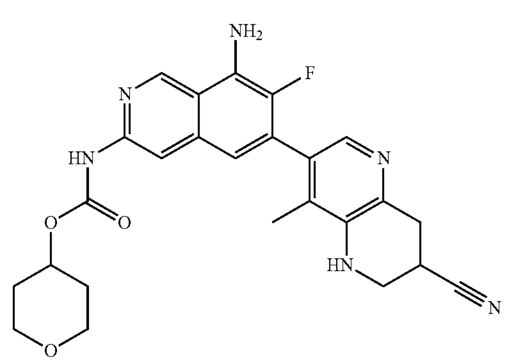 [SMILES: Cc1c(-c2cc3cc(NC(=O)OC4CCOCC4)ncc3c(N)c2F)cnc2c1NCC(C#N)C2] | Tetrahydro-2H-pyran-4-yl (8-amino-6-(7-cyano-4-methyl-5,6,7,8-tetrahydro-1,5-naphthyridin-3-yl)-7-fluoroisoquinolin-3-yl)carbamate; |

-continued

| No. | Structure | Name |
|---|---|---|
| 459 | 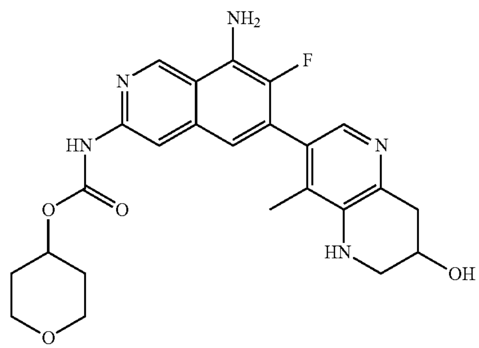 [SMILES: Cc1c(-c2cc3cc(NC(=O)OC4CCOCC4)ncc3c(N)c2F)cnc2c1NCC(O)C2] | Tetrahydro-2H-pyran-4-yl (8-amino-7-fluoro-6-(7-hydroxy-4-methyl-5,6,7,8-tetrahydro-1,5-naphthyridin-3-yl)isoquinolin-3-yl)carbamate; |
| 460 | 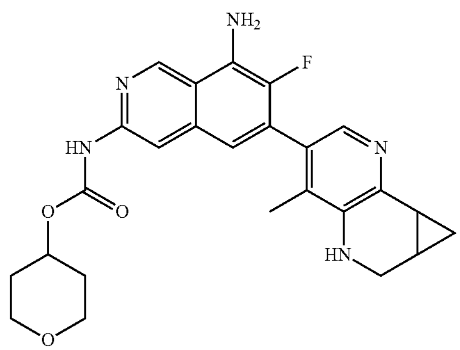 [SMILES: Cc1c(-c2cc3cc(NC(=O)OC4CCOCC4)ncc3c(N)c2F)cnc2c1NCC1CC21] | Tetrahydro-2H-pyran-4-yl (8-amino-7-fluoro-6-(4-methyl-6,6a,7,7a-tetrahydro-5H-cyclopropa[c][1,5]naphthyridin-3-yl)isoquinolin-3-yl)carbamate; |
| 461 | 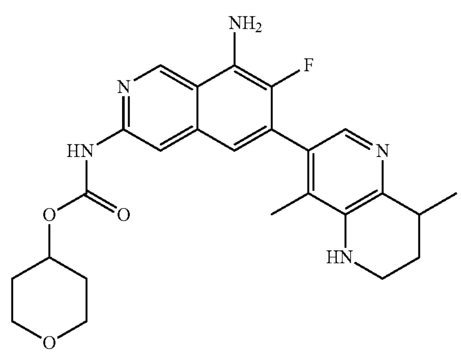 [SMILES: Cc1c(-c2cc3cc(NC(=O)OC4CCOCC4)ncc3c(N)c2F)cnc2c1NCCC2C] | Tetrahydro-2H-pyran-4-yl (8-amino-6-(4,8-dimethyl-5,6,7,8-tetrahydro-1,5-naphthyridin-3-yl)-7-fluoroisoquinolin-3-yl)carbamate; |
| 461a | | Tetrahydro-2H-pyran-4-yl (R)-(8-amino-6-(4,8-dimethyl-5,6,7,8-tetrahydro-1,5-naphthyridin-3-yl)-7-fluoroisoquinolin-3-yl)carbamate; |
| 461b | | Tetrahydro-2H-pyran-4-yl (S)-(8-amino-6-(4,8-dimethyl-5,6,7,8-tetrahydro-1,5-naphthyridin-3-yl)-7-fluoroisoquinolin-3-yl)carbamate; |
| 462 | 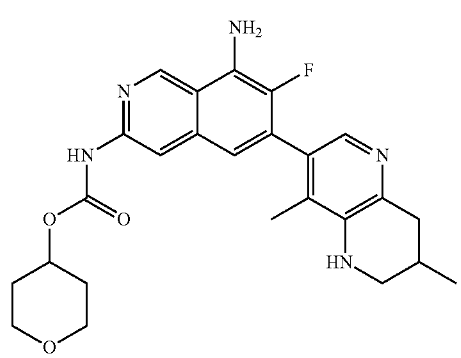 [SMILES: Cc1c(-c2cc3cc(NC(=O)OC4CCOCC4)ncc3c(N)c2F)cnc2c1NCC(C)C2] | Tetrahydro-2H-pyran-4-yl (8-amino-6-(4,7-dimethyl-5,6,7,8-tetrahydro-1,5-naphthyridin-3-yl)-7-fluoroisoquinolin-3-yl)carbamate; |

| No. | Structure | Name |
|---|---|---|
| 463 | 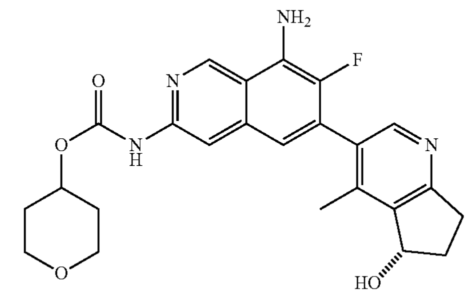 [SMILES: Cc1c(-c2cc3cc(NC(=O)OC4CCOCC4)ncc3c(N)c2F)cnc2c1[C@@H](O)CC2] | Tetrahydro-2H-pyran-4-yl-(8-amino-7-fluoro-6-(5-hydroxy-4-methyl-6,7-dihydro-5H-cyclopenta[b]pyridin-3-yl)isoquinolin-3-yl)carbamate; |
| 464 | 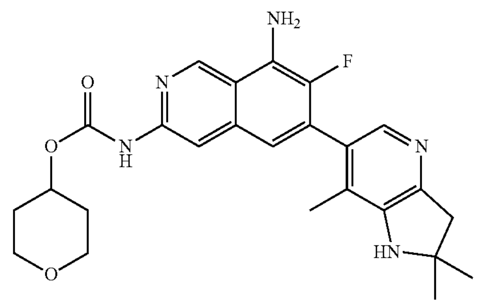 [SMILES: Cc1c(-c2cc3cc(NC(=O)OC4CCOCC4)ncc3c(N)c2F)cnc2c1NC(C)(C)C2] | Tetrahydro-2H-pyran-4-yl (8-amino-7-fluoro-6-(2,2,7-trimethyl-2,3-dihydro-1H-pyrrolo[3,2-b]pyridin-6-yl)isoquinolin-3-yl)carbamate; |
| 465 | 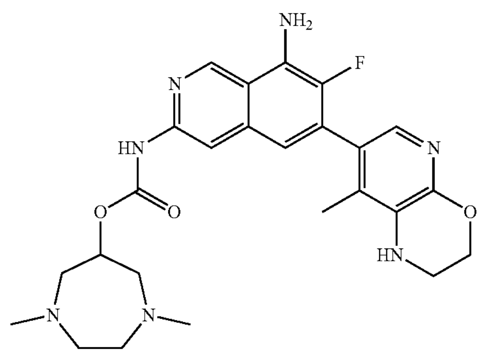 [SMILES: Cc1c(-c2cc3cc(NC(=O)OC4CN(C)CCN(C)C4)ncc3c(N)c2F)cnc2c1NCCO2] | 1,4-Dimethyl-1,4-diazepan-6-yl (8-amino-7-fluoro-6-(8-methyl-2,3-dihydro-1H-pyrido[2,3-b][1,4]oxazin-7-yl)isoquinolin-3-yl)carbamate; |
| 466 | 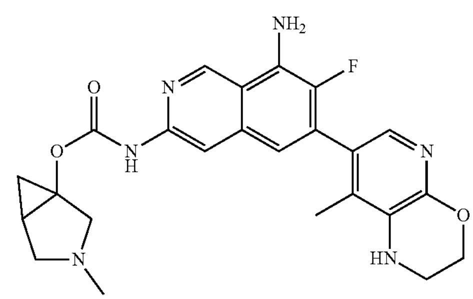 [SMILES: Cc1c(-c2cc3cc(NC(=O)OC45CC4CN(C)C5)ncc3c(N)c2F)cnc2c1NCCO2] | 3-Methyl-3-azabicyclo[3.1.0]hexan-1-yl (8-amino-7-fluoro-6-(8-methyl-2,3-dihydro-1H-pyrido[2,3-b][1,4]oxazin-7-yl)isoquinolin-3-yl)carbamate; |
| 467 | 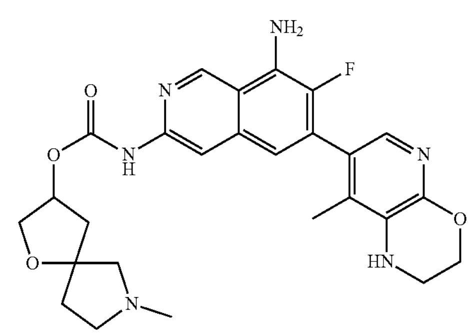 [SMILES: Cc1c(-c2cc3cc(NC(=O)OC4COC5(CCN(C)C5)C4)ncc3c(N)c2F)cnc2c1NCCO2] | 7-Methyl-1-oxa-7-azaspiro[4.4]nonan-3-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 467a | | (3S,5S)-7-Methyl-1-oxa-7-azaspiro[4.4]nonan-3-yl (8-amino-7-fluoro-6-(8-methyl-2,3-dihydro-1H-pyrido[2,3-b][1,4]oxazin-7-yl)isoquinolin-3-yl)carbamate; |
| 467b | | (3R,5R)-7-Methyl-1-oxa-7-azaspiro[4.4]nonan-3-yl (8-amino-7-fluoro-6-(8-methyl-2,3-dihydro-1H-pyrido[2,3-b][1,4]oxazin-7-yl)isoquinolin-3-yl)carbamate; |
| 467c | | (3S,5R)-7-Methyl-1-oxa-7-azaspiro[4.4]nonan-3-yl (8-amino-7-fluoro-6-(8-methyl-2,3-dihydro-1H-pyrido[2,3-b][1,4]oxazin-7-yl)isoquinolin-3-yl)carbamate; |
| 467d | | (3R,5S)-7-Methyl-1-oxa-7-azaspiro[4.4]nonan-3-yl (8-amino-7-fluoro-6-(8-methyl-2,3-dihydro-1H-pyrido[2,3-b][1,4]oxazin-7-yl)isoquinolin-3-yl)carbamate; |
| 468 | 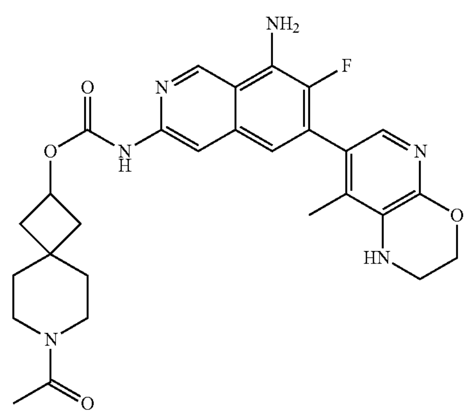 [SMILES: CC(=O)N1CCC2(CC1)CC(OC(=O)Nc1cc3cc(-c4cnc5c(c4C)NCCO5)c(F)c(N)c3cn1)C2] | 7-Acetyl-7-azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate; |
| 469 | 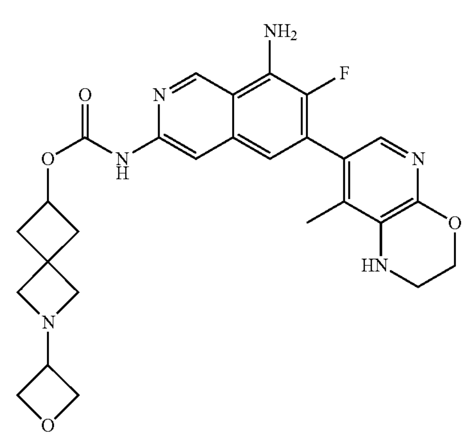 [SMILES: Cc1c(-c2cc3cc(NC(=O)OC4CC5(C4)CN(C4COC4)C5)ncc3c(N)c2F)cnc2c1NCCO2] | 2-(Oxetan-3-yl)-2-azaspiro[3.3]heptan-6-yl (8-amino-7-fluoro-6-(4-methyl-5,6,7,8-tetrahydro-1,5-naphthyridin-3-yl)isoquinolin-3-yl)carbamate; |

| No. | Structure | Name |
|---|---|---|
| 470 | 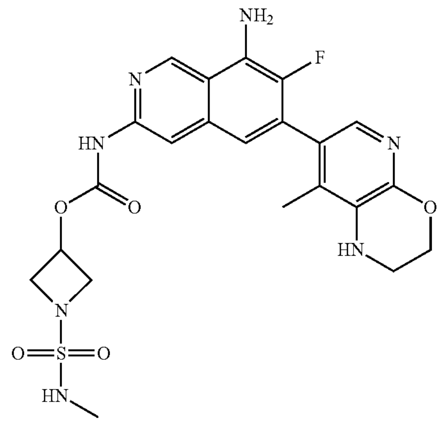 [SMILES: CNS(=O)(=O)N1CC(OC(=O)Nc2cc3cc(-c4cnc5c(c4C)NCCO5)c(F)c(N)c3cn2)C1] | 1-(N-Methylsulfamoyl)azetidin-3-yl(8-amino-7-fluoro-6-(8-methyl-2,3-dihydro-1H-pyrido[2,3-b][1,4]oxazin-7-yl)isoquinolin-3-yl)carbamate; |
| 471 | 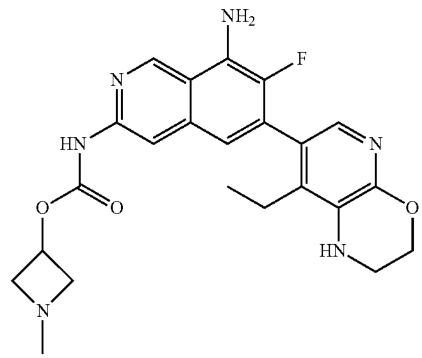 [SMILES: CCc1c(-c2cc3cc(NC(=O)OC4CN(C)C4)ncc3c(N)c2F)cnc2c1NCCO2] | 1-Methylazetidin-3-yl (8-amino-6-(8-ethyl-2,3-dihydro-1H-pyrido[2,3-b][1,4]oxazin-7-yl)-7-fluoroisoquinolin-3-yl)carbamate; |
| 472 | 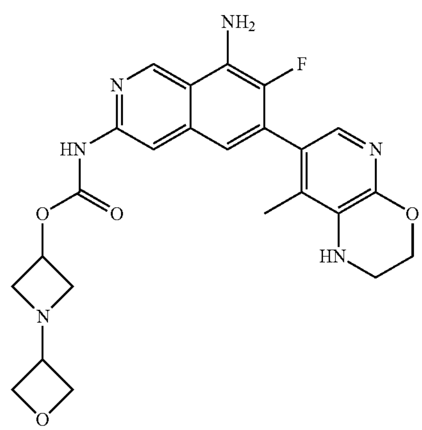 [SMILES: Cc1c(-c2cc3cc(NC(=O)OC4CN(C5COC5)C4)ncc3c(N)c2F)cnc2c1NCCO2] | 1-(Oxetan-3-yl)azetidin-3-yl (8-amino-7-fluoro-6-(8-methyl-2,3-dihydro-1H-pyrido[2,3-b][1,4]oxazin-7-yl)isoquinolin-3-yl)carbamate; |
| 473 | 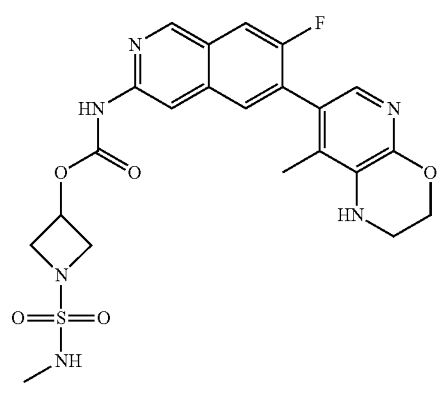 [SMILES: CNS(=O)(=O)N1CC(OC(=O)Nc2cc3cc(-c4cnc5c(c4C)NCCO5)c(F)cc3cn2)C1] | 1-(N-Methylsulfamoyl)azetidin-3-yl (7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 474 | 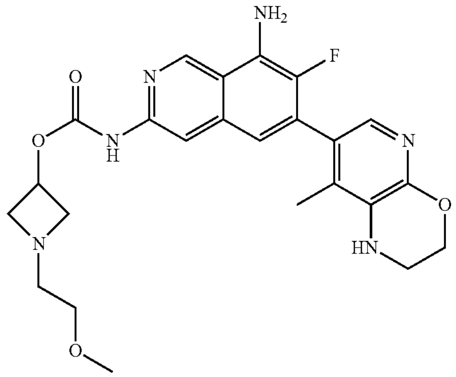 [SMILES: COCCN1CC(OC(=O)Nc2cc3cc(-c4cnc5c(c4C)NCCO5)c(F)c(N)c3cn2)C1] | 1-(2-Methoxyethyl)azetidin-3-yl (8-amino-7-fluoro-6-(8-methyl-2,3-dihydro-1H-pyrido[2,3-b][1,4]oxazin-7-yl)isoquinolin-3-yl)carbamate; |
| 475 | 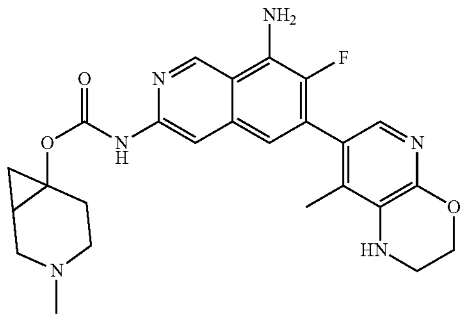 [SMILES: Cc1c(-c2cc3cc(NC(=O)OC45CCN(C)CC4C5)ncc3c(N)c2F)cnc2c1NCCO2] | 3-Methyl-3-azabicyclo[4.1.0]heptan-6-yl (8-amino-7-fluoro-6-(8-methyl-2,3-dihydro-1H-pyrido[2,3-b][1,4]oxazin-7-yl)isoquinolin-3-yl)carbamate; |
| 476 | 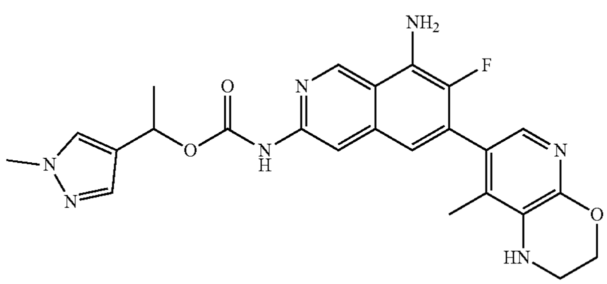 [SMILES: Cc1c(-c2cc3cc(NC(=O)OC(C)c4cnn(C)c4)ncc3c(N)c2F)cnc2c1NCCO2] | 1-(1-Methyl-1H-pyrazol-4-yl)ethyl (8-amino-7-fluoro-6-(8-methyl-2,3-dihydro-1H-pyrido[2,3-b][1,4]oxazin-7-yl)isoquinolin-3-yl)carbamate; |
| 477 | 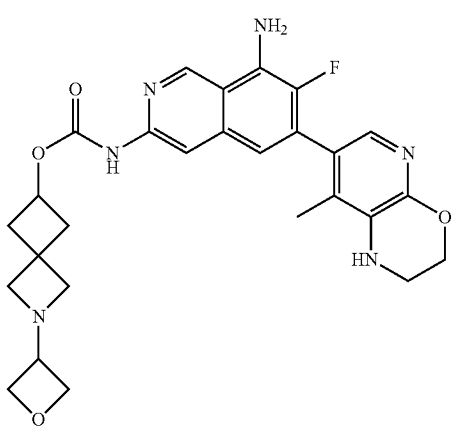 [SMILES: Cc1c(-c2cc3cc(NC(=O)OC4CC5(C4)CN(C4COC4)C5)ncc3c(N)c2F)cnc2c1NCCO2] | 4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 477a 477b | | (trans)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4R)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| | | (3S,4S)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 477c | | (cis)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 477d | | (3S,4R)-4-Fluorotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| | | (3R,4S)-4-Fluorotetrahydrofuran-3-yl(8-amino-7-fluoro-6-(8-methyl-2,3-dihydro-1H-pyrido[2,3-b][1,4]oxazin-7-yl)isoquinolin-3-yl)carbamate; |
| 478 | 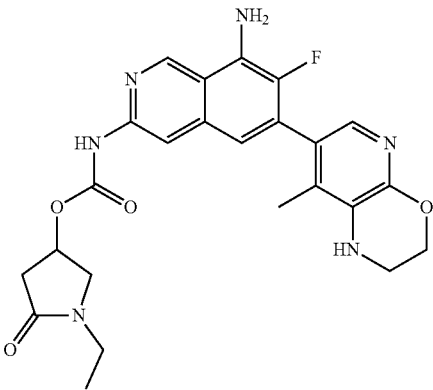 [SMILES: CCN1CC(OC(=O)Nc2cc3cc(-c4cnc5c(c4C)NCCO5)c(F)c(N)c3cn2)CC1=O] | 1-Ethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 478a | | (R)-1-Ethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 478b | | (S)-1-Ethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 479 | 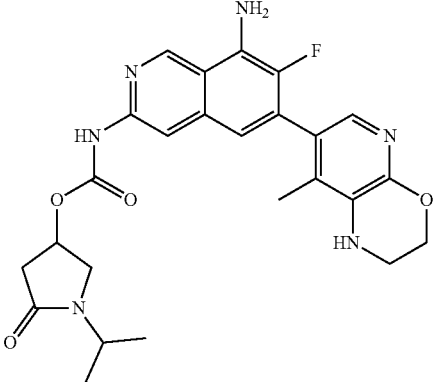 [SMILES: Cc1c(-c2cc3cc(NC(=O)OC4CC(=O)N(C(C)C)C4)ncc3c(N)c2F)cnc2c1NCCO2] | 1-Isopropyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 479a | | (S)-1-Isopropyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 479b | | (R)-1-Isopropyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 480 | 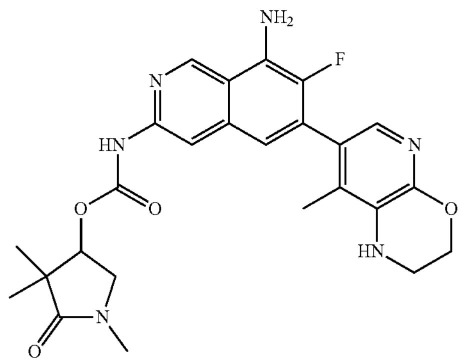 [SMILES: Cc1c(-c2cc3cc(NC(=O)OC4CN(C)C(=O)C4(C)C)ncc3c(N)c2F)cnc2c1NCCO2] | 1,4,4-Trimethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 480a | | (S)-1,4,4-Trimethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 480b | | (R)-1,4,4-Trimethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate; |
| 481 | 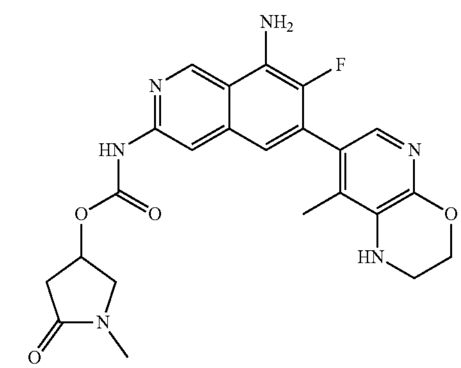 [SMILES: Cc1c(-c2cc3cc(NC(=O)OC4CC(=O)N(C)C4)ncc3c(N)c2F)cnc2c1NCCO2] | 1-Methyl-5-oxopyrrolidin-3-yl (8-amino-7-fluoro-6-(4-methyl-5,6,7,8-tetrahydro-1,5-naphthyridin-3-yl)isoquinolin-3-yl)carbamate; |
| 481a | | (S)-1-Methyl-5-oxopyrrolidin-3-yl (8-amino-7-fluoro-6-(4-methyl-5,6,7,8-tetrahydro-1,5-naphthyridin-3-yl)isoquinolin-3-yl)carbamate; |
| 481b | | (R)-1-Methyl-5-oxopyrrolidin-3-yl (8-amino-7-fluoro-6-(4-methyl-5,6,7,8-tetrahydro-1,5-naphthyridin-3-yl)isoquinolin-3-yl)carbamate; |
| 482 | 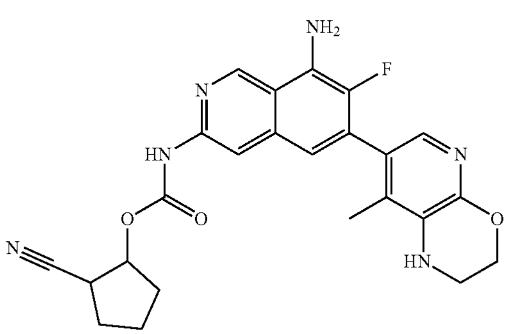 [SMILES: Cc1c(-c2cc3cc(NC(=O)OC4CCCC4C#N)ncc3c(N)c2F)cnc2c1NCCO2] | 2-Cyanocyclopentyl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 482a | | (trans)-2-Cyanocyclopentyl (8-amino-7-fluoro-6-(8-methyl-2,3-dihydro-1H-pyrido[2,3-b][1,4]oxazin-7-yl)isoquinolin-3-yl)carbamate;<br>(1R,2S)-2-Cyanocyclopentyl (8-amino-7-fluoro-6-(8-methyl-2,3-dihydro-1H-pyrido[2,3-b][1,4]oxazin-7-yl)isoquinolin-3-yl)carbamate;<br>(1S,2R)-2-Cyanocyclopentyl (8-amino-7-fluoro-6-(8-methyl-2,3-dihydro-1H-pyrido[2,3-b][1,4]oxazin-7-yl)isoquinolin-3-yl)carbamate; |
| 482b | | |
| 482c | | (cis)-2-Cyanocyclopentyl (8-amino-7-fluoro-6-(8-methyl-2,3-dihydro-1H-pyrido[2,3-b][1,4]oxazin-7-yl)isoquinolin-3-yl)carbamate;<br>(1S,2S)-2-Cyanocyclopentyl (8-amino-7-fluoro-6-(8-methyl-2,3-dihydro-1H-pyrido[2,3-b][1,4]oxazin-7-yl)isoquinolin-3-yl)carbamate;<br>(1R,2R)-2-Cyanocyclopentyl (8-amino-7-fluoro-6-(8-methyl-2,3-dihydro-1H-pyrido[2,3-b][1,4]oxazin-7-yl)isoquinolin-3-yl)carbamate; |
| 482d | | |
| 483 | 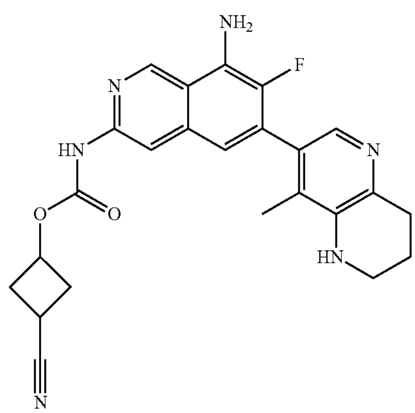 [SMILES: Cc1c(-c2cc3cc(NC(=O)OC4CC(C#N)C4)ncc3c(N)c2F)cnc2c1NCCC2] | 3-Cyanocyclobutyl (8-amino-7-fluoro-6-(4-methyl-5,6,7,8-tetrahydro-1,5-naphthyridin-3-yl)isoquinolin-3-yl)carbamate; |
| 483a | | (1s,3s)-3-cyanocyclobutyl (8-amino-7-fluoro-6-(4-methyl-5,6,7,8-tetrahydro-1,5-naphthyridin-3-yl)isoquinolin-3-yl)carbamate; |
| 483b | | (1r,3r)-3-cyanocyclobutyl (8-amino-7-fluoro-6-(4-methyl-5,6,7,8-tetrahydro-1,5-naphthyridin-3-yl)isoquinolin-3-yl)carbamate; |
| 484 | 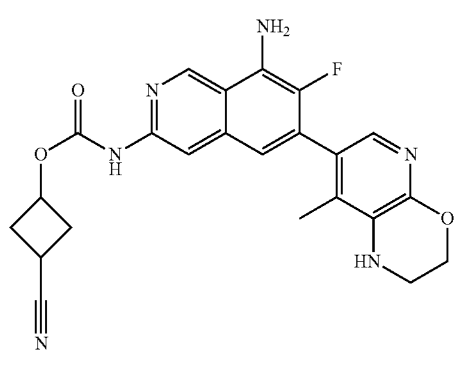 [SMILES: Cc1c(-c2cc3cc(NC(=O)OC4CC(C#N)C4)ncc3c(N)c2F)cnc2c1NCCO2] | 3-Cyanocyclobutyl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 484a | | (1s,3r)-3-Cyanocyclobutyl (8-amino-7-fluoro-6-(8-methyl-2,3-dihydro-1H-pyrido[2,3-b][1,4]oxazin-7-yl)isoquinolin-3-yl)carbamate; |
| 484b | | (1r,3r)-3-Cyanocyclobutyl (8-amino-7-fluoro-6-(8-methyl-2,3-dihydro-1H-pyrido[2,3-b][1,4]oxazin-7-yl)isoquinolin-3-yl)carbamate; |
| 485 | 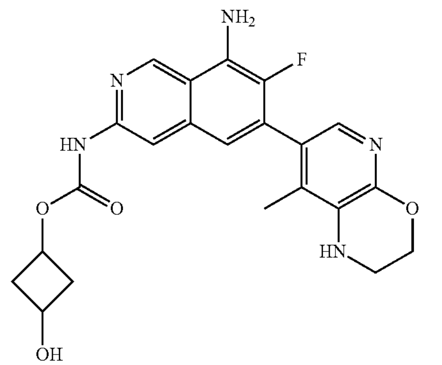 [SMILES: Cc1c(-c2cc3cc(NC(=O)OC4CC(O)C4)ncc3c(N)c2F)cnc2c1NCCO2] | 3-Hydroxycyclobutyl (8-amino-7-fluoro-6-(8-methyl-2,3-dihydro-1H-pyrido[2,3-b][1,4]oxazin-7-yl)isoquinolin-3-yl)carbamate; |
| 485a | | (1s,3r)-3-Hydroxycyclobutyl (8-amino-7-fluoro-6-(8-methyl-2,3-dihydro-1H-pyrido[2,3-b][1.4]oxazin-7-yl)isoquinolin-3-yl)carbamate; |
| 485b | | (1r,3r)-3-Hydroxycyclobutyl (8-amino-7-fluoro-6-(8-methyl-2,3-dihydro-1H-pyrido[2,3-b][1.4]oxazin-7-yl)isoquinolin-3-yl)carbamate; |
| 486 | 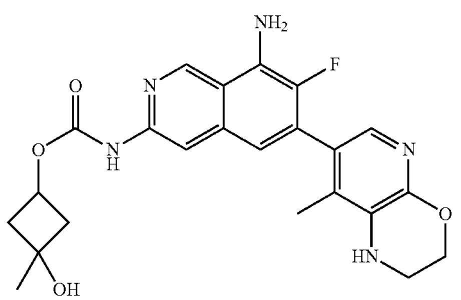 [SMILES: Cc1c(-c2cc3cc(NC(=O)OC4CC(C)(O)C4)ncc3c(N)c2F)cnc2c1NCCO2] | 3-Hydroxy-3-methylcyclobutyl (8-amino-7-fluoro-6-(8-methyl-2,3-dihydro-1H-pyrido[2,3-b][1.4]oxazin-7-yl)isoquinolin-3-yl)carbamate; |
| 486a | | (1s,3s)-3-Hydroxy-3-methylcyclobutyl (8-amino-7-fluoro-6-(8-methyl-2,3-dihydro-1H-pyrido[2,3-b][1,4]oxazin-7-yl)isoquinolin-3-yl)carbamate; |
| 486b | | (1r,3r)-3-Hydroxy-3-methylcyclobutyl (8-amino-7-fluoro-6-(8-methyl-2,3-dihydro-1H-pyrido[2,3-b][1,4]oxazin-7-yl)isoquinolin-3-yl)carbamate; |
| 487 | 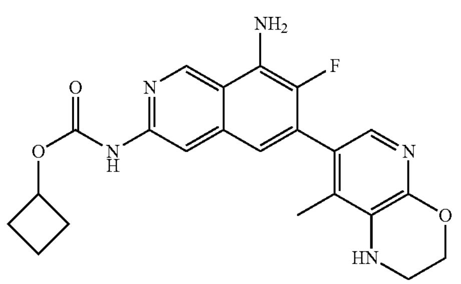 [SMILES: Cc1c(-c2cc3cc(NC(=O)OC4CCC4)ncc3c(N)c2F)cnc2c1NCCO2] | Cyclobutyl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 488 | 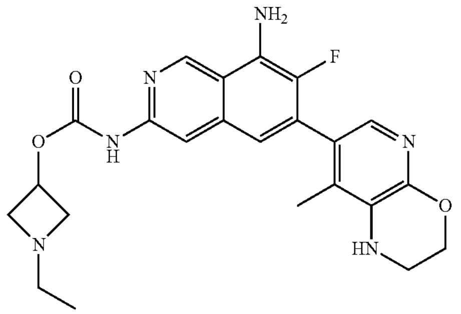 [SMILES: CCN1CC(OC(=O)Nc2cc3cc(-c4cnc5c(c4C)NCCO5)c(F)c(N)c3cn2)C1] | 1-Ethylazetidin-3-yl (8-amino-7-fluoro-6-(8-methyl-2,3-dihydro-1H-pyrido[2,3-b][1,4]oxazin-7-yl)isoquinolin-3-yl)carbamate; |
| 489 | 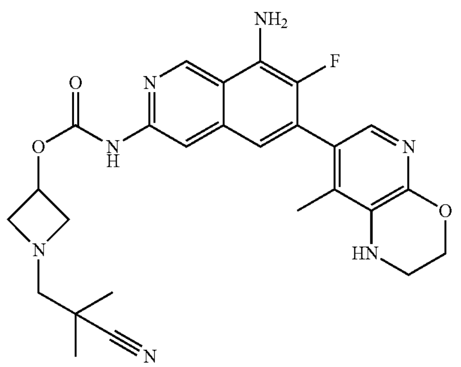 [SMILES: Cc1c(-c2cc3cc(NC(=O)OC4CN(CC(C)(C)C#N)C4)ncc3c(N)c2F)cnc2c1NCCO2] | 1-(2-Cyano-2-methylpropyl)azetidin-3-yl (8-amino-7-fluoro-6-(8-methyl-2,3-dihydro-1H-pyrido[2,3-b][1,4]oxazin-7-yl)isoquinolin-3-yl)carbamate; |
| 490 | 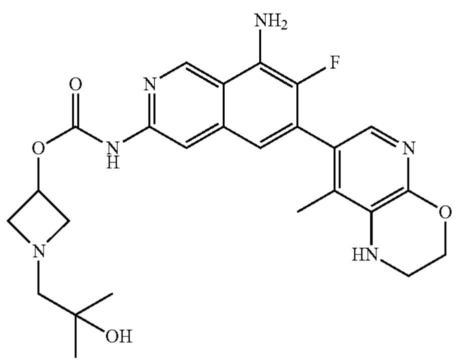 [SMILES: Cc1c(-c2cc3cc(NC(=O)OC4CN(CC(C)(C)O)C4)ncc3c(N)c2F)cnc2c1NCCO2] | 1-(2-Hydroxy-2-methylpropyl)azetidin-3-yl (8-amino-7-fluoro-6-(8-methyl-2,3-dihydro-1H-pyrido[2,3-b][1,4]oxazin-7-yl)isoquinolin-3-yl)carbamate; |
| 491 | 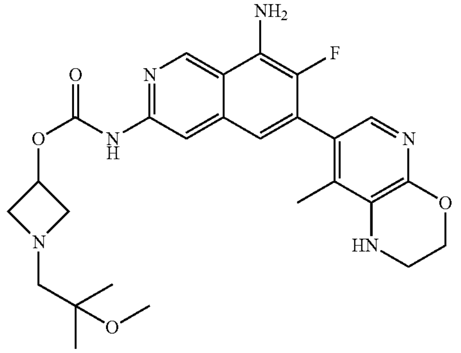 [SMILES: COC(C)(C)CN1CC(OC(=O)Nc2cc3cc(-c4cnc5c(c4C)NCCO5)c(F)c(N)c3cn2)C1] | 1-(2-Methoxy-2-methylpropyl)azetidin-3-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 492 | 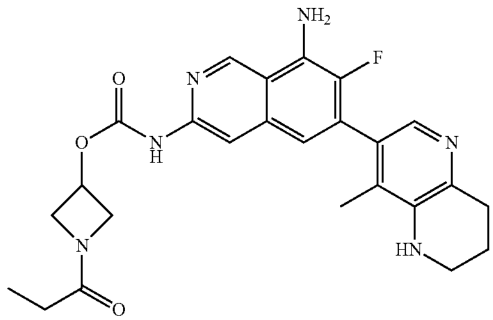 [SMILES: CCC(=O)N1CC(OC(=O)Nc2cc3cc(-c4cnc5c(c4C)NCCC5)c(F)c(N)c3cn2)C1] | 1-Propionylazetidin-3-yl (8-amino-7-fluoro-6-(4-methyl-5,6,7,8-tetrahydro-1,5-naphthyridin-3-yl)isoquinolin-3-yl)carbamate; |
| 493 | 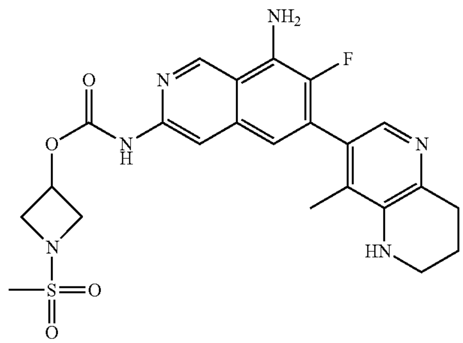 [SMILES: Cc1c(-c2cc3cc(NC(=O)OC4CN(S(C)(=O)=O)C4)ncc3c(N)c2F)cnc2c1NCCC2] | 1-(Methylsulfonyl)azetidin-3-yl (8-amino-7-fluoro-6-(4-methyl-5,6,7,8-tetrahydro-1,5-naphthyridin-3-yl)isoquinolin-3-yl)carbamate; |
| 494 | 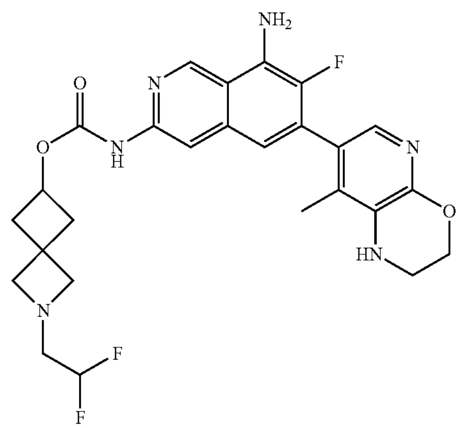 [SMILES: Cc1c(-c2cc3cc(NC(=O)OC4CC5(C4)CN(CC(F)F)C5)ncc3c(N)c2F)cnc2c1NCCO2] | 2-(2,2-Difluoroethyl)-2-azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate; |
| 495 | 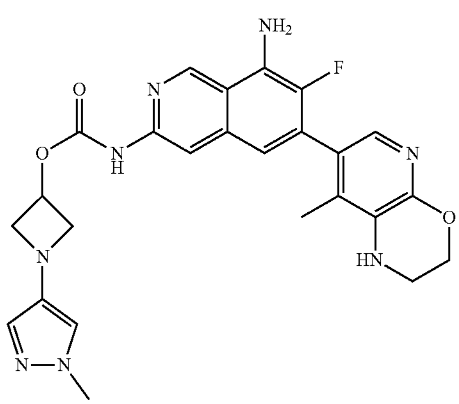 [SMILES: Cc1c(-c2cc3cc(NC(=O)OC4CN(c5cnn(C)c5)C4)ncc3c(N)c2F)cnc2c1NCCO2] | 1-(1-Methyl-1H-pyrazol-4-yl)azetidin-3-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 496 | 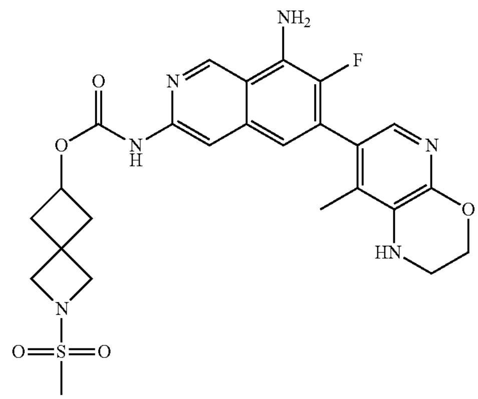 [SMILES: Cc1c(-c2cc3cc(NC(=O)OC4CC5(C4)CN(S(C)(=O)=O)C5)ncc3c(N)c2F)cnc2c1NCCO2] | 2-(Methylsulfonyl)-2-azaspiro[3.3]heptan-6-yl (8-amino-7-fluoro-6-(8-methyl-2,3-dihydro-1H-pyrido[2,3-b][1,4]oxazin-7-yl)isoquinolin-3-yl)carbamate; |
| 497 | 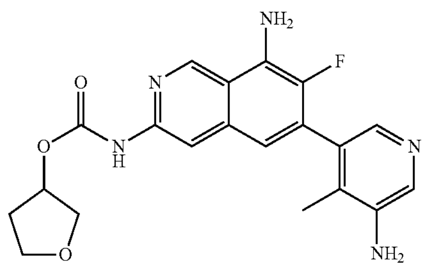 [SMILES: Cc1c(N)cncc1-c1cc2cc(NC(=O)OC3CCOC3)ncc2c(N)c1F] | Tetrahydrofuran-3-yl (8-amino-6-(5-amino-4-methylpyridin-3-yl)-7-fluoroisoquinolin-3-yl)carbamate; |
| 498 | 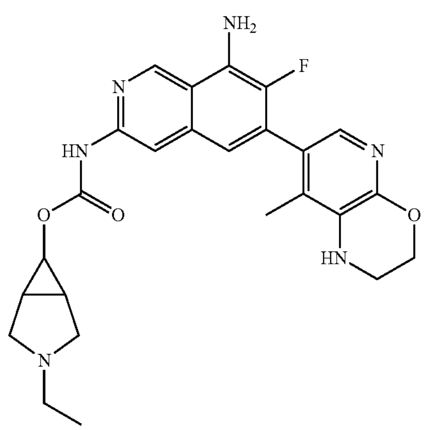 [SMILES: CCN1CC2C(C1)C2OC(=O)Nc1cc2cc(-c3cnc4c(c3C)NCCO4)c(F)c(N)c2cn1] | 3-Ethyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |
| 499 | 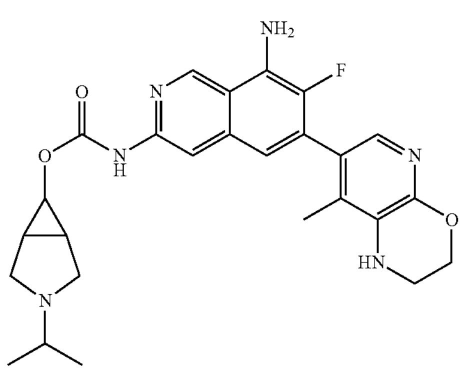 [SMILES: Cc1c(-c2cc3cc(NC(=O)OC4C5CN(C(C)C)CC54)ncc3c(N)c2F)cnc2c1NCCO2] | 3-Isopropyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 499a | | (1R,5S,6r)-3-Isopropyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |
| 499b | | (1R,5S,6s)-3-Isopropyl-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |
| 500 | 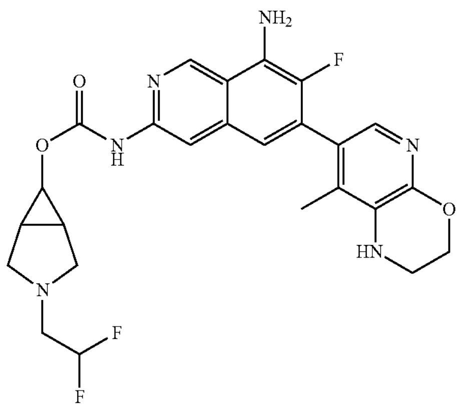 [SMILES: Cc1c(-c2cc3cc(NC(=O)OC4C5CN(CC(F)F)CC54)ncc3c(N)c2F)cnc2c1NCCO2] | 3-(2,2-Difluoroethyl)-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |
| 501 | 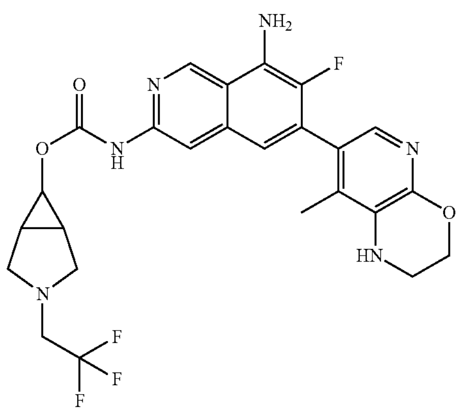 [SMILES: Cc1c(-c2cc3cc(NC(=O)OC4C5CN(CC(F)(F)F)CC54)ncc3c(N)c2F)cnc2c1NCCO2] | 3-(2,2,2-Trifluoroethyl)-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |
| 502 | 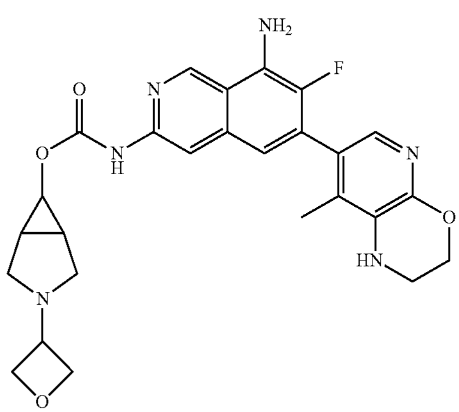 [SMILES: Cc1c(-c2cc3cc(NC(=O)OC4C5CN(C6COC6)CC54)ncc3c(N)c2F)cnc2c1NCCO2] | 3-(Oxetan-3-yl)-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 502a | | (1R,5S,6r)-3-(oxetan-3-yl)-3-azabicyclo[3.1.0]hexan-6-yl (8-amino-7-fluoro-6-(8-methyl-2,3-dihydro-1/7-pyrido[2,3-b][1,4]oxazin-7-yl)isoquinolin-3-yl)carbamate; |
| 502b | | (1R,5S,6s)-3-(oxetan-3-yl)-3-azabicyclo[3.1.0]hexan-6-yl (8-amino-7-fluoro-6-(8-methyl-2,3-dihydro-1/7-pyrido[2,3-b][1,4]oxazin-7-yl)isoquinolin-3-yl)carbamate; |
| 503 | 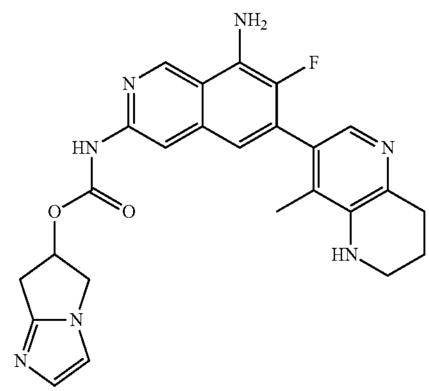 [SMILES: Cc1c(-c2cc3cc(NC(=O)OC4Cc5nccn5C4)ncc3c(N)c2F)cnc2c1NCCC2] | 6,7-Dihydro-5H-pyrrolo[1,2-a]imidazol-6-yl (8-amino-7-fluoro-6-(4-methyl-5,6,7,8-tetrahydro-1,5-naphthyridin-3-yl)isoquinolin-3-yl)carbamate; |
| 504 | 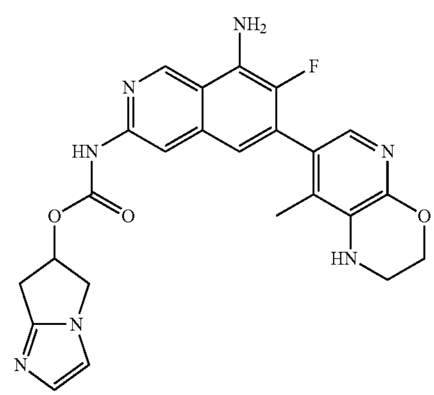 [SMILES: Cc1c(-c2cc3cc(NC(=O)OC4Cc5nccn5C4)ncc3c(N)c2F)cnc2c1NCCO2] | 6,7-Dihydro-5H-pyrrolo[1,2-aimidazol-6-yl (8-amino-7-fluoro-6-(8-methyl-2,3-dihydro-1H-pyrido[2,3-b][1,4]oxazin-7-yl)isoquinolin-3-yl)carbamate; |
| 504a | | (R)-6,7-dihydro-5H-pyrrolo[1,2-a]imidazol-6-yl (8-amino-7-fluoro-6-(8-methyl-2,3-dihydro-1H-pyrido[2,3-b][1,4]oxazin-7-yl)isoquinolin-3-yl)carbamate; (S)-6,7-dihydro-5H-pyrrolo[1,2-a]imidazol-6-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 504b | | |
| 505 | 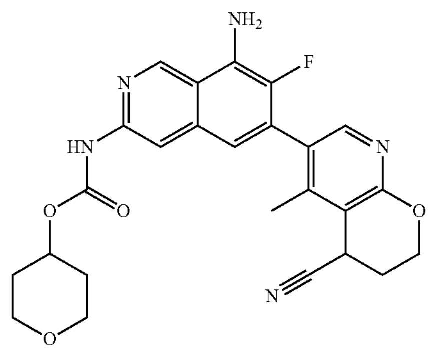 [SMILES: Cc1c(-c2cc3cc(NC(=O)OC4CCOCC4)ncc3c(N)c2F)cnc2c1C(C#N)CCO2] | Tetrahydro-2H-pyran-4-yl (8-amino-6-(4-cyano-5-methyl-3,4-dihydro-2H-pyrano[2,3-b]pyridin-6-yl)-7-fluoroisoquinolin-3-yl)carbamate; |
| 506 | 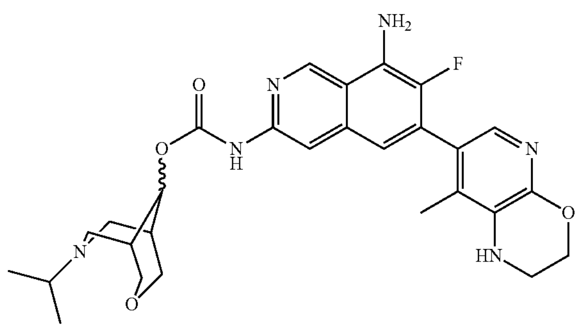 [SMILES: Cc1c(-c2cc3cc(NC(=O)OC4C5COCC4CN(C(C)C)C5)ncc3c(N)c2F)cnc2c1NCCO2] | 7-Isopropyl-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; |
| 506a | | (1R,5S,9s)-7-isopropyl-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; |
| 506b | | (1R,5S,9r)-7-isopropyl-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; |
| 507 | 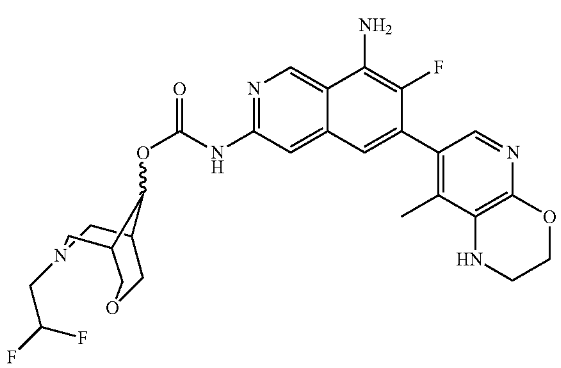 [SMILES: Cc1c(-c2cc3cc(NC(=O)OC4C5COCC4CN(CC(F)F)C5)ncc3c(N)c2F)cnc2c1NCCO2] | 7-(2,2-Difluoroethyl)-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; |
| 507a 507b | | (1R,5S,9s)-7-(2,2-difluoroethyl)-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; (IR,5S,9r)-7-(2,2-difluoroethyl)-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 508 | 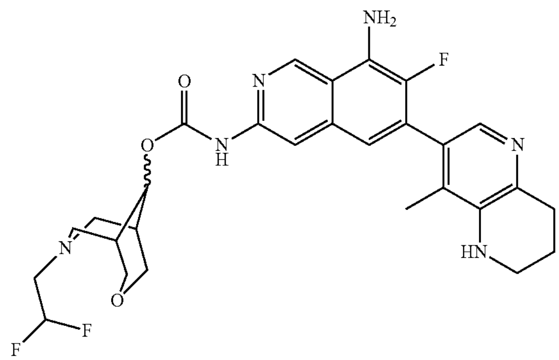 [SMILES: Cc1c(-c2cc3cc(NC(=O)OC4C5COCC4CN(CC(F)F)C5)ncc3c(N)c2F)cnc2c1NCCC2] | 7-(2,2-Difluoroethyl)-3-oxa-7-azabicyclo[3.3.1]nonan-9-yl (8-amino-7-fluoro-6-(4-methyl-5,6,7,8-tetrahydro-1,5-naphthyridin-3-yl)isoquinolin-3-yl)carbamate; |
| 509 | 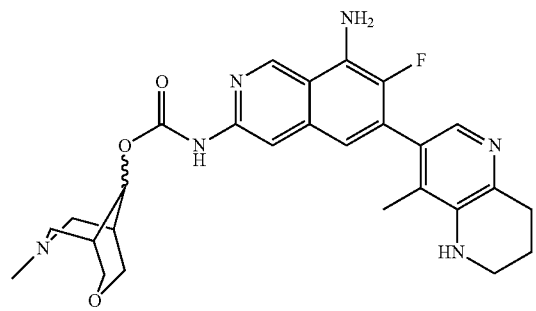 [SMILES: Cc1c(-c2cc3cc(NC(=O)OC4C5COCC4CN(C)C5)ncc3c(N)c2F)cnc2c1NCCC2] | 7-Methyl-3-oxa-7-azabicyclo[3.3.1]nonan-9-yl (8-amino-7-fluoro-6-(4-methyl-5,6,7,8-tetrahydro-1,5-naphthyridin-3-yl)isoquinolin-3-yl)carbamate; |
| 510 | 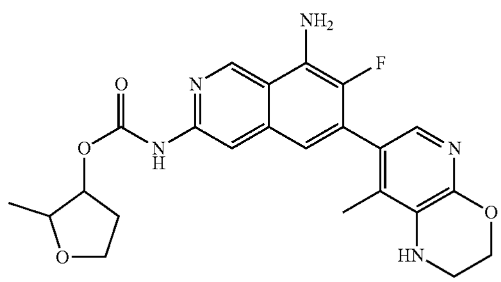 [SMILES: Cc1c(-c2cc3cc(NC(=O)OC4CCOC4C)ncc3c(N)c2F)cnc2c1NCCO2] | 2-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 510a | | (trans)-2-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3S,4R)-2-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4S)-2-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (cis)-2-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4R)-2-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3S,4S)-2-Methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 510b | | |
| 510c | | |
| 510d | | |

| No. | Structure | Name |
|---|---|---|
| 511 | 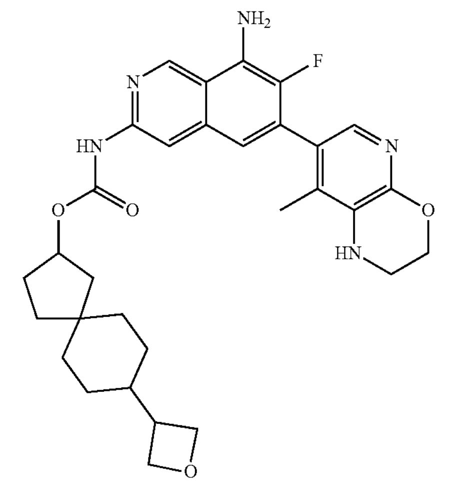 | 8-(Oxetan-3-yl)-8-azaspiro[4.5]decan-2-yl (8-amino-7-fluoro-6-(8-methyl-2,3-dihydro-1H-pyrido[2,3-b][1,4]oxazin-7-yl)isoquinolin-3-yl)carbamate; |
| 511a | | (R)-8-(Oxetan-3-yl)-8-azaspiro[4.5]decan-2-yl (8-amino-7-fluoro-6-(8-methyl-2,3-dihydro-1H-pyrido[2,3-b][1,4]oxazin-7-yl)isoquinolin-3-yl)carbamate; |
| 511b | | (S)-8-(Oxetan-3-yl)-8-azaspiro[4.5]decan-2-yl (8-amino-7-fluoro-6-(8-methyl-2,3-dihydro-1H-pyrido[2,3-b][1,4]oxazin-7-yl)isoquinolin-3-yl)carbamate; |
| 512 | 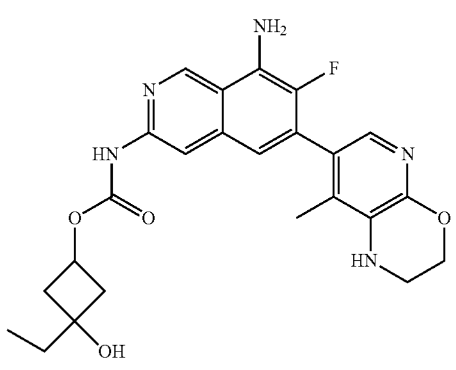 [SMILES: CCC1(O)CC(OC(=O)Nc2cc3cc(-c4cnc5c(c4C)NCCO5)c(F)c(N)c3cn2)C1] | 3-Ethyl-3-hydroxycyclobutyl (8-amino-7-fluoro-6-(8-methyl-2,3-dihydro-1H-pyrido[2,3-b][1,4]oxazin-7-yl)isoquinolin-3-yl)carbamate; |
| 512a | | (1s,3r)-3-Ethyl-3-hydroxycyclobutyl (8-amino-7-fluoro-6-(8-methyl-2,3-dihydro-1H-pyrido[2,3-b][1,4]oxazin-7-yl)isoquinolin-3-yl)carbamate; |
| 512b | | (1r,3s)-3-Ethyl-3-hydroxycyclobutyl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 513 | 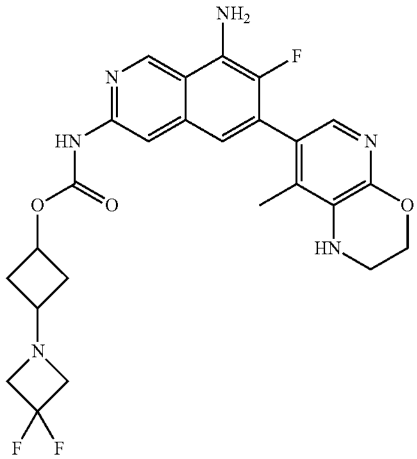 [SMILES: Cc1c(-c2cc3cc(NC(=O)OC4CC(N5CC(F)(F)C5)C4)ncc3c(N)c2F)cnc2c1NCCO2] | 3-(3,3-Difluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate; |
| 513a 513b | | (1s,3s)-3-(3,3-Difluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate; (1r,3r)-3-(3,3-Difluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate; |
| 514 | 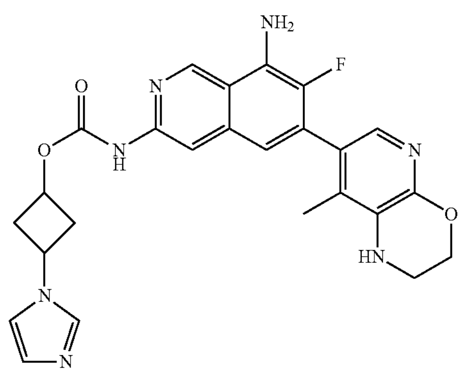 [SMILES: Cc1c(-c2cc3cc(NC(=O)OC4CC(n5ccnc5)C4)ncc3c(N)c2F)cnc2c1NCCO2] | 3-(1H-Imidazol-1-yl)cyclobutyl (8-amino-7-fluoro-6-(8-methyl-2,3-dihydro-1H-pyrido[2,3-b][1,4]oxazin-7-yl)isoquinolin-3-yl)carbamate; |
| 514a 514b | | (1r,3)-3-(1H-Imidazol-1-yl)cyclobutyl (8-amino-7-fluoro-6-(8-methyl-2,3-dihydro-1H-pyrido[2,3-b][1,4]oxazin-7-yl)isoquinolin-3-yl)carbamate; (1s,3s)-3-(1H-Imidazol-1-yl)cyclobutyl (8-amino-7-fluoro-6-(8-methyl-2,3-dihydro-1H-pyrido[2,3-b][1,4]oxazin-7-yl)isoquinolin-3-yl)carbamate; |
| 515 | 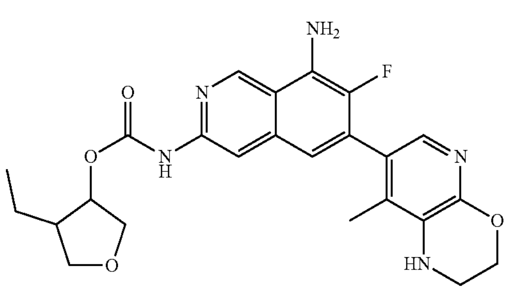 [SMILES: CCC1COCC1OC(=O)Nc1cc2cc(-c3cnc4c(c3C)NCCO4)c(F)c(N)c2cn1] | 4-Ethyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 515a 515b | | (trans)-4-Ethyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3S,4R)-4-Ethyltetrahydrofuran-3-yl (8-amino-7-fluoro-6-(8-methyl-2,3-dihydro-1H-pyrido[2,3-b][1,4]oxazin-7- |

-continued

| No. | Structure | Name |
|---|---|---|
| | | yl)isoquinolin-3-yl)carbamate;<br>(3R,4S)-4-Ethyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 515c<br>515d | | (cis)-4-Ethyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate;<br>(3R,4R)-4-Ethyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate;<br>(3S,4S)-4-Ethyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 516 | ![structure] | 4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 516a<br>516b | | (trans)-4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate;<br>(3R,4S)-4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate;<br>(3S,4R)-4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 516c<br>516d | | (cis)-4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate;<br>(3R,4R)-4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate;<br>(3S,4S)-4-Cyclopropyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 517 | ![structure] | 3-(Azetidine-1-carbonyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 517a | | (1s,3s)-3-(Azetidine-1-carbonyl)cyclobutyl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 517b | | (1r,3r)-3-(Azetidine-1-carbonyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 518 | 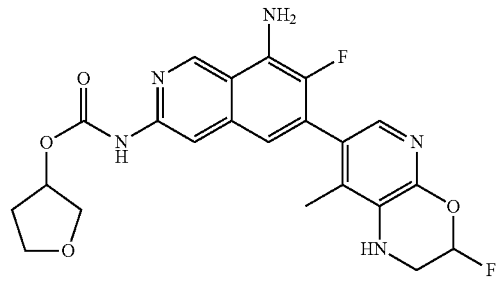 [SMILES: Cc1c(-c2cc3cc(NC(=O)OC4CCOC4)ncc3c(N)c2F)cnc2c1NCC(F)O2] | Tetrahydrofuran-3-yl (8-amino-7-fluoro-6-(3-fluoro-8-methyl-2,3-dihydro-1H-yl)isoquinolin-3-yl)carbamate; pyrido[2,3-b][1,4]oxazin-7- |
| 518a | | (R)-Tetrahydrofuran-3-yl (8-amino-7-fluoro-6-(3-fluoro-8-methyl-2,3-dihydro-1H-pyrido[2,3-b][1,4]oxazin-7-yl)isoquinolin-3-yl)carbamate; (R)-Tetrahydrofuran-3-yl (8-amino-7-fluoro-6-((R)-3-fluoro-8-methyl-2,3-dihydro-1H-pyrido[2,3-b][1,4]oxazin-7-yl)isoquinolin-3-yl)carbamate; (R)-Tetrahydrofuran-3-yl (8-amino-7-fluoro-6-((S)-3-fluoro-8-methyl-2,3-dihydro-1H-pyrido[2,3-b][1,4]oxazin-7-yl)isoquinolin-3-yl)carbamate; |
| 518b | | |
| 518c | | (S)-tetrahydrofuran-3-yl (8-amino-7-fluoro-6-(3-fluoro-8-methyl-2,3-dihydro-1H-pyrido[2,3-b][1,4]oxazin-7-yl)isoquinolin-3-yl)carbamate; (S)-tetrahydrofuran-3-yl (8-amino-7-fluoro-6-((S)-3-fluoro-8-methyl-2,3-dihydro-1H-pyrido[2,3-b][1,4]oxazin-7-yl)isoquinolin-3-yl)carbamate; (S)-tetrahydrofuran-3-yl (8-amino-7-fluoro-6-((S)-3-fluoro-8-methyl-2,3-dihydro-1H-pyrido[2,3-b][1,4]oxazin-7-yl)isoquinolin-3-yl)carbamate; |
| 518d | | |
| 519 | 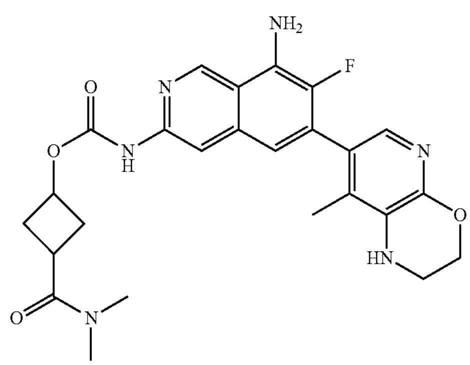 [SMILES: Cc1c(-c2cc3cc(NC(=O)OC4CC(C(=O)N(C)C)C4)ncc3c(N)c2F)cnc2c1NCCO2] | 3-(Dimethylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 519a | | (1s,3s)-3-(Dimethylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 519b | | (1r,3r)-3-(Dimethylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 520 | 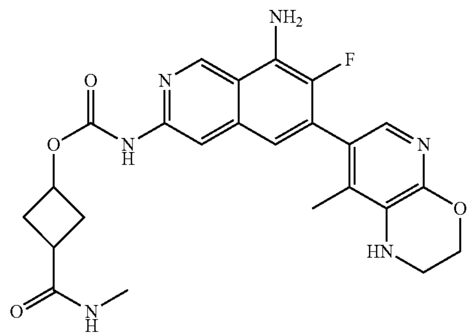 [SMILES: CNC(=O)C1CC(OC(=O)Nc2cc3cc(-c4cnc5c(c4C)NCCO5)c(F)c(N)c3cn2)C1] | 3-(Methylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 520a | | (1s,3s)-3-(Methylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 520b | | (1r,3r)-3-(Methylcarbamoyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 521 | 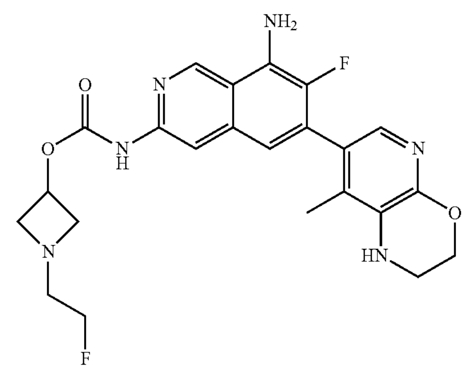 [SMILES: Cc1c(-c2cc3cc(NC(=O)OC4CN(CCF)C4)ncc3c(N)c2F)cnc2c1NCCO2] | 1-(2-Fluoroethyl)azetidin-3-yl (8-amino-7-fluoro-6-(8-methyl-2,3-dihydro-1H-pyrido[2,3-b][1,4]oxazin-7-yl)isoquinolin-3-yl)carbamate; |
| 522 | 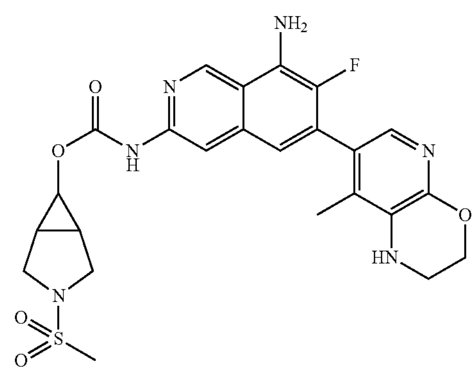 [SMILES: Cc1c(-c2cc3cc(NC(=O)OC4C5CN(S(C)(=O)=O)CC54)ncc3c(N)c2F)cnc2c1NCCO2] | 3-(Methylsulfonyl))-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |
| 522a | | (1R,5S,6s)-3-(Methylsulfonyl)-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |
| 522b | | (1R,5S,6r)-3-(Methylsulfonyl)-3-azabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 523 | 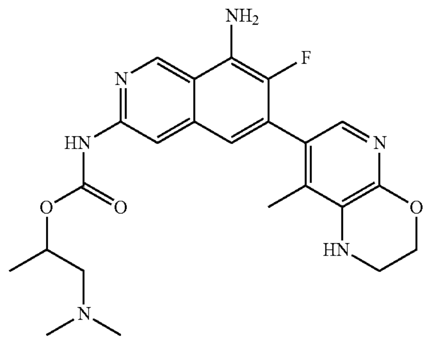 [SMILES: Cc1c(-c2cc3cc(NC(=O)OC(C)CN(C)C)ncc3c(N)c2F)cnc2c1NCCO2] | 1-(Dimethylamino)propan-2-yl(8-amino-7-fluoro-6-(8-methyl-2,3-dihydro-1H-pyrido[2,3-b][1,4]oxazin-7-yl)isoquinolin-3-yl)carbamate; |
| 523a 523b | | (R)-1-(Dimethylamino)propan-2-yl (8-amino-7-fluoro-6-(8-methyl-2,3-dihydro-1H-pyrido[2,3-b][1,4]oxazin-7-yl)isoquinolin-3-yl)carbamate; (S)-1-(Dimethylamino)propan-2-yl (8-amino-7-fluoro-6-(8-methyl-2,3-dihydro-1H-pyrido[2,3-b][1,4]oxazin-7-yl)isoquinolin-3-yl)carbamate; |
| 524 | 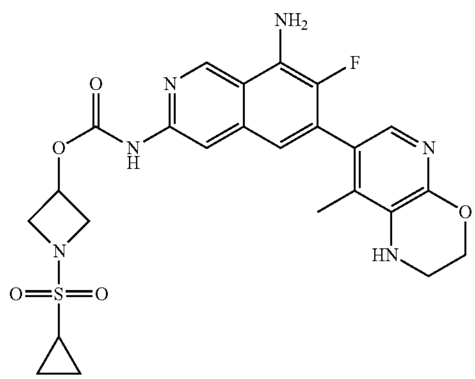 [SMILES: Cc1c(-c2cc3cc(NC(=O)OC4CN(S(=O)(=O)C5CC5)C4)ncc3c(N)c2F)cnc2c1NCCO2] | 1-(Cyclopropylsulfonyl)azetidin-3-yl (8-amino-7-fluoro-6-(8-methyl-2,3-dihydro-1H-pyrido[2,3-b][1,4]oxazin-7-yl)isoquinolin-3-yl)carbamate; |
| 525 | 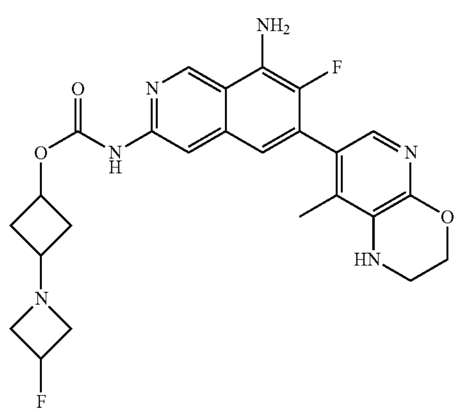 [SMILES: Cc1c(-c2cc3cc(NC(=O)OC4CC(N5CC(F)C5)C4)ncc3c(N)c2F)cnc2c1NCCO2] | 3-(3-Fluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate; |
| 525a 525b | | (1s,3s)-3-(3-Fluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate; (1r,3r)-3-(3-Fluoroazetidin-1-yl)cyclobutyl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 526 | 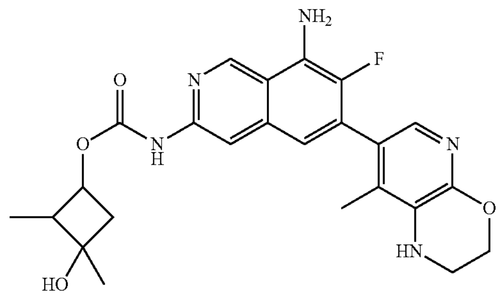 [SMILES: Cc1c(-c2cc3cc(NC(=O)OC4CC(C)(O)C4C)ncc3c(N)c2F)cnc2c1NCCO2] | 3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate; |
| 526a 526b | | (1R,2R,3S)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate; (1S,2S,3R)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate; |
| 526c 526d | | (1S,2R,3S)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate; (1R,2S,3R)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate; |
| 526e 526f 526g 526h | | (1R,2S,3S)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate; (1S,2R,3R)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate; (1S,2S,3S)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate; (1R,2R,3R)-3-Hydroxy-2,3-dimethylcyclobutyl (8-amino-7-fluoro-6-(8-methyl-2,3-dihydro-1H-pyrido[2,3-b][1,4]oxazin-7-yl)isoquinolin-3-yl)carbamate; |
| 527 | 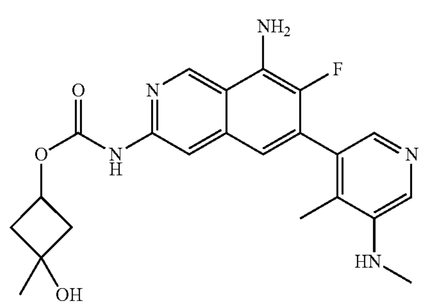 [SMILES: CNc1cncc(-c2cc3cc(NC(=O)OC4CC(C)(O)C4)ncc3c(N)c2F)c1C] | 3-Hydroxy-3-methylcyclobutyl (8-amino-7-fluoro-6-(4-methyl-5-(methylamino)pyridin-3-yl)isoquinolin-3-yl)carbamate; |
| 527a 527b | | (1s,3s)-3-Hydroxy-3-methylcyclobutyl (8-amino-7-fluoro-6-(4-methyl-5-(methylamino)pyridin-3-yl)isoquinolin-3-yl)carbamate; (1r,3r)-3-hydroxy-3-methylcyclobutyl (8-amino-7-fluoro-6-(4-methyl-5-(methylamino)pyridin-3-yl)isoquinolin-3-yl)carbamate; |

-continued

| No. | Structure | Name |
|---|---|---|
| 528 | 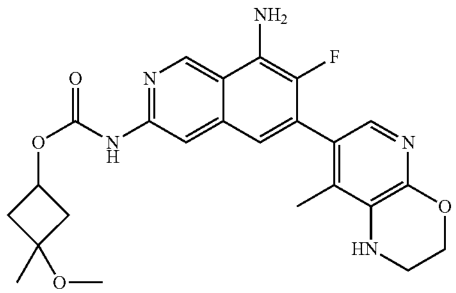 [SMILES: COC1(C)CC(OC(=O)Nc2cc3cc(-c4cnc5c(c4C)NCCO5)c(F)c(N)c3cn2)C1] | 3-Methoxy-3-methylcyclobutyl (8-amino-7-fluoro-6-(8-methyl-2,3-dihydro-1/7-pyrido[2,3-b][1,4]oxazin-7-yl)isoquinolin-3-yl)carbamate; |
| 528a | | (1s,3s)-3-Methoxy-3-methylcyclobutyl (8-amino-7-fluoro-6-(8-methyl-2,3-dihydro-1H-pyrido[2,3-b][1,4]oxazin-7-yl)isoquinolin-3-yl)carbamate; |
| 528b | | (1r,3r)-3-Methoxy-3-methylcyclobutyl (8-amino-7-fluoro-6-(8-methyl-2,3-dihydro-1H-pyrido[2,3-b][1,4]oxazin-7-yl)isoquinolin-3-yl)carbamate; |
| 529 | 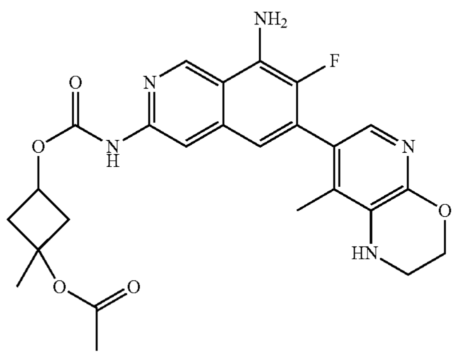 [SMILES: CC(=O)OC1(C)CC(OC(=O)Nc2cc3cc(-c4cnc5c(c4C)NCCO5)c(F)c(N)c3cn2)C1] | 3-(((8-Amino-7-fluoro-6-(8-methyl-2,3-dihydro-1H-pyrido[2,3-b][1,4]oxazin-7-yl)isoquinolin-3-yl)carbamoyl)oxy)-1-methylcyclobutylacetate; |
| 529a | | (1r,3r)-3-(((8-Amino-7-fluoro-6-(8-methyl-2,3-dihydro-1H-pyrido[2,3-b][1,4]oxazin-7-yl)isoquinolin-3-yl)carbamoyl)oxy)-1-methylcyclobutyl acetate; |
| 529b | | (1s,3s)-3-(((8-Amino-7-fluoro-6-(8-methyl-2,3-dihydro-1H-pyrido[2,3-b][1,4]oxazin-7-yl)isoquinolin-3-yl)carbamoyl)oxy)-1-methylcyclobutyl acetate; |
| 530 | 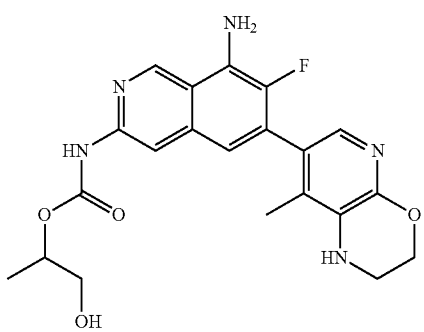 [SMILES: Cc1c(-c2cc3cc(NC(=O)OC(C)CO)ncc3c(N)c2F)cnc2c1NCCO2] | l-Hydroxypropan-2-yl (8-amino-7-fluoro-6-(8-methyl-2,3-dihydro-1H-pyrido[2,3-b][1,4]oxazin-7-yl)isoquinolin-3-yl)carbamate; |
| 530a 530b | | (R)-1-Hydroxypropan-2-yl (8-amino-7-fluoro-6-(8-methyl-2,3-dihydro-1H-pyrido[2,3-b][1,4]oxazin-7-yl)isoquinolin-3-yl)carbamate; (S)-1-Hydroxypropan-2-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 531 | 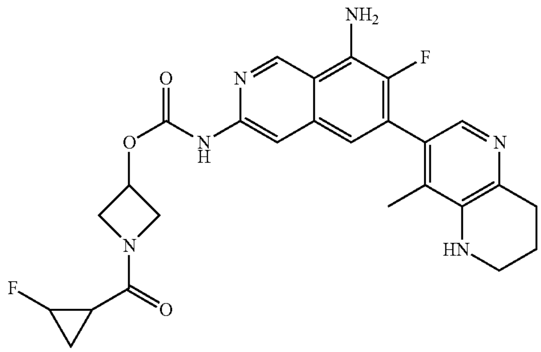 [SMILES: Cc1c(-c2cc3cc(NC(=O)OC4CN(C(=O)C5CC5F)C4)ncc3c(N)c2F)cnc2c1NCCC2] | 1-(2-Fluorocyclopropane-1-carbonyl)azetidin-3-yl (8-amino-7-fluoro-6-(4-methyl-5,6,7,8-tetrahydro-F5-naphthyridin-3-yl)isoquinolin-3-yl)carbamate; |
| 531a | | 1-(trans-2-Fluorocyclopropane-1-carbonyl)azetidin-3-yl (8-amino-7-fluoro-6-(4-methyl-5,6,7,8-tetrahydro-1,5-naphthyridin-3-yl)isoquinolin-3-yl)carbamate; 1-((1R,2S)-2-Fluorocyclopropane-1-carbonyl)azetidin-3-yl (8-amino-7-fluoro-6-(4-methyl-5,6,7,8-tetrahydro-1,5-naphthyridin-3-yl)isoquinolin-3-yl)carbamate; 1-((1S,2R)-2-Fluorocyclopropane-1-carbonyl)azetidin-3-yl (8-amino-7-fluoro-6-(4-methyl-5,6,7,8-tetrahydro-1,5-naphthyridin-3-yl)isoquinolin-3-yl)carbamate; |
| 531b | | |
| 531c | | 1-(cis-2-fluorocyclopropane-1-carbonyl)azetidin-3-yl (8-amino-7-fluoro-6-(4-methyl-5,6,7,8-tetrahydro-1,5-naphthyridin-3-yl)isoquinolin-3-yl)carbamate; 1-((1R,2R)-2-fluorocyclopropane-1-carbonyl)azetidin-3-yl (8-amino-7-fluoro-6-(4-methyl-5,6,7,8-tetrahydro-1,5-naphthyridin-3-yl)isoquinolin-3-yl)carbamate; 1-((1S,2S)-2-fluorocyclopropane-1-carbonyl)azetidin-3-yl (8-amino-7-fluoro-6-(4-methyl-5,6,7,8-tetrahydro-1,5-naphthyridin-3-yl)isoquinolin-3-yl)carbamate; |
| 531d | | |
| 532 | 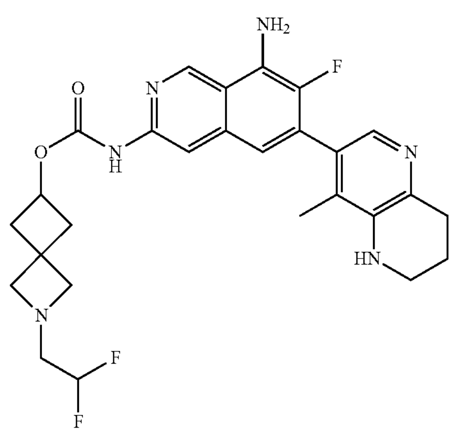 [SMILES: Cc1c(-c2cc3cc(NC(=O)OC4CC5(C4)CN(CC(F)F)C5)ncc3c(N)c2F)cnc2c1NCCC2] | 2-(2,2-Difluoroethyl)-2-azaspiro[3.3]heptan-6-yl (8-amino-7-fluoro-6-(4-methyl-5,6,7,8-tetrahydro-1,5-naphthyridin-3-yl)isoquinolin-3-yl)carbamate; |

| No. | Structure | Name |
|---|---|---|
| 533 | 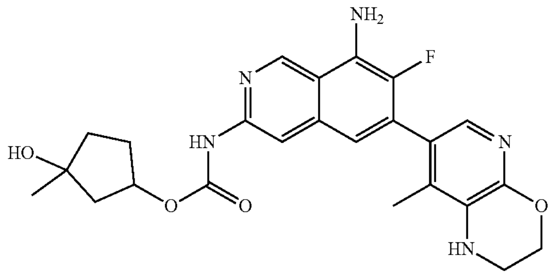 [SMILES: Cc1c(-c2cc3cc(NC(=O)OC4CCC(C)(O)C4)ncc3c(N)c2F)cnc2c1NCCO2] | 3-Hydroxy-3-methylcyclopentyl (8-amino-7-fluoro-6-(8-methyl-2,3-dihydro-1H-pyrido[2,3-b][1,4]oxazin-7-yl)isoquinolin-3-yl)carbamate; |
| 533a 533b 533c 533d | | (1R,3S)-3-hydroxy-3-methylcyclopentyl (8-amino-7-fluoro-6-(8-methyl-2,3-dihydro-1H-pyrido[2,3-b][1,4]oxazin-7-yl)isoquinolin-3-yl)carbamate; (1S,3R)-3-hydroxy-3-methylcyclopentyl (8-amino-7-fluoro-6-(8-methyl-2,3-dihydro-1H-pyrido[2,3-b][1,4]oxazin-7-yl)isoquinolin-3-yl)carbamate; (1R,3R)-3-hydroxy-3-methylcyclopentyl (8-amino-7-fluoro-6-(8-methyl-2,3-dihydro-1H-pyrido[2,3-b][1,4]oxazin-7-yl)isoquinolin-3-yl)carbamate; (1S,3S)-3-hydroxy-3-methylcyclopentyl (8-amino-7-fluoro-6-(8-methyl-2,3-dihydro-1H-pyrido[2,3-b][1,4]oxazin-7-yl)isoquinolin-3-yl)carbamate; |
| 534 | 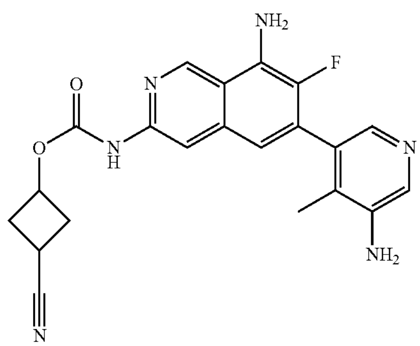 [SMILES: Cc1c(N)cncc1-c1cc2cc(NC(=O)OC3CC(C#N)C3)ncc2c(N)c1F] | 3-Cyanocyclobutyl (8-amino-6-(5-amino-4-methylpyridin-3-yl)-7-fluoroisoquinolin-3-yl)carbamate; |
| 534a | | (1s,3s)-3-Cyanocyclobutyl (8-amino-6-(5-amino-4-methylpyridin-3-yl)-7-fluoroisoquinolin-3-yl)carbamate; |
| 534b | | (1r,3r)-3-Cyanocyclobutyl (8-amino-6-(5-amino-4-methylnyridin-3-yl)-7-fluoroisoquinolin-3-yl)carbamate; |
| 535 | 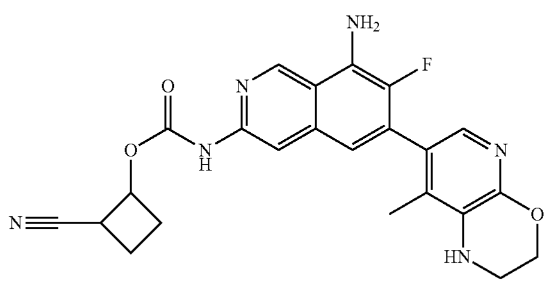 [SMILES: Cc1c(-c2cc3cc(NC(=O)OC4CCC4C#N)ncc3c(N)c2F)cnc2c1NCCO2] | 2-Cyanocyclobutyl (8-amino-7-fluoro-6-(8-methyl-2,3-dihydro-1H-pyrido[2,3-b][1,4]oxazin-7-yl)isoquinolin-3-yl)carbamate; |
| 535a 535b | | trans-2-Cyanocyclobutyl (8-amino-7-fluoro-6-(8-methyl-2,3-dihydro-1H-pyrido[2,3-b][1,4]oxazin-7-yl)isoquinolin-3-yl)carbamate; (1S,2R)-2-Cyanocyclobutyl (8-amino-7-fluoro-6-(8-methyl-2,3-dihydro-1H-pyrido[2,3-b][1,4]oxazin-7-yl)isoquinolin-3-yl)carbamate; (1R,2S)-2-Cyanocyclobutyl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 535c 535d | | cis-2-Cyanocyclobutyl (8-amino-7-fluoro-6-(8-methyl-2,3-dihydro-1H-pyrido[2,3-b][1,4]oxazin-7-yl)isoquinolin-3-yl)carbamate; (1S,2S)-2-Cyanocyclobutyl (8-amino-7-fluoro-6-(8-methyl-2,3-dihydro-1H-pyrido[2,3-b][1,4]oxazin-7-yl)isoquinolin-3-yl)carbamate; (1R,2R)-2-Cyanocyclobutyl (8-amino-7-fluoro-6-(8-methyl-2,3-dihydro-1H-pyrido[2,3-b][1,4]oxazin-7-yl)isoquinolin-3-yl)carbamate; |
| 536 | | 3-(Cyanomethyl)cyclobutyl (8-amino-7-fluoro-6-(8-methyl-2,3-dihydro-1/7-pyrido[2,3-b][1,4]oxazin-7-yl)isoquinolin-3-yl)carbamate; |
| 536a 536b | | (1r,3s)-3-(Cyanomethy)cyclobutyl (8-amino-7-fluoro-6-(8-methyl-2,3-dihydro-1H-pyrido[2,3-b][1,4]oxazin-7-yl)isoquinolin-3-yl)carbamate; (1s,3r)-3-(Cyanomethyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 537 | | 3-Cyano-3-methylcyclobutyl (8-amino-7-fluoro-6-(8-methyl-2,3-dihydro-1H-pyrido[2,3-b][1,4]oxazin-7-yl)isoquinolin-3-yl)carbamate; |
| 537a 537b | | (1s,3s)-3-Cyano-3-methylcyclobutyl (8-amino-7-fluoro-6-(8-methyl-2,3-dihydro-1H-pyrido[2,3-b][1,4]oxazin-7-yl)isoquinolin-3-yl)carbamate; (1r,3r)-3-Cyano-3-methylcyclobutyl (8-amino-7-fluoro-6-(8-methyl-2,3-dihydro-1H-pyrido[2,3-b][1,4]oxazin-7-yl)isoquinolin-3-yl)carbamate; |
| 538 | | 4-Cyanotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 538a 538b | | trans-4-Cyanotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 538c 538d | | (3S,4R)-4-Cyanotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4S)-4-Cyanotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; cis-2-4-Cyanotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3S,4S)-4-Cyanotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4R)-4-cyanotetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 539 | 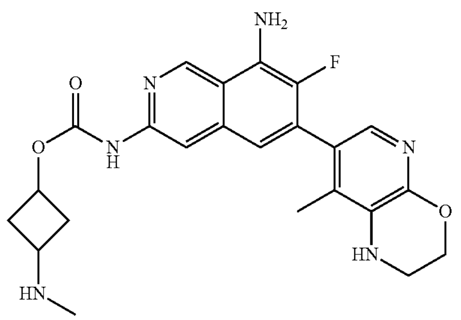 [SMILES: CNC1CC(OC(=O)Nc2cc3cc(-c4cnc5c(c4C)NCCO5)c(F)c(N)c3cn2)C1] | 3-(Methylamino)cyclobutyl (8-amino-7-fluoro-6-(8-methyl-2,3-dihydro-1H-pyrido[2,3-b][1,4]oxazin-7-yl)isoquinolin-3-yl)carbamate; |
| 539a | | (1r,3r)-3-(Methylamino)cyclobutyl (8-amino-7-fluoro-6-(8-methyl-2,3-dihydro-1H-pyrido[2,3-b][1,4]oxazin-7-yl)isoquinolin-3-yl)carbamate; |
| 539b | | (1s,3s)-3-(Methylamino)cyclobutyl (8-amino-7-fluoro-6-(8-methyl-2,3-dihydro-1H-pyrido[2,3-b][1,4]oxazin-7-yl)isoquinolin-3-yl)carbamate; |
| 540 | 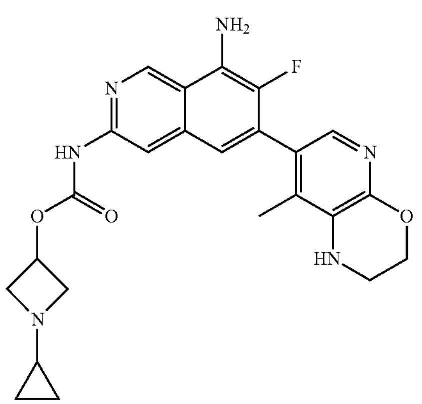 [SMILES: Cc1c(-c2cc3cc(NC(=O)OC4CN(C5CC5)C4)ncc3c(N)c2F)cnc2c1NCCO2] | 1-Cyclopropylazetidin-3-yl (8-amino-7-fluoro-6-(8-methyl-2,3-dihydro-1H-pyrido[2,3-b][1,4]oxazin-7-yl)isoquinolin-3-yl)carbamate; |
| 541 | 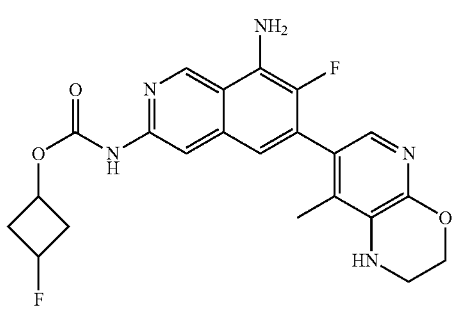 [SMILES: Cc1c(-c2cc3cc(NC(=O)OC4CC(F)C4)ncc3c(N)c2F)cnc2c1NCCO2] | 3-Fluorocyclobutyl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 541a | | (1s,3s)-3-Fluorocyclobutyl (8-amino-7-fluoro-6-(8-methyl-2,3-dihydro-1H-pyrido[2,3-b][1,4]oxazin-7-yl)isoquinolin-3-yl)carbamate; |
| 541b | | (1r,3r)-3-Fluorocyclobutyl (8-amino-7-fluoro-6-(8-methyl-2,3-dihydro-1H-pyrido[2,3-b][1,4]oxazin-7-yl)isoquinolin-3-yl)carbamate; |
| 542 | 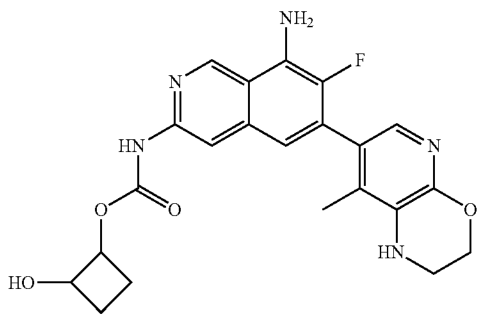 [SMILES: Cc1c(-c2cc3cc(NC(=O)OC4CCC4O)ncc3c(N)c2F)cnc2c1NCCO2] | 2-Hydroxycyclobutyl (8-amino-7-fluoro-6-(8-methyl-2,3-dihydro-1H-pyrido[2,3-b][1,4]oxazin-7-yl)isoquinolin-3-yl)carbamate; |
| 542a 542b | | cis-2-Hydroxycyclobutyl (8-amino-7-fluoro-6-(8-methyl-2,3-dihydro-1/7-pyrido[2,3-b][1,4]oxazin-7-yl)isoquinolin-3-yl)carbamate; (1S,2R)-2-Hydroxycyclobutyl (8-amino-7-fluoro-6-(8-methyl-2,3-dihydro-1/7-pyrido[2,3-b][1,4]oxazin-7-yl)isoquinolin-3-yl)carbamate; (1R,2S)-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate; |
| 542c 542d | | trans-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate; (1S,2S)-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate; (1R,2R)-2-Hydroxycyclobutyl (8-amino-7-fluoro-6-(8-methyl-2,3-dihydro-1H-pyrido[2,3-b][1,4]oxazin-7-yl)isoquinolin-3-yl)carbamate; |
| 543 | 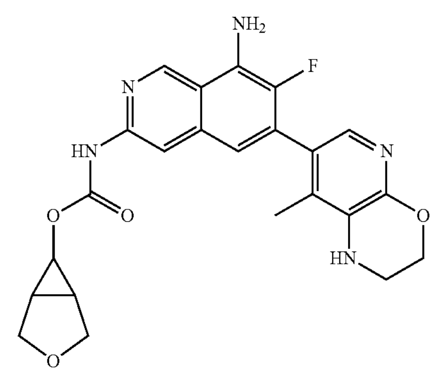 [SMILES: Cc1c(-c2cc3cc(NC(=O)OC4C5COCC54)ncc3c(N)c2F)cnc2c1NCCO2] | 3-Oxabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |
| 543a 543b | | (1R,5S,6s)-3-Oxabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; (1R,5S,6r)-3-Oxabicyclo[3.1.0]hexan-6-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 544 | | 4-Methyltetrahydrofuran-3-yl (8-amino-6-(5-amino-4-methylpyridin-3-yl)-7-fluoroisoquinolin-3-yl)carbamate; |
| 544a  544b | | trans-4-Methyltetrahydrofuran-3-yl (8-amino-6-(5-amino-4-methylpyridin-3-yl)-7-fluoroisoquinolin-3-yl)carbamate; (3R,4S)-4-Methyltetrahydrofuran-3-yl (8-amino-6-(5-amino-4-methyl)pyridin-3-yl)-7-fluoroisoquinolin-3-yl)carbamate; (3S,4R)-4-Methyltetrahydrofuran-3-yl (8-amino-6-(5-amino-4-methylpyridin-3-yl)-7-fluoroisoquinolin-3-yl)carbamate; |
| 544c  544d | | cis-4-Methyltetrahydrofuran-3-yl (8-amino-6-(5-amino-4-methyl)pyridin-3-yl)-7-fluoroisoquinolin-3-yl)carbamate; (3R,4R)-4-Methyltetrahydrofuran-3-yl (8-amino-6-(5-amino-4-methyl)pyridin-3-yl)-7-fluoroisoquinolin-3-yl)carbamate; (3S,4S)-4-Methyltetrahydrofuran-3-yl (8-amino-6-(5-amino-4-methyl)pyridin-3-yl)-7-fluoroisoquinolin-3-yl)carbamate; |
| 545 | | 1-(2-Fuorocyclopropane-1-carbonyl)azetidin-3-yl (8-amino-7-fluoro-6-(8-methyl-2,3-dihydro-1H-pyrido[2,3-b][1,4]oxazin-7-yl)isoquinolin-3-yl)carbamate; |
| 545a  545b | | 1-(trans-2-Fuorocyclopropane-1-carbonyl)azetidin-3-yl (8-amino-7-fluoro-6-(8-methyl-2,3-dihydro-1H-pyrido[2,3-b][1,4]oxazin-7-yl)isoquinolin-3-yl)carbamate; 1-((1R,2S)-2-Fluorocyclopropane-1-carbonyl)azetidin-3-yl (8-amino-7-fluoro-6-(8-methyl-2,3-dihydro-1H-pyrido[2,3-b][1,4]oxazin-7-yl)isoquinolin-3-yl)carbamate; 1-((1S,2R)-2-fluorocyclopropane-1-carbonyl)azetidin-3-yl (8-amino-7-fluoro-6-(8-methyl-2,3-dihydro-1H-pyrido[2,3-b][1,4]oxazin-7-yl)isoquinolin-3-yl)carbamate; |
| 545c  545d | | 1-(cis-2-Fuorocyclopropane-1-carbonyl)azetidin-3-yl (8-amino-7-fluoro-6-(8-methyl-2,3-dihydro-1H-pyrido[2,3-b][1,4]oxazin-7-yl)isoquinolin-3-yl)carbamate; 1-((1R,2R)-2-Fluorocyclopropane-1-carbonyl)azetidin-3-yl (8-amino-7-fluoro-6-(8-methyl-2,3-dihydro-1H-pyrido[2,3-b][1,4]oxazin-7-yl)isoquinolin-3-yl)carbamate; 1-((1S,2S)-2-Fluorocyclopropane-1-carbonyl)azetidin-3-yl (8-amino-7-fluoro- |

| No. | Structure | Name |
|---|---|---|
| | | 6-(8-methyl-2,3-dihydro-1H-pyrido[2,3-b][1,4]oxazin-7-yl)isoquinolin-3-yl)carbamate; |
| 546 | 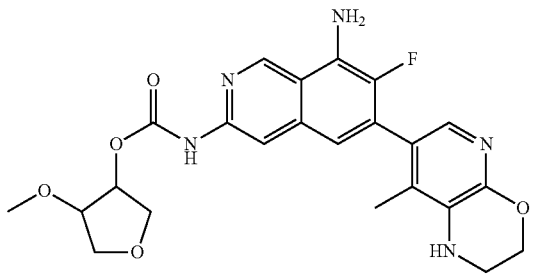 [SMILES: COC1COCC1OC(=O)Nc1cc2cc(-c3cnc4c(c3C)NCCO4)c(F)c(N)c2cn1] | 4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 546a | | trans-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 546b | | (3S,4S)-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4R)-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 546c | | cis-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 546d | | (3S,4R)-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate; (3R,4S)-4-Methoxytetrahydrofuran-3-yl (8-amino-7-fluoro-6-(8-methyl-2,3-dihydro-1H-pyrido[2,3-b][1,4]oxazin-7-yl)isoquinolin-3-yl)carbamate; |
| 547 | 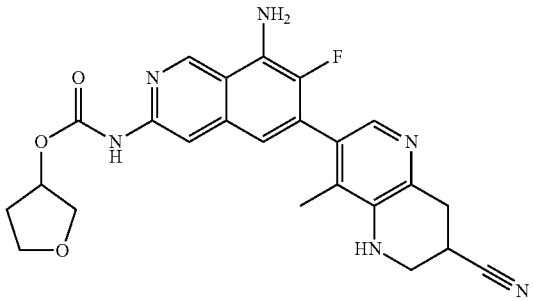 [SMILES: Cc1c(-c2cc3cc(NC(=O)OC4CCOC4)ncc3c(N)c2F)cnc2c1NCC(C#N)C2] | Tetrahydrofuran-3-yl (8-amino-6-(7-cyano-4-methyl-5,6,7,8-tetrahydro-1,5-naphthyridin-3-yl)-7-fluoroisoquinolin-3-yl)carbamate; |
| 547a | | (R)-Tetrahydrofuran-3-yl (8-amino-6-(7-cyano-4-methyl-5,6,7,8-tetrahydro-1,5-naphthyridin-3-yl)-7-fluoroisoquinolin-3-yl)carbamate; |
| 547b | | (S)-Tetrahydrofuran-3-yl (8-amino-6-(7-cyano-4-methyl-5,6,7,8-tetrahydro-1,5-naphthyridin-3-yl)-7-fluoroisoquinolin-3-yl)carbamate; |

| No. | Structure | Name |
|---|---|---|
| 548 | 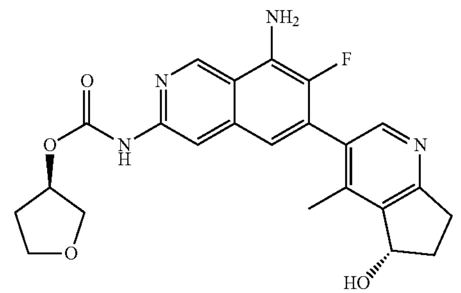 [SMILES: Cc1c(-c2cc3cc(NC(=O)O[C@@H]4CCOC4)ncc3c(N)c2F)cnc2c1[C@@H](O)CC2] | Tetrahydrofuran-3-yl (8-amino-7-fluoro-6-(5-hydroxy-4-methyl-6,7-dihydro-5H-cyclopentar[b]pyridin-3-yl)isoquinolin-3-yl)carbamate; |
| 548a | | (R)-tetrahydrofuran-3-yl (8-amino-7-fluoro-6-(5-hydroxy-4-methyl-6,7-dihydro-5H-cyclopenta[b]pyridin-3-yl)isoquinolin-3-yl)carbamate; |
| 548b | | (R)-tetrahydrofuran-3-yl (8-amino-7-fluoro-6-((S)-5-hydroxy-4-methyl-6,7-dihydro-5H-cyclopenta[b]pyridin-3-yl)isoquinolin-3-yl)carbamate; |
| 548c | | (R)-tetrahydrofuran-3-yl (8-amino-7-fluoro-6-((R)-5-hydroxy-4-methyl-6,7-dihydro-5H-cyclopenta[b]pyridin-3-yl)isoquinolin-3-yl)carbamate; |
| 548d | | (S)-tetrahydrofuran-3-yl (8-amino-7-fluoro-6-(5-hydroxy-4-methyl-6,7-dihydro-5H-cyclopenta[b]pyridin-3-yl)isoquinolin-3-yl)carbamate; (S)-tetrahydrofuran-3-yl (8-amino-7-fluoro-6-((S)-5-hydroxy-4-methyl-6,7-dihydro-5H-cyclopenta[b]pyridin-3-yl)isoquinolin-3-yl)carbamate; (S)-tetrahydrofuran-3-yl (8-amino-7-fluoro-6-((R)-5-hydroxy-4-methyl-6,7-dihydro-5H-cyclopenta[b]pyridin-3-yl)isoquinolin-3-yl)carbamate; |
| 549 | 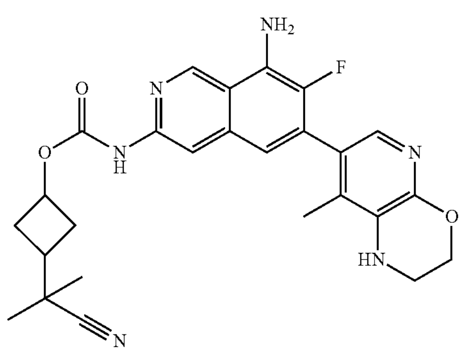 [SMILES: Cc1c(-c2cc3cc(NC(=O)OC4CC(C(C)(C)C#N)C4)ncc3c(N)c2F)cnc2c1NCCO2] | 3-(2-Cyanopropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate; |
| 549a | | (1s,3s)-3-(2-Cyanopropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate; |
| 549b | | (1r,3r)-3-(2-Cyanopropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 550 | 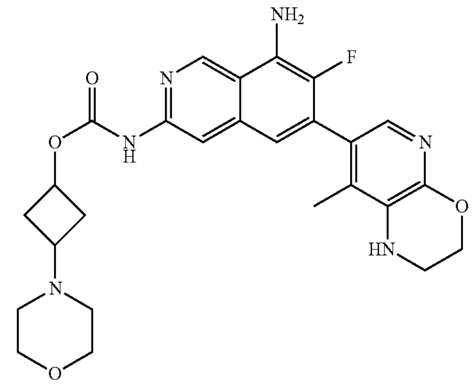 [SMILES: Cc1c(-c2cc3cc(NC(=O)OC4CC(N5CCOCC5)C4)ncc3c(N)c2F)cnc2c1NCCO2] | 3-Morpholinocyclobutyl (8-amino-7-fluoro-6-(8-methyl-2,3-dihydro-1H-pyrido[2,3-b][1,4]oxazin-7-yl)isoquinolin-3-yl)carbamate; |
| 550a | | (1r,3r)-3-Morpholinocyclobutyl (8-amino-7-fluoro-6-(8-methyl-2,3-dihydro-1H-pyrido[2,3-b][1,4]oxazin-7-yl)isoquinolin-3-yl)carbamate; |
| 550b | | (1s,3s)-3-Morpholinocyclobutyl (8-amino-7-fluoro-6-(8-methyl-2,3-dihydro-1H-pyrido[2,3-b][1,4]oxazin-7-yl)isoquinolin-3-yl)carbamate; |
| 551 | 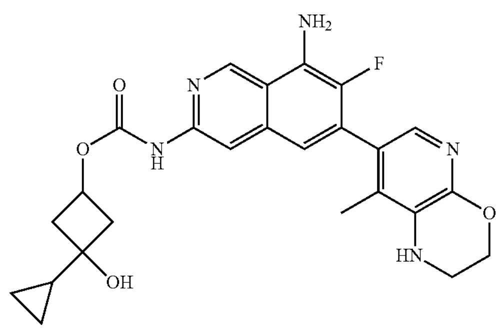 [SMILES: Cc1c(-c2cc3cc(NC(=O)OC4CC(O)(C5CC5)C4)ncc3c(N)c2F)cnc2c1NCCO2] | 3-Cyclopropyl-3-hydroxycyclobutyl (8-amino-7-fluoro-6-(8-methyl-2,3-dihydro-1H-pyrido[2,3-b][1,4]oxazin-7-yl)isoquinolin-3-yl)carbamate; |
| 551a | | (1s,3s)-3-Cyclopropyl-3-hydroxycyclobutyl (8-amino-7-fluoro-6-(8-methyl-2,3-dihydro-1H-pyrido[2,3-b][1,4]oxazin-7-yl)isoquinolin-3-yl)carbamate; |
| 551b | | (1r,3r)-3-Cyclopropyl-3-hydroxycyclobutyl (8-amino-7-fluoro-6-(8-methyl-2,3-dihydro-1H-pyrido[2,3-b][1,4]oxazin-7-yl)isoquinolin-3-yl)carbamate; |
| 552 | 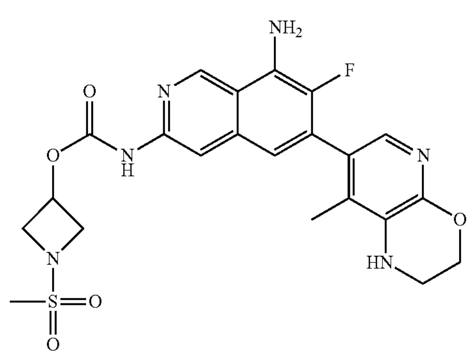 [SMILES: Cc1c(-c2cc3cc(NC(=O)OC4CN(S(C)(=O)=O)C4)ncc3c(N)c2F)cnc2c1NCCO2] | 1-(Methylsulfonyl)azetidin-3-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 553 | 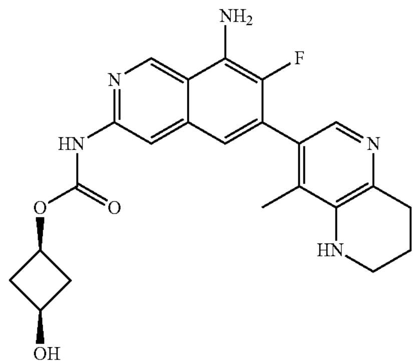 [SMILES: Cc1c(-c2cc3cc(NC(=O)O[C@H]4C[C@@H](O)C4)ncc3c(N)c2F)cnc2c1NCCC2] | 3-Hydroxycyclobutyl (8-amino-7-fluoro-6-(4-methyl-5,6,7,8-tetrahydro-1,5-naphthyridin-3-yl)isoquinolin-3-yl)carbamate; |
| 553a | | (1s,3s)-3-hydroxycyclobutyl (8-amino-7-fluoro-6-(4-methyl-5,6,7,8-tetrahydro-1,5-naphthyridin-3-yl)isoquinolin-3-yl)carbamate; |
| 553b | | (1r,3r)-3-hydroxycyclobutyl (8-amino-7-fluoro-6-(4-methyl-5,6,7,8-tetrahydro-1,5-naphthyridin-3-yl)isoquinolin-3-yl)carbamate; |
| 554 | 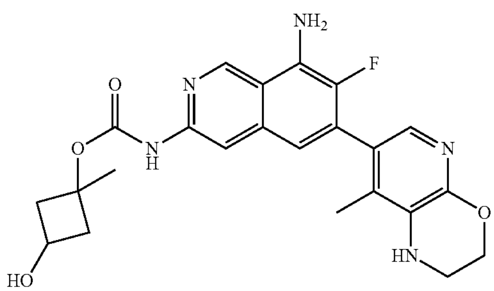 [SMILES: Cc1c(-c2cc3cc(NC(=O)OC4(C)CC(O)C4)ncc3c(N)c2F)cnc2c1NCCO2] | 3-Hydroxy-1-methylcyclobutyl (8-amino-7-fluoro-6-(8-methyl-2,3-dihydro-1H-pyrido[2,3-b][1,4]oxazin-7-yl)isoquinolin-3-yl)carbamate; |
| 554a | | (1s,3s)-3-Hydroxy-1-methylcyclobutyl (8-amino-7-fluoro-6-(8-methyl-2,3-dihydro-1H-pyrido[2,3-b][1,4]oxazin-7-yl)isoquinolin-3-yl)carbamate; |
| 554b | | (1r,3r)-3-Hydroxy-1-methylcyclobutyl (8-amino-7-fluoro-6-(8-methyl-2,3-dihydro-1H-pyrido[2,3-b][1,4]oxazin-7-yl)isoquinolin-3-yl)carbamate; |
| 555 | 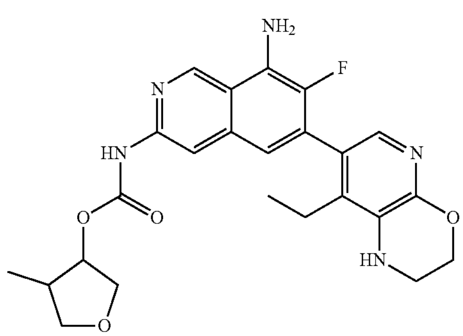 [SMILES: CCc1c(-c2cc3cc(NC(=O)OC4COCC4C)ncc3c(N)c2F)cnc2c1NCCO2] | 4-Methyltetrahydrofuran-3-yl (8-amino-6-(8-ethyl-2,3-dihydro-1H-pyrido[2,3-b][1,4]oxazin-7-yl)-7-fluoroisoquinolin-3-yl)carbamate; |
| 555a | | trans-4-Methyltetrahydrofuran-3-yl (8-amino-6-(8-ethyl-2,3-dihydro-1H-pyrido[2,3-b][1,4]oxazin-7-yl)-7-fluoroisoquinolin-3-yl)carbamate; |
| 555b | | (3R,4S)-4-Methyltetrahydrofuran-3-yl (8-amino-6-(8-ethyl-2,3-dihydro-1H-pyrido[2,3-b][1,4]oxazin-7-yl)-7-fluoroisoquinolin-3-yl)carbamate; |
| | | (3S,4R)-4-Methyltetrahydrofuran-3-yl (8-amino-6-(8-ethyl-2,3-dihydro-1H-pyrido[2,3-b][1,4]oxazin-7-yl)-7-fluoroisoquinolin-3-yl)carbamate; |
| 555c | | cis-4-Methyltetrahydrofuran-3-yl (8- |
| 555d | | amino-6-(8-ethyl-2,3-dihydro-1H- |

| No. | Structure | Name |
|---|---|---|
| | | pyrido[2,3-b][1,4]oxazin-7-yl)-7-fluoroisoquinolin-3-yl)carbamate;<br>(3R,4R)-4-methyltetrahydrofuran-3-yl (8-amino-6-(8-ethyl-2,3-dihydro-1H-pyrido[2,3-b][1,4]oxazin-7-yl)-7-fluoroisoquinolin-3-yl)carbamate;<br>(3S,4S)-4-methyltetrahydrofuran-3-yl (8-amino-6-(8-ethyl-2,3-dihydro-1H-pyrido[2,3-b][1,4]oxazin-7-yl)-7-fluoroisoquinolin-3-yl)carbamate; |
| 556 | 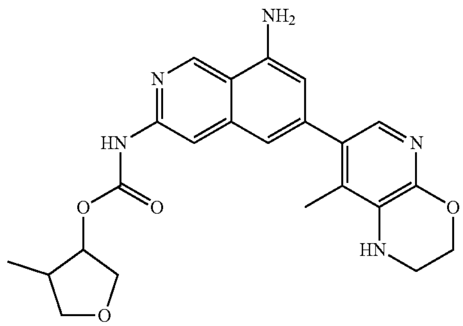 [SMILES: Cc1c(-c2cc(N)c3cnc(NC(=O)OC4COCC4C)cc3c2)cnc2c1NCCO2] | 4-Methyltetrahydrofuran-3-yl (8-amino-6-(8-methyl-2,3-dihydro-1H-pyrido[2,3-b][1,4]oxazin-7-yl)isoquinolin-3-yl)carbamate; |
| 556a<br>556b | | trans-4-Methyltetrahydrofuran-3-yl (8-amino-6-(8-methyl-2,3-dihydro-1H-pyrido[2,3-b][1,4]oxazin-7-yl)isoquinolin-3-yl)carbamate;<br>(3R,4S)-4-Methyltetrahydrofuran-3-yl (8-amino-6-(8-methyl-2,3-dihydro-1H-pyrido[2,3-b][1,4]oxazin-7-yl)isoquinolin-3-yl)carbamate;<br>(3S,4R)-4-Methyltetrahydrofuran-3-yl (8-amino-6-(8-methyl-2,3-dihydro-1H-pyrido[2,3-b][1,4]oxazin-7-yl)isoquinolin-3-yl)carbamate; |
| 556c<br>556d | | cis-4-Methyltetrahydrofuran-3-yl (8-amino-6-(8-methyl-2,3-dihydro-1H-pyrido[2,3-b][1,4]oxazin-7-yl)isoquinolin-3-yl)carbamate;<br>(3R,4R)-4-Methyltetrahydrofuran-3-yl (8-amino-6-(8-methyl-2,3-dihydro-1H-pyrido[2,3-b][1,4]oxazin-7-yl)isoquinolin-3-yl)carbamate;<br>(3S,4S)-4-Methyltetrahydrofuran-3-yl (8-amino-6-(8-methyl-2,3-dihydro-1H-pyrido[2,3-b][1,4]oxazin-7-yl)isoquinolin-3-yl)carbamate; |
| 557 | 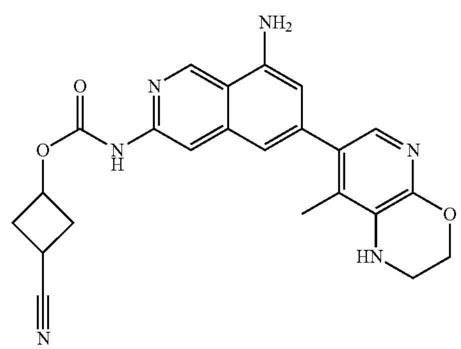 [SMILES: Cc1c(-c2cc(N)c3cnc(NC(=O)OC4CC(C#N)C4)cc3c2)cnc2c1NCCO2] | 3-Cyanocyclobutyl (8-amino-6-(8-methyl-2,3-dihydro-1H-pyrido[2,3-b][1,4]oxazin-7-yl)isoquinolin-3-yl)carbamate; |
| 557a<br>557b | | (1s,3s)-3-Cyanocyclobutyl (8-amino-6-(8-methyl-2,3-dihydro-1H-pyrido[2,3-b][1,4]oxazin-7-yl)isoquinolin-3-yl)carbamate;<br>(1r,3r)-3-Cyanocyclobutyl(8-amino-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 558 | | 4-Methyltetrahydrofuran-3-yl (8-amino-7-fluoro-6-(8-methyl-2-oxo-2,3-dihydro-1H-pyrido[2,3-b][1,4]oxazin-7-yl)isoquinolin-3-yl)carbamate; |
| 558a 558b | | trans-4-Methyltetrahydrofuran-3-yl (8-amino-7-fluoro-6-(8-methyl-2-oxo-2,3-dihydro-1H-pyrido[2,3-b][1,4]oxazin-7-yl)isoquinolin-3-yl)carbamate; (3R,4S)-4-Methyltetrahydrofuran-3-yl (8-amino-7-fluoro-6-(8-methyl-2-oxo-2,3-dihydro-1H-pyrido[2,3-b][1,4]oxazin-7-yl)isoquinolin-3-yl)carbamate; (I3S,4R)-4-Methyltetrahydrofuran-3-yl (8-amino-7-fluoro-6-(8-methyl-2-oxo-2,3-dihydro-1H-pyrido[2,3-b][1,4]oxazin-7-yl)isoquinolin-3-yl)carbamate; |
| 558c 558d | | cis-4-Methyltetrahydrofuran-3-yl (8-amino-7-fluoro-6-(8-methyl-2-oxo-2,3-dihydro-1H-pyrido[2,3-b][1,4]oxazin-7-yl)isoquinolin-3-yl)carbamate; (3R,4R)-4-Methyltetrahydrofuran-3-yl (8-amino-7-fluoro-6-(8-methyl-2-oxo-2,3-dihydro-1H-pyrido[2,3-b][1,4]oxazin-7-yl)isoquinolin-3-yl)carbamate; (3S,4S)-4-Methyltetrahydrofuran-3-yl (8-amino-7-fluoro-6-(8-methyl-2-oxo-2,3-dihydro-1H-pyrido[2,3-b][1,4]oxazin-7-yl)isoquinolin-3-yl)carbamate; |
| 559 | | 2-Methylcyclobutyl (8-amino-7-fluoro-6-(8-methyl-2,3-dihydro-1H-pyrido[2,3-b][1,4]oxazin-7-yl)isoquinolin-3-yl)carbamate; |
| 559a 559b | | cis-2-Methylcyclobutyl (8-amino-7-fluoro-6-(8-methyl-2,3-dihydro-1H-pyrido[2,3-b][1,4]oxazin-7-yl)isoquinolin-3-yl)carbamate; (1R,2S)-2-Methylcyclobutyl (8-amino-7-fluoro-6-(8-methyl-2,3-dihydro-1H-pyrido[2,3-b][1,4]oxazin-7-yl)isoquinolin-3-yl)carbamate; (1S,2R)-2-Methylcyclobutyl (8-amino-7-fluoro-6-(8-methyl-2,3-dihydro-1H-pyrido[2,3-b][1,4]oxazin-7-yl)isoquinolin-3-yl)carbamate; |
| 559c 559d | | trans-2-Methylcyclobutyl (8-amino-7-fluoro-6-(8-methyl-2,3-dihydro-1H-pyrido[2,3-b][1,4]oxazin-7-yl)isoquinolin-3-yl)carbamate; (1R,2R)-2-Methylcyclobutyl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| | | (1S,2S)-2-Methylcyclobutyl (8-amino-7-fluoro-6-(8-methyl-2,3-dihydro-1H-pyrido[2,3-b][1,4]oxazin-7-yl)isoquinolin-3-yl)carbamate; |
| 560 | ![structure] | 3-Hydroxycyclobutyl (8-amino-6-(4,7-dimethyl-5,6,7,8-tetrahydro-1,5-naphthyridin-3-yl)-7-fluoroisoquinolin-3-yl)carbamate; |
| 560a 560b 560c 560d | | (1s,3s)-3-Hydroxycyclobutyl (8-amino-6-((S)-4,7-dimethyl-5,6,7,8-tetrahydro-1,5-naphthyridin-3-yl)-7-fluoroisoquinolin-3-yl)carbamate; (1s,3s)-3-Hydroxycyclobutyl (8-amino-6-((R)-4,7-dimethyl-5,6,7,8-tetrahydro-1,5-naphthyridin-3-yl)-7-fluoroisoquinolin-3-yl)carbamate; (1r,3r)-3-Hydroxycyclobutyl (8-amino-6-((R)-4,7-dimethyl-5,6,7,8-tetrahydro-1,5-naphthyridin-3-yl)-7-fluoroisoquinolin-3-yl)carbamate; (1r,3r)-3-Hydroxycyclobutyl (8-amino-6-((7?)-4,7-dimethyl-5,6,7,8-tetrahydro-1,5-naphthyridin-3-yl)-7-fluoroisoquinolin-3-yl)carbamate; |
| 561 | ![structure] | 4-Methyltetrahydrofuran-3-yl (8-amino-7-cyano-6-(8-methyl-2,3-dihydro-1H-pyrido[2,3-b][1,4]oxazin-7-yl)isoquinolin-3-yl)carbamate; |
| 561a 561b | | trans-4-Methyltetrahydrofuran-3-yl (8-amino-7-cyano-6-(8-methyl-2,3-dihydro-1H-pyrido[2,3-b][1,4]oxazin-7-yl)isoquinolin-3-yl)carbamate; (3R,4S)-4-Methyltetrahydrofuran-3-yl (8-amino-7-cyano-6-(8-methyl-2,3-dihydro-1H-pyrido[2,3-b][1,4]oxazin-7-yl)isoquinolin-3-yl)carbamate; (3S,4R)-4-Methyltetrahydrofuran-3-yl (8-amino-7-cyano-6-(8-methyl-2,3-dihydro-1H-pyrido[2,3-b][1,4]oxazin-7-yl)isoquinolin-3-yl)carbamate; |
| 561c 561d | | cis-4-Methyltetrahydrofuran-3-yl (8-amino-7-cyano-6-(8-methyl-2,3-dihydro-1H-pyrido[2,3-b][1,4]oxazin-7-yl)isoquinolin-3-yl)carbamate; (3S,4S)-4-Methyltetrahydrofuran-3-yl (8-amino-7-cyano-6-(8-methyl-2,3-dihydro-1H-pyrido[2,3-b][1,4]oxazin-7-yl)isoquinolin-3-yl)carbamate; (3R,4R)-4-Methyltetrahydrofuran-3-yl (8-amino-7-cyano-6-(8-methyl-2,3-dihydro-1H-pyrido[2,3-b][1,4]oxazin-7-yl)isoquinolin-3-yl)carbamate; |

| No. | Structure | Name |
|---|---|---|
| 562 | | Tetrahydrofuran-3-yl (8-amino-6-(4-cyano-5-methyl-3,4-dihydro-2H-pyrano[2,3-b]pyridin-6-yl)-7-fluoroisoquinolin-3-yl)carbamate; |
| 562a 562b | | (R)-Tetrahydrofuran-3-yl (8-amino-6-(4-cyano-5-methyl-3,4-dihydro-2H-pyrano[2,3-b]pyridin-6-yl)-7-fluoroisoquinolin-3-yl)carbamate; (R)-Tetrahydrofuran-3-yl (8-amino-6-((R)-4-cyano-5-methyl-3,4-dihydro-2H-pyrano[2,3-b]pyridin-6-yl)-7-fluoroisoquinolin-3-yl)carbamate; (R)-Tetrahydrofuran-3-yl (8-amino-6-((S)-4-cyano-5-methyl-3,4-dihydro-2H-pyrano[2,3-b]pyridin-6-yl)-7-fluoroisoquinolin-3-yl)carbamate; |
| 562c 562d | | (S)-Tetrahydrofuran-3-yl (8-amino-6-(4-cyano-5-methyl-3,4-dihydro-2H-pyrano[2,3-b]pyridin-6-yl)-7-fluoroisoquinolin-3-yl)carbamate; (S)-Tetrahydrofuran-3-yl (8-amino-6-((R)-4-cyano-5-methyl-3,4-dihydro-2H-pyrano[2,3-b]pyridin-6-yl)-7-fluoroisoquinolin-3-yl)carbamate; (S)-tetrahydrofuran-3-yl (8-amino-6-((S)-4-cyano-5-methyl-3,4-dihydro-2H-pyrano[2,3-b]pyridin-6-yl)-7-fluoroisoquinolin-3-yl)carbamate; |
| 563 | | Hexahydrofuro[3,4-b]furan-3-yl (8-amino-7-fluoro-6-(8-methyl-2,3-dihydro-1H-pyrido[2,3-b][1,4]oxazin-7-yl)isoquinolin-3-yl)carbamate; |
| 563a 563b | | (3S,3aR,6aR)-Hexahydrofuro[3,4-b]furan-3-yl (8-amino-7-fluoro-6-(8-methyl-2,3-dihydro-1H-pyrido[2,3-b][1,4]oxazin-7-yl)isoquinolin-3-yl)carbamate; (3R,3aS,6aS)-Hexahydrofuro[3,4-b]furan-3-yl (8-amino-7-fluoro-6-(8-methyl-2,3-dihydro-1H-pyrido[2,3-b][1,4]oxazin-7-yl)isoquinolin-3-yl)carbamate; |
| 563c 563d | | (3R,3aR,6aR)-Hexahydrofuro[3,4-b]furan-3-yl (8-amino-7-fluoro-6-(8-methyl-2,3-dihydro-1H-pyrido[2,3-b][1,4]oxazin-7-yl)isoquinolin-3-yl)carbamate; (3S,3aS,6aS)-Hexahydrofuro[3,4-b]furan-3-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 566 | 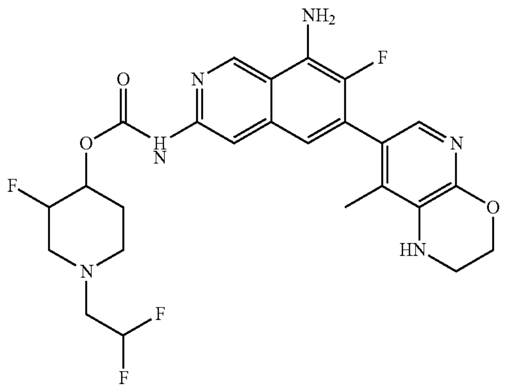 [SMILES: Cc1c(-c2cc3cc(NC(=O)OC4CCN(CC(F)F)CC4F)ncc3c(N)c2F)cnc2c1NCCO2] | 1-(2,2-Difluoroethyl)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate; |
| 566a<br>566b | | cis-1-(2,2-Difluoroethyl)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate;<br>(3S,4S)-1-(2,2-Difluoroethyl)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate;<br>(3R,4R)-1-(2,2-Difluoroethyl)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate; |
| 566c<br>566d | | trans-1-(2,2-Difluoroethyl)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate;<br>(3S,4S)-1-(2,2-Difluoroethyl)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate;<br>(3R,4R)-1-(2,2-Difluoroethyl)-3-fluoropiperidin-4-yl (8-amino-7-fluoro-6-(8-methyl-2,3-dihydro-1H-pyrido[2,3-b][1,4]oxazin-7-yl)isoquinolin-3-yl)carbamate; |
| 567 | 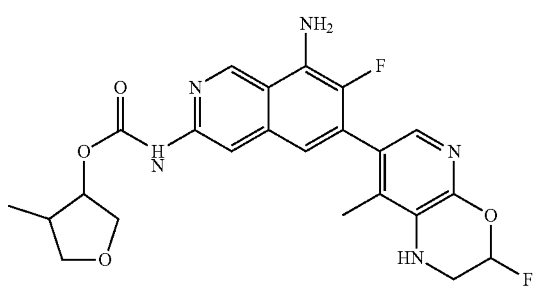 [SMILES: Cc1c(-c2cc3cc(NC(=O)OC4COCC4C)ncc3c(N)c2F)cnc2c1NCC(F)O2] | 4-Methyltetrahydrofuran-3-yl (8-amino-7-fluoro-6-(3-fluoro-8-methyl-2,3-dihydro-1H-pyrido[2,3-b][1,4]oxazin-7-yl)isoquinolin-3-yl)carbamate; |
| 567a<br>567b | | (3R,4S)-4-Methyltetrahydrofuran-3-yl (8-amino-7-fluoro-6-(3-fluoro-8-methyl-2,3-dihydro-1H-pyrido[2,3-b][1,4]oxazin-7-yl)isoquinolin-3-yl)carbamate;<br>(3R,4S)-4-Methyltetrahydrofuran-3-yl (8-amino-7-fluoro-6-((S)-3-fluoro-8-methyl-2,3-dihydro-1H-pyrido[2,3-b][1,4]oxazin-7-yl)isoquinolin-3-yl)carbamate;<br>(3R,4S)-4-Methyltetrahydrofuran-3-yl (8-amino-7-fluoro-6-((R)-3-fluoro-8-methyl-2,3-dihydro-1H-pyrido[2,3-b][1,4]oxazin-7-yl)isoquinolin-3-yl)carbamate; |
| 567c<br>567d | | (3S,4R)-4-Methyltetrahydrofuran-3-yl (8-amino-7-fluoro-6-(3-fluoro-8-methyl-2,3-dihydro-1H-pyrido[2,3-b][1,4]oxazin-7-yl)isoquinolin-3-yl)carbamate; |

-continued

| No. | Structure | Name |
|---|---|---|
| 567e | | (3S,4R)-4-Methyltetrahydrofuran-3-yl (8-amino-7-fluoro-6-((S)-3-fluoro-8-methyl-2,3-dihydro-1H-pyrido[2,3-b][1,4]oxazin-7-yl)isoquinolin-3-yl)carbamate; |
| 567f | | (3S,4R)-4-Methyltetrahydrofuran-3-yl (8-amino-7-fluoro-6-((R)-3-fluoro-8-methyl-2,3-dihydro-1H-pyrido[2,3-b][1,4]oxazin-7-yl)isoquinolin-3-yl)carbamate; |
| | | (3R,4R)-4-Methyltetrahydrofuran-3-yl (8-amino-7-fluoro-6-(3-fluoro-8-methyl-2,3-dihydro-1H-pyrido[2,3-b][1,4]oxazin-7-yl)isoquinolin-3-yl)carbamate; |
| | | (3R,4R)-4-Methyltetrahydrofuran-3-yl (8-amino-7-fluoro-6-((S)-3-fluoro-8-methyl-2,3-dihydro-1H-pyrido[2,3-b][1,4]oxazin-7-yl)isoquinolin-3-yl)carbamate; |
| | | (3R,4R)-4-Methyltetrahydrofuran-3-yl (8-amino-7-fluoro-6-((R)-3-fluoro-8-methyl-2,3-dihydro-1H-pyrido[2,3-b][1,4]oxazin-7-yl)isoquinolin-3-yl)carbamate; |
| 567g | | (3S,4S)-4-Methyltetrahydrofuran-3-yl (8-amino-7-fluoro-6-(3-fluoro-8-methyl-2,3-dihydro-1H-pyrido[2,3-b][1,4]oxazin-7-yl)isoquinolin-3-yl)carbamate; |
| 567h | | (3S,4S)-4-Methyltetrahydrofuran-3-yl (8-amino-7-fluoro-6-((S)-3-fluoro-8-methyl-2,3-dihydro-1H-pyrido[2,3-b][1,4]oxazin-7-yl)isoquinolin-3-yl)carbamate; |
| | | (3S,4S)-4-Methyltetrahydrofuran-3-yl (8-amino-7-fluoro-6-((R)-3-fluoro-8-methyl-2,3-dihydro-1H-pyrido[2,3-b][1,4]oxazin-7-yl)isoquinolin-3-yl)carbamate; |
| 568 | | Hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate; |
| 568a | | (3R,3aR,6aS)-Hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate; |
| 568b | | (3S,3aS,6aR)-Hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate; |
| 568c | | (3S,3aR,6aS)-Hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate; |
| 568d | | (3R,3aS,6aR)-Hexahydrofuro[2,3-b]furan-3-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 569 | | 3-Fluoro-1-(tetrahydrofuran-3-yl))piperidin-4-yl (8-amino-7-fluoro-6-(8-methyl-2,3-dihydro-1H-pyrido[2,3-b][1,4]oxazin-7-yl)isoquinolin-3-yl)carbamate; |
| 569a | | cis-3-Fluoro-1-(tetrahydrofuran-3-yl))piperidin-4-yl (8-amino-7-fluoro-6-(8-methyl-2,3-dihydro-1H-pyrido[2,3-b][1,4]oxazin-7-yl)isoquinolin-3-yl)carbamate; |
| 569b | | (3S,4R)-3-Fluoro-1-((S)-tetrahydrofuran-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; |
| 569c | | (3S,4R)-3-Fluoro-1-((R)-tetrahydrofuran-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; |
| 569d | | (3R,4S)-3-Fluoro-1-((S)-tetrahydrofuran-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; |
|  | | (3R,4S)-3-Fluoro-1-((R)-tetrahydrofuran-3-yl)piperidin-4-yl (8-amino-7-fluoro-6-(8-methyl-2,3-dihydro-1H-pyrido[2,3-b][1,4]oxazin-7-yl)isoquinolin-3-yl)carbamate; |
| 570 | | 3-Fluoro-1-(2-methoxyethyl)piperidin-4-yl (8-amino-7-fluoro-6-(8-methyl-2,3-dihydro-1H-pyrido[2,3-b][1,4]oxazin-7-yl)isoquinolin-3-yl)carbamate; |
| 570a | | (3R,4S)-3-fluoro-1-(2-methoxyethyl))piperidin-4-yl (8-amino-7-fluoro-6-(8-methyl-2,3-dihydro-1H-pyrido[2,3-b][1,4]oxazin-7-yl)isoquinolin-3-yl)carbamate; |
| 570b | | (3S,4R)-3-Fluoro-1-(2-methoxyethyl))piperidin-4-yl (8-amino-7-fluoro-6-(8-methyl-2,3-dihydro-1H-pyrido[2,3-b][1,4]oxazin-7-yl)isoquinolin-3-yl)carbamate; |
| 570c | | (3R,4R)-3-Fluoro-1-(2-methoxyethyl))piperidin-4-yl (8-amino-7-fluoro-6-(8-methyl-2,3-dihydro-1H-pyrido[2,3-b][1,4]oxazin-7-yl)isoquinolin-3-yl)carbamate; |
| 570d | | |

| No. | Structure | Name |
|---|---|---|
| | | (3S,4S)-3-fluoro-1-(2-methoxyethyl))piperidin-4-yl (8-amino-7-fluoro-6-(8-methyl-2,3-dihydro-1H-pyrido[2,3-b][1,4]oxazin-7-yl)isoquinolin-3-yl)carbamate; |
| 571 | 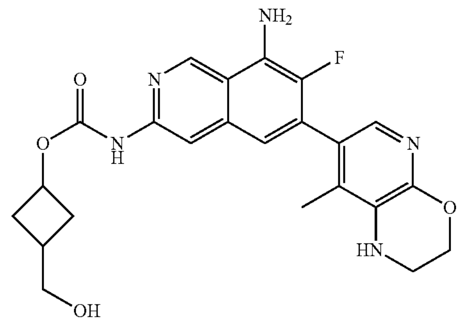 [SMILES: Cc1c(-c2cc3cc(NC(=O)OC4CC(CO)C4)ncc3c(N)c2F)cnc2c1NCCO2] | 3-(Hydroxymethyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 571a | | (1r,3r)-3-(Hydroxymethyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 571b | | (1s,3s)-3-(Hydroxymethyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 572 | 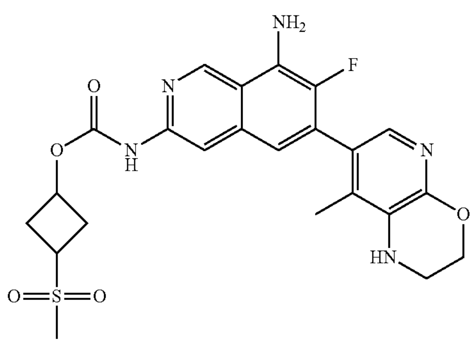 [SMILES: Cc1c(-c2cc3cc(NC(=O)OC4CC(S(C)(=O)=O)C4)ncc3c(N)c2F)cnc2c1NCCO2] | 3-(Methylsulfonyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 572a | | (1s,3s)-3-(Methylsulfonyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 572b | | (1r,3r)-3-(Methylsulfonyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 573 | 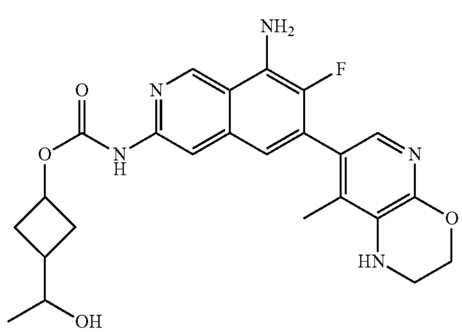 [SMILES: Cc1c(-c2cc3cc(NC(=O)OC4CC(C(C)O)C4)ncc3c(N)c2F)cnc2c1NCCO2] | 3-(1-Hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 573a | | (1S,3s)-3-((R)-1-Hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate; (1S,3r)-3-((S)-1-Hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate; (1R,3r)-3-((R)-1-Hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate; (1R,3s)-3-((S)-1-Hydroxyethyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 573b | | |
| 573c | | |
| 573d | | |
| 574 | 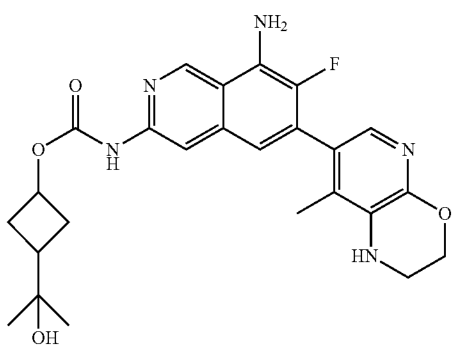 [SMILES: Cc1c(-c2cc3cc(NC(=O)OC4CC(C(C)(C)O)C4)ncc3c(N)c2F)cnc2c1NCCO2] | 3-(2-Hydroxypropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate; |
| 574a | | (1r,3r)-3-(2-Hydroxypropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate; (1s,3s)-3-(2-Hydroxypropan-2-yl)cyclobutyl (8-amino-7-fluoro-6-(8-methyl-2,3-dihydro-1H-pyrido[2,3-b][1,4]oxazin-7-yl)isoquinolin-3-yl)carbamate; |
| 574b | | |
| 575 | 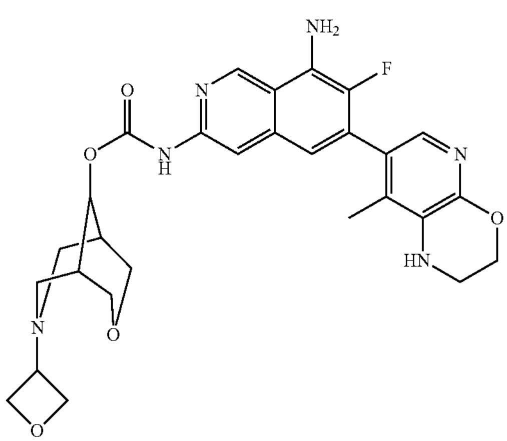 [SMILES: Cc1c(-c2cc3cc(NC(=O)OC4C5COCC4CN(C4COC4)C5)ncc3c(N)c2F)cnc2c1NCCO2] | 7-(Oxetan-3-yl)-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 575a | | (1R,5S,9s)-7-(Oxetan-3-yl)-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; |
| 575b | | (1R,5S,9r)-7-(oxetan-3-yl)-3-oxa-7-azabicyclo[3.3.1]nonan-9-yl (8-amino-7-fluoro-6-(8-methyl-2,3-dihydro-1H-pyrido[2,3-b][1,4]oxazin-7-yl)isoquinolin-3-yl)carbamate; |
| 576 | 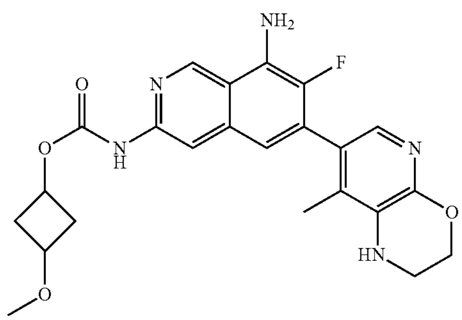 [SMILES: COC1CC(OC(=O)Nc2cc3cc(-c4cnc5c(c4C)NCCO5)c(F)c(N)c3cn2)C1] | 3-Methoxycyclobutyl (8-amino-7-fluoro-6-(8-methyl-2,3-dihydro-1H-pyrido[2,3-b][1,4]oxazin-7-yl)isoquinolin-3-yl)carbamate; |
| 576a 576b | | (1r,3r)-3-Methoxycyclobutyl (8-amino-7-fluoro-6-(8-methyl-2,3-dihydro-1H-pyrido[2,3-b][1,4]oxazin-7-yl)isoquinolin-3-yl)carbamate; (1s,3s)-3-Methoxycyclobutyl (8-amino-7-fluoro-6-(8-methyl-2,3-dihydro-1H-pyrido[2,3-b][1,4]oxazin-7-yl)isoquinolin-3-yl)carbamate; |
| 577 | 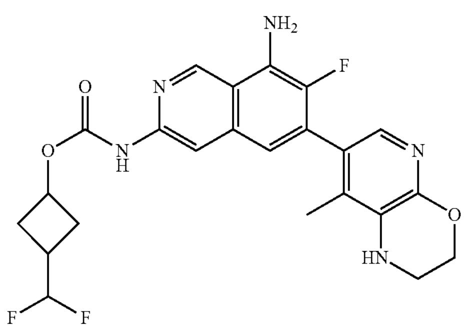 [SMILES: Cc1c(-c2cc3cc(NC(=O)OC4CC(C(F)F)C4)ncc3c(N)c2F)cnc2c1NCCO2] | 3-(Difluoromethyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 577a 577b | | (1s,3s)-3-(Difluoromethyl)cyclobutyl (8-amino-7-fluoro-6-(8-methyl-2,3-dihydro-1H-pyrido[2,3-b][1,4]oxazin-7-yl)isoquinolin-3-yl)carbamate; (1r,3r)-3-(Difluoromethyl)cyclobutyl (8-amino-7-fluoro-6-(8-methyl-2,3-dihydro-1H-pyrido[2,3-b][1,4]oxazin-7-yl)isoquinolin-3-yl)carbamate; |
| 578 | 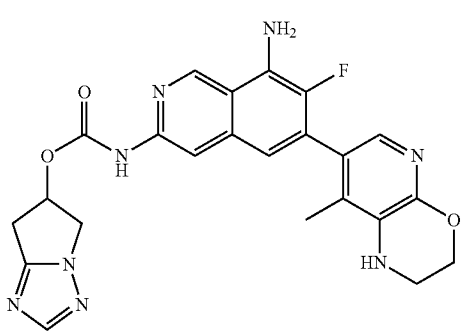 [SMILES: Cc1c(-c2cc3cc(NC(=O)OC4Cc5ncnn5C4)ncc3c(N)c2F)cnc2c1NCCO2] | 6,7-Dihydro-5H-pyrrolo[1,2-b][1,2,4]triazol-6-yl (8-amino-7-fluoro-6-(8-methyl-2,3-dihydro-1H-pyrido[2,3-b][1,4]oxazin-7-yl)isoquinolin-3-yl)carbamate; |

-continued

| No. | Structure | Name |
|---|---|---|
| 578a 578b | | (R)-6,7-Dihydro-5H-pyrrolo[1,2-b][1,2,4]triazol-6-yl (8-amino-7-fluoro-6-(8-methyl-2,3-dihydro-1H-pyrido[2,3-b][1,4]oxazin-7-yl)isoquinolin-3-yl)carbamate; (S)-6,7-Dihydro-5H-pyrrolo[1,2-b][1,2,4]triazol-6-yl (8-amino-7-fluoro-6-(8-methyl-2,3-dihydro-1H-pyrido[2,3-b][1,4]oxazin-7-yl)isoquinolin-3-yl)carbamate; |
| 579 | 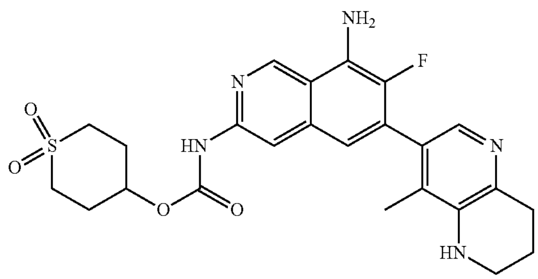 [SMILES: Cc1c(-c2cc3cc(NC(=O)OC4CCS(=O)(=O)CC4)ncc3c(N)c2F)cnc2c1NCCC2] | 1,1-Dioxidotetrahydro-2H-thiopyran-4-yl (8-amino-7-fluoro-6-(4-methyl-5,6,7,8-tetrahydro-1,5-naphthyridin-3-yl)isoquinolin-3-yl)carbamate; |
| 580 | 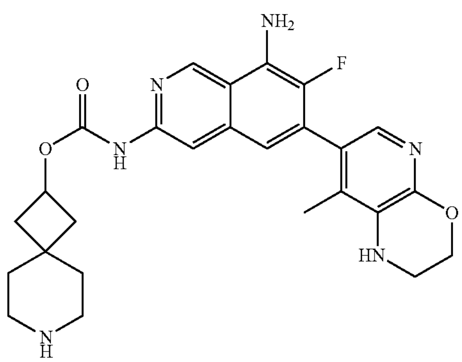 [SMILES: Cc1c(-c2cc3cc(NC(=O)OC4CC5(CCNCC5)C4)ncc3c(N)c2F)cnc2c1NCCO2] | 7-Azaspiro[3.5]nonan-2-yl (8-amino-7-fluoro-6-(8-methyl-2,3-dihydro-1H-pyrido[2,3-b][1,4]oxazin-7-yl)isoquinolin-3-yl)carbamate; |
| 581 | 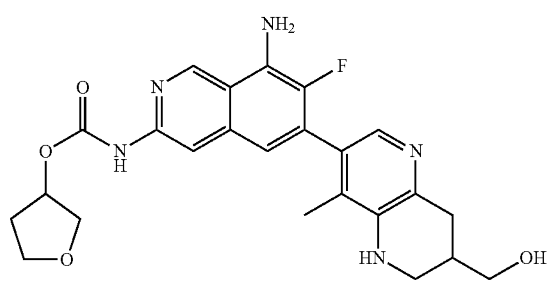 [SMILES: Cc1c(-c2cc3cc(NC(=O)OC4CCOC4)ncc3c(N)c2F)cnc2c1NCC(CO)C2] | Tetrahydrofuran-3-yl (8-amino-7-fluoro-tetrahydro-1,5-naphthyridin-3-6-(7-(hydroxymethyl)-4-methyl-5,6,7,8-yl)isoquinolin-3-yl)carbamate; |
| 581a 581b | | (R)-tetrahydrofuran-3-yl (8-amino-7-fluoro-6-(7-(hydroxymethyl)-4-methyl-5,6,7,8-tetrahydro-1,5-naphthyridin-3-yl)isoquinolin-3-yl)carbamate; (R)-tetrahydrofuran-3-yl (8-amino-7-fluoro-6-((R)-7-(hydroxymethyl)-4-methyl-5,6,7,8-tetrahydro-1,5-naphthyridin-3-yl)isoquinolin-3-yl)carbamate; (R)-tetrahydrofuran-3-yl (8-amino-7-fluoro-6-((S)-7-(hydroxymethyl)-4-methyl-5,6,7,8-tetrahydro-1,5-naphthyridin-3-yl)isoquinolin-3-yl)carbamate; |
| 581c 581d | | (S)-Tetrahydrofuran-3-yl (8-amino-7-fluoro-6-(7-(hydroxymethyl)-4-methyl-5,6,7,8-tetrahydro-1,5-naphthyridin-3-yl)isoquinolin-3-yl)carbamate; (S)-Tetrahydrofuran-3-yl (8-amino-7-fluoro-6-((R)-7-(hydroxymethyl)-4-methyl-5,6,7,8-tetrahydro-1,5-naphthyridin-3-yl)isoquinolin-3-yl)carbamate; |

| No. | Structure | Name |
|---|---|---|
| | | (S)-tetrahydrofuran-3-yl (8-amino-7-fluoro-6-((S)-7-(hydroxymethyl)-4-methyl-5,6,7,8-tetrahydro-1,5-naphthyridin-3-yl)isoquinolin-3-yl)carbamate; |
| 582 | | 3-Hydroxycyclonentyl (8-amino-7-fluoro-6-(8-methyl-2,3-dihydro-1H-pyrido[2,3-b][1,4]oxazin-7-yl)isoquinolin-3-yl)carbamate; |
| 582a 582b | | cis-3-Hydroxycyclopentyl (8-amino-7-fluoro-6-(8-methyl-2,3-dihydro-1H-pyrido[2,3-b][1.4]oxazin-7-yl)isoquinolin-3-yl)carbamate; (1S,3R)-3-Hydroxycyclopentyl (8-amino-7-fluoro-6-(8-methyl-2,3-dihydro-1H-pyrido[2,3-b][1.4]oxazin-7-yl)isoquinolin-3-yl)carbamate; (1R,3S)-3-Hydroxycyclopentyl (8-amino-7-fluoro-6-(8-methyl-2,3-dihydro-1H-pyrido[2,3-b][1,4]oxazin-7-yl)isoquinolin-3-yl)carbamate; |
| 582c 582d | | trans-3-Hydroxycyclopentyl (8-amino-7-fluoro-6-(8-methyl-2,3-dihydro-1H-pyrido[2,3-b][1,4]oxazin-7-yl)isoquinolin-3-yl)carbamate; (1S,3S)-3-Hydroxycyclopentyl (8-amino-7-fluoro-6-(8-methyl-2,3-dihydro-1H-pyrido[2,3-b][1,4]oxazin-7-yl)isoquinolin-3-yl)carbamate; (1R,3R)-3-Hydroxycyclopentyl (8-amino-7-fluoro-6-(8-methyl-2,3-dihydro-1H-pyrido[2,3-b][1,4]oxazin-7-yl)isoquinolin-3-yl)carbamate; |
| 583 | | 3-Methoxytetrahydro-2H-pyran-4-yl (8-amino-7-fluoro-6-(8-methyl-2,3-dihydro-1H-pyrido[2,3-b][1,4]oxazin-7-yl)isoquinolin-3-yl)carbamate; |
| 583a 583b 583c 583d | | (3S,4S)-3-Methoxytetrahydro-2H-pyran-4-yl (8-amino-7-fluoro-6-(8-methyl-2,3-dihydro-1H-pyrido[2,3-b][1,4]oxazin-7-yl)isoquinolin-3-yl)carbamate; (3S,4R)-3-Methoxytetrahydro-2H-pyran-4-yl (8-amino-7-fluoro-6-(8-methyl-2,3-dihydro-1H-pyrido[2,3-b][1,4]oxazin-7-yl)isoquinolin-3-yl)carbamate; (3R,4S)-3-Methoxytetrahydro-2H-pyran-4-yl (8-amino-7-fluoro-6-(8-methyl-2,3-dihydro-1H-pyrido[2,3-b][1,4]oxazin-7-yl)isoquinolin-3-yl)carbamate; (3R,4R)-3-Methoxytetrahydro-2H-pyran-4-yl (8-amino-7-fluoro-6-(8-methyl-2,3-dihydro-1H-pyrido[2,3-b][1,4]oxazin-7-yl)isoquinolin-3-yl)carbamate; |

| No. | Structure | Name |
|---|---|---|
| 584 | 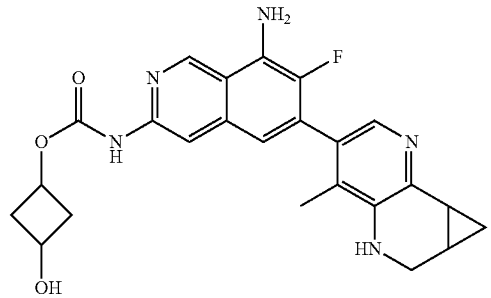 [SMILES: Cc1c(-c2cc3cc(NC(=O)OC4CC(O)C4)ncc3c(N)c2F)cnc2c1NCC1CC21] | 3-Hyroxycyclobutyl (8-amino-7-fluoro-6-(4-methyl-6,6a,7,7a-tetrahydro-5H-cyclopropa[c][1,5]naphthyridin-3-yl)isoquinolin-3-yl)carbamate; |
| 584a<br>584b<br>584c<br>584d | | (1s,3R)-3-Hydroxycyclobutyl (8-amino-7-fluoro-6-((6aR,7aS)-4-methyl-6,6a,7,7a-tetrahydro-5H-cyclopropa[c][1,5]naphthyridin-3-yl)isoquinolin-3-yl)carbamate;<br>(1s,3S)-3-Hydroxycyclobutyl (8-amino-7-fluoro-6-((6aS,7aR)-4-methyl-6,6a,7,7a-tetrahydro-5H-cyclopropa[c][1,5]naphthyridin-3-yl)isoquinolin-3-yl)carbamate;<br>(1r,3S)-3-Hydroxycyclobutyl (8-amino-7-fluoro-6-((6aR,7aS)-4-methyl-6,6a,7,7a-tetrahydro-5H-cyclopropa[c][1,5]naphthyridin-3-yl)isoquinolin-3-yl)carbamate; and<br>(1r,3R)-3-hydroxycyclobutyl (8-amino-7-fluoro-6-((6aS,7aR)-4-methyl-6,6a,7,7a-tetrahydro-5H-cyclopropa[c][1,5]naphthyridin-3-yl)isoquinolin-3-yl)carbamate. |

28. A pharmaceutical composition comprising the compound of claim 1, or a pharmaceutically acceptable salt thereof; and a pharmaceutically acceptable excipient.

29. The pharmaceutical composition of claim 28, wherein said composition comprises a chemotherapeutic agent.

* * * * *